US012448389B2

(12) United States Patent
Lu et al.

(10) Patent No.: US 12,448,389 B2
(45) Date of Patent: Oct. 21, 2025

(54) BRM TARGETING COMPOUNDS AND ASSOCIATED METHODS OF USE

(71) Applicant: Prelude Therapeutics Incorporated, Wilmington, DE (US)

(72) Inventors: Liang Lu, Hockessin, DE (US); Andrew Paul Combs, Kennett Square, PA (US); Corey Howard Basch, Delmar, DE (US); Rupa Shetty, Blue Bell, PA (US); Chaofeng Dai, Hockessin, DE (US); Klare Lazor Bersch, Glen Mills, PA (US); John A. Rose, Wilmington, DE (US); Danielle Julie Beam, Newark, DE (US); Song Mei, Wilmington, DE (US)

(73) Assignee: Prelude Therapeutics Incorporated, Wilmington, DE (US)

( * ) Notice: Subject to any disclaimer, the term of this patent is extended or adjusted under 35 U.S.C. 154(b) by 444 days.

(21) Appl. No.: 17/521,195

(22) Filed: Nov. 8, 2021

(65) Prior Publication Data

US 2023/0083376 A1 Mar. 16, 2023

Related U.S. Application Data

(60) Provisional application No. 63/110,688, filed on Nov. 6, 2020.

(51) Int. Cl.
*C07D 487/14* (2006.01)
*C07D 519/00* (2006.01)

(52) U.S. Cl.
CPC ......... *C07D 487/14* (2013.01); *C07D 519/00* (2013.01)

(58) Field of Classification Search
None
See application file for complete search history.

(56) References Cited

U.S. PATENT DOCUMENTS

| | | | | |
|---|---|---|---|---|
| 3,657,744 | A | 4/1972 | Ersek | |
| 4,739,762 | A | 4/1988 | Palmaz | |
| 5,040,548 | A | 8/1991 | Yock | |
| 5,061,273 | A | 10/1991 | Yock | |
| 5,195,984 | A | 3/1993 | Schatz | |
| 5,292,331 | A | 3/1994 | Boneau | |
| 5,451,233 | A | 9/1995 | Yock | |
| 5,496,346 | A | 3/1996 | Horewski | |
| 5,674,278 | A | 10/1997 | Boneau | |
| 5,879,382 | A | 3/1999 | Boneau | |
| 6,344,053 | B1 | 2/2002 | Boneau | |
| 2023/0103415 | A1 * | 4/2023 | Zhang | C07D 213/75 514/250 |
| 2023/0365576 | A1 * | 11/2023 | Rose | A61P 35/02 |
| 2024/0018158 | A1 * | 1/2024 | Lin | C07D 519/00 |

FOREIGN PATENT DOCUMENTS

| | | | |
|---|---|---|---|
| WO | 2016105518 | 6/2016 | |
| WO | 2019084026 | 5/2019 | |
| WO | 2019084030 | 5/2019 | |
| WO | 2019195201 | 10/2019 | |
| WO | WO-2020010227 A1 * | 1/2020 | A61P 35/00 |
| WO | 2021133917 | 7/2021 | |
| WO | 2021252666 | 12/2021 | |

OTHER PUBLICATIONS

Wang et al., Acta Pharmaceutica Sinica B, vol. 10, Issue 2, 2020, pp. 207-238 (Year: 2020).*
Maniaci C. et al., *Bioorg Med Chem.* 2019, 27(12): 2466-2479.
Lai A.C., Crews C.M. *Nat Rev Drug Discov.* 2017;16(2): 101-114.

* cited by examiner

*Primary Examiner* — Jeffrey S Lundgren
*Assistant Examiner* — Anthony Joseph Seitz
(74) *Attorney, Agent, or Firm* — BakerHostetler

(57) ABSTRACT

The present disclosure provides bifunctional compounds comprising a target protein binding moiety and a E3 ubiquitin ligase binding moiety, and associated methods of use.

29 Claims, No Drawings

BRM TARGETING COMPOUNDS AND ASSOCIATED METHODS OF USE

CROSS REFERENCE TO RELATED APPLICATIONS

This application claims the benefit of U.S. Provisional Application No. 63/110,688, filed Nov. 6, 2020, the entirety of which is incorporated by reference herein.

TECHNICAL FIELD

The description provides bifunctional compounds comprising a target protein binding moiety and a E3 ubiquitin ligase binding moiety, and associated methods of use. The bifunctional compounds are useful as modulators of targeted ubiquitination, especially with respect to Switch/Sucrose Non-Fermentable (SWI/SNF)-Related, Matrix-Associated, Actin-Dependent Regulator of Chromatin, Subfamily A, Member 2 (SMARCA2) (i.e. BRAHMA or BRM), which are degraded and/or otherwise inhibited by bifunctional compounds according to the present disclosure.

BACKGROUND

The human SWItch/Sucrose Non-Fermentable (SWI/SNF) complexes are ATP-dependent chromatin remodelers. These large complexes play important roles in essential cellular processes, such as transcription, DNA repair and replication by regulating DNA accessibility.

Mutations in the genes encoding up to 20 canonical SWI/SNF subunits are observed in nearly 20% of all human cancers with the highest frequency of mutations observed in rhabdoid tumors, female cancers (including ovarian, uterine, cervical and endometrial), lung adenocarcinoma, gastric adenocarcinoma, melanoma, esophageal, and renal clear cell carcinoma.

SMARCA2 (BRM) and SMARCA4 (BRG1) are the subunits containing catalytic ATPase domains and they are essential for the function of SWI/SNF in perturbation of histone-DNA contacts, thereby providing access points to transcription factors and cognate DNA elements that facilitate gene activation and repression.

SMARCA2 and SMARCA4 shares a high degree of homology (up to 75%). SMARCA4 is frequently mutated in primary tumors (i.e., deleted or inactivated), particularly in lung cancer (12%), melanoma, liver cancer and pancreatic cancer. SMARCA2 is one of the top essential genes in SMARCA4-mutant (deleted) cancer cell line. This is because SMARCA4 deleted cancer cells exclusively rely on SMARCA2 ATPase activity for their chromatin remodeling activity for cellular functions such as cell proliferation, survival and growth. Thus, targeting SMARCA2 may be promising therapeutic approach in SMARCA4-related or deficient cancers (genetic synthetic lethality).

Previous studies have demonstrated the strong synthetic lethality using gene expression manipulation such as RNAi; downregulating SMARCA2 gene expression in SMARCA4 mutated cancer cells results in suppression of cancer cell proliferation. However, SMARCA2/4 bromodomain inhibitors (e.g. PFI-3) exhibit none to minor effects on cell proliferation inhibition [Vangamudi et al. Cancer Res 2015]. This phenotypic discrepancy between gene expression downregulation and small molecule-based approach lead us to investigating protein degradation bispecific molecules in SMARCA4 deficient cancers.

SMARCA2 is also reported to play roles in multiple myeloma expressing t(4;14) chromosomal translocation [Chooi et al. Cancer Res abstract 2018]. SMARCA2 interacts with NSD2 and regulates gene expression such as PRL3 and CCND1. SMARCA2 gene expression downregulation with shRNA reduces cell cycle S phase and suppresses cell proliferation of t(4;14) MM cells.

Therapeutic compounds that inhibit SMARCA2 and/or SMARCA4 are needed.

SUMMARY

The present disclosure is directed to compounds of Formula (I):

PTM-ULM (I)

or a pharmaceutically acceptable salt or solvate thereof, wherein

PTM is a moiety of Formula IA:

(IA)

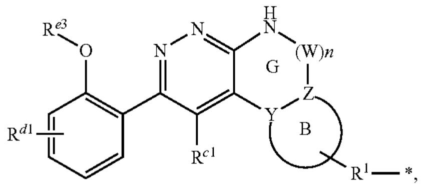

wherein $R^1$ is a covalent bond, or chemical moiety that links PTM and ULM;

* is a point of attachment to ULM;

n=0-3;

each W is independently optionally substituted —$CH_2$—, —C(O)—, —S(O)—, or —$S(O)_2$—, wherein when n=2 or 3, only one W is —C(O)—, —S(O)—, or —$S(O)_2$— and the other W are —$CH_2$— or substituted —$CH_2$—;

$R^{c1}$ and $R^{d1}$ are independently H, D, Halo, $C_{1-3}$ alkyl, $C_{1-3}$ haloalkyl, or $C_{1-4}$ alkoxyl;

$R^{e3}$ is H, —C(O)$R^f$, or —P(O)$(OR^g)_2$; wherein $R^f$ and $R^g$ are independently H, $C_{1-4}$ alkyl, $C_{1-4}$ substituted alkyl, $C_{3-8}$ cyclcoalkyl, $C_{3-8}$ substituted cyclcoalkyl, $C_{3-8}$ heterocyclcoalkyl, or $C_{3-8}$ substituted heterocyclcoalkyl;

Z and Y are each independently N, $CR^h$ wherein $R^h$═H or absent; or, if $R^l$ is attached to Z, then Z is C and Y is N or $CR^h$ wherein $R^h$ is H; or if $R^l$ is attached to Y, then Y is C and Z is N or $CR^h$ wherein $R^h$ is H;

B is an optionally substituted 5-7 membered cycloalkyl ring, an optionally substituted 5-7 membered heteroaryl ring, or an optionally substituted 5-7 membered heterocyclic ring, wherein ring B is fused to ring G through Y and Z; and ULM is a small molecule E3 Ubiquitin Ligase binding moiety that binds a Cereblon E3 Ubiquitin Ligase.

DETAILED DESCRIPTION OF ILLUSTRATIVE EMBODIMENTS

Unless otherwise defined, all technical and scientific terms used herein have the same meaning as commonly understood by one of ordinary skill in the art to which this disclosure pertains. The terminology used in the description is for describing particular embodiments only and is not intended to be limiting of the disclosure.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

The following terms are used to describe the present disclosure. In instances where a term is not specifically defined herein, that term is given an art-recognized meaning by those of ordinary skill applying that term in context to its use in describing the present disclosure.

The articles "a" and "an" as used herein and in the appended claims are used herein to refer to one or to more than one (e.g., to at least one) of the grammatical object of the article unless the context clearly indicates otherwise. By way of example, "an element" means one element or more than one element.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are co-administered in combination with at least one additional bioactive agent, especially including an anticancer agent. In particularly preferred aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives, including prodrug and/or deuterated forms thereof where applicable, in context. Deuterated small molecules contemplated are those in which one or more of the hydrogen atoms contained in the drug molecule have been replaced by deuterium.

Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder.

The term "ubiquitin ligase" refers to a family of proteins that facilitate the transfer of ubiquitin to a specific substrate protein, targeting the substrate protein for degradation. For example, an E3 ubiquitin ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

As used herein, "Cereblon (CRBN) E3 Ubiquitin Ligase" refers to the substrate recognition subunit of the Cullin RING E3 ubiquitin ligase complexes. CRBN are one of the most popular E3 ligases recruited by bifunctional Proteolysis-targeting chimeras (PROTACs) to induce ubiquitination and subsequent proteasomal degradation of a target protein (Maniaci C. et al., *Bioorg fed Chem.* 2019, 27(12): 2466-2479).

As used herein, the term "alkyl", by itself or as part of another substituent, means, unless otherwise stated, a straight or branched chain hydrocarbon radical having up to twelve carbon atoms. In some embodiments, the number of carbon atoms is designated (i.e., $C_1$-$C_8$ means one to eight carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. Alkyl groups may be optionally substituted as provided herein. In some embodiments, the alkyl group is a $C_1$-$C_6$ alkyl; in some embodiments, it is a $C_1$-$C_4$ alkyl.

When a range of carbon atoms is used herein, for example, $C_1$-$C_6$, all ranges, as well as individual numbers of carbon atoms are encompassed. For example, "$C_1$-$C_3$" includes $C_1$-$C_3$, $C_1$-$C_2$, $C_2$-$C_3$, $C_1$, $C_2$, and $C_3$.

The term "optionally substituted", as used in combination with a substituent defined herein, means that the substituent may, but is not required to, have one or more hydrogens replaced with one or more suitable functional groups or other substituents as provided herein. For example, a substituent may be optionally substituted with one or more of: —H, D, -halo, —$C_1$-$C_8$alkyl, —O—$C_1$-$C_8$alkyl, —$C_1$-$C_6$haloalkyl, —S—$C_1$-$C_8$alkyl, —NH$C_1$-$C_8$alkyl, —N($C_1$-$C_8$alkyl)2, 3-11 membered cycloalkyl, aryl, heteroaryl, 3-11 membered heterocyclyl, —O-(3-11 membered cycloalkyl), —S-(3-11 membered cycloalkyl), NH-(3-11 membered cycloalkyl), N(3-11 membered cycloalkyl)$_2$, N-(3-11 membered cycloalkyl)($C_1$-$C_8$alkyl), —OH, —$NH_2$, —SH, —$SO_2C_1$-$C_8$alkyl, SO(NH)$C_1$-$C_8$alkyl, P(O)(O$C_1$-$C_8$alkyl)($C_1$-$C_8$alkyl), —P(O)(O$C_1$-$C_8$alkyl)$_2$, —C≡C—$C_1$-$C_8$alkyl, —C≡CH, —CH=CH($C_1$-$C_8$alkyl), —C($C_1$-$C_8$alkyl)=CH($C_1$-$C_8$alkyl), —C($C_1$-$C_8$alkyl)=C($C_1$-$C_8$alkyl)$_2$, —Si(OH)$_3$, —Si($C_1$-$C_8$alkyl)$_3$, —Si(OH)($C_1$-$C_8$alkyl)$_2$, —C(O)$C_1$-$C_8$alkyl, —$CO_2H$, —CN, —$CF_3$, —$CHF_2$, —$CH_2F$, —$NO_2$, —$SF_5$, —$SO_2NHC_1$-$C_8$alkyl, —$SO_2N$($C_1$-$C_8$alkyl)$_2$, —SO(NH)NH$C_1$-$C_8$alkyl, —SO(NH)N($C_1$-$C_8$alkyl)$_2$, —SONH$C_1$-$C_8$alkyl, —SON($C_1$-$C_8$alkyl)$_2$, —$CONHC_1$-$C_8$alkyl, —$CON(C_1$-$C_8alkyl)_2$, —$N(C_1$-$C_8$alkyl)$CONH(C_1$-$C_8$alkyl), —$N(C_1$-$C_8$alkyl)$CON(C_1$-$C_8alkyl)_2$, —$NHCONH(C_1$-$C_8$alkyl), —$NHCON(C_1$-$C_8alkyl)_2$, —$NHCONH_2$, —$N(C_1$-$C_8$alkyl)$SO_2NH(C_1$-$C_8$alkyl), —$N(C_1$-$C_8$alkyl)$SO_2N(C_1$-$C_8alkyl)_2$, —$NHSO_2NH(C_1$-$C_8$alkyl), —$NHSO_2N(C_1$-$C_8alkyl)_2$, or —$NHSO_2NH_2$. In some embodiments, each of the above optional substituents are themselves optionally substituted by one or two groups.

The term "optionally substituted —$CH_2$—," refers to "—$CH_2$—" or substituted —$CH_2$—." A substituted —$CH_2$— may also be referred to as —CH(substituent)- or —C(substituent)(substituent)-, wherein each substituent is independently selected from the optional substituents described herein.

The term "cycloalkyl" as used herein refers to a 3-12 membered cyclic alkyl group, and includes bridged and spirocycles (e.g., adamantine). Cycloalkyl groups may be fully saturated or partially unsaturated. The term "cycloalkyl" also includes multiple condensed ring systems (e.g., ring systems comprising 2, 3 or 4 rings) wherein a single cycloalkyl ring (as defined above) can be condensed with one or more groups selected from heterocycles, carbocycles, aryls, or heteroaryls to form the multiple condensed ring system. Such multiple condensed ring systems may be optionally substituted with one or more (e.g., 1, 2, 3 or 4) oxo groups on the carbocycle or heterocycle portions of the multiple condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a cycloalkyl) can be at any position of the cycloalkylic ring. Examples of cycloalkyl groups include cyclopropyl, cyclobutyl, cyclopentyl, cycloheptyl, cyclohexyl, cycloheptyl, cyclooctyl, indenyl, bicyclo[2.2.1]heptanyl, bicyclo[3.1.1]heptanyl, bicyclo[4.1.0]heptanyl, spiro[3.3]heptanyl, and spiro[3.4]octanyl. In some embodiments, the cycloalkyl group is a 3-7 membered cycloalkyl.

The term "alkenyl" as used herein refers to $C_2$-$C_{12}$ alkyl group that contains at least one carbon-carbon double bond. In some embodiments, the alkenyl group is optionally substituted. In some embodiments, the alkenyl group is a $C_2$-$C_6$ alkenyl.

The term "akynyl" as used herein refers to $C_2$-$C_{12}$ alkyl group that contains at least one carbon-carbon triple bond. In some embodiments, the alkenyl group is optionally substituted. In some embodiments, the alkynyl group is a $C_2$-$C_6$ alkynyl.

The terms "alkoxy," "alkylamino" and "alkylthio", are used in their conventional sense, and refer to those alkyl groups attached to the remainder of the molecule via an oxygen atom ("oxy"), an amino group ("amino") or thio group. The term "alkylamino" includes mono-di-alkylamino groups, the alkyl portions can be the same or different.

The terms "halo" or "halogen", by itself or as part of another substituent, means a fluorine, chlorine, bromine, or iodine atom.

The term "heteroalkyl" refers to an alkyl group in which one or more carbon atom has been replaced by a heteroatom selected from S, O, P and N. Exemplary heteroalkyls include alkyl ethers, secondary and tertiary alkyl amines, alkyl amides, alkyl sulfides, and the like. The group may be a terminal group or a bridging group. As used herein reference to the normal chain when used in the context of a bridging group refers to the direct chain of atoms linking the two terminal positions of the bridging group.

The term "aryl" as used herein refers to a single, all carbon aromatic ring or a multiple condensed all carbon ring system wherein at least one of the rings is aromatic. For example, in certain embodiments, an aryl group has 6 to 12 carbon atoms. Aryl includes a phenyl radical. Aryl also includes multiple condensed ring systems (e.g., ring systems comprising 2, 3 or 4 rings) having about 9 to 12 carbon atoms in which at least one ring is aromatic and wherein the other rings may be aromatic or not aromatic. Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the aromatic ring. Non-limiting examples of aryl groups include, but are not limited to, phenyl, indenyl, naphthyl, 1,2,3,4-tetrahydronaphth-yl, and the like.

The term "heteroaryl" as used herein refers to a single aromatic ring that has at least one atom other than carbon in the ring, wherein the atoms are selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example a naphthyridinyl such as 1,8-naphthyridinyl), heterocycles, (to form for example a 1, 2, 3, 4-tetra-hydronaphthyridinyl such as 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. A heteroaryl (a single aromatic ring or multiple condensed ring system) can also have about 5 to 12 or about 5 to 10 members within the heteroaryl ring. Multiple condensed ring systems may be optionally substituted with one or more (e.g., 1, 2, 3 or 4) oxo groups on the carbocycle or heterocycle portions of the condensed ring. The rings of a multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the heteroaryl ring. It is also to be understood that the point of attachment for a heteroaryl or heteroaryl multiple condensed ring system can be at any suitable atom of the heteroaryl ring including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5,6,7-tetrahydro-1H-indazole and 3b,4,4a,5-tetrahydro-1H-cyclopropa[3,4]cyclopenta[1,2-c]pyrazole. In one embodiment the term "heteroaryl" refers to a single aromatic ring containing at least one heteroatom. For example, the term includes 5-membered and 6-membered monocyclic aromatic rings that include one or more heteroatoms. Non-limiting examples of heteroaryl include but are not limited to pyridyl, furyl, thiazole, pyrimidine, oxazole, and thiadiazole.

The term "heterocyclyl" or "heterocycle" as used herein refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from heterocycles (to form for example a 1,8-decahydronapthyridinyl), carbocycles (to form for example a decahydroquinolyl) and aryls to form the multiple condensed ring system. Thus, a heterocycle (a single saturated or single partially unsaturated ring or multiple condensed ring system) has about 2-20 carbon atoms and 1-6 heteroatoms within the heterocycle ring. Such multiple condensed ring systems may be optionally substituted with one or more (e.g., 1, 2, 3 or 4) oxo groups on the carbocycle or heterocycle portions of the multiple condensed ring. The rings of the multiple condensed ring system can be connected to each other via fused, spiro and bridged bonds when allowed by valency requirements. It is to be understood that the individual rings of the multiple condensed ring system may be connected in any order relative to one another. Accordingly, a heterocycle (a single saturated or single partially unsaturated ring or multiple condensed ring system) has about 3-20 atoms including about 1-6 heteroatoms within the heterocycle ring system. It is also to be understood that the point of attachment of a multiple condensed ring system (as defined above for a heterocyclyl) can be at any position of the heterocyclic ring. It is also to be understood that the point of attachment for a heterocycle or heterocycle multiple condensed ring system can be at any suitable atom of the heterocyclic ring including a carbon atom and a heteroatom (e.g., a nitrogen). In one embodiment the term heterocycle includes a $C_{2-20}$ heterocycle. In one embodiment the term heterocycle includes a $C_{2-7}$ heterocycle. In one embodiment the term heterocycle includes a $C_{2-5}$ heterocycle. In one embodiment the term heterocycle includes a $C_{2-4}$ heterocycle. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzo-furanyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one N-methylpiperidine, imidazolidine, pyrazolidine, butyrolactam, valerolactam, imidazolidinone, hydantoin, dioxolane, phthalimide, 1,4-dioxane, thiomorpholine, thiomorpholine-S-oxide, thiomorpholine-S,S-oxide, pyran, 3-pyrroline, thiopyran, pyrone, tetrahydrothiophene, quinuclidine, tropane, 2-azaspiro[3.3]-heptane, (1R,5S)-3-azabicyclo[3.2.1]octane, (1s,4s)-2-azabicyclo[2.2.2]octane, (1R,4R)-2-oxa-5-azabicyclo[2.2.2]octane and pyrrolidin-2-one. In one embodiment the term "heterocycle" refers to a monocyclic, saturated or partially unsaturated, 3-8 membered ring having at least one heteroatom. For example, the term includes a monocyclic, saturated or partially unsaturated, 4, 5, 6, or 7 membered ring having at least one heteroatom. Non-limiting examples of heterocycle include aziridine, azetidine, pyrrolidine, piperidine, piperidine, piperazine, oxirane, morpholine, and thiomorpholine. The term "9- or 10-membered heterobicyclic" as used herein refers to a partially unsaturated or aromatic fused bicyclic ring system having at least one heteroatom. For example, the term 9- or 10-membered heterobicyclic includes a bicyclic ring system having a benzo ring fused to a 5-membered or 6-membered saturated, partially unsaturated, or aromatic ring that contains one or more heteroatoms.

As used herein, the term "heteroatom" is meant to include oxygen (O), nitrogen (N), sulfur (S) and silicon (Si). The nitrogen and sulfur can be in an oxidized form when feasible.

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution but differ with regard to the arrangement of the atoms or groups in space, e.g., enantiomers, diastereomers, tautomers.

The term "patient" or "subject" is used throughout the specification to describe an animal, preferably a human or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, e.g., in humans.

"Pharmaceutically acceptable salt" refers to a salt of a compound of the disclosure that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

A "solvate" refers to a physical association of a compound of Formula I with one or more solvent molecules.

"Treating" or "treatment" of any disease or disorder refers, in one embodiment, to ameliorating the disease or disorder (e.g., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

In one aspect, the disclosure is directed to a compound of Formula (I):

PTM-ULM (I)

or a pharmaceutically acceptable salt or solvate thereof, wherein PTM (Protein Targeting Moiety) is a moiety of Formula IA:

(IA)

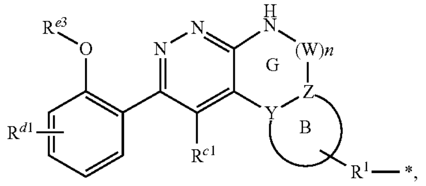

wherein $R^1$ is a covalent bond or a chemical moiety that links PTM and ULM; * is a point of attachment to ULM;

n=0-3;

each W is independently optionally substituted —$CH_2$—, —C(O)—, —S(O)—, or —$S(O)_2$—, wherein when n=2 or 3, only one W is —C(O)—, —S(O)—, or —$S(O)_2$— and the other W are —$CH_2$— or substituted —$CH_2$—;

$R^{c1}$ and $R^{d1}$ are independently H, D, Halo, $C_{1-3}$ alkyl, $C_{1-3}$ haloalkyl, or $C_{1-4}$ alkoxyl;

$R^{e3}$ is H, —C(O)$R^f$, or —P(O)$(OR^g)_2$; wherein $R^f$ and $R^g$ are independently H, $C_{1-4}$ alkyl, $C_{1-4}$ substituted alkyl, $C_{3-8}$ cyclcoalkyl, $C_{3-8}$ substituted cyclcoalkyl, $C_{3-8}$ heterocyclcoalkyl, or $C_{3-8}$ substituted heterocyclcoalkyl;

Z and Y are each independently N, or $CR^h$ wherein $R^h$=H or absent or, if $R^l$ is attached to Z, then Z is C and Y is N or $CR^h$ wherein $R^h$ is H; or if $R^l$ is attached to Y, then Y is C and Z is N or $CR^h$ wherein $R^h$ is H;

B is an optionally substituted 5-7 membered cycloalkyl ring, an optionally substituted 5-7 membered heteroaryl ring, or an optionally substituted 5-7 membered heterocyclic ring, wherein ring B is fused to ring G through Y and Z; and ULM is a small molecule E3 Ubiquitin Ligase binding moiety that binds a Cereblon E3 Ubiquitin Ligase.

In some aspects, the compounds of Formula I includes a PTM. According to the disclosure, the PTM in the compounds of Formula I is a moiety of Formula IA (IA)

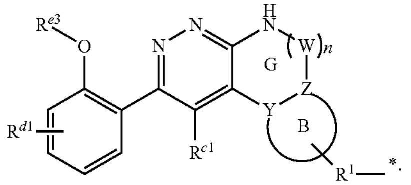

According to the disclosure, B is a ring fused to ring "C" via Y and Z.

In some aspects, B in Formula IA is an optionally substituted 5-7 membered cycloalkyl ring, an optionally substituted 5-7 membered heteroaryl ring, or an optionally substituted 5-7 membered heterocyclic ring.

In some embodiments, B in Formula IA is an optionally substituted 5-7 membered cycloalkyl ring.

In some embodiments, B in Formula IA is an usubstituted 5-7 membered cycloalkyl ring. In some embodiments, B is Formula IA is a substituted 5-7 membered cycloalkyl ring wherein the substituents are hydroxy, halogen, alkoxy, alkyl, haloalkyl, amino, alkylamino, or cyano.

In some embodiments, B in Formula IA is an unsubstituted 5-7 membered heteroaryl ring.

In some embodiments, B in Formula IA is an unsubstituted 5-7 membered heteroaryl ring. In some embodiments, B in Formula IA is a substituted 5-7 membered heteroaryl ring, wherein substituents are hydroxy, halogen, alkoxy, alkyl, haloalkyl, amino, alkylamino, or cyano.

In other embodiments, B in Formula IA is an unsubstituted 5-7 membered heterocyclic ring.

In some embodiments, B in Formula IA is an unsubstituted 5-7 membered heterocyclic ring. In some embodiments, B in Formula IA is a substituted 5-7 membered heterocyclic ring, wherein the substituents are hydroxy, halogen, alkoxy, alkyl, haloalkyl, amino, alkylamino, cyano.

In some aspects, n in Formula IA is 0, 1, 2 or 3. In some embodiments, n=0. In other embodiments, n=1. In other embodiments, n=2. In other embodiments, n=3.

In some aspects, each W in Formula IA is independently optionally substituted —$CH_2$—, —C(O)—, —S(O)—, or —$S(O)_2$—, wherein when n=2 or 3, only one W may be —C(O)—, —S(O)—, or —$S(O)_2$— and the other W are —$CH_2$— or substituted —$CH_2$—. Preferred substituents when W is substituted —$CH_2$— include D, $C_{1-3}$alkyl, $C_{1-3}$haloalkyl, and $C_{1-4}$alkoxyl.

In some embodiments, W in Formula IA is optionally substituted —$CH_2$—. In other embodiments, W in Formula IA is —$CH_2$—. Preferred substituents when W is substituted —$CH_2$— include D, $C_{1-3}$alkyl, $C_{1-3}$haloalkyl, and $C_{1-4}$alkoxyl.

In some embodiments, W in Formula IA is —C(O)—.

In some embodiments, W in Formula IA is —S(O)—.

In some embodiments, W in Formula IA is —$S(O)_2$—.

In embodiments of the disclosure wherein n is 2 or 3, then only one W may be —C(O)—, —S(O)—, or —$S(O)_2$— and the other W are —$CH_2$— or substituted —$CH_2$—. Preferred substituents when W is substituted —$CH_2$— include D, $C_{1-3}$alkyl, $C_{1-3}$haloalkyl, and $C_{1-4}$alkoxyl.

In some aspects, $R^{c1}$ and $R^{d1}$ in Formula IA are independently H, D, halo, $C_{1-3}$ alkyl, $C_{1-3}$ haloalkyl, or $C_{1-4}$ alkoxyl.

In some embodiments, $R^{c1}$ is H.

In some embodiments, $R^{c1}$ is D.

In some embodiments, $R^{c1}$ is halo, e.g., —F, —Cl, —Br, or —I.

In some embodiments, $R^{c1}$ is $C_{1-3}$ alkyl, e.g., —$C_1$ alkyl, —$C_2$ alkyl, —$C_3$ alkyl, —$CH_3$, —$CH_2CH_3$, and the like.

In some embodiments, $R^{c1}$ is $C_{1-3}$ haloalkyl, e.g., —$C_1$ haloalkyl, —$C_2$ haloalkyl, —$C_3$ haloalkyl, —$CF_3$, —$CH_2CF_3$, and the like.

In some embodiments, $R^{c1}$ is $C_{1-4}$ alkoxyl, e.g., —$C_1$ alkoxyl, —$C_2$ alkoxyl, —$C_3$ alkoxyl, —$C_4$ alkoxyl, —$OCH_3$, —$OCH_2CH_3$, and the like.

In some embodiments, $R^{d1}$ is H.

In some embodiments, $R^{d1}$ is D.

In some embodiments, $R^{d1}$ is halo, e.g., —F, —Cl, —Br, or —I.

In some embodiments, $R^{d1}$ is $C_{1-3}$ alkyl, e.g., —$C_1$ alkyl, —$C_2$ alkyl, —$C_3$ alkyl, —$CH_3$, —$CH_2CH_3$, and the like.

In some embodiments, $R^{d1}$ is $C_{1-3}$ haloalkyl, e.g., —$C_1$ haloalkyl, —$C_2$ haloalkyl, —$C_3$ haloalkyl, —$CF_3$, —$CH_2CF_3$, and the like.

In some embodiments, $R^{d1}$ is $C_{1-4}$ alkoxyl, e.g., —$C_1$ alkoxyl, —$C_2$ alkoxyl, —$C_3$ alkoxyl, —$C_4$ alkoxyl, —$OCH_3$, —$OCH_2CH_3$, and the like.

In some aspects, $R^{e3}$ in Formula IA is H, —C(O)$R^f$, or —P(O)$(OR^g)_2$; wherein $R^f$ and $R^g$ are independently H, $C_{1-4}$ alkyl, $C_{1-4}$ substituted alkyl, $C_{3-8}$ cyclcoalkyl, $C_{3-8}$ substituted cyclcoalkyl, $C_{3-8}$ heterocyclcoalkyl, or $C_{3-8}$ substituted heterocyclcoalkyl.

In some embodiments, $R^{e3}$ is H.

In other embodiments, $R^{e3}$ is —C(O)R wherein $R^f$ is H, $C_{1-4}$ alkyl, $C_{1-4}$ substituted alkyl, $C_{3-8}$ cyclcoalkyl, $C_{3-8}$ substituted cyclcoalkyl, $C_{3-8}$ heterocyclcoalkyl, or $C_{3-8}$ substituted heterocyclcoalkyl.

In other embodiments, $R^{e3}$ is —C(O)R wherein $R^f$ is H. In other embodiments, $R^{e3}$ is —C(O)R wherein $R^f$ is $C_{1-4}$ alkyl, e.g., —$C_1$ alkyl, —$C_2$ alkyl, —$C_3$ alkyl, —$C_4$ alkyl, —$CH_3$, —$CH_2CH_3$, and the like.

In other embodiments, $R^{e3}$ is —C(O)R wherein $R^f$ is $C_{1-4}$ substituted alkyl, e.g., —$C_1$ substituted alkyl, —$C_2$ substituted alkyl, —$C_3$ substituted alkyl, and —$C_4$ substituted alkyl.

In other embodiments, $R^{e3}$ is —C(O)R wherein $R^f$ is $C_{3-8}$ cyclcoalkyl, e.g., $C_3$ cyclcoalkyl, $C_4$ cyclcoalkyl, $C_5$ cyclcoalkyl, $C_6$ cyclcoalkyl, $C_7$ cyclcoalkyl, and $C_8$ cyclcoalkyl.

In other embodiments, $R^{e3}$ is —C(O)R wherein $R^f$ is $C_{3-8}$ substituted cyclcoalkyl, e.g., $C_3$ substituted cyclcoalkyl, $C_4$ substituted cyclcoalkyl, $C_5$ substituted cyclcoalkyl, $C_6$ substituted cyclcoalkyl, $C_7$ substituted cyclcoalkyl, and $C_8$ substituted cyclcoalkyl.

In other embodiments, $R^{e3}$ is —C(O)R wherein $R^f$ is $C_{3-8}$ heterocyclcoalkyl, e.g., $C_3$ heterocyclcoalkyl, $C_4$ heterocyclcoalkyl, $C_5$ heterocyclcoalkyl, $C_6$ heterocyclcoalkyl, $C_7$ heterocyclcoalkyl, and $C_8$ heterocyclcoalkyl.

In other embodiments, $R^{e3}$ is —C(O)R wherein $R^f$ is $C_{3-8}$ substituted heterocyclcoalkyl, e.g., $C_3$ substituted heterocyclcoalkyl, $C_4$ substituted heterocyclcoalkyl, $C_5$ substituted heterocyclcoalkyl, $C_6$ substituted heterocyclcoalkyl, $C_7$ substituted heterocyclcoalkyl, and $C_8$ substituted heterocyclcoalkyl.

In other embodiments, $R^{e3}$ is —P(O)$(OR^g)_2$; wherein each $R^g$ is independently H, $C_{1-4}$ alkyl, $C_{1-4}$ substituted alkyl, $C_{3-8}$ cyclcoalkyl, $C_{3-8}$ substituted cyclcoalkyl, $C_{3-8}$ heterocyclcoalkyl, or $C_{3-8}$ substituted heterocyclcoalkyl.

In other embodiments, $R^{e3}$ is —P(O)$(OR^g)_2$; wherein each $R^g$ is H.

In other embodiments, $R^{e3}$ is —P(O)$(OR^g)_2$; wherein each $R^g$ is $C_{1-4}$ alkyl, e.g., —$C_1$ alkyl, —$C_2$ alkyl, —$C_3$ alkyl, —$C_4$ alkyl, —$CH_3$, —$CH_2CH_3$, and the like.

In other embodiments, $R^{e3}$ is —P(O)$(OR^g)_2$; wherein one $R^g$ is H and the other $R^g$ is $C_{1-4}$ alkyl, e.g., —$C_1$ alkyl, —$C_2$ alkyl, —$C_3$ alkyl, —$C_4$ alkyl, —$CH_3$, —$CH_2CH_3$, and the like.

In other embodiments, $R^{e3}$ is —P(O)$(OR^g)_2$; wherein at least one $R^g$ is $C_{1-4}$ substituted alkyl, e.g., —$C_1$ substituted alkyl, —$C_2$ substituted alkyl, —$C_3$ substituted alkyl, and —$C_4$ substituted alkyl.

In other embodiments, $R^{e3}$ is —P(O)$(OR^g)_2$; wherein at least one $R^g$ is $C_{3-8}$ cyclcoalkyl, e.g., $C_3$ cyclcoalkyl, $C_4$ cyclcoalkyl, $C_5$ cyclcoalkyl, $C_6$ cyclcoalkyl, $C_7$ cyclcoalkyl, and $C_8$ cyclcoalkyl.

In other embodiments, $R^{e3}$ is —P(O)$(OR^g)_2$; wherein at least one $R^g$ is $C_{3-8}$ substituted cyclcoalkyl, e.g., $C_3$ substituted cyclcoalkyl, $C_4$ substituted cyclcoalkyl, $C_5$ substituted cyclcoalkyl, $C_6$ substituted cyclcoalkyl, $C_7$ substituted cyclcoalkyl, and $C_8$ substituted cyclcoalkyl.

In other embodiments, $R^{e3}$ is —P(O)$(OR^g)_2$; wherein at least one $R^g$ is $C_{3-8}$ heterocyclcoalkyl, e.g., $C_3$ heterocyclcoalkyl, $C_4$ heterocyclcoalkyl, $C_5$ heterocyclcoalkyl, $C_6$ heterocyclcoalkyl, $C_7$ heterocyclcoalkyl, and $C_8$ heterocyclcoalkyl.

In other embodiments, $R^{e3}$ is —P(O)$(OR^g)_2$; wherein at least one $R^g$ is $C_{3-8}$ substituted heterocyclcoalkyl, e.g., $C_3$ substituted heterocyclcoalkyl, $C_4$ substituted heterocyclcoalkyl, $C_5$ substituted heterocyclcoalkyl, $C_6$ substituted heterocyclcoalkyl, $C_7$ substituted heterocyclcoalkyl, and $C_8$ substituted heterocyclcoalkyl.

In some aspects, Z and Y in Formula IA are each independently N or $CR^h$, wherein $R^h$=H or may be absent when n=1-3 such that a double bond is formed between Z and Y, or, if $R^1$ is attached to Z, then Z is C and Y is N or $CR^h$ wherein $R^h$ is H; or if $R^1$ is attached to Y, then Y is C and Z is N or $CR^h$ wherein $R^h$ is H. Examples of these embodiments include:

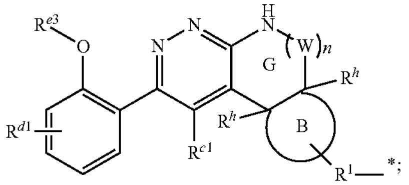

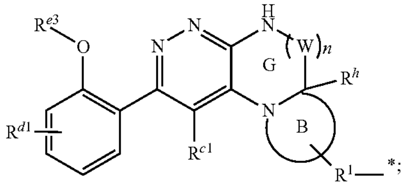

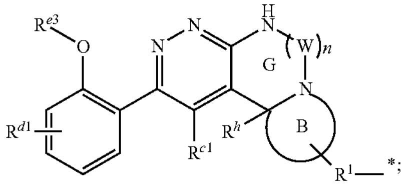

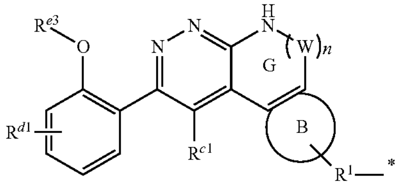

(n =1-3);

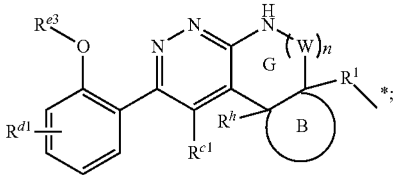

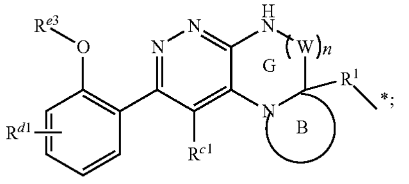

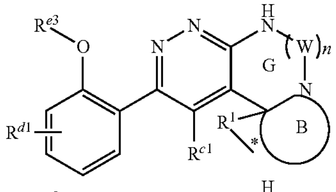

; and

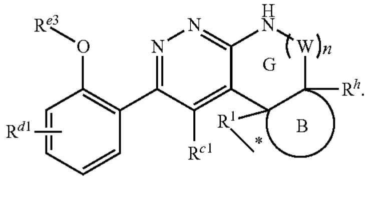

In some embodiments, Z is N.

In other embodiments, Z is $CR^h$ wherein $R^h$=H.

In other embodiments, Z is $CR^h$ wherein $R^h$=absent, and Z is bonded to Y by a double bond.

In some embodiments, Z is C and is attached to $R^1$.

In some embodiments, Y is N.

In other embodiments, Y is $CR^h$ wherein $R^h$=H.

In other embodiments, Y is $CR^h$ wherein $R^h$=absent, and Y is bonded to Z by a double bond.

In some embodiments, Y is C and is attached to $R^1$.

In some embodiments, the PTM is a moiety of Formula IA wherein * is a point of attachment to ULM.

In some aspects, $R^1$ in Formula IA is a covalent bond, or chemical moiety that links PTM and ULM.

In some embodiments, $R^1$ in Formula IA is a covalent bond.

In other embodiments, $R^1$ in Formula IA is a chemical moiety that links PTM and ULM.

Chemical moieties that are used to link PTM and ULM moieties are known in the art. These moieties are sometimes referred to as "linkers" in the art. In some embodiments, $R^1$ in Formula IA is a chemical moiety that is used to link a PTM and ULM that is known in the art.

In some embodiments, $R^1$ in Formula IA is a chemical moiety that is used to link a PTM and ULM as described in U.S. Patent Application Publication No. 2019/0300521, the entirety of which is incorporated by reference herein.

In other embodiments, $R^1$ in Formula IA is a chemical moiety that is used to link a PTM and ULM as described in U.S. Patent Application Publication No. 2019/0255066, the entirety of which is incorporated by reference herein.

In other embodiments, $R^1$ in Formula IA is a chemical moiety that is used to link a PTM and ULM as described in WO 2019/084030, the entirety of which is incorporated by reference herein.

In other embodiments, $R^1$ in Formula IA is a chemical moiety that is used to link a PTM and ULM as described in WO 2019/084026, the entirety of which is incorporated by reference herein.

In some embodiments, $R^1$ in Formula IA is a chemical structural unit represented by the formula:

$$-(A)_q-,$$

wherein:

q is an integer from 1 to 14;

each A is independently selected from the group consisting of a bond, $CR^{1a}R^{1b}$, O, S, SO, $SO_2$, $NR^{1c}$, $SO_2NR^{1c}$, $SONR^{1c}$, $SO(=NR^{1c})$, $SO(=NR^{1c})NR^{1d}$, $CONR^{1c}$, $NR^{1c}CONR^{1d}$, $NR^{1c}C(O)O$, $NR^{1c}SO_2NR^{1d}$, CO, $CR^{1a}=CR^{1b}$, C≡C, $SiR^{1a}R^{1b}$, $P(O)R^{1a}$, $P(O)OR^{1a}$, $(CR^{1a}R^{1b})_{1-4}$, $-(CR^{1a}R^{1b})_{1-4}O(CR^{1a}R^{1b})_{1-4}$, $-(CR^{1a}R^{1b})_{1-4}S(CR^{1a}R^{1b})_{1-4}$, $-(CR^{1a}R^{1b})_{1-4}NR(CR^{1a}R^{1b})_{1-4}$, $NR^{1c}C(=NCN)NR^{1d}NR^{1c}C(=NCN)$, $NR^{1c}C(=CNO_2)NR^{1d}$, 3-11 membered cycloalkyl, optionally substituted with 0-6 $R^{1a}$ and/or $R^{1b}$ groups, 3-11 membered heteocyclyl optionally substituted with 0-6 $R^{1a}$ and/or $R^{1b}$ groups, aryl optionally substituted with 0-6 $R^{1a}$ and/or $R^{1b}$ groups, heteroaryl optionally substituted with 0-6 $R^{1a}$ and/or $R^{1b}$ groups, and $R^{1a}$, $R^{1b}$, $R^{1c}$, $R^{1d}$ and $R^{1e}$ are each independently, —H, D, -halo, —$C_1$-$C_8$alkyl, —$C_1$-$C_6$haloalkyl, —O—$C_1$-$C_8$alkyl, —S—$C_1$-$C_8$alkyl, —NH$C_1$-$C_8$alkyl, —N($C_1$-$C_8$alkyl)2, 3-11 membered cycloalkyl, aryl, heteroaryl, 3-11 membered heterocyclyl, —O-(3-11 membered cycloalkyl), —S-(3-11 membered cycloalkyl), NH-(3-11 membered cycloalkyl), N(3-11 membered cycloalkyl)$_2$, N-(3-11 membered cycloalkyl)($C_1$-$C_8$alkyl), —OH, —$NH_2$, —SH, —$SO_2C_1$-$C_8$alkyl, SO(NH)$C_1$-$C_8$alkyl, P(O)(O$C_1$-$C_8$alkyl)($C_1$-$C_8$alkyl), —P(O)(O$C_1$-$C_8$alkyl)$_2$, —C≡C—$C_1$-$C_8$alkyl, —C≡CH, —CH═CH($C_1$-$C_8$alkyl), —C($C_1$-$C_8$alkyl)═CH ($C_1$-$C_8$alkyl), —C($C_1$-$C_8$alkyl)═C($C_1$-$C_8$alkyl)$_2$, —Si(OH)$_3$, —Si($C_1$-$C_8$alkyl)$_3$, —Si(OH)($C_1$-$C_8$alkyl)$_2$, —C(O)$C_1$-$C_8$alkyl, —$CO_2H$, —CN, —$CF_3$, —$CHF_2$, —$CH_2F$, —$NO_2$, —$SF_5$, —$SO_2NHC_1$-$C_8$alkyl, —$SO_2N$ ($C_1$-$C_8$alkyl)$_2$, —SO(NH)$NHC_1$-$C_8$alkyl, —SO(NH)N($C_1$-$C_8$alkyl)$_2$, —$SONHC_1$-$C_8$alkyl, —SON($C_1$-$C_8$alkyl)$_2$, —$CONHC_1$-$C_8$alkyl, —CON($C_1$-$C_8$alkyl)$_2$, —N($C_1$-$C_8$alkyl)CONH($C_1$-$C_8$alkyl), —N($C_1$-$C_8$alkyl)CON($C_1$-$C_8$alkyl)$_2$, —NHCONH($C_1$-$C_8$alkyl), —NHCON($C_1$-$C_8$alkyl)$_2$, —$NHCONH_2$, —N($C_1$-$C_8$alkyl)$SO_2NH$($C_1$-$C_8$alkyl), —N($C_1$-$C_8$alkyl)$SO_2N$($C_1$-$C_8$alkyl)$_2$, —$NHSO_2NH$($C_1$-$C_8$alkyl), —$NHSO_2N$($C_1$-$C_8$alkyl)$_2$, or —$NHSO_2NH_2$; or where the context permits, $R^{1a}$ or $R^{1b}$, are linked to other groups, or to each other, to form a cycloalkyl and/or a heterocyclyl moiety, optionally substituted with 0-4 $R^{1e}$ groups.

In these embodiments, q represents the number of connected A groups. For example, when q=1, -$(A)_q$- is -$A_1$-; when q=2, -$(A)_q$- is -$A_1$-$A_2$-; when q=3, -$(A)_q$- is -$A_1$-$A_2$-$A_3$-; when q=4, -$(A)_q$- is -$A_1$-$A_2$-$A_3$-$A_4$-; when q=5, -$(A)_q$- is -$A_1$-$A_2$-$A_3$-$A_4$-$A_5$-; when q=6, -$(A)_q$- is -$A_1$-$A_2$-$A_3$-$A_4$-$A_5$-$A_6$-; when q=7, -$(A)_q$- is -$A_1$-$A_2$-$A_3$-$A_4$-$A_5$-$A_6$-$A_7$-; when q=8, -$(A)_q$- is -$A_1$-$A_2$-$A_3$-$A_4$-$A_5$-$A_6$-$A_7$-$A_8$-; when q=9, -$(A)_q$- is -$A_1$-$A_2$-$A_3$-$A_4$-$A_5$-$A_6$-$A_7$-$A_8$-$A_9$-; when q=10, -$(A)_q$- is -$A_1$-$A_2$-$A_3$-$A_4$-$A_5$-$A_6$-$A_7$-$A_8$-$A_9$-$A_{10}$-; when q=11, -$(A)_q$- is -$A_1$-$A_2$-$A_3$-$A_4$-$A_5$-$A_6$-$A_7$-$A_8$-$A_9$-$A_{10}$-$A_{11}$-; when q=12, -$(A)_q$- is -$A_1$-$A_2$-$A_3$-$A_4$-$A_5$-$A_6$-$A_7$-$A_8$-$A_9$-$A_{10}$-$A_{11}$-$A_{12}$-; when q=13, -$(A)_q$- is -$A_1$-$A_2$-$A_3$-$A_4$-$A_5$-$A_6$-$A_7$-$A_8$-$A_9$-$A_{10}$-$A_{11}$-$A_{12}$-$A_{13}$-; and when q=14, -$(A)_q$- is -$A_1$-$A_2$-$A_3$-$A_4$-$A_5$-$A_6$-$A_7$-$A_8$-$A_9$-$A_{10}$-Ain-$A_{12}$-$A_{13}$-$A_{14}$-.

In some embodiments, q=5 and $R^1$ is a chemical moiety represented by the formula: -$A_1$-$A_2$-$A_3$-$A_4$-$A_5$-, wherein each of $A_1$, $A_3$ and $A_5$ is independently selected from the group consisting of a bond, —$(CR^{1a}R^{1b})_{0-4}O(CR^{1a}R^{1b})_{0-4}$, —$(CR^{1a}R^{1b})_{0-4}S(CR^{1a}R^{1b})_{0-4}$, —$(CR^{1a}R^{1b})_{0-4}NR^{1c}(CR^{1a}R^{1b})_{0-4}$, —$(CR^{1a}R^{1b})_{0-4}SO(CR^{1a}R^{1b})_{0-4}$, —$(CR^{1a}R^{1b})_{0-4}SO_2(CR^{1a}R^{1b})_{0-4}$, —$(CR^{1a}R^{1b})_{0-4}$ $SO_2NR^{1c}(CR^{1a}R^{1b})_{0-4}$, —$(CR^{1a}R^{1b})_{0-4}SONR^{1c}(CR^{1a}R^{1b})_{0-4}$, —$(CR^{1a}R^{1b})_{0-4}SO(═NR^{1c})(CR^{1a}R^{1b})_{0-4}$, —$(CR^{1a}R^{1b})_{0-4}$ $SO(═NR^{1c})NR^{1d}(CR^{1a}R^{1b})_{0-4}$, —$(CR^{1a}R^{1b})_{0-4}CONR^{1c}(CR^{1a}R^{1b})_{0-4}$, —$(CR^{1a}R^{1b})_{0-4}C(O)O(CR^{1a}R^{1b})_{0-4}$, —$(CR^{1a}R^{1b})_{0-4}NR^{1c}CONR^{1d}(CR^{1a}R^{1b})_{0-4}$, —$(CR^{1a}R^{1b})_{0-4}NR^{1c}C(O)O(CR^{1a}R^{1b})_{0-4}$, —$(CR^{1a}R^{1b})_{0-4}$ $NR^{1c}SO_2NR^{1d}(CR^{1a}R^{1b})_{0-4}$, —$(CR^{1a}R^{1b})_{0-4}C(O)(CR^{1a}R^{1b})_{0-4}$, —$(CR^{1a}R^{1b})_{0-4}CR^{1a}═CR^{1b}(CR^{1a}R^{1b})_{0-4}$, —$(CR^{1a}R^{1b})_{0-4}C≡C(CR^{1a}R^{1b})_{0-4}$, —$(CR^{1a}R^{1b})_{0-4}SiR^{1a}R^{1b}(CR^{1a}R^{1b})_{0-4}$, —$(CR^{1a}R^{1b})_{0-4}P(O)R^{1a}(CR^{1a}R^{1b})_{0-4}$, —$(CR^{1a}R^{1b})_{0-4}P(O)OR^{1a}(CR^{1a}R^{1b})_{0-4}$, $(CR^{1a}R^{1b})_{1-4}$, optionally substituted 3-11 membered cycloalkyl, 3-11 membered heterocyclyl, aryl, and heteroaryl; wherein each of $A_2$ and $A_4$ is independently selected from the group consisting of is independently selected from the group consisting of a bond, $(CR^{1a}R^{1b})_{1-4}$, optionally substituted 3-11 membered cycloalkyl, 3-11 membered heterocyclyl, aryl, and heteroaryl; wherein $R^{1a}$ and $R^{1b}$ are each independently selected from the group consisting of —H, D, -halo, —$C_1$-$C_8$alkyl, —O—$C_1$-$C_8$alkyl, —$C_1$-$C_6$haloalkyl, —S—$C_1$-$C_8$alkyl, —$NHC_1$-$C_8$alkyl, —N($C_1$-$C_8$alkyl)2, 3-11 membered cycloalkyl, aryl, heteroaryl, 3-11 membered heterocyclyl, —O-(3-11 membered cycloalkyl), —S-(3-11 membered cycloalkyl), NH-(3-11 membered cycloalkyl), N(3-11 membered cycloalkyl)$_2$, N-(3-11 membered cycloalkyl)($C_1$-$C_8$alkyl), —OH, —$NH_2$, —SH, —$SO_2C_1$-$C_8$alkyl, SO(NH)$C_1$-$C_8$alkyl, P(O)($OC_1$-$C_8$alkyl)($C_1$-$C_8$alkyl), —P(O)($OC_1$-$C_8$alkyl)$_2$, —C≡C—$C_1$-$C_8$alkyl, —C≡CH, —CH═CH($C_1$-$C_8$alkyl), —C($C_1$-$C_8$alkyl)═CH($C_1$-$C_8$alkyl), —C($C_1$-$C_8$alkyl)═C($C_1$-$C_8$alkyl)$_2$, —Si(OH)$_3$, —Si($C_1$-$C_8$alkyl)$_3$, —Si(OH)($C_1$-$C_8$alkyl)$_2$, —C(O)$C_1$-$C_8$alkyl, —$CO_2H$, —CN, —$NO_2$, —$SF_5$, —$SO_2NHC_1$-$C_8$alkyl, —$SO_2N$($C_1$-$C_8$alkyl)$_2$, —SO(NH)$NHC_1$-$C_8$alkyl, —SO(NH)N($C_1$-$C_8$alkyl)$_2$, —$SONHC_1$-$C_8$alkyl, —SON($C_1$-$C_8$alkyl)$_2$, —$CONHC_1$-$C_8$alkyl, —CON($C_1$-$C_8$alkyl)$_2$, —N($C_1$-$C_8$alkyl)CONH($C_1$-$C_8$alkyl), —N($C_1$-$C_8$alkyl)CON($C_1$-$C_8$alkyl)$_2$, —NHCONH($C_1$-$C_8$alkyl), —NHCON($C_1$-$C_8$alkyl)$_2$, —$NHCONH_2$, —N($C_1$-$C_8$alkyl)$SO_2NH$($C_1$-$C_8$alkyl), —N($C_1$-$C_8$alkyl)$SO_2N$($C_1$-$C_8$alkyl)$_2$, —$NHSO_2NH$($C_1$-$C_8$alkyl), —$NHSO_2N$($C_1$-$C_8$alkyl)$_2$, or —$NHSO_2NH_2$; and $R^{1c}$ and $R^{1d}$ are each independently selected from the group consisting of H, D, optionally substituted $C_{1-4}$ alkyl, $C_{3-8}$ cyclcoalkyl, $C_{3-8}$ heterocyclcoalkyl, aryl, or heteroaryl.

In some embodiments, q=4 and $R^1$ is a chemical moiety represented by the formula: -$A_1$-$A_2$-$A_3$-$A_4$-, wherein each of $A_{14}$ is independently selected from the group consisting of O, S, SO, $SO_2$, $NR^{1c}$, $SO_2NR^{1c}$, $SONR^{1c}$, $SO(═NR^{1c})$, $SO(═NR^{1c})NR^{1d}$, $CONR^{1c}$, $NR^{1c}CONR^{1d}$, $NR^{1c}C(O)O$, $NR^{1c}SO_2NR^{1d}$, CO, $CR^{1a}═CR^{1b}$, C≡C, $SiR^{1a}R^{1b}$, $P(O)R^{1a}$, $P(O)OR^{1a}$, $(CR^{1a}R^{1b})_{1-4}$, —$(CR^{1a}R^{1b})_{1-4}O(CR^{1a}R^{1b})_{1-4}$, —$(CR^{1a}R^{1b})_{1-4}S(CR^{1a}R^{1b})_{1-4}$, —$(CR^{1a}R^{1b})_{1-4}NR(CR^{1a}R^{1b})_{1-4}$, optionally substituted 3-11 membered cycloalkyl, 3-11 membered heterocyclyl, aryl, and heteroaryl; wherein $R^{1a}$ and $R^{1b}$ are each independently selected from the group consisting of —H, D, -halo, —$C_1$-$C_8$alkyl, —O—$C_1$-$C_8$alkyl, —$C_1$-$C_6$haloalkyl, —S—$C_1$-$C_8$alkyl, —$NHC_1$-$C_8$alkyl, —N($C_1$-$C_8$alkyl)2, 3-11 membered cycloalkyl, aryl, heteroaryl, 3-11 membered heterocyclyl, —O-(3-11 membered cycloalkyl), —S-(3-11 membered cycloalkyl), NH-(3-11 membered cycloalkyl), N(3-11 membered cycloalkyl)$_2$, N-(3-11 membered cycloalkyl)($C_1$-$C_8$alkyl), —OH, —$NH_2$, —SH, —$SO_2C_1$-$C_8$alkyl, SO(NH)$C_1$-$C_8$alkyl, P(O)($OC_1$-$C_8$alkyl)($C_1$-$C_8$alkyl), —P(O)($OC_1$-$C_8$alkyl)$_2$, —C≡C—$C_1$-$C_8$alkyl, —C≡CH, —CH═CH($C_1$-$C_8$alkyl), —C($C_1$-$C_8$alkyl)═CH($C_1$-$C_8$alkyl), —C($C_1$-$C_8$alkyl)═C($C_1$-$C_8$alkyl)$_2$, —Si(OH)$_3$, —Si($C_1$-$C_8$alkyl)$_3$, —Si(OH)($C_1$-$C_8$alkyl)$_2$, —C(O)$C_1$-$C_8$alkyl, —$CO_2H$, —CN, —$NO_2$, —$SF_5$, —$SO_2NHC_1$-$C_8$alkyl, —$SO_2N$($C_1$-$C_8$alkyl)$_2$, —SO(NH)$NHC_1$-$C_8$alkyl, —SO(NH)N($C_1$-$C_8$alkyl)$_2$, —$SONHC_1$-$C_8$alkyl, —SON($C_1$-$C_8$alkyl)$_2$, —$CONHC_1$-$C_8$alkyl, —CON($C_1$-$C_8$alkyl)$_2$, —N($C_1$-$C_8$alkyl)CONH($C_1$-$C_8$alkyl), —N($C_1$-$C_8$alkyl)CON($C_1$-$C_8$alkyl)$_2$, —NHCONH($C_1$-$C_8$alkyl), —NHCON($C_1$-$C_8$alkyl)$_2$, —$NHCONH_2$, —N($C_1$-$C_8$alkyl)$SO_2NH$($C_1$-$C_8$alkyl), —N($C_1$-$C_8$alkyl)$SO_2N$($C_1$-$C_8$alkyl)$_2$, —$NHSO_2NH$($C_1$-$C_8$alkyl), —$NHSO_2N$($C_1$-$C_8$alkyl)$_2$, or —$NHSO_2NH_2$; and $R^{1c}$ and $R^{1d}$ are each independently selected from the group consisting of H, D, optionally substituted $C_{1-4}$ alkyl, $C_{3-8}$ cyclcoalkyl, $C_{3-8}$ heterocyclcoalkyl, aryl, or heteroaryl.

In other embodiments, q=3 and $R^1$ is a chemical moiety represented by the formula: -$A_1$-$A_2$-$A_3$-, wherein each of $A_{1-3}$ is independently selected from the group consisting of O, S, SO, $SO_2$, $NR^{1c}$, $SO_2NR^{1c}$, $SONR^{1c}$, $SO(═NR^{1c})$, $SO(═NR^{1c})NR^{1d}$, $CONR^{1c}$, $NR^{1c}CONR^{1d}$, $NR^{1c}C(O)O$, $NR^{1c}SO_2NR^{1d}$, CO, $CR^{1a}═CR^{1b}$, C≡C, $SiR^{1a}R^{1b}$, $P(O)R^{1a}$, $P(O)OR^{1a}$, $(CR^{1a}R^{1b})_{1-4}$, —$(CR^{1a}R^{1b})_{1-4}O(CR^{1a}R^{1b})_{1-4}$, —$(CR^{1a}R^{1b})_{1-4}S(CR^{1a}R^{1b})_{1-4}$, —$(CR^{1a}R^{1b})_{1-4}NR(CR^{1a}R^{1b})_{1-4}$, optionally substituted 3-11 membered cycloalkyl, 3-11 membered heterocyclyl, aryl, and heteroaryl; wherein $R^{1a}$ and $R^{1b}$ are each independently selected from the group consisting of —H, D, -halo, —$C_1$-$C_8$alkyl, —O—$C_1$-$C_8$alkyl, —$C_1$-$C_6$haloalkyl, —S—$C_1$-$C_8$alkyl, —$NHC_1$-$C_8$alkyl, —N($C_1$-$C_8$alkyl)2, 3-11 membered cycloalkyl, aryl, heteroaryl, 3-11 membered heterocyclyl, —O-(3-11 membered cycloalkyl), —S-(3-11 membered cycloalkyl), NH-(3-11 membered cycloalkyl), N(3-11 membered cycloalkyl)$_2$, N-(3-11 membered cycloalkyl)($C_1$-$C_8$alkyl), —OH, —$NH_2$, —SH, —$SO_2C_1$-$C_8$alkyl, SO(NH)$C_1$-$C_8$alkyl, P(O)(O$C_1$-$C_8$alkyl)($C_1$-$C_8$alkyl), —P(O)(O$C_1$-$C_8$alkyl)$_2$, —C≡C—$C_1$-$C_8$alkyl, —C≡CH, —CH═CH($C_1$-$C_8$alkyl), —C($C_1$-$C_8$alkyl)═CH($C_1$-$C_8$alkyl), —C($C_1$-$C_8$alkyl)═C($C_1$-$C_8$alkyl)$_2$, —Si(OH)$_3$, —Si($C_1$-$C_8$alkyl)$_3$, —Si(OH)($C_1$-$C_8$alkyl)$_2$, —C(O)$C_1$-$C_8$alkyl, —$CO_2$H, —CN, —$NO_2$, —$SF_5$, —$SO_2NHC_1$-$C_8$alkyl, —$SO_2$N($C_1$-$C_8$alkyl)$_2$, —SO(NH)NH$C_1$-$C_8$alkyl, —SO(NH)N($C_1$-$C_8$alkyl)$_2$, —SONH$C_1$-$C_8$alkyl, —SON($C_1$-$C_8$alkyl)$_2$, —CONH$C_1$-$C_8$alkyl, —CON($C_1$-$C_8$alkyl)$_2$, —N($C_1$-$C_8$alkyl)CONH($C_1$-$C_8$alkyl), —N($C_1$-$C_8$alkyl)CON($C_1$-$C_8$alkyl)$_2$, —NHCONH($C_1$-$C_8$alkyl), —NHCON($C_1$-$C_8$alkyl)$_2$, —$NHCONH_2$, —N($C_1$-$C_8$alkyl)$SO_2$NH($C_1$-$C_8$alkyl), —N($C_1$-$C_8$alkyl)$SO_2$N($C_1$-$C_8$alkyl)$_2$, —$NHSO_2$NH($C_1$-$C_8$alkyl), —$NHSO_2$N($C_1$-$C_8$alkyl)$_2$, or —$NHSO_2NH_2$; and $R^{1c}$ and $R^{1d}$ are each independently selected from the group consisting of H, D, optionally substituted $C_{1-4}$ alkyl, $C_{3-8}$ cyclcoalkyl, $C_{3-8}$ heterocyclcoalkyl, aryl, or heteroaryl.

In other embodiments, q=2 and $R^1$ is a chemical moiety represented by the formula: -$A_1$-$A_2$-, wherein each of $A_{1-2}$ is independently selected from the group consisting of O, S, SO, $SO_2$, $NR^{1c}$, $SO_2NR^{1c}$, $SONR^{1c}$, SO(═$NR^{1c}$), SO(═$NR^{1c}$)$NR^{1d}$, $CONR^{1c}$, $NR^{1c}CONR^{1d}$, $NR^{1c}$C(O)O, $NR^{1c}SO_2NR^{1d}$, CO, $CR^{1a}$═$CR^{1b}$, C≡C, $SiR^{1a}R^{1b}$, P(O)$R^{1a}$, P(O)$OR^{1a}$, $(CR^{1a}R^{1b})_{1-4}$, —$(CR^{1a}R^{1b})_{1-4}$O$(CR^{1a}R^{1b})_{1-4}$, —$(CR^{1a}R^{1b})_{1-4}$S$(CR^{1a}R^{1b})_{1-4}$, —$(CR^{1a}R^{1b})_{1-4}$NR$(CR^{1a}R^{1b})_{1-4}$, optionally substituted 3-11 membered cycloalkyl, 3-11 membered heterocyclyl, aryl, and heteroaryl; wherein $R^{1a}$ and $R^{1b}$ are each independently selected from the group consisting of —H, D, -halo, —$C_1$-$C_8$alkyl, —O—$C_1$-$C_8$alkyl, —$C_1$-$C_6$haloalkyl, —S—$C_1$-$C_8$alkyl, —NH$C_1$-$C_8$alkyl, —N($C_1$-$C_8$alkyl)2, 3-11 membered cycloalkyl, aryl, heteroaryl, 3-11 membered heterocyclyl, —O-(3-11 membered cycloalkyl), —S-(3-11 membered cycloalkyl), NH-(3-11 membered cycloalkyl), N(3-11 membered cycloalkyl)$_2$, N-(3-11 membered cycloalkyl)($C_1$-$C_8$alkyl), —OH, —$NH_2$, —SH, —$SO_2C_1$-$C_8$alkyl, SO(NH)$C_1$-$C_8$alkyl, P(O)(O$C_1$-$C_8$alkyl)($C_1$-$C_8$alkyl), —P(O)(O$C_1$-$C_8$alkyl)$_2$, —C≡C—$C_1$-$C_8$alkyl, —C≡CH, —CH═CH($C_1$-$C_8$alkyl), —C($C_1$-$C_8$alkyl)═CH($C_1$-$C_8$alkyl), —C($C_1$-$C_8$alkyl)═C($C_1$-$C_8$alkyl)$_2$, —Si(OH)$_3$, —Si($C_1$-$C_8$alkyl)$_3$, —Si(OH)($C_1$-$C_8$alkyl)$_2$, —C(O)$C_1$-$C_8$alkyl, —$CO_2$H, —CN, —$NO_2$, —$SF_5$, —$SO_2NHC_1$-$C_8$alkyl, —$SO_2$N($C_1$-$C_8$alkyl)$_2$, —SO(NH)NH$C_1$-$C_8$alkyl, —SO(NH)N($C_1$-$C_8$alkyl)$_2$, —SONH$C_1$-$C_8$alkyl, —SON($C_1$-$C_8$alkyl)$_2$, —CONH$C_1$-$C_8$alkyl, —CON($C_1$-$C_8$alkyl)$_2$, —N($C_1$-$C_8$alkyl)CONH($C_1$-$C_8$alkyl), —N($C_1$-$C_8$alkyl)CON($C_1$-$C_8$alkyl)$_2$, —NHCONH($C_1$-$C_8$alkyl), —NHCON($C_1$-$C_8$alkyl)$_2$, —$NHCONH_2$, —N($C_1$-$C_8$alkyl)$SO_2$NH($C_1$-$C_8$alkyl), —N($C_1$-$C_8$alkyl)$SO_2$N($C_1$-$C_8$alkyl)$_2$, —$NHSO_2$NH($C_1$-$C_8$alkyl), —$NHSO_2$N($C_1$-$C_8$alkyl)$_2$, or —$NHSO_2NH_2$; and $R^{1c}$ and $R^{1d}$ are each independently selected from the group consisting of H, D, optionally substituted $C_{1-4}$ alkyl, $C_{3-8}$ cyclcoalkyl, $C_{3-8}$ heterocyclcoalkyl, aryl, or heteroaryl.

In other embodiments, q=1 and $R^1$ is a chemical moiety represented by the formula: -$A_1$, wherein $A_1$ is selected from the group consisting of O, S, SO, $SO_2$, $NR^{1c}$, $SO_2NR^{1c}$, $SONR^{1c}$, SO(═$NR^{1c}$), SO(═$NR^{1c}$)$NR^{1d}$, $CONR^{1c}$, $NR^{1c}CONR^{1d}$, $NR^{1c}$C(O)O, $NR^{1c}SO_2NR^{1d}$, CO, $CR^{1a}$═$CR^{1b}$, C≡C, $SiR^{1a}R^{1b}$, P(O)$R^{1a}$, P(O)$OR^{1a}$, $(CR^{1a}R^{1b})_{1-4}$, —$(CR^{1a}R^{1b})_{1-4}$O$(CR^{1a}R^{1b})_{1-4}$, —$(CR^{1a}R^{1b})_{1-4}$S$(CR^{1a}R^{1b})_{1-4}$, —$(CR^{1a}R^{1b})_{1-4}$NR$(CR^{1a}R^{1b})_{1-4}$, optionally substituted 3-11 membered cycloalkyl, 3-11 membered heterocyclyl, aryl, and heteroaryl; wherein $R^{1a}$ and $R^{1b}$ are each independently selected from the group consisting of —H, D, -halo, —$C_1$-$C_8$alkyl, —O—$C_1$-$C_8$alkyl, —$C_1$-$C_6$haloalkyl, —S—$C_1$-$C_8$alkyl, —NH$C_1$-$C_8$alkyl, —N($C_1$-$C_5$alkyl)2, 3-11 membered cycloalkyl, aryl, heteroaryl, 3-11 membered heterocyclyl, —O-(3-11 membered cycloalkyl), —S-(3-11 membered cycloalkyl), NH-(3-11 membered cycloalkyl), N(3-11 membered cycloalkyl)$_2$, N-(3-11 membered cycloalkyl)($C_1$-$C_5$alkyl), —OH, —$NH_2$, —SH, —$SO_2C_1$-$C_8$alkyl, SO(NH)$C_1$-$C_5$alkyl, P(O)(O$C_1$-$C_8$alkyl)($C_1$-$C_8$alkyl), —P(O)(O$C_1$-$C_8$alkyl)$_2$, —C≡C—$C_1$-$C_8$alkyl, —C≡CH, —CH═CH($C_1$-$C_8$alkyl), —C($C_1$-$C_8$alkyl)═CH($C_1$-$C_8$alkyl), —C($C_1$-$C_8$alkyl)═C($C_1$-$C_8$alkyl)$_2$, —Si(OH)$_3$, —Si($C_1$-$C_8$alkyl)$_3$, —Si(OH)($C_1$-$C_8$alkyl)$_2$, —C(O)$C_1$-$C_8$alkyl, —$CO_2$H, —CN, —$NO_2$, —$SF_5$, —$SO_2NHC_1$-$C_8$alkyl, —$SO_2$N($C_1$-$C_8$alkyl)$_2$, —SO(NH)NH$C_1$-$C_8$alkyl, —SO(NH)N($C_1$-$C_8$alkyl)$_2$, —SONH$C_1$-$C_8$alkyl, —SON($C_1$-$C_8$alkyl)$_2$, —CONH$C_1$-$C_8$alkyl, —CON($C_1$-$C_8$alkyl)$_2$, —N($C_1$-$C_8$alkyl)CONH($C_1$-$C_8$alkyl), —N($C_1$-$C_8$alkyl)CON($C_1$-$C_8$alkyl)$_2$, —NHCONH($C_1$-$C_8$alkyl), —NHCON($C_1$-$C_8$alkyl)$_2$, —$NHCONH_2$, —N($C_1$-$C_8$alkyl)$SO_2$NH($C_1$-$C_8$alkyl), —N($C_1$-$C_8$alkyl)$SO_2$N($C_1$-$C_8$alkyl)$_2$, —$NHSO_2$NH($C_1$-$C_8$alkyl), —$NHSO_2$N($C_1$-$C_8$alkyl)$_2$, or —$NHSO_2NH_2$; and $R^{1c}$ and $R^{1d}$ are each independently selected from the group consisting of H, D, optionally substituted $C_{1-4}$ alkyl, $C_{3-8}$ cyclcoalkyl, $C_{3-8}$ heterocyclcoalkyl, aryl, or heteroaryl.

In some embodiments, $R^1$ is a covalent bond, 3-11 membered cycloalkyl optionally substituted with 0-6 $R^{1a}$ and/or $R^{1b}$ groups, 3-11 membered heterocyclyl optionally substituted with 0-6 $R^{1a}$ and/or $R^{1b}$ groups, —$(CR^{1a}R^{1b})_{1-5}$, —($CR^{1a}$═$CR^{1b}$)—, —$(CR^{1a}R^{1b})_{1-5}$-A- wherein A is O, S, or $NR^{1c}$, —$(CR^{1a}R^{1b})_{1-5}$-A-$(CR^{1a}R^{1b})_{1-5}$— wherein A is O, S, or $NR^{1c}$, —$(CR^{1a}R^{1b})_{1-5}$-A-$(CR^{1a}R^{1b})_{1-5}$-A- wherein A is O, S, or $NR^{1c}$, —$(CR^{1a}R^{1b})_{1-5}$—($CR^{1a}$═$CR^{1b}$)—$(CR^{1a}R^{1b})_{1-5}$—, —$(CR^{1a}R^{1b})_{1-5}$-($CR^{1a}$═$CR^{1b}$)—$(CR^{1a}R^{1b})_{1-5}$-A- wherein A is O, S, or $NR^{1c}$, —$(CR^{1a}R^{1b})_{1-5}$—(C≡C)—$(CR^{1a}R^{1b})_{1-5}$—, —$(CR^{1a}R^{1b})_{1-5}$—(C≡C)—$(CR^{1a}R^{1b})_{1-5}$-A- wherein A is O, S, or $NR^{1c}$, —(C≡C)—$(CR^{1a}R^{1b})_{1-5}$-A-$(CR^{1a}R^{1b})_{1-5}$— wherein A is O, S, or $NR^{1c}$, —(C≡C)—$(CR^{1a}R^{1b})_{1-5}$, —$(CR^{1a}R^{1b})_{1-5}$-(3-11 membered cycloalkyl optionally substituted with 0-6 $R^{1a}$ and/or $R^{1b}$ groups)-, —$(CR^{1a}R^{1b})_{1-5}$-(3-11 membered heterocyclyl optionally substituted with 0-6 $R^{1a}$ and/or $R^{1b}$ groups)-, -(3-11 membered cycloalkyl optionally substituted with 0-6 $R^{1a}$ and/or $R^{1b}$ groups)-$(CR^{1a}R^{1b})_{1-5}$—, -(3-11 membered heterocyclyl optionally substituted with 0-6 $R^{1a}$ and/or $R^{1b}$ groups) —$(CR^{1a}R^{1b})_{1-5}$—, —$(CR^{1a}R^{1b})_{1-5}$-(3-11 membered cycloalkyl optionally substituted with 0-6 $R^{1a}$ and/or $R^{1b}$ groups)-A-, —$(CR^{1a}R^{1b})_{1-5}$-(3-11 membered heterocyclyl optionally substituted with 0-6 $R^{1a}$ and/or $R^{1b}$ groups)-A-, —$(CR^{1a}R^{1b})_{1-5}$-(3-11 membered cycloalkyl optionally substituted with 0-6 $R^{1a}$ and/or $R^{1b}$ groups)-$(CR^{1a}R^{1b})_{1-5}$, —$(CR^{1a}R^{1b})_{1-5}$-(3-11 membered cycloalkyl optionally substituted with 0-6 $R^{1a}$ and/or $R^{1b}$ groups)-A- wherein A is O, S, or $NR^{1c}$, —$(CR^{1a}R^{1b})_{1-5}$-(3-11 membered cycloalkyl optionally substituted with 0-6 $R^{1a}$ and/or $R^{1b}$ groups)-$(CR^{1a}R^{1b})_{1-5}$-A- wherein A is O, S, or $NR^{1c}$, —$(CR^{1a}R^{1b})_{1-5}$-A-(3-11 membered cycloalkyl optionally substituted with 0-6 $R^{1a}$ and/or $R^{1b}$ groups)- wherein A is O, S, or $NR^{1c}$—$(CR^{1a}R^{1b})_{1-5}$-(3-11 membered heterocyclyl optionally substituted with 0-6 $R^{1a}$ and/or $R^{1b}$ groups)-$(CR^{1a}R^{1b})_{1-5}$, —$(CR^{1a}R^{1b})_{1-5}$-(3-11 membered heterocyclyl optionally substituted with 0-6 $R^{1a}$ and/or $R^{1b}$ groups)-

$(CR^{1a}R^{1b})_{1-5}$-A- wherein A is O, S, or $NR^{1c}$—$(CR^{1a}R^{1b})_{1-5}$-(3-11 membered heterocyclyl optionally substituted with 0-6 $R^{1a}$ and/or $R^{1b}$ groups)-A- wherein A is O, S, or $NR^{1c}$, —$(CR^{1a}R^{1b})_{1-5}$-A-(3-11 membered heterocyclyl optionally substituted with 0-6 $R^{1a}$ and/or $R^{1b}$ groups)- wherein A is O, S, or $NR^{1c}$—$(CR^{1a}R^{1b})_{1-5}$-(3-11 membered cycloalkyl optionally substituted with 0-6 $R^{1a}$ and/or $R^{1b}$ groups)-$(CR^{1a}R^{1b})_{1-5}$-A- wherein A is O, S, or $NR^{1c}$—$(CR^{1a}R^{1b})_{1-5}$-A-(3-11 membered cycloalkyl optionally substituted with 0-6 $R^{1a}$ and/or $R^{1b}$ groups)- wherein A is O, S, or $NR^{1c}$—$(CR^{1a}R^{1b})_{1-5}$-A-(3-11 membered cycloalkyl optionally substituted with 0-6 $R^{1a}$ and/or $R^{1b}$ groups)-$(CR^{1a}R^{1b})_{1-5}$-A- wherein each A is independently O, S, or $NR^{1c}$—$(CR^{1a}R^{1b})_{1-5}$-A-(3-11 membered heterocyclyl optionally substituted with 0-6 $R^{1a}$ and/or $R^{1b}$ groups)-$(CR^{1a}R^{1b})_{1-5}$-A- wherein each A is independently O, S, or $NR^{1c}$, —$(CR^{1a}R^{1b})_{1-5}$-A-$(CR^{1a}R^{1b})_{1-5}$-A- wherein A is O, S, or $NR^{1c}$—$(CR^{1a}R^{1b})_{1-5}$-A-$(CR^{1a}R^{1b})_{1-5}$-A-$(CR^{1a}R^{1b})_{1-5}$-A-$(CR^{1a}R^{1b})_{1-5}$-A- wherein A is O, S, or $NR^{1c}$—$(CR^{1a}R^{1b})_{1-5}$-A-(CO) wherein A is O, S, or $NR^{1c}$, —$(CR^{1a}R^{1b})_{1-5}$—$(CR^{1a}$═$CR^{1b})$—$(CR^{1a}R^{1b})_{1-5}$-A-(CO)— wherein A is O, S, or $NR^{1c}$, —$(CR^{1a}R^{1b})_{1-5}$—(C≡C)—$(CR^{1a}R^{1b})_{1-5}$-A-(CO)— wherein A is O, S, or $NR^{1c}$, —$(CR^{1a}R^{1b})_{1-5}$-(3-11 membered cycloalkyl optionally substituted with 0-6 $R^{1a}$ and/or $R^{1b}$ groups)-$(CR^{1a}R^{1b})_{1-5}$-A-(CO)— wherein A is O, S, or $NR^{1c}$, —$(CR^{1a}R^{1b})_{1-5}$-A-(CO)-(3-11 membered cycloalkyl optionally substituted with 0-6 $R^{1a}$ and/or $R^{1b}$ groups)- wherein A is O, S, or $NR^{1c}$, —$(CR^{1a}R^{1b})_{1-5}$-(3-11 membered heterocyclyl optionally substituted with 0-6 $R^{1a}$ and/or $R^{1b}$ groups)-$(CR^{1a}R^{1b})_{1-5}$-A-(CO)— wherein A is O, S, or $NR^{1c}$, —$(CR^{1a}R^{1b})_{1-5}$-A-(CO)-(3-11 membered heterocyclyl optionally substituted with 0-6 $R^{1a}$ and/or $R^{1b}$ groups)- wherein A is O, S, or $NR^{1c}$—$(CR^{1a}R^{1b})_{1-5}$-A-(3-11 membered cycloalkyl optionally substituted with 0-6 $R^{1a}$ and/or $R^{1b}$ groups)-A-(CO)— wherein each A is independently O, S, or $NR^{1c}$, -(3-11 membered cycloalkyl optionally substituted with 0-6 $R^{1a}$ and/or $R^{1b}$ groups)-CO—$(CR^{1a}R^{1b})_{1-5}$-A- wherein A is O, S, or $NR^{1c}$, —$(CR^{1a}R^{1b})_{1-5}$-(3-11 membered cycloalkyl optionally substituted with 0-6 $R^{1a}$ and/or $R^{1b}$ groups)-$(CR^{1a}R^{1b})_{1-5}$-A-(CO)— wherein A is O, S, or $NR^{1c}$, —$(CR^{1a}R^{1b})_{1-5}$-(3-11 membered heterocyclyl optionally substituted with 0-6 $R^{1a}$ and/or $R^{1b}$ groups)-$(CR^{1a}R^{1b})_{1-5}$-A-(CO)— wherein A is O, S, or $NR^{1c}$, -(3-11 membered cycloalkyl optionally substituted with 0-6 Ria and/or $R^{1b}$ groups)-$(CR^{1a}R^{1b})_{1-5}$—, or -(3-11 membered heterocyclyl optionally substituted with 0-6$R^{1a}$ and/or $R^{1b}$ groups)-$(CR^{1a}R^{1b})_{1-5}$—.

In some embodiments, $R^1$ is —$CR^{1a}$═$CR^{1b}$—, such as, for example, —CH═CH—.

In some embodiments, $R^1$ is —$(CR^{1a}R^{1b})_{1-5}$, for example —$(CH_2)_{1-5}$—, —$CH_2$—, —$CH_2CH_2CH_2$— and the like.

In some embodiments, $R^1$ is —$(CR^{1a}R^{1b})_{1-5}$-A- wherein A is O, S, or $NR^{1c}$, such as for example, —$(CH_2)_{1-5}$—O—, —$(CH_2)_{1-5}$—S—, —$(CH_2)_{1-5}$—NH—, or —$(CH_2)_{0-2}$—$(C(CH_3)_2)$—$(CH_2)_{0-2}$—O—.

In other embodiments, $R^1$ is —$(CR^{1a}R^{1b})_{1-5}$-A-$(CR^{1a}R^{1b})_{1-5}$— wherein A is O, S, or $NR^{1c}$ such as, for example, —$(CH_2)_{1-5}$—O—$(CH_2)_{1-5}$—, —$(CH_2)_{1-5}$—S—$(CH_2)_{1-5}$—, —$(CH_2)_{1-5}$—NH—$(CH_2)_{1-5}$—.

In some embodiments, $R^1$ is —(C≡C)—$(CR^{1a}R^{1b})_{1-5}$, such as, for example, —(C≡C)—$(CH_2)_2$—, and the like.

In some embodiments, $R^1$ is —$(CR^{1a}R^{1b})_{1-5}$-(3-11 membered cycloalkyl optionally substituted with 0-6 $R^{1a}$ and/or $R^{1b}$ groups)-, such as, for example, —$CH_2$-cyclobutyl-.

In some embodiments, $R^1$ is —$(CR^{1a}R^{1b})_{1-5}$-(3-11 membered cycloalkyl optionally substituted with 0-6 $R^{1a}$ and/or $R^{1b}$ groups)-$(CR^{1a}R^{1b})_{1-5}$, such as, for example, —$CH_2$-cyclobutyl-$CH_2$— and the like.

In some embodiments, $R^1$ is —$(CR^{1a}R^{1b})_{1-5}$-(3-11 membered heterocyclyl optionally substituted with 0-6 $R^{1a}$ and/or $R^{1b}$ groups)-$(CR^{1a}R^{1b})_{1-5}$, such as, for example, —$CH_2$-azetidinyl-$CH_2$—.

In some embodiments, $R^1$ is —$(CR^{1a}R^{1b})_{1-5}$-(3-11 membered heterocyclyl optionally substituted with 0-6 $R^{1a}$ and/or $R^{1b}$ groups)-, such as, for example, —$CH_2$-azetidinyl-.

In some embodiments, $R^1$ is -(3-11 membered heterocyclyl optionally substituted with 0-6$R^{1a}$ and/or $R^{1b}$ groups)—$(CR^{1a}R^{1b})_{1-5}$—, such as, for example, -azetidinyl-$CH_2$—, -pyrolidnyl-$CH_2$—, -piperidinyl-$CH_2$—, and the like.

In some embodiments, $R^1$ is —$(CR^{1a}R^{1b})_{1-5}$-(3-11 membered cycloalkyl optionally substituted with 0-6 $R^{1a}$ and/or $R^{1b}$ groups)-$(CR^{1a}R^{1b})_{1-5}$-A- wherein A is O, S, or $NR^{1c}$, such as, for example, —$CH_2$-cyclopropyl-$CH_2$—O—, and the like.

In some embodiments, $R^1$ is —$(CR^{1a}R^{1b})_{1-5}$-(3-11 membered heterocyclyl optionally substituted with 0-6 $R^{1a}$ and/or $R^{1b}$ groups)-$(CR^{1a}R^{1b})_{1-5}$-A- wherein A is O, S, or $NR^{1c}$, such as, for example, —$CH_2$-piperidinyl-$CH_2CH_2$—O—, and the like.

In some embodiments, $R^1$ is —$(CR^{1a}R^{1b})_{1-5}$-(3-11 membered heterocyclyl optionally substituted with 0-6 $R^{1a}$ and/or $R^{1b}$ groups)-A- wherein A is O, S, or $NR^{1c}$, such as, for example, —$CH_2$-azetidinyl-O—, and the like.

In some embodiments, $R^1$ is —$(CR^{1a}R^{1b})_{1-5}$-A-(3-11 membered heterocyclyl optionally substituted with 0-6 $R^{1a}$ and/or $R^{1b}$ groups)- wherein A is O, S, or $NR^{1c}$, such as, for example, —$CH_2$—O-azetidinyl-, —$CH_2$—NH-azetidinyl-, and the like.

In other embodiments, $R^1$ is —$(CR^{1a}R^{1b})_{1-5}$-A-(3-11 membered cycloalkyl optionally substituted with 0-6 $R^{1a}$ and/or $R^{1b}$ groups)- wherein A is O, S, or $NR^{1c}$, such as —$CH_2$—O— cyclobutylene-, —$CH_2$—NH-cyclobutylene-, and the like.

In some embodiments, $R^1$ is —$(CR^{1a}R^{1b})_{1-5}$-A-$(CR^{1a}R^{1b})_{1-5}$-A- wherein A is O, S, or $NR^{1c}$ such as, for example, —$CH_2$—O—$CH_2CH_2$—O—.

In some aspects, the Y in the compound of Formula IA is $CR^h$ wherein $R^h$ is H, and the compound of Formula IA has Formula IA-1:

(IA-1)

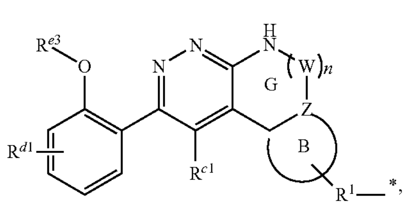

wherein $R^{c1}$, $R^{d1}$, $R^{e3}$, W, Z, B, n, and $R^1$ are as described above for Formula IA.

In some embodiments, n in Formula IA-1 is 1.

In some embodiments of the compound of Formula IA-1, at least one W is optionally substituted —$CH_2$—.

In some embodiments of the compound of Formula IA-1, at least one W is —$CH_2$— or substituted —$CH_2$— wherein the substituents are alkyl, alkoxy, alkylamino.

In some embodiments of the compound of Formula IA-1, at least one W is —$CH_2$—.

In some embodiments of the compound of Formula IA-1, one W is —C(O)—.

In some embodiments of the compound of Formula IA-1, one W is —S(O)—.

In some embodiments of the compound of Formula IA-1, one W is —$S(O)_2$—.

In some embodiments, B in Formula IA-1 is an optionally substituted 5-7 membered cycloalkyl ring.

In some embodiments, B in Formula IA-1 is an optionally substituted 5-7 membered cycloalkyl ring wherein the optional substituents are hydroxy, halogen, alkoxy, alkyl, haloalkyl, amino, alkylamino, or cyano.

In other embodiments, B in Formula IA-1 is an optionally substituted 5-7 membered heterocyclic ring.

In some embodiments, B in Formula IA-1 is an optionally substituted 5-7 membered heterocyclic ring wherein the optional substituents are hydroxy, halogen, alkoxy, alkyl, haloalkyl, amino, alkylamino, cyano.

In other aspects, the Y in the compound of Formula IA is N, and Z is $CR^h$ wherein $R^h$ is H, and the compound of Formula IA has Formula IA-2:

(IA-2)

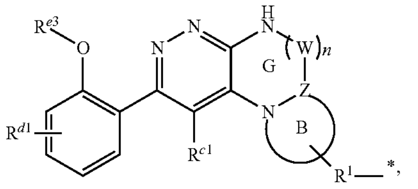

wherein $R^{c1}$, $R^{d1}$, $R^{e3}$, W, B, n, and $R^1$ are as described above for Formula IA.

In some embodiments, n in Formula IA-2 is 1.

In some embodiments of the compound of Formula IA-2, at least one W is —$CH_2$— or substituted —$CH_2$—.

In some embodiments of the compound of Formula IA-2, at least one W is —$CH_2$— or substituted —$CH_2$— wherein the substituents are alkyl, alkoxy, alkylamino.

In some embodiments of the compound of Formula IA-2, at least one W is —$CH_2$—.

In some embodiments of the compound of Formula IA-2, one W is —C(O)—.

In some embodiments of the compound of Formula IA-2, one W is —S(O)—.

In some embodiments of the compound of Formula IA-2, one W is —$S(O)_2$—.

In some embodiments, B in Formula IA-2 is an optionally substituted 5-7 membered heterocyclic ring.

In some embodiments, B in Formula IA-2 is an optionally substituted 5-7 membered heterocyclic ring wherein the optional substituents are hydroxy, halogen, alkoxy, alkyl, haloalkyl, amino, alkylamino, cyano.

In other embodiments, B in Formula IA-2 is an optionally substituted 5-7 membered heterocyclic ring.

In some embodiments, B in Formula IA-2 is an optionally substituted 5-7 membered heterocyclic ring wherein the optional substituents are hydroxy, halogen, alkoxy, alkyl, haloalkyl, amino, alkylamino, or cyano.

In some aspects, the compound of Formula IA is a compound of Formula IA-3:

(IA-3)

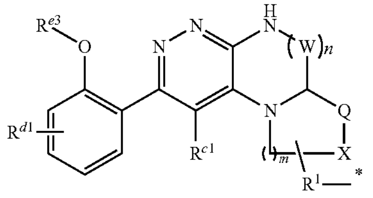

wherein m=1 to 3;

X is optionally substituted —$CH_2$—, or NH; or, if $R^1$ is attached to X, then X is —CH— or N; Q is optionally substituted —$CH_2$—, optionally substituted —$(CH_2)_2$—, —C(O)—, optionally substituted —$CH_2C(O)$—, —S(O)—, —$S(O)_2$—, optionally substituted —$CH_2S(O)_2$—, or optionally substituted —$CH_2S(O)$—; and wherein $R^{c1}$, $R^{d1}$, $R^{e3}$, W, Z, B, n, and $R^1$ are as described above for Formula IA.

In some embodiments of the compound of Formula IA-3, n=1. In other embodiments of the compound of Formula IA-3, n=2. In other embodiments of the compound of Formula IA-3, n=3.

In some embodiments of the compound of Formula IA-3, X is —CH—.

In other embodiments of the compound of Formula IA-3, X is NH.

In some of those embodiments of the compound of Formula IA-3 wherein $R^1$ is attached to X, then X is CH.

In other of those embodiments of the compound of Formula IA-3 wherein $R^1$ is attached to X, then X is N.

In some embodiments of the compound of Formula IA-3, Q is optionally substituted —$CH_2$—.

In some embodiments of the compound of Formula IA-3, Q is optionally substituted —$CH_2$— wherein the optional substituents are alkyl, alkoxy, or alkylamino.

In some embodiments of the compound of Formula IA-3, Q is optionally substituted —$(CH_2)_2$—.

In some embodiments of the compound of Formula IA-3, Q is optionally substituted —$(CH_2)_2$— wherein the optional substituents are alkyl, alkoxy, or alkylamino.

In some embodiments of the compound of Formula IA-3, Q is —C(O)—.

In some embodiments of the compound of Formula IA-3, Q is optionally substituted —$CH_2C(O)$—.

In some embodiments of the compound of Formula IA-3, Q is —S(O)—.

In some embodiments of the compound of Formula IA-3, Q is —$S(O)_2$—.

In some embodiments of the compound of Formula IA-3, Q is optionally substituted —$CH_2S(O)_2$—.

In some embodiments of the compound of Formula IA-3, Q is optionally substituted —$CH_2S(O)$—.

In some aspects, the compound of Formula IA is a compound of Formula IA-4

(IA-4)

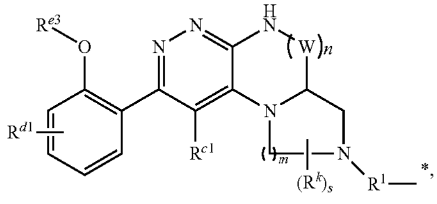

wherein $R^k$=H, D, F, $C_{1-3}$ alkyl, $C_{1-3}$ haloalkyl, $C_{1-4}$ alkoxyl, substituted $C_{1-3}$ alkyl, substituted $C_{1-3}$ haloalkyl, or substituted $C_{1-4}$ alkoxyl; s=0-7; and m=1-3; and wherein $R^{c1}$, $R^{d1}$, $R^{e3}$, W, n, and $R^1$ are as described above for Formula IA.

In some embodiments of the compound of Formula IA-4, n=1. In other embodiments of the compound of Formula IA-4, n=2. In other embodiments of the compound of Formula IA-4, n=3.

In some embodiments of the compound of Formula IA-4, m=1. In other embodiments of the compound of Formula IA-4, m=2. In other embodiments of the compound of Formula IA-4, m=3.

In some embodiments of the compound of Formula IA-4, s=0. In some embodiments of the compound of Formula IA-4, s=1. In other embodiments of the compound of Formula IA-4, s=2. In other embodiments of the compound of Formula IA-4, s=3.

In some embodiments of the compound of Formula IA-4, $R^k$=H.

In some embodiments of the compound of Formula IA-4, $R^k$=D.

In some embodiments of the compound of Formula IA-4, $R^k$=F.

In some embodiments of the compound of Formula IA-4, $R^k$=$C_{1-3}$ alkyl, for example, $C_1$ alkyl, $C_2$ alkyl, $C_3$ alkyl, —$CH_3$, —$CH_2CH_3$, and the like.

In some embodiments of the compound of Formula IA-4, $R^k$=$C_{1-3}$ haloalkyl, for example, $C_1$ haloalkyl, $C_2$ haloalkyl, $C_3$ haloalkyl, —$CF_3$, —$CH_2CF_3$, and the like.

In some embodiments of the compound of Formula IA-4, $R^k$=$C_{1-4}$ alkoxyl, for example, $C_1$ alkoxyl, $C_2$ alkoxyl, $C_3$ alkoxyl, —$OCH_3$, —$OCH_2CH_3$, and the like.

In some embodiments of the compound of Formula IA-4, $R^k$=substituted $C_{1-3}$ alkyl, for example, substituted $C_1$ alkyl, substituted $C_2$ alkyl, substituted $C_3$ alkyl, and the like.

In some embodiments of the compound of Formula IA-4, $R^k$=substituted $C_{1-3}$ haloalkyl, for example, substituted $C_1$ haloalkyl, substituted $C_2$ haloalkyl, substituted $C_3$ haloalkyl, and the like.

In some embodiments of the compound of Formula IA-4, $R^k$=substituted $C_{1-4}$ alkoxyl, for example, substituted $C_1$ alkoxyl, substituted $C_2$ alkoxyl, substituted $C_3$ alkoxyl, and the like.

In some aspects, the compound of Formula IA is a compound of Formula IA-5:

(IA-5)

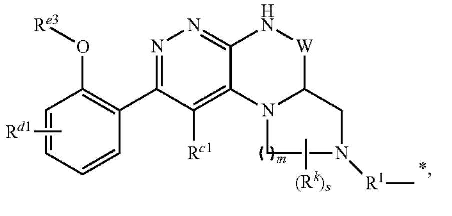

wherein $R^k$=H, D, F, $C_{1-3}$ alkyl, $C_{1-3}$ haloalkyl, or $C_{1-4}$ alkoxyl; m=1-3; and s=0-3, and wherein $R^{c1}$, $R^{d1}$, $R^{e3}$, W, and $R^1$ are as described above for Formula IA.

In some embodiments of the compound of Formula IA-5, m=1. In other embodiments of the compound of Formula IA-5, m=2. In other embodiments of the compound of Formula IA-5, m=3.

In some embodiments of the compound of Formula IA-5, s=0. In some embodiments of the compound of Formula IA-5, s=1. In other embodiments of the compound of Formula IA-5, s=2. In other embodiments of the compound of Formula IA-5, s=3.

In some embodiments of the compound of Formula IA-5, $R^k$=H.

In some embodiments of the compound of Formula IA-5, $R^k$=D.

In some embodiments of the compound of Formula IA-5, $R^k$=F.

In some embodiments of the compound of Formula IA-5, $R^k$=$C_{1-3}$ alkyl, for example, $C_1$ alkyl, $C_2$ alkyl, $C_3$ alkyl, —$CH_3$, —$CH_2CH_3$, and the like.

In some embodiments of the compound of Formula IA-5, $R^k$=$C_{1-3}$ haloalkyl, for example, $C_1$ haloalkyl, $C_2$ haloalkyl, $C_3$ haloalkyl, —$CF_3$, —$CH_2CF_3$, and the like.

In some embodiments of the compound of Formula IA-5, $R^k$=H. or $C_{1-4}$ alkoxyl, for example, $C_1$ alkoxyl, $C_2$ alkoxyl, $C_3$ alkoxyl, —$OCH_3$, —$OCH_2CH_3$, and the like.

In some aspects, the compound of Formula IA is a compound of Formula IA-6, Formula IA-6a or Formula IA-6b:

(IA-6)

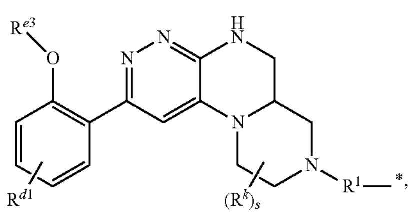

(IA-6a)

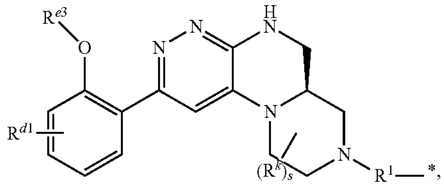

or (IA-6b)

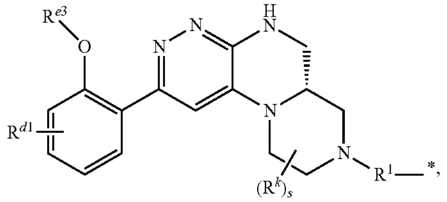

wherein $R^k$=H, D, F, $C_{1-3}$ alkyl, $C_{1-3}$ haloalkyl, or $C_{1-4}$ alkoxyl; and s=0-3, and wherein $R^{c1}$, $R^{d1}$, $R^{e3}$, and $R^1$ are as described above for Formula IA.

In some embodiments, the compound is a compound of Formula IA-6. In some embodiments, the compound is a compound of Formula IA-6a. In some embodiments, the compound is a compound of Formula IA-6b.

In some embodiments of the compound of Formula IA-6, IA-6a or IA-6b, s=0. In some embodiments of the compound of Formula IA-6, IA-6a or IA-6b, s=1. In other embodiments of the compound of Formula IA-6, IA-6a or IA-6b, s=2. In other embodiments of the compound of Formula IA-6, IA-6a or IA-6b, s=3.

In some embodiments of the compound of Formula IA-6, IA-6a or IA-6b, $R^k$=H.

In some embodiments of the compound of Formula IA-6, IA-6a or IA-6b, $R^k$=D.

In some embodiments of the compound of Formula IA-6, IA-6a or IA-6b, $R^k$=F.

In some embodiments of the compound of Formula IA-6, IA-6a or IA-6b, $R^k$=$C_{1-3}$ alkyl, for example, $C_1$ alkyl, $C_2$ alkyl, $C_3$ alkyl, —$CH_3$, —$CH_2CH_3$, and the like.

In some embodiments of the compound of Formula IA-6, IA-6a or IA-6b, $R^k$=$C_{1-3}$ haloalkyl, for example, $C_1$ haloalkyl, $C_2$ haloalkyl, $C_3$ haloalkyl, —$CF_3$, —$CH_2CF_3$, and the like.

In some embodiments of the compound of Formula IA-6, IA-6a or IA-6b, $R^k$=H. or $C_{1-4}$ alkoxyl, for example, $C_1$ alkoxyl, $C_2$ alkoxyl, $C_3$ alkoxyl, —$OCH_3$, —$OCH_2CH_3$, and the like.

In some aspects, the ULM moiety in the compounds of the disclosure is a small molecule E3 Ubiquitin Ligase binding moiety that binds a Cereblon E3 Ubiquitin Ligase (CRBN). Such ULM moieties that bind to CRBN are known to those of skill in the art. Methods of determining whether a small molecule binds a Cereblon E3 Ubiguitin Ligase are known in the art, for example, see Lai A. C., Crews C. M. *Nat Rev Drug Discov.* 2017; 16(2):101-114.

In some embodiments, the ULM is a previously described ULM.

In some embodiments, the ULM is a ULM moiety described in WO 2020/010227, the entirety of which is incorporated by reference herein.

In other embodiments, the ULM is a ULM moiety described in WO 2020/081450, the entirety of which is incorporated by reference herein.

In other embodiments, the ULM is a ULM moiety described in WO 2018/102725, the entirety of which is incorporated by reference herein.

In some embodiments, the ULM is a moiety having the Formula ULM-I (ULM-I)

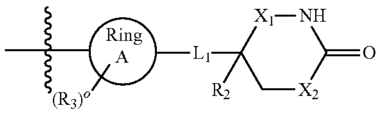

wherein:

∿∿∿ is a point of attachment to $R^1$ of PTM Formula IA;

Ring A is a monocyclic, bicyclic or tricyclic aryl, heteroaryl or heterocycloalkyl group, $L_1$ is a bond, —O—, —S—, —$NR^a$—, —$C(R^a)_2$—C(O)$NR^a$—;

$X_1$ is a bond, —C(O)—, —C(S)—, —$CH_2$—, —$CHCF_3$—, $SO_2$—, —S(O), P(O)$R^b$— or —P(O)$OR^b$—;

$X_2$ is —$C(R^a)_2$—, —$NR^a$— or —S—;

$R_2$ is H, D, optionally substituted $C_{1-4}$ alkyl, $C_{1-4}$ alkoxyl, $C_{1-4}$ haloalkyl, —CN, —$OR^a$, —$OR^b$ or —$SR^b$;

each $R_3$ is independently H, D, halogen, oxo, —OH, —CN, —$NO_2$, —$C_1$-$C_6$alkyl, —$C_2$-$C_6$alkenyl, —$C_2$-$C_6$alkynyl, $C_0$-$C_1$alk-aryl, $C_0$-$C_1$alk-heteroaryl, cycloalkyl, cycloalkenyl, heterocycloalkyl, or heterocycloalkenyl, —$OR^a$, —$SR^a$, —$NR^cR^d$, —$NR^aR^c$, —C(O)$R^b$, —OC(O)$R^a$, —C(O)$OR^a$, —C(O)$NR^cR^d$, —S(O)$R^b$, —$S(O)_2NR^cR^d$, —S(O)(=NR)$R^b$, —$SF_5$, —P(O)$R^bR^b$, —P(O)($OR^b$)($OR^b$), —B($OR^d$)($OR^c$) or —$S(O)_2R^b$;

each $R^a$ is independently H, D, —C(O)$R^b$, —C(O)$OR^c$, —C(O)$NR^cR^d$, —C(=NR)$NR^bR^c$, —C(=$NOR^b$)$NR^bR^c$, —C(=NCN)$NR^bR^c$, —$P(OR^c)_2$, —P(O)$R^cR^b$, —P(O)$OR^cOR^b$, —S(O)$R^b$, —S(O)$NR^cR^d$, —$S(O)_2R^b$, —$S(O)_2NR^cR^d$, $SiR_3$, —$C_1$-$C_{10}$alkyl, —$C_2$-$C_{10}$ alkenyl, —$C_2$-$C_{10}$ alkynyl, aryl, cycloalkyl, cycloalkenyl, heteroaryl, heterocycloalkyl, or heterocycloalkenyl;

each $R^b$, is independently H, D, —$C_1$-$C_6$ alkyl, —$C_2$-$C_6$ alkenyl, —$C_2$-$C_6$ alkynyl, aryl, cycloalkyl, cycloalkenyl, heteroaryl, heterocycloalkyl, or heterocycloalkenyl;

each $R^c$ or $R^d$ is independently H, D, —$C_1$-$C_{10}$ alkyl, —$C_2$-$C_6$ alkenyl, —$C_2$-$C_6$ alkynyl, —$OC_1$-$C_6$alkyl, —O-cycloalkyl, aryl, heteroaryl, cycloalkyl, cycloalkenyl, heterocycloalkyl, or heterocycloalkenyl;

or $R^c$ and $R^d$, together with the atom to which they are both attached, form a monocyclic or multicyclic heterocycloalkyl, or a monocyclic or multicyclic heterocyclo-alkenyl group;

is 1, 2, 3, 4, or 5.

In some embodiments of ULM-I, Ring A is a bicyclic or tricyclic heteroaryl or heterocycloalkyl group. In some embodiments of ULM-1, Ring A is heteroaryl bicyclic. In some embodiments of ULM-1, Ring A is heteroaryl tricyclic. In some embodiments of ULM-1, Ring A is heterobicycloalkyl. In some embodiments of ULM-1, Ring A is heterotricycloalkyl.

In other embodiments of ULM-I, Ring A is a monocyclic heteroaryl having at least one N atom. In other embodiments of ULM-I, Ring A is a pyridine or a pyridazine. In other embodiments of ULM-I, Ring A is

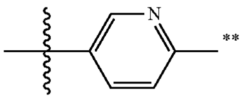

or

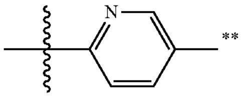

wherein ∿∿∿ is a point of attachment to PTM and ** is a point of attachment to $L_1$.

In yet other embodiments, Ring A is

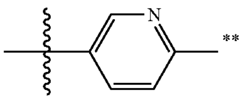 [SMILES: *c1ccc(C)nc1]

wherein ∿∿∿ is a point of attachment to PTM and ** is a point of attachment to $L_1$. In yet other embodiments, Ring A is

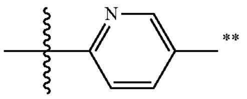 [SMILES: *c1ccc(C)cn1]

wherein ∿∿∿ is a point of attachment to PTM and ** is a point of attachment to $L_1$.

In other embodiments of ULM-I, Ring A is a bicyclic heteroaryl having at least one N atom. In other embodiments of ULM-I, Ring A is an isoindolin-one, an isoindolin-dione, an isoquinolin-one or an an isoquinolin-dione. In other embodiments of ULM-I, Ring A is

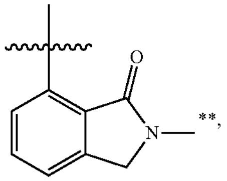

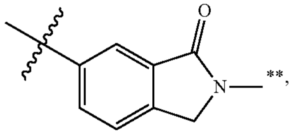

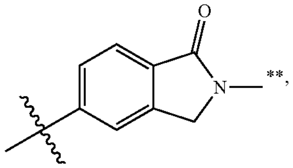

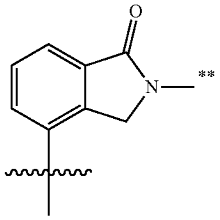

or

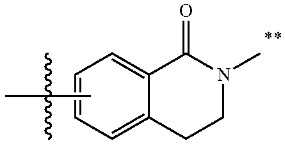

;

wherein ∿∿∿ is a point of attachment to PTM and ** is a point of attachment to $L_1$.

In yet other embodiments, Ring A is

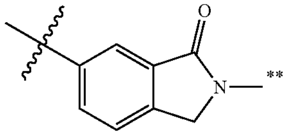 [SMILES: *c1ccc2c(c1)C(=O)N(C)C2]

wherein ∿∿∿ is a point of attachment to PTM and ** is a point of attachment to $L_1$. In yet other embodiments, Ring A is

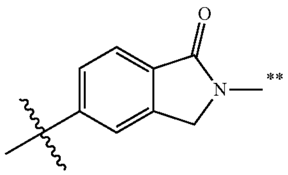 [SMILES: *c1ccc2c(c1)CN(C)C2=O]

wherein ∿∿∿ is a point of attachment to PTM and ** is a point of attachment to $L_1$.

In yet other embodiments of ULM-I, Ring A is

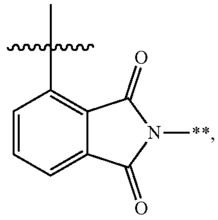

wherein ∿∿∿ is a point of attachment to PTM and ** is a point of attachment to $L_1$. In yet other embodiments of ULM-I, Ring A is

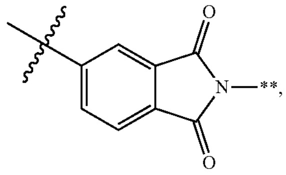

wherein ∿∿∿ is a point of attachment to PTM and ** is a point of attachment to $L_1$.

In yet other embodiments of ULM-I, Ring A is

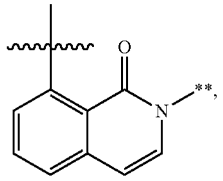

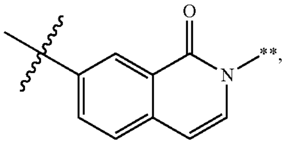

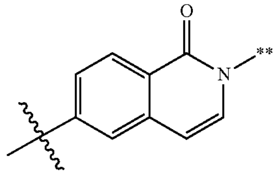

or

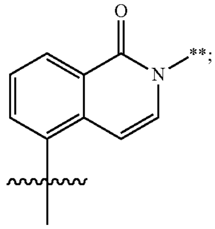

wherein ∿∿∿ is a point of attachment to PTM and ** is a point of attachment to $L_1$.

In yet other embodiments of ULM-I, Ring A is a tricyclic heteroaryl having at least one N atom. In yet other embodiments of ULM-I, Ring A is a carbazole, a pyrido-indole or a pyrrolo-dipyridine. In yet other embodiments of ULM-I, Ring A is

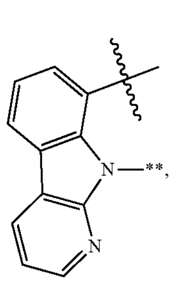

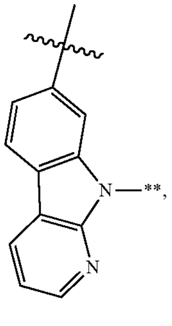

-continued

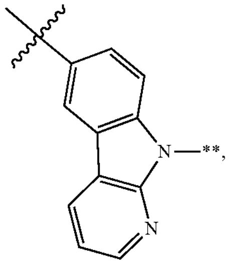

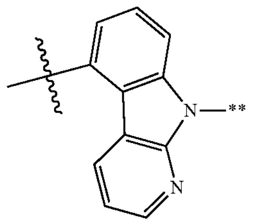

or

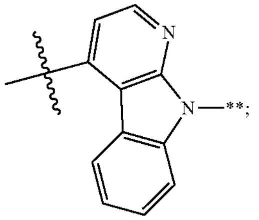

wherein ∿∿ is a point of attachment to PTM and ** is a point of attachment to $L_1$.

In yet other embodiments of ULM-I, Ring A is

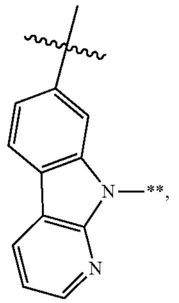

wherein ∿∿ is a point of attachment to PTM and ** is a point of attachment to $L_1$. In yet other embodiments of ULM-I, Ring A is

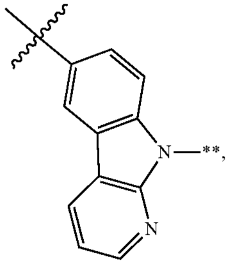

wherein ∿∿ is a point of attachment to PTM and ** is a point of attachment to $L_1$.

In some embodiments of ULM-I, $L_1$ is a bond, —O—, —S—, —$NR^a$—, —$C(R^a)_2$—C(O)$NR^a$—. In some embodiments of ULM-I, $L^1$ is a bond. In some embodiments of ULM-I, $L^1$ is $C_1$-$C_6$ alkylene. In some embodiments of ULM-I, $L^1$ is —C(O)$NR^a$—.

In some embodiments of ULM-I, $X_1$ is a bond, —C(O)—, —C(S)—, —$CH_2$—, —$CHCF_3$—, $SO_2$—, —S(O), P(O)$R^b$— or —P(O)$OR^b$—. In some embodiments of ULM-I, $X_1$ is a bond. In some embodiments of ULM-I, $X_1$ is —C(O)—. In some embodiments of ULM-I, $X_1$ is —$CH_2$—. In some embodiments of ULM-I, $X_1$ is -$CHCF_3$—.

In some embodiments of ULM-I, $X_2$ is —$C(R^a)_2$—, —$NR^a$— or —S—. In some embodiments, $X_2$ is —$C(R^a)_2$—.

In some embodiments of ULM-I, $R_2$ is H, D, optionally substituted $C_{1-4}$ alkyl, $C_{1-4}$ alkoxyl, $C_{1-4}$ haloalkyl, —CN, —$OR^a$, —$OR^b$ or —SR. In some embodiments of ULM-I, $R_2$ is H. In some embodiments of ULM-I, $R_2$ is optionally substituted $C_{1-4}$ alkyl.

In some embodiments of ULM-I, each $R_3$ is independently H, D, halogen, oxo, —OH, —CN, —$NO_2$, —$C_1$-$C_6$alkyl, —$C_2$-$C_6$alkenyl, —$C_2$-$C_6$alkynyl, $C_0$-$C_1$alk-aryl, $C_0$-$C_1$alk-heteroaryl, cycloalkyl, cycloalkenyl, heterocycloalkyl, or heterocycloalkenyl, —$OR^a$, —$SR^a$, —$NR^cR^d$—$NR^aR^c$—C(O)$R^b$, —OC(O)$R^a$, —C(O)$OR^a$, —C(O)$NR^cR^d$, —S(O)$R^b$, —$S(O)_2NR^cR^d$, —S(O)(=$NR^b$)$R^b$, —$SF_5$, —P(O)$R^bR^b$, —P(O)($OR^b$)($OR^b$), —B($OR^d$)($OR^c$) or —$S(O)_2R^b$. In some embodiments of ULM-I, at least one $R_3$ is H. In some embodiments of ULM-I, each $R_3$ is H. In some embodiments of ULM-I, at least one $R_3$ is $C_{1-6}$alkyl.

In some embodiments of ULM-I, each $R^a$ is independently H, D, —C(O)$R^b$, —C(O)$OR^c$, —C(O)$NR^cR^d$, —C(=$NR^b$)$NR^bR^c$, —C(=$NOR^b$)$NR^bR^c$, —C(=NCN)$NR^bR^c$, —$P(OR^c)_2$, —P(O)$R^cR^b$, —P(O)$OR^cOR^b$, —S(O)$R^b$, —S(O)$NR^cR^d$, —$S(O)_2R^b$, —$S(O)_2NR^cR^d$, $SiR_3$, —$C_1$-$C_{10}$alkyl, —$C_2$-$C_{10}$ alkenyl, —$C_2$-$C_{10}$ alkynyl, aryl, cycloalkyl, cycloalkenyl, heteroaryl, heterocycloalkyl, or heterocycloalkenyl. In some embodiments of ULM-I, $R^a$ is H. In some embodiments, $R^a$ is D. In some embodiments, $R^a$ is —C(O)$R^b$. In some embodiments, $R^a$ is —C(O)$OR^c$. In some embodiments, $R^a$ is —C(O)$NR^cR^d$. In some embodiments, $R^a$ is —C(=$NR^b$)$NR^bR^c$. In some embodiments, $R^a$ is C(=$NOR^b$)$NR^bR^c$. In some embodiments, $R^a$ is —C(=NCN)$NR^bR^c$. In other embodiments, $R^a$ is —$P(OR^c)_2$, —P(O)$R^cR^b$, —P(O)$OR^cOR^b$, —S(O)$R^b$, —S(O)$NR^cR^d$, —$S(O)_2R^b$, —$S(O)_2NR^cR^d$, $SiR^b_3$, and the like. In yet other embodiments, $R^a$ is —$C_1$-$C_{10}$alkyl, —$C_2$-$C_{10}$ alkenyl, —$C_2$-$C_{10}$ alkynyl, aryl, cycloalkyl, cycloalkenyl, heteroaryl, heterocycloalkyl, heterocycloalkenyl, and the like.

In some embodiments of ULM-I, each $R^b$, is independently H, D, —$C_1$-$C_6$ alkyl, —$C_2$-$C_6$ alkenyl, —$C_2$-$C_6$ alkynyl, aryl, cycloalkyl, cycloalkenyl, heteroaryl, heterocycloalkyl, or heterocycloalkenyl. In some embodiments, $R^b$ is H. In some embodiments, $R^b$ is D. In some embodiments, $R^b$ is —$C_1$-$C_6$ alkyl. In some embodiments, $R^b$ is —$C_2$-$C_6$ alkenyl. In some embodiments, $R^b$ is —$C_2$-$C_6$ alkynyl. In other embodiments, $R^b$ is aryl. In other embodiments, $R^b$ is cycloalkyl. In other embodiments, $R^b$ is cycloalkenyl. In other embodiments, $R^b$ is heteroaryl. In other embodiments, $R^b$ is heterocycloalkyl. In other embodiments, $R^b$ is heterocycloalkenyl.

In some embodiments of ULM-I, each $R^c$ or $R^d$ is independently H, D, —$C_1$-$C_{10}$ alkyl, —$C_2$-$C_6$ alkenyl, —$C_2$-$C_6$ alkynyl, —$OC_1$-$C_6$alkyl, —O-cycloalkyl, aryl, heteroaryl, cycloalkyl, cycloalkenyl, heterocycloalkyl, or heterocycloalkenyl. In some embodiments, $R^c$ or $R^d$ is H. In some embodiments, $R^c$ or $R^d$ is D. In some embodiments, $R^c$ or $R^d$ is —$C_1$-$C_{10}$ alkyl. In some embodiments, $R^c$ or $R^d$ is —$C_2$-$C_6$ alkenyl. In some embodiments, $R^c$ or $R^d$ is —$C_2$-$C_6$ alkynyl. In other embodiments, $R^c$ or $R^d$ is —$OC_1$-$C_6$alkyl. In other embodiments, $R^c$ or $R^d$ is —O-cycloalkyl. In other embodiments, $R^c$ or $R^d$ is aryl. In other embodiments, $R^c$ or $R^d$ is cycloalkyl. In other embodiments, $R^c$ or $R^d$ is cycloalkenyl. In other embodiments, $R^c$ or $R^d$ is heteroaryl. In other embodiments, $R^c$ or $R^d$ is heterocycloalkyl.

In other embodiments of ULM-I, $R^c$ and $R^d$, together with the atom to which they are both attached, form a monocyclic or multicyclic heterocycloalkyl, or a monocyclic or multicyclic heterocyclo-alkenyl group. In other embodiments, $R^c$ or $R^d$ is heterocycloalkenyl. In yet other embodiments, $R^c$ and $R^d$, together with the atom to which they are both attached, form a monocyclic or multicyclic heterocycloalkyl, or a monocyclic or multicyclic heterocyclo-alkenyl group. In yet other embodiments, $R^c$ and $R^d$ form a monocyclic heterocycloalkyl. In yet other embodiments, $R^c$ and $R^d$ form a multicyclic heterocycloalkyl. In yet other embodiments, $R^c$ and $R^d$ form a monocyclic heterocyclo-alkenyl group. In yet other embodiments, $R^c$ and $R^d$ form a multicyclic heterocyclo-alkenyl group.

In some embodiments of ULM-1, o is 1, 2, 3, 4 or 5. In some embodiments, o is 1. In some embodiments, o is 2. In other embodiments, o is 3. In other embodiments, o is 4. In yet other embodiments, o is 5.

In some embodiments, ULM-I is a compound of formula:

(ULM-IA)

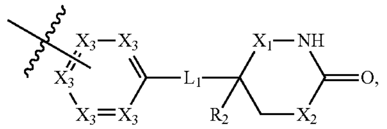

wherein each $X_3$ is independently N,N-oxide or $CR^3$ and at least one $X_3$ is N or N-oxide; wherein ∿∿ is a point of attachment to PTM; or (ULM-IB)

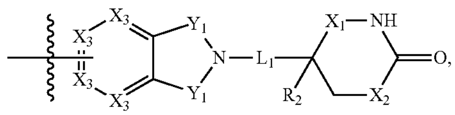

wherein each $X_3$ is independently N,N-oxide or $CR^3$; wherein each Y is independently —C(O)— or —$C(R^a)_2$— and at least one Y is —C(O)—; and wherein ∿∿ is a point of attachment to PTM; or (ULM-IC)

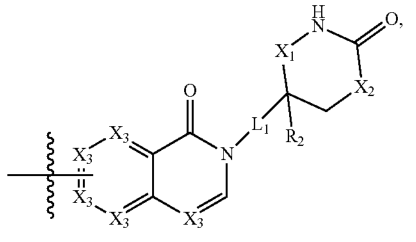

wherein each $X_3$ is independently N,N-oxide or $CR^3$ and wherein ∿∿ is a point of attachment to PTM; or (ULM-ID)

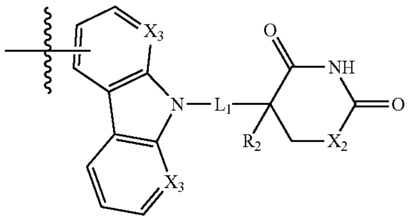

wherein each $X_3$ is independently N,N-oxide or $CR^3$ and wherein ∿∿ is a point of attachment to PTM.

In some embodiments of ULM-IA, ULM-IB, ULM-IC, or ULM-ID, $X_2$ is —$C(R^a)_2$— and and $R_2$ is H.

In some embodiments, the compounds of Formula I are those having the Formula IA-7, Formula IA-8, Formula IA-9, Formula IA-10, Formula IA-11, Formula IA-12 or Formula IA-13:

(IA-7)

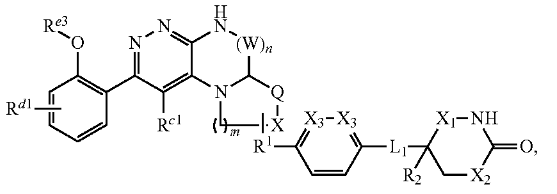

or (IA-8)

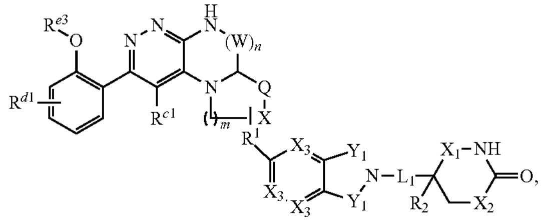

or (IA-9)

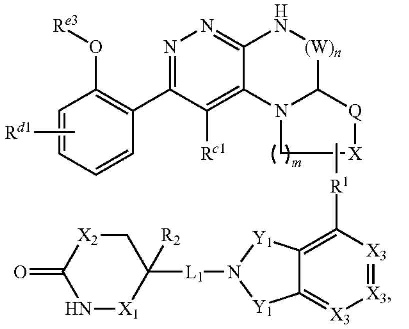

or (IA-10)

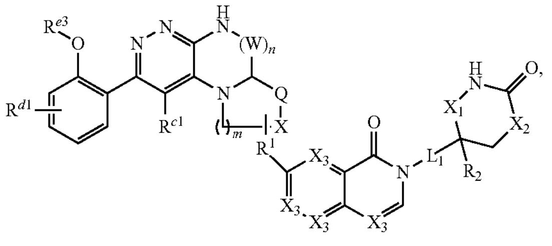

or

-continued (IA-11)

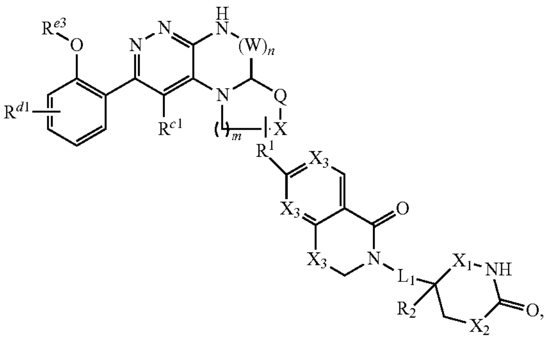

or (IA-12)

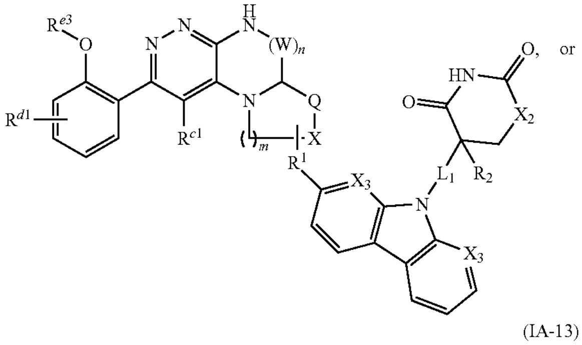

or (IA-13)

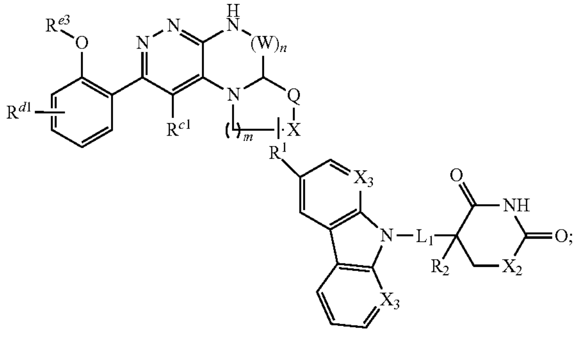

;

wherein:

each W is independently optionally substituted —$CH_2$—, —C(O)—, —S(O)—, or —$S(O)_2$—; wherein when n=2 or 3, only one W may be —C(O)—, —S(O)—, or —$S(O)_2$—, and the other W are —$CH_2$— or substituted —$CH_2$—;

n=0-3;

m=1-3;

X is optionally substituted —$CH_2$—, or NH; or, if $R^1$ is attached to X, then X is —CH— or N;

Q is optionally substituted —$CH_2$—, optionally substituted —$(CH_2)_2$—, —C(O)—, optionally substituted —$CH_2C(O)$—, —S(O)—, —$S(O)_2$—, optionally substituted —$CH_2S(O)_2$—, or optionally substituted —$CH_2S(O)$—;

$R^{c1}$ and $R^{d1}$ are independently H, D, Halo, $C_{1-3}$ alkyl, $C_{1-3}$ haloalkyl, or $C_{1-4}$ alkoxyl;

$R^{e3}$ is H, —$C(O)R^f$, or —$P(O)(OR^g)_2$; wherein $R^f$ and $R^g$ are independently H, $C_{1-4}$ alkyl, $C_{1-4}$ substituted alkyl, $C_{3-8}$ cyclcoalkyl, $C_{3-8}$ substituted cyclcoalkyl, $C_{3-8}$ heterocyclcoalkyl, or $C_{3-8}$ substituted heterocyclcoalkyl;

$R^1$ is a covalent bond, 3-11 membered cycloalkyl optionally substituted with 0-6 $R^{1a}$ and/or $R^{1b}$ groups, 3-11 membered heterocyclyl optionally substituted with 0-6 $R^{1a}$ and/or $R^{1b}$ groups, —$(CR^{1a}R^{1b})_{1-5}$, —$(CR^{1a}{=}CR^{1b})$—, —$(CR^{1a}R^{1b})_{1-5}$-A- wherein A is O, S, or $NR^{1c}$, —$(CR^{1a}R^{1b})_{1-5}$-A-$(CR^{1a}R^{1b})_{1-5}$— wherein A is O, S, or $NR^{1c}$, —$(CR^{1a}R^{1b})_{1-5}$-A-$(CR^{1a}R^{1b})_{1-5}$-A- wherein A is O, S, or $NR^{1c}$, —$(CR^{1a}R^{1b})_{1-5}$—$(CR^{1a}{=}CR^{1b})$—$(CR^{1a}R^{1b})_{1-5}$—, —$(CR^{1a}R^{1b})_{1-5}$—, —$(CR^{1a}{=}CR^{1b})$—$(CR^{1a}R^{1b})_{1-5}$-A- wherein A is O, S, or $NR^{1c}$, —$(CR^{1a}R^{1b})_{1-5}$—(C≡C)—$(CR^{1a}R^{1b})_{1-5}$—, —$(CR^{1a}R^{1b})_{1-5}$—(C≡C)—$(CR^{1a}R^{1b})_{1-5}$-A- wherein A is O, S, or $NR^{1c}$, —(C≡C)—$(CR^{1a}R^{1b})_{1-5}$-A-$(CR^{1a}R^{1b})_{1-5}$— wherein A is O, S, or $NR^{1c}$, —(C≡C)—$(CR^{1a}R^{1b})_{1-5}$, —$(CR^{1a}R^{1b})_{1-5}$-(3-11 membered cycloalkyl optionally substituted with 0-6 $R^{1a}$ and/or $R^{1b}$ groups)-, —$(CR^{1a}R^{1b})_{1-5}$—(3-11 membered heterocyclyl optionally substituted with 0-6 $R^{1a}$ and/or $R^{1b}$ groups)-, -(3-11 membered cycloalkyl optionally substituted with 0-6 $R^{1a}$ and/or $R^{1b}$ groups)-, —$(CR^{1a}R^{1b})_{1-5}$—, -(3-11 membered heterocyclyl optionally substituted with 0-6 $R^{1a}$ and/or $R^{1b}$ groups) —$(CR^{1a}R^{1b})_{1-5}$—, —$(CR^{1a}R^{1b})_{1-5}$-(3-11 membered cycloalkyl optionally substituted with 0-6 $R^{1a}$ and/or $R^{1b}$ groups)-A-, —$(CR^{1a}R^{1b})_{1-5}$-(3-11 membered heterocyclyl optionally substituted with 0-6 $R^{1a}$ and/or $R^{1b}$ groups)-A-, —$(CR^{1a}R^{1b})_{1-5}$-(3-11 membered cycloalkyl optionally substituted with 0-6 $R^{1a}$ and/or $R^{1b}$ groups)-$(CR^{1a}R^{1b})_{1-5}$, —$(CR^{1a}R^{1b})_{1-5}$-(3-11 membered cycloalkyl optionally substituted with 0-6 $R^{1a}$ and/or $R^{1b}$ groups)-A- wherein A is O, S, or $NR^{1c}$—$(CR^{1a}R^{1b})_{1-5}$-(3-11 membered cycloalkyl optionally substituted with 0-6 $R^{1a}$ and/or $R^{1b}$ groups)-$(CR^{1a}R^{1b})_{1-5}$-A- wherein A is O, S, or $NR^{1c}$, —$(CR^{1a}R^{1b})_{1-5}$-A-(3-11 membered cycloalkyl optionally substituted with 0-6 $R^{1a}$ and/or $R^{1b}$ groups)- wherein A is O, S, or $NR^{1c}$—$(CR^{1a}R^{1b})_{1-5}$-(3-11 membered heterocyclyl optionally substituted with 0-6 $R^{1a}$ and/or $R^{1b}$ groups)-$(CR^{1a}R^{1b})_{1-5}$, —$(CR^{1a}R^{1b})_{1-5}$-(3-11 membered heterocyclyl optionally substituted with 0-6 $R^{1a}$ and/or $R^{1b}$ groups)-$(CR^{1a}R^{1b})_{1-5}$-A- wherein A is O, S, or $NR^{1c}$, —$(CR^{1a}R^{1b})_{1-5}$-(3-11 membered heterocyclyl optionally substituted with 0-6 $R^{1a}$ and/or $R^{1b}$ groups)-A- wherein A is O, S, or $NR^{1c}$, —$(CR^{1a}R^{b})_{1-5}$-A-(3-11 membered heterocyclyl optionally substituted with 0-6 Ria and/or $R^{1b}$ groups)- wherein A is O, S, or $NR^{1c}$—$(CR^{1a}R^{1b})_{1-5}$-(3-11 membered cycloalkyl optionally substituted with 0-6 $R^{1a}$ and/or $R^{1b}$ groups)-$(CR^{1a}R^{1b})_{1-5}$-A- wherein A is O, S, or $NR^{1c}$, —$(CR^{1a}R^{1b})_{1-5}$-A-(3-11 membered cycloalkyl optionally substituted with 0-6 $R^{1a}$ and/or $R^{1b}$ groups)- wherein A is O, S, or $NR^{1c}$, —$(CR^{1a}R^{1b})_{1-5}$-A-(3-11 membered cycloalkyl optionally substituted with 0-6 $R^{1a}$ and/or $R^{1b}$ groups)-$(CR^{1a}R^{1b})_{1-5}$-A- wherein each A is independently O, S, or $NR^{1c}$, —$(CR^{1a}R^{1b})_{1-5}$-A-(3-11 membered heterocyclyl optionally substituted with 0-6 $R^{1a}$ and/or $R^{1b}$ groups)-$(CR^{1a}R^{1b})_{1-5}$-A- wherein each A is independently O, S, or $NR^{1c}$, —$(CR^{1a}R^{b})_{1-5}$-A-$(CR^{1a}R^{b})_{1-5}$-A- wherein A is O, S, or $NR^{1C}$, —$(CR^{1a}R^{1b})_{1-5}$-A-$(CR^{1a}R^{1b})_{1-5}$-A-$(CR^{1a}R^{1b})_{1-5}$-A-$(CR^{1a}R^{1b})_{1-5}$-A- wherein A is O, S, or $NR^{1c}$—$(CR^{1a}R^{1b})_{1-5}$-A-(CO) wherein A is O, S, or $NR^{1c}$—$(CR^{1a}R^{1b})_{1-5}$—$(CR^{1a}{=}CR^{1b})$—$(CR^{1a}R^{1b})_{1-5}$-A-(CO)— wherein A is O, S, or $NR^{1c}$, —$(CR^{1a}R^{1b})_{1-5}$—(C≡C)—$(CR^{1a}R^{1b})_{1-5}$-A-(CO)— wherein A is O, S, or $NR^{1c}$—$(CR^{1a}R^{1b})_{1-5}$-(3-11 membered cycloalkyl optionally substituted with 0-6 $R^{1a}$ and/or $R^{1b}$ groups)-$(CR^{1a}R^{1b})_{1-5}$-A-(CO)— wherein A is O, S, or $NR^{1c}$, $—(CR^{1a}R^{b})_{1-5}$-A-(CO)-(3-11 membered cycloalkyl optionally substituted with 0-6 $R^{1a}$ and/or $R^{1b}$ groups)- wherein A is O, S, or $NR^{1c}—(CR^{1a}R^{1b})_{1-5}$-(3-11 membered heterocyclyl optionally substituted with 0-6 $R^{1a}$ and/or $R^{1b}$ groups)-$(CR^{1a}R^{1b})_{1-5}$-A-(CO)— wherein A is O, S, or $NR^{1c}$, $—(CR^{1a}R^{1b})_{1-5}$-A-(CO)-(3-11 membered heterocyclyl optionally substituted with 0-6 $R^{1a}$ and/or $R^{1b}$ groups)- wherein A is O, S, or $NR^{1c}—(CR^{1a}R^{1b})_{1-5}$-A-(3-11 membered cycloalkyl optionally substituted with 0-6 $R^{1a}$ and/or $R^{1b}$ groups)-A-(CO)— wherein each A is independently O, S, or $NR^{1c}$, -(3-11 membered cycloalkyl optionally substituted with 0-6 $R^{1a}$ and/or $R^{1b}$ groups)-CO—$(CR^{1a}R^{1b})_{1-5}$-A- wherein A is O, S, or $NR^{1c}—(CR^{1a}R^{1b})_{1-5}$-(3-11 membered cycloalkyl optionally substituted with 0-6 $R^{1a}$ and/or $R^{1b}$ groups)-$(CR^{1a}R^{1b})_{1-5}$-A-(CO)— wherein A is O, S, or $NR^{1c}$, $—(CR^{1a}R^{1b})_{1-5}$-(3-11 membered heterocyclyl optionally substituted with 0-6 Ria and/or $R^{1b}$ groups)-$(CR^{1a}R^{1b})_{1-5}$-A-(CO)— wherein A is O, S, or $NR^{1c}$, -(3-11 membered cycloalkyl optionally substituted with 0-6 $R^{1a}$ and/or $R^{1b}$ groups)-$(CR^{1a}R^{1b})_{1-5}$—, or -(3-11 membered heterocyclyl optionally substituted with 0-6 $R^{1a}$ and/or $R^{1b}$ groups)-$(CR^{1a}R^{1b})_{1-5}$—;

$L_1$ is a bond, —O—, —S—, $—NR^a—$, $—C(R^a)_2—C(O)NR^a—$;

$X_1$ is a bond, —C(O)—, —C(S)—, $—CH_2—$, $—CHCF_3—$, $SO_2—$, —S(O), $P(O)R^b—$ or $—P(O)OR^b—$;

$X_2$ is $—C(R^a)_2—$, $—NR^a—$ or —S—;

$R_2$ is H, D, optionally substituted $C_{1-4}$ alkyl, $C_{1-4}$ alkoxyl, $C_{1-4}$ haloalkyl, —CN, $—OR^a$, $—OR^b$ or —SR;

each $X_3$ is independently N,N-oxide or $CR^3$; and each Y is independently —C(O)— or $—C(R^a)_2—$ and at least one Y is —C(O)—.

In some embodiments of the compound of Formula IA-7, Formula IA-8, Formula IA-9, Formula IA-10, Formula IA-11, Formula IA-12 and Formula IA-13, n=1. In other embodiments of the compound of Formula IA-7, Formula IA-8, Formula IA-9, Formula IA-10, Formula IA-11, Formula IA-12 and Formula IA-13, n=2. In other embodiments of the compound of Formula IA-7, Formula IA-8, Formula IA-9, Formula IA-10, Formula IA-11, Formula IA-12 and Formula IA-13, n=3.

In some embodiments of the compound of Formula IA-7, Formula IA-8, Formula IA-9, Formula IA-10, Formula IA-11, Formula IA-12 and Formula IA-13, m=1. In other embodiments of the compound of Formula IA-7, Formula IA-8, Formula IA-9, Formula IA-10, Formula IA-11, Formula IA-12 and Formula IA-13, m=2. In other embodiments of the compound of Formula IA-7, Formula IA-8, Formula IA-9, Formula IA-10, Formula IA-11, Formula IA-12 and Formula IA-13, m=3.

In some embodiments of the compound of Formula IA-7, Formula IA-8, Formula IA-9, Formula IA-10, Formula IA-11, Formula IA-12 and Formula IA-13, $R^{c1}$ and $R^{d1}$ are each H.

In some embodiments of the compound of Formula IA-7, Formula IA-8, Formula IA-9, Formula IA-10, Formula IA-11, Formula IA-12 and Formula IA-13, $R^{e3}$ is H.

In some embodiments of the compound of Formula IA-7, Formula IA-8, Formula IA-9, Formula IA-10, Formula IA-11, Formula IA-12 and Formula IA-13, $R^{c1}$, $R^{d1}$, and $R^{e3}$ are each H.

In some embodiments, the compounds of Formula I are those having the Formula IA-7a, Formula IA-8a, Formula IA-9a, Formula IA-10a, Formula IA-11a, Formula IA-12a or Formula IA-13a:

(IA-7a)

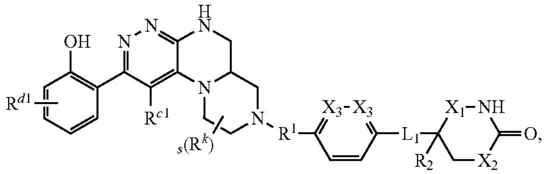

or (IA-8a)

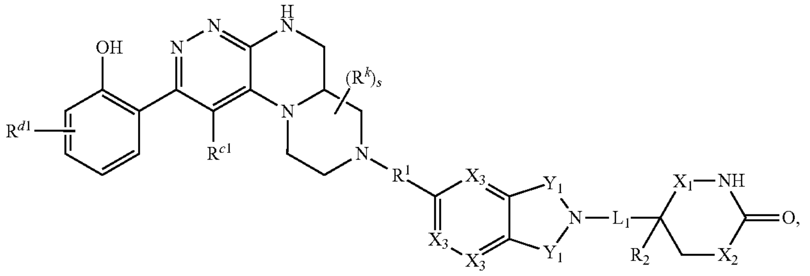

or

-continued (IA-9a)

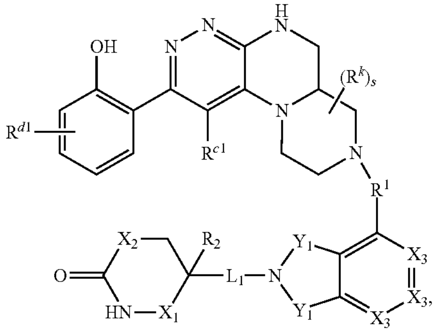

or (IA-10a)

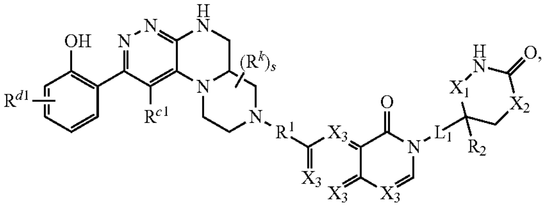

or (IA-11a)

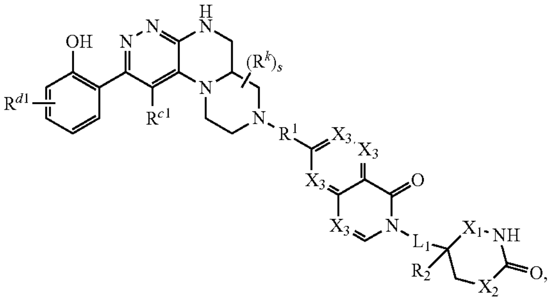

or (IA-12a)

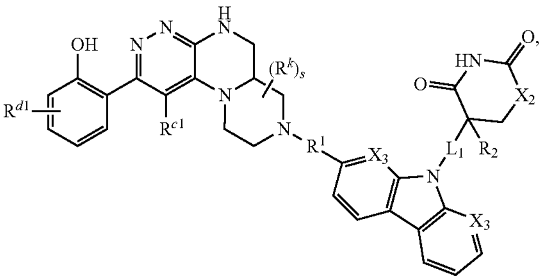

or (IA-13a)

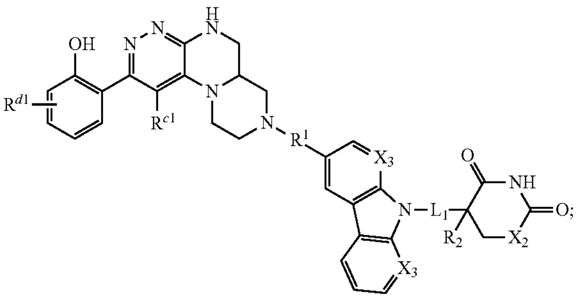

wherein each $R^k$ is independently H, D, F, $C_{1-3}$ alkyl, $C_{1-3}$ haloalkyl, $C_{1-4}$ alkoxyl, substituted $C_{1-3}$ alkyl, substituted $C_{1-3}$ haloalkyl, or substituted $C_{1-4}$ alkoxyl;

s is 0, 1, 2, 3 or 4;

each $Y_1$ is independently —C(O)— or —$CH_2$— and at least one $Y_1$ is —C(O)—; and $R^{d1}$, $R^{c1}$, $R^1$, $R^2$, $X_1$, $X_2$ and $X_3$ are as defined herein.

In some embodiments of the compounds of Formula IA-7a, Formula IA-8a, Formula IA-9a, Formula IA-10a, Formula IA-11a, Formula IA-12a and Formula IA-13a, s is 0. In some embodiments of the compounds of Formula IA-7a, Formula IA-8a, Formula IA-9a, Formula IA-10a, Formula IA-11a, Formula IA-12a and Formula IA-13a, S is 1. In some embodiments of the compounds of Formula IA-7a, Formula IA-8a, Formula IA-9a, Formula IA-10a, Formula IA-11a, Formula IA-12a and Formula IA-13a, S is 2. In some embodiments of the compounds of Formula IA-7a, Formula IA-8a, Formula IA-9a, Formula IA-10a, Formula IA-11a, Formula IA-12a and Formula IA-13a, S is 3. In some embodiments of the compounds of Formula IA-7a, Formula IA-8a, Formula IA-9a, Formula IA-10a, Formula IA-11a, Formula IA-12a and Formula IA-13a, S is 4.

In some embodiments of the compounds of Formula IA-7a, Formula IA-8a, Formula IA-9a, Formula IA-10a, Formula IA-11a, Formula IA-12a and Formula IA-13a, at least one $R^k$ is H. In some embodiments of the compounds of Formula IA-7a, Formula IA-8a, Formula IA-9a, Formula IA-10a, Formula IA-11a, Formula IA-12a and Formula IA-13a, at least two $R^k$ are H. In some embodiments of the compounds of Formula IA-7a, Formula IA-8a, Formula IA-9a, Formula IA-10a, Formula IA-11a, Formula IA-12a and Formula IA-13a, each $R^k$ is H.

In some embodiments of the compounds of Formula IA-7a, Formula IA-8a, Formula IA-9a, Formula IA-10a, Formula IA-11a, Formula IA-12a and Formula IA-13a, at least one $R^k$ is $C_{1-6}$alkyl. In some embodiments of the compounds of Formula IA-7a, Formula IA-8a, Formula IA-9a, Formula IA-10a, Formula IA-11a, Formula IA-12a and Formula IA-13a, at least two $R^k$ are $C_{1-6}$alkyl. In some embodiments of the compounds of Formula IA-7a, Formula IA-8a, Formula IA-9a, Formula IA-10a, Formula IA-11a, Formula IA-12a and Formula IA-13a, each $R^k$ is $C_{1-6}$alkyl.

In some embodiments of the compounds of Formula IA-7a, Formula IA-8a, Formula IA-9a, Formula IA-10a, Formula IA-11a, Formula IA-12a and Formula IA-13a, at least one $R^k$ is methyl. In some embodiments of the compounds of Formula IA-7a, Formula IA-8a, Formula IA-9a, Formula IA-10a, Formula IA-11a, Formula IA-12a and Formula IA-13a, at least two $R^k$ are methyl. In some embodiments of the compounds of Formula IA-7a, Formula IA-8a, Formula IA-9a, Formula IA-10a, Formula IA-11a, Formula IA-12a and Formula IA-13a, each $R^k$ is methyl.

In some embodiments of the compounds of Formula IA-7a, Formula IA-8a, Formula IA-9a, Formula IA-10a, Formula IA-11a, Formula IA-12a and Formula IA-13a, at least one $Y_1$ is —C(O)—. In some embodiments of the compounds of Formula IA-7a, Formula IA-8a, Formula IA-9a, Formula IA-10a, Formula IA-11a, Formula IA-12a and Formula IA-13a, each $Y_1$ is —C(O)—.

In some embodiments of the compounds of Formula IA-7a, Formula IA-8a, Formula IA-9a, Formula IA-10a, Formula IA-11a, Formula IA-12a and Formula IA-13a, at least one $Y_1$ is —$CH_2$—. In some embodiments of the compounds of Formula IA-7a, Formula IA-8a, Formula IA-9a, Formula IA-10a, Formula IA-11a, Formula IA-12a and Formula IA-13a, each $Y_1$ is —$CH_2$—.

In some embodiments of the compounds of Formula IA-7a, Formula IA-8a, Formula IA-9a, Formula IA-10a, Formula IA-11a, Formula IA-12a and Formula IA-13a, one $Y_1$ is —$CH_2$— and the other $Y_1$ is —C(O)—.

In some embodiments, the compounds of Formula I are those having the Formula IA-7b, Formula IA-8b, Formula IA-9b, Formula IA-10b, Formula IA-11 b, Formula IA-12b or Formula IA-13b:

(IA-7b)

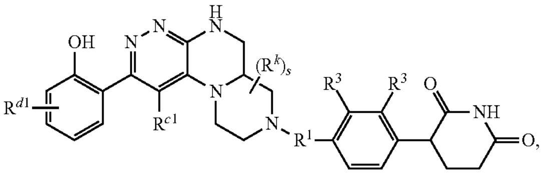

or (IA-8b)

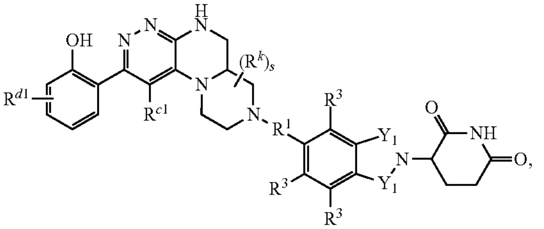

or (IA-9b)

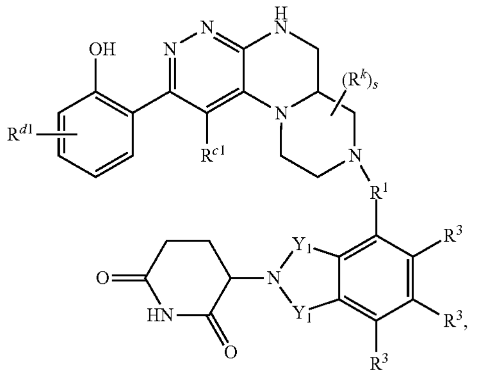

or (IA-10b)

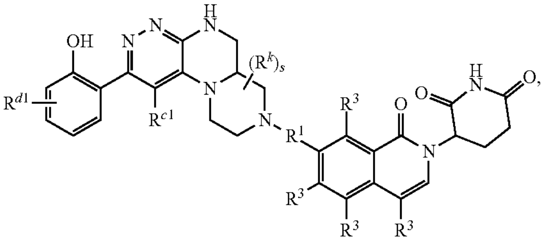

or (IA-11b)

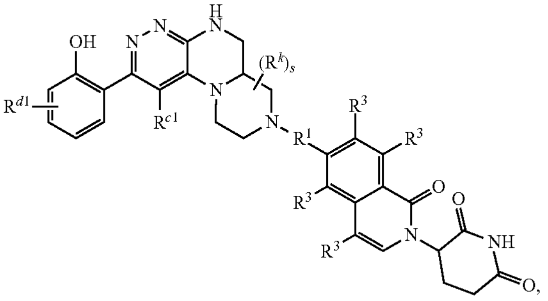

or

-continued (IA-12b)

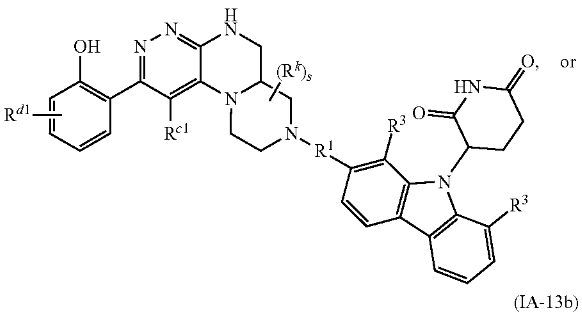

or (IA-13b)

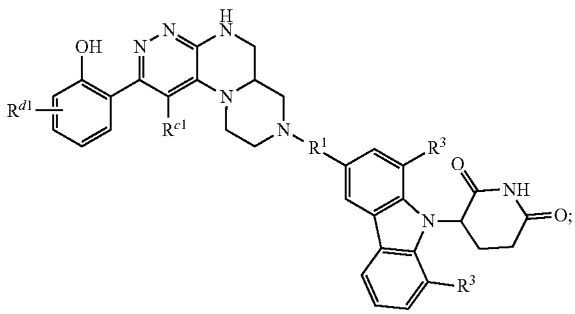

;

wherein each $R^k$ is independently H, D, F, $C_{1-3}$ alkyl, $C_{1-3}$ haloalkyl, $C_{1-4}$ alkoxyl, substituted $C_{1-3}$ alkyl, substituted $C_{1-3}$ haloalkyl, or substituted $C_{1-4}$ alkoxyl;

s is 0, 1, 2, 3 or 4;

each $Y_1$ is independently —C(O)— or —$CH_2$— and at least one $Y_1$ is —C(O)—; and $R^{d1}$, $R^{c1}$, $R^1$ and $R^3$ are as defined herein.

In some embodiments of the compounds of Formula IA-7b, Formula IA-8b, Formula IA-9b, Formula IA-10b, Formula IA-11b, Formula IA-12b and Formula IA-13b, s is 0. In some embodiments of the compounds of Formula IA-7b, Formula IA-8b, Formula IA-9b, Formula IA-10b, Formula IA-11b, Formula IA-12b and Formula IA-13b, s is 1. In some embodiments of the compounds of Formula Formula IA-7b, Formula IA-8b, Formula IA-9b, Formula IA-10b, Formula IA-11 b, Formula IA-12b and Formula IA-13b, s is 2. In some embodiments of the compounds of Formula Formula IA-7b, Formula IA-8b, Formula IA-9b, Formula IA-10b, Formula IA-11 b, Formula IA-12b and Formula IA-13b, s is 3. In some embodiments of the compounds of Formula Formula IA-7b, Formula IA-8b, Formula IA-9b, Formula IA-10b, Formula IA-11 b, Formula IA-12b and Formula IA-13b, s is 4.

In some embodiments of the compounds of Formula IA-7b, Formula IA-8b, Formula IA-9b, Formula IA-10b, Formula IA-11 b, Formula IA-12b and Formula IA-13b, at least one $R^k$ is H. In some embodiments of the compounds of Formula IA-7b, Formula IA-8b, Formula IA-9b, Formula IA-10b, Formula IA-11 b, Formula IA-12b and Formula IA-13b, at least two $R^k$ are H. In some embodiments of the compounds of Formula Formula IA-7b, Formula IA-8b, Formula IA-9b, Formula IA-10b, Formula IA-11b, Formula IA-12b and Formula IA-13b, each $R^k$ is H.

In some embodiments of the compounds of Formula IA-7b, Formula IA-8b, Formula IA-9b, Formula IA-10b, Formula IA-1 b, Formula IA-12b and Formula IA-13b, at least one $R^k$ is $C_{1-6}$alkyl. In some embodiments of the compounds of Formula IA-7b, Formula IA-8b, Formula IA-9b, Formula IA-10b, Formula IA-11b, Formula IA-12b and Formula IA-13b, at least two $R^k$ are $C_{1-6}$alkyl. In some embodiments of the compounds of Formula IA-7b, Formula IA-8b, Formula IA-9b, Formula IA-10b, Formula IA-11b, Formula IA-12b and Formula IA-13b, each $R^k$ is $C_{1-6}$alkyl.

In some embodiments of the compounds of Formula IA-7b, Formula IA-8b, Formula IA-9b, Formula IA-10b, Formula IA-1 b, Formula IA-12b and Formula IA-13b, at least one $R^k$ is methyl. In some embodiments of the compounds of Formula IA-7b, Formula IA-8b, Formula IA-9b, Formula IA-10b, Formula IA-1 b, Formula IA-12b and Formula IA-13b, at least two $R^k$ are methyl. In some embodiments of the compounds of Formula IA-7b, Formula IA-8b, Formula IA-9b, Formula IA-10b, Formula IA-1 b, Formula IA-12b and Formula IA-13b, each $R^k$ is methyl.

In some embodiments of the compounds of Formula IA-7b, Formula IA-8b, Formula IA-9b, Formula IA-10b, Formula IA-1 b, Formula IA-12b and Formula IA-13b, at least one $Y_1$ is —C(O)—. In some embodiments of the compounds of Formula IA-7b, Formula IA-8b, Formula IA-9b, Formula IA-10b, Formula IA-1 b, Formula IA-12b and Formula IA-13b, each $Y_1$ is —C(O)—.

In some embodiments of the compounds of Formula IA-7b, Formula IA-8b, Formula IA-9b, Formula IA-10b, Formula IA-1 b, Formula IA-12b and Formula IA-13b, at least one $Y_1$ is —$CH_2$—. In some embodiments of the compounds of Formula IA-7b, Formula IA-8b, Formula IA-9b, Formula IA-10b, Formula IA-1 b, Formula IA-12b and Formula IA-13b, each $Y_1$ is —$CH_2$—.

In some embodiments of the compounds of Formula Formula IA-7b, Formula IA-8b, Formula IA-9b, Formula IA-10b, Formula IA-11b, Formula IA-12b and Formula IA-13b, one $Y_1$ is —$CH_2$— and the other $Y_1$ is —C(O)—.

In some embodiments, the compounds of Formula I are those having the Formula IA-7c, Formula IA-8c, Formula IA-9c, Formula IA-10c, Formula IA-11c, Formula IA-12c or Formula IA-13c:

(IA-7c)

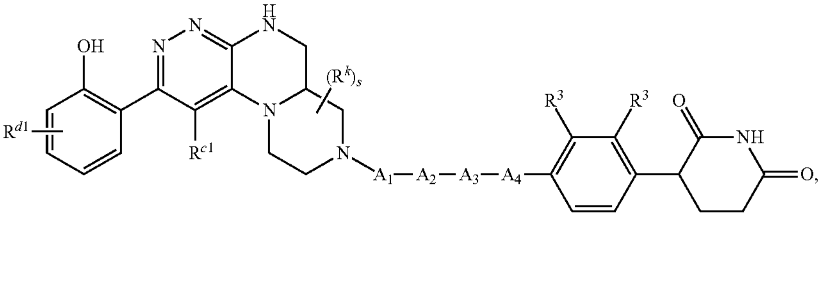

or

-continued
(IA-8c)
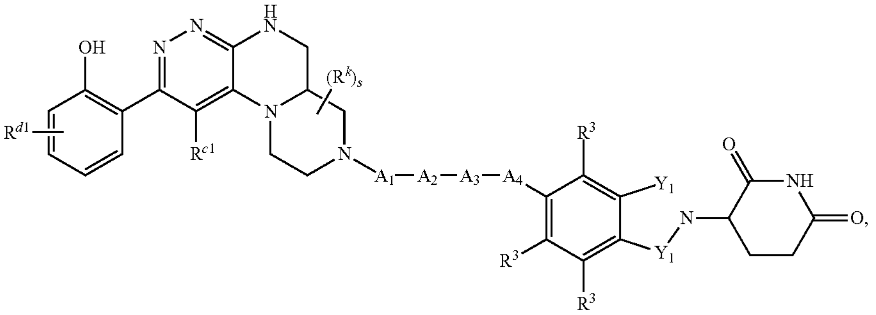
or
(IA-9c)
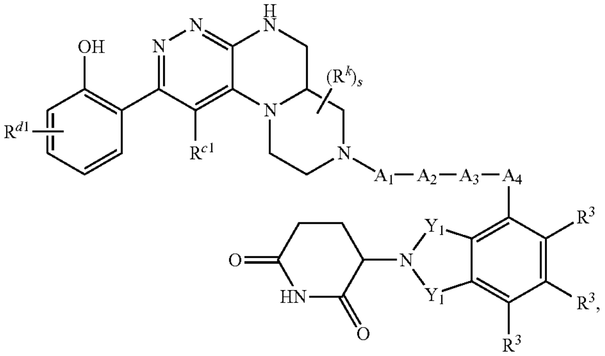
or
(IA-10c)
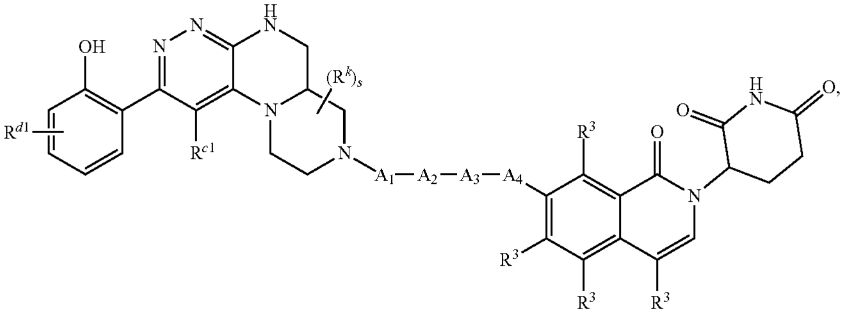
or
(IA-11c)
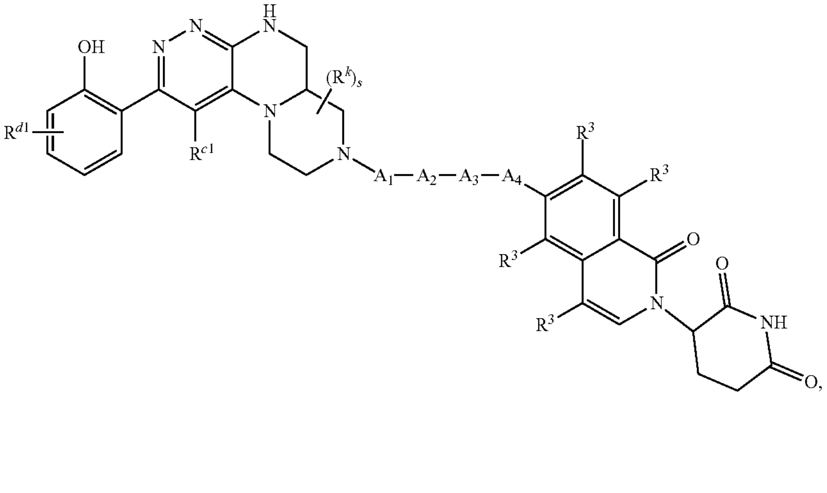
or -continued (IA-12c)

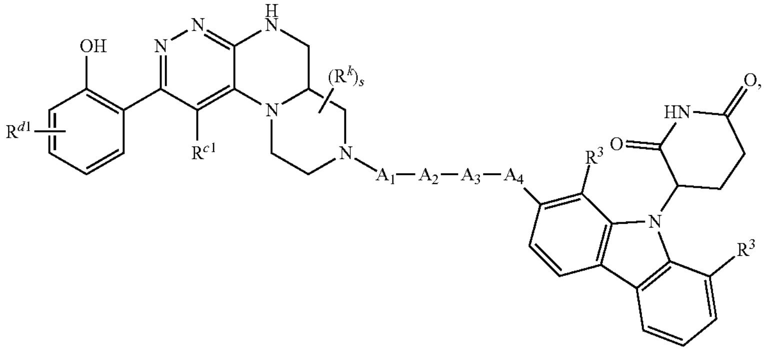

, or (IA-13c)

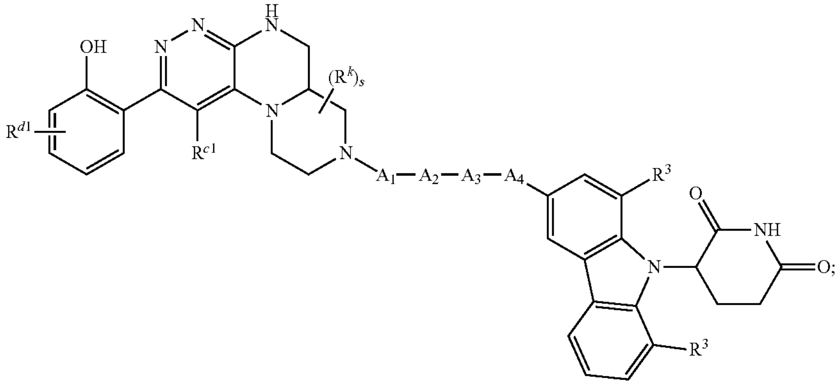

;

wherein each $R^k$ is independently H, D, F, $C_{1-3}$ alkyl, $C_{1-3}$ haloalkyl, $C_{1-4}$ alkoxyl, substituted $C_{1-3}$ alkyl, substituted $C_{1-3}$ haloalkyl, or substituted $C_{1-4}$ alkoxyl;

s is 0, 1, 2, 3 or 4;

each $Y_1$ is independently —C(O)— or —$CH_2$— and at least one $Y_1$ is —C(O)—;

$A_1$ is a bond, —$(CR^1R^2)_n$, —C═O, —C(═O)O, —C(═O)$NR^3$, —$SO_2$, —SO, aryl, heteroaryl, cycloalkyl, or heterocycloalkyl;

$A_2$ is a bond, alkyl, cycloalkyl, heteroaryl or heterocycloalkyl;

$A_3$ is a bond, —$(CR^1R^2)_n$, —C═O, —$SO_2$, SO, aryl, heteroaryl, cycloalkyl or heterocycloalkyl;

$A_4$ is a bond, alkyl, cycloalkyl, heteroaryl or heterocycloalkyl;

wherein each of $A_1$, $A_2$, $A_3$ and $A_4$ is optionally substituted with D, halo, alkyl, haloalkyl, —CN, —$OR^3$, $NR^cR^d$, $NO_2$, —$SR^3$, —C═$OR^b$, —C(═O)$OR^b$, —C(═O)$NR^3R^3$, —$SO_2R^b$, —$SOR^b$, —S(═O)(═$NR^b$)N, cycloalkyl or heterocycloalkyl; and wherein two substituents on each $A_1$, $A_2$, $A_3$, $A_4$ can be joined to form an additional 3-8 membered ring, such as a spirocycle; and $R^{d1}$, $R^{c1}$ and $R^3$ are as defined herein.

In some embodiments of the compounds of Formula IA-7c, Formula IA-8c, Formula IA-9c, Formula IA-10c, Formula IA-11c, Formula IA-12c or Formula IA-13c, $A_1$ is a bond. In some embodiments of the compounds of Formula IA-7c, Formula IA-8c, Formula IA-9c, Formula IA-10c, Formula IA-11c, Formula IA-12c or Formula IA-13c, $A_1$ is —$(CR^1R^2)_n$. In some embodiments of the compounds of Formula IA-7c, Formula IA-8c, Formula IA-9c, Formula IA-10c, Formula IA-11c, Formula IA-12c or Formula IA-13c, $A_1$ is —C═O. In some embodiments of the compounds of Formula IA-7c, Formula IA-8c, Formula IA-9c, Formula IA-10c, Formula IA-11c, Formula IA-12c or Formula IA-13c, $A_1$ is-C(═O)O. In some embodiments of the compounds of Formula IA-7c, Formula IA-8c, Formula IA-9c, Formula IA-10c, Formula IA-11c, Formula IA-12c or Formula IA-13c, $A_1$ is —C(═O)$NR^3$. In some embodiments of the compounds of Formula IA-7c, Formula IA-8c, Formula IA-9c, Formula IA-10c, Formula IA-11c, Formula IA-12c or Formula IA-13c, $A_1$ is —$SO_2$. In some embodiments of the compounds of Formula IA-7c, Formula IA-8c, Formula IA-9c, Formula IA-10c, Formula IA-11c, Formula IA-12c or Formula IA-13c, $A_1$ is —SO. In some embodiments of the compounds of Formula IA-7c, Formula IA-8c, Formula IA-9c, Formula IA-10c, Formula IA-11c, Formula IA-12c or Formula IA-13c, $A_1$ is aryl. In some embodiments of the compounds of Formula IA-7c, Formula IA-8c, Formula IA-9c, Formula IA-10c, Formula IA-11c, Formula IA-12c or Formula IA-13c, $A_1$ is heteroaryl. In some embodiments of the compounds of Formula IA-7c, Formula IA-8c, Formula IA-9c, Formula IA-10c, Formula IA-11c, Formula IA-12c or Formula IA-13c, $A_1$ is cycloalkyl. In some embodiments of the compounds of Formula IA-7c, Formula IA-8c, Formula IA-9c, Formula IA-10c, Formula IA-11c, Formula IA-12c or Formula IA-13c, $A_1$ is heterocycloalkyl.

In some embodiments of the compounds of Formula IA-7c, Formula IA-8c, Formula IA-9c, Formula IA-10c, Formula IA-11c, Formula IA-12c or Formula IA-13c, $A_1$ is optionally substituted with D, halo, alkyl, haloalkyl, —CN, —$OR^3$, $NR^cR^d$, $NO_2$, —$SR^3$, —C═$OR^b$, —C(═O)$OR^b$, —C(═O)$NR^3R^3$, —$SO_2R^b$, —$SOR^b$, —S(═O)(═$NR^b$)N, cycloalkyl or heterocycloalkyl.

In some embodiments of the compounds of Formula IA-7c, Formula IA-8c, Formula IA-9c, Formula IA-10c, Formula IA-11c, Formula IA-12c or Formula IA-13c, $A_2$ is a bond. In some embodiments of the compounds of Formula IA-7c, Formula IA-8c, Formula IA-9c, Formula IA-10c, Formula IA-11c, Formula IA-12c or Formula IA-13c, $A_2$ is alkyl. In some embodiments of the compounds of Formula IA-7c, Formula IA-8c, Formula IA-9c, Formula IA-10c, Formula IA-11c, Formula IA-12c or Formula IA-13c, $A_2$ is heterocycloalkyl. In some embodiments of the compounds of Formula IA-7c, Formula IA-8c, Formula IA-9c, Formula IA-10c, Formula IA-11c, Formula IA-12c or Formula IA-13c, $A_2$ is heteroaryl. In some embodiments of the compounds of Formula IA-7c, Formula IA-8c, Formula IA-9c, Formula IA-10c, Formula IA-11c, Formula IA-12c or Formula IA-13c, $A_2$ is cycloalkyl. In some embodiments of the compounds of Formula IA-7c, Formula IA-8c, Formula IA-9c, Formula IA-10c, Formula IA-11c, Formula IA-12c or Formula IA-13c, $A_2$ is heteroaryl.

In some embodiments of the compounds of Formula IA-7c, Formula IA-8c, Formula IA-9c, Formula IA-10c, Formula IA-11c, Formula IA-12c or Formula IA-13c, $A_2$ is optionally substituted with D, halo, alkyl, haloalkyl, —CN, —$OR^3$, $NR^cR^d$, $NO_2$, —$SR^3$, —C═$OR^b$, —C(═O)$OR^b$, —C(═O)$NR^3R^3$, —$SO_2R^b$, —$SOR^b$, —S(═O)(═$NR^b$)N, cycloalkyl or heterocycloalkyl.

In some embodiments of the compounds of Formula IA-7c, Formula IA-8c, Formula IA-9c, Formula IA-10c, Formula IA-11c, Formula IA-12c or Formula IA-13c, $A_3$ is a bond. In some embodiments of the compounds of Formula IA-7c, Formula IA-8c, Formula IA-9c, Formula IA-10c, Formula IA-11c, Formula IA-12c or Formula IA-13c, $A_3$ is —$(CR^1R^2)_n$. In some embodiments of the compounds of Formula IA-7c, Formula IA-8c, Formula IA-9c, Formula IA-10c, Formula IA-11c, Formula IA-12c or Formula IA-13c, $A_3$ is —C═O. In some embodiments of the compounds of Formula IA-7c, Formula IA-8c, Formula IA-9c, Formula IA-10c, Formula IA-11c, Formula IA-12c or Formula IA-13c, $A_3$ is —$SO_2$. In some embodiments of the compounds of Formula IA-7c, Formula IA-8c, Formula IA-9c, Formula IA-10c, Formula IA-11c, Formula IA-12c or Formula IA-13c, $A_3$ is SO. In some embodiments of the compounds of Formula IA-7c, Formula IA-8c, Formula IA-9c, Formula IA-10c, Formula IA-11c, Formula IA-12c or Formula IA-13c, $A_3$ is aryl. In some embodiments of the compounds of Formula IA-7c, Formula IA-8c, Formula IA-9c, Formula IA-10c, Formula IA-11c, Formula IA-12c or Formula IA-13c, $A_3$ is heteroaryl. In some embodiments of the compounds of Formula IA-7c, Formula IA-8c, Formula IA-9c, Formula IA-10c, Formula IA-11c, Formula IA-12c or Formula IA-13c, $A_3$ is cycloalkyl. In some embodiments of the compounds of Formula IA-7c, Formula IA-8c, Formula IA-9c, Formula IA-10c, Formula IA-11c, Formula IA-12c or Formula IA-13c, $A_3$ is heterocycloalkyl.

In some embodiments of the compounds of Formula IA-7c, Formula IA-8c, Formula IA-9c, Formula IA-10c, Formula IA-11c, Formula IA-12c or Formula IA-13c, $A_3$ is optionally substituted with D, halo, alkyl, haloalkyl, —CN, —$OR^3$, $NR^cR^d$, $NO_2$, —$SR^3$, —C═OR, —C(═O)OR, —C(═O)$NR^3R^3$, —$SO_2R^b$, —SOR, —S(═O)(═NR)N, cycloalkyl or heterocycloalkyl.

In some embodiments of the compounds of Formula IA-7c, Formula IA-8c, Formula IA-9c, Formula IA-10c, Formula IA-11c, Formula IA-12c or Formula IA-13c, $A_4$ is a bond. In some embodiments of the compounds of Formula IA-7c, Formula IA-8c, Formula IA-9c, Formula IA-10c, Formula IA-11c, Formula IA-12c or Formula IA-13c, $A_4$ is alkyl. In some embodiments of the compounds of Formula IA-7c, Formula IA-8c, Formula IA-9c, Formula IA-10c, Formula IA-11c, Formula IA-12c or Formula IA-13c, $A_4$ is heterocycloalkyl. In some embodiments of the compounds of Formula IA-7c, Formula IA-8c, Formula IA-9c, Formula IA-10c, Formula IA-11c, Formula IA-12c or Formula IA-13c, $A_4$ is heteroaryl. In some embodiments of the compounds of Formula IA-7c, Formula IA-8c, Formula IA-9c, Formula IA-10c, Formula IA-11c, Formula IA-12c or Formula IA-13c, $A_4$ is cycloalkyl. In some embodiments of the compounds of Formula IA-7c, Formula IA-8c, Formula IA-9c, Formula IA-10c, Formula IA-11c, Formula IA-12c or Formula IA-13c, $A_4$ is heteroaryl.

In some embodiments of the compounds of Formula IA-7c, Formula IA-8c, Formula IA-9c, Formula IA-10c, Formula IA-11c, Formula IA-12c or Formula IA-13c, $A_4$ is optionally substituted with D, halo, alkyl, haloalkyl, —CN, —$OR^3$, $NR^cR^d$, $NO_2$, —$SR^3$, —C═OR, —C(═O)OR, —C(═O)$NR^3R^3$, —$SO_2R^b$, —$SOR^b$, —S(═O)(═$NR^b$)N, cycloalkyl or heterocycloalkyl.

In some embodiments of the compounds of Formula IA-7c, Formula IA-8c, Formula IA-9c, Formula IA-10c, Formula IA-11c, Formula IA-12c or Formula IA-13c, two substituents on each $A_1$, $A_2$, $A_3$, $A_4$ can be joined to form an additional 3-8 membered ring. In some embodiments, the 3-8 membered ring is a spirocycle.

In some embodiments, the compounds of Formula I are those having the Formula IA-7d, Formula IA-8d1, Formula IA-8d2, Formula IA-8d3, Formula IA-9d1, Formula IA-9d2, Formula IA-9d3, Formula IA-10d, Formula IA-11d, Formula IA-12d or Formula IA-13d:

(IA-7d)

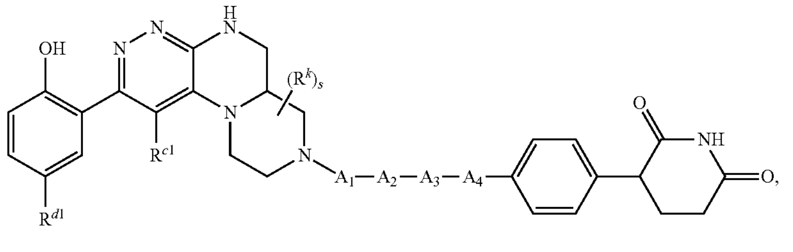

or

-continued
(IA-8d1)
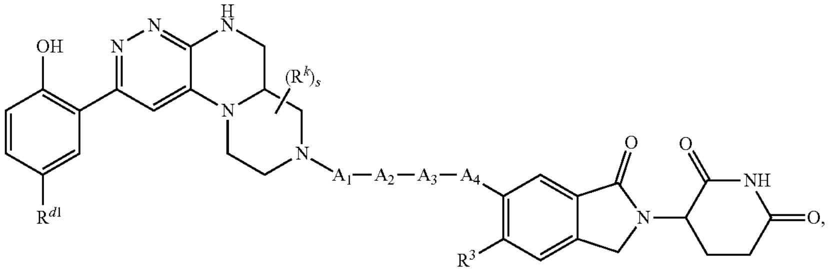
or
(IA-8d2)
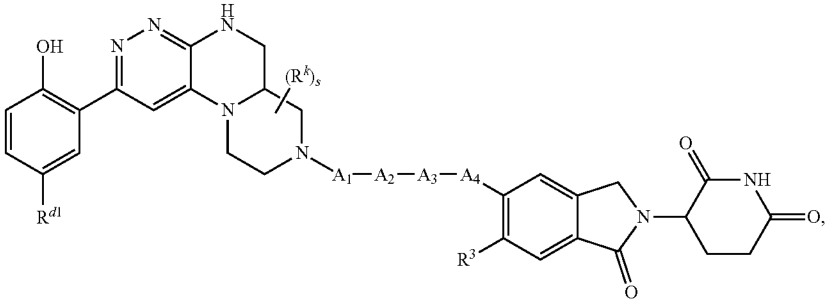
or
(IA-8d3)
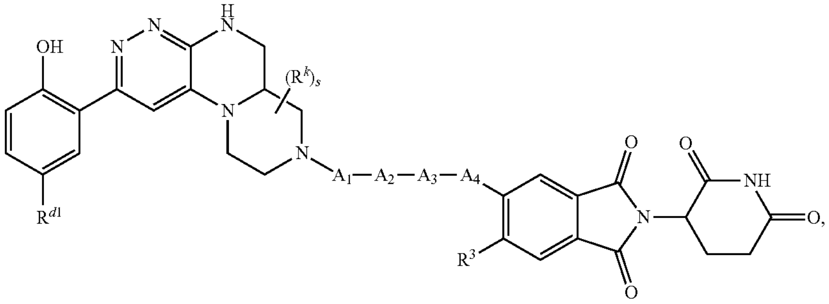
or
(IA-9d1)
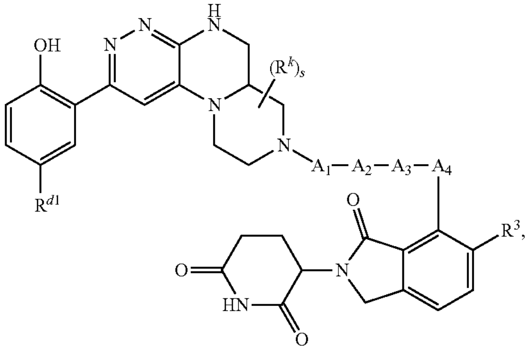
or
(IA-9d2)
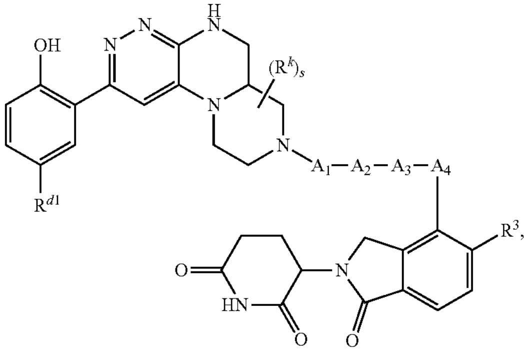
or
(IA-9d3)
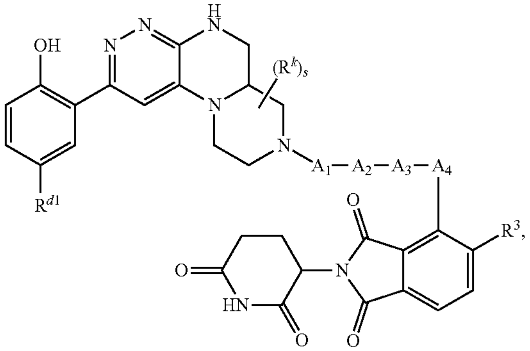
or -continued (IA-10d)

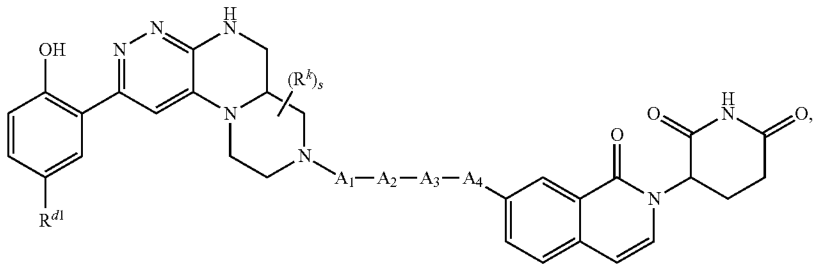

or (IA-IId)

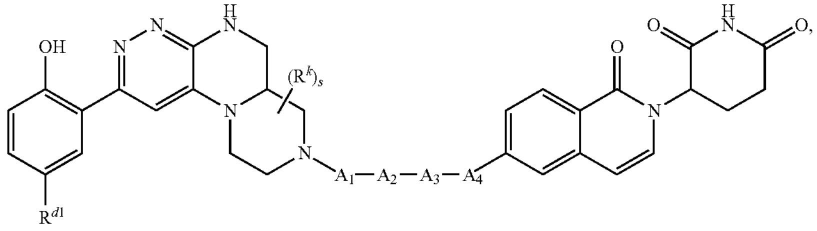

or (IA-12d)

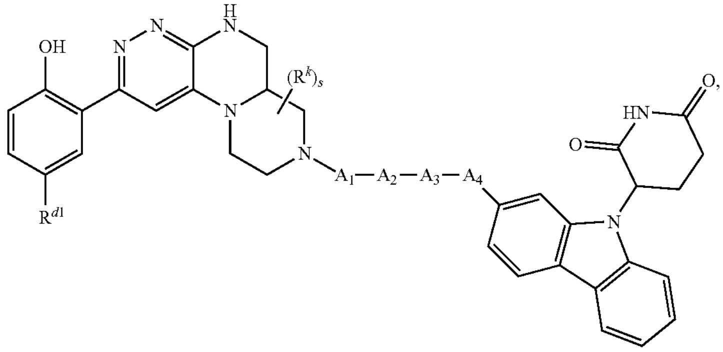

or (IA-13d)

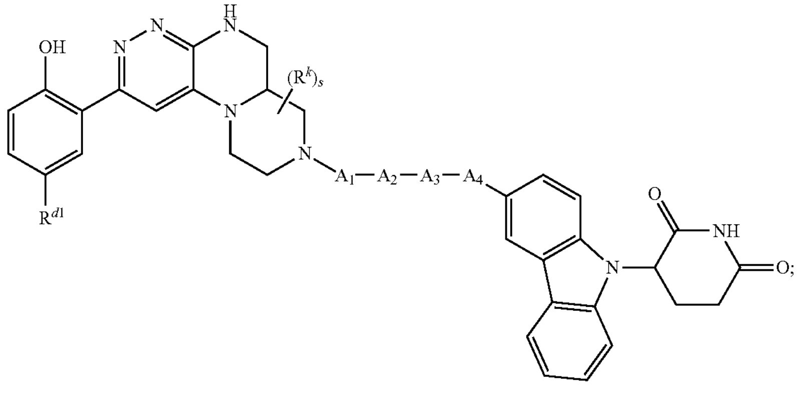

wherein each $R^k$ is independently H or $C_{1-6}$alkyl;

s is 0, 1, 2, 3 or 4;

$R^{d1}$ is H or F;

$R^3$ is H or F;

$A_1$ is —$CR^1R^2$ or —C═O;

$A_2$ is 3-8 membered heterocycloalkyl or 3-8 membered cycloalkyl;

$A_3$ is —$CR^1R^2$ or —C═O; and $A_4$ is 3-8 membered heterocycloalkyl or 3-8 membered cycloalkyl.

In some embodiments of the compounds of Formula IA-7c, Formula IA-8c, Formula IA-9c, Formula IA-10c, Formula IA-11c, Formula IA-12c or Formula IA-13c, $R^{d1}$ is H or F. In some embodiments of the compounds of Formula IA-7c, Formula IA-8c, Formula IA-9c, Formula IA-10c, Formula IA-11c, Formula IA-12c or Formula IA-13c, $R^{d1}$ is H. In some embodiments of the compounds of Formula IA-7c, Formula IA-8c, Formula IA-9c, Formula IA-10c, Formula IA-11c, Formula IA-12c or Formula IA-13c, $R^{d1}$ is F.

In some embodiments of the compounds of Formula IA-7c, Formula IA-8c, Formula IA-9c, Formula IA-10c, Formula IA-11c, Formula IA-12c or Formula IA-13c, $R^3$ is H or F. In some embodiments of the compounds of Formula IA-7c, Formula IA-8c, Formula IA-9c, Formula IA-10c, Formula IA-11c, Formula IA-12c or Formula IA-13c, $R^3$ is H. In some embodiments of the compounds of Formula IA-7c, Formula IA-8c, Formula IA-9c, Formula IA-10c, Formula IA-11c, Formula IA-12c or Formula IA-13c, $R^3$ is F.

In some embodiments of the compounds of Formula IA-7c, Formula IA-8c, Formula IA-9c, Formula IA-10c, Formula IA-11c, Formula IA-12c or Formula IA-13c, $A_1$ is —$CR^1R^2$ or —C═O. In some embodiments of the compounds of Formula IA-7c, Formula IA-8c, Formula IA-9c, Formula IA-10c, Formula IA-11c, Formula IA-12c or Formula IA-13c, $A_1$ is —$CR^1R^2$. In some embodiments of the compounds of Formula IA-7c, Formula IA-8c, Formula IA-9c, Formula IA-10c, Formula IA-11c, Formula IA-12c or Formula IA-13c, $A_1$ is —C═O. In some embodiments of the compounds of Formula IA-7c, Formula IA-8c, Formula IA-9c, Formula IA-10c, Formula IA-11c, Formula IA-12c or Formula IA-13c, $A_1$ is —$CH_2$.

In some embodiments of the compounds of Formula IA-7c, Formula IA-8c, Formula IA-9c, Formula IA-10c, Formula IA-11c, Formula IA-12c or Formula IA-13c, $A_2$ is 3-8 membered heterocycloalkyl or 3-8 membered cycloalkyl. In some embodiments of the compounds of Formula IA-7c, Formula IA-8c, Formula IA-9c, Formula IA-10c, Formula IA-11c, Formula IA-12c or Formula IA-13c, $A_2$ is a 3-8 membered heterocycloalkyl. In some embodiments of the compounds of Formula IA-7c, Formula IA-8c, Formula IA-9c, Formula IA-10c, Formula IA-11c, Formula IA-12c or Formula IA-13c, $A_2$ is a 3-8 membered cycloalkyl.

In some embodiments of the compounds of Formula IA-7c, Formula IA-8c, Formula IA-9c, Formula IA-10c, Formula IA-11c, Formula IA-12c or Formula IA-13c, $A_3$ is —$CR^1R^2$ or —C═O. In some embodiments of the compounds of Formula IA-7c, Formula IA-8c, Formula IA-9c, Formula IA-10c, Formula IA-11c, Formula IA-12c or Formula IA-13c, $A_3$ is —$CR^1R^2$. In some embodiments of the compounds of Formula IA-7c, Formula IA-8c, Formula IA-9c, Formula IA-10c, Formula IA-11c, Formula IA-12c or Formula IA-13c, $A_3$ is —C═O.

In some embodiments of the compounds of Formula IA-7c, Formula IA-8c, Formula IA-9c, Formula IA-10c, Formula IA-11c, Formula IA-12c or Formula IA-13c, $A_4$ is 3-8 membered heterocycloalkyl or 3-8 membered cycloalkyl. In some embodiments of the compounds of Formula IA-7c, Formula IA-8c, Formula IA-9c, Formula IA-10c, Formula IA-11c, Formula IA-12c or Formula IA-13c, $A_4$ is a 3-8 membered heterocycloalkyl. In some embodiments of the compounds of Formula IA-7c, Formula IA-8c, Formula IA-9c, Formula IA-10c, Formula IA-11c, Formula IA-12c or Formula IA-13c, $A_4$ is a 3-8 membered cycloalkyl.

In some embodiments of the compounds of Formula IA-7c, Formula IA-8c, Formula IA-9c, Formula IA-10c, Formula IA-11c, Formula IA-12c or Formula IA-13c, $A_2$ is a piperidine, a piperazine, an azetidine or a pyrrolidine. In some embodiments of the compounds of Formula IA-7c, Formula IA-8c, Formula IA-9c, Formula IA-10c, Formula IA-11c, Formula IA-12c or Formula IA-13c, $A_2$ is a piperidine. In some embodiments of the compounds of Formula IA-7c, Formula IA-8c, Formula IA-9c, Formula IA-10c, Formula IA-11c, Formula IA-12c or Formula IA-13c, $A_2$ is a piperazine. In some embodiments of the compounds of Formula IA-7c, Formula IA-8c, Formula IA-9c, Formula IA-10c, Formula IA-11c, Formula IA-12c or Formula IA-13c, $A_2$ is a pyrrolidine. In some embodiments of the compounds of Formula IA-7c, Formula IA-8c, Formula IA-9c, Formula IA-10c, Formula IA-11c, Formula IA-12c or Formula IA-13c, $A_2$ is an azetidine.

In some embodiments of the compounds of Formula IA-7c, Formula IA-8c, Formula IA-9c, Formula IA-10c, Formula IA-11c, Formula IA-12c or Formula IA-13c, $A_4$ is a piperidine, a piperazine, an azetidine or a pyrrolidine. In some embodiments of the compounds of Formula IA-7c, Formula IA-8c, Formula IA-9c, Formula IA-10c, Formula IA-11c, Formula IA-12c or Formula IA-13c, $A_4$ is a piperidine. In some embodiments of the compounds of Formula IA-7c, Formula IA-8c, Formula IA-9c, Formula IA-10c, Formula IA-11c, Formula IA-12c or Formula IA-13c, $A_4$ is a piperazine. In some embodiments of the compounds of Formula IA-7c, Formula IA-8c, Formula IA-9c, Formula IA-10c, Formula IA-11c, Formula IA-12c or Formula IA-13c, $A_4$ is a pyrrolidine. In some embodiments of the compounds of Formula IA-7c, Formula IA-8c, Formula IA-9c, Formula IA-10c, Formula IA-11c, Formula IA-12c or Formula IA-13c, $A_4$ is an azetidine.

In some embodiments, the compounds of Formula I are those having the Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b:

(IA-8d1a)

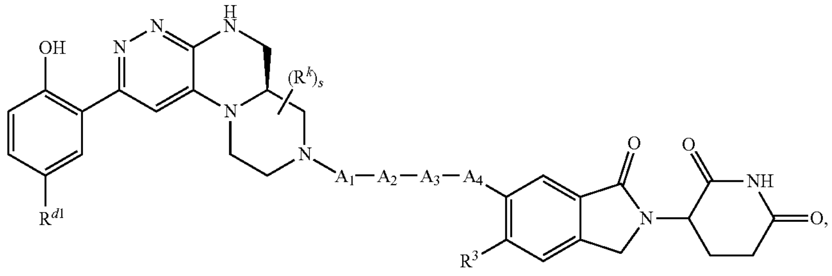

or

-continued
(IA-8d1b)
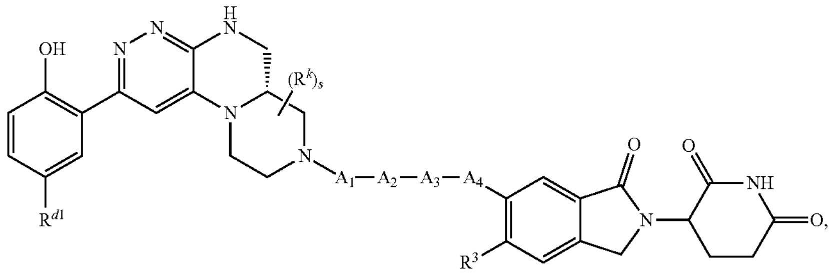
or
(IA-8d2a)
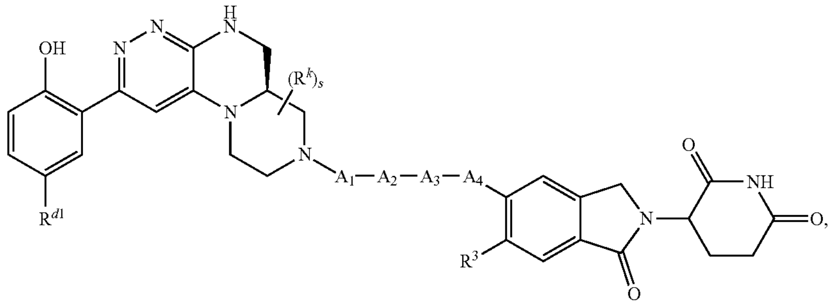
or
(IA-8d2b)
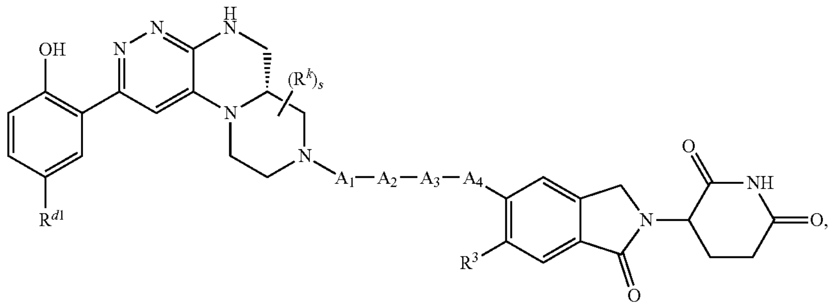
or
(IA-8d3a)
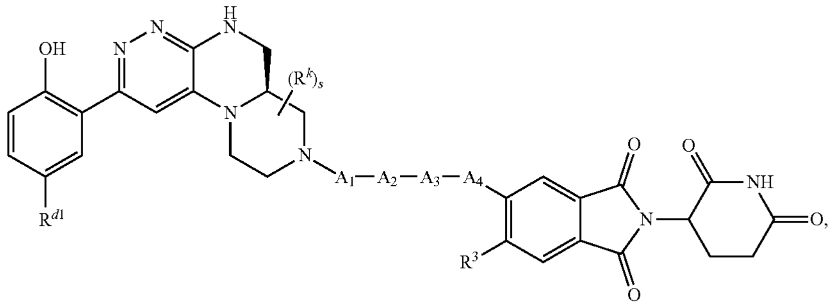
or
(IA-8d3b)
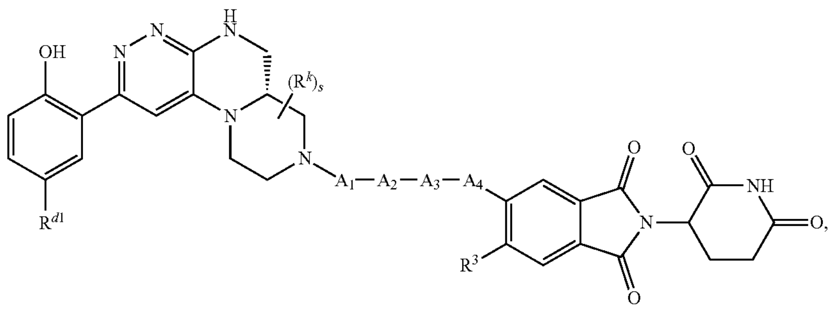
or -continued (IA-9d1a)

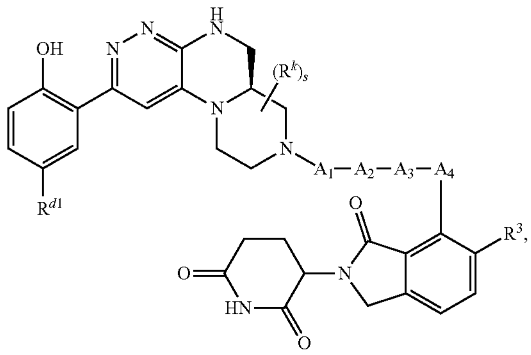

or (IA-9d1b)

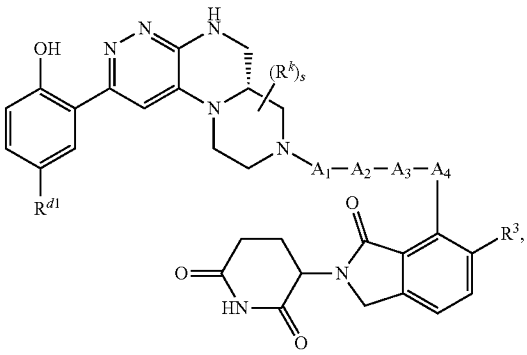

or (IA-9d2a)

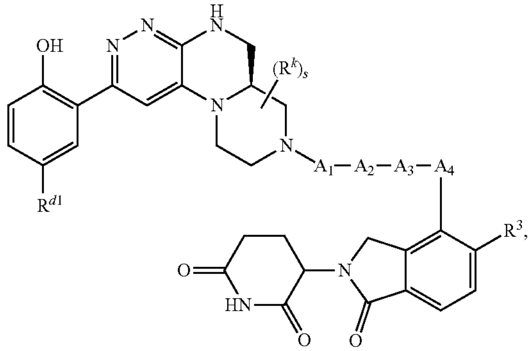

or (IA-9d2b)

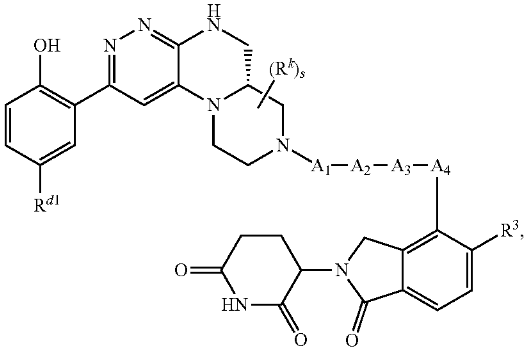

or (IA-9d3a)

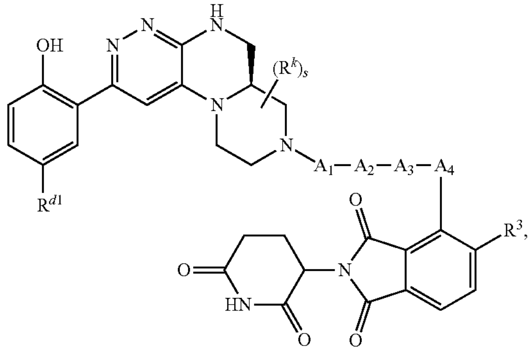

or (IA-9d3b)

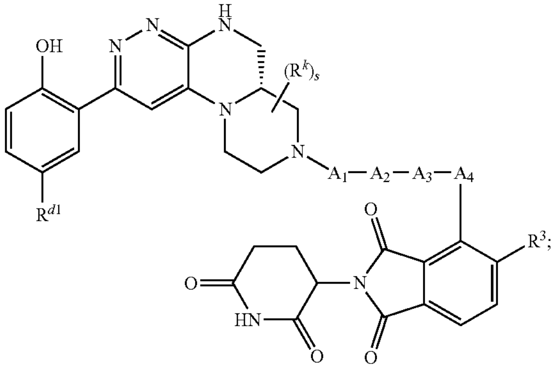

;

wherein each $R^k$ is independently H or $C_{1-6}$alkyl;

s is 0, 1, 2, 3 or 4;

$R^{d1}$ is H or F;

$R^3$ is H or F;

$A_1$ is —$CH_2$ or —C═O;

$A_2$ is 3-8 membered heterocycloalkyl or 3-8 membered cycloalkyl;

$A_3$ is —$CR^1R^2$ or —C═O; and $A_4$ is 3-8 membered heterocycloalkyl or 3-8 membered cycloalkyl.

In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $R^{d1}$ is H or F. In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $R^{d1}$ is H. In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $R^{d1}$ is F.

In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $R^3$ is H or F. In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $R^3$ is H. In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $R^3$ is F.

In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $A_1$ is $—CH_2$ or —C═O. In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $A_1$ is $—CH_2$. In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $A_1$ is —C═O.

In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $A_2$ is 3-8 membered heterocycloalkyl or 3-8 membered cycloalkyl. In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $A_2$ is 3-8 membered heterocycloalkyl. In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $A_2$ is 3-8 membered cycloalkyl.

In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $A_2$ is a piperidine, a piperazine, an azetidine or a pyrrolidine.

In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $A_2$ is a piperidine. In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $A_2$ is a piperazine. In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $A_2$ is an azetidine. In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $A_2$ is a pyrrolidine.

In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $A_3$ is $—CR^1R^2$ or —C═O. In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $A_3$ is $—CR^1R^2$. In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $A_3$ is —C═O.

In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $A_4$ is 3-8 membered heterocycloalkyl or 3-8 membered cycloalkyl. In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $A_4$ is 3-8 membered heterocycloalkyl. In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $A_4$ is 3-8 membered cycloalkyl.

In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $A_4$ is a piperidine, a piperazine, an azetidine or a pyrrolidine.

In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $A_4$ is a piperidine. In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $A_4$ is a piperazine. In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $A_4$ is an azetidine. In some embodiments of the compounds of Formula IA-8d1a, Formula IA-8d1b, Formula IA-8d2a, Formula IA-8d2b, Formula IA-8d3a, Formula IA-8d3b, Formula IA-9d1a, Formula IA-9d1b, Formula IA-9d2a, Formula IA-9d2b, Formula IA-9d3a, or Formula IA-9d3b, $A_4$ is a pyrrolidine.

It will be apparent that the compounds of the invention, including all subgenera described herein, may have multiple stereogenic centers. As a result, there exist multiple stereoisomers (enantiomers and diastereomers) of the compounds (and subgenera described herein). The present disclosure contemplates and encompasses each stereoisomer of any compound of encompassed by the disclosure as well as mixtures of said stereoisomers.

Pharmaceutically acceptable salts and solvates of the compounds of the disclosure (including all subgenera described herein) are also within the scope of the disclosure.

Isotopic variants of the compounds of the disclosure (including all subgenera described herein) are also contemplated by the present disclosure.

Pharmaceutical Compositions and Methods of Administration

The subject pharmaceutical compositions are typically formulated to provide a therapeutically effective amount of a compound of the present disclosure as the active ingredient, or a pharmaceutically acceptable salt, ester, prodrug, solvate, hydrate or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the one or more compounds of the invention and other agent(s) may be mixed into a preparation or both components may be formulated into separate preparations to use them in combination separately or at the same time.

In some embodiments, the concentration of one or more compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v or v/v.

In some embodiments, the concentration of one or more compounds of the invention is greater than 90%, 80%, 70%, 60%, 50%, 40%, 30%, 20%, 19.75%, 19.50%, 19.25%, 19%, 18.75%, 18.50%, 18.25% 18%, 17.75%, 17.50%, 17.25% 17%, 16.75%, 16.50%, 16.25%, 16%, 15.75%, 15.50%, 15.25% 15%, 14.75%, 14.50%, 14.25% 14%, 13.75%, 13.50%, 13.25%, 13%, 12.75%, 12.50%, 12.25%, 12%, 11.75%, 11.50%, 11.25% 11%, 10.75%, 10.50%, 10.25% 10%, 9.75%, 9.50%, 9.25%, 9%, 8.75%, 8.50%, 8.25% 8%, 7.75%, 7.50%, 7.25%, 7%, 6.75%, 6.50%, 6.25%, 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v, or v/v.

In some embodiments, the concentration of one or more compounds of the invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds of the invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g (or a number in the range defined by and including any two numbers above).

In some embodiments, the amount of one or more compounds of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g (or a number in the range defined by and including any two numbers above).

In some embodiments, the amount of one or more compounds of the invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

A pharmaceutical composition of the invention typically contains an active ingredient (e.g., a compound of the disclosure) of the present invention or a pharmaceutically acceptable salt and/or coordination complex thereof, and one or more pharmaceutically acceptable excipients, carriers, including but not limited to inert solid diluents and fillers, diluents, sterile aqueous solution and various organic solvents, permeation enhancers, solubilizers and adjuvants.

Described below are non-limiting exemplary pharmaceutical compositions and methods for preparing the same.

Pharmaceutical Compositions for Oral Administration

In some embodiments, the invention provides a pharmaceutical composition for oral administration containing a compound of the invention, and a pharmaceutical excipient suitable for oral administration.

In some embodiments, the invention provides a solid pharmaceutical composition for oral administration containing: (i) an effective amount of a compound of the invention; optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or nonaqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, microcrystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions.

Hydrophilic surfactants are generally considered to be those compounds having an HLB value greater than about 10, as well as anionic, cationic, or zwitterionic compounds for which the HLB scale is not generally applicable. Similarly, lipophilic (e.g., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof, polyoxyethylated vitamins and derivatives thereof, polyoxyethylene-polyoxypropylene block copolymers; and mixtures thereof, polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-lOoleate, Tween 40, Tween 60, sucrose monostearate, sucrose mono laurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, F-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, F-caprolactone and isomers thereof, 6-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of 10%, 25%o, 50%), 100%o, or up to about 200%> by weight, based on the combined weight of the drug, and other excipients. If desired, very small amounts of solubilizer may also be used, such as 5%>, 2%>, 1%) or even less. Typically, the solubilizer may be present in an amount of about 1%> to about 100%, more typically about 5%> to about 25%> by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Compositions for Injection.

In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical (e.g. Transdermal) Delivery

In some embodiments, the invention provides a pharmaceutical composition for transdermal delivery containing a compound of the present invention and a pharmaceutical excipient suitable for transdermal delivery.

Compositions of the present invention can be formulated into preparations in solid, semisolid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation.

Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical Compositions for Inhalation

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other Pharmaceutical Compositions

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins, 2000; Martindale, The Extra Pharmacopoeia, Thirty-Second Edition (The Pharmaceutical Press, London, 1999); all of which are incorporated by reference herein in their entirety.

Administration of the compounds or pharmaceutical composition of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Compounds can also be administered intraadiposally or intrathecally.

In some embodiments, the compounds or pharmaceutical composition of the present invention are administered by intravenous injection.

The amount of the compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose.

Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis.

A variety of stent devices which may be used as described are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762; 5,195,984; 5,292,331; 5,674,278; 5,879,382; 6,344,053.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention is administered in a composition that comprises one or more agents, and the agent has a shorter half-life than the compound of the invention unit dose forms of the agent and the compound of the invention may be adjusted accordingly.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc. Exemplary parenteral administration forms include solutions or suspensions of active compound in sterile aqueous solutions, for example, aqueous propylene glycol or dextrose solutions. Such dosage forms can be suitably buffered, if desired.

Methods of Use

The method typically comprises administering to a subject a therapeutically effective amount of a compound of the invention. The therapeutically effective amount of the subject combination of compounds may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or downregulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

In certain embodiment, the present invention provides a pharmaceutical composition comprising a compound of bispecific formula, or pharmaceutically acceptable salt thereof.

In certain embodiment, the present invention provides a pharmaceutical composition comprising a compound of bispecific formula for use in degrading a target protein in a cell.

In certain embodiment, a method of degrading a target protein comprising administering to a cell therapeutically effective amount of a bispecific compound, or pharmaceutically acceptable salt, wherein the compound is effective for degrading the target protein.

In certain embodiment, the present invention provides a pharmaceutical composition comprising a compound of bispecific formula, for use in treating or preventing of a disease or disorder in which SMARCA2 and/or SMARCA4 plays a role.

In certain embodiment, the present invention provides a pharmaceutical composition comprising a compound of bispecific formula, for use in treating or preventing of a disease or disorder in which SWI/SNF mutations plays a role.

In certain embodiment, target proteins are SMARCA2, SMARCA4 and/or PB1.

In certain embodiment, target protein complex is SWI/SNF in a cell.

In certain embodiment, diseases or disorders dependent on SMARCA2 or SMARCA4 include cancers.

In certain embodiment, diseases or disorders dependent on SWI/SNF complex include cancers.

Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas.

In certain embodiments, the cancers which may be treated using compounds according to the present disclosure include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

In certain further embodiment, the cancer is a SMARCA2 and/or SMARAC4-dependent cancer.

In certain embodiment, the present invention provides a pharmaceutical composition comprising a compound of bispecific formula for use in the diseases or disorders dependent upon SMARCA2 and/or SMARCA4 is cancer.

Compounds of the disclosure, as well as pharmaceutical compositions comprising them, can be administered to treat any of the described diseases, alone or in combination with a medical therapy. Medical therapies include, for example, surgery and radiotherapy (e.g., gamma-radiation, neutron beam radiotherapy, electron beam radiotherapy, proton therapy, brachytherapy, systemic radioactive isotopes).

In other aspects, compounds of the disclosure, as well as pharmaceutical compositions comprising them, can be administered to treat any of the described diseases, alone or in combination with one or more other agents.

In other methods, the compounds of the disclosure, as well as pharmaceutical compositions comprising them, can be administered in combination with agonists of nuclear receptors agents.

In other methods, the compounds of the disclosure, as well as pharmaceutical compositions comprising them, can be administered in combination with antagonists of nuclear receptors agents.

In other methods, the compounds of the disclosure, as well as pharmaceutical compositions comprising them, can be administered in combination with an anti-proliferative agent.

Combination Therapies

For treating cancer and other proliferative diseases, the compounds of the invention can be used in combination with chemotherapeutic agents, agonists or antagonists of nuclear receptors, or other anti-proliferative agents. The compounds of the invention can also be used in combination with a medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, all-trans retinoic acid, altretamine, anastrozole, arsenic trioxide, asparaginase, azacitidine, bendamustine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panobinostat, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinstat and zoledronate.

In some embodiments, the compounds of the invention can be used in combination with a therapeutic agent that targets an epigenetic regulator. Examples of epigenetic regulators include bromodomain inhibitors, the histone lysine methyltransferase inhibitors, histone arginine methyl transferase inhibitors, histone demethylase inhibitors, histone deacetylase inhibitors, histone acetylase inhibitors, and DNA methyltransferase inhibitors. Histone deacetylase inhibitors include, e.g., vorinostat. Histone arginine methyl transferase inhibitors include inhibitors of protein arginine methyltransferases (PRMTs) such as PRMT5, PRMT1 and PRMT4. DNA methyltransferase inhibitors include inhibitors of DNMT1 and DNMT3.

For treating cancer and other proliferative diseases, the compounds of the invention can be used in combination with targeted therapies, including JAK kinase inhibitors (e.g. Ruxolitinib), PI3 kinase inhibitors including PI3K-delta selective and broad spectrum PI3K inhibitors, MEK inhibitors, Cyclin Dependent kinase inhibitors, including CDK4/6 inhibitors and CDK9 inhibitors, BRAF inhibitors, mTOR inhibitors, proteasome inhibitors (e.g. Bortezomib, Carfilzomib), HDAC inhibitors (e.g. panobinostat, vorinostat), DNA methyl transferase inhibitors, dexamethasone, bromo and extra terminal family member (BET) inhibitors, BTK inhibitors (e.g. ibrutinib, acalabrutinib), BCL2 inhibitors (e.g. venetoclax), dual BCL2 family inhibitors (e.g. BCL2/BCLxL), PARP inhibitors, FLT3 inhibitors, or LSD1 inhibitors.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), or PDR001. In some embodiments, the anti-PD-1 monoclonal antibody is nivolumab or pembrolizumab. In some embodiments, the anti-PD1 antibody is pembrolizumab. In some embodiments, the inhibitor of an immune checkpoint molecule is an inhibitor of PD-L1, e.g., an anti-PD-L1 monoclonal antibody. In some embodiments, the anti-PD-L1 monoclonal antibody is atezolizumab, durvalumab, or BMS-935559. In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

Compounds of the present invention include, but are not limited to, those shown in Table

TABLE 1

| Example | Structure | Name |
|---|---|---|
| | Compounds | |
| 1 | 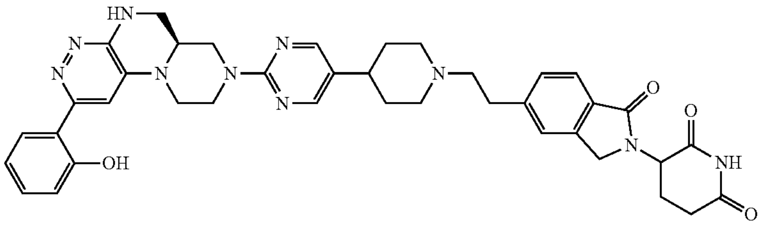 [SMILES: O=C1CCC(N2Cc3cc(CCN4CCC(c5cnc(N6CCN7c8cc(-c9ccccc9O)nnc8NC[C@H]7C6)nc5)CC4)ccc3C2=O)C(=O)N1] | 3-(5-(2-(4-(2-((S)-2-(2-hydroxyphenyl)-5,6,6a,7,9,10-hexahydro-8H-pyrazino[1',2':4,5]pyrazino[2,3-c]pyridazin-8-yl)pyrimidin-5-yl)piperidin-1-yl)ethyl)-1-oxoisoindolin-2-yl)piperidine-2,6-dione |
| 2 | 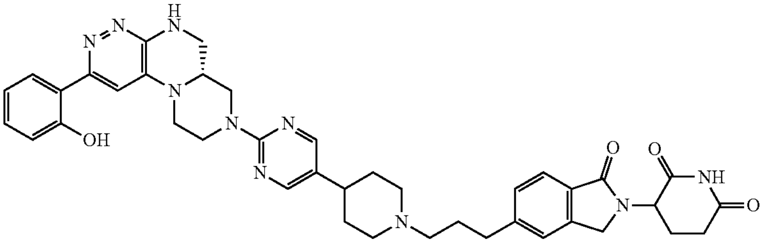 [SMILES: O=C1CCC(N2Cc3cc(CCCN4CCC(c5cnc(N6CCN7c8cc(-c9ccccc9O)nnc8NC[C@@H]7C6)nc5)CC4)ccc3C2=O)C(=O)N1] | 3-(5-(3-(4-(2-((R)-2-(2-hydroxyphenyl)-5,6,6a,7,9,10-hexahydro-8H-pyrazino[1',2':4,5]pyrazino[2,3-c]pyridazin-8-yl)pyrimidin-5-yl)piperidin-1-yl)propyl)-1-oxoisoindolin-2-yl)piperidine-2,6-dione |
| 3 | 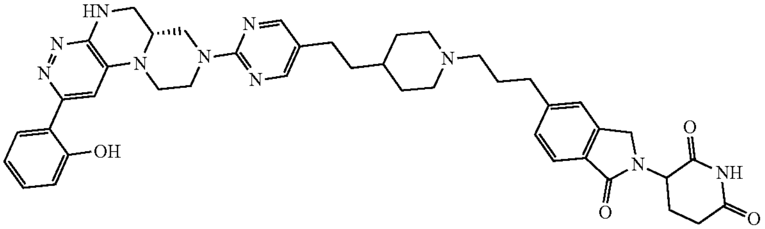 [SMILES: O=C1CCC(N2Cc3cc(CCCN4CCC(CCc5cnc(N6CCN7c8cc(-c9ccccc9O)nnc8NC[C@@H]7C6)nc5)CC4)ccc3C2=O)C(=O)N1] | 3-(5-(3-(4-(2-(2-((R)-2-(2-hydroxyphenyl)-5,6,6a,7,9,10-hexahydro-8H-pyrazino[1',2':4,5]pyrazino[2,3-c]pyridazin-8-yl)pyrimidin-5-yl)ethyl)piperidin-1-yl)propyl)-1-oxoisoindolin-2-yl)piperidine-2,6-dione |

TABLE 1-continued

| Compounds | | |
|---|---|---|
| Example | Structure | Name |
| 4 | 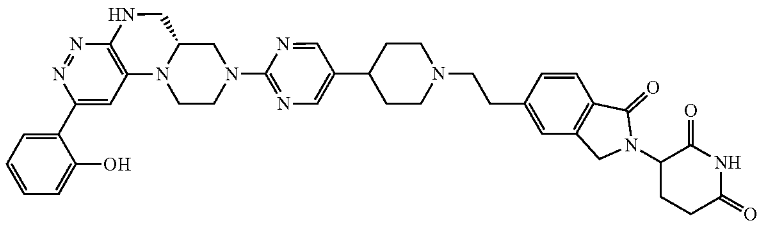 [SMILES: O=C1CCC(N2Cc3cc(CCN4CCC(c5cnc(N6CCN7c8cc(-c9ccccc9O)nnc8NC[C@@H]7C6)nc5)CC4)ccc3C2=O)C(=O)N1] | 3-(5-(2-(4-(2-((R)-2-(2-hydroxyphenyl)-5,6,6a,7,9,10-hexahydro-8H-pyrazino[1',2':4,5]pyrazino[2,3-c]pyridazin-8-yl)pyrimidin-5-yl)piperidin-1-yl)ethyl)-1-oxoisoindolin-2-yl)piperidine-2,6-dione |
| 5 | 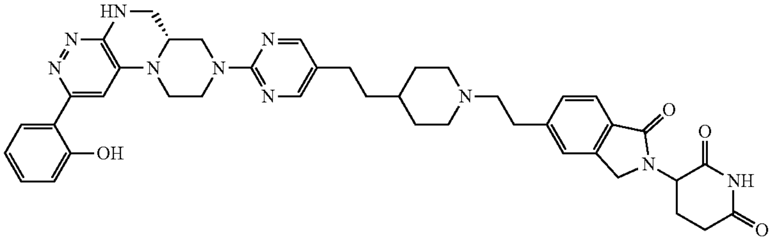 [SMILES: O=C1CCC(N2Cc3cc(CCN4CCC(CCc5cnc(N6CCN7c8cc(-c9ccccc9O)nnc8NC[C@@H]7C6)nc5)CC4)ccc3C2=O)C(=O)N1] | 3-(5-(2-(4-(2-(2-((R)-2-(2-hydroxyphenyl)-5,6,6a,7,9,10-hexahydro-8H-pyrazino[1',2':4,5]pyrazino[2,3-c]pyridazin-8-yl)pyrimidin-5-yl)ethyl)piperidin-1-yl)ethyl)-1-oxoisoindolin-2-yl)piperidine-2,6-dione |
| 6 | 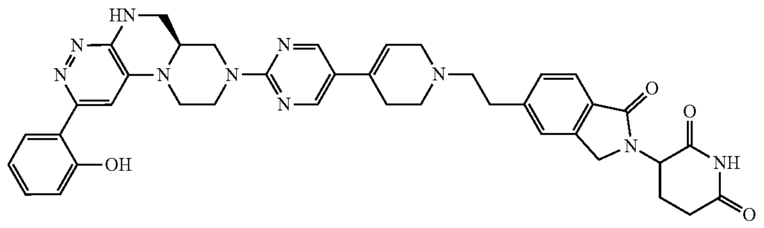 | 3-(5-(2-(4-(2-((S)-2-(2-hydroxyphenyl)-5,6,6a,7,9,10-hexahydro-8H-pyrazino[1',2':4,5]pyrazino[2,3-c]pyridazin-8-yl)pyrimidin-5-yl)-3,6-dihydropyridin-1(2H)-yl)ethyl)-1-oxoisoindolin-2-yl)piperidine-2,6-dione |
| 7 | 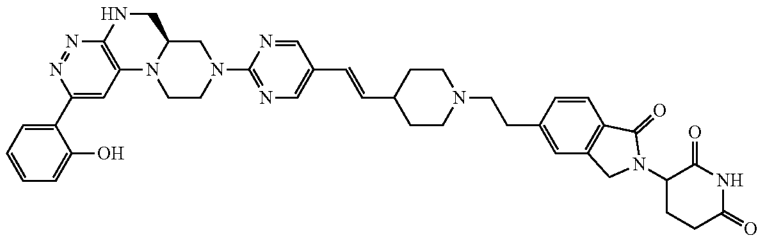 [SMILES: O=C1CCC(N2Cc3cc(CCN4CCC(/C=C/c5cnc(N6CCN7c8cc(-c9ccccc9O)nnc8NC[C@H]7C6)nc5)CC4)ccc3C2=O)C(=O)N1] | 3-(5-(2-(4-((E)-2-(2-((S)-2-(2-hydroxyphenyl)-5,6,6a,7,9,10-hexahydro-8H-pyrazino[1',2':4,5]pyrazino[2,3-c]pyridazin-8-yl)pyrimidin-5-yl)vinyl)piperidin-1-yl)ethyl)-1-oxoisoindolin-2-yl)piperidine-2,6-dione |
| 8 | 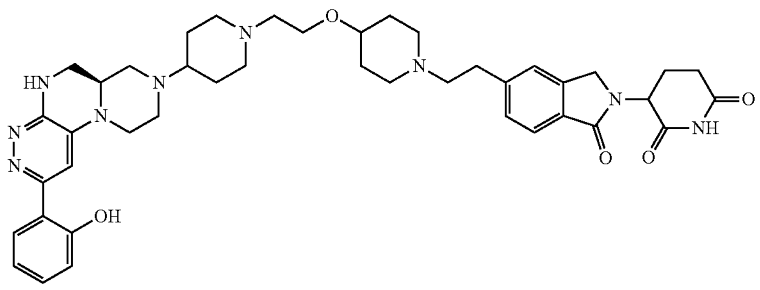 [SMILES: O=C1CCC(N2Cc3cc(CCN4CCC(OCCN5CCC(N6CCN7c8cc(-c9ccccc9O)nnc8NC[C@H]7C6)CC5)CC4)ccc3C2=O)C(=O)N1] | 3-(5-(2-(4-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethoxy)piperidin-1-yl)ethyl)-1-oxoisoindolin-2-yl)piperidine-2,6-dione |
| 9 | 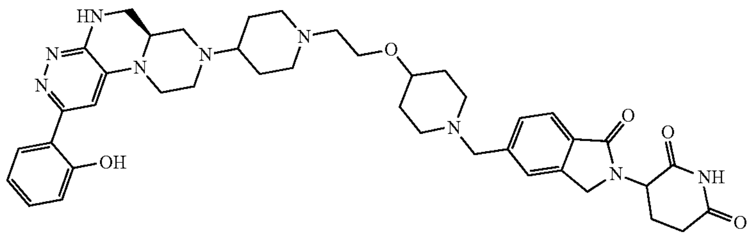 [SMILES: O=C1CCC(N2Cc3cc(CN4CCC(OCCN5CCC(N6CCN7c8cc(-c9ccccc9O)nnc8NC[C@H]7C6)CC5)CC4)ccc3C2=O)C(=O)N1] | 3-(5-((4-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethoxy)piperidin-1-yl)methyl)-1-oxoisoindolin-2-yl)piperidine-2,6-dione |

TABLE 1-continued

Compounds

| Exam-ple | Structure | Name |
|---|---|---|
| 10 | 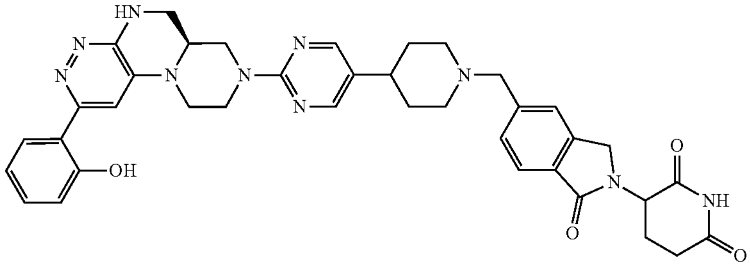 [SMILES: O=C1CCC(N2Cc3cc(CN4CCC(c5cnc(N6CCN7c8cc(-c9ccccc9O)nnc8NC[C@H]7C6)nc5)CC4)ccc3C2=O)C(=O)N1] | 3-(5-((4-(2-((S)-2-(2-hydroxyphenyl)-5,6,6a,7,9,10-hexahydro-8H-pyrazino[1',2':4,5]pyrazino[2,3-c]pyridazin-8-yl)pyrimidin-5-yl)piperidin-1-yl)methyl)-1-oxoisoindolin-2-yl)piperidine-2,6-dione |
| 11 | 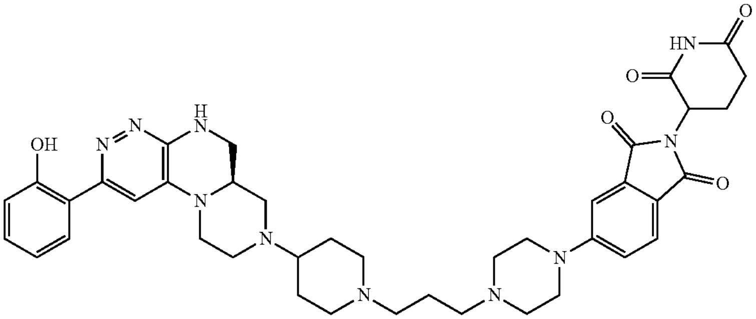 [SMILES: O=C1CCC(N2C(=O)c3ccc(N4CCN(CCCN5CCC(N6CCN7c8cc(-c9ccccc9O)nnc8NC[C@H]7C6)CC5)CC4)cc3C2=O)C(=O)N1] | 2-(2,6-Dioxopiperidin-3-yl)-5-(4-(3-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propyl)piperazin-1-yl)isoindoline-1,3-dione |
| 12 | 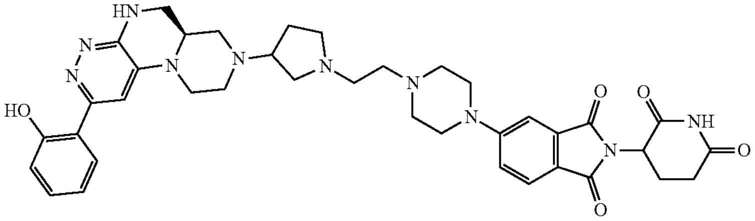 [SMILES: O=C1CCC(N2C(=O)c3ccc(N4CCN(CCN5CCC(N6CCN7c8cc(-c9ccccc9O)nnc8NC[C@H]7C6)C5)CC4)cc3C2=O)C(=O)N1] | 2-(2,6-Dioxopiperidin-3-yl)-5-(4-(2-(3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)ethyl)piperazin-1-yl)isoindoline-1,3-dione |
| 13 | 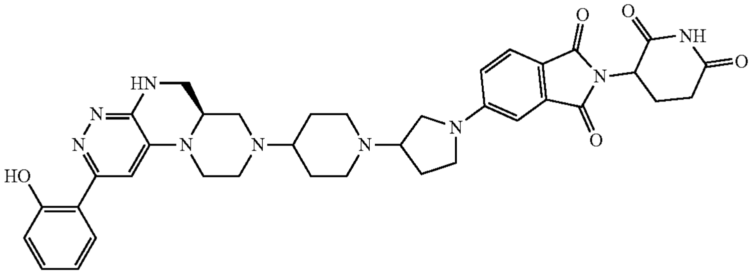 [SMILES: O=C1CCC(N2C(=O)c3ccc(N4CCC(N5CCC(N6CCN7c8cc(-c9ccccc9O)nnc8NC[C@H]7C6)CC5)C4)cc3C2=O)C(=O)N1] | 2-(2,6-Dioxopiperidin-3-yl)-5-(3-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)pyrrolidin-1-yl)isoindoline-1,3-dione |
| 14 | 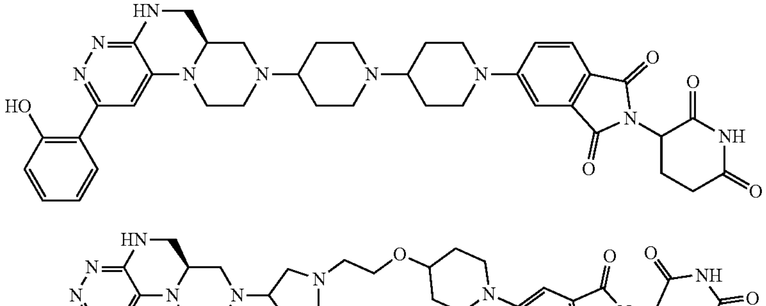 | 2-(2,6-Dioxopiperidin-3-yl)-5-(4-((S)-2-(2-hydroxyphenyl)-5,6,6a,7,9,10-hexahydro-8H-pyrazino[1',2':4,5]pyrazino[2,3-c]pyridazin-8-yl)-[1,4'-bipiperidin]-1'-yl)isoindoline-1,3-dione |
| 15 | 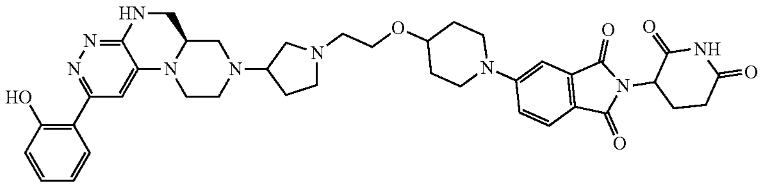 [SMILES: O=C1CCC(N2C(=O)c3ccc(N4CCC(OCCN5CCC(N6CCN7c8cc(-c9ccccc9O)nnc8NC[C@H]7C6)C5)CC4)cc3C2=O)C(=O)N1] | 2-(2,6-Dioxopiperidin-3-yl)-5-(4-(2-(3-((S)-2-(2-hydroxyphenyl)-8H-pyrazino[1',2':4,5]pyrazino[2,3-c]pyridazin-8-yl)pyrrolidin-1-yl)ethoxy)piperidin-1-yl)isoindoline-1,3-dione |

TABLE 1-continued

| Compounds | | |
|---|---|---|
| Example | Structure | Name |
| 16 | 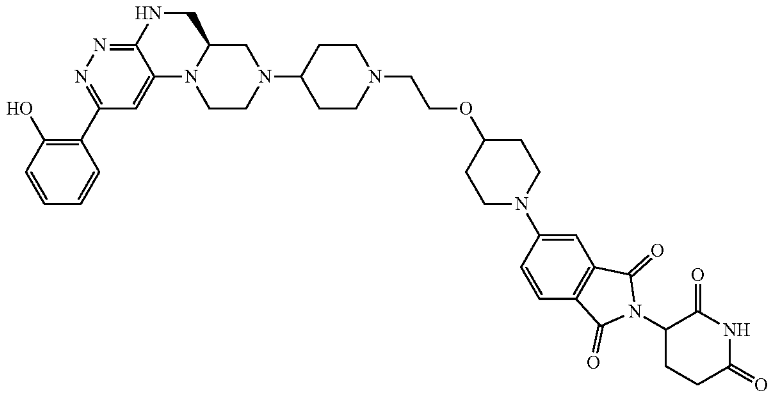 [SMILES: O=C1CCC(N2C(=O)c3ccc(N4CCC(OCCN5CCC(N6CCN7c8cc(-c9ccccc9O)nnc8NC[C@H]7C6)CC5)CC4)cc3C2=O)C(=O)N1] | 2-(2,6-Dioxopiperidin-3-yl)-5-(4-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethoxy)piperidin-1-yl)isoindoline-1,3-dione |
| 17 | 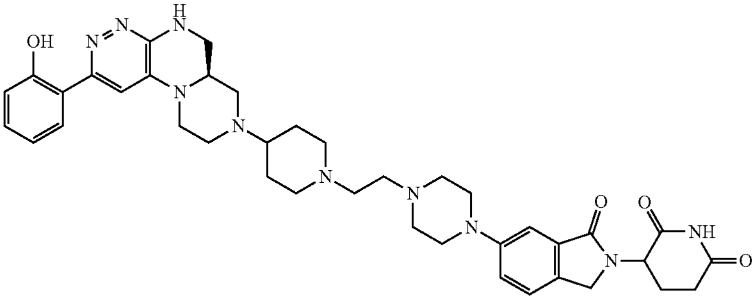 [SMILES: O=C1CCC(N2Cc3ccc(N4CCN(CCN5CCC(N6CCN7c8cc(-c9ccccc9O)nnc8NC[C@H]7C6)CC5)CC4)cc3C2=O)C(=O)N1] | 3-(6-(4-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethyl)piperazin-1-yl)-1-oxoisoindolin-2-yl)piperidine-2,6-dione |
| 18 | 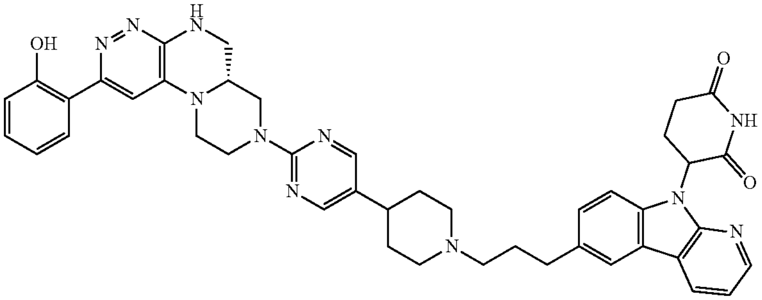 [SMILES: O=C1CCC(n2c3ccc(CCCN4CCC(c5cnc(N6CCN7c8cc(-c9ccccc9O)nnc8NC[C@@H]7C6)nc5)CC4)cc3c3cccnc32)C(=O)N1] | 3-(6-(3-(4-(2-((R)-2-(2-hydroxyphenyl)-5,6,6a,7,9,10-hexahydro-8H-pyrazino-[1',2':4,5]pyrazino[2,3-c]pyridazin-8-yl)pyrimidin-5-yl)piperidin-1-yl)propyl)-9H-pyrido[2,3-b]indol-9-yl)piperidine-2,6-dione |
| 19 | 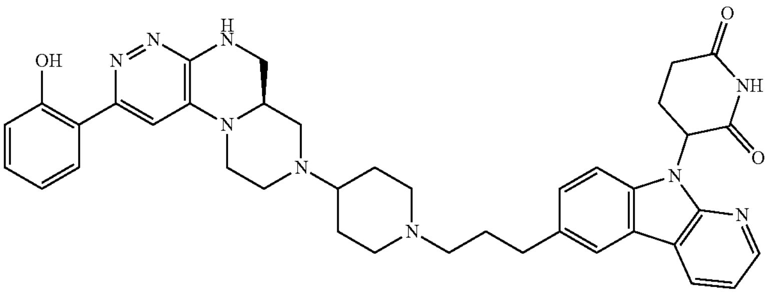 [SMILES: O=C1CCC(n2c3ccc(CCCN4CCC(N5CCN6c7cc(-c8ccccc8O)nnc7NC[C@H]6C5)CC4)cc3c3cccnc32)C(=O)N1] | 3-(6-(3-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propyl)-9H-pyrido[2,3-b]indol-9-yl)piperidine-2,6-dione |

TABLE 1-continued

| Compounds | | |
|---|---|---|
| Example | Structure | Name |
| 20 | 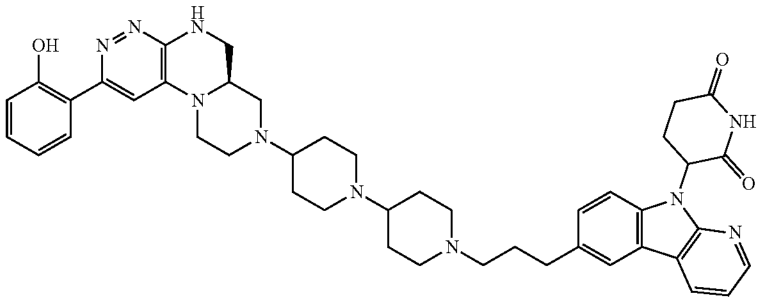 [SMILES: O=C1CCC(n2c3ccc(CCCN4CCC(N5CCC(N6CCN7c8cc(-c9ccccc9O)nnc8NC[C@H]7C6)CC5)CC4)cc3c3cccnc32)C(=O)N1] | 3-(6-(3-(4-((S)-2-(2-hydroxyphenyl)-5,6,6a,7,9,10-hexahydro-8H-pyrazino[1',2':4,5]pyrazino[2,3-c]pyridazin-8-yl)-[1,4'-bipiperidin]-1'-yl)propyl)-9H-pyrido[2,3-b]indol-9-yl)piperidine-2,6-dione |
| 21 | 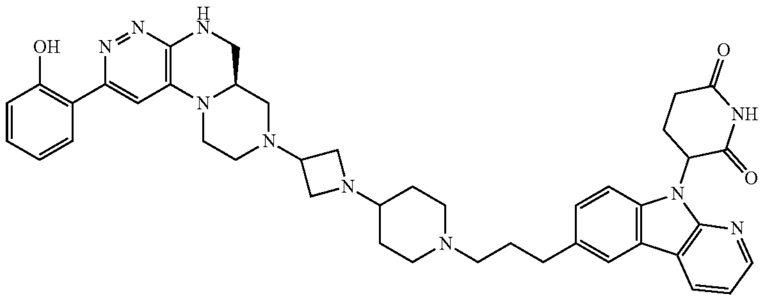 [SMILES: O=C1CCC(n2c3ccc(CCCN4CCC(N5CC(N6CCN7c8cc(-c9ccccc9O)nnc8NC[C@H]7C6)C5)CC4)cc3c3cccnc32)C(=O)N1] | 3-(6-(3-(4-(3-((S)-2-(2-hydroxyphenyl)-5,6,6a,7,9,10-hexahydro-8H-pyrazino[1',2':4,5]pyrazino[2,3-c]pyridazin-8-yl)azetidin-1-yl)piperidin-1-yl)propyl)-9H-pyrido[2,3-b]indol-9-yl)piperidine-2,6-dione |
| 22 | 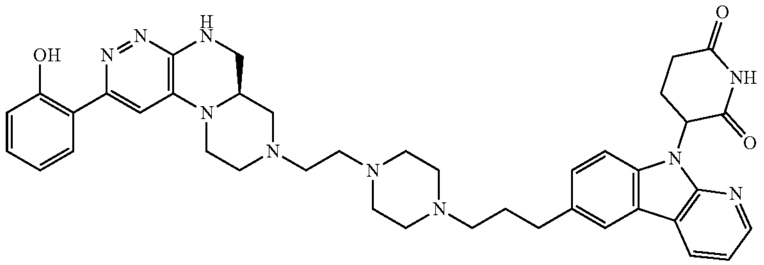 [SMILES: O=C1CCC(n2c3ccc(CCCN4CCN(CCN5CCN6c7cc(-c8ccccc8O)nnc7NC[C@H]6C5)CC4)cc3c3cccnc32)C(=O)N1] | 3-(6-(3-(4-(2-((S)-2-(2-hydroxyphenyl)-5,6,6a,7,9,10-hexahydro-8H-pyrazino[1',2':4,5]pyrazino[2,3-c]pyridazin-8-yl)ethyl)piperazin-1-yl)propyl)-9H-pyrido[2,3-b]indol-9-yl)piperidine-2,6-dione |
| 23 | 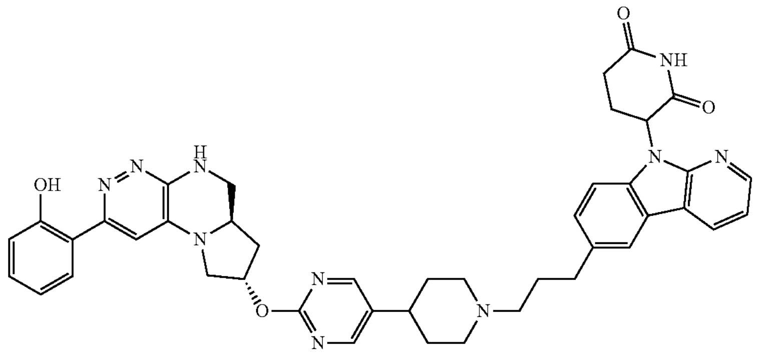 [SMILES: O=C1CCC(n2c3ccc(CCCN4CCC(c5cnc(O[C@H]6C[C@@H]7CNc8nnc(-c9ccccc9O)cc8N7C6)nc5)CC4)cc3c3cccnc32)C(=O)N1] | 3-(6-(3-(4-(2-(((6aR,8S)-2-(2-hydroxyphenyl)-5,6,6a,7,8,9-hexahydropyrrolo[1',2':4,5]pyrazino[2,3-c]pyridazin-8-yl)oxy)pyrimidin-5-yl)piperidin-1-yl)propyl)-9H-pyrido[2,3-b]indol-9-yl)piperidine-2,6-dione |
| 24 | 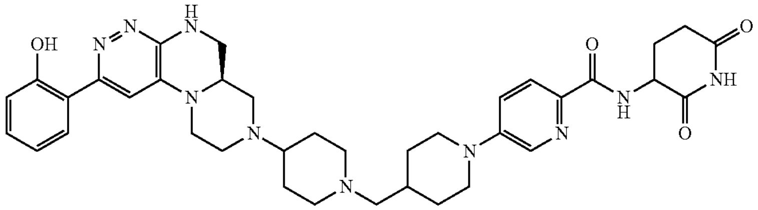 [SMILES: O=C1CCC(NC(=O)c2ccc(N3CCC(CN4CCC(N5CCN6c7cc(-c8ccccc8O)nnc7NC[C@H]6C5)CC4)CC3)cn2)C(=O)N1] | N-(2,6-dioxopiperidin-3-yl)-5-(4-((4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)methyl)piperidin-1-yl)picolinamide |

TABLE 1-continued

| Compounds | | |
|---|---|---|
| Example | Structure | Name |
| 25 | 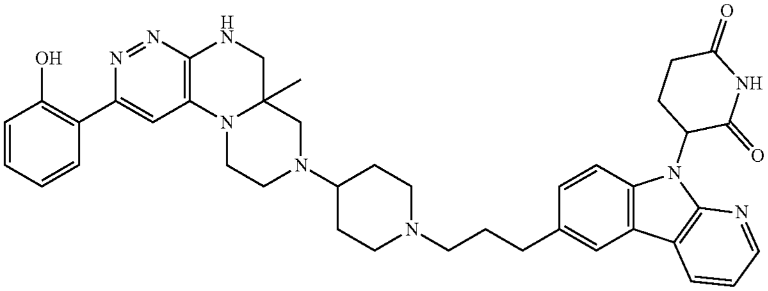 [SMILES: CC12CNc3nnc(-c4ccccc4O)cc3N1CCN(C1CCN(CCCc3ccc4c(c3)c3cccnc3n4C3CCC(=O)NC3=O)CC1)C2] | 3-(6-(3-(4-(2-(2-hydroxyphenyl)-6a-methyl-5,6,6a,7,9,10-hexahydro-8H-pyrazino[1',2':4,5]pyrazino[2,3-c]pyridazin-8-yl)piperidin-1-yl)propyl)-9H-pyrido[2,3-b]indol-9-yl)piperidine-2,6-dione |
| 26 | 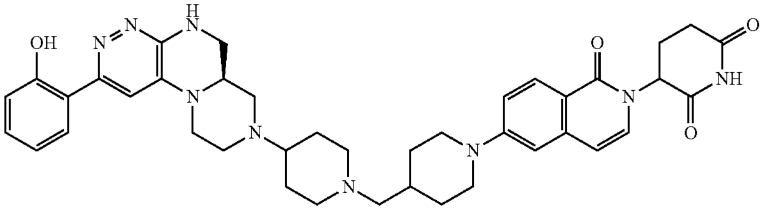 [SMILES: O=C1CCC(n2ccc3cc(N4CCC(CN5CCC(N6CCN7c8cc(-c9ccccc9O)nnc8NC[C@H]7C6)CC5)CC4)ccc3c2=O)C(=O)N1] | 3-(6-(4-((4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)methyl)piperidin-1-yl)-1-oxoisoquinolin-2(1H)-yl)piperidine-2,6-dione |
| 27 | 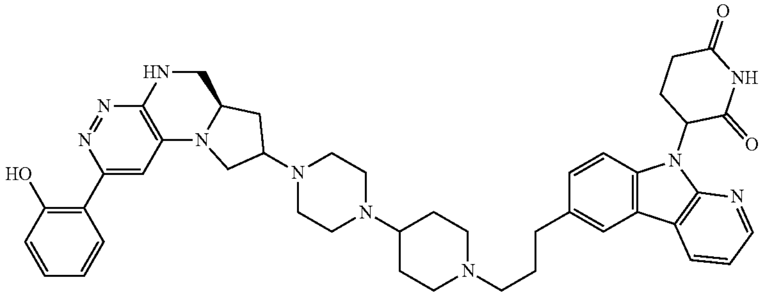 [SMILES: O=C1CCC(n2c3ccc(CCCN4CCC(N5CCN(C6C[C@@H]7CNc8nnc(-c9ccccc9O)cc8N7C6)CC5)CC4)cc3c3cccnc32)C(=O)N1] | 3-(6-(3-(4-(4-((6aR)-2-(2-hydroxyphenyl)-5,6,6a,7,8,9-hexahydropyrrolo[1',2':4,5]pyrazino[2,3-c]pyridazin-8-yl)piperazin-1-yl)piperidin-1-yl)propyl)-9H-pyrido[2,3-b]indol-9-yl)piperidine-2,6-dione |
| 28 | 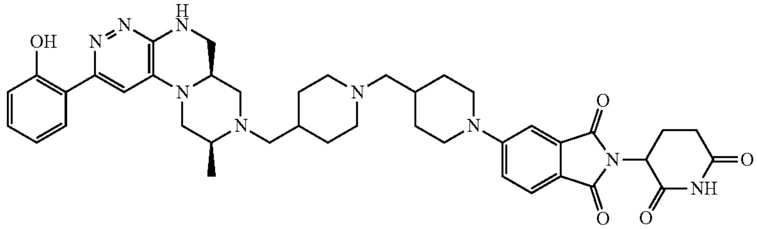 [SMILES: C[C@H]1CN2c3cc(-c4ccccc4O)nnc3NC[C@H]2CN1CC1CCN(CC2CCN(c3ccc4c(c3)C(=O)N(C3CCC(=O)NC3=O)C4=O)CC2)CC1] | 2-(2,6-dioxopiperidin-3-yl)-5-(4-((4-(((6aS,9S)-2-(2-hydroxyphenyl)-9-methyl-5,6,6a,7,9,10-hexahydro-8H-pyrazino[1',2':4,5]pyrazino[2,3-c]pyridazin-8-yl)methyl)piperidin-1-yl)methyl)piperidin-1- |
| 29 | 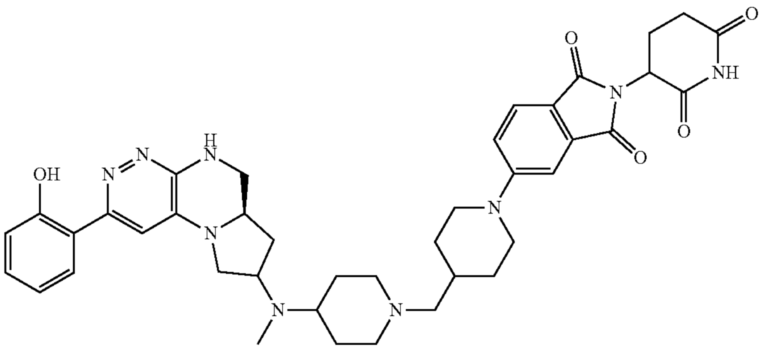 [SMILES: CN(C1CCN(CC2CCN(c3ccc4c(c3)C(=O)N(C3CCC(=O)NC3=O)C4=O)CC2)CC1)C1C[C@@H]2CNc3nnc(-c4ccccc4O)cc3N2C1] | 2-(2,6-dioxopiperidin-3-yl)-5-(4-((4-(((6aR)-2-(2-hydroxyphenyl)-5,6,6,a,7,8,9-hexahydropyrrolo[1',2':4,5]pyrazino[2,3-c]pyridazin-8-yl)(methyl)amino)piperidin-1-yl)methyl)piperidin-1-yl)isoindolin-1,3-dione |

TABLE 1-continued

| Compounds | | |
|---|---|---|
| Example | Structure | Name |
| 30 | 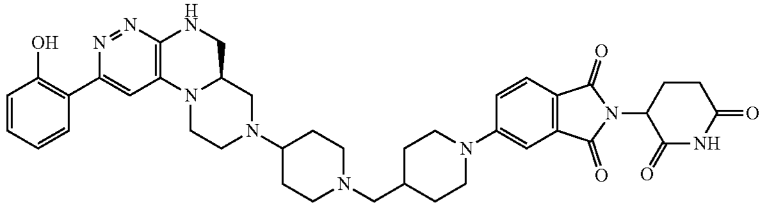 [SMILES: O=C1CCC(N2C(=O)c3ccc(N4CCC(CN5CCC(N6CCN7c8cc(-c9ccccc9O)nnc8NC[C@H]7C6)CC5)CC4)cc3C2=O)C(=O)N1] | 2-(2,6-dioxopiperidin-3-yl)-5-(4-((4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)methyl)piperidin-1-yl)isoindoline-1,3-dione |
| 31 | 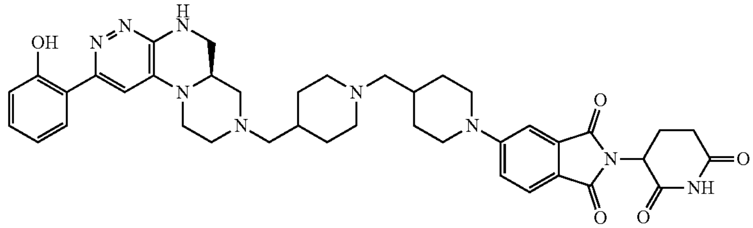 | 2-(2,6-dioxopiperidin-3-yl)-5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl)isoindoline-1,3-dione |
| 32 | 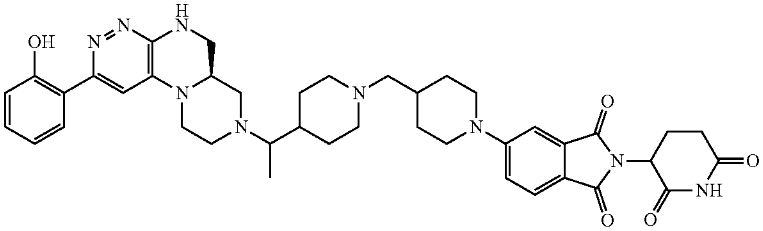 [SMILES: CC(C1CCN(CC2CCN(c3ccc4c(c3)C(=O)N(C3CCC(=O)NC3=O)C4=O)CC2)CC1)N1CCN2c3cc(-c4ccccc4O)nnc3NC[C@H]2C1] | 2-(2,6-dioxopiperidin-3-yl)-5-(4-((4-(1-((S)-2-(2-hydroxyphenyl)-5,6,6a,7,9,10-hexahydro-8H-pyrazino[1',2':4,5]pyrazino[2,3-c]pyridazin-8-yl)ethyl)piperidin-1-yl)methyl)piperidin-1-yl)isoindoline-1,3-dione |
| 33 | 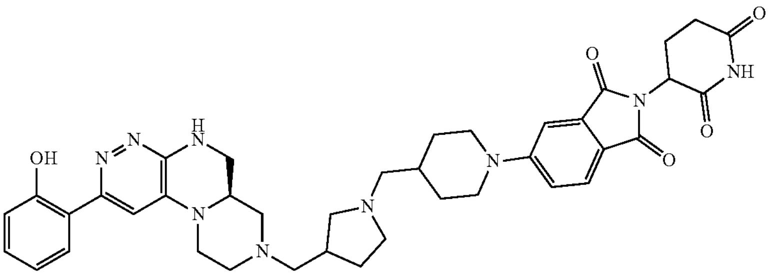 [SMILES: O=C1CCC(N2C(=O)c3ccc(N4CCC(CN5CCC(CN6CCN7c8cc(-c9ccccc9O)nnc8NC[C@H]7C6)C5)CC4)cc3C2=O)C(=O)N1] | 2-(2,6-dioxopiperidin-3-yl)-5-(4-((3-(((S)-2-(2-hydroxyphenyl)-5,6,6a,7,9,10-hexahydro-8H-pyrazino[1',2':4,5]pyrazino[2,3-c]pyridazin-8-yl)methyl)pyrrolidin-1-yl)methyl)piperidin-1-yl)isoindoline-1,3-dione |
| 34 | 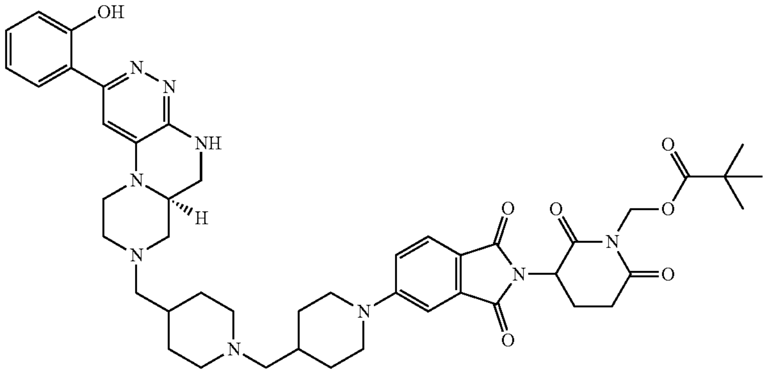 [SMILES: CC(C)(C)C(=O)OCN1C(=O)CCC(N2C(=O)c3ccc(N4CCC(CN5CCC(CN6CCN7c8cc(-c9ccccc9O)nnc8NC[C@H]7C6)CC5)CC4)cc3C2=O)C1=O] | (3-(5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl)-1,3-dioxoisoindolin-2-yl)-2,6-dioxopiperidin-1-yl)methyl pivalate |
| 35 | 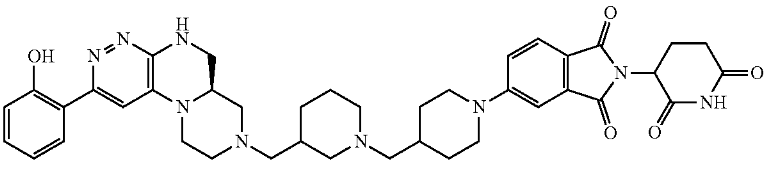 [SMILES: O=C1CCC(N2C(=O)c3ccc(N4CCC(CN5CCCC(CN6CCN7c8cc(-c9ccccc9O)nnc8NC[C@H]7C6)C5)CC4)cc3C2=O)C(=O)N1] | 2-(2,6-dioxopiperidin-3-yl)-5-(4-((3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl)isoindoline-1,3-dione |

TABLE 1-continued

| Compounds | | |
|---|---|---|
| Example | Structure | Name |
| 36 | 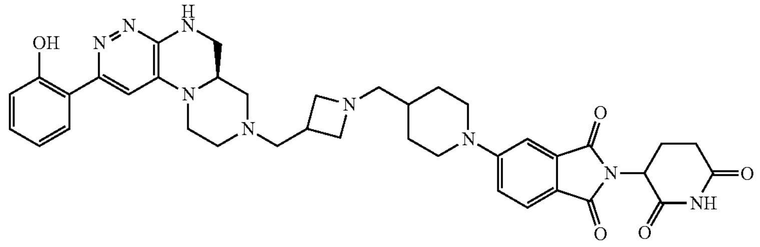 [SMILES: O=C1CCC(N2C(=O)c3ccc(N4CCC(CN5CC(CN6CCN7c8cc(-c9ccccc9O)nnc8NC[C@H]7C6)C5)CC4)cc3C2=O)C(=O)N1] | 2-(2,6-dioxopiperidin-3-yl)-5-(4-((3-(((S)-2-(2-hydroxyphenyl)-5,6,6a,7,9,10-hexahydro-8H-pyrazino[1',2':4,5]pyrazino[2,3-c]pyridazin-8-yl)methyl)azetidin-1-yl)methyl)piperidin-1-yl)isoindoline-1,3-dione |
| 37 | 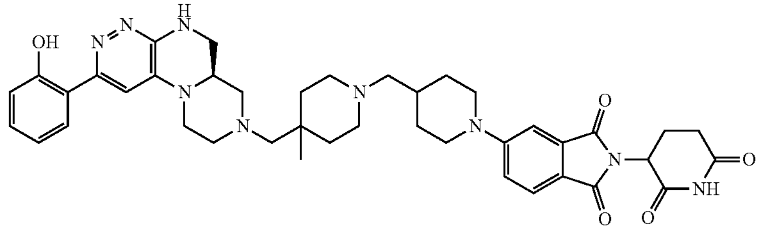 | 2-(2,6-dioxopiperidin-3-yl)-5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)-4-methylpiperidin-1-yl)methyl)piperidin-1-yl)isoindoline-1,3-dione |
| 38 | 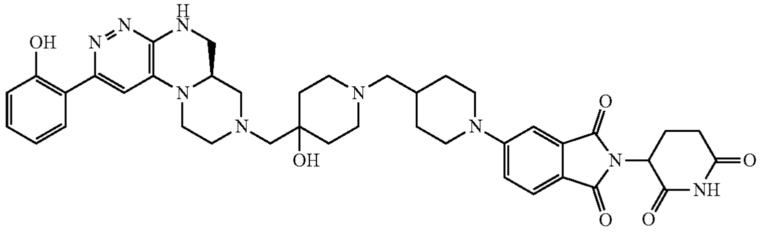 [SMILES: O=C1CCC(N2C(=O)c3ccc(N4CCC(CN5CCC(O)(CN6CCN7c8cc(-c9ccccc9O)nnc8NC[C@H]7C6)CC5)CC4)cc3C2=O)C(=O)N1] | 2-(2,6-dioxopiperidin-3-yl)-5-(4-((4-hydroxy-4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl)isoindoline-1,3-dione |
| 39 | 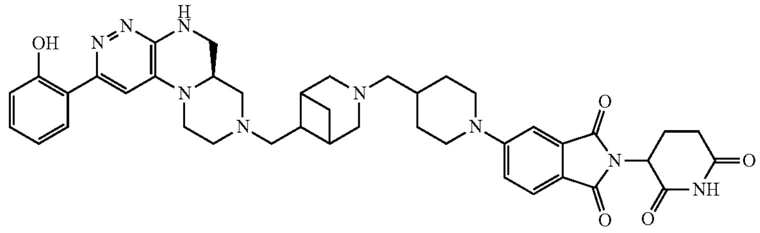 [SMILES: O=C1CCC(N2C(=O)c3ccc(N4CCC(CN5CC6CC(C5)C6CN5CCN6c7cc(-c8ccccc8O)nnc7NC[C@H]6C5)CC4)cc3C2=O)C(=O)N1] | 2-(2,6-dioxopiperidin-3-yl)-5-(4-((6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.1]heptan-3-yl)methyl)piperidin-1-yl)isoindoline-1,3-dione |
| 40 | 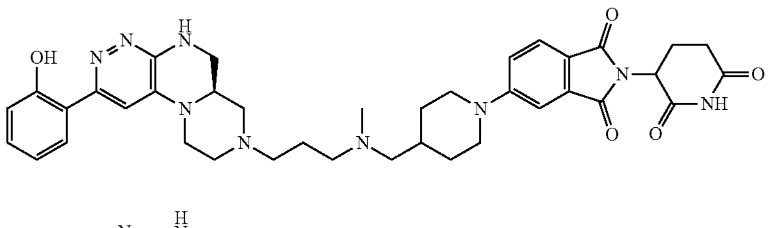 | 2-(2,6-dioxopiperidin-3-yl)-5-(4-(((3-((S)-2-(2-hydroxyphenyl)-5,6,6a,7,9,10-hexahydro-8H-pyrazino[1',2':4,5]pyrazino[2,3-c]pyridazin-8-yl)propyl)(methyl)amino)methyl)piperidin-1-yl)isoindoline-1,3-dione |
| 41 | 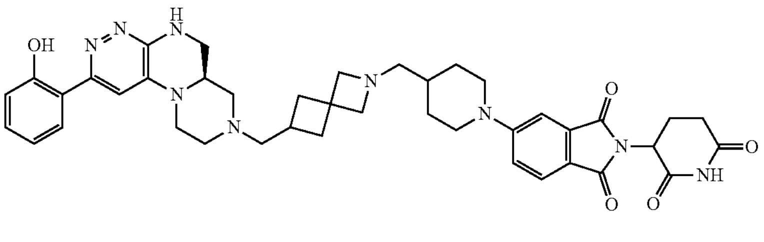 [SMILES: O=C1CCC(N2C(=O)c3ccc(N4CCC(CN5CC6(CC(CN7CCN8c9cc(-c%10ccccc%10O)nnc9NC[C@H]8C7)C6)C5)CC4)cc3C2=O)C(=O)N1] | 2-(2,6-dioxopiperidin-3-yl)-5-(4-((6-(((S)-2-(2-hydroxyphenyl)-5,6,6a,7,9,10-hexahydro-8H-pyrazino[1',2':4,5]pyrazino[2,3-c]pyridazin-8-yl)methyl)-2-azaspiro[3.3]heptan-2-yl)methyl)piperidin-1-yl)isoindoline-1,3-dione |

TABLE 1-continued

| Compounds | | |
|---|---|---|
| Example | Structure | Name |
| 42 | 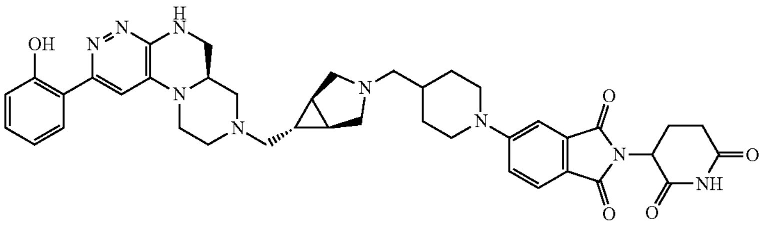 [SMILES: O=C1CCC(N2C(=O)c3ccc(N4CCC(CN5C[C@@H]6[C@H](C5)[C@H]6CN5CCN6c7cc(-c8ccccc8O)nnc7NC[C@H]6C5)CC4)cc3C2=O)C(=O)N1] | 2-(2,6-dioxopiperidin-3-yl)-5-(4-(((1R,5S,6r)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)piperidin-1-yl)isoindoline-1,3-dione |
| 43 | 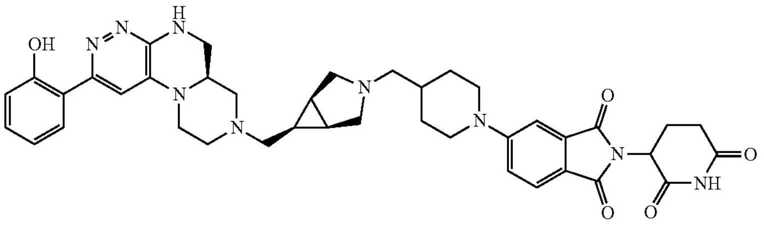 [SMILES: O=C1CCC(N2C(=O)c3ccc(N4CCC(CN5C[C@@H]6[C@H](C5)[C@@H]6CN5CCN6c7cc(-c8ccccc8O)nnc7NC[C@H]6C5)CC4)cc3C2=O)C(=O)N1] | 2-(2,6-dioxopiperidin-3-yl)-5-(4-(((1R,5S,6s)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)piperidin-1-yl)isoindoline-1,3-dione |
| 44 | 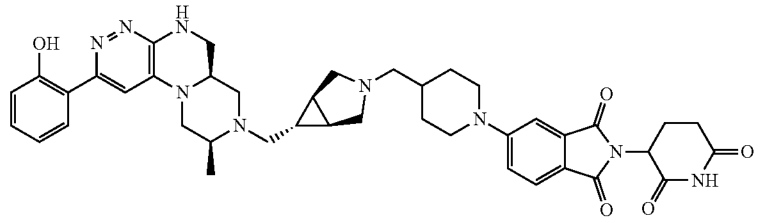 [SMILES: C[C@H]1CN2c3cc(-c4ccccc4O)nnc3NC[C@H]2CN1C[C@H]1[C@@H]2CN(CC3CCN(c4ccc5c(c4)C(=O)N(C4CCC(=O)NC4=O)C5=O)CC3)C[C@@H]21] | 2-(2,6-dioxopiperidin-3-yl)-5-(4-(((1R,5S,6r)-6-(((6aS,9S)-2-(2-hydroxyphenyl)-9-methyl-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)piperidin-1-yl)isoindoline-1,3-dione |
| 45 | 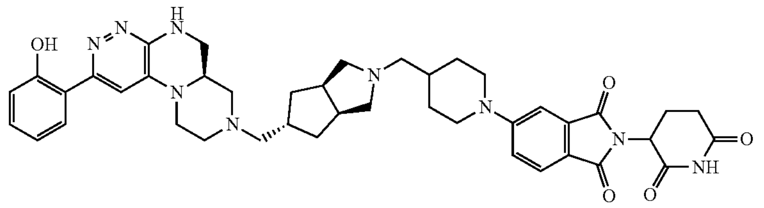 [SMILES: O=C1CCC(N2C(=O)c3ccc(N4CCC(CN5C[C@H]6C[C@H](CN7CCN8c9cc(-c%10ccccc%10O)nnc9NC[C@H]8C7)C[C@H]6C5)CC4)cc3C2=O)C(=O)N1] | 2-(2,6-dioxopiperidin-3-yl)-5-(4-(((3aR,5s,6aS)-5-(((S)-2-(2-hydroxyphenyl)-5,6,6a,7,9,10-hexahydro-8H-pyrazino[1',2':4,5]pyrazino[2,3-c]pyridazin-8-yl)methyl)hexahydrocyclopenta[c]pyrrol-2(1H)-yl)methyl)piperidin-1-yl)isoindoline-1,3-dione |
| 46 | 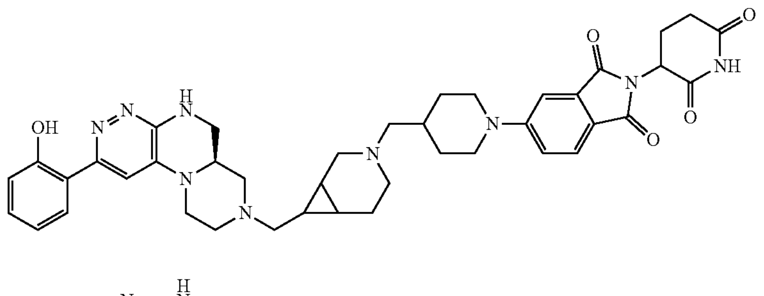 | 2-(2,6-dioxopiperidin-3-yl)-5-(4-((7-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[4.1.0]heptan-3-yl)methyl)piperidin-1-yl)isoindoline-1,3-dione |
| 47 | 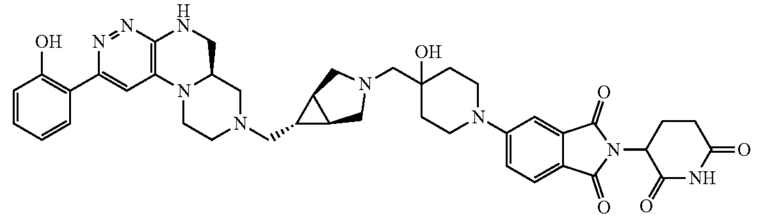 [SMILES: O=C1CCC(N2C(=O)c3ccc(N4CCC(O)(CN5C[C@@H]6[C@@H](CN7CCN8c9cc(-c%10ccccc%10O)nnc9NC[C@H]8C7)[C@@H]6C5)CC4)cc3C2=O)C(=O)N1] | 2-(2,6-dioxopiperidin-3-yl)-5-(4-hydroxy-4-(((1R,5S,6s)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)piperidin-1-yl)isoindoline-1,3-dione |

TABLE 1-continued

| Compounds | | |
|---|---|---|
| Exam-ple | Structure | Name |
| 48 | 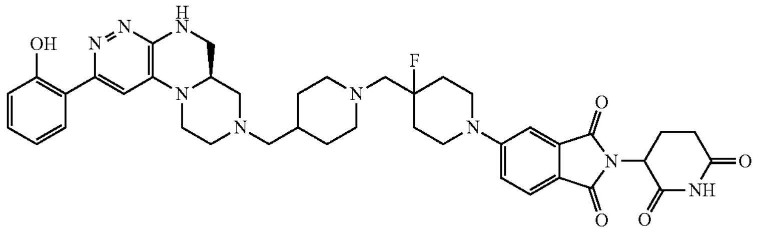 [SMILES: O=C1CCC(N2C(=O)c3ccc(N4CCC(F)(CN5CCC(CN6CCN7c8cc(-c9ccccc9O)nnc8NC[C@H]7C6)CC5)CC4)cc3C2=O)C(=O)N1] | 2-(2,6-dioxopiperidin-3-yl)-5-(4-fluoro-4-((4-(((S)-2-(2-hydroxyphenyl)-5,6,6a,7,9,10-hexahydro-8H-pyrazino [1',2':4,5]pyrazino[2,3-c] pyridazin-8-yl)methyl) piperidin-1-yl)methyl)piperidin-1-yl)isoindoline-1,3-dione |
| 49 | 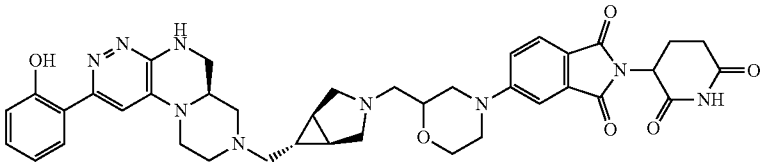 [SMILES: O=C1CCC(N2C(=O)c3ccc(N4CCOC(CN5C[C@@H]6[C@H](C5)[C@H]6CN5CCN6c7cc(-c8ccccc8O)nnc7NC[C@H]6C5)C4)cc3C2=O)C(=O)N1] | 2-(2,6-dioxopiperidin-3-yl)-5-(2-(((1R,5S,6s)-6-(((S)-2-(2-hydroxyphenyl)-5,6,6a,7,9,10-hexahydro-8H-pyrazino [1',2':4,5]pyrazino[2,3-c] pyridazin-8-yl)methyl)-3-azabicyclo[3.1.0]hexan-3-yl) methyl)morpholino)isoindoline-1,3-dione |
| 50 | 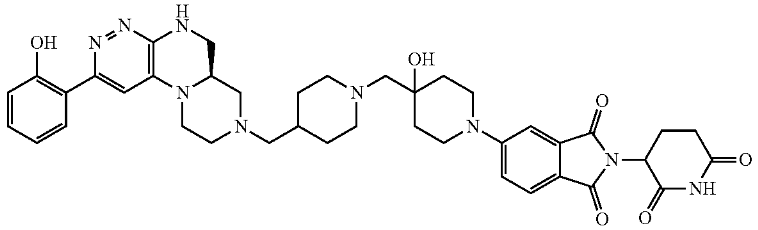 [SMILES: O=C1CCC(N2C(=O)c3ccc(N4CCC(O)(CN5CCC(CN6CCN7c8cc(-c9ccccc9O)nnc8NC[C@H]7C6)CC5)CC4)cc3C2=O)C(=O)N1] | 2-(2,6-dioxopiperidin-3-yl)-5-(4-hydroxy-4-((4-(((S)-2-(2-hydroxyphenyl)-5,6,6a,7,9,10-hexahydro-8H-pyrazino [1',2':4,5]pyrazino[2,3-c] pyridazin-8-yl)methyl)piperidin-1-yl)methyl)piperidin-1-yl) isoindoline-1,3-dione |
| 51 | 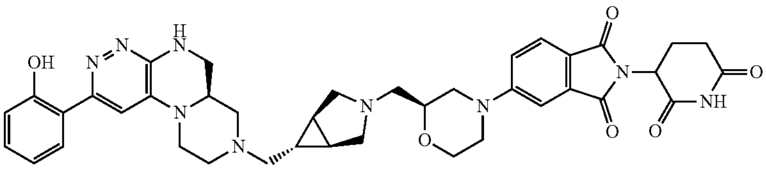 [SMILES: O=C1CCC(N2C(=O)c3ccc(N4CCO[C@@H](CN5C[C@@H]6[C@H](C5)[C@H]6CN5CCN6c7cc(-c8ccccc8O)nnc7NC[C@H]6C5)C4)cc3C2=O)C(=O)N1] | 2-(2,6-dioxopiperidin-3-yl)-5-((S)-2-(((1R,5S,6R)-6-(((S)-2-(2-hydroxyphenyl)-5,6,6a,7,9,10-hexahydo-8H-pyrazino [1',2':4,5]pyrazino[2,3-c] pyridazin-8-yl)methyl)-3-azabicyclo[3.1.0]hexan-3-yl) methyl)morpholino)isoindoline-2,3-dione |
| 52 | 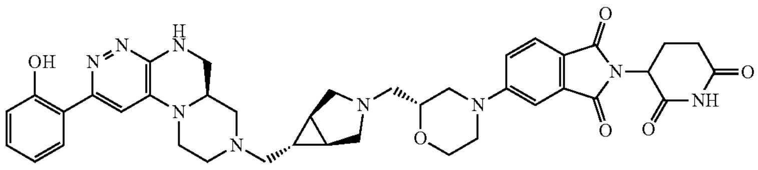 | 2-(2,6-dioxopiperidin-3-yl)-5-((R)-2-(((1R,5S,6S)-6-(((S)-2-(2-hydroxphenyl)-5,6,6a,7,9,10-hexahydro-8H-pyrazino [1',2':4,5]pyrazino[2,3-c] pyridazin-8-yl)methyl)-3-azabicyclo[3.1.0]hexan-3-yl) methyl)morpholino)isoindoline-1,3-dione |
| 53 | 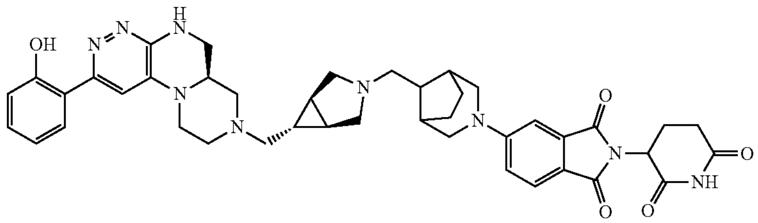 [SMILES: O=C1CCC(N2C(=O)c3ccc(N4CC5CCC(C4)C5CN4C[C@@H]5[C@H](C4)[C@H]5CN4CCN5c6cc(-c7ccccc7O)nnc6NC[C@H]5C4)cc3C2=O)C(=O)N1] | 2-(2,6-dioxopiperidin-3-yl)-5-(8-(((1R,5S,6r)-6-(((S)-2-(2-hydroxyphenyl)-5,6,6a,7,9,10-hexahydro-8H-pyrazino [1',2':4,5]pyrazino[2,3-c] pyridazin-8-yl)methyl)-3-azabicyclo[3.1.0]hexan-3-yl)methyl)-3-azabicyclo [3.2.1]octan-3-yl)isoindoline-1,3-dione |
| 54 | 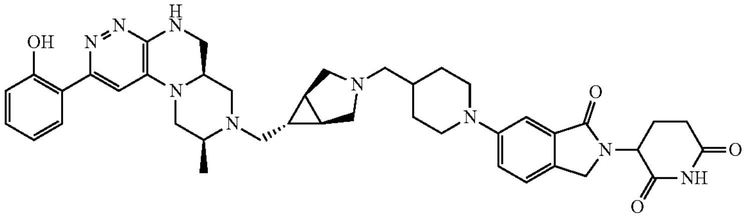 [SMILES: C[C@H]1CN2c3cc(-c4ccccc4O)nnc3NC[C@H]2CN1C[C@H]1[C@@H]2CN(CC3CCN(c4ccc5c(c4)C(=O)N(C4CCC(=O)NC4=O)C5)CC3)C[C@@H]21] | 3-(6-(4-(((1R,5S,6r)-6-(((6aS,9S)-2-(2-hydroxyphenyl)-9-methyl-5,6,6a,7,9,10-hexahydro-8H-pyrazino[1',2':4,5]pyrazino[2,3-c] pyridazin-8-yl)methyl)-3-azabicyclo[3.1.0]hexan-3-yl)methyl)piperidin-1-yl)-1-oxoisoindolin-2-yl)piperidine-2,6-dione |

TABLE 1-continued

| Compounds | | |
|---|---|---|
| Example | Structure | Name |
| 55 | 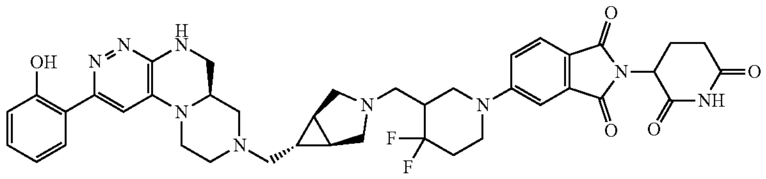 [SMILES: O=C1CCC(N2C(=O)c3ccc(N4CCC(F)(F)C(CN5C[C@@H]6[C@H](C5)[C@H]6CN5CCN6c7cc(-c8ccccc8O)nnc7NC[C@H]6C5)C4)cc3C2=O)C(=O)N1] | 5-(4,4-difluoro-3-(((1R,5S,6r)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)piperidin-1-yl)-2-(2,6-dioxopiperidin-3-yl)isoindoline-1,3-dione |
| 56 | 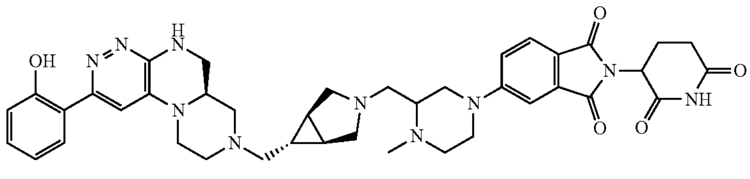 [SMILES: CN1CCN(c2ccc3c(c2)C(=O)N(C2CCC(=O)NC2=O)C3=O)CC1CN1C[C@@H]2[C@H](C1)[C@H]2CN1CCN2c3cc(-c4ccccc4O)nnc3NC[C@H]2C1] | 2-(2,6-dioxopiperidin-3-yl)-5-(3-(((1R,5S,6r)-6-(((S)-2-(2-hydroxyphenyl)-5,6,6a,7,9,10-hexahydro-8H-[1',2':4,5]pyrazino[2,3-c]pyridazin-8-yl)methyl)-3-azabicyclo[3.1.0]hexan-3-yl)methyl)-4-methylpiperazin-1-yl)isoindoline-1,3-dione |
| 57 | 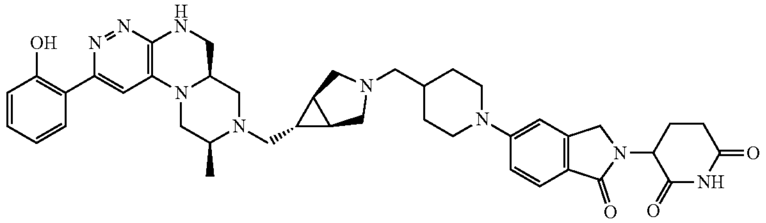 [SMILES: C[C@H]1CN2c3cc(-c4ccccc4O)nnc3NC[C@H]2CN1C[C@H]1[C@@H]2CN(CC3CCN(c4ccc5c(c4)CN(C4CCC(=O)NC4=O)C5=O)CC3)C[C@@H]21] | 3-(5-(4-(((1R,5S,6r)-6-(((6aS,9S)-2-(2-hydroxyphenyl)-9-methyl-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)piperidin-1-yl)-1-oxoisoindolin-2-yl)piperidine-2,6-dione |
| 58 | 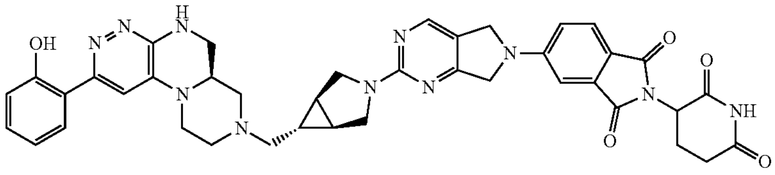 [SMILES: O=C1CCC(N2C(=O)c3ccc(N4Cc5cnc(N6C[C@@H]7[C@@H](CN8CCN9c%10cc(-c%11ccccc%11O)nnc%10NC[C@H]9C8)[C@@H]7C6)nc5C4)cc3C2=O)C(=O)N1] | 2-(2,6-dioxopiperidin-3-yl)-5-(2-((1R,5S,6s)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)-5,7-dihydro-6H-pyrrolo[3,4-d]pyrimidin-6-yl)isoindoline-1,3-dione |
| 59 | 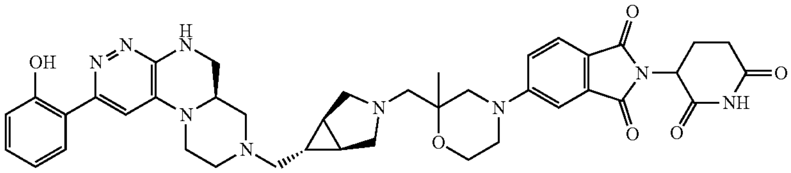 [SMILES: CC1(CN2C[C@@H]3[C@@H](CN4CCN5c6cc(-c7ccccc7O)nnc6NC[C@H]5C4)[C@@H]3C2)CN(c2ccc3c(c2)C(=O)N(C2CCC(=O)NC2=O)C3=O)CCO1] | 2-(2,6-dioxopiperidin-3-yl)-5-(2-(((1R,5S,6s)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)-2-methylmorpholino)isoindoline-1,3-dione |
| 60 | 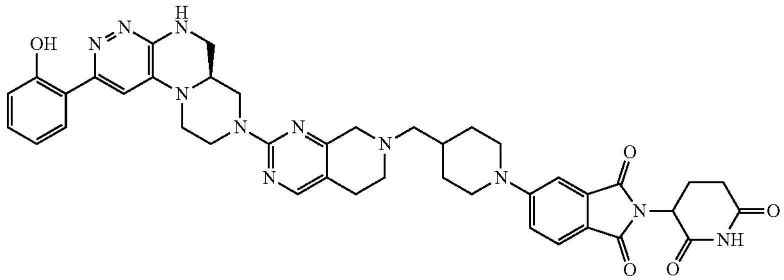 [SMILES: O=C1CCC(N2C(=O)c3ccc(N4CCC(CN5CCc6cnc(N7CCN8c9cc(-c%10ccccc%10O)nnc9NC[C@H]8C7)nc6C5)CC4)cc3C2=O)C(=O)N1] | 2-(2,6-dioxopiperidin-3-yl)-5-(4-((2-((S)-2-(2-hydroxyphenyl)-5,6,6a,7,9,10-hexahydro-8H-pyrazino[1',2':4,5]pyrazino[2,3-c]pyridazin-8-yl)-5,8-dihydropyrido[3,4-d]pyrimidin-7(6H)-yl)methyl)piperidin-1-yl)isoindoline-1,3-dione |

TABLE 1-continued

| Compounds | | |
|---|---|---|
| Example | Structure | Name |
| 61 | 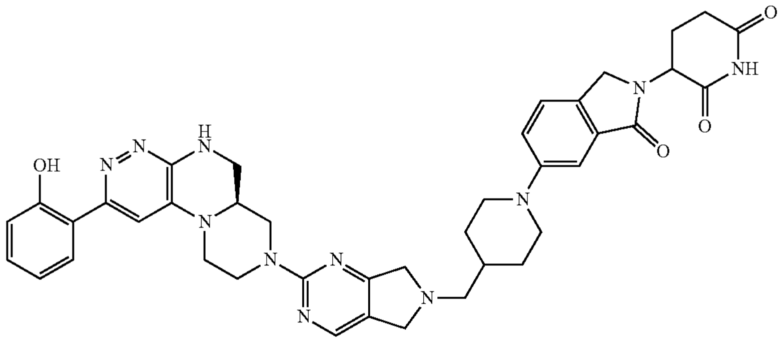 [SMILES: O=C1CCC(N2Cc3ccc(N4CCC(CN5Cc6cnc(N7CCN8c9cc(-c%10ccccc%10O)nnc9NC[C@H]8C7)nc6C5)CC4)cc3C2=O)C(=O)N1] | 3-(6-(4-((2-((S)-2-(2-hydroxyphenyl)-5,6,6a,7,9,10-hexahydro-8H-pyrazino[1',2':4,5]pyrazino[2,3-c]pyridazin-8-yl)-5,7-dihydro-6H-pyrrolo[3,4-d]pyrimidin-6-yl)methyl)piperidin-1-yl)-1-oxoisoindolin-2-yl)piperidine-2,6-dione |
| 62 | 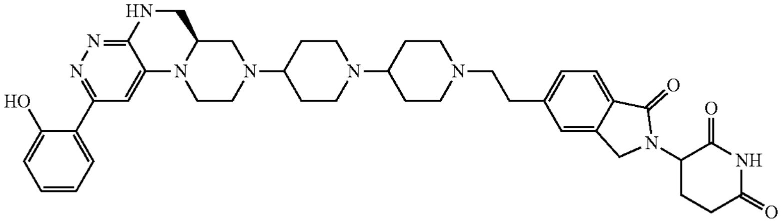 [SMILES: O=C1CCC(N2Cc3cc(CCN4CCC(N5CCC(N6CCN7c8cc(-c9ccccc9O)nnc8NC[C@H]7C6)CC5)CC4)ccc3C2=O)C(=O)N1] | 3-(5-(2-(4-((S)-2-(2-hydroxyphenyl)-5,6,6a,7,9,10-hexahydro-8H-pyrazino[1',2':4,5]pyrazino[2,3-c]pyridazin-8-yl)-[1,4'-bipiperidin]-1'-yl)ethyl)-1-oxoisoindolin-2-yl)piperidine-2,6-dione |
| 63 | 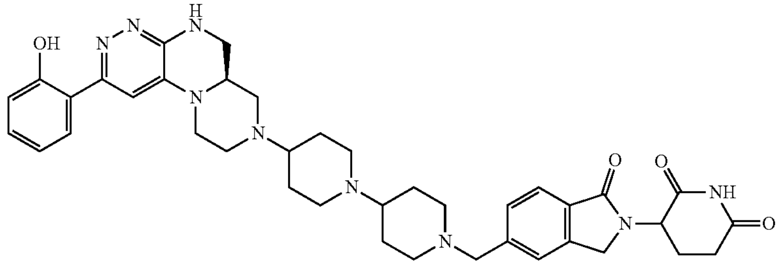 [SMILES: O=C1CCC(N2Cc3cc(CN4CCC(N5CCC(N6CCN7c8cc(-c9ccccc9O)nnc8NC[C@H]7C6)CC5)CC4)ccc3C2=O)C(=O)N1] | 3-(5-((4-((S)-2-(2-hydroxyphenyl)-5,6,6a,7,9,10-hexahydro-8H-pyrazino[1',2':4,5]pyrazino[2,3-c]pyridazin-8-yl)-[1,4'-bipiperidin]-1'-yl)methyl)-1-oxoisoindolin-2-yl)piperidine-2,6-dione |
| 64 | 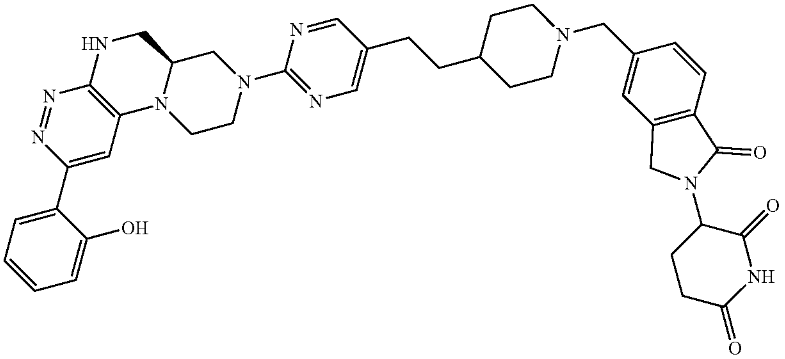 [SMILES: O=C1CCC(N2Cc3cc(CN4CCC(CCc5cnc(N6CCN7c8cc(-c9ccccc9O)nnc8NC[C@H]7C6)nc5)CC4)ccc3C2=O)C(=O)N1] | 3-(5-((4-(2-(2-((S)-2-(2-hydroxyphenyl)-5,6,6a,7,9,10-hexahydro-8H-pyrazino[1',2':4,5]pyrazino[2,3-c]pyridazin-8-yl)pyrimidin-5-yl)ethyl)piperidin-1-yl)methyl)-1-oxoisoindolin-2-yl)piperidine-2,6-dione |
| 65 | 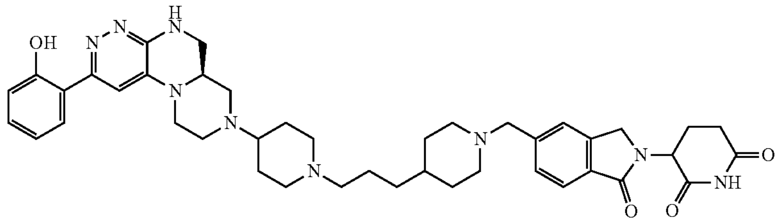 [SMILES: O=C1CCC(N2Cc3cc(CN4CCC(CCCN5CCC(N6CCN7c8cc(-c9ccccc9O)nnc8NC[C@H]7C6)CC5)CC4)ccc3C2=O)C(=O)N1] | 3-(5-((4-(3-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propyl)piperidin-1-yl)methyl)-1-oxoisoindolin-2-yl)piperidine-2,6-dione |

TABLE 1-continued

| Compounds | | |
|---|---|---|
| Example | Structure | Name |
| 66 | 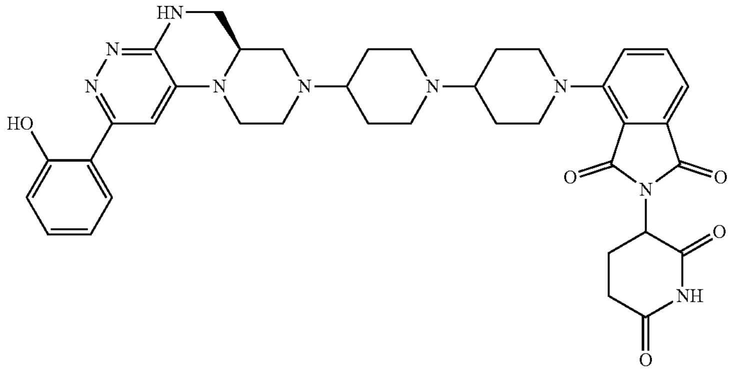 [SMILES: O=C1CCC(N2C(=O)c3cccc(N4CCC(N5CCC(N6CCN7c8cc(-c9ccccc9O)nnc8NC[C@H]7C6)CC5)CC4)c3C2=O)C(=O)N1] | 2-(2,6-dioxopiperidin-3-yl)-4-(4-((S)-2-(2-hydroxyphenyl)-5,6,6a,7,9,10-hexahydro-8H-pyrazino[1',2':4,5]pyrazino[2,3-c]pyridazin-8-yl)-[1,4'-bipiperidin]-1'-yl)isoindoline-1,3-dione |
| 67 | 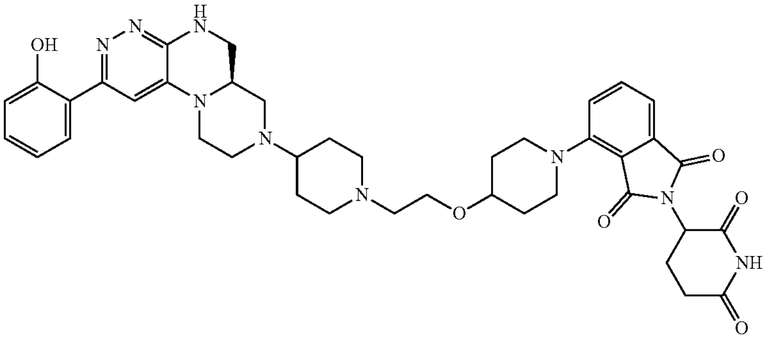 [SMILES: O=C1CCC(N2C(=O)c3cccc(N4CCC(OCCN5CCC(N6CCN7c8cc(-c9ccccc9O)nnc8NC[C@H]7C6)CC5)CC4)c3C2=O)C(=O)N1] | 2-(2,6-dioxopiperidin-3-yl)-4-(4-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)isoindoline-1,3-dione |
| 68 | 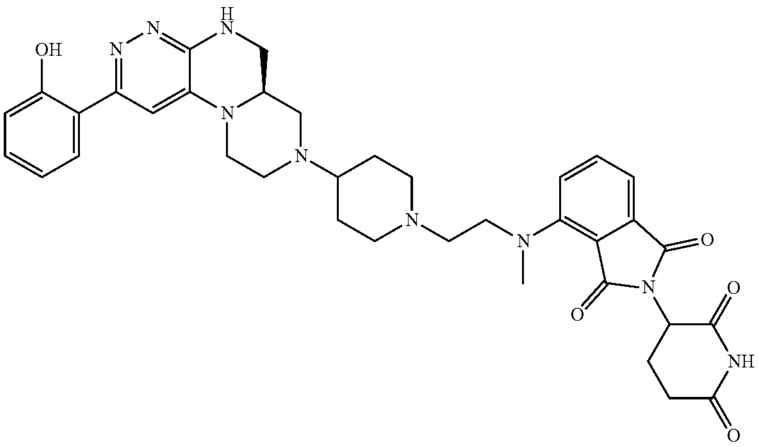 [SMILES: CN(CCN1CCC(N2CCN3c4cc(-c5ccccc5O)nnc4NC[C@H]3C2)CC1)c1cccc2c1C(=O)N(C1CCC(=O)NC1=O)C2=O] | 2-(2,6-dioxopiperidin-3-yl)-4-((2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethyl)(methyl)amino)isoindoline-1,3-dione |
| 69 | 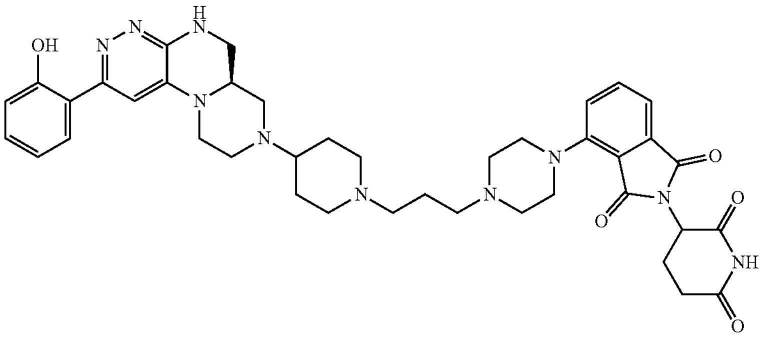 [SMILES: O=C1CCC(N2C(=O)c3cccc(N4CCN(CCCN5CCC(N6CCN7c8cc(-c9ccccc9O)nnc8NC[C@H]7C6)CC5)CC4)c3C2=O)C(=O)N1] | 2-(2,6-dioxopiperidin-3-yl)-4-(4-(3-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propyl)piperazin-1-yl)isoindoline-1,3-dione |

TABLE 1-continued

| Example | Structure | Name |
|---|---|---|
| 70 | 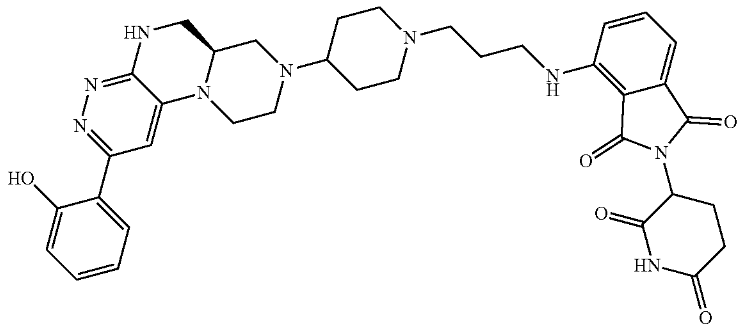 [SMILES: O=C1CCC(N2C(=O)c3cccc(NCCCN4CCC(N5CCN6c7cc(-c8ccccc8O)nnc7NC[C@H]6C5)CC4)c3C2=O)C(=O)N1] | 2-(2,6-dioxopiperidin-3-yl)-4-((3-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propyl)amino)isoindoline-1,3-dione |
| 71 | 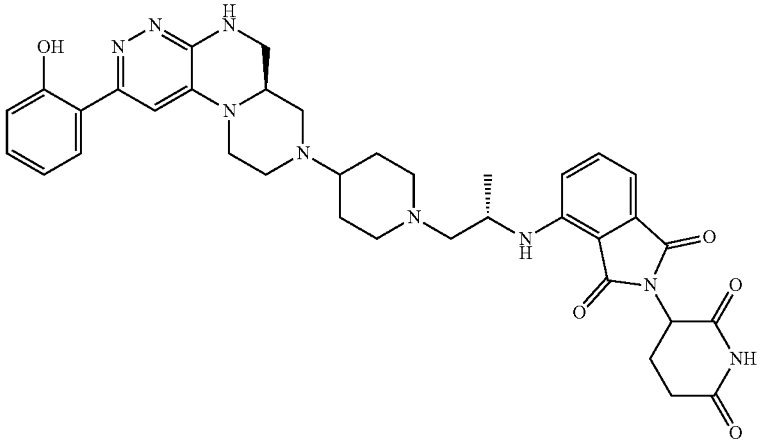 [SMILES: C[C@@H](CN1CCC(N2CCN3c4cc(-c5ccccc5O)nnc4NC[C@H]3C2)CC1)Nc1cccc2c1C(=O)N(C1CCC(=O)NC1=O)C2=O] | 2-(2,6-dioxopiperidin-3-yl)-4-(((S)-1-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propan-2-yl)amino)isoindoline-1,3-dione |
| 72 | 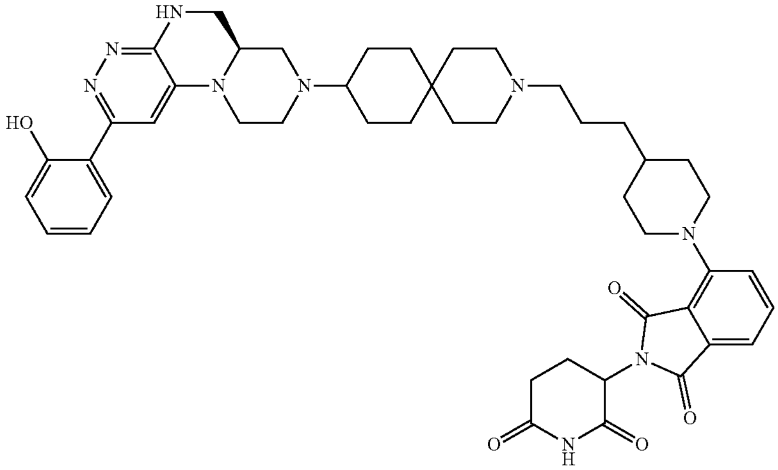 [SMILES: O=C1CCC(N2C(=O)c3cccc(N4CCC(CCCN5CCC6(CCC(N7CCN8c9cc(-c%10ccccc%10O)nnc9NC[C@H]8C7)CC6)CC5)CC4)c3C2=O)C(=O)N1] | 2-(2,6-dioxopiperidin-3-yl)-4-(4-(3-(9-((S)-2-(2-hydroxyphenyl)-5,6,6a,7,9,10-hexahydro-8H-pyrazino[1',2':4,5]pyrazino[2,3-c]pyridazin-8-yl)-3-azaspiro[5.5]undecan-3-yl)propyl)piperidin-1-yl)isoindoline-1,3-dione |

TABLE 1-continued

| Compounds | | |
|---|---|---|
| Example | Structure | Name |
| 73 | 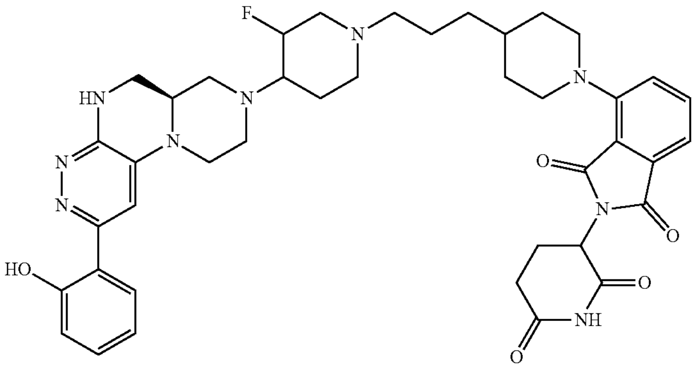 [SMILES: O=C1CCC(N2C(=O)c3cccc(N4CCC(CCCN5CCC(N6CCN7c8cc(-c9ccccc9O)nnc8NC[C@H]7C6)C(F)C5)CC4)c3C2=O)C(=O)N1] | 2-(2,6-dioxopiperidin-3-yl)-4-(4-(3-(3-fluoro-4-((S)-2-(2-hydroxyphenyl)-5,6,6a,7,9,10-hexahydro-8H-pyrazino[1',2':4,5]pyrazino[2,3-c] pyridazin-8-yl)piperidin-1-yl)propyl)piperidin-1-yl)isoindoline-1,3-dione |
| 74 | 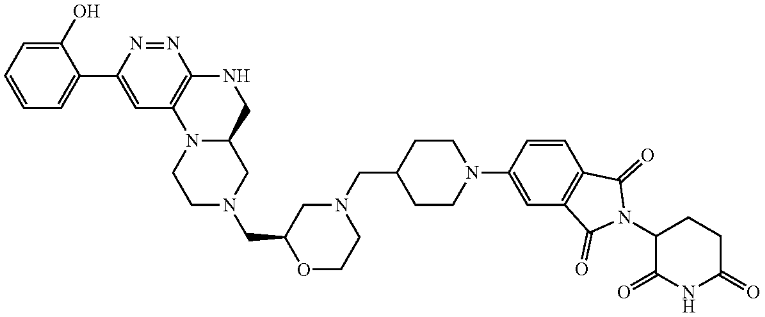 [SMILES: O=C1CCC(N2C(=O)c3ccc(N4CCC(CN5CCO[C@@H](CN6CCN7c8cc(-c9ccccc9O)nnc8NC[C@H]7C6)C5)CC4)cc3C2=O)C(=O)N1] | 2-(2,6-dioxopiperidin-3-yl)-5-(4-((S)-2-(((S)-2-(2-hydroxyphenyl)-5,6,6a,7,9,10-hexahydro-8H-pyrazino[1',2':4,5]pyrazino[2,3-c] pyridazin-8-yl)methyl) morpholino)piperidin-1-yl)isoindoline-1,3-dione |
| 75 | 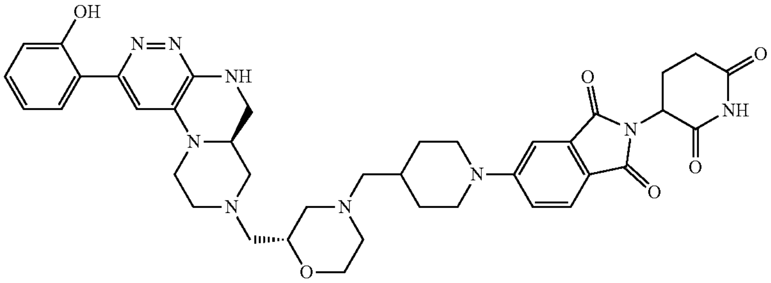 [SMILES: O=C1CCC(N2C(=O)c3ccc(N4CCC(CN5CCO[C@H](CN6CCN7c8cc(-c9ccccc9O)nnc8NC[C@H]7C6)C5)CC4)cc3C2=O)C(=O)N1] | 2-(2,6-dioxopiperidin-3-yl)-5-(4-(((R)-2-(((S)-2-(2-hydroxyphenyl)-5,6,6a,7,9,10-hexahydro-8H-pyrazino[1',2':4,5]pyrazino[2,3-c] pyridazin-8-yl)methyl) morpholino)methyl)piperidin-1-yl)isoindoline-1,3-dione |
| 76 | 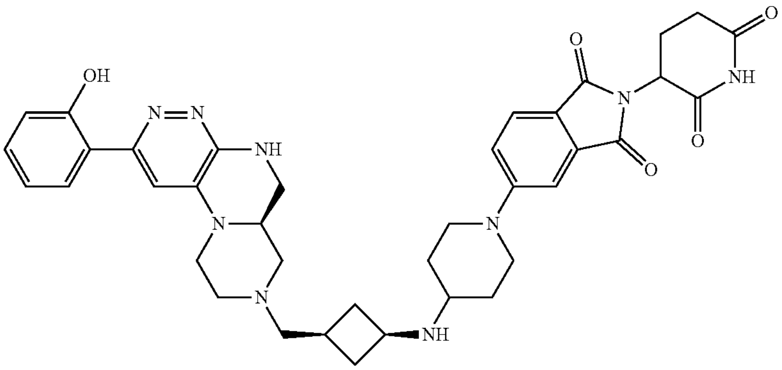 [SMILES: O=C1CCC(N2C(=O)c3ccc(N4CCC(N[C@H]5C[C@@H](CN6CCN7c8cc(-c9ccccc9O)nnc8NC[C@H]7C6)C5)CC4)cc3C2=O)C(=O)N1] | 2-(2,6-dioxopiperidin-3-yl)-5-(4-(((1R,3s)-3-(((S)-2-(2-hydroxyphenyl)-5,6,6a,7,9,10-hexahydro-8H-pyrazino[1',2':4,5]pyrazino[2,3-c] pyridazin-8-yl)methyl) cyclobutyl)amino)piperidin-1-yl)isoindoline-1,3-dione |

TABLE 1-continued

| Compounds | | |
|---|---|---|
| Example | Structure | Name |
| 77 | 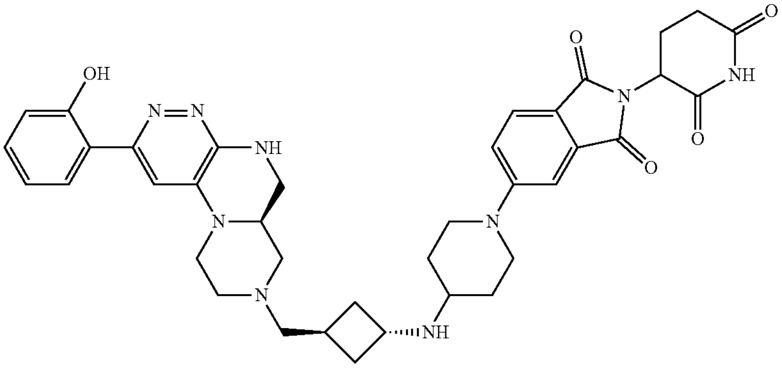 [SMILES: O=C1CCC(N2C(=O)c3ccc(N4CCC(N[C@H]5C[C@H](CN6CCN7c8cc(-c9ccccc9O)nnc8NC[C@H]7C6)C5)CC4)cc3C2=O)C(=O)N1] | 2-(2,6-dioxopiperidin-3-yl)-5-(4-(((1S,3r)-3-(((S)-2-(2-hydroxyphenyl)-5,6,6a,7,9,10-hexahydro-8H-pyrazino[1',2':4,5]pyrazino[2,3-c]pyridazin-8-yl)methyl)cyclobutyl)amino)piperidin-1-yl)isoindoline-1,3-dione |
| 78 | 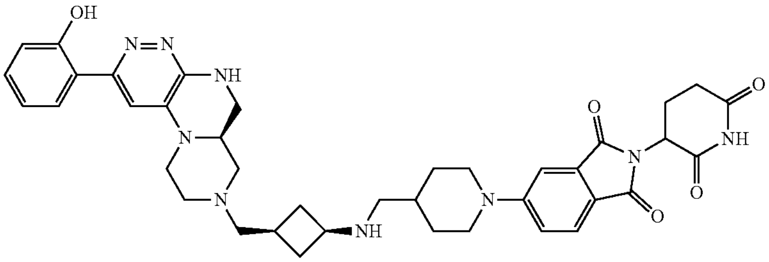 [SMILES: O=C1CCC(N2C(=O)c3ccc(N4CCC(CN[C@H]5C[C@@H](CN6CCN7c8cc(-c9ccccc9O)nnc8NC[C@H]7C6)C5)CC4)cc3C2=O)C(=O)N1] | 2-(2,6-dioxopiperidin-3-yl)-5-(4-((((1R,3s)-3-(((S)-2-(2-hydroxyphenyl)-5,6,6a,7,9,10-hexahydro-8H-pyrazino[1',2':4,5]pyrazino[2,3-c]pyridazin-8-yl)methyl)cyclobutyl)amino)methyl)piperidin-1-yl)isoindoline-1,3-dione |
| 79 | 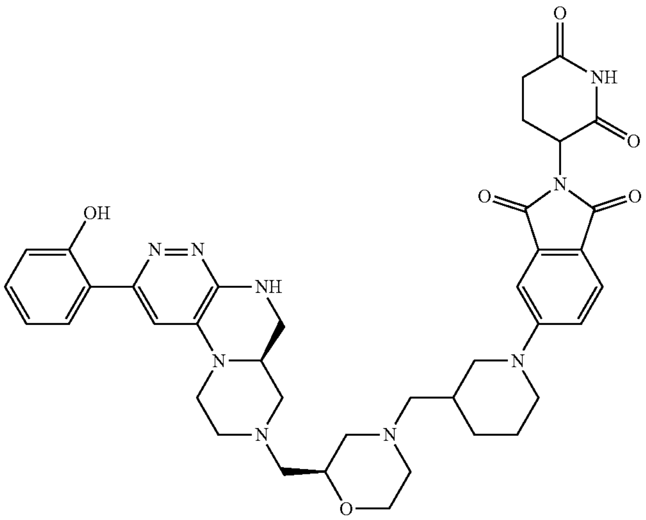 [SMILES: O=C1CCC(N2C(=O)c3ccc(N4CCCC(CN5CCO[C@@H](CN6CCN7c8cc(-c9ccccc9O)nnc8NC[C@H]7C6)C5)C4)cc3C2=O)C(=O)N1] | 2-(2,6-dioxopiperidin-3-yl)-5-(3-(((S)-2-(((S)-2-(2-hydroxyphenyl)-5,6,6a,7,9,10-hexahydro-8H-pyrazino[1',2':4,5]pyrazino[2,3-c]pyridazin-8-yl)methyl)morpholino)methyl)piperidin-1-yl)isoindoline-1,3-dione |
| 80 | 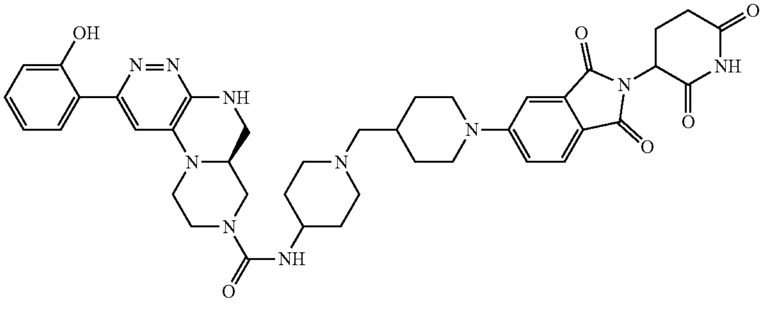 [SMILES: O=C1CCC(N2C(=O)c3ccc(N4CCC(CN5CCC(NC(=O)N6CCN7c8cc(-c9ccccc9O)nnc8NC[C@H]7C6)CC5)CC4)cc3C2=O)C(=O)N1] | (6aS)-N-(1-((1-(2-(2,6-dioxopiperidin-3-yl)-1,3-dioxoisoindolin-5-yl)piperidin-4-yl)methyl)piperidin-4-yl)-2-(2-hydroxyphenyl)-5,6,6a,7,9,10-hexahydro-8H-pyrazino[1',2':4,5]pyrazino[2,3-c]pyridazine-8-carboxamide |

TABLE 1-continued

| Example | Structure | Name |
|---|---|---|
| 81 | 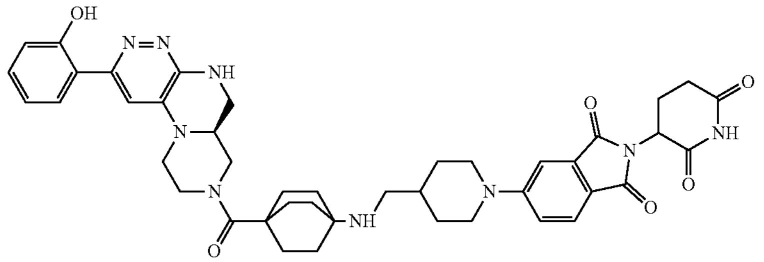 [SMILES: O=C1CCC(N2C(=O)c3ccc(N4CCC(CNC56CCC(C(=O)N7CCN8c9cc(-c%10ccccc%10O)nnc9NC[C@H]8C7)(CC5)CC6)CC4)cc3C2=O)C(=O)N1] | 2-(2,6-dioxopiperidin-3-yl)-5-(4-(((4-((S)-2-(2-hydroxyphenyl)-6,6a,7,8,9,10-hexahydro-5H-pyrazino[1',2':4,5]pyrazino[2,3-c]pyridazine-8-carbonyl)bicyclo[2.2.2]octan-1-yl)amino)methyl)piperidin-1-yl)isoindoline-1,3-dione |
| 82 | 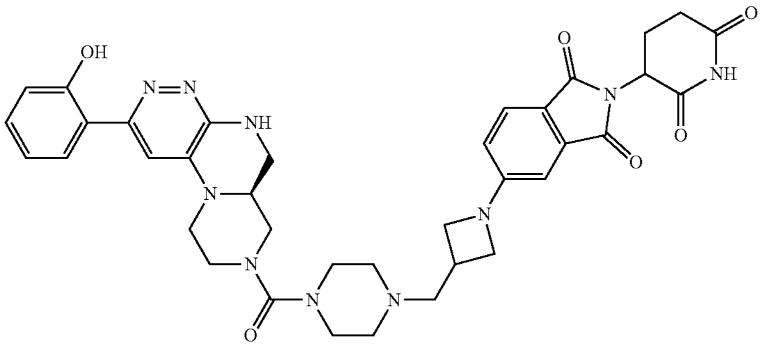 [SMILES: O=C1CCC(N2C(=O)c3ccc(N4CC(CN5CCN(C(=O)N6CCN7c8cc(-c9ccccc9O)nnc8NC[C@H]7C6)CC5)C4)cc3C2=O)C(=O)N1] | 2-(2,6-dioxopiperidin-3-yl)-5-(3-((4-((S)-2-(2-hydroxyphenyl)-6,6a,7,8,9,10-hexahydro-5H-pyrazino[1',2':4,5]pyrazino[2,3-c]pyridazine-8-carbonyl)piperazin-1-yl)methyl)azetidin-1-yl)isoindoline-1,3-dione |
| 83 | 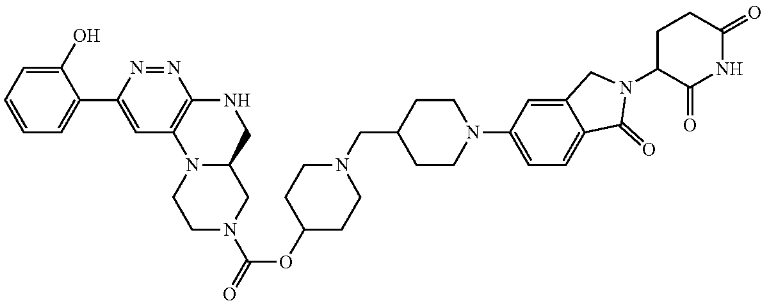 [SMILES: O=C1CCC(N2Cc3cc(N4CCC(CN5CCC(OC(=O)N6CCN7c8cc(-c9ccccc9O)nnc8NC[C@H]7C6)CC5)CC4)ccc3C2=O)C(=O)N1] | 1-((1-(2-(2,6-dioxopiperidin-3-yl)-1-oxoisoindolin-5-yl)piperidin-4-yl)methyl)piperidin-4-yl (6aS)-2-(2-hydroxyphenyl)-5,6,6a,7,9,10-hexahydro-8H-pyrazino[1',2':4,5]pyrazino[2,3-c]pyridazine-8-carboxylate |
| 84 | 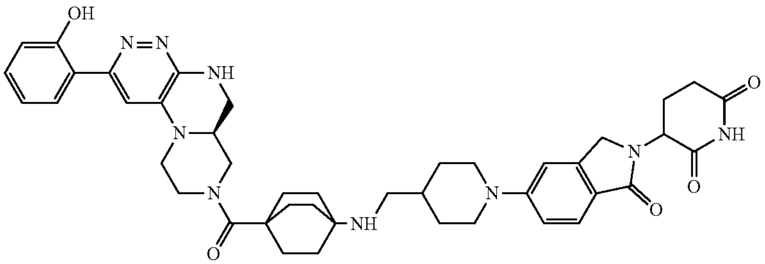 [SMILES: O=C1CCC(N2Cc3cc(N4CCC(CNC56CCC(C(=O)N7CCN8c9cc(-c%10ccccc%10O)nnc9NC[C@H]8C7)(CC5)CC6)CC4)ccc3C2=O)C(=O)N1] | 3-(5-(4-(((4-((S)-2-(2-hydroxyphenyl)-6,6a,7,8,9,10-hexahydro-5H-pyrazino[1',2':4,5]pyrazino[2,3-c]pyridazine-8-carbonyl)bicyclo[2.2.2]octan-1-yl)amino)methyl)piperidin-1-yl)-1-oxoisoindolin-2-yl)piperidine-2,6-dione |
| 85 | 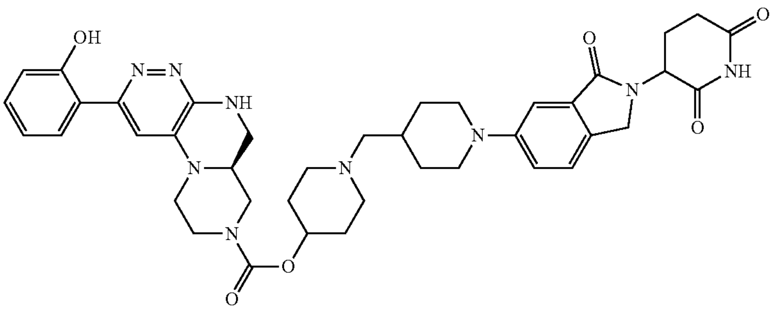 [SMILES: O=C1CCC(N2Cc3ccc(N4CCC(CN5CCC(OC(=O)N6CCN7c8cc(-c9ccccc9O)nnc8NC[C@H]7C6)CC5)CC4)cc3C2=O)C(=O)N1] | 1-((1-(2-(2,6-dioxopiperidin-3-yl)-3-oxoisoindolin-5-yl)piperidin-4-yl)methyl)piperidin-4-yl (6aS)-2-(2-hydroxyphenyl)-5,6,6a,7,9,10-hexahydro-8H-pyrazino[1',2':4,5]pyrazino[2,3-c]pyridazine-8-carboxylate |

TABLE 1-continued

| Compounds | | |
|---|---|---|
| Example | Structure | Name |
| 86 | 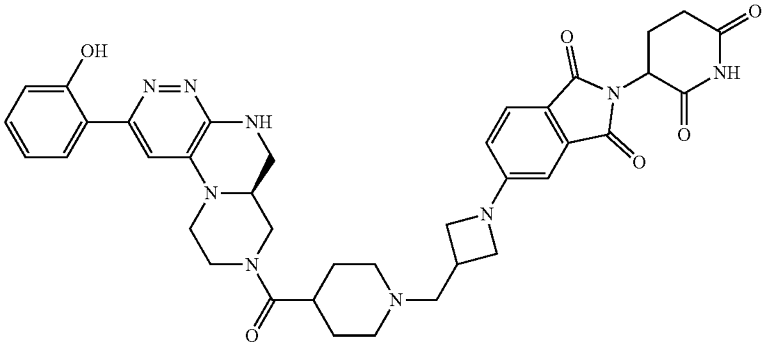 [SMILES: O=C1CCC(N2C(=O)c3ccc(N4CC(CN5CCC(C(=O)N6CCN7c8cc(-c9ccccc9O)nnc8NC[C@H]7C6)CC5)C4)cc3C2=O)C(=O)N1] | 2-(2,6-dioxopiperidin-3-yl)-5-(3-((4-((S)-2-(2-hydroxyphenyl)-6,6a,7,8,9,10-hexahydro-5H-pyrazino[1',2':4,5]pyrazino[2,3-c]pyridazine-8-carbonyl)piperidin-1-yl)methyl)azetidin-1-yl)isoindoline-1,3-dione |
| 87 | 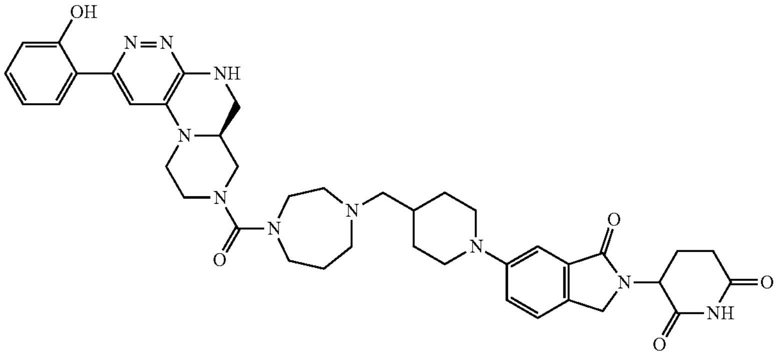 [SMILES: O=C1CCC(N2Cc3ccc(N4CCC(CN5CCCN(C(=O)N6CCN7c8cc(-c9ccccc9O)nnc8NC[C@H]7C6)CC5)CC4)cc3C2=O)C(=O)N1] | 3-(5-(4-((4-((S)-2-(2-hydroxyphenyl)-6,6a,7,8,9,10-hexahydro-5H-pyrazino[1',2':4,5]pyrazino[2,3-c]pyridazine-8-carbonyl)-1,4-diazepan-1-yl)methyl)piperidin-1-yl)-1-oxoisoindolin-2-yl)piperidine-2,6-dione |
| 88 | 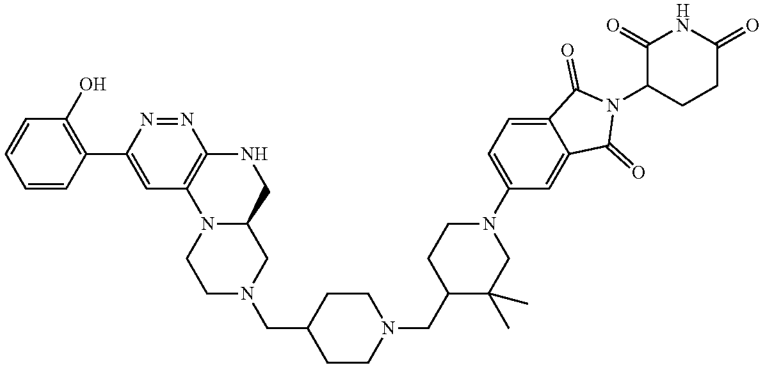 [SMILES: CC1(C)CN(c2ccc3c(c2)C(=O)N(C2CCC(=O)NC2=O)C3=O)CCC1CN1CCC(CN2CCN3c4cc(-c5ccccc5O)nnc4NC[C@H]3C2)CC1] | 2-(2,6-dioxopiperidin-3-yl)-5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)-3,3-dimethylpiperidin-1-yl)isoindoline-1,3-dione |
| 89 | 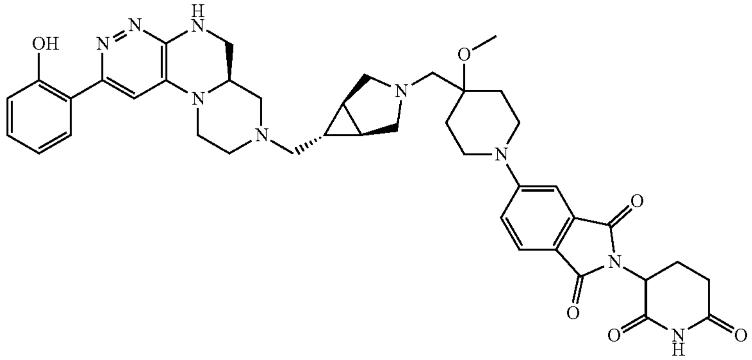 [SMILES: COC1(CN2C[C@@H]3[C@@H](CN4CCN5c6cc(-c7ccccc7O)nnc6NC[C@H]5C4)[C@@H]3C2)CCN(c2ccc3c(c2)C(=O)N(C2CCC(=O)NC2=O)C3=O)CC1] | 2-(2,6-dioxopiperidin-3-yl)-5-(4-(((1R,5S,6s)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)-4-methoxypiperidin-1-yl)isoindoline-1,3-dione |

TABLE 1-continued

| Compounds | | |
|---|---|---|
| Exam-ple | Structure | Name |
| 90 | 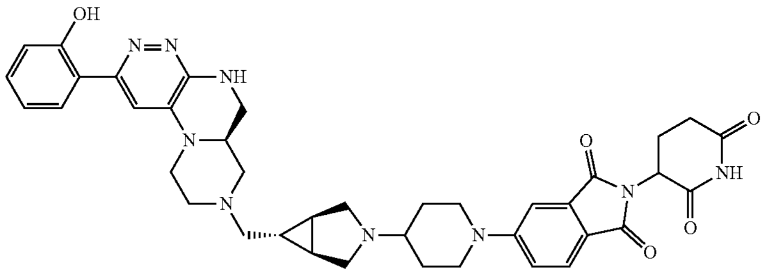 [SMILES: O=C1CCC(N2C(=O)c3ccc(N4CCC(N5C[C@@H]6[C@@H](CN7CCN8c9cc(-c%10ccccc%10O)nnc9NC[C@H]8C7)[C@@H]6C5)CC4)cc3C2=O)C(=O)N1] | 2-(2,6-dioxopiperidin-3-yl)-5-(4-((1R,5S,6s)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)piperidin-1-yl)isoindoline-1,3-dione |
| 91 | 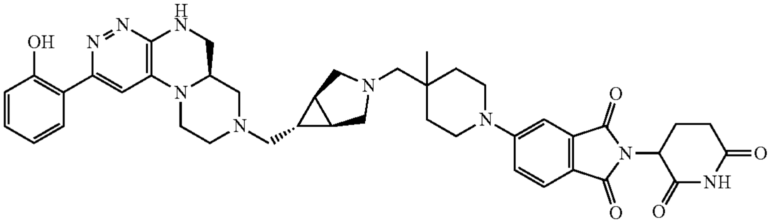 | 2-(2,6-dioxopiperidin-3-yl)-5-(4-(((1R,5S,6r)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)-4-methylpiperidin-1-yl)isoindoline-1,3-dione |
| 92 | 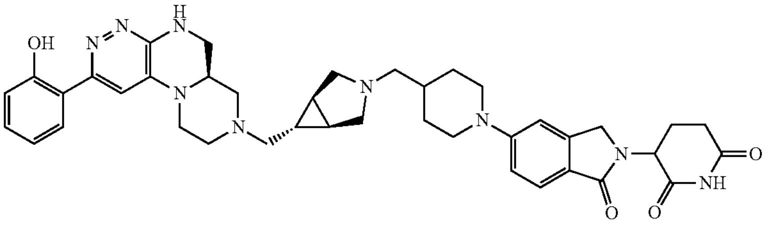 [SMILES: O=C1CCC(N2Cc3cc(N4CCC(CN5C[C@@H]6[C@H](C5)[C@H]6CN5CCN6c7cc(-c8ccccc8O)nnc7NC[C@H]6C5)CC4)ccc3C2=O)C(=O)N1] | 3-(5-(4-(((1R,5S,6r)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)piperidin-1-yl)-1-oxoisoindolin-2-yl)piperidine-2,6-dione |
| 93 | 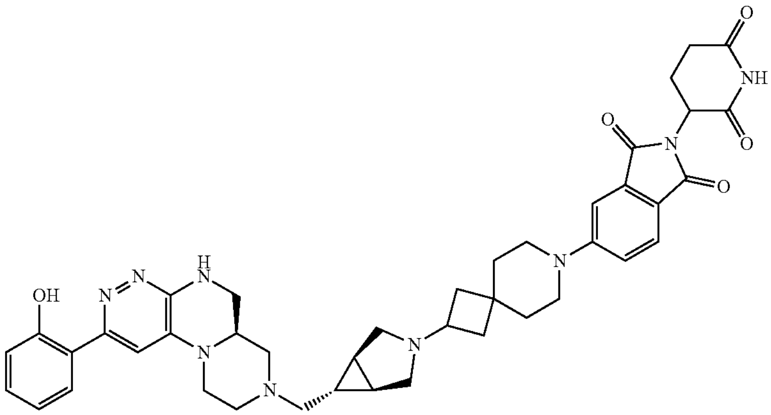 [SMILES: O=C1CCC(N2C(=O)c3ccc(N4CCC5(CC4)CC(N4C[C@@H]6[C@@H](CN7CCN8c9cc(-c%10ccccc%10O)nnc9NC[C@H]8C7)[C@@H]6C4)C5)cc3C2=O)C(=O)N1] | 2-(2,6-dioxopiperidin-3-yl)-5-(2-((1R,5S,6s)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)-7-azaspiro[3.5]nonan-7-yl)isoindoline-1,3-dione |
| 94 | 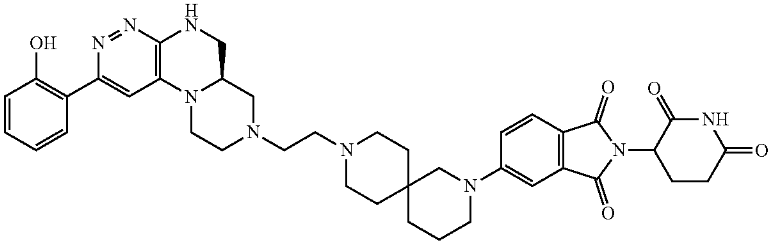 [SMILES: O=C1CCC(N2C(=O)c3ccc(N4CCCC5(CCN(CCN6CCN7c8cc(-c9ccccc9O)nnc8NC[C@H]7C6)CC5)C4)cc3C2=O)C(=O)N1] | 2-(2,6-dioxopiperidin-3-yl)-5-(9-(2-((S)-2-(2-hydroxyphenyl)-5,6,6a,7,9,10-hexahydro-8H-pyrazino[1',2':4,5]pyrazino[2,3-c]pyridazin-8-yl)ethyl)-2,9-diazaspiro[5.5]undecan-2-yl)isoindoline-1,3-dione |

TABLE 1-continued

| Example | Structure | Name |
| --- | --- | --- |
| | Compounds | |
| 95 | 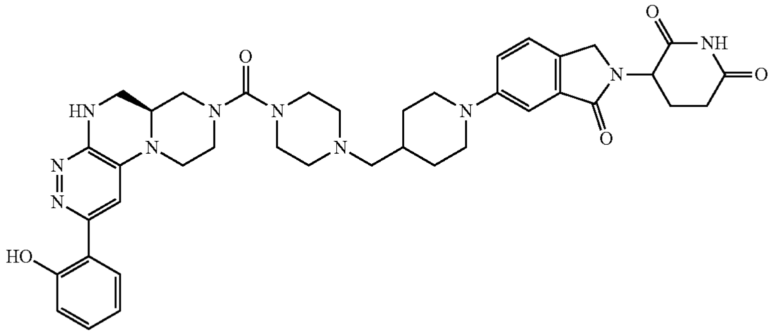 [SMILES: O=C1CCC(N2Cc3ccc(N4CCC(CN5CCN(C(=O)N6CCN7c8cc(-c9ccccc9O)nnc8NC[C@H]7C6)CC5)CC4)cc3C2=O)C(=O)N1] | 3-(6-(4-((4-((S)-2-(2-hydroxyphenyl)-6,6a,7,8,9,10-hexahydro-5H-pyrazino[1',2':4,5]pyrazino[2,3-c]pyridazine-8-carbonyl)piperazin-1-yl)methyl)piperidin-1-yl)-1-oxoisoindolin-2-yl)piperidine-2,6-dione |
| 96 | 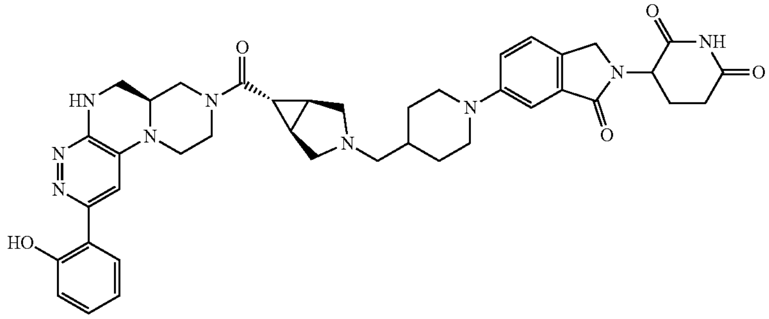 [SMILES: O=C1CCC(N2Cc3ccc(N4CCC(CN5C[C@@H]6[C@H](C5)[C@H]6C(=O)N5CCN6c7cc(-c8ccccc8O)nnc7NC[C@H]6C5)CC4)cc3C2=O)C(=O)N1] | 3-(6-(4-(((1R,5S,6r)-6-((S)-2-(2-hydroxyphenyl)-6,6a,7,8,9,10-hexahydro-5H-pyrazino[1',2':4,5]pyrazino[2,3-c]pyridazine-8-carbonyl)-3-azabicyclo[3.1.0]hexan-3-yl)methyl)piperidin-1-yl)-1-oxoisoindolin-2-yl)piperidine-2,6-dione |
| 97 | 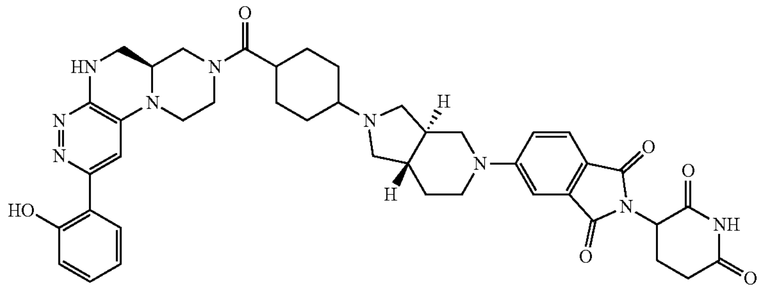 [SMILES: O=C1CCC(N2C(=O)c3ccc(N4CC[C@@H]5CN(C6CCC(C(=O)N7CCN8c9cc(-c%10ccccc%10O)nnc9NC[C@H]8C7)CC6)C[C@H]5C4)cc3C2=O)C(=O)N1] | 2-(2,6-dioxopiperidin-3-yl)-5-((3aS,7aS)-2-(4-((S)-2-(2-hydroxyphenyl)-5H-pyrazino[1',2':4,5]pyrazino[2,3-c]pyridazine-8-carbonyl)cyclohexyl)octahydro-5H-pyrrolo[3,4-c]pyridin-5-yl)isoindoline-1,3-dione |
| 98 | 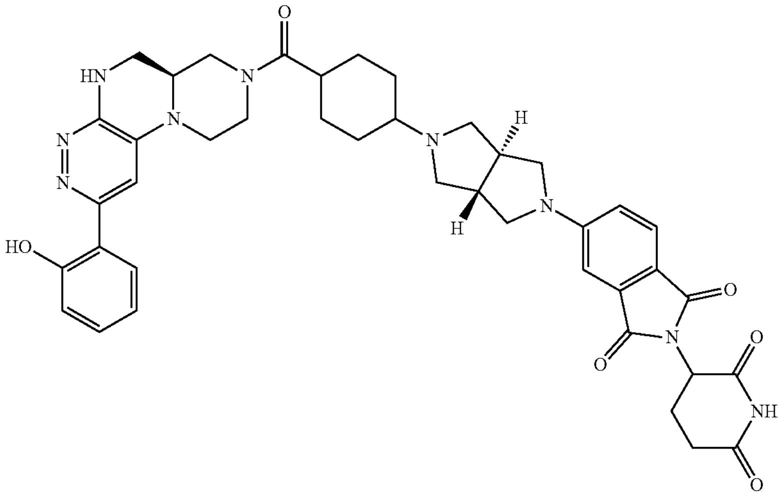 [SMILES: O=C1CCC(N2C(=O)c3ccc(N4C[C@@H]5CN(C6CCC(C(=O)N7CCN8c9cc(-c%10ccccc%10O)nnc9NC[C@H]8C7)CC6)C[C@H]5C4)cc3C2=O)C(=O)N1] | 2-(2,6-dioxopiperidin-3-yl)-5-((3aS,6aS)-5-(4-((S)-2-(2-hydroxyphenyl)-6,6a,7,8,9,10-hexahydro-5H-pyrazino[1',2':4,5]pyrazino[2,3-c]pyridazine-8-carbonyl)cyclohexyl)hexahydropyrrolo[3,4-c]pyrrol-2(1H)-yl)isoindoline-1,3-dione |

TABLE 1-continued

| Compounds | | |
|---|---|---|
| Example | Structure | Name |
| 99 | 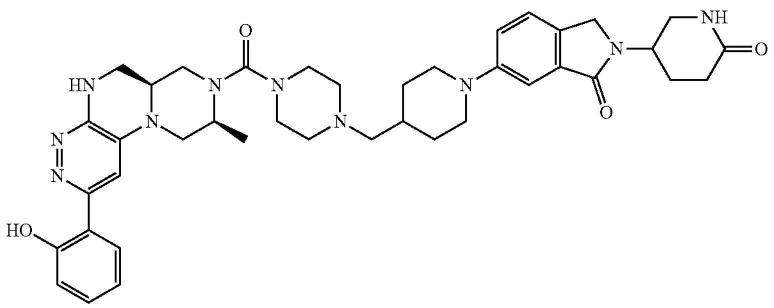 [SMILES: C[C@H]1CN2c3cc(-c4ccccc4O)nnc3NC[C@H]2CN1C(=O)N1CCN(CC2CCN(c3ccc4c(c3)C(=O)N(C3CCC(=O)NC3)C4)CC2)CC1] | 3-(6-(4-((4-((6aS,9S)-2-(2-hydroxyphenyl)-9-methyl-6,6a,7,8,9,10-hexahydro-5H-pyrazino[1',2':4,5]pyrazino[2,3-c]pyridazine-8-carbonyl)piperazin-1-yl)methyl)piperidin-1-yl)-1-oxoisoindolin-2-yl)piperidine-2,6-dione |
| 100 | 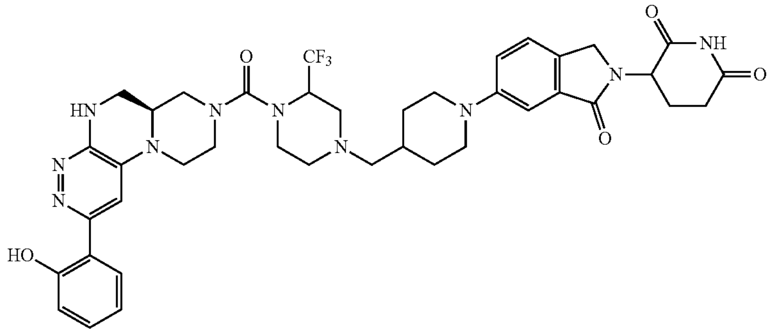 | 3-(6-(4-((4-((S)-2-(2-hydroxyphenyl)-6,6a,7,8,9,10-hexahydro-5H-pyrazino[1',2':4,5]pyrazino[2,3-c]pyridazine-8-carbonyl)-3-(trifluoromethyl)piperazin-1-yl)methyl)piperidin-1-yl)-1-oxoisoindolin-2-yl)piperidine-2,6-dione |
| 101 | 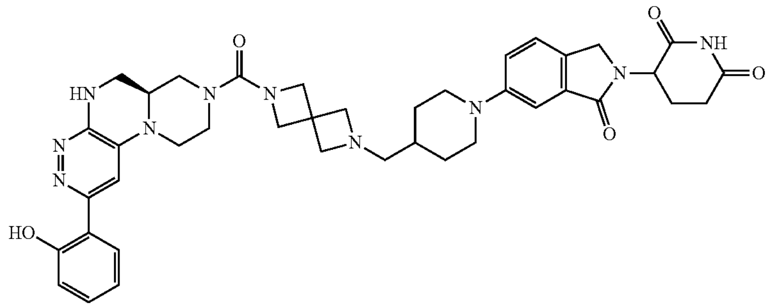 [SMILES: O=C1CCC(N2Cc3ccc(N4CCC(CN5CC6(C5)CN(C(=O)N5CCN7c8cc(-c9ccccc9O)nnc8NC[C@H]7C5)C6)CC4)cc3C2=O)C(=O)N1] | 3-(6-(4-((6-((S)-2-(2-hydroxyphenyl)-6,6a,7,8,9,10-hexahydro-5H-pyrazino[1',2':4,5]pyrazino[2,3-c]pyridazine-8-carbonyl)-2,6-diazaspiro[3.3]heptan-2-yl)methyl)piperidin-1-yl)-1-oxoisoindolin-2-yl)piperidine-2,6-dione |
| 102 | 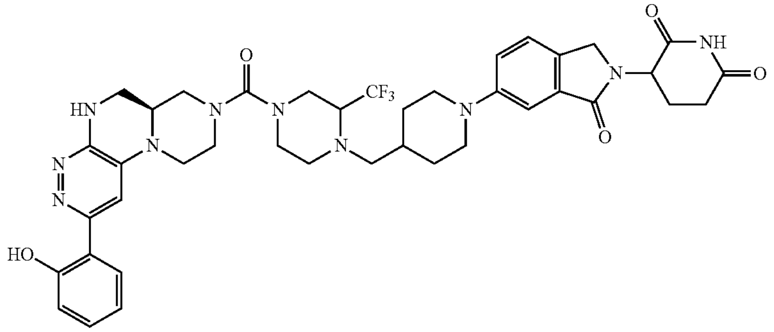 [SMILES: O=C1CCC(N2Cc3ccc(N4CCC(CN5CCN(C(=O)N6CCN7c8cc(-c9ccccc9O)nnc8NC[C@H]7C6)CC5C(F)(F)F)CC4)cc3C2=O)C(=O)N1] | 3-(6-(4-((4-((S)-2-(2-hydroxyphenyl)-6,6a,7,8,9,10-hexahydro-5H-pyrazino[1',2':4,5]pyrazino[2,3-c]pyridazine-8-carbonyl)-2-(trifluoromethyl)piperazin-1-yl)methyl)piperidin-1-yl)-1-oxoisoindolin-2-yl)piperidine-2,6-dione |

TABLE 1-continued

| Compounds | | |
|---|---|---|
| Example | Structure | Name |
| 103 | 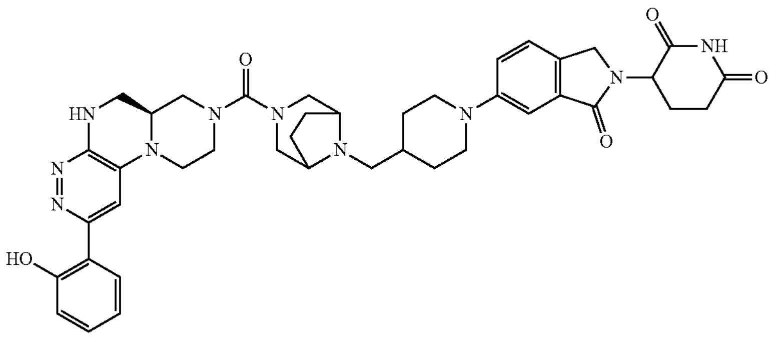 [SMILES: O=C1CCC(N2Cc3ccc(N4CCC(CN5C6CCC5CN(C(=O)N5CCN7c8cc(-c9ccccc9O)nnc8NC[C@H]7C5)C6)CC4)cc3C2=O)C(=O)N1] | 3-(6-(4-((3-((S)-2-(2-hydroxyphenyl)-6,6a,7,8,9,10-hexahydro-5H-pyrazino[1',2':4,5]pyrazino[2,3-c]pyridazine-8-carbonyl)-3,8-diazaspiro[3.2.1]octan-8-yl)methyl)piperidin-1-yl)-1-oxoisoindolin-2-yl)piperidine-2,6-dione |
| 104 | 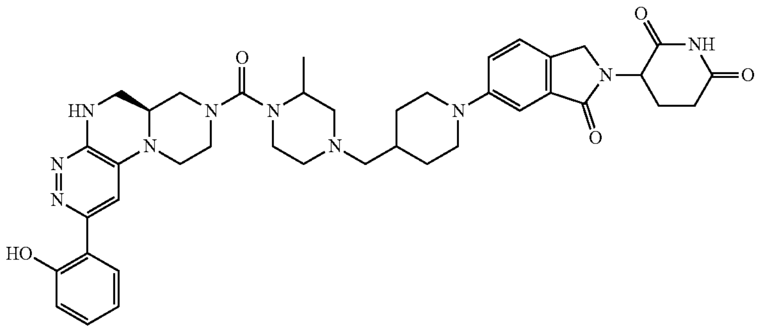 | 3-(6-(4-((4-((S)-2-(2-hydroxyphenyl)-6,6a,7,8,9,10-hexahydro-5H-pyrazino[1',2':4,5]pyrazino[2,3-c]pyridazine-8-carbonyl)-3-methylpiperazin-1-yl)methyl)piperidin-1-yl)-1-oxoisoindolin-2-yl)piperidine-2,6-dione |
| 105 | 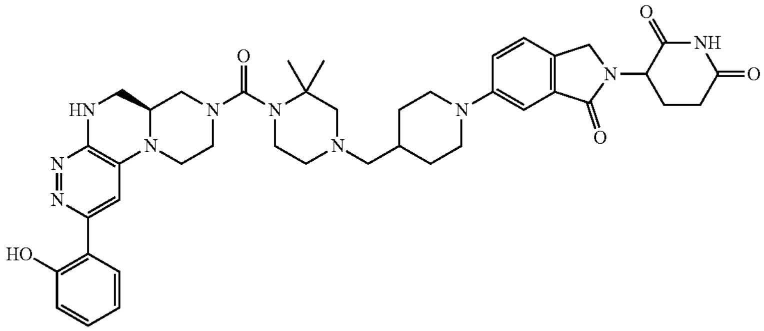 [SMILES: CC1(C)CN(CC2CCN(c3ccc4c(c3)C(=O)N(C3CCC(=O)NC3=O)C4)CC2)CCN1C(=O)N1CCN2c3cc(-c4ccccc4O)nnc3NC[C@H]2C1] | 3-(6-(4-((4-((S)-2-(2-hydroxyphenyl)-6,6a,7,8,9,10-hexahydro-5H-pyrazino[1',2':4,5]pyrazino[2,3-c]pyridazine-8-carbonyl)-3,3-dimethylpiperazin-1-yl)methyl)piperidin-1-yl)-1-oxoisoindolin-2-yl)piperidine-2,6-dione |
| 106 | 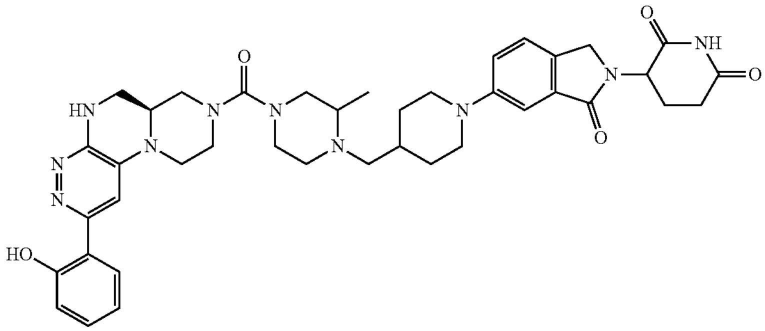 [SMILES: CC1CN(C(=O)N2CCN3c4cc(-c5ccccc5O)nnc4NC[C@H]3C2)CCN1CC1CCN(c2ccc3c(c2)C(=O)N(C2CCC(=O)NC2=O)C3)CC1] | 3-(6-(4-((4-((S)-2-(2-hydroxyphenyl)-6,6a,7,8,9,10-hexahydro-5H-pyrazino[1',2':4,5]pyrazino[2,3-c]pyridazine-8-carbonyl)-2-methylpiperazin-1-yl)methyl)piperidin-1-yl)-1-oxoisoindolin-2-yl)piperidine-2,6-dione |

TABLE 1-continued

| Compounds | | |
|---|---|---|
| Example | Structure | Name |
| 107 | 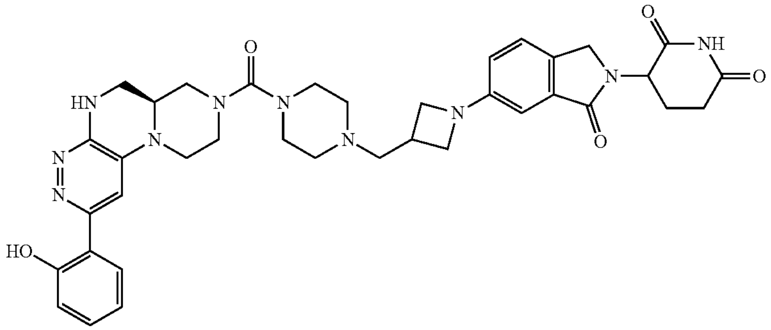 [SMILES: O=C1CCC(N2Cc3ccc(N4CC(CN5CCN(C(=O)N6CCN7c8cc(-c9ccccc9O)nnc8NC[C@H]7C6)CC5)C4)cc3C2=O)C(=O)N1] | 3-(6-(3-((4-((S)-2-(2-hydroxyphenyl)-6,6a,7,8,9,10-hexahydro-5H-pyrazino[1',2':4,5]pyrazino[2,3-c] pyridazine-8-carbonyl) piperazin-1-yl)methyl)azetidin-1-yl)-1-oxoisoindolin-2-yl)piperidine-2,6-dione |
| 108 | 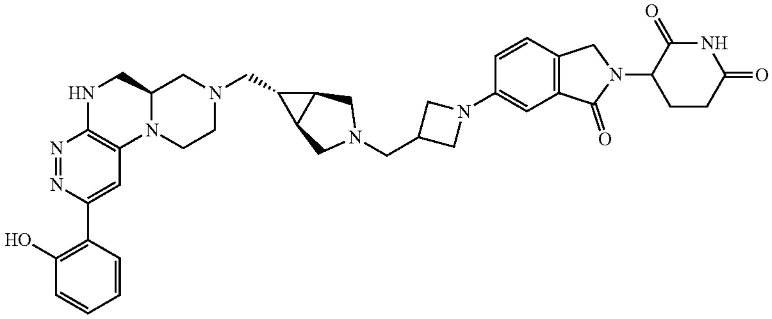 [SMILES: O=C1CCC(N2Cc3ccc(N4CC(CN5C[C@@H]6[C@H](C5)[C@H]6CN5CCN6c7cc(-c8ccccc8O)nnc7NC[C@H]6C5)C4)cc3C2=O)C(=O)N1] | 3-(6-(3-(((1R,5S,6r)-6-(((S)-2-(2-hydroxyphenyl)-5,6,6a,7,9,10-hexahydro-8H-pyrazino[1',2':4,5]pyrazino[2,3-c] pyridazin-8-yl)methyl)-3-azabicyclo[3.1.0]hexan-3-yl)methyl)azetidin-1-yl)-1-oxoisoindolin-2-yl)piperidine-2,6-dione |
| 109 | 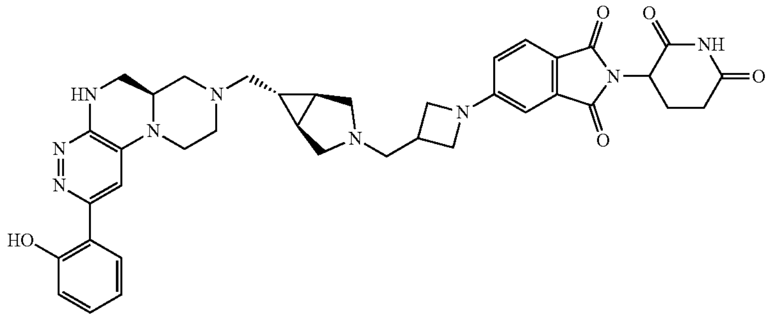 [SMILES: O=C1CCC(N2C(=O)c3ccc(N4CC(CN5C[C@@H]6[C@H](C5)[C@H]6CN5CCN6c7cc(-c8ccccc8O)nnc7NC[C@H]6C5)C4)cc3C2=O)C(=O)N1] | 2-(2,6-dioxopiperidin-3-yl)-5-(3-(((1R,5S,6r)-6-(((S)-2-(2-hydroxyphenyl)-5,6,6a,7,9,10-hexahydro-8H-pyrazino[1',2':4,5]pyrazino[2,3-c] pyridazin-8-yl)methyl)-3-azabicyclo[3.1.0]hexan-3-yl)methyl)azetidin-1-yl)isoindoline-1,3-dione |
| 110 | 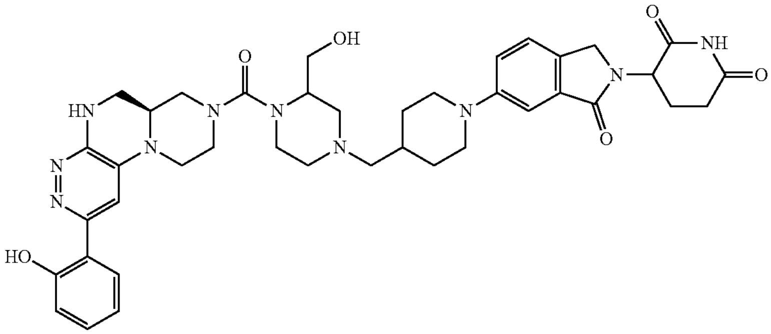 [SMILES: O=C1CCC(N2Cc3ccc(N4CCC(CN5CCN(C(=O)N6CCN7c8cc(-c9ccccc9O)nnc8NC[C@H]7C6)C(CO)C5)CC4)cc3C2=O)C(=O)N1] | 3-(6-(4-((3-(hydroxymethyl)-4-((S)-2-(2-hydroxyphenyl)-6,6a,7,8,9,10-hexahydro-5H-pyrazino[1',2':4,5]pyrazino[2,3-c] pyridazine-8-carbonyl)piperazin-1-yl)methyl)piperidin-1-yl)-1-oxoisoindolin-2-yl)piperidine-2,6-dione |

TABLE 1-continued

| Compounds | | |
|---|---|---|
| Example | Structure | Name |
| 111 | 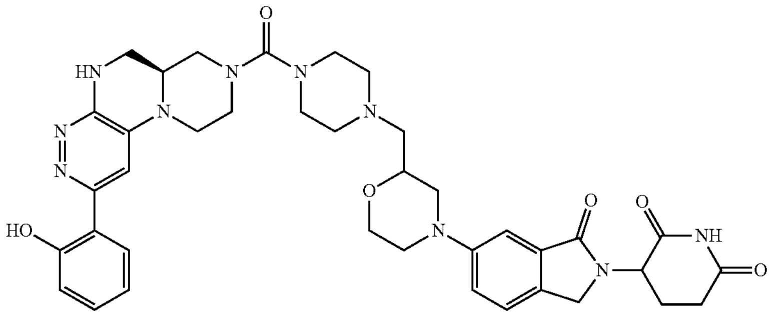 | 3-(6-(2-((4-((S)-2-(2-hydroxyphenyl)-6,6a,7,8,9,10-hexahydro-5H-pyrazino[1',2':4,5]pyrazino[2,3-c]pyridazine-8-carbonyl)piperazin-1-yl)methyl)morpholino)-1-oxoisoindolin-2-yl)piperidine-2,6-dione |
| 112 | 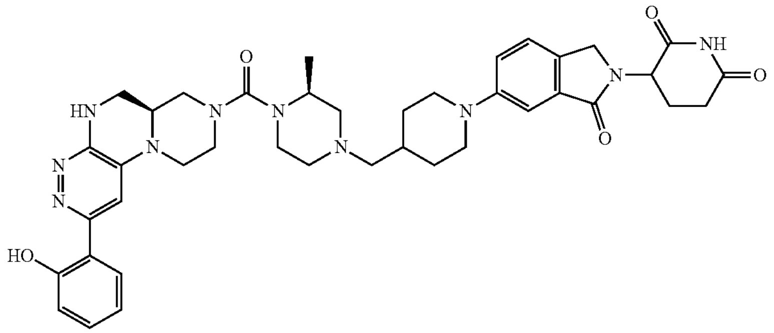 [SMILES: C[C@H]1CN(CC2CCN(c3ccc4c(c3)C(=O)N(C3CCC(=O)NC3=O)C4)CC2)CCN1C(=O)N1CCN2c3cc(-c4ccccc4O)nnc3NC[C@H]2C1] | 3-(6-(4-(((S)-4-((S)-2-(2-hydroxyphenyl)-6,6a,7,8,9,10-hexahydro-5H-pyrazino[1',2':4,5]pyrazino[2,3-c]pyridazine-8-carbonyl)-3-methylpiperazin-1-yl)methyl)piperidin-1-yl)-1-oxoisoindolin-2-yl)piperidine-2,6-dione |
| 113 | 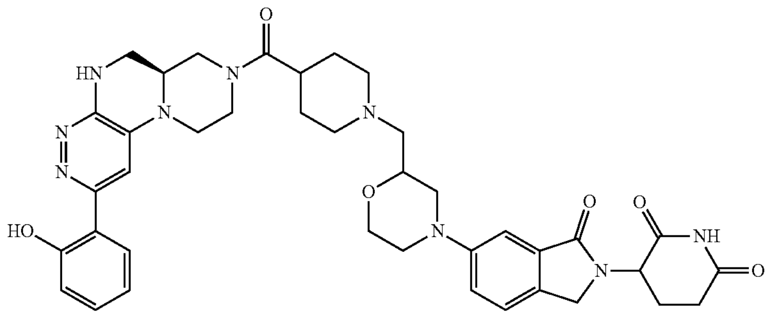 | 3-(6-(2-((4-((S)-2-(2-hydroxyphenyl)-6,6a,7,8,9,10-hexahydro-5H-pyrazino[1',2':4,5]pyrazino[2,3-c]pyridazine-8-carbonyl)piperidin-1-yl)methyl)morpholino)-1-oxoisoindolin-2-yl)piperidine-2,6-dione |
| 114 | 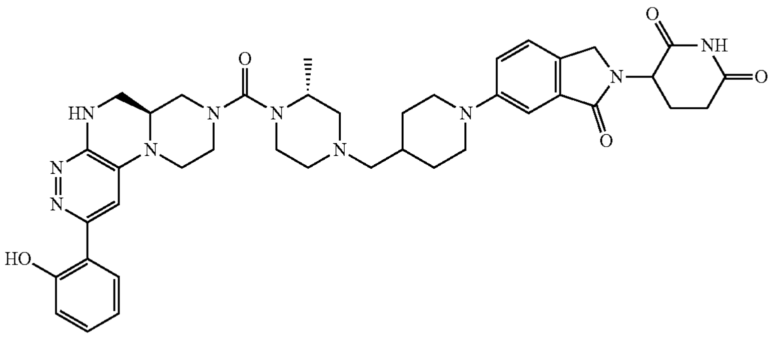 [SMILES: C[C@@H]1CN(CC2CCN(c3ccc4c(c3)C(=O)N(C3CCC(=O)NC3=O)C4)CC2)CCN1C(=O)N1CCN2c3cc(-c4ccccc4O)nnc3NC[C@H]2C1] | 3-(6-(4-(((R)-4-((S)-2-(2-hydroxyphenyl)-6,6a,7,8,9,10-hexahydro-5H-pyrazino[1',2':4,5]pyrazino[2,3-c]pyridazine-8-carbonyl)-3-methylpiperazin-1-yl)methyl)piperidin-1-yl)-1-oxoisoindolin-2-yl)piperidine-2,6-dione |

TABLE 1-continued

| Compounds | | |
|---|---|---|
| Example | Structure | Name |
| 115 | 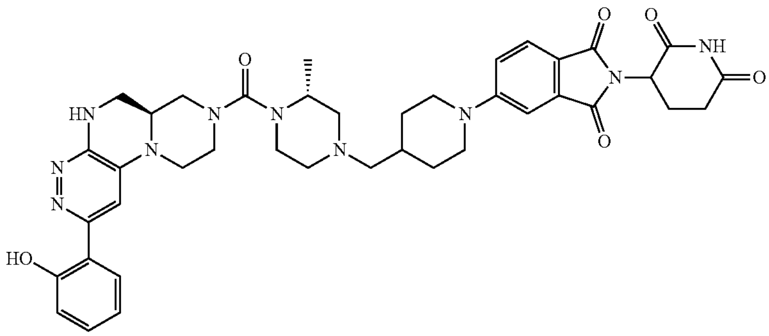 [SMILES: C[C@@H]1CN(CC2CCN(c3ccc4c(c3)C(=O)N(C3CCC(=O)NC3=O)C4=O)CC2)CCN1C(=O)N1CCN2c3cc(-c4ccccc4O)nnc3NC[C@H]2C1] | 2-(2,6-dioxopiperidin-3-yl)-5-(4-(((R)-4-((S)-2-(2-hydroxyphenyl)-6,6a,7,8,9,10-hexahydro-5H-pyrazino[1',2':4,5]pyrazino[2,3-c]pyridazine-8-carbonyl)-3-methylpiperazin-1-yl)methyl)piperidin-1-yl)isoindoline-1,3-dione |
| 116 | 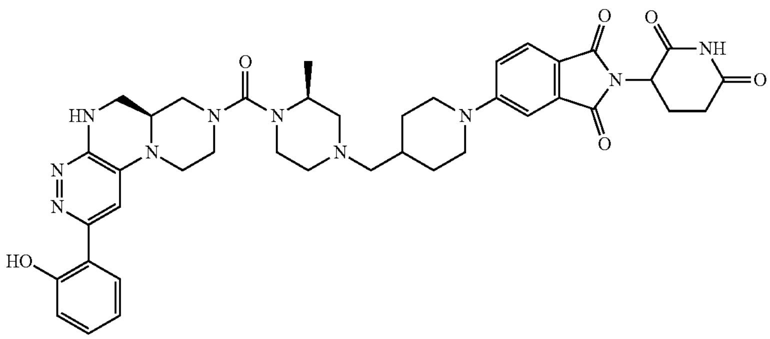 [SMILES: C[C@H]1CN(CC2CCN(c3ccc4c(c3)C(=O)N(C3CCC(=O)NC3=O)C4=O)CC2)CCN1C(=O)N1CCN2c3cc(-c4ccccc4O)nnc3NC[C@H]2C1] | 2-(2,6-dioxopiperidin-3-yl)-5-(4-(((S)-4-((S)-2-(2-hydroxyphenyl)-6,6a,7,8,9,10-hexahydro-5H-pyrazino[1',2':4,5]pyrazino[2,3-c]pyridazine-8-carbonyl)-3-methylpiperazin-1-yl)methyl)piperidin-1-yl)isoindoline-1,3-dione |
| 117 | 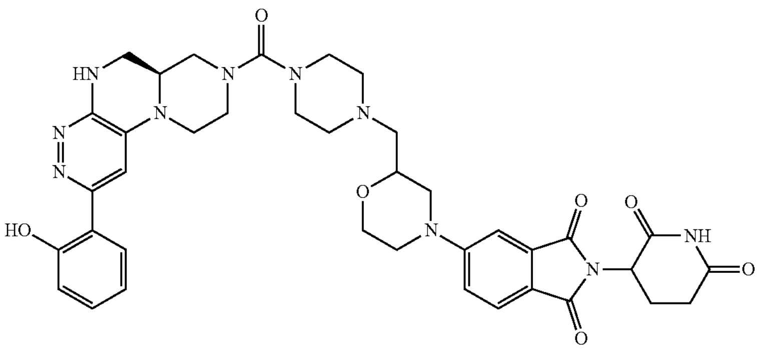 [SMILES: O=C1CCC(N2C(=O)c3ccc(N4CCOC(CN5CCN(C(=O)N6CCN7c8cc(-c9ccccc9O)nnc8NC[C@H]7C6)CC5)C4)cc3C2=O)C(=O)N1] | 2-(2,6-dioxopiperidin-3-yl)-5-(2-((4-((S)-2-(2-hydroxyphenyl)-6,6a,7,8,9,10-hexahydro-5H-pyrazino[1',2':4,5]pyrazino[2,3-c]pyridazine-8-carbonyl)piperazin-1-yl)methyl)morpholino)isoindoline-1,3-dione |
| 118 | 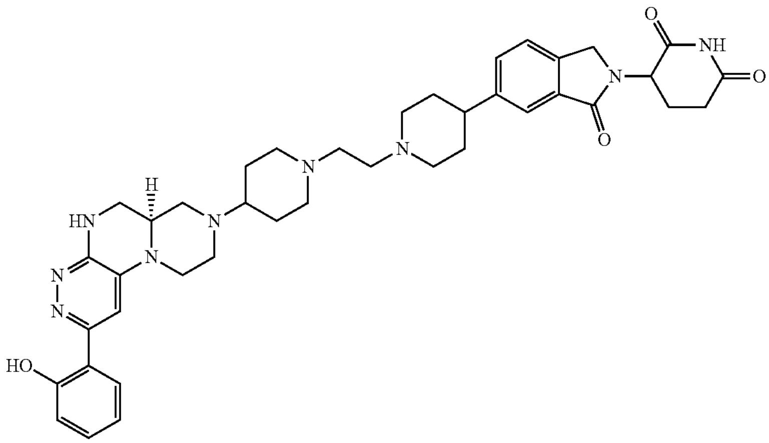 [SMILES: O=C1CCC(N2Cc3ccc(C4CCN(CCN5CCC(N6CCN7c8cc(-c9ccccc9O)nnc8NC[C@H]7C6)CC5)CC4)cc3C2=O)C(=O)N1] | 3-(6-(1-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethyl)piperidin-4-yl)-1-oxoisoindolin-2-yl)piperidine-2,6-dione |

TABLE 1-continued

| Compounds | | |
|---|---|---|
| Example | Structure | Name |
| 119 | 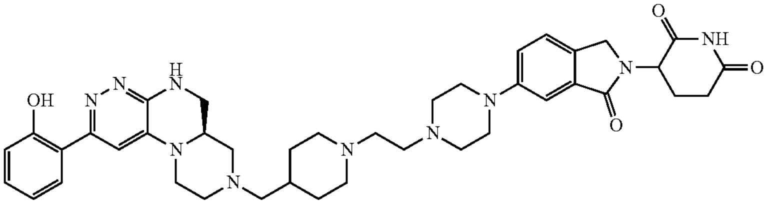 [SMILES: O=C1CCC(N2Cc3ccc(N4CCN(CCN5CCC(CN6CCN7c8cc(-c9ccccc9O)nnc8NC[C@H]7C6)CC5)CC4)cc3C2=O)C(=O)N1] | 3-(6-(4-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethyl)piperazin-1-yl)-1-oxoisoindolin-2-yl)piperidine-2,6-dione |
| 120 | 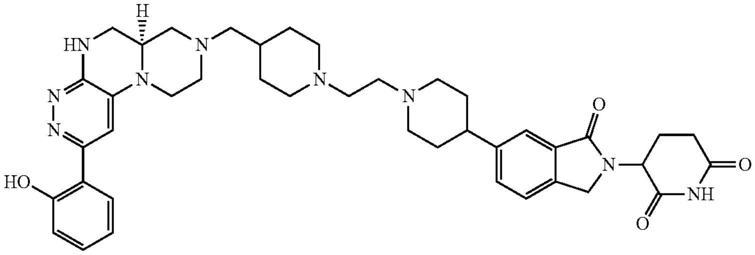 [SMILES: O=C1CCC(N2Cc3ccc(C4CCN(CCN5CCC(CN6CCN7c8cc(-c9ccccc9O)nnc8NC[C@H]7C6)CC5)CC4)cc3C2=O)C(=O)N1] | 3-(6-(1-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethyl)piperidin-4-yl)-1-oxoisoindolin-2-yl)piperidine-2,6-dione |
| 121 | 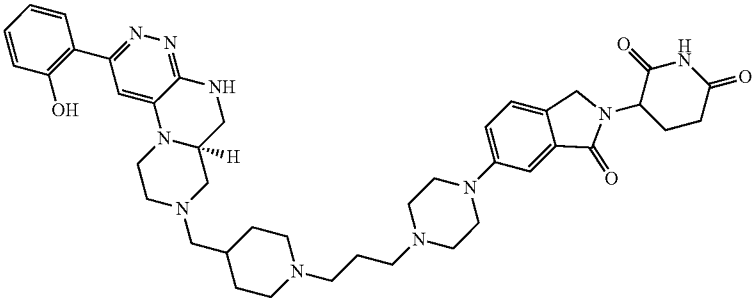 [SMILES: O=C1CCC(N2Cc3ccc(N4CCN(CCCN5CCC(CN6CCN7c8cc(-c9ccccc9O)nnc8NC[C@H]7C6)CC5)CC4)cc3C2=O)C(=O)N1] | 3-(6-(4-(3-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propyl)piperazin-1-yl)-1-oxoisoindolin-2-yl)piperidine-2,6-dione |
| 122 | 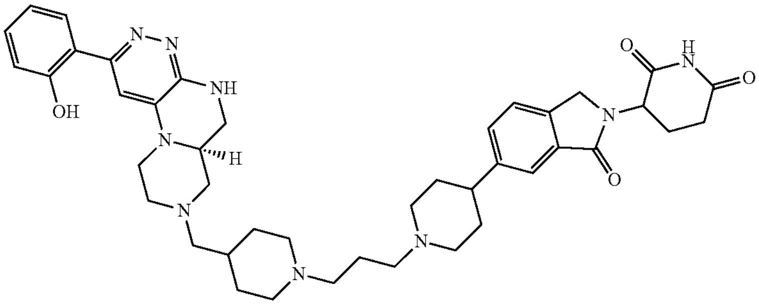 [SMILES: O=C1CCC(N2Cc3ccc(C4CCN(CCCN5CCC(CN6CCN7c8cc(-c9ccccc9O)nnc8NC[C@H]7C6)CC5)CC4)cc3C2=O)C(=O)N1] | 3-(6-(1-(3-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propyl)piperidin-4-yl)-1-oxoisoindolin-2-yl)piperidine-2,6-dione |
| 123 | 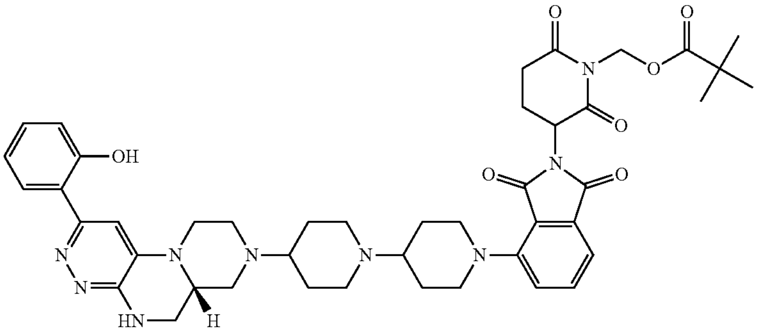 [SMILES: CC(C)(C)C(=O)OCN1C(=O)CCC(N2C(=O)c3cccc(N4CCC(N5CCC(N6CCN7c8cc(-c9ccccc9O)nnc8NC[C@H]7C6)CC5)CC4)c3C2=O)C1=O] | 3-(4-(4-((S)-2-(2-hydroxyphenyl)-5,6,6a,7,9,10-hexahydro-8H-pyrazino[1',2':4,5]pyrazino[2,3-c]pyridazin-8-yl)-[1,4'-bipiperidin]-1'-yl)-1,3-dioxoisoindolin-2-yl)-2,6-dioxopiperidin-1-yl)methyl pivalate |

TABLE 1-continued

| Compounds | | |
|---|---|---|
| Example | Structure | Name |
| 124 | 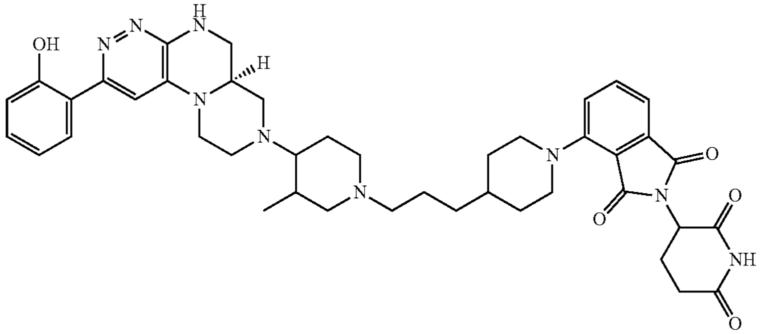 [SMILES: CC1CN(CCCC2CCN(c3cccc4c3C(=O)N(C3CCC(=O)NC3=O)C4=O)CC2)CCC1N1CCN2c3cc(-c4ccccc4O)nnc3NC[C@H]2C1] | 2-(2,6-dioxopiperidin-3-yl)-4-(4-(3-(4-((S)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)propyl)piperidin-1-yl)isoindoline-1,3-dione |
| 125 | 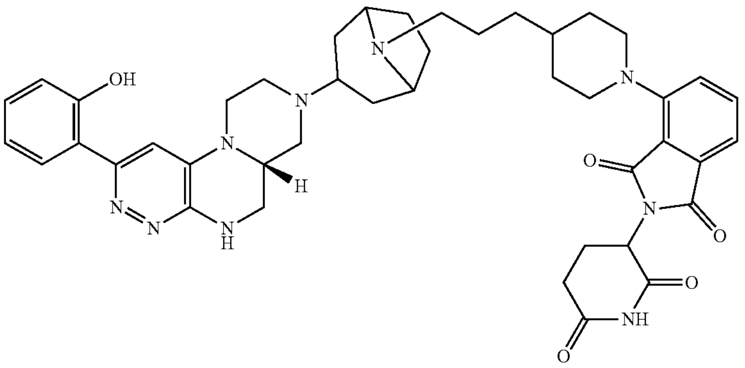 [SMILES: O=C1CCC(N2C(=O)c3cccc(N4CCC(CCCN5C6CCC5CC(N5CCN7c8cc(-c9ccccc9O)nnc8NC[C@H]7C5)C6)CC4)c3C2=O)C(=O)N1] | 2-(2,6-dioxopiperidin-3-yl)-4-(4-(3-(3-((S)-2-(2-hydroxyphenyl)-5,6,6a,7,9,10-hexahydro-8H-pyrazino[1',2':4,5]pyrazino[2,3-c]pyridazin-8-yl)-8-azabicyclo[3.2.1]octan-8-yl)propyl)piperidin-1-yl)isoindoline-1,3-dione |
| 126 | 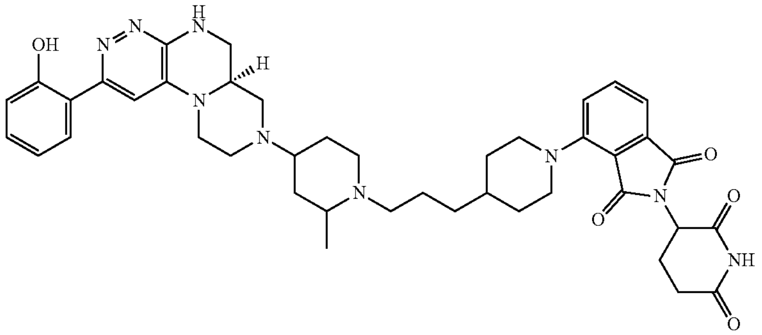 [SMILES: CC1CC(N2CCN3c4cc(-c5ccccc5O)nnc4NC[C@H]3C2)CCN1CCCC1CCN(c2cccc3c2C(=O)N(C2CCC(=O)NC2=O)C3=O)CC1] | 2-(2,6-dioxopiperidin-3-yl)-4-(4-(3-(4-((S)-2-(2-hydroxyphenyl)-5,6,6a,7,9,10-hexahydro-8H-pyrazino[1',2':4,5]pyrazino[2,3-c]pyridazin-8-yl)-2-methylpiperidin-1-yl)propyl)piperidin-1-yl)isoindoline-1,3-dione |
| 127 | 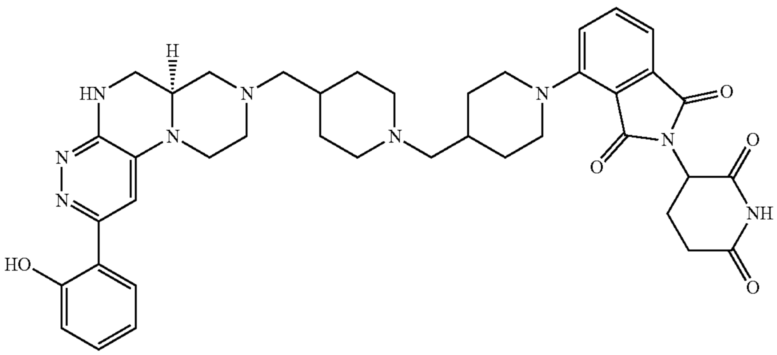 [SMILES: O=C1CCC(N2C(=O)c3cccc(N4CCC(CN5CCC(CN6CCN7c8cc(-c9ccccc9O)nnc8NC[C@H]7C6)CC5)CC4)c3C2=O)C(=O)N1] | 2-(2,6-dioxopiperidin-3-yl)-4-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl)isoindoline-1,3-dione |

TABLE 1-continued

| Compounds | | |
|---|---|---|
| Example | Structure | Name |
| 128 | 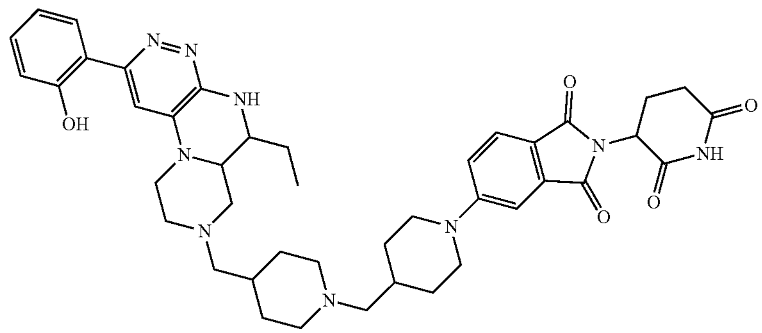 [SMILES: CCC1Nc2nnc(-c3ccccc3O)cc2N2CCN(CC3CCN(CC4CCN(c5ccc6c(c5)C(=O)N(C5CCC(=O)NC5=O)C6=O)CC4)CC3)CC12] | 2-(2,6-dioxopiperidin-3-yl)-5-(4-((4-((6-ethyl-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl)isoindoline-1,3-dione |
| 129 | 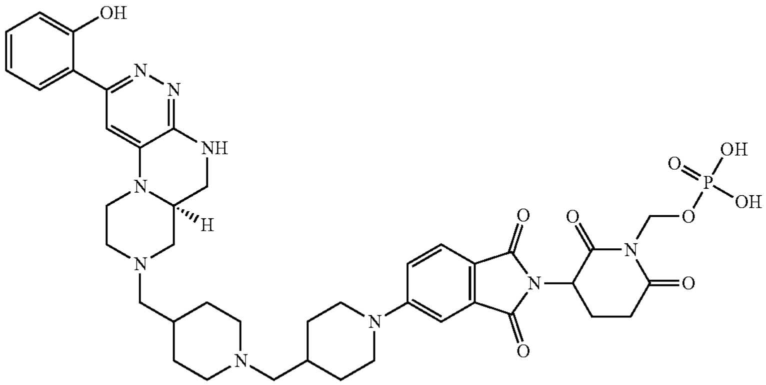 [SMILES: O=C1CCC(N2C(=O)c3ccc(N4CCC(CN5CCC(CN6CCN7c8cc(-c9ccccc9O)nnc8NC[C@H]7C6)CC5)CC4)cc3C2=O)C(=O)N1COP(=O)(O)O] | (3-(5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl)-1,3-dioxoisoindolin-2-yl)-2,6-dioxopiperidin-1-yl)methyl) dihydrogen phosphate |
| 130 | 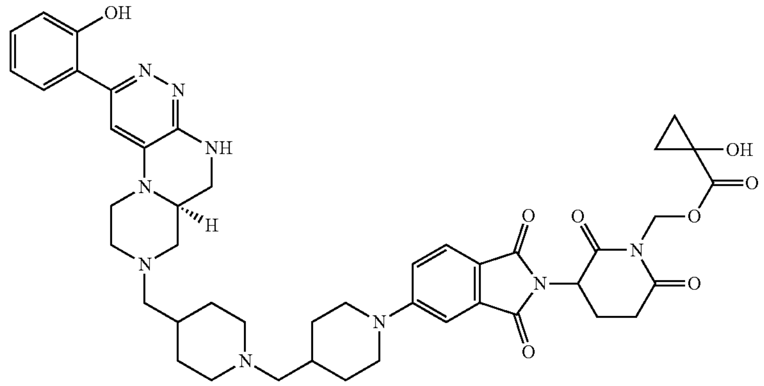 [SMILES: O=C1CCC(N2C(=O)c3ccc(N4CCC(CN5CCC(CN6CCN7c8cc(-c9ccccc9O)nnc8NC[C@H]7C6)CC5)CC4)cc3C2=O)C(=O)N1COC(=O)C1(O)CC1] | (3-(5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl)-1,3-dioxoisoindolin-2-yl)-2,6-dioxopiperidin-1-yl)methyl-1-hydroxycyclopropane-1-carboxylate |
| 131 | 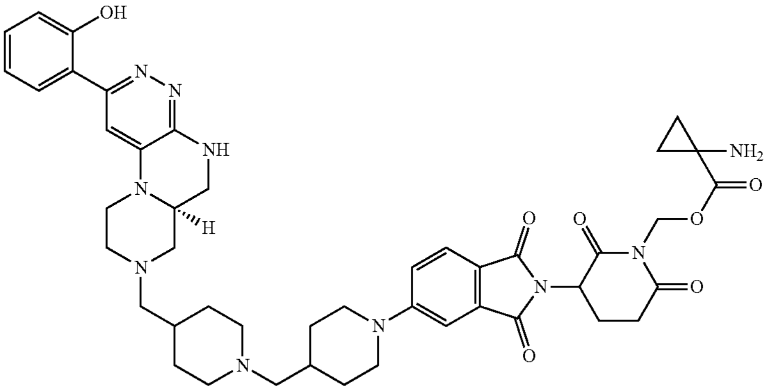 [SMILES: NC1(C(=O)OCN2C(=O)CCC(N3C(=O)c4ccc(N5CCC(CN6CCC(CN7CCN8c9cc(-c%10ccccc%10O)nnc9NC[C@H]8C7)CC6)CC5)cc4C3=O)C2=O)CC1] | (3-(5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl)-1,3-dioxoisoindolin-2-yl)-2,6-dioxopiperidin-1-yl)methyl 1-aminocyclopropane-1-carboxylate |

TABLE 1-continued

| Compounds | | |
|---|---|---|
| Example | Structure | Name |
| 132 | 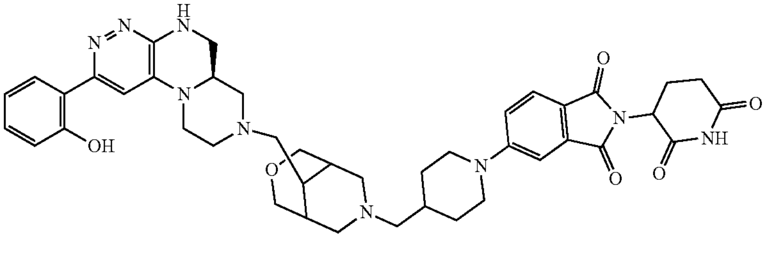 [SMILES: O=C1CCC(N2C(=O)c3ccc(N4CCC(CN5CC6COCC(C5)C6CN5CCN6c7cc(-c8ccccc8O)nnc7NC[C@H]6C5)CC4)cc3C2=O)C(=O)N1] | 2-(2,6-dioxopiperidin-3-yl)-5-(4-((9-(((S)-2-(2-hydroxyphenyl)-5,6,6a,7,9,10-hexahydro-8H-pyrazino[1',2':4,5]pyrazino[2,3-c]pyridazin-8-yl)methyl)-3-oxa-7-azabicyclo[3.3.1]nonan-7-yl)methyl)piperidin-1-yl)isoindoline-1,3-dione |
| 133 | 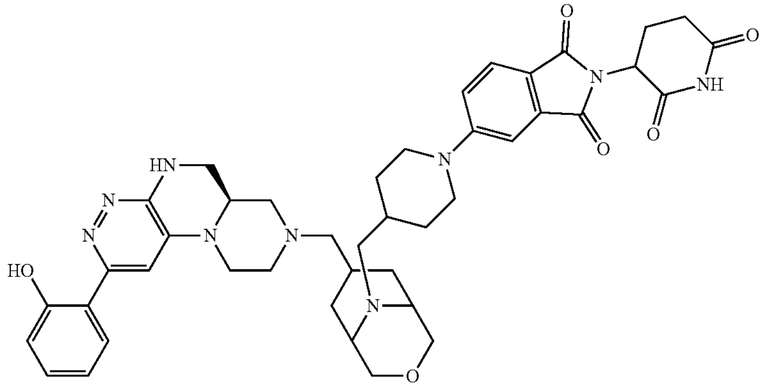 [SMILES: O=C1CCC(N2C(=O)c3ccc(N4CCC(CN5C6COCC5CC(CN5CCN7c8cc(-c9ccccc9O)nnc8NC[C@H]7C5)C6)CC4)cc3C2=O)C(=O)N1] | 2-(2,6-dioxopiperidin-3-yl)-5-(4-((7-(((S)-2-(2-hydroxyphenyl)-5,6,6a,7,9,10-hexahydro-8H-pyrazino[1',2':4,5]pyrazino[2,3-c]pyridazin-8-yl)methyl)-3-oxa-9-azabicyclo[3.3.1]nonan-9-yl)methyl)piperidin-1-yl)isoindoline-1,3-dione |
| 134 | 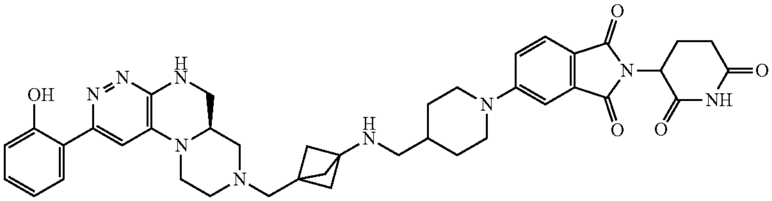 [SMILES: O=C1CCC(N2C(=O)c3ccc(N4CCC(CNC56CC(CN7CCN8c9cc(-c%10ccccc%10O)nnc9NC[C@H]8C7)(C5)C6)CC4)cc3C2=O)C(=O)N1] | 2-(2,6-dioxopiperidin-3-yl)-5-(4-(((3-(((S)-2-(2-hydroxyphenyl)-5,6,6a,7,9,10-hexahydro-8H-pyrazino[1',2':4,5]pyrazino[2,3-c]pyridazin-8-yl)methyl)bicyclo[1.1.1]pentan-1-yl)amino)methyl)piperidin-1-yl)isoindoline-1,3-dione |
| 135 | 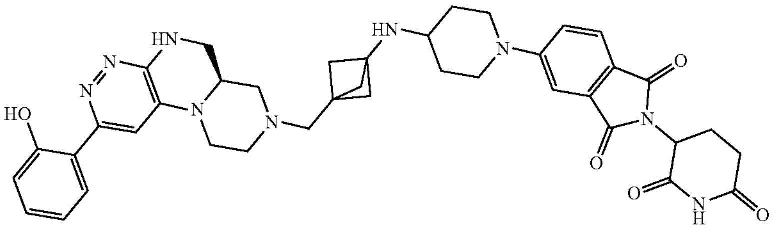 [SMILES: O=C1CCC(N2C(=O)c3ccc(N4CCC(NC56CC(CN7CCN8c9cc(-c%10ccccc%10O)nnc9NC[C@H]8C7)(C5)C6)CC4)cc3C2=O)C(=O)N1] | 2-(2,6-dioxopiperidin-3-yl)-5-(4-((3-(((S)-2-(2-hydroxyphenyl)-5,6,6a,7,9,10-hexahydro-8H-pyrazino[1',2':4,5]pyrazino[2,3-c]pyridazin-8-yl)methyl)bicyclo[1.1.1]pentan-1-yl)amino)piperidin-1-yl)isoindoline-1,3-dione |
| 136 | 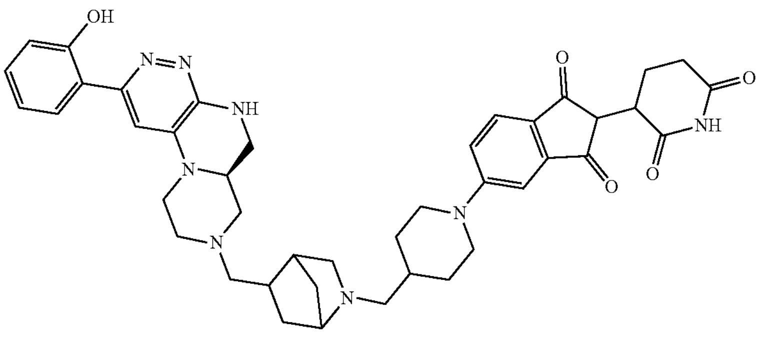 [SMILES: O=C1CCC(C2C(=O)c3ccc(N4CCC(CN5CC6CC5CC6CN5CCN6c7cc(-c8ccccc8O)nnc7NC[C@H]6C5)CC4)cc3C2=O)C(=O)N1] | 2-(2,6-dioxopiperidin-3-yl)-5-(4-((5-(((S)-2-(2-hydroxyphenyl)-5,6,6a,7,9,10-hexahydro-8H-pyrazino[1',2':4,5]pyrazino[2,3-c]pyridazin-8-yl)methyl)-2-azabicyclo[2.2.1]heptan-2-yl)methyl)piperidin-1-yl)isoindoline-1,3-dione |

TABLE 1-continued

Compounds

| Example | Structure | Name |
|---|---|---|
| 137 | 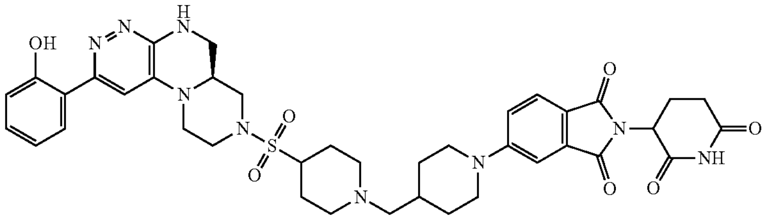 [SMILES: O=C1CCC(N2C(=O)c3ccc(N4CCC(CN5CCC(S(=O)(=O)N6CCN7c8cc(-c9ccccc9O)nnc8NC[C@H]7C6)CC5)CC4)cc3C2=O)C(=O)N1] | 2-(2,6-dioxopiperidin-3-yl)-5-(4-((4-(((S)-2-(2-hydroxyphenyl)-5,6,6a,7,9,10-hexahydro-8H-pyrazino[1',2':4,5]pyrazino[2,3-c]pyridazin-8-yl)sulfonyl)piperidin-1-yl)methyl)piperidin-1-yl)isoindoline-1,3-dione |
| 138 | 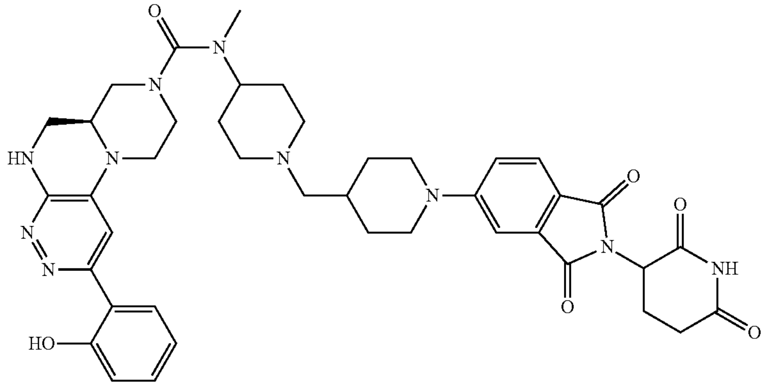 [SMILES: CN(C(=O)N1CCN2c3cc(-c4ccccc4O)nnc3NC[C@H]2C1)C1CCN(CC2CCN(c3ccc4c(c3)C(=O)N(C3CCC(=O)NC3=O)C4=O)CC2)CC1] | (6aS)-N-(1-((1-(2-(2,6-dioxopiperidin-3-yl)-1,3-dioxoisoindolin-5-yl)piperidin-4-yl)methyl)piperidin-4-yl)-2-(2-hydroxyphenyl)-N-methyl-5,6,6a,7,9,10-hexahydro-8H-pyrazino[1',2':4,5]pyrazino[2,3-c]pyridazine-8-carboxamide |
| 139 | 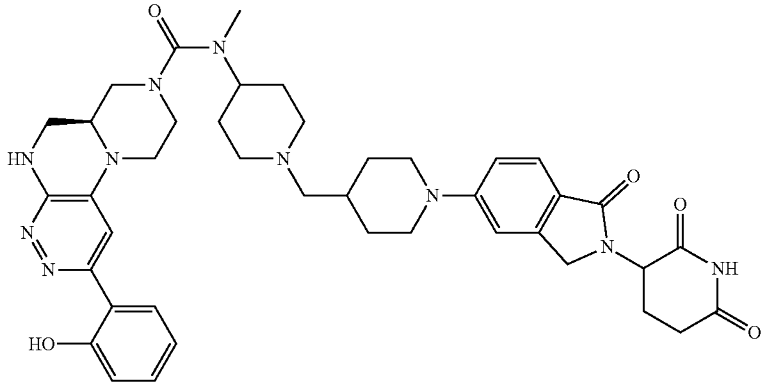 [SMILES: CN(C(=O)N1CCN2c3cc(-c4ccccc4O)nnc3NC[C@H]2C1)C1CCN(CC2CCN(c3ccc4c(c3)CN(C3CCC(=O)NC3=O)C4=O)CC2)CC1] | (6aS)-N-(1-((1-(2-(2,6-dioxopiperidin-3-yl)-1-oxoisoindolin-5-yl)piperidin-4-yl)methyl)piperidin-4-yl)-2-(2-hydroxyphenyl)-N-methyl-5,6,6a,7,9,10-hexahydro-8H-pyrazino[1',2':4,5]pyrazino[2,3-c]pyridazine-8-carboxamide |
| 140 | 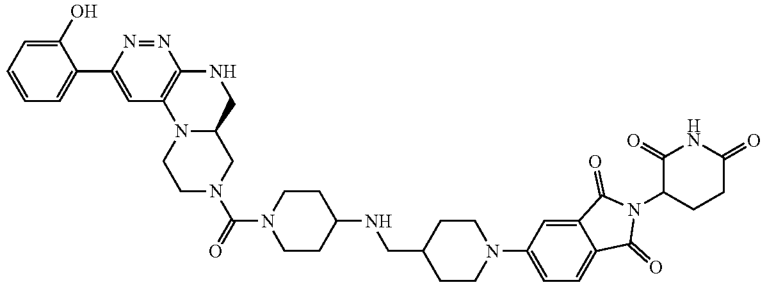 [SMILES: O=C1CCC(N2C(=O)c3ccc(N4CCC(CNC5CCN(C(=O)N6CCN7c8cc(-c9ccccc9O)nnc8NC[C@H]7C6)CC5)CC4)cc3C2=O)C(=O)N1] | 2-(2,6-dioxopiperidin-3-yl)-5-(4-(((1-((S)-2-(2-hydroxyphenyl)-6,6a,7,8,9,10-hexahydro-5H-pyrazino[1',2':4,5]pyrazino[2,3-c]pyridazine-8-carbonyl)piperidin-4-yl)amino)methyl)piperidin-1-yl)isoindoline-1,3-dione |
| 141 | 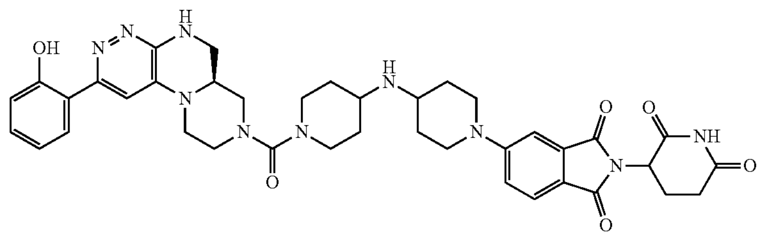 [SMILES: O=C1CCC(N2C(=O)c3ccc(N4CCC(NC5CCN(C(=O)N6CCN7c8cc(-c9ccccc9O)nnc8NC[C@H]7C6)CC5)CC4)cc3C2=O)C(=O)N1] | 2-(2,6-dioxopiperidin-3-yl)-5-(4-((1-((S)-2-(2-hydroxyphenyl)-6,6a,7,8,9,10-hexahydro-5H-pyrazino[1',2':4,5]pyrazino[2,3-c]pyridazine-8-carbonyl)piperidin-4-yl)amino)piperidin-1-yl)isoindoline-1,3-dione |

TABLE 1-continued

Compounds

| Exam-ple | Structure | Name |
| --- | --- | --- |
| 142 | 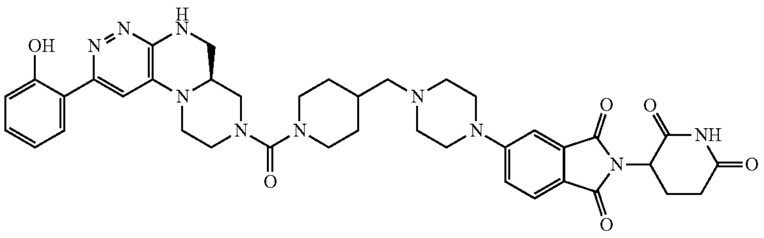 [SMILES: O=C1CCC(N2C(=O)c3ccc(N4CCN(CC5CCN(C(=O)N6CCN7c8cc(-c9ccccc9O)nnc8NC[C@H]7C6)CC5)CC4)cc3C2=O)C(=O)N1] | 2-(2,6-dioxopiperidin-3-yl)-5-(4-((1-((S)-2-(2-hydroxyphenyl)-6,6a,7,8,9,10-hexahydro-5H-pyrazino[1',2':4,5]pyrazino[2,3-c]pyridazine-8-carbonyl)piperidin-4-yl)methyl)piperazin-1-yl)isoindoline-1,3-dione |
| 143 | 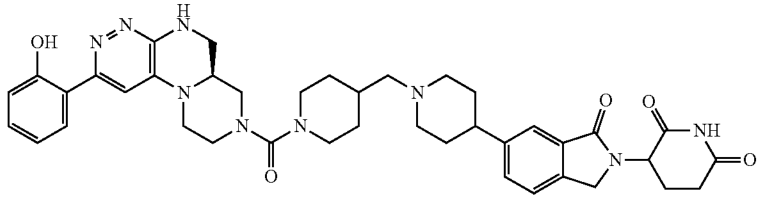 [SMILES: O=C1CCC(N2Cc3ccc(C4CCN(CC5CCN(C(=O)N6CCN7c8cc(-c9ccccc9O)nnc8NC[C@H]7C6)CC5)CC4)cc3C2=O)C(=O)N1] | 3-(6-(1-((1-((S)-2-(2-hydroxyphenyl)-6,6a,7,8,9,10-hexahydro-5H-pyrazino[1',2':4,5]pyrazino[2,3-c]pyridazine-8-carbonyl)piperidin-4-yl)methyl)piperidin-4-yl)-1-oxoisoindolin-2-yl)piperidine-2,6-dione |
| 144 | 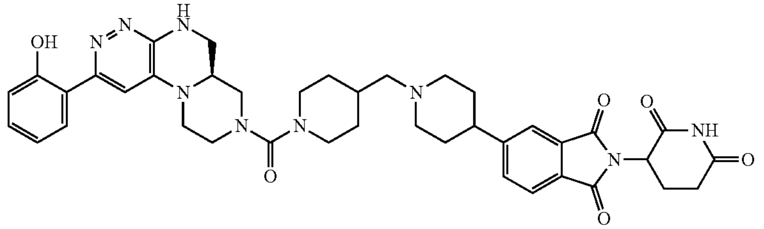 [SMILES: O=C1CCC(N2C(=O)c3ccc(C4CCN(CC5CCN(C(=O)N6CCN7c8cc(-c9ccccc9O)nnc8NC[C@H]7C6)CC5)CC4)cc3C2=O)C(=O)N1] | 2-(2,6-dioxopiperidin-3-yl)-5-(1-((1-((S)-2-(2-hydroxyphenyl)-6,6a,7,8,9,10-hexahydro-5H-pyrazino[1',2':4,5]pyrazino[2,3-c]pyridazine-8-carbonyl)piperidin-4-yl)methyl)piperidin-4-yl)isoindoline-1,3-dione |
| 145 | 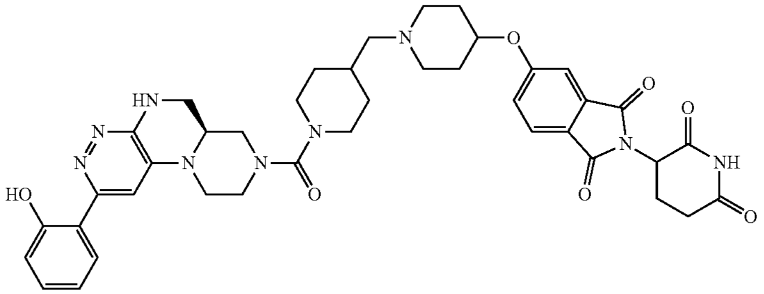 [SMILES: O=C1CCC(N2C(=O)c3ccc(OC4CCN(CC5CCN(C(=O)N6CCN7c8cc(-c9ccccc9O)nnc8NC[C@H]7C6)CC5)CC4)cc3C2=O)C(=O)N1] | 2-(2,6-dioxopiperidin-3-yl)-5-((1-((1-((S)-2-(2-hydroxyphenyl)-6,6a,7,8,9,10-hexahydro-5H-pyrazino[1',2':4,5]pyrazino[2,3-c]pyridazine-8-carbonyl)piperidin-4-yl)methyl)piperidin-4-yl)oxy)isoindoline-1,3-dione |
| 146 | 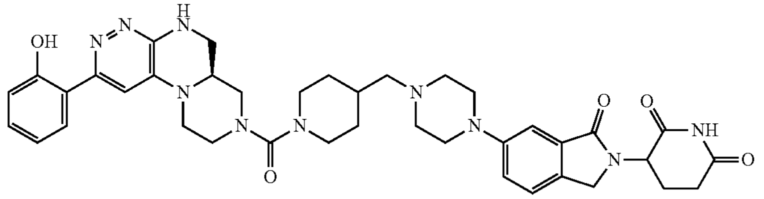 [SMILES: O=C1CCC(N2Cc3ccc(N4CCN(CC5CCN(C(=O)N6CCN7c8cc(-c9ccccc9O)nnc8NC[C@H]7C6)CC5)CC4)cc3C2=O)C(=O)N1] | 3-(6-(4-((1-((S)-2-(2-hydroxyphenyl)-6,6a,7,8,9,10-hexahydro-5H-pyrazino[1',2':4,5]pyrazino[2,3-c]pyridazine-8-carbonyl)piperidin-4-yl)methyl)piperazin-1-yl)-1-oxoisoindolin-2-yl)piperidine-2,6-dione |
| 147 | 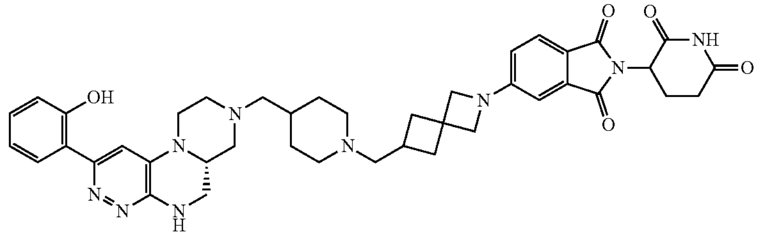 [SMILES: O=C1CCC(N2C(=O)c3ccc(N4CC5(CC(CN6CCC(CN7CCN8c9cc(-c%10ccccc%10O)nnc9NC[C@H]8C7)CC6)C5)C4)cc3C2=O)C(=O)N1] | 2-(2,6-dioxopiperidin-3-yl)-5-(6-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)-2-azaspiro[3.3]heptan-2-yl)isoindoline-1,3-dione |

TABLE 1-continued

| Example | Structure | Name |
|---|---|---|
| 148 | 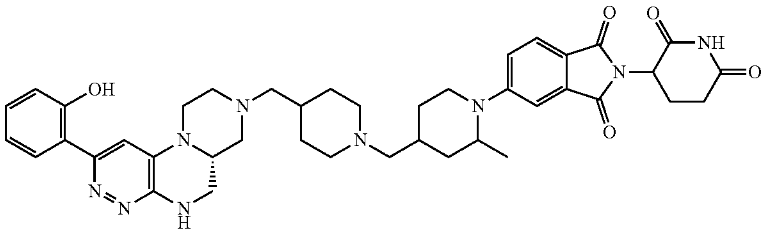 [SMILES: CC1CC(CN2CCC(CN3CCN4c5cc(-c6ccccc6O)nnc5NC[C@H]4C3)CC2)CCN1c1ccc2c(c1)C(=O)N(C1CCC(=O)NC1=O)C2=O] | 2-(2,6-dioxopiperidin-3-yl)-5-(4-((4-(((S)-2-(2-hydroxyphenyl)-5,6,6a,7,9,10-hexahydro-8H-pyrazino[1',2':4,5]pyrazino[2,3-c] pyridazin-8-yl)methyl) piperidin-1-yl)methyl)-2-methylpiperidin-1-yl) isoindoline-1,3-dione |
| 149 | 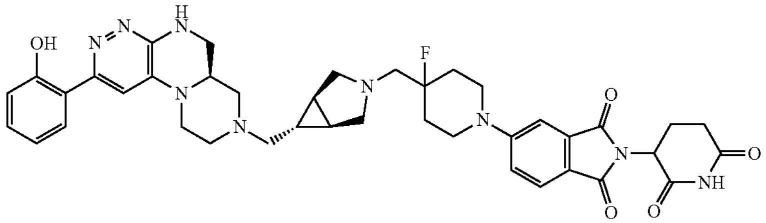 [SMILES: O=C1CCC(N2C(=O)c3ccc(N4CCC(F)(CN5C[C@@H]6[C@@H](CN7CCN8c9cc(-c%10ccccc%10O)nnc9NC[C@H]8C7)[C@@H]6C5)CC4)cc3C2=O)C(=O)N1] | 2-(2,6-dioxopiperidin-3-yl)-5-(4-fluoro-4-(((1R,5S,6s)-6-(((S)-2-(2-hydroxyphenyl)-5,6,6a,7,9,10-hexahydro-8H-pyrazino[1',2':4,5]pyrazino[2,3-c] pyridazin-8-yl)methyl)-3-azabicyclo[3.1.0]hexan-3-yl) methyl)piperidin-1-yl)isoindoline-1,3-dione |
| 150 | 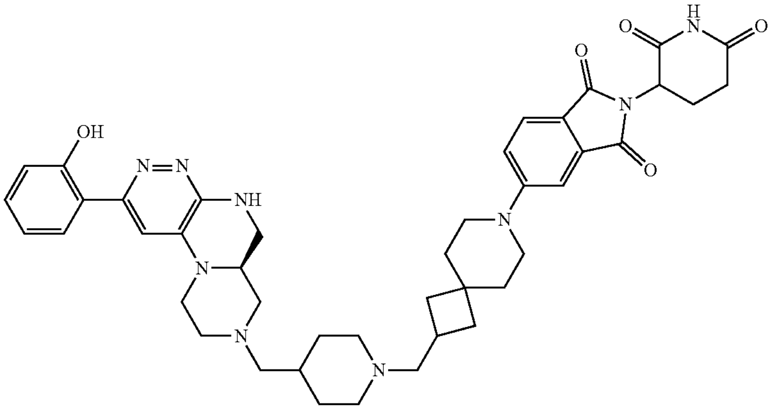 [SMILES: O=C1CCC(N2C(=O)c3ccc(N4CCC5(CC4)CC(CN4CCC(CN6CCN7c8cc(-c9ccccc9O)nnc8NC[C@H]7C6)CC4)C5)cc3C2=O)C(=O)N1] | 2-(2,6-dioxopiperidin-3-yl)-5-(2-((4-(((S)-2-(2-hydroxyphenyl)-5,6,6a,7,9,10-hexahydro-8H-pyrazino[1',2':4,5]pyrazino[2,3-c] pyridazin-8-yl)methyl) piperidin-1-yl)methyl)-7-azaspiro[3.5]nonan-7-yl) isoindoline-1,3-dione |
| 151 | 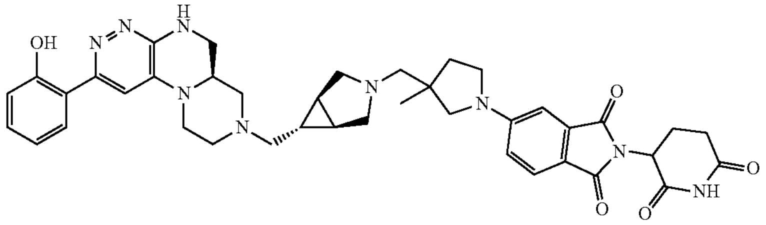 [SMILES: CC1(CN2C[C@@H]3[C@@H](CN4CCN5c6cc(-c7ccccc7O)nnc6NC[C@H]5C4)[C@@H]3C2)CCN(c2ccc3c(c2)C(=O)N(C2CCC(=O)NC2=O)C3=O)C1] | 2-(2,6-dioxopiperidin-3-yl)-5-(3-(((1R,5S,6r)-6-(((S)-2-(2-hydroxyphenyl)-5,6,6a,7,9,10-hexahydro-8H-pyrazino[1',2':4,5]pyrazino[2,3-c] pyridazin-8-yl)methyl)-3-azabicyclo[3.1.0]hexan-3-yl)methyl)-3-methylpyrrolidin-1-yl)isoindoline-1,3-dione |
| 152 | 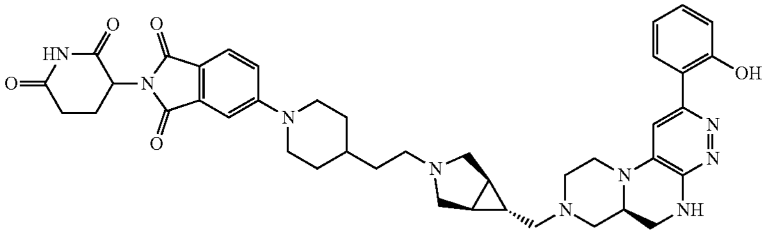 [SMILES: O=C1CCC(N2C(=O)c3ccc(N4CCC(CCN5C[C@@H]6[C@H](C5)[C@H]6CN5CCN6c7cc(-c8ccccc8O)nnc7NC[C@H]6C5)CC4)cc3C2=O)C(=O)N1] | 2-(2,6-dioxopiperidin-3-yl)-5-(4-(2-((1R,5S,6r)-6-(((S)-2-(2-hydroxyphenyl)-5,6,6a,7,9,10-hexahydro-8H-pyrazino[1',2':4,5]pyrazino[2,3-c] pyridazin-8-yl)methyl)-3-azabicyclo[3.1.0]hexan-3-yl)ethyl)piperidin-1-yl)isoindoline-1,3-dione |

TABLE 1-continued

| Example | Structure | Name |
|---|---|---|
| | Compounds | |
| 153 | 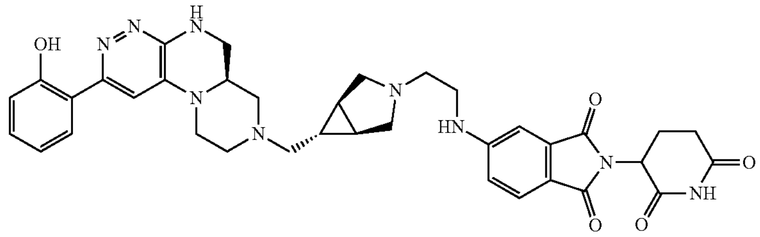 [SMILES: O=C1CCC(N2C(=O)c3ccc(NCCN4C[C@@H]5[C@H](C4)[C@H]5CN4CCN5c6cc(-c7ccccc7O)nnc6NC[C@H]5C4)cc3C2=O)C(=O)N1] | 2-(2,6-dioxopiperidin-3-yl)-5-((2-((1R,5S,6r)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)ethyl)amino)isoindoline-1,3-dione |
| 154 | 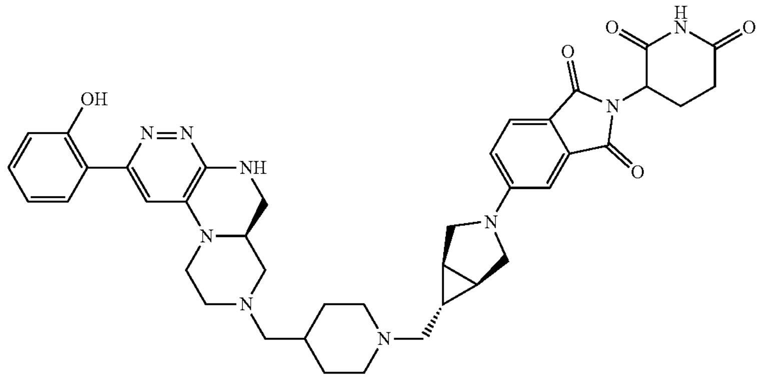 [SMILES: O=C1CCC(N2C(=O)c3ccc(N4C[C@@H]5[C@@H](CN6CCC(CN7CCN8c9cc(-c%10ccccc%10O)nnc9NC[C@H]8C7)CC6)[C@@H]5C4)cc3C2=O)C(=O)N1] | 2-(2,6-dioxopiperidin-3-yl)-5-((1R,5S,6s)-6-((4-(((S)-2-(2-hydroxyphenyl)-5,6,6a,7,9,10-hexahydro-8H-pyrazino pyrazino[1',2':4,5]pyrazino[2,3-c]pyridazin-8-yl)methyl)piperidin-1-yl)methyl)-3-azabicyclo[3.1.0]hexan-3-yl)isoindoline-1,3-dione |
| 155 | 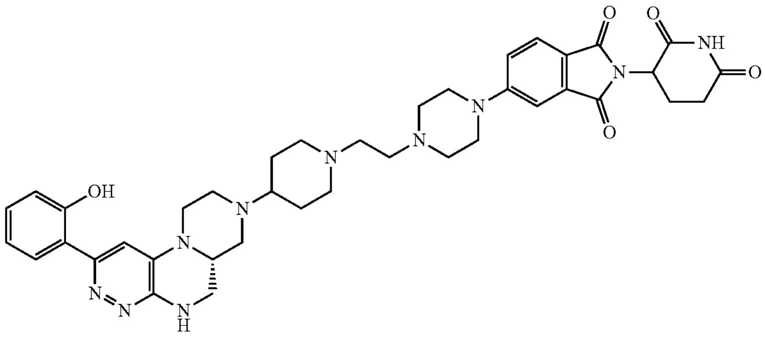 [SMILES: O=C1CCC(N2C(=O)c3ccc(N4CCN(CCN5CCC(N6CCN7c8cc(-c9ccccc9O)nnc8NC[C@H]7C6)CC5)CC4)cc3C2=O)C(=O)N1] | 2-(2,6-dioxopiperidin-3-yl)-5-(4-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethyl)piperazin-1-yl)isoindoline-1,3-dione |
| 156 | 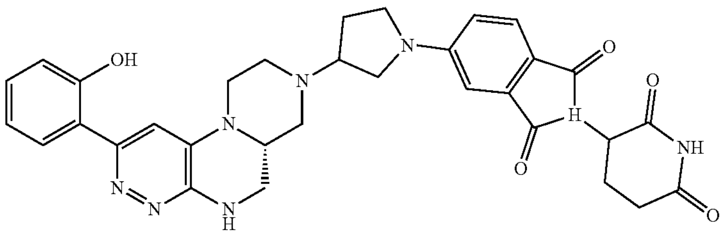 | 2-(2,6-dioxopiperidin-3-yl)-5-(3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)isoindoline-1,3-dione |

TABLE 1-continued

| Compounds | | |
|---|---|---|
| Example | Structure | Name |
| 157 | 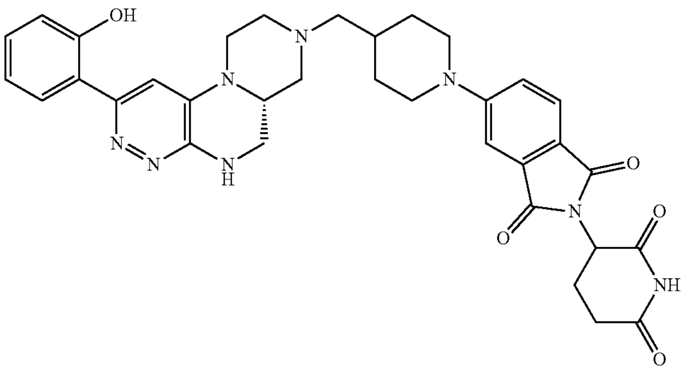 [SMILES: O=C1CCC(N2C(=O)c3ccc(N4CCC(CN5CCN6c7cc(-c8ccccc8O)nnc7NC[C@H]6C5)CC4)cc3C2=O)C(=O)N1] | 2-(2,6-dioxopiperidin-3-yl)-5-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)isoindoline-1,3-dione |
| 158 | 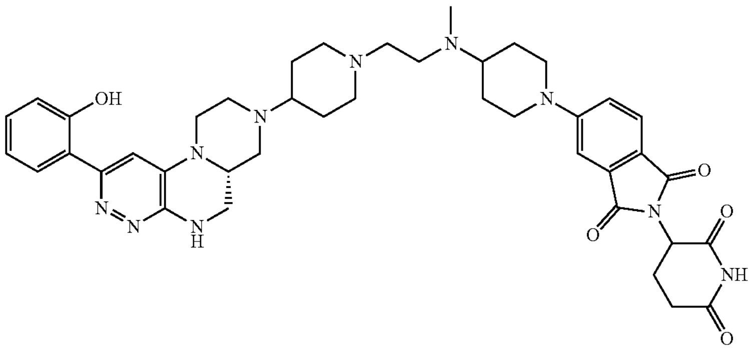 [SMILES: CN(CCN1CCC(N2CCN3c4cc(-c5ccccc5O)nnc4NC[C@H]3C2)CC1)C1CCN(c2ccc3c(c2)C(=O)N(C2CCC(=O)NC2=O)C3=O)CC1] | 2-(2,6-dioxopiperidin-3-yl)-5-(4-((2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethyl)(methyl)amino)piperidin-1-yl)isoindoline-1,3-dione |
| 159 | 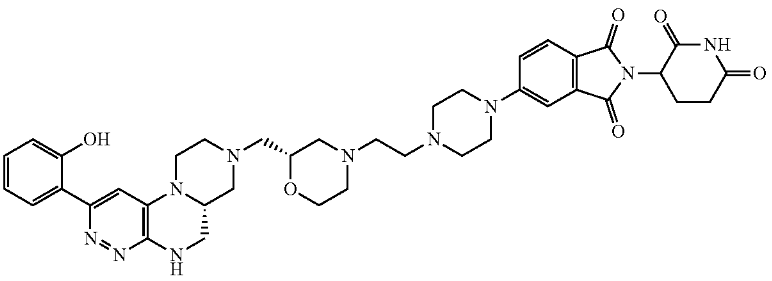 [SMILES: O=C1CCC(N2C(=O)c3ccc(N4CCN(CCN5CCO[C@H](CN6CCN7c8cc(-c9ccccc9O)nnc8NC[C@H]7C6)C5)CC4)cc3C2=O)C(=O)N1] | 2-(2,6-dioxopiperidin-3-yl)-5-(4-(2-((R)-2-(((S)-2-(2-hydroxyphenyl)-5,6,6a,7,9,10-hexahydro-8H-pyrazino[1',2':4,5]pyrazino[2,3-c]pyridazin-8-yl)methyl)morpholino)ethyl)piperazin-1-yl)isoindoline-1,3-dione |
| 160 | 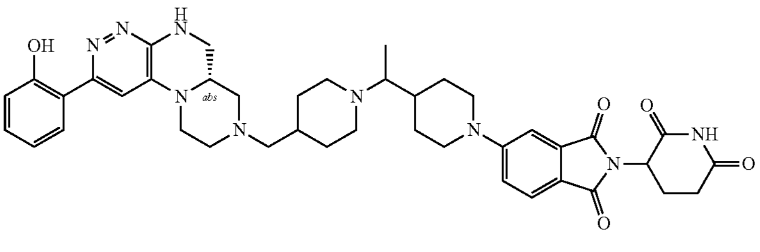 [SMILES: CC(C1CCN(c2ccc3c(c2)C(=O)N(C2CCC(=O)NC2=O)C3=O)CC1)N1CCC(CN2CCN3c4cc(-c5ccccc5O)nnc4NC[C@@H]3C2)CC1] | 2-(2,6-dioxopiperidin-3-yl)-5-[4-[1-[4-[[(10S)-4-(2-hydroxyphenyl)-1,5,6,8,12-pentazatricyclo[8.4.0.02,7]tetradeca-2(7),3,5-trien-12-yl]methyl]piperidin-1-yl]ethyl]piperidin-1-yl]isoindole-1,3-dione |
| 161 | 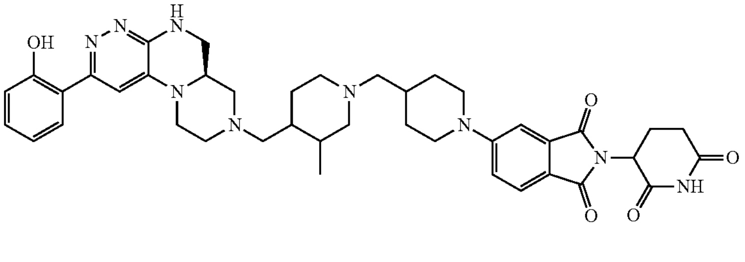 [SMILES: CC1CN(CC2CCN(c3ccc4c(c3)C(=O)N(C3CCC(=O)NC3=O)C4=O)CC2)CCC1CN1CCN2c3cc(-c4ccccc4O)nnc3NC[C@H]2C1] | 2-(2,6-dioxopiperidin-3-yl)-5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)-3-methylpiperidin-1-yl)methyl)piperidin-1-yl)isoindoline-1,3-dione |

TABLE 1-continued

| Compounds | | |
|---|---|---|
| Example | Structure | Name |
| 162 | 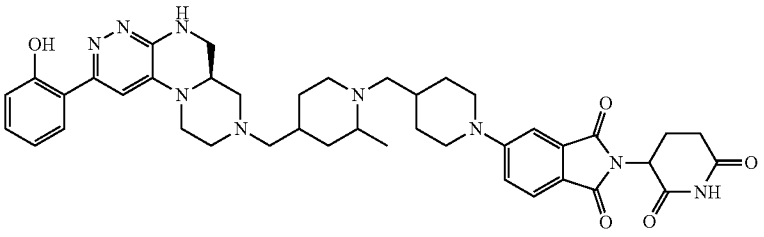 [SMILES: CC1CC(CN2CCN3c4cc(-c5ccccc5O)nnc4NC[C@H]3C2)CCN1CC1CCN(c2ccc3c(c2)C(=O)N(C2CCC(=O)NC2=O)C3=O)CC1] | 2-(2,6-dioxopiperidin-3-yl)-5-[4-[[4-[[(10S)-4-(2-hydroxyphenyl)-1,5,6,8,12-pentazatricyclo[8.4.0.02,7]tetradeca-2,4,6-trien-12-yl]methyl]-2-methylpiperidine-1-yl]methyl]piperidin-1-yl]isoindole-1,3-dione |
| 163 | 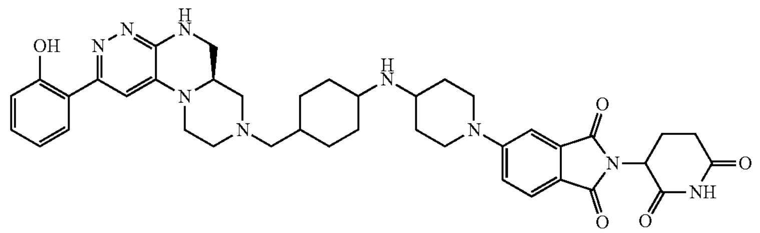 [SMILES: O=C1CCC(N2C(=O)c3ccc(N4CCC(NC5CCC(CN6CCN7c8cc(-c9ccccc9O)nnc8NC[C@H]7C6)CC5)CC4)cc3C2=O)C(=O)N1] | 2-(2,6-dioxopiperidin-3-yl)-5-[4-[[4-[[(10S)-4-(2-hydroxyphenyl)-1,5,6,8,12-pentazatricyclo[8.4.0.02,7]tetradeca-2,4,6-trien-12-yl]methyl]cyclohexyl]amino]piperidin-1-yl]isoindole-1,3-dione |
| 164 | 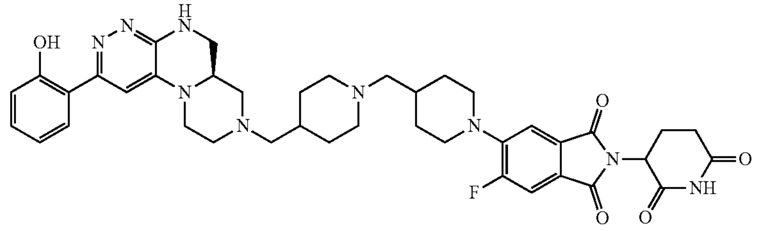 | 2-(2,6-dioxopiperidin-3-yl)-5-fluoro-6-[4-[[4-[[(10S)-4-(2-hydroxyphenyl)-1,5,6,8,12-pentazatricyclo[8.4.0.02,7]tetradeca-2,4,6-trien-12-yl]methyl]piperidin-1-yl]methyl]piperidin-1-yl]isoindole-1,3-dione |
| 165 | 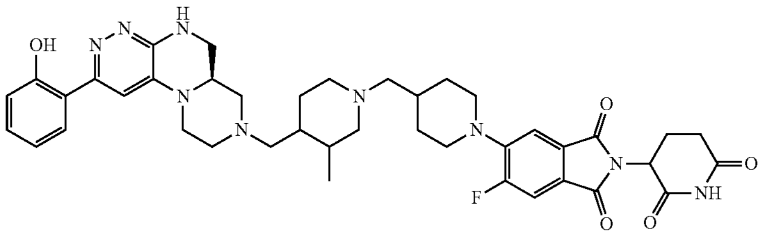 [SMILES: CC1CN(CC2CCN(c3cc4c(cc3F)C(=O)N(C3CCC(=O)NC3=O)C4=O)CC2)CCC1CN1CCN2c3cc(-c4ccccc4O)nnc3NC[C@H]2C1] | 2-(2,6-dioxopiperidin-3-yl)-5-fluoro-6-[4-[[4-[[(10S)-4-(2-hydroxyphenyl)-1,5,6,8,12-pentazatricyclo[8.4.0.02,7]tetradeca-2,4,6-trien-12-yl]methyl]-3-methylpiperidin-1-yl]methyl]piperidin-1-yl]isoindole-1,3-dione |
| 166 | 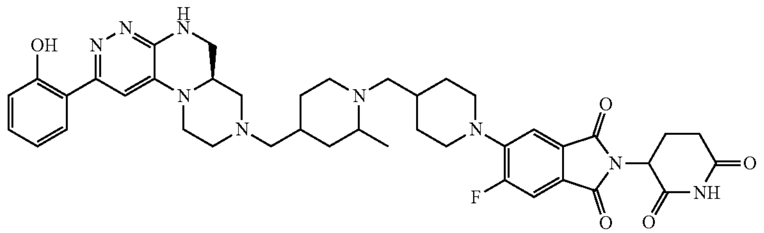 [SMILES: CC1CC(CN2CCN3c4cc(-c5ccccc5O)nnc4NC[C@H]3C2)CCN1CC1CCN(c2cc3c(cc2F)C(=O)N(C2CCC(=O)NC2=O)C3=O)CC1] | 2-(2,6-dioxopiperidin-3-yl)-5-fluoro-6-[4-[[4-[[(10S)-4-(2-hydroxyphenyl)-1,5,6,8,12-pentazatricyclo[8.4.0.02,7]tetradeca-2,4,6-trien-12-yl]methyl]-2-methylpiperidin-1-yl]methyl]piperidin-1-yl]isoindole-1,3-dione |
| 167 | 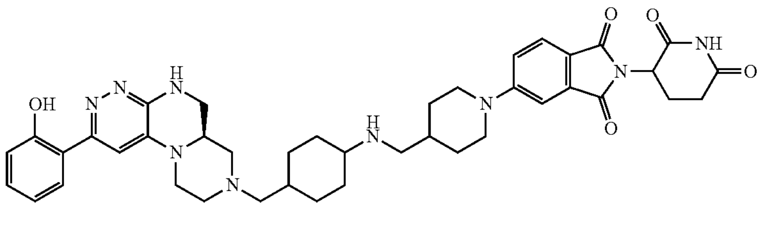 [SMILES: O=C1CCC(N2C(=O)c3ccc(N4CCC(CNC5CCC(CN6CCN7c8cc(-c9ccccc9O)nnc8NC[C@H]7C6)CC5)CC4)cc3C2=O)C(=O)N1] | 2-(2,6-dioxopiperidin-3-yl)-5-[4-[[[4-[[(10S)-4-(2-hydroxyphenyl)-1,5,6,8,12-pentazatricyclo[8.4.0.02,7]tetradeca-2,4,6-trien-12-yl]methyl]cyclohexyl]amino]methyl]piperidin-1-yl]isoindole-1,3-dione |

TABLE 1-continued

| Compounds | | |
|---|---|---|
| Example | Structure | Name |
| 168 | 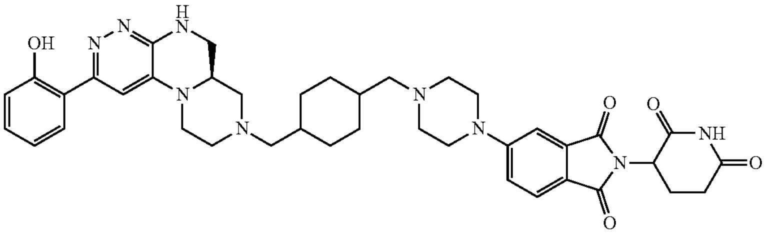 [SMILES: O=C1CCC(N2C(=O)c3ccc(N4CCN(CC5CCC(CN6CCN7c8cc(-c9ccccc9O)nnc8NC[C@H]7C6)CC5)CC4)cc3C2=O)C(=O)N1] | 2-(2,6-dioxopiperidin-3-yl)-5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)cyclohexyl)methyl)piperazin-1-yl)isoindoline-1,3-dione |
| 169 | 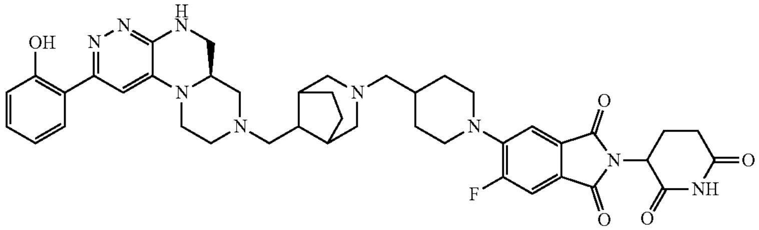 [SMILES: O=C1CCC(N2C(=O)c3cc(F)c(N4CCC(CN5CC6CCC(C5)C6CN5CCN6c7cc(-c8ccccc8O)nnc7NC[C@H]6C5)CC4)cc3C2=O)C(=O)N1] | 2-(2,6-dioxopiperidin-3-yl)-5-fluoro-6-[4-[[8-[[(10S)-4-(2-hydroxyphenyl)-1,5,6,8,12-pentazatricyclo[8.4.0.02,7]tetradeca-2,4,6-trien-12-yl]methyl]-3-azabicyclo[3.2.1]octan-3-yl]methyl]piperidin-1-yl]isoindole-1,3-dione |
| 170 | 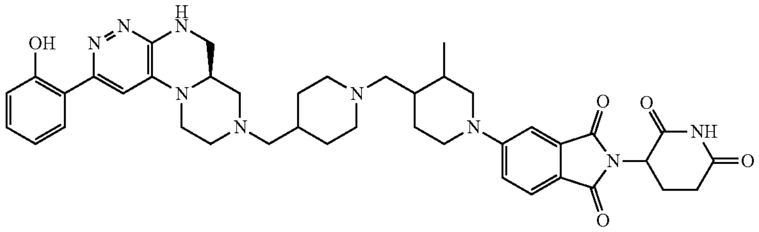 [SMILES: CC1CN(c2ccc3c(c2)C(=O)N(C2CCC(=O)NC2=O)C3=O)CCC1CN1CCC(CN2CCN3c4cc(-c5ccccc5O)nnc4NC[C@H]3C2)CC1] | 2-(2,6-dioxopiperidin-3-yl)-5-[4-[[4-[[(10S)-4-(2-hydroxyphenyl)-1,5,6,8,12-pentazatricyclo[8.4.0.02,7]tetradeca-2(7),3,5-trien-12-yl]methyl]piperidin-1-yl]methyl]-3-methylpiperidin-1-yl]isoindole-1,3-dione |
| 171 | 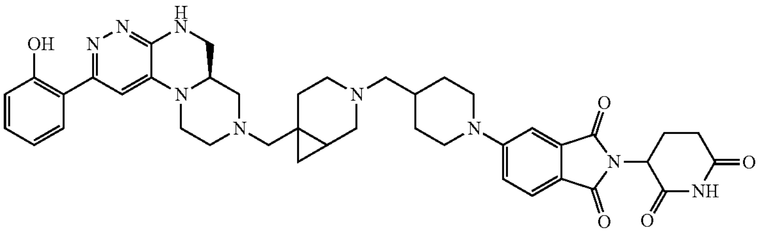 [SMILES: O=C1CCC(N2C(=O)c3ccc(N4CCC(CN5CCC6(CN7CCN8c9cc(-c%10ccccc%10O)nnc9NC[C@H]8C7)CC6C5)CC4)cc3C2=O)C(=O)N1] | 2-(2,6-dioxopiperidin-3-yl)-5-[4-[[6-[[(10S)-4-(2-hydroxyphenyl)-1,5,6,8,12-pentazatricyclo[8.4.0.02,7]tetradeca-2,4,6-trien-12-yl]methyl]-3-azabicyclo[4.1.0]heptan-3-yl]methyl]piperidin-1-yl]isoindole-1,3-dione |
| 172 | 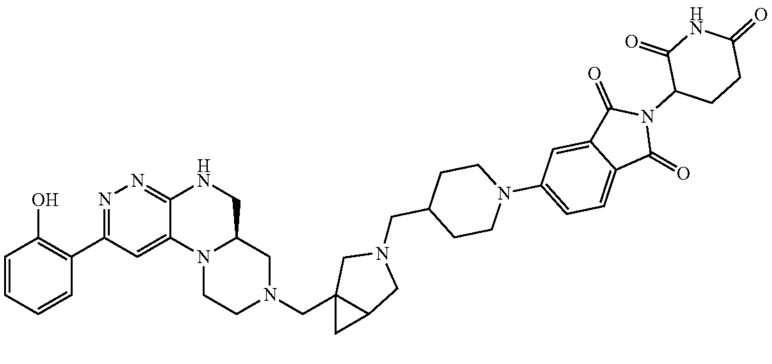 [SMILES: O=C1CCC(N2C(=O)c3ccc(N4CCC(CN5CC6CC6(CN6CCN7c8cc(-c9ccccc9O)nnc8NC[C@H]7C6)C5)CC4)cc3C2=O)C(=O)N1] | 2-(2,6-dioxopiperidin-3-yl)-5-[4-[[1-[[(10S)-4-(2-hydroxyphenyl)-1,5,6,8,12-pentazatricyclo[8.4.0.02,7]tetradeca-2,4,6-trien-12-yl]methyl]-3-azabicyclo[3.1.0]hexan-3-yl]methyl]piperidin-1-yl]isoindole-1,3-dione |
| 173 | 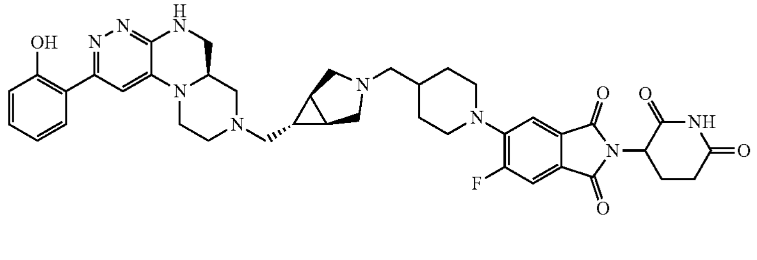 [SMILES: O=C1CCC(N2C(=O)c3cc(F)c(N4CCC(CN5C[C@@H]6[C@H](C5)[C@H]6CN5CCN6c7cc(-c8ccccc8O)nnc7NC[C@H]6C5)CC4)cc3C2=O)C(=O)N1] | 2-(2,6-dioxopiperidin-3-yl)-5-fluoro-6-[4-[[(1S,5R)-6-[[(10S)-4-(2-hydroxyphenyl)-1,5,6,8,12-pentazatricyclo[8.4.0.02,7]tetradeca-2,4,6-trien-12-yl]methyl]-3-azabicyclo[3.1.0]hexan-3-yl]methyl]piperidin-1-yl]isoindole-1,3-dione |

TABLE 1-continued

| Compounds | | |
|---|---|---|
| Example | Structure | Name |
| 174 | 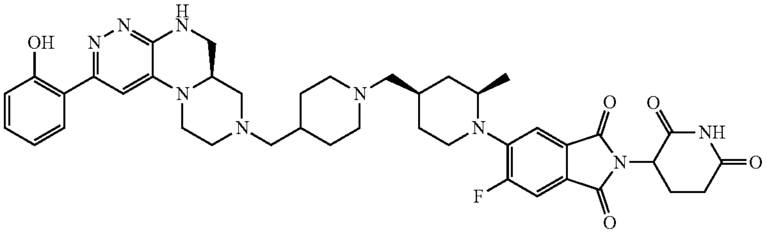 [SMILES: C[C@@H]1C[C@H](CN2CCC(CN3CCN4c5cc(-c6ccccc6O)nnc5NC[C@H]4C3)CC2)CCN1c1cc2c(cc1F)C(=O)N(C1CCC(=O)NC1=O)C2=O] | 2-(2,6-dioxopiperidin-3-yl)-5-fluoro-6-[(2R,4R)-4-[[4-[[(10S)-4-(2-hydroxyphenyl)-1,5,6,8,12-pentazatricyclo[8.4.0.02,7]tetradeca-2,4,6-trien-12-yl]methyl]piperidin-1-yl]methyl]-2-methylpiperidin-1-yl]isoindole-1,3-dione |
| 175 | 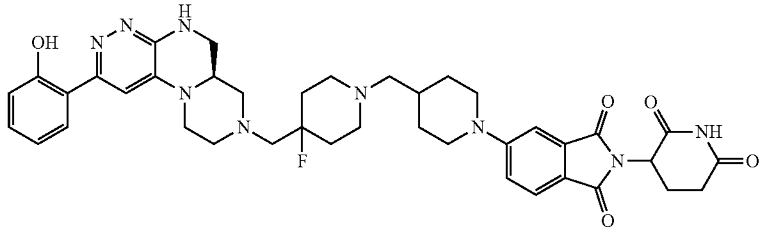 [SMILES: O=C1CCC(N2C(=O)c3ccc(N4CCC(CN5CCC(F)(CN6CCN7c8cc(-c9ccccc9O)nnc8NC[C@H]7C6)CC5)CC4)cc3C2=O)C(=O)N1] | 2-(2,6-dioxopiperidin-3-yl)-5-[4-[[4-fluoro-4-[[(10S)-4-(2-hydroxyphenyl)-1,5,6,8,12-pentazatricyclo[8.4.0.02,7]tetradeca-2,4,6-trien-12-yl]methyl]piperidin-1-yl]methyl]piperidin-1-yl]isoindole-1,3-dione |
| 176 | 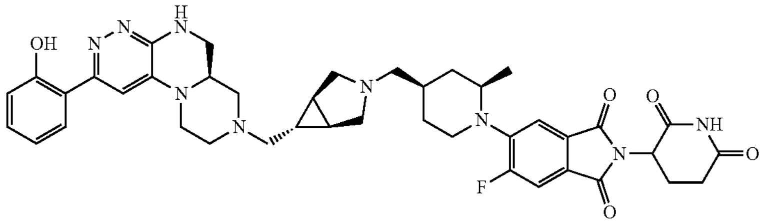 [SMILES: C[C@@H]1C[C@H](CN2C[C@@H]3[C@H](C2)[C@H]3CN2CCN3c4cc(-c5ccccc5O)nnc4NC[C@H]3C2)CCN1c1cc2c(cc1F)C(=O)N(C1CCC(=O)NC1=O)C2=O] | 2-(2,6-dioxopiperidin-3-yl)-5-fluoro-6-[(2R,4R)-4-[[(1S,5R)-6-[[(10S)-4-(2-hydroxyphenyl)-1,5,6,8,12-pentazatricyclo[8.4.0.02,7]tetradeca-2,4,6-trien-12-yl]methyl]-3-azabicyclo[3.1.0]hexan-3-yl]methyl]-2-methylpiperidin-1-yl]isoindole- |
| 177 | 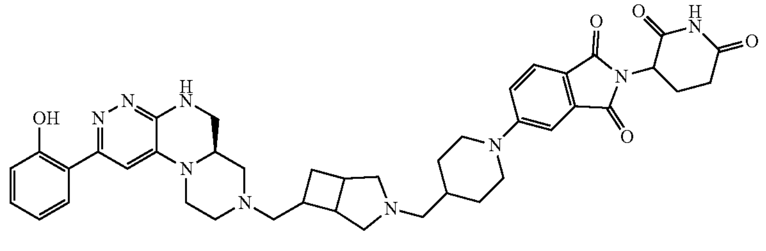 [SMILES: O=C1CCC(N2C(=O)c3ccc(N4CCC(CN5CC6CC(CN7CCN8c9cc(-c%10ccccc%10O)nnc9NC[C@H]8C7)C6C5)CC4)cc3C2=O)C(=O)N1] | 2-(2,6-dioxopiperidin-3-yl)-5-[4-[[6-[[(10S)-4-(2-hydroxyphenyl)-1,5,6,8,12-pentazatricyclo[8.4.0.02,7]tetradeca-2,4,6-trien-12-yl]methyl]-3-azabicyclo[3.2.0]heptan-3-yl]methyl]piperidin-1-yl]isoindole-1,3-dione |
| 178 | 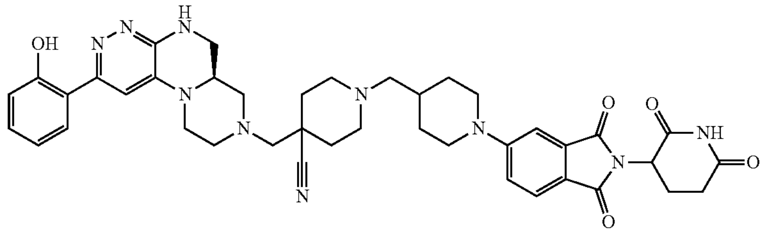 [SMILES: N#CC1(CN2CCN3c4cc(-c5ccccc5O)nnc4NC[C@H]3C2)CCN(CC2CCN(c3ccc4c(c3)C(=O)N(C3CCC(=O)NC3=O)C4=O)CC2)CC1] | 1-[[1-[2-(2,6-dioxopiperidin-3-yl)-1,3-dioxoisoindol-5-yl]piperidin-4-yl]methyl]-4-[[(10S)-4-(2-hydroxyphenyl)-1,5,6,8,12-pentazatricyclo[8.4.0.02,7]tetradeca-2,4,6-trien-12-yl]methyl]piperidine-4-carbonitrile |
| 179 | 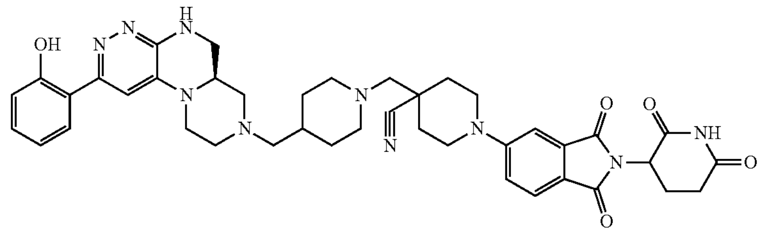 [SMILES: N#CC1(CN2CCC(CN3CCN4c5cc(-c6ccccc6O)nnc5NC[C@H]4C3)CC2)CCN(c2ccc3c(c2)C(=O)N(C2CCC(=O)NC2=O)C3=O)CC1] | 1-[2-(2,6-dioxopiperidin-3-yl)-1,3-dioxoisoindol-5-y]-4-[[4-[[(10S)-4-(2-hydroxyphenyl)-1,5,6,8,12-pentazatricyclo[8.4.0.02,7]tetradeca-2,4,6-trien-12-yl]methyl]piperidin-1-yl]methyl]piperidine-4-carbonitrile |

TABLE 1-continued

| Compounds | | |
|---|---|---|
| Example | Structure | Name |
| 180 | 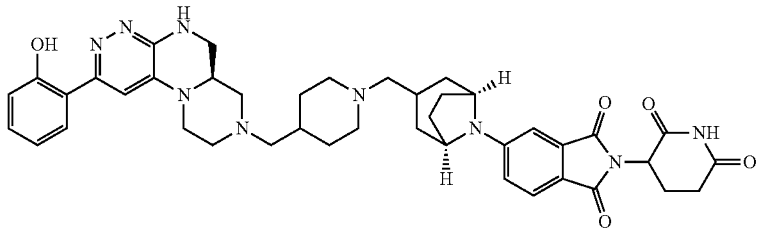 [SMILES: O=C1CCC(N2C(=O)c3ccc(N4[C@@H]5CC[C@H]4CC(CN4CCC(CN6CCN7c8cc(-c9ccccc9O)nnc8NC[C@H]7C6)CC4)C5)cc3C2=O)C(=O)N1] | 2-(2,6-dioxopiperidin-3-yl)-5-[(1S,5R)-3-[[4-[[(10S)-4-(2-hydroxyphenyl)-1,5,6,8,12-pentazatricyclo[8.4.0.02,7]tetradeca-2,4,6-trien-12-yl]methyl]piperidin-1-yl]methyl]-8-azabicyclo[3.2.1]octan-8-yl]isoindole-1,3-dione |
| 181 | 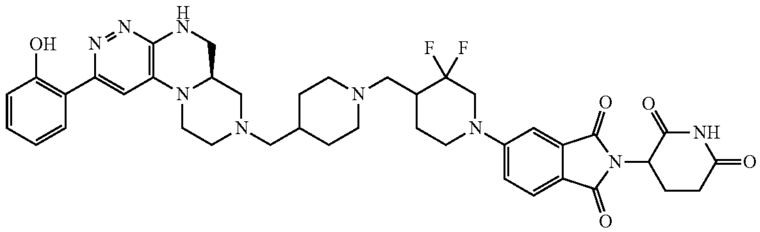 [SMILES: O=C1CCC(N2C(=O)c3ccc(N4CCC(CN5CCC(CN6CCN7c8cc(-c9ccccc9O)nnc8NC[C@H]7C6)CC5)C(F)(F)C4)cc3C2=O)C(=O)N1] | 5-[3,3-difluoro-4-[[4-[[(10S)-4-(2-hydroxyphenyl)-1,5,6,8,12-pentazatricyclo[8.4.0.02,7]tetradeca-2,4,6-trien-12-yl]methyl]piperidin-1-yl]mehtyl]piperidin-1-yl]-2-(2,6-dioxopiperidin-3-yl)isoindoline-1,3-dione |
| 182 | 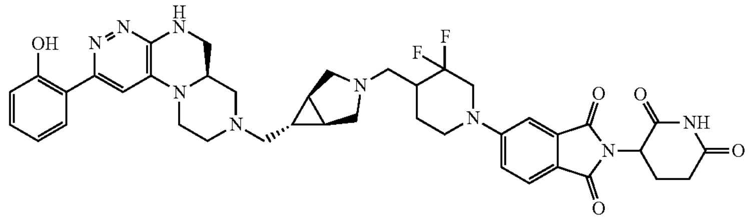 [SMILES: O=C1CCC(N2C(=O)c3ccc(N4CCC(CN5C[C@@H]6[C@H](C5)[C@H]6CN5CCN6c7cc(-c8ccccc8O)nnc7NC[C@H]6C5)C(F)(F)C4)cc3C2=O)C(=O)N1] | 5-[3,3-difluoro-4-[[(1S,5R)-6-[[(10S)-4-(2-hydroxyphenyl)-1,5,6,8,12-pentazatricyclo[8.4.0.02,7]tetradeca-2(7),3,5-trien-12-yl]methyl]-3-azabicyclo[3.1.0]hexan-3-yl]methyl]piperidin-1-yl]-2-(2,6-dioxopiperidin-3-yl)isoindole-1,3-dione |
| 183 | 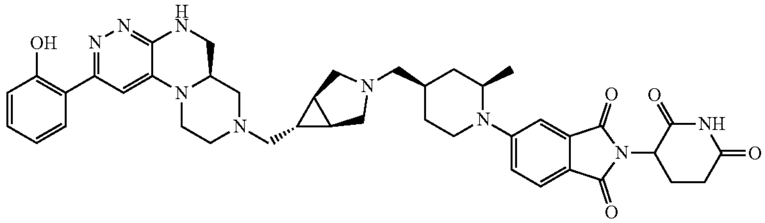 [SMILES: C[C@@H]1C[C@H](CN2C[C@@H]3[C@H](C2)[C@H]3CN2CCN3c4cc(-c5ccccc5O)nnc4NC[C@H]3C2)CCN1c1ccc2c(c1)C(=O)N(C1CCC(=O)NC1=O)C2=O] | 2-(2,6-dioxopiperidin-3-yl)-5-[(2R,4R)-4-[[(1S,5R)-6-[[(10S)-4-(2-hydroxyphenyl)-1,5,6,8,12-pentazatricyclo[8.4.0.02,7]tetradeca-2,4,6-trien-12-yl]methyl]-3-azabicyclo[3.1.0]hexan-3-yl]methyl]-2-methylpiperidin-1-yl]isoindole-1,3-dione |
| 184 | 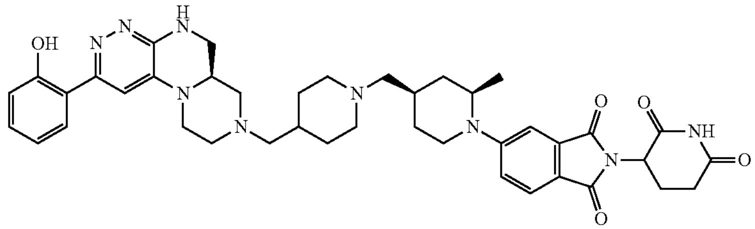 [SMILES: C[C@@H]1C[C@H](CN2CCC(CN3CCN4c5cc(-c6ccccc6O)nnc5NC[C@H]4C3)CC2)CCN1c1ccc2c(c1)C(=O)N(C1CCC(=O)NC1=O)C2=O] | 2-(2,6-dioxopiperidin-3-yl)-5-[(2R,4R)-4-[[4-[[(10S)-4-(2-hydroxyphenyl)-1,5,6,8,12-pentazatricyclo[8.4.0.02,7]tetradeca-2,4,6-trien-12-yl]methyl]piperidin-1-yl]methyl]-2-methylpiperidin-1-yl]isoindole-1,3-dione |
| 185 | 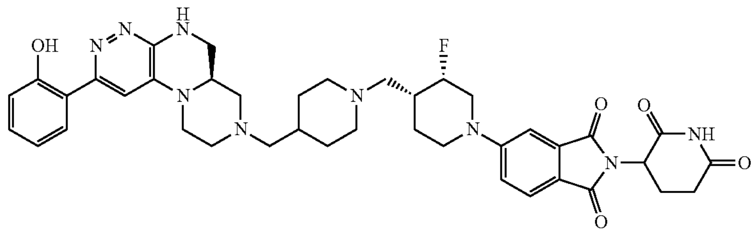 [SMILES: O=C1CCC(N2C(=O)c3ccc(N4CC[C@H](CN5CCC(CN6CCN7c8cc(-c9ccccc9O)nnc8NC[C@H]7C6)CC5)[C@H](F)C4)cc3C2=O)C(=O)N1] | 2-(2,6-dioxopiperidin-3-yl)-5-[(3S,4R)-3-fluoro-4-[[4-[[(10S)-4-(2-hydroxyphenyl)-1,5,6,8,12-pentazatricyclo[8.4.0.02,7]tetradeca-2(7),3,5-trien-12-yl]methyl]piperidin-1-yl]methyl]piperidin-1-yl]isoindole-1,3-dione |

TABLE 1-continued

| Compounds | | |
|---|---|---|
| Example | Structure | Name |
| 186 | 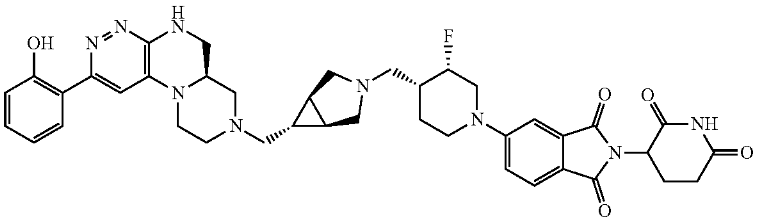 [SMILES: O=C1CCC(N2C(=O)c3ccc(N4CC[C@H](CN5C[C@@H]6[C@H](C5)[C@H]6CN5CCN6c7cc(-c8ccccc8O)nnc7NC[C@H]6C5)[C@H](F)C4)cc3C2=O)C(=O)N1] | 2-(2,6-dioxopiperidin-3-yl)-5-[(3S,4R)-3-fluoro-4-[[(1S,5R)-6-[[(10S)-4-(2-hydroxyphenyl)-1,5,6,8,12-pentazatricyclo[8.4.0.02,7]tetradeca-2(7),3,5-trien-12-yl]methyl]-3-azabicyclo[3.1.0]hexan-3-yl]methyl]piperidin-1-yl]isoindole-1,3-dione |
| 187 | 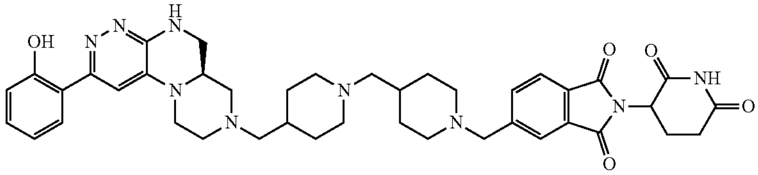 [SMILES: O=C1CCC(N2C(=O)c3ccc(CN4CCC(CN5CCC(CN6CCN7c8cc(-c9ccccc9O)nnc8NC[C@H]7C6)CC5)CC4)cc3C2=O)C(=O)N1] | 2-(2,6-dioxopiperidin-3-yl)-5-[[4-[[4-[[(10S)-4-(2-hydroxyphenyl)-1,5,6,8,12-pentazatricyclo[8.4.0.02,7]tetradeca-2,4,6-trien-12-yl]methyl]piperidin-1-yl]methyl]piperidin-1-yl]methyl] Isoindole-1,3-dione |
| 188 | 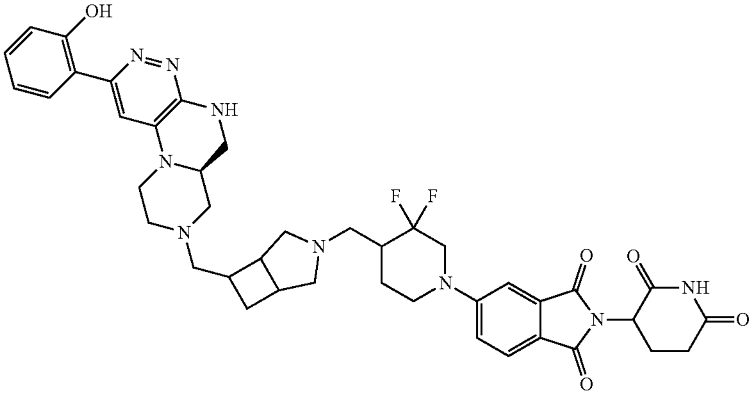 [SMILES: O=C1CCC(N2C(=O)c3ccc(N4CCC(CN5CC6CC(CN7CCN8c9cc(-c%10ccccc%10O)nnc9NC[C@H]8C7)C6C5)C(F)(F)C4)cc3C2=O)C(=O)N1] | 5-[3,3-difluoro-4-[[6-[[(10S)-4-(2-hydroxyphenyl)-1,5,6,8,12-pentazatricyclo[8.4.0.02,7]tetradeca-2(7),3,5-trien-12-yl]methyl]-3-azabicyclo[3.2.0]heptan-3-yl]methyl]piperidin-1-yl]-2-(2,6-dioxopiperidin-3-yl)isoindole-1,3-dione |
| 189 | 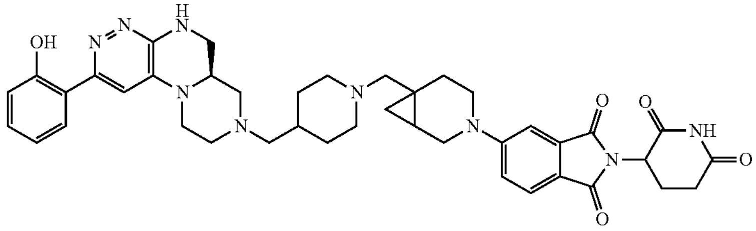 [SMILES: O=C1CCC(N2C(=O)c3ccc(N4CCC5(CN6CCC(CN7CCN8c9cc(-c%10ccccc%10O)nnc9NC[C@H]8C7)CC6)CC5C4)cc3C2=O)C(=O)N1] | 2-(2,6-dioxopiperidin-3-yl)-5-[6-[[4-[[(10S)-4-(2-hydroxyphenyl)-1,5,6,8,12-pentazatricyclo[8.4.0.02,7]tetradeca-2(7),3,5-trien-12-yl]methyl]piperidin-1-yl]methyl]-3-azabicyclo[4.1.0]heptan-3-yl]isoindole-1,3-dione |
| 190 | 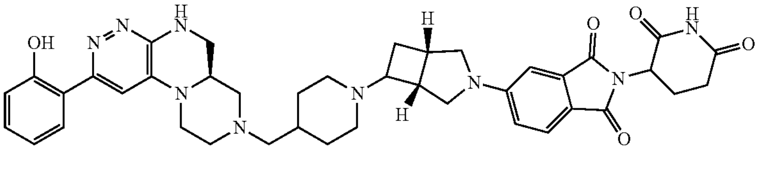 [SMILES: O=C1CCC(N2C(=O)c3ccc(N4C[C@H]5CC(N6CCC(CN7CCN8c9cc(-c%10ccccc%10O)nnc9NC[C@H]8C7)CC6)[C@H]5C4)cc3C2=O)C(=O)N1] | 2-(2,6-dioxopiperidin-3-yl)-5-[(1S,5R)-6-[4-[[(10S)-4-(2-hydroxyphenyl)-1,5,6,8,12-pentazatricyclo[8.4.0.02,7]tetradeca-2(7),3,5-trien-12-yl]methyl]piperidin-1-yl]-3-azabicyclo[3.2.0]heptan-3-yl]isoindole-1,3-dione |

TABLE 1-continued

| Example | Structure | Name |
|---|---|---|
| | Compounds | |
| 191 | 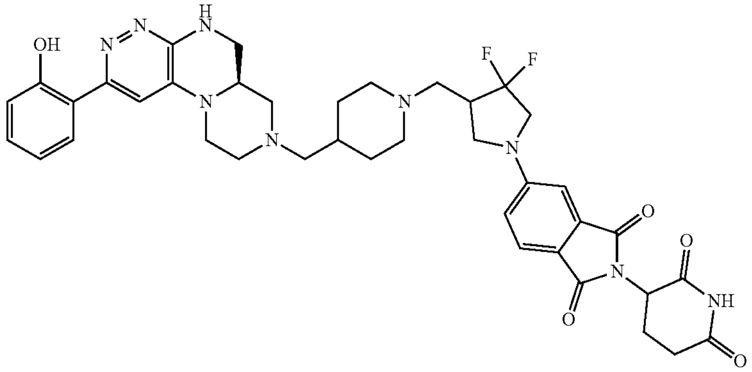 [SMILES: O=C1CCC(N2C(=O)c3ccc(N4CC(CN5CCC(CN6CCN7c8cc(-c9ccccc9O)nnc8NC[C@H]7C6)CC5)C(F)(F)C4)cc3C2=O)C(=O)N1] | 5-[3,3-difluoro-4-[[4-[[(10S)-4-(2-hydroxyphenyl)-1,5,6,8,12-pentazatricyclo[8.4.0.02,7]tetradeca-2(7),3,5-trien-12-yl]methyl]piperidin-1-yl]methyl]pyrrolidin-1-yl]-2-(2,6-dioxopiperidin-3-yl)isoindole-1,3-dione |
| 192 | 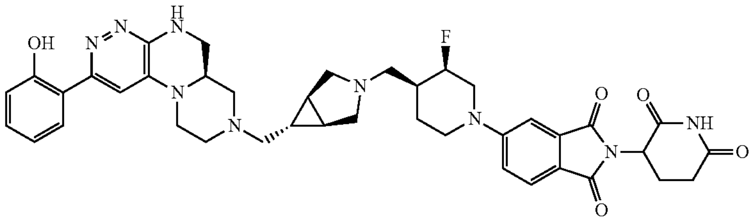 [SMILES: O=C1CCC(N2C(=O)c3ccc(N4CC[C@@H](CN5C[C@@H]6[C@H](C5)[C@H]6CN5CCN6c7cc(-c8ccccc8O)nnc7NC[C@H]6C5)[C@@H](F)C4)cc3C2=O)C(=O)N1] | 2-(2,6-dioxopiperidin-3-yl)-5-[(3R,4R)-3-fluoro-4-[[(1S,5R)-6-[[(10S)-4-(2-hydroxyphenyl)-1,5,6,8,12-pentazatricyclo[8.4.0.02,7]tetradeca-2(7),3,5-trien-12-yl]methyl]-3-azabicyclo[3.1.0]hexan-3-yl]methyl]piperidin-1-yl]isoindole-1,3-dione |
| 193 | 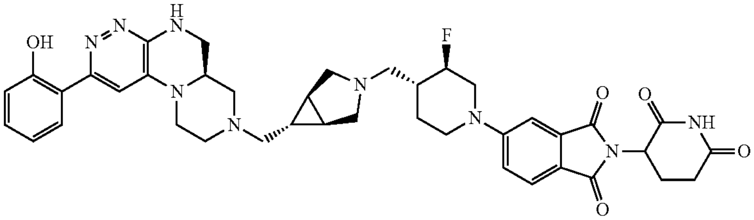 [SMILES: O=C1CCC(N2C(=O)c3ccc(N4CC[C@H](CN5C[C@@H]6[C@H](C5)[C@H]6CN5CCN6c7cc(-c8ccccc8O)nnc7NC[C@H]6C5)[C@@H](F)C4)cc3C2=O)C(=O)N1] | 2-(2,6-dioxopiperidin-3-yl)-5-[(3R,4R)-3-fluoro-4-[[(1S,5R)-6-[[(10S)-4-(2-hydroxyphenyl)-1,5,6,8,12-pentazatricyclo[8.4.0.02,7]tetradeca-2(7),3,5-trien-12-yl]methyl]-3-azabicyclo[3.1.0]hexan-3-yl]methyl]piperidin-1-yl]isoindole-1,3-dione |
| 194 | 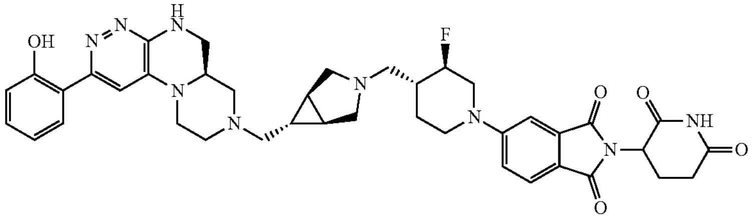 [SMILES: O=C1CCC(N2C(=O)c3ccc(N4CC[C@H](CN5C[C@@H]6[C@H](C5)[C@H]6CN5CCN6c7cc(-c8ccccc8O)nnc7NC[C@H]6C5)[C@@H](F)C4)cc3C2=O)C(=O)N1] | 2-(2,6-dioxopiperidin-3-yl)-5-[(3R,4R)-3-fluoro-4-[[(1S,5R)-6-[[(10S)-4-(2-hydroxyphenyl)-1,5,6,8,12-pentazatricyclo[8.4.0.02,7]tetradeca-2(7),3,5-trien-12-yl]methyl]-3-azabicyclo[3.1.0]hexan-3-yl]methyl]piperidin-1-yl]isoindole-1,3-dione |
| 195 | 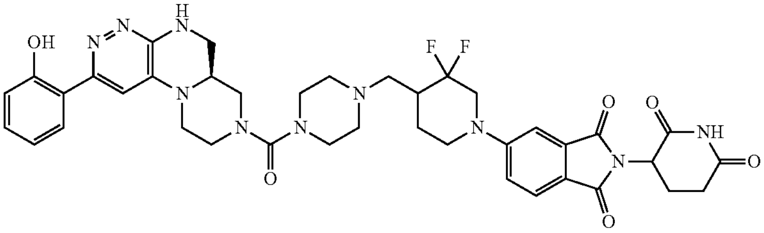 [SMILES: O=C1CCC(N2C(=O)c3ccc(N4CCC(CN5CCN(C(=O)N6CCN7c8cc(-c9ccccc9O)nnc8NC[C@H]7C6)CC5)C(F)(F)C4)cc3C2=O)C(=O)N1] | 5-[3,3-difluoro-4-[[4-[(10S)-4-(2-hydroxyphenyl)-1,5,6,8,12-pentazatricyclo[8.4.0.02,7]tetradeca-2(7),3,5-trien-12-carbonyl]piperazin-1-yl]methyl]piperidin-1-yl]-2-(2,6-dioxopiperidin-3-yl)isoindole-1,3-dione |
| 196 | 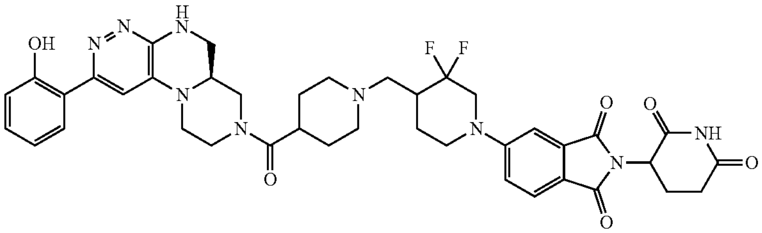 [SMILES: O=C1CCC(N2C(=O)c3ccc(N4CCC(CN5CCC(C(=O)N6CCN7c8cc(-c9ccccc9O)nnc8NC[C@H]7C6)CC5)C(F)(F)C4)cc3C2=O)C(=O)N1] | 5-[3,3-difluoro-4-[[4-[(10S)-4-(2-hydroxyphenyl)-1,5,6,8,12-pentazatricyclo[8.4.0.02,7]tetradeca-2(7),3,5-trien-12-carbonyl]piperidin-1-yl]methyl]piperidin-1-yl]-2-(2,6-dioxopiperidin-3-yl)isoindole-1,3-dione |

TABLE 1-continued

| Compounds | | |
|---|---|---|
| Example | Structure | Name |
| 197 | 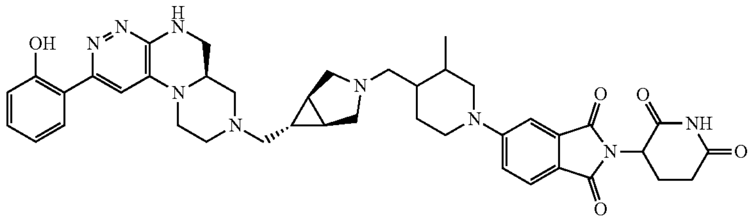 [SMILES: CC1CN(c2ccc3c(c2)C(=O)N(C2CCC(=O)NC2=O)C3=O)CCC1CN1C[C@@H]2[C@H](C1)[C@H]2CN1CCN2c3cc(-c4ccccc4O)nnc3NC[C@H]2C1] | 2-(2,6-dioxopiperidin-3-yl)-5-(4-(((1R,5S,6r)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl-3-methylpiperidin-1-yl)isoindoline-1,3-dione |
| 198 | 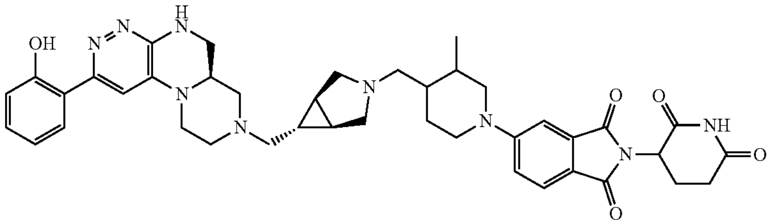 [SMILES: CC1CN(c2ccc3c(c2)C(=O)N(C2CCC(=O)NC2=O)C3=O)CCC1CN1C[C@@H]2[C@H](C1)[C@H]2CN1CCN2c3cc(-c4ccccc4O)nnc3NC[C@H]2C1] | 2-(2,6-dioxopiperidin-3-yl)-5-(4-(((1R,5S,6r)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)-3-methylpiperidin-1-yl)isoindoline-1,3-dione |
| 199 | 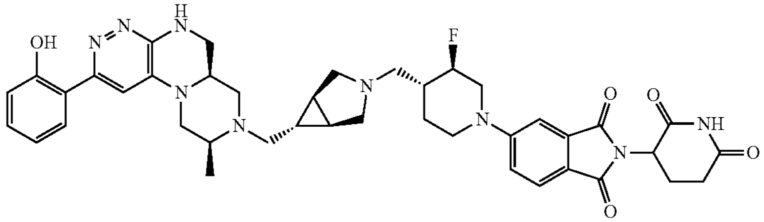 [SMILES: C[C@H]1CN2c3cc(-c4ccccc4O)nnc3NC[C@H]2CN1C[C@H]1[C@@H]2CN(C[C@H]3CCN(c4ccc5c(c4)C(=O)N(C4CCC(=O)NC4=O)C5=O)C[C@@H]3F)C[C@@H]21] | 2-(2,6-dioxopiperidin-3-yl)-5-[(3R,4R)-3-fluoro-4-[[(1S,5R)-6-[[(10S,13S)-4-(2-hydroxyphenyl)-13-methyl-1,5,6,8,12-pentazatricyclo[8.4.0.02,7]tetradeca-2(7),3,5-trien-12-yl]methyl]-3-azabicyclo[3.1.0]hexan-3-yl]methyl]piperidin-1-yl]isoindole-1,3-dione |
| 200 | 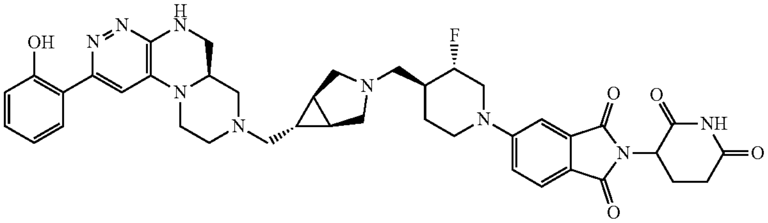 [SMILES: O=C1CCC(N2C(=O)c3ccc(N4CC[C@@H](CN5C[C@@H]6[C@H](C5)[C@H]6CN5CCN6c7cc(-c8ccccc8O)nnc7NC[C@H]6C5)[C@H](F)C4)cc3C2=O)C(=O)N1] | 2-(2,6-dioxopiperidin-3-yl)-5-[(3S,4S)-3-fluoro-4-[[(1S,5R)-6-[[(10S)-4-(2-hydroxyphenyl)-1,5,6,8,12-pentazatricyclo[8.4.0.02,7]tetradeca-2(7),3,5-trien-12-yl]methyl]-3-azabicyclo[3.1.0]hexan-3-yl]methyl]piperidin-1-yl]isoindole-1,3-dione |
| 201 | 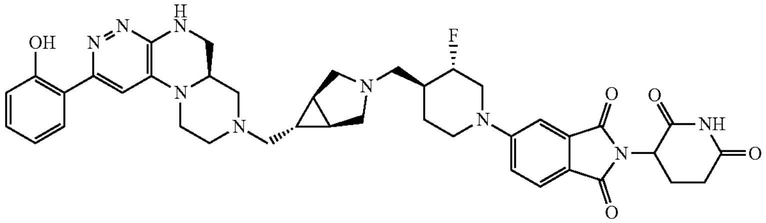 [SMILES: O=C1CCC(N2C(=O)c3ccc(N4CC[C@@H](CN5C[C@@H]6[C@H](C5)[C@H]6CN5CCN6c7cc(-c8ccccc8O)nnc7NC[C@H]6C5)[C@H](F)C4)cc3C2=O)C(=O)N1] | 2-(2,6-dioxopiperidin-3-yl)-5-[(3S,4S)-3-fluoro-4-[[(1S,5R)-6-[[(10S)-4-(2-hydroxyphenyl)-1,5,6,8,12-pentazatricyclo[8.4.0.02,7]tetradeca-2(7),3,5-trien-12-yl]methyl]-3-azabicyclo[3.1.0]hexan-3-yl]methyl]piperidin-1-yl]isoindole-1,3-dione |
| 202 | 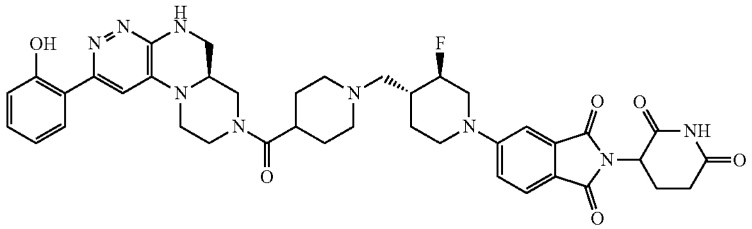 [SMILES: O=C1CCC(N2C(=O)c3ccc(N4CC[C@H](CN5CCC(C(=O)N6CCN7c8cc(-c9ccccc9O)nnc8NC[C@H]7C6)CC5)[C@@H](F)C4)cc3C2=O)C(=O)N1] | 2-(2,6-dioxopiperidin-3-yl)-5-[(3R,4R)-3-fluoro-4-[[4-[(10S)-4-(2-hydroxyphenyl)-1,5,6,8,12-pentazatricyclo[8.4.0.02,7]tetradeca-2(7),3,5-trien-12-carbonyl]piperidin-1-yl]methyl]piperidin-1-yl]isoindole-1,3-dione |

TABLE 1-continued

| Compounds | | |
|---|---|---|
| Exam-ple | Structure | Name |
| 203 | 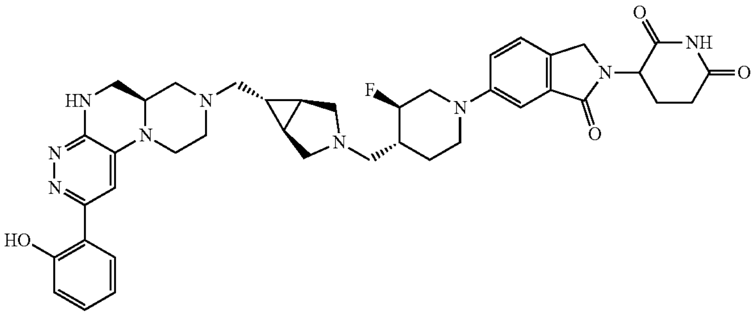 [SMILES: O=C1CCC(N2Cc3ccc(N4CC[C@H](CN5C[C@@H]6[C@H](C5)[C@H]6CN5CCN6c7cc(-c8ccccc8O)nnc7NC[C@H]6C5)[C@@H](F)C4)cc3C2=O)C(=O)N1] | 3-(6-((3R,4R)-3-fluoro-4-(((1R,5S,6R)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)piperidin-1-yl)-1-oxoisoindolin-2-yl)piperidine-2,6-dione |
| 204 | 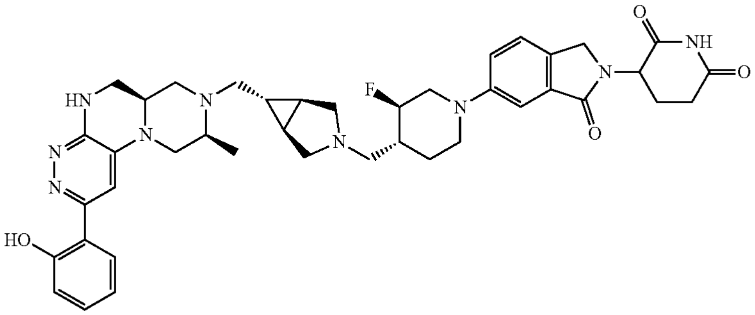 [SMILES: C[C@H]1CN2c3cc(-c4ccccc4O)nnc3NC[C@H]2CN1C[C@H]1[C@@H]2CN(C[C@H]3CCN(c4ccc5c(c4)C(=O)N(C4CCC(=O)NC4=O)C5)C[C@@H]3F)C[C@@H]21] | 3-[5-[(3R,4R)-3-fluoro-4-[[(1S,5R)-6-[[(10S,13S)-4-(2-hydroxyphenyl)-13-methyl-1,5,6,8,12-pentazatricyclo[8.4.0.02,7]tetradeca-2,4,6-trien-12-yl]methyl]-3-azabicyclo[3.1.0]hexan-3-yl]methyl]piperidin-1-yl]-3-oxo-1H-isoindol-2-yl]piperidine-2,6-dione |
| 205 | 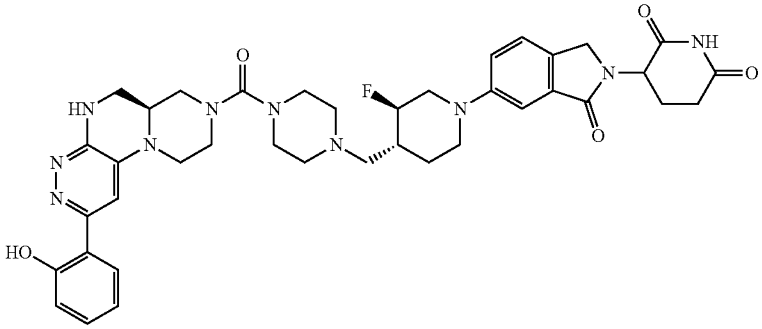 | 3-[5-[(3R,4R)-3-fluoro-4-[[4-[(10S)-4-(2-hydroxyphenyl)-1,5,6,8,12-pentazatricyclo[8.4.0.02,7]tetradeca-2,4,6-triene-12-carbonyl]piperazin-1-yl]methyl]piperidin-1-yl]-3-oxo-1H-isoindol-2-yl]piperidine-2,6-dione |
| 206 | 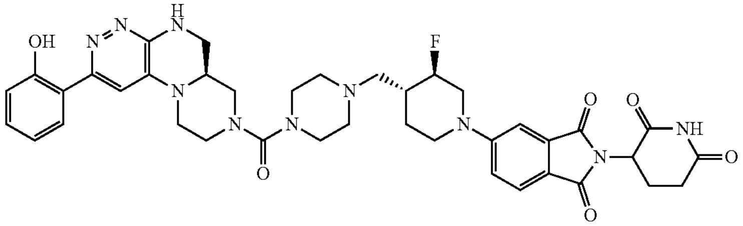 [SMILES: O=C1CCC(N2C(=O)c3ccc(N4CC[C@H](CN5CCN(C(=O)N6CCN7c8cc(-c9ccccc9O)nnc8NC[C@H]7C6)CC5)[C@@H](F)C4)cc3C2=O)C(=O)N1] | 2-(2,6-dioxopiperidin-3-yl)-5-[(3R,4R)-3-fluoro-4-[[4-[(10S)-4-(2-hydroxyphenyl)-1,5,6,8,12-pentazatricyclo[8.4.0.02,7]tetradeca-2(7),3,5-triene-12-carbonyl]piperazin-1-yl]methyl]piperidin-1-yl]isoindole-1,3-dione |
| 207 | 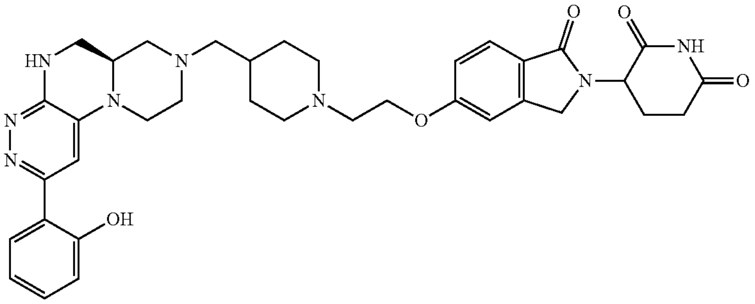 [SMILES: O=C1CCC(N2Cc3cc(OCCN4CCC(CN5CCN6c7cc(-c8ccccc8O)nnc7NC[C@H]6C5)CC4)ccc3C2=O)C(=O)N1] | 3-(5-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)-1-oxoisoindolin-2-yl)piperidine-2,6-dione |

TABLE 1-continued

| Example | Structure | Name |
|---|---|---|
| | Compounds | |
| 208 | 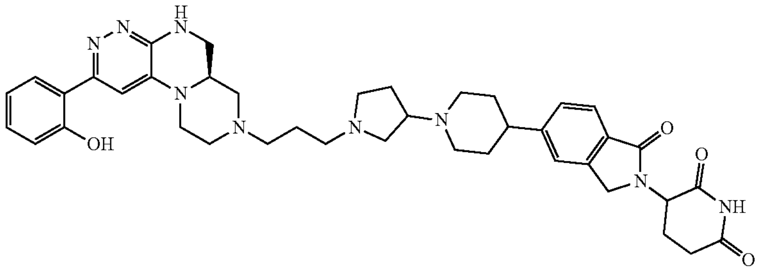 [SMILES: O=C1CCC(N2Cc3cc(C4CCN(C5CCN(CCCN6CCN7c8cc(-c9ccccc9O)nnc8NC[C@H]7C6)C5)CC4)ccc3C2=O)C(=O)N1] | 3-(5-(1-(1-(3-((S)-2-(2-hydroxyphenyl)-5,6,6a,7,9,10-hexahydro-8H-pyrazino[1',2':4,5]pyrazino[2,3-c]pyridazin-8-yl)propyl)pyrrolidin-3-yl)piperidin-4-yl)-1-oxoisoindolin-2-yl)piperidine-2,6-dione |
| 209 | 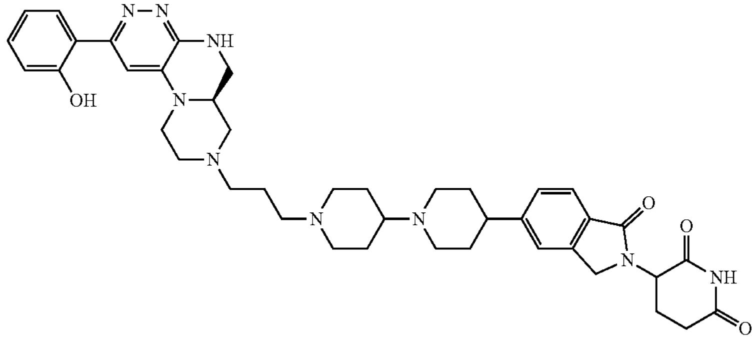 [SMILES: O=C1CCC(N2Cc3cc(C4CCN(C5CCN(CCCN6CCN7c8cc(-c9ccccc9O)nnc8NC[C@H]7C6)CC5)CC4)ccc3C2=O)C(=O)N1] | 3-(5-(1'-(3-((S)-2-(2-hydroxyphenyl)-5,6,6a,7,9,10-hexahydro-8H-pyrazino[1',2':4,5]pyrazino[2,3-c]pyridazin-8-yl)propyl)-[1,4'-bipiperidin]-4-yl)-1-oxoisoindolin-2-yl)piperidine-2,6-dione |
| 210 | 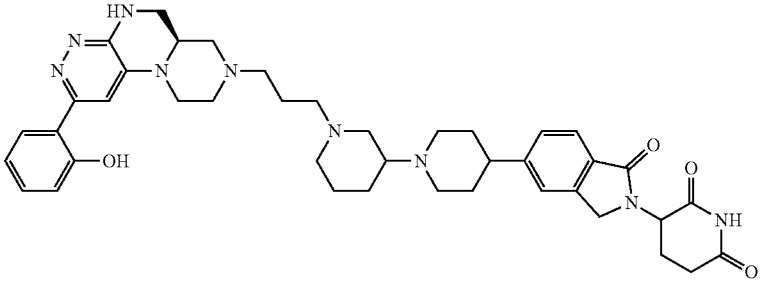 [SMILES: O=C1CCC(N2Cc3cc(C4CCN(C5CCCN(CCCN6CCN7c8cc(-c9ccccc9O)nnc8NC[C@H]7C6)C5)CC4)ccc3C2=O)C(=O)N1] | 3-(5-(1'-(3-((S)-2-(2-hydroxyphenyl)-5,6,6a,7,9,10-hexahydro-8H-pyrazino[1',2':4,5]pyrazino[2,3-c]pyridazin-8-yl)propyl)-[1,3'-bipiperidin]-4-yl)-1-oxoisoindolin-2-yl)piperidine-2,6-dione |
| 211 | 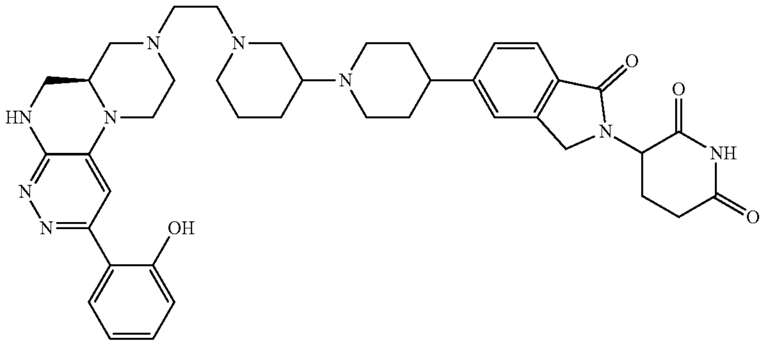 [SMILES: O=C1CCC(N2Cc3cc(C4CCN(C5CCCN(CCN6CCN7c8cc(-c9ccccc9O)nnc8NC[C@H]7C6)C5)CC4)ccc3C2=O)C(=O)N1] | 3-(5-(1'-(2-((S)-2-(2-hydroxyphenyl)-5,6,6a,7,9,10-hexahydro-8H-pyrazino[1',2':4,5]pyrazino[2,3-c]pyridazin-8-yl)ethyl)-[1,3'-bipiperidin]-4-yl)-1-oxoisoindolin-2-yl)piperidine-2,6-dione |

TABLE 1-continued

| Example | Structure | Name |
|---|---|---|
| 212 | 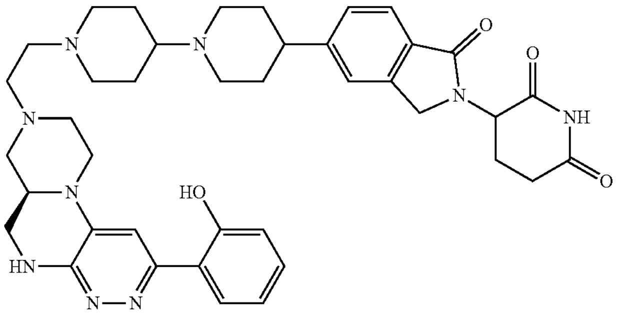 [SMILES: O=C1CCC(N2Cc3cc(C4CCN(C5CCN(CCN6CCN7c8cc(-c9ccccc9O)nnc8NC[C@H]7C6)CC5)CC4)ccc3C2=O)C(=O)N1] | 3-(5-(1'-(2-((S)-2-(2-hydroxyphenyl)-5,6,6a,7,9,10-hexahydro-8H-pyrazino[1',2':4,5]pyrazino[2,3-c]pyridazin-8-yl)ethyl)-[1,4'-bipiperidin]-4-yl)-1-oxoisoindolin-2-yl)piperidine-2,6-dione |
| 213 | 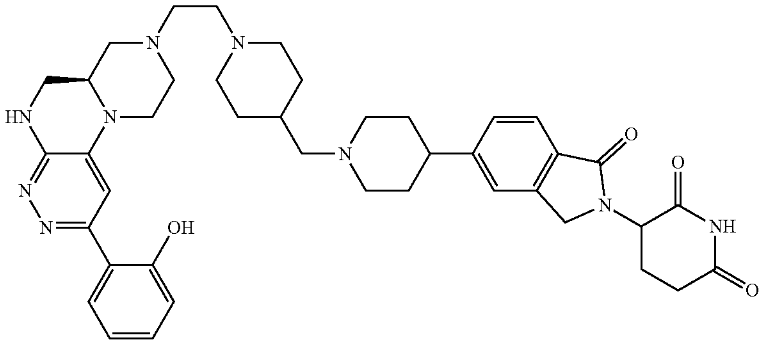 [SMILES: O=C1CCC(N2Cc3cc(C4CCN(CC5CCN(CCN6CCN7c8cc(-c9ccccc9O)nnc8NC[C@H]7C6)CC5)CC4)ccc3C2=O)C(=O)N1] | 3-(5-(1-((1-(2-((S)-2-(2-hydroxyphenyl)-5,6,6a,7,9,10-hexahydro-8H-pyrazino[1',2':4,5]pyrazino[2,3-c]pyridazin-8-yl)ethyl)piperidin-4-yl)methyl)piperidin-4-yl)-1-oxoisoindolin-2-yl)piperidine-2,6-dione |
| 214 | 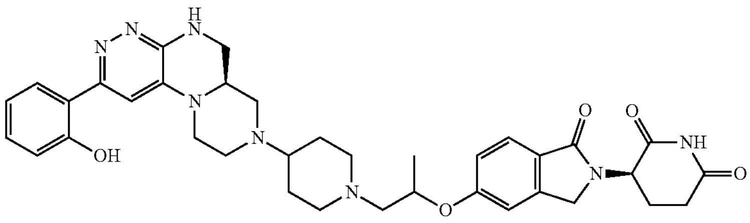 [SMILES: CC(CN1CCC(N2CCN3c4cc(-c5ccccc5O)nnc4NC[C@H]3C2)CC1)Oc1ccc2c(c1)CN([C@@H]1CCC(=O)NC1=O)C2=O] | (3R)-3-(5-((1-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propan-2-yl)oxy)-1-oxoisoindolin-2-yl)piperidine-2,6-dione |
| 215 | 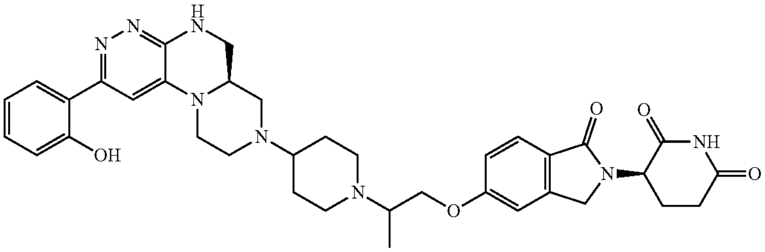 [SMILES: CC(COc1ccc2c(c1)CN([C@@H]1CCC(=O)NC1=O)C2=O)N1CCC(N2CCN3c4cc(-c5ccccc5O)nnc4NC[C@H]3C2)CC1] | (3R)-3-(5-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propoxy)-1-oxoisoindolin-2-yl)piperidine-2,6-dione |
| 216 | 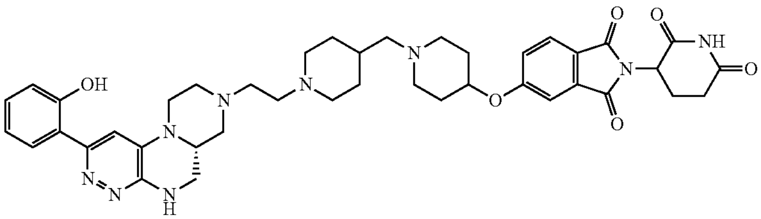 [SMILES: O=C1CCC(N2C(=O)c3ccc(OC4CCN(CC5CCN(CCN6CCN7c8cc(-c9ccccc9O)nnc8NC[C@H]7C6)CC5)CC4)cc3C2=O)C(=O)N1] | 2-(2,6-dioxopiperidin-3-yl)-5-((1-((1-(2-((S)-2-(2-hydroxyphenyl)-5,6,6a,7,9,10-hexahydro-8H-pyrazino[1',2':4,5]pyrazino[2,3-c]pyridazin-8-yl)ethyl)piperidin-4-yl)methyl)piperidin-4-yl)oxy)isoindoline-1,3-dione |

TABLE 1-continued

| Compounds | | |
|---|---|---|
| Exam-ple | Structure | Name |
| 217 | 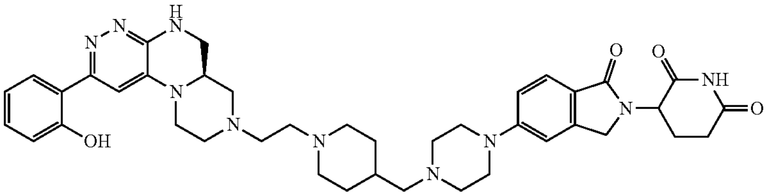 [SMILES: O=C1CCC(N2Cc3cc(N4CCN(CC5CCN(CCN6CCN7c8cc(-c9ccccc9O)nnc8NC[C@H]7C6)CC5)CC4)ccc3C2=O)C(=O)N1] | 3-(5-(4-((1-(2-((S)-2-(2-hydroxyphenyl)-5,6,6a,7,9,10-hexahydro-8H-pyrazino[1',2':4,5]pyrazino[2,3-c]pyridazin-8-yl)ethyl)piperidin-4-yl)methyl)piperazin-1-yl)-1-oxoisoindolin-2-yl)piperidine-2,6-dione |
| 218 | 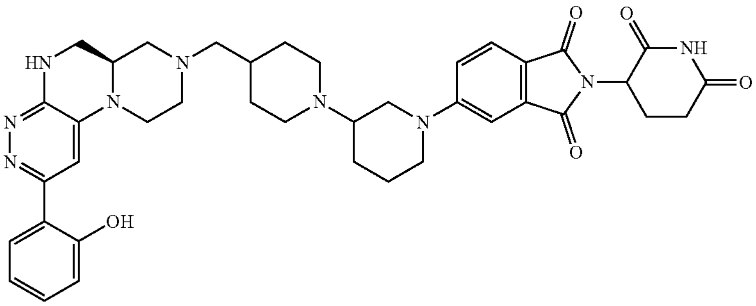 [SMILES: O=C1CCC(N2C(=O)c3ccc(N4CCCC(N5CCC(CN6CCN7c8cc(-c9ccccc9O)nnc8NC[C@H]7C6)CC5)C4)cc3C2=O)C(=O)N1] | 2-(2,6-dioxopiperidin-3-yl)-5-(4-(((S)-2-(2-hydroxyphenyl)-5,6,6a,7,9,10-hexahydro-8H-pyrazino[1',2':4,5]pyrazino[2,3-c]pyridazin-8-yl)methyl)-[1,3'-bipiperidin]-1'-yl)isoindoline-1,3-dione |
| 219 | 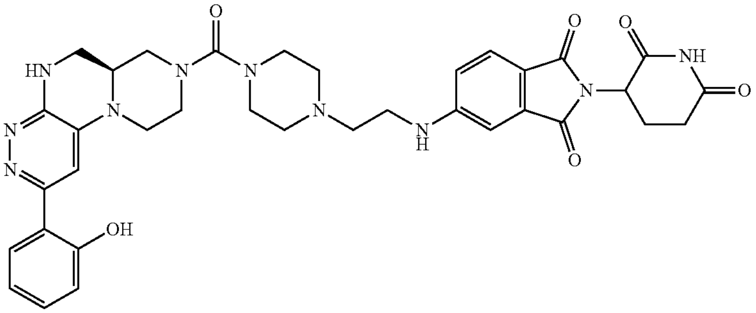 | 2-(2,6-dioxopiperidin-3-yl)-5-((2-(4-((S)-2-(2-hydroxyphenyl)-6,6a,7,8,9,10-hexahydro-5H-pyrazino[1',2':4,5]pyrazino[2,3-c]pyridazine-8-carbonyl)piperazin-1-yl)ethyl)amino)isoindoline-1,3-dione |
| 220 | 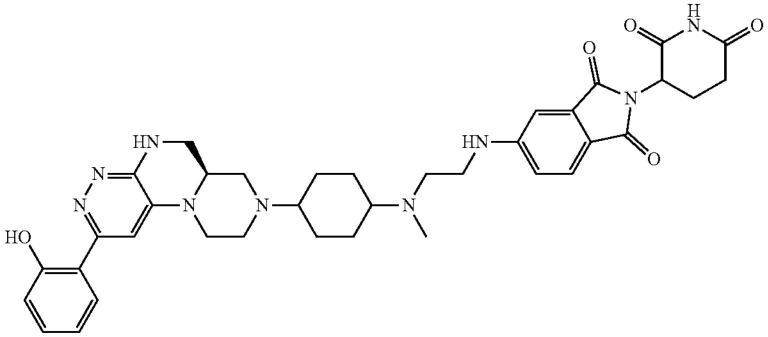 [SMILES: CN(CCNc1ccc2c(c1)C(=O)N(C1CCC(=O)NC1=O)C2=O)C1CCC(N2CCN3c4cc(-c5ccccc5O)nnc4NC[C@H]3C2)CC1] | 2-(2,6-dioxopiperidin-3-yl)-5-((2-((4-((S)-2-(2-hydroxyphenyl)-5,6,6a,7,9,10-hexahydro-8H-pyrazino[1',2':4,5]pyrazino[2,3-c]pyridazin-8-yl)cyclohexyl)(methyl)amino)ethyl)amino)isoindoline-1,3-dione |

TABLE 1-continued

Compounds

| Example | Structure | Name |
|---|---|---|
| 221 | 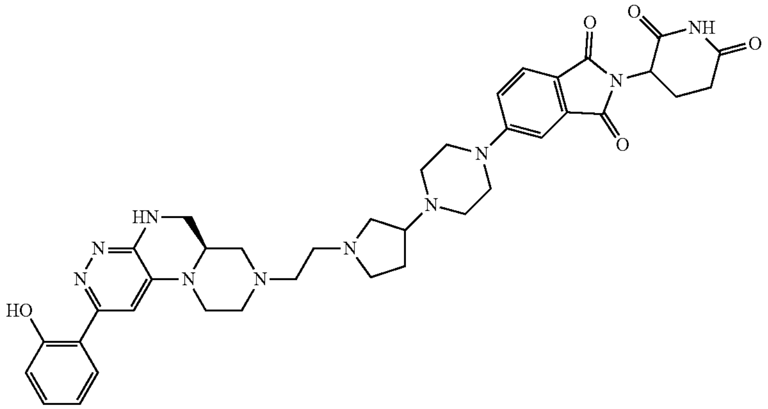 [SMILES: O=C1CCC(N2C(=O)c3ccc(N4CCN(C5CCN(CCN6CCN7c8cc(-c9ccccc9O)nnc8NC[C@H]7C6)C5)CC4)cc3C2=O)C(=O)N1] | 2-(2,6-dioxopiperidin-3-yl)-5-(4-(1-(2-((S)-2-(2-hydroxyphenyl)-5,6,6a,7,9,10-hexahydro-8H-pyrazino[1',2':4,5]pyrazino[2,3-c]pyridazin-8-yl)ethyl)pyrrolidin-3-yl)piperazin-1-yl)isoindoline-1,3-dione |
| 222 | 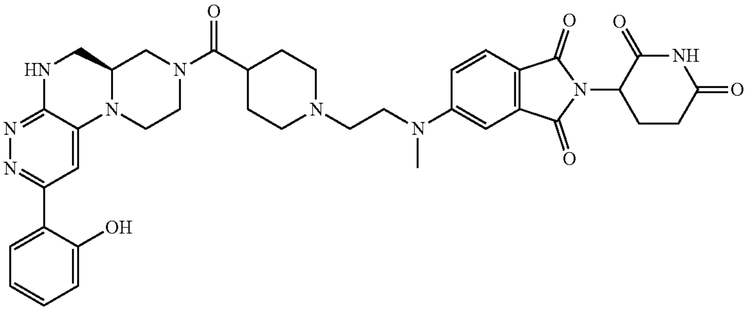 [SMILES: CN(CCN1CCC(C(=O)N2CCN3c4cc(-c5ccccc5O)nnc4NC[C@H]3C2)CC1)c1ccc2c(c1)C(=O)N(C1CCC(=O)NC1=O)C2=O] | 2-(2,6-dioxopiperidin-3-yl)-5-((2-(4-((S)-2-(2-hydroxyphenyl)-6,6a,7,8,9,10-hexahydro-5H-pyrazino[1',2':4,5]pyrazino[2,3-c]pyridazine-8-carbonyl)piperidin-1-yl)ethyl)(methyl)amino)isoindoline-1,3-dione |
| 223 | 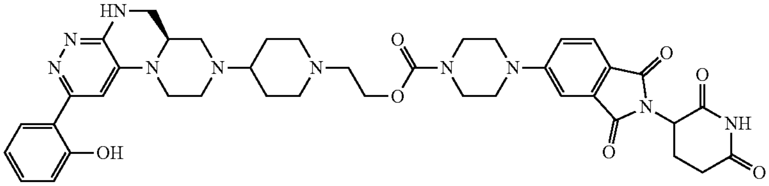 [SMILES: O=C1CCC(N2C(=O)c3ccc(N4CCN(C(=O)OCCN5CCC(N6CCN7c8cc(-c9ccccc9O)nnc8NC[C@H]7C6)CC5)CC4)cc3C2=O)C(=O)N1] | 2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethyl 4-(2-(2,6-dioxopiperidin-3-yl)-1,3-dioxoisoindolin-5-yl)piperazine-1-carboxylate |
| 224 | 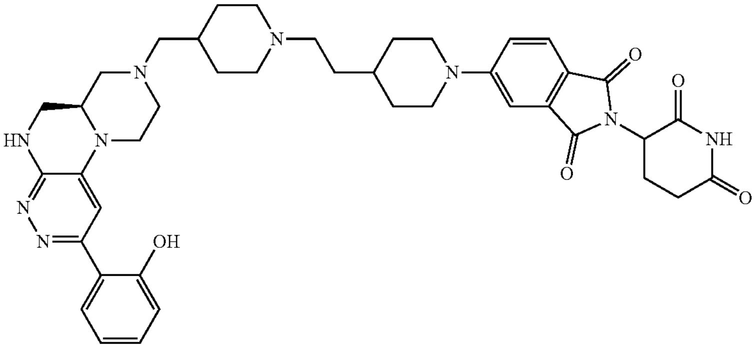 [SMILES: O=C1CCC(N2C(=O)c3ccc(N4CCC(CCN5CCC(CN6CCN7c8cc(-c9ccccc9O)nnc8NC[C@H]7C6)CC5)CC4)cc3C2=O)C(=O)N1] | 2-(2,6-dioxopiperidin-3-yl)-5-(4-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethyl)piperidin-1-yl)isoindoline-1,3-dione |

TABLE 1-continued

| Compounds | | |
|---|---|---|
| Example | Structure | Name |
| 225 | 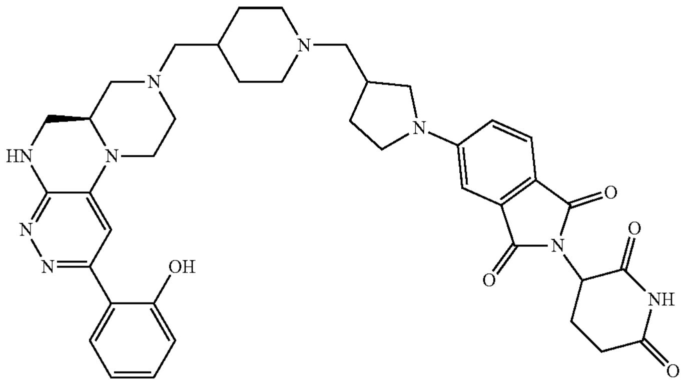 [SMILES: O=C1CCC(N2C(=O)c3ccc(N4CCC(CN5CCC(CN6CCN7c8cc(-c9ccccc9O)nnc8NC[C@H]7C6)CC5)C4)cc3C2=O)C(=O)N1] | 2-(2,6-dioxopiperidin-3-yl)-5-(3-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)pyrrolidin-1-yl)isoindoline-1,3-dione |
| 226 | 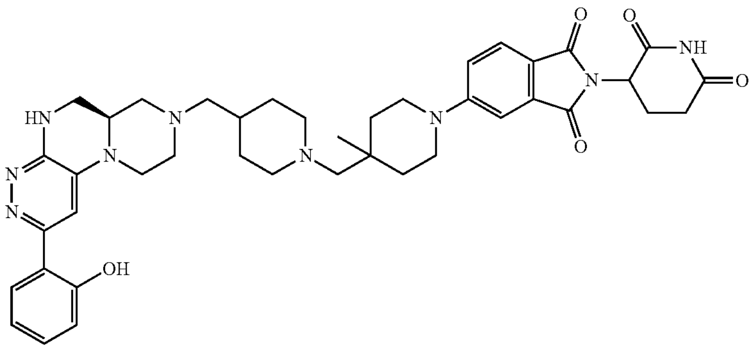 [SMILES: CC1(CN2CCC(CN3CCN4c5cc(-c6ccccc6O)nnc5NC[C@H]4C3)CC2)CCN(c2ccc3c(c2)C(=O)N(C2CCC(=O)NC2=O)C3=O)CC1] | 2-(2,6-dioxopiperidin-3-yl)-5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)-4-methylpiperidin-1-yl)isoindoline-1,3-dione |
| 227 | 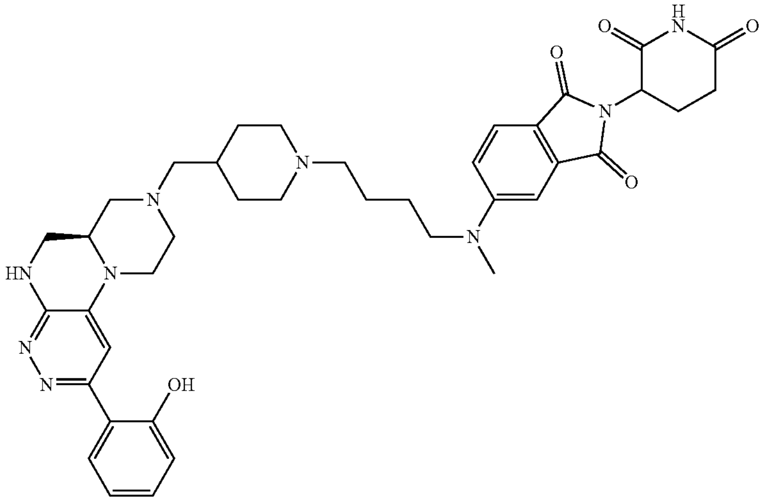 [SMILES: CN(CCCCN1CCC(CN2CCN3c4cc(-c5ccccc5O)nnc4NC[C@H]3C2)CC1)c1ccc2c(c1)C(=O)N(C1CCC(=O)NC1=O)C2=O] | 2-(2,6-dioxopiperidin-3-yl)-5-((4-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)butyl)(methyl)amino)isoindoline-1,3-dione |

TABLE 1-continued

| Compounds | | |
|---|---|---|
| Example | Structure | Name |
| 228 | 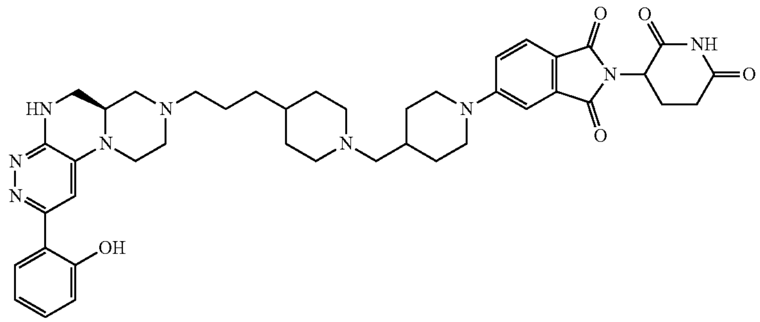 [SMILES: O=C1CCC(N2C(=O)c3ccc(N4CCC(CN5CCC(CCCN6CCN7c8cc(-c9ccccc9O)nnc8NC[C@H]7C6)CC5)CC4)cc3C2=O)C(=O)N1] | 2-(2,6-dioxopiperidin-3-yl)-5-(4-((4-(3-((S)-2-(2-hydroxyphenyl)-5,6,6a,7,9,10-hexahydro-8H-pyrazino[1',2':4,5]pyrazino[2,3-c]pyridazin-8-yl)propyl)piperidin-1-yl)methyl)piperidin-1-yl)isoindoline-1,3-dione |
| 229 | 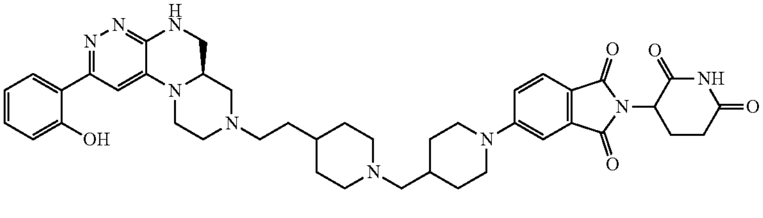 [SMILES: O=C1CCC(N2C(=O)c3ccc(N4CCC(CN5CCC(CCN6CCN7c8cc(-c9ccccc9O)nnc8NC[C@H]7C6)CC5)CC4)cc3C2=O)C(=O)N1] | 2-(2,6-dioxopiperidin-3-yl)-5-(4-((4-(2-((S)-2-(2-hydroxyphenyl)-5,6,6a,7,9,10-hexahydro-8H-pyrazino[1',2':4,5]pyrazino[2,3-c]pyridazin-8-yl)ethyl)piperidin-1-yl)methyl)piperidin-1-yl)isoindoline-1,3-dione |
| 230 | 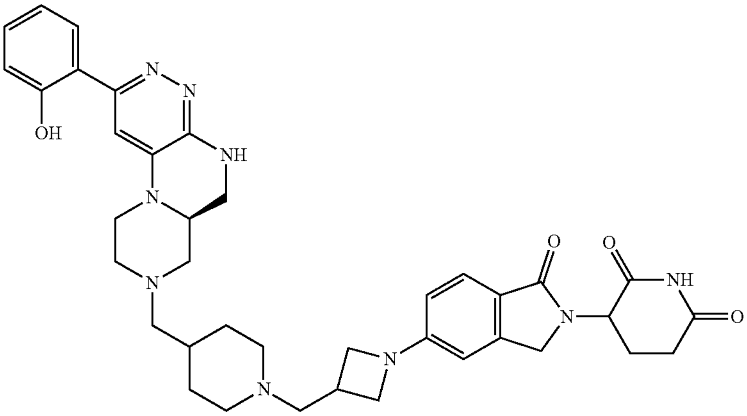 [SMILES: O=C1CCC(N2Cc3cc(N4CC(CN5CCC(CN6CCN7c8cc(-c9ccccc9O)nnc8NC[C@H]7C6)CC5)C4)ccc3C2=O)C(=O)N1] | 3-(5-(3-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)azetidin-1-yl)-1-oxoisoindolin-2-yl)piperidine-2,6-dione |
| 231 | 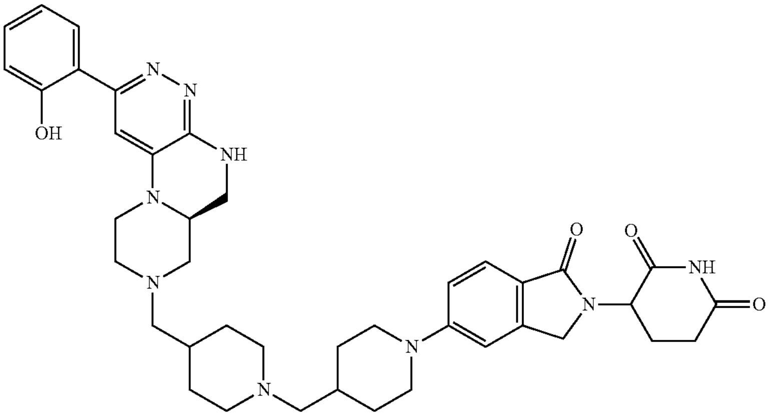 [SMILES: O=C1CCC(N2Cc3cc(N4CCC(CN5CCC(CN6CCN7c8cc(-c9ccccc9O)nnc8NC[C@H]7C6)CC5)CC4)ccc3C2=O)C(=O)N1] | 3-(5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl)-1-oxoisoindolin-2-yl)piperidine-2,6-dione |

TABLE 1-continued

| Example | Structure | Name |
|---|---|---|
| 232 | 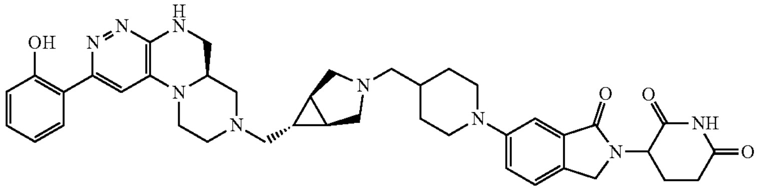 [SMILES: O=C1CCC(N2Cc3ccc(N4CCC(CN5C[C@@H]6[C@H](C5)[C@H]6CN5CCN6c7cc(-c8ccccc8O)nnc7NC[C@H]6C5)CC4)cc3C2=O)C(=O)N1] | 3-(6-(4-(((1R,5S,6r)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)piperidin-1-yl)-1-oxoisoindolin-2-yl)piperidine-2,6-dione |
| 233 | 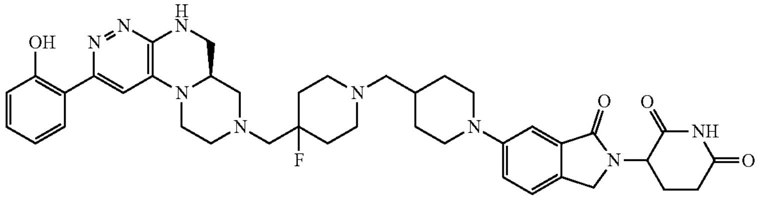 [SMILES: O=C1CCC(N2Cc3ccc(N4CCC(CN5CCC(F)(CN6CCN7c8cc(-c9ccccc9O)nnc8NC[C@H]7C6)CC5)CC4)cc3C2=O)C(=O)N1] | 3-(6-(4-((4-fluoro-4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl)-1-oxoisoindolin-2-yl)piperidine-2,6-dione |
| 234 | 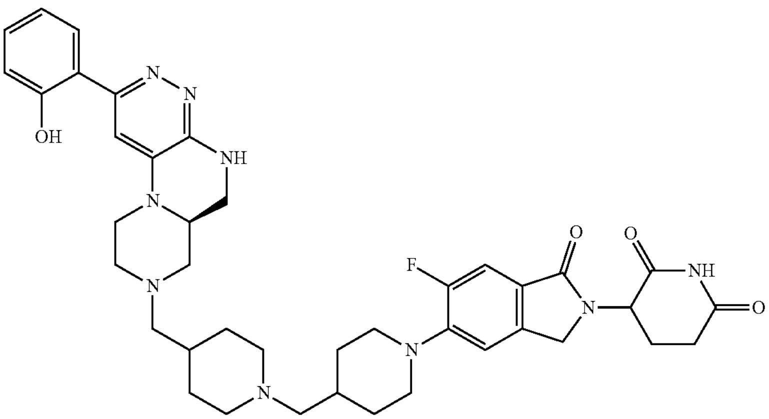 [SMILES: O=C1CCC(N2Cc3cc(N4CCC(CN5CCC(CN6CCN7c8cc(-c9ccccc9O)nnc8NC[C@H]7C6)CC5)CC4)c(F)cc3C2=O)C(=O)N1] | 3-(6-fluoro-5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl)-1-oxoisoindolin-2-yl)piperidine-2,6-dione |
| 235 | 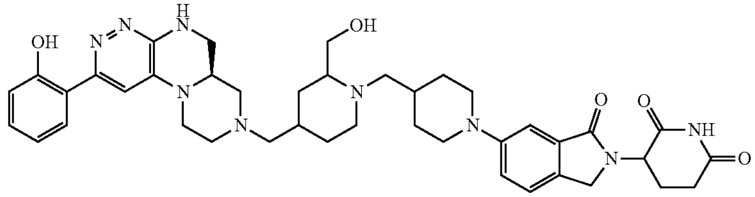 | 3-(6-(4-((2-(hydroxymethyl)-4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl)-1-oxoisoindolin-2-yl)piperidine-2,6-dione |
| 236 | 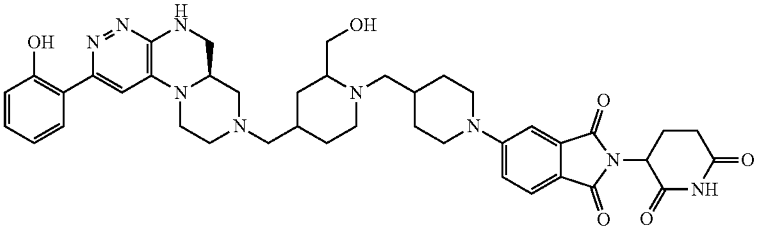 [SMILES: O=C1CCC(N2C(=O)c3ccc(N4CCC(CN5CCC(CN6CCN7c8cc(-c9ccccc9O)nnc8NC[C@H]7C6)CC5CO)CC4)cc3C2=O)C(=O)N1] | 2-(2,6-dioxopiperidin-3-yl)-5-(4-((2-(hydroxymethyl)-4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl)isoindoline-1,3-dione |
| 237 | 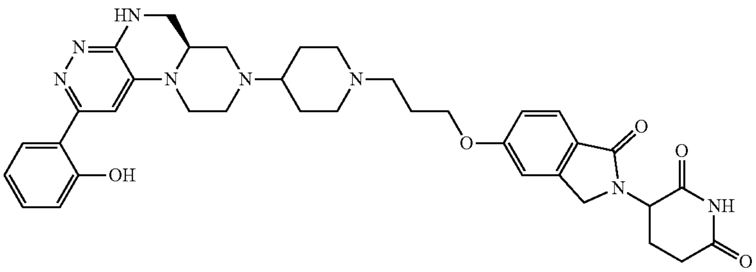 [SMILES: O=C1CCC(N2Cc3cc(OCCCN4CCC(N5CCN6c7cc(-c8ccccc8O)nnc7NC[C@H]6C5)CC4)ccc3C2=O)C(=O)N1] | 3-(5-(3-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propoxy)-1-oxoisoindolin-2-yl)piperidine-2,6-dione |

TABLE 1-continued

| Example | Structure | Name |
|---|---|---|
| 238 | 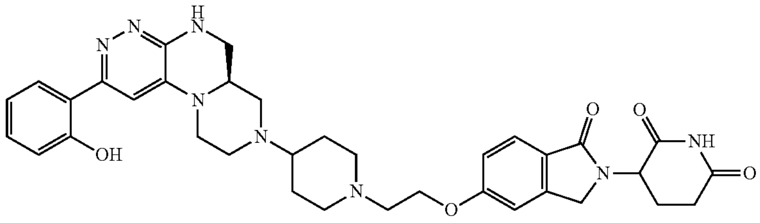 [SMILES: O=C1CCC(N2Cc3cc(OCCN4CCC(N5CCN6c7cc(-c8ccccc8O)nnc7NC[C@H]6C5)CC4)ccc3C2=O)C(=O)N1] | 3-(5-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethoxy)-1-oxoisoindolin-2-yl)piperidine-2,6-dione |
| 239 | 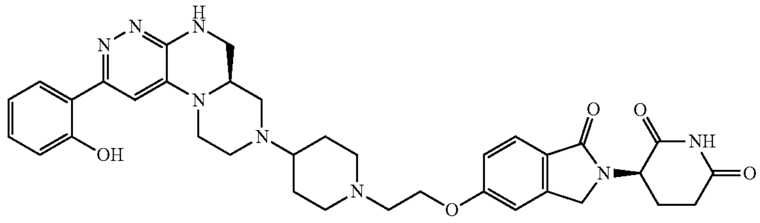 [SMILES: O=C1CC[C@@H](N2Cc3cc(OCCN4CCC(N5CCN6c7cc(-c8ccccc8O)nnc7NC[C@H]6C5)CC4)ccc3C2=O)C(=O)N1] | (R)-3-(5-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethoxy)-1-oxoisoindolin-2-yl)piperidine-2,6-dione |
| 240 | 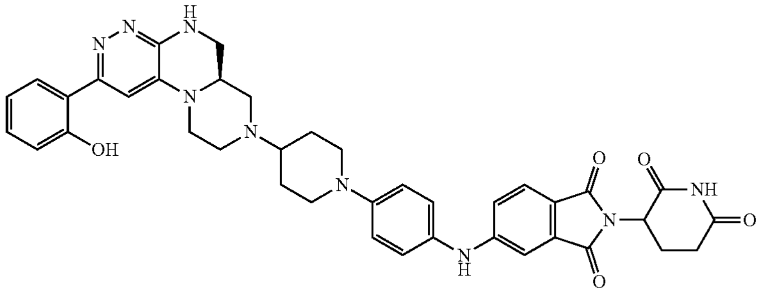 [SMILES: O=C1CCC(N2C(=O)c3ccc(Nc4ccc(N5CCC(N6CCN7c8cc(-c9ccccc9O)nnc8NC[C@H]7C6)CC5)cc4)cc3C2=O)C(=O)N1] | 2-(2,6-dioxopiperidin-3-yl)-5-((4-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)phenyl)amino)isoindoline-1,3-dione |
| 241 | 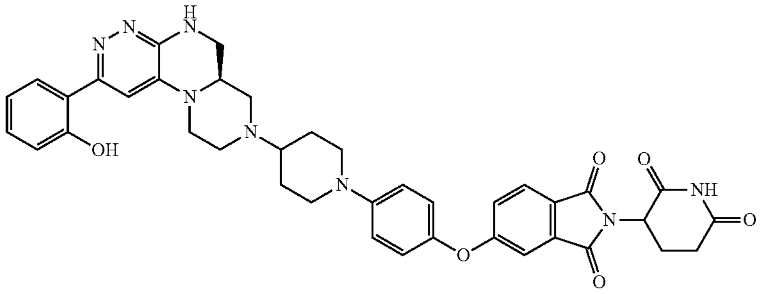 [SMILES: O=C1CCC(N2C(=O)c3ccc(Oc4ccc(N5CCC(N6CCN7c8cc(-c9ccccc9O)nnc8NC[C@H]7C6)CC5)cc4)cc3C2=O)C(=O)N1] | 2-(2,6-dioxopiperidin-3-yl)-5-(4-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)phenoxy)isoindoline-1,3-dione |
| 242 | 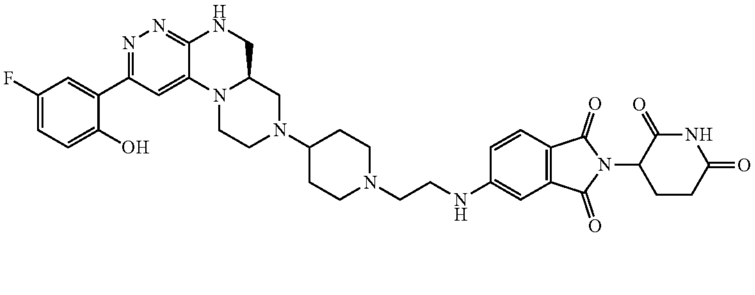 [SMILES: O=C1CCC(N2C(=O)c3ccc(NCCN4CCC(N5CCN6c7cc(-c8cc(F)ccc8O)nnc7NC[C@H]6C5)CC4)cc3C2=O)C(=O)N1] | 2-(2,6-dioxopiperidin-3-yl)-5-((2-(4-((S)-2-(5-fluoro-2-hydroxyphenyl)-5,6,6a,7,9,10-hexahydro-8H-pyrazino[1',2':4,5]pyrazino[2,3-c]pyridazin-8-yl)piperidin-1-yl)ethyl)amino)isoindoline-1,3-dione |

TABLE 1-continued

| Compounds | | |
|---|---|---|
| Example | Structure | Name |
| 243 | 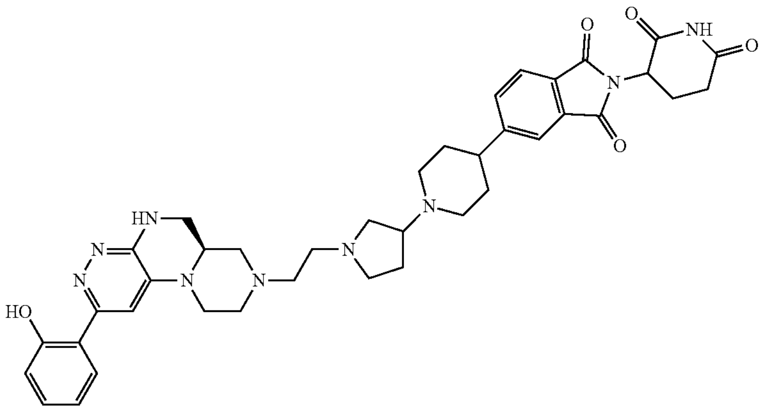 | 2-(2,6-dioxopiperidin-3-yl)-5-(1-(1-(2-((S)-2-(2-hyroxyphenyl)-5,6,6a,7,9,10-hexahydro-8H-pyrazino[1',2':4,5]pyrazino[2,3-c]pyridazin-8-yl)ethyl)pyrrolidin-3-yl)piperidin-4-yl)isoindoline-1,3-dione |
| 244 | 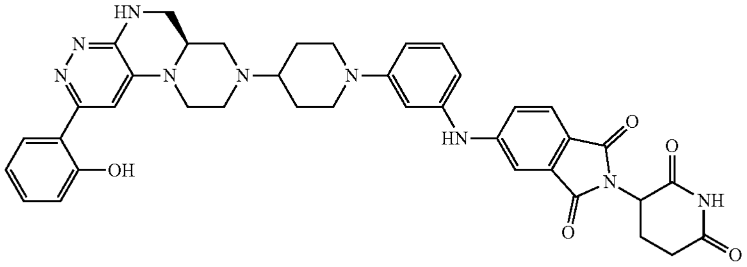 [SMILES: O=C1CCC(N2C(=O)c3ccc(Nc4cccc(N5CCC(N6CCN7c8cc(-c9ccccc9O)nnc8NC[C@H]7C6)CC5)c4)cc3C2=O)C(=O)N1] | 2-(2,6-dioxopiperidin-3-yl)-5-((3-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)phenyl)amino)isoindoline-1,3-dione |
| 245 | 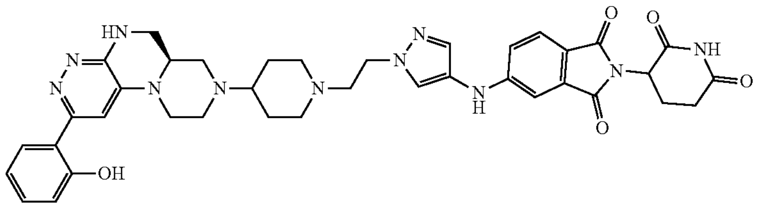 [SMILES: O=C1CCC(N2C(=O)c3ccc(Nc4cnn(CCN5CCC(N6CCN7c8cc(-c9ccccc9O)nnc8NC[C@H]7C6)CC5)c4)cc3C2=O)C(=O)N1] | 2-(2,6-dioxopiperidin-3-yl)-5-((1-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethyl)-1H-pyrazol-4-yl)amino)isoindoline-1,3-dione |
| 246 | 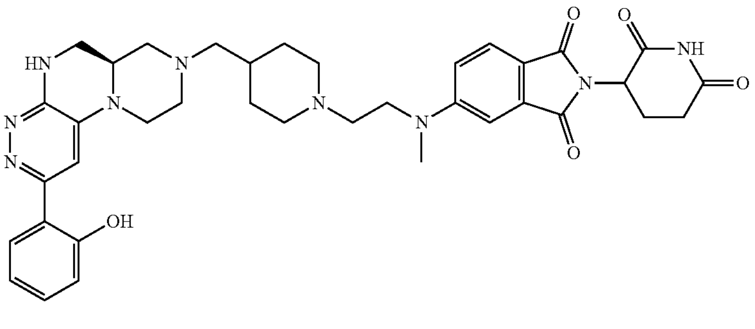 [SMILES: CN(CCN1CCC(CN2CCN3c4cc(-c5ccccc5O)nnc4NC[C@H]3C2)CC1)c1ccc2c(c1)C(=O)N(C1CCC(=O)NC1=O)C2=O] | 2-(2,6-dioxopiperidin-3-yl)-5-((2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethyl)(methyl)amino)isoindoline-1,3-dione |

TABLE 1-continued

| Example | Structure | Name |
|---|---|---|
| | Compounds | |
| 247 | 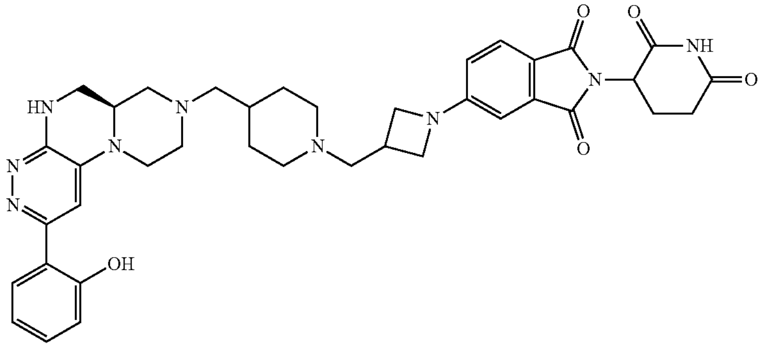 [SMILES: O=C1CCC(N2C(=O)c3ccc(N4CC(CN5CCC(CN6CCN7c8cc(-c9ccccc9O)nnc8NC[C@H]7C6)CC5)C4)cc3C2=O)C(=O)N1] | 2-(2,6-dioxopiperidin-3-yl)-5-(3-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)azetidin-1-yl)isoindoline-1,3-dione |
| 248 | 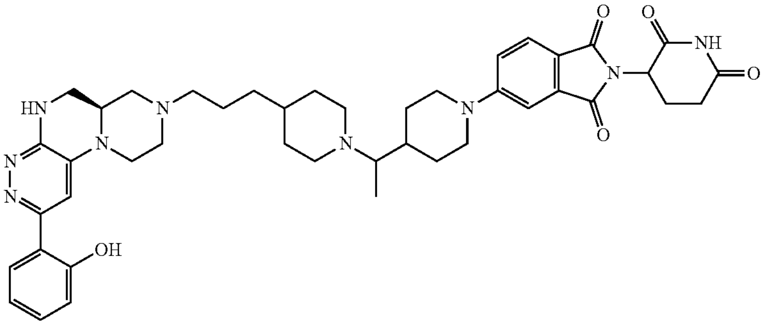 | 2-(2,6-dioxopiperidin-3-yl)-5-(4-(1-(4-(3-((S)-2-(2-hydroxyphenyl)-5,6,6a,7,9,10-hexahydro-8H-pyrazino[1',2':4,5]pyrazino[2,3-c]pyridazin-8-yl)propyl)piperidin-1-yl)ethyl)piperidin-1-yl)isoindoline-1,3-dione |
| 249 | 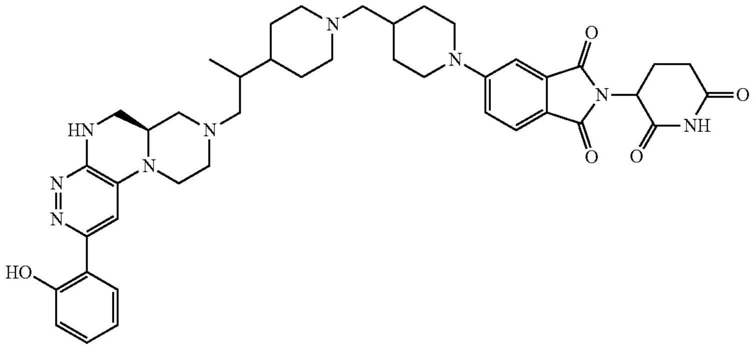 [SMILES: CC(CN1CCN2c3cc(-c4ccccc4O)nnc3NC[C@H]2C1)C1CCN(CC2CCN(c3ccc4c(c3)C(=O)N(C3CCC(=O)NC3=O)C4=O)CC2)CC1] | 2-(2,6-dioxopiperidin-3-yl)-5-(4-((4-(1-((S)-2-(2-hydroxyphenyl)-5,6,6a,7,9,10-hexahydro-8H-pyrazino[1',2':4,5]pyrazino[2,3-c]pyridazin-8-yl)propan-2-yl)piperidin-1-yl)methyl)piperidin-1-yl)isoindoline-1,3-dione |
| 250 | 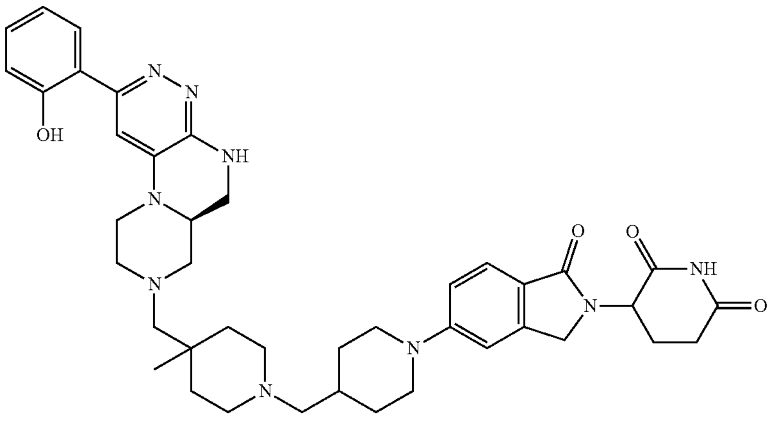 [SMILES: CC1(CN2CCN3c4cc(-c5ccccc5O)nnc4NC[C@H]3C2)CCN(CC2CCN(c3ccc4c(c3)CN(C3CCC(=O)NC3=O)C4=O)CC2)CC1] | 3-(5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)-4-methylpiperidin-1-yl)methyl)piperidin-1-yl)-1-oxoisoindolin-2-yl)piperidine-2,6-dione |

TABLE 1-continued

| Compounds | | |
|---|---|---|
| Example | Structure | Name |
| 251 | 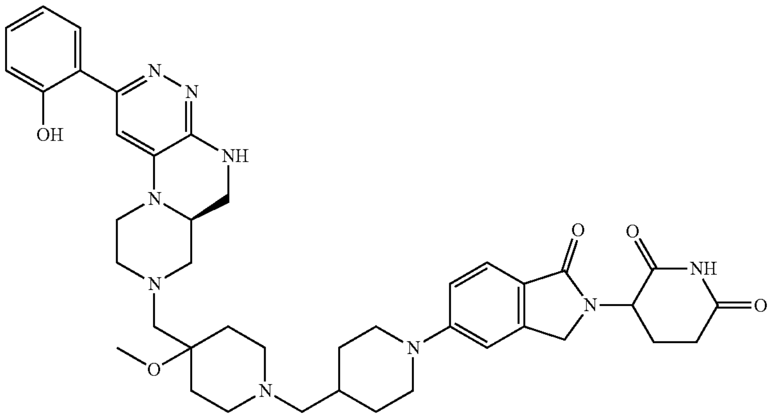 [SMILES: COC1(CN2CCN3c4cc(-c5ccccc5O)nnc4NC[C@H]3C2)CCN(CC2CCN(c3ccc4c(c3)CN(C3CCC(=O)NC3=O)C4=O)CC2)CC1] | 3-(5-(4-((4-(((S)-2-(2-hydroxyphenyl)-5,6,6a,7,9,10-hexahydro-8H-pyrazino[1',2':4,5]pyrazino[2,3-c] pyridazin-8-yl)methyl)-4-methoxypiperidin-1-yl)methyl) piperidin-1-yl)-1-oxoisoindolin-2-yl)piperidine-2,6-dione |
| 252 | 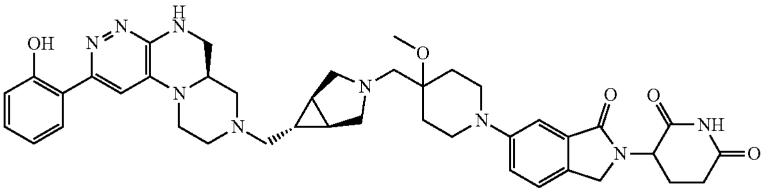 [SMILES: COC1(CN2C[C@@H]3[C@@H](CN4CCN5c6cc(-c7ccccc7O)nnc6NC[C@H]5C4)[C@@H]3C2)CCN(c2ccc3c(c2)C(=O)N(C2CCC(=O)NC2=O)C3)CC1] | 3-(6-(4-(((1R,5S,6s)-6-(((S)-2-(2-hydroxyphenyl)-5,6,6a,7,9,10-hexhydro-8H-pyrazino[1',2':4,5]pyrazino[2,3-c] pyridazin-8-yl)methyl)-3-azabicyclo[3.1.0]hexan-3-yl)methyl)-4-methoxypiperidin-1-yl)-1-oxoisoindolin-2-yl) piperidine-2,6-dione |
| 253 | 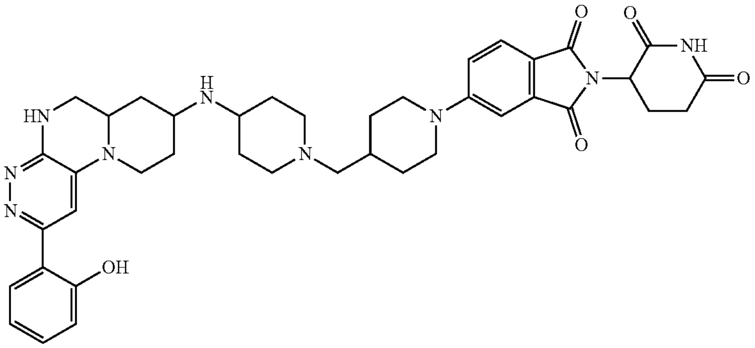 [SMILES: O=C1CCC(N2C(=O)c3ccc(N4CCC(CN5CCC(NC6CCN7c8cc(-c9ccccc9O)nnc8NCC7C6)CC5)CC4)cc3C2=O)C(=O)N1] | 2-(2,6-dioxopiperidin-3-yl)-5-(4-((4-((2-(2-hydroxyphenyl)-6,6a,7,8,9,10-hexahydro-5H-pyrido[1',2':4,5]pyrazino[2,3-c] pyridazin-8-yl)amino) piperidin-1-yl)methyl)piperidin-1-yl)isoindoline-1,3-dione |
| 254 | 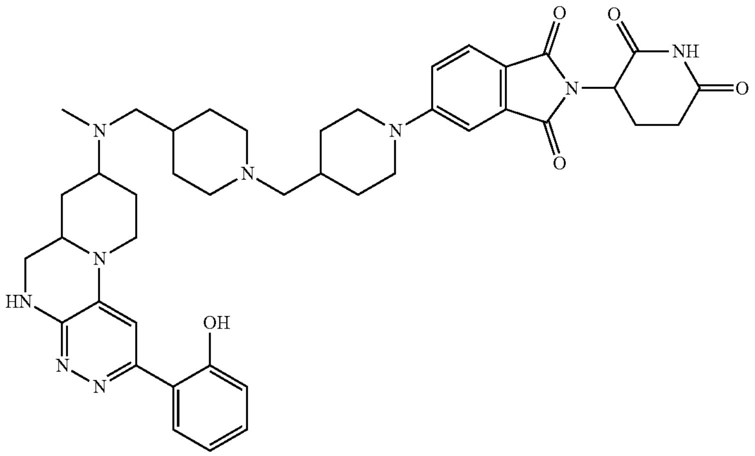 [SMILES: CN(CC1CCN(CC2CCN(c3ccc4c(c3)C(=O)N(C3CCC(=O)NC3=O)C4=O)CC2)CC1)C1CCN2c3cc(-c4ccccc4O)nnc3NCC2C1] | 2-(2,6-dioxopiperidin-3-yl)-5-(4-((4-(((2-(2-hydroxyphenyl)-6,6a,7,8,9,10-hexahydro-5H-pyrido[1',2':4,5]pyrazino[2,3-c] pyridazin-8-yl)(methyl) amino)methyl)piperidin-1-yl) methyl)piperidin-1-yl) isoindoline-1,3-dione |

TABLE 1-continued

| Compounds | | |
|---|---|---|
| Example | Structure | Name |
| 255 | 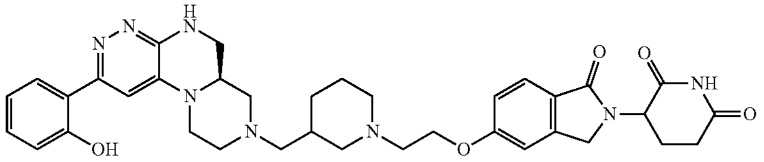 [SMILES: O=C1CCC(N2Cc3cc(OCCN4CCCC(CN5CCN6c7cc(-c8ccccc8O)nnc7NC[C@H]6C5)C4)ccc3C2=O)C(=O)N1] | 3-(5-(2-(3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)-1-oxoisoindolin-2-yl)piperidine-2,6-dione |
| 256 | 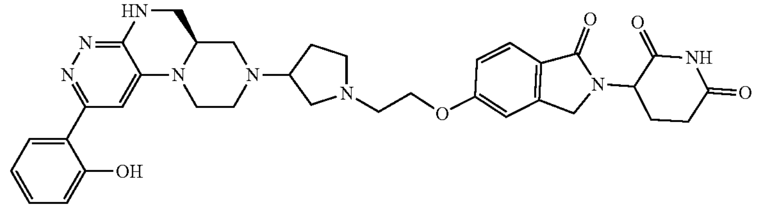 [SMILES: O=C1CCC(N2Cc3cc(OCCN4CCC(N5CCN6c7cc(-c8ccccc8O)nnc7NC[C@H]6C5)C4)ccc3C2=O)C(=O)N1] | 3-(5-(2-(3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)ethoxy)-1-oxoisoindolin-2-yl)piperidine-2,6-dione |
| 257 | 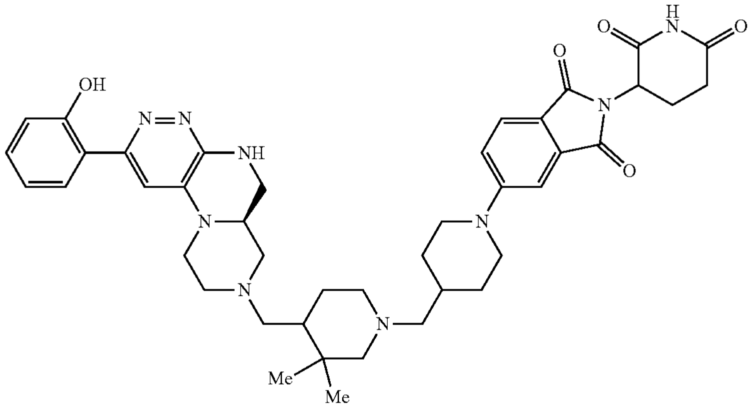 [SMILES: CC1(C)CN(CC2CCN(c3ccc4c(c3)C(=O)N(C3CCC(=O)NC3=O)C4=O)CC2)CCC1CN1CCN2c3cc(-c4ccccc4O)nnc3NC[C@H]2C1] | 2-(2,6-dioxopiperidin-3-yl)-5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)-3,3-dimethylpiperidin-1-yl)methyl)piperidin-1-yl)isoindoline-1,3-dione |
| 258 | 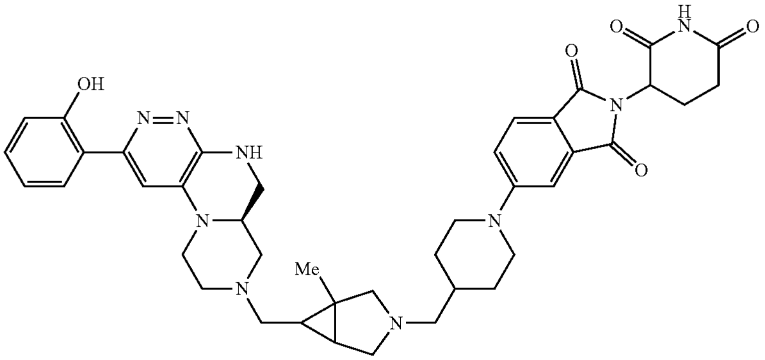 [SMILES: CC12CN(CC3CCN(c4ccc5c(c4)C(=O)N(C4CCC(=O)NC4=O)C5=O)CC3)CC1C2CN1CCN2c3cc(-c4ccccc4O)nnc3NC[C@H]2C1] | 2-(2,6-dioxopiperidin-3-yl)-5-(4-((6-(((S)-2-(2-hydroxyphenyl)-5,6,6a,7,9,10-hexahydro-8H-pyrazino[1',2':4,5]pyrazino[2,3-c]pyridazin-8-yl)methyl)-1-methyl-3-azabicyclo[3.1.0]hexan-3-yl)methyl)piperidin-1-yl)isoindoline-1,3-dione |
| 259 | 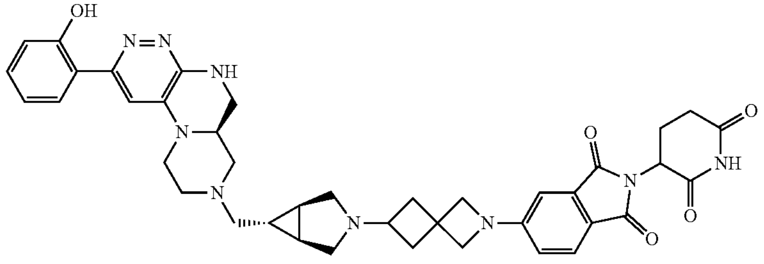 [SMILES: O=C1CCC(N2C(=O)c3ccc(N4CC5(CC(N6C[C@@H]7[C@@H](CN8CCN9c%10cc(-c%11ccccc%11O)nnc%10NC[C@H]9C8)[C@@H]7C6)C5)C4)cc3C2=O)C(=O)N1] | 2-(2,6-dioxopiperidin-3-yl)-5-(6-((1R,5S,6s)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)-2-azaspiro[3.3]heptan-2-yl)isoindoline-1,3-dione |

TABLE 1-continued

Compounds

| Example | Structure | Name |
|---|---|---|
| 260 | 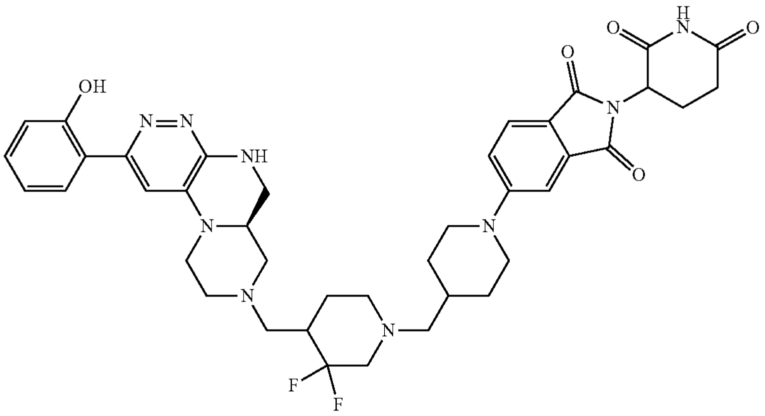 [SMILES: O=C1CCC(N2C(=O)c3ccc(N4CCC(CN5CCC(CN6CCN7c8cc(-c9ccccc9O)nnc8NC[C@H]7C6)C(F)(F)C5)CC4)cc3C2=O)C(=O)N1] | 5-(4-((3-difluoro-4-(((S)-2-(2-hydroxyphenyl)-5,6,6a,7,9,10-hexahydro-8H-pyrazino[1',2':4,5]pyrazino[2,3-c] pyridazin-8-yl)methyl) piperidin-1-yl)methyl)piperidin-1-yl)-2-(2,6-dioxopiperidin-3-yl) isoindoline-1,3-dione |
| 261 | 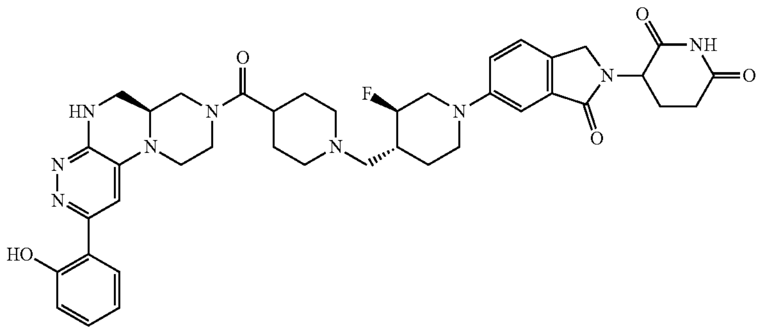 [SMILES: O=C1CCC(N2Cc3ccc(N4CC[C@H](CN5CCC(C(=O)N6CCN7c8cc(-c9ccccc9O)nnc8NC[C@H]7C6)CC5)[C@@H](F)C4)cc3C2=O)C(=O)N1] | 3-(6-((3R,4R)-3-fluoro-4-((4-((S)-2-(2-hydroxyphenyl)-6,6a,7,8,9,10-hexahydro-5H-pyrazino[1',2':4,5]pyrazino[2,3-c] pyridazine-8-carbonyl) piperidin-1-yl)methyl)piperidin-1-yl)-1-oxoisoindolin-2-yl)piperidine-2,6-dione |
| 262 | 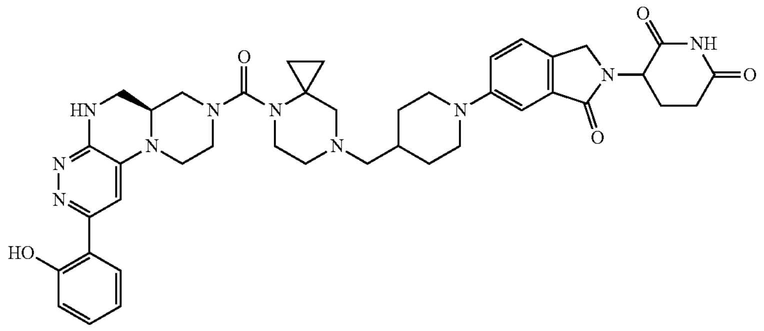 [SMILES: O=C1CCC(N2Cc3ccc(N4CCC(CN5CCN(C(=O)N6CCN7c8cc(-c9ccccc9O)nnc8NC[C@H]7C6)C6(CC6)C5)CC4)cc3C2=O)C(=O)N1] | 3-(6-(4-((4-((S)-2-(2-hydroxyphenyl)-6,6a,7,8,9,10-hexahydro-5H-pyrazino[1',2':4,5]pyrazino[2,3-c] pyridazine-8-carbonyl)-4,7-diazaspiro[2.5]octan-7-yl)methyl)piperidin-1-yl)-1-oxoisoindolin-2-yl)piperidine-2,6-dione |
| 263 | 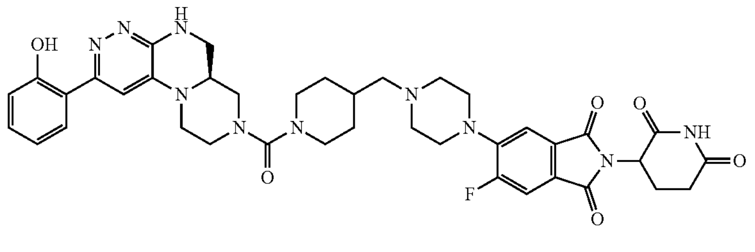 [SMILES: O=C1CCC(N2C(=O)c3cc(F)c(N4CCN(CC5CCN(C(=O)N6CCN7c8cc(-c9ccccc9O)nnc8NC[C@H]7C6)CC5)CC4)cc3C2=O)C(=O)N1] | 2-(2,6-dioxopiperidin-3-yl)-5-fluoro-6-(4-((1-((S)-2-(2-hydroxyphenyl)-6,6a,7,8,9,10-hexahydro-5H-pyrazino[1',2':4,5]pyrazino[2,3-c] pyridazine-8-carbonyl) piperidin-4-yl)methyl) piperazin-1-yl)isoindoline-1,3-dione |

TABLE 1-continued

| Compounds | | |
|---|---|---|
| Example | Structure | Name |
| 264 | 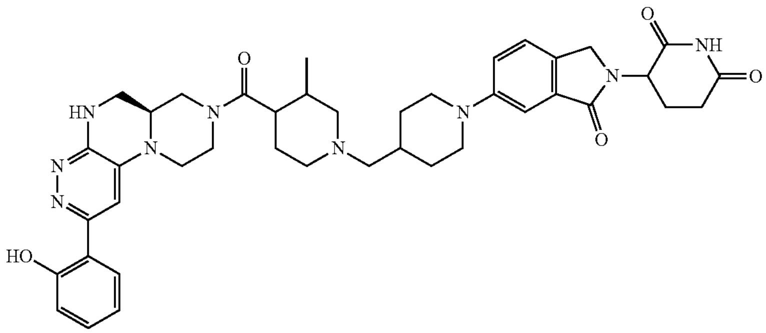 [SMILES: CC1CN(CC2CCN(c3ccc4c(c3)C(=O)N(C3CCC(=O)NC3=O)C4)CC2)CCC1C(=O)N1CCN2c3cc(-c4ccccc4O)nnc3NC[C@H]2C1] | 3-(6-(4-((4-((S)-2-(2-hydroxyphenyl)-6,6a,7,8,9,10-hexahydro-5H-pyrazino[1',2':4,5]pyrazino[2,3-c]pyridazine-8-carbonyl)-3-methylpiperidin-1-yl)methyl)piperidin-1-yl)-1-oxoisoindolin-2-yl)piperidine-2,6-dione |
| 265 | 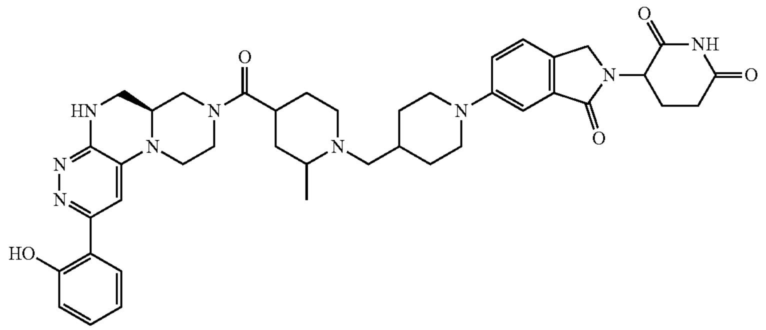 [SMILES: CC1CC(C(=O)N2CCN3c4cc(-c5ccccc5O)nnc4NC[C@H]3C2)CCN1CC1CCN(c2ccc3c(c2)C(=O)N(C2CCC(=O)NC2=O)C3)CC1] | 3-(6-(4-((4-((S)-2-(2-hydroxyphenyl)-6,6a,7,8,9,10-hexahydro-5H-pyrazino[1',2':4,5]pyrazino[2,3-c]pyridazine-8-carbonyl)-2-methylpiperidin-1-yl)methyl)piperidin-1-yl)-1-oxoisoindolin-2-yl)piperidine-2,6-dione |
| 266 | 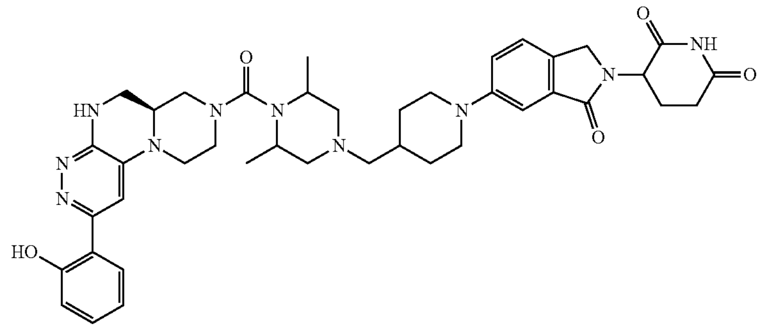 [SMILES: CC1CN(CC2CCN(c3ccc4c(c3)C(=O)N(C3CCC(=O)NC3=O)C4)CC2)CC(C)N1C(=O)N1CCN2c3cc(-c4ccccc4O)nnc3NC[C@H]2C1] | 3-(6-(4-((4-((S)-2-(2-hydroxyphenyl)-6,6a,7,8,9,10-hexahydro-5H-pyrazino[1',2':4,5]pyrazino[2,3-c]pyridazine-8-carbonyl)-3,5-dimethylpiperazin-1-yl)methyl)piperidin-1-yl)-1-oxoisoinolin-2-yl)piperidine-2,6-dione |
| 267 | 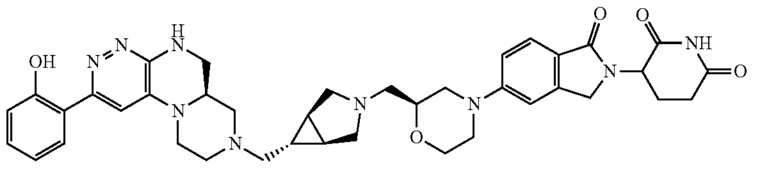 [SMILES: O=C1CCC(N2Cc3cc(N4CCO[C@@H](CN5C[C@@H]6[C@H](C5)[C@H]6CN5CCN6c7cc(-c8ccccc8O)nnc7NC[C@H]6C5)C4)ccc3C2=O)C(=O)N1] | 3-(5-((S)-2-(((1R,5S,6R)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)morpholino)-1-oxoisoindolin-2-yl)piperidine-2,6-dione |
| 268 | 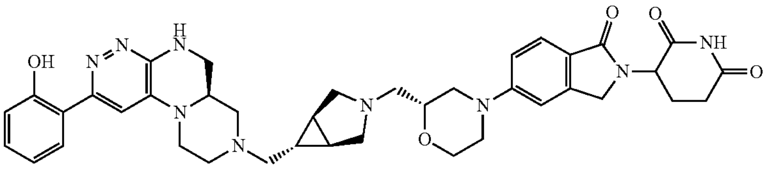 [SMILES: O=C1CCC(N2Cc3cc(N4CCO[C@H](CN5C[C@@H]6[C@H](C5)[C@H]6CN5CCN6c7cc(-c8ccccc8O)nnc7NC[C@H]6C5)C4)ccc3C2=O)C(=O)N1] | 3-(5-((R)-2-(((1R,5S,6S)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)morpholino)-1-oxoisoindolin-2-yl)piperidine-2,6-dione |

TABLE 1-continued

| Compounds | | |
|---|---|---|
| Example | Structure | Name |
| 269 | 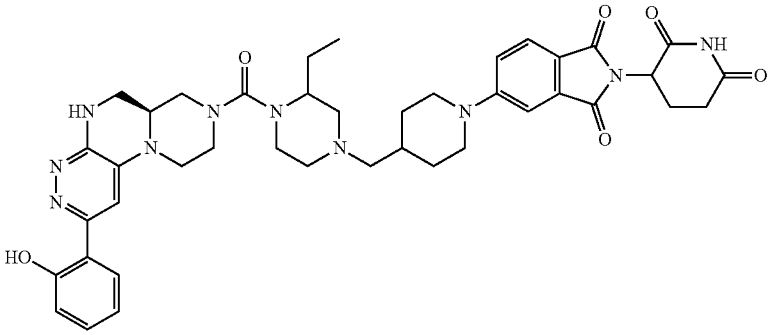 [SMILES: CCC1CN(CC2CCN(c3ccc4c(c3)C(=O)N(C3CCC(=O)NC3=O)C4=O)CC2)CCN1C(=O)N1CCN2c3cc(-c4ccccc4O)nnc3NC[C@H]2C1] | 2-(2,6-dioxopiperidin-3-yl)-5-(4-((3-ethyl-4-((S)-2-(2-hydroxyphenyl)-6,6a,7,8,9,10-hexahydro-5H-pyrazino[1',2':4,5]pyrazino[2,3-c]pyridazine-8-carbonyl)-piperazin-1-yl)mehtyl)piperidin-1-yl)isoindoline-1,3-dione |
| 270 | 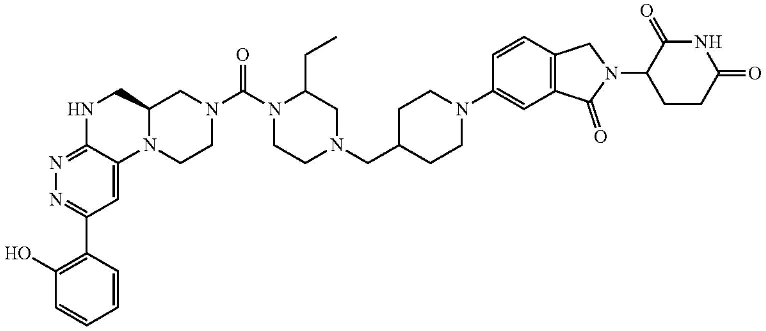 [SMILES: CCC1CN(CC2CCN(c3ccc4c(c3)C(=O)N(C3CCC(=O)NC3=O)C4)CC2)CCN1C(=O)N1CCN2c3cc(-c4ccccc4O)nnc3NC[C@H]2C1] | 3-(6-(4-((3-ethyl-4-((S)-2-(2-hydroxyphenyl)-6,6a,7,8,9,10-hexahydro-5H-pyrazino[1',2':4,5]pyrazino[2,3-c]pyridazine-8-carbonyl)piperazin-1-yl)methyl)piperidin-1-yl)-1-oxoisoindolin-2-yl)piperidine-2,6-dione |
| 271 | 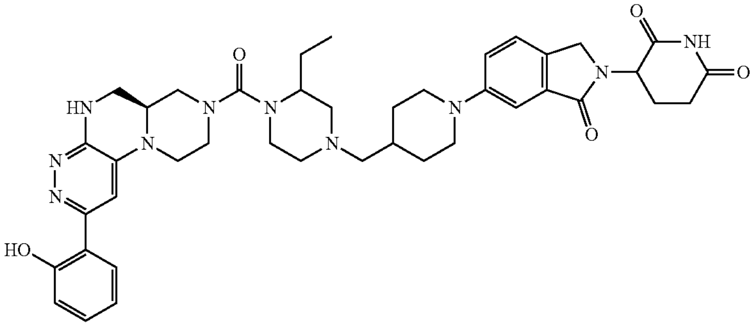 [SMILES: CCC1CN(CC2CCN(c3ccc4c(c3)C(=O)N(C3CCC(=O)NC3=O)C4)CC2)CCN1C(=O)N1CCN2c3cc(-c4ccccc4O)nnc3NC[C@H]2C1] | 3-(6-(4-((3-ethyl-4-((S)-2-(2-hydroxyphenyl)-6,6a,7,8,9,10-hexahydro-5H-pyrazino[1',2':4,5]pyrazino[2,3-c]pyridazine-8-carbonyl)piperazin-1-yl)methyl)piperidin-1-yl)-1-oxoisoindolin-2-yl)piperidine-2,6-dione |
| 272 | 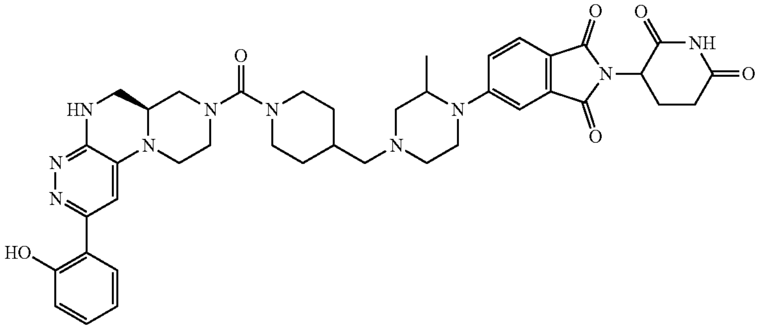 [SMILES: CC1CN(CC2CCN(C(=O)N3CCN4c5cc(-c6ccccc6O)nnc5NC[C@H]4C3)CC2)CCN1c1ccc2c(c1)C(=O)N(C1CCC(=O)NC1=O)C2=O] | 2-(2,6-dioxopiperidin-3-yl)-5-(4-((1-((S)-2-(2-hydroxyphenyl)-6,6a,7,8,9,10-hexahydro-5H-pyrazino[1',2':4,5]pyrazino[2,3-c]pyridazine-8-carbonyl)piperidin-4-yl)methyl)-2-methylpiperazin-1-yl)isoindoline-1,3-dione |

TABLE 1-continued

| Compounds | | |
|---|---|---|
| Example | Structure | Name |
| 273 | 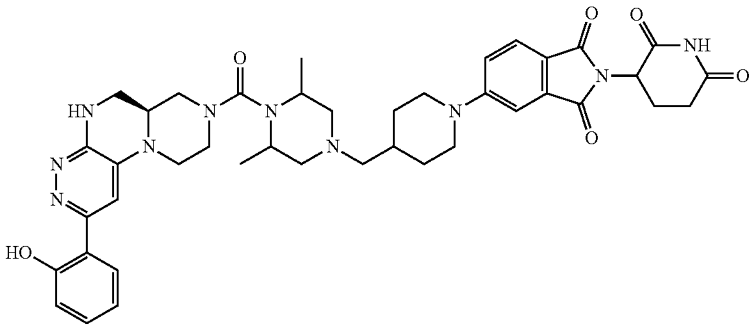 [SMILES: CC1CN(CC2CCN(c3ccc4c(c3)C(=O)N(C3CCC(=O)NC3=O)C4=O)CC2)CC(C)N1C(=O)N1CCN2c3cc(-c4ccccc4O)nnc3NC[C@H]2C1] | 2-(2,6-dioxopiperidin-3-yl)-5-(4-((4-((S)-2-(2-hydroxyphenyl)-6,6a,7,8,9,10-hexahydro-5H-pyrazino[1',2':4,5]pyrazino[2,3-c] pyridazine-8-carbonyl)-3,5-dimethylpiperazin-1-yl)methyl)piperidin-1-yl)isoindoline-1,3-dione |
| 274 | 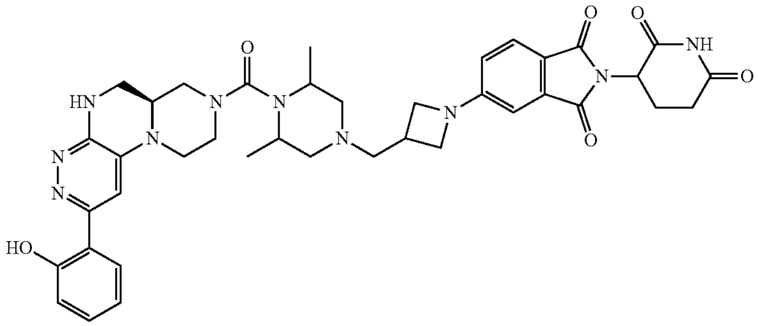 [SMILES: CC1CN(CC2CN(c3ccc4c(c3)C(=O)N(C3CCC(=O)NC3=O)C4=O)C2)CC(C)N1C(=O)N1CCN2c3cc(-c4ccccc4O)nnc3NC[C@H]2C1] | 2-(2,6-dioxopiperidin-3-yl)-5-(3-((4-((S)-2-(2-hydroxyphenyl)-6,6a,7,8,9,10-hexahydro-5H-pyrazino[1',2':4,5]pyrazino[2,3-c] pyridazine-8-carbonyl)-3,5-dimethylpiperazin-1-yl)methyl)azetidin-1-yl)isoindoline-1,3-dione |
| 275 | 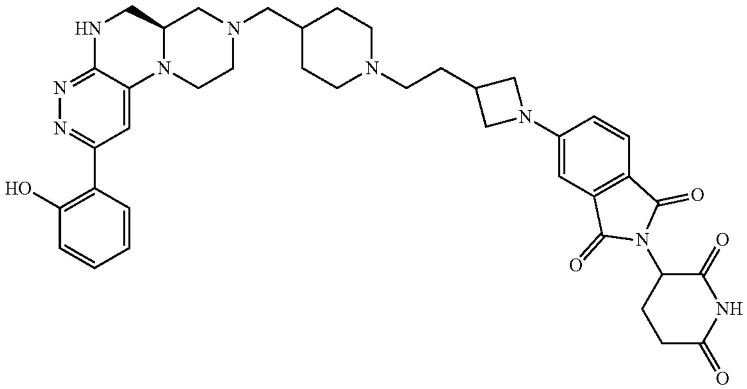 [SMILES: O=C1CCC(N2C(=O)c3ccc(N4CC(CCN5CCC(CN6CCN7c8cc(-c9ccccc9O)nnc8NC[C@H]7C6)CC5)C4)cc3C2=O)C(=O)N1] | 2-(2,6-dioxopiperidin-3-yl)-5-(3-(2-(4-((S)-2-(2-hydroxyphenyl)-5,6,6a,7,9,10-hexahydro-8H-pyrazino[1',2':4,5]pyrazino[2,3-c] pyridazin-8-yl)methyl) piperidin-1-yl)ethyl)azetidin-1-yl)isoindoline-1,3-dione |
| 276 | 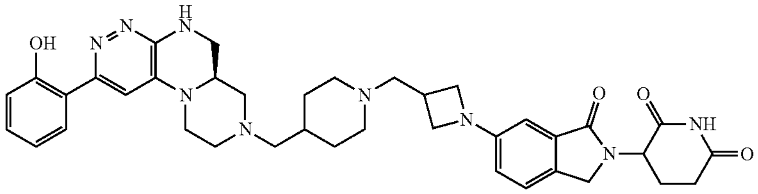 [SMILES: O=C1CCC(N2Cc3ccc(N4CC(CN5CCC(CN6CCN7c8cc(-c9ccccc9O)nnc8NC[C@H]7C6)CC5)C4)cc3C2=O)C(=O)N1] | 3-(6-(3-((4-(((S)-2-(2-hydroxyphenyl)-5,6,6a,7,9,10-hexahydro-8H-pyrazino[1',2':4,5]pyrazino[2,3-c] pyridazin-8-yl)methyl) piperidin-1-yl)methyl)azetidin-1-yl)-1-oxoisoindolin-2-yl) piperidine-2,6-dione |
| 277 | 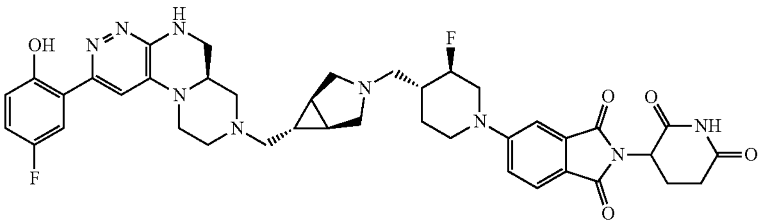 [SMILES: O=C1CCC(N2C(=O)c3ccc(N4CC[C@H](CN5C[C@@H]6[C@H](C5)[C@H]6CN5CCN6c7cc(-c8cc(F)ccc8O)nnc7NC[C@H]6C5)[C@@H](F)C4)cc3C2=O)C(=O)N1] | 2-(2,6-dioxopiperidin-3-yl)-5-((3R,4R)-3-fluoro-4-(((1R,5S,6R)-6-(((S)-2-(5-fluoro-2-hydroxyphenyl)-5,6,6a,7,9,10-hexahydro-8H-pyrazino[1',2':4,5]pyrazino[2,3-c] pyridazin-8-yl)methyl)-3-azabicyclo[3.1.0]hexan-3-yl)methyl)piperidin-1-yl)isoindoline-1,3-dione |

TABLE 1-continued

| Compounds | | |
|---|---|---|
| Example | Structure | Name |
| 278 | 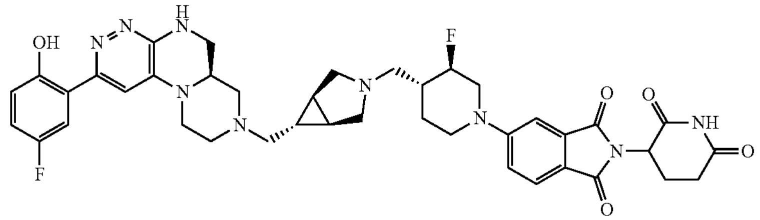 [SMILES: O=C1CCC(N2C(=O)c3ccc(N4CC[C@H](CN5C[C@@H]6[C@H](C5)[C@H]6CN5CCN6c7cc(-c8cc(F)ccc8O)nnc7NC[C@H]6C5)[C@@H](F)C4)cc3C2=O)C(=O)N1] | 2-(2,6-dioxopiperidin-3-yl)-5-((3R,4R)-3-fluoro-4-(((1R,5S,6R)-6-(((S)-2-(5-fluoro-2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)piperidin-1-yl)isoindoline-1,3-dione |
| 279 | 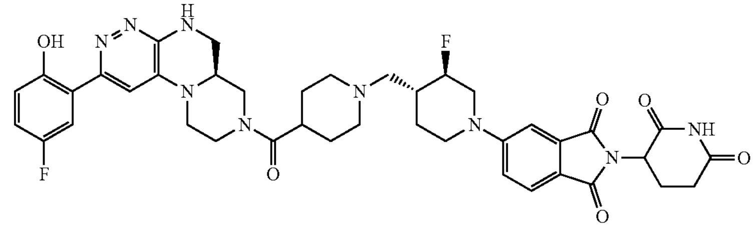 [SMILES: O=C1CCC(N2C(=O)c3ccc(N4CC[C@H](CN5CCC(C(=O)N6CCN7c8cc(-c9cc(F)ccc9O)nnc8NC[C@H]7C6)CC5)[C@@H](F)C4)cc3C2=O)C(=O)N1] | 2-(2,6-dioxopiperidin-3-yl)-5-((3R,4R)-3-fluoro-4-((4-((S)-2-(5-fluoro-2-hydroxyphenyl)-6,6a,7,8,9,10-hexahydro-5H-pyrazino[1',2':4,5]pyrazino[2,3-c]pyridazine-8-carbonyl)piperidin-1-yl)methyl)piperidin-1-yl)isoindoline-1,3-dione |
| 280 | 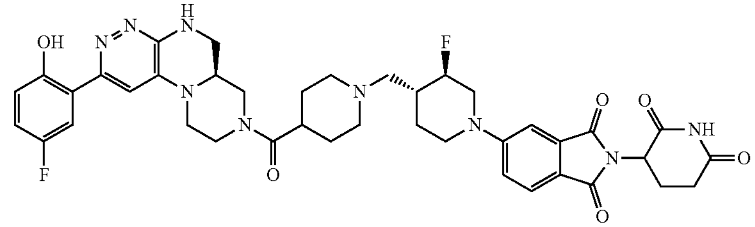 [SMILES: O=C1CCC(N2C(=O)c3ccc(N4CC[C@H](CN5CCC(C(=O)N6CCN7c8cc(-c9cc(F)ccc9O)nnc8NC[C@H]7C6)CC5)[C@@H](F)C4)cc3C2=O)C(=O)N1] | 2-(2,6-dioxopiperidin-3-yl)-5-((3R,4R)-3-fluoro-4-((4-((S)-2-(5-fluoro-2-hydroxyphenyl)-6,6a,7,8,9,10-hexahydro-5H-pyrazino[1',2':4,5]pyrazino[2,3-c]pyridazine-8-carbonyl)piperidin-1-yl)methyl)piperidin-1-yl)isoindoline-1,3-dione |
| 281 | 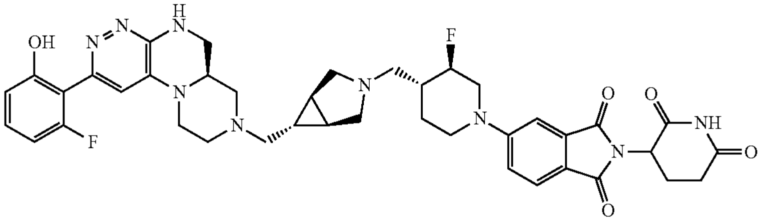 [SMILES: O=C1CCC(N2C(=O)c3ccc(N4CC[C@H](CN5C[C@@H]6[C@H](C5)[C@H]6CN5CCN6c7cc(-c8c(O)cccc8F)nnc7NC[C@H]6C5)[C@@H](F)C4)cc3C2=O)C(=O)N1] | 2-(2,6-dioxopiperidin-3-yl)-5-((3R,4R)-3-fluoro-4-(((1R,5S,6R)-6-(((S)-2-(2-fluoro-6-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)piperidin-1-yl)isoindoline-1,3-dione |
| 282 | 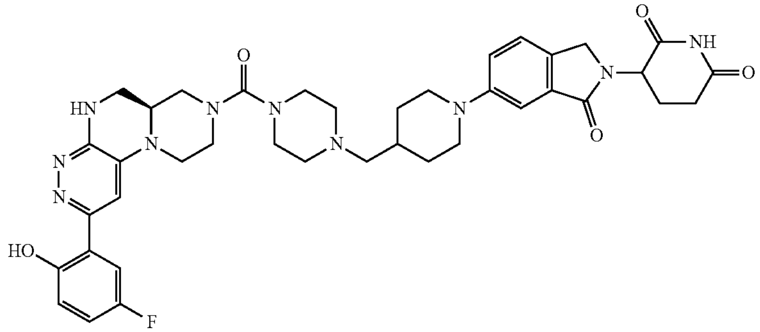 [SMILES: O=C1CCC(N2Cc3ccc(N4CCC(CN5CCN(C(=O)N6CCN7c8cc(-c9cc(F)ccc9O)nnc8NC[C@H]7C6)CC5)CC4)cc3C2=O)C(=O)N1] | 3-(6-(4-((4-((S)-2-(5-fluoro-2-hydroxyphenyl)-6,6a,7,8,9,10-hexahydro-5H-pyrazino[1',2':4,5]pyrazino[2,3-c]pyridazine-8-carbonyl)piperazin-1-yl)methyl)piperidin-1-yl)-1-oxoisoindolin-2-yl)piperidine-2,6-dione |

Compounds of the invention can be prepared using numerous preparatory reactions known in the literature. The Schemes below provide general guidance in connection with preparing the compounds of the invention. One skilled in the art would understand that the preparations shown in the Schemes can be modified or optimized using general knowledge of organic chemistry to prepare various compounds of the invention. Example synthetic methods for preparing compounds of the invention are provided in the Schemes below.

The following Examples are provided to illustrate some of the concepts described within this disclosure. While the Examples are considered to provide an embodiment, it should not be considered to limit the more general embodiments described herein.

EXAMPLES

General Synthetic Procedures

The compounds described herein may be prepared according to the following synthetic schemes and general synthetic procedures.

Scheme I

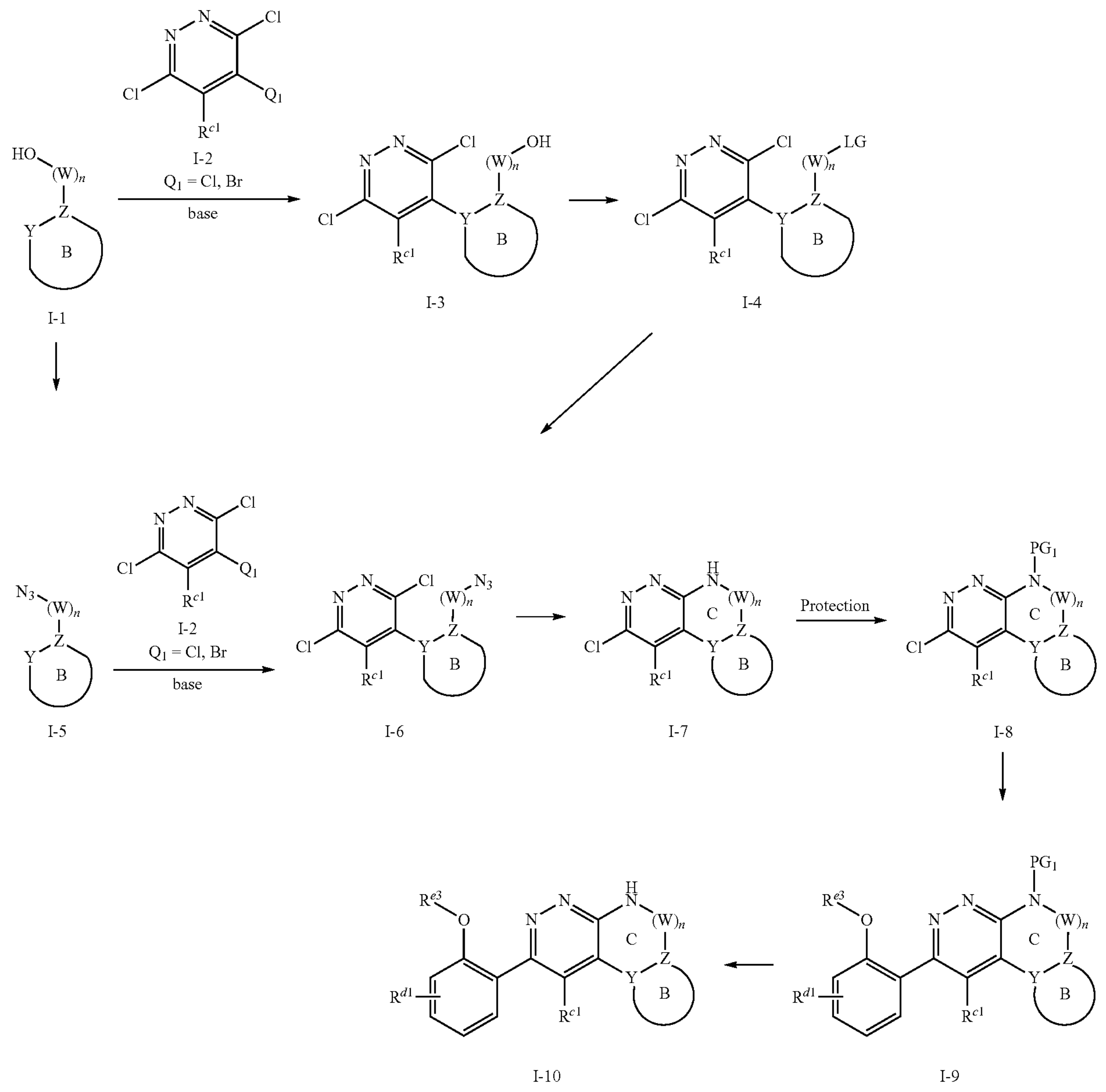

Compounds of formula I-10 can be synthesized using, for example, the sequences shown in Scheme I. $S_NAr$ reaction between I-1 and compound I-2 in the presence of a base (e.g., $Cs_2CO_3$, $NaHCO_3$, DIPEA) at elevated temperatures can give alcohol I-3. Conversion of the hydroxyl group of I-3 to a leaving group (LG) under appropriate conditions (such as, but not limited to, treatment with $SOCl_2$, or $CBr_4/PPh_3$, or $MsCl/Et_3N$) can afford compounds I-4, which can be transformed to the corresponding azid I-6 using $NaN_3$. Alternatively, compound I-1 can be converted to azide I-5 upon treatment with $PPh_3/NaN_3$/DEAD. $S_NAr$ reaction between I-5 and compound 1-2 in the presence of a base can yield compounds 1-6. Reduction of the azido group of compounds I-6 using $PPh_3$ or $Pd/H_2$ to the corresponding amines, followed by intramolecular cyclization can afford compounds I-7. Protection of the —NH group with an appropriate group (e.g., Boc, SEM, Bn, etc.) can give compounds I-8, which can be converted to compounds I-9 under standard Suzuki conditions (e.g., in the presence of a palladium catalyst, such as but not limited to tetrakis (triphenylphosphine)palladium(0) or [1,1'-bis (diphenylphosphino)ferrocene]dichloropalladium (11), complex with dichloromethane and a base (e.g., a carbonate base)) using the appropriate boronic acid or ester (e.g., 2-hydroxyphenylboronic acid). Removal of the protecting groups can yield compounds I-10, wherein W, Y, Z, B, C, n, $R^{c1}$, $R^{d1}$, and $R^{e3}$ are as defined herein and above.

Scheme II

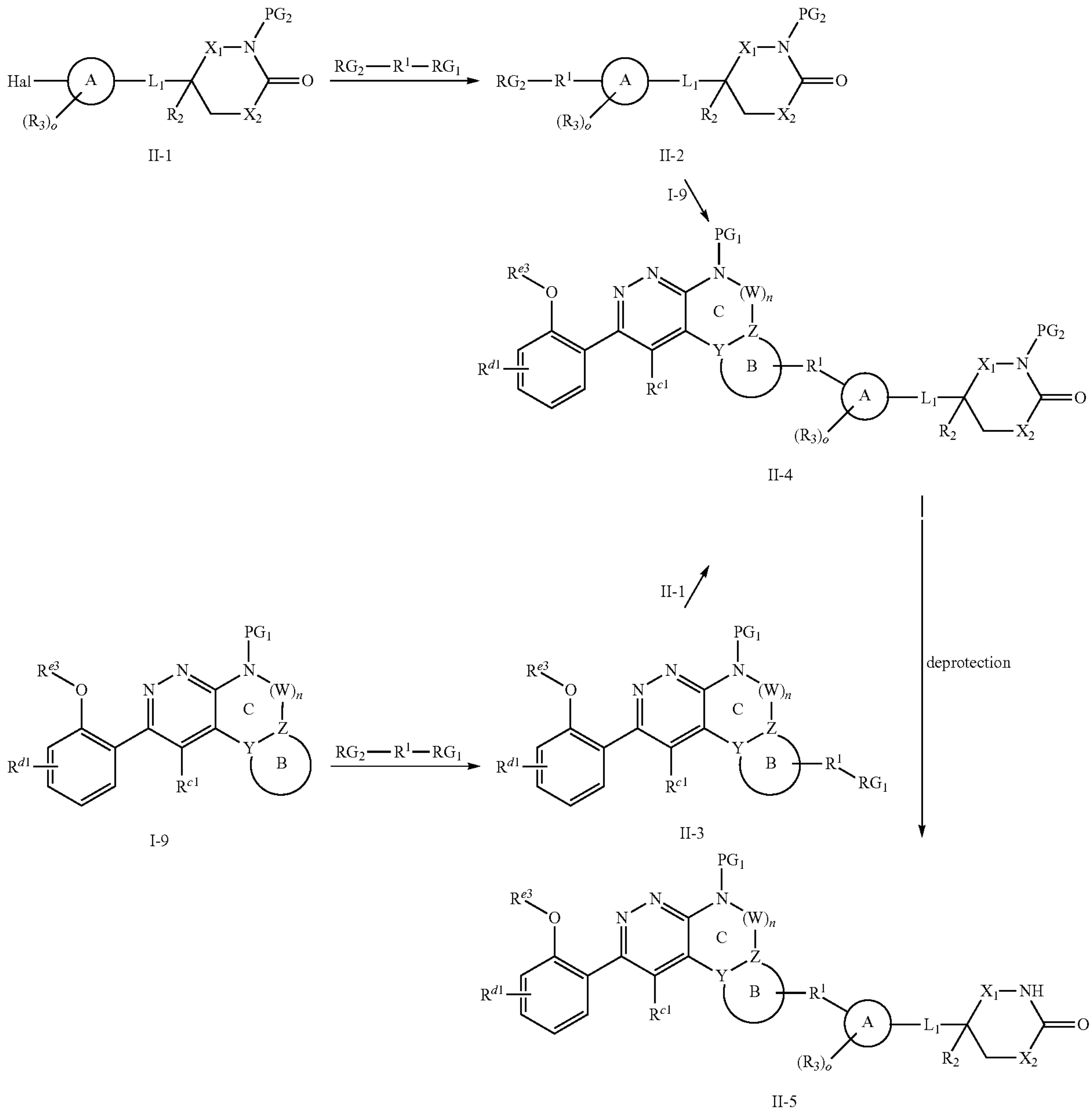

II-1 II-2 II-4 II-3 I-9 II-5

$RG_1$ and $RG_2$ = reacting groups
$PG_1$ and $PG_2$ = protecting groups

Compounds of formula II-5 can be synthesized using, for example, the sequences shown in Scheme II. Coupling of compounds II-1 with $R_1$ using appropriate synthetic methods (such as but not limited to $S_NAr$ reaction, Suzuki coupling, Buchwald reaction, or copper(I)-catalyzed alkynylation, etc) can afford compounds II-2. Compounds I-8 can be introduced using appropriate synthetic methods (such as, but not limited to, $S_N2$ reaction, $S_NAr$ reaction, reductive amination, Buchwald reaction, amide formation, Mitsunobu reaction, olefin metathesis, etc.) to give compounds II-4. Alternatively, the synthesis of II-4 can be achieved by the coupling of I-9 with $R_1$, followed by the introduction of II-1 using appropriate synthetic methods mentioned above. Removal of the protecting groups can afford compounds of formula II-5, wherein W, B, C, Y, Z, X, $X_1$, $X_2$, $L_1$, n, o, $R^1$, $R_2$, $R_3$, $R^{c1}$, $R^{d1}$, and $R^{e3}$ are as defined herein and above.

Scheme III

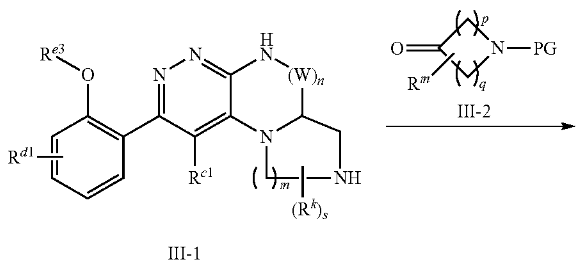

III-1 III-2

-continued

-continued

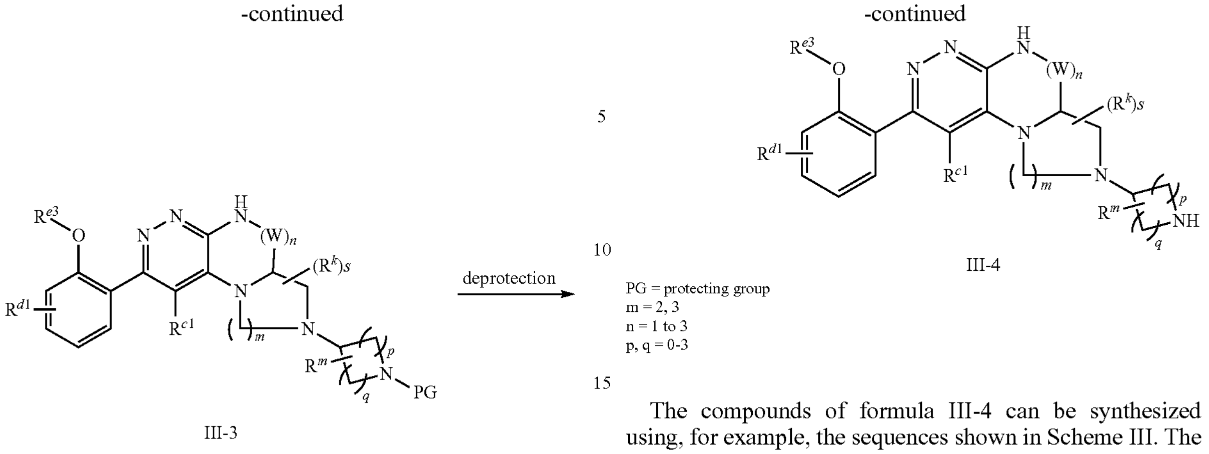

III-3

III-4

The compounds of formula III-4 can be synthesized using, for example, the sequences shown in Scheme III. The reductive amination between compounds III-1 and III-2 under reducing conditions (e.g., $NaBH_3CN$) can provide compounds III-3. Removal of the protecting groups, under standard conditions (e.g., PG=Boc, deprotect with TFA) can give compounds of formula III-4, wherein W, X, Q, m, n, p, q, $R^{c1}$, $R^{d1}$, $R^m$, $R^k$ and $R^{e3}$ are as defined herein and above.

Scheme IV

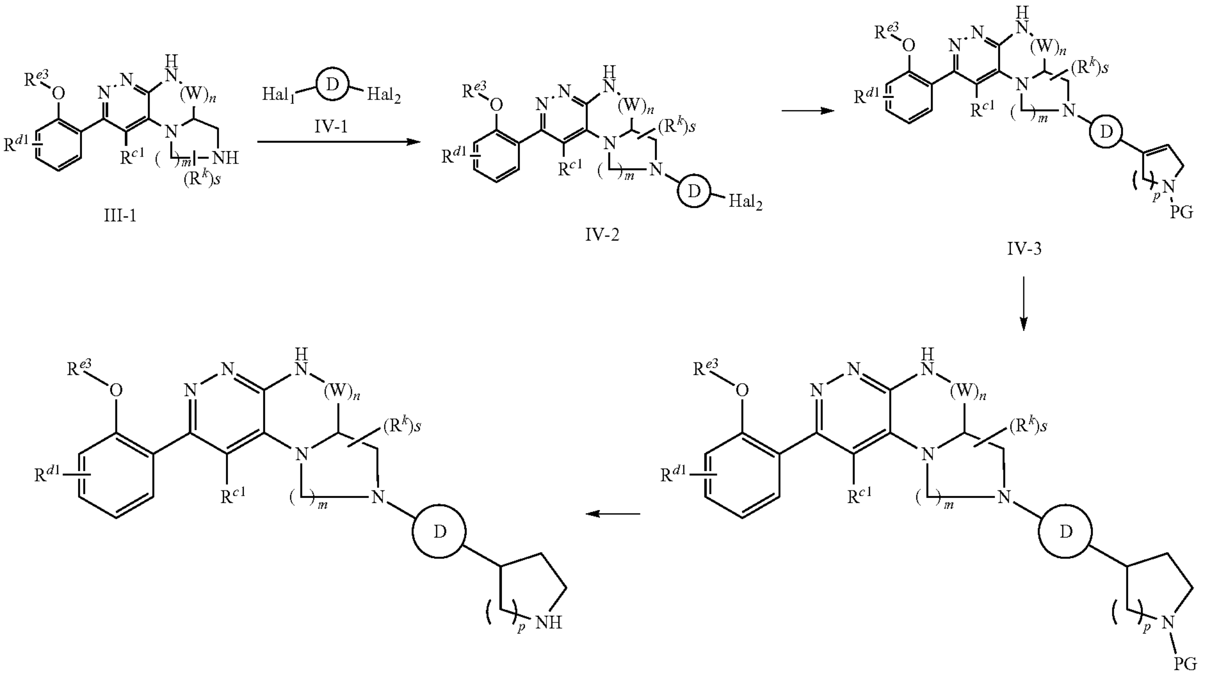

III-1

IV-1

IV-2

IV-3

IV-4

IV-5

PG = protecting group
Hal1 and Hal2 = halogens
m = 2, 3
n = 1 to 3
p = 1 to 3
Ring D is optionally substituted aryl or heteroaryl The compounds of formula IV-5 can be synthesized using, for example, the sequences shown in Scheme TV. The $S_NAr$ reaction between compounds ITT-1 and 5-bromo-2-chloropyrimidine can provide compounds IV-2. The following Suzuki reaction can afford compounds IV-3. The reduction of the alkene under the appropriate conditions (e.g., Pd/C catalyzed hydrogenation) followed by the removal of the protecting group (e.g., PG=Boc, deprotect with TFA) can afford the compounds of formula IV-5, wherein W, D, m, n, p, s, $R^{c1}$, $R^{d1}$, $R^k$ and $R^{e3}$ are as defined herein and above.

Scheme V

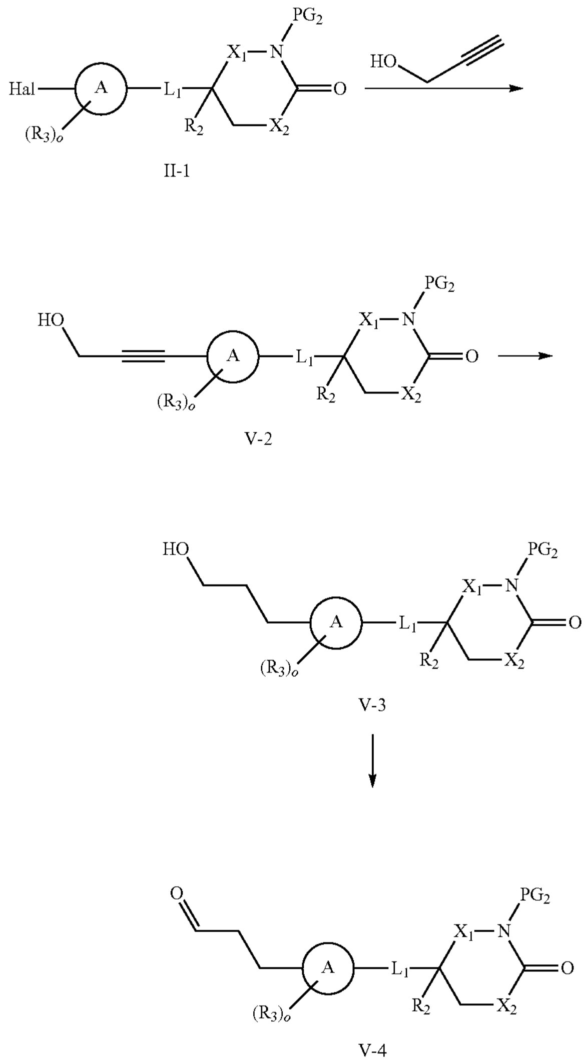

II-1

V-2

V-3

V-4

$PG_2$ = protecting group

The compounds of formula V-4 can be synthesized using, for example, the sequences shown in Scheme V. The Cu (I)-catalyzed alkynylation of compounds II-1 can provide compounds V-2. The reduction of the alkyne under appropriate conditions (e.g., Pd/C catalyzed hydrogenation) followed by the oxidation (e.g., Dess-Martin reagent or TEMPO) of the hydroxyl group afford the aldehydes of formula V-4, wherein $X_1$, $X_2$, $L_1$, o, $R_2$, and $R_3$ are as defined herein and above.

Scheme VI

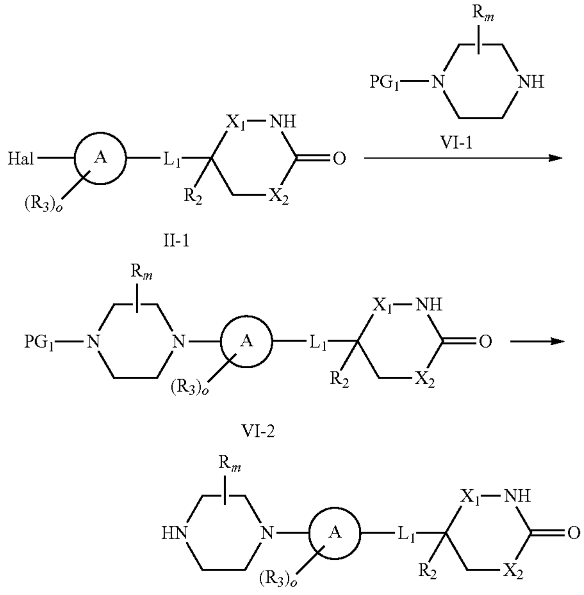

VI-1

II-1

VI-2

VI-3

$PG_1$ = protecting group

The compounds of formula VI-3 can be synthesized using, for example, the sequences shown in Scheme VI. The coupling between compounds II-1 and VI-1 using synthetic methods (such as but not limited to $S_NAr$ reaction, Buchwald reaction, etc.) can afford compounds VI-2. Removal of the protecting group can yield the compounds of formula VI-3, wherein $X_1$, $X_2$, $L_1$, o, $R_2$, $R_m$, and $R_3$ are as defined herein and above.

Scheme VII

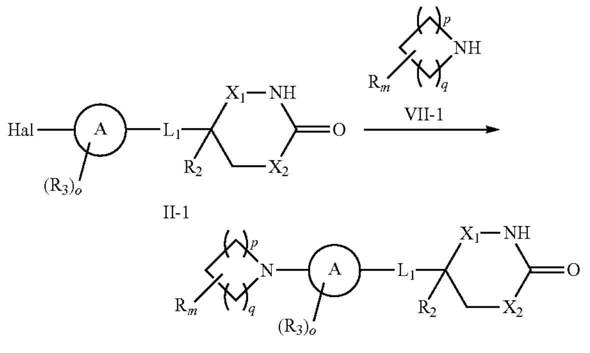

VII-1

II-1

VII-2 p, q = 0 to 3

The compounds of formula VII-2 can be synthesized using, for example, the sequences shown in Scheme VII. The coupling between compounds II-1 and VII-1 using synthetic methods (such as but not limited to SNAr reaction, Buchwald reaction, etc.) can afford compounds VII-2, wherein $X_1$, $X_2$, $L_1$, o, p, q, $R_2$, $R_m$, and $R_3$ are as defined herein and above.

Intermediate 1: (R)-2-(6,6a,7,8,9,10-hexahydro-5H-pyrazino[1',2':4,5]pyrazino[2,3-c]pyridazin-2-yl) phenol (Int-1)

Int-1

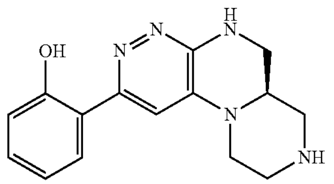

Step 1: Synthesis of tert-butyl (R)-4-(3,6-dichloro-pyridazin-4-yl)-3-(hydroxymethyl)piperazine-1-carboxylate

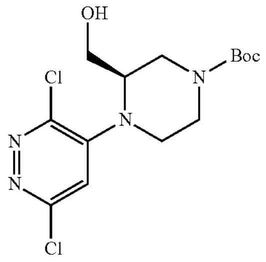 [SMILES: CC(C)(C)OC(=O)N1CCN(c2cc(Cl)nnc2Cl)[C@@H](CO)C1]

To a solution of 3,4,6-trichloropyridazine (5.7 g, 31.08 mmol) in DMF (24 mL) was added N,N-diisopropylethylamine (5.95 mL, 34.2 mmol) and tert-butyl (R)-3-(hydroxymethyl) piperazine-1-carboxylate (7.1 g, 32.8 mmol). The reaction was stirred at 80° C. overnight. The reaction was cooled to 45° C. and water (17 mL) was added slowly. The resulted clear solution was stirred at 35° C. for 30 min until precipitate formed. Another portion of water (23 mL) was charged slowly and the mixture was stirred at 0° C. for an additional 1 h. The mixture was filtered and the resulting solid was washed with water and dried under vacuum to give tert-butyl (R)-4-(3,6-dichloropyridazin-4-yl)-3-(hydroxymethyl)piperazine-1-carboxylate (8.5 g, 75.3% yield) as an off-white solid. LCMS m/z calcd for $C_{14}H_{21}Cl_2N_4O_3$ $[M+H]^+$: 363.1; found: 363.1.

Step 2: Synthesis of tert-butyl (R)-3-(azidomethyl)-4-(3,6-dichloropyridazin-4-yl)piperazine-1-carboxylate

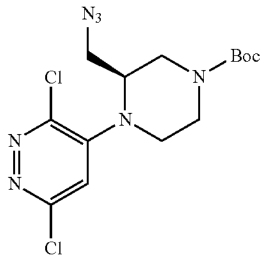 [SMILES: CC(C)(C)OC(=O)N1CCN(c2cc(Cl)nnc2Cl)[C@@H](CN=[N+]=[N-])C1]

To a solution of tert-butyl (R)-4-(3,6-dichloropyridazin-4-yl)-3-(hydroxymethyl) piperazine-1-carboxylate (5.45 g, 15 mmol) and triphenylphosphine (4.72 g, 18 mmol) in THF (150 mL) was added diisopropyl azodicarboxylate (3.54 mL, 18 mmol) and DPPA (3.9 mL, 18 mmol) at 0° C. The reaction was then stirred at RT overnight. The reaction mixture was cooled to 0° C., quenched with water and extracted with EtOAc. The combined organic layers were washed with brine and water, dried over $Na_2SO_4$ and filtered. The filtrate was concentrated under reduced pressure to give crude tert-butyl (R)-3-(azidomethyl)-4-(3,6-dichloropyridazin-4-yl)piperazine-1-carboxylate (19.4 g, 100% yield), which was used without further purification. Assumed 100% yield, 30% purity. LCMS m/z calcd for $C_{14}H_{20}Cl_2N_7O_2$ $[M+H]^+$: 388.1; found: 388.0.

Step 3: Synthesis of tert-butyl (S)-2-chloro-5,6,6a,7,9,10-hexahydro-8H-pyrazino[1',2':4,5]pyrazino[2,3-c]pyridazine-8-carboxylate

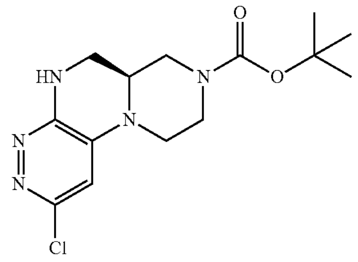 [SMILES: CC(C)(C)OC(=O)N1CCN2c3cc(Cl)nnc3NC[C@H]2C1]

To a stirred solution of crude tert-butyl (R)-3-(azidomethyl)-4-(3,6-dichloropyridazin-4-yl) piperazine-1-carboxylate (30% purity, 20.3 g, 15.7 mmol) in THF (200 mL), triphenylphosphine (4.94 g, 18.8 mmol) was added. The resulted solution was stirred at 60° C. for 3 h. Water (20 mL) and N,N-diisopropylethylamine (8.2 mL, 47.1 mmol) were added sequentially. After 20 h, the reaction mixture was diluted with EtOAc (100 mL) and water (100 mL). The aqueous layer was separated and extracted with EtOAc. The combined organic layers were washed with brine, dried over $Na_2SO_4$ and filtered. The filtrate was concentrated under reduced pressure. The residue was purified by silica gel chromatography, eluting with 0-100% EtOAc/hexanes to give tert-butyl (S)-2-chloro-5,6,6a,7,9,10-hexahydro-8H-pyrazino[1',2':4,5]pyrazino[2,3-c]pyridazine-8-carboxylate (3.1 g, 60% yield) as an off-white solid. LCMS m/z calcd for $C_{14}H_{21}ClN_5O_2[M+H]^+$: 326.1; found: 326.2.

Step 4: Synthesis of di-tert-butyl (R)-2-chloro-6a,7,9,10-tetrahydro-5H-pyrazino[1',2':4,5]pyrazino[2,3-c]pyridazine-5,8(6H)-dicarboxylate

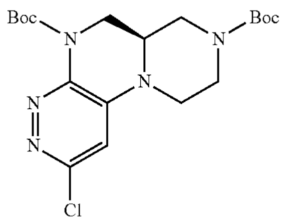 [SMILES: CC(C)(C)OC(=O)N1CCN2c3cc(Cl)nnc3N(C(=O)OC(C)(C)C)C[C@H]2C1]

To a stirred solution of tert-butyl (S)-2-chloro-5,6,6a,7,9,10-hexahydro-8H-pyrazino [1',2':4,5]pyrazino[2,3-c]pyridazine-8-carboxylate (3.1 g, 9.52 mmol) in DCM (120 mL), di-tert butyl dicarbonate (6.23 g, 28.6 mmol) and 4-(dimethylamino)pyridine (1.16 g, 9.52 mmol) were added at RT. After 1 h, the reaction was diluted with DCM (120 mL) and sat. aq. $NH_4Cl$ (50 mL). After another 1 h, the aqueous layer was separated and extracted with DCM. The organic layers were combined, washed with brine, dried over $Na_2SO_4$ and filtered. The filtrate was concentrated under reduced pressure. The residue was purified by silica gel chromatography, eluting with 50% EtOAc/hexanes to give di-tert-butyl (R)-2-chloro-6a,7,9,10-tetrahydro-5H-pyrazino[1',2':4,5]pyrazino[2,3-c]pyridazine-5,8(6H)-dicarboxylate (3.9 g, 96% yield). LCMS m/z calcd for $C_{19}H_{29}ClN_5O_4$[M+H]$^+$: 426.2; found: 426.3.

Step 5: Synthesis of di-tert-butyl (R)-2-(2-hydroxyphenyl)-6a, 7,9,10-tetrahydro-5H-pyrazino [1',2':4,5]pyrazino[2,3-c]pyridazine-5,8(6H)-dicarboxylate

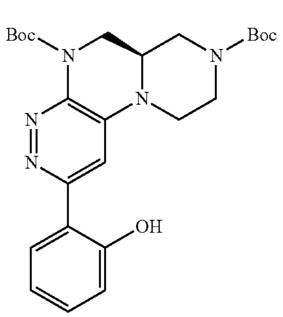 [SMILES: CC(C)(C)OC(=O)N1CCN2c3cc(-c4ccccc4O)nnc3N(C(=O)OC(C)(C)C)C[C@H]2C1]

To a solution of di-tert-butyl (R)-2-chloro-6a,7,9,10-tetrahydro-5H-pyrazino[1',2':4,5]pyrazino[2,3-c]pyridazine-5,8(6H)-dicarboxylate and 2-hydroxyphenyl boronic acid (1.94 g, 14.1 mmol) in 1,4-dioxane (110 mL) was added potassium carbonate (3.89 g, 28.2 mmol) and [1,1'-bis(diphenylphosphino)ferrocene]dichloropalladium(II), complex with dichloromethane (0.58 g, 0.70 mmol) at RT. The mixture was stirred at 105° C. for 18 h. The reaction was concentrated and the residue was purified by flash chromatography ($SiO_2$, 200-300 mesh, EtOAc/hexanes=2/1) to give di-tert-butyl (R)-2-(2-hydroxyphenyl)-6a,7,9,10-tetrahydro-5H-pyrazino[1',2':4,5]pyrazino [2,3-c]pyridazine-5,8(6H)-dicarboxylate (2.6 g, 5.4 mmol, 76.3% yield) as a white solid. LCMS m/z calcd for $C_{25}H_{34}N_5O_5$ [M+H]$^+$: 484.3; found: 484.3.

Step 6: Synthesis of (R)-2-(6,6a, 7,8,9,10-hexahydro-5H-pyrazino[1',2':4,5]pyrazino[2,3-c]pyridazin-2-yl)phenol To a stirred solution of di-tert-butyl (R)-2-(2-hydroxyphenyl)-6a,7,9,10-tetrahydro-5H-pyrazino[1',2':4,5]pyrazino[2,3-c]pyridazine-5,8(6H)-dicarboxylate (1.3 g, 2.69 mmol) in DCM (10 mL), 2,2,2-trifluoroacetic acid (4.1 mL) was added at RT. After 1 h, the reaction mixture was concentrated to dryness under reduced pressure. The residue was dissolved in MeOH/DCM (1/6, 400 mL) and saturated aqueous $NaHCO_3$ (80 mL) was added. The resulted mixture was stirred at 30° C. for 30 min. The aqueous layer was separated and extracted with MeOHDCM (1/6, 80 mL×4). The combined organic layers were washed with brine, dried over $Na_2SO_4$ and filtered. The filtrate was concentrated under reduced pressure to give crude (R)-2-(6,6a,7,8,9,10-hexahydro-5H-pyrazino[1',2':4,5]pyrazino[2,3-c]pyridazin-2-yl)phenol (700 mg, 92% yield) as a beige solid. LCMS m/z calcd for $C_{15}H_{18}N_5O$ [M+H]$^+$: 284.2; found: 284.1. $^1H$ NMR (400 MHz, DMSO-$d_6$) δ14.8 (s, 1H), 7.91 (s, 1H), 7.30 (s, 1H), 7.19 (s, 2H), 6.83-6.86 (m, 2H), 3.92-3.94 (m, 1H), 3.40-3.44 (m, 1H), 3.13-3.15 (m, 2H), 3.00-3.11 (m, 2H), 2.66-2.76 (m, 2H), 2.45-2.50 (m, 1H), 2.28-2.33 (m, 1H).

Intermediate 2: (S)-2-(6,6a,7,8,9,10-hexahydro-5H-pyrazino[1',2':4,5]pyrazino[2,3-c]pyridazin-2-yl) phenol (Int-2)

Int-2

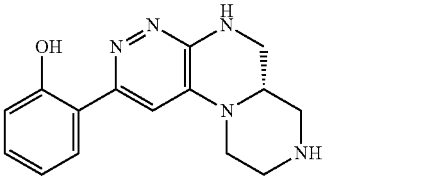

The title compound was prepared using procedure analogous to those described for Intermediate 1, with tert-butyl (S)-3-(hydroxymethyl)piperazine-1-carboxylate replacing tert-butyl (R)-3-(hydroxymethyl)piperazine-1-carboxylate in step 1. LCMS m/z calcd for $C_{15}H_{18}N_5O$ [M+H]$^+$: 284.2; found: 284.1.

Intermediate 3: (S)-2-(8-(piperidin-4-yl)-6,6a,7,8,9,10-hexahydro-5H-pyrazino[1',2':4,5]pyrazino[2,3-c]pyridazin-2-yl)phenol (Int-3)

Int-3

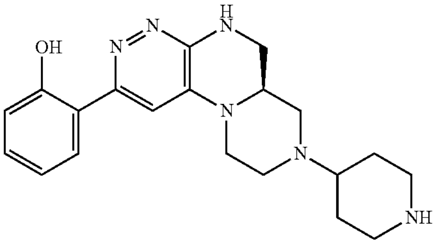

Step 1: Synthesis of tert-butyl (S)-4-(2-(2-hydroxyphenyl)-5,6,6a, 7,9,10-hexahydro-8H-pyrazino [1',2':4,5]pyrazino[2,3-c]pyridazin-8-yl)piperidine-1-carboxylate

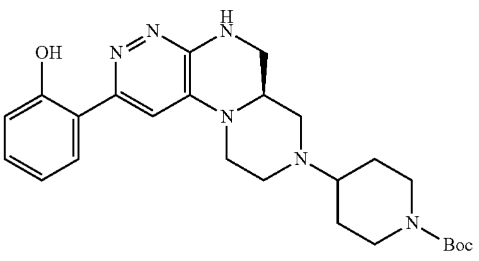 [SMILES: CC(C)(C)OC(=O)N1CCC(N2CCN3c4cc(-c5ccccc5O)nnc4NC[C@H]3C2)CC1]

To a solution of (R)-2-(6,6a,7,8,9,10-hexahydro-5H-pyrazino[1',2':4,5]pyrazino[2,3-c]pyridazin-2-yl)phenol (350 mg, 1.24 mmol) and Boc-piperidone (1.23 g, 6.18 mmol) in methanol (5 mL) was added sodium cyanoborohydride (233 mg, 3.71 mmol) and acetic acid (74.2 mg, 1.24 mmol) at RT. The resulted mixture was stirred at RT for 16 h then concentrated to dryness under reduced pressure. The crude residue was purified by column chromatography ($SiO_2$, 200-300 mesh size, DCM/MeOH=1/20) to give tert-butyl (S)-4-(2-(2-hydroxyphenyl)-5,6,6a,7,9,10-hexahydro-8H-pyrazino[1',2':4,5]pyrazino[2,3-c]pyridazin-8-yl)piperidine-1-carboxylate (380 mg, 0.81 mmol, 65.9% yield) as a solid. LCMS m/z calcd for $C_{25}H_{35}N_6O_3$ $[M+H]^+$: 467.3; found: 467.2.

Step 2: Synthesis of (S)-2-(8-(piperidin-4-yl)-6,6a,7,8,9,10-hexahydro-5H-pyrazino[1',2':4,5]pyrazino[2,3-c]pyridazin-2-yl)phenol To a solution of tert-butyl (S)-4-(2-(2-hydroxyphenyl)-5,6,6a,7,9,10-hexahydro-8H-pyrazino[1',2':4,5]pyrazino[2,3-c]pyridazin-8-yl)piperidine-1-carboxylate (200 mg, 0.43 mmol) in DCM (3 mL) was added 2,2,2-trifluoroacetic acid (3.0 mL) at RT. The resulted mixture was stirred at RT. for 16 h. The reaction was concentrated to dryness under reduced pressure to give crude (S)-2-(8-(piperidin-4-yl)-6,6a,7,8,9,10-hexahydro-5H-pyrazino[1',2':4,5]pyrazino[2,3-c]pyridazin-2-yl)phenol (150 mg, 0.41 mmol, 95.5% yield), which was used in the next step without further purification. LCMS m/z calcd for $C_{20}H_{27}N_6O$ [M+H]+=367.2; found: 367.2.

Intermediate 4: 2-((6aS)-8-(pyrrolidin-3-yl)-6,6a,7,8,9,10-hexahydro-5H-pyrazino[1',2':4,5]pyrazino[2,3-c]pyridazin-2-yl)phenol (Int-4)

Int-4

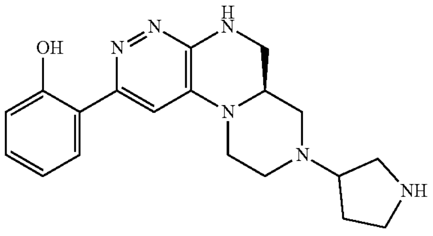

The title compound was prepared using procedure analogous to those described for Intermediate 3, with Boc-3-pyrrolidinone replacing Boc-piperidone in step 1. LCMS calcd for $C_{19}H_{25}N_6O$ $(M+H)^+$ m/z=353.2; found: 353.3.

Intermediate 5: 3-(6-bromo-3-oxo-1H-isoindol-2-yl)piperidine-2,6-dione (Int-5)

Int-5

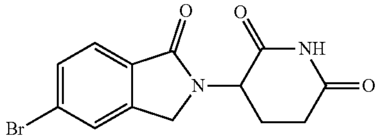

To a solution of methyl 4-bromo-2-(bromomethyl)benzoate (3.08 g, 10 mmol) in DMF (30 mL) was added 3-aminopiperidine-2,6-dione, HCl (Accela, catalog #: SY030429, 1.81 g, 11 mmol) and potassium carbonate (4.15 g, 30 mmol). The reaction mixture was heated at 70° C. for 20 h. The reaction was cooled to RT and concentrated to dryness under reduced pressure. Water (50 mL) was added to the residue and the mixture was stirred at RT for 30 min then filtered. The resulting solid was washed with EtOAc to give 3-(6-bromo-3-oxo-1H-isoindol-2-yl)piperidine-2,6-dione (2.1 g, 65% yield) as a pale-grey solid. LCMS m/z calcd for $C_{13}H_{12}BrN_2O_3$ $[M+H]^+$: 323.0; found: 323.1.

Intermediate 6: 2-(2,6-dioxopiperidin-3-yl)-1-oxoisoindoline-5-carbaldehyde (Int-6)

Int-6

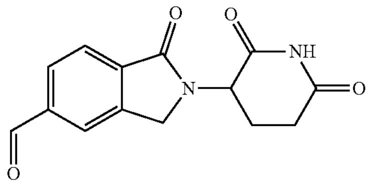

Step 1: Synthesis of 3-(1-oxo-5-vinylisoindolin-2-yl)piperidine-2,6-dione

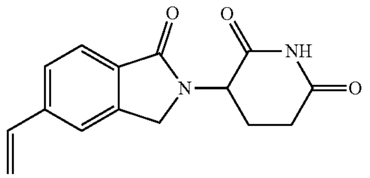 [SMILES: C=Cc1ccc2c(c1)CN(C1CCC(=O)NC1=O)C2=O]

A mixture of 3-(6-bromo-3-oxo-1H-isoindol-2-yl)piperidine-2,6-dione (100 mg, 0.31 mmol), [1,1'-bis(diphenylphosphino)ferrocene]dichloropalladium(II), complex with dichloromethane (25 mg, 0.03 mmol), potassium vinyltrifluoroborate (83 mg, 0.62 mmol) and cesium carbonate (302 mg, 0.93 mmol) in 1,4-Dioxane (2.4 mL) was stirred at 80° C. for 16 hours under $N_2$. After the reaction was cooled to RT, water (30 mL) was added. The reaction mixture was extracted with MeOH/DCM (1/6), washed with brine, dried over $Na_2SO_4$ and filtered. The resulting filtrate was concentrated under reduced pressure and purified by silica gel chromatography with 0~5% MeOH/DCM to give 3-(1-oxo-5-vinylisoindolin-2-yl)piperidine-2,6-dione (80 mg, 96% yield) as an orange solid. LCMS m/z calcd for $C_{15}H_{15}N_2O_3$ $[M+H]^+$: 271.1; found: 271.1.

Step 2: Synthesis of 2-(2,6-dioxopiperidin-3-yl)-1-oxoisoindoline-5-carbaldehyde To a solution of 3-(1-oxo-5-vinylisoindolin-2-yl)piperidine-2,6-dione (70 mg, 0.26 mmol) in 1,4-dioxane (2 mL) and water (2 mL) at 0° C. was added sodium periodate (222 mg, 1.04 mmol) and potassium osmate (8.6 mg, 0.03 mmol), followed by 2,6-lutidine (60 uL, 0.52 mmol). The reaction was stirred at 0° C. for 1 hour then diluted with water and extracted with MeOH/DCM (1/6), the combined organic phases were washed with $Na_2SO_3$ and brine, dried over $Na_2SO_4$ and filtered. The filtrate was concentrated under reduced pressure. The residue was purified by silica gel chromatography, eluting with 0%-5% MeOH/DCM, to give 2-(2,6-dioxopiperidin-3-yl)-1-oxoisoindoline-5-carbaldehyde (45 mg, 64% yield) as a pale-yellow solid. LCMS m/z calcd for $C_{14}H_{13}N_2O_4$ $[M+H]^+$: 273.1; found: 273.2.

Intermediate 7: 2-(2-(2,6-dioxopiperidin-3-yl)-1-oxoisoindolin-5-yl)acetaldehyde (Int-7)

Int-7

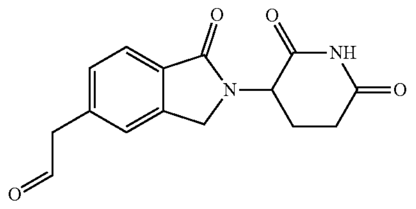

To a 5 mL vial containing $Pd(t-Bu_3P)_2$ (158 mg, 0.31 mmol) and anhydrous zinc fluoride, (320 mg, 3.09 mmol) under a $N_2$ atmosphere was added DMF (4 mL). The mixture was stirred at RT for 15 min. 3-(6-Bromo-3-oxo-1H-isoindol-2-yl)piperidine-2,6-dione (200 mg, 0.62 mmol) in DMF (4 mL) was added followed by vinlyoxy-trimethylsilane (0.92 mL, 6.19 mmol). The reaction mixture was heated at 80° C. for 1 hour, diluted with MeOH/DCM (1/6, 40 mL, washed with water, extracted with DCM/MeOH twice then washed with brine. The combined organic phases were dried over $Na_2SO_4$ and filtered. The filtrate was concentrated under reduced pressure then purified by silica gel chromatography, eluting with 5% MeOH/DCM, to give 2-(2-(2,6-dioxopiperidin-3-yl)-1-oxoisoindolin-5-yl)acetaldehyde (108 mg, 61% yield). LCMS m/z calcd for $C_{15}H_{15}N_2O_4$ $[M+H]^+$: 287.1; found: 287.2.

Intermediate 8: 3-(2-(2,6-dioxopiperidin-3-yl)-1-oxoisoindolin-5-yl)propanal (Int-8)

Int-8

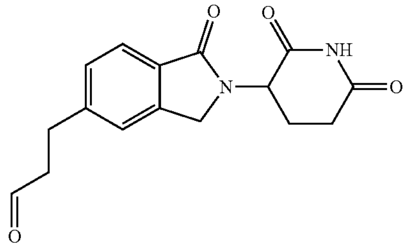

Step 1: Synthesis of 3-(5-(3-hydroxyprop-1-yn-1-yl)-1-oxoisoindolin-2-yl)piperidine-2,6-dione

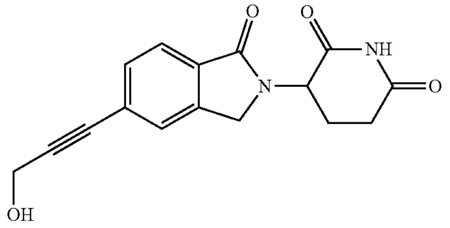 [SMILES: O=C1CCC(N2Cc3cc(C#CCO)ccc3C2=O)C(=O)N1]

A 4 mL vial with septum cap containing a mixture of 3-(6-bromo-3-oxo-1H-isoindol-2-yl)piperidine-2,6-dione (168.0 mg, 0.52 mmol), copper(I) iodide (9.9 mg, 0.05 mmol), and bis(triphenylphosphine)palladium(II) dichloride (37 mg, 0.05 mmol) under $N_2$ was charged with DMF (3 mL) and N,N-diisopropylethylamine (0.9 mL, 5.2 mmol). The mixture was sparged with $N_2$ continuously for 3 min and charged with prop-2-yn-1-ol (90 μL, 1.56 mmol) 1 min into sparging. The mixture was heated at 60° C. for 20 h. After cooling to RT, the reaction mixture was diluted with MeOH/DCM (1/6, 30 mL) and filtered through a short pad of celite. The resulting filtrated was washed with $NH_4Cl$ and brine, dried over $Na_2SO_4$, filtered and concentrated under reduced pressure. The residue was purified by silica chromatography, eluting with 0-10% MeOH/DCM to give 3-(5-(3-hydroxyprop-1-yn-1-yl)-1-oxoisoindolin-2-yl)piperidine-2,6-dione (136 mg, 88% yield) as a white solid. LCMS m/z calcd for $C_{16}H_{15}N_2O_4$ $[M+H]^+$: 299.1; found: 299.1.

Step 2: Synthesis of 3-(5-(3-hydroxypropyl)-1-oxoisoindolin-2-yl)piperidine-2,6-dione

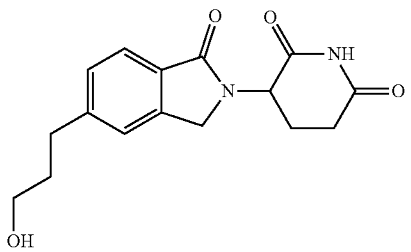 [SMILES: O=C1CCC(N2Cc3cc(CCCO)ccc3C2=O)C(=O)N1]

A mixture of 3-(5-(3-hydroxyprop-1-yn-1-yl)-1-oxoisoindolin-2-yl)piperidine-2,6-dione (100 mg, 0.34 mmol) and 10% palladium on carbon (36 mg, 0.34 mmol) in methanol (10 mL) was stirred at RT under a $H_2$ atmosphere overnight. The mixture was passed through a syringe filter and the resulting solution was charged fresh 10% palladium on carbon (36 mg, 0.34 mmol). The mixture was stirred under a $H_2$ atmosphere for 3 h. The reaction was filtered and the resulting solution was concentrated under reduced pressure. The residue was purified by silica gel chromatography, eluting with 0-10% MeOH/DCM to give 3-(5-(3-hydroxypropyl)-1-oxoisoindolin-2-yl)piperidine-2,6-dione (60 mg, 59% yield). LCMS m/z calcd for $C_{16}H_{19}N_2O_4$ $[M+H]^+$: 303.1; found: 303.1.

Step 3: 3-(2-(2,6-dioxopiperidin-3-yl)-1-oxoisoindolin-5-yl)propanal

To a suspension of 3-(5-(3-hydroxypropyl)-1-oxoisoindolin-2-yl)piperidine-2,6-dione (12 mg, 0.04 mmol) in DCM (1 mL) and THE (1 mL) was added Dess-Martin periodinane (33 mg, 0.08 mmol). The reaction was stirred at RT for 2 hours. $NaHCO_3$ sat. aq. (10 mL) was added and the reaction was extracted with MeOH/DCM (1/6, 10 mL×3). The combined organic phases were washed with brine, dried over $Na_2SO_4$ and filtered. The filtrate was concentrated under reduced pressure then purified by silica gel chromatography, eluting with 5% MeOH/DCM to give 3-(2-(2,6-dioxopiperidin-3-yl)-1-oxoisoindolin-5-yl)propanal (8 mg, 67% yield) as an off-white solid. LCMS m/z calcd for $C_{16}H_{17}N_2O_4$ $[M+H]^+$: 301.1; found: 301.1.

Intermediate 9: (R)-2-(8-(5-(piperidin-4-yl)pyrimidin-2-yl)-6,6a,7,8,9,10-hexahydro-5H-pyrazino[1',2':4,5]pyrazino[2,3-c]pyridazin-2-yl)phenol (Int-9)

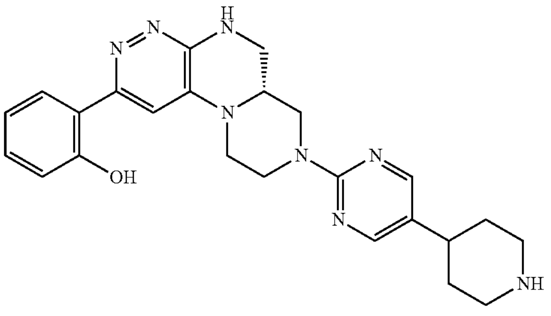 [SMILES: Oc1ccccc1-c1cc2c(nn1)NC[C@@H]1CN(c3ncc(C4CCNCC4)cn3)CCN21]

Step 1: Synthesis of (R)-2-(8-(5-bromopyrimidin-2-yl)-6,6a, 7,8,9,10-hexahydro-5H-pyrazino [1',2':4,5] pyrazino[2,3-c]pyridazin-2-yl)phenol

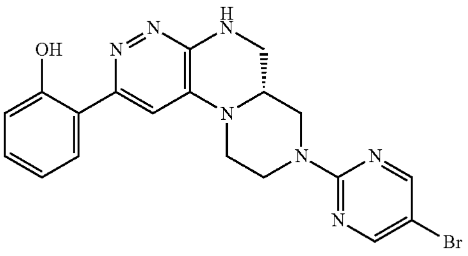 [SMILES: Oc1ccccc1-c1cc2c(nn1)NC[C@@H]1CN(c3ncc(Br)cn3)CCN21]

A 20 mL vial with septum containing a mixture of 5-bromo-2-chloropyrimidine (75 mg, 0.39 mmol) and (S)-2-(6,6a,7,8,9,10-hexahydro-5H-pyrazino[1',2':4,5]pyrazino [2,3-c]pyridazin-2-yl)phenol (100 mg, 0.35 mmol) under $N_2$ was charged with ethanol (2 mL) and DMF (1.5 mL), followed by $Et_3N$ (60 μL, 0.43 mmol). The reaction mixture was stirred at 95° C. for 2 h to yield crude (R)-2-(8-(5-bromopyrimidin-2-yl)-6,6a,7,8,9,10-hexahydro-5H-pyrazino[1',2':4,5]pyrazino [2,3-c]pyridazin-2-yl)phenol as a beige precipitate suspension. The crude suspension was used in the following reaction. LCMS m/z calcd for $C_{19}H_{19}BrN_7O$ $(M+H)^+$: 440.1/442.1; found: 439.9/441.9.

Step 2: Synthesis of tert-butyl (R)-4-(2-(2-(2-hydroxyphenyl)-5,6,6a, 7,9,10-hexahydro-8H-pyrazino [1',2':4,5]pyrazino[2,3-c]pyridazin-8-yl)pyrimidin-5-yl)-3,6-dihydropyridine-1(2H)-carboxylate

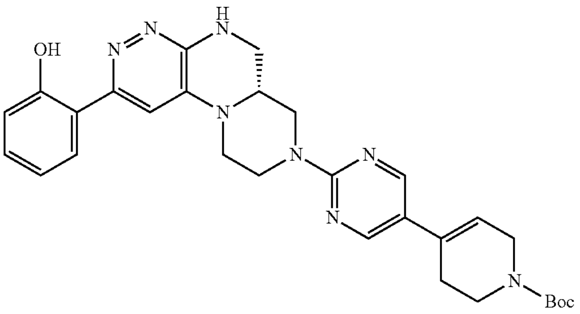 [SMILES: CC(C)(C)OC(=O)N1CC=C(c2cnc(N3CCN4c5cc(-c6ccccc6O)nnc5NC[C@@H]4C3)nc2)CC1]

A 20 mL vial with septum cap containing a crude suspension of (R)-2-(8-(5-bromopyrimidin-2-yl)-6,6a,7,8,9,10-hexahydro-5H-pyrazino[1',2':4,5]pyrazino[2,3-c]pyridazin-2-yl)phenol in DMF (1.1 mL) and ethanol (1.5 mL) was charged with N-Boc-1,2,3,6-tetrahydropyridine-4-boronic acid pinacol ester (97 mg, 0.31 mmol), potassium carbonate (98 mg, 0.71 mmol), [1,1'-bis(diphenylphosphino)ferrocene]dichloropalladium (II), complex with dichloromethane (21 mg, 0.03 mmol), and additional DMF (0.70 mL). The reaction mixture was sparged with $N_2$ for 2 min, then stirred at 100° C. for 2 h. The reaction mixture was diluted with EtOAc (50 mL), washed with sat. $NH_4Cl$ (10 mL) and water (50 mL), and brine (2×20 mL). The organic layer was dried over $Na_2SO_4$, filtered, concentrated under reduced pressure then purified by flash column chromatography (25 g $SiO_2$, 0→6% MeOH in DCM, wet-loaded in DCM). Fractions containing desired product were combined and concentrated under reduced pressure and heat (~50° C.) to yield tert-butyl (R)-4-(2-(2-(2-hydroxyphenyl)-5,6,6a,7,9,10-hexahydro-8H-pyrazino[1',2':4,5]pyrazino[2,3-c]pyridazin-8-yl)pyrimidin-5-yl)-3,6-dihydropyridine-1(2H)-carboxylate (86 mg, 0.16 mmol, 61% yield over two steps) as a beige solid. LCMS m/z calcd for $C_{29}H_{35}N_8O_3$ $(M+H)^+$: 543.3; found: 543.1.

Step 3: tert-butyl (R)-4-(2-(2-(2-hydroxyphenyl)-5, 6,6a, 7,9,10-hexahydro-8H-pyrazino [1',2':4,5] pyrazino[2,3-c]pyridazin-8-yl)pyrimidin-5-yl)piperidine-1-carboxylate

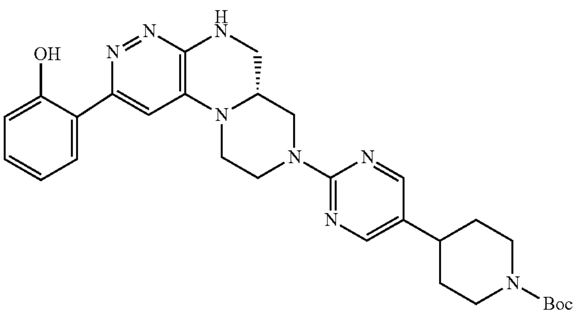 [SMILES: CC(C)(C)OC(=O)N1CCC(c2cnc(N3CCN4c5cc(-c6ccccc6O)nnc5NC[C@@H]4C3)nc2)CC1]

A 4 mL vial with septa cap containing a mixture of tert-butyl (R)-4-(2-(2-(2-hydroxyphenyl)-5,6,6a,7,9,10-hexahydro-8H-pyrazino[1',2':4,5]pyrazino[2,3-c]pyridazin-8-yl)pyrimidin-5-yl)-3,6-dihydropyridine-1(2H)-carboxylate (86.5 mg, 0.16 mmol) and 10 wt % dihydroxypalladium (wet) (23 mg, 0.02 mmol) was charged with methanol (0.30 mL) and THE (3 mL). The mixture was sparged with $N_2$ for 30 s, then $H_2$ for 2 min, and topped with a $H_2$ balloon. The reaction mixture was stirred at rt for 1 d. The reaction mixture was sparged with $N_2$, charged with additional 10 wt % dihydroxypalladium (wet) (25 mg, 0.02 mmol), sparged with $N_2$ for 30 s, then $H_2$ for 2 min, and topped with an $H_2$ balloon. The reaction mixture was stirred at rt for an additional 1 d. The reaction mixture was sparged with $N_2$, charged with additional 10 wt % dihydroxypalladium (wet) (10 mg, 0.01 mmol), sparged with $N_2$ for 30 s, then $H_2$ for 2 min, and topped with an $H_2$ balloon. The reaction mixture was stirred at 40° C. for 1 d. The reaction mixture was filtered through 0.45 um PTFE and concentrated under reduced pressure to yield crude tert-butyl (R)-4-(2-(2-(2-hydroxyphenyl)-5,6,6a,7,9,10-hexahydro-8H-pyrazino[1',2':4,5]pyrazino[2,3-c]pyridazin-8-yl)pyrimidin-5-yl)piperidine-1-carboxylate (87 mg, 0.16 mmol, 100% yield) as a beige solid. LCMS m/z calcd for $C_{29}H_{37}N_8O_3$ $(M+H)^+$: 545.3; found: 545.1.

Step 4: (R)-2-(8-(5-(piperidin-4-yl)pyrimidin-2-yl)-6,6a, 7,8,9,1O-hexahydro-5H-pyrazino [1',2':4,5] pyrazino[2,3-c]pyridazin-2-yl)phenol A 20 mL vial with septa cap containing tert-butyl (R)-4-(2-(2-(2-hydroxyphenyl)-5,6,6a,7,9,10-hexahydro-8H-pyrazino[1',2':4,5]pyrazino[2,3-c]pyridazin-8-yl)pyrimidin-5-yl)piperidine-1-carboxylate (87 mg, 0.16 mmol) was charged with DCM (2.5 mL) followed by TFA (600 mL, 7.8 mmol). The reaction mixture was stirred at rt for 1 d. The reaction mixture was concentrated under reduced pressure to yield the TFA salt of (R)-2-(8-(5-(piperidin-4-yl)pyrimidin-2-yl)-6,6a,7,8,9,10-hexahydro-5H-pyrazino[1',2':4,5]pyrazino[2,3-c]pyridazin-2-yl)phenol (120 mg) as a black residue. LCMS m/z calcd for $C_{24}H_{29}N_8O$ $(M+H)^+$: 445.2; found: 445.0.

Intermediate 10: (S)-2-(8-(5-(piperidin-4-yl)pyrimidin-2-yl)-6,6a,7,8,9,10-hexahydro-5H-pyrazino[1',2':4,5]pyrazino[2,3-c]pyridazin-2-yl)phenol Int-10

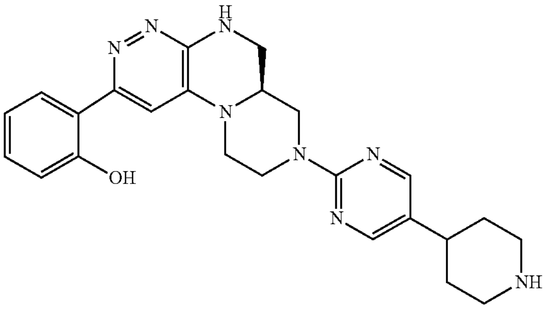

The title compound was prepared using procedure analogous to those described for Intermediate 9, with (R)-2-(6,6a,7,8,9,10-hexahydro-5H-pyrazino[1',2':4,5]pyrazino[2,3-c]pyridazin-2-yl)phenol replacing (S)-2-(6,6a,7,8,9,10-hexahydro-5H-pyrazino[1',2':4,5]pyrazino[2,3-c]pyridazin-2-yl)phenol in step 1. LCMS m/z calcd for $C_{24}H_{29}N_8O$ $(M+H)^+$: 445.2; found: 445.1.

Intermediate 11 (S)-2-(8-(5-(1,2,3,6-tetrahydropyridin-4-yl)pyrimidin-2-yl)-6,6a,7,8,9,10-hexahydro-5H-pyrazino[1',2':4,5]pyrazino[2,3-c]pyridazin-2-yl) phenol (Int-11)

Int-11

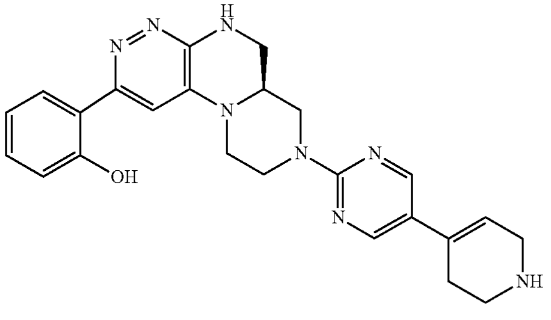

Step 1: tert-butyl (S)-4-(2-(2-(2-hydroxyphenyl)-5,6,6a, 7,9,10-hexahydro-8H-pyrazino [1',2':4,5] pyrazino[2,3-c]pyridazin-8-yl)pyrimidin-5-yl)-3,6-dihydropyridine-1(2H)-carboxylate

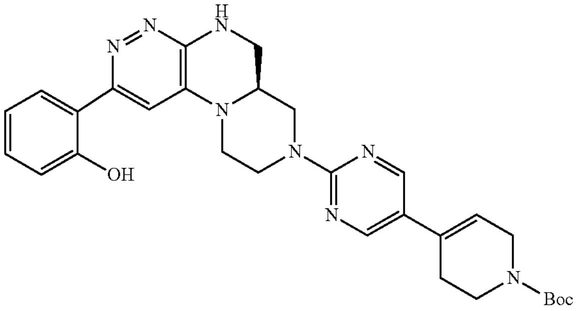 [SMILES: CC(C)(C)OC(=O)N1CC=C(c2cnc(N3CCN4c5cc(-c6ccccc6O)nnc5NC[C@H]4C3)nc2)CC1]

The title compound was prepared using procedure analogous to those described for Intermediate 9, step 1 to step 2 with (R)-2-(6,6a,7,8,9,10-hexahydro-5H-pyrazino[1',2':4,5]pyrazino[2,3-c]pyridazin-2-yl)phenol replacing (S)-2-(6,6a,7,8,9,10-hexahydro-5H-pyrazino [1',2':4,5]pyrazino[2,3-c]pyridazin-2-yl)phenol in step 1. LCMS m/z calcd for $C_{29}H_{35}N_8O_3$ $[M+H]^+$: 543.3; Found: 543.2 Step 2: (S)-2-(8-(5-(1,2,3,6-tetrahydropyridin-4-yl)pyrimidin-2-yl)-6,6a,7,8,9,10-hexahydro-5H-pyrazino[1',2':4,5]pyrazino[2,3-c]pyridazin-2-yl)phenol To a solution of: tert-butyl (S)-4-(2-(2-(2-hydroxyphenyl)-5,6,6a,7,9,10-hexahydro-8H-pyrazino[1',2':4,5]pyrazino[2,3-c]pyridazin-8-yl)pyrimidin-5-yl)-3,6-dihydropyridine-1(2H)-carboxylate (65 mg, 0.12 mmol) in DCM (2 mL) was added TFA (0.46 mL). The reaction mixture was stirred at RT for 1 h. The reaction was concentrated to dryness and the was redissolved in DCM/MeOH 1:6 (50 mL), to which $NaHCO_3$ (10 mL) was charged and the mixture was stirred at RT for 30 min. The phases were separated, and the aqueous layer was extracted with DCM/MeOH (1:6). The combined organic phase was washed with brine, dried over $Na_2SO_4$, filtered, and concentrated under vacuum to give the desired product (48 mg, 90% yield). LCMS m/z calcd for $C_{24}H_{27}N_8O$ $[M+H]^+$: 443.2; Found: 443.2.

Intermediate 12: (R)-2-(8-(5-(2-(piperidin-4-yl) ethyl)pyrimidin-2-yl)-6,6a,7,8,9,10-hexahydro-5H-pyrazino[1',2':4,5]pyrazino[2,3-c]pyridazin-2-yl) phenol (Int-12)

Int-12

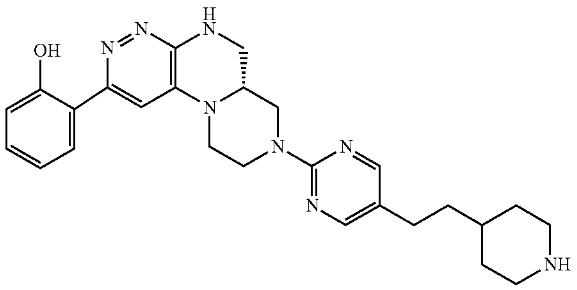

Step 1: tert-butyl (R,E)-4-(2-(2-(2-(2-hydroxyphenyl)-5,6,6a, 7,9,10-hexahydro-8H-pyrazino [1',2':4, 5]pyrazino[2,3-c]pyridazin-8-yl)pyrimidin-5-yl)vinyl)piperidine-1-carboxylate

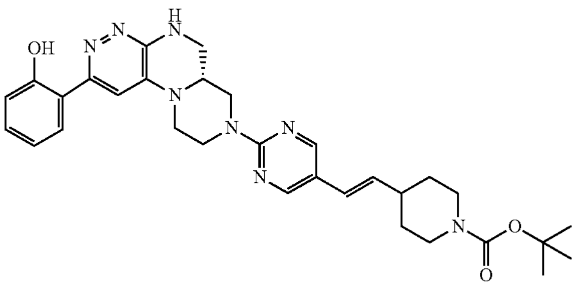 [SMILES: CC(C)(C)OC(=O)N1CCC(/C=C/c2cnc(N3CCN4c5cc(-c6ccccc6O)nnc5NC[C@@H]4C3)nc2)CC1]

A 4 mL vial with septum cap containing a mixture of (E)-tert-butyl 4-(2-(4,4,5,5-tetramethyl-1,3,2-dioxaborolan-2-yl)vinyl)piperidine-1-carboxylate (35 mg, 0.10 mmol), potassium carbonate (33 mg, 0.24 mmol), and [1,1'-bis (diphenylphosphino)ferrocene]dichloropalladium(II), complex with dichloromethane (7.1 mg, 0.01 mmol) under $N_2$ was charged with the telescoped, crude reaction mixture of (R)-2-(8-(5-bromopyrimidin-2-yl)-6,6a,7,8,9,10-hexahydro-5H-pyrazino[1',2':4,5]pyrazino[2,3-c]pyridazin-2-yl) phenol (0.9 mL, 0.09 mmol) in DMF (0.37 mL), and ethanol (0.49 mL)). The reaction mixture was diluted with additional DMF (0.65 mL) (due to solubility issues), sparged with $N_2$ for 1 min, and stirred at 100° C. for 10 h. The reaction mixture was diluted with EtOAc (10 mL), sat. $NH_4Cl$ (5 mL), and water (5 mL), and vacuum filtered through a PE frit with Celite plug. The solids were rinsed with additional EtOAc and water. The organic fraction was separated, washed with water (20 mL), and brine (20 mL). The aqueous fractions were combined, extracted with EtOAc (20 mL), washed with water (10 mL), and brine (10 mL). The organic layers were combined, dried over $Na_2SO_4$, filtered, concentrated under reduced pressure, and purified by FCC (12 g $SiO_2$, 0→5% MeOH in DCM, wet-loaded in DCM). Fractions containing desired product were combined and concentrated under reduced pressure and heat (~50° C.) to yield tert-butyl (R,E)-4-(2-(2-(2-(2-hydroxyphenyl)-5,6,6a,7,9,10-hexahydro-8H-pyrazino[1',2':4,5]pyrazino[2,3-c] pyridazin-8-yl)pyrimidin-5-yl)vinyl)piperidine-1-carboxylate (35 mg, 0.061 mmol, 70% yield) as a tan foam. LCMS m/z calcd for $C_{31}H_{39}N_8O_3$ $(M+H)^+$: 571.3; found: 571.2.

Step 2: tert-butyl (R)-4-(2-(2-(2-(2-hydroxyphenyl)-5,6,6a, 7,9,10-hexahydro-8H-pyrazino [1',2':4,S] pyrazino[2,3-c]pyridazin-8-yl)pyrimidin-5-yl)ethyl) piperidine-1-carboxylate

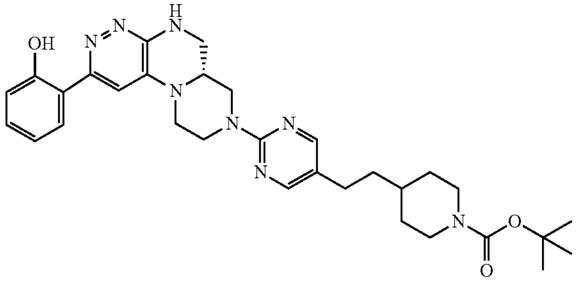 [SMILES: CC(C)(C)OC(=O)N1CCC(CCc2cnc(N3CCN4c5cc(-c6ccccc6O)nnc5NC[C@@H]4C3)nc2)CC1]

A 4 mL vial with septa cap containing a mixture of tert-butyl (R,E)-4-(2-(2-(2-(2-hydroxyphenyl)-5,6,6a,7,9,10-hexahydro-8H-pyrazino[1',2':4,5]pyrazino[2,3-c] pyridazin-8-yl) pyrimidin-5-yl)vinyl)piperidine-1-carboxylate (35 mg, 0.06 mmol) and 10 wt % dihydroxypalladium (wet) (11.5 mg, 0.01 mmol) was charged with methanol (100 uL) and THF (1 mL). The mixture was sparged with $N_2$ for 30 s, then $H_2$ for 1 min, and topped with a $H_2$ balloon. The reaction mixture was stirred at rt for 2 d. The reaction mixture was filtered through 0.45 um PTFE frit and concentrated under reduced pressure to yield crude tert-butyl (R)-4-(2-(2-(2-(2-hydroxyphenyl)-5,6,6a,7,9,10-hexahydro-8H-pyrazino[1',2':4,5]pyrazino[2,3-c] pyridazin-8-yl)pyrimidin-5-yl)ethyl)piperidine-1-carboxylate (35 mg, 0.061 mmol, 100% yield) as a beige solid. LCMS m/z calcd for $C_{31}H_{41}N_8O_3$ $(M+H)^+$: 573.3; found: 573.2.

Step 3: (R)-2-(8-(5-(2-(piperidin-4-yl)ethyl)pyrimidin-2-yl)-6,6a, 7,8,9,10-hexahydro-5H-pyrazino[1', 2':4,5]pyrazino[2,3-c]pyridazin-2-yl)phenol A 4 mL vial with septa cap containing tert-butyl (R)-4-(2-(2-(2-(2-hydroxyphenyl)-5,6,6a,7,9,10-hexahydro-8H-pyrazino[1',2':4,5]pyrazino[2,3-c]pyridazin-8-yl)pyrimidin-5-yl) ethyl)piperidine-1-carboxylate (35 mg, 0.06 mmol) was charged with DCM (1 mL) followed by TFA (300 mL, 3.9 mmol). The reaction mixture was stirred at rt for 1 d. The reaction mixture was concentrated under reduced pressure to yield the TFA salt of (R)-2-(8-(5-(2-(piperidin-4-yl) ethyl) pyrimidin-2-yl)-6,6a,7,8,9,10-hexahydro-5H-pyrazino[1',2':4,5]pyrazino[2,3-c]pyridazin-2-yl)phenol (45 mg) as a black residue. LCMS m/z calcd for $C_{26}H_{33}N_8O$ $(M+H)^+$: 473.3; found: 473.0.

Intermediate 13: (S,E)-2-(8-(5-(2-(piperidin-4-yl) vinyl)pyrimidin-2-yl)-6,6a,7,8,9,10-hexahydro-5H-pyrazino[1',2':4,5]pyrazino[2,3-c]pyridazin-2-yl) phenol (Int-13)

Int-13

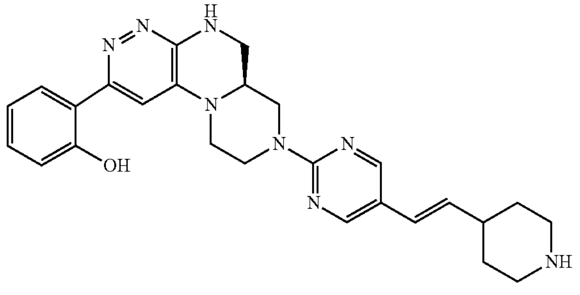

Step 1:tert-butyl (S,E)-4-(2-(2-(2-(2-hydroxyphenyl)-5,6,6a, 7,9,10-hexahydro-8H-pyrazino [1',2':4,5]pyrazino[2,3-c]pyridazin-8-yl)pyrimidin-5-yl)vinyl)piperidine-1-carboxylate

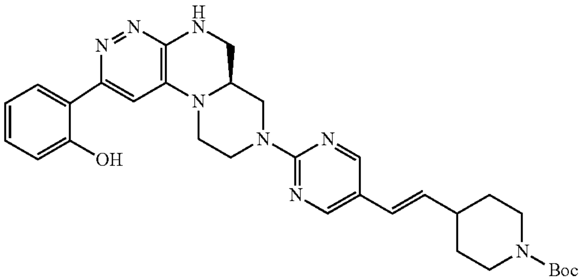 [SMILES: CC(C)(C)OC(=O)N1CCC(/C=C/c2cnc(N3CCN4c5cc(-c6ccccc6O)nnc5NC[C@H]4C3)nc2)CC1]

The title compound was prepared using procedure analogous to those described for Intermediate 12, step 1, with (S)-2-(8-(5-bromopyrimidin-2-yl)-6,6a,7,8,9,10-hexahydro-5H-pyrazino[1',2':4,5]pyrazino[2,3-c]pyridazin-2-yl)phenol replacing (R)-2-(8-(5-bromopyrimidin-2-yl)-6,6a,7,8,9,10-hexahydro-5H-pyrazino[1',2':4,5]pyrazino[2,3-c]pyridazin-2-yl)phenol. LCMS m/z calcd for $C_{31}H_{39}N_8O_3$ $[M+H]^+$: 571.3; Found: 571.2.

Step 2: (S,E)-2-(8-(5-(2-(piperidin-4-yl)vinyl)pyrimidin-2-yl)-6,6a, 7,8,9,10-hexahydro-5H-pyrazino [1',2':4,5]pyrazino[2,3-c]pyridazin-2-yl)phenol To a solution of tert-butyl (S,E)-4-(2-(2-(2-(2-hydroxyphenyl)-5,6,6a,7,9,10-hexahydro-8H-pyrazino[1',2':4,5] pyrazino[2,3-c]pyridazin-8-yl)pyrimidin-5-yl)vinyl)piperidine-1-carboxylate (12.0 mg, 0.02 mmol) in DCM (1 mL) was added TFA (0.3 mL). The reaction was stirred at rt for 1 h. The reaction was concentrated to dryness and was redissolved in DCM/MeOH (1/6, 30 mL). Saturated aqueous $NaHCO_3$ (10 mL) was added and the mixture was stirred at rt for 30 min. The aqueous layer was extracted with DCM/MeOH (1/6). The combined organic layers were washed with brine, dried over $Na_2SO_4$, and filtered. The resulting filtrate was concentrated under vacuum to give (S,E)-2-(8-(5-(2-(piperidin-4-yl)vinyl)pyrimidin-2-yl)-6,6a,7,8,9,10-hexahydro-5H-pyrazino[1',2':4,5]pyrazino[2,3-c]pyridazin-2-yl)phenol (8 mg, 81% yield). LCMS m/z calcd for $C_{26}H_{31}N_8O$ $[M+H]^+$: 471.2; Found: 471.2.

Intermediate 14: (S)-2-(8-(1-(2-(piperidin-4-yloxy) ethyl)piperidin-4-yl)-6,6a,7,8,9,10-hexahydro-5H-pyrazino[1',2':4,5]pyrazino[2,3-c]pyridazin-2-yl) phenol (Int-14)

Int-14

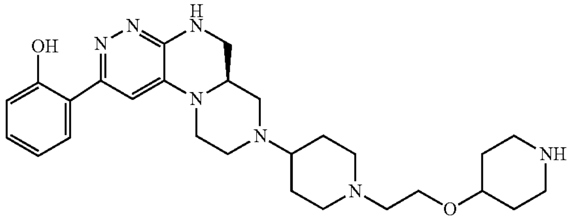

Step 1: tert-butyl (S)-4-(2-(4-(2-(2-hydroxyphenyl)-5,6,6a, 7,9,1O-hexahydro-8H-pyrazino [1',2':4,5] pyrazino[2,3-c]pyridazin-8-yl)piperidin-1-yl)ethoxy) piperidine-1-carboxylate

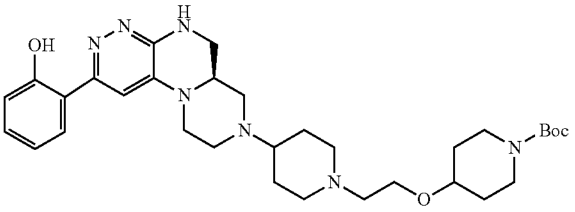 [SMILES: CC(C)(C)OC(=O)N1CCC(OCCN2CCC(N3CCN4c5cc(-c6ccccc6O)nnc5NC[C@H]4C3)CC2)CC1]

To a stirred solution of (R)-2-(6,6a,7,8,9,10-hexahydro-5H-pyrazino[1',2':4,5]pyrazino [2,3-c]pyridazin-2-yl)phenol (18 mg, 0.05 mmol) and tert-butyl 4-(2-oxoethoxy) piperidine-1-carboxylate (14 mg, 0.06 mmol) in DMF (2 mL), Sodium triacetoxyborohydride (31 mg, 0.15 mmol) was added at rt. After 15 min, the reaction mixture was diluted with MeOH and purified with Prep-HPLC. The fractions were collected and neutralized with $NaHCO_3$. The volatiles were removed under reduced pressure, and the residue was extracted with DCM. The combined organic layers were washed with brine, dried over $Na_2SO_4$, and filtered. The resulting filtrate was concentrated under vacuum to give tert-butyl (S)-4-(2-(4-(2-(2-hydroxyphenyl)-5,6,6a,7,9,10-hexahydro-8H-pyrazino[1',2':4,5]pyrazino[2,3-c]pyridazin-8-yl)piperidin-1-yl)ethoxy) piperidine-1-carboxylate (16 mg, 55% yield). LCMS m/z calcd for $C_{32}H_{48}N_7O_4$ $[M+H]^+$: 594.4; Found: 594.3.

Step 2: (S)-2-(8-(1-(2-(piperidin-4-yloxy)ethyl)piperidin-4-yl)-6,6a, 7,8,9,10-hexahydro-5H-pyrazino [1',2':4,5]pyrazino[2,3-c]pyridazin-2-yl)phenol To a stirred solution of tert-butyl (S)-4-(2-(4-(2-(2-hydroxyphenyl)-5,6,6a,7,9,10-hexahydro-8H-pyrazino[1',2':4,5]pyrazino[2,3-c]pyridazin-8-yl)piperidin-1-yl)ethoxy) piperidine-1-carboxylate (16 mg, 0.03 mmol) in DCM (2 mL) was added TFA (0.21 mL) at rt. After 1 h, the reaction was concentrated to dryness and was redissolved in DCM/MeOH (1/6, 30 mL). Saturated aqueous $NaHCO_3$ (10 mL) was added and the mixture was stirred at rt for 30 min. The aqueous layer was extracted with DCM/MeOH (1/6). The combined organic layers were washed with brine, dried over $Na_2SO_4$, and filtered. The resulting filtrate was concentrated under vacuum to give (S)-2-(8-(1-(2-(piperidin-4-yloxy)ethyl)piperidin-4-yl)-6,6a,7,8,9,10-hexahydro-5H-pyrazino[1',2':4,5]pyrazino[2,3-c]pyridazin-2-yl)phenol (12 mg, 90% yield). LCMS m/z calcd for $C_{27}H_{40}N_7O_2$ $[M+H]^+$: 494.3; Found: 494.2.

Intermediate 15: 3-(1-oxo-6-(piperazin-1-yl) isoindolin-2-yl)piperidine-2,6-dione (Int-15)

Int-15

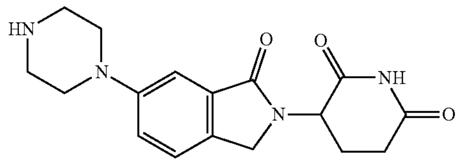

Step 1: ethyl 5-bromo-2-(chloromethyl)benzoate

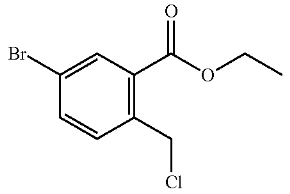

To a 100 mL round-bottom flask containing 6-bromoisobenzofuran-1(3H)-one (1.56 g, 7.33 mmol) was added anhydrous Ethanol (22 mL). The solution was heated to 72° C. then Thionyl chloride (3.12 mL, 43.0 mmol) was added in portions over 6 hours. The reaction mixture was diluted in water on ice then extracted with EtOAc three times. The organic layers were combined and dried over sodium sulfate, filtered, and concentrated. Crude product was purified by FCC (12 g $SiO_2$, 0-100% EtOAc in Hexanes). Fractions containing desired product were combined and concentrated to yield ethyl 5-bromo-2-(chloromethyl)benzoate (1.57 g, 5.65 mmol, 77.1% yield) as a tan oil/solid.

Step 2: 3-(6-bromo-1-oxoisoindolin-2-yl)piperidine-2,6-dione

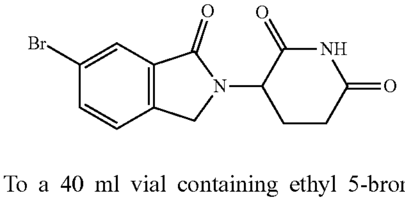

To a 40 ml vial containing ethyl 5-bromo-2-(chloromethyl)benzoate (1.57 g, 5.66 mmol), 3-aminopiperidine-2,6-dione, HCl (1.08 g, 6.56 mmol) and DMF (8 mL) was added N,N-Diisopropylethylamine (4.0 mL, 22.96 mmol). The solution was heated to 90° C. overnight. The reaction was cooled and added dropwise to 50 mL of water. The resulted mixture was stirred at 0° C. for 1 hour then was filtered. The solid was washed with EtOAc, hexane and minimal methanol to yield a pale purple solid 3-(6-bromo-1-oxoisoindolin-2-yl)piperidine-2,6-dione (1.12 g, 3.46 mmol, 61.2% yield). $^1H$ NMR (400 MHz, DMSO-d6) δ 11.02 (s, 1H), 7.90-7.79 (m, 2H), 7.60 (d, J=8.0 Hz, 1H), 5.17-5.07 (m, 1H), 4.45 (d, J=17.6 Hz, 1H), 4.32 (d, J=17.5 Hz, 1H), 2.98-2.84 (m, 1H), 2.65-2.55 (m, 1H), 2.39 (q, J=12.3, 16.3 Hz, 1H), 2.05-1.97 (m, 1H). LCMS m/z calcd for $C_{13}H_{12}BrN_2O_3$ $(M+H)^+$: 323.0/325.0; found: 323.1/324.9.

Step 3: tert-butyl 4-(2-(2,6-dioxopiperidin-3-yl)-3-oxoisoindolin-5-yl)piperazine-1-carboxylate

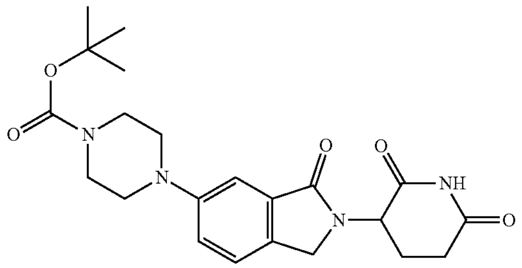 [SMILES: CC(C)(C)OC(=O)N1CCN(c2ccc3c(c2)C(=O)N(C2CCC(=O)NC2=O)C3)CC1]

To a vial containing 3-(6-bromo-1-oxoisoindolin-2-yl)piperidine-2,6-dione (176.0 mg, 0.54 mmol), tert-butyl 1-piperazinecarboxylate (166.0 mg, 0.89 mmol), RuPhosPd G2 (49.0 mg, 0.06 mmol) and Cesium carbonate (400.0 mg, 1.23 mmol) was added DMSO (2 mL). The solution was sparged for 3 min with nitrogen then heated to 100° C. overnight. The reaction was quenched with 4N HCl in Dioxane (adjusted to pH-7) and diluted to 50 mg/ml in DMSO. Solution was further diluted to ~12 mg/ml with acetonitrile and filtered. The filtrate was purified using a prep-LCMS (5 μm 10×3 cm Waters Sunfire C18, 29.8-49.8% acetonitrile in water (0.1% TFA), wet loaded) to yield tert-butyl 4-(2-(2,6-dioxopiperidin-3-yl)-3-oxoisoindolin-5-yl)piperazine-1-carboxylate (48 mg, 0.11 mmol, 20.5% yield) as a white solid. LCMS m/z calcd for $C_{22}H_{29}N_4O_5$ $(M+H)^+$: 429.2; found: 429.1.

Step 4: 3-(1-oxo-6-(piperazin-1-yl) isoindolin-2-yl)piperidine-2,6-dione

To a 20 ml vial containing tert-butyl 4-(2-(2,6-dioxopiperidin-3-yl)-3-oxoisoindolin-5-yl)piperazine-1-carboxylate (48.0 mg, 0.11 mmol) and 1,4-Dioxane (0.50 mL) was added 4N HCl in dioxane (0.5 mL, 2 mmol) dropwise. The solution was stirred at room temperature for 2 h. The volatiles were removed under reduced pressure to yield 3-(3-oxo-5-piperazin-1-yl-1H-isoindol-2-yl)piperidine-2,6-dione as its HCl salt (37 mg, 0.10 mmol, 90.5% yield). LCMS m/z calcd for $C_{17}H_{21}N_4O_3$ $(M+H)^+$: 329.2; found: 329.0.

Intermediate 16: (S)-2-(4-(2-(2-hydroxyphenyl)-5,6,6a,7,9,10-hexahydro-8H-pyrazino [1',2':4,5]pyrazino [2,3-c]pyridazin-8-yl)piperidin-1-yl)acetaldehyde Int-16

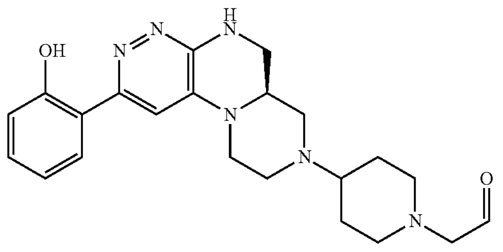

Step 1: (S)-2-(8-(1-(2,2-dimethoxyethyl)piperidin-4-yl)-6,6a, 7,8,9,10-hexahydro-5H-pyrazino [1',2':4,5] pyrazino[2,3-c]pyridazin-2-yl)phenol

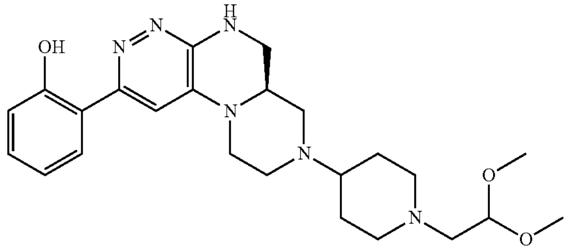 [SMILES: COC(CN1CCC(N2CCN3c4cc(-c5ccccc5O)nnc4NC[C@H]3C2)CC1)OC]

To a 20 ml vial containing (S)-2-(8-(piperidin-4-yl)-6,6a,7,8,9,10-hexahydro-5H-pyrazino [1',2':4,5]pyrazino[2,3-c] pyridazin-2-yl)phenol (11.0 mg, 0.03 mmol), Sodium bicarbonate (29.0 mg, 0.35 mmol) and DMF (300 uL) was added 2-Bromo-1,1-dimethoxyethane (5.0 uL, 0.04 mmol). The reaction was heated to 80° C. overnight. The reaction was diluted with 5 ml of MeOH and 5 ml of acetonitrile then filtered. Solution was purified using a prep-LCMS (5 m 10×3 cm Waters Sunfire C18, 5-25% acetonitrile in water (0.1% TFA), wet loaded) to yield (S)-2-(8-(1-(2,2-dimethoxyethyl)piperidin-4-yl)-6,6a,7,8,9,10-hexahydro-5H-pyrazino[1',2':4,5]pyrazino [2,3-c]pyridazin-2-yl)phenol as its TFA salt (9.3 mg, 0.013 mmol, 40.6% yield). LCMS m/z calcd for $C_{24}H_{35}N_6O_3$ $[M+H]^+$: 455.3; found 455.1.

Step 2: (S)-2-(4-(2-(2-hydroxyphenyl)-5,6,6a, 7,9,10-hexahydro-8H-pyrazino[1',2':4,S]pyrazino [2,3-c] pyridazin-8-yl)piperidin-1-yl)acetaldehyde To a vial containing (S)-2-(8-(1-(2,2-dimethoxyethyl)piperidin-4-yl)-6,6a,7,8,9,10-hexahydro-5H-pyrazino[1',2':4,5]pyrazino[2,3-c]pyridazin-2-yl)phenol; di-2,2,2-trifluoroacetic acid (9.3 mg, 0.01 mmol) was added 1,4-Dioxane (200 µL) and 6 M Hydrochloric acid (aq) (200.0 µL, 1.2 mmol). The solution was heated to 70° C. for 1 h. After cooled to rt, the volatiles were removed under reduced pressure to yield (S)-2-(4-(2-(2-hydroxyphenyl)-5,6,6a,7,9,10-hexahydro-8H-pyrazino[1',2':4,5]pyrazino[2,3-c] pyridazin-8-yl)piperidin-1-yl)acetaldehyde as its HCl salt (6.5 mg, 0.013 mmol, 99.1% yield) as a yellow solid. LCMS m/z calcd for $C_{22}H_{31}N_6O_3$ $[M+H_2O+H]^+$: 427.2; found: 427.1.

Intermediate 17: 3-(9-(2,6-dioxopiperidin-3-yl)-9H-pyrido[2,3-b]indol-6-yl)propanal (Int-17)

Int-17

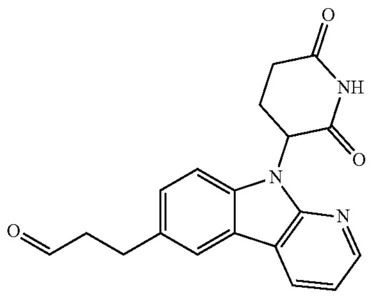

Step 1: 3-(6-(3-hydroxyprop-1-yn-1-yl)-9H-pyrido [2,3-b]indol-9-yl)piperidine-2,6-dione

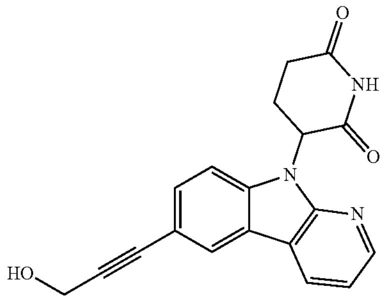 [SMILES: O=C1CCC(n2c3ccc(C#CCO)cc3c3cccnc32)C(=O)N1]

To a mixture of 3-(6-bromo-9H-pyrido[2,3-b]indol-9-yl) piperidine-2,6-dione (prepared using the procedure described in WO2020010227, 356.4 mg, 1.0 mmol), bis (triphenyl-phosphine)palladium(II) dichloride (69.8 mg, 0.10 mmol), and copper(I) iodide (18.9 mg, 0.10 mmol) in DMF (5 mL) was added N,N-Diisopropylethylamine (1.73 mL, 9.95 mmol). The mixture was sparged with $N_2$ for 1 min. Prop-2-yn-1-ol (0.17 mL, 2.99 mmol) was added and the mixture was sparged with $N_2$ for 2 min. Heated to 60° C. with stirring overnight. The reaction mixture was allowed to cool to RT and additional bis(triphenylphosphine)palladium (II) dichloride (139.7 mg, 0.20 mmol), copper(I) iodide (37.9 mg, 0.20 mmol) and prop-2-yn-1-ol (0.17 mL, 2.99 mmol) was added. The reaction mixture was sparged again with $N_2$ for 2 min then stirred at 60° C. for 2 h. The mixture was allowed to cool to RT then concentrated under reduced pressure. The residue was purified via silica gel chromatography (0-100% EtOAc/hexanes) to obtain 3-(6-(3-hydroxyprop-1-yn-1-yl)-9H-pyrido[2,3-b]indol-9-yl) piperidine-2,6-dione (135 mg, 0.41 mmol, 41% yield) as an orange solid. LCMS calcd for $C_{19}H_{16}N_3O_3$ $[M+H]^+$ m/z=334.1; found: 333.9.

Step 2: 3-(6-(3-hydroxypropyl)-9H-pyrido[2,3-b]indol-9-yl)piperidine-2,6-dione

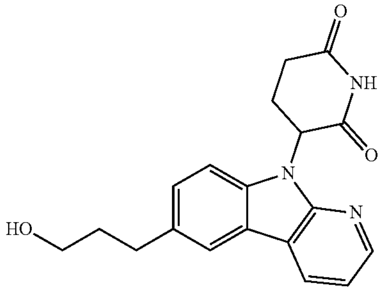 [SMILES: O=C1CCC(n2c3ccc(CCCO)cc3c3cccnc32)C(=O)N1]

A vial containing 3-(6-(3-hydroxyprop-1-yn-1-yl)-9H-pyrido[2,3-b]indol-9-yl) piperidine-2,6-dione (133.0 mg, 0.40 mmol) and Pd/C (10 wt % Pd, 44.0 mg) was evacuated and backfilled with $N_2$ (4×). EtOAc (8 mL) and MeOH (3.2 mL) were slowly added and the vial was evacuated and backfilled with $N_2$ (4×). The vial was then evacuated and backfilled with $H_2$ (balloon) (4×). The resulted mixture was stirred at room temperature for three days. The vial was evacuated and backfilled with $N_2$ (4×) and additional Pd/C (10 wt % Pd, 88.0 mg). The reaction mixture was put under an $H_2$ atmosphere as described above and stirring was resumed for two additional days at RT. Filtration through celite and washing of the celite pad with MeOH, followed by concentration of the filtrate, gave crude 3-(6-(3-hydroxypropyl)-9H-pyrido[2,3-b]indol-9-yl)piperidine-2,6-dione (~70% purity, approx. 90 mg desired product, 68% yield) which was used directly in the next step without further purification. LCMS calcd for $C_{19}H_{20}N_3O_3$ $[M+H]^+$ m/z=338.1; found: 338.0.

Step 3: 3-(9-(2,6-dioxopiperidin-3-yl)-9H-pyrido[2,3-b]indol-6-yl)propanal

To crude 3-(6-(3-hydroxypropyl)-9H-pyrido[2,3-b]indol-9-yl)piperidine-2,6-dione (84.0 mg, 0.25 mmol) in DCM (4 mL) at 0° C. was added Dess-Martin Periodinane (158.41 mg, 0.37 mmol). The reaction mixture was stirred at 0° C. for 20 min then allowed to room temperature. After 3 h of stirring at rt, the reaction was diluted with 2 mL saturated aq. $Na_2CO_3$ and 2 mL saturated aq. $Na_2S_2O_3$. The mixture was extracted with 1:1 THF/EtOAc (3×20 mL). The combined organic layers were washed with brine (50 mL), dried with $MgSO_4$, filtered and concentrated to afford crude 3-(9-(2,6-dioxopiperidin-3-yl)-9H-pyrido[2,3-b]indol-6-yl) propanal (~60% purity) as an orange solid which was used in the next step without further purification. LCMS calcd for $C_{19}H_{18}N_3O_3$ $[M+H]^+$ m/z=336.1; found: 336.0.

Intermediate 18: (R)-4-fluoro-2-(6,6a,7,8,9,10-hexahydro-5H-pyrazino[1',2':4,5]pyrazino [2,3-c]pyridazin-2-yl)phenol Int-18

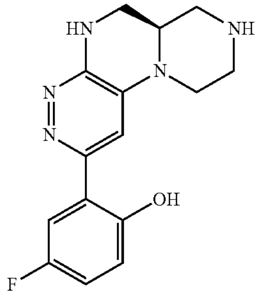

14231 Int-18 was prepared by the procedures described for preparing Int-1 using appropriate starting materials. LCMS m/z calcd $[M+H]^+$: 302.1; found: 302.1.

Intermediates 19-46

The intermediates shown below in Table 2 were prepared by the method used in preparing nt-3 using appropriate starting materials.

TABLE 2

Intermediates 19-46

| Int. | Structure | Name | Calcd. $(M + H)^+$ m/z | Found $(M + H)^+$ m/z |
|---|---|---|---|---|
| Int-19 | 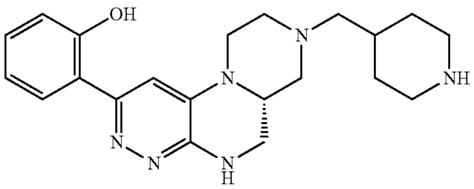 [SMILES: Oc1ccccc1-c1cc2c(nn1)NC[C@H]1CN(CC3CCNCC3)CCN21] | (S)-2-(8-(piperidin-4-ylmethyl)-6,6a,7,8,9,10-hexahydro-5H-pyrazino[1',2':4,5]pyrazino[2,3-c] pyridazin-2-yl)phenol | 381.2 | 381.2 |
| Int-20 | 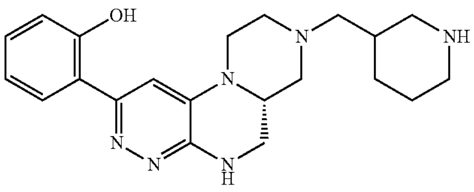 [SMILES: Oc1ccccc1-c1cc2c(nn1)NC[C@H]1CN(CC3CCCNC3)CCN21] | 2-((6aS)-8-(piperidin-3-ylmethyl)-6,6a,7,8,9,10-hexahydro-5H-pyrazino [1',2':4,5]pyrazino[2,3-c] pyridazin-2-yl)phenol | 381.2 | 381.3 |

TABLE 2-continued

| Int. | Structure | Name | Calcd. (M + H)+ m/z | Found (M + H)+ m/z |
|---|---|---|---|---|
| Intermediates 19-46 | | | | |
| Int-21 | 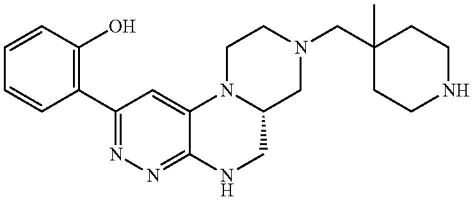 [SMILES: CC1(CN2CCN3c4cc(-c5ccccc5O)nnc4NC[C@H]3C2)CCNCC1] | (S)-2-(8-((4-methylpiperidin-4-yl)methyl)-6,6a,7,8,9,10-hexahydro-5H-pyrazino [1',2':4,5]pyrazino[2,3-c] pyridazin-2-yl)phenol | 395.2 | 395.2 |
| Int-22 | 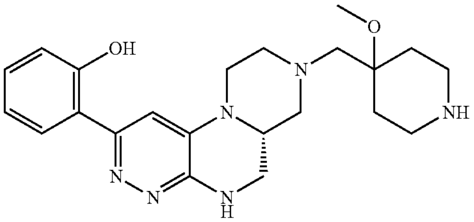 [SMILES: COC1(CN2CCN3c4cc(-c5ccccc5O)nnc4NC[C@H]3C2)CCNCC1] | (S)-2-(8-((4-methoxypiperidin-4-yl)methyl)-6,6a,7,8,9,10-hexahydro-5H-pyrazino [1',2':4,5]pyrazino[2,3-c] pyridazin-2-yl)phenol | 411.2 | 411.3 |
| Int-23 | 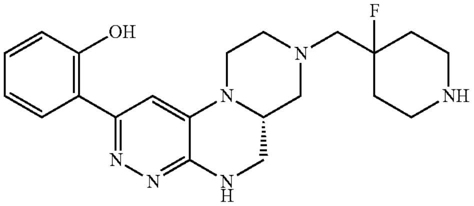 [SMILES: Oc1ccccc1-c1cc2c(nn1)NC[C@H]1CN(CC3(F)CCNCC3)CCN21] | (S)-2-(8-((4-fluoropiperidin-4-yl)methyl)-6,6a,7,8,9,10-hexahydro-5H-pyrazino [1',2':4,5]pyrazino[2,3-c] pyridazin-2-yl)phenol | 399.2 | 399.2 |
| Int-24 | 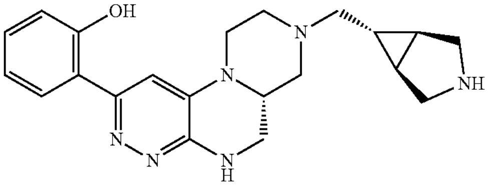 [SMILES: Oc1ccccc1-c1cc2c(nn1)NC[C@H]1CN(C[C@H]3[C@@H]4CNC[C@@H]43)CCN21] | 2-((S)-8-(((1R,5S,6r)-3-azabicyclo[3.1,0]hexan-6-yl) methyl)-6,6a,7,8,9,10-hexahydro-5H-pyrazino[1',2':4,5]pyrazino [2,3-c] pyridazin-2-yl)phenol | 379.2 | 379.1 |
| Int-25 | 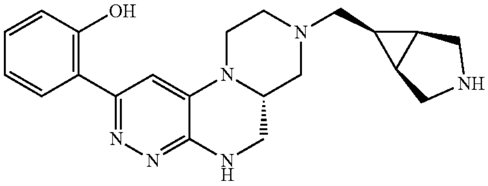 [SMILES: Oc1ccccc1-c1cc2c(nn1)NC[C@H]1CN(C[C@@H]3[C@@H]4CNC[C@@H]43)CCN21] | 2-((S)-8-(((1R,5S,6s)-3-azabicyclo[3.1,0]hexan-6-yl) methyl)-6,6a,7,8,9,10-hexahydro-5H-pyrazino[1',2':4,5]pyrazino [2,3-c] pyridazin-2-yl)phenol | 379.2 | 379.2 |
| Int-26 | 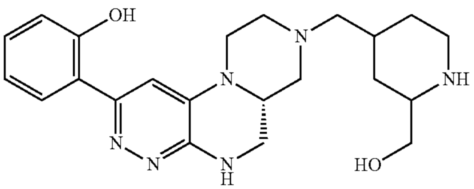 [SMILES: OCC1CC(CN2CCN3c4cc(-c5ccccc5O)nnc4NC[C@H]3C2)CCN1] | 2-((6aS)-8-((2-(hydroxymethyl)piperidin-4-yl) methyl)-6,6a,7,8,9,10-hexahydro-5H-pyrazino[1',2':4,5]pyrazino [2,3-c]pyridazin-2-yl)phenol | 411.2 | 411.0 |
| Int-27 | 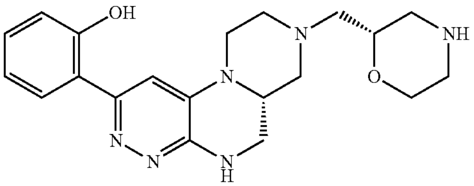 [SMILES: Oc1ccccc1-c1cc2c(nn1)NC[C@H]1CN(C[C@@H]3CNCCO3)CCN21] | 2-((S)-8-(((S)-morpholin-2-yl)methyl)-6,6a,7,8,9,10-hexahydro-5H-pyrazino [1',2':4,5]pyrazino[2,3-c] pyridazin-2-yl)phenol | 383.2 | 383.2 |

TABLE 2-continued

| Int. | Structure | Name | Calcd. (M + H)+ m/z | Found (M + H)+ m/z |
|---|---|---|---|---|
| Intermediates 19-46 | | | | |
| Int-28 | 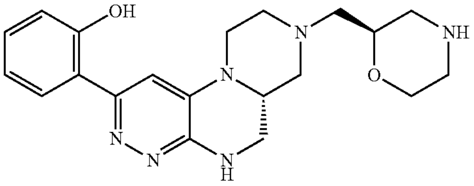 [SMILES: Oc1ccccc1-c1cc2c(nn1)NC[C@H]1CN(C[C@H]3CNCCO3)CCN21] | 2-((S)-8-(((R)-morpholin-2-yl) methyl)-6,6a,7,8,9,10-hexahydro-5H-pyrazino[1',2':4,5]pyrazino [2,3-c] pyridazin-2-yl)phenol | 383.2 | 383.1 |
| Int-29 | 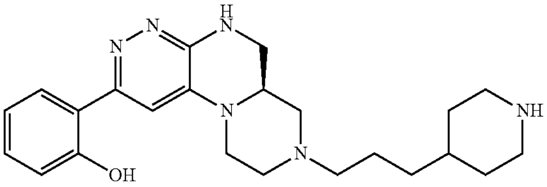 [SMILES: Oc1ccccc1-c1cc2c(nn1)NC[C@H]1CN(CCCC3CCNCC3)CCN21] | (S)-2-(8-(3-(piperidin-4-yl) propyl)-6,6a,7,8,9,10-hexahydro-5H-pyrazino[1',2':4,5]pyrazino [2,3-c] pyridazin-2-yl)phenol | 409.3 | 409.3 |
| Int-30 | 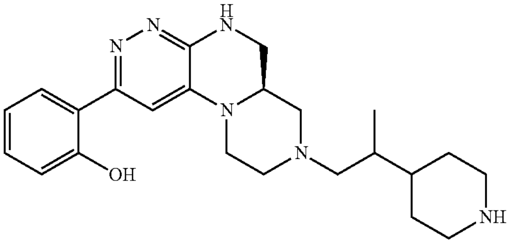 [SMILES: CC(CN1CCN2c3cc(-c4ccccc4O)nnc3NC[C@H]2C1)C1CCNCC1] | 2-((6aS)-8-(2-(piperidin-4-yl) propyl)-6,6a,7,8,9,10-hexahydro-5H-pyrazino[1',2':4,5]pyrazino [2,3-c] pyridazin-2-yl)phenol | 409.3 | 409.2 |
| Int-31 | 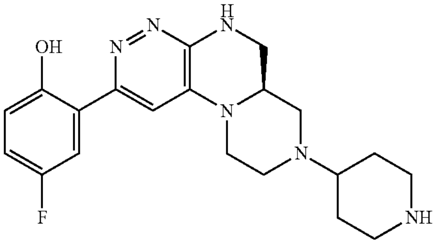 [SMILES: Oc1ccc(F)cc1-c1cc2c(nn1)NC[C@H]1CN(C3CCNCC3)CCN21] | (S)-4-fluoro-2-(8-(piperidin-4-yl)-6,6a,7,8,9,10-hexahydro-5H-pyrazino[1',2':4,5]pyrazino[2,3-c] pyridazin-2-yl)phenol | 385.2 | 385.3 |
| Int-32 | 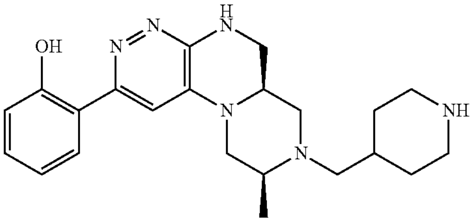 [SMILES: C[C@H]1CN2c3cc(-c4ccccc4O)nnc3NC[C@H]2CN1CC1CCNCC1] | 2-((6aS,9S)-9-methyl-8-(piperidin-4-ylmethyl)-6,6a,7,8,9,10-hexahydro-5H-pyrazino[1',2':4,5]pyrazino[2,3-c] pyridazin-2-yl)phenol | 395.3 | 395.2 |
| Int-33 | 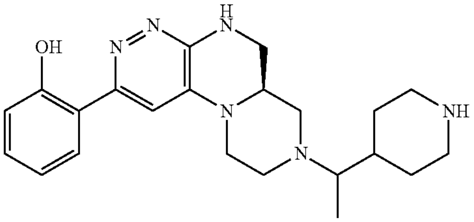 [SMILES: CC(C1CCNCC1)N1CCN2c3cc(-c4ccccc4O)nnc3NC[C@H]2C1] | 2-((6aS)-8-(1-(piperidin-4-yl) ethyl)-6,6a,7,8,9,10-hexahydro-5H-pyrazino[1',2':4,5]pyrazino [2,3-c] pyridazin-2-yl)phenol | 395.3 | 395.2 |

TABLE 2-continued

| Int. | Structure | Name | Calcd. (M + H)+ m/z | Found (M + H)+ m/z |
|---|---|---|---|---|
| | Intermediates 19-46 | | | |
| Int-34 | 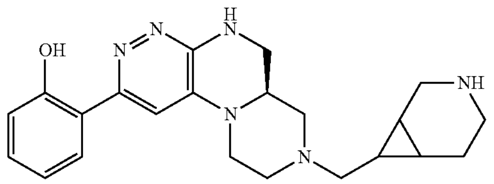 [SMILES: Oc1ccccc1-c1cc2c(nn1)NC[C@H]1CN(CC3C4CCNCC43)CCN21] | 2-((6aS)-8-((3-azabicyclo [4.1,0]heptan-7-yl)methyl)-6,6a,7,8,9,10-hexahydro-5H-pyrazino[1',2':4,5]pyrazino[2,3-c] pyridazin-2-yl)phenol | 393.2 | 393.1 |
| Int-35 | 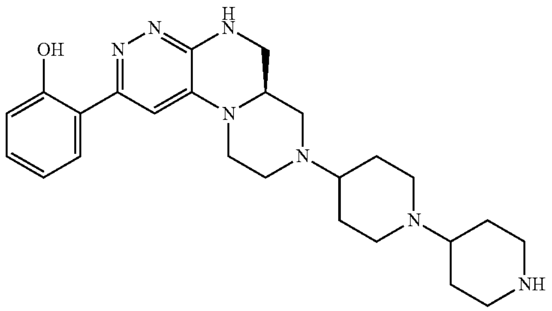 [SMILES: Oc1ccccc1-c1cc2c(nn1)NC[C@H]1CN(C3CCN(C4CCNCC4)CC3)CCN21] | (S)-2-(8-([1,4'-bipiperidin]-4-yl)-6,6a,7,8,9,10-hexahydro-5H-pyrazino[1',2':4,5]pyrazino[2,3-c]pyridazin-2-yl)phenol | 450.3 | 450.2 |
| Int-36 | 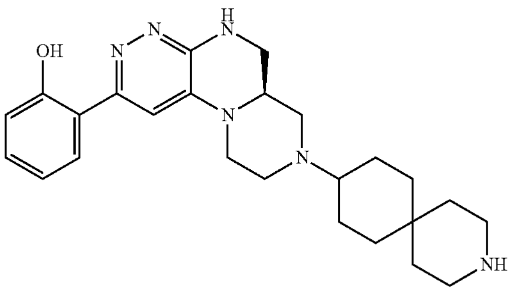 [SMILES: Oc1ccccc1-c1cc2c(nn1)NC[C@H]1CN(C3CCC4(CCNCC4)CC3)CCN21] | (S)-2-(8-(3-azaspiro[5.5]undecan-9-yl)-6,6a,7,8,9,10-hexahydro-5H-pyrazino[1',2':4,5]pyrazino[2,3-c]pyridazin-2-yl)phenol | 435.3 | 435.2 |
| Int-37 | 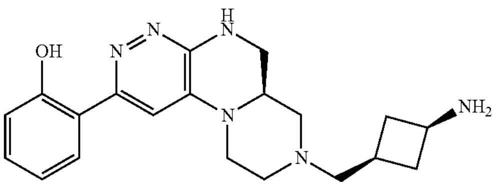 [SMILES: N[C@H]1C[C@@H](CN2CCN3c4cc(-c5ccccc5O)nnc4NC[C@H]3C2)C1] | 2-((S)-8-(((1s,3R)-3-aminocyclobutyl)methyl)-6,6a,7,8,9,10-hexahydro-5H-pyrazino[1',2':4,5]pyrazino[2,3-c]pyridazin-2-yl)phenol | 367.2 | 367.1 |
| Int-38 | 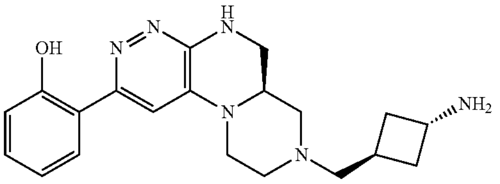 [SMILES: N[C@H]1C[C@H](CN2CCN3c4cc(-c5ccccc5O)nnc4NC[C@H]3C2)C1] | 2-((S)-8-(((1r,3S)-3-aminocyclobutyl)methyl)-6,6a,7,8,9,10-hexahydro-5H-pyrazino[1',2':4,5]pyrazino[2,3-c]pyridazin-2-yl)phenol | 367.2 | 367.2 |
| Int-39 | 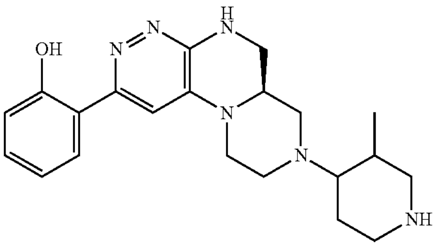 [SMILES: CC1CNCCC1N1CCN2c3cc(-c4ccccc4O)nnc3NC[C@H]2C1] | 2-((6aS)-8-(3-methylpiperidin-4-yl)-6,6a,7,8,9,10-hexahydro-5H-pyrazino[1',2':4,5]pyrazino[2,3-c]pyridazin-2-yl)phenol | 381.2 | 381.1 |

TABLE 2-continued

| Int. | Structure | Name | Calcd. (M + H)+ m/z | Found (M + H)+ m/z |
|---|---|---|---|---|
| | Intermediates 19-46 | | | |
| Int-40 | 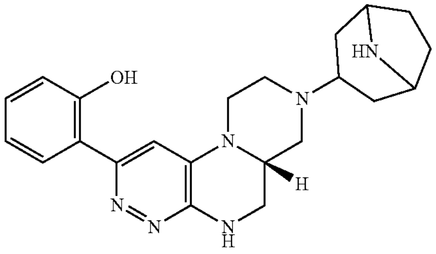 [SMILES: Oc1ccccc1-c1cc2c(nn1)NC[C@H]1CN(C3CC4CCC(C3)N4)CCN21] | 2-((6aS)-8-(8-azabicyclo[3.2.1]octan-3-yl)-6,6a,7,8,9,10-hexahydro-5H-pyrazino[1',2':4,5]pyrazino[2,3-c]pyridazin-2-yl)phenol | 393.2 | 393.2 |
| Int-41 | 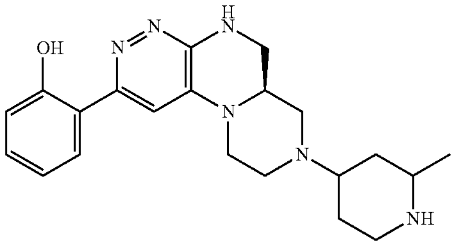 [SMILES: CC1CC(N2CCN3c4cc(-c5ccccc5O)nnc4NC[C@H]3C2)CCN1] | 2-((6aS)-8-(2-methylpiperidin-4-yl)-6,6a,7,8,9,10-hexahydro-5H-pyrazino[1',2':4,5]pyrazino[2,3-c]pyridazin-2-yl)phenol | 381.2 | 381.2 |
| Int-42 | 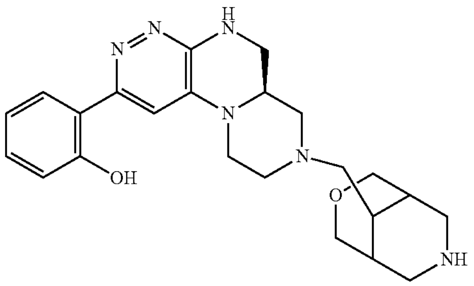 [SMILES: Oc1ccccc1-c1cc2c(nn1)NC[C@H]1CN(CC3C4CNCC3COC4)CCN21] | 2-((6aS)-8-((3-oxa-7-azabicyclo[3.3.1]nonan-9-yl)methyl)-6,6a,7,8,9,10-hexahydro-5H-pyrazino[1',2':4,5]pyrazino[2,3-c]pyridazin-2-yl)phenol | 423.2 | 423.1 |
| Int-43 | 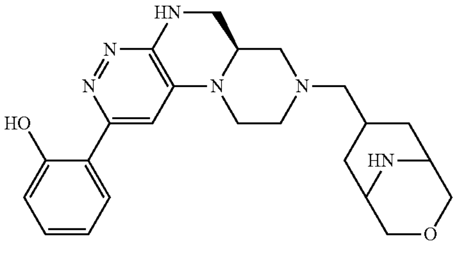 [SMILES: Oc1ccccc1-c1cc2c(nn1)NC[C@H]1CN(CC3CC4COCC(C3)N4)CCN21] | 2-((6aS)-8-((3-oxa-9-azabicyclo[3.3.1]nonan-7-yl)methyl)-6,6a,7,8,9,10-hexahydro-5H-pyrazino[1',2':4,5]pyrazino[2,3-c] pyridazin-2-yl)phenol | 423.2 | 423.2 |
| Int-44 | 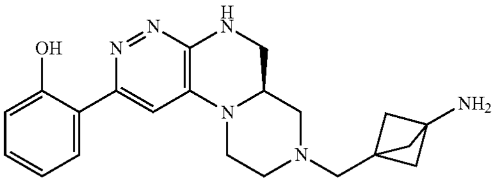 [SMILES: NC12CC(CN3CCN4c5cc(-c6ccccc6O)nnc5NC[C@H]4C3)(C1)C2] | (S)-2-(8-((3-aminobicyclo[1.1.1]pentan-1-yl)methyl)-6,6a,7,8,9,10-hexahydro-5H-pyrazino[1',2':4,5]pyrazino[2,3-c] pyridazin-2-yl)phenol | 379.2 | 379.0 |

TABLE 2-continued

| Intermediates 19-46 | | | | |
|---|---|---|---|---|
| Int. | Structure | Name | Calcd. (M + H)+ m/z | Found (M + H)+ m/z |
| Int-45 | 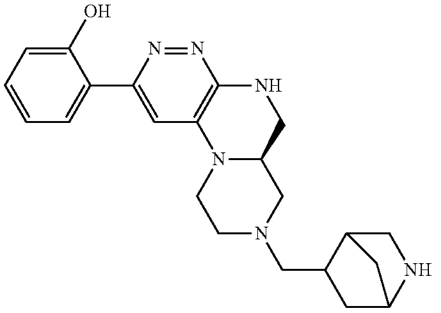 [SMILES: Oc1ccccc1-c1cc2c(nn1)NC[C@H]1CN(CC3CC4CC3CN4)CCN21] | 2-((6aS)-8-((2-azabicyclo [2.2.1]heptan-5-yl)methyl)-6,6a,7,8,9,10-hexahydro-5H-pyrazino[1',2':4,5]pyrazino[2,3-c] pyridazin-2-yl)phenol | 393.2 | 393.1 |
| Int-46 | 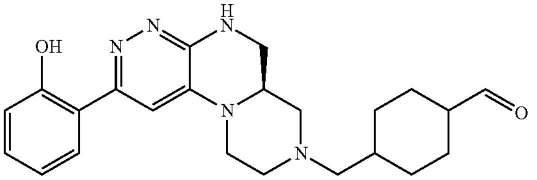 [SMILES: O=CC1CCC(CN2CCN3c4cc(-c5ccccc5O)nnc4NC[C@H]3C2)CC1] | (S)-4-((2-(2-hydroxyphenyl)-5,6,6a,7,9,10-hexahydro-8H-pyrazino[1',2':4,5]pyrazino[2,3-c]pyridazin-8-yl)methyl) cyclohexane-1-carbaldehyde | 408.2 | 408.2 |

Intermediate 47: 2-((2-(2,6-dioxopiperidin-3-yl)-1-oxoisoindolin-5-yl)oxy)acetaldehyde Int-47

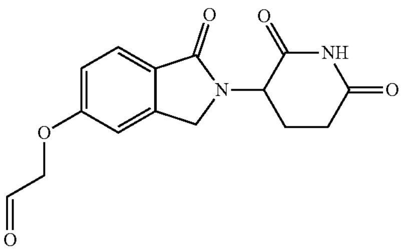

Step 1: 3-(5-(allyloxy)-1-oxoisoindolin-2-yl)piperidine-2,6-dione

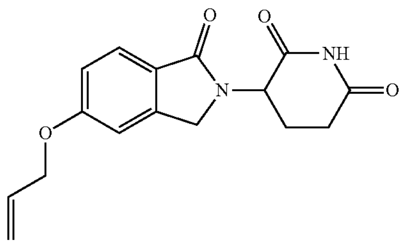 [SMILES: C=CCOc1ccc2c(c1)CN(C1CCC(=O)NC1=O)C2=O]

To a stirred mixture of 3-(6-hydroxy-3-oxo-1H-isoindol-2-yl)piperidine-2,6-dione (prepared using the procedure described in WO 2018/071606, 200 mg, 0.77 mmol) and $K_2CO_3$ (106 mg, 0.77 mmol) in DMF (2.5 mL) at 0° C. was slowly added allyl bromide (102 mg, 0.85 mmol). After 30 min, the cooling bath was removed, and the reaction mixture was warmed up to 25° C. After additional 14 h, the mixture was purified by prep-HPLC on a C18 column (20-35 μM, 100 A, 80 g) with mobile phase: $H_2O$ (0.100 TFA)/MeOH at flow rate: 50 mL/min to give the desired product as its TFA salt (52 mg, 0.17 mmol, 22.5% yield). LCMS calcd. for $C_{16}H_{17}N_2O_4$ $(M+H)^+$ m/z=301.1; found: 301.2.

Step 2: 2-((2-(2,6-dioxopiperidin-3-yl)-1-oxoisoindolin-5-yl)oxy)acetaldehyde (Int-18)

To a stirred mixture of 3-(3-oxo-6-prop-2-enoxy-1H-isoindol-2-yl)piperidine-2,6-dione (177 mg, 0.59 mmol) in DCM (30 mL) was added $O_3$ at −78° C. After 10 min, dimethyl sulfide was added. After another 1 h, the mixture was concentrated to give the crude product 2-[[2-(2,6-dioxopiperidin-3-yl)-1-oxo-3H-isoindol-5-yl]oxy]acetaldehyde (170 mg, 0.45 mmol, 76.3% yield). LCMS calcd. for $C_{15}H_{15}N_2O_5$ $(M+H)^+$ m/z=303.1; found: 303.1.

Intermediate 48: tert-butyl (R)-5-amino-4-(5-hydroxy-1-oxoisoindolin-2-yl)-5-oxopentanoate Int-48

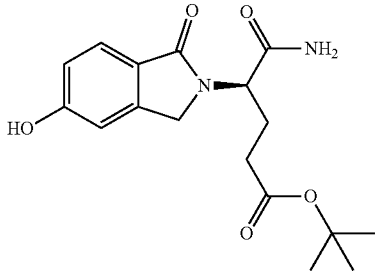

Step 1: 1-(4-((tert-butyldimethylsilyl)oxy)-2-methylphenyl)ethan-1-one

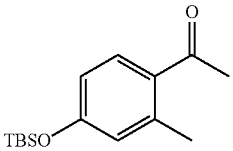 [SMILES: CC(=O)c1ccc(O[Si](C)(C)C(C)(C)C)cc1C]

To a stirred solution of methyl 4-hydroxy-2-methylbenzoate (25.0 g, 150 mmol) and imidazole (51.2 g, 752 mmol) in DCM (200 mL) was added TBSCl (34.0 g, 226 mmol) at rt. After 16 h, the mixture was diluted with water (100 mL) and extracted with DCM (300 mL). The organic layer was washed with water and brine, dried with $MgSO_4$, filtered and concentrated. The residue was purified by column chromatography on a silica gel column (PE/EA=20/1) to the desired product (46.2 g, 140 mmol, 93.1% yield). LCMS calculated for $C_{15}H_{25}O_2Si(M+H)^+$ m/z=265.2; found: 265.3. 1H NMR (400 MHz, $CDCl_3$) δ7.64 (d, J=8.8 Hz, 1H), 6.44-6.47 (m, 2H), 3.63 (S, 3H), 2.34 (S, 3H), 0.77 (S, 9H), 0.00 (S, 6H).

Step 2: methyl 2-(bromomethyl)-4-[tert-butyl(dimethyl)silyl]oxybenzoate

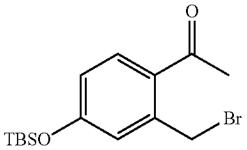 [SMILES: CC(=O)c1ccc(O[Si](C)(C)C(C)(C)C)cc1CBr]

To a stirred solution of methyl 4-[tert-butyl(dimethyl)silyl]oxy-2-methylbenzoate (3.0 g, 10.7 mmol) in carbon tetrachloride (40 mL) were added NBS (2.3 g, 12.8 mmol) and AIBN (0.09 g, 0.53 mmol) at rt. The resulted mixture was stirred at 15° C. for 0.5 hour, then heated to 80° C. After another 2.5 hours, the reaction mixture was poured into water (100 mL), and the organic layer was separated. The aqueous layer was extracted with dichloromethane (100 mL×2). The combined organic layers were washed with saturated brine (100 mL×2), dried over sodium sulfate, filtered, and concentrated under reduced pressure. The residue was purified by column chromatography on a silica gel column (PE) to afford methyl 2-(bromomethyl)-4-[tert-butyl(dimethyl)silyl]oxybenzoate (3.0 g, 8.3 mmol, 78% yield). LCMS calculated for $C_{15}H_{24}BrO_2Si$ $(M+H)^+$ m/z=343.1; found: 343.1. $^1H$ NMR (400 MHz, $CDCl_3$) δ 7.81 (d, J=8.4 Hz, 1H), 6.82 (d, J=2.4 Hz, 1H), 6.69 (dd, J=8.4, 2.4 Hz, 1H), 4.83 (S, 2H), 3.80 (S, 3H), 0.89 (S, 9H), 0.13 (S, 6H).

Step 3: tert-butyl (R)-5-amino-4-(5-hydroxy-1-oxoisoindolin-2-yl)-5-oxopentanoate (Int-19)

To a mixture of methyl 2-(bromomethyl)-4-[tert-butyl(dimethyl)silyl]oxybenzoate (5.0 g, 13.91 mmol) and tert-butyl (4R)-4,5-diamino-5-oxopentanoate (2.81 g, 13.91 mmol) in MeCN (70 mL) was added DIEA (9.2 mL, 55.66 mmol). The mixture was stirred at 80° C. for 12 hrs.

The reaction mixture was quenched by water (50 mL), extracted with EA (50 mL×4), the combined organic phase was washed with brine (50 mL), dried over anhydrous sodium sulfate, filtered, and concentrated under reduced pressure. The residue was purified by column chromatography on a silica gel column (DCM/MeOH=20/1) to afford the desired product (2.0 g, 5.5 mmol, 39.6% yield). LCMS calculated for $C_{17}H_{23}N_2O_5(M+H)^+$ m/z=335.16; found: 335.2.

Intermediate 49: 2-(2,6-dioxopiperidin-3-yl)-5-(piperidin-4-yl) isoindoline-1,3-dione Int-49

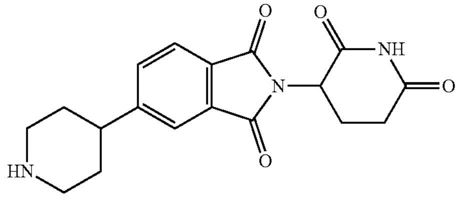

Step 1: tert-butyl 4-[2-(2,6-dioxopiperidin-3-yl)-1,3-dioxoisoindol-5-yl]-3,6-dihydro-2H-pyridine-1-carboxylate

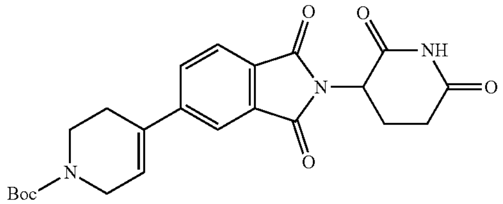 [SMILES: CC(C)(C)OC(=O)N1CC=C(c2ccc3c(c2)C(=O)N(C2CCC(=O)NC2=O)C3=O)CC1]

A solution of 5-bromo-2-(2,6-dioxopiperidin-3-yl) isoindole-1,3-dione (500 mg, 1.48 mmol), N-Boc-1,2,3,6-tetrahydropyridine-4-boronic acid pinacol ester (459 mg, 1.48 mmol), $K_3PO_4$ (787 mg, 3.71 mmol) and $Pd(dppf)_2Cl_2$ (218 mg, 0.30 mmol) in DMF (10 mL) was stirred at 90° C. for 2 h under nitrogen. The resulted mixture was diluted with water, and extracted with EA. The organic layers were combined, washed with brine, dried over $Na_2SO_4$, filtered, and concentrated. The residue was purified by silica gel chromatography (PE/EA=1/1) to afford the desired product (532 mg, 82% yield) as a yellow oil. LCMS calculated for $C_{23}H_{26}N_3O_6$ $(M+H)^+$ m/z=440.2; found: 384.0 (M+H−56).

Step 2: tert-butyl 4-[2-(2,6-dioxopiperidin-3-yl)-1,3-dioxoisoindol-5-yl]piperidine-1-carboxylate

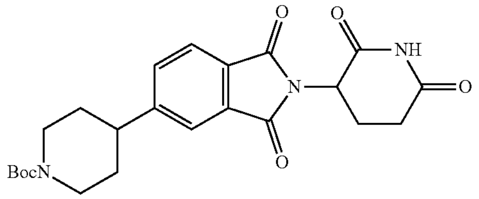 [SMILES: CC(C)(C)OC(=O)N1CCC(c2ccc3c(c2)C(=O)N(C2CCC(=O)NC2=O)C3=O)CC1]

A mixture of tert-butyl 4-[2-(2,6-dioxopiperidin-3-yl)-1,3-dioxoisoindol-5-yl]-3,6-dihydro-2H-pyridine-1-carboxylate (638 mg, 1.45 mmol) and Pd/C (10%, 15.4 mg, 0.15 mmol) in THE (5 mL) was stirred at 25° C. under hydrogen overnight. The resulted mixture was filtered, and the filtrate was concentrated to afford the desired product (523 mg, 82% yield) as a white solid. LCMS calculated for $C_{23}H_{28}N_3O_6$ $(M+H)^+$ m/z=442.2; found: 386.0 (M+H−56).

Step 3: 2-(2,6-dioxopiperidin-3-yl)-5-piperidin-4-ylisoindole-1,3-dione

A mixture of tert-butyl 4-[2-(2,6-dioxopiperidin-3-yl)-1,3-dioxoisoindol-5-yl]piperidine-1-carboxylate (523 mg, 1.18 mmol) and HCl/1,4-dioxane (4 M, 3 mL, 11.9 mmol) in DCM (4 mL) was stirred at 25° C. for 1 h. The resulted mixture was concentrated to afford the desired product as its HCl salt (403 mg, 100% yield). LCMS calculated for $C_{18}H_{20}N_3O_4$ $(M+H)^+$ m/z=342.2; found: 342.0.

Intermediate 50: 3-(1-oxo-6-(piperidin-4-yl) isoindolin-2-yl)piperidine-2,6-dione Int-50

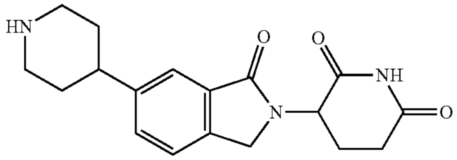

The title compound was prepared using procedure analogous to those described for Intermediate 49, using appropriate starting materials. LCMS m/z calcd for $C_{18}H_{22}N_3O_3$ $(M+H)^+$: 328.2; found: 328.2.

Intermediate 51: 2-(2,6-dioxopiperidin-3-yl)-5-(piperidin-4-yloxy) isoindoline-1,3-dione Int-51

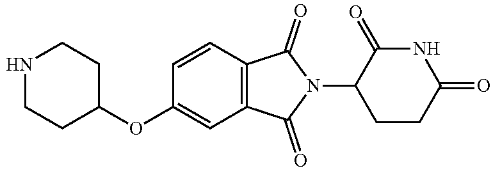

Step 1: tert-butyl 4-((2-(2,6-dioxopiperidin-3-yl)-1,3-dioxoisoindolin-5-yl)oxy)piperidine-1-carboxylate

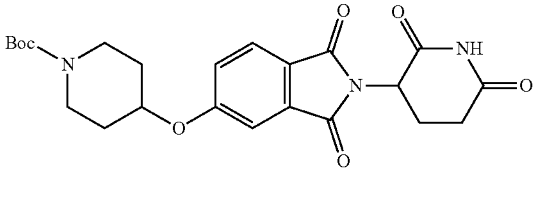 [SMILES: CC(C)(C)OC(=O)N1CCC(Oc2ccc3c(c2)C(=O)N(C2CCC(=O)NC2=O)C3=O)CC1]

To a stirred solution of 2-(2,6-dioxopiperidin-3-yl)-5-hydroxyisoindole-1,3-dione (prepared using the procedure described in US20180099940, 500 mg, 1.82 mmol), tert-butyl 4-(4-methylphenyl)sulfonyloxypiperidine-1-carboxylate (648 mg, 1.82 mmol) in DMF (10 mL), was added $K_2CO_3$ (756 mg, 5.47 mmol). The resulted mixture was heated to 80° C. After 16 h, the mixture was diluted with water, extracted with EA. The organic layers were combined, washed with brine, dried over $Na_2SO_4$, and filtered. The filtrate was concentrated to afford crude tert-butyl 4-((2-(2,6-dioxopiperidin-3-yl)-1,3-dioxoisoindolin-5-yl)oxy)piperidine-1-carboxylate (680 mg, 1.49 mmol, 81.5% yield). LCMS calculated for $C_{23}H_{28}N_3O_7$ (M+H)+m/z=458.2; found: $(M+H-100)^+$=358.2.

Step 2: 2-(2,6-dioxopiperidin-3-yl)-5-(piperidin-4-yloxy) isoindoline-1,3-dione

To a stirred solution of tert-butyl 4-[2-(2,6-dioxopiperidin-3-yl)-1,3-dioxoisoindol-5-yl]oxypiperidine-1-carboxylate (200 mg, 0.44 mmol) in DCM (5 mL), was added 4M HCl in dioxane (1.25 mL, 5 mmol) at rt. After 2 h, the volatiles were removed under reduced pressure to afford the desired product as its TFA salt (128 mg, 0.36 mmol, 81.9% yield). LCMS calculated for $C_{18}H_{20}N_3O_5$ (M+H)+m/z=358.2; found: 358.2.

Intermediate 52: 2-(2,6-dioxopiperidin-3-yl)-5-[4-(hydroxymethyl)piperidin-1-yl]isoindole-1,3-dione Int-52

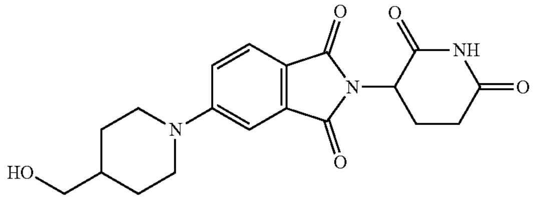

To a stirring solution of 2-(2,6-Dioxo-3-piperidinyl)-5-fluoro-1H-isoindole-1,3(2H)-dione (1.00 g, 3.62 mmol) and 4-Piperidinemethanol (625 mg, 5.43 mmol) in N-methylpyrrolidone (7.2 mL) was added N,N-diisopropylethyl amine (2.52 mL, 14.5 mmol). The reaction mixture was heated to 120° C. and stirred form 1.5 hours. The product mixture was diluted with ethyl acetate (80 mL) and washed with saturated sodium chloride aqueous solution (60 mL) and then water (60 mL). The organic layer was dried with sodium sulfate. The dried organic layer was filtered, and the filtrate was concentrated under reduced pressure The residue obtained was purified with flash column chromatography eluting with 0-100% ethyl acetate-hexanes to obtain 2-(2,6-dioxopiperidin-3-yl)-5-[4-(hydroxymethyl)piperidin-1-yl] isoindole-1,3-dione (1.22 g, 910) as a yellow solid. LCMS m/z calcd for $C_{19}H_{21}N_3O_5$ $[M+H]^+$: 372.1; found: 372.1.

Intermediates 53-60

The intermediates shown below in Table 3 were prepared by the method used in preparing Int-52 using appropriate starting materials.

TABLE 3

| Intermediates 53-60 | | | | |
|---|---|---|---|---|
| Int. | Structure | Name | Calcd. (M + H)+ m/z | Found (M + H)+ m/z |
| Int-53 | 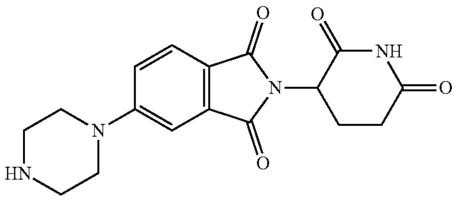 [SMILES: O=C1CCC(N2C(=O)c3ccc(N4CCNCC4)cc3C2=O)C(=O)N1] | 2-(2,6-dioxopiperidin-3-yl)-5-(piperazin-1-yl) isoindoline-1,3-dione | 343.1 | 343.1 |
| Int-54 | 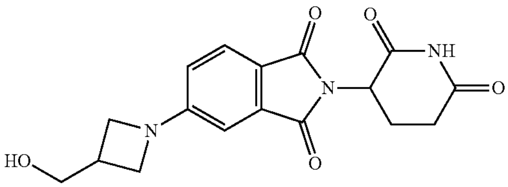 [SMILES: O=C1CCC(N2C(=O)c3ccc(N4CC(CO)C4)cc3C2=O)C(=O)N1] | 2-(2,6-dioxopiperidin-3-yl)-5-[3-(hydroxymethyl) azetidin-1-yl]isoindole-1,3-dione | 344.1 | 344.1 |
| Int-55 | 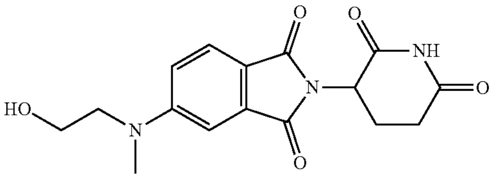 [SMILES: CN(CCO)c1ccc2c(c1)C(=O)N(C1CCC(=O)NC1=O)C2=O] | 2-(2,6-dioxopiperidin-3-yl)-5-[2-hydroxyethyl (methyl) amino]isoindole-1,3-dione | 332.1 | 332.2 |
| Int-56 | 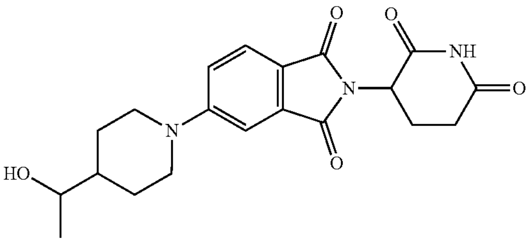 [SMILES: CC(O)C1CCN(c2ccc3c(c2)C(=O)N(C2CCC(=O)NC2=O)C3=O)CC1] | 2-(2,6-dioxopiperidin-3-yl)-5-(4-(1-hydroxyethyl)piperidin-1-yl)isoindoline-1,3-dione | 386.2 | 386.1 |
| Int-57 | 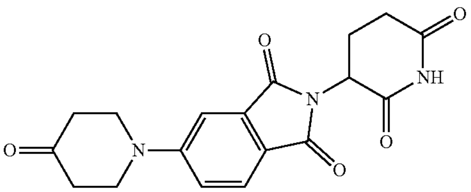 [SMILES: O=C1CCN(c2ccc3c(c2)C(=O)N(C2CCC(=O)NC2=O)C3=O)CC1] | 2-(2,6-dioxopiperidin-3-yl)-5-(4-oxopiperidin-1-yl) isoindoline-1,3-dione | 356.1 | 356.0 |
| Int-58 | 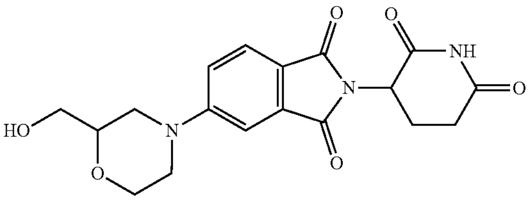 [SMILES: O=C1CCC(N2C(=O)c3ccc(N4CCOC(CO)C4)cc3C2=O)C(=O)N1] | 2-(2,6-dioxopiperidin-3-yl)-5-(2-(hydroxymethyl) morpholino)isoindoline-1,3-dione | 374.1 | 374.1 |

TABLE 3-continued

| Intermediates 53-60 | | | | |
|---|---|---|---|---|
| Int. | Structure | Name | Calcd. (M + H)+ m/z | Found (M + H)+ m/z |
| Int-59 | 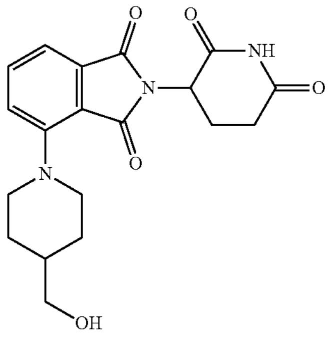 [SMILES: O=C1CCC(N2C(=O)c3cccc(N4CCC(CO)CC4)c3C2=O)C(=O)N1] | 2-(2,6-dioxopiperidin-3-yl)-4-(4-(hydroxymethyl)piperidin-1-yl)isoindoline-1,3-dione | 372.2 | 372.2 |

Intermediate 60: 1-(2-(2,6-dioxopiperidin-3-yl)-1,3-dioxoisoindolin-5-yl)piperidine-4-carbaldehyde Int-60

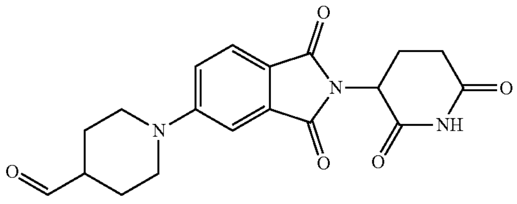

To a stirred solution of 2-(2,6-dioxopiperidin-3-yl)-5-(4-(hydroxymethyl)piperidin-1-yl) isoindoline-1,3-dione (500 mg, 1.35 mmol) in DCM (25 mL) was added Dess-Martin periodinane (1.71 g, 4.04 mmol) at 0° C. After 2 h, the volatiles were removed and the residue was purified by Prep-HPLC on a C18 column (20-35 μm, 100 A, 80 g) with mobile phase: $H_2O$ (0.1% TFA)/MeCN at flow rate: 50 mL/min to afford 1-(2-(2,6-dioxopiperidin-3-yl)-1,3-dioxoisoindolin-5-yl)piperidine-4-carbaldehyde (447 mg, 0.63 mmol, 46.7% yield). LCMS calculated for $C_{19}H_{20}N_3O_5$ $(M+H)^+$ m/z=370.2; found: 370.0.

Intermediate 61: 1-(2-(2,6-dioxopiperidin-3-yl)-1,3-dioxoisoindolin-4-yl)piperidine-4-carbaldehyde Int-61

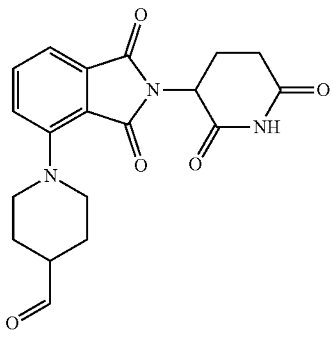

The title compound was prepared using procedure analogous to those described for Intermediate 60, using appropriate starting materials. LCMS m/z calcd for $C_{19}H_{20}N_3O_5$ $(M+H)^+$: 370.1; found: 370.0.

Intermediate 62: (S)-(2-(2-hydroxyphenyl)-5,6,6a,7,9,10-hexahydro-8H-pyrazino[1',2':4,5]pyrazino[2,3-c]pyridazin-8-yl)(piperidin-4-yl)methanone Int-62

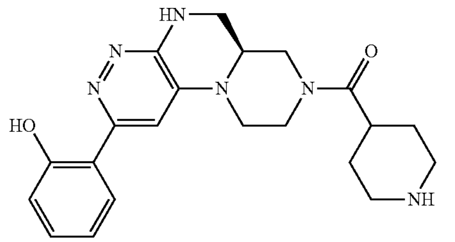

Step 1: Synthesis of tert-butyl (S)-4-(2-(2-hydroxyphenyl)-6,6a, 7,8,9,10-hexahydro-5H-pyrazino [1',2':4,5]pyrazino[2,3-c]pyridazine-8-carbonyl)piperidine-1-carboxylate

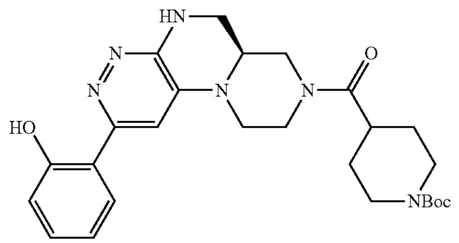 [SMILES: CC(C)(C)OC(=O)N1CCC(C(=O)N2CCN3c4cc(-c5ccccc5O)nnc4NC[C@H]3C2)CC1]

To a stirring solution of N-Boc-isonipecotic acid (60 mg, 0.262 mmol) in N,N-dimethylformamide (3 mL) at 0° C. was added 1-[Bis(dimethylamino)-methylene]-1H-1,2,3-triazolo[4,5-b]pyridinium 3-oxid hexafluorophosphate (150 mg, 0.394 mmol) and triethylamine (211 μL, 1.52 mmol).

The reaction mixture was stirred at 0° C. for 15 minutes. Then 2-[(10R)-1,5,6,8,12-pentazatricyclo[8.4.0.02,7]tetradeca-2,4,6-trien-4-yl]phenol; dihydrochloride (80 mg, 0.253 mmol) was added, and the reaction mixture was stirred for an additional 2 hours while warming to 23° C. The product mixture was purified directly using a prep-LCMS (5 m 10×3 cm Waters CSH—C18, 20.2-40.2% acetonitrile in water (0.1% TFA), wet loaded) to yield the trifluoroacetic acid salt of tert-butyl (S)-4-(2-(2-hydroxyphenyl)-6,6a,7,8,9,10-hexahydro-5H-pyrazino[1',2':4,5]pyrazino[2,3-c] pyridazine-8-carbonyl)piperidine-1-carboxylate (113 mg, 73%) as an off white solid. LCMS m/z calcd for $C_{26}H_{34}N_6O_4$ $[M+H]^+$: 495.3; found: 495.2.

Step 2: Synthesis of (S)-(2-(2-hydroxyphenyl)-5,6,6a,7,9,10-hexahydro-8H-pyrazino[1',2':4,5]pyrazino[2,3-c]pyridazin-8-yl)(piperidin-4-yl)methanone To a stirring solution of the trifluoroacetic acid salt tert-butyl (S)-4-(2-(2-hydroxyphenyl)-6,6a,7,8,9,10-hexahydro-5H-pyrazino[1',2':4,5]pyrazino[2,3-c]pyridazine-8-carbonyl)piperidine-1-carboxylate (113 mg, 0.186 mmol) in dichloromethane (7.1 mL) was added trifluoroacetic acid (956 μL, 12.5 mmol). The reaction mixture was stirred for 1 hour. The product mixture was concentrated under reduced pressure to obtain the trifluoroacetic acid salt of (S)-(2-(2-hydroxyphenyl)-5,6,6a,7,9,10-hexahydro-8H-pyrazino[1',2':4,5]pyrazino[2,3-c]pyridazin-8-yl)(piperidin-4-yl)methanone (94 mg, 99%) as an off white oil. LCMS m/z calcd for $C_{21}H_{26}N_6O_2$ $[M+H]^+$: 395.2; found: 395.1.

Intermediates 63-64

The intermediates shown below in Table 4 were prepared by the method used in preparing Int-62 using appropriate starting materials.

TABLE 4

Intermediates 63-64

| Int. | Structure | Name | Calcd. (M + H)+ m/z | Found (M + H)+ m/z |
|---|---|---|---|---|
| Int-63 | 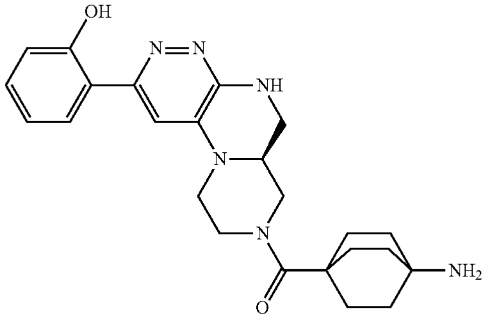 [SMILES: NC12CCC(C(=O)N3CCN4c5cc(-c6ccccc6O)nnc5NC[C@H]4C3)(CC1)CC2] | (S)-(4-aminobicyclo[2.2.2] octan-1-yl)(2-(2-hydroxyphenyl)-5,6,6a,7,9,10-hexahydro-8H-pyrazino [1',2':4,5] pyrazino[2,3-c]pyridazin-8-yl)methanone | 435.2 | 435.1 |
| Int-64 | 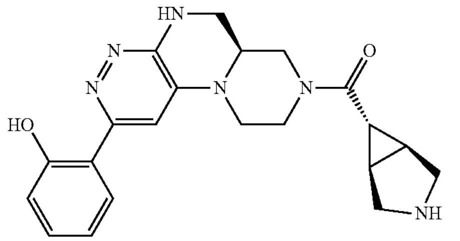 [SMILES: O=C([C@H]1[C@@H]2CNC[C@@H]21)N1CCN2c3cc(-c4ccccc4O)nnc3NC[C@H]2C1] | ((1R,5S,6r)-3-azabicyclo [3.1.0]hexan-6-yl)((S)-2-(2-hydroxyphenyl)-5,6,6a,7,9,10-hexahydro-8H-pyrazino [1',2':4,5] pyrazino[2,3-c]pyridazin-8-yl)methanone | 393.2 | 393.1 |

Intermediate 65: 3-(6-(4-(hydroxymethyl)piperidin-1-yl)-1-oxoisoindolin-2-yl)piperidine-2,6-dione Int-65

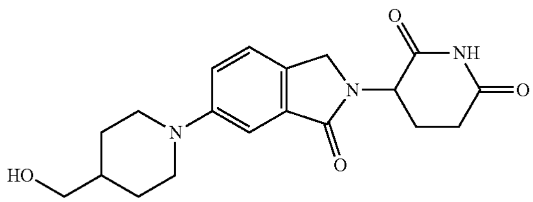

Step 1: Synthesis of methyl 2-cyano-5-(4-(hydroxymethyl)piperidin-1-yl)benzoate

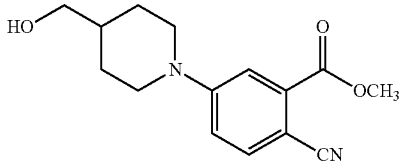 [SMILES: COC(=O)c1cc(N2CCC(CO)CC2)ccc1C#N]

To a solution of methyl 2-cyano-5-fluorobenzoate (2.00 g, 11.2 mmol) and 4-piperidinemethanol (1.67 g, 14.5 mmol) in dimethyl sulfoxide (22.3 mL) was added N,N-diisopropylethylamine (5.83 mL, 33.5 mmol). The reaction mixture was heated to 110° C. and stirred for 1.5 hours. The product mixture was diluted with ethyl acetate (100 mL) and transferred to a separatory funnel. The diluted reaction mixture was washed with saturated sodium chloride aqueous solution (50 mL×2). The organic layer was dried with sodium sulfate. The dried organic layer was filtered, and the filtrate was concentrated under reduced pressure. The residue obtained was purified with flash column chromatography eluting with 0-100% ethyl acetate-hexanes to obtain methyl 2-cyano-5-(4-(hydroxymethyl)piperidin-1-yl)benzoate (3.02 g, 98% yield) as a yellow oil. LCMS m/z calcd for $C_{15}H_{18}N_2O_3$ $[M+H]^+$: 275.1; found: 275.1.

Step 2: Synthesis of methyl 2-formyl-5-(4-(hydroxymethyl)piperidin-1-yl)benzoate

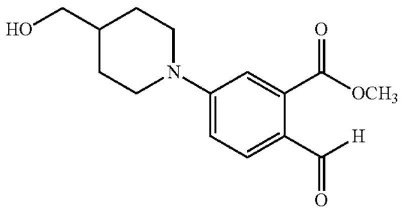 [SMILES: COC(=O)c1cc(N2CCC(CO)CC2)ccc1C=O]

To a solution of methyl 2-cyano-5-(4-(hydroxymethyl) piperidin-1-yl)benzoate (3.00 g, 10.9 mmol), sodium hypophosphite monohydrate (11.7 g, 111 mmol), and acetic acid (12.7 mL, 222 mmol) in pyridine (26.3 mL) was added Raney nickel (1.97 g, 33.6 mmol) as a slurry in water (28 mL). The reaction mixture was heated to 70° C. and stirred for 8 hours. The product mixture was filter through celite, and the celite was washed with ethyl acetate (50 mL×2). The filtrate was transferred to a separatory funnel. The diluted product mixture was washed with water (150 mL). The aqueous layer was extracted with ethyl acetate (75×2). The combined organic layers were dried with sodium sulfate. The dried organic layers were filtered, and the filtrate was concentrated under reduced pressure. The residue obtained was purified with flash column chromatography eluting with 0-100% ethyl acetate-hexanes to obtain methyl 2-formyl-5-(4-(hydroxymethyl)piperidin-1-yl)benzoate (2.31 g, 76%) as a yellow oil. LCMS m/z calcd for $C_{15}H_{19}NO_4$ $[M+H]^+$: 278.1; found: 278.1.

Step 3: Synthesis of 3-(6-(4-(hydroxymethyl)piperidin-1-yl)-1-oxoisoindolin-2-yl)piperidine-2,6-dione To a stirring solution of methyl 2-formyl-5-(4-(hydroxymethyl)piperidin-1-yl)benzoate (2.40 g, 8.65 mmol) in dichloromethane (48.8 mL) and N,N-dimethylformamide (48.8 mL) was added 3-aminopiperidine-2,6-dione hydrochloride (1.85 g, 11.3 mmol) followed by N,N-diisopropylethylamine (3.77 mL, 21.6 mmol). The reaction mixture was stirred at 23° C. for 3 hours. The reaction mixture was cooled to 0° C. To the cooled reaction mixture was added acetic acid (5.94 mL, 104 mmol) followed by sodium triacetoxyborohydride (5.50 g, 26.0 mmol). The reaction mixture was allowed to slowly warm to 23° C. and was stirred for an additional 3 hours. The product mixture was diluted with water (10 mL). The diluted product mixture was basified with saturated sodium bicarbonate aqueous solution until no further evolution of gas was observed. The basified product mixture was filtered. The retentate was washed with water (10 mL×2). The retentate was collected and place under vacuum to obtain 3-(6-(4-(hydroxymethyl)piperidin-1-yl)-1-oxoisoindolin-2-yl)piperidine-2,6-dione (1.95 g, 63%) as a grey-white solid. LCMS m/z calcd for $C_{19}H_{23}N_3O_4$ $[M+H]^+$: 358.1; found: 358.1.

Intermediates 66-67

The intermediates shown below in Table 5 were prepared by the method used in preparing Int-65 using appropriate starting materials.

TABLE 5

| Intermediates 66-67 | | | | |
|---|---|---|---|---|
| Int. | Structure | Name | Calcd. $(M + H)^+$ m/z | Found $(M + H)^+$ m/z |
| Int-66 | 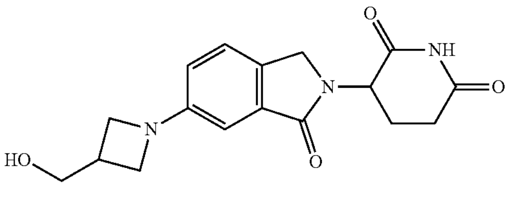 [SMILES: O=C1CCC(N2Cc3ccc(N4CC(CO)C4)cc3C2=O)C(=O)N1] | 3-(6-(3-(hydroxymethyl) azetidin-1-yl)-1-oxoisoindolin-2-yl) piperidine-2,6-dione | 330.1 | 330.2 |
| Int-67 | 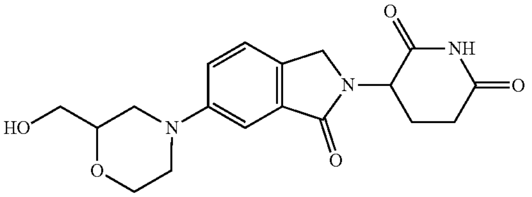 [SMILES: O=C1CCC(N2Cc3ccc(N4CCOC(CO)C4)cc3C2=O)C(=O)N1] | 3-(6-(2-(hydroxymethyl) morpholino)-1-oxoisoindolin-2-yl) piperidine-2,6-dione | 360.1 | 360.1 |

Intermediate 68: 1-(2-(2,6-dioxopiperidin-3-yl)-3-oxoisoindolin-5-yl)piperidine-4-carbaldehyde Int-68

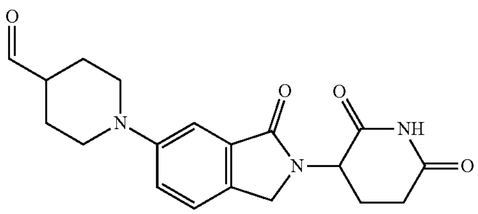

To a stirred solution of 3-(6-(4-(hydroxymethyl)piperidin-1-yl)-1-oxoisoindolin-2-yl)piperidine-2,6-dione (191 mg, 0.53 mmol) in DCM (10 mL) and DMF (2 mL), was added Dess-Martin periodinane (453 mg, 1.07 mmol) at 0° C. After 2 h, the volatiles were removed and the residue was purified by Prep-HPLC on a C18 column (20-35 μm, 100 A, 80 g) with mobile phase: $H_2O$ (0.1% $NH_4HCO_3$)/MeCN at flow rate: 50 mL/min to afford the desired product (116 mg, 0.33 mmol, 61.1% yield). LCMS calculated for $C_{19}H_{22}N_3O_4$ $(M+H)^+$ m/z=356.2; found: 356.2.

Intermediate 69: tert-butyl 4-formyl-2-(hydroxymethyl)piperidine-1-carboxylate

Int-69

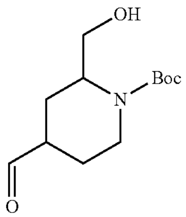

Step 1: 1-O-tert-butyl 2-O-methyl (4E)-4-(methoxymethylidene)piperidine-1,2-dicarboxylate

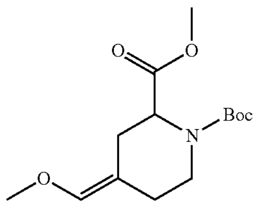 [SMILES: CO/C=C1/CCN(C(=O)OC(C)(C)C)C(C(=O)OC)C1]

To a stirred solution of (methoxymethyl)triphenylphosphonium chloride (3.36 g, 9.79 mmol) in THE (45 mL), was added potassium tert-butoxide (1.10 g, 9.79 mmol) at 0° C. After 0.5 h. A solution of 1-O-tert-butyl 2-O-methyl 4-oxopiperidine-1,2-dicarboxylate (840 mg, 3.26 mmol) in THE (6 mL) was added. The resulted mixture was warmed up to rt and stirred for additional 2 h. The reaction mixture was diluted with water, and extracted with EA. The combined organic phases was washed with brine, dried over sodium sulfate, and filtered. The filtrate was concentrated and the residue was purified by silica gel column with (PE/EA=5/1) to afford 1-O-tert-butyl 2-O-methyl (4E)-4-(methoxymethylidene)piperidine-1,2-dicarboxylate (795 mg, 2.79 mmol, 85.3% yield). LCMS calculated for $C_{14}H_{24}NO_5$ $(M+H)^+$ m/z=286.2; found: 186.2 (M+H−100).

Step 2: tert-butyl (4Z)-2-(hydroxymethyl)-4-(methoxymethylidene)piperidine-1-carboxylate

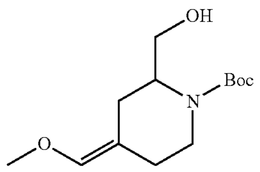 [SMILES: CO/C=C1/CCN(C(=O)OC(C)(C)C)C(CO)C1]

To a stirred solution of 1-O-tert-butyl 2-O-methyl (4Z)-4-(methoxymethylidene) piperidine-1,2-dicarboxylate (795 mg, 2.79 mmol) in THF (50 mL) and MeOH (2.6 mL), was added $LiBH_4$ (606 mg, 27.86 mmol) at rt. After 16 h, the resulted mixture was diluted with water, and extracted with EA. The combined organic phases was washed with brine, dried over sodium sulfate, and filtered. The filtrate was concentrated to afford tert-butyl (4Z)-2-(hydroxymethyl)-4-(methoxymethylidene)piperidine-1-carboxylate (902 mg, 2.63 mmol, 94.4% yield). LCMS calculated for $C_{13}H_{24}NO_4$ $(M+H)^+$ m/z=258.2; found: 158.2 (M+H−100).

Step 3: 2-(hydroxymethyl)piperidine-4-carbaldehyde

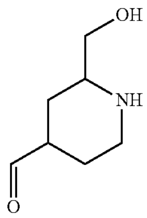

To a stirred solution of tert-butyl (4Z)-2-(hydroxymethyl)-4-(methoxymethylidene) piperidine-1-carboxylate (902 mg, 3.51 mmol) in THE (20 mL), was added 6N HCl (5.80 mL, 34.80 mmol). at 25° C. After 20 h, the resulted mixture was diluted with aqueous $NaHCO_3$, and extracted with EA. The aqueous phase was lyophilized to afford 2-(hydroxymethyl)piperidine-4-carbaldehyde (480 mg, 3.35 mmol, 95.6% yield) as crude. LCMS calculated for $C_7H_{14}NO_2$ $(M+H)^+$ m/z=144.2; found: 144.2.

Step 4: tert-butyl 4-formyl-2-(hydroxymethyl)piperidine-1-carboxylate

To a solution of 2-(hydroxymethyl)piperidine-4-carbaldehyde (480 mg, 3.35 mmol) in water (5 mL), were added TEA (1.40 mL, 10.1 mmol), DMAP (41.0 mg, 0.34 mmol), and $(Boc)_2O$ (1.46 g, 6.70 mmol). The reaction mixture was stirred at 25° C. for 20 h. The resulted mixture was extracted with EA. The combined organic phases was washed with brine, dried over sodium sulfate, and filtered. The filtrate was concentrated to afford tert-butyl 4-formyl-2-(hydroxymethyl)piperidine-1-carboxylate (247 mg, 1.02 mmol, 30.3% yield) as crude. LCMS calculated for $C_{12}H_{22}NO_4$ $(M+H)^+$ m/z=244.2; found: 144.2 (M+H−100).

Intermediate 70: [(10S)-4-(2-hydroxyphenyl)-1,5,6,8,12-pentazatricyclo[8.4.0.02,7]tetradeca-2,4,6-trien-12-yl]-piperazin-1-ylmethanone

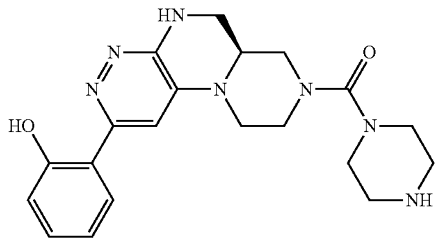

Int-70

Step 1: tert-butyl 4-[(10S)-4-(2-hydroxyphenyl)-1,5,6,8,12-pentazatricyclo[8.4.0.02,7]tetradeca-2(7),3,5-triene-12-carbonyl]piperazine-1-carboxylate

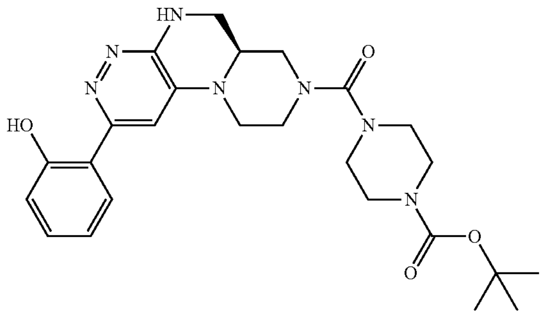 [SMILES: CC(C)(C)OC(=O)N1CCN(C(=O)N2CCN3c4cc(-c5ccccc5O)nnc4NC[C@H]3C2)CC1]

To a stirring solution of tert-butyl 1-piperazinecarboxylate (237 mg, 1.27 mmol, 3 equiv) and pyridine (171 μL, 2.12 mmol, 5.0 equiv) in dichloromethane (4.2 mL) at 0° C. was added triphosgene (189 mg, 0.635 mmol, 1.5 equiv). The reaction mixture was warmed to room temperature and stirred for 1.5 hours. The product mixture was diluted with dichloromethane (50 mL) and transferred to a separatory funnel containing 1 N aqueous hydrochloric acid solution. The aqueous layer was extracted with dichloromethane (50 mL×2). The combined organic layers were dried with sodium sulfate. The dried organic layers with filtered, and the filtrate was concentrated under reduced pressure. The residue was obtained was dissolved in dichloromethane (4.2 mL). To a stirring solution of the residue in dichloromethane was added 2-[(10R)-1,5,6,8,12-pentazatricyclo[8.4.0.02,7]tetradeca-2(7),3,5-trien-4-yl]phenol (120 mg, 0.424 mmol, 1.00 equiv) and added triethylamine (295 μL, 2.12 mmol, 5.00 equiv). The reaction mixture was stirred at 23° C. for 2 hours. The resulting produce mixture was diluted with methanol (16 mL) and directly purified using a prep-LCMS (5 m 10×3 cm Waters CSH-C18, 18.6-38.6% acetonitrile in water (0.1% TFA), wet loaded) to yield the trifluoroacetic acid salt of tert-butyl 4-[(10S)-4-(2-hydroxyphenyl)-1,5,6,8,12-pentazatricyclo[8.4.0.02,7]tetradeca-2(7),3,5-triene-12-carbonyl]piperazine-1-carboxylate (235 mg, 91%) as a clear oil. LCMS m/z calcd for $C_{25}H_{33}N_7O_4$ $[M+H]^+$: 496.3; found: 496.2.

Step 2: [(10S)-4-(2-hydroxyphenyl)-1,5,6,8,12-pentazatricyclo[8.4.0.02,7]tetradeca-2,4,6-trien-12-yl]-piperazin-1-ylmethanone To a stirring solution of the trifluoroacetic acid salt of tert-butyl 4-[(10S)-4-(2-hydroxyphenyl)-1,5,6,8,12-pentazatricyclo[8.4.0.02,7]tetradeca-2,4,6-triene-12-carbonyl]piperazine-1-carboxylate (220 mg, 361 mmol, 1.00 equiv) in dichloromethane (7.2 mL) was added 2,2,2-trifluoroacetic acid (911 μL, 11.9 mmol, 33 equiv). The reaction mixture was stirred 1.5 hours then concentrated under reduced pressure to yield the trifluoroacetic acid salt of [(10S)-4-(2-hydroxyphenyl)-1,5,6,8,12-pentazatricyclo[8.4.0.02,7]tetradeca-2,4,6-trien-12-yl]-piperazin-1-ylmethanone (182 mg, 99%) as a pink oil. LCMS m/z calcd for $C_{20}H_{25}N_7O_2$ $[M+H]^+$: 396.2; found: 396.2.

Intermediates 71-86

The intermediates shown below in Table 6 were prepared by the method used in preparing Int-70 using appropriate starting materials.

TABLE 6

Intermediates 71-86

| Int. | Structure | Name | Calcd. $(M + H)^+$ m/z | Found $(M + H)^+$ m/z |
|---|---|---|---|---|
| Int-71 | 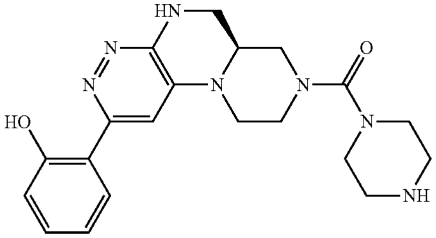 [SMILES: O=C(N1CCNCC1)N1CCN2c3cc(-c4ccccc4O)nnc3NC[C@H]2C1] | (S)-(2-(2-hydroxyphenyl)-5,6,6a,7,9,10-hexahydro-8H-pyrazino[1',2':4,5]pyrazino[2,3-c]pyridazin-8-yl)(piperazin-1-yl)methanone | 396.2 | 396.1 |

TABLE 6-continued

| Int. | Structure | Name | Calcd. (M + H)+ m/z | Found (M + H)+ m/z |
|---|---|---|---|---|
| | Intermediates 71-86 | | | |
| Int-72 | 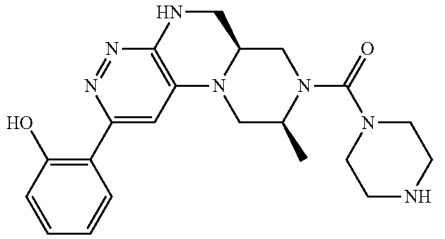 [SMILES: C[C@H]1CN2c3cc(-c4ccccc4O)nnc3NC[C@H]2CN1C(=O)N1CCNCC1] | ((6aS,9S)-2-(2-hydroxyphenyl)-9-methyl-5,6,6a,7,9,10-hexahydro-8H-pyrazino[1',2':4,5]pyrazino[2,3-c]pyridazin-8-yl)(piperazin-1-yl)methanone | 410.2 | 410.1 |
| Int-73 | 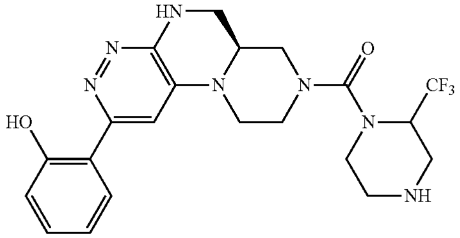 [SMILES: O=C(N1CCN2c3cc(-c4ccccc4O)nnc3NC[C@H]2C1)N1CCNCC1C(F)(F)F] | ((S)-2-(2-hydroxyphenyl)-5,6,6a,7,9,10-hexahydro-8H-pyrazino[1',2':4,5]pyrazino[2,3-c]pyridazin-8-yl)(2-(trifluoromethyl)piperazin-1-yl)methanone | 464.2 | 464.2 |
| Int-74 | 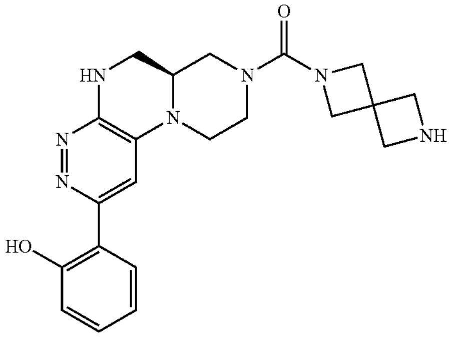 [SMILES: O=C(N1CCN2c3cc(-c4ccccc4O)nnc3NC[C@H]2C1)N1CC2(CNC2)C1] | (S)-(2-(2-hydroxyphenyl)-5,6,6a,7,9,10-hexahydro-8H-pyrazino[1',2':4,5]pyrazino[2,3-c]pyridazin-8-yl)(2,6-diazaspiro[3.3]heptan-2-yl)methanone | 408.2 | 408.1 |
| Int-75 | 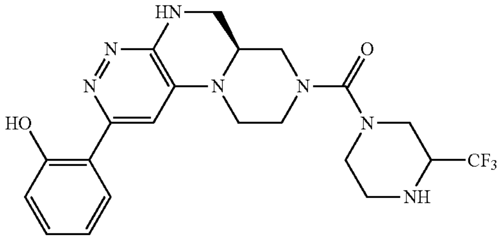 [SMILES: O=C(N1CCNC(C(F)(F)F)C1)N1CCN2c3cc(-c4ccccc4O)nnc3NC[C@H]2C1] | ((S)-2-(2-hydroxyphenyl)-5,6,6a,7,9,10-hexahydro-8H-pyrazino[1',2':4,5]pyrazino[2,3-c]pyridazin-8-yl)(3-(trifluoromethyl)piperazin-1-yl)methanone | 464.2 | 464.1 |
| Int-76 | 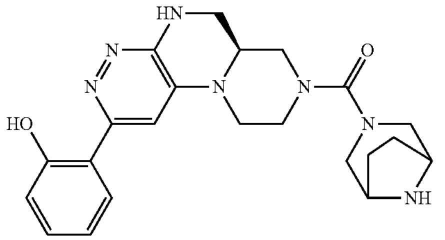 [SMILES: O=C(N1CC2CCC(C1)N2)N1CCN2c3cc(-c4ccccc4O)nnc3NC[C@H]2C1] | (3,8-diazabicyclo[3.2.1]octan-3-yl)((S)-2-(2-hydroxyphenyl)-5,6,6a,7,9,10-hexahydro-8H-pyrazino[1',2':4,5]pyrazino[2,3-c]pyridazin-8-yl)methanone | 422.2 | 422.1 |

TABLE 6-continued

| Intermediates 71-86 | | | | |
|---|---|---|---|---|
| Int. | Structure | Name | Calcd. (M + H)+ m/z | Found (M + H)+ m/z |
| Int-77 | 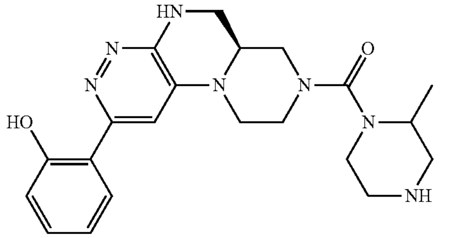 [SMILES: CC1CNCCN1C(=O)N1CCN2c3cc(-c4ccccc4O)nnc3NC[C@H]2C1] | ((S)-2-(2-hydroxyphenyl)-5,6,6a,7,9,10-hexahydro-8H-pyrazino[1',2':4,5]pyrazino[2,3-c]pyridazin-8-yl)(2-methyl-piperazin-1-yl)methanone | 410.2 | 410.1 |
| Int-78 | 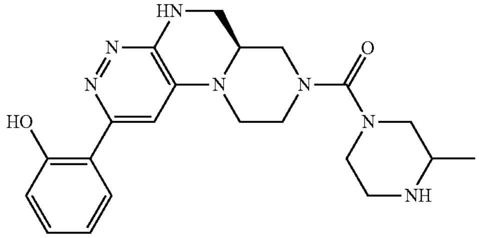 [SMILES: CC1CN(C(=O)N2CCN3c4cc(-c5ccccc5O)nnc4NC[C@H]3C2)CCN1] | ((S)-2-(2-hydroxyphenyl)-5,6,6a,7,9,10-hexahydro-8H-pyrazino[1',2':4,5]pyrazino[2,3-c]pyridazin-8-yl)(3-methyl-piperazin-1-yl)methanone | 410.2 | 410.1 |
| Int-79 | 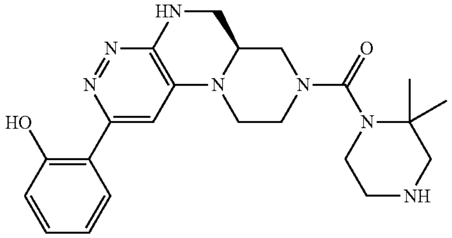 [SMILES: CC1(C)CNCCN1C(=O)N1CCN2c3cc(-c4ccccc4O)nnc3NC[C@H]2C1] | (S)-(2,2-dimethylpiperazin-1-yl)(2-(2-hydroxyphenyl)-5,6,6a,7,9,10-hexahydro-8H-pyrazino[1',2':4,5]pyrazino[2,3-c]pyridazin-8-yl)methanone | 424.2 | 424.1 |
| Int-80 | 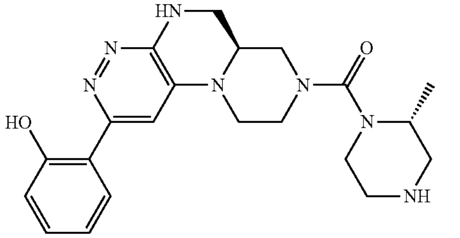 [SMILES: C[C@@H]1CNCCN1C(=O)N1CCN2c3cc(-c4ccccc4O)nnc3NC[C@H]2C1] | ((S)-2-(2-hydroxyphenyl)-5,6,6a,7,9,10-hexahydro-8H-pyrazino[1',2':4,5]pyrazino[2,3-c]pyridazin-8-yl)((R)-2-methyl-piperazin-1-yl)methanone | 410.2 | 410.1 |
| Int-81 | 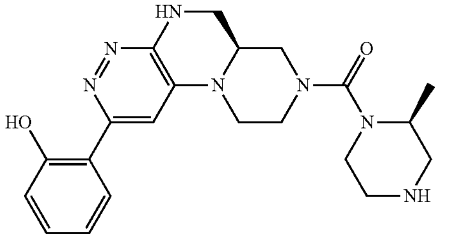 [SMILES: C[C@H]1CNCCN1C(=O)N1CCN2c3cc(-c4ccccc4O)nnc3NC[C@H]2C1] | ((S)-2-(2-hydroxyphenyl)-5,6,6a,7,9,10-hexahydro-8H-pyrazino[1',2':4,5]pyrazino[2,3-c]pyridazin-8-yl)((S)-2-methyl-piperazin-1-yl)methanone | 410.2 | 410.1 |
| Int-82 | 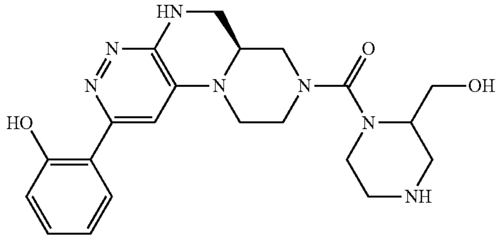 [SMILES: O=C(N1CCN2c3cc(-c4ccccc4O)nnc3NC[C@H]2C1)N1CCNCC1CO] | (2-(hydroxymethyl)piperazin-1-yl)((S)-2-(2-hydroxyphenyl)-5,6,6a,7,9,10-hexahydro-8H-pyrazino[1',2':4,5]pyrazino[2,3-c]pyridazin-8-yl)methanone | 426.2 | 426.1 |

TABLE 6-continued

| Intermediates 71-86 | | | | |
|---|---|---|---|---|
| Int. | Structure | Name | Calcd. (M + H)$^+$ m/z | Found (M + H)$^+$ m/z |
| Int-83 | 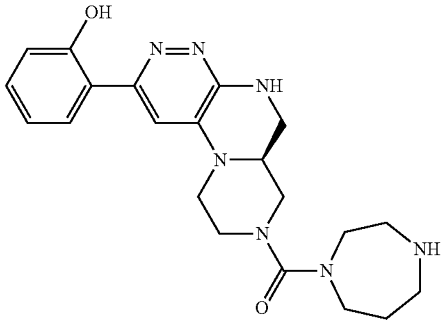 [SMILES: O=C(N1CCCNCC1)N1CCN2c3cc(-c4ccccc4O)nnc3NC[C@H]2C1] | (S)-(1,4-diazepan-1-yl)(2-(2-hydroxyphenyl)-5,6,6a,7,9,10-hexahydro-8H-pyrazino [1',2':4,5]pyrazino[2,3-c] pyridazin-8-yl)methanone | 410.2 | 410.1 |
| Int-84 | 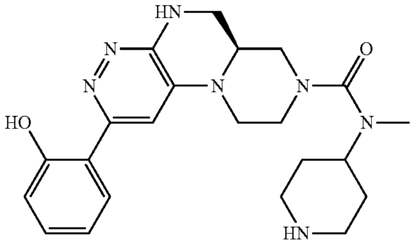 [SMILES: CN(C(=O)N1CCN2c3cc(-c4ccccc4O)nnc3NC[C@H]2C1)C1CCNCC1] | (S)-2-(2-hydroxyphenyl)-N-methyl-N-(piperidin-4-yl)-5,6,6a,7,9,10-hexahydro-8H-pyrazino[1',2':4,5]pyrazino[2,3-c]pyridazine-8-carboxamide | 424.2 | 424.2 |
| Int-85 | 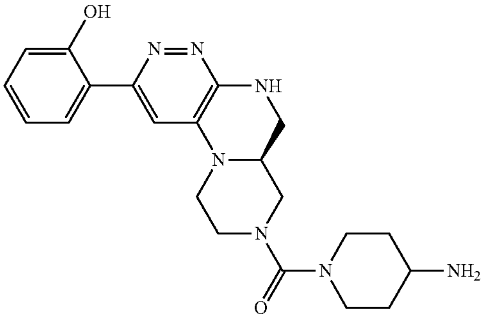 [SMILES: NC1CCN(C(=O)N2CCN3c4cc(-c5ccccc5O)nnc4NC[C@H]3C2)CC1] | (S)-(4-aminopiperidin-1-yl)(2-(2-hydroxyphenyl)-5,6,6a,7,9,10-hexahydro-8H-pyrazino[1',2':4,5]pyrazino[2,3-c]pyridazin-8-yl)methanone | 410.2 | 410.0 |
| Int-86 | 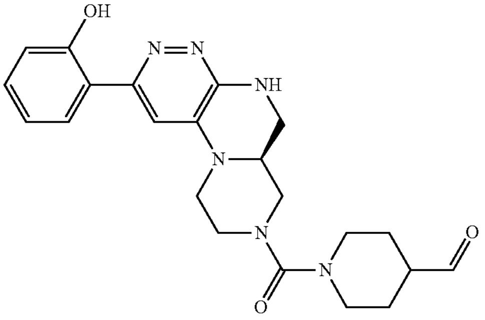 [SMILES: O=CC1CCN(C(=O)N2CCN3c4cc(-c5ccccc5O)nnc4NC[C@H]3C2)CC1] | (S)-1-(2-(2-hydroxyphenyl)-6,6a,7,8,9,10-hexahydro-5H-pyrazino[1',2':4,5]pyrazino[2,3-c]pyridazine-8-carbonyl) piperidine-4-carbaldehyde | 423.2 | 423.1 |

Intermediate 87: (S)-2-(8-(3-bromopropyl)-6,6a,7,8,9,1O-hexahydro-511-pyrazino[1',2':4,5]pyrazino[2,3-c]pyridazin-2-yl)phenol Int-87

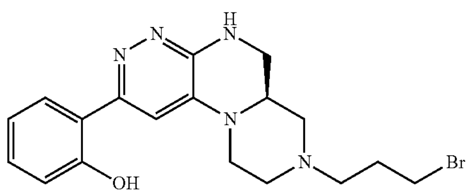

To a stirred solution of (R)-2-(6,6a,7,8,9,10-hexahydro-5H-pyrazino[1',2':4,5]pyrazino [2,3-c]pyridazin-2-yl)phenol (50 mg, 0.18 mmol) and 1,3-dibromopropane (39 mg, 0.19 mmol) in DMF (0.50 mL), was added DIPEA (0.09 mL, 0.53 mmol) at rt. After 16 h, the resulted mixture was purified by prep-LCMS to afford the desired product (13 mg, 0.032 mmol, 18.2% yield). LCMS calculated for $C_{18}H_{23}BrN_5O$ $(M+H)^+$ m/z=404.1; found: 404.0.

Intermediate 88: (S)-2-(8-(2-bromoethyl)-6,6a,7,8,9,10-hexahydro-5H-pyrazino[1',2':4,5]pyrazino[2,3-c]pyridazin-2-yl)phenol Int-88

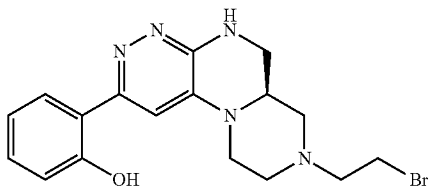

Int-88 was prepared by the procedures described for preparing Int-87 using appropriate starting materials. LCMS m/z calcd $[M+H]^+$: 390.1; found: 390.1.

Intermediate 89: tert-butyl 4-formyl-3,3-dimethylpiperidine-1-carboxylate

Int-89

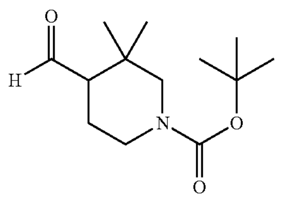

Step 1: tert-butyl 4-(methoxymethylene)-3,3-dimethylpiperidine-1-carboxylate

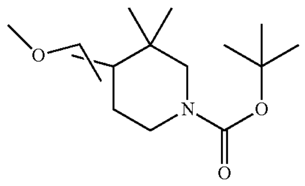

To a stirred solution of (methoxymethyl)-triphenylphosphonium chloride (1.5 g, 4.4 mmol) in THE (10 mL) was added NaHMDS (2 M in THF, 2.2 mL, 4.4 mmol) at 0° C. After 1 h, 3,3-dimethyl-4-oxopiperidine-1-carboxylic acid t-butyl ester (500 mg, 2.2 mmol) in THE (6 mL) was added slowly. The resulted mixture was stirred at 0° C. to 25° C. for additional 3 h. The reaction was diluted with $H_2O$ (20 mL) and extracted with EA (20 mL). The organic layer was concentrated and the residue was purified by silica gel column (PE:EA=5:1) to get the desired product (170 mg, 0.53 mmol, 24.2% yield) as an colorless oil. LCMS calc'd for $C_{14}H_{26}NO_3$ $(M+H)^+$ m/z: 256.2; Found: LCMS [M+H]: 256.3.

Step 2: tert-butyl 4-formyl-3,3-dimethylpiperidine-1-carboxylate

To a stirred solution of tert-butyl (4E)-4-(methoxymethylidene)-3,3-dimethylpiperidine-1-carboxylate (170.0 mg, 0.67 mmol) in DCM (3 mL) and water (1 mL) was added 2,2,2-trichloroacetic acid (653 mg, 4.0 mmol) at 25° C. After 2 h, the mixture was diluted with $H_2O$ (20.0 mL) and extracted with DCM (20.0 mL×3). The combined the organic phases were washed with brine (30.0 mL), dried over $Na_2SO_4$, filtered and concentrated under vacuum to give tert-butyl 4-formyl-3,3-dimethylpiperidine-1-carboxylate (150 mg, 0.55 mmol, 84.0% yield). LCMS calc'd for $C_{13}H_{24}NO_3$: 242.2; Found: LCMS [M+H]: 242.3.

Intermediate 89: 2-(6a-methyl-6,6a,7,8,9,10-hexahydro-5H-pyrazino[1',2':4,5]pyrazino[2,3-c]pyridazin-2-yl)phenol Int-90

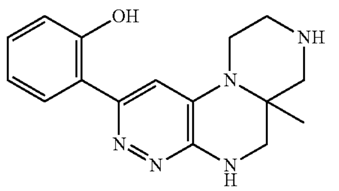

Step 1: 1,4-di-tert-butyl 2-methyl piperazine-1,2,4-tricarboxylate

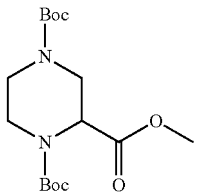 [SMILES: COC(=O)C1CN(C(=O)OC(C)(C)C)CCN1C(=O)OC(C)(C)C]

To a solution of 1,4-bis(tert-butoxycarbonyl)piperazine-2-carboxylic acid (5.0 g, 15.1 mmol) and potassium carbonate (4.18 g, 30.3 mmol) in acetone (50 mL) was added iodomethane (2.17 g, 15.3 mmol) at rt. The mixture was stirred at rt for 16 h. The reaction mixture was filtered and the filtrate was concentrated in vacuum. The residue was dissolved in EA (100 mL) and washed with brine (100 mL×2). The organic layer was concentrated in vacuum to give 1,4-di-tert-butyl 2-methyl piperazine-1,2,4-tricarboxylate (5.2 g, 15.1 mmol, 99.7% yield) as a white solid. LCMS calc'd for $C_{16}H_{29}N_2O_6[M+H]^+$: 345.2; Found: 345.2.

Step 2: 1,4-di-tert-butyl 2-methyl 2-methylpiperazine-1,2,4-tricarboxylate

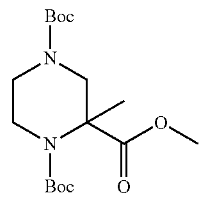 [SMILES: COC(=O)C1(C)CN(C(=O)OC(C)(C)C)CCN1C(=O)OC(C)(C)C]

To a solution of 1,4-di-tert-butyl 2-methyl piperazine-1,2,4-tricarboxylate (5.2 g, 15.1 mmol) in THE (100 mL) was added LiHMDS (2.8 g, 16.6 mmol) at −78° C. The mixture was stirred at −78° C. for 2 h then iodomethane (6.4 g, 45.3 mmol) was added at −78° C. The resulted mixture was stirred at rt. for 16 h. The reaction was quenched with saturated aqueous $NH_4Cl$ (100 mL) at 0° C., diluted with EA (200 mL), and washed with water (2×100 mL) then brine (50 mL). The organic layer was dried ($MgSO_4$), filtered, and the filtrate was concentrated to dryness. The crude was purified by silica gel column chromatography (100-200 mesh size), eluted with PE:EA=3:1 to 1:1 to give 1,4-di-tert-butyl 2-methyl 2-methylpiperazine-1,2,4-tricarboxylate (5.0 g, 13.9 mmol, 91.4% yield) as a yellow oil. LCMS calc'd for $C_{17}H_{31}N_2O_6$ $[M+H]^+$: 359.2; Found: 359.3.

Step 3: 1,4-bis(tert-butoxycarbonyl)-2-methylpiperazine-2-carboxylic acid

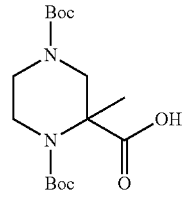 [SMILES: CC(C)(C)OC(=O)N1CCN(C(=O)OC(C)(C)C)C(C)(C(=O)O)C1]

To a solution of 1,4-di-tert-butyl 2-methyl 2-methylpiperazine-1,2,4-tricarboxylate (5.0 g, 13.9 mmol) in THE (12 mL)/methanol (2 mL)/water (2 mL) was added LiOH (713 mg, 17.0 mmol). The mixture was stirred at 50° C. for 16 h. TLC showed the reaction was complete. The reaction mixture was washed with PE (100 mL×2). The pH of the aqueous layer was adjusted to 3-4 with 1 N HCl, then extracted with EA (100 mL×3). The organic layers were combined, washed with brine (50 mL), and concentrated under reduced pressure to give the product 1,4-bis(tert-butoxycarbonyl)-2-methylpiperazine-2-carboxylic acid (4.5 g, 13.1 mmol, 93.7% yield) as a white solid. LCMS calc'd for $C_{16}H_{29}N_2O_6[M+H]^+$: 345.2; Found: 345.2.

Step 4: tert-butyl 2-chloro-6a-methyl-6-oxo-5,6,6a,7,9,10-hexahydro-8H-pyrazino[1',2':4,5]pyrazino[2,3-c]pyridazine-8-carboxylate

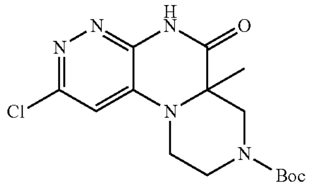 [SMILES: CC(C)(C)OC(=O)N1CCN2c3cc(Cl)nnc3NC(=O)C2(C)C1]

To a solution of 1,4-bis(tert-butoxycarbonyl)-2-methylpiperazine-2-carboxylic acid (4.2 g, 12.2 mmol) in DCM (25 mL) was added DMF (1 mL) and oxalyl chloride (4.6 g, 36.6 mmol). The mixture was stirred at rt for 30 min. The volatiles were removed under reduced pressure and DMF (25 mL), DIEA (10.1 mL, 61.0 mmol) and 5-bromo-6-chloropyridazin-3-amine (5.1 g, 24.4 mmol) were added sequentially. The resulted mixture was stirred at 120° C. for 16 h. The reaction mixture was diluted with EA (100 mL) and washed with brine (30 mL×2). The organic layer was concentrated in vacuum and purified by prep-TLC, eluting with PE:EA=1:1 to give tert-butyl 2-chloro-6a-methyl-6-oxo-5,6,6a,7,9,10-hexahydro-8H-pyrazino[1',2':4,5]pyrazino[2,3-c]pyridazine-8-carboxylate (1.5 g, 4.2 mmol, 34.7% yield) as a yellow solid. LCMS calc'd for $C_{15}H_{21}ClN_5O_3[M+H]^+$: 354.1; Found: 354.1.

Step 5: tert-butyl 2-chloro-6a-methyl-5,6,6a, 7,9,10-hexahydro-8H-pyrazino[1',2':4,5]pyrazino [2,3-c]pyridazine-8-carboxylate

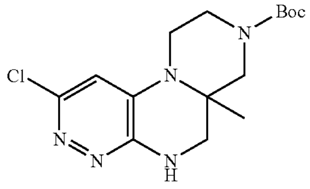 [SMILES: CC(C)(C)OC(=O)N1CCN2c3cc(Cl)nnc3NCC2(C)C1]

To a solution of tert-butyl 2-chloro-6a-methyl-6-oxo-5,6,6a,7,9,10-hexahydro-8H-pyrazino[1',2':4,5]pyrazino[2,3-c]pyridazine-8-carboxylate (87.3 mg, 0.25 mmol) in THE (8 mL) was added $BH_3$ in THE (1 M, 0.74 mL, 0.74 mmol). The resulted mixture was stirred at 80° C. for 16 h. The reaction was diluted with MeOH (20 mL) and was stirred at 80° C. for additional 16 h. The volatiles were removed under reduce pressure and the residue was purified by prep-TLC (DCM:MeOH=10:1) to give tert-butyl 2-chloro-6a-methyl-5,6,6a,7,9,10-hexahydro-8H-pyrazino[1',2':4,5]pyrazino[2,3-c]pyridazine-8-carboxylate (40.0 mg, 0.12 mmol, 47.7% yield) as a yellow solid. LCMS calc'd for $C_{15}H_{23}ClN_5O_2$ $[M+H]^+$: 340.2; Found: 340.1. Step 6: tert-butyl 2-(2-hydroxyphenyl)-6a-methyl-5,6,6a, 7,9,10-hexahydro-8H-pyrazino [1',2':4,5]pyrazino[2,3-c]pyridazine-8-carboxylate

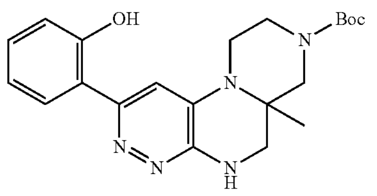 [SMILES: CC(C)(C)OC(=O)N1CCN2c3cc(-c4ccccc4O)nnc3NCC2(C)C1]

To a solution of 2-hydroxyphenylboronic acid (731 mg, 5.3 mmol), potassium carbonate (1.1 g, 7.95 mmol) and tert-butyl 2-chloro-6a-methyl-5,6,6a,7,9,10-hexahydro-8H-pyrazino[1',2':4,5]pyrazino[2,3-c]pyridazine-8-carboxylate (900 mg, 2.65 mmol) in 1,4-dioxane (10 mL) and water (1 mL) was added $Pd(dppf)_2Cl_2$ (216 mg, 0.26 mmol). The mixture was stirred at 105° C. for 16 h under $N_2$. The reaction was diluted with EA (200 mL) and washed with brine (100 mL×2). The organic layer was concentrated and the residue was purified by silica gel column chromatography (100-200 mesh size), eluting with PE:EA=3:1 to 1:1 to give tert-butyl 2-(2-hydroxyphenyl)-6a-methyl-5,6,6a,7,9,10-hexahydro-8H-pyrazino[1',2':4,5]pyrazino[2,3-c]pyridazine-8-carboxylate (1.0 g, 2.51 mmol, 95.0% yield) as a yellow solid. LCMS calc'd for $C_{21}H_{28}N_5O_3$ $[M+H]^+$: 398.2; Found: 398.2.

Step 7:_2-(6a-methyl-6,6a, 7,8,9,10-hexahydro-5H-pyrazino[1',2':4,5]pyrazino[2,3-c]pyridazin-2-yl) phenol To a solution of tert-butyl 2-(2-hydroxyphenyl)-6a-methyl-5,6,6a,7,9,10-hexahydro-8H-pyrazino[1',2':4,5]pyrazino[2,3-c]pyridazine-8-carboxylate (60.0 mg, 0.15 mmol) in DCM (1 mL) was added TFA (1.2 mL). The mixture was stirred at 25° C. for 2 h. The volatiles were removed under reduced pressure and the residue was purified by prep-HPLC, eluting with $CH_3CN$ in $H_2O$ (0.1% HCl) from 5.0% to 95% to get 2-(6a-methyl-6,6a,7,8,9,10-hexahydro-5H-pyrazino[1',2':4,5]pyrazino[2,3-c]pyridazin-2-yl) phenol as its HCl salt (45.0 mg, 0.13 mmol, 87.9% yield). $^1H$ NMR (400 MHz, CD3OD) δ 7.54-7.52 (m, 1H), 7.45-7.41 (m, 1H), 7.26 (s, 1H), 7.06-7.01 (m, 2H), 4.26-4.22 (m, 1H), 3.65-3.44 (m, 5H), 3.24-3.12 (m, 2H), 1.55 (m, 3H). LCMS calc'd for $C_{16}H_{20}N_5O$ $[M+H]^+$: 298.2; Found: 298.2.

Intermediate 91: 2-((6aR,9S)-9-methyl-6,6a,7,8,9,10-hexahydro-5H-pyrazino[1',2':4,5]pyrazino[2,3-c]pyridazin-2-yl)phenol

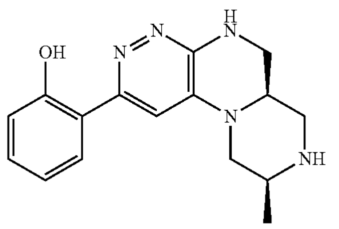 [SMILES: C[C@H]1CN2c3cc(-c4ccccc4O)nnc3NC[C@H]2CN1]

Step 1: methyl O-benzyl-N-(tert-butoxycarbonyl)-L-seryl-L-alaninate

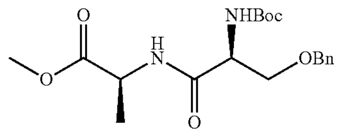 [SMILES: COC(=O)[C@H](C)NC(=O)[C@H](COCc1ccccc1)NC(=O)OC(C)(C)C]

To a stirred suspension solution of O-benzyl-N-(tert-butoxycarbonyl)-L-serine (20.0 g, 67.7 mmol) and 1-hydroxybenzotriazole hydrate (11.0 g, 81.3 mmol) in $CH_2C_2$ (451 mL) was added DIPEA (14.2 mL, 81.3 mmol) at 0° C. The reaction mixture was added EDCI (15.6 g, 81.3 mmol) and stirred at 0° C. for 15 minutes. Then, the reaction mixture was added the mixture solution of L-serine methyl ester hydrochloride (11.3 g, 81.3 mmol) in DIPEA (14.2 mL, 81.3 mmol) and DMF (30 mL) dropwise at 0° C. over 5 minutes. The reaction was warmed up to room temperature and stirred for 3 hours. The reaction was added water (500 mL) and extracted with DCM (300 mL×3). The organic phases were dried over $Na_2SO_4$, filtered and concentrated. The residue was purified by flash silica gel column chromatography (ethyl acetate and heptane, 0% to 100%) to give methyl O-benzyl-N-(tert-butoxycarbonyl)-L-seryl-L-alaninate (26.1 g, yield: 99%). LCMS calculated for $C_{19}H_{29}N_2O_6$ $(M+H)^+$: m/z=381.2; found: 381.0.

Step 2: methyl O-benzyl-L-seryl-L-alaninate

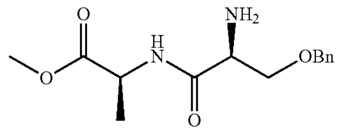 [SMILES: COC(=O)[C@H](C)NC(=O)[C@@H](N)COCc1ccccc1]

To a solution of methyl O-benzyl-N-(tert-butoxycarbonyl)-L-seryl-L-alaninate (26.1 g, 68.6 mmol) in DCM (260 mL) was added TFA (51.4 mL, 672.3 mmol) at room temperature. The reaction was stirred at room temperature for 3 hours. The reaction mixture was basified to between pH 7 and pH 8 via saturated aqueous $NaHCO_3$ solution, extracted with DCM (100 mL×3), and washed with brine (100 mL×1). The combined organic phases were dried over $Na_2SO_4$, filtered and concentrated. The residue was directly used for the next step without purification (16.9 g crude). LCMS calculated for $C_{14}H_{21}N_2O_4$ $(M+H)^+$: m/z=281.1; found: 281.0.

Step 3: (3S,6S)-3-((benzyloxy)methyl)-6-methylpiperazine-2,5-dione

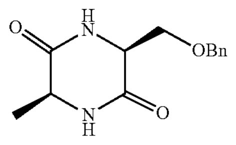 [SMILES: C[C@@H]1NC(=O)[C@H](COCc2ccccc2)NC1=O]

To a solution of methyl O-benzyl-L-seryl-L-alaninate (16.9 g, 60.3 mmol) in dioxane (169 mL) was stirred at 100°

C. for overnight. The reaction was cooled to room temperature (white solid was precipitated out). The white precipitate was filtered, collected, and washed with cold MTBE (100 mL) to give (3S,6S)-3-((benzyloxy)methyl)-6-methylpiperazine-2,5-dione (11 g, yield: 73%).

Step 4: (2R,5S)-2-((benzyloxy)methyl)-5-methylpiperazine

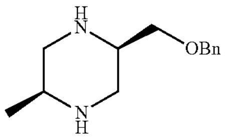 [SMILES: C[C@H]1CN[C@@H](COCc2ccccc2)CN1]

To a solution of (3S,6S)-3-((benzyloxy)methyl)-6-methylpiperazine-2,5-dione (9.0 g, 36.3 mmol) in THE (201 mL) was added borane dimethyl sulfide complex (27.5 mL, 290 mmol) under ice-water bath. The reaction was stirred at 60° C. for overnight. The reaction was cooled under ice-water bath, and slowly added MeOH (200 mL). The reaction mixture was warmed up to room temperature, added 1 N HCl aqueous solution to pH 3, and then stirred at 50° C. for 3 hours. The reaction mixture was basified to pH 12 with 1 N NaOH aqueous solution and extracted with $CHCl_3$ (200 mL×3). The combined organic phases were dried over $Na_2SO_4$, filtered and concentrated. The residue was directly used for the next step without purification (9.8 g crude). LCMS calculated for $C_{13}H_{21}N_2O$ $(M+H)^+$: m/z=221.2; found: 221.2.

Step 5: ((2R,5S)-5-methylpiperazin-2-yl)methanol

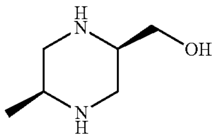

To a solution of (2R,5S)-2-((benzyloxy)methyl)-5-methylpiperazine (0.29 g, 1.3 mmol) in DCM (13 mL) was added 1 M $BCl_3$ in DCM solution (5.2 mL, 5.2 mmol) at −78° C. The reaction was slowly warmed up to room temperature and stirred for overnight. The reaction was cooled under ice-water bath, and slowly added MeOH (10 mL). The reaction mixture was concentrated to dryness. The residue was directly used for the next step without purification (0.23 g crude). LCMS calculated for $C_6H_{15}N_2O$ $(M+H)^+$: m/z=131.1; found: 131.0.

Step 6: di-tert-butyl (2R,5S)-2-(hydroxymethyl)-5-methylpiperazine-1,4-dicarboxylate

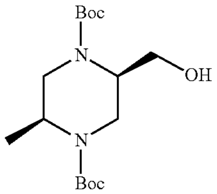 [SMILES: C[C@H]1CN(C(=O)OC(C)(C)C)[C@@H](CO)CN1C(=O)OC(C)(C)C]

To a solution of ((2R,5S)-5-methylpiperazin-2-yl)methanol (9.0 g, 69.1 mmol) in DCM (376 mL) was added TEA (120.0 mL, 864.0 mmol), and di-tert-butyl dicarbonate (45.3 g, 207.0 mmol) at 0° C. The reaction was stirred at room temperature for overnight, and then concentrated to dryness. The residue was directly used for the next step without purification (24.0 g crude). LCMS calculated for $C_{16}H_{31}N_2O_5$ $(M+H)^+$: m/z=331.2; found: 331.0.

Step 7: tert-butyl (2S,5R)-5-(hydroxymethyl)-2-methylpiperazine-1-carboxylate

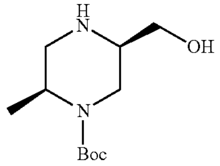 [SMILES: C[C@H]1CN[C@@H](CO)CN1C(=O)OC(C)(C)C]

To a solution of di-tert-butyl (2R,5S)-2-(hydroxymethyl)-5-methylpiperazine-1,4-dicarboxylate (14.0 g, 42.4 mmol) in EtOH (78.5 mL) was added a solution of NaOH (8.5 g, 211.9 mmol) in water (78.5 mL). The reaction mixture was stirred at 80° C. for overnight. The reaction was cooled to room temperature, added 1 N HCl aqueous solution to pH 9, and extracted with $CHCl_3$ (100 mL×3). The combined organic phases were dried over $Na_2SO_4$, filtered and concentrated. The residue was purified by flash silica gel column chromatography (DCM and MeOH with 0.1% TEA, 0% to 10%) to give tert-butyl (2S,5R)-5-(hydroxymethyl)-2-methylpiperazine-1-carboxylate (2.7 g, yield: 28%). LCMS calculated for $C_{11}H_{23}N_2O_3$ $(M+H)^+$: m/z=231.2; found: 231.1.

Step 8: tert-Butyl (2S,5R)-4-(3,6-dichloropyridazin-4-yl)-5-(hydroxymethyl)-2-methylpiperazine-1-carboxylate

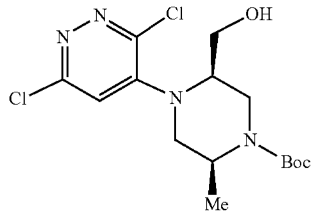 [SMILES: C[C@H]1CN(c2cc(Cl)nnc2Cl)[C@@H](CO)CN1C(=O)OC(C)(C)C]

To a solution of 3,4,6-trichloropyridazine (406 mg, 2.21 mmol) in DMF (1.75 mL) was added DIPEA (0.59 mL, 3.39 mmol) and tert-butyl (2S,5R)-5-(hydroxymethyl)-2-methylpiperazine-1-carboxylate (300 mg, 1.3 mmol) in DMF (1.75 mL) at ambient temperature. The reaction was stirred at 80° C. for overnight. The reaction was cooled to ambient temperature, diluted with water (15 mL), and extracted with EtOAc (15 mL×3). The combined organic phase was collected and dried over $Na_2SO_4$, filtered and evaporated under reduced pressure. The crude material was purified by flash column chromatography eluted with a mixture of EtOAc and heptanes (10~100%) to give the desired product, tert-Butyl (2S,5R)-4-(3,6-dichloropyridazin-4-yl)-5-(hydroxymethyl)-2-methylpiperazine-1-carboxylate (408 mg), as yellow viscous oil. LCMS calc. for $C_{15}H_{23}C_{12}N_4O_3$ $[M+H]^+$: m/z=377.1; Found: 377.0.

Step 9: tert-butyl (2S,5R)-5-(azidomethyl)-4-(3,6-dichloropyridazin-4-yl)-2-methylpiperazine-1-carboxylate

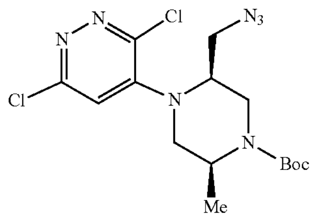 [SMILES: C[C@H]1CN(c2cc(Cl)nnc2Cl)[C@@H](CN=[N+]=[N-])CN1C(=O)OC(C)(C)C]

To a solution of tert-butyl (2S,5R)-4-(3,6-dichloropyridazin-4-yl)-5-(hydroxymethyl)-2-methylpiperazine-1-carboxylate (408 mg, 1.08 mmol) and triphenylphosphine (397 mg, 1.51 mmol) in THE (7.8 mL) was added DIAD (0.298 mL, 1.51 mmol) slowly at 0° C. The reaction mixture was stirred at 0° C. for 10 minutes. Then DPPA (0.328 mL, 1.51 mmol) was added slowly. The reaction mixture was stirred at ambient temperature for overnight, when LC-MS indicated the formation of the product and HPLC analysis confirmed the disappearance of the starting material. The solvent THE was evaporated and added sat. $NaHCO_3$ (15 mL). The mixture was extracted with EtOAc (15 mL×3). The combined organic layers were collected and dried over $Na_2SO_4$. The crude product was purified by flash column chromatography eluted with a mixture of EtOAc and heptanes (10~50%) to give the desired product, tert-butyl (2S,5R)-5-(azidomethyl)-4-(3,6-dichloropyridazin-4-yl)-2-methylpiperazine-1-carboxylate (608 mg), as yellow oil. LCMS calc. for $C_{15}H_{22}C_{12}N_7O_2$ $[M+H]^+$: m/z=402.1; Found: 401.8.

Step 10: tert-butyl (6aS,9S)-2-chloro-9-methyl-5,6,6a, 7,9,10-hexahydro-8H-pyrazino[1',2':4,5]pyrazino[2,3-c]pyridazine-8-carboxylate

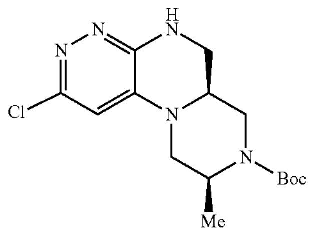 [SMILES: C[C@H]1CN2c3cc(Cl)nnc3NC[C@H]2CN1C(=O)OC(C)(C)C]

The solution of triphenylphosphine (5.5 g, 20.8 mmol) and tert-butyl (2S,5R)-5-(azidomethyl)-4-(3,6-dichloropyridazin-4-yl)-2-methylpiperazine-1-carboxylate (7 g, 17.3 mmol) in THE (45 mL) was heated at 60° C. for 3 h. Water (4.5 mL) and DIPEA (9 mL, 51.9 mmol) was charged to the reaction mixture. The reaction was stirred at 60° C. for overnight. The reaction was cooled to ambient temperature and solvent was removed by evaporation under reduced pressure. The residual oil was diluted with water (40 mL) and extracted with EtOAc (50 mL×3). The combined organic layers were dried over $Na_2SO_4$, filtered, and evaporated in vacuo. The crude residue was purified by flash column chromatography eluted with a mixture of EtOAc and heptanes (10~100%) to give the desired product, tert-butyl (6aS,9S)-2-chloro-9-methyl-5,6,6a,7,9,10-hexahydro-8H-pyrazino[1',2':4,5]pyrazino[2,3-c]pyridazine-8-carboxylate (1.5 g), as yellow solid. LCMS calc. for $C_{15}H_{23}ClN_5O_2[M+H]^+$: m/z=340.2; Found: 340.0.

Step 11: di-tert-butyl (6aR,9S)-2-chloro-9-methyl-6a, 7,9,10-tetrahydro-5H-pyrazino[1',2':4,5]pyrazino[2,3-c]pyridazine-5,8(6H)-dicarboxylate

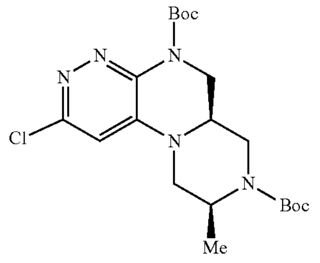 [SMILES: C[C@H]1CN2c3cc(Cl)nnc3N(C(=O)OC(C)(C)C)C[C@H]2CN1C(=O)OC(C)(C)C]

The solution of tert-butyl (6aS,9S)-2-chloro-9-methyl-5,6,6a,7,9,10-hexahydro-8H-pyrazino[1',2':4,5]pyrazino[2,3-c]pyridazine-8-carboxylate (1.5 g, 4.41 mmol) in DCM (24 mL) was added TEA (1.23 mL, 8.83 mmol), and Boc anhydride (1.35 g, 6.18 mmol) at 0° C. The reaction was stirred at ambient temperature overnight. The starting material was not completely consumed and DMAP (54 mg, 0.44 mmol) and extra Boc anhydride (0.675 g, 0.70 equiv.) were added. The reaction was further stirred at ambient temperature 3 h, when HPLC analysis indicated the disappearance of the starting material. The reaction was added $NH_4Cl$ (30 mL), extracted with DCM (30 mL×3), dried over $Na_2SO_4$, filtered, and evaporated under reduced pressure. The crude material was purified by flash column chromatography eluted with a mixture of EtOAc and heptanes (10~50%) to give the desired product, di-tert-butyl (6aR,9S)-2-chloro-9-methyl-6a,7,9,10-tetrahydro-5H-pyrazino[1',2':4,5]pyrazino[2,3-c]pyridazine-5,8(6H)-dicarboxylate (1.1 g), as white solid. LCMS calc. for $C_{24}H_{31}ClN_5O_4[M+H]^+$: m/z=440.2; Found: 440.1.

Step 12: di-tert-butyl (6aR,9S)-2-(2-hydroxyphenyl)-9-methyl-6a, 7,9,10-tetrahydro-5H-pyrazino[1',2':4,5]pyrazino[2,3-c]pyridazine-5,8(6H)-dicarboxylate

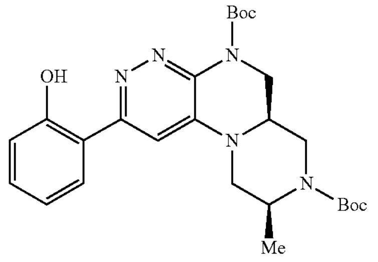 [SMILES: C[C@H]1CN2c3cc(-c4ccccc4O)nnc3N(C(=O)OC(C)(C)C)C[C@H]2CN1C(=O)OC(C)(C)C]

The mixture of di-tert-butyl (6aR,9S)-2-chloro-9-methyl-6a,7,9,10-tetrahydro-5H-pyrazino[1',2':4,5]pyrazino[2,3-c]pyridazine-5,8(6H)-dicarboxylate (1.1 g, 2.5 mmol), 2-hydroxyphenylboronic acid (0.345 g, 2.5 mmol), $K_3PO_4$ (1.33 g, 6.25 mmol), and Xphos Pd G2 (79 mg, 0.1 mmol) in 1,4-dioxane (39 mL) and water (3.8 mL) was stirred at 60°

C. for overnight. The reaction was cooled to ambient and extra 2-hydroxyphenylboronic acid (0.207 g, 1.5 mmol), $K_3PO_4$ (0.319 g, 1.5 mmol) were added. The reaction was stirred at 60° C. for another overnight. The solvent was evaporated, and the crude was diluted with water (60 mL) and extracted with DCM (60 mL×3). The organic phase was dried over $Na_2SO_4$, concentrated and purified by flash column chromatography eluted with a mixture of EtOAc and heptanes (10~50%) to give the desired product, di-tert-butyl (6aR,9S)-2-(2-hydroxyphenyl)-9-methyl-6a,7,9,10-tetra-hydro-5H-pyrazino[1',2':4,5]pyrazino[2,3-c]pyridazine-5,8 (6H)-dicarboxylate (1.07 g), as white solid. LCMS calc. for $C_{26}H_{36}N_5O_5$ $[M+H]^+$: m/z=498.3; Found: 498.4.

Step 13: 2-((6aR,9S)-9-methyl-6,6a, 7,8,9,10-hexa-hydro-5H-pyrazino[1',2':4,5]pyrazino[2,3-c] pyridazin-2-yl)phenol 2 M HCl in i-PrOAc (21 mL) was added to di-tert-butyl (6aR,9S)-2-(2-hydroxyphenyl)-9-methyl-6a,7,9,10-tetra-hydro-5H-pyrazino[1',2':4,5]pyrazino[2,3-c]pyridazine-5,8 (6H)-dicarboxylate (1.07 g, 2.15 mmol). The reaction was stirred at ambient temperature overnight. The starting material was dissolved initially and precipitated out after 5 min. The solid was filtered off, washed with EtOAc and heptanes in small portions, dried under air-flow to give the desired product, 2-((6aR,9S)-9-methyl-6,6a,7,8,9,10-hexahydro-5H-pyrazino[1',2':4,5]pyrazino[2,3-c]pyridazin-2-yl)phenol (626 mg), as white solid. LCMS calc. for $C_{16}H_{20}N_5O$ $[M+H]^+$: m/z=298.2; Found: 298.0. $^1H$ NMR (300 MHz, $CDCl_3$) δ 7.55 (d, J=9.0 Hz, 1H), 7.44 (t, J=6.0 Hz, 1H), 7.30 (s, 1H), 7.04 (t, J=6.0, 2H), 4.25 (dd, J=15.0, 3.0, 1H), 4.10-4.03 (m, 2H), 3.74 (dd, J=12.0, 6.0, 2H), 3.55-3.37 (m, 3H), 1.48 (d, J=6.0, 3H).

Intermediate 92: 2-(9-ethyl-6,6a,7,8,9,10-hexa-hydro-5H-pyrazino[1',2':4,5]pyrazino[2,3-c] pyridazin-2-yl)phenol Int-92

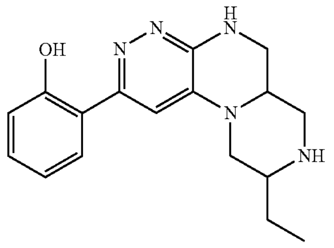

The title compound was prepared using procedure analogous to those described for Intermediate 91, using appropriate starting materials. LCMS m/z calcd for for $C_{17}H_{22}N_5O$ $[M+H]^+$: m/z=312.2; Found: 312.1.

Intermediate 93: tert-butyl 7-formyl-3-azabicyclo [4.1.0]heptane-3-carboxylate

Int-93

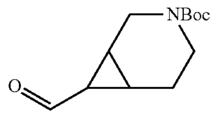

Step 1: tert-butyl 7-(hydroxymethyl)-3-azabicyclo [4.1.0]heptane-3-carboxylate

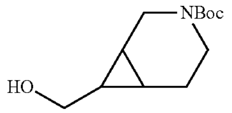 [SMILES: CC(C)(C)OC(=O)N1CCC2C(CO)C2C1]

To a stirring solution of 3-(tert-butyl) 7-ethyl 3-azabicyclo [4.1.0]heptane-3,7-dicarboxylate (136 mg, 0.51 mmol) in THE (5 mL) at 0° C. was added lithium aluminum hydride (1 M, 0.51 mL, 0.51 mmol). After 10 min, the reaction was allowed to warm to room temperature and stirring was continued for 1.5 h. The reaction was cooled back to 0° C. then additional lithium aluminum hydride (1 M, 0.15 mL, 0.15 mmol) was added dropwise. After 5 min, the reaction was allowed to warm to room temperature and stir for an additional 30 min. The reaction was quenched with saturated. aq $Na_2SO_4$ at 0° C. then allowed to warm to room temperature. The mixture was filtered and the filtrate was extracted with MTBE (2×). The combined organic layers were washed with brine (1×), dried with $MgSO_4$, filtered then concentrated to afford tert-butyl 7-(hydroxymethyl)-3-azabicyclo[4.1.0]heptane-3-carboxylate (80 mg, 0.35 mmol, 70%) which was used directly without further purification. LCMS calcd. for $C_8H_{14}NO_3^+[M-tBu+2H]^+$ m/z=172.1; found: 172.0.

Step 2: tert-butyl 7-formyl-3-azabicyclo[4.1.0]heptane-3-carboxylate

To tert-butyl 7-(hydroxymethyl)-3-azabicyclo[4.1.0]heptane-3-carboxylate (40 mg, 0.18 mmol) in DCM (1.8 mL) was added Dess-Martin Periodinane (187 mg, 0.44 mmol) at room temperature. The reaction was stirred for 30 min then quenched with saturated aq $Na_2CO_3$ (2 mL). The mixture was diluted with water and extracted with DCM (2×). The combined DCM layers were washed with brine (1×), dried with $MgSO_4$, filtered and concentrated to afford tert-butyl 7-formyl-3-azabicyclo[4.1.0]heptane-3-carboxylate (assumed quantitative yield of 40 mg) which was used directly without further purification. LCMS calcd. for $C_8H_{12}NO_3^+$ $[M-tBu+2H]^+$ m/z=170.1; found: 169.9.

Intermediate 94: Piperidin-4-yl (S)-2-(2-hydroxy-phenyl)-5,6,6a,7,9,10-hexahydro-8H-pyrazino[1',2':4,5]pyrazino[2,3-c]pyridazine-8-carboxylate Int-94

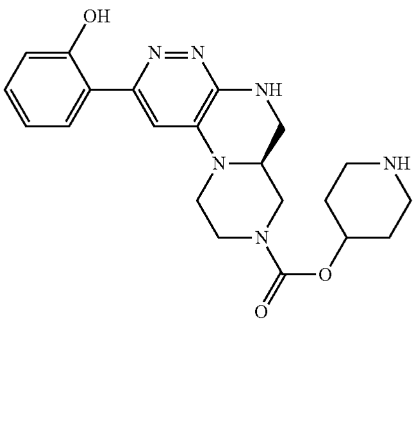

Step 1: 1-(tert-butoxycarbonyl)piperidin-4-yl (S)-2-(2-hydroxyphenyl)-5,6,6a, 7,9,10-hexahydro-8H-pyrazino[1',2':4,5]pyrazino[2,3-c]pyridazine-8-carboxylate

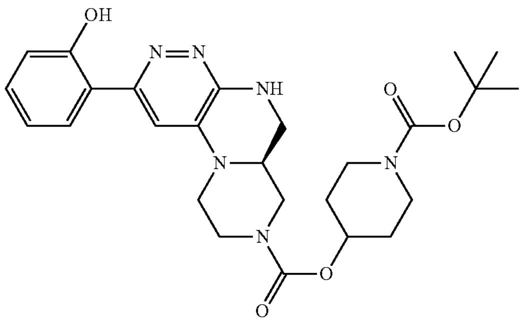 [SMILES: CC(C)(C)OC(=O)N1CCC(OC(=O)N2CCN3c4cc(-c5ccccc5O)nnc4NC[C@H]3C2)CC1]

To a 20 mL vial containing tert-butyl 4-hydroxypiperidine-1-carboxylate (69.6 mg, 0.35 mmol) and 1,1'-carbonyldiimidazole (90.7 mg, 0.56 mmol) in DMF (1.2 mL) was added N,N-diisopropylethylamine (0.2 mL, 1.15 mmol) and the reaction mixture was stirred at room temperature. After 1.5 hours, the reaction mixture was added dropwise to a stirring solution of (R)-2-(6,6a,7,8,9,10-hexahydro-5H-pyrazino[1',2':4,5]pyrazino[2,3-c]pyridazin-2-yl)phenol (104.0 mg, 0.29 mmol) in DMF (0.8 mL) and the reaction was stirred at 80° C. for 1.5 hours. The reaction mixture was then cooled to room temperature and stored overnight in the freezer. The reaction mixture was then warmed to room temperature, diluted in 15 mL MeOH, filtered through a syringe filter, and purified on the prep-LCMS (CSH-C18, 23.2-43.2% ACN/water with 0.1% TFA, 5 min) to yield the desired product as a powder. Assumed quantitative yield for next step.

Step 2: piperidin-4-yl (S)-2-(2-hydroxyphenyl)-5,6,6a, 7,9,10-hexahydro-8H-pyrazino[1',2':4,5]pyrazino[2,3-c]pyridazine-8-carboxylate To a 20 mL vial containing 1-(tert-butoxycarbonyl)piperidin-4-yl (S)-2-(2-hydroxyphenyl)-5,6,6a,7,9,10-hexahydro-8H-pyrazino[1',2':4,5]pyrazino[2,3-c]pyridazine-8-carboxylate in 1,4-dioxane (2.75 mL) was added HCl in 1,4-dioxane (4 M, 2.74 mL, 10.95 mmol). The reaction mixture was stirred at room temperature for 1 hour, then directly condensed under reduced pressure to yield the HCl salt of piperidin-4-yl (S)-2-(2-hydroxyphenyl)-5,6,6a,7,9,10-hexahydro-8H-pyrazino[1',2':4,5]pyrazino[2,3-c]pyridazine-8-carboxylate (50.6 mg, 0.08 mmol) as a beige powder. LCMS calcd for $C_{21}H_{27}N_6O_3$ $[M+H]^+$ m/z=411.2; found: 411.1.+.

Intermediate 95: (S)-2-(2-hydroxyphenyl)-N-(piperidin-4-yl)-5,6,6a,7,9,10-hexahydro-8H-pyrazino[1',2':4,5]pyrazino[2,3-c]pyridazine-8-carboxamide Int-95

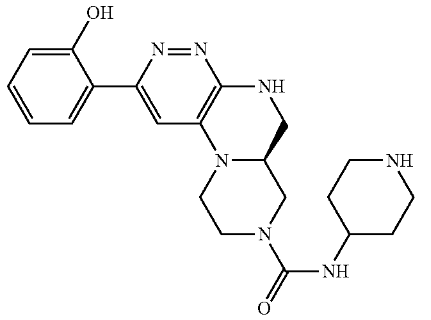

The title compound was prepared as a HCl salt using a procedure analogous to that used for Intermediate 94 using appropriate starting materials. LCMS calcd for $C_{21}H_{28}N_7O_2$ $[M+H]^+$ m/z=410.2; found: 410.1.

Intermediate 96: 3-(5-(3-(hydroxymethyl)azetidin-1-yl)-1-oxoisoindolin-2-yl)piperidine-2,6-dione Int-96

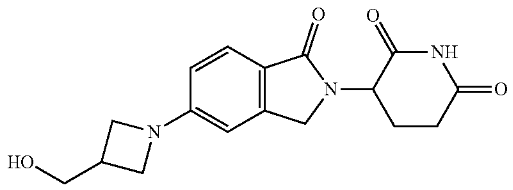

Step 1: methyl 2-cyano-4-(3-(hydroxymethyl)azetidin-1-yl)benzoate

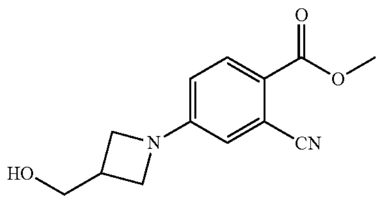 [SMILES: COC(=O)c1ccc(N2CC(CO)C2)cc1C#N]

A solution of methyl 2-cyano-4-fluorobenzoate (2.70 g, 15.1 mmol), $K_2CO_3$ (7.80 g, 60.3 mmol) and azetidin-3-ylmethanol hydrochloride (2.05 g, 16.6 mmol) in DMSO (30 mL) was stirred at 110° C. overnight. The mixture was diluted with water and extracted with EA (50 mL×2). The combined organic layers were washed with water and brine, dried and concentrated. The residue was purified by silica gel chromatography (PE/EA=5/1) to afford methyl 2-cyano-4-[3-(hydroxymethyl)azetidin-1-yl]benzoate (2.80 g, 11.4 mmol, 75.4% yield) as a yellow solid. LCMS calculated for $C_{13}H_{15}N_2O_3$ $(M+H)^+$ m/z=247.1; found: 247.2.

Step 2: methyl 2-formyl-4-(3-(hydroxymethyl)azetidin-1-yl)benzoate

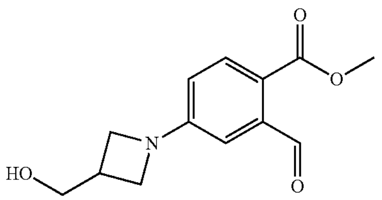 [SMILES: COC(=O)c1ccc(N2CC(CO)C2)cc1C=O]

To a solution of sodium hypophosphite hydrate (3.84 g, 44.7 mmol), methyl 2-cyano-4-[3-(hydroxymethyl)azetidin-1-yl]benzoate (1.10 g, 4.47 mmol) in water (4 mL), acetic acid (4 mL) and pyridine (8 mL) was added Raney Ni (236 mg, 2.23 mmol). The reaction mixture was stirred at 70° C. overnight. The resulted mixture was diluted with water and extracted with EA (50 mL×2). The combined organic layers were washed with water and brine, dried and concentrated. The residue was purified by silica gel chromatography (PE/EA=5/1) to afford the desired product (500 mg, 2.00 mmol, 44.9% yield) as a yellow solid. LCMS calculated for $C_{13}H_{16}NO_4$ $(M+H)^+$ m/z=250.1; found: 250.0.

Step 3: 3-(5-(3-(hydroxymethyl)azetidin-1-yl)-1-oxoisoindolin-2-yl)piperidine-2,6-dione To a stirred solution of methyl 2-formyl-4-(3-(hydroxymethyl)azetidin-1-yl)benzoate (250 mg, 1.00 mmol), 3-aminopiperidine-2,6-dione hydrochloride (198 mg, 1.20 mmol) and DIPEA (0.27 mL, 1.63 mmol) in DMF (5 mL) was added AcOH (0.54 mL, 9.41 mmol) at rt. After 1 h. NaBH$(OAc)_3$ (638 mg, 3.01 mmol) was added. After another 16 h, the resulted mixture was purified by a Prep-HPLC on a C18 column (20-35 μm, 100 A, 80 g) with mobile phase: $H_2O$ (0.1% TFA)/ACN at flow rate: 50 mL/min to afford the desired product (180 mg, 0.55 mmol, 54.5% yield). LCMS calculated for $C_{17}H_{20}N_3O_4$ $(M+H)^+$ m/z=330.1; found: 330.0.

Intermediate 97: 3-(5-(4-(hydroxymethyl)piperidin-1-yl)-1-oxoisoindolin-2-yl)piperidine-2,6-dione Int-97

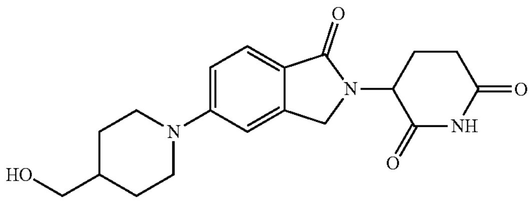

The title compound was prepared using procedure analogous to those described for Intermediate 96 using appropriate starting materials. LCMS m/z calcd $[M+H]^+$: m/z=358.2; Found: 358.0.

Intermediate 98: tert-butyl 9-formyl-3-oxa-7-azabicyclo[3.3.1]nonane-7-carboxylate Int-98

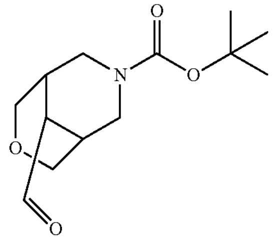

Step 1: tert-butyl 9-(hydroxymethyl)-3-oxa-7-azabicyclo[3.3.1]nonane-7-carboxylate

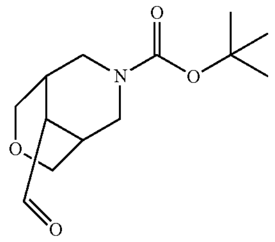 [SMILES: CC(C)(C)OC(=O)N1CC2COCC(C1)C2CC=O]

To borane tetrahydrofuran (0.98 mL, 0.98 mmol) in THF (1 mL) at 0° C. was added 2,3-dimethyl-2-butene (0.12 mL, 0.98 mmol) over 15 min. The mixture was stirred at 0° C. for 3 h. Next, a solution of tert-butyl 9-methylidene-3-oxa-7-azabicyclo[3.3.1]nonane-7-carboxylate (50.0 mg, 0.21 mmol) in 0.5 mL THF was added slowly. The reaction was warmed to room temperature and stirred overnight. The reaction was cooled to 0° C. and slowly added 5% aqueous 1 M solution of sodium hydroxide (1.0 mL, 1 mmol) followed by hydrogen peroxide 30 wt % in water (0.09 mL, 3.07 mmol). The mixture was warmed to RT. After stirring for 3 hour, the mixture was concentrated, diluted with water, extracted with DCM (3×), dried with sodium sulfate and condensed to give tert-butyl 9-(hydroxymethyl)-3-oxa-7-azabicyclo[3.3.1]nonane-7-carboxylate (53 mg, 0.21 mmol, 98.6% yield). LCMS m/z calcd for $C_8H_{16}NO_2$ $(M+H-100)^+$: 158.1; found: 158.0.

Step 2: tert-butyl 9-formyl-3-oxa-7-azabicyclo[3.3.1]nonane-7-carboxylate

To a vial containing tert-butyl 9-(hydroxymethyl)-3-oxa-7-azabicyclo[3.3.1]nonane-7-carboxylate (50.0 mg, 0.19 mmol) was added Dess-Martin Periodinane (173.0 mg, 0.41 mmol) and DCM (2 mL). The reaction stirred at RT for 3 hour. Then saturated bicarbonate was added and the solution stirred for 15 min. Product was extracted from the water layer with DCM. Organic layer was dried with sodium sulfate, filtered and condensed to yield tert-butyl 9-formyl-3-oxa-7-azabicyclo[3.3.1]nonane-7-carboxylate (49 mg, 0.19 mmol, 98.8% yield) as a white solid. Yield was assumed to be quantitative. LCMS m/z calcd for $C_8H_{14}NO_2$ $(M+H-100)^+$: 156.1; found: 156.0.

Intermediates 99-100

The intermediates shown below in Table 7 were prepared by the method used in preparing Int-98 using appropriate starting materials.

TABLE 7

| Intermediates 99-100 | | | | |
|---|---|---|---|---|
| Int. | Structure | Name | Calcd. (M + H-Boc)$^+$ m/z | Found (M + H-Boc)$^+$ m/z |
| Int-99 | 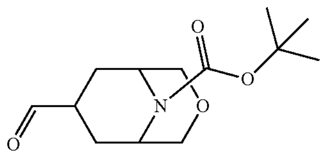 [SMILES: CC(C)(C)OC(=O)N1C2COCC1CC(C=O)C2] | tert-butyl 7-formyl-3-oxa-9-azabicyclo[3.3.1] nonane-9-carboxylate | 156.1 | 156.0 |
| Int-100 | 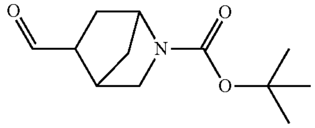 [SMILES: CC(C)(C)OC(=O)N1CC2CC1CC2C=O] | tert-butyl 5-formyl-2-azabicyclo[2.2.1]heptane-2-carboxylate | 126.1 | 126.0 |

Intermediate 101: (3-(4-fluoro-1,3-dioxoisoindolin-2-yl)-2,6-dioxopiperidin-1-yl)methyl pivalate Int-101

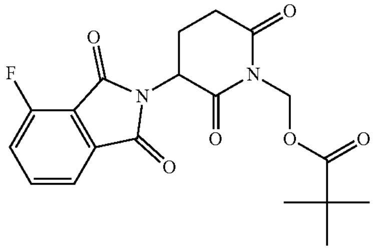

To a solution of cesium carbonate (324.0 mg, 1 mmol) in DMF (3 mL) was added 2-(2,6-Dioxo-piperidin-3-yl)-4-fluoroisoindoline-1,3-dione (250.0 mg, 0.91 mmol) and the mixture was stirred for a few minutes until total dissolution. Chloromethyl pivalate (200.0 μL, 1.39 mmol) in DMF (1 mL) was added over 30 minutes. The resulted mixture was stirred at rt overnight. The reaction mixture was diluted with water and extracted with DCM and EtOAc. Organic layers were condensed and wet loaded in DCM onto a 12 g silica column and purified using 0-60% EtOAC in hexane over 20 min to yield (3-(4-fluoro-1,3-dioxoisoindolin-2-yl)-2,6-dioxopiperidin-1-yl)methyl pivalate (250 mg, 0.64 mmol, 70.8% yield) as an clear oil. LCMS m/z calcd for $C_{19}H_{19}FN_2NaO_6$ (M+Na)$^+$: 413.1; found 412.9.

Intermediate 102: di-tert-butyl ((3-(5-fluoro-1,3-dioxoisoindolin-2-yl)-2,6-dioxopiperidin-1-yl) methyl) phosphate Int-102

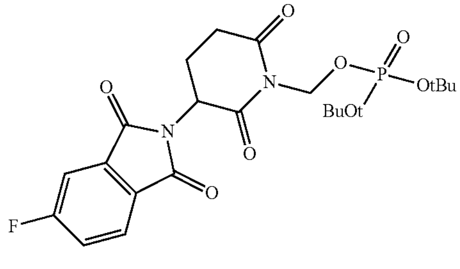

Step 1: 5-fluoro-2-(1-(hydroxymethyl)-2,6-dioxopiperidin-3-yl) isoindoline-1,3-dione

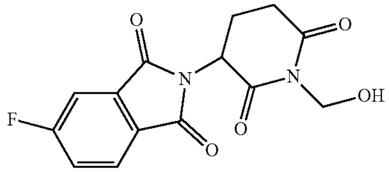 [SMILES: O=C1CCC(N2C(=O)c3ccc(F)cc3C2=O)C(=O)N1CO]

To a solution of 2-(2,6-dioxopiperidin-3-yl)-5-fluoroisoindole-1,3-dione (1.3 g, 4.71 mmol) was added paraformaldehyde 37% in water (5.0 mL, 67.16 mmol). After 2 hours at 100° C., another portion of paraformaldehyde 37% in water (5.0 mL, 67.16 mmol) was added. The resulted mixture was stirred at rt overnight. Reaction was diluted in water and filtered to yield 5-fluoro-2-(1-(hydroxymethyl)-2,6-dioxopiperidin-3-yl) isoindoline-1,3-dione (1.2 g, 3.91 mmol, 83.3% yield) as a white solid. $^1$H NMR (400 MHz, DMSO-d6) δ 8.02 (dd, J=4.5, 8.3 Hz, 1H), 7.85 (dd, J=2.3, 7.4 Hz, 1H), 7.73 (ddd, J=2.4, 8.3, 10.6 Hz, 1H), 6.18 (t, J=7.4 Hz, 1H), 5.26 (dd, J=5.3, 13.2 Hz, 1H), 5.12-4.99 (m, 2H), 3.03 (ddd, J=5.5, 13.9, 17.4 Hz, 1H), 2.78 (ddd, J=2.4, 4.5, 17.4 Hz, 1H), 2.59 (qd, J=4.4, 13.3 Hz, 1H), 2.09 (dtd, J=2.4, 5.4, 13.0 Hz, 1H).

Step 2: 2-(1-(chloromethyl)-2,6-dioxopiperidin-3-yl)-5-fluoroisoindoline-1,3-dione

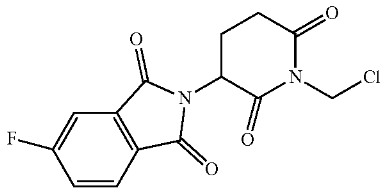 [SMILES: O=C1CCC(N2C(=O)c3ccc(F)cc3C2=O)C(=O)N1CCl]

Thionyl chloride (360.0 μL, 4.96 mmol) was added dropwise to a solution of 5-fluoro-2-(1-(hydroxymethyl)-2,6-dioxopiperidin-3-yl) isoindoline-1,3-dione (600.0 mg, 1.96 mmol) in DMF (8.1 mL) on ice. The reaction mixture was stirred for 1 hour at room temperature then was slowly added to a stirring solution of water (30 mL). Precipitate formed, was filtered, and washed with water and hexane to yield 2-(1-(chloromethyl)-2,6-dioxopiperidin-3-yl)-5-fluoroisoindoline-1,3-dione (575 mg, 1.77 mmol, 90.4% yield) as a white solid. Product did not ionize in LC-MS and was used directly in next step.

Step 3: di-tert-butyl ((3-(5-fluoro-1,3-dioxoisoindolin-2-yl)-2,6-dioxopiperidin-1-yl)methyl) phosphate To a vial containing 2-(1-(chloromethyl)-2,6-dioxopiperidin-3-yl)-5-fluoroisoindoline-1,3-dione (200.0 mg, 0.62 mmol) was added potassium di-tert-butyl phosphate (200.0 mg, 0.81 mmol), DMF (6.1597 mL) and N,N-diisopropylethylamine (150.0 μL, 0.86 mmol). The resulted mixture was stirred at 55° C. for 6 hours. Reaction was diluted in DCM and washed with water. Water layer was extracted 2× with DCM. Organic layers were dried with sodium sulfate and condensed to yield di-tert-butyl ((3-(5-fluoro-1,3-dioxoisoindolin-2-yl)-2,6-dioxopiperidin-1-yl)methyl) phosphate (300 mg, 0.60 mmol, 97.7% yield). LCMS m/z calcd for $C_{14}H_{13}FN_2O_8P$ $(M-3tBu+1)^+$: 387.0; found 386.9.

Intermediates 103-104

The intermediates shown below in Table 8 were prepared by the method used in preparing Int-102 using appropriate starting materials.

dihydrochloride (30.0 mg, 0.08 mmol) in DMF (1 mL) was added tert-Butyl 4-(chlorosulfonyl)piperidine-1-carboxylate (30.0 mg, 0.11 mmol) and N,N-Diisopropylethylamine (40.0 μL, 0.23 mmol) at 0° C. After being stirred overnight at rt, reaction was diluted in 10 mL of methanol, filtered and purified by prep-LCMS (CSH-C18, 23.8-43.8% Acetonitrile in water 0.1% TFA over 5 min) to yield tert-butyl (S)-4-((2-(2-hydroxyphenyl)-5,6,6a,7,9,10-hexahydro-8H-pyrazino[1',2':4,5]pyrazino[2,3-c]pyridazin-8-yl)sulfonyl) piperidine-1-carboxylate. Tert-butyl (S)-4-((2-(2-hydroxyphenyl)-5,6,6a,7,9,10-hexahydro-8H-pyrazino[1',2':4,5]pyrazino[2,3-c]pyridazin-8-yl)sulfonyl)piperidine-1-carboxylate was then dissolved in 0.5 mL of 4 M HCl Dioxane and 0.5 mL of dioxane and stirred for 2 hours at rt. The volatiles were removed to yield (S)-2-(8-(piperidin-4-ylsulfonyl)-6,6a,7,8,9,10-hexahydro-5H-pyrazino[1',2':4,5]pyrazino[2,3-c]pyridazin-2-yl)phenol as its HCl salt (10 mg, 0.019 mmol, 23.6% yield). LCMS m/z calcd for $C_{20}H_{27}N_6O_3S$ $(M+H)^+$: 431.2; found 431.0.

TABLE 8

Intermediates 103-104

| Int. | Structure | Name | Calcd. $(M + H)^+$ m/z | Found $(M + H)^+$ m/z |
|---|---|---|---|---|
| Int-103 | 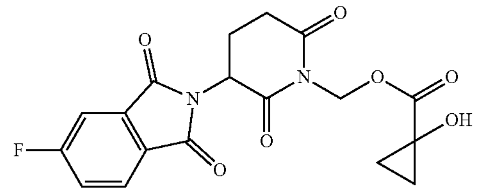 [SMILES: O=C1CCC(N2C(=O)c3ccc(F)cc3C2=O)C(=O)N1COC(=O)C1(O)CC1] | (3-(5-fluoro-1,3-dioxoisoindolin-2-yl)-2,6-dioxopiperidin-1-yl)methyl 1-hydroxycyclopropane-1-carboxylate | 391.1 | 391.0 |
| Int-104 | 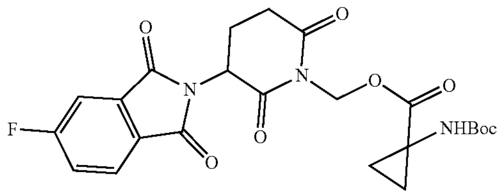 [SMILES: CC(C)(C)OC(=O)NC1(C(=O)OCN2C(=O)CCC(N3C(=O)c4ccc(F)cc4C3=O)C2=O)CC1] | (3-(5-fluoro-1,3-dioxoisoindolin-2-yl)-2,6-dioxopiperidin-1-yl)methyl 1-((tert-butoxycarbonyl) amino)cyclopropane-1-carboxylate | 490.1 | 390.0 $(M-Boc + H)^+$ |

Intermediate 105: (S)-2-(8-(piperidin-4-ylsulfonyl)-6,6a,7,8,9,10-hexahydro-5H-pyrazino [1',2':4,5] pyrazino[2,3-c]pyridazin-2-yl)phenol Int-105

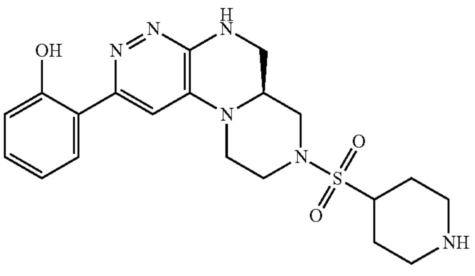

To a solution of (R)-2-(6,6a,7,8,9,10-hexahydro-5H-pyrazino[1',2':4,5]pyrazino[2,3-c]pyridazin-2-yl)phenol;

Intermediate 106: 2-(6-methyl-6,6a,7,8,9,10-hexahydro-5H-pyrazino[1',2':4,5]pyrazino[2,3-c]pyridazin-2-yl)phenol Int-106

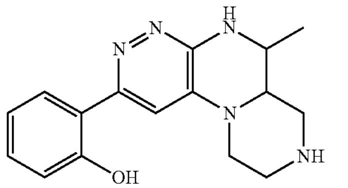

Step 1: tert-butyl 4-(3,6-dichloropyridazin-4-yl)-3-formylpiperazine-1-carboxylate To a solution of tert-butyl 4-(3,6-dichloropyridazin-4-yl)-3-(hydroxymethyl)piperazine-1-carboxylate (3.96 g, 10.9 mmol) in DCM (70 mL) was added Dess-Martin periodinane (9.25 g, 21.8 mmol) at 0° C. The mixture was stirred at 0° C. for 1 h. The reaction was quenched with saturated aqueous $Na_2S_2O_3$ (80 mL) and extracted with DCM (80.0 mL×3). The organic layers were combined, dried over $Na_2SO_4$, filtered, and concentrated reduced pressure to give crude tert-butyl 4-(3,6-dichloropyridazin-4-yl)-3-formylpiperazine-1-carboxylate (3.6 g, 9.97 mmol, 91.4% yield). LCMS m/z calcd for $C_{14}H_{19}C_{12}N_4O_3$ $[M+H]^+$: 361.1; Found: 361.1.

Step 2: tert-butyl 4-(3,6-dichloropyridazin-4-yl)-3-(1-hydroxyethyl)piperazine-1-carboxylate To a solution of tert-butyl 4-(3,6-dichloropyridazin-4-yl)-3-formylpiperazine-1-carboxylate (3.6 g, 9.97 mmol) in THF (70 mL) was added $CH_3MgBr$ (1M in $Et_2O$, 19.9 mL, 19.9 mmol) at 0° C. The mixture was stirred at 0° C. for 2 h. The reaction was quenched with saturated aqueous $NH_4Cl$ (80 mL) and extracted with EA (80 mL×3). The organic layers were combined, dried over $Na_2SO_4$, filtered, and concentrated reduced pressure. The residue was purified by silica gel chromatography (PE:EA=3:1) to give tert-butyl 4-(3,6-dichloropyridazin-4-yl)-3-(1-hydroxyethyl)piperazine-1-carboxylate (2.1 g, 5.6 mmol, 56.9% yield) as a yellow solid. LCMS m/z calcd for $C_{15}H_{23}C_{12}N_4O_3$ $[M+H]^+$: 377.1; Found: 377.0.

Step 3 to step 7: 2-(6-methyl-6,6a, 7,8,9,10-hexahydro-5H-pyrazino[1',2':4,5]pyrazino[2,3-c]pyridazin-2-yl)phenol The title compound was prepared using procedures analogous to those described for Int-1, from step 2 to step 6, with appropriate starting materials. LCMS m/z calcd for $C_{16}H_{20}N_5O$ $[M+H]^+$: 298.2; Found: 298.2.

Intermediate 107: 2-(6-ethyl-6,6a,7,8,9,10-hexahydro-5H-pyrazino[1',2':4,5]pyrazino[2,3-c]pyridazin-2-yl)phenol Int-107

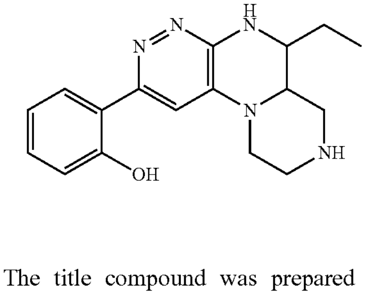

The title compound was prepared using a procedure analogous to that used for Intermediate 106 using appropriate starting materials. LCMS calcd for $C_{17}H_{22}N_5O$ $[M+H]^+$ m/z=312.2; found: 312.1.

Intermediate 108: 2- [(10S)-12-[(3,3-Dimethylpiperidin-4-yl)methyl]-1,5,6,8,12-pentazatricyclo[8.4.0.02,7]tetradeca-2(7),3,5-trien-4-yl]phenol Int-108

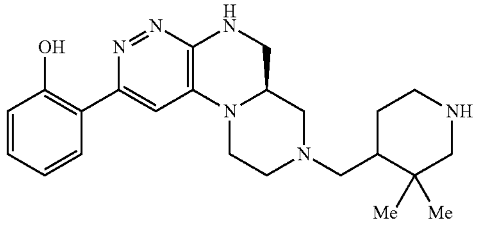

Step 1. tert-Butyl 4-[(10S)-4-(2-hydroxyphenyl)-1,5,6,8,12-pentazatricyclo[8.4.0.02,7]tetradeca-2(7),3,5-triene-12-carbonyl]-3,3-dimethylpiperidine-1-carboxylate To a solution of 2-[(10R)-1,5,6,8,12-pentazatricyclo[8.4.0.02,7]tetradeca-2(7),3,5-trien-4-yl]phenol dihydrochloride (97 mg, 0.27 mmol) in DMF (1.3 mL) was added DIPEA (0.20 mL, 1.17 mmol). The reaction was stirred at rt for 10 minutes. The reaction was added 3,3-dimethyl-1-[(2-methylpropan-2-yl)oxycarbonyl]piperidine-4-carboxylic acid (50 mg, 0.19 mmol) followed by adding HATU (103 mg, 0.27 mmol, 1.40 equiv.). The reaction was stirred at ambient temperature for 18 h. The reaction was added water (15 mL) and extracted with DCM (15 mL×3). The combined organic layers were washed with water (15 mL), dried over $Na_2SO_4$, filtered and concentrated. The crude material was purified by flash column chromatography (0~100% EtOAc in heptanes, then 100-95% EtOAc in MeOH) to give the desired product (121 mg). LCMS calculated for $C_{28}H_{39}N_6O_4$ $(M+H)^+$: m/z=523.3; found: 523.2.

Step 2. 2- [(10S)-12-[(3,3-Dimethylpiperidin-4-yl)methyl]-1,5,6,8,12-pentazatricyclo[8.4.0.02,7]tetradeca-2(7),3,5-trien-4-yl]phenol To a solution of tert-Butyl 4-[(10S)-4-(2-hydroxyphenyl)-1,5,6,8,12-pentazatricyclo[8.4.0.02,7]tetradeca-2(7),3,5-triene-12-carbonyl]-3,3-dimethylpiperidine-1-carboxylate (60 mg, 0.04 mmol) in THF (1.1 mL) was added $BH_3$-THF solution (1.38 mL) at ambient temperature. The reaction was stirred at 66° C. for 18 h The solvent was evaporated. The crude material (88 mg) was directly used for the next step. The crude material was added 0.8 mL DCM and 0.2 mL TFA. The reaction was stirred at ambient temperature for 2 h. Volatiles were evaporated in vacuo and the residue was purified by Prep-HPLC (10~100% MeCN in water with 0.1% TFA) to give the desired product (8 mg, TFA salt). LCMS calculated for $C_{23}H_{33}N_6O$ $(M+H)^+$: m/z=409.3; found: 409.3.

Intermediate 109: tert-Butyl 6-formyl-1-methyl-3-azabicyclo[3.1.0]hexane-3-carboxylate Step 1. 1-Benzyl-3-methylpyrrole-2,5-dione 3-methylfuran-2,5-dione (2.0 mL; 22.3 mmol) was placed in a 100 mL flask under nitrogen at 0° C. and benzylamine (2.43 mL; 22.3 mmol) was added dropwise. The resulting mixture was then heated at 120° C. for 18 h. The reaction mixture was then allowed to cool to ambient temperature and purified by silica gel flash column chromatography eluting with a mixture of EtOAc and heptanes (1:2) to give the desired product as a colorless oil (2.4 g, Yield: 53.6%). LCMS calculated for $C_{12}H_{12}NO_2$ $(M+H)^+$: m/z=202.1; found: 202.1.

Step 2. Ethyl 5-benzyl-6a-methyl-4,6-dioxo-1,3a-dihydropyrrolo[3,4-c]pyrazole-3-carboxylate To a solution of 1-benzyl-3-methylpyrrole-2,5-dione (2 g, 9.94 mmol) in THF (50 mL) as added ethyl diazoacetate (15% in toluene; 18 mL) at ambient temperature. The reaction was heated to 65° C. for 18 h and evaporated to dryness. The crude material was purified by flash column chromatography (40% EtOAc in heptanes) to give the desired product (1.2 g; Yield: 38.3%). LCMS calculated for $C_{16}H_{18}N_3O_4$ $(M+H)^+$: m/z=316.1; found: 316.0.

Step 3. Ethyl 3-benzyl-1-methyl-2,4-dioxo-3-azabicyclo[3.1.0]hexane-6-carboxylate The ethyl 5-benzyl-6a-methyl-4,6-dioxo-1,3a-dihydropyrrolo[3,4-c]pyrazole-3-carboxylate (1.1 g, 3.6 mmol) was placed in the round-bottom flask. The material was heated to 170° C. for 6 hours. The crude was directly purified by flash column chromatography (0~75% EtOAc in heptanes) to give the desired product (553 mg; Yield: 53.0%). LCMS calculated for $C_{16}H_{18}NO_4$ $(M+H)^+$: m/z=288.1; found: 288.1.

Step 4. (3-Benzyl-1-methyl-3-azabicyclo[3.1.0]hexan-6-yl)methanol

To a stirred suspension of $LiAlH_4$ (292 mg, 1.11 mmol) in THF (55 mL) at 0° C. was added a solution of ethyl 3-benzyl-1-methyl-2,4-dioxo-3-azabicyclo[3.1.0]hexane-6-carboxylate (553 mg, 0.28 mmol.) in 5.5 mL THF dropwise. The reaction was heated to 66° C. for 18 h. The reaction was cooled in ice-water bath and slowly added 0.6 mL 15% NaOH solution and 2 mL water. The reaction was added 1 g $Na_2SO_4$. The reaction was filtered through a pad celite. The solvent was evaporated. The crude material was purified by flash column chromatography (0~100% EtOAc in heptanes and then 100~95% EtOAc in MeOH) to give the desired product (278 mg; Yield: 66.5%). LCMS calculated for $C_{14}H_{20}NO$ $(M+H)^+$: m/z=218.2; found: 218.3.

Step 5. tert-Butyl 6-(hydroxymethyl)-1-methyl-3-azabicyclo[3.1.0]hexane-3-carboxylate The (3-benzyl-1-methyl-3-azabicyclo[3.1.0]hexan-6-yl) methanol (144 mg, 0.66 mmol) in MeOH (7.8 mL) was added $Pd(OH)_2$ (19 mg, 0.133 mmol) and $(Boc)_2O$ (217 mg, 0.994 mmol). The reaction was stirred at ambient temperature under 55 psi $H_2$ for 18 h. The reaction mixture was filtered through a pad of Celite and the filter cake was washed in small portions of MeOH. The combined filtrate was concentrated and the residue was purified by flash column chromatography (0~100% EtOAc in heptanes) to obtain the desired product (25 mg; Yield: 16.6%). LCMS calculated for $C_8H_{14}NO_3$ $(M+H\text{-}^tBu)^+$: m/z=172.1; found: 172.3.

Step 6. tert-Butyl 6-formyl-1-methyl-3-azabicyclo[3.1.0]hexane-3-carboxylate

To a solution of tert-butyl 6-(hydroxymethyl)-1-methyl-3-azabicyclo[3.1.0]hexane-3-carboxylate (25 mg, 0.11 mmol, 1.00 equiv.) in DCM (0.55 mL) was added Dess-Martin periodinane (56 mg, 0.132 mmol, 1.20 equiv.) in portions under an ice bath. The reaction was stirred at ambient temperature for 4 h. The reaction was filtered through a pad of celite and the filter cake was washed with DCM (20 mL). The combined filtrate was added saturated sodium bicarbonate $NaHCO_3$ solution (15 mL) The organic layer was separated from the aqueous layer and extracted with DCM (15 mL×2). The combined organic layers were dried over $Na_2SO_4$, filtered and concentrated under reduced pressure. The residue was purified by auto flash column chromatography (5~100% EtOAc in heptanes) to afford the desired product (20 mg; Yield: 80.7%) as a colorless oil. LCMS calculated for $C_8H_{12}NO_3$ $(M+H\text{-}^tBu)^+$: m/z=170.1; found: 170.1.

Intermediate 110: 2- [(10S)-12-[(3,3-Difluoropiperidin-4-yl)methyl]-1,5,6,8,12-pentazatricyclo[8.4.0.02,7]tetradeca-2(7),3,5-trien-4-yl]phenol Int-110

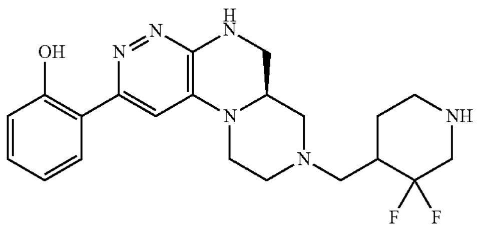

Step 1. tert-Butyl 3,3-difluoro-4-(trifluoromethylsulfonyloxymethyl)piperidine-1-carboxylate To a solution of tert-butyl 3,3-difluoro-4-(hydroxymethyl)piperidine-1-carboxylate (25 mg, 0.10 mmol) and pyridine (0.024 mL, 0.30 mmol) in DCM (1 mL) was added $Tf_2O$ (0.021 mL, 0.12 mmol) at 0° C. The reaction mixture was stirred at 20° C. for 2 h. The reaction was evaporated to dryness. The crude product was used in the next step without further purification.

Step 2. tert-Butyl 3,3-difluoro-4-[[(10S)-4-(2-hydroxyphenyl)-1,5,6,8,12-pentazatricyclo [8.4.0.02,7] tetradeca-2(7),3,5-trien-12-yl]methyl]piperidine-1-carboxylate To a solution of 2-[(10R)-1,5,6,8,12-pentazatricyclo [8.4.0.02,7]tetradec-5-en-4-yl]phenol dihydrochloride (43 mg, 0.12 mmol) in THF (1 mL) was added DIPEA (92.2 mg, 0.71 mmol) at rt and stirred for 10 minutes. The solution was added to tert-butyl 3,3-difluoro-4-(trifluoromethylsulfonyloxymethyl)piperidine-1-carboxylate (38 mg crude). The reaction was stirred at 40° C. for 18 h. The reaction was evaporated to dryness and directly purified flash column chromatography (30~100% EtOAc in heptanes) to give the desired product, tert-butyl 3,3-difluoro-4-[[(10S)-4-(2-hydroxyphenyl)-1,5,6,8,12-pentazatricyclo[8.4.0.02,7]tetradeca-2(7),3,5-trien-12-yl]methyl]piperidine-1-carboxylate (40 mg, 0.077 mmol, 78.1% yield), as yellow solid. LCMS calculated for $C_{26}H_{35}F2N_6O_3(M+H)^+$: m/z=517.3; found: 517.4.

Step 3. 2- [(10S)-12-[(3,3-Difluoropiperidin-4-yl) methyl]-1,5,6,8,12-pentazatricyclo [8.4.0.02,7]tetradeca-2(7),3,5-trien-4-yl]phenol To a stirred solution of tert-butyl 3,3-difluoro-4-[[(10S)-4-(2-hydroxyphenyl)-1,5,6,8,12-pentazatricyclo[8.4.0.02,7] tetradeca-2(7),3,5-trien-12-yl]methyl]piperidine-1-carboxylate (40 mg, 0.078 mmol) in DCM (0.8 mL) was added TFA (0.2 mL). The resulting mixture was stirred at rt for 3 h. The reaction was evaporated to dryness to obtain crude material (61 mg, as TFA salt), which was used in the next step without further purification. LCMS calculated for $C_{21}H_{27}F_2N_6O$ $(M+H)^+$: m/z=417.2; found: 417.2.

Example 1: 3-(5-(2-(4-(2-((S)-2-(2-hydroxyphenyl)-5,6,6a,7,9,10-hexahydro-8H-pyrazino [1',2':4,5] pyrazino[2,3-c]pyridazin-8-yl)pyrimidin-5-yl)piperidin-1-yl)ethyl)-1-oxoiso-indolin-2-yl)piperidine-2,6-dione Ex.1

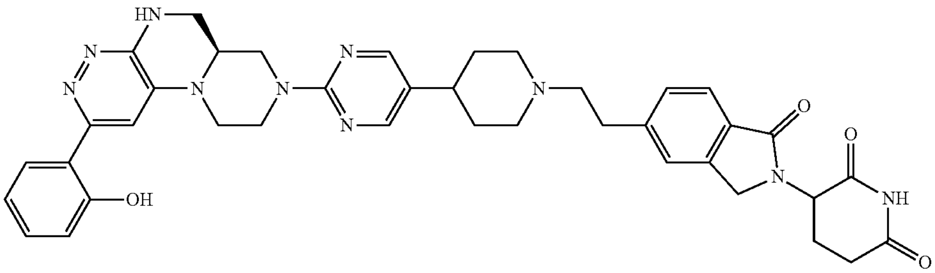

To a stirred solution of 2-[2-(2,6-dioxopiperidin-3-yl)-1-oxo-3H-isoindol-5-yl]acetaldehyde (42.5 mg, 0.07 mmol) in DMF (2 mL) was added (S)-2-(8-(5-(piperidin-4-yl) pyrimidin-2-yl)-6,6a,7,8,9,10-hexahydro-5H-pyrazino[1',2':4,5] pyrazino[2,3-c]pyridazin-2-yl) phenol (22.0 mg, 0.05 mmol) and acetic acid (28 μL, 0.50 mmol) at rt. After 1 h, sodium triacetoxyborohydride (31.3 mg, 0.15 mmol) was added. After additional 2 h, another batch of sodium triacetoxyborohydride (31.3 mg, 0.15 mmol) was added. The resulted mixture was stirred overnight at rt. The reaction was diluted with MeOH (10 mL), filtered through a syringe filter, and the filtrate was purified by prep-HPLC to give 3-(5-(2-(4-(2-((S)-2-(2-hydroxyphenyl)-5,6,6a,7,9,10-hexahydro-8H-pyrazino[1',2':4,5]pyrazino[2,3-c]pyridazin-8-yl)pyrimidin-5-yl) piperidin-1-yl)ethyl)-1-oxoisoindolin-2-yl)piperidine-2,6-dione (28 mg, 60% yield) as it's TFA salt. LCMS m/z calcd for $C_{39}H_{43}N_{10}O_4$ $[M+H]^+$: 715.3; Found: 715.2.

Examples in Table 9 were prepared using the procedure described in the synthesis of Example 1 with appropriate intermediates.

TABLE 9

| Examples 2-10 and 62-65 | | | |
|---|---|---|---|
| Example | Structure/Name | Calcd. $(M + H)^+$ m/z | Found $(M + H)^+$ m/z |
| 2 | 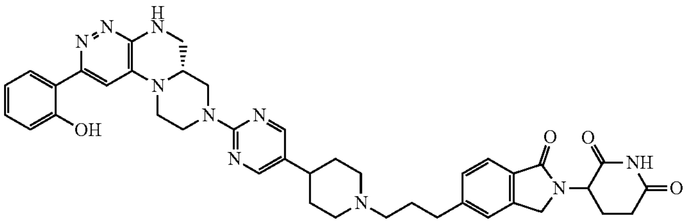 [SMILES: O=C1CCC(N2Cc3cc(CCCN4CCC(c5cnc(N6CCN7c8cc(-c9ccccc9O)nnc8NC[C@@H]7C6)nc5)CC4)ccc3C2=O)C(=O)N1] 3-(5-(3-(4-(2-((R)-2-(2-hydroxyphenyl)-5,6,6a,7,9,10-hexahydro-8H-pyrazino[1',2':4,5]pyrazino[2,3-c] pyridazin-8-yl)pyrimidin-5-yl)piperidin-1-yl)propyl)-1-oxoisoindolin-2-yl)piperidine-2,6-dione | 729.4 | 729.3 |

TABLE 9-continued

| Example | Structure/Name | Calcd. (M + H)+ m/z | Found (M + H)+ m/z |
|---|---|---|---|
| | Examples 2-10 and 62-65 | | |
| 3 | 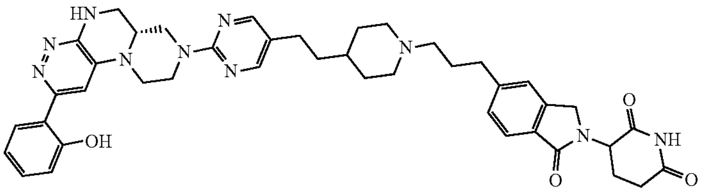 [SMILES: O=C1CCC(N2Cc3cc(CCCN4CCC(CCc5cnc(N6CCN7c8cc(-c9ccccc9O)nnc8NC[C@@H]7C6)nc5)CC4)ccc3C2=O)C(=O)N1] 3-(5-(3-(4-(2-(2-((R)-2-(2-hydroxyphenyl)-5,6,6a,7,9,10-hexahydro-8H-pyrazino[1',2':4,5]pyrazino[2,3-c]pyridazin-8-yl)pyrimidin-5-yl)ethyl)piperidin-1-yl)propyl)-1-oxoisoindolin-2-yl)piperidine-2,6-dione | 757.4 | 757.2 |
| 4 | 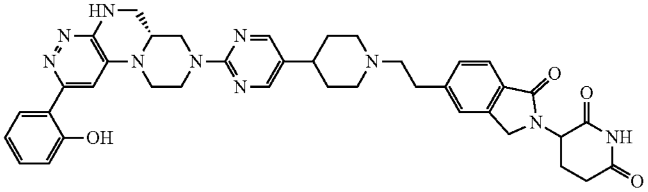 [SMILES: O=C1CCC(N2Cc3cc(CCN4CCC(c5cnc(N6CCN7c8cc(-c9ccccc9O)nnc8NC[C@@H]7C6)nc5)CC4)ccc3C2=O)C(=O)N1] 3-(5-(2-(4-(2-((R)-2-(2-hydroxyphenyl)-5,6,6a,7,9,10-hexahydro-8H-pyrazino[1',2':4,5]pyrazino[2,3-c]pyridazin-8-yl)pyrimidin-5-yl)piperidin-1-yl)ethyl)-1-oxoisoindolin-2-yl)piperidine-2,6-dione | 715.3 | 715.2 |
| 5 | 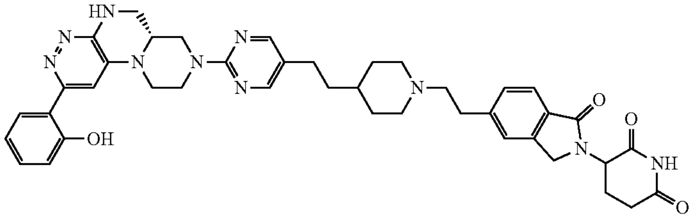 [SMILES: O=C1CCC(N2Cc3cc(CCN4CCC(CCc5cnc(N6CCN7c8cc(-c9ccccc9O)nnc8NC[C@@H]7C6)nc5)CC4)ccc3C2=O)C(=O)N1] 3-(5-(2-(4-(2-(2-((R)-2-(2-hydroxyphenyl)-5,6,6a,7,9,10-hexahydro-8H-pyrazino[1',2':4,5]pyrazino[2,3-c]pyridazin-8-yl)pyrimidin-5-yl)ethyl)piperidin-1-yl)ethyl)-1-oxoisoindolin-2-yl)piperidine-2,6-dione | 743.4 | 743.2 |
| 6 | 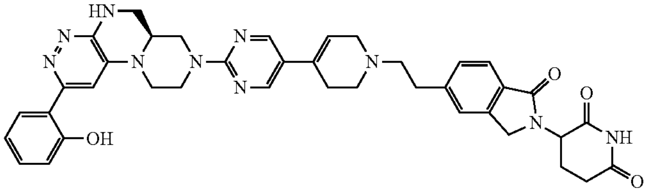 [SMILES: O=C1CCC(N2Cc3cc(CCN4CC=C(c5cnc(N6CCN7c8cc(-c9ccccc9O)nnc8NC[C@H]7C6)nc5)CC4)ccc3C2=O)C(=O)N1] 3-(5-(2-(4-(2-((S)-2-(2-hydroxyphenyl)-5,6,6a,7,9,10-hexahydro-8H-pyrazino[1',2':4,5]pyrazino[2,3-c]pyridazin-8-yl)pyrimidin-5-yl)-3,6-dihydropyridin-1(2H)-yl)ethyl)-1-oxoisoindolin-2-yl)piperidine-2,6-dione | 713.3 | 713.2 |
| 7 | 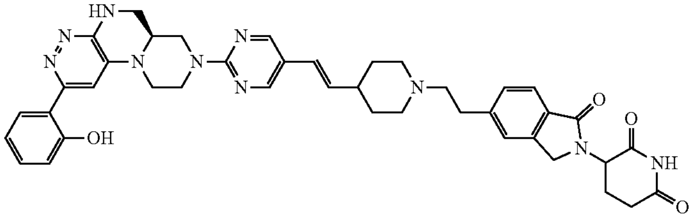 [SMILES: O=C1CCC(N2Cc3cc(CCN4CCC(/C=C/c5cnc(N6CCN7c8cc(-c9ccccc9O)nnc8NC[C@H]7C6)nc5)CC4)ccc3C2=O)C(=O)N1] 3-(5-(2-(4-((E)-2-(2-((S)-2-(2-hydroxyphenyl)-5,6,6a,7,9,10-hexahydro-8H-pyrazino[1',2':4,5]pyrazino[2,3-c]pyridazin-8-yl)pyrimidin-5-yl)vinyl)piperidin-1-yl)ethyl)-1-oxoisoindolin-2-yl)piperidine-2,6-dione | 741.3 | 741.2 |

TABLE 9-continued

Examples 2-10 and 62-65

| Example | Structure/Name | Calcd. (M + H)+ m/z | Found (M + H)+ m/z |
| --- | --- | --- | --- |
| 8 | 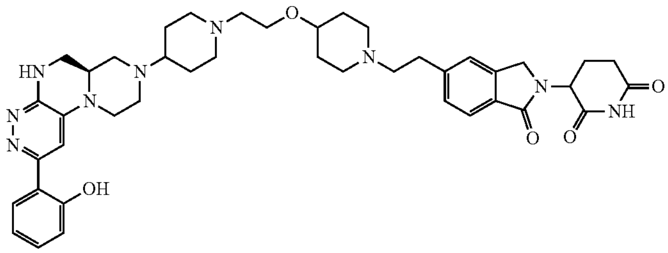 [SMILES: O=C1CCC(N2Cc3cc(CCN4CCC(OCCN5CCC(N6CCN7c8cc(-c9ccccc9O)nnc8NC[C@H]7C6)CC5)CC4)ccc3C2=O)C(=O)N1] 3-(5-(2-(4-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethoxy)piperidin-1-yl)ethyl)-1-oxoisoindolin-2-yl)piperidine-2,6-dione | 764.4 | 764.2 |
| 9 | 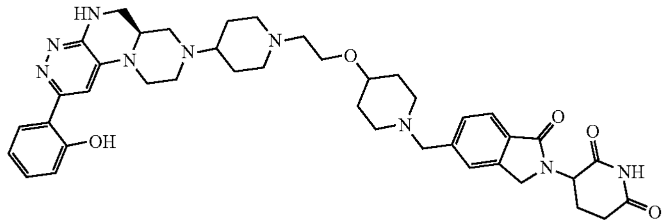 [SMILES: O=C1CCC(N2Cc3cc(CN4CCC(OCCN5CCC(N6CCN7c8cc(-c9ccccc9O)nnc8NC[C@H]7C6)CC5)CC4)ccc3C2=O)C(=O)N1] 3-(5-((4-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethoxy)piperidin-1-yl)methyl)-1-oxoisoindolin-2-yl)piperidine-2,6-dione | 750.4 | 750.2 |
| 10 | 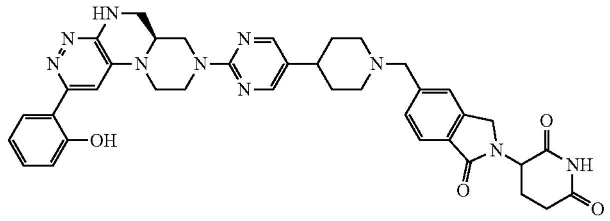 [SMILES: O=C1CCC(N2Cc3cc(CN4CCC(c5cnc(N6CCN7c8cc(-c9ccccc9O)nnc8NC[C@H]7C6)nc5)CC4)ccc3C2=O)C(=O)N1] 3-(5-((4-(2-((S)-2-(2-hydroxyphenyl)-5,6,6a,7,9,10-hexahydro-8H-pyrazino[1',2':4,5]pyrazino[2,3-c]pyridazin-8-yl)pyrimidin-5-yl)piperidin-1-yl)methyl)-1-oxoisoindolin-2-yl)piperidine-2,6-dione | 701.3 | 701.2 |
| 62 | 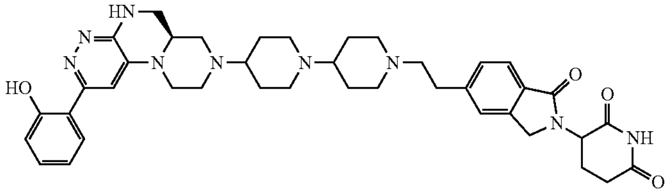 [SMILES: O=C1CCC(N2Cc3cc(CCN4CCC(N5CCC(N6CCN7c8cc(-c9ccccc9O)nnc8NC[C@H]7C6)CC5)CC4)ccc3C2=O)C(=O)N1] 3-(5-(2-(4-((S)-2-(2-hydroxyphenyl)-5,6,6a,7,9,10-hexahydro-8H-pyrazino[1',2':4,5]pyrazino[2,3-c]pyridazin-8-yl)-[1,4'-bipiperidin]-1'-yl)ethyl)-1-oxoisoindolin-2-yl)piperidine-2,6-dione | 720.4 | 720.3 |
| 63 | 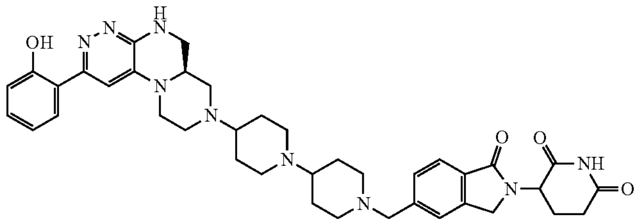 [SMILES: O=C1CCC(N2Cc3cc(CN4CCC(N5CCC(N6CCN7c8cc(-c9ccccc9O)nnc8NC[C@H]7C6)CC5)CC4)ccc3C2=O)C(=O)N1] 3-(5-((4-((S)-2-(2-hydroxyphenyl)-5,6,6a,7,9,10-hexahydro-8H-pyrazino[1',2':4,5]pyrazino[2,3-c]pyridazin-8-yl)-[1,4'-bipiperidin]-1'-yl)methyl)-1-oxoisoindolin-2-yl)piperidine-2,6-dione | 706.3 | 706.2 |

TABLE 9-continued

| Example | Structure/Name | Calcd. (M + H)+ m/z | Found (M + H)+ m/z |
|---|---|---|---|
| | Examples 2-10 and 62-65 | | |
| 64 | 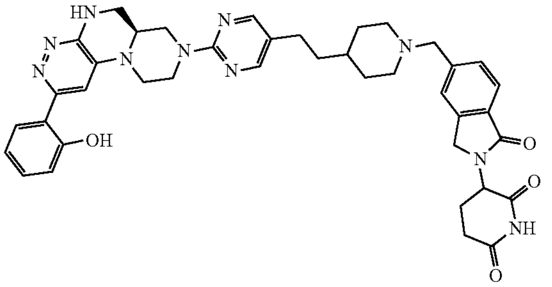 [SMILES: O=C1CCC(N2Cc3cc(CN4CCC(CCc5cnc(N6CCN7c8cc(-c9ccccc9O)nnc8NC[C@H]7C6)nc5)CC4)ccc3C2=O)C(=O)N1] 3-(5-((4-(2-(2-((S)-2-(2-hydroxyphenyl)-5,6,6a,7,9,10-hexahydro-8H-pyrazino[1',2':4,5]pyrazino[2,3-c]pyridazin-8-yl)pyrimidin-5-yl)ethyl)piperidin-1-yl)methyl)-1-oxoisoindolin-2-yl)piperidine-2,6-dione | 729.4 | 729.2 |
| 65 | 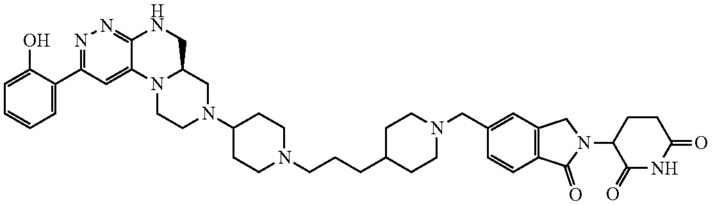 [SMILES: O=C1CCC(N2Cc3cc(CN4CCC(CCCN5CCC(N6CCN7c8cc(-c9ccccc9O)nnc8NC[C@H]7C6)CC5)CC4)ccc3C2=O)C(=O)N1] 3-(5-((4-(3-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propyl)piperidin-1-yl)methyl)-1-oxoisoindolin-2-yl)piperidine-2,6-dione | 748.4 | 748.2 |

Example 11: 2-(2,6-Dioxopiperidin-3-yl)-5-(4-(3-(4-((S)-2-(2-hydroxyphenyl)-5,6,6a,7,9,10-hexahydro-8H-pyrazino[1',2':4,5]1pyrazino[2,3-c]pyridazin-8-yl)piperidin-1-yl)propyl) piperazin-1-yl) isoindoline-1,3-dione Ex.11

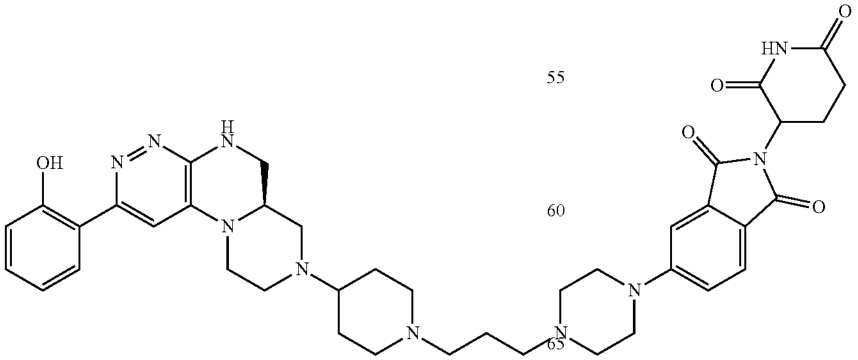

Step 1: (S)-2-(8-(1-(3-(piperazin-1-yl)propyl)piperidin-4-yl)-6, 6a, 7,8,9,10-hexahydro-5H-pyrazino[1',2':4,5]pyrazino[2,3-c]pyridazin-2-yl)phenol

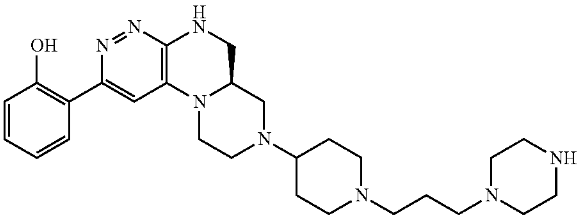 [SMILES: Oc1ccccc1-c1cc2c(nn1)NC[C@H]1CN(C3CCN(CCCN4CCNCC4)CC3)CCN21]

To a stirred solution of (S)-2-(8-(piperidin-4-yl)-6,6a,7,8,9,10-hexahydro-5H-pyrazino [1',2':4,5]pyrazino[2,3-c]pyridazin-2-yl)phenol (10.0 mg, 0.03 mmol) in DMF (0.50 mL) was added the triethylamine (0.02 mL, 0.11 mmol) and tert-butyl 4-(3-bromopropyl)piperazine-1-carboxylate (25.1 mg, 0.08 mmol) sequentially at 50° C. After 12 h, the reaction mixture was diluted with water and extracted with ethyl acetate. The combined organic layers were washed with brine, dried over $Na_2SO_4$, and filtered. The resulting filtrate was concentrated under vacuum. The crude was dissolved in Ethyl acetate (1 mL) and treated with hydrochloric acid (0.2 mL, 1.2 mmol) and stirred at room temperature for 2 h. The reaction mixture was concentrated under vacuum to give (S)-2-(8-(1-(3-(piperazin-1-yl)propyl)piperidin-4-yl)-6,6a,7,8,9,10-hexahydro-5H-pyrazino[1',2':4,5]pyrazino[2,3-c]pyridazin-2-yl)phenol as its HCl salt (6 mg, 0.011 mmol, 41% yield). LCMS m/z calcd for $C_{27}H_{41}N_8O$ $[M+H]^+$: 493.3; found: 493.1.

Step 2: 2-(2,6-dioxopiperidin-3-yl)-5-(4-(3-(4-((S)-2-(2-hydroxyphenyl)-5,6,6a, 7,9,10-hexahydro-8H-pyrazino[1',2':4,5]pyrazino[2,3-c]pyridazin-8-yl) piperidin-1-yl)propyl)piperazin-1-yl) isoindoline-1,3-dione

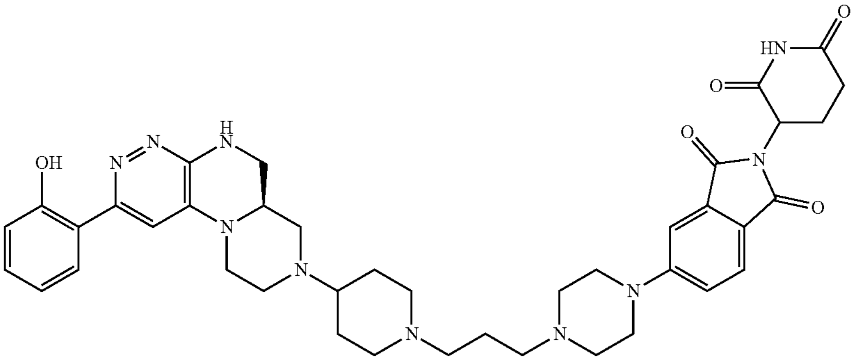 [SMILES: O=C1CCC(N2C(=O)c3ccc(N4CCN(CCCN5CCC(N6CCN7c8cc(-c9ccccc9O)nnc8NC[C@H]7C6)CC5)CC4)cc3C2=O)C(=O)N1]

To (S)-2-(8-(1-(3-(piperazin-1-yl)propyl)piperidin-4-yl)-6,6a,7,8,9,10-hexahydro-5H-pyrazino[1',2':4,5]pyrazino[2,3-c]pyridazin-2-yl)phenol; hydrochloride (5.54 mg, 0.01 mmol) in NMP (1 mL) in a microwave tube was added the N,N-Diisopropylethylamine (0.01 mL, 0.05 mmol), and 2-(2,6-dioxopiperidin-3-yl)-5-fluoroisoindole-1,3-dione (2.97 mg, 0.01 mmol). The reaction was heated at 150° C. for 2 h. The reaction mixture was directly purified without any workup on prep LC/MS using C-18 column to give 2-(2,6-dioxopiperidin-3-yl)-5-(4-(3-(4-((S)-2-(2-hydroxyphenyl)-5,6,6a,7,9,10-hexahydro-8H-pyrazino[1',2':4,5]pyrazino[2,3-c]pyridazin-8-yl) piperidin-1-yl)propyl)piperazin-1-yl) isoindoline-1,3-dione as its TFA salt (2.1 mg, 0.0021 mmol, 20% yield). LCMS m/z calcd for $C_{40}H_{49}N_{10}O_5$ $[M+H]^+$: 749.3; found: 749.2.

Example 12: 2-(2,6-Dioxopiperidin-3-yl)-5-(4-(2-(3-((S)-2-(2-hydroxyphenyl)-5,6,6a,7,9,10-hexahydro-8H-pyrazino[1',2':4,5]pyrazino[2,3-c]pyridazin-8-yl) pyrrolidin-1-yl)ethyl) piperazin-1-yl) isoindoline-1,3-dione Ex.12

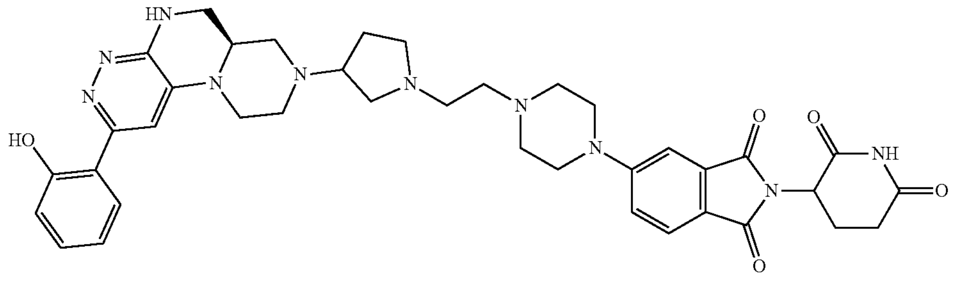

The title compound was prepared using procedure analogous to those described for Example 11, using 2-((6aS)-8-(1-(2-(piperazin-1-yl)ethyl)pyrrolidin-3-yl)-6,6a,7,8,9,10-hexahydro-5H-pyrazino[1',2':4,5]pyrazino[2,3-c]pyridazin-2-yl)phenol replacing (S)-2-(8-(1-(3-(piperazin-1-yl)propyl) piperidin-4-yl)-6,6a,7,8,9,10-hexahydro-5H-pyrazino[1',2': 4,5]pyrazino [2,3-c]pyridazin-2-yl)phenol and tert-butyl 4-(2-bromoethyl)piperazine-1-carboxylate replacing tert-butyl 4-(3-bromopropyl)piperazine-1-carboxylate in step 1. LCMS m/z calcd for $C_{38}H_{45}N_{10}O_5$ $[M+H]^+$: 721.3; found: 721.1.

Example 13: 2-(2,6-Dioxopiperidin-3-yl)-5-(3-(4-((S)-2-(2-hydroxyphenyl)-5,6,6a,7,9,10-hexahydro-8H-pyrazino[1',2':4,5]pyrazino[2,3-c]pyridazin-8-yl) piperidin-1-yl)pyrrolidin-1-yl) isoindoline-1,3-dione Ex.13

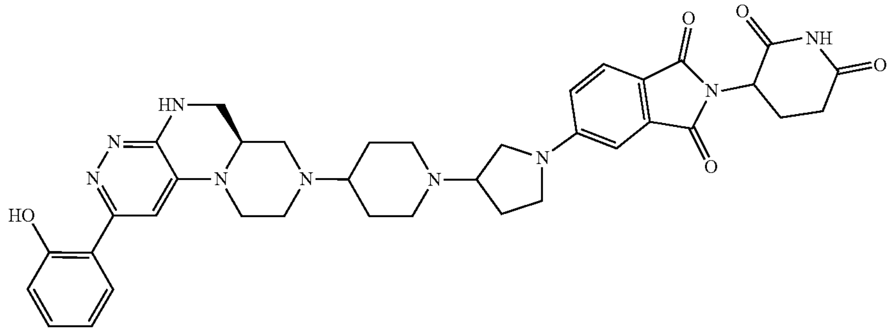

Step 1: 2-((6aS)-8-(1-(pyrrolidin-3-yl)piperidin-4-yl)-6,6a, 7,8,9,1O-hexahydro-5H-pyrazino [1',2':4,5] pyrazino[2,3-c]pyridazin-2-yl)phenol

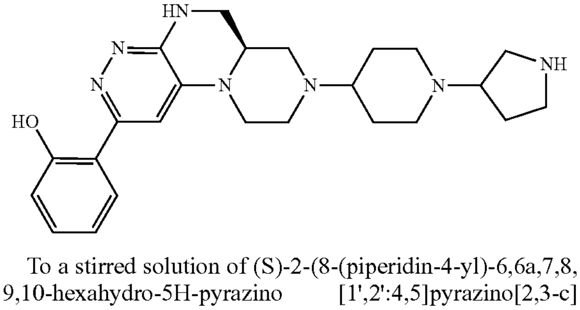

To a stirred solution of (S)-2-(8-(piperidin-4-yl)-6,6a,7,8,9,10-hexahydro-5H-pyrazino [1',2':4,5]pyrazino[2,3-c]pyridazin-2-yl)phenol (40.0 mg, 0.11 mmol) in methanol (3 mL) was added tert-butyl 3-oxopyrrolidine-1-carboxylate (44.5 mg, 0.24 mmol) and sodium triacetoxyborohydride (92.1 mg, 0.44 mmol) sequentially at rt. After 12 h, the volatiles were removed under reduced pressure and the residue was diluted with DCM. The organic layer was washed with saturated sodium bicarbonate, dried over sodium sulfate, filtered, and concentrated. The crude was purified by silica gel chromatography using 10% MeOH in DCM with 0.1% $NH_{40}H$. The purified compound was dissolved in Ethyl acetate (3 mL) and treated with 6M Hydrochloric acid (aq) (0.25 mL, 1.5 mmol). After 2 h, the reaction mixture was concentrated under vacuum to give 2-((6aS)-8-(1-(pyrrolidin-3-yl)piperidin-4-yl)-6,6a,7,8,9,10-hexahydro-5H-pyrazino[1',2':4,5]pyrazino[2,3-c]pyridazin-2-yl) phenol as its hydrochloride acid (25 mg, 0.053 mmol, 48.5% yield). LCMS m/z calcd for $C_{24}H_{34}N_7O$ $[M+H]^+$: 436.3; found: 436.1.

Step 2: 2-(2,6-dioxopiperidin-3-yl)-5-(3-(4-((S)-2-(2-hydroxyphenyl)-5,6,6a, 7,9,10-hexahydro-8H-pyrazino[1',2':4,5]pyrazino[2,3-c]pyridazin-8-yl) piperidin-1-yl)pyrrolidin-1-yl) isoindoline-1,3-dione The title compound was prepared using procedure analogous to those described for Example 11, Step 2, using 2-((6aS)-8-(1-(pyrrolidin-3-yl)piperidin-4-yl)-6,6a,7,8,9,10-hexahydro-5H-pyrazino[1',2':4,5]pyrazino[2,3-c] pyridazin-2-yl)phenol replacing (S)-2-(8-(1-(3-(piperazin-1-yl)propyl)piperidin-4-yl)-6,6a,7,8,9,10-hexahydro-5H-pyrazino[1',2':4,5]pyrazino [2,3-c]pyridazin-2-yl)phenol. LCMS m/z calcd for $C_{37}H_{42}N_9O_5$ [M+H]$^+$: 692.3; found: 692.1.

Example 14: 2-(2,6-dioxopiperidin-3-yl)-5-(4-((S)-2-(2-hydroxyphenyl)-5,6,6a,7,9,10-hexahydro-8H-pyrazino[1',2':4,5]pyrazino[2,3-c]pyridazin-8-yl)-[1,4'-bipiperidin]-1'-yl) isoindoline-1,3-dione Ex.14

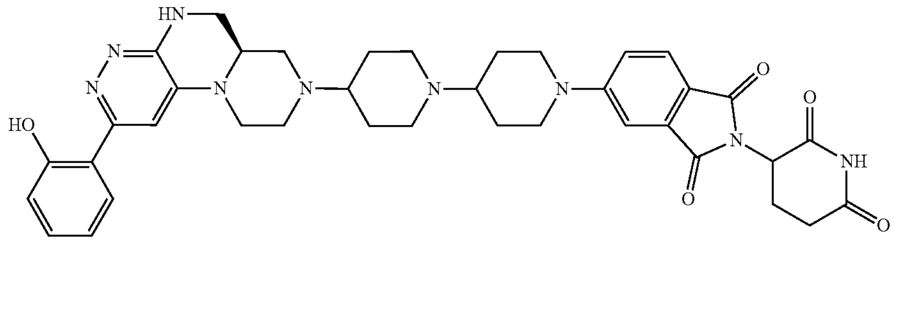

The title compound was prepared using procedure analogous to those described for Example 13, using tert-butyl 4-oxopiperidine-1-carboxylate replacing tert-butyl 3-oxo-pyrrolidine-1-carboxylate in step 1. LCMS m/z calcd for $C_{38}H_{44}N_9O_5$ [M+H]$^+$: 706.3; found: 706.2.

Example 15: 2-(2,6-Dioxopiperidin-3-yl)-5-(4-(2-(3-((S)-2-(2-hydroxyphenyl)-5,6,6a,7,9,10-hexahydro-8H-pyrazino[1',2':4,5]pyrazino[2,3-c]pyridazin-8-yl) pyrrolidin-1-yl)ethoxy) piperidin-1-yl) isoindoline-1,3-dione Ex.15

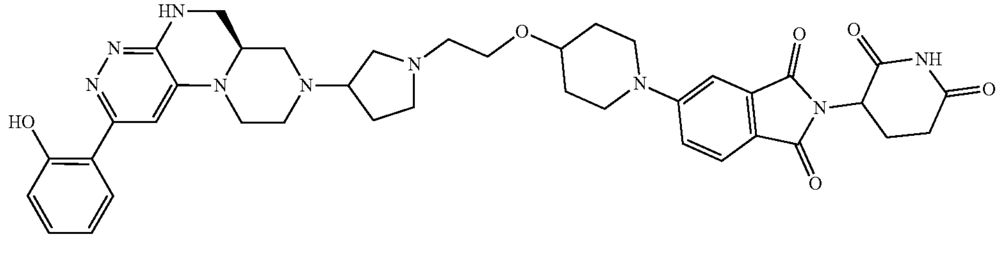

Step 1: 2-((6aS)-8-(1-(2-(piperidin-4-yloxy)ethyl) pyrrolidin-3-yl)-6,6a, 7,8,9,10-hexahydro-5H-pyrazino[1',2':4,5]pyrazino[2,3-c]pyridazin-2-yl) phenol

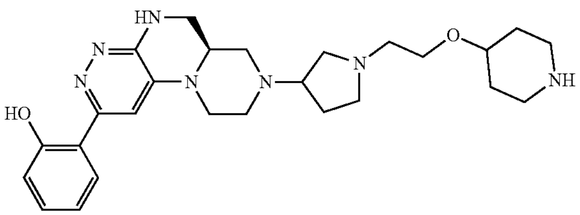 [SMILES: Oc1ccccc1-c1cc2c(nn1)NC[C@H]1CN(C3CCN(CCOC4CCNCC4)C3)CCN21]

The title compound was prepared using procedure analogous to those described for Intermediate 14, using 2-((6aS)-8-(pyrrolidin-3-yl)-6,6a,7,8,9,10-hexahydro-5H-pyrazino[1',2':4,5]pyrazino[2,3-c]pyridazin-2-yl)phenol replacing (S)-2-(8-(piperidin-4-yl)-6,6a,7,8,9,10-hexahydro-5H-pyrazino[1',2':4,5]pyrazino[2,3-c]pyridazin-2-yl)phenol in step 1. LCMS m/z calcd for $C_{26}H_{38}N_7O_2$ $(M+H)^+$: 480.3; found: 480.1.

Step 2: 2-(2,6-dioxopiperidin-3-yl)-5-(4-(2-(3-((S)-2-(2-hydroxyphenyl)-5,6,6a, 7,9,10-hexahydro-8H-pyrazino[1',2':4,5]pyrazino[2,3-c]pyridazin-8-yl) pyrrolidin-1-yl)ethoxy)piperidin-1-yl) isoindoline-1,3-dione The title compound was prepared using procedure analogous to those described for Example 11, Step 2, using 2-((6aS)-8-(1-(2-(piperidin-4-yloxy)ethyl)pyrrolidin-3-yl)-6,6a,7,8,9,10-hexahydro-5H-pyrazino[1',2':4,5]pyrazino[2,3-c]pyridazin-2-yl)phenol replacing (S)-2-(8-(1-(3-(piperazin-1-yl)propyl)piperidin-4-yl)-6,6a,7,8,9,10-hexahydro-5H-pyrazino [1',2':4,5]pyrazino[2,3-c]pyridazin-2-yl) phenol. LCMS m/z calcd for $C_{39}H_4N_9O_6(M+H)^+$: 736.3; found: 736.2.

Example 16: 2-(2,6-Dioxopiperidin-3-yl)-5-(4-(2-(4-((S)-2-(2-hydroxyphenyl)-5,6,6a,7,9,10-hexahydro-8H-pyrazino[1',2':4,5]pyrazino[2,3-c]pyridazin-8-yl) piperidin-1-yl)ethoxy) piperidin-1-yl) isoindoline-1,3-dione Ex.16

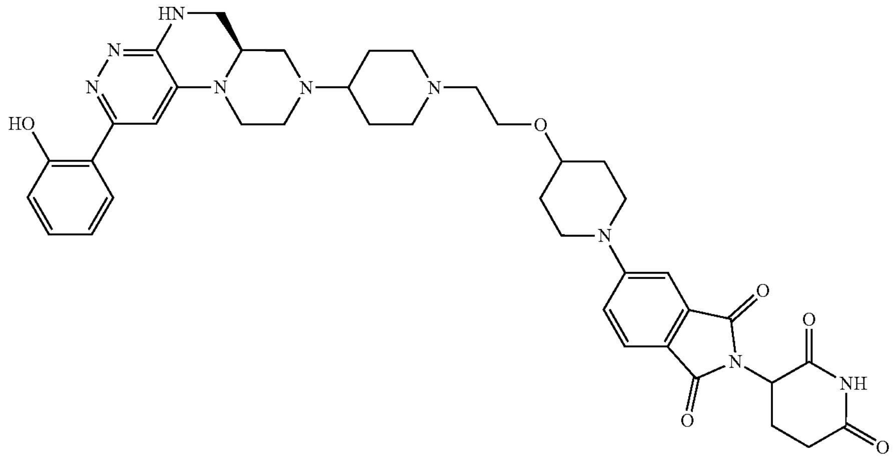

The title compound was prepared using procedure analogous to those described for Example 11, Step 2, using (S)-2-(8-(1-(2-(piperidin-4-yloxy)ethyl)piperidin-4-yl)-6,6a,7,8,9,10-hexahydro-5H-pyrazino[1',2':4,5]pyrazino[2,3-c]pyridazin-2-yl)phenol replacing (S)-2-(8-(1-(3-(piperazin-1-yl)propyl)piperidin-4-yl)-6,6a,7,8,9,10-hexahydro-5H-pyrazino[1',2':4,5]pyrazino [2,3-c]pyridazin-2-yl)phenol. LCMS m/z calcd for $C_{40}H_{48}N_9O_6$ $(M+H)^+$: 750.4; found: 750.2.

Example 17: 3-(6-(4-(2-(4-((S)-2-(2-hydroxyphenyl)-5,6,6a,7,9,10-hexahydro-8H-pyrazino [1',2':4,5] pyrazino[2,3-c]pyridazin-8-yl)piperidin-1-yl)ethyl) piperazin-1-yl)-1-oxoisoindolin-2-yl)piperidine-2,6-dione Ex.17

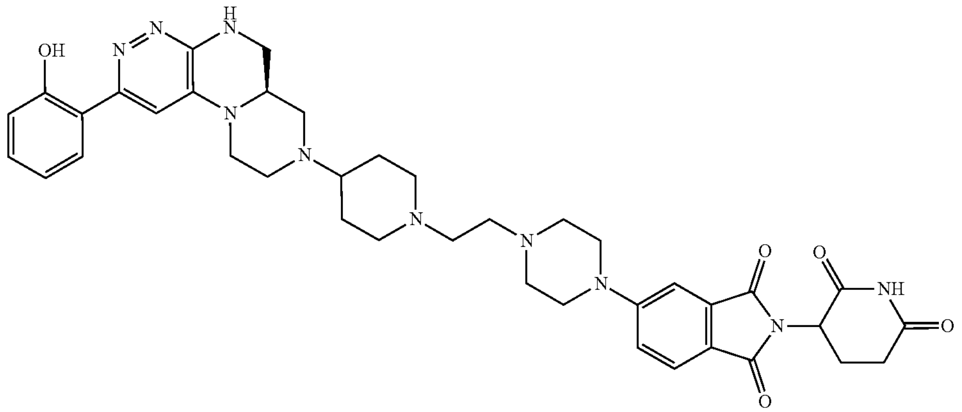

To a stirred solution of 3-(1-oxo-6-(piperazin-1-yl) isoindolin-2-yl)piperidine-2,6-dione; hydrochloride (6.1 mg, 0.02 mmol) and (S)-2-(4-(2-(2-hydroxyphenyl)-5,6,6a,7,9,10-hexahydro-8H-pyrazino[1',2':4,5]pyrazino[2,3-c] pyridazin-8-yl)piperidin-1-yl) acetaldehyde; dihydrochloride (6.5 mg, 0.01 mmol) in DCM (200 μL) and Methanol (10 μL) was added sodium acetate (6.5 mg, 0.08 mmol) at rt. After 10 min, sodium cyanoborohydride (4.3 mg, 0.07 mmol) was added. After another 1 hour, the reaction was diluted in 10 mL of MeOH and purified using prep-LCMS (5 m 10×3 cm Waters Sunfire C18, 5.3-25.3% acetonitrile in water (0.1% TFA), wet loaded) to yield 3-(6-(4-(2-(4-((S)-2-(2-hydroxyphenyl)-5,6,6a,7,9,10-hexahydro-8H-pyrazino [1',2':4,5]pyrazino[2,3-c]pyridazin-8-yl)piperidin-1-yl) ethyl)piperazin-1-yl)-1-oxoisoindolin-2-yl)piperidine-2,6-dione as its TFA salt (0.90 mg, 0.00063 mmol, 4.6% yield) as a white solid. LCMS m/z calcd for $C_{39}H_{49}N_{10}O_4$ $(M+H)^+$: 721.4; found 721.1.

Example 18: 3-(6-(3-(4-(2-((R)-2-(2-hydroxyphenyl)-5,6,6a,7,9,10-hexahydro-8H-pyrazino [1',2':4,5] pyrazino[2,3-c]pyridazin-8-yl)pyrimidin-5-yl)piperidin-1-yl)propyl)-9H-pyrido [2,3-b]indol-9-yl) piperidine-2,6-dione To a mixture of (R)-2-(8-(5-(piperidin-4-yl)pyrimidin-2-yl)-6,6a,7,8,9,10-hexahydro-5H-pyrazino[1',2':4,5]pyrazino [2,3-c]pyridazin-2-yl)phenol (50.9 mg, 0.098 mmol) in DMF (7.6 mL) was added 3-(9-(2,6-dioxopiperidin-3-yl)-9H-pyrido[2,3-b]indol-6-yl)propanal (~60% purity, 55 mg, 0.098 mmol), sodium triacetoxyborohydride (62 mg, 0.295 mmol) and acetic acid (17 μL, 0.295 mmol). The mixture was stirred at room temperature for 1 h. The mixture was diluted with water and MeCN and purified by prep-LCMS (5 m 10×3 cm Waters CSH Fluoro-Phenyl, 16-30% MeCN in $H_2O$ (0.1% TFA) to afford 3-(6-(3-(4-(2-((R)-2-(2-hydroxyphenyl)-5,6,6a,7,9,10-hexahydro-8H-pyrazino[1',2':4,5] pyrazino[2,3-c]pyridazin-8-yl)pyrimidin-5-yl)piperidin-1-yl) propyl)-9H-pyrido[2,3-b]indol-9-yl)piperidine-2,6-dione as its TFA slat (30 mg, 0.302 mmol, 31% yield). LCMS calcd. for $C_{43}H_{46}N_{11}O_3$ $[M+H]^+$ m/z=764.4; found: 764.2. $^1H$ NMR (400 MHz, DMSO) δ 14.19 (bs, 1H), 11.13 (s, 1H), 9.33 (bs, 1H), 8.52 (dd, J=7.7, 1.6 Hz, 1H), 8.43 (dd, J=4.8, 1.8 Hz, 1H), 8.34 (s, 2H), 8.10 (s, 2H), 7.64-7.45 (m, 2H), 7.46-7.33 (m, 2H), 7.28 (dd, J=7.7, 4.9 Hz, 1H), 7.20 (s, 1H), 7.07-6.92 (m, 2H), 6.04 (bs, 1H), 4.72 (d, J=11.2 Hz, 1H), 4.67-4.58 (m, 1H), 4.29-4.18 (m, 1H), 3.74-3.57 (m, Ex.18

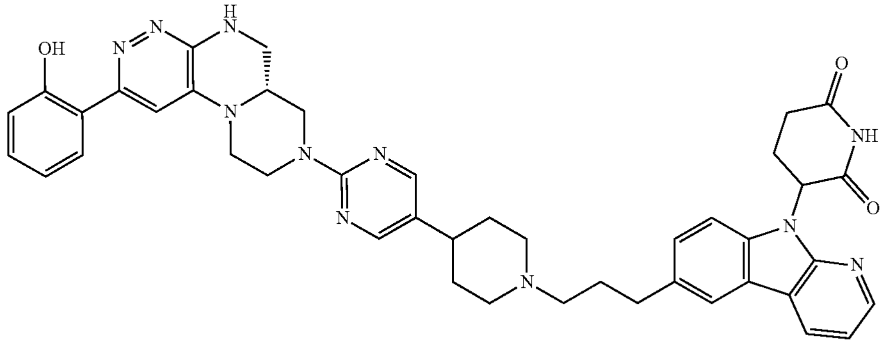

4H), 3.40-3.21 (m, 4H), 3.20-3.10 (m, 2H), 3.10-2.87 (m, 5H), 2.84 (t, J=7.2 Hz, 2H), 2.79-2.68 (m, 2H), 2.17-1.95 (m, 5H), 1.92-1.74 (m, 2H).

-

Example 19: 3-(6-(3-(4-((S)-2-(2-hydroxyphenyl)-5,6,6a,7,9,10-hexahydro-8H-pyrazino [1',2':4,5]pyrazino[2,3-c]pyridazin-8-yl)piperidin-1-yl)propyl)-9H-pyrido[2,3-b]indol-9-yl) piperidine-2,6-dione Ex.19

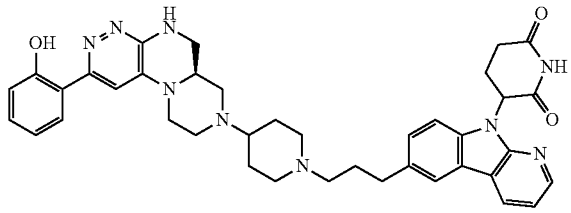

The title compound was prepared using procedure analogous to those described for Example 18, using (S)-2-(8-(piperidin-4-yl)-6,6a,7,8,9,10-hexahydro-5H-pyrazino[1',2':4,5]pyrazino[2,3-c]pyridazin-2-yl)phenol replacing (R)-2-(8-(5-(piperidin-4-yl)pyrimidin-2-yl)-6,6a,7,8,9,10-hexahydro-5H-pyrazino[1',2':4,5]pyrazino[2,3-c]pyridazin-2-yl)phenol. LCMS calcd. for $C_{39}H_{44}N_9O_3$ $[M+H]^+$ m/z=686.4; found: 686.2.

Example 20: 3-(6-(3-(4-((S)-2-(2-hydroxyphenyl)-5,6,6a,7,9,10-hexahydro-8H-pyrazino [1',2':4,5]pyrazino[2,3-c]pyridazin-8-yl)-[1,4'-bipiperidin]-1'-yl)propyl)-9H-pyrido[2,3-b]indol-9-yl)piperidine-2,6-dione Ex.20

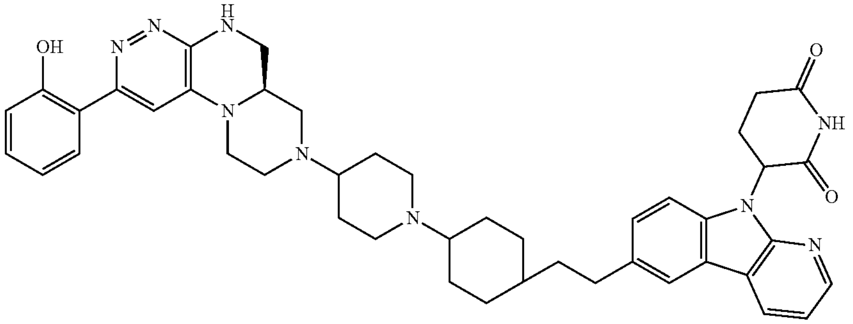

The title compound was prepared using procedure analogous to those described for Example 18, using (S)-2-(8-([1,4'-bipiperidin]-4-yl)-6,6a,7,8,9,10-hexahydro-5H-pyrazino[1',2':4,5]pyrazino[2,3-c]pyridazin-2-yl)phenol replacing (R)-2-(8-(5-(piperidin-4-yl)pyrimidin-2-yl)-6,6a,7,8,9,10-hexahydro-5H-pyrazino[1',2':4,5]pyrazino[2,3-c]pyridazin-2-yl)phenol. LCMS calcd. for $C_{44}H_{53}N_{10}O_3[M+H]^+$ m/z=769.4; found: 769.2.

Example 21: 3-(6-(3-(4-(3-((S)-2-(2-hydroxyphenyl)-5,6,6a,7,9,10-hexahydro-8H-pyrazino [1',2':4,5] pyrazino[2,3-c]pyridazin-8-yl)azetidin-1-yl)piperidin-1-yl)propyl)-9H-pyrido[2,3-b]indol-9-yl) piperidine-2,6-dione Ex.21

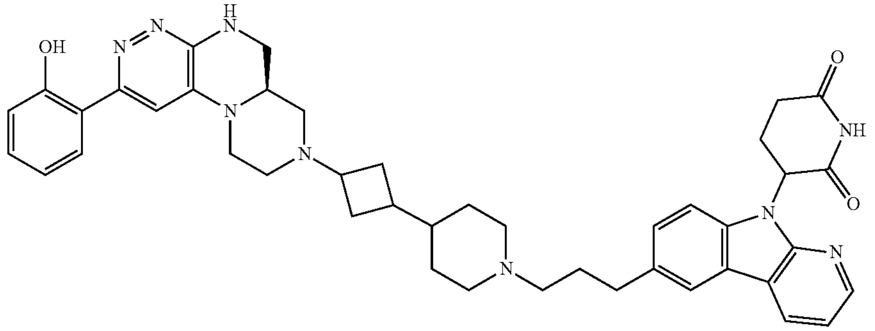

Step 1: tert-butyl (S)-3-(2-(2-hydroxyphenyl)-5,6,6a, 7,9,10-hexahydro-8H-pyrazino[1',2':4,5]pyrazino [2,3-c]pyridazin-8-yl)azetidine-1-carboxylate

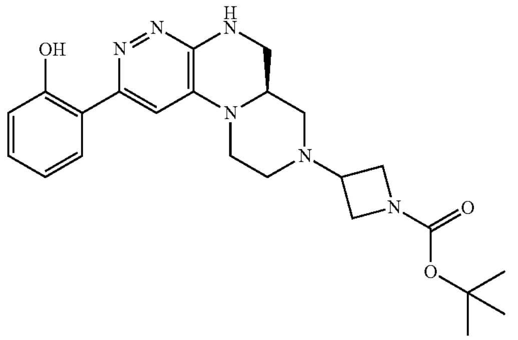 [SMILES: CC(C)(C)OC(=O)N1CC(N2CCN3c4cc(-c5ccccc5O)nnc4NC[C@H]3C2)C1]

A vial with septum containing a solution of (R)-2-(6,6a,7,8,9,10-hexahydro-5H-pyrazino [1',2':4,5]pyrazino[2,3-c] pyridazin-2-yl)phenol (20 mg, 0.071 mmol) and tert-butyl 3-oxo-azetidine-1-carboxylate (12.1 mg, 0.071 mmol) in DCM (1 mL) was charged with acetic acid (4 μL, 0.071 mmol) and sodium triacetoxyborohydride (45 mg, 0.212 mmol). The mixture was stirred at room temperature overnight then charged with additional tert-butyl 3-oxoazetidine-1-carboxylate (24 mg, 0.14 mmol), sodium triacetoxyborohydride (30 mg, 0.14 mmol) and DMF (1 mL). The reaction was stirred at RT for 12-18 h. The reaction mixture was diluted with water and MeCN and purified by prep-LCMS (Waters SunFire C18, 5 μm particle size, 30×100 mm, mobile phase: Aq(0.1% TFA)/ACN @ 60 mL/min, gradient: 13.9-33.9% ACN over 5 min) to afford tert-butyl (S)-3-(2-(2-hydroxyphenyl)-5,6,6a,7,9,10-hexahydro-8H-pyrazino [1',2':4,5]pyrazino[2,3-c]pyridazin-8-yl)azetidine-1-carboxylate as its TFA salt (21.5 mg, 0.039 mmol, 55% yield). LCMS calcd. for $C_{23}H_{31}N_6O_3$ $[M+H]^+$ m/z=439.2; found: 439.1.

Step 2: (S)-2-(8-(azetidin-3-yl)-6,6a, 7,8,9,10-hexahydro-5H-pyrazino[1',2':4,5]pyrazino[2,3-c] pyridazin-2-yl)phenol

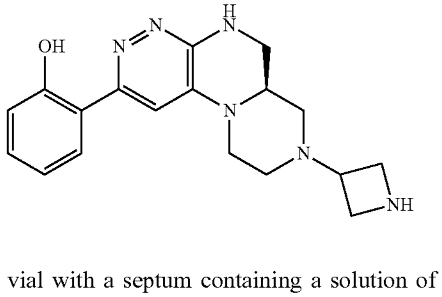

A vial with a septum containing a solution of tert-butyl (S)-3-(2-(2-hydroxyphenyl)-5,6,6a,7,9,10-hexahydro-8H-pyrazino[1',2':4,5]pyrazino[2,3-c]pyridazin-8-yl)azetidine-1-carboxylate (21.5 mg, 0.039 mmol) in DCM (1 mL) was charged with trifluoroacetic acid (60 μL, 0.778 mmol). The reaction solution was stirred overnight and then concentrated under reduced pressure to yield (S)-2-(8-(azetidin-3-yl)-6,6a,7,8,9,10-hexahydro-5H-pyrazino[1',2':4,5]pyrazino [2,3-c]pyridazin-2-yl)phenol as its TFA salt (assumed quantitative yield, 0.039 mmol). LCMS calcd. for $C_{18}H_{23}N_6O$ $(M+H)^+$ m/z: 339.2; found: 339.0.

Step 3: tert-butyl (S)-4-(3-(2-(2-hydroxyphenyl)-5,6,6a,7,9,10-hexahydro-8H-pyrazino[1',2':4,5]pyrazino[2,3-c]pyridazin-8-yl)azetidin-1-yl)piperidine-1-carboxylate

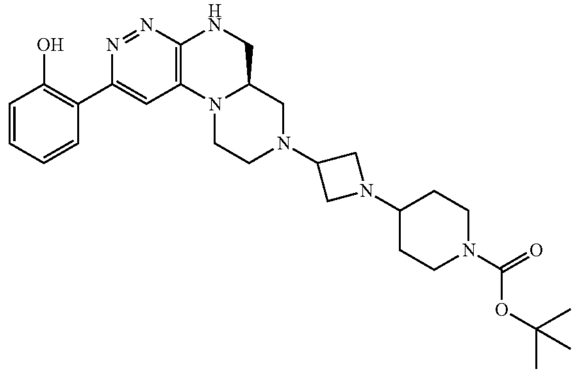 [SMILES: CC(C)(C)OC(=O)N1CCC(N2CC(N3CCN4c5cc(-c6ccccc6O)nnc5NC[C@H]4C3)C2)CC1]

A vial with a septum containing a solution of tert-butyl (S)-3-(2-(2-hydroxyphenyl)-5,6,6a,7,9,10-hexahydro-8H-pyrazino[1',2':4,5]pyrazino[2,3-c]pyridazin-8-yl)azetidine-1-carboxylate (21.5 mg, 0.039 mmol) and tert-butyl 4-oxopiperidine-1-carboxylate (39 mg, 0.195 mmol) in DMF (1.3 mL) was charged with acetic acid (2.2 μL, 0.039 mmol) and sodium triacetoxyborohydride (41 mg, 0.195 mmol). The reaction mixture was stirred at RT overnight and then diluted with water and MeCN and purified by prep-LCMS (Waters SunFire C18, 5 μm particle size, 30×100 mm, mobile phase: Aq(0.1% TFA)/ACN @ 60 mL/min, gradient: 12.9-32.9% ACN over 5 min) to afford tert-butyl (S)-4-(3-(2-(2-hydroxyphenyl)-5,6,6a,7,9,10-hexahydro-8H-pyrazino[1',2':4,5]pyrazino[2,3-c]pyridazin-8-yl)azetidin-1-yl)piperidine-1-carboxylate as its TFA salt (6.8 mg, 0.009 mmol, 23% yield). LCMS calcd. for $C_{28}H_{40}N_7O_3$ $[M+H]^+$ m/z=522.3; found: 522.3.

Step 4: (S)-2-(8-(1-(piperidin-4-yl)azetidin-3-yl)-6,6a,7,8,9,10-hexahydro-5H-pyrazino[1',2':4,5]pyrazino[2,3-c]pyridazin-2-yl)phenol

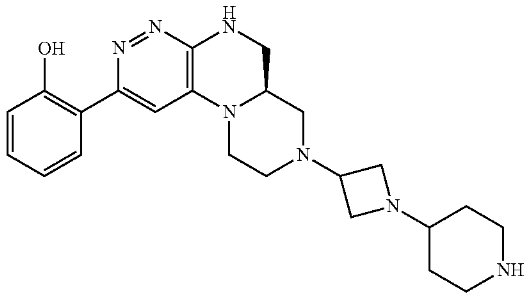 [SMILES: Oc1ccccc1-c1cc2c(nn1)NC[C@H]1CN(C3CN(C4CCNCC4)C3)CCN21]

A vial with a septum containing a solution of tert-butyl (S)-3-(2-(2-hydroxyphenyl)-5,6,6a,7,9,10-hexahydro-8H-pyrazino[1',2':4,5]pyrazino[2,3-c]pyridazin-8-yl)azetidine-1-carboxylate (6.8 mg, 0.009 mmol) in DCM (1 mL) was charged with trifluoroacetic acid (14 μL, 0.181 mmol). The reaction solution was stirred at RT overnight and then concentrated under reduced pressure to yield (S)-2-(8-(1-(piperidin-4-yl)azetidin-3-yl)-6,6a,7,8,9,10-hexahydro-5H-pyrazino[1',2':4,5]pyrazino[2,3-c]pyridazin-2-yl)phenol as its TFA salt (assumed quantitative yield, 0.009 mmol). LCMS calcd. for $C_{23}H_{32}N_7O$ $(M+H)^+$ m/z: 422.3; found: 422.2.

Step 4: 3-(6-(3-(4-(3-((S)-2-(2-hydroxyphenyl)-5,6,6a,7,9,10-hexahydro-8H-pyrazino[1',2':4,5]pyrazino[2,3-c]pyridazin-8-yl)azetidin-1-yl)piperidin-1-yl)propyl)-9H-pyrido[2,3-b]indol-9-yl)piperidine-2,6-dione The title compound was prepared using procedure analogous to those described for Example 18, using (S)-2-(8-(1-(piperidin-4-yl)azetidin-3-yl)-6,6a,7,8,9,10-hexahydro-5H-pyrazino[1',2':4,5]pyrazino[2,3-c]pyridazin-2-yl)phenol replacing (R)-2-(8-(5-(piperidin-4-yl) pyrimidin-2-yl)-6,6a,7,8,9,10-hexahydro-5H-pyrazino[1',2':4,5]pyrazino[2,3-c]pyridazin-2-yl) phenol. LCMS calcd. for $C_{42}H_{49}N_{10}O_3[M+H]^+$ m/z=741.4; found: 741.2.

Example 22: 3-(6-(3-(4-(2-((S)-2-(2-hydroxyphenyl)-5,6,6a,7,9,10-hexahydro-8H-pyrazino [1',2':4,5]pyrazino[2,3-c]pyridazin-8-yl)ethyl)piperazin-1-yl)propyl)-9H-pyrido[2,3-b]indol-9-yl)piperidine-2,6-dione Ex.22

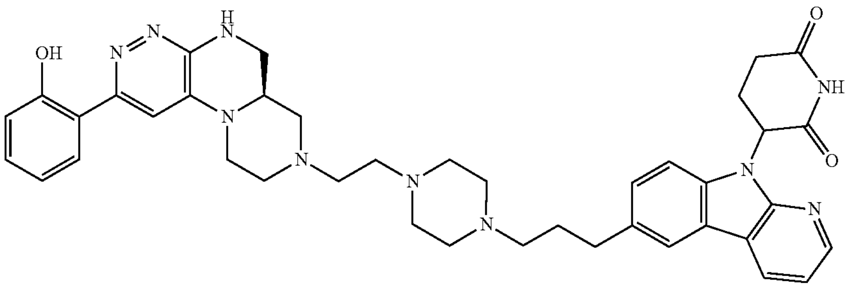

Step 1: tert-butyl (S)-4-(2-(2-(2-hydroxyphenyl)-5,6,6a, 7,9,10-hexahydro-8H-pyrazino[1',2':4,5]pyrazino[2,3-c]pyridazin-8-yl)ethyl)piperazine-1-carboxylate

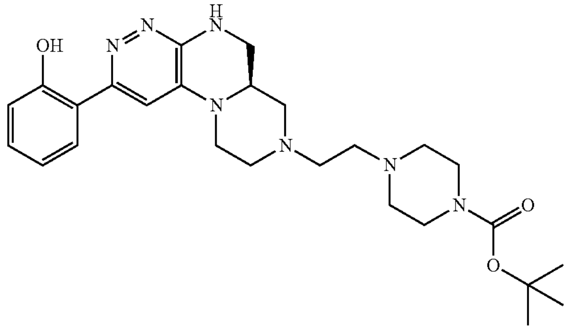 [SMILES: CC(C)(C)OC(=O)N1CCN(CCN2CCN3c4cc(-c5ccccc5O)nnc4NC[C@H]3C2)CC1]

To a mixture of (S)-2-(8-(1-(piperidin-4-yl)azetidin-3-yl)-6,6a,7,8,9,10-hexahydro-5H-pyrazino[1',2':4,5]pyrazino[2,3-c]pyridazin-2-yl)phenol tris(2,2,2-trifluoroacetate) (15.0 mg, 0.053 mmol) and tert-butyl 4-(2-oxoethyl)piperazine-1-carboxylate (16.3 mg, 0.071 mmol) in MeOH (2 mL) was added sodium triacetoxyborohydride (33.7 mg, 0.159 mmol). The mixture was stirred at rt for 1 h then charged with additional tert-butyl 4-(2-oxoethyl)piperazine-1-carboxylate (18.0 mg, 0.079 mmol) and sodium triacetoxyborohydride (35.0 mg, 0.165 mmol). The mixture was stirred for 20 min then diluted with water and MeOH/MeCN and purified by prep-LCMS (Waters SunFire C18, 5 μm particle size, 30×100 mm, mobile phase: Aq(0.1% TFA)/ACN @ 60 mL/min, gradient: 12.6-32.6% ACN over 5 min) to afford tert-butyl (S)-4-(2-(2-(2-hydroxyphenyl)-5,6,6a,7,9,10-hexahydro-8H-pyrazino[1',2':4,5]pyrazino[2,3-c]pyridazin-8-yl)ethyl)piperazine-1-carboxylateas as its TFA salt (15.6 mg, 0.022 mmol, 41% yield). LCMS calcd for $C_{26}H_{38}N_7O_3$ $[M+H]^+$ m/z=496.3; found: 496.2.

Step 2: (S)-2-(8-(2-(piperazin-1-yl)ethyl)-6,6a, 7,8,9,10-hexahydro-5H-pyrazino[1',2':4,5]pyrazino[2,3-c]pyridazin-2-yl)phenol

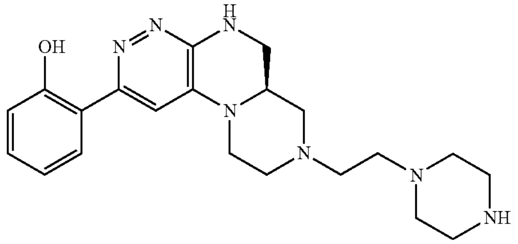 [SMILES: Oc1ccccc1-c1cc2c(nn1)NC[C@H]1CN(CCN3CCNCC3)CCN21]

A vial with a septum containing a solution of tert-butyl (S)-4-(2-(2-(2-hydroxyphenyl)-5,6,6a,7,9,10-hexahydro-8H-pyrazino[1',2':4,5]pyrazino[2,3-c]pyridazin-8-yl)ethyl)piperazine-1-carboxylateas (10.9 mg, 0.022 mmol) in DCM (1 mL) was charged with trifluoroacetic acid (33 μL, 0.431 mmol). The reaction solution was stirred at rt overnight and then concentrated under reduced pressure to yield (S)-2-(8-(2-(piperazin-1-yl)ethyl)-6,6a,7,8,9,10-hexahydro-5H-pyrazino[1',2':4,5]pyrazino[2,3-c]pyridazin-2-yl)phenol as its TFA salt (assumed quantitative yield, 0.022 mmol). LCMS calcd for $C_{21}H_{30}N_7O$ $(M+H)^+$ m/z: 396.3; found: 396.2.

Step 3: 3-(6-(3-(4-(2-((S)-2-(2-hydroxyphenyl)-5,6,6a, 7,9,10-hexahydro-8H-pyrazino[1',2':4,5]pyrazino[2,3-c]pyridazin-8-yl)ethyl)piperazin-1-yl)propyl)-9H-pyrido[2,3-b]indol-9-yl) piperidine-2,6-dione The title compound was prepared using procedure analogous to those described for Example 18, using (S)-2-(8-(2-(piperazin-1-yl)ethyl)-6,6a,7,8,9,10-hexahydro-5H-pyrazino [1',2':4,5]pyrazino[2,3-c]pyridazin-2-yl)phenol replacing (R)-2-(8-(5-(piperidin-4-yl)pyrimidin-2-yl)-6,6a,7,8,9,10-hexahydro-5H-pyrazino[1',2':4,5]pyrazino[2,3-c]pyridazin-2-yl)phenol. LCMS calcd for $C_{42}H_{49}N_{10}O_3[M+H]^+$ m/z=715.4; found: 715.2.

Example 23: 3-(6-(3-(4-(2-(((6aR,8S)-2-(2-hydroxyphenyl)-5,6,6a,7,8,9-hexahydro-pyrrolo[1',2':4,5]pyrazino[2,3-c]pyridazin-8-yl)oxy)pyrimidin-5-yl)piperidin-1-yl)propyl)-9H-pyrido[2,3-b]indol-9-yl)piperidine-2,6-dione Ex.23

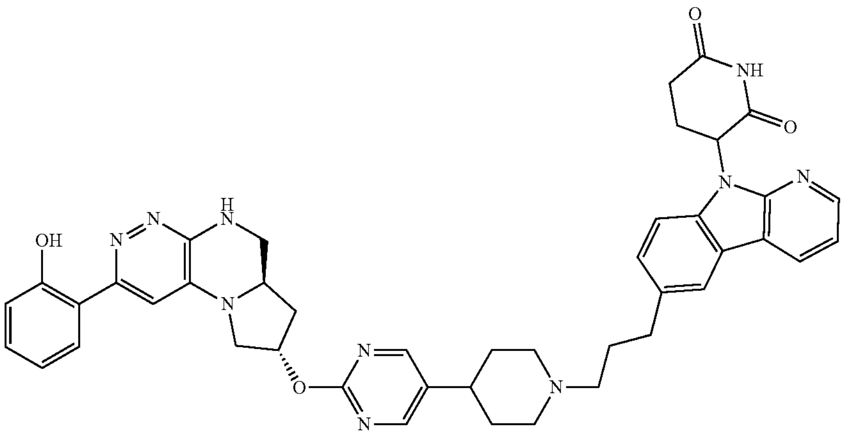

Step 1: (2R,4S)-1-(tert-butoxycarbonyl)-4-((tert-butyldimethylsilyl)oxy)pyrrolidine-2-carboxylic acid

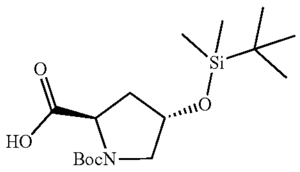 [SMILES: CC(C)(C)OC(=O)N1C[C@@H](O[Si](C)(C)C(C)(C)C)C[C@@H]1C(=O)O]

A round-bottomed flask containing a solution of (2R,4S)-1-(tert-butoxycarbonyl)-4-hydroxypyrrolidine-2-carboxylic acid (1.0 g, 4.3 mmol) and imidazole (1.47 g, 21.6 mmol) in DCM (7 mL) and DMF (1.4 mL) was charged with tert-butyldimethylsilyl chloride (1.43 g, 9.51 mmol). The reaction mixture was stirred at rt for 18 h, then poured into water, extracted with DCM (25 mL), and concentrated under reduced pressure. The residue was dissolved in 20% MTBE/hexanes (v/v) (50 mL), washed with brine and concentrated. The residue was dissolved in MeOH (7 mL) and THF (7 mL). Lithium hydroxide (176 mg) in water (9 mL) was added and the mixture was stirred at rt for three hours. The mixture was poured into water, acidified to pH ~2 with 1 N HCl, extracted with 20% MTBE/hexanes (v/v) (3×50 mL), and washed with brine (50 mL). The organic fraction was dried with $MgSO_4$, filtered and concentrated to give (2R, 4S)-1-(tert-butoxycarbonyl)-4-((tert-butyldimethylsilyl)oxy)pyrrolidine-2-carboxylic acid (assumed quantitative yield, 4.3 mmol). LCMS calcd for $C_{11}H_{24}NO_3Si$ $(M+2H-Boc)^+$ m/z: 246.2; found: 246.1.

Step 2: tert-butyl (2R,4S)-4-((tert-butyldimethylsilyl)oxy)-2-(hydroxymethyl)pyrrolidine-1-carboxylate

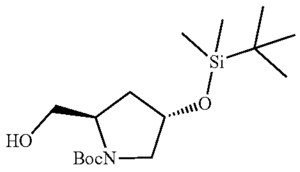 [SMILES: CC(C)(C)OC(=O)N1C[C@@H](O[Si](C)(C)C(C)(C)C)C[C@@H]1CO]

A round-bottomed flask containing a solution of (2R,4S)-1-(tert-butoxycarbonyl)-4-((tert-butyldimethylsilyl)oxy) pyrrolidine-2-carboxylic acid (1.5 g, 4.3 mmol) in THF (16 mL) at 0° C. was charged with $BH_3 \cdot SMe_2$ (0.82 mL, 8.6 mmol) dropwise. The solution was allowed to warm to rt and stir for 24 h. The reaction was quenched with saturated aqueous $NH_4Cl$, extracted with EtOAc (2×25 mL), washed with brine (25 mL), dried with $MgSO_4$, filtered, and concentrated to give tert-butyl (2R,4S)-4-((tert-butyldimethylsilyl)oxy)-2-(hydroxymethyl)pyrrolidine-1-carboxylate (assumed quantitative yield, 4.3 mmol). LCMS calcd for $C_{12}H_{26}NO_4Si$ $(M+2H-tBu)^+$ m/z: 276.2; found: 276.0.

Step 3: tert-butyl (2R,4S)-4-((tert-butyldimethylsilyl)oxy)-2-((tosyloxy)methyl)pyrrolidine-1-carboxylate

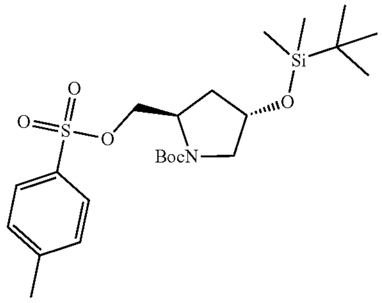 [SMILES: Cc1ccc(S(=O)(=O)OC[C@H]2C[C@H](O[Si](C)(C)C(C)(C)C)CN2C(=O)OC(C)(C)C)cc1]

To a solution of tert-butyl (2R,4S)-4-((tert-butyldimethylsilyl)oxy)-2-(hydroxymethyl) pyrrolidine-1-carboxylate (1.4 g, 4.3 mmol) and 4-methylbenzenesulfonyl chloride (1.0 g, 5.4 mmol) in DCM (8.6 mL) at 0° C. was added pyridine (2.6 mL). The reaction was allowed to warm to rt and stirred for 23 h. The reaction was diluted with DCM, washed with water (2×50 mL), 10 wt % citric acid (2×50 mL), brine (50 mL), and dried with $MgSO_4$. The mixture was filtered and concentrated. The residue was purified by column chromatography on a silica gel column (0-100% EtOAc/hexanes) to give tert-butyl (2R,4S)-4-((tert-butyldimethylsilyl)oxy)-2-((tosyloxy)methyl) pyrrolidine-1-carboxylate (1.6 g, 3.3 mmol, 76% yield) as a clear oil. LCMS calcd for $C_{18}H_{32}NO_4SSi$ (M+2H-Boc)+m/z: 386.2; found: 386.1.

Step 4: tert-butyl (2R,4S)-2-(azidomethyl)-4-((tert-butyldimethylsilyl)oxy)pyrrolidine-1-carboxylate

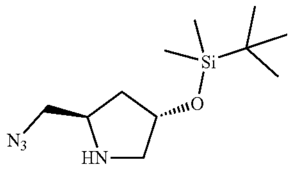 [SMILES: CC(C)(C)[Si](C)(C)O[C@@H]1CN[C@@H](CN=[N+]=[N-])C1]

To a solution of tert-butyl (2R,4S)-4-((tert-butyldimethylsilyl)oxy)-2-((tosyloxy) methyl)pyrrolidine-1-carboxylate (500 mg, 1.0 mmol) in DMSO (5.1 mL) was added sodium azide (170 mg, 2.6 mmol). The reaction mixture was stirred at 65° C. for 22 h. The reaction mixture was allowed to cool to rt, diluted with MTBE, then washed with water (4×50 mL) and brine (50 mL). The organic layer was dried over $MgSO_4$, filtered, and concentrated to afford tert-butyl (2R, 4S)-2-(azidomethyl)-4-((tert-butyldimethylsilyl)oxy)pyrrolidine-1-carboxylate (343 mg, 94% yield) as a clear oil which was taken on without further purification. LCMS calcd for $C_{12}H_{25}N_4O_3Si$ $(M+2H-tBu)^+$ m/z: 301.2; found 301.0.

Step 5: (2R,4S)-2-(azidomethyl)-4-((tert-butyldimethylsilyl)oxy)pyrrolidine

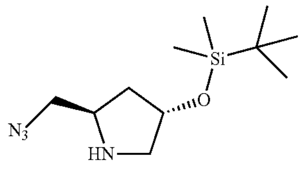 [SMILES: CC(C)(C)[Si](C)(C)O[C@@H]1CN[C@@H](CN=[N+]=[N-])C1]

To a solution of tert-butyl (2R,4S)-2-(azidomethyl)-4-((tert-butyldimethylsilyl)oxy) pyrrolidine-1-carboxylate (343 mg, 0.96 mmol) in DCM (1.5 mL) was added trifluoroacetic acid (1.5 mL, 19 mmol). The reaction mixture was stirred at rt for 1 h and basified to pH~12 with 2 N $NaOH_{(aq)}$. The reaction mixture was extracted with DCM (3×25 mL), washed with brine (25 mL), dried with $MgSO_4$, filtered and concentrated to afford (2R,4S)-2-(azidomethyl)-4-((tert-butyldimethylsilyl)oxy)pyrrolidine (165 mg, 67% yield) as a clear oil which was taken on without further purification. LCMS calcd for $C_{11}H_{25}N_4OSi$ $(M+H)^+$ m/z: 257.2; found: 257.1.

Step 4: 4-((2R,4S)-2-(azidomethyl)-4-((tert-butyldimethylsilyl)oxy)pyrrolidin-1-yl)-3,6-dichloropyridazine

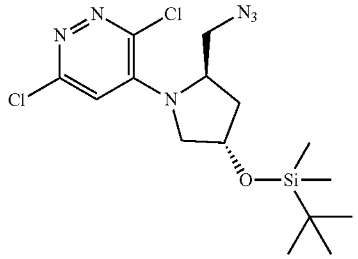 [SMILES: CC(C)(C)[Si](C)(C)O[C@H]1C[C@H](CN=[N+]=[N-])N(c2cc(Cl)nnc2Cl)C1]

To a solution of (2R,4S)-2-(azidomethyl)-4-((tert-butyldimethylsilyl)oxy)pyrrolidine (1.48 g, 5.8 mmol, 1.5 eq) and 3,4,6-trichloropyridazine (124 mg, 0.68 mmol) in DMF (1 mL) was added N,N-diisopropylethylamine (120 μL, 0.71 mmol). The reaction was stirred at 80° C. for 20 h, then poured into water and extracted with EtOAc (2×25 mL). The combined organic layers were washed with water (4×50 mL), then brine (50 mL), then dried with $MgSO_4$ and filtered. The filtrate was concentrated to afford 4-((2R,4S)-2-(azidomethyl)-4-((tert-butyldimethylsilyl)oxy) pyrrolidin-1-yl)-3,6-dichloropyridazine (144 mg, 56% yield) which was taken on without further purification. LCMS calcd for $C_{15}H_{25}C_{12}N_6OSi$ $(M+H)^+$ m/z: 403.1/405.1; found: 403.0/405.0. $^1H$ NMR (400 MHz, DMSO) δ 7.41 (s, 1H), 4.59 (tt, J=7.6, 3.7 Hz, 1H), 4.56-4.51 (m, 1H), 3.93 (dd, J=11.3, 3.4 Hz, 1H), 3.69 (dd, J=13.2, 4.5 Hz, 1H), 3.39-3.28 (m, 5H), 2.08-1.95 (m, 2H), 0.77 (s, 9H), 0.06 (s, 3H).

Step 5: (6aR,8S)-8-((tert-butyldimethylsilyl)oxy)-2-chloro-5,6,6a, 7,8,9-hexahydropyrrolo [1',2':4,5] pyrazino[2,3-c]pyridazine

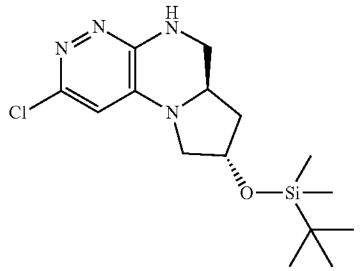 [SMILES: CC(C)(C)[Si](C)(C)O[C@H]1C[C@@H]2CNc3nnc(Cl)cc3N2C1]

To a solution of 4-((2R,4S)-2-(azidomethyl)-4-((tert-butyldimethylsilyl)oxy)pyrrolidin-1-yl)-3,6-dichloropyridazine (144 mg, 0.36 mmol) in THF (4 mL) was added triphenylphosphine (103 mg, 0.39 mmol). The reaction mixture was stirred at 60° C. for 80 min. Water (0.4 mL) and N,N-diisopropylethylamine (190 μL, 1.1 mmol) were added and the reaction mixture was stirred at 60° C. for 24 h. The mixture was allowed to cool to rt and then was extracted with EtOAc (3×25 mL). The combined organic layers were washed with brine (25 mL), dried with $MgSO_4$, filtered and concentrated to afford tert-butyl (6aR,8S)-8-((tert-butyldimethylsilyl)oxy)-2-chloro-5,6,6a, 7,8,9-hexahydropyrrolo[1',2':4,5]pyrazino[2,3-c]pyridazine (120 mg crude, 0.36 mmol, assumed quant. yield) which was taken on without further purification. LCMS calcd for $C_{15}H_{26}ClN_7OSi$ $(M+H)^+$ m/z: 341.2/343.2; found 341.0/342.9.

Step 6: tert-butyl (6aR,8S)-8-((tert-butyldimethylsilyl)oxy)-2-chloro-6a, 7,8,9-tetrahydropyrrolo [1',2':4,5]pyrazino[2,3-c]pyridazine-5(6H)-carboxylate

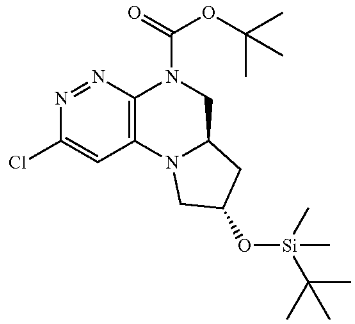 [SMILES: CC(C)(C)OC(=O)N1C[C@H]2C[C@H](O[Si](C)(C)C(C)(C)C)CN2c2cc(Cl)nnc21]

To a mixture of tert-butyl (6aR,8S)-8-((tert-butyldimethylsilyl)oxy)-2-chloro-5,6,6a,7,8,9-hexahydropyrrolo[1',2':4,5]pyrazino[2,3-c]pyridazine (120 mg, 0.36 mmol, 1.0 eq) in DCM (3.6 mL) was added di-tert-butyl dicarbonate (234 mg, 1.1 mmol) and 4-(dimethylamino)pyridine (43.6 mg, 0.36 mmol). The mixture was stirred at rt for 1 h then charged with additional di-tert-butyl dicarbonate (156 mg, 0.71 mmol) and 4-(dimethylamino)pyridine (21.8 mg, 0.18 mmol). The mixture was stirred at rt for 20 min then concentrated under reduced pressure and purified via silica gel chromatography (0-100% EtOAc/hexanes) to afford tert-butyl (6aR,8S)-8-((tert-butyl-dimethylsilyl)oxy)-2-chloro-6a,7,8,9-tetrahydropyrrolo[1',2':4,5]pyrazino[2,3-c]

pyridazine-5(6H)-carboxylate (97 mg, 0.22 mmol, 62% yield) as a white solid. LCMS calcd for $C_{20}H_{34}ClN_4O_3Si$ $(M+H)^+$ m/z=441.2/443.2; found: 441.1/443.0.

Step 7: tert-butyl (6aR,8S)-2-chloro-8-hydroxy-6a, 7,8,9-tetrahydropyrrolo[1',2':4,5]pyrazino [2,3-c] pyridazine-5(6H)-carboxylate

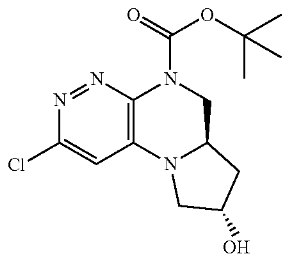 [SMILES: CC(C)(C)OC(=O)N1C[C@H]2C[C@H](O)CN2c2cc(Cl)nnc21]

To a solution of tert-butyl (6aR,8S)-8-((tert-butyldimethylsilyl)oxy)-2-chloro-6a,7,8,9-tetrahydropyrrolo[1',2':4,5] pyrazino[2,3-c]pyridazine-5(6H)-carboxylate (550 mg, 1.25 mmol) in THF (25 mL) at 0° C. was added tetrabutylammonium fluoride (1 M in THF, 3.1 mL, 3.1 mmol). The mixture was stirred at 0° C. for 5 min then allowed to stir at rt for 19 h. $NH_4Cl$ (sat., aq.) was added to the reaction and the mixture was extracted with DCM (3×25 mL). The combined organic layers were washed with brine (25 mL), dried with $MgSO_4$, filtered and concentrated. The residue was purified via silica gel chromatography (0-100% EtOAc/hexanes) to afford tert-butyl (6aR,8S)-2-chloro-8-hydroxy-6a,7,8,9-tetrahydropyrrolo[1',2':4,5]pyrazino[2,3-c] pyridazine-5(6H)-carboxylate (251 mg, 0.77 mmol, 62% yield) as an yellow-orange solid. LCMS calcd for $C_{14}H_{20}ClN_4O_3(M+H)^+$ m/z=327.1/329.1; found: 327.0/328.9.

Step 8: tert-butyl (6aR,8S)-8-((5-(1-(tert-butoxycarbonyl)-1,2,3,6-tetrahydropyridin-4-yl) pyrimidin-2-yl)oxy)-2-chloro-6a, 7,8,9-tetrahydropyrrolo[1',2':4,5]pyrazino[2,3-c]pyridazine-5(6H)-carboxylate

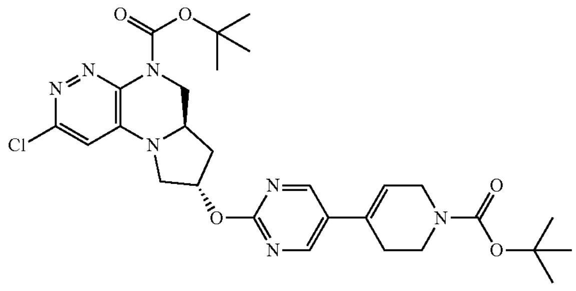 [SMILES: CC(C)(C)OC(=O)N1CC=C(c2cnc(O[C@H]3C[C@@H]4CN(C(=O)OC(C)(C)C)c5nnc(Cl)cc5N4C3)nc2)CC1]

To a mixture of tert-butyl (6aR,8S)-2-chloro-8-hydroxy-6a,7,8,9-tetrahydropyrrolo [1',2':4,5]pyrazino[2,3-c] pyridazine-5(6H)-carboxylate (22 mg, 1.25 mmol) and tert-butyl 4-(2-chloropyrimidin-5-yl)-3,6-dihydropyridine-1(2H)-carboxylate in DMF (1 mL) at 0° C. was added sodium hydride (5.0 mg, 0.125 mmol, 60 wt % dispersion in mineral oil). The reaction mixture was allowed to warm to rt over 10 min, then heated to 60° C. with stirring for 3 h. The reaction was allowed to cool to rt and charged with additional sodium hydride (5.5 mg, 0.14 mmol, 60 wt % dispersion in mineral oil). The mixture was stirred at 60° C. for an additional 2 h, then quenched with water and extracted with EtOAc (3×25 mL), washed with water and brine (25 mL), dried with $MgSO_4$, filtered and concentrated. The residue was purified via silica gel chromatography (0-100% EtOAc/hexanes) to afford as an tert-butyl (6aR,8S)-8-((5-(1-(tert-butoxycarbonyl)-1,2,3,6-tetrahydropyridin-4-yl)pyrimidin-2-yl)oxy)-2-chloro-6a,7,8,9-tetrahydropyrrolo[1',2':4,5]pyrazino[2,3-c] pyridazine-5(6H)-carboxylate (13 mg, 0.022 mmol, 44% yield) as a yellow oil. LCMS calcd for $C_{28}H_{37}ClN_7O_5(M+H)^+$ m/z=586.3/588.3; found: 586.1/588.1.

Step 9: tert-butyl (6aR,8S)-8-((5-(1-(tert-butoxycarbonyl)-1,2,3,6-tetrahydropyridin-4-yl) pyrimidin-2-yl)oxy)-2-(2-hydroxyphenyl)-6a, 7,8,9-tetrahydropyrrolo[1',2':4,5]pyrazino[2,3-c]pyridazine-5(6H)-carboxylate

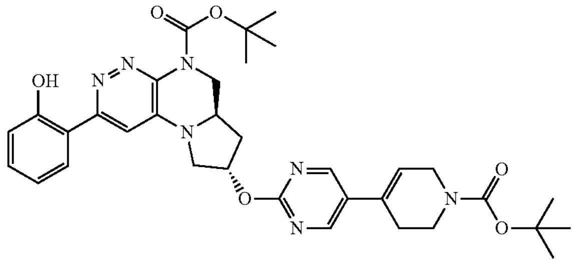 [SMILES: CC(C)(C)OC(=O)N1CC=C(c2cnc(O[C@H]3C[C@@H]4CN(C(=O)OC(C)(C)C)c5nnc(-c6ccccc6O)cc5N4C3)nc2)CC1]

A mixture of tert-butyl (6aR,8S)-8-((5-(1-(tert-butoxycarbonyl)-1,2,3,6-tetrahydro-pyridin-4-yl)pyrimidin-2-yl) oxy)-2-chloro-6a,7,8,9-tetrahydropyrrolo[1',2':4,5]pyrazino [2,3-c]pyridazine-5(6H)-carboxylate (13 mg, 0.022 mmol), 2-hydroxyphenylboronic acid (6.1 mg, 0.044 mmol), [1,1'-bis(diphenylphosphino)ferrocene]dichloropalladium(II) (dichloromethane adduct) (1.8 mg, 0.002 mmol) and potassium carbonate (12 mg, 0.089 mmol) in 1,4-dioxane (2 mL) and water (0.2 mL) was sparged with $N_2$ for 5 min. The reaction mixture was stirred at 100° C. for 2 h then charged with additional 2-hydroxyphenylboronic acid (6.0 mg, 0.044 mmol), [1,1'-bis(diphenylphosphino)ferrocene]dichloropalladium(II) (dichloromethane adduct) (5 mg, 0.006 mmol), potassium carbonate (12 mg, 0.087 mmol) and water (0.2 mL). The reaction mixture was stirred at 100° C. for 18 h then concentrated. The residue was purified by silica gel chromatography (0-10% MeOH/DCM) to give tert-butyl (6aR,8S)-8-((5-(1-(tert-butoxycarbonyl)-1,2,3,6-tetrahydro-pyridin-4-yl)pyrimidin-2-yl)oxy)-2-(2-hydroxyphenyl)-6a, 7,8,9-tetrahydro-pyrrolo [1',2':4,5]pyrazino[2,3-c] pyridazine-5(6H)-carboxylate (11 mg, 0.017 mmol, 77% yield). LCMS calcd for $C_{34}H_{42}N_7O_6$ $(M+H)^+$ m/z=644.3; found: 644.2.

Step 10: tert-butyl (6aR,8S)-8-((5-(1-(tert-butoxy-carbonyl)piperidin-4-yl)pyrimidin-2-yl)oxy)-2-(2-hydroxyphenyl)-6a, 7,8,9-tetrahydropyrrolo[1',2':4,5]pyrazino[2,3-c]pyridazine-5(6H)-carboxylate

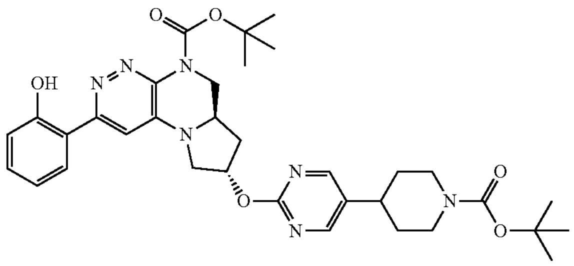 [SMILES: CC(C)(C)OC(=O)N1CCC(c2cnc(O[C@H]3C[C@@H]4CN(C(=O)OC(C)(C)C)c5nnc(-c6ccccc6O)cc5N4C3)nc2)CC1]

A vial with a septum containing a mixture tert-butyl (6aR,8S)-8-((5-(1-(tert-butoxycarbonyl)-1,2,3,6-tetrahydro-pyridin-4-yl)pyrimidin-2-yl)oxy)-2-(2-hydroxyphenyl)-6a, 7,8,9-tetrahydropyrrolo[1',2':4,5]pyrazino[2,3-c]pyridazine-5(6H)-carboxylate (11 mg, 0.017 mmol) and $Pd(OH)_2/C$ (10 wt % Pd (wet), 8.6 mg) was evacuated and backfilled with $N_2$ (×3). The vial was charged with THF (2 mL), MeOH (0.5 mL) and formic acid (1.3 μL, 0.034 mmol). The vial was evacuated and quickly backfilled with $N_2$ (×3). The vial was evacuated and quickly backfilled with $H_2$ (×5, balloon) and the mixture was stirred at 40° C. overnight. The mixture was allowed to cool to rt and was purged with $N_2$. Additional $Pd(OH)_2/C$ (10 wt % Pd (wet), 4.3 mg) was added, followed by formic acid (25 μL, 0.66 mmol), THE (1 mL) and MeOH (0.1 mL). The vial was evacuated and quickly backfilled with $N_2$ (×3). The vial was evacuated and quickly backfilled with $H_2$ (×5, balloon) and the mixture was stirred at 40° C. for three days. The mixture was purged with $N_2$ and filtered through a celite pad, which was subsequently washed with MeOH. The resulting solution was concentrated to dryness to and purified by prep-HPLCMS (Waters SunFire C18, 5 μm particle size, 30×100 mm, mobile phase: Aq(0.1% TFA)/ACN @ 60 mL/min, gradient: 34.0-54.0% ACN over 5 min to obtain tert-butyl (6aR,8S)-8-((5-(1-(tert-butoxycarbonyl)piperidin-4-yl)pyrimidin-2-yl)oxy)-2-(2-hydroxyphenyl)-6a,7,8,9-tetrahydro-pyrrolo[1',2':4,5]pyrazino[2,3-c]pyridazine-5(6H)-carboxylate (2 mg, 0.003 mmol) as its TFA salt. LCMS m/z calcd for $C_{34}H_{44}N_7O_6$ $(M+H)^+$: 646.3; found: 646.3.

Step 11: 2-((6aR,8S)-8-((5-(piperidin-4-yl)pyrimidin-2-yl)oxy)-5,6,6a, 7,8,9-hexahydropyrrolo [1',2':4,5]pyrazino[2,3-c]pyridazin-2-yl)phenol

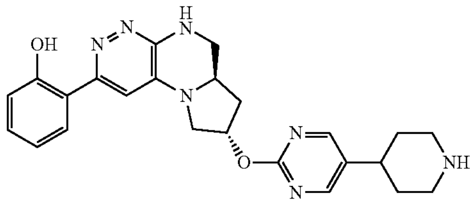 [SMILES: Oc1ccccc1-c1cc2c(nn1)NC[C@H]1C[C@H](Oc3ncc(C4CCNCC4)cn3)CN21]

A vial with a septum containing a solution of tert-butyl (6aR,8S)-8-((5-(1-(tert-butoxy-carbonyl)piperidin-4-yl)pyrimidin-2-yl)oxy)-2-(2-hydroxyphenyl)-6a,7,8,9-tetrahydro-pyrrolo [1',2':4,5]pyrazino[2,3-c]pyridazine-5(6H)-carboxylate (2 mg, 0.0026 mmol) in DCM (2 mL) was charged with trifluoroacetic acid (12 μL, 0.16 mmol). The reaction mixture was stirred at rt overnight then concentrated to afford 2-((6aR,8S)-8-((5-(piperidin-4-yl)pyrimidin-2-yl)oxy)-5,6,6a,7,8,9-hexahydropyrrolo[1',2':4,5]pyrazino [2,3-c]pyridazin-2-yl)phenol (assumed quantitative yield, 0.0026 mmol) as its TFA salt which was used in the next step without further purification. LCMS m/z calcd for $C_{24}H_{28}N_7O_2$ $(M+H)^+$: 446.2; found: 446.2.

Step 12: 3-(6-(3-(4-(2-(((6aR,8S)-2-(2-hydroxyphenyl)-5,6,6a, 7,8,9-hexahydropyrrolo [1',2':4,5] pyrazino[2,3-c]pyridazin-8-yl)oxy)pyrimidin-5-yl) piperidin-1-yl)propyl)-9H-pyrido[2,3-b]indol-9-yl) piperidine-2,6-dione The title compound was prepared using procedure analogous to those described for Example 18, using 2-((6aR,8S)-8-((5-(piperidin-4-yl)pyrimidin-2-yl)oxy)-5,6,6a,7,8,9-hexahydro-pyrrolo[1',2':4,5]pyrazino[2,3-c]pyridazin-2-yl) phenol replacing (R)-2-(8-(5-(piperidin-4-yl) pyrimidin-2-yl)-6,6a,7,8,9,10-hexahydro-5H-pyrazino[1',2':4,5]pyrazino [2,3-c]pyridazin-2-yl) phenol. LCMS calcd for $C_{43}H_{45}N_{10}O_4$ $[M+H]^+$ m/z=765.4; found: 765.1.

Example 24: N-(2,6-dioxopiperidin-3-yl)-5-(4-((4-((S)-2-(2-hydroxyphenyl)-5,6,6a,7,9,10-hexahydro-8H-pyrazino[1',2':4,5]pyrazino[2,3-c]pyridazin-8-yl) piperidin-1-yl)methyl) piperidin-1-yl)picolinamide Ex. 24

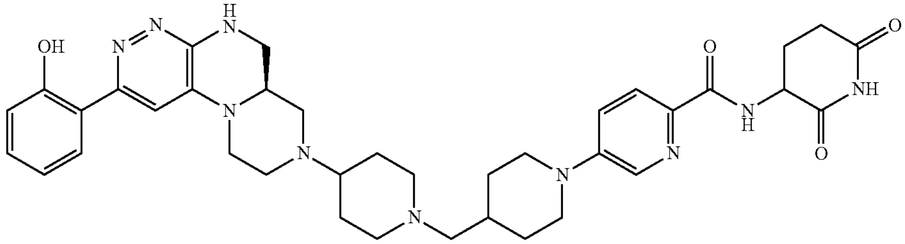

Step 1: methyl 5-(4-(hydroxymethyl)piperidin-1-yl)picolinate

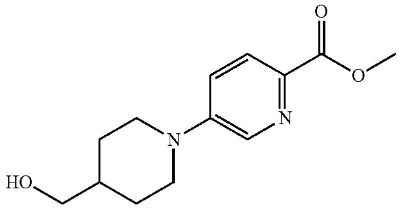 [SMILES: COC(=O)c1ccc(N2CCC(CO)CC2)cn1]

To methyl 5-fluoropicolinate (500 mg, 3.22 mmol) in DMSO (1.6 mL) was added $K_2CO_3$ (535 mg, 3.87 mmol) and piperidin-4-ylmethanol (445 mg, 3.87 mmol). The reaction was stirred at 110° C. for 45 min then poured into water and extracted with DCM (3×). The combined DCM layers were washed with brine (1×), dried with $MgSO_4$, filtered then concentrated to afford methyl 5-(4-(hydroxymethyl) piperidin-1-yl)picolinate (assumed quantitative yield of 807 mg) which was used directly without further purification. LCMS calcd. for $C_{13}H_{19}N_2O_{32}{}^+$[M+H]$^+$ m/z=251.1; found: 251.0.

Step 2: 5-(4-(hydroxymethyl)piperidin-1-yl)picolinic acid

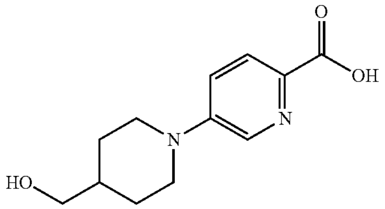 [SMILES: O=C(O)c1ccc(N2CCC(CO)CC2)cn1]

To methyl 5-(4-(hydroxymethyl)piperidin-1-yl)picolinate (807 mg, 3.22 mmol) in THF (5 mL) was added NaOH (653 mg, 16.3 mmol) in water (10 mL). The reaction was stirred at room temperature for 40 min. Aqueous HCl (6 N, 3.3 mL, 19.8 mmol) was added slowly and the reaction was stirred for 5 min then concentrated. Toluene (~5 mL) was added to the residue. The mixture was sonicated for –1 min then concentrated to afford crude 5-(4-(hydroxymethyl)piperidin-1-yl)picolinic acid (assumed quantitative yield of 762 mg as HCl salt) as a yellow semi-solid which was used directly without further purification. LCMS calcd. for $C_{12}H_{17}N_2O_3$ [M+H]$^+$ m/z=237.1; found: 237.0.

Step 3: N-(2,6-dioxopiperidin-3-yl)-5-(4-(hydroxymethyl)piperidin-1-yl)picolinamide

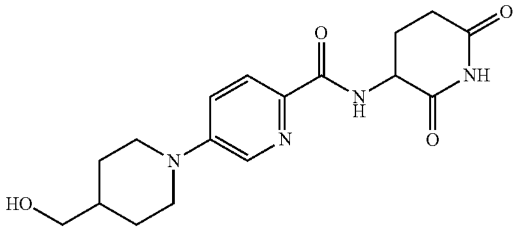 [SMILES: O=C1CCC(NC(=O)c2ccc(N3CCC(CO)CC3)cn2)C(=O)N1]

To a suspension of crude 5-(4-(hydroxymethyl)piperidin-1-yl)picolinic acid (100 mg, 0.37 mmol) as its HCl salt in DCM (4 mL) was added triethylamine (0.36 mL, 2.57 mmol). The mixture was sonicated for ~1 min then stirred for 2 min. HATU (209 mg, 0.55 mmol) was added and the mixture was stirred for another 2 min. 3-Aminopiperidine-2,6-dione (121 mg, 0.73 mmol) was added and the reaction was stirred at room temperature for 1 h. The mixture was filtered through a PTFE frit and the filtrate was concentrated. The residue was purified via silica gel chromatography (0-10% MeOH/DCM) to afford N-(2,6-dioxopiperidin-3-yl)-5-(4-(hydroxymethyl)piperidin-1-yl)picolinamide (45 mg, 0.13 mmol, 35%) as an off-white solid. LCMS calcd. for $C_{17}H_{23}N_4O_4{}^+$[M+H]$^+$ m/z=347.2; found: 347.1.

Step 3: N-(2,6-dioxopiperidin-3-yl)-5-(4-formylpiperidin-1-yl)picolinamide

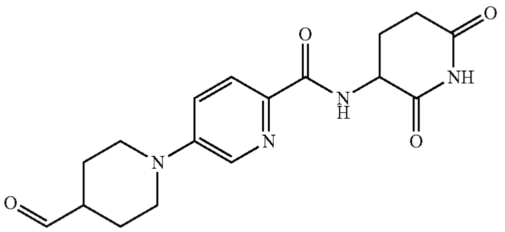 [SMILES: O=CC1CCN(c2ccc(C(=O)NC3CCC(=O)NC3=O)nc2)CC1]

To N-(2,6-dioxopiperidin-3-yl)-5-(4-(hydroxymethyl)piperidin-1-yl)picolinamide (10 mg, 0.03 mmol) in MeCN (1 mL) at 0° C. was added Dess-Martin Periodinane (18 mg, 0.04 mmol). The reaction was allowed to warm to room temperature and stirred for 1 h. Additional Dess-Martin Periodinane (37 mg, 0.09 mmol) was added, followed by stirring at room temperature for 2.5 h then filtration of the mixture through a PTFE frit. After washing the filter cake with MeCN/DCM the filtrate was concentrated and purified via silica gel chromatography (0-5% MeOH/DCM). The fractions containing desired product were concentrated then taken up in DCM (~5 mL) and concentrated again to give N-(2,6-dioxopiperidin-3-yl)-5-(4-formylpiperidin-1-yl)picolinamide (7.4 mg, 0.02 mmol, 74%). LCMS calcd. for $C_{17}H_{21}N_4O_4{}^+$[M+H]$^+$ m/z=345.2; found: 345.1.

Step 4: N-(2,6-dioxopiperidin-3-yl)-5-(4-((4-((S)-2-(2-hydroxyphenyl)-5,6,6a, 7,9,10-hexahydro-8H-pyrazino[1',2':4,5]pyrazino[2,3-c]pyridazin-8-yl) piperidin-1-yl)methyl)piperidin-1-yl)picolinamide To N-(2,6-dioxopiperidin-3-yl)-5-(4-(hydroxymethyl)piperidin-1-yl)picolinamide (10 mg, 0.03 mmol) and (S)-2-(8-(piperidin-4-yl)-6,6a,7,8,9,10-hexahydro-5H-pyrazino [1',2':4,5]pyrazino[2,3-c]pyridazin-2-yl)phenol (17 mg, 0.35 mmol) as its tris(HCl) salt in DMF (1 mL) was added sodium triacetoxyborohydride (25 mg, 0.12 mmol) then AcOH (6.6 μL, 0.12 mmol). The reaction was stirred at room temperature for 40 min then diluted with water and MeCN to 5 mL and purified via prep-HPLCMS (Waters SunFire C18, 5 μm particle size, 30×100 mm, mobile phase: Aq(0.1% TFA)/MeCN @ 60 mL/min, gradient: 6.2-26.2% MeCN over 5 min). The product was further purified via an additional prep-HPLCMS run (Waters CSH Fluoro-Phenyl, 5 μm particle size, 30×100 mm, mobile phase: Aq(0.1% TFA)/MeCN @ 60 mL/min, gradient: 5-25% MeCN over 5 min) to afford N-(2,6-dioxopiperidin-3-yl)-5-(4-((4-((S)-2-(2-hydroxyphenyl)-5,6,6a,7,9,10-hexahydro-8H-pyrazino [1',2':4,5]pyrazino[2,3-c]pyridazin-8-yl)piperidin-1-yl) methyl)piperidin-1-yl)picolinamide (1.0 mg, 1.0 μmol, 3%) as its tris(2,2,2-trifluoroacetic acid) salt as an off-white solid. LCMS calcd. for $C_{37}H_{47}N_{10}O_4{}^+$[M+H]$^+$ m/z=695.4; found: 695.2.

Example 25: 3-(6-(3-(4-(2-(2-hydroxyphenyl)-6a-methyl-5,6,6a,7,9,10-hexahydro-8H-pyrazino[1',2':4,5]pyrazino[2,3-c]pyridazin-8-yl)piperidin-1-yl)propyl)-9H-pyrido[2,3-b]indol-9-yl)piperidine-2,6-dione Ex.25

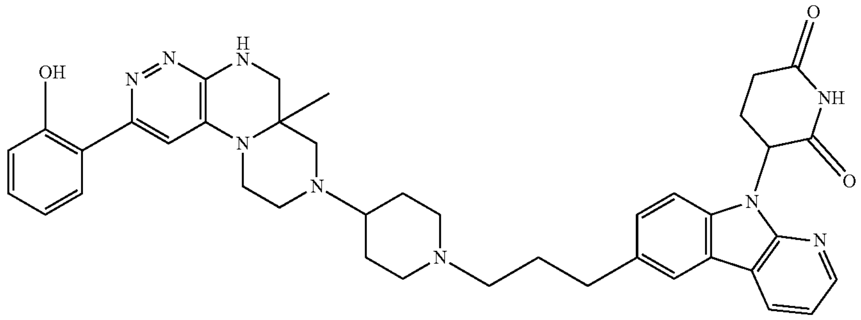

The title compound was prepared using procedure analogous to those described for Example 18, using 2-(6a-methyl-8-(piperidin-4-yl)-6,6a,7,8,9,10-hexahydro-5H-pyrazino[1',2':4,5]pyrazino[2,3-c]pyridazin-2-yl)phenol instead of (R)-2-(8-(5-(piperidin-4-yl)pyrimidin-2-yl)-6,6a,7,8,9,10-hexahydro-5H-pyrazino[1',2':4,5]pyrazino[2,3-c]pyridazin-2-yl)phenol. LCMS calcd. for $C_{40}H_{46}N_9O_3[M+H]^+$ m/z=700.4; found: 700.2.

Example 26: 3-(6-(4-((4-((S)-2-(2-hydroxyphenyl)-5,6,6a,7,9,10-hexahydro-8H-pyrazino [1',2':4,5]pyrazino[2,3-c]pyridazin-8-yl)piperidin-1-yl)methyl)piperidin-1-yl)-1-oxoisoquinolin-2(1H)-yl)piperidine-2,6-dione Ex. 26

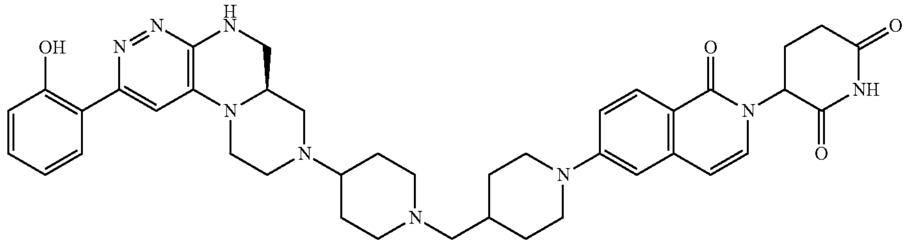

Step 1: 6-(4-(hydroxymethyl)piperidin-1-yl) isoquinolin-1(2H)-one

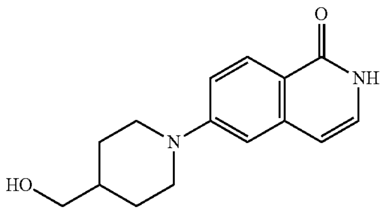 [SMILES: O=c1[nH]ccc2cc(N3CCC(CO)CC3)ccc12]

To 6-fluoroisoquinolin-1(2H)-one (500 mg, 3.06 mmol) in DMSO (4.4 mL) was added N,N-diisopropylethylamine followed by piperidin-4-ylmethanol. Stirred at 120° C. for 48 h. Let cool to room temperature then diluted with 8 mL water. Stirred suspension for 5 min then filtered through PTFE filter. Washed solid with water 3× then air dried. Obtained 6-(4-(hydroxymethyl)piperidin-1-yl) isoquinolin-1(2H)-one (790 mg, 3.06 mmol, quantitative). LCMS calcd. for $C_{15}H_{19}N_2O_2^+$ [M+H]$^+$ m/z=259.1; found: 259.0.

Step 2: 6-(4-(((tert-butyldimethylsilyl)oxy)methyl) piperidin-1-yl) isoquinolin-1(2H)-one

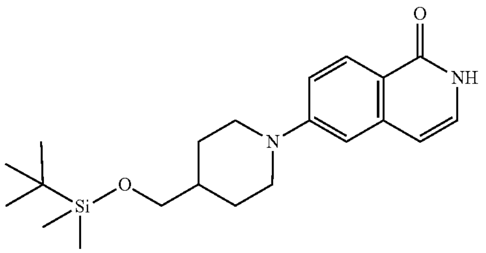 [SMILES: CC(C)(C)[Si](C)(C)OCC1CCN(c2ccc3c(=O)[nH]ccc3c2)CC1]

To 6-(4-(hydroxymethyl)piperidin-1-yl) isoquinolin-1 (2H)-one (790 mg, 3.06 mmol) and imidazole (458 mg, 6.73 mmol) in DMF (7.65 mL) was added tert-butyldimethylsilyl chloride (922 mg, 6.12 mmol). Stirred at 60° C. for 50 min. Let cool to room temperature and stored overnight in −20° C. freezer. Let warm to room temperature then diluted with 2 mL water. Filtered through PTFE filter and washed solid with water 3× and air dried. Obtained 6-(4-(((tert-butyldimethylsilyl)oxy)methyl)piperidin-1-yl) isoquinolin-1(2H)-one (1110 mg, 2.98 mmol, 97%). LCMS calcd. for $C_{21}H_{33}N_2O_2Si^+$ [M+H]$^+$ m/z=373.2; found: 373.2.

Step 3: 3-(6-(4-(((tert-butyldimethylsilyl)oxy) methyl)piperidin-1-yl)-1-oxoisoquinolin-2(1H)-yl)-1-(4-methoxybenzyl)piperidine-2,6-dione

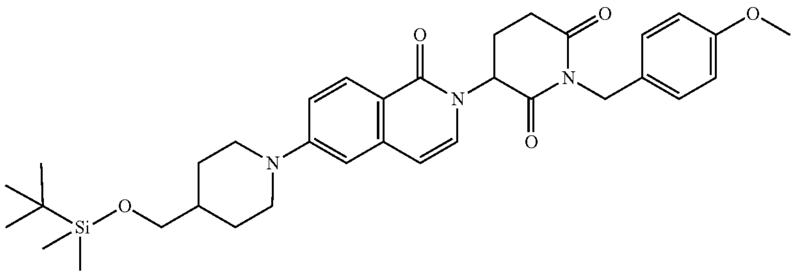 [SMILES: COc1ccc(CN2C(=O)CCC(n3ccc4cc(N5CCC(CO[Si](C)(C)C(C)(C)C)CC5)ccc4c3=O)C2=O)cc1]

To 6-(4-(((tert-butyldimethylsilyl)oxy)methyl)piperidin-1-yl) isoquinolin-1(2H)-one (293 mg, 0.79 mmol) and 18-crown-6 (42 mg, 0.16 mmol) in THF (4 mL) at 0° C. was added sodium hydride (38 mg, 0.94 mmol, 60 wt % dispersion in mineral oil). Let stir for 30 min at 0° C. 1-(4-methoxybenzyl)-2,6-dioxopiperidin-3-yl trifluoromethanesulfonate (300 mg, 0.78 mmol) in THF (2 mL) was added dropwise and the reaction stirred for ~2 h then quenched with saturated aq $NH_4Cl$. The aqueous layer was extracted with EtOAc (3×) and the combined organic layers were washed with brine 1×, dried with $MgSO_4$, filtered then concentrated. The resulting solid was transferred to a PTFE frit filter and washed with MeOH (3×). Obtained 3-(6-(4-(((tert-butyldimethylsilyl)oxy)methyl)piperidin-1-yl)-1-oxoisoquinolin-2(1H)-yl)-1-(4-methoxybenzyl)piperidine-2,6-dione (265 mg, 0.44 mmol, 56%) as an off-white solid. LCMS calcd. for $C_{34}H_{46}N_3O_5Si^+$ [M+H]$^+$ m/z=604.3; found: 604.2.

Step 4: 3-(6-(4-(hydroxymethyl)piperidin-1-yl)-1-oxoisoquinolin-2(1H)-yl)piperidine-2,6-dione

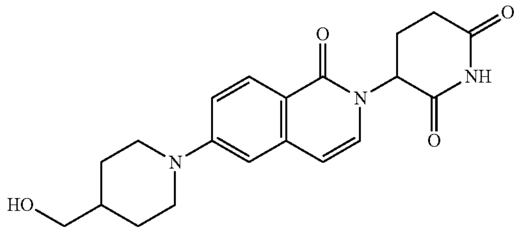 [SMILES: O=C1CCC(n2ccc3cc(N4CCC(CO)CC4)ccc3c2=O)C(=O)N1]

To 3-(6-(4-(((tert-butyldimethylsilyl)oxy)methyl)piperidin-1-yl)-1-oxoisoquinolin-2(1H)-yl)-1-(4-methoxybenzyl) piperidine-2,6-dione (100 mg, 0.17 mmol) in DCM (5.5 mL) was added TfOH (1.32 mL, 14.9 mmol). Stirred at 50° C. overnight. Cooled the reaction to 0° C. then slowly neutralized with saturated aq $NaHCO_3$. The aqueous layer was extracted with DCM (5×) then dried with $MgSO_4$, filtered and concentrated. The residue was purified via prep-HPLCMS (Waters SunFire C18, 5 μm particle size, 30×100 mm, mobile phase: Aq(0.1% TFA)/MeCN @ 60 mL/min, gradient: 6.3-26.3% MeCN over 5 min) to afford 3-(6-(4-(hydroxymethyl)piperidin-1-yl)-1-oxoisoquinolin-2(1H)-yl) piperidine-2,6-dione as it's TFA salt (72 mg, 0.15 mmol, 90%). LCMS calcd. for $C_{20}H_{24}N_3O_4^+$[M+H]$^+$ m/z=370.2; found: 370.1.

Step 5: 1-(2-(2,6-dioxopiperidin-3-yl)-1-oxo-1,2-dihydroisoquinolin-6-yl)piperidine-4-carbaldehyde

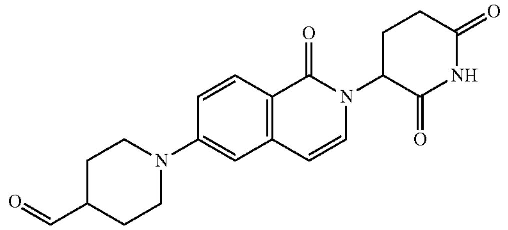 [SMILES: O=CC1CCN(c2ccc3c(=O)n(C4CCC(=O)NC4=O)ccc3c2)CC1]

To 3-(6-(4-(hydroxymethyl)piperidin-1-yl)-1-oxoisoquinolin-2(1H)-yl)piperidine-2,6-dione (72 mg, 0.15 mmol) in MeCN (5 mL) at 0° C. was added Dess-Martin Periodinane (95 mg, 0.22 mmol). The reaction was stirred and allowed to warm to room temperature. After 15 min, additional MeCN (5 mL) was added and stirring at room temperature was continued. After 3 h, diluted with saturated aq $Na_2SO_3$ (5 mL) and saturated. aq $Na_2CO_3$ (5 mL) and stirred vigorously for ~5 min. The aqueous layer was extracted with 1:1 THF/EtOAc (3×20 mL). The combined organic layers were washed with brine (1×), dried with $MgSO_4$, filtered then concentrated. to give 1-(2-(2,6-dioxopiperidin-3-yl)-1-oxo-1,2-dihydroisoquinolin-6-yl)piperidine-4-carbaldehyde (assumed quantitative yield of 55 mg) which was used directly without further purification. LCMS calcd. for $C_{20}H_{22}N_3O_4^+$ $[M+H]^+$ m/z=368.2; found: 368.1.

Step 6: 3-(6-(4-((4-((S)-2-(2-hydroxyphenyl)-5,6,6a,7,9,10-hexahydro-8H-pyrazino [1',2':4,5]pyrazino[2,3-c]pyridazin-8-yl)piperidin-1-yl)methyl)piperidin-1-yl)-1-oxoisoquinolin-2(1H)-yl)piperidine-2,6-dione To crude 1-(2-(2,6-dioxopiperidin-3-yl)-1-oxo-1,2-dihydroisoquinolin-6-yl)piperidine-4-carbaldehyde (4 mg, 0.01 mmol) and (S)-2-(8-(piperidin-4-yl)-6,6a,7,8,9,10-hexahydro-5H-pyrazino[1',2':4,5]pyrazino[2,3-c]pyridazin-2-yl)phenol in DMF (1 mL) was added sodium triacetoxyborohydride (12 mg, 0.05 mmol) then acetic acid (3 µL, 0.5 mmol). The reaction was stirred for 1 h then diluted with water and MeCN to 5 mL and purified via prep-HPLCMS (Waters SunFire C18, 5 µm particle size, 30×100 mm, mobile phase: Aq(0.1% TFA)/MeCN @ 60 mL/min, gradient: 6.7-26.7% MeCN over 5 min). Obtained 3-(6-(4-((4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)methyl)piperidin-1-yl)-1-oxoisoquinolin-2(1H)-yl) piperidine-2,6-dione (0.8 mg, 0.75 µmol, 7%) as its tris(2,2,2-trifluoroacetic acid) salt as an off-white solid. LCMS calcd. for $C_{40}H_{48}N_9O_4^+[M+H]^+$ m/z=718.4; found: 718.2.

Example 27: 3-(6-(3-(4-(4-((6aR)-2-(2-hydroxyphenyl)-5,6,6a,7,8,9-hexahydropyrrolo [1',2':4,5] pyrazino[2,3-c]pyridazin-8-yl)piperazin-1-yl)piperidin-1-yl)propyl)-9H-pyrido[2,3-b]indol-9-yl) piperidine-2,6-dione Ex. 27

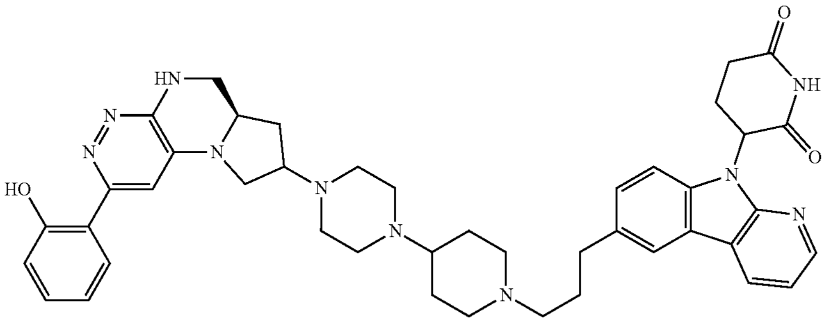

Step 1: tert-butyl (R)-2-chloro-8-oxo-6a, 7,8,9-tetrahydropyrrolo[1',2':4,5]pyrazino[2,3-c]pyridazine-5 (6H)-carboxylate

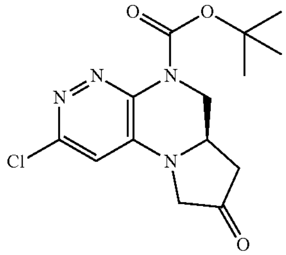 [SMILES: CC(C)(C)OC(=O)N1C[C@H]2CC(=O)CN2c2cc(Cl)nnc21]

To oxalyl chloride (58 µL, 0.67 mmol) in DCM (2 mL) at −78° C. was added DMSO (97 µL, 1.37 mmol). The solution was stirred at −78° C. for 30 min. A solution of tert-butyl (6aR,8S)-2-chloro-8-hydroxy-6a,7,8,9-tetrahydropyrrolo[1',2':4,5]pyrazino[2,3-c]pyridazine-5(6H)-carboxylate (100 mg, 0.31 mmol) in DCM (8 mL) was added and the reaction was stirred at −78° C. for 1 h. Triethylamine (0.21 mL, 1.53 mmol) was added and the reaction was allowed to warm to room temperature and stir overnight. The reaction was diluted with water and extracted with DCM (3×). The combined DCM layers were washed with brine (1×), dried with $MgSO_4$, filtered and concentrated. The residue was purified via column chromatography (SiO2, 0-100% EtOAc/hexanes) to afford tert-butyl (R)-2-chloro-8-oxo-6a,7,8,9-tetrahydropyrrolo [1',2':4,5]pyrazino[2,3-c]pyridazine-5(6H)-carboxylate (35 mg, 0.11 mmol, 35% yield). LCMS calcd. for $C_{14}H_{18}ClN_4O_3[M+H]^+$ m/z=325.1; found: 325.0.

Step 2: tert-butyl (6aR)-8-(4-(tert-butoxycarbonyl)piperazin-1-yl)-2-chloro-6a, 7,8,9-tetrahydropyrrolo[1',2':4,5]pyrazino[2,3-c]pyridazine-5(6H)-carboxylate

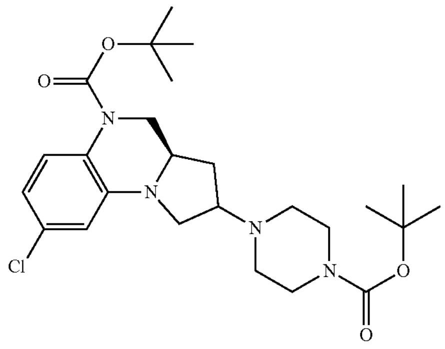 [SMILES: CC(C)(C)OC(=O)N1CCN(C2C[C@@H]3CN(C(=O)OC(C)(C)C)c4ccc(Cl)cc4N3C2)CC1]

To crude tert-butyl (R)-2-chloro-8-oxo-6a,7,8,9-tetrahydropyrrolo[1',2':4,5]pyrazino[2,3-c]pyridazine-5(6H)-carboxylate (~40-50% purity, 18 mg, 0.057 mmol) and tert-butyl piperazine-1-carboxylate (16 mg, 0.085 mmol) in DCM (1 mL) was added acetic acid (3.2 µL, 0.057 mmol). The reaction was stirred for 20 min at room temperature. Sodium triacetoxyborohydride (36 mg, 0.17 mmol) was added and the reaction was stirred for 48 h. The mixture was diluted with DCM and washed with saturated aq $NaHCO_3$, followed by brine (1×). The DCM layer was dried with $MgSO_4$, filtered and concentrated to afford tert-butyl (6aR)-8-(4-(tert-butoxycarbonyl)piperazin-1-yl)-2-chloro-6a,7,8,9-tetrahydropyrrolo[1',2':4,5]pyrazino[2,3-c]pyridazine-5(6H)-carboxylate (assumed quantitative yield, 28 mg) which was used in the next step without further purification. LCMS calcd. for $C_{23}H_{36}ClN_6O_4[M+H]^+$ m/z=495.2; found: 495.1.

Step 3: 2-((6aR)-8-(piperazin-1-yl)-5,6,6a, 7,8,9-hexahydropyrrolo[1',2':4,5]pyrazino[2,3-c]pyridazin-2-yl)phenol

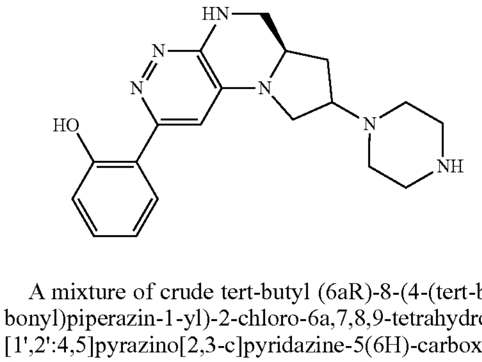

A mixture of crude tert-butyl (6aR)-8-(4-(tert-butoxycarbonyl)piperazin-1-yl)-2-chloro-6a,7,8,9-tetrahydropyrrolo[1',2':4,5]pyrazino[2,3-c]pyridazine-5(6H)-carboxylate (~14 mg, ~0.028 mmol), $K_2CO_3$ (54 mg, 0.39 mmol), 2-hydroxyphenylboronic acid (23.5 mg, 0.17 mmol), and $PdCl_2(dppf)$ $CH_2Cl_2$ (14 mg, 0.017 mmol) in dioxane (1 mL) and water (0.25 mL) was sparged with $N_2$ for 5 min. The mixture was stirred at 100° C. for 1 h then allowed to cool to room temperature. The reaction was concentrated. DCM (1 mL) and TFA (1 mL, 13.1 mmol) were added to the residue and the reaction was stirred at room temperature until complete deprotection was observed by LC-MS. The reaction was concentrated and the residue was purified via prep-HPLCMS (Waters SunFire C18, 5 µm particle size, 30×100 mm, mobile phase: Aq(0.1% TFA)/MeCN @ 60 mL/min, gradient: 5-25% MeCN over 5 min) to give 2-((6aR)-8-(piperazin-1-yl)-5,6,6a,7,8,9-hexahydropyrrolo[1',2':4,5]pyrazino[2,3-c]pyridazin-2-yl)phenol as its tris(2,2,2-trifluoroacetate) salt (assumed quantitative yield of ~20 mg). LCMS calcd. for $C_{19}H_{25}N_6O^+$ $[M+H]^+$ m/z=353.2; found: 353.1.

Step 4: tert-butyl 4-(4-((6aR)-2-(2-hydroxyphenyl)-5,6,6a, 7,8,9-hexahydropyrrolo [1',2':4,5]pyrazino[2,3-c]pyridazin-8-yl)piperazin-1-yl)piperidine-1-carboxylate

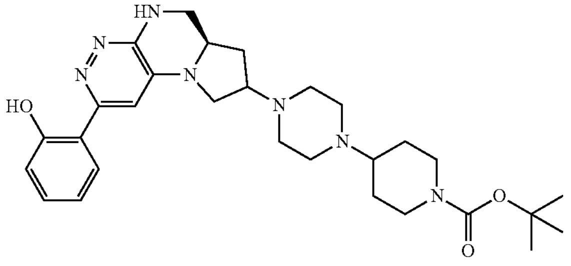 [SMILES: CC(C)(C)OC(=O)N1CCC(N2CCN(C3C[C@@H]4CNc5nnc(-c6ccccc6O)cc5N4C3)CC2)CC1]

To 2-((6aR)-8-(piperazin-1-yl)-5,6,6a,7,8,9-hexahydropyrrolo[1',2':4,5]pyrazino[2,3-c]pyridazin-2-yl)phenol (6 mg, 0.009 mmol) and tert-butyl 4-oxopiperidine-1-carboxylate (6.9 mg, 0.035 mmol) in DMF (1 mL) was added acetic acid (2 µL, 0.035 mmol) and sodium triacetoxyborohydride (9.2 mg, 0.043 mmol). The reaction was stirred at 60° C. for 1 h. Additional tert-butyl 4-oxopiperidine-1-carboxylate (3.4 mg, 0.017 mmol), acetic acid (2 µL, 0.035 mmol) and sodium triacetoxyborohydride (9.2 mg, 0.043 mmol) were added and the reaction was stirred at 60° C. for 2 h. The reaction was quenched with MeOH and water, stirred briefly, diluted with MeCN, and purified via prep-HPLCMS (Waters SunFire C18, 5 µm particle size, 30×100 mm, mobile phase: Aq(0.1% TFA)/MeCN @ 60 mL/min, gradient: 12.6-32.6% MeCN over 5 min) to afford tert-butyl 4-(4-((6aR)-2-(2-hydroxyphenyl)-5,6,6a,7,8,9-hexahydropyrrolo[1',2':4,5]pyrazino[2,3-c]pyridazin-8-yl)piperazin-1-yl)piperidine-1-carboxylate as its tris(2,2,2-trifluoroacetate) salt (assumed quantitative yield of 7.6 mg). LCMS calcd. for $C_{29}H_{42}N_7O_3$ $[M+H]^+$ m/z=536.3; found: 536.3.

Step 5: 2-((6aR)-8-(4-(piperidin-4-yl)piperazin-1-yl)-5,6,6a, 7,8,9-hexahydropyrrolo [1',2':4,5]pyrazino[2,3-c]pyridazin-2-yl)phenol

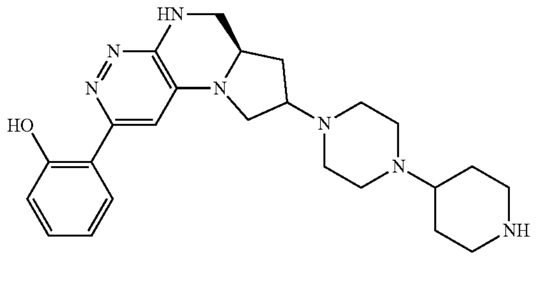 [SMILES: Oc1ccccc1-c1cc2c(nn1)NC[C@H]1CC(N3CCN(C4CCNCC4)CC3)CN21]

To tert-butyl 4-(4-((6aR)-2-(2-hydroxyphenyl)-5,6,6a,7,8,9-hexahydropyrrolo[1',2':4,5]pyrazino[2,3-c]pyridazin-8-yl)piperazin-1-yl)piperidine-1-carboxylate as its tris(2,2,2-trifluoroacetate) salt (7.6 mg, 0.014 mmol) in MeOH (1 mL) was added HCl (4 N in dioxane, 0.43 mL, 1.73 mmol). The reaction was stirred at room temperature until complete deprotection was observed by LC-MS. The reaction was concentrated to afford 2-((6aR)-8-(4-(piperidin-4-yl)piperazin-1-yl)-5,6,6a,7,8,9-hexahydropyrrolo[1',2':4,5]pyrazino[2,3-c]pyridazin-2-yl)phenol as its tetrahydrochloride salt (assumed quantitative yield of 5 mg) which was used in the next step without further purification. LCMS calcd. for $C_{24}H_{34}N_7O$ $[M+H]^+$ m/z=436.3; found: 436.2.

Step 6: 3-(6-(3-(4-(4-((6aR)-2-(2-hydroxyphenyl)-5,6,6a, 7,8,9-hexahydropyrrolo [1',2':4,5]pyrazino[2,3-c]pyridazin-8-yl)piperazin-1-yl)piperidin-1-yl)propyl)-9H-pyrido[2,3-b]indol-9-yl)piperidine-2,6-dione To 2-((6aR)-8-(4-(piperidin-4-yl)piperazin-1-yl)-5,6,6a,7,8,9-hexahydropyrrolo [1',2':4,5]pyrazino[2,3-c]pyridazin-2-yl)phenol as its tetrahydrochloride salt (4 mg, 0.007 mmol) and 3-[9-(2,6-dioxopiperidin-3-yl)pyrido[2,3-b]indol-6-yl]propanal (~60% purity, 5 mg, 0.009 mmol) in DMF (1 mL) was added sodium triacetoxyborohydride (4.8 mg, 0.022 mmol) then acetic acid (2 μL, 0.035 mmol). The reaction was stirred at room temperature for 1 h then quenched with water and diluted with MeCN. The reaction was purified via prep-HPLCMS (Waters CSH Fluoro-Phenyl, 5 μm particle size, 30×100 mm, mobile phase: Aq(0.1% TFA)/MeCN @ 60 mL/min, gradient: 7.7-27.7% MeCN over 5 min) to afford 3-(6-(3-(4-(4-((6aR)-2-(2-hydroxyphenyl)-5,6,6a,7,8,9-hexahydropyrrolo[1',2':4,5]pyrazino[2,3-c]pyridazin-8-yl)piperazin-1-yl)piperidin-1-yl)propyl)-9H-pyrido[2,3-b]indol-9-yl)piperidine-2,6-dione as its tetra(2,2,2-trifluoroacetate) salt (0.8 mg, 0.66 μmol, 10% yield) as an off-white solid. LCMS calcd. for $C_{43}H_{51}N_{10}O_3$ $[M+H]^+$ m/z=755.4; found: 755.2.

Example 28: 2-(2,6-dioxopiperidin-3-yl)-5-(4-((4-(((6aS,9S)-2-(2-hydroxyphenyl)-9-methyl-5,6,6a,7,9,10-hexahydro-8H-pyrazino[1',2':4,5]pyrazino[2,3-c]pyridazin-8-yl)methyl) piperidin-1-yl)methyl) piperidin-1-yl) isoindoline-1,3-dione Ex. 28

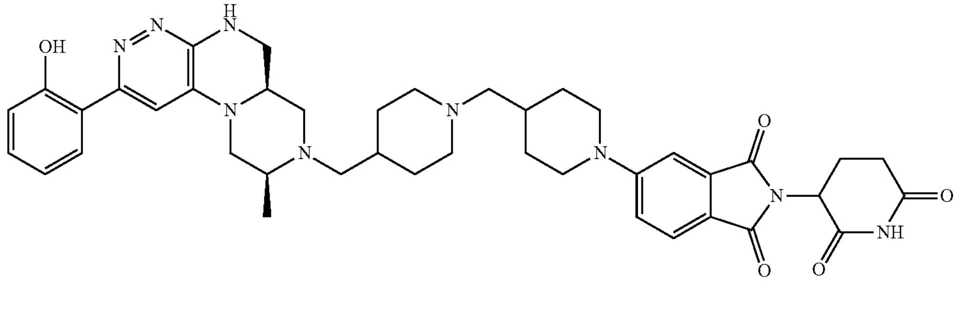

To 1-(2-(2,6-dioxopiperidin-3-yl)-1,3-dioxoisoindolin-5-yl)piperidine-4-carbaldehyde (7.6 mg, 0.02 mmol) in DMF (1 mL) was added 2-((6aS,9S)-9-methyl-8-(piperidin-4-ylmethyl)-6,6a,7,8,9,10-hexahydro-5H-pyrazino[1',2':4,5]pyrazino[2,3-c]pyridazin-2-yl)phenol (6.1 mg, 0.01 mmol), followed by acetic acid (2 uL, 0.03 mmol) and sodium triacetoxyborohydride (8.8 mg, 0.04 mmol). The reaction was stirred at room temperature for 1 h then diluted with MeOH, water, and MeCN, stirred briefly then filtered through a PTFE filter and purified via prep-HPLCMS (Waters CSH Fluoro-Phenyl, 5 μm particle size, 30×100 mm; mobile phase: Aq(0.1% TFA)/MeCN @ 60 mL/min; gradient: 6.6-26.6% MeCN over 5 min). Obtained 2-(2,6-dioxopiperidin-3-yl)-5-(4-((4-(((6aS,9S)-2-(2-hydroxyphenyl)-9-methyl-5,6,6a,7,9,10-hexahydro-8H-pyrazino[1',2':4,5]pyrazino[2,3-c]pyridazin-8-yl)methyl)piperidin-1-yl)methyl)piperidin-1-yl) isoindoline-1,3-dione (3.9 mg, 3.2 μmol, 39%) as its tris(2,2,2-trifluoroacetic acid) salt as a yellow solid. LCMS calcd. for $C_{41}H_{50}N_9O_5^+$ $[M+H]^+$ m/z=748.4; found: 748.2.

Example 29: 2-(2,6-dioxopiperidin-3-yl)-5-(4-((4-(((6aR)-2-(2-hydroxyphenyl)-5,6,6a,7,8,9-hexahydropyrrolo[1',2':4,5]pyrazino[2,3-c]pyridazin-8-yl)(methyl)amino)piperidin-1-yl)methyl)piperidin-1-yl) isoindoline-1,3-dione The title compound was prepared using procedure analogous to those described for Example 27, using appropriate starting materials. LCMS calcd. for $C_{40}H_{48}N_9O_5$+[M+H]+ m/z=734.4; found: 734.2.

Examples 30-33, 35-46, 49, 51-53, 55, 56, 59, 92, 93 and 257-260

Examples in Table 10 were prepared using the procedure described in the synthesis of Example 28 with appropriate intermediates.

TABLE 10

Examples 30-33, 35-46, 49, 51-53, 55, 56, 59, 92, 93 and 257-260

| Ex. | Structure/Name | Calcd. (M + H)+ m/z | Found (M + H)+ m/z |
|---|---|---|---|
| 30 | 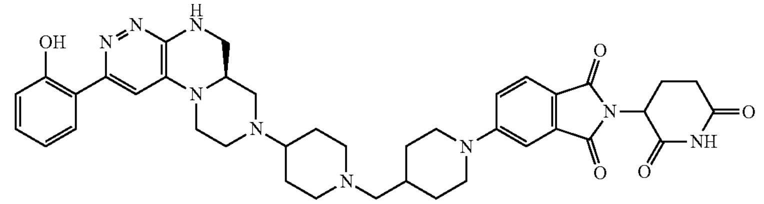 [SMILES: O=C1CCC(N2C(=O)c3ccc(N4CCC(CN5CCC(N6CCN7c8cc(-c9ccccc9O)nnc8NC[C@H]7C6)CC5)CC4)cc3C2=O)C(=O)N1]<br>2-(2,6-dioxopiperidin-3-yl)-5-(4-((4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)methyl)piperidin-1-yl)isoindoline-1,3-dione | 720.4 | 720.2 |
| 31 | 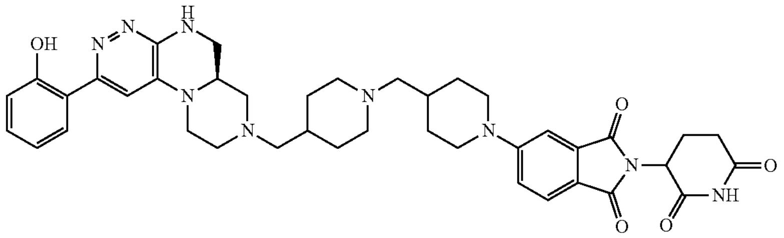<br>2-(2,6-dioxopiperidin-3-yl)-5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl)isoindoline-1,3-dione<br><br>$^1$H NMR (400 MHz, DMSO) δ 11.07 (s, 1H), 8.90 (s, 1H), 8.13 (s, 1H), 7.68 (d, J = 8.6 Hz, 1H), 7.55-7.45 (m, 1H), 7.41 (t, J = 7.7 Hz, 1H), 7.38-7.33 (m, 1H), 7.27 (dd, J = 8.5, 2.3 Hz, 1H), 7.23-7.12 (m, 1H), 7.04 (d, J = 8.3 Hz, 1H), 6.99 (t, J = 7.5 Hz, 1H), 5.07 (dd, J = 12.9, 5.4 Hz, 1H), 4.10 (d, J = 12.9 Hz, 2H), 3.77-3.36 (m, 9H), 3.32-3.13 (m, 3H), 3.13-2.95 (m, 5H), 2.95-2.79 (m, 3H), 2.65-2.52 (m, 2H), 2.20-2.08 (m, 1H), 2.06-1.98 (m, 1H), 1.97-1.89 (m, 2H), 1.88-1.75 (m, 3H), 1.54-1.34 (m, 2H), 1.34-1.20 (m, 2H). | 734.4 | 734.3 |
| 32 | 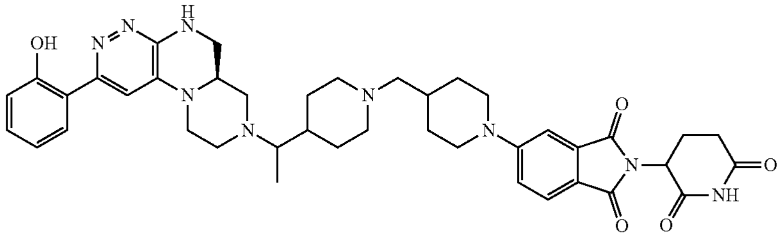 [SMILES: CC(C1CCN(CC2CCN(c3ccc4c(c3)C(=O)N(C3CCC(=O)NC3=O)C4=O)CC2)CC1)N1CCN2c3cc(-c4ccccc4O)nnc3NC[C@H]2C1]<br>2-(2,6-dioxopiperidin-3-yl)-5-(4-((4-(1-((S)-2-(2-hydroxyphenyl)-5,6,6a,7,9,10-hexahydro-8H-pyrazino[1',2':4,5]pyrazino[2,3-c]pyridazin-8-yl)ethyl)piperidin-1-yl)methyl)piperidin-1-yl)isoindoline-1,3-dione | 748.4 | 748.2 |
| 33 | 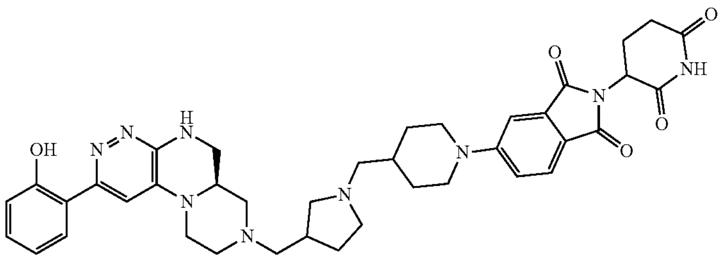 [SMILES: O=C1CCC(N2C(=O)c3ccc(N4CCC(CN5CCC(CN6CCN7c8cc(-c9ccccc9O)nnc8NC[C@H]7C6)C5)CC4)cc3C2=O)C(=O)N1]<br>2-(2,6-dioxopiperidin-3-yl)-5-(4-((3-(((S)-2-(2-hydroxyphenyl)-5,6,6a,7,9,10-hexahydro-8H-pyrazino[1',2':4,5]pyrazino[2,3-c]pyridazin-8-yl)methyl)pyrrolidin-1-yl)methyl)piperidin-1-yl)isoindoline-1,3-dione | 720.4 | 720.1 |

TABLE 10-continued

| Ex. | Structure/Name | Calcd. (M + H)+ m/z | Found (M + H)+ m/z |
|---|---|---|---|
| | Examples 30-33, 35-46, 49, 51-53, 55, 56, 59, 92, 93 and 257-260 | | |
| 35 | 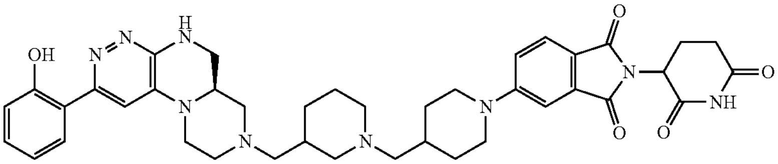 [SMILES: O=C1CCC(N2C(=O)c3ccc(N4CCC(CN5CCCC(CN6CCN7c8cc(-c9ccccc9O)nnc8NC[C@H]7C6)C5)CC4)cc3C2=O)C(=O)N1] 2-(2,6-dioxopiperidin-3-yl)-5-(4-((3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl)isoindoline-1,3-dione | 734.4 | 734.2 |
| 36 | 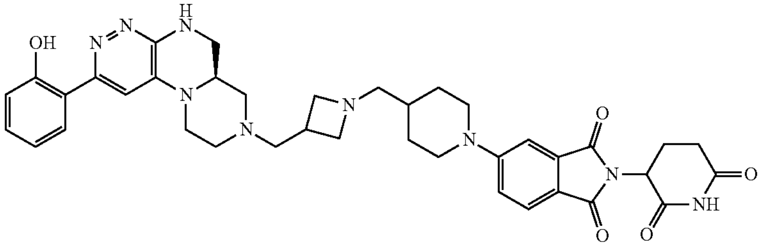 [SMILES: O=C1CCC(N2C(=O)c3ccc(N4CCC(CN5CC(CN6CCN7c8cc(-c9ccccc9O)nnc8NC[C@H]7C6)C5)CC4)cc3C2=O)C(=O)N1] 2-(2,6-dioxopiperidin-3-yl)-5-(4-((3-(((S)-2-(2-hydroxyphenyl)-5,6,6a,7,9,10-hexahydro-8H-pyrazino[1',2':4,5]pyrazino[2,3-c]pyridazin-8-yl)methyl)azetidin-1-yl)methyl)piperidin-1-yl)isoindoline-1,3-dione | 706.3 | 706.3 |
| 37 | 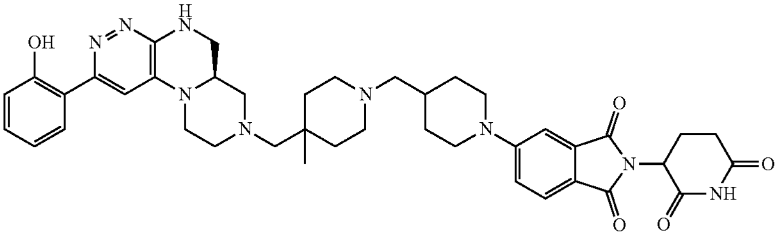 [SMILES: CC1(CN2CCN3c4cc(-c5ccccc5O)nnc4NC[C@H]3C2)CCN(CC2CCN(c3ccc4c(c3)C(=O)N(C3CCC(=O)NC3=O)C4=O)CC2)CC1] 2-(2,6-dioxopiperidin-3-yl)-5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)-4-methylpiperidin-1-yl)methyl)piperidin-1-yl)isoindoline-1,3-dione | 748.4 | 748.3 |
| 38 | 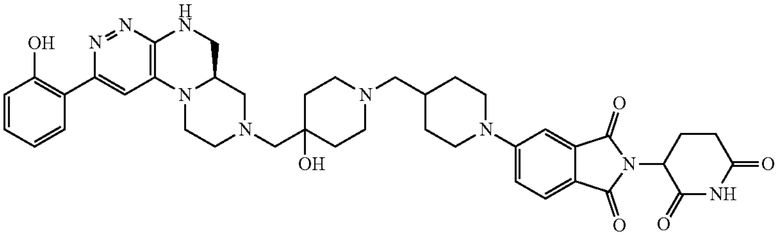 [SMILES: O=C1CCC(N2C(=O)c3ccc(N4CCC(CN5CCC(O)(CN6CCN7c8cc(-c9ccccc9O)nnc8NC[C@H]7C6)CC5)CC4)cc3C2=O)C(=O)N1] 2-(2,6-dioxopiperidin-3-yl)-5-(4-((4-hydroxy-4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl)isoindoline-1,3-dione | 750.4 | 750.2 |

TABLE 10-continued

Examples 30-33, 35-46, 49, 51-53, 55, 56, 59, 92, 93 and 257-260

| Ex. | Structure/Name | Calcd. (M + H)+ m/z | Found (M + H)+ m/z |
|---|---|---|---|
| 39 | 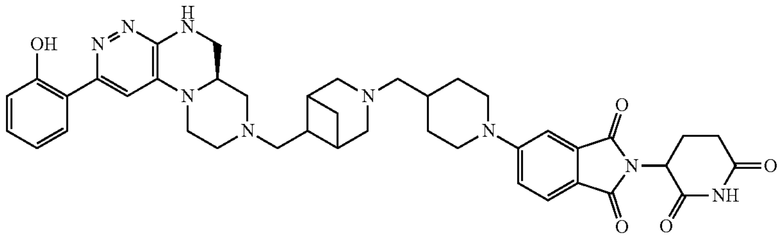 [SMILES: O=C1CCC(N2C(=O)c3ccc(N4CCC(CN5CC6CC(C5)C6CN5CCN6c7cc(-c8ccccc8O)nnc7NC[C@H]6C5)CC4)cc3C2=O)C(=O)N1] 2-(2,6-dioxopiperidin-3-yl)-5-(4-((6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.1]heptan-3-yl)methyl)piperidin-1-yl)isoindoline-1,3-dione | 746.4 | 746.2 |
| 40 | 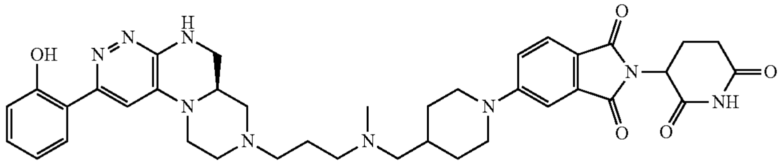 [SMILES: CN(CCCN1CCN2c3cc(-c4ccccc4O)nnc3NC[C@H]2C1)CC1CCN(c2ccc3c(c2)C(=O)N(C2CCC(=O)NC2=O)C3=O)CC1] 2-(2,6-dioxopiperidin-3-yl)-5-(4-(((3-((S)-2-(2-hydroxyphenyl)-5,6,6a,7,9,10-hexahydro-8H-pyrazino[1',2':4,5]pyrazino[2,3-c]pyridazin-8-yl)propyl)(methyl)amino)methyl)piperidin-1-yl)isoindoline-1,3-dione | 708.4 | 708.2 |
| 41 | 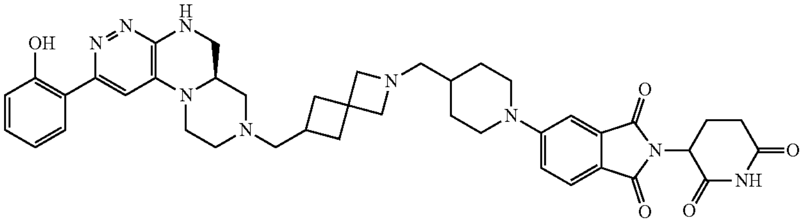 [SMILES: O=C1CCC(N2C(=O)c3ccc(N4CCC(CN5CC6(CC(CN7CCN8c9cc(-c%10ccccc%10O)nnc9NC[C@H]8C7)C6)C5)CC4)cc3C2=O)C(=O)N1] 2-(2,6-dioxopiperidin-3-yl)-5-(4-((6-(((S)-2-(2-hydroxyphenyl)-5,6,6a,7,9,10-hexahydro-8H-pyrazino[1',2':4,5]pyrazino[2,3-c]pyridazin-8-yl)methyl)-2-azaspiro[3.3]heptan-2-yl)methyl)piperidin-1-yl)isoindoline-1,3-dione | 746.4 | 746.2 |
| 42 | 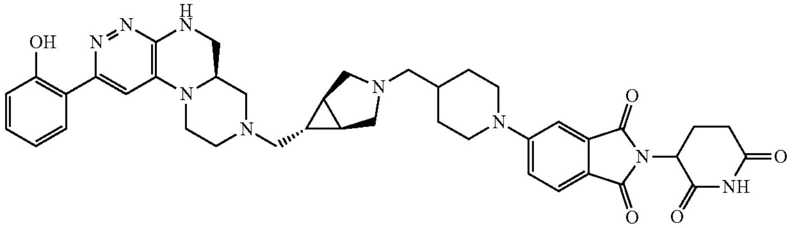 [SMILES: O=C1CCC(N2C(=O)c3ccc(N4CCC(CN5C[C@@H]6[C@H](C5)[C@H]6CN5CCN6c7cc(-c8ccccc8O)nnc7NC[C@H]6C5)CC4)cc3C2=O)C(=O)N1] 2-(2,6-dioxopiperidin-3-yl)-5-(4-(((1R,5S,6r)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)piperidin-1-yl)isoindoline-1,3-dione | 732.4 | 732.2 |
| 43 | 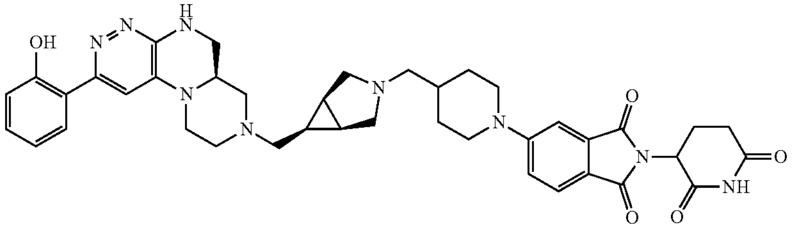 [SMILES: O=C1CCC(N2C(=O)c3ccc(N4CCC(CN5C[C@@H]6[C@H](C5)[C@@H]6CN5CCN6c7cc(-c8ccccc8O)nnc7NC[C@H]6C5)CC4)cc3C2=O)C(=O)N1] 2-(2,6-dioxopiperidin-3-yl)-5-(4-(((1R,5S,6s)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)piperidin-1-yl)isoindoline-1,3-dione | 732.4 | 732.3 |

TABLE 10-continued

Examples 30-33, 35-46, 49, 51-53, 55, 56, 59, 92, 93 and 257-260

| Ex. | Structure/Name | Calcd. (M + H)+ m/z | Found (M + H)+ m/z |
|---|---|---|---|
| 44 | 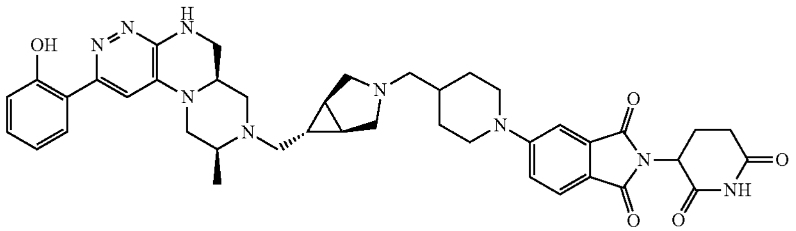 [SMILES: C[C@H]1CN2c3cc(-c4ccccc4O)nnc3NC[C@H]2CN1C[C@H]1[C@@H]2CN(CC3CCN(c4ccc5c(c4)C(=O)N(C4CCC(=O)NC4=O)C5=O)CC3)C[C@@H]21] 2-(2,6-dioxopiperidin-3-yl)-5-(4-(((1R,5S,6r)-6-(((6aS,9S)-2-(2-hydroxyphenyl)-9-methyl-5,6,6a,7,9,10-hexahydro-8H-pyrazino [1',2':4,5]pyrazino[2,3-c]pyridazin-8-yl)methyl)-3-azabicyclo [3.1.0]hexan-3-yl)methyl)piperidin-1-yl)isoindoline-1,3-dione | 746.4 | 746.3 |
| | $^1$H NMR (400 MHz, MeOD) δ 7.68 (d, J = 8.5 Hz, 1H), 7.54 (dd, J = 7.7, 1.7 Hz, 1H), 7.44 (td, J = 7.8, 1.7 Hz, 1H), 7.37-7.30 (m, 2H), 7.23 (dd, J = 8.7, 2.3 Hz, 1H), 7.08-7.00 (m, 2H), 5.07 (dd, J = 12.5, 5.4 Hz, 1H), 4.33 (d, J = 14.3 Hz, 1H), 4.17-3.87 (m, 6H), 3.82-3.67 (m, 2H), 3.59-3.49 (m, 2H), 3.44 (dd, J = 12.4, 7.5 Hz, 1H), 3.27-3.14 (m, 4H), 3.10-2.93 (m, 4H), 2.92-2.80 (m, 1H), 2.79-2.65 (m, 2H), 2.17-1.98 (m, 4H), 1.98-1.86 (m, 2H), 1.72-1.59 (m, 1H), 1.49-1.30 (m, 5H). | | |
| 45 | 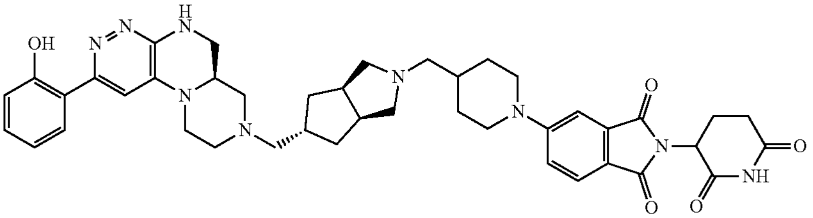 [SMILES: O=C1CCC(N2C(=O)c3ccc(N4CCC(CN5C[C@H]6C[C@H](CN7CCN8c9cc(-c%10ccccc%10O)nnc9NC[C@H]8C7)C[C@H]6C5)CC4)cc3C2=O)C(=O)N1] 2-(2,6-dioxopiperidin-3-yl)-5-(4-(((3aR,5s,6aS)-5-(((S)-2-(2-hydroxyphenyl)-5,6,6a,7,9,10-hexahydro-8H-pyrazino [1',2':4,5] pyrazino[2,3-c]pyridazin-8-yl)methyl) hexahydrocyclopenta [c]pyrrol-2(1H)-yl)methyl)piperidin-1-yl)isoindoline-1,3-dione | 760.4 | 760.2 |
| 46 | 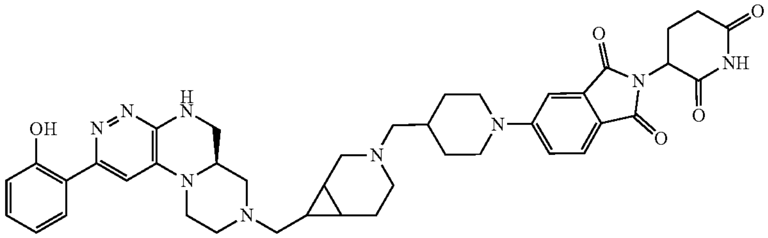 [SMILES: O=C1CCC(N2C(=O)c3ccc(N4CCC(CN5CCC6C(C5)C6CN5CCN6c7cc(-c8ccccc8O)nnc7NC[C@H]6C5)CC4)cc3C2=O)C(=O)N1] 2-(2,6-dioxopiperidin-3-yl)-5-(4-((7-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[4.1,0]heptan-3-yl)methyl)piperidin-1-yl)isoindoline-1,3-dione | 746.4 | 746.2 |
| 49 | 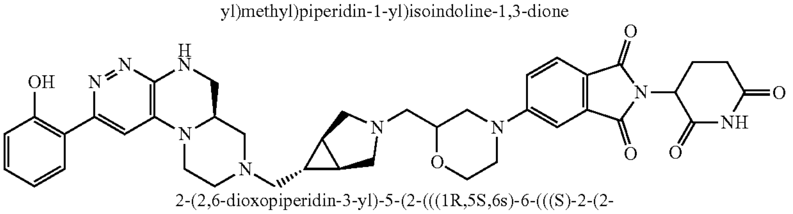 2-(2,6-dioxopiperidin-3-yl)-5-(2-(((1R,5S,6s)-6-(((S)-2-(2-hydroxyphenyl)-5,6,6a,7,9,10-hexahydro-8H-pyrazino [1',2':4,5]pyrazino[2,3-c]pyridazin-8-yl)methyl)-3-azabicyclo [3.1.0]hexan-3-yl)methyl)morpholino)isoindoline-1,3-dione | 734.3 | 734.2 |
| | $^1$H NMR (400 MHz, MeOD) δ 7.73 (d, J = 8.5 Hz, 1H), 7.53 (dd, J = 7.7, 1.7 Hz, 1H), 7.46-7.39 (m, 2H), 7.28 (dd, J = 8.5, 2.3 Hz, 1H), 7.23 (s, 1H), 7.08-7.00 (m, 2H), 5.08 (dd, J = 12.5, 5.4 Hz, 1H), 4.33-4.22 (m, 1H), 4.18-4.09 (m, 1H), 4.05-3.94 (m, 1H), 3.95-3.76 (m, 5H), 3.72 (dd, J = 12.2, 4.0 Hz, 1H), 3.60-3.50 (m, 1H), 3.51-3.35 (m, 6H), 3.33 (s, 1H), 3.34-3.32 (m, 1H), 3.11-2.99 (m, 1H), 2.94-2.62 (m, 7H), 2.56-2.42 (m, 1H), 2.11 (ddd, J = 13.0, 5.4, 2.8 Hz, 1H), 2.04-1.89 (m, 2H), 1.56-1.39 (m, 1H). | | |

TABLE 10-continued

| Ex. | Structure/Name | Calcd. (M + H)+ m/z | Found (M + H)+ m/z |
|---|---|---|---|
| 51 | 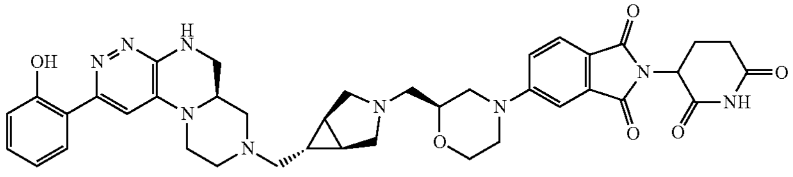 2-(2,6-dioxopiperidin-3-yl)-5-((S)-2-(((1R,5S,6R)-6-(((S)-2-(2-hydroxyphenyl)-5,6,6a,7,9,10-hexahydro-8H-pyrazino [1',2':4,5]pyrazino[2,3-c]pyridazin-8-yl)methyl)-3-azabicyclo [3.1.0]hexan-3-yl)methyl)morpholino)isoindoline-1,3-dione | 734.3 | 734.2 |
| 52 | 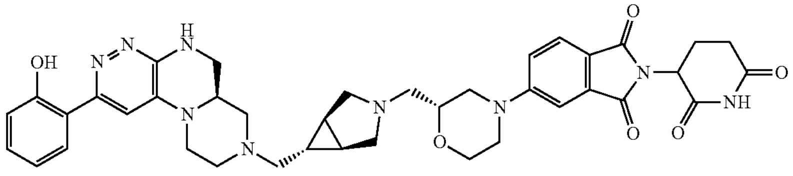 [SMILES: O=C1CCC(N2C(=O)c3ccc(N4CCOC(CN5C[C@@H]6[C@H](C5)[C@H]6CN5CCN6c7cc(-c8ccccc8O)nnc7NC[C@H]6C5)C4)cc3C2=O)C(=O)N1] 2-(2,6-dioxopiperidin-3-yl)-5-((R)-2-(((1R,5S,6S)-6-(((S)-2-(2-hydroxyphenyl)-5,6,6a,7,9,10-hexahydro-8H-pyrazino [1',2':4,5]pyrazino[2,3-c]pyridazin-8-yl)methyl)-3-azabicyclo [3.1.0]hexan-3-yl)methyl)morpholino)isoindoline-1,3-dione | 734.3 | 734.2 |
| 53 | 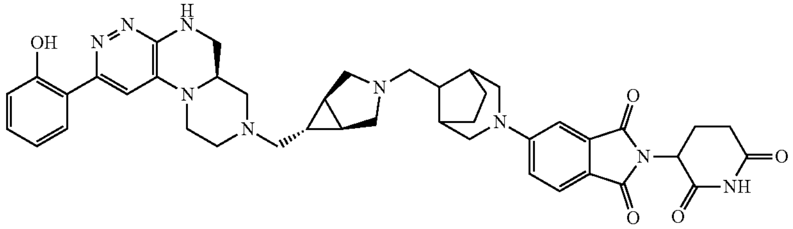 [SMILES: O=C1CCC(N2C(=O)c3ccc(N4CC5CCC(C4)C5CN4C[C@@H]5[C@H](C4)[C@H]5CN4CCN5c6cc(-c7ccccc7O)nnc6NC[C@H]5C4)cc3C2=O)C(=O)N1] 2-(2,6-dioxopiperidin-3-yl)-5-(8-(((1R,5S,6r)-6-(((S)-2-(2-hydroxyphenyl)-5,6,6a,7,9,10-hexahydro-8H-pyrazino [1',2':4,5] pyrazino[2,3-c]pyridazin-8-yl)methyl)-3-azabicyclo [3.1,0]hexan-3-yl)methyl)-3-azabicyclo[3.2.1]octan-3-yl)isoindoline-1,3-dione | 758.4 | 758.3 |
| 55 | 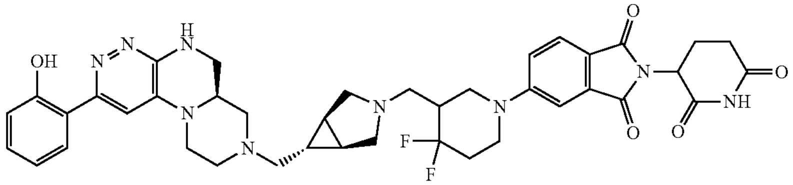 [SMILES: O=C1CCC(N2C(=O)c3ccc(N4CCC(F)(F)C(CN5C[C@@H]6[C@H](C5)[C@H]6CN5CCN6c7cc(-c8ccccc8O)nnc7NC[C@H]6C5)C4)cc3C2=O)C(=O)N1] 5-(4,4-difluoro-3-(((1R,5S,6r)-6-(((S)-2-(2-hydroxyphenyl)-5,6,6a,7,9,10-hexahydro-8H-pyrazino[1',2':4,5]pyrazino[2,3-c] pyridazin-8-yl)methyl)-3-azabicyclo[3.1.0]hexan-3-yl)methyl) piperidin-1-yl)-2-(2,6-dioxopiperidin-3-yl)isoindoline-1,3-dione<br>$^{1}$H NMR (400 MHz, MeOD) δ 7.75-7.68 (m, 1H), 7.54 (dd, J = 7.8, 1.8 Hz, 1H), 7.51-7.46 (m, 1H), 7.46-7.39 (m, 1H), 7.39-7.32 (m, 1H), 7.28 (s, 1H), 7.09-7.00 (m, 2H), 5.07 (dd, J = 12.5, 5.4 Hz, 1H), 4.37 (d, J = 14.0 Hz, 1H), 4.28-4.08 (m, 1H), 4.06-3.86 (m, 3H), 3.84-3.71 (m, 2H), 3.71-3.57 (m, 3H), 3.57-3.45 (m, 3H), 3.41 (dd, J = 12.4, 7.5 Hz, 2H), 3.36-3.33 (m, 1H), 3.28-3.15 (m, 1H), 2.98 (d, J = 7.1 Hz, 3H), 2.92-2.66 (m, 4H), 2.67-2.50 (m, 1H), 2.30-2.06 (m, 3H), 2.04-1.90 (m, 2H), 1.72-1.58 (m, 1H). | 768.3 | 768.3 |

Table header line: Examples 30-33, 35-46, 49, 51-53, 55, 56, 59, 92, 93 and 257-260

TABLE 10-continued

Examples 30-33, 35-46, 49, 51-53, 55, 56, 59, 92, 93 and 257-260

| Ex. | Structure/Name | Calcd. (M + H)+ m/z | Found (M + H)+ m/z |
|---|---|---|---|
| 56 | 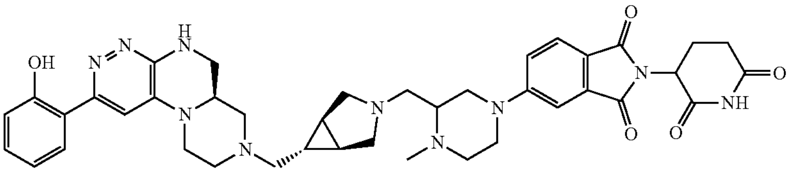 [SMILES: CN1CCN(c2ccc3c(c2)C(=O)N(C2CCC(=O)NC2=O)C3=O)CC1CN1C[C@@H]2[C@H](C1)[C@H]2CN1CCN2c3cc(-c4ccccc4O)nnc3NC[C@H]2C1] 2-(2,6-dioxopiperidin-3-yl)-5-(3-(((1R,5S,6r)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)-4-methylpiperazin-1-yl)isoindoline-1,3-dione<br><br>$^1$H NMR (400 MHz, MeOD) δ 7.77 (d, J = 8.4 Hz, 1H), 7.55 (d, J = 7.7 Hz, 1H), 7.48-7.41 (m, 2H), 7.35-7.29 (m, 2H), 7.08-7.01 (m, 2H), 5.08 (dd, J = 12.5, 5.4 Hz, 1H), 4.47 (d, J = 14.4 Hz, 1H), 4.13-4.00 (m, 1H), 4.00-3.73 (m, 5H), 3.72-3.50 (m, 5H), 3.47-3.33 (m, 2H), 3.29-3.16 (m, 3H), 3.16-3.03 (m, 3H), 3.01 (s, 3H), 2.99-2.86 (m, 2H), 2.86-2.77 (m, 1H), 2.78-2.57 (m, 4H), 2.15-2.06 (m, 1H), 1.75-1.60 (m, 3H). | 747.4 | 747.2 |
| 59 | 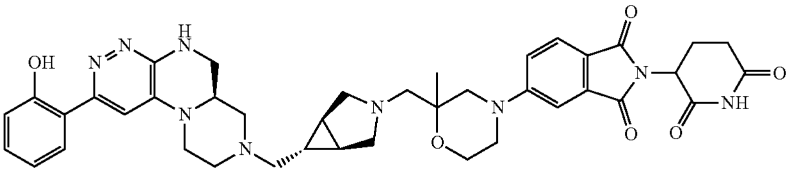 [SMILES: CC1(CN2C[C@@H]3[C@@H](CN4CCN5c6cc(-c7ccccc7O)nnc6NC[C@H]5C4)[C@@H]3C2)CN(c2ccc3c(c2)C(=O)N(C2CCC(=O)NC2=O)C3=O)CCO1] 2-(2,6-dioxopiperidin-3-yl)-5-(2-(((1R,5S,6s)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)-2-methylmorpholino)isoindoline-1,3-dione | 748.4 | 748.3 |
| 92 | 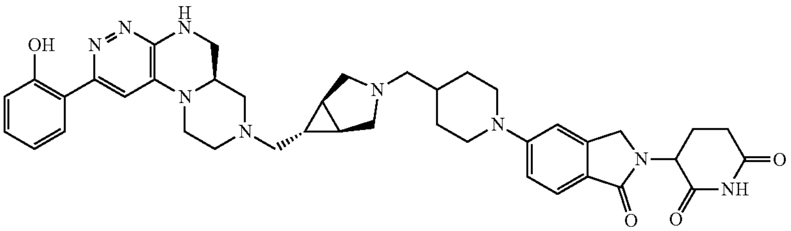 [SMILES: O=C1CCC(N2Cc3cc(N4CCC(CN5C[C@@H]6[C@H](C5)[C@H]6CN5CCN6c7cc(-c8ccccc8O)nnc7NC[C@H]6C5)CC4)ccc3C2=O)C(=O)N1] 3-(5-(4-(((1R,5S,6r)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)piperidin-1-yl)-1-oxoisoindolin-2-yl)piperidine-2,6-dione<br><br>$^1$H NMR (400 MHz, DMSO) δ 11.08 (s, 1H), 8.27 (s, 1H), 7.91 (d, J = 7.0Hz, 1H), 7.71 (d, J = 8.5 Hz, 1H), 7.38-7.07 (m, 5H), 6.85-6.82 (m, 2H), 5.07-5.06 (m, 1H), 4.06-3.82 (m, 4H), 3.61-3.58 (m, 2H), 3.09-3.05 (m, 6H), 2.95-2.85 (m, 3H), 2.72-2.52 (m, 5H), 2.20-2.17 (m, 7H), 1.76-1.73 (m, 1H), 1.22 (m, 3H). | 718.4 | 718.3 |
| 93 | 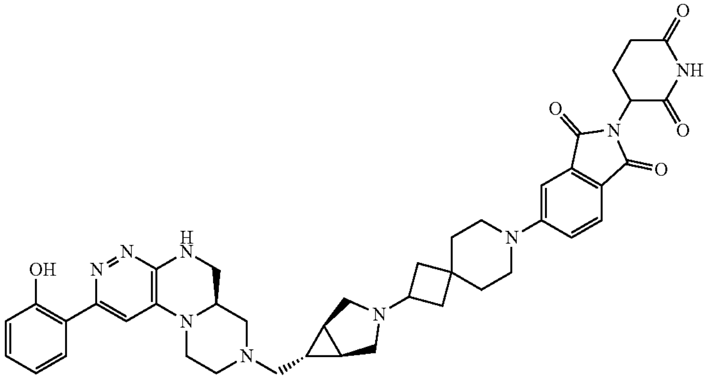 [SMILES: O=C1CCC(N2C(=O)c3ccc(N4CCC5(CC4)CC(N4C[C@@H]6[C@@H](CN7CCN8c9cc(-c%10ccccc%10O)nnc9NC[C@H]8C7)[C@@H]6C4)C5)cc3C2=O)C(=O)N1] 2-(2,6-dioxopiperidin-3-yl)-5-(2-((1R,5S,6s)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)-7-azaspiro[3.5]nonan-7-yl)isoindoline-1,3-dione | 758.4 | 758.5 |

TABLE 10-continued

| Ex. | Examples 30-33, 35-46, 49, 51-53, 55, 56, 59, 92, 93 and 257-260<br>Structure/Name | Calcd. (M + H)+ m/z | Found (M + H)+ m/z |
|---|---|---|---|
| | $^1$H NMR (400 MHz, DMSO) δ 11.08 (s, 1H), 8.27 (s, 1H), 7.91 (d, J = 7.0 Hz, 1H), 7.71 (d, J = 8.5 Hz, 1H), 7.38-7.07 (m, 5H), 6.85-6.82 (m, 2H), 5.07-5.06 (m, 1H), 4.06-3.82 (m, 4H), 3.61-3.58 (m, 2H), 3.09-3.05 (m, 6H), 2.95-2.85 (m, 3H), 2.72-2.52 (m, 5H), 2.20-2.17 (m, 7H), 1.76-1.73 (m, 1H), 1.22 (m, 3H). | | |
| 257 | 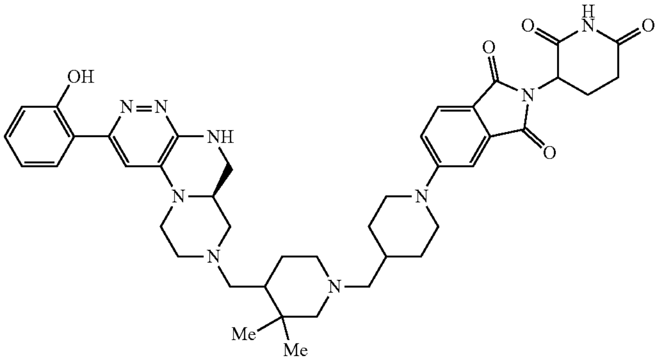 [SMILES: CC1(C)CN(CC2CCN(c3ccc4c(c3)C(=O)N(C3CCC(=O)NC3=O)C4=O)CC2)CCC1CN1CCN2c3cc(-c4ccccc4O)nnc3NC[C@H]2C1]<br>2-(2,6-dioxopiperidin-3-yl)-5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)-3,3-dimethylpiperidin-1-yl)methyl)piperidin-1-yl)isoindoline-1,3-dione | 762.4 | 762.5 |
| 258 | 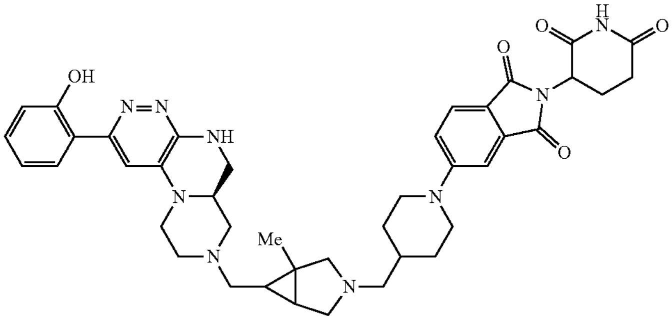 [SMILES: CC12CN(CC3CCN(c4ccc5c(c4)C(=O)N(C4CCC(=O)NC4=O)C5=O)CC3)CC1C2CN1CCN2c3cc(-c4ccccc4O)nnc3NC[C@H]2C1]<br>2-(2,6-dioxopiperidin-3-yl)-5-(4-((6-(((S)-2-(2-hydroxyphenyl)-5,6,6a,7,9,10-hexahydro-8H-pyrazino[1',2':4,5]pyrazino[2,3-c]pyridazin-8-yl)methyl)-1-methyl-3-azabicyclo[3.1.0]hexan-3-yl)methyl)piperidin-1-yl)isoindoline-1,3-dione | 746.4 | 746.4 |
| 259 | 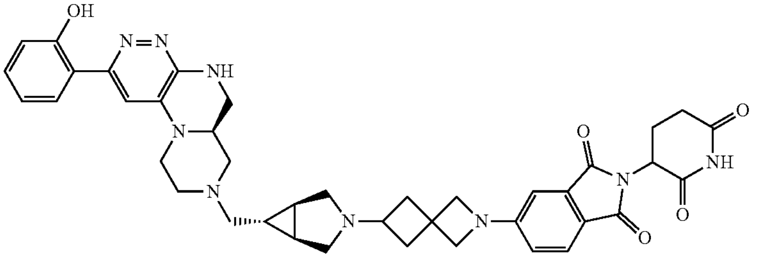 [SMILES: O=C1CCC(N2C(=O)c3ccc(N4CC5(CC(N6C[C@@H]7[C@@H](CN8CCN9c%10cc(-c%11ccccc%11O)nnc%10NC[C@H]9C8)[C@@H]7C6)C5)C4)cc3C2=O)C(=O)N1]<br>2-(2,6-dioxopiperidin-3-yl)-5-(6-((1R,5S,6s)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1,0]hexan-3-yl)-2-azaspiro[3.3]heptan-2-yl)isoindoline-1,3-dione | 730.4 | 730.3 |

TABLE 10-continued

| Examples 30-33, 35-46, 49, 51-53, 55, 56, 59, 92, 93 and 257-260 | | | |
|---|---|---|---|
| Ex. | Structure/Name | Calcd. (M + H)+ m/z | Found (M + H)+ m/z |
| 260 | 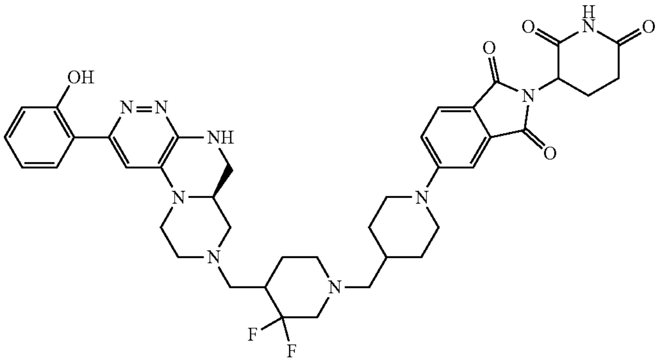 [SMILES: O=C1CCC(N2C(=O)c3ccc(N4CCC(CN5CCC(CN6CCN7c8cc(-c9ccccc9O)nnc8NC[C@H]7C6)C(F)(F)C5)CC4)cc3C2=O)C(=O)N1] 5-(4-((3,3-difluoro-4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl)-2-(2,6-dioxopiperidin-3-yl)isoindoline-1,3-dione | 770.4 | 770.5 |

Example 47: 2-(2,6-dioxopiperidin-3-yl)-5-(4-hydroxy-4-(((1R,5S,6s)-6-(((S)-2-(2-hydroxyphenyl)-5,6,6a,7,9,10-hexahydro-811-pyrazino[1',2':4,5]pyrazino[2,3-c]pyridazin-8-yl)methyl)-3-azabicyclo[3.1.0]hexan-3-yl)methyl)piperidin-1-yl)isoindoline-1,3-dione Ex. 47

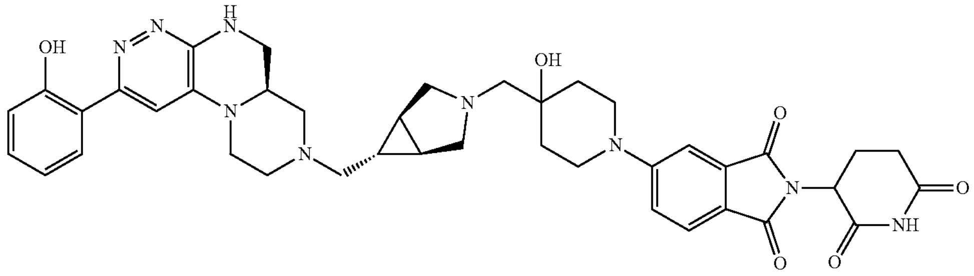

Step 1: tert-butyl 4-hydroxy-4-(((1R,5S,6r)-6-(hydroxymethyl)-3-azabicyclo[3.1.0]hexan-3-yl)methyl)piperidine-1-carboxylate

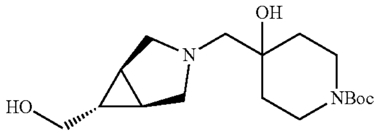 [SMILES: CC(C)(C)OC(=O)N1CCC(O)(CN2C[C@@H]3[C@@H](CO)[C@@H]3C2)CC1]

To ((1R,5S,6r)-3-azabicyclo[3.1.0]hexan-6-yl)methanol (150 mg, 0.70 mmol) and tert-butyl 1-oxa-6-azaspiro[2.5]octane-6-carboxylate (96 mg, 0.84 mmol) in DMSO (5 mL) was added N,N-diisopropylethylamine (0.17 mL, 0.99 mmol). The reaction was stirred at 120° C. for ~20 h then allowed to cool to room temperature. The reaction was diluted with MeOH and purified via prep-HPLCMS (Waters SunFire C18, 5 μm particle size, 30×100 mm; mobile phase: Aq(0.1% TFA)/MeCN @ 60 mL/min; gradient: 10-30% MeCN over 5 min). The combined fractions were basified to pH>10 with saturated aq $Na_2CO_3$ then extracted with DCM (3×40 mL). The combined DCM layers were washed with brine (1×30 mL), dried with $MgSO_4$, filtered and concentrated to afford tert-butyl 4-hydroxy-4-(((1R,5S,6r)-6-(hydroxymethyl)-3-azabicyclo[3.1.0]hexan-3-yl)methyl)piperidine-1-carboxylate (159 mg, 0.49 mmol, 69%). LCMS calcd. for $C_{17}H_{31}N_2O_4^+$[M+H]+ m/z=327.2; found: 327.1.

Step 2: 4-(((1R,5S,6r)-6-(hydroxymethyl)-3-azabicyclo[3.1.0]hexan-3-yl)methyl)piperidin-4-ol

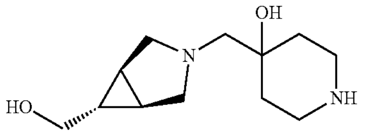 [SMILES: OC[C@@H]1[C@H]2CN(CC3(O)CCNCC3)C[C@@H]12]

To tert-butyl 4-hydroxy-4-(((1R,5S,6r)-6-(hydroxymethyl)-3-azabicyclo[3.1.0]hexan-3-yl)methyl)piperidine-1-carboxylate (159 mg, 0.49 mmol) was added 4 N HCl in dioxane (6.1 mL, 24.4 mmol). After the reaction was stirred at room temperature for 5 min, MeOH (3 mL) was added. After stirring at room temperature for an additional 50 min, the reaction was concentrated to afford 4-(((1R,5S,6r)-6-(hydroxymethyl)-3-azabicyclo[3.1.0]hexan-3-yl)methyl)piperidin-4-ol (assumed quantitative yield of 146 mg) as its bis(HCl) salt which was used directly without further purification. LCMS calcd. for $C_{12}H_{23}N_2O_2^+[M+H]^+$ m/z=227.2; found: 227.0.

Step 3: 2-(2,6-dioxopiperidin-3-yl)-5-(4-hydroxy-4-(((R,5S,6r)-6-(hydroxymethyl)-3-azabicyclo[3.1.0]hexan-3-yl)methyl)piperidin-1-yl) isoindoline-1,3-dione

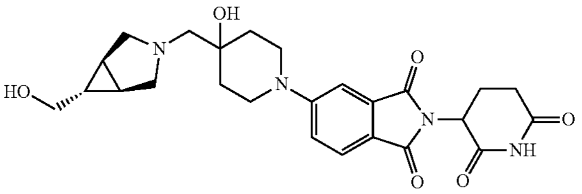 [SMILES: O=C1CCC(N2C(=O)c3ccc(N4CCC(O)(CN5C[C@@H]6[C@@H](CO)[C@@H]6C5)CC4)cc3C2=O)C(=O)N1]

To 4-(((1R,5S,6r)-6-(hydroxymethyl)-3-azabicyclo[3.1.0]hexan-3-yl)methyl)piperidin-4-ol (146 mg, 0.49 mmol) as its bis(HCl) salt and 2-(2,6-dioxopiperidin-3-yl)-5-fluoroisoindoline-1,3-dione (90 mg, 0.33 mmol) in NMP (2 mL) was added N,N-diisopropylethylamine (0.28 mL, 1.63 mmol). The reaction was stirred at 110° C. for 2 h then allowed to cool to room temperature. The reaction was purified via prep-HPLCMS (Waters CSH-C18, 5 µm particle size, 30×100 mm; mobile phase: Aq(0.1% TFA)/MeCN @ 60 mL/min; gradient: 7.2-27.2% MeCN over 5 min). The combined fractions were basified with saturated aq $Na_2CO_3$, diluted with water, extracted with DCM (2-3×). The combined organic layers were washed with brine, dried with $MgSO_4$, filtered and concentrated to afford 2-(2,6-dioxopiperidin-3-yl)-5-(4-hydroxy-4-(((1R,5S,6r)-6-(hydroxymethyl)-3-azabicyclo[3.1.0]hexan-3-yl)methyl)piperidin-1-yl) isoindoline-1,3-dione (34 mg, 0.07 mmol, 22%). LCMS calcd. for $C_{25}H_{31}N_4O_6^+[M+H]^+$ m/z=483.2; found: 483.1.

Step 4: (1R,5S,6r)-3-((1-(2-(2,6-dioxopiperidin-3-yl)-1,3-dioxoisoindolin-5-yl)-4-hydroxypiperidin-4-yl)methyl)-3-azabicyclo[3.1.0]hexane-6-carbaldehyde

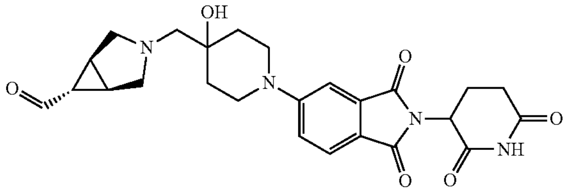 [SMILES: O=C[C@@H]1[C@H]2CN(CC3(O)CCN(c4ccc5c(c4)C(=O)N(C4CCC(=O)NC4=O)C5=O)CC3)C[C@@H]12]

To 2-(2,6-dioxopiperidin-3-yl)-5-(4-hydroxy-4-(((1R,5S,6r)-6-(hydroxymethyl)-3-azabicyclo[3.1.0]hexan-3-yl)methyl)piperidin-1-yl) isoindoline-1,3-dione (34 mg, 0.07 mmol) in DCM (2 mL) was added Dess-Martin Periodinane (75 mg, 0.18 mmol). The reaction was stirred at room temperature for 50 min at which point additional Dess-Martin Periodinane (75 mg, 0.18 mmol) and DCM (2 mL) were added. The reaction was stirred at room temperature for 2 h then quenched with saturated aq $Na_2CO_3$ (5 mL), diluted with water and extracted with DCM. The combined organic layers were washed with brine, dried with $MgSO_4$, filtered and concentrated to afford crude (1R,5S,6r)-3-((1-(2-(2,6-dioxopiperidin-3-yl)-1,3-dioxoisoindolin-5-yl)-4-hydroxypiperidin-4-yl)methyl)-3-azabicyclo[3.1.0]hexane-6-carbaldehyde (16.9 mg, 0.04 mmol, 50%) which was used directly without further purification. LCMS calcd. for $C_{25}H_{29}N_4O_6^+$ $[M+H]^+$ m/z=481.2; found: 481.1.

Step 5: 2-(2,6-dioxopiperidin-3-yl)-5-(4-hydroxy-4-(((1R, 5S,6s)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)piperidin-1-yl) isoindoline-1,3-dione (R)-2-(6,6a,7,8,9,10-hexahydro-5H-pyrazino[1',2':4,5]pyrazino[2,3-c]pyridazin-2-yl)phenol (15 mg, 0.04 mmol) as its bis(hydrochloric acid) salt and N,N-diisopropylethylamine (15 µL, 0.08 mmol) in DCM (1 mL) was added to (1R,5S,6r)-3-((1-(2-(2,6-dioxopiperidin-3-yl)-1,3-dioxoisoindolin-5-yl)-4-hydroxypiperidin-4-yl)methyl)-3-azabicyclo[3.1.0]hexane-6-carbaldehyde (16.9 mg, 0.04 mmol). AcOH (10 µL, 0.18 mmol), sodium triacetoxyborohydride (30 mg, 0.14 mmol) and DMF (1 mL) were added. The reaction was stirred at room temperature for 1 h then purified via prep-HPLCMS (Waters SunFire C18, 5 µm particle size, 30×100 mm; mobile phase: Aq(0.1% TFA)/MeCN @ 60 mL/min; gradient: 5-23% MeCN over 12 min) to afford 2-(2,6-dioxopiperidin-3-yl)-5-(4-hydroxy-4-(((1R,5S,6s)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)piperidin-1-yl) isoindoline-1,3-dione (13 mg, 12 µmol, 34%) as a yellow solid. LCMS calcd. for $C_{40}H_{46}N_9O_6^+$ $[M+H]^+$ m/z=748.4; found: 748.3.

Examples 48 and 50

Examples in Table 11 were prepared using the procedure described in the synthesis of Example 47 with appropriate intermediates.

TABLE 11

Examples 48 and 50

| Ex. | Structure/Name | Calcd. (M + H)+ m/z | Found (M + H)+ m/z |
|---|---|---|---|
| 48 | 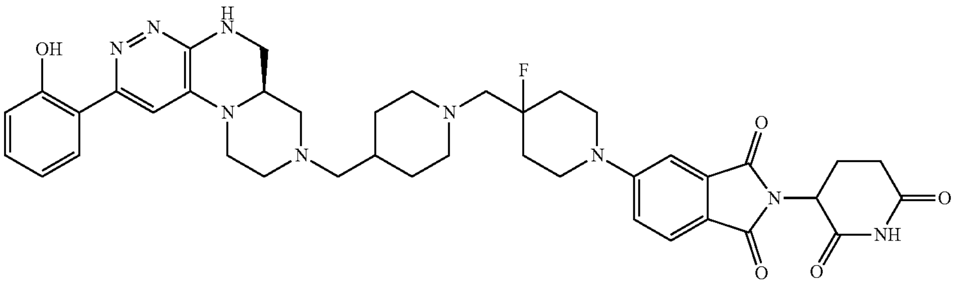 [SMILES: O=C1CCC(N2C(=O)c3ccc(N4CCC(F)(CN5CCC(CN6CCN7c8cc(-c9ccccc9O)nnc8NC[C@H]7C6)CC5)CC4)cc3C2=O)C(=O)N1] 2-(2,6-dioxopiperidin-3-yl)-5-(4-fluoro-4-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl)isoindoline-1,3-dione | 752.4 | 752.3 |
| 50 | 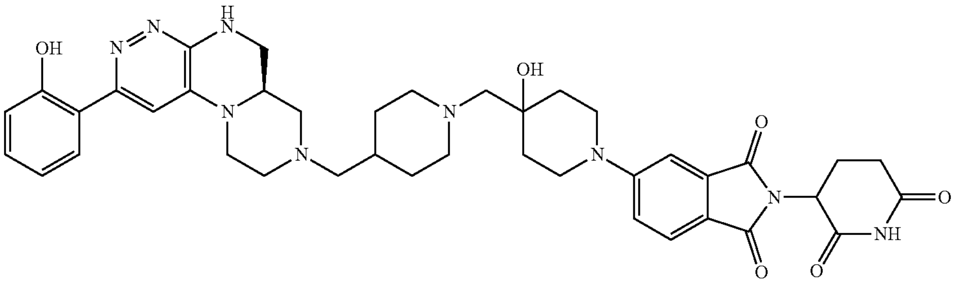 [SMILES: O=C1CCC(N2C(=O)c3ccc(N4CCC(O)(CN5CCC(CN6CCN7c8cc(-c9ccccc9O)nnc8NC[C@H]7C6)CC5)CC4)cc3C2=O)C(=O)N1] 2-(2,6-dioxopiperidin-3-yl)-5-(4-hydroxy-4-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl)isoindoline-1,3-dione | 750.4 | 750.3 |

Example 54: 3-(6-(4-(((1R,5S,6r)-6-(((6aS,9S)-2-(2-hydroxyphenyl)-9-methyl-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)piperidin-1-yl)-1-oxoisoindolin-2-yl)piperidine-2,6-dione Ex. 54

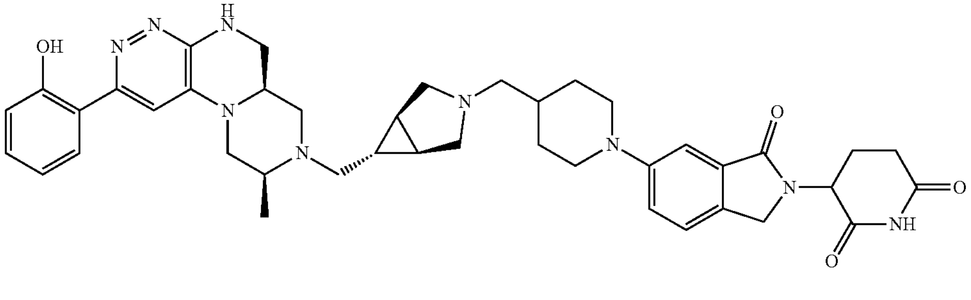

To 2-((6aS,9S)-8-(((1R,5S,6r)-3-azabicyclo[3.1.0]hexan-6-yl)methyl)-9-methyl-6,6a,7,8,9,10-hexahydro-5H-pyrazino[1',2':4,5]pyrazino[2,3-c]pyridazin-2-yl)phenol (20 mg, 0.03 mmol) as its tris(2,2,2-trifluoroacetic acid) salt in DMF (2 mL) was added 1-(2-(2,6-dioxopiperidin-3-yl)-3-oxoisoindolin-5-yl)piperidine-4-carbaldehyde (29 mg, 0.06 mmol) as its TFA salt. AcOH (8 μL, 0.14 mmol) and sodium triacetoxyborohydride (24 mg, 0.11 mmol) were added. The reaction was stirred at room temperature for 1 h then diluted with MeCN/TFA and a few drops of water. Purification of the crude reaction via prep-HPLCMS (Waters SunFire C18, 5 μm particle size, 30×100 mm; mobile phase: Aq(0.1% TFA)/MeCN @ 60 mL/min; gradient: 6-26% MeCN over 5 min) afforded 3-(6-(4-(((1R,5S,6r)-6-(((6aS,9S)-2-(2-hydroxyphenyl)-9-methyl-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)piperidin-1-yl)-1-oxoisoindolin-2-yl)piperidine-2,6-dione (5 mg, 4.7 μmol, 17%). LCMS calcd. for $C_{41}H_{50}N_9O_4$+[M+H]$^+$ m/z=732.4; found: 732.2.

Example 58: 2-(2,6-dioxopiperidin-3-yl)-5-(2-((1R,5S,6s)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)-5,7-dihydro-6H-pyrrolo[3,4-d]pyrimidin-6-yl)isoindoline-1,3-dione Ex. 58

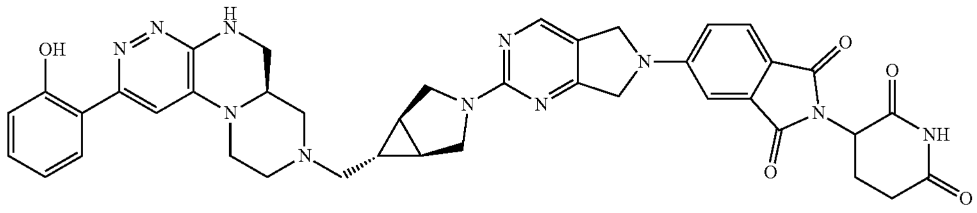

Step 1: tert-butyl 2-((1R,5S,6r)-6-(hydroxymethyl)-3-azabicyclo[3.1.0]hexan-3-yl)-5,7-dihydro-6H-pyrrolo[3,4-d]pyrimidine-6-carboxylate

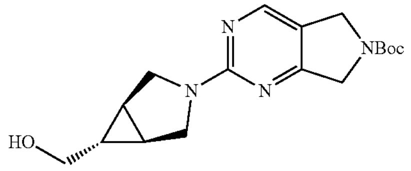 [SMILES: CC(C)(C)OC(=O)N1Cc2cnc(N3C[C@@H]4[C@@H](CO)[C@@H]4C3)nc2C1]

To tert-butyl 2-chloro-5,7-dihydro-6H-pyrrolo[3,4-d]pyrimidine-6-carboxylate (50 mg, 0.20 mmol) and (1R,5S,6r)-3-azabicyclo[3.1.0]hexan-6-yl)methanol (33 mg, 0.29 mmoL) in NMP (2 mL) was added N,N-diisopropylethylamine (55 μL, 0.31 mmol). The reaction was stirred at 100° C. for 3.5 h then allowed to cool to room temperature. The reaction was diluted with MeCN and purified via prep-HPLCMS (Waters SunFire C18, 5 μm particle size, 30×100 mm; mobile phase: Aq(0.1% TFA)/MeCN @ 60 mL/min; gradient: 19-39% MeCN over 5 min). The combined fractions containing product were basified with saturated aq $Na_2CO_3$ to pH>10 then extracted with DCM (2×). The combined DCM layers were dried with $MgSO_4$, filtered then concentrated to afford tert-butyl 2-((1R,5S,6r)-6-(hydroxymethyl)-3-azabicyclo[3.1.0]hexan-3-yl)-5,7-dihydro-6H-pyrrolo[3,4-d]pyrimidine-6-carboxylate (46 mg, 0.14 mmol, 71%) as a white solid. LCMS calcd. for $C_{17}H_{25}N_4O_3^+[M+H]^+$ m/z=333.2; found: 333.1.

Step 2: ((1R,5S,6r)-3-(6,7-dihydro-5H-pyrrolo[3,4-d]pyrimidin-2-yl)-3-azabicyclo[3.1.0]hexan-6-yl)methanol

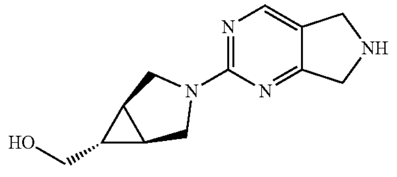 [SMILES: OC[C@@H]1[C@H]2CN(c3ncc4c(n3)CNC4)C[C@@H]12]

To tert-butyl 2-((1R,5S,6r)-6-(hydroxymethyl)-3-azabicyclo[3.1.0]hexan-3-yl)-5,7-dihydro-6H-pyrrolo[3,4-d]pyrimidine-6-carboxylate (46 mg, 0.14 mmol) in DCM (1 mL) was added TFA (1.05 mL, 13.8 mmol). The reaction was stirred at room temperature for ~1.5 h then concentrated. The residue was dissolved in a mixture of MeOH (1 mL), THF (1 mL) and water (1 mL). Solid NaOH (37 mg, 0.91 mmol) was added and the reaction was stirred at 60° C. for ~ 1 h then allowed to cool to room temperature. A minimal amount of 2 N HCl (aq) was added followed by neutralization with saturated aq $NaHCO_3$. The reaction was concentrated to afford crude ((1R,5S,6r)-3-(6,7-dihydro-5H-pyrrolo[3,4-d]pyrimidin-2-yl)-3-azabicyclo[3.1.0]hexan-6-yl)methanol (assumed quantitative yield of 32 mg) which was used directly without further purification. LCMS calcd. for $C_{12}H_{17}N_4O^+$ $[M+H]^+$ m/z=233.1; found: 233.1.

Step 3: 2-(2,6-dioxopiperidin-3-yl)-5-(2-((1R,5S,6r)-6-(hydroxymethyl)-3-azabicyclo[3.1.0]hexan-3-yl)-5,7-dihydro-6H-pyrrolo[3,4-d]pyrimidin-6-yl)isoindoline-1,3-dione

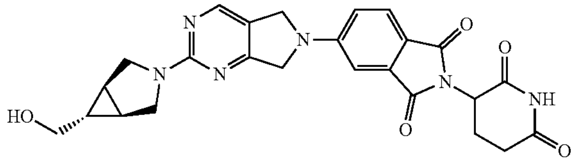 [SMILES: O=C1CCC(N2C(=O)c3ccc(N4Cc5cnc(N6C[C@@H]7[C@@H](CO)[C@@H]7C6)nc5C4)cc3C2=O)C(=O)N1]

To crude ((1R,5S,6r)-3-(6,7-dihydro-5H-pyrrolo[3,4-d]pyrimidin-2-yl)-3-azabicyclo[3.1.0]hexan-6-yl)methanol (32 mg, 0.14 mmol) and 2-(2,6-dioxopiperidin-3-yl)-5-fluoroisoindoline-1,3-dione (76 mg, 0.28 mmol) in NMP (1 mL) was added N,N-diisopropylethylamine (72 μL, 0.41 mmol). The reaction was stirred at 110° C. for ~1.5 h then allowed to cool to room temperature. Additional N,N-diisopropylethylamine (120 μL, 0.69 mmol) was added and the reaction was stirred at 130° C. overnight. The reaction was allowed to cool to room temperature then purified via prep-HPLCMS (Waters CSH Fluoro-Phenyl, 5 μm particle size, 30×100 mm; mobile phase: Aq(0.1% TFA)/MeCN @ 60 mL/min; gradient: 13.7-33.7% MeCN over 5 min). The combined fractions containing product were basified with triethylamine to pH-10-11 then concentrated to afford crude 2-(2,6-dioxopiperidin-3-yl)-5-(2-((1R,5S,6r)-6-(hydroxymethyl)-3-azabicyclo[3.1.0]hexan-3-yl)-5,7-dihydro-6H-pyrrolo[3,4-d]pyrimidin-6-yl) isoindoline-1,3-dione (assumed quantitative yield of 67 mg) which was used directly without further purification. LCMS calcd. for $C_{25}H_{25}N_6O_5$ [M+H]$^+$ m/z=489.2; found: 489.1.

Step 3: 2-(2,6-dioxopiperidin-3-yl)-5-(2-((1R,5S,6r)-6-(hydroxymethyl)-3-azabicyclo [3.1.0]hexan-3-yl)-5,7-dihydro-6H-pyrrolo[3,4-d]pyrimidin-6-yl) isoindoline-1,3-dione To crude 2-(2,6-dioxopiperidin-3-yl)-5-(2-((1R,5S,6r)-6-(hydroxymethyl)-3-azabicyclo[3.1.0]hexan-3-yl)-5,7-dihydro-6H-pyrrolo[3,4-d]pyrimidin-6-yl) isoindoline-1,3-dione (67 mg, 0.14 mmol) and triethylamine (154 µL, 1.1 mmol) in DMSO (1 mL) was added a solution of sulfur trioxide pyridine (66 mg, 0.41 mmol) in DMSO (1 mL). The reaction was stirred at room temperature for ~2.5 h. (R)-2-(6,6a,7,8,9,10-hexahydro-5H-pyrazino[1',2':4,5]pyrazino[2,3-c]pyridazin-2-yl)phenol (25 mg, 0.07 mmol) as its bis (HCl) salt and triethylamine (19 µL, 0.14 mmol) in MeCN (2 mL) were added, followed by AcOH (0.12 mL, 2.07 mmol) and sodium triacetoxyborohydride (123 mg, 0.58 mmol). The reaction was stirred at room temperature for ~1 h then stored in −80° C. freezer overnight. After allowing the reaction to warm to room temperature, a 1.5 mL aliquot was diluted with MeCN/MeOH/water, filtered through a 0.45 µm PTFE syringe filter, then purified via prep-HPLCMS (Waters CSH Fluoro-Phenyl, 5 µm particle size, 30×100 mm; mobile phase: Aq(0.1% TFA)/MeCN @ 60 mL/min; gradient: 10-30% MeCN over 5 min) to afford 2-(2,6-dioxopiperidin-3-yl)-5-(2-((1R,5S,6r)-6-(hydroxymethyl)-3-azabicyclo[3.1.0]hexan-3-yl)-5,7-dihydro-6H-pyrrolo[3,4-d]pyrimidin-6-yl) isoindoline-1,3-dione (10 mg, 9.4 µmol, 14%) as its tris(2,2,2-trifluoroacetic acid) salt. LCMS calcd. for $C_{40}H_{40}N_{11}O_5^+$[M+H]$^+$ m/z=754.3; found: 754.2.

Example 60: 2-(2,6-dioxopiperidin-3-yl)-5-(4-((2-((S)-2-(2-hydroxyphenyl)-5,6,6a,7,9,10-hexahydro-8H-pyrazino[1',2':4,5]pyrazino[2,3-c]pyridazin-8-yl)-5,8-dihydropyrido[3,4-d]pyrimidin-7(6H)-yl) methyl)piperidin-1-yl) isoindoline-1,3-dione Step 1: tert-butyl (S)-2-(2-(2-hydroxyphenyl)-5,6,6a, 7,9,10-hexahydro-8H-pyrazino[1',2':4,5]pyrazino [2,3-c]pyridazin-8-yl)-5,8-dihydropyrido[3,4-d]pyrimidine-7(6H)-carboxylate

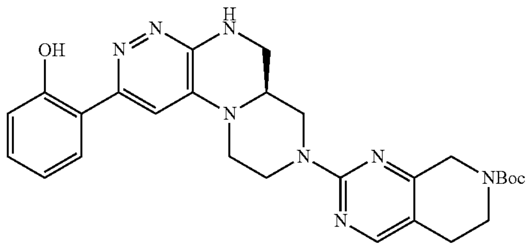 [SMILES: CC(C)(C)OC(=O)N1CCc2cnc(N3CCN4c5cc(-c6ccccc6O)nnc5NC[C@H]4C3)nc2C1]

To (R)-2-(6,6a,7,8,9,10-hexahydro-5H-pyrazino[1',2':4,5]pyrazino[2,3-c] pyridazin-2-yl)phenol (40 mg, 0.11 mmol) as its bis(HCl) salt in NMP (1 mL) was added N,N-diisopropylethylamine (65 µL, 0.37 mmol). tert-Butyl 2-chloro-5,8-dihydropyrido[3,4-d]pyrimidine-7(6H)-carboxylate (25 mg, 0.09 mmol) was added and the reaction was stirred at 110° C. for 4 h. The reaction was allowed to cool to room temperature then stored in −80° C. freezer overnight. After allowing the reaction to warm to room temperature, it was purified via prep-HPLCMS (Waters CSH Fluoro-Phenyl, 5 µm particle size, 30×100 mm; mobile phase: Aq(0.1% TFA)/MeCN @ 60 mL/min; gradient: 22.1-42.1% MeCN over 5 min). The combined fractions containing product were lyophilized to give tert-butyl (S)-2-(2-(2-hydroxyphenyl)-5,6,6a,7,9,10-hexahydro-8H-pyrazino[1',2':4,5]pyrazino[2,3-c]pyridazin-8-yl)-5,8-dihydropyrido[3,4-d]pyrimidine-7(6H)-carboxylate (21 mg, 0.03 mmol, 30%) as its bis(2,2,2-trifluoroacetic acid) salt as a beige lyophilate. LCMS calcd. for $C_{27}H_{33}N_8O_3^+$[M+H]$^+$ m/z=517.3; found: 517.1.

Ex. 60

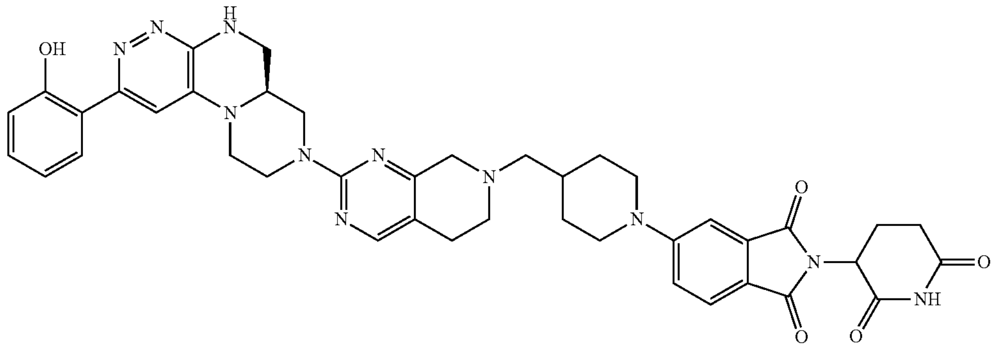

Step 2: (S)-2-(8-(5,6,7,8-tetrahydropyrido[3,4-d]pyrimidin-2-yl)-6,6a, 7,8,9,10-hexahydro-5H-pyrazino[1',2':4,5]pyrazino[2,3-c]pyridazin-2-yl)phenol

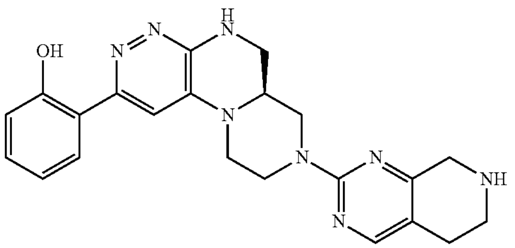 [SMILES: Oc1ccccc1-c1cc2c(nn1)NC[C@H]1CN(c3ncc4c(n3)CNCC4)CCN21]

To tert-butyl (S)-2-(2-(2-hydroxyphenyl)-5,6,6a,7,9,10-hexahydro-8H-pyrazino[1',2':4,5]pyrazino[2,3-c]pyridazin-8-yl)-5,8-dihydropyrido[3,4-d]pyrimidine-7(6H)-carboxylate (21 mg, 0.03 mmol) as its bis(2,2,2-trifluoroacetic acid) in DCM (1 mL) was added TFA (0.22 mL, 2.82 mmol). The reaction was stirred at room temperature for 35 min then was stored at −80° C. overnight. The reaction was allowed to warm to room temperature then concentrated to afford (S)-2-(8-(5,6,7,8-tetrahydropyrido[3,4-d]pyrimidin-2-yl)-6,6a,7,8,9,10-hexahydro-5H-pyrazino [1',2':4,5]pyrazino[2,3-c]pyridazin-2-yl)phenol (assumed quantitative yield of 21 mg) as its tris(2,2,2-trifluoroacetic acid) salt. LCMS calcd. for $C_{22}H_{25}N_8O^+$ [M+H]$^+$ m/z=417.2; found: 417.2.

Step 2: 2-(2,6-dioxopiperidin-3-yl)-5-(4-((2-((S)-2-(2-hydroxyphenyl)-5,6,6a, 7,9,10-hexahydro-8H-pyrazino[1',2':4,5]pyrazino[2,3-c]pyridazin-8-yl)-5,8-dihydropyrido[3,4-d]pyrimidin-7(6H)-yl)methyl)piperidin-1-yl) isoindoline-1,3-dione To (S)-2-(8-(5,6,7,8-tetrahydropyrido[3,4-d]pyrimidin-2-yl)-6,6a,7,8,9,10-hexahydro-5H-pyrazino[1',2':4,5]pyrazino[2,3-c]pyridazin-2-yl)phenol (11 mg, 0.74 mmol) as its tris(2,2,2-trifluoroacetic acid) salt in DMF (1 mL) was added 1-(2-(2,6-dioxopiperidin-3-yl)-1,3-dioxoisoindolin-5-yl)piperidine-4-carbaldehyde (7.0 mg, 0.02 mmol), followed by AcOH (5.4 μL, 0.09 mmol). The reaction was stirred briefly. Sodium triacetoxyborohydride (16 mg, 0.08 mmol) was added and the reaction was stirred at room temperature for 40 min then diluted with MeOH and purified via prep-HPLCMS (Waters CSH-C18, 5 μm particle size, 30×100 mm; mobile phase: Aq(0.1% TFA)/MeCN @ 60 mL/min; gradient: 13.8-33.8% MeCN over 5 min) to afford Step 2: 2-(2,6-dioxopiperidin-3-yl)-5-(4-((2-((S)-2-(2-hydroxyphenyl)-5,6,6a,7,9,10-hexahydro-8H-pyrazino[1',2':4,5]pyrazino[2,3-c]pyridazin-8-yl)-5,8-dihydropyrido[3,4-d]pyrimidin-7(6H)-yl)methyl)piperidin-1-yl) isoindoline-1,3-dione (6 mg, 5.5 μmol, 29%) as its tris(2,2,2-trifluoroacetic acid) salt as a yellow solid. LCMS calcd. for $C_{41}H_{44}N_{11}O_5^+$ [M+H]$^+$ m/z=770.4; found: 770.3.

Example 61: 3-(6-(4-((2-((S)-2-(2-hydroxyphenyl)-5,6,6a,7,9,10-hexahydro-8H-pyrazino[1',2':4,5]pyrazino[2,3-c]pyridazin-8-yl)-5,7-dihydro-6H-pyrrolo[3,4-d]pyrimidin-6-yl)methyl)piperidin-1-yl)-1-oxoisoindolin-2-yl)piperidine-2,6-dione Ex. 61

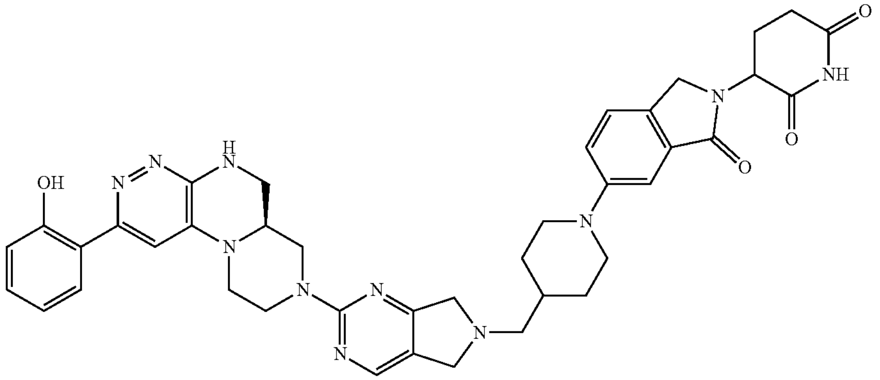

Step 1: tert-butyl (S)-2-(2-(2-hydroxyphenyl)-5,6,6a, 7,9,10-hexahydro-8H-pyrazino[1',2':4,5]pyrazino[2,3-c]pyridazin-8-yl)-5,7-dihydro-6H-pyrrolo[3,4-d]pyrimidine-6-carboxylate

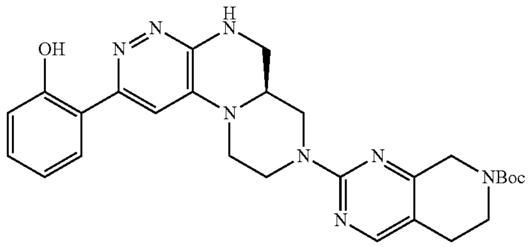 [SMILES: CC(C)(C)OC(=O)N1CCc2cnc(N3CCN4c5cc(-c6ccccc6O)nnc5NC[C@H]4C3)nc2C1]

To (R)-2-(6,6a,7,8,9,10-hexahydro-5H-pyrazino[1',2':4,5]pyrazino[2,3-c]pyridazin-2-yl)phenol (41 mg, 0.0.12 mmol) as its bis(HCl) salt in NMP (1 mL) was added N,N-diisopropylethylamine (65 μL, 0.37 mmol). The mixture was sonicated briefly (until homogeneous). tert-Butyl 2-chloro-5,7-dihydro-6H-pyrrolo[3,4-d]pyrimidine-6-carboxylate (24 mg, 0.09 mmol) was added and the reaction was stirred at 110° C. for 4 h. The reaction was allowed to cool to room temperature then stored in −80° C. freezer overnight. After allowing the reaction to warm to room temperature, it was purified via prep-HPLCMS (Waters CSH Fluoro-Phenyl, 5 μm particle size, 30×100 mm; mobile phase: Aq(0.1% TFA)/MeCN @ 60 mL/min; gradient: 20.3-40.3% MeCN over 5 min) to give tert-butyl (S)-2-(2-(2-hydroxyphenyl)-5,6,6a,7,9,10-hexahydro-8H-pyrazino[1',2':4,5]pyrazino[2,3-c]pyridazin-8-yl)-5,7-dihydro-6H-pyrrolo[3,4-d]pyrimidine-6-carboxylate (45 mg, 0.06 mmol, 67%) as its bis(2,2,2-trifluoroacetic acid) salt as a beige solid. LCMS calcd. for $C_{26}H_{31}N_8O_3^+$[M+H]$^+$ m/z=503.3; found: 503.1.

Step 2: (S)-2-(8-(6,7-dihydro-5H-pyrrolo[3,4-d]pyrimidin-2-yl)-6,6a, 7,8,9,10-hexahydro-5H-pyrazino[1',2':4,5]pyrazino[2,3-c]pyridazin-2-yl)phenol

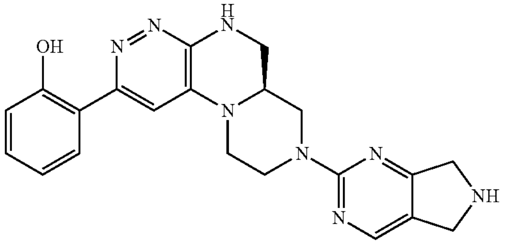 [SMILES: Oc1ccccc1-c1cc2c(nn1)NC[C@H]1CN(c3ncc4c(n3)CNC4)CCN21]

To tert-butyl (S)-2-(2-(2-hydroxyphenyl)-5,6,6a,7,9,10-hexahydro-8H-pyrazino[1',2':4,5]pyrazino[2,3-c]pyridazin-8-yl)-5,7-dihydro-6H-pyrrolo[3,4-d]pyrimidine-6-carboxylate (45 mg, 0.06 mmol) as its bis(2,2,2-trifluoroacetic acid) salt in DCM (2 mL) was added TFA (0.47 mL, 6.16 mmol). The reaction was stirred at room temperature for 2 h, stored overnight at −80° C., then concentrated to afford (S)-2-(8-(6,7-dihydro-5H-pyrrolo[3,4-d]pyrimidin-2-yl)-6,6a,7,8,9,10-hexahydro-5H-pyrazino[1',2':4,5]pyrazino[2,3-c]pyridazin-2-yl)phenol (assumed quantitative yield of 46 mg) as its tris(2,2,2-trifluoroacetic acid) salt which was used directly without further purification. LCMS calcd. for $C_{21}H_{23}N_8O^+$ [M+H]$^+$ m/z=403.2; found: 403.1.

Step 3: 3-(6-(4-((2-((S)-2-(2-hydroxyphenyl)-5,6,6a,7,9,10-hexahydro-8H-pyrazino[1',2':4,5]pyrazino[2,3-c]pyridazin-8-yl)-5,7-dihydro-6H-pyrrolo[3,4-d]pyrimidin-6-yl)methyl)piperidin-1-yl)-1-oxoisoindolin-2-yl)piperidine-2,6-dione To 3-(6-(4-(hydroxymethyl)piperidin-1-yl)-1-oxoisoindolin-2-yl)piperidine-2,6-dione (10 mg, 0.03 mmol) and triethylamine (23 μL, 0.17 mmol) in DMSO (0.25 mL) was added a solution of sulfur trioxide pyridine (13 mg, 0.08 mmol) in DMSO (0.25 mL) at room temperature. The reaction was stirred at room temperature for 40 min. (S)-2-(8-(6,7-dihydro-5H-pyrrolo[3,4-d]pyrimidin-2-yl)-6,6a,7,8,9,10-hexahydro-5H-pyrazino[1',2':4,5]pyrazino[2,3-c]pyridazin-2-yl)phenol (12 mg, 0.02 mmol) as its tris(2,2,2-trifluoroacetic acid) salt in DMF (1 mL) was added, followed by AcOH (19 μL, 0.34 mmol) then sodium triacetoxyborohydride (24 mg, 0.11 mmol). The reaction was stirred at room temperature for 40 min then diluted with MeCN (~1 mL) and stirred for an additional 15 min. The mixture was filtered through a 0.45 μm PP syringe filter and purified via prep-HPLCMS (Waters CSH Fluoro-Phenyl, 5 μm particle size, 30×100 mm; mobile phase: Aq(0.1% TFA)/MeCN @ 60 mL/min; gradient: 6.1-26.1% MeCN over 5 min) to give 3-(6-(4-((2-((S)-2-(2-hydroxyphenyl)-5,6,6a,7,9,10-hexahydro-8H-pyrazino [1',2':4,5]pyrazino[2,3-c]pyridazin-8-yl)-5,7-dihydro-6H-pyrrolo[3,4-d]pyrimidin-6-yl)methyl) piperidin-1-yl)-1-oxoisoindolin-2-yl) piperidine-2,6-dione (9.2 mg, 8.5 μmol, 30%) as its tris(2,2-trifluoroacetic acid) salt as a white solid. LCMS calcd. for $C_{40}H_{44}N_{11}O_4^+$[M+H]$^+$ m/z=742.4; found: 742.3.

Example 66: 2-(2,6-dioxopiperidin-3-yl)-4-(4-((S)-2-(2-hydroxyphenyl)-5,6,6a,7,9,10-hexahydro-8H-pyrazino[1',2':4,5]pyrazino[2,3-c]pyridazin-8-yl)-[1,4'-bipiperidin]-1'-yl) isoindoline-1,3-dione Ex. 66

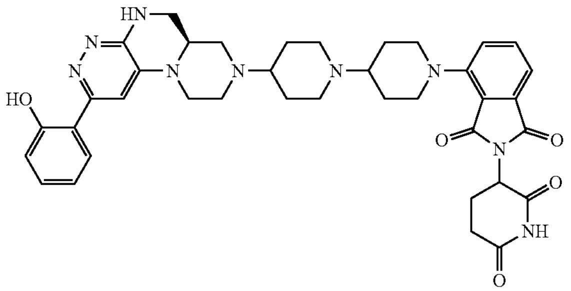

A mixture of (S)-2-(8-([1,4'-bipiperidin]-4-yl)-6,6a,7,8,9,10-hexahydro-5H-pyrazino [1',2':4,5] pyrazino[2,3-c] pyridazin-2-yl)phenol (10.0 mg, 0.02 mmol), 2-(2,6-Dioxopiperidin-3-yl)-4-fluoroisoindoline-1,3-dione (12.29 mg, 0.04 mmol), and N,N-Diisopropylethylamine (11.62 uL, 0.07 mmol) in DMSO (0.50 mL) was stirred at 100° C. for 3 h. The reaction mixture was diluted with MeOH 4 mL and filtered through a syringe filter. The resulting solution was purified by Prep-HPLC to give the tile compound (8 mg, 51% yield) as a yellow solid. LCMS calcd. for $C_{38}H_{44}N_9O_5$ [M+H]+m/z=706.3; found: 706.2.

Examples 67-73

Examples in Table 12 were prepared using the procedure described in the synthesis of Example 66 with appropriate intermediates.

TABLE 12

| Ex. | Structure Name | Calcd. $(M + H)^+$ m/z | Found $(M + H)^+$ m/z |
| --- | --- | --- | --- |
| | Examples 67-73 | | |
| 67 | 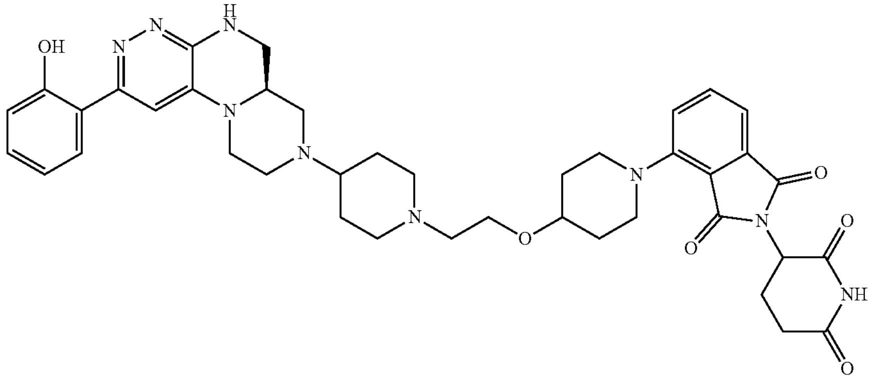 [SMILES: O=C1CCC(N2C(=O)c3cccc(N4CCC(OCCN5CCC(N6CCN7c8cc(-c9ccccc9O)nnc8NC[C@H]7C6)CC5)CC4)c3C2=O)C(=O)N1] 2-(2,6-dioxopiperidin-3-yl)-4-(4-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethoxy)piperidin-1-yl)isoindoline-1,3-dione | 750.4 | 750.2 |
| 68 | 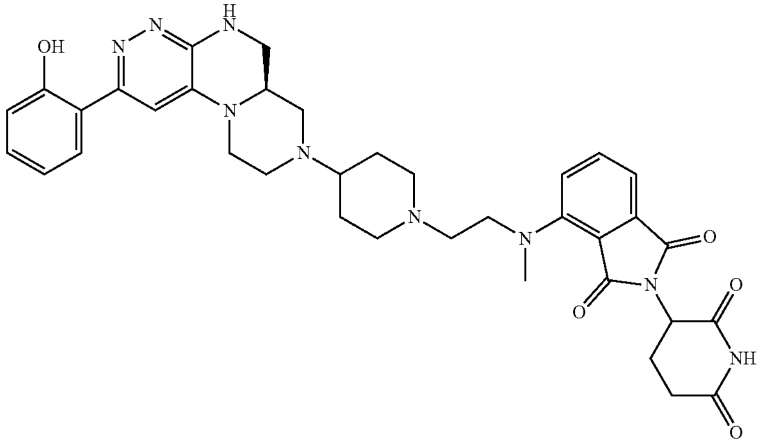 [SMILES: CN(CCN1CCC(N2CCN3c4cc(-c5ccccc5O)nnc4NC[C@H]3C2)CC1)c1cccc2c1C(=O)N(C1CCC(=O)NC1=O)C2=O] 2-(2,6-dioxopiperidin-3-yl)-4-((2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1 -yl)ethyl)(methyl)amino)isoindoline-1,3-dione | | |
| 69 | 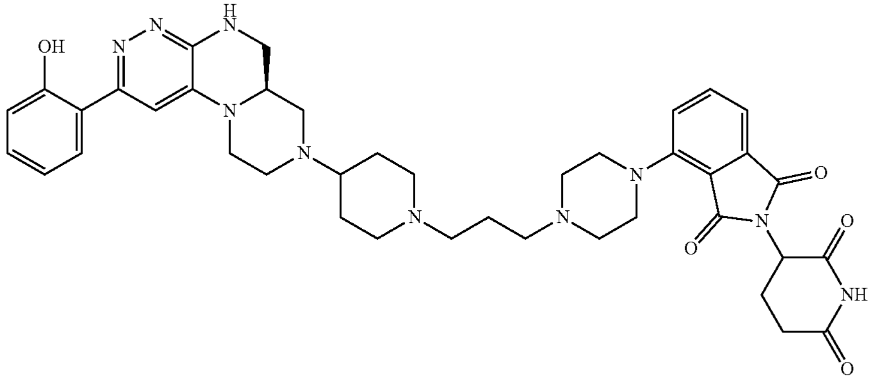 [SMILES: O=C1CCC(N2C(=O)c3cccc(N4CCN(CCCN5CCC(N6CCN7c8cc(-c9ccccc9O)nnc8NC[C@H]7C6)CC5)CC4)c3C2=O)C(=O)N1] 2-(2,6-dioxopiperidin-3-yl)-4-(4-(3-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propyl)piperazin-1-yl)isoindoline-1,3-dione | 749.4 | 749.2 |

TABLE 12-continued

Examples 67-73

| Ex. | Structure Name | Calcd. (M + H)+ m/z | Found (M + H)+ m/z |
|---|---|---|---|
| 70 | 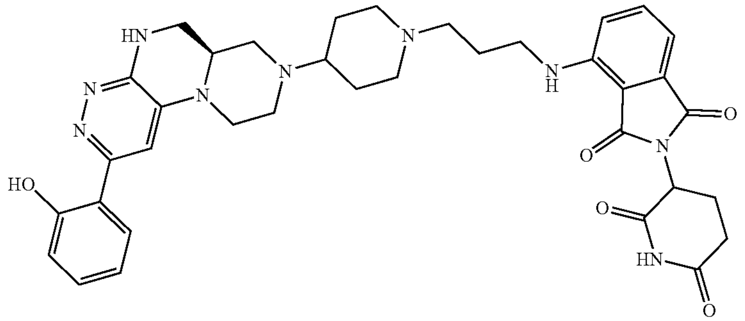 2-(2,6-dioxopiperidin-3-yl)-4-((3-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propyl)amino)isoindoline-1,3-dione | 680.4 | 680.2 |
| 71 | 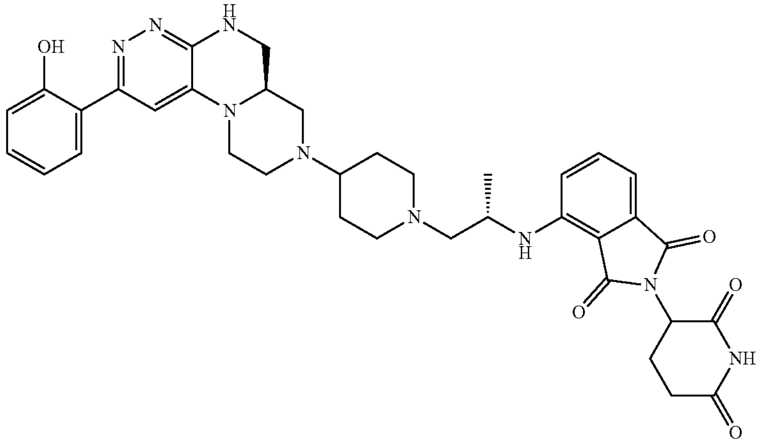 [SMILES: C[C@@H](CN1CCC(N2CCN3c4cc(-c5ccccc5O)nnc4NC[C@H]3C2)CC1)Nc1cccc2c1C(=O)N(C1CCC(=O)NC1=O)C2=O] 2-(2,6-dioxopiperidin-3-yl)-4-(((S)-1-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propan-2-yl)ammo)isoindoline-1,3-dione | 680.4 | 680.2 |
| 72 | 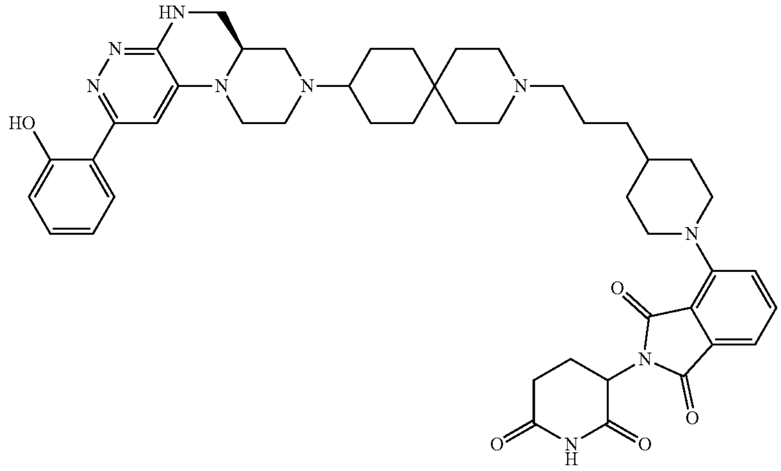 [SMILES: O=C1CCC(N2C(=O)c3cccc(N4CCC(CCCN5CCC6(CCC(N7CCN8c9cc(-c%10ccccc%10O)nnc9NC[C@H]8C7)CC6)CC5)CC4)c3C2=O)C(=O)N1] 2-(2,6-dioxopiperidin-3-yl)-4-(4-(3-(9-((S)-2-(2-hydroxyphenyl)-5,6,6a,7,9,10-hexahydro-8H-pyrazino[1',2':4,5]pyrazino[2,3-c]pyridazin-8-yl)-3-azaspiro[5.5]undecan-3-yl)propyl)piperidin-1-yl)isoindoline-1,3-dione | 816.4 | 816.3 |

TABLE 12-continued

Examples 67-73

| Ex. | Structure Name | Calcd. (M + H)+ m/z | Found (M + H)+ m/z |
|---|---|---|---|
| 73 | 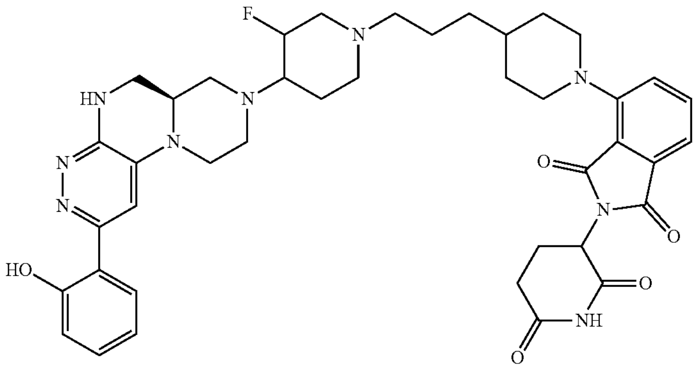 [SMILES: O=C1CCC(N2C(=O)c3cccc(N4CCC(CCCN5CCC(N6CCN7c8cc(-c9ccccc9O)nnc8NC[C@H]7C6)C(F)C5)CC4)c3C2=O)C(=O)N1] 2-(2,6-dioxopiperidin-3-yl)-4-(4-(3-(3-fluoro-4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propyl)piperidin-1-yl)isoindoline-1,3- | 766.4 | 766.2 |

Example 74: 2-(2,6-dioxopiperidin-3-yl)-5-(4-((S)-2-(((S)-2-(2-hydroxyphenyl)-5,6,6a,7,9,10-hexahydro-8H-pyrazino[1',2':4,5]pyrazino[2,3-c]pyridazin-8-yl)methyl)morpholino) piperidin-1-yl)isoindoline-1,3-dione Ex. 74

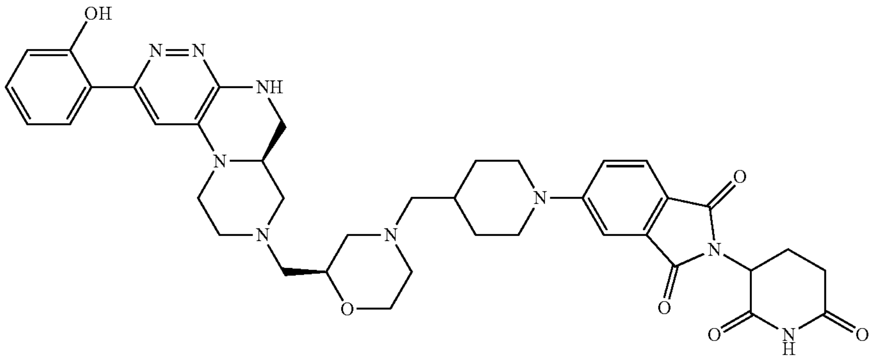

To a 4 mL vial containing 2-((S)-8-(((R)-morpholin-2-yl)methyl)-6,6a,7,8,9,10-hexahydro-5H-pyrazino[1',2':4,5]pyrazino[2,3-c]pyridazin-2-yl)phenol (15.7 mg, 0.03 mmol), sodium acetate (6.0 mg, 0.05 mmol), 1-(2-(2,6-dioxopiperidin-3-yl)-1,3-dioxoisoindolin-5-yl)piperidine-4-carbaldehyde (16.9 mg, 0.05 mmol), and ethanol (0.2 mL) was added DCM (0.6 mL). The reaction mixture was heated to 35° C. and stirred for 10 minutes, after which time sodium triacetoxyborohydride (19.0 mg, 0.09 mmol) was added and the reaction stirred at room temperature for 1.5 hours. The reaction mixture was then quenched with water (0.5 mL), diluted in 10 mL MeOH, filtered through a syringe filter, and purified on the prep-LCMS using a CSH-C18 column with a gradient of 7.8-27.8% ACN/water with 0.1% TFA over 5 minutes to yield the TFA salt of 2-(2,6-dioxopiperidin-3-yl)-5-(4-((S)-2-(((S)-2-(2-hydroxyphenyl)-5,6,6a,7,9,10-hexahydro-8H-pyrazino[1',2':4,5]pyrazino[2,3-c]pyridazin-8-yl)methyl)morpholino)piperidin-1-yl) isoindoline-1,3-dione as a yellow powder. LCMS calcd for $C_{39}H_{46}N_9O_6$ $[M+H]^+$ m/z=736.3; found: 736.2.

Examples 75-81

Examples in Table 13 were prepared using the procedure described in the synthesis of Example 74 with appropriate intermediates.

TABLE 13

| Ex. | Examples 75-81<br>Structure Name | Calcd. (M + H)+ m/z | Found (M + H)+ m/z |
|---|---|---|---|
| 75 | 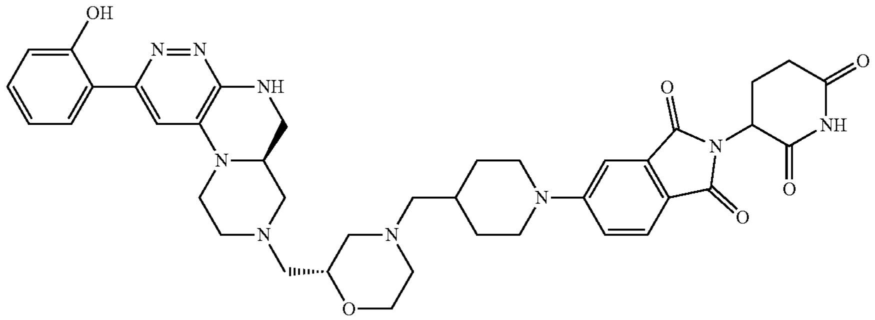 [SMILES: O=C1CCC(N2C(=O)c3ccc(N4CCC(CN5CCO[C@H](CN6CCN7c8cc(-c9ccccc9O)nnc8NC[C@H]7C6)C5)CC4)cc3C2=O)C(=O)N1]<br>2-(2,6-dioxopiperidin-3-yl)-5-(4-(((R)-2-(((S)-2-(2-hydroxyphenyl)-5,6,6a,7,9,10-hexahydro-8H-pyrazino[1',2':4,5]pyrazino[2,3-c]pyridazin-8-yl)methyl)morpholino)methyl)piperidin-1-yl)isoindoline-1,3-dione | 736.4 | 736.2 |
| 76 | 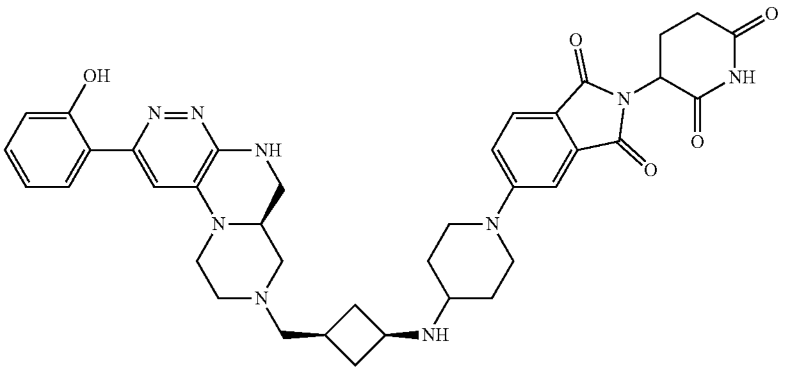 [SMILES: O=C1CCC(N2C(=O)c3ccc(N4CCC(N[C@H]5C[C@@H](CN6CCN7c8cc(-c9ccccc9O)nnc8NC[C@H]7C6)C5)CC4)cc3C2=O)C(=O)N1]<br>2-(2,6-dioxopiperidin-3-yl)-5-(4-(((1R,3s)-3-(((S)-2-(2-hydroxyphenyl)-5,6,6a,7,9,10-hexahydro-8H-pyrazino[1',2':4,5]pyrazino[2,3-c]pyridazin-8-yl)methyl)cyclobutyl)amino)piperidin-1-yl)isoindoline-1,3-dione | 706.3 | 706.2 |
| 77 | 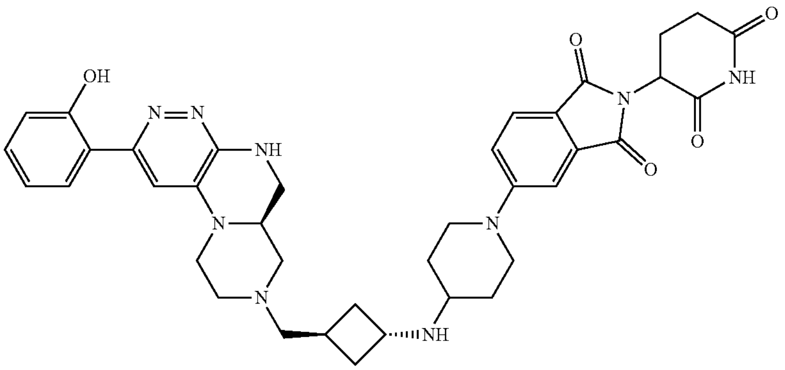 [SMILES: O=C1CCC(N2C(=O)c3ccc(N4CCC(N[C@H]5C[C@H](CN6CCN7c8cc(-c9ccccc9O)nnc8NC[C@H]7C6)C5)CC4)cc3C2=O)C(=O)N1]<br>2-(2,6-dioxopiperidin-3-yl)-5-(4-(((1S,3r)-3-(((S)-2-(2-hydroxyphenyl)-5,6,6a,7,9,10-hexahydro-8H-pyrazino[1',2':4,5]pyrazino[2,3-c]pyridazin-8-yl)methyl)cyclobutyl)amino)piperidin-1-yl)isoindoline-1,3-dione | 706.3 | 706.1 |

TABLE 13-continued

| Ex. | Structure Name | Calcd. (M + H)+ m/z | Found (M + H)+ m/z |
|---|---|---|---|
| | Examples 75-81 | | |
| 78 | 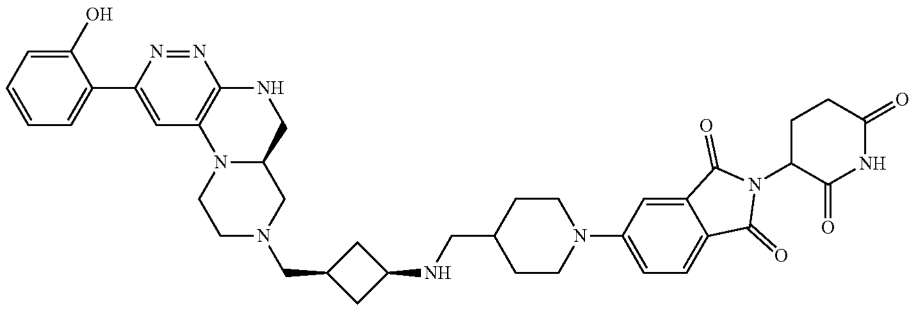 [SMILES: O=C1CCC(N2C(=O)c3ccc(N4CCC(CN[C@H]5C[C@@H](CN6CCN7c8cc(-c9ccccc9O)nnc8NC[C@H]7C6)C5)CC4)cc3C2=O)C(=O)N1] 2-(2,6-dioxopiperidin-3-yl)-5-(4-((((1R,3s)-3-(((S)-2-(2-hydroxyphenyl)-5,6,6a,7,9,10-hexahydro-8H-pyrazino [1',2':4,5]pyrazino[2,3-c]pyridazin-8-yl)methyl) cyclobutyl)amino)methyl)piperidin-1-yl)isoindolme-1,3-dione | 720.4 | 720.2 |
| 79 | 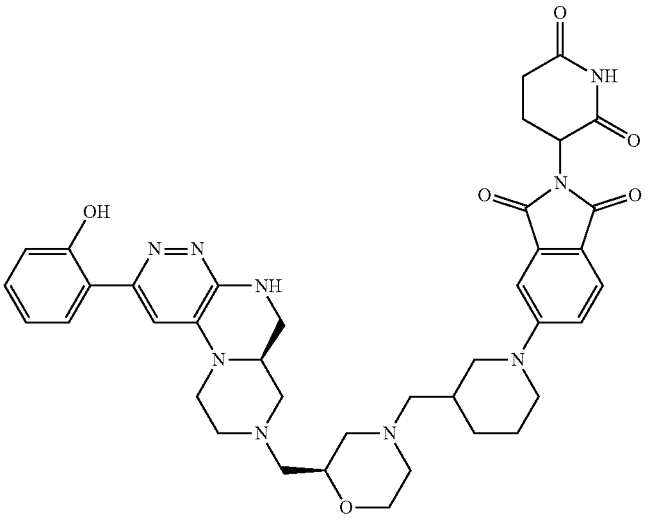 [SMILES: O=C1CCC(N2C(=O)c3ccc(N4CCCC(CN5CCO[C@@H](CN6CCN7c8cc(-c9ccccc9O)nnc8NC[C@H]7C6)C5)C4)cc3C2=O)C(=O)N1] 2-(2,6-dioxopiperidin-3-yl)-5-(3-(((S)-2-(((S)-2-(2-hydroxyphenyl)-5,6,6a,7,9,10-hexahydro-8H-pyrazino [1',2':4,5]pyrazino[2,3-c]pyridazin-8-yl)methyl) morpholino)methyl)piperidin-1-yl)isoindoline-1,3-dione | 736.4 | 736.2 |
| 80 | 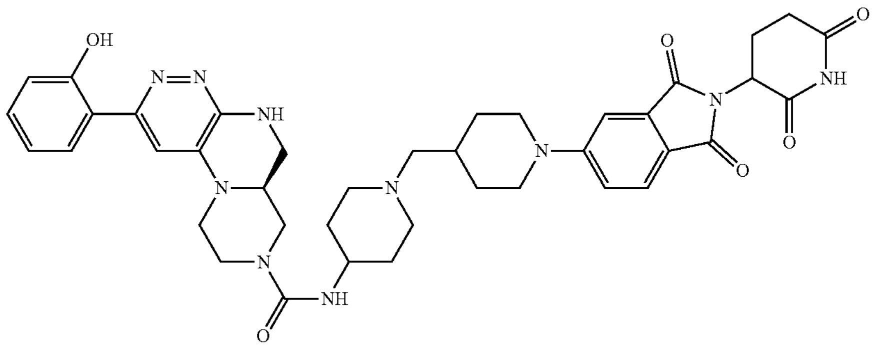 [SMILES: O=C1CCC(N2C(=O)c3ccc(N4CCC(CN5CCC(NC(=O)N6CCN7c8cc(-c9ccccc9O)nnc8NC[C@H]7C6)CC5)CC4)cc3C2=O)C(=O)N1] (6aS)-N-(1-((1-(2-(2,6-dioxopiperidin-3-yl)-1,3-dioxoisoindolin-5-yl)piperidin-4-yl)methyl)piperidin-4-yl)-2-(2-hydroxyphenyl)-5,6,6a,7,9,10-hexahydro-8H-pyrazino[1',2':4,5]pyrazino[2,3-c]pyridazine-8-carboxamide | 763.3 | 763.2 |

TABLE 13-continued

| Ex. | Structure Name | Calcd. (M + H)+ m/z | Found (M + H)+ m/z |
|---|---|---|---|
| | Examples 75-81 | | |
| 81 | 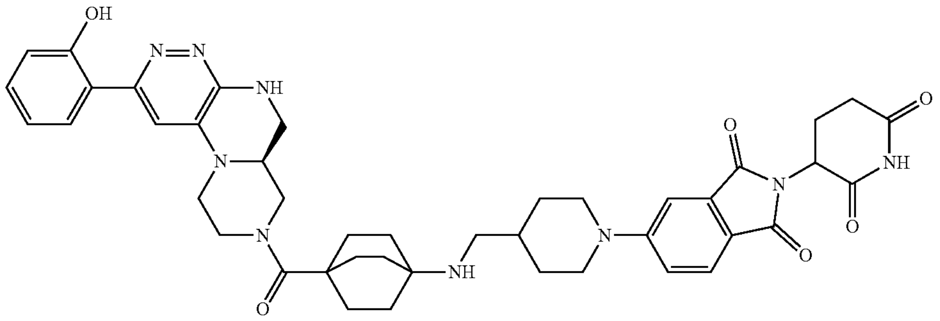 [SMILES: O=C1CCC(N2C(=O)c3ccc(N4CCC(CNC56CCC(C(=O)N7CCN8c9cc(-c%10ccccc%10O)nnc9NC[C@H]8C7)(CC5)CC6)CC4)cc3C2=O)C(=O)N1] 2-(2,6-dioxopiperidin-3-yl)-5-(4-(((4-((S)-2-(2-hydroxyphenyl)-6,6a,7,8,9,10-hexahydro-5H-pyrazino [1',2':4,5]pyrazino[2,3-c]pyridazine-8-carbonyl)bicyclo [2.2.2]octan-1-yl)amino)methyl)piperidin-1-yl)isoindoline-1 dione | 788.4 | 788.3 |

Example 82: 2-(2,6-dioxopiperidin-3-yl)-5-(3-((4-((S)-2-(2-hydroxyphenyl)-6,6a,7,8,9,10-hexahydro-511-pyrazino[1',2':4,5]pyrazino[2,3-c]pyridazine-8-carbonyl)piperazin-1-yl)methyl)azetidin-1-yl) isoindoline-1,3-dione

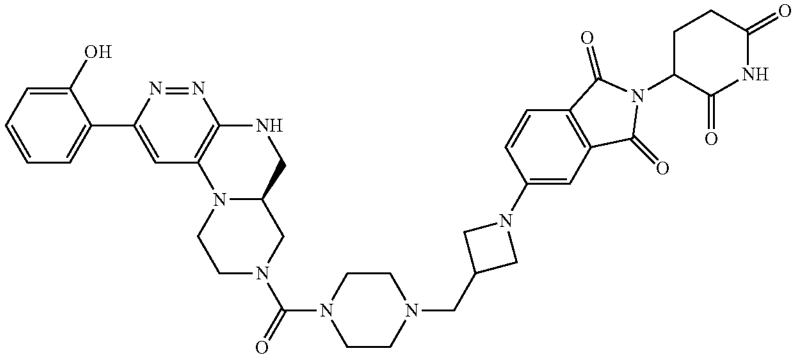

Ex. 85

To a 4 mL vial containing 2-(2,6-dioxopiperidin-3-yl)-5-(3-(hydroxymethyl)azetidin-1-yl) isoindoline-1,3-dione (28.7 mg, 0.08 mmol) in DMSO (1 mL) was added and Triethylamine; TEA (0.07 mL, 0.50 mmol) and the reaction mixture was cooled to 0° C. A solution of sulfurtrioxide pyridine (40.1 mg, 0.25 mmol) in DMSO (0.50 mL) was added dropwise and the mixture was then allowed to warm up to room temperature. Reaction mixture stirred at room temperature and monitored by LCMS. After 2.5 hours, reaction mixture was returned to 0° C. and added a solution of (S)-(2-(2-hydroxyphenyl)-5,6,6a,7,9,10-hexahydro-8H-pyrazino[1',2':4,5]pyrazino[2,3-c]pyridazin-8-yl)(piperazin-1-yl)methanone (22.0 mg, 0.05 mmol) in DMSO (0.50 mL), followed by acetic acid (0.1 mL, 1.67 mmol), followed by sodium triacetoxyborohydride (88.5 mg, 0.42 mmol), followed by ACN (0.2 mL). Stirred at room temperature for 20 minutes, then quenched with water (2 mL), diluted with ACN (1 mL), filtered through a syringe filter, and purified on the Prep-LCMS using a CSH-C18 column with a gradient of 9-29% ACN/water with 0.1% TFA over 5 minutes to yield the TFA salt of 2-(2,6-dioxopiperidin-3-yl)-5-(3-((4-((S)-2-(2-hydroxyphenyl)-6,6a,7,8,9,10-hexahydro-5H-pyrazino [1',2':4,5]pyrazino[2,3-c]pyridazine-8-carbonyl)piperazin-1-yl)methyl)azetidin-1-yl) isoindoline-1,3-dione (11.8 mg, 0.012 mmol) as a yellow powder. LCMS calcd for $C_{37}H_{41}N_{10}O_6$ $[M+H]^+$ m/z=721.3; found: 721.1.

Examples 83-87

Examples in Table 14 were prepared using the procedure described in the synthesis of Example 82 with appropriate intermediates.

TABLE 14

| Ex. | Structure Name | Calcd. (M + H)+ m/z | Found (M + H)+ m/z |
|---|---|---|---|
| Examples 83-87, and 247 | | | |
| 83 | 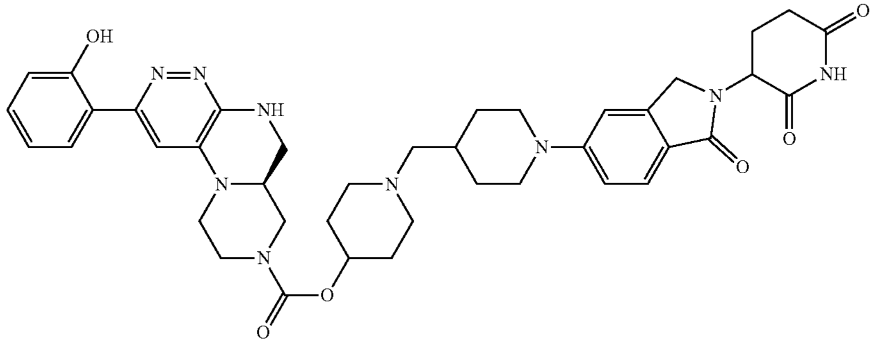 [SMILES: O=C1CCC(N2Cc3cc(N4CCC(CN5CCC(OC(=O)N6CCN7c8cc(-c9ccccc9O)nnc8NC[C@H]7C6)CC5)CC4)ccc3C2=O)C(=O)N1] 1-((1-(2-(2,6-dioxopiperidin-3-yl)-1-oxoisoindolin-5-yl)piperidin-4-yl)methyl)piperidin-4-yl (6aS)-2-(2-hydroxyphenyl)-5,6,6a,7,9,10-hexahydro-8H-pyrazino [1',2':4,5]pyrazino[2,3-c]pyridazine-8-carboxylate | 750.4 | 750.2 |
| 84 | 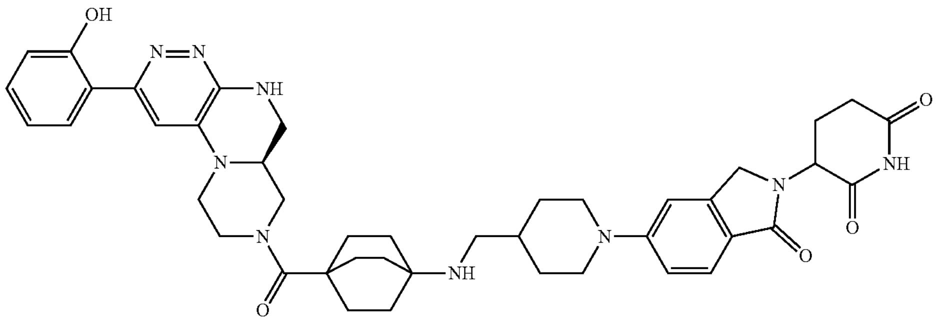 [SMILES: O=C1CCC(N2Cc3cc(N4CCC(CNC56CCC(C(=O)N7CCN8c9cc(-c%10ccccc%10O)nnc9NC[C@H]8C7)(CC5)CC6)CC4)ccc3C2=O)C(=O)N1] 3-(5-(4-(((4-((S)-2-(2-hydroxyphenyl)-6,6a,7,8,9,10-hexahydro-5H-pyrazino[1 ',2':4,5]pyrazino[2,3-c]pyridazine-8-carbonyl)bicyclo[2.2.2]octan-1-yl)amino)methyl)piperidin-1-yl)-1-oxoisoindolin-2-yl)piperidine-2,6-dione | 774.4 | 774.3 |
| 85 | 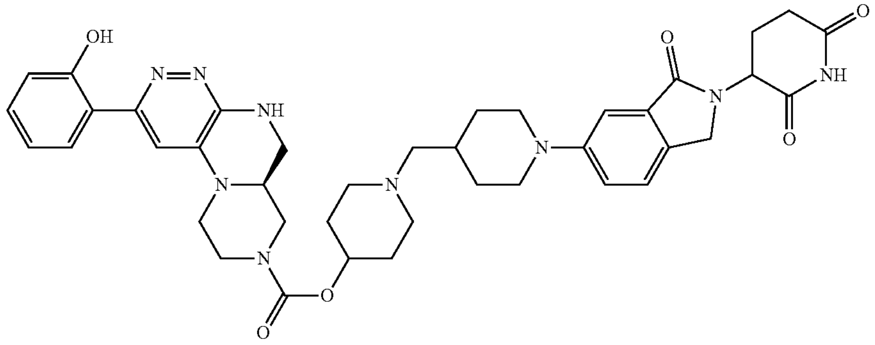 [SMILES: O=C1CCC(N2Cc3ccc(N4CCC(CN5CCC(OC(=O)N6CCN7c8cc(-c9ccccc9O)nnc8NC[C@H]7C6)CC5)CC4)cc3C2=O)C(=O)N1] l-((l-(2-(2,6-dioxopiperidin-3-yl)-3-oxoisoindolin-5-yl)piperidin-4-yl)methyl)piperidin-4-yl (6aS)-2-(2-hydroxyphenyl)-5,6,6a,7,9,10-hexahydro-8H-pyrazino [1',2':4,5]pyrazino[2,3-c]pyridazine-8-carboxylate | 750.4 | 750.3 |

TABLE 14-continued

| Ex. | Structure Name | Calcd. (M + H)+ m/z | Found (M + H)+ m/z |
|---|---|---|---|
| | Examples 83-87, and 247 | | |
| 86 | 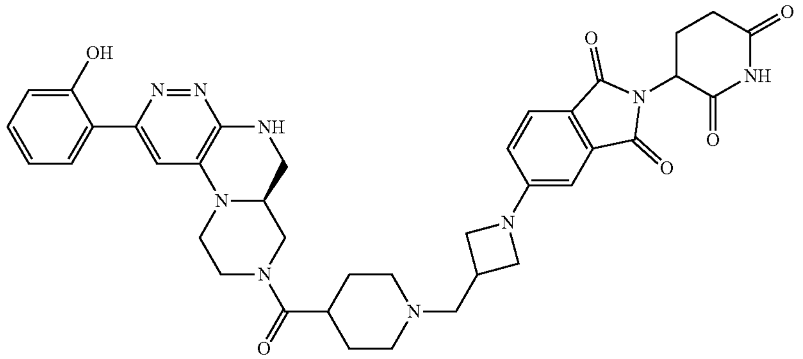 2-(2,6-dioxopiperidin-3-yl)-5-(3-((4-((S)-2-(2-hydroxyphenyl)-6,6a,7,8,9,10-hexahydro-5H-pyrazino [1',2':4,5]pyrazino[2,3-c]pyridazine-8-carbonyl)piperidin-1-yl)methyl)azetidin-1-yl)isoindoline-1,3-dione <br> $^1$H NMR (400 MHz, DMSO) δ 14.24 (s, 1H), 11.07 (s, 1H), 9.38 (s, 1H), 8.10 (s, 1H), 7.69 (d, J = 8.3 Hz, 1H), 7.51 (s, 1H), 7.40 (t, J = 7.8 Hz, 1H), 7.22-7.17 (m, 1H), 7.01 (dt, J = 15.1, 7.9 Hz, 2H), 6.82 (s, 1H), 6.72-6.65 (m, 1H), 5.06 (dd, J = 12.8, 5.4 Hz, 1H), 4.43 (dd, J = 40.6. 12.9 Hz, 1H), 4.29-4.08 (m, 4H), 3.84 (t, J = 7.0 Hz. 2H), 3.66 (s, 6H), 3.31-3.06 (m, 1H), 3.06-2.81 (m, 4H), 2.71-2.52 (m, 2H), 2.05-1.77 (m, 7H). | 720.3 | 720.2 |
| 87 | 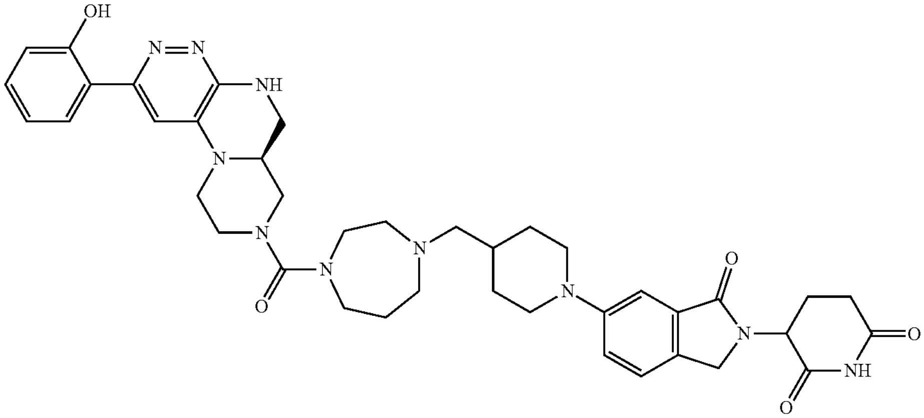 [SMILES: O=C1CCC(N2Cc3ccc(N4CCC(CN5CCCN(C(=O)N6CCN7c8cc(-c9ccccc9O)nnc8NC[C@H]7C6)CC5)CC4)cc3C2=O)C(=O)N1] 3-(5-(4-((4-((S)-2-(2-hydroxyphenyl)-6,6a,7,8,9,10-hexahydro-5H-pyrazino[1',2':4,5]pyrazino[2,3-c]pyridazine-8-carbonyl)-1,4-diazepan-1-yl)methyl)piperidin-1-yl)-1-oxoisoindolin-2-yl)piperidine-2,6-dione | 749.4 | 749.2 |
| 247 | 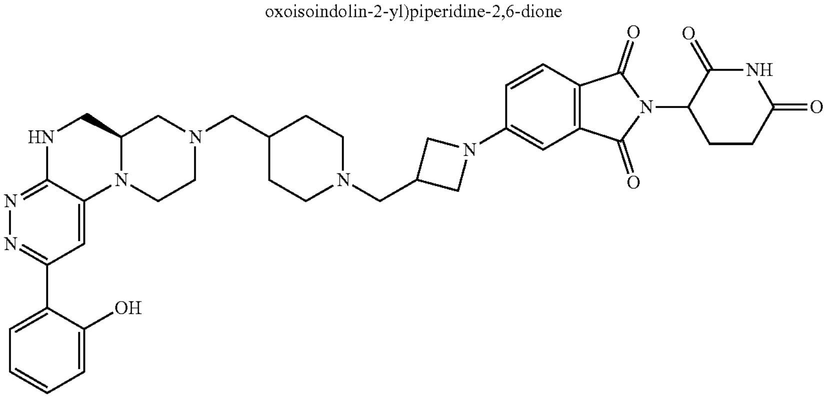 2-(2,6-dioxopiperidin-3-yl)-5-(3-((4-(((S)-2-(2-hydroxyphenyl)-5,6,6a,7,9,10-hexahydro-8H-pyrazino [1',2':4,5]pyrazino[2,3-c]pyridazin-8-yl)methyl)piperidin-1-yl)methyl)azetidin-1-yl)isoindoline-1,3-dione | 706.3 | 706.2 |

Example 94: 2-(2,6-dioxopiperidin-3-yl)-5-(9-(2-((S)-2-(2-hydroxyphenyl)-5,6,6a,7,9,10-hexahydro-8H-pyrazino[1',2':4,5]pyrazino[2,3-c]pyridazin-8-yl) ethyl)-2,9-diazaspiro [5.5]undecan-2-yl) isoindoline-1,3-dione Ex. 94

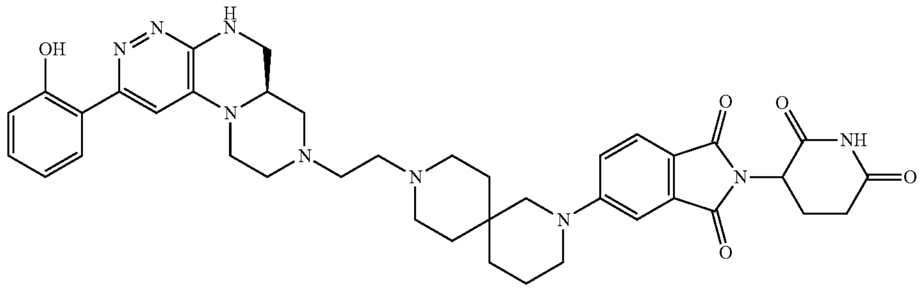

Step 1: Synthesis of tert-butyl 2-(2-(2,6-dioxopiperidin-3-yl)-1,3-dioxoisoindolin-5-yl)-2,9-diazaspiro [5.5]undecane-9-carboxylate

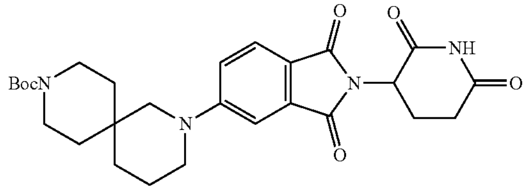 [SMILES: CC(C)(C)OC(=O)N1CCC2(CCCN(c3ccc4c(c3)C(=O)N(C3CCC(=O)NC3=O)C4=O)C2)CC1]

To a stirring solution of 2-(2,6-dioxopiperidin-3-yl)-5-fluoroisoindole-1,3-dione (50 mg, 0.181 mmol) and tert-butyl 2,9-diazaspiro[5.5]undecane-9-carboxylate (69.1 mg, 0.272 mmol) in N-methyl-2-pyrrolidone (1.8 mL) was added N,N-Diisopropylethylamine (126 μL, 0.724 mmol). The reaction mixture was heated to 110° C. and stirred for 6 hours. The product mixture was diluted with ethyl acetate (50 mL) and washed with saturated sodium carbonate aqueous solution (50 mL×2). The organic layer was dried with sodium sulfate. The dried organic layer was filtered, and the filtrate was concentrated under reduced pressure. The residue obtained was purified with flash column chromatography eluting with 0-100% ethyl acetate-hexanes to obtain tert-butyl 2-(2-(2,6-dioxopiperidin-3-yl)-1,3-dioxoisoindolin-5-yl)-2,9-diazaspiro[5.5]undecane-9-carboxylate (74 mg, 80%) as a yellow oil. LCMS m/z calcd for $C_{28}H_{38}N_4O_6$ $[M+H]^+$: 511.3; found: 511.2.

Step 2: Synthesis of 2-(2,6-dioxopiperidin-3-yl)-5-(2,9-diazaspiro[5.5]undecan-2-yl) isoindoline-1,3-dione

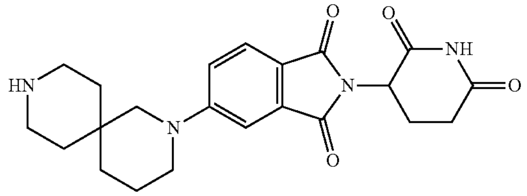 [SMILES: O=C1CCC(N2C(=O)c3ccc(N4CCCC5(CCNCC5)C4)cc3C2=O)C(=O)N1]

To a stirring solution of tert-butyl 2-(2-(2,6-dioxopiperidin-3-yl)-1,3-dioxoisoindolin-5-yl)-2,9-diazaspiro[5.5]undecane-9-carboxylate (74 mg, 0.141 mmol) in dichloromethane (2.6 mL) was added 4 N hydrochloric acid in dioxanes (0.176 mL, 0.703 mmol). The reaction mixture was stirred for 12 hours. The product mixture was concentrated under reduced pressure to obtain the hydrochloric acid salt of 2-(2,6-dioxopiperidin-3-yl)-5-(2,9-diazaspiro[5.5]undecan-2-yl) isoindoline-1,3-dione (57 mg, 99%) as a yellow solid. LCMS m/z calcd for $C_{22}H_{26}N_4O_4$ $[M+H]^+$: 411.2; found: 411.2.

Step 3: Synthesis of 2-(2,6-dioxopiperidin-3-yl)-5-(9-(2-hydroxyethyl)-2,9-diazaspiro[5.5]undecan-2-yl) isoindoline-1,3-dione

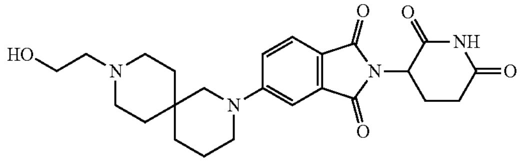 [SMILES: O=C1CCC(N2C(=O)c3ccc(N4CCCC5(CCN(CCO)CC5)C4)cc3C2=O)C(=O)N1]

To a stirring solution of the hydrochloric acid salt of 2-(2,6-dioxopiperidin-3-yl)-5-(2,9-diazaspiro [5.5]undecan-2-yl) isoindoline-1,3-dione (34.8 mg, 0.078 mmol) and triethylamine (109 μL, 0.780 mmol) in acetonitrile (2 mL) was added 2-bromoethanol (8.35 μL, 0.117 mmol). The reaction mixture was heated to 50° C. and allowed to stir for 3 hours. The product mixture was diluted with methanol (7 mL) and purified directly using a prep-LCMS (5 m 10×3 cm Waters CSH-Fluoro-Phenyl, 8.5-28.5% acetonitrile in water (0.1% TFA), wet loaded) to yield the trifluoroacetic acid salt of 2-(2,6-dioxopiperidin-3-yl)-5-(9-(2-hydroxyethyl)-2,9-diazaspiro [5.5]undecan-2-yl) isoindoline-1,3-dione (28 mg, 67%) as a yellow solid. LCMS m/z calcd for $C_{24}H_{30}N_4O_5$ $[M+H]^+$: 455.2; found 455.1.

Step 4: Synthesis of 5-(9-(2-chloroethyl)-2,9-diazaspiro[5.5]undecan-2-yl)-2-(2,6-dioxopiperidin-3-yl) isoindoline-1,3-dione

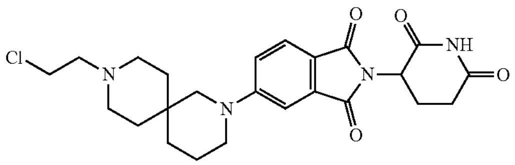 [SMILES: O=C1CCC(N2C(=O)c3ccc(N4CCCC5(CCN(CCCl)CC5)C4)cc3C2=O)C(=O)N1]

To a stirring solution of the trifluoroacetic acid salt of 2-(2,6-dioxopiperidin-3-yl)-5-(9-(2-hydroxyethyl)-2,9-diazaspiro[5.5]undecan-2-yl) isoindoline-1,3-dione (18 mg, 0.0396 mmol) and triethylamine (44.2 μL, 0.317 mmol) in dichloromethane (1 mL) at 0° C. was added methanesulfonyl chloride (6.1 μL, 0.0792 mmol). The reaction mixture was allowed to warm to 23° C. and stirred 1 hour. The product mixture was diluted with acetonitrile (3.5 mL) and and purified directly using a prep-LCMS (5 m 10×3 cm Waters CSH-Fluoro-Phenyl, 8.5-28.5% acetonitrile in water (0.1% TFA), wet loaded) to yield the trifluoroacetic acid salt of 5-(9-(2-chloroethyl)-2,9-diazaspiro[5.5]undecan-2-yl)-2-(2,6-dioxopiperidin-3-yl) isoindoline-1,3-dione (10 mg, 53%) as a yellow solid. LCMS m/z calcd for $C_{24}H_{29}ClN_4O_4$ $[M+H]^+$: 473.2; found 473.2.

Step 5: Synthesis of 2-(2,6-dioxopiperidin-3-yl)-5-(9-(2-((S)-2-(2-hydroxyphenyl)-5,6,6a, 7,9,10-hexahydro-8H-pyrazino[1',2': 4,5]pyrazino[2,3-c] pyridazin-8-yl)ethyl)-2,9-diazaspiro[5.5]undecan-2-yl) isoindoline-1,3-dione To a stirring solution of 2-[(10R)-1,5,6,8,12-pentazatricyclo[8.4.0.02,7]tetradeca-2(7),3,5-trien-4-yl]phenol; dihydrochloride (11.3 mg, 0.0317 mmol) and the trifluoroacetic acid salt of 5-[2-(2-chloroethyl)-2,9-diazaspiro[5.5]undecan-9-yl]-2-(2,6-dioxopiperidin-3-yl) isoindole-1,3-dione (12.4 mg, 0.0211 mmol) in acetonitrile (1 mL) was added sodium iodide (3.2 mg, 0.0211 mmol) and potassium carbonate (14.6 mg, 0.106 mmol). The reaction mixture was heated to 60° C. and stirred for 2 hours. The product mixture was diluted with acetonitrile (3.5 mL) and filtered. The filtrate was directly purified using a prep-LCMS (5 m 10×3 cm Waters CSH-Fluoro-Phenyl, 6.9-26.9% acetonitrile in water (0.1% TFA), wet loaded) to yield the trifluoroacetic acid salt of 2-(2,6-dioxopiperidin-3-yl)-5-(9-(2-((S)-2-(2-hydroxyphenyl)-5,6,6a,7,9,10-hexahydro-8H-pyrazino[1',2':4,5]pyrazino[2,3-c]pyridazin-8-yl)ethyl)-2,9-diazaspiro[5.5]undecan-2-yl) isoindoline-1,3-dione (4.2 mg, 19%) as a yellow solid. LCMS m/z calcd for $C_{39}H_{45}N_9O_5$ $[M+H]^+$: 720.3; found 720.2.

Example 95: 3-(6-(4-((4-((S)-2-(2-hydroxyphenyl)-6,6a,7,8,9,10-hexahydro-5H-pyrazino [1',2':4,5] pyrazino[2,3-c]pyridazine-8-carbonyl)piperazin-1-yl)methyl)piperidin-1-yl)-1-oxoisoindolin-2-yl) piperidine-2,6-dione Ex. 95

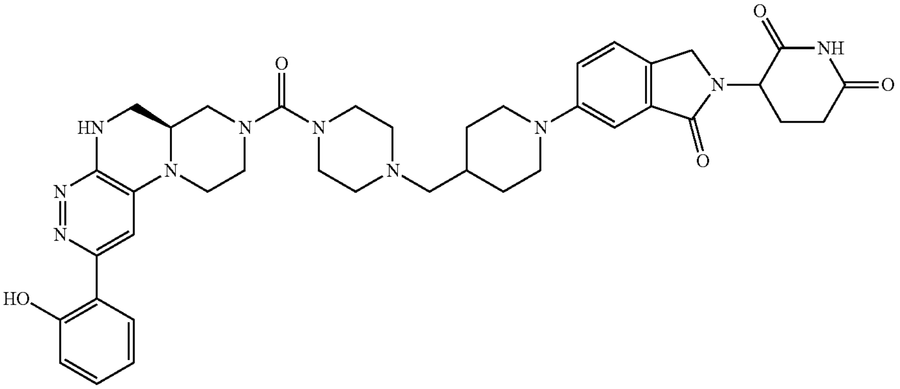

To a stirring solution of 3-[5-[4-(hydroxymethyl)piperidin-1-yl]-3-oxo-1H-isoindol-2-yl]piperidine-2,6-dione (421 mg, 1.18 mmol) and triethylamine (985 μL, 7.07 mmol, 12 equiv) in dimethyl sulfoxide (5.9 mL) was added sulfur trioxide-pyridine (562 mg, 3.53 mmol) in dimethyl sulfoxide (1.5 mL). The reaction mixture was stirred for 1 hour. After 1 hour, the trifluoroacetic acid salt of ([(10S)-4-(2-hydroxyphenyl)-1,5,6,8,12-pentazatricyclo[8.4.0.02,7]tetradeca-2,4,6-trien-12-yl]-piperazin-1-ylmethanone (300 mg, 0.589 mmol) in N,N-dimethylformamide (6.0 mL) was added to the reaction mixture. The reaction mixture was cooled to 0° C. To the cooled reaction mixture was added acetic acid (842 μL, 14.7 mmol) followed by sodium triacetoxyborohydride (749 mg, 3.53 mmol). The reaction mixture was stirred at 0° C. for 1 hour then allowed to warm to room temperature. The product mixture was diluted with water (1.5 mL) then stirred for 30 minutes. The diluted product mixture was filtered through celite and purified directly using a prep-LCMS (5 m 10×3 cm Waters CSH-Fluoro-Phenyl, 8.8-28.7% acetonitrile in water (0.1% TFA), wet loaded) to yield the trifluoroacetic acid salt of 3-(6-(4-((4-((S)-2-(2-hydroxyphenyl)-6,6a,7,8,9,10-hexahydro-5H-pyrazino[1',2':4,5]pyrazino[2,3-c]pyridazine-8-carbonyl) piperazin-1-yl)methyl)piperidin-1-yl)-1-oxoisoindolin-2-yl) piperidine-2,6-dione (54 mg, 48%) as a white solid. LCMS m/z calcd for $C_{39}H_{46}N_{10}O_5$ $[M+H]^+$: 735.4; found: 735.3. $^1H$ NMR (400 MHz, DMSO) δ 10.97 (s, 1H), 9.41 (s, 1H), 8.18 (s, 1H), 7.51-7.38 (m, 3H), 7.29 (dd, J=8.5, 2.4 Hz, 1H), 7.21 (d, J=2.3 Hz, 1H), 7.17 (s, 1H), 7.06 (d, J=8.2 Hz, 1H), 7.01 (td, J=7.5, 1.0 Hz, 1H), 5.09 (dd, J=13.3, 5.1 Hz, 1H), 4.35 (d, J=16.8 Hz, 1H), 4.22 (d, J=16.8 Hz, 1H), 4.14 (d, J=13.1 Hz, 1H), 3.86-3.62 (m, 8H), 3.53 (d, J=11.5 Hz, 2H), 3.31-3.17 (m, 4H), 3.16-3.00 (m, 5H), 2.98-2.83 (m, 2H), 2.78 (t, J=11.9 Hz, 2H), 2.61 (d, J=17.4 Hz, 1H), 2.39 (dd, J=13.2, 4.4 Hz, 1H), 2.12-1.95 (in, 2H), 1.85 (d, J=12.6 Hz, 2H), 1.37 (q, J=12.3 Hz, 2H).

Examples 96, 99-117, 138-141, 203-205, 261, 262, 264-266, 269-275 and 282

Examples in Table 15 were prepared using the procedure described in the synthesis of Example 95 with appropriate intermediates.

TABLE 15

Examples 96, 99-117, 138-141, 203-205, 261, 262, 264-266, 269-275 and 282

| Ex. | Structure Name | Calcd. $(M + H)^+$ m/z | Found $(M + H)^+$ m/z |
|---|---|---|---|
| 96 | 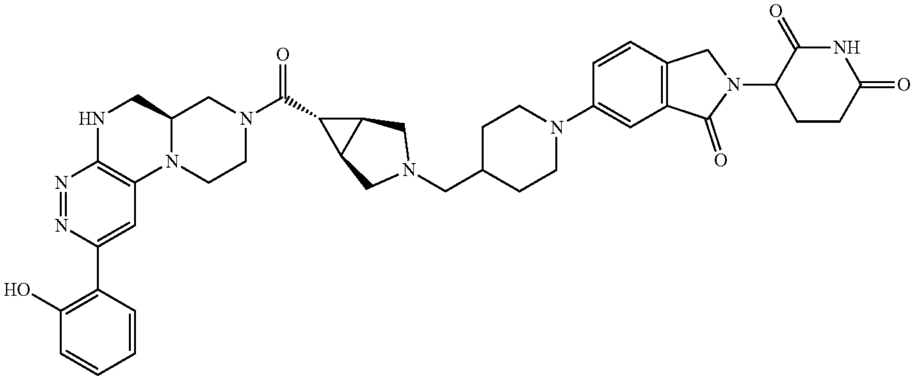 [SMILES: O=C1CCC(N2Cc3ccc(N4CCC(CN5C[C@@H]6[C@H](C5)[C@H]6C(=O)N5CCN6c7cc(-c8ccccc8O)nnc7NC[C@H]6C5)CC4)cc3C2=O)C(=O)N1] 3-(6-(4-(((1R,5S,6r)-6-((S)-2-(2-hydroxyphenyl)-6,6a,7,8,9,10-hexahydro-5H-pyrazino[1',2':4,5]pyrazino[2,3-c]pyridazine-8-carbonyl)-3-azabicyclo[3.1.0]hexan-3-yl)methyl)piperidin-1-yl)-1-oxoisoindolin-2-yl)piperidine-2,6-dione | 732.3 | 732.2 |
| 99 | 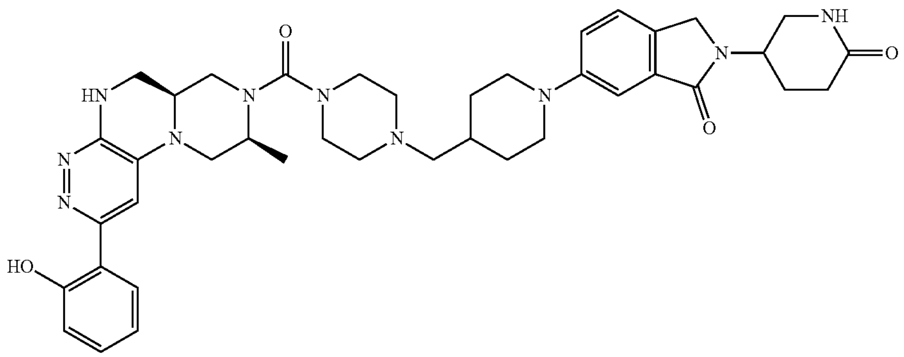 [SMILES: C[C@H]1CN2c3cc(-c4ccccc4O)nnc3NC[C@H]2CN1C(=O)N1CCN(CC2CCN(c3ccc4c(c3)C(=O)N(C3CCC(=O)NC3)C4)CC2)CC1] 3-(6-(4-((4-((6aS,9S)-2-(2-hydroxyphenyl)-9-methyl-6,6a,7,8,9,10-hexahydro-5H-pyrazino[1',2':4,5]pyrazino[2,3-c]pyridazine-8-carbonyl)piperazin-1-yl)methyl)piperidin-1-yl)-1-oxoisoindolin-2-yl)piperidine-2,6-dione | 749.4 | 749.4 |
| 100 | 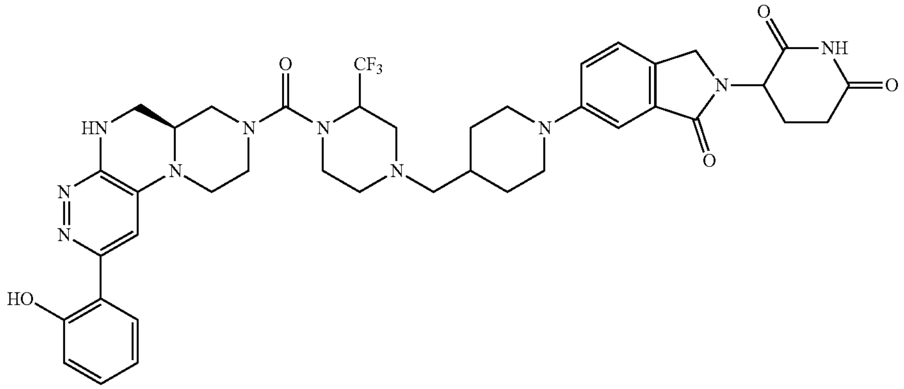 [SMILES: O=C1CCC(N2Cc3ccc(N4CCC(CN5CCN(C(=O)N6CCN7c8cc(-c9ccccc9O)nnc8NC[C@H]7C6)C(C(F)(F)F)C5)CC4)cc3C2=O)C(=O)N1] 3-(6-(4-((4-((S)-2-(2-hydroxyphenyl)-6,6a,7,8,9,10-hexahydro-5H-pyrazino[1',2':4,5]pyrazino[2,3-c]pyridazine- | 803.4 | 803.3 |

TABLE 15-continued

| Ex. | Structure Name | Calcd. (M + H)+ m/z | Found (M + H)+ m/z |
|---|---|---|---|
| | 8-carbonyl)-3-(trifluoromethyl)piperazin-1-yl)methyl)piperidin-1-yl)-1-oxoisoindolin-2-yl)piperidine-2,6-dione | | |
| 101 | 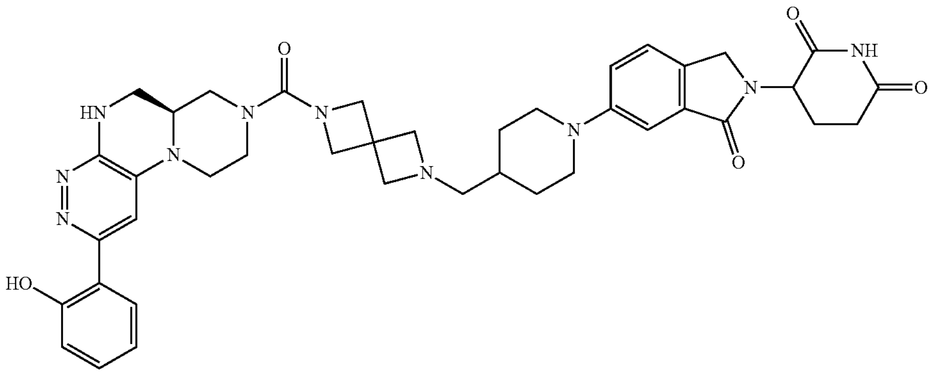 [SMILES: O=C1CCC(N2Cc3ccc(N4CCC(CN5CC6(C5)CN(C(=O)N5CCN7c8cc(-c9ccccc9O)nnc8NC[C@H]7C5)C6)CC4)cc3C2=O)C(=O)N1] 3-(6-(4-((6-((S)-2-(2-hydroxyphenyl)-6,6a,7,8,9,10-hexahydro-5H-pyrazino[1',2':4,5]pyrazino[2,3-c]pyridazine-8-carbonyl)-2,6-diazaspiro[3.3]heptan-2-yl)methyl)piperidin-1-yl)-1-oxoisoindolin-2-yl)piperidine-2,6-dione | 747.4 | 747.4 |
| 102 | 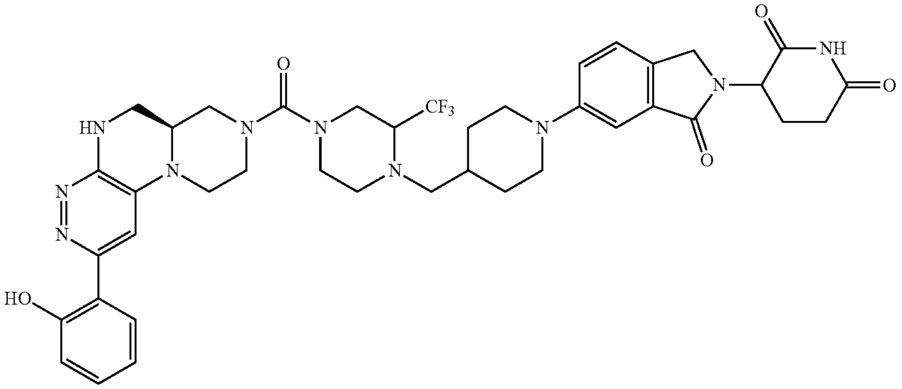 [SMILES: O=C1CCC(N2Cc3ccc(N4CCC(CN5CCN(C(=O)N6CCN7c8cc(-c9ccccc9O)nnc8NC[C@H]7C6)CC5C(F)(F)F)CC4)cc3C2=O)C(=O)N1] 3-(6-(4-((4-((S)-2-(2-hydroxyphenyl)-6,6a,7,8,9,10-hexahydro-5H-pyrazino[1',2':4,5]pyrazino[2,3-c]pyridazine-8-carbonyl)-2-(trifluoromethyl)piperazin-1-yl)methyl)piperidin-1-yl)-1-oxoisoindolin-2-yl)piperidine-2,6-dione | 803.4 | 803.3 |
| 103 | 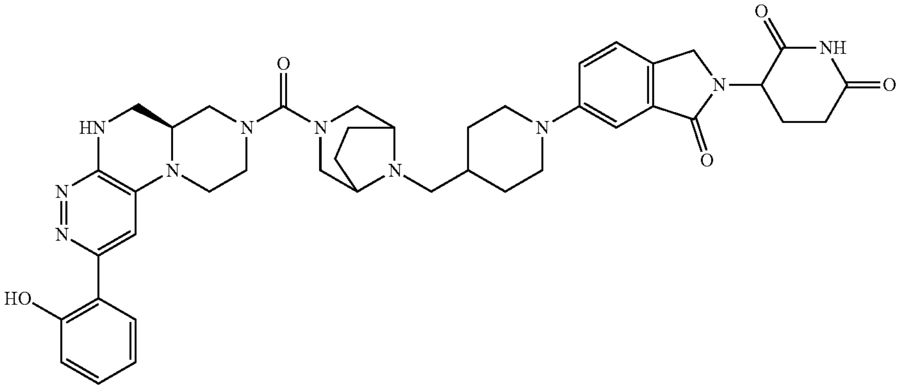 [SMILES: O=C1CCC(N2Cc3ccc(N4CCC(CN5C6CCC5CN(C(=O)N5CCN7c8cc(-c9ccccc9O)nnc8NC[C@H]7C5)C6)CC4)cc3C2=O)C(=O)N1] 3-(6-(4-((3-((S)-2-(2-hydroxyphenyl)-6,6a,7,8,9,10-hexahydro-5H-pyrazino[1',2':4,5]pyrazino[2,3-c]pyridazine-8-carbonyl)-3,8-diazabicyclo[3.2.1]octan-8-yl)methyl)piperidin-1-yl)-1-oxoisoindolin-2-yl)piperidine-2,6-dione | 761.4 | 761.3 |

TABLE 15-continued

| Ex. | Structure Name | Calcd. (M + H)+ m/z | Found (M + H)+ m/z |
|---|---|---|---|
| | Examples 96, 99-117, 138-141, 203-205, 261, 262, 264-266, 269-275 and 282 | | |
| 104 | 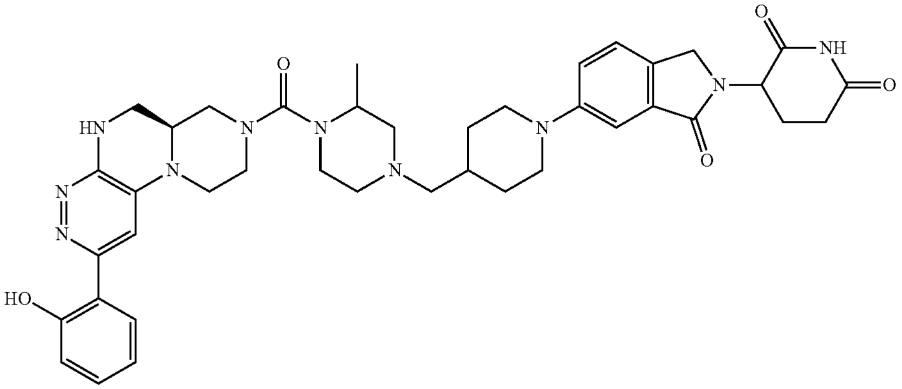 3-(6-(4-((4-((S)-2-(2-hydroxyphenyl)-6,6a,7,8,9,10-hexahydro-5H-pyrazino[1',2':4,5]pyrazino[2,3-c]pyridazine-8-carbonyl)-3-methylpiperazin-1-yl)methyl)piperidin-1-yl)-1-oxoisoindolin-2-yl)piperidine-2,6-dione | 749.4 | 749.3 |
| 105 | 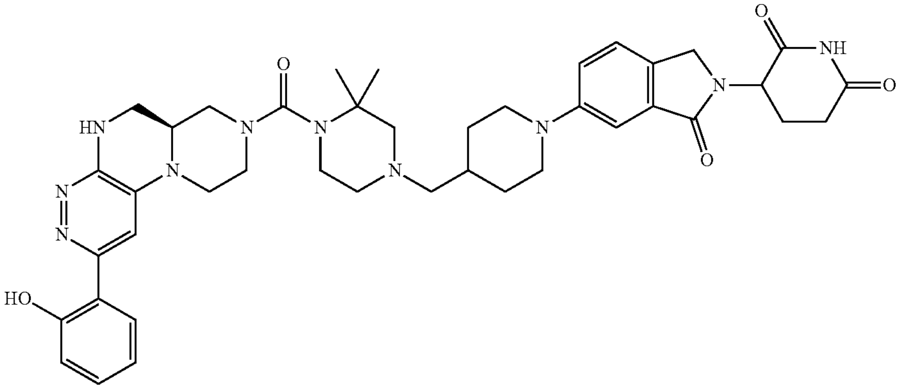 [SMILES: CC1(C)CN(CC2CCN(c3ccc4c(c3)C(=O)N(C3CCC(=O)NC3=O)C4)CC2)CCN1C(=O)N1CCN2c3cc(-c4ccccc4O)nnc3NC[C@H]2C1] 3-(6-(4-((4-((S)-2-(2-hydroxyphenyl)-6,6a,7,8,9,10-hexahydro-5H-pyrazino[1',2':4,5]pyrazino[2,3-c]pyridazine-8-carbonyl)-3,3-dimethylpiperazin-1-yl)methyl)piperidin-1-yl)-1-oxoisoindolin-2-yl)piperidine-2,6-dione | 763.4 | 763.4 |
| 106 | 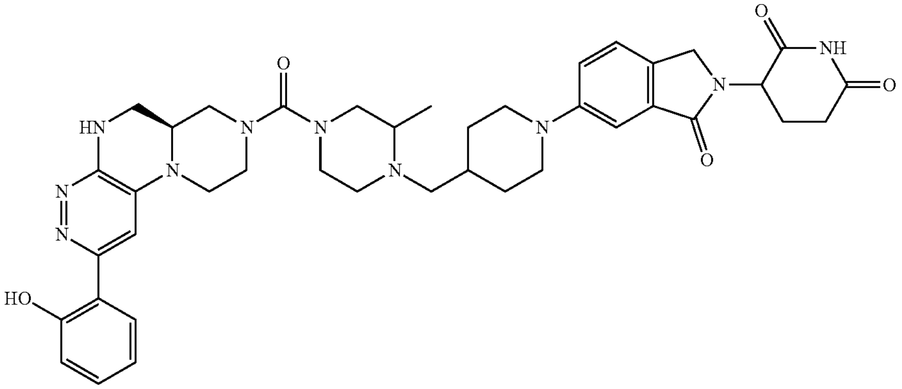 [SMILES: CC1CN(C(=O)N2CCN3c4cc(-c5ccccc5O)nnc4NC[C@H]3C2)CCN1CC1CCN(c2ccc3c(c2)C(=O)N(C2CCC(=O)NC2=O)C3)CC1] 3-(6-(4-((4-((S)-2-(2-hydroxyphenyl)-6,6a,7,8,9,10-hexahydro-5H-pyrazino[1',2':4,5]pyrazino[2,3-c]pyridazine-8-carbonyl)-2-methylpiperazin-1-yl)methyl)piperidin-1-yl)-1-oxoisoindolin-2-yl)piperidine-2,6-dione | 749.4 | 749.3 |

TABLE 15-continued

| Ex. | Structure Name | Calcd. (M + H)+ m/z | Found (M + H)+ m/z |
|---|---|---|---|
| Examples 96, 99-117, 138-141, 203-205, 261, 262, 264-266, 269-275 and 282 | | | |
| 107 | 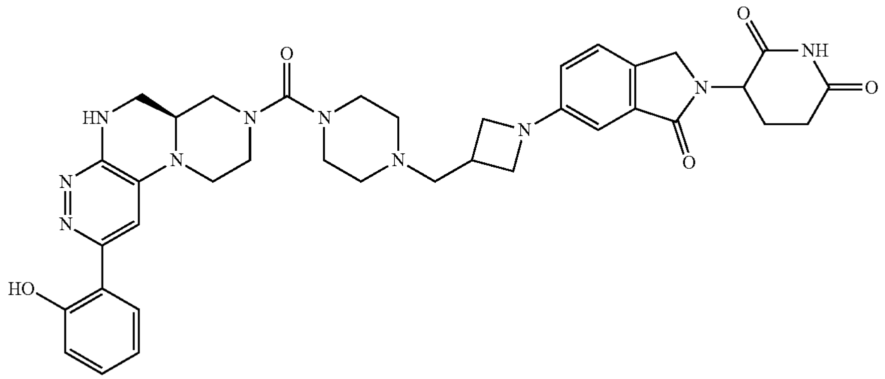 [SMILES: O=C1CCC(N2Cc3ccc(N4CC(CN5CCN(C(=O)N6CCN7c8cc(-c9ccccc9O)nnc8NC[C@H]7C6)CC5)C4)cc3C2=O)C(=O)N1] 3-(6-(3-((4-((S)-2-(2-hydroxyphenyl)-6,6a,7,8,9,10-hexahydro-5H-pyrazino[1',2':4,5]pyrazino[2,3-c]pyridazine-8-carbonyl)piperazin-1-yl)methyl)azetidin-1-yl)-1-oxoisoindolin-2-yl)piperidine-2,6-dione<br>$^1$H NMR (400 MHz, DMSO) δ 10.89 (s, 1H), 8.06 (s, 1H), 7.42 (d, J = 7.8 Hz, 1H), 7.38-7.31 (m, 2H), 7.10 (s, 1H), 6.98 (d, J = 8.2 Hz, 1H), 6.93 (t, J = 7.5 Hz, 1H), 6.70-6.61 (m, 2H), 5.00 (dd, J = 13.2, 5.2 Hz, 1H), 4.26 (d, J = 16.7 Hz, 1H), 4.14 (d, J = 16.7 Hz, 1H), 4.08-3.98 (m, 3H), 3.75-3.63 (m, 4H), 3.63-3.54 (m, 5H), 3.46-3.40 (m, 4H), 3.19-3.10 (m, 4H), 3.01 (t, J = 11.2 Hz, 2H), 2.88-2.73 (m, 2H), 2.63-2.50 (m, 1H), 2.35-2.23 (m, 1H), 1.96-1.88 (m, 1H), 1.25-1.12 (m, 1H). | 707.3 | 707.2 |
| 108 | 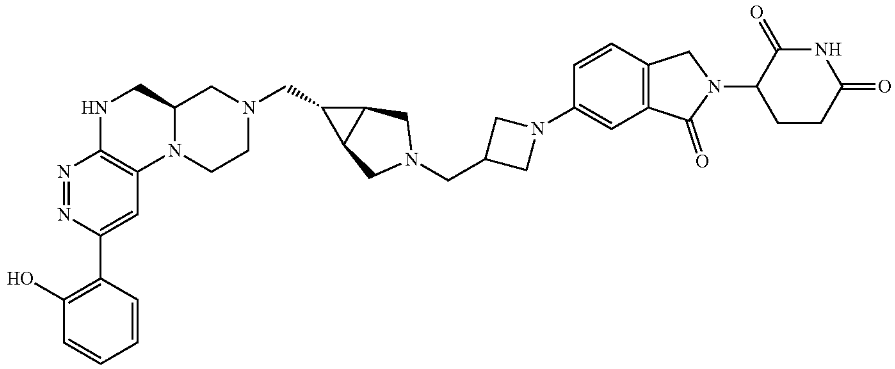 [SMILES: O=C1CCC(N2Cc3ccc(N4CC(CN5C[C@@H]6[C@H](C5)[C@H]6CN5CCN6c7cc(-c8ccccc8O)nnc7NC[C@H]6C5)C4)cc3C2=O)C(=O)N1] 3-(6-(3-(((1R,5S,6r)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1,0]hexan-3-yl)methyl)azetidin-1-yl)-1-oxoisoindolin-2-yl)piperidine-2,6-dione | 690.3 | 690.2 |
| 109 | 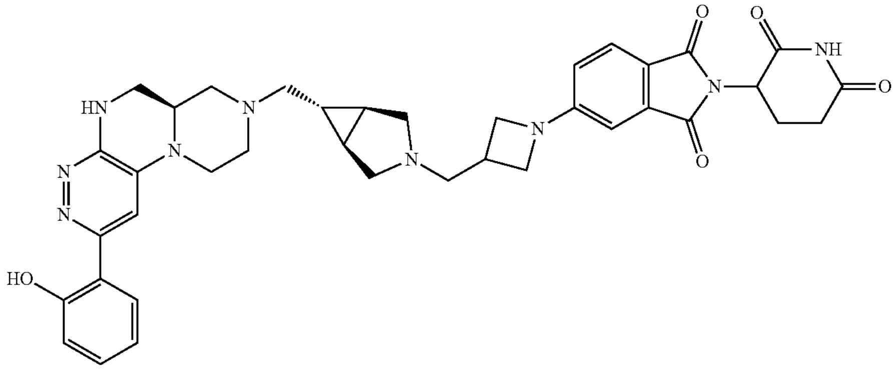 [SMILES: O=C1CCC(N2C(=O)c3ccc(N4CC(CN5C[C@@H]6[C@H](C5)[C@H]6CN5CCN6c7cc(-c8ccccc8O)nnc7NC[C@H]6C5)C4)cc3C2=O)C(=O)N1] 2-(2,6-dioxopiperidin-3-yl)-5-(3-(((1R,5S,6r)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)azetidin-1-yl)isoindoline-1,3-dione | 704.3 | 704.2 |

TABLE 15-continued

| Ex. | Structure Name | Calcd. (M + H)+ m/z | Found (M + H)+ m/z |
|---|---|---|---|
| | Examples 96, 99-117, 138-141, 203-205, 261, 262, 264-266, 269-275 and 282 | | |
| 110 | 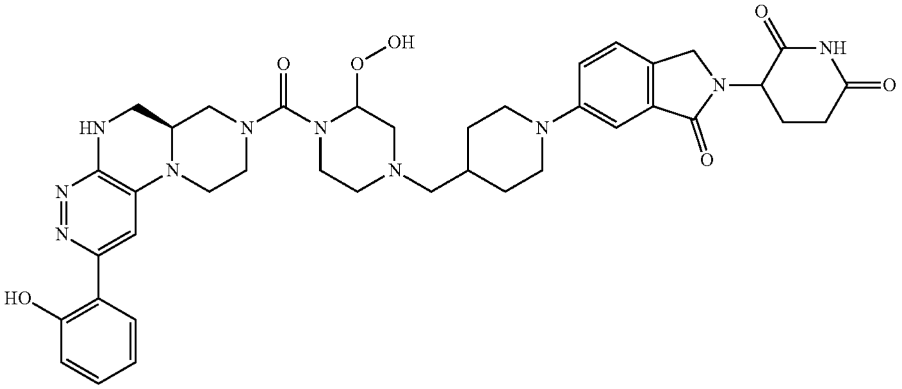 [SMILES: O=C1CCC(N2Cc3ccc(N4CCC(CN5CCN(C(=O)N6CCN7c8cc(-c9ccccc9O)nnc8NC[C@H]7C6)C(OO)C5)CC4)cc3C2=O)C(=O)N1] 3-(6-(4-((3-(hydroxymethyl)-4-((S)-2-(2-hydroxyphenyl)-6,6a,7,8,9,10-hexahydro-5H-pyrazino[1',2':4,5]pyrazino[2,3-c]pyridazine-8-carbonyl)piperazin-1-yl)methyl)piperidin-1-yl)-1-oxoisoindolin-2-yl)piperidine-2,6-dione | 765.4 | 765.3 |
| 111 | 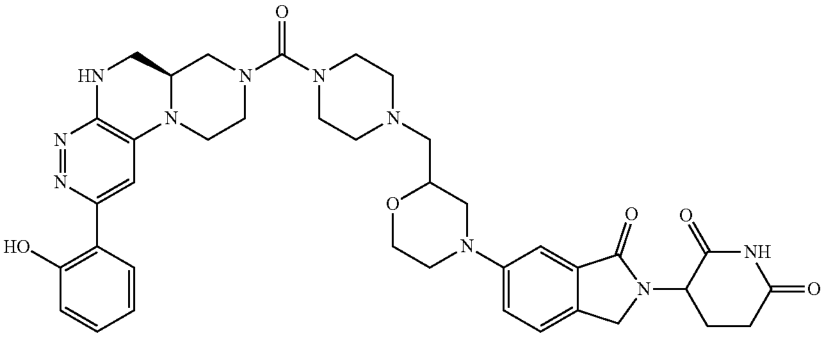 [SMILES: O=C1CCC(N2Cc3ccc(N4CCOC(CN5CCN(C(=O)N6CCN7c8cc(-c9ccccc9O)nnc8NC[C@H]7C6)CC5)C4)cc3C2=O)C(=O)N1] 3-(6-(2-((4-((S)-2-(2-hydroxyphenyl)-6,6a,7,8,9,10-hexahydro-5H-pyrazino[1',2':4,5]pyrazino[2,3-c]pyridazine-8-carbonyl)piperazin-1-yl)methyl)morpholino)-1-oxoisoindolin-2-yl)piperidine-2,6-dione | 737.3 | 737.2 |
| 112 | 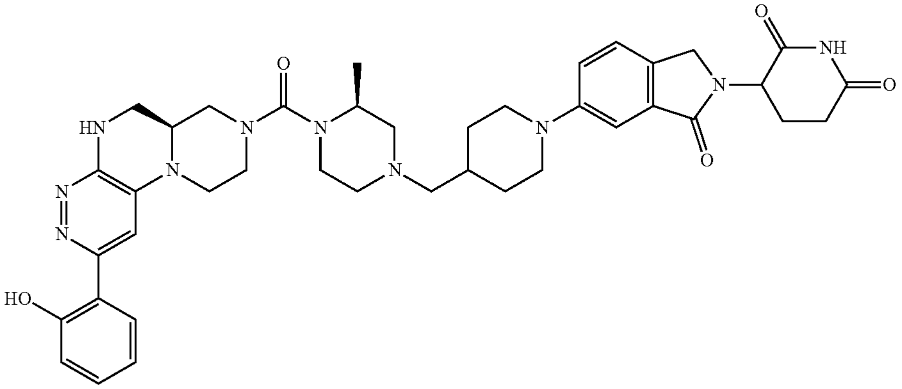 [SMILES: C[C@H]1CN(CC2CCN(c3ccc4c(c3)C(=O)N(C3CCC(=O)NC3=O)C4)CC2)CCN1C(=O)N1CCN2c3cc(-c4ccccc4O)nnc3NC[C@H]2C1] 3-(6-(4-(((S)-4-((S)-2-(2-hydroxyphenyl)-6,6a,7,8,9,10-hexahydro-5H-pyrazino[1',2':4,5]pyrazino[2,3-c]pyridazine-8-carbonyl)-3-methylpiperazin-1-yl)methyl)piperidin-1-yl)-1-oxoisoindolin-2-yl)piperidine-2,6-dione | 749.4 | 749.3 |

TABLE 15-continued

| Ex. | Structure Name | Calcd. (M + H)+ m/z | Found (M + H)+ m/z |
|---|---|---|---|
| Examples 96, 99-117, 138-141, 203-205, 261, 262, 264-266, 269-275 and 282 | | | |
| 113 | 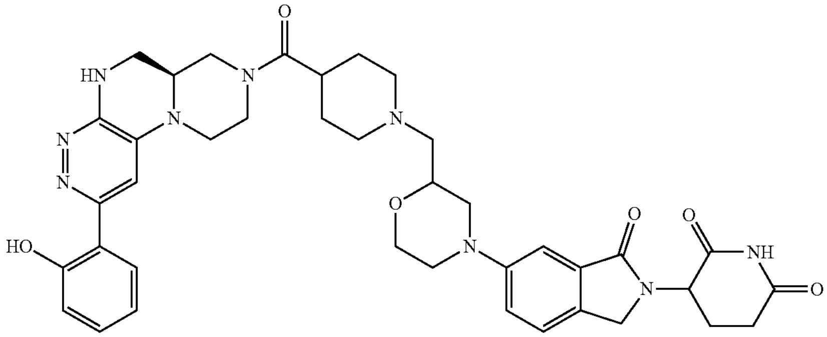 [SMILES: O=C1CCC(N2Cc3ccc(N4CCOC(CN5CCC(C(=O)N6CCN7c8cc(-c9ccccc9O)nnc8NC[C@H]7C6)CC5)C4)cc3C2=O)C(=O)N1] 3-(6-(2-((4-((S)-2-(2-hydroxyphenyl)-6,6a,7,8,9,10-hexahydro-5H-pyrazino[1',2':4,5]pyrazino[2,3-c]pyridazine-8-carbonyl)piperidin-1-yl)methyl)morpholino)-1-oxoisoindolin-2-yl)piperidine-2,6-dione | 736.3 | 736.2 |
| 114 | 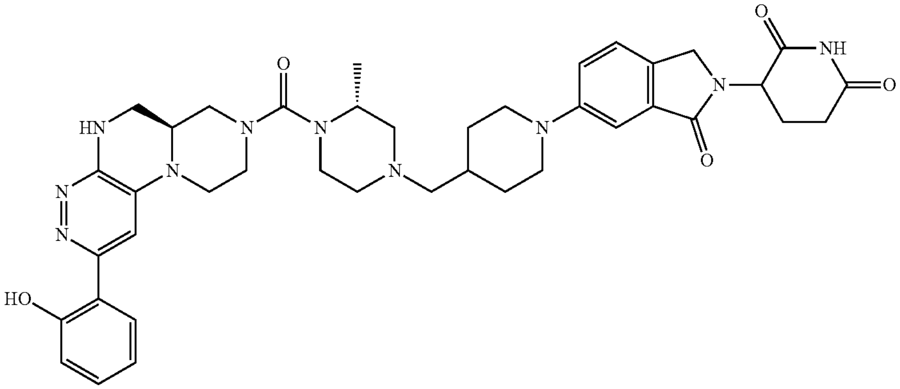 [SMILES: C[C@@H]1CN(CC2CCN(c3ccc4c(c3)C(=O)N(C3CCC(=O)NC3=O)C4)CC2)CCN1C(=O)N1CCN2c3cc(-c4ccccc4O)nnc3NC[C@H]2C1] 3-(6-(4-(((R)-4-((S)-2-(2-hydroxyphenyl)-6,6a,7,8,9,10-hexahydro-5H-pyrazino[1',2':4,5]pyrazino[2,3-c]pyridazine-8-carbonyl)-3-methylpiperazin-1-yl)methyl)piperidin-1-yl)-1-oxoisoindolin-2-yl)piperidine-2,6-dione | 749.4 | 749.4 |
| 115 | 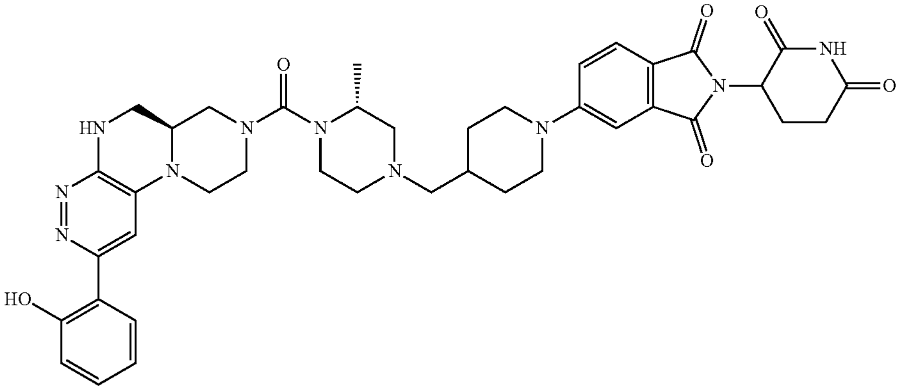 [SMILES: C[C@@H]1CN(CC2CCN(c3ccc4c(c3)C(=O)N(C3CCC(=O)NC3=O)C4=O)CC2)CCN1C(=O)N1CCN2c3cc(-c4ccccc4O)nnc3NC[C@H]2C1] 2-(2,6-dioxopiperidin-3-yl)-5-(4-(((R)-4-((S)-2-(2-hydroxyphenyl)-6,6a,7,8,9,10-hexahydro-5H-pyrazino[1',2':4,5]pyrazino[2,3-c]pyridazine-8-carbonyl)-3-methyl-piperazin-1-yl)methyl)piperidin-1-yl)isoindoline-1,3-dione | 763.4 | 763.3 |

$^1$H NMR (400 MHz, DMSO) δ 11.07 (s, 1H), 9.37 (s, 1H), 8.18 (s, 1H), 7.68 (d, J = 8.5 Hz, 1H), 7.48 (dd, J = 7.7, 1.7 Hz, 1H), 7.41 (ddd, J = 8.9, 7.3, 1.7 Hz, 1H), 7.36 (d, J = 2.2 Hz, 1H), 7.27 (dd, J = 8.8, 2.3 Hz, 1H), 7.16 (s, 1H), 7.06 (dd, J = 8.3, 1.1 Hz, 1H), 6.99 (td, J = 7.5, 1.1 Hz, 1H), 5.07 (dd, J = 12.9, 5.4 Hz, 1H), 4.12 (d, J = 12.9 Hz, 3H), 3.78-3.63 (m, 5H), 3.61-3.45 (m, 5H), 3.37-3.17 (m, 4H), 3.15-2.80 (m, 8H), 2.66-2.52 (m, 2H), 2.09 (br, 1H), 2.06-1.95 (m, 1H), 1.92 (br, 1H), 1.72 (d, J = 12.5 Hz, 1H), 1.31 (m, 5H).

TABLE 15-continued

| Ex. | Structure Name | Calcd. (M + H)+ m/z | Found (M + H)+ m/z |
|---|---|---|---|
| | Examples 96, 99-117, 138-141, 203-205, 261, 262, 264-266, 269-275 and 282 | | |
| 116 | 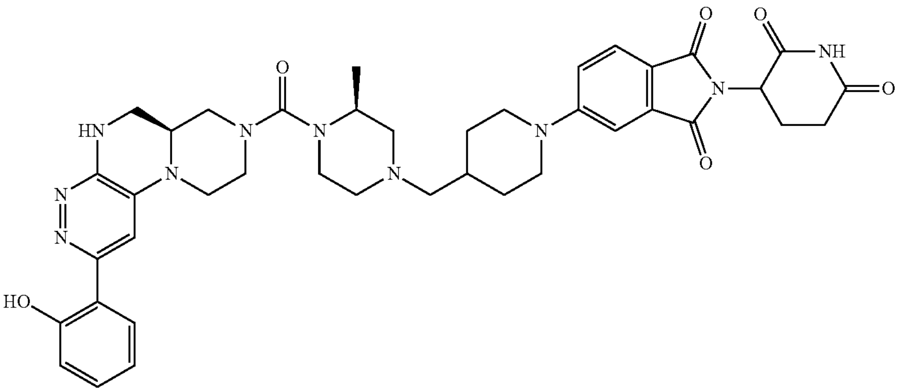 [SMILES: C[C@H]1CN(CC2CCN(c3ccc4c(c3)C(=O)N(C3CCC(=O)NC3=O)C4=O)CC2)CCN1C(=O)N1CCN2c3cc(-c4ccccc4O)nnc3NC[C@H]2C1] 2-(2,6-dioxopiperidin-3-yl)-5-(4-(((S)-4-((S)-2-(2-hydroxyphenyl)-6,6a,7,8,9,10-hexahydro-5H-pyrazino[1',2':4,5]pyrazino[2,3-c]pyridazine-8-carbonyl)-3-methylpiperazin-1-yl)methyl)piperidin-1-yl)isoindoline-1,3-dione <br> $^1$H NMR (400 MHz, DMSO) δ 11.07 (s, 1H), 9.37 (s, 1H), 8.18 (s, 1H), 7.68 (d, J = 8.5 Hz, 1H), 7.48 (dd, J = 7.7, 1.7 Hz, 1H), 7.41 (ddd, J = 8.9, 7.3, 1.7 Hz, 1H), 7.36 (d, J = 2.2 Hz, 1H), 7.27 (dd, J = 8.8, 2.3 Hz, 1H), 7.16 (s, 1H), 7.06 (dd, J = 8.3, 1.1 Hz, 1H), 6.99 (td, J = 7.5, 1.1 Hz, 1H), 5.07 (dd, J = 12.9, 5.4 Hz, 1H), 4.12 (d, J = 12.9 Hz, 3H), 3.78-3.63 (m, 5H), 3.61-3.45 (m, 5H), 3.37-3.17 (m, 4H), 3.15-2.80 (m, 8H), 2.66-2.52 (m, 2H), 2.09 (br, 1H), 2.06-1.95 (m, 1H), 1.92 (br, 1H), 1.72 (d, J = 12.5 Hz, 1H), 1.31 (m, 5H). | 763.4 | 763.3 |
| 117 | 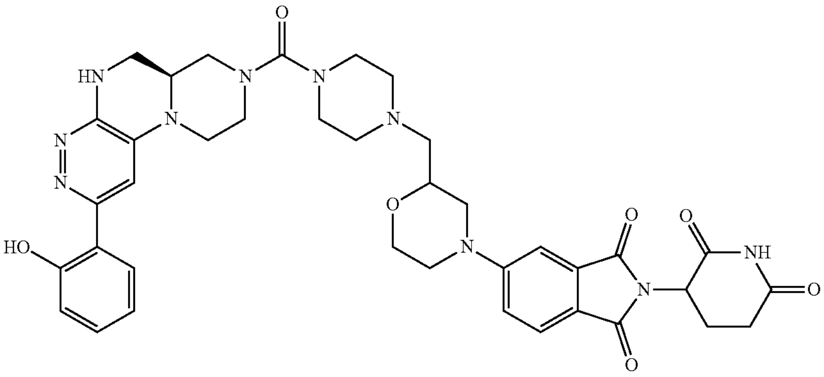 [SMILES: O=C1CCC(N2C(=O)c3ccc(N4CCOC(CN5CCN(C(=O)N6CCN7c8cc(-c9ccccc9O)nnc8NC[C@H]7C6)CC5)C4)cc3C2=O)C(=O)N1] 2-(2,6-dioxopiperidin-3-yl)-5-(2-((4-((S)-2-(2-hydroxyphenyl)-6,6a,7,8,9,10-hexahydro-5H-pyrazino[1',2':4,5]pyrazino[2,3-c]pyridazine-8-carbonyl)piperazin-1-yl)methyl)morpholino)isoindoline-1,3-dione | 751.3 | 751.2 |
| 138 | 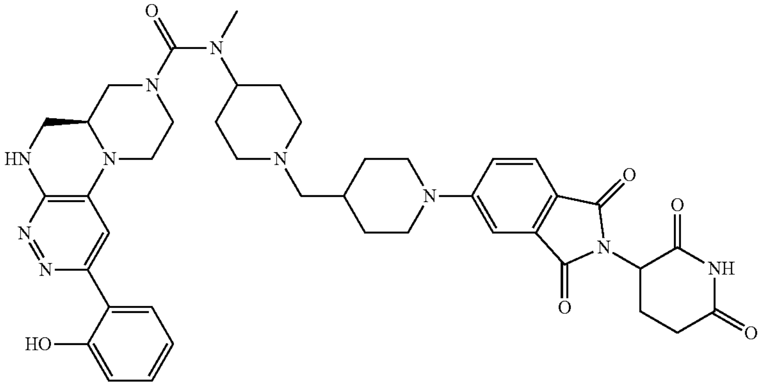 [SMILES: CN(C(=O)N1CCN2c3cc(-c4ccccc4O)nnc3NC[C@H]2C1)C1CCN(CC2CCN(c3ccc4c(c3)C(=O)N(C3CCC(=O)NC3=O)C4=O)CC2)CC1] | 777.4 | 777.3 |

TABLE 15-continued

| Ex. | Examples 96, 99-117, 138-141, 203-205, 261, 262, 264-266, 269-275 and 282<br>Structure Name | Calcd. $(M + H)^+$ m/z | Found $(M + H)^+$ m/z |
|---|---|---|---|
| | (6aS)-N-(1-((1-(2-(2,6-dioxopiperidin-3-yl)-1,3-dioxoisoindolin-5-yl)piperidin-4-yl)methyl)piperidin-4-yl)-2-(2-hydroxyphenyl)-N-methyl-5,6,6a,7,9,10-hexahydro-8H-pyrazino[1',2':4,5]pyrazino[2,3-c]pyridazine-8-carboxamide | | |
| 139 | 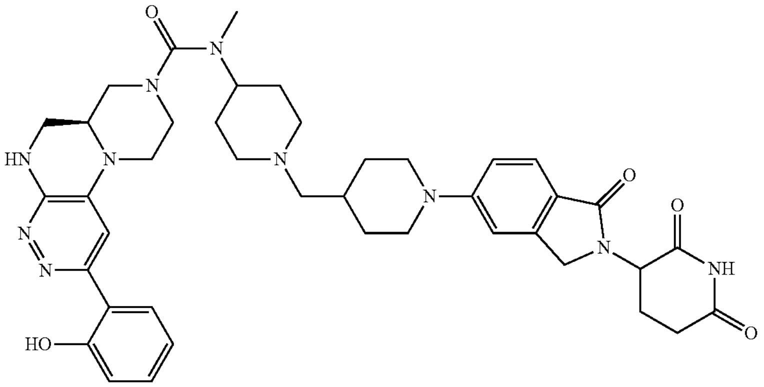 [SMILES: CN(C(=O)N1CCN2c3cc(-c4ccccc4O)nnc3NC[C@H]2C1)C1CCN(CC2CCN(c3ccc4c(c3)CN(C3CCC(=O)NC3=O)C4=O)CC2)CC1]<br>(6aS)-N-(1-((1-(2-(2,6-dioxopiperidin-3-yl)-1-oxoisoindolin-5-yl)piperidin-4-yl)methyl)piperidin-4-yl)-2-(2-hydroxyphenyl)-N-methyl-5,6,6a,7,9,10-hexahydro-8H-pyrazino[1',2':4,5]pyrazino[2,3-c]pyridazine-8-carboxamide | 763.4 | 763.3 |
| 140 | 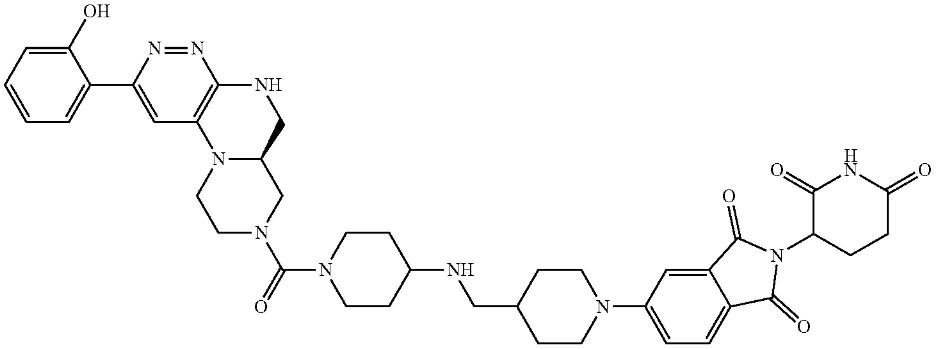 [SMILES: O=C1CCC(N2C(=O)c3ccc(N4CCC(CNC5CCN(C(=O)N6CCN7c8cc(-c9ccccc9O)nnc8NC[C@H]7C6)CC5)CC4)cc3C2=O)C(=O)N1]<br>2-(2,6-dioxopiperidin-3-yl)-5-(4-(((l-((S)-2-(2-hydroxyphenyl)-6,6a,7,8,9,10-hexahydro-5H-pyrazino[1',2':4,5]pyrazino[2,3-c]pyridazine-8-carbonyl)piperidin-4-yl)amino)methyl)piperidin-1-yl)isoindoline-1,3-dione | 763.4 | 763.2 |
| 141 | 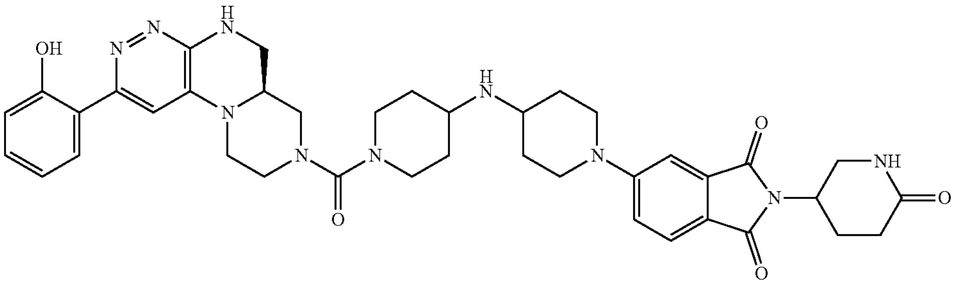 [SMILES: O=C1CCC(N2C(=O)c3ccc(N4CCC(NC5CCN(C(=O)N6CCN7c8cc(-c9ccccc9O)nnc8NC[C@H]7C6)CC5)CC4)cc3C2=O)CN1]<br>2-(2,6-dioxopiperidin-3-yl)-5-(4-((1-((S)-2-(2-hydroxyphenyl)-6,6a,7,8,9,10-hexahydro-5H-pyrazino[1',2':4,5]pyrazino[2,3-c]pyridazine-8-carbonyl)piperidin-4-yl)amino)piperidin-1-yl)isoindoline-1,3-dione | 749.3 | 749.2 |

TABLE 15-continued

| Ex. | Structure Name | Calcd. (M + H)+ m/z | Found (M + H)+ m/z |
|---|---|---|---|
| | Examples 96, 99-117, 138-141, 203-205, 261, 262, 264-266, 269-275 and 282 | | |
| 203 | 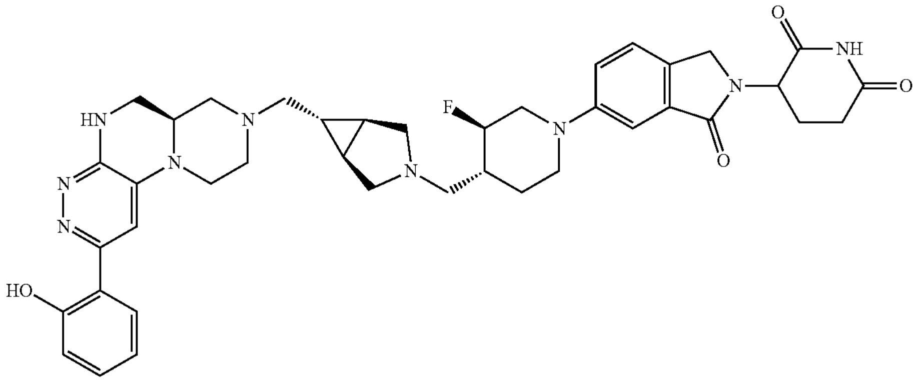 [SMILES: O=C1CCC(N2Cc3ccc(N4CC[C@H](CN5C[C@@H]6[C@H](C5)[C@H]6CN5CCN6c7cc(-c8ccccc8O)nnc7NC[C@H]6C5)[C@@H](F)C4)cc3C2=O)C(=O)N1] 3-(6-((3R,4R)-3-fluoro-4-(((1R,5S,6R)-6-(((S)-2-(2-hydroxyphenyl)-5,6,6a,7,9,10-hexahydro-8H-pyrazino [1',2':4,5]pyrazino[2,3-c]pyridazin-8-yl)methyl)-3-azabicyclo [3.1.0]hexan-3-yl)methyl)piperidin-1-yl)-1-oxoisoindolin-2-yl)piperidine-2,6-dione | 736.4 | 736.3 |
| 204 | 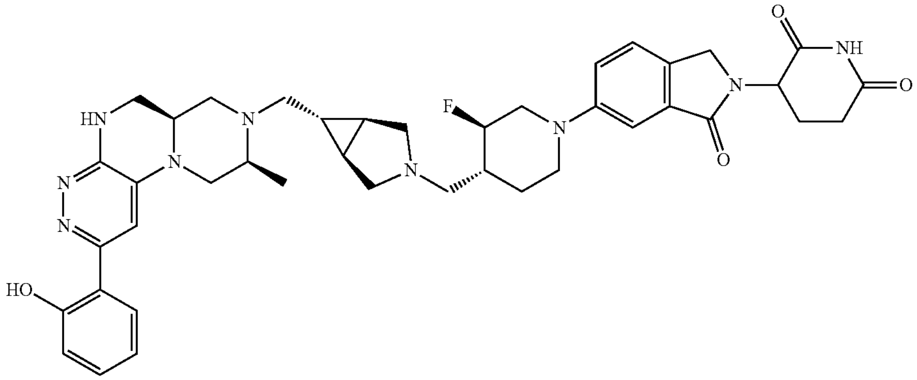 [SMILES: C[C@H]1CN2c3cc(-c4ccccc4O)nnc3NC[C@H]2CN1C[C@H]1[C@@H]2CN(C[C@H]3CCN(c4ccc5c(c4)C(=O)N(C4CCC(=O)NC4=O)C5)C[C@@H]3F)C[C@@H]21] 3-[5-[(3R,4R)-3-fluoro-4-[[(1S,5R)-6-[[(10S,13S)-4-(2-hydroxyphenyl)-13-methyl-1,5,6,8,12-pentazatricyclo [8.4.0.02,7]tetradeca-2,4,6-trien-12-yl]methyl]-3-azabicyclo [3.1.0]hexan-3-yl]methyl]piperidin-1-yl]-3-oxo-1H-isoindol-2-yl]piperidine-2,6-dione | 750.4 | 750.4 |
| 205 | 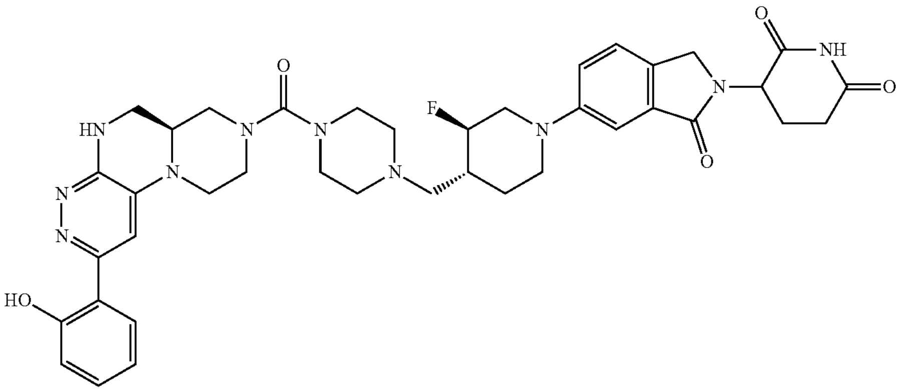 [SMILES: O=C1CCC(N2Cc3ccc(N4CC[C@H](CN5CCN(C(=O)N6CCN7c8cc(-c9ccccc9O)nnc8NC[C@H]7C6)CC5)[C@@H](F)C4)cc3C2=O)C(=O)N1] 3-[5-[(3R.4R)-3-fluoro-4-[[4-[(10S)-4-(2-hydroxyphenyl)-1,5,6,8,12-pentazatricyclo[8.4.0.02,7]tetradeca-2,4,6-triene-12-carbonyl]piperazin-1 -yl]methyl]piperidin-1-yl]-3-oxo-1H-isoindol-2-yl]piperidine-2.6-dione | 753.4 | 753.3 |

TABLE 15-continued

| Ex. | Structure Name | Calcd. (M + H)+ m/z | Found (M + H)+ m/z |
|---|---|---|---|
| | Examples 96, 99-117, 138-141, 203-205, 261, 262, 264-266, 269-275 and 282 | | |
| 261 | 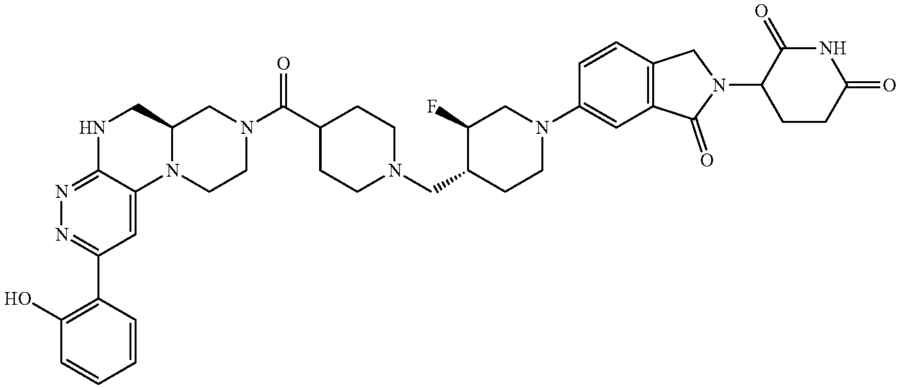 [SMILES: O=C1CCC(N2Cc3ccc(N4CC[C@H](CN5CCC(C(=O)N6CCN7c8cc(-c9ccccc9O)nnc8NC[C@H]7C6)CC5)[C@@H](F)C4)cc3C2=O)C(=O)N1] 3-(6-((3R,4R)-3-fluoro-4-((4-((S)-2-(2-hydroxyphenyl)-6,6a,7,8,9,10-hexahydro-5H-pyrazino[1',2':4,5]pyrazino[2,3-c]pyridazine-8-carbonyl)piperidin-1-yl)methyl)piperidin-1-yl)-1-oxoisoindolin-2-yl)piperidine-2,6-dione | 752.4 | 752.4 |
| 262 | 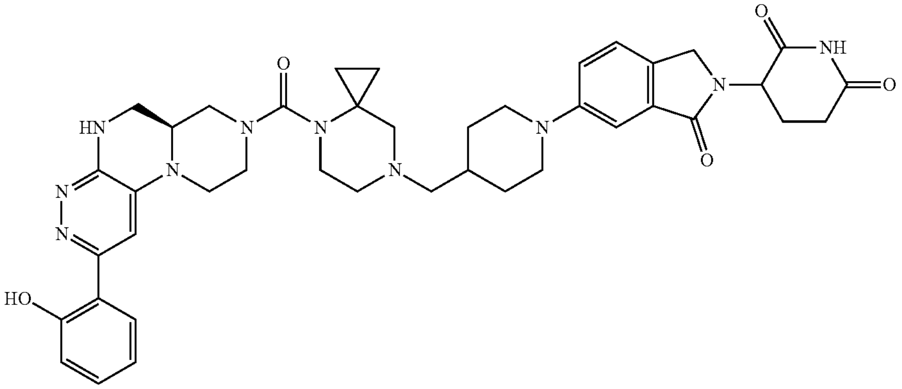 [SMILES: O=C1CCC(N2Cc3ccc(N4CCC(CN5CCN(C(=O)N6CCN7c8cc(-c9ccccc9O)nnc8NC[C@H]7C6)C6(CC6)C5)CC4)cc3C2=O)C(=O)N1] 3-(6-(4-((4-((S)-2-(2-hydroxyphenyl)-6,6a,7,8,9,10-hexahydro-5H-pyrazino[1',2':4,5]pyrazino[2,3-c]pyridazine-8-carbonyl)-4,7-diazaspiro[2.5]octan-7-yl)methyl)piperidin-1-yl)-1-oxoisoindolin-2-yl)piperidine-2,6-dione | 761.4 | 761.2 |
| 264 | 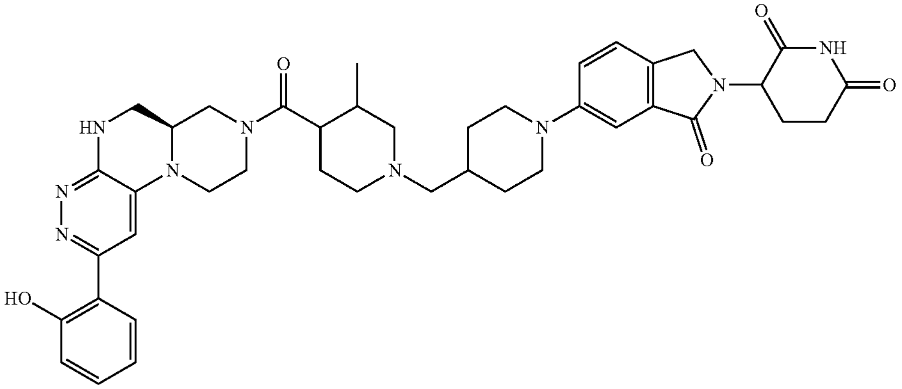 [SMILES: CC1CN(CC2CCN(c3ccc4c(c3)C(=O)N(C3CCC(=O)NC3=O)C4)CC2)CCC1C(=O)N1CCN2c3cc(-c4ccccc4O)nnc3NC[C@H]2C1] 3-(6-(4-((4-((S)-2-(2-hydroxyphenyl)-6,6a,7,8,9,10-hexahydro-5H-pyrazino[1',2':4,5]pyrazino[2,3-c]pyridazine-8-carbonyl)-3-methylpiperidin-1-yl)methyl)piperidin-1-yl)-1-oxoisoindolin-2-yl)piperidine-2,6-dione | 748.4 | 748.3 |

TABLE 15-continued

Examples 96, 99-117, 138-141, 203-205, 261, 262, 264-266, 269-275 and 282

| Ex. | Structure Name | Calcd. (M + H)+ m/z | Found (M + H)+ m/z |
|---|---|---|---|
| 265 | 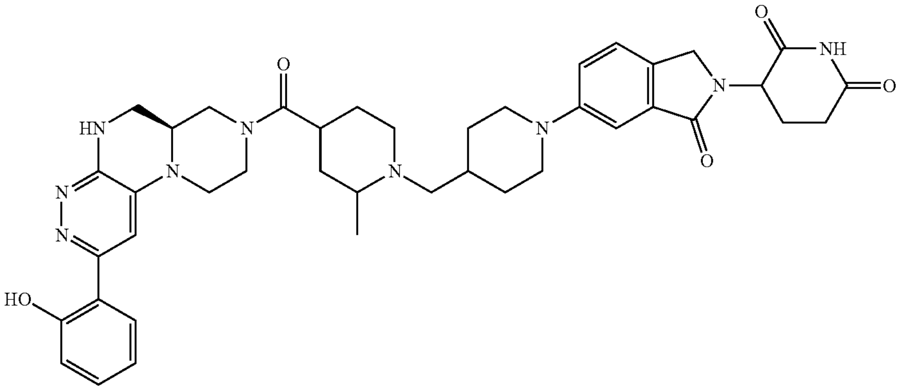 [SMILES: CC1CC(C(=O)N2CCN3c4cc(-c5ccccc5O)nnc4NC[C@H]3C2)CCN1CC1CCN(c2ccc3c(c2)C(=O)N(C2CCC(=O)NC2=O)C3)CC1] 3-(6-(4-((4-((S)-2-(2-hydroxyphenyl)-6,6a,7,8,9,10-hexahydro-5H-pyrazino[1',2':4,5]pyrazino[2,3-c]pyridazine-8-carbonyl)-2-methylpiperidin-1-yl)methyl)piperidin-1-yl)-1-oxoisoindolin-2-yl)piperidine-2,6-dione | 748.4 | 748.2 |
| 266 | 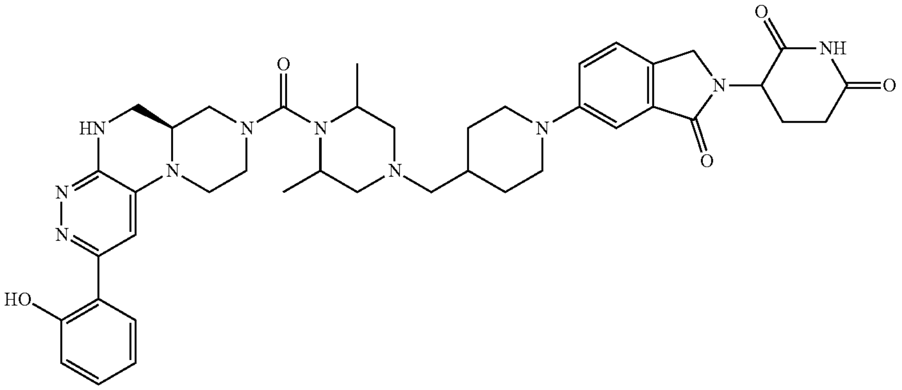 [SMILES: CC1CN(CC2CCN(c3ccc4c(c3)C(=O)N(C3CCC(=O)NC3=O)C4)CC2)CC(C)N1C(=O)N1CCN2c3cc(-c4ccccc4O)nnc3NC[C@H]2C1] 3-(6-(4-((4-((S)-2-(2-hydroxyphenyl)-6,6a,7,8,9,10-hexahydro-5H-pyrazino[1',2':4,5]pyrazino[2,3-c]pyridazine-8-carbonyl)-3,5-dimethylpiperazin-1-yl)methyl)piperidin-1-yl)-1-oxoisoindolin-2-yl)piperidine-2,6-dione | 763.4 | 763.4 |
| 269 | 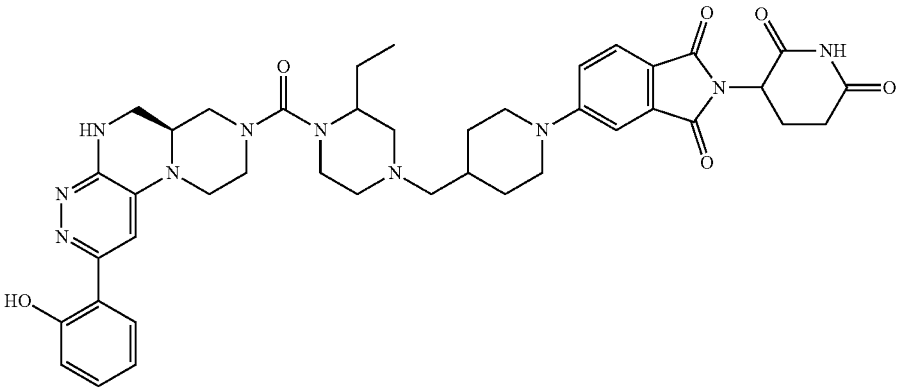 [SMILES: CCC1CN(CC2CCN(c3ccc4c(c3)C(=O)N(C3CCC(=O)NC3=O)C4=O)CC2)CCN1C(=O)N1CCN2c3cc(-c4ccccc4O)nnc3NC[C@H]2C1] 2-(2,6-dioxopiperidin-3-yl)-5-(4-((3-ethyl-4-((S)-2-(2-hydroxyphenyl)-6,6a,7,8,9,10-hexahydro-5H-pyrazino[1',2':4,5]pyrazino[2,3-c]pyridazine-8-carbonyl)piperazin-1-yl)methyl)piperidin-1-yl)isoindoline-1,3-dione | 777.4 | 777.2 |

TABLE 15-continued

| Ex. | Structure Name | Calcd. (M + H)+ m/z | Found (M + H)+ m/z |
|---|---|---|---|
| | Examples 96, 99-117, 138-141, 203-205, 261, 262, 264-266, 269-275 and 282 | | |
| 270 | 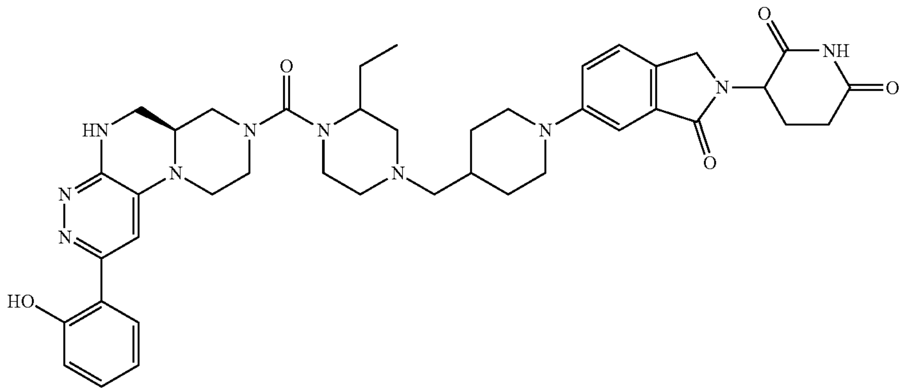 [SMILES: CCC1CN(CC2CCN(c3ccc4c(c3)C(=O)N(C3CCC(=O)NC3=O)C4)CC2)CCN1C(=O)N1CCN2c3cc(-c4ccccc4O)nnc3NC[C@H]2C1] 3-(6-(4-((3-ethyl-4-((S)-2-(2-hydroxyphenyl)-6,6a,7,8,9,10-hexahydro-5H-pyrazino[1',2':4,5]pyrazino[2,3-c]pyridazine-8-carbonyl)piperazin-1-yl)methyl)piperidin-1-yl)-1-oxoisoindolin-2-yl)piperidine-2,6-dione | 763.4 | 763.4 |
| 271 | 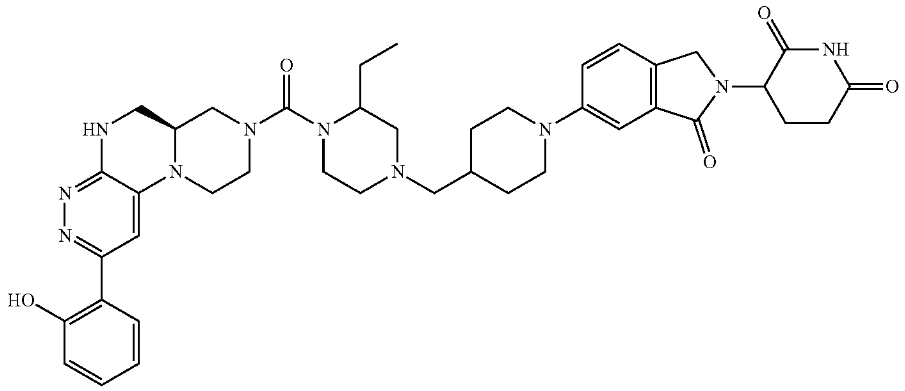 [SMILES: CCC1CN(CC2CCN(c3ccc4c(c3)C(=O)N(C3CCC(=O)NC3=O)C4)CC2)CCN1C(=O)N1CCN2c3cc(-c4ccccc4O)nnc3NC[C@H]2C1] 3-(6-(4-((3-ethyl-4-((S)-2-(2-hydroxyphenyl)-6,6a,7,8,9,10-hexahydro-5H-pyrazino[1',2':4,5]pyrazino[2,3-c]pyridazine-8-carbonyl)piperazin-1-yl)methyl)piperidin-1-yl)-1-oxoisoindolin-2-yl)piperidine-2,6-dione | 763.4 | 763.3 |
| 272 | 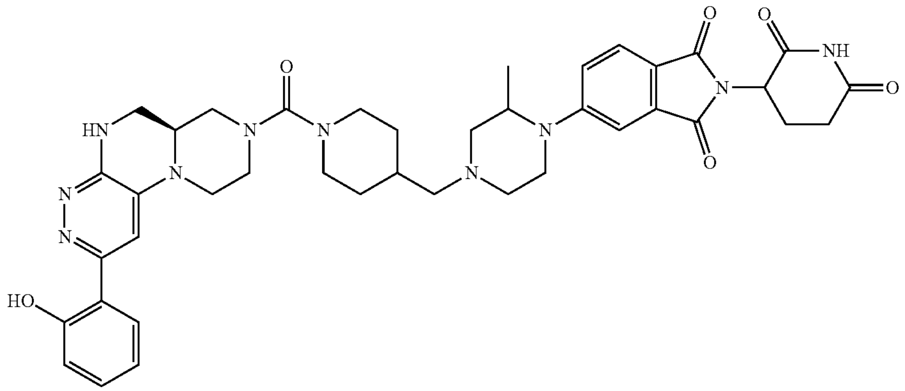 [SMILES: CC1CN(CC2CCN(C(=O)N3CCN4c5cc(-c6ccccc6O)nnc5NC[C@H]4C3)CC2)CCN1c1ccc2c(c1)C(=O)N(C1CCC(=O)NC1=O)C2=O] 2-(2,6-dioxopiperidin-3-yl)-5-(4-((1-((S)-2-(2-hydroxyphenyl)-6,6a,7,8,9,10-hexahydro-5H-pyrazino[1',2':4,5]pyrazino[2,3-c]pyridazine-8-carbonyl)piperidin-4-yl)methyl)-2-methylpiperazin-1-yl)isoindoline-1,3-dione | 763.4 | 763.2 |

TABLE 15-continued

| Ex. | Structure Name | Calcd. (M + H)+ m/z | Found (M + H)+ m/z |
|---|---|---|---|
| Examples 96, 99-117, 138-141, 203-205, 261, 262, 264-266, 269-275 and 282 | | | |
| 273 | 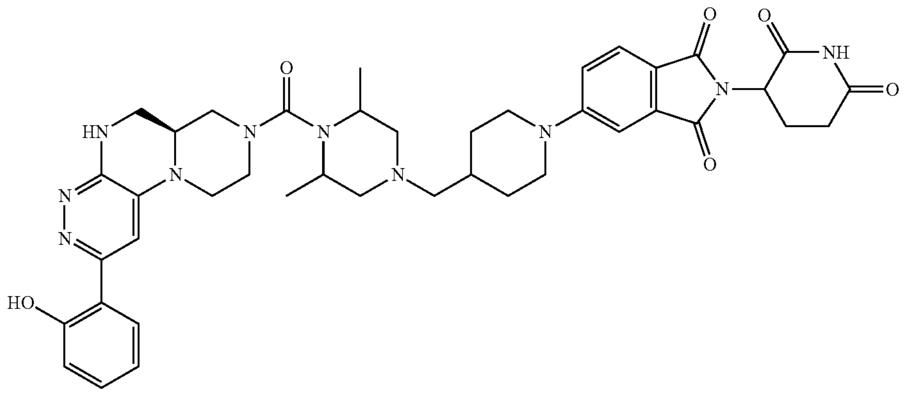 [SMILES: CC1CN(CC2CCN(c3ccc4c(c3)C(=O)N(C3CCC(=O)NC3=O)C4=O)CC2)CC(C)N1C(=O)N1CCN2c3cc(-c4ccccc4O)nnc3NC[C@H]2C1] 2-(2,6-dioxopiperidin-3-yl)-5-(4-((4-((S)-2-(2-hydroxyphenyl)-6,6a,7,8,9,10-hexahydro-5H-pyrazino[1',2':4,5]pyrazino[2,3-c]pyridazine-8-carbonyl)-3,5-dimethylpiperazin-1-yl)methyl)piperidin-1-yl)isoindoline-1,3-dione | 777.4 | 777.2 |
| 274 | 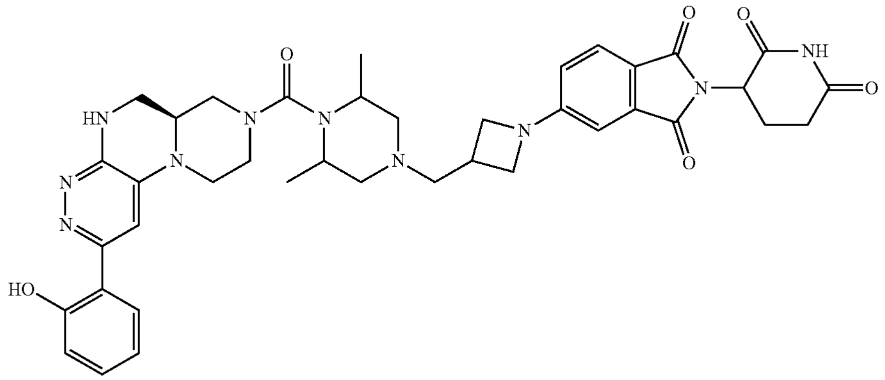 [SMILES: CC1CN(CC2CN(c3ccc4c(c3)C(=O)N(C3CCC(=O)NC3=O)C4=O)C2)CC(C)N1C(=O)N1CCN2c3cc(-c4ccccc4O)nnc3NC[C@H]2C1] 2-(2,6-dioxopiperidin-3-yl)-5-(3-((4-((S)-2-(2-hydroxyphenyl)-6,6a,7,8,9,10-hexahydro-5H-pyrazino[1 ',2':4,5]pyrazino[2,3-c]pyridazine-8-carbonyl)-3,5-dimethylpiperazin-1-yl)methyl)azetidin-1-yl)isoindoline-1,3-dione | 749.3 | 749.3 |
| 275 | 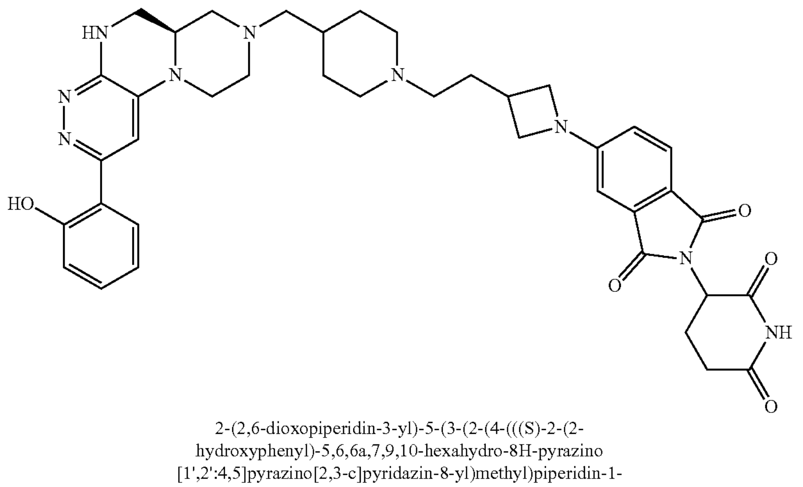 2-(2,6-dioxopiperidin-3-yl)-5-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethyl)azetidin-1-yl)isoindoline-1,3-dione | 720.4 | 720.2 |

TABLE 15-continued

| Examples 96, 99-117, 138-141, 203-205, 261, 262, 264-266, 269-275 and 282 | | | |
|---|---|---|---|
| Ex. | Structure Name | Calcd. (M + H)+ m/z | Found (M + H)+ m/z |
| 282 | 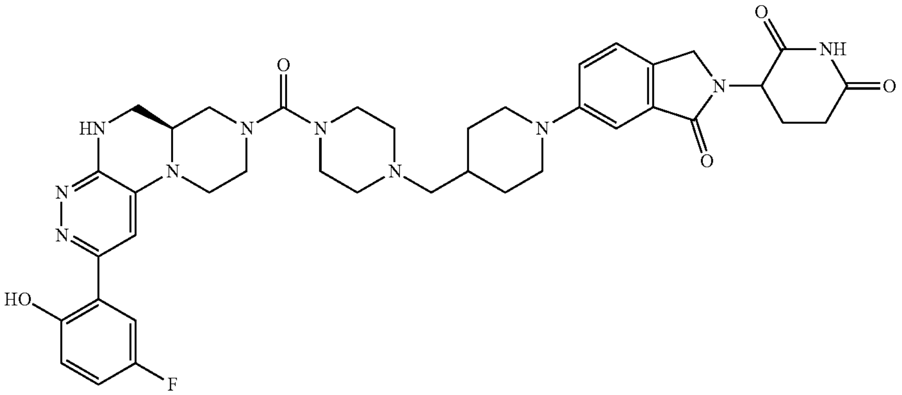 [SMILES: O=C1CCC(N2Cc3ccc(N4CCC(CN5CCN(C(=O)N6CCN7c8cc(-c9cc(F)ccc9O)nnc8NC[C@H]7C6)CC5)CC4)cc3C2=O)C(=O)N1] 3-(6-(4-((4-((S)-2-(5-fluoro-2-hydroxyphenyl)-6,6a,7,8,9,10-hexahydro-5H-pyrazino[1',2':4,5]pyrazino[2,3-c]pyridazine-8-carbonyl)piperazin-1-yl)methyl)piperidin-1-yl)-1-oxoisoindolin-2-yl)piperidine-2,6-dione | 753.4 | 753.4 |

Example 97: 2-(2,6-dioxopiperidin-3-yl)-5-((3aS, 7aS)-2-(4-((S)-2-(2-hydroxyphenyl)-6,6a,7,8,9,10-hexahydro-5H-pyrazino[1',2':4,5]pyrazino[2,3-c]pyridazine-8-carbonyl)cyclohexyl)octahydro-5H-pyrrolo[3,4-c]pyridin-5-yl) isoindoline-1,3-dione Ex. 97

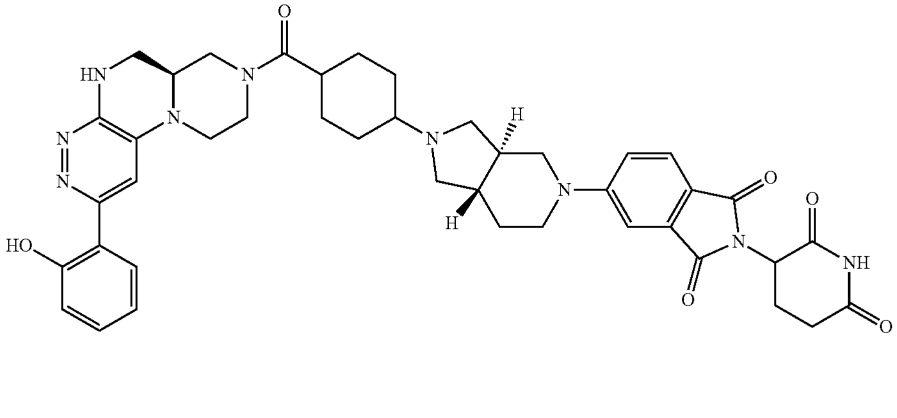

Step 1: Synthesis of tert-butyl (3aR,7aS)-5-(2-(2,6-dioxopiperidin-3-yl)-1,3-dioxoisoindolin-5-yl)octahydro-2H-pyrrolo[3,4-c]pyridine-2-carboxylate

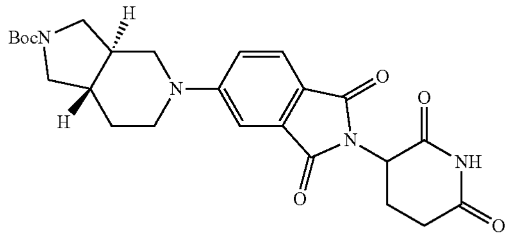 [SMILES: CC(C)(C)OC(=O)N1C[C@H]2CCN(c3ccc4c(c3)C(=O)N(C3CCC(=O)NC3=O)C4=O)C[C@@H]2C1]

To a stirring solution of 2-(2,6-Dioxo-3-piperidinyl)-5-fluoro-1H-isoindole-1,3(2H)-dione (60 mg, 0.265 mmol) and 2-Methyl-2-propanyl (3aR,7aS)-octahydro-2H-pyrrolo[3,4-c]pyridine-2-carboxylate (95.2 mg, 0.345 mmol) in N-methyl-2-pyrrolidinone (2.5 mL) was added N,N-diisopropylethylamine (123 μL, 0.707 mmol). The reaction mixture was heated to 120° C. and stirred for 5 hours. The product mixture was diluted with ethyl acetate (60 mL) and washed with saturated sodium chloride aqueous solution (50 mL×2). The organic layer was dried with sodium sulfate. The dried organic layer was filtered, and the filtrate was concentrated. The residue obtained was purified with flash column chromatography eluting with 0-100% ethyl acetate-hexanes followed by 20% methanol-hexanes to obtain tert-butyl (3aR,7aS)-5-(2-(2,6-dioxopiperidin-3-yl)-1,3-dioxoisoindolin-5-yl)octahydro-2H-pyrrolo[3,4-c]pyridine-2-carboxylate (90 mg, 70%) as a yellow oil. LCMS m/z calcd for $C_{25}H_{30}N_4O_6$ $[M+H]^+$: 483.2; found 483.2.

Step 2: Synthesis of 2-(2,6-dioxopiperidin-3-yl)-5-((3aS,7aS)-octahydro-5H-pyrrolo[3,4-c]pyridin-5-yl) isoindoline-1,3-dione

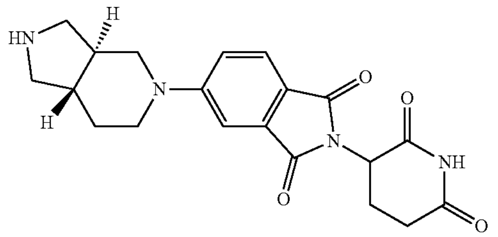 [SMILES: O=C1CCC(N2C(=O)c3ccc(N4CC[C@@H]5CNC[C@H]5C4)cc3C2=O)C(=O)N1]

To a stirring solution of tert-butyl (3aR,7aS)-5-(2-(2,6-dioxopiperidin-3-yl)-1,3-dioxoisoindolin-5-yl)octahydro-2H-pyrrolo[3,4-c]pyridine-2-carboxylate (90.0 mg, 0.187 mmol) in dichloromethane (4 mL) was added trifluoroacetic acid (800 μL, 10.5 mmol). The reaction mixture was stirred 1.5 hours. The product mixture was concentrated under reduced pressure to give the trifluoroacetic acid salt of 2-(2,6-dioxopiperidin-3-yl)-5-((3aS,7aS)-octahydro-5H-pyrrolo[3,4-c]pyridin-5-yl) isoindoline-1,3-dione (91 mg, 99%) as a yellow oil. LCMS m/z calcd for $C_{20}H_{22}N_4O_4$ $[M+H]^+$: 383.2; found 383.1.

Step 3: Synthesis of 4-((3aS,7aS)-5-(2-(2,6-dioxopiperidin-3-yl)-1,3-dioxoisoindolin-5-yl)octahydro-2H-pyrrolo[3,4-c]pyridin-2-yl)cyclohexane-1-carboxylic acid

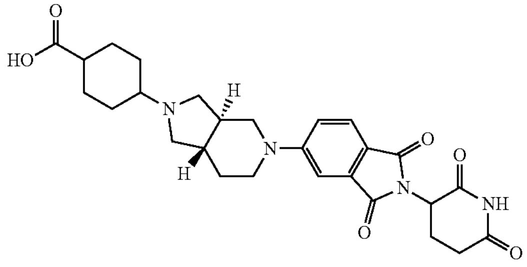 [SMILES: O=C1CCC(N2C(=O)c3ccc(N4CC[C@@H]5CN(C6CCC(C(=O)O)CC6)C[C@H]5C4)cc3C2=O)C(=O)N1]

To a stirring solution of the trifluoroacetic acid salt of 2-(2,6-dioxopiperidin-3-yl)-5-((3aS,7aS)-octahydro-5H-pyrrolo[3,4-c]pyridin-5-yl) isoindoline-1,3-dion (22.5 mg, 0.0589 mmol) and 4-oxocyclohexane-1-carboxylic acid (83.7 mg, 0.589 mmol) in N,N-dimethylformamide (500 μL) and acetonitrile (500 μL) was added acetic acid (16.8 μL, 0.295 mmol) followed by sodium triacetoxyborohydride (25 mg, 0.118 mmol). The reaction mixture was heated to 60° C. and stirred for 3 hours. The product mixture was diluted with acetonitrile. The diluted product mixture was filtered and the filtrate was purified directly using a prep-LCMS (5 m 10×3 cm Waters CSH-C18, 21.1-41.1% acetonitrile in water (0.1% TFA), wet loaded) to yield the trifluoroacetic acid salt of 4-((3aS,7aS)-5-(2-(2,6-dioxopiperidin-3-yl)-1,3-dioxoisoindolin-5-yl)octahydro-2H-pyrrolo[3,4-c]pyridin-2-yl)cyclohexane-1-carboxylic acid (15 mg, 45%) as a yellow solid. LCMS m/z calcd for $C_{27}H_{32}N_4O_6$ $[M+H]^+$: 509.2; found 509.2.

Step 4: Synthesis of 2-(2,6-dioxopiperidin-3-yl)-5-((3aS,7aS)-2-(4-((S)-2-(2-hydroxyphenyl)-6,6a, 7,8, 9,10-hexahydro-5H-pyrazino[1',2':4,5]pyrazino[2,3-c]pyridazine-8-carbonyl) cyclohexyl)octahydro-5H-pyrrolo[3,4-c]pyridin-5-yl) isoindoline-1,3-dione To a stirring solution of the trifluoroacetic acid salt of 4-((3aS,7aS)-5-(2-(2,6-dioxopiperidin-3-yl)-1,3-dioxoisoindolin-5-yl)octahydro-2H-pyrrolo[3,4-c]pyridin-2-yl)cyclohexane-1-carboxylic acid (15.0 mg, 0.0241 mmol) in N,N-dimethylformamide (1 mL) at 0° C. was added 1-[Bis(dimethylamino)-methylene]-1H-1,2,3-triazolo[4,5-b]pyridinium 3-oxid hexafluorophosphate (14.3 mg, 0.0376) followed by triethylamine (20.1 μL, 0.145 mmol). The reaction mixture was stirred at 0° C. for 15 minutes. Then to the stirring reaction mixture at 0° C. was added 2-[(10R)-1,5,6,8,12-pentazatricyclo[8.4.0.02,7]tetradeca-2,4,6-trien-4-yl]phenol; dihydrochloride (10.3 mg, 0.0289 mmol). The reaction mixture was allowed to warm to 23° C. and stir an additional 1 hour. The product mixture was diluted with acetonitrile (3.5 mL) and directly purified using a prep-LCMS (5 m 10×3 cm Waters CSH-C18, 12.5-32.5% acetonitrile in water (0.1% TFA), wet loaded) to yield the trifluoroacetic acid salt of 2-(2,6-dioxopiperidin-3-yl)-5-((3aS,7aS)-2-(4-((S)-2-(2-hydroxyphenyl)-6,6a,7,8,9,10-hexahydro-5H-pyrazino[1',2':4,5]pyrazino[2,3-c]pyridazine-8-carbonyl)cyclohexyl)octahydro-5H-pyrrolo[3,4-c]pyridin-5-yl) isoindoline-1,3-dione (6.1 mg, 25.3%) as a yellow solid. LCMS m/z calcd for $C_{42}H_{47}N_9O_6$ $[M+H]^+$: 774.4; found 774.3.

Example 98: 2-(2,6-dioxopiperidin-3-yl)-5-((3aS, 6aS)-5-(4-((S)-2-(2-hydroxyphenyl)-6,6a,7,8,9,10-hexahydro-5H-pyrazino[1',2':4,5]pyrazino[2,3-c]pyridazine-8-carbonyl)cyclohexyl)hexahydropyrrolo[3,4-c]pyrrol-2(1H)-yl) isoindoline-1,3-dione Ex. 98

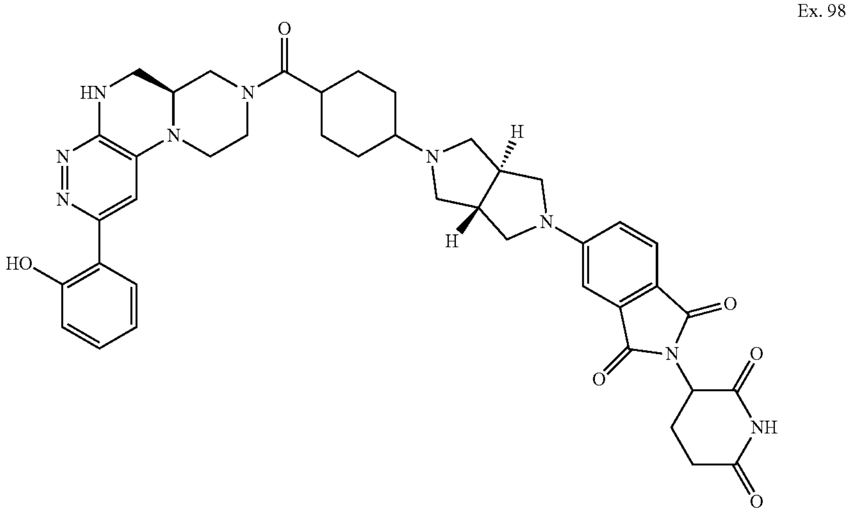 [SMILES: O=C1CCC(N2C(=O)c3ccc(N4C[C@@H]5CN(C6CCC(C(=O)N7CCN8c9cc(-c%10ccccc%10O)nnc9NC[C@H]8C7)CC6)C[C@H]5C4)cc3C2=O)C(=O)N1]

The title compound was prepared using procedure analogous to those described for Example 97, using appropriate starting materials. LCMS calcd. for $C_{40}H_{46}N_9O_3[M+H]^+$ m/z=700.4; found: 700.2.

Examples 118-122

Examples in Table 16 were prepared using the procedure described in the synthesis of Example 17 with appropriate intermediates.

TABLE 16

Examples 118-122

| Ex. | Structure/Name | Calcd. $(M + H)^+$ m/z | Found $(M + H)^+$ m/z |
|---|---|---|---|
| 118 | 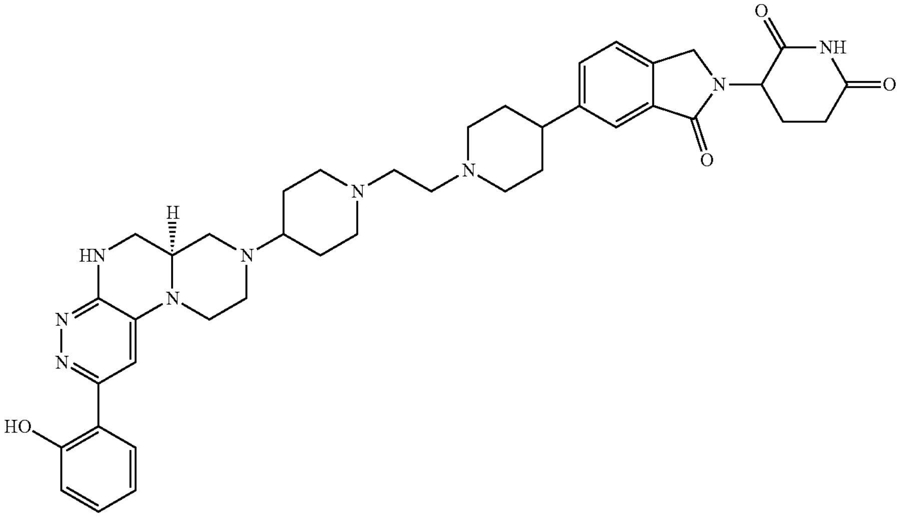 3-(6-(1-(2-(4-((S)-2-(2-hydroxyphenyl)-5,6,6a,7,9,10-hexahydro-8H-pyrazino[1′,2′:4,5]pyrazino[2,3-c]pyridazin-8-yl)piperidin-1-yl)ethyl)piperidin-4-yl)-1-oxoisoindolin-2-yl)piperidine-2,6-dione | 720.40 | 720.3 |

TABLE 16-continued

| Ex. | Structure/Name | Calcd. (M + H)+ m/z | Found (M + H)+ m/z |
|---|---|---|---|
| | Examples 118-122 | | |
| 119 | 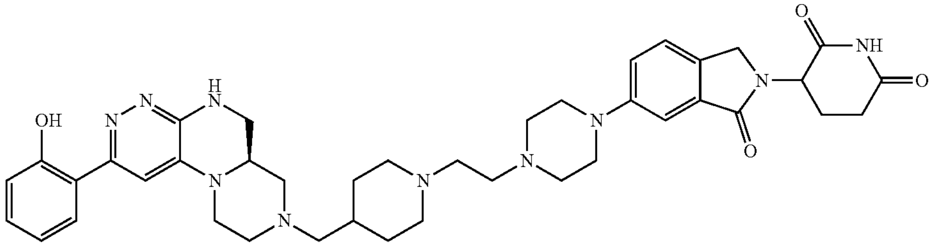 3-(6-(4-(2-(4-(((S)-2-(2-hydroxyphenyl)-5,6,6a,7,9,10-hexahydro-8H-pyrazino[1′,2′:4,5]pyrazino[2,3-c]pyridazin-8-yl)methyl)piperidin-1-yl)ethyl)piperazin-1-yl)-1-oxoisoindolin-2-yl)piperidine-2,6-dione | 735.4 | 735.3 |
| 120 | 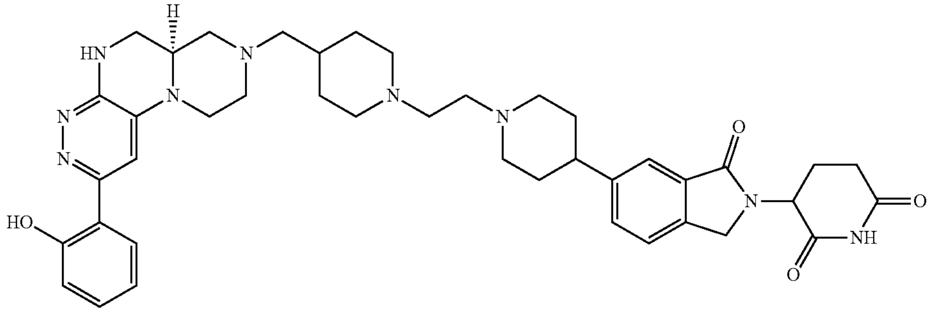 3-(6-(1-(2-(4-(((S)-2-(2-hydroxyphenyl)-5,6,6a,7,9,10-hexahydro-8H-pyrazino[1′,2′:4,5]pyrazino[2,3-c]pyridazin-8-yl)methyl)piperidin-1-yl)ethyl)piperidin-4-yl)-1-oxoisoindolin-2-yl)piperidine-2,6-dione | 734.4 | 734.2 |
| 121 | 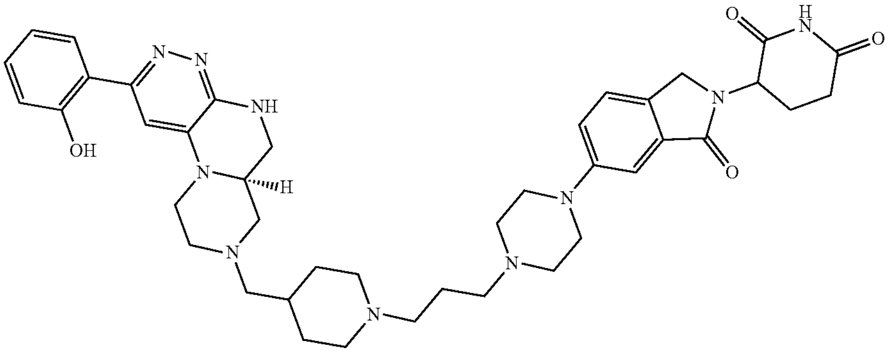 3-(6-(4-(3-(4-(((S)-2-(2-hydroxyphenyl)-5,6,6a,7,9,10-hexahydro-8H-pyrazino[1′,2′:4,5]pyrazino[2,3-c]pyridazin-8-yl)methyl)piperidin-1-yl)propyl)piperazin-1-yl)-1-oxoisoindolin-2-yl)piperidine-2,6-dione | 749.4 | 749.4 |
| 122 | 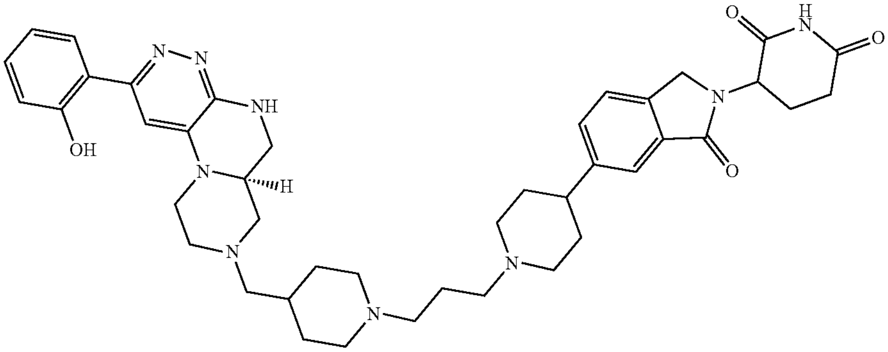 3-(6-(1-(3-(4-(((S)-2-(2-hydroxyphenyl)-5,6,6a,7,9,10-hexahydro-8H-pyrazino[1′,2′:4,5]pyrazino[2,3-c]pyridazin-8-yl)methyl)piperidin-1-yl)propyl)piperidin-4-yl)-1-oxoisoindolin-2-yl)piperidine-2,6-dione | 748.43 | 748.2 |

Example 123: (3-(4-(4-((S)-2-(2-hydroxyphenyl)-5,6,6a,7,9,10-hexahydro-811-pyrazino [1',2':4,5] pyrazino[2,3-c]pyridazin-8-yl)-[1,4'-bipiperidin]-1'-yl)-1,3-dioxoisoindolin-2-yl)-2,6-dioxopiperidin-1-yl)methyl pivalate Ex. 123

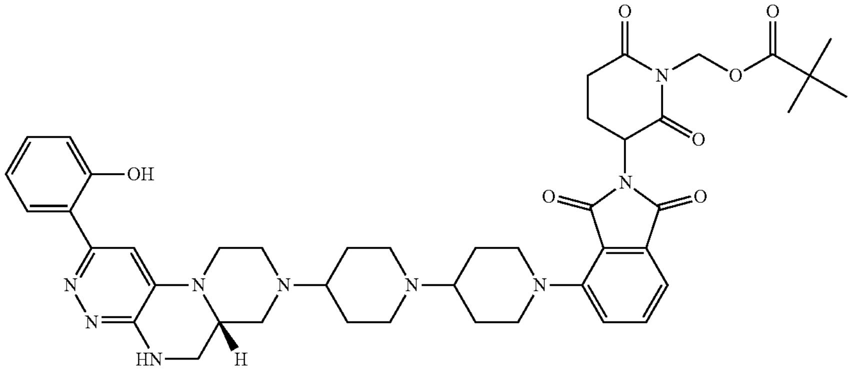

To a vial containing (S)-2-(8-([1,4'-bipiperidin]-4-yl)-6,6a,7,8,9,10-hexahydro-5H-pyrazino[1',2':4,5]pyrazino[2,3-c]pyridazin-2-yl)phenol;2,2,2-trifluoroacetic acid (102.0 mg, 0.13 mmol), [3-(4-fluoro-1,3-dioxoisoindol-2-yl)-2,6-dioxopiperidin-11-yl]methyl 2,2-dimethylpropanoate (50.3 mg, 0.13 mmol), and NMP (1.3 mL) was added N,N-diisopropylethyl amine (150.0 μL, 0.86 mmol). The resulted mixture was heated to 110° C. for 6.5 hours. The reaction was quenched with 4 N HCl dioxane (0.23 mL, 0.90 mmol). Crude was diluted into 25 mL of Methanol, filtered, and purified using prep-LCMS (5 μm 10×3 cm CSH-F1-Ph column, 14.4-34.3%$_0$ acetonitrile in water (0.100 TFA), wet loaded, over 5 min) to yield (3-(4-(4-((S)-2-(2-hydroxyphenyl)-5,6,6a,7,9,10-hexahydro-8H-pyrazino[1',2':4,5]pyrazino[2,3-c]pyridazin-8-yl)-[1,4'-bipiperidin]-1'-yl)-1,3-dioxoisoindolin-2-yl)-2,6-dioxopiperidin-11-yl)methyl pivalate; 2,2,2-tri fluoroacetic acid (24.8 mg, 0.023 mmol, 18.1% yield) as a yellow powder. LCMS m/z calcd for $C_{44}H_{54}N_9O_7$ $(M+H)^+$: 820.41; found 820.3.

Examples 34 and 129-131

Examples in Table 17 were prepared using the procedure described in the synthesis of Example 123 with appropriate intermediates.

TABLE 17

| Ex. | Structure/Name | Calcd. $(M + H)^+$ m/z | Found $(M + H)^+$ m/z |
|---|---|---|---|
| | Examples 34 and 129-131 | | |
| 34 | 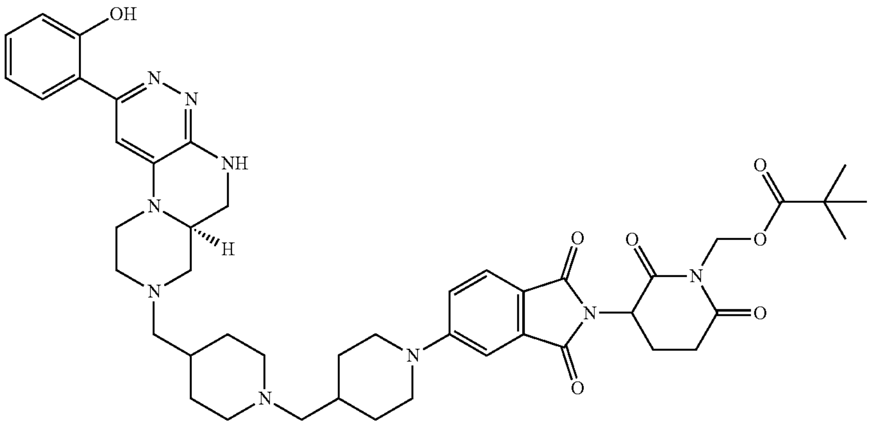 (3-(5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl)-1,3-dioxoisoindolin-2-yl)-2,6-dioxopiperidin-1-yl)methyl pivalate | 848.4 | 848.3 |

TABLE 17-continued

| Ex. | Examples 34 and 129-131<br>Structure/Name | Calcd. (M + H)+ m/z | Found (M + H)+ m/z |
|---|---|---|---|
| 129 | 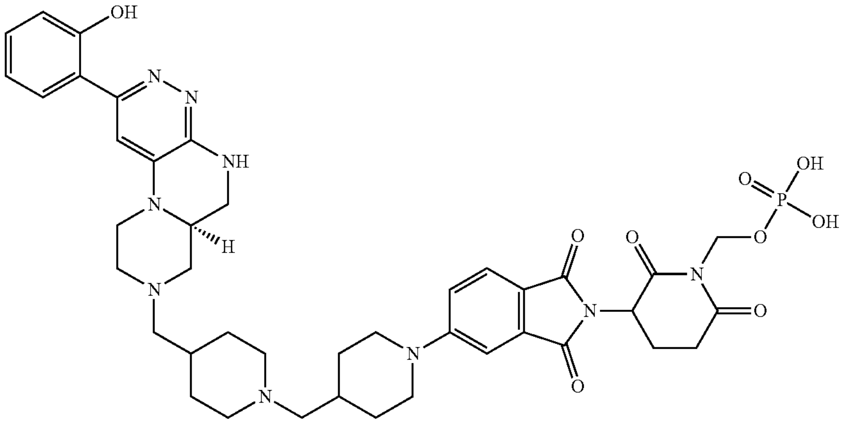<br>(3-(5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl)-1,3-dioxoisoindolin-2-yl)-2,6-dioxopiperidin-1-yl)methyl dihydrogen phosphate | 844.3 | 844.3 |
| 130 | 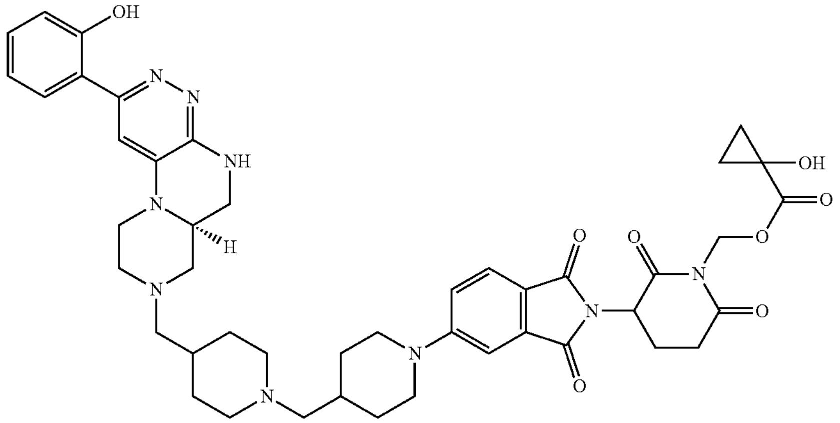<br>(3-(5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl)-1,3-dioxoisoindolin-2-yl)-2,6-dioxopiperidin-1-yl)methyl 1-hydroxycyclopropane-1-carboxylate | 848.4 | 848.4 |
| 131 | 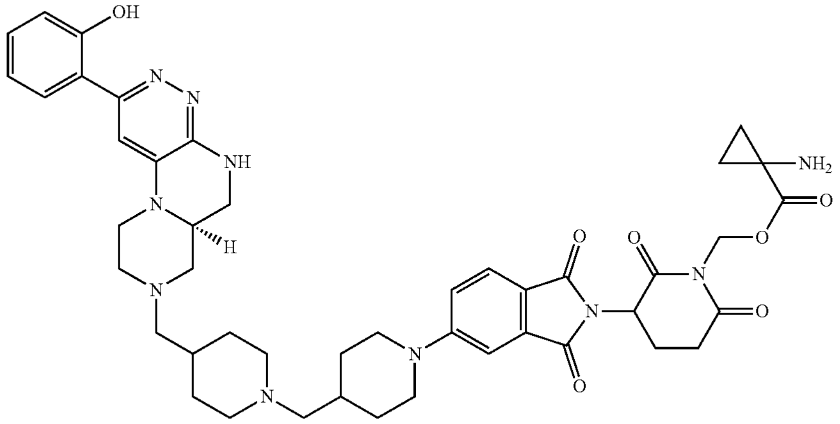<br>(3-(5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl)-1,3-dioxoisoindolin-2-yl)-2,6-dioxopiperidin-1-yl)methyl 1-aminocyclopropane-1-carboxylate | 847.4 | 847.3 |

Example 124: 2-(2,6-dioxopiperidin-3-yl)-4-(4-(3-(4-((S)-2-(2-hydroxyphenyl)-5,6,6a,7,9,10-hexahydro-811-pyrazino[1',2':4,5]pyrazino[2,3-c]pyridazin-8-yl)-3-methylpiperidin-1-yl)propyl)piperidin-1-yl) isoindoline-1,3-dione Ex. 124

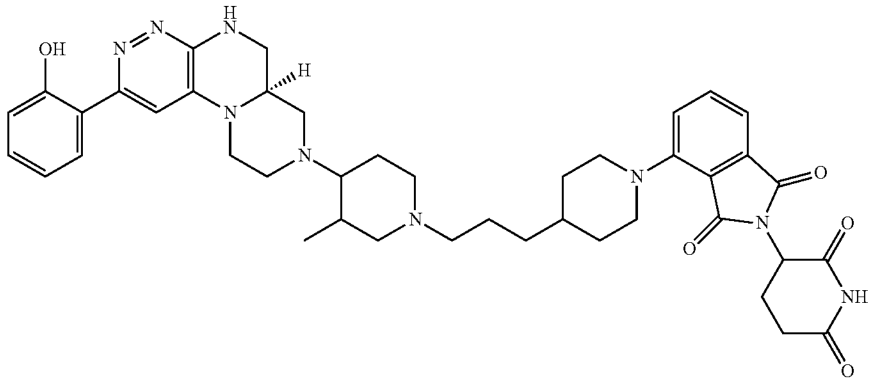

Step 1: 2-((6aS)-8-(3-methyl-1-(3-(piperidin-4-yl)propyl)piperidin-4-yl)-6,6a, 7,8,9,10-hexahydro-5H-pyrazino[1',2':4,5]pyrazino[2,3-c]pyridazin-2-yl)phenol

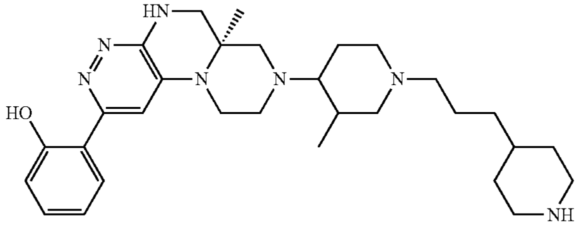 [SMILES: CC1CN(CCCC2CCNCC2)CCC1N1CCN2c3cc(-c4ccccc4O)nnc3NC[C@@]2(C)C1]

To a vial containing 2-((6aS)-8-(3-methylpiperidin-4-yl)-6,6a,7,8,9,10-hexahydro-5H-pyrazino[1',2':4,5]pyrazino[2,3-c]pyridazin-2-yl)phenol; dihydrochloride (20.0 mg, 0.04 mmol) and tert-butyl 4-(3-oxopropyl)piperidine-1-carboxylate (13.33 mg, 0.06 mmol) was added DCM (1 mL) and Ethanol (0.20 mL). The resulted mixture was stirred for 5 minutes then sodium triacetoxyborohydride (26.58 mg, 0.13 mmol) was added. After another 16 h, the reaction was dissolved in 10 mL of MeOH filtered and purified using prep-LCMS (5 m 10×3 cm Sunfire C18 column, 14.1-34.1% acetonitrile in water (0.1% TFA), wet loaded, over 5 min) to yield tert-butyl 4-(3-(4-((S)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)propyl)piperidine-1-carboxylate. Tert-butyl 4-(3-(4-((S)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)propyl)piperidine-1-carboxylate was then dissolved in DCM (1 mL) and 2,2,2-trifluoroacetic acid (0.3 mL, 3.92 mmol). After 15 min, the volatiles were removed to yield 2-(2,6-dioxopiperidin-3-yl)-4-(4-(3-(4-((S)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)propyl)piperidin-1-yl) isoindoline-1,3-dione as its TFA salt (30 mg, 0.04 mmol, 92.7% yield). LCMS m/z calcd for $C_{29}H_{44}N_7O$ $(M+H)^+$: 506.4; found 506.2.

Step 2: 2-(2,6-dioxopiperidin-3-yl)-4-(4-(3-(4-((S)-2-(2-hydroxyphenyl)-5,6,6a, 7,9,10-hexahydro-8H-pyrazino[1',2':4,5]pyrazino[2,3-c]pyridazin-8-yl)-3-methylpiperidin-1-yl)propyl)piperidin-1-yl) isoindoline-1,3-dione To a vial containing N,N-Diisopropylethylamine (60.0 uL, 0.34 mmol), 2-((6aS)-8-(3-methylpiperidin-4-yl)-6,6a,7,8,9,10-hexahydro-5H-pyrazino[1',2':4,5]pyrazino[2,3-c]pyridazin-2-yl)phenol; dihydrochloride;2,2,2-trifluoroacetic acid (30.0 mg, 0.04 mmol) and DMSO (700 uL) was added 2-(2,6-Dioxo-piperidin-3-yl)-4-fluoroisoindoline-1,3-dione (15.0 mg, 0.05 mmol). After 3 hour at 100° C., the reaction was diluted in 5 mL of MeOH filtered and purified using prep-LCMS (5 m 10×3 cm Sunfire C18 column, 13-33% acetonitrile in water (0.1% TFA), wet loaded, over 5 min). Product was lyophilized to yield 2-(2,6-dioxopiperidin-3-yl)-4-[4-[3-[4-[(10S)-4-(2-hydroxyphenyl)-1,5,6,8,12-pentazatricyclo[8.4.0.02,7]tetradeca-2(7),3,5-trien-12-yl]-3-methylpiperidin-1-yl]propyl]piperidin-11-yl]isoindole-1,3-dione as its TFA salt (3 mg, 0.00264 mmol, 6.445300 yield). LCMS m/z calcd for $C_{42}H_{52}N_9O_5$ $(M+H)^+$: 762.4; found 762.2.

Examples 125 and 126

Examples in Table 18 were prepared using the procedure described in the synthesis of Example 124 with appropriate intermediates.

TABLE 18

Examples 125 and 126

| Ex. | Structure/Name | Calcd. (M + H)+ m/z | Found (M + H)+ m/z |
|---|---|---|---|
| 125 | 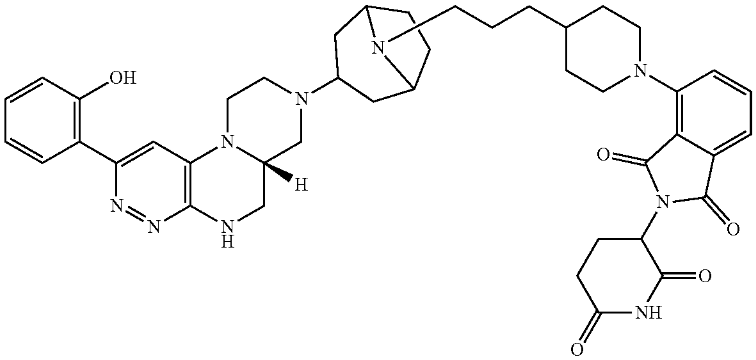 2-(2,6-dioxopiperidin-3-yl)-4-(4-(3-(3-((S)-2-(2-hydroxyphenyl)-5,6,6a,7,9,10-hexahydro-8H-pyrazino[1′,2′:4,5]pyrazino[2,3-c]pyridazin-8-yl)-8-azabicyclo[3.2.1]octan-8-yl)propyl)piperidin-1-yl)isoindoline-1,3-dione | 774.4 | 774.2 |
| 126 | 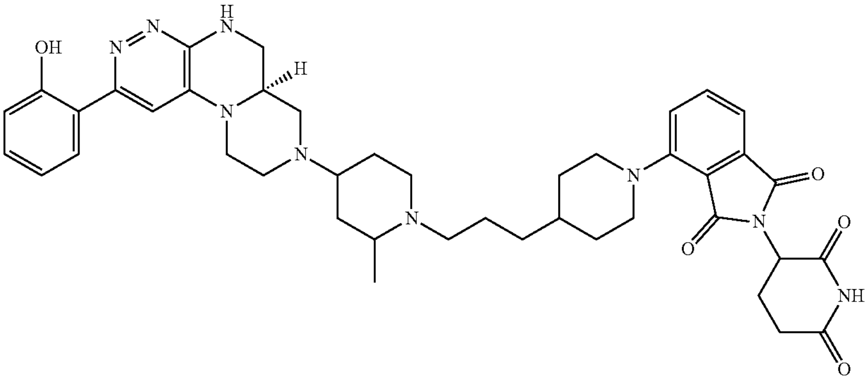 2-(2,6-dioxopiperidin-3-yl)-4-(4-(3-(4-((S)-2-(2-hydroxyphenyl)-5,6,6a,7,9,10-hexahydro-8H-pyrazino[1′,2′:4,5]pyrazino[2,3-c]pyridazin-8-yl)-2-methylpiperidin-1-yl)propyl)piperidin-1-yl)isoindoline-1,3-dione | 762.4 | 762.2 |

Example 127: 2-(2,6-dioxopiperidin-3-yl)-4-(4-((4-(((S)-2-(2-hydroxyphenyl)-5,6,6a,7,9,10-hexahydro-8H-pyrazino[1',2':4,5]pyrazino[2,3-c]pyridazin-8-yl) methyl)piperidin-1-yl) methyl)piperidin-1-yl) isoindoline-1,3-dione Ex.127

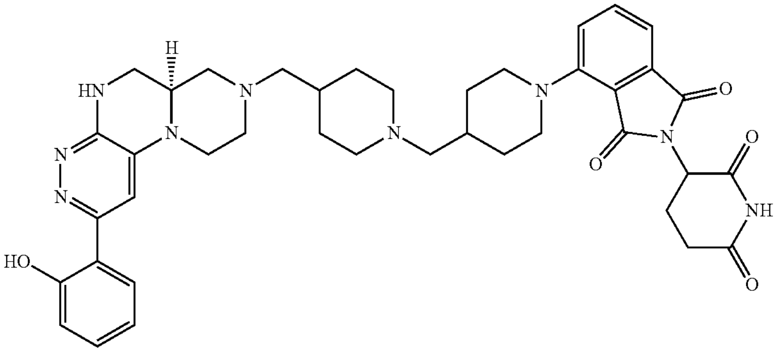

To 1-[2-(2,6-dioxopiperidin-3-yl)-1,3-dioxoisoindol-4-yl]piperidine-4-carbaldehyde (30.0 mg, 0.05 mmol) was added (S)-2-(8-(piperidin-4-ylmethyl)-6,6a,7,8,9,10-hexahydro-5H-pyrazino[1',2':4,5]pyrazino[2,3-c]pyridazin-2-yl) phenol; dihydrochloride (30.0 mg, 0.06 mmol) in DCM (700 uL) and Ethanol (150 μL), followed by sodium acetate (20.0 mg, 0.24 mmol) and magnesium sulfate (2.0 mg, 0.02 mmol). The resulted mixture was stirred for 30 min at 35° C. before sodium triacetoxyborohydride (30.0 mg, 0.14 mmol) was added. After additional 1 hour, the reaction mixture was diluted into 10 mL of MeOH, filtered and purified using prep-LCMS (5 m 10×3 cm CSH-FP column, 5-26% acetonitrile in water (0.1% TFA), wet loaded, over 5 min) to yield 2-(2,6-dioxopiperidin-3-yl)-4-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl) isoindoline-1,3-dione as its TFA salt (15 mg, 0.01369 mmol, 26.761% yield) as a yellow solid. LCMS m/z calcd for $C_{40}H_{48}N_9O_5$ $(M+H)^+$: 734.4; found 734.2.

Examples 128, 132-137 and 142-146

Examples in Table 19 were prepared using the procedure described in the synthesis of Example 127 with appropriate intermediates.

TABLE 19

Examples 128, 132-137 and 142-146

| Ex. | Structure/Name | Calcd. $(M + H)^+$ m/z | Found $(M + H)^+$ m/z |
|---|---|---|---|
| 128 | 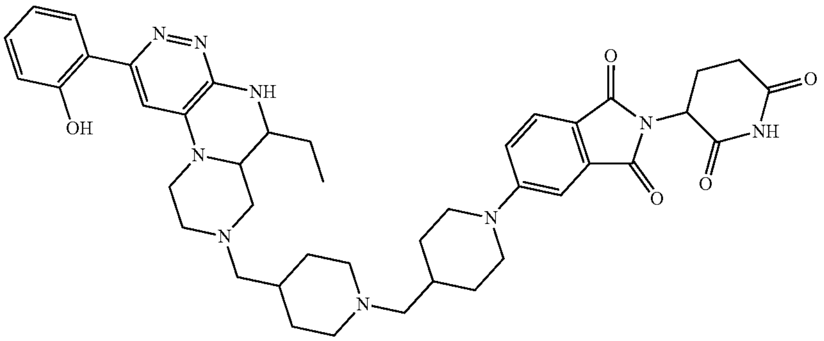 2-(2,6-dioxopiperidin-3-yl)-5-(4-((4-((6-ethyl-2-(2-hydroxyphenyl)-5,6,6a,7,9,10-hexahydro-8H-pyrazino[1′,2′:4,5]pyrazino[2,3-c]pyridazin-8-yl)methyl)piperidin-1-yl)methyl)piperidin-1-yl)isoindoline-1,3-dione | 762.4 | 762.3 |
| 132 | 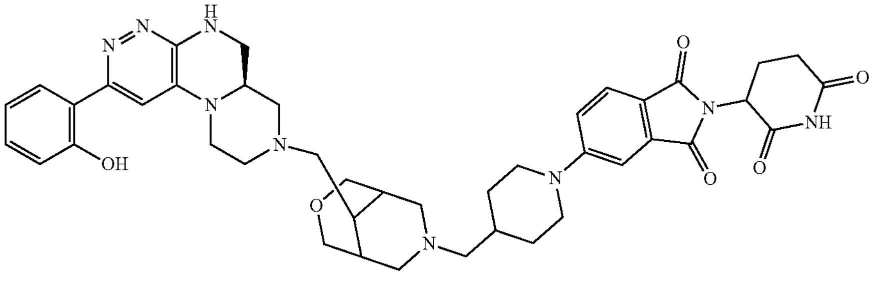 2-(2,6-dioxopiperidin-3-yl)-5-(4-((9-(((S)-2-(2-hydroxyphenyl)-5,6,6a,7,9,10-hexahydro-8H-pyrazino[1′,2′:4,5]pyrazino[2,3-c]pyridazin-8-yl)methyl)-3-oxa-7-azabicyclo[3.3.1]nonan-7-yl)methyl)piperidin-1-yl)isoindoline-1,3-dione | 776.4 | 776.2 |

TABLE 19-continued

| Ex. | Structure/Name | Calcd. (M + H)+ m/z | Found (M + H)+ m/z |
|---|---|---|---|
| | Examples 128, 132-137 and 142-146 | | |
| 133 | 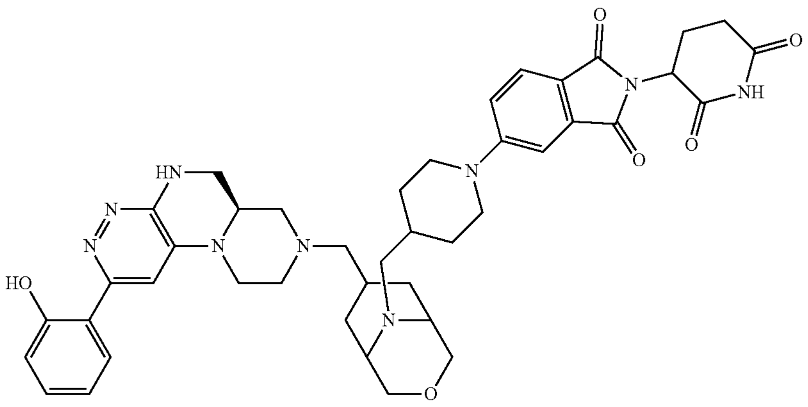 2-(2,6-dioxopiperidin-3-yl)-5-(4-((7-(((S)-2-(2-hydroxyphenyl)-5,6,6a,7,9,10-hexahydro-8H-pyrazino[1′,2′:4,5]pyrazino[2,3-c]pyridazin-8-yl)methyl)-3-oxa-9-azabicyclo[3.3.11nonan-9-yl)methyl)piperidin-1-yl)isoindoline-1,3-dione | 776.4 | 776.3 |
| 134 | 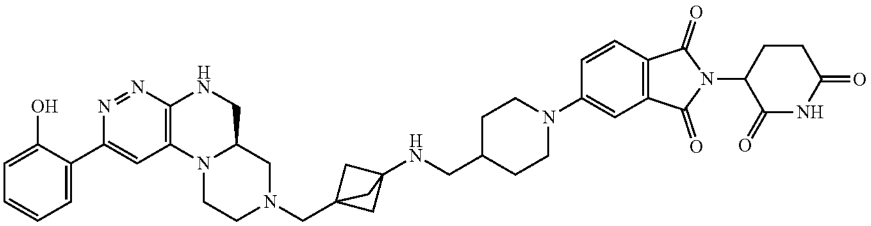 2-(2,6-dioxopiperidin-3-yl)-5-(4-(((3-(((S)-2-(2-hydroxyphenyl)-5,6,6a,7,9,10-hexahydro-8H-pyrazino[1′,2′:4,5]pyrazino[2,3-c]pyridazin-8-yl)methyl)bicyclo[1.1.1]pentan-1-yl)amino)methyl)piperidin-1-yl)isoindoline-1,3-dione | 732.4 | 732.2 |
| 135 | 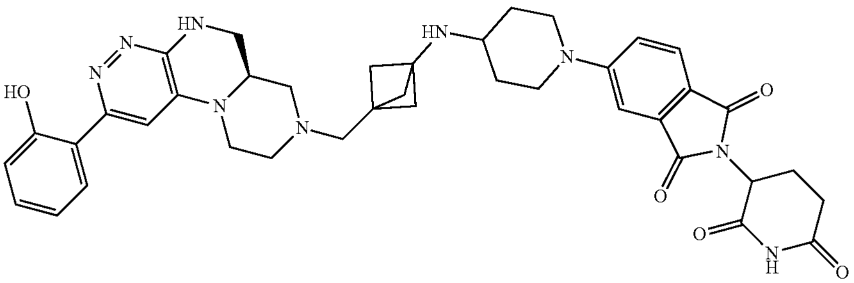 2-(2,6-dioxopiperidin-3-yl)-5-(4-((3-(((S)-2-(2-hydroxyphenyl)-5,6,6a,7,9,10-hexahydro-8H-pyrazino[1′,2′:4,5]pyrazino[2,3-c]pyridazin-8-yl)methyl)bicyclo[1.1.1]pentan-1-yl)amino)piperidin-1-yl)isoindoline-1,3-dione | 718.3 | 718.2 |

TABLE 19-continued

| Ex. | Structure/Name | Calcd. (M + H)+ m/z | Found (M + H)+ m/z |
|---|---|---|---|
| 136 | 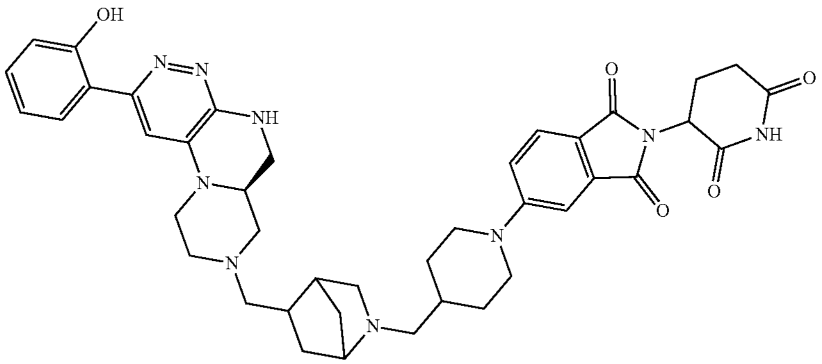 2-(2,6-dioxopiperidin-3-yl)-5-(4-((5-(((S)-2-(2-hydroxyphenyl)-5,6,6a,7,9,10-hexahydro-8H-pyrazino[1′,2′:4,5]pyrazino[2,3-c]pyridazin-8-yl)methyl)-2-azabicyclo[2.2.1]heptan-2-yl)methyl)piperidin-1-yl)isoindoline-1,3-dione | 746.4 | 746.2 |
| 137 | 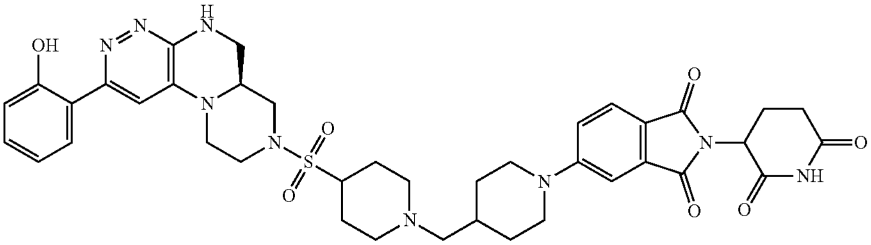 2-(2,6-dioxopiperidin-3-yl)-5-(4-((4-(((S)-2-(2-hydroxyphenyl)-5,6,6a,7,9,10-hexahydro-8H-pyrazino[1′,2′:4,5]pyrazino[2,3-c]pyridazin-8-yl)sulfonyl)piperidin-1-yl)methyl)piperidin-1-yl)isoindoline-1,3-dione | 784.3 | 784.2 |
| 142 | 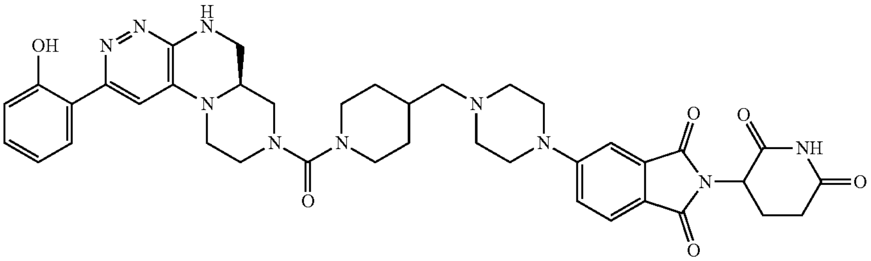 2-(2,6-dioxopiperidin-3-yl)-5-(4-((1-((S)-2-(2-hydroxyphenyl)-6,6a,7,8,9,10-hexahydro-5H-pyrazino[1′,2′:4,5]pyrazino[2,3-c]pyridazine-8-carbonyl)piperidin-4-yl)methyl)piperazin-1-yl)isoindoline-1,3-dione<br>$^1$H NMR (400 MHz, DMSO) δ 11.09 (s, 1H), 8.14 (s, 1H), 7.77 (d, J = 8.4 Hz 1H), 7.51-7.45 (m, 2H), 7.44-7.34 (m, 2H), 7.15 (s, 1H), 7.05 (d, J = 8.2 Hz, 1H), 6.99 (td, J = 7.5, 1.1 Hz, 1H), 5.09 (dd, J = 12.9, 5.4 Hz, 1H), 4.29-4.04 (m, 3H), 3.72-3.60 (m, 9H), 3.28-2.98 (m, 9H), 2.95-2.73 (m, 5H), 2.69-2.54 (m, 2H), 2.03 (d, J = 13.2 Hz, 2H), 1.76 (d, J = 12.4 Hz, 2H), 1.19 (s, 2H). | 749.3 | 749.2 |
| 143 | 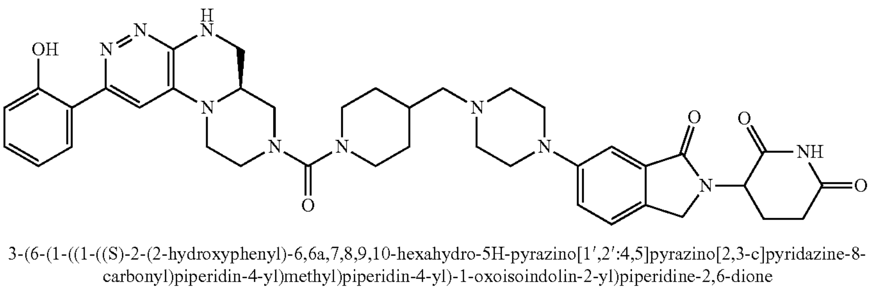 [SMILES: O=C1CCC(N2Cc3ccc(N4CCN(CC5CCN(C(=O)N6CCN7c8cc(-c9ccccc9O)nnc8NC[C@H]7C6)CC5)CC4)cc3C2=O)C(=O)N1] 3-(6-(1-((1-((S)-2-(2-hydroxyphenyl)-6,6a,7,8,9,10-hexahydro-5H-pyrazino[1′,2′:4,5]pyrazino[2,3-c]pyridazine-8-carbonyl)piperidin-4-yl)methyl)piperidin-4-yl)-1-oxoisoindolin-2-yl)piperidine-2,6-dione | 734.4 | 734.2 |

Examples 128, 132-137 and 142-146

TABLE 19-continued

| Ex. | Structure/Name | Calcd. (M + H)+ m/z | Found (M + H)+ m/z |
|---|---|---|---|
| | Examples 128, 132-137 and 142-146 | | |
| 144 | 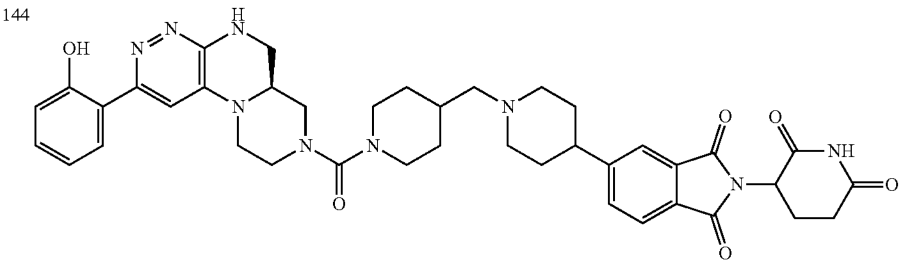 2-(2,6-dioxopiperidin-3-yl)-5-(1-((1-((S)-2-(2-hydroxyphenyl)-6,6a,7,8,9,10-hexahydro-5H-pyrazino[1′,2′:4,5]pyrazino[2,3-c]pyridazine-8-carbonyl)piperidin-4-yl)methyl)piperidin-4-yl)isoindoline-1,3-dione | 748.4 | 748.2 |
| 145 | 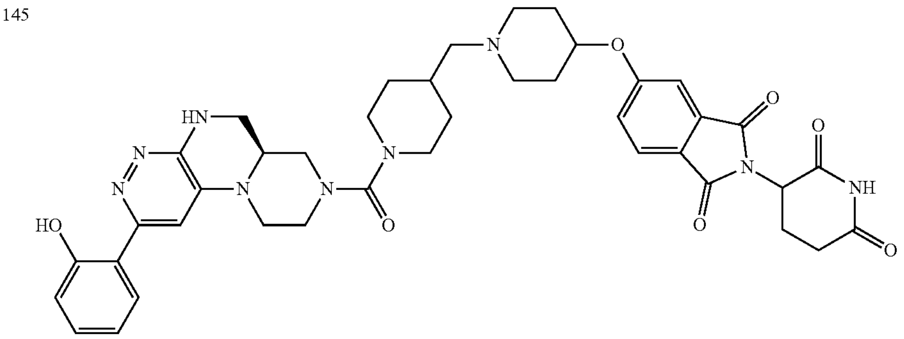 2-(2,6-dioxopiperidin-3-yl)-5-((1-((1-((S)-2-(2-hydroxyphenyl)-6,6a,7,8,9,10-hexahydro-5H-pyrazino[1′,2′:4,5]pyrazino[2,3-c]pyridazine-8-carbonyl)piperidin-4-yl)methyl)piperidin-4-yl)oxy)isoindoline-1,3-dione | 764.3 | 764.2 |
| 146 | 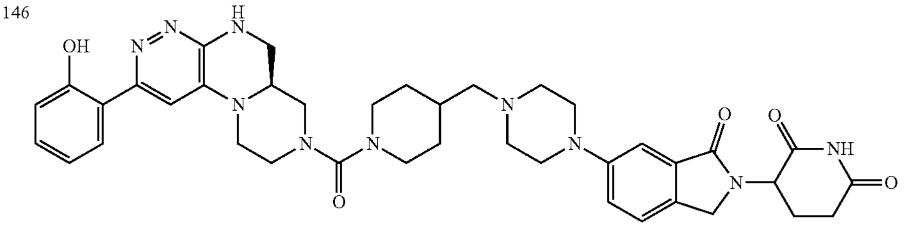 3-(6-(4-((1-((S)-2-(2-hydroxyphenyl)-6,6a,7,8,9,10-hexahydro-5H-pyrazino[1′,2′:4,5]pyrazino[2,3-c]pyridazine-8-carbonyl)piperidin-4-yl)methyl)piperazin-1-yl)-1-oxoisoindolin-2-yl)piperidine-2,6-dione | 735.4 | 735.2 |

$^1$H NMR (400 MHz, DMSO) δ 10.97 (s, 1H), 8.17 (s, 1H), 7.54-7.44 (m, 2H), 7.41 (ddd, J = 8.8, 7.3, 1.7 Hz, 1H), 7.36-7.25 (m, 2H), 7.15 (s, 1H), 7.08-6.95 (m, 2H), 5.10 (dd, J = 13.2, 5.1 Hz, 1H), 4.37 (d, J = 16.9 Hz, 1H), 4.24 (d, J = 16.9 Hz, 2H), 4.12 (d, J = 13.0 Hz, 1H), 3.93 (d, J = 11.9 Hz, 2H), 3.74-3.55 (m, 8H), 3.29-2.98 (m, 9H), 2.98-2.74 (m, 4H), 2.70-2.53 (m, 1H), 2.45-2.30 (m, 1H), 2.07 (s, 2H), 1.76 (d, J = 12.4 Hz, 2H), 1.27-1.10 (m, 2H).

Example 160: 2-(2,6-dioxopiperidin-3-yl)-5-[4-[1-[4-[[(10S)-4-(2-hydroxyphenyl)-1,5,6,8,12-pentazatricyclo[8.4.0.02,7]tetradeca-2(7),3,5-trien-12-yl]methyl]piperidin-1-yl]ethyl]piperidin-1-yl]isoindole-1,3-dione

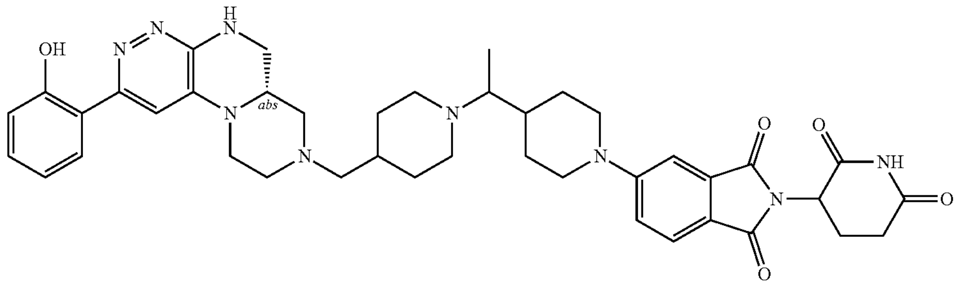

Ex.160

Step 1: 1-[1-[2-(2,6-dioxopiperidin-3-yl)-1,3-dioxoisoindol-5-yl]piperidin-4-yl]ethyl 4-methylbenzenesulfonate

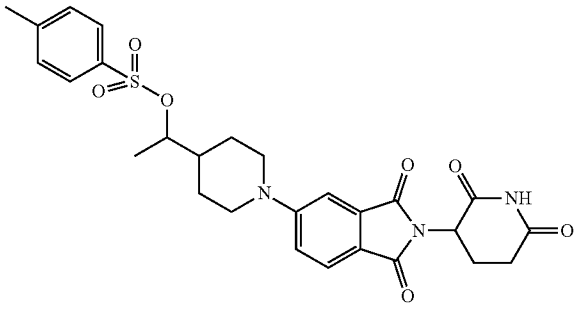 [SMILES: Cc1ccc(S(=O)(=O)OC(C)C2CCN(c3ccc4c(c3)C(=O)N(C3CCC(=O)NC3=O)C4=O)CC2)cc1]

To a mixture of 2-(2,6-dioxopiperidin-3-yl)-5-[4-(1-hydroxyethyl)piperidin-1-yl]isoindole-1,3-dione (210 mg, 0.54 mmol) in pyridine (2.0 mL, 24.73 mmol) was added tosyl chloride (156 mg, 0.82 mmol). The mixture was stirred at rt for 1 h. Additional TsCl was added every 2 h until the starting material was mostly consumed. The mixture was diluted with DCM, washed with water, concentrated and purified on silica gel column (0-100% EA/DCM) to give 1-[1-[2-(2,6-dioxopiperidin-3-yl)-1,3-dioxoisoindol-5-yl]piperidin-4-yl]ethyl 4-methylbenzenesulfonate (165 mg, 0.30578 mmol, 56.12% yield). LCMS m/z calcd for $C_{27}H_{30}N_3O_7S$ $[M+H]^+$: 540.2; found: 540.2.

Step 2: 2-(2,6-dioxopiperidin-3-yl)-5-[4-[1-[4-[[(10S)-4-(2-hydroxyphenyl)-1,5,6,8,12-pentazatricyclo[8.4.0.02,7]tetradeca-2(7),3,5-trien-12-yl]methyl]piperidin-1-yl]ethyl]piperidin-1-yl]isoindole-1,3-dione A mixture of 1-[1-[2-(2,6-dioxopiperidin-3-yl)-1,3-dioxoisoindol-5-yl]piperidin-4-yl]ethyl 4-methylbenzenesulfonate (143 mg, 0.27 mmol), 2-[(10S)-12-(piperidin-4-ylmethyl)-1,5,6,8,12-pentazatricyclo[8.4.0.02,7]tetradeca-2(7),3,5-trien-4-yl]phenol; trihydrochloride (65 mg, 0.13 mmol), Sodium iodide (199 mg, 1.33 mmol) and N,N-diisopropylethylamine (0.14 mL, 0.80 mmol) in DMF (3 mL) was stirred at 130° C. for 1 h. The mixture was purified on prep-LCMS (pH 2, CSHC18) to give 2-(2,6-dioxopiperidin-3-yl)-5-[4-[1-[4-[[(10S)-4-(2-hydroxyphenyl)-1,5,6,8,12-pentazatricyclo[8.4.0.02,7]tetradeca-2(7),3,5-trien-12-yl]methyl]piperidin-1-yl]ethyl]piperidin-1-yl]isoindole-1,3-dione (10 mg, 0.013 mmol, 10.1% yield). LCMS m/z calcd for $C_{41}H_{50}N_9O_5[M+H]^+$: 748.4; found: 748.2.

Examples 181, 182, 185, 186, 188, 191-196, 199-202, 206 and 276-281

Examples in Table 20 were prepared using the procedure described in the synthesis of Example 160 with appropriate intermediates.

TABLE 20

| Ex. | Structure/Name | Calcd. (M + H)+ m/z | Found (M + H)+ m/z |
|---|---|---|---|
| | Examples 181, 182, 185, 186, 188, 191-196, 199-202, 206 and 276-281 | | |
| 181 | 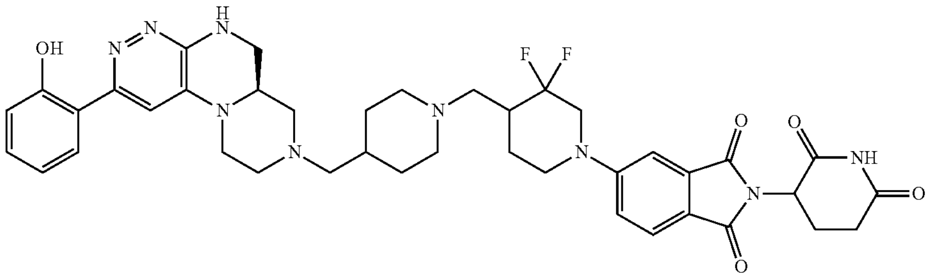 5-[3,3-difluoro-4-[[4-[[(10S)-4-(2-hydroxyphenyl)-1,5,6,8,12-pentazatricyclo[8.4.0.02,7]tetradeca-2(7),3,5-trien-12-yl]methyl]piperidin-1-yl]methyl]piperidin-1-yl]-2-(2,6-dioxopiperidin-3-yl)isoindole-1,3-dione | 770.4 | 770.3 |
| 182 | 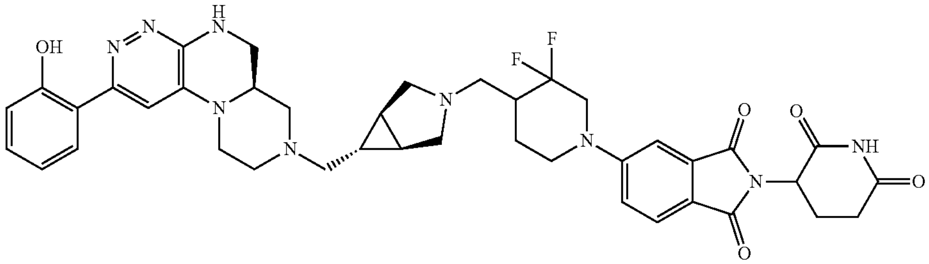 5-[3,3-difluoro-4-[[(1S,5R)-6-[[(10S)-4-(2-hydroxyphenyl)-1,5,6,8,12-pentazatricyclo[8.4.0.02,7]tetradeca-2(7),3,5-trien-12-yl]methyl1-3-azabicyclo[3.1.0]hexan-3-yl]methyl]piperidin-1-yl]-2-(2,6-dioxopiperidin-3-yl)isoindole-1,3-dione | 768.4 | 768.2 |
| 185 | 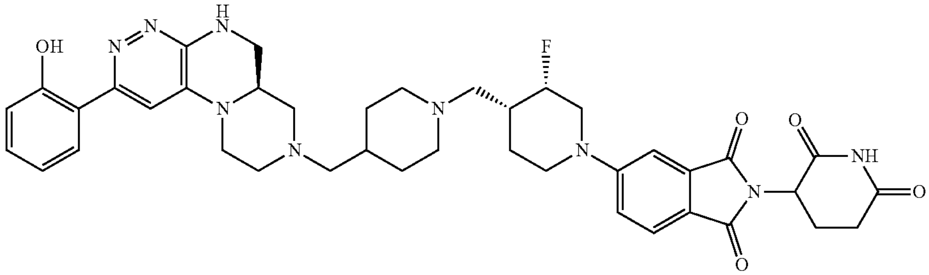 2-(2,6-dioxopiperidin-3-yl)-5-[(3S,4R)-3-fluoro-4-[[4-[[(10S)-4-(2-hydroxyphenyl)-1,5,6,8,12-pentazatricyclo[8.4.0.02,7]tetradeca-2(7),3,5-trien-12-yl]methyl]piperidin-1-yl]methyl]piperidin-1-yl]isoindole-1,3-dione | 752.4 | 752.2 |
| 186 | 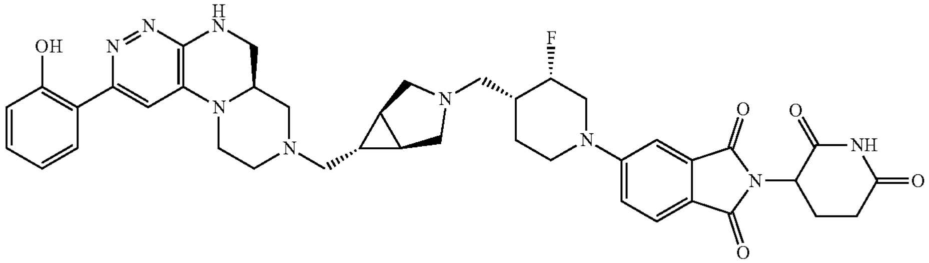 2-(2,6-dioxopiperidin-3-yl)-5-[(3S,4R)-3-fluoro-4-[[(1S,5R)-6-[[(10S)-4-(2-hydroxyphenyl)-1,5,6,8,12-pentazatricyclo[8.4.0.02,7]tetradeca-2(7),3,5-trien-12-yl]methyl]-3-azabicyclo[3.1.0]hexan-3-yl]methyl]piperidin-1-yl]isoindole-1,3-dione | 750.3 | 750.2 |

TABLE 20-continued

| Ex. | Examples 181, 182, 185, 186, 188, 191-196, 199-202, 206 and 276-281 Structure/Name | Calcd. (M + H)+ m/z | Found (M + H)+ m/z |
|---|---|---|---|
| 188 | 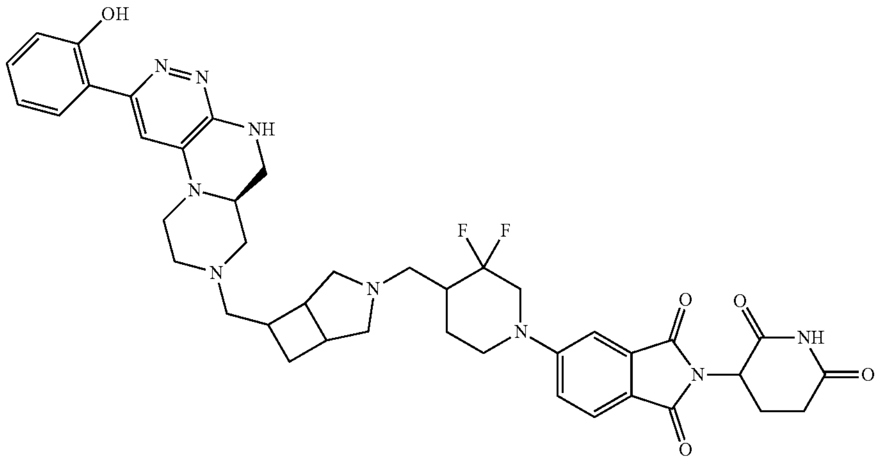 5-[3,3-difluoro-4-[[6-[[(10S)-4-(2-hydroxyphenyl)-1,5,6,8,12-pentazatricyclo[8.4.0.02,7]tetradeca-2(7),3,5-trien-12-yl]methyl]-3-azabicyclo[3.2.0]heptan-3-yl]methyl]piperidin-1-yl]-2-(2,6-dioxopiperidin-3-yl)isoindole-1,3-dione | 782.4 | 782.2 |
| 191 | 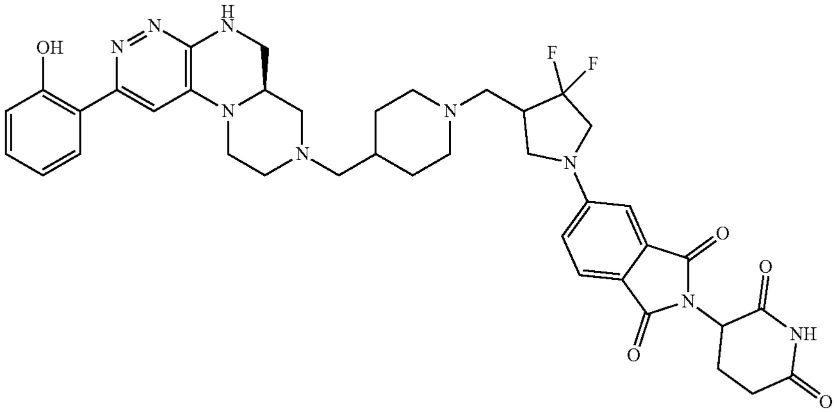 5-[3,3-difluoro-4-[[4-[[(10S)-4-(2-hydroxyphenyl)-1,5,6,8,12-pentazatricyclo[8.4.0.02,7]tetradeca-2(7),3,5-trien-12-yl]methyl]piperidin-1-yl]methyl]pyrrolidin-1-yl]-2-(2,6-dioxopiperidin-3-yl)isoindole-1,3-dione | 756.3 | 756.2 |
| 192 | 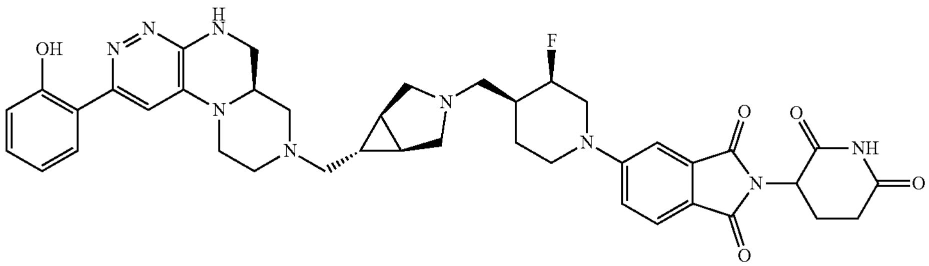 2-(2,6-dioxopiperidin-3-yl)-5-[(3R,4S)-3-fluoro-4-[[(1S,5R)-6-[[(10S)-4-(2-hydroxyphenyl)-1,5,6,8,12-pentazatricyclo[8.4.0.02,7]tetradeca-2(7),3,5-trien-12-yl]methyl]-3-azabicyclo[3.1.0]hexan-3-yl]methyl]piperidin-1-yl]isoindole-1,3-dione | 750.3 | 750.2 |

TABLE 20-continued

| Ex. | Structure/Name | Calcd. (M + H)+ m/z | Found (M + H)+ m/z |
|---|---|---|---|
| | Examples 181, 182, 185, 186, 188, 191-196, 199-202, 206 and 276-281 | | |
| 193 | 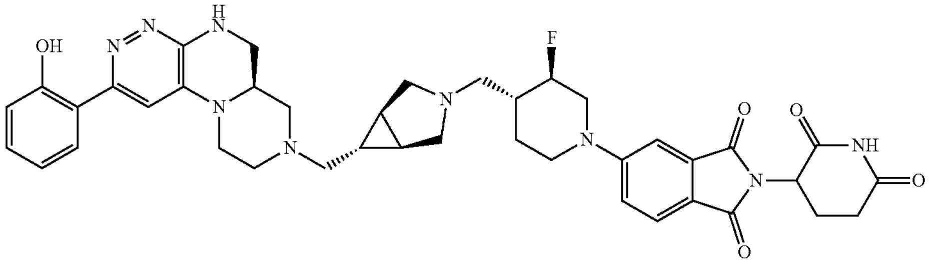 2-(2,6-dioxopiperidin-3-yl)-5-[(3R,4R)-3-fluoro-4-[[(1S,5R)-6-[[(10S)-4-(2-hydroxyphenyl)-1,5,6,8,12-pentazatricyclo[8.4.0.02,7]tetradeca-2(7),3,5-trien-12-yl]methyl]-3-azabicyclo[3.1.0]hexan-3-yl]methyl]piperidin-1-yl]isoindole-1,3-dione | 750.3 | 750.2 |
| 194 | 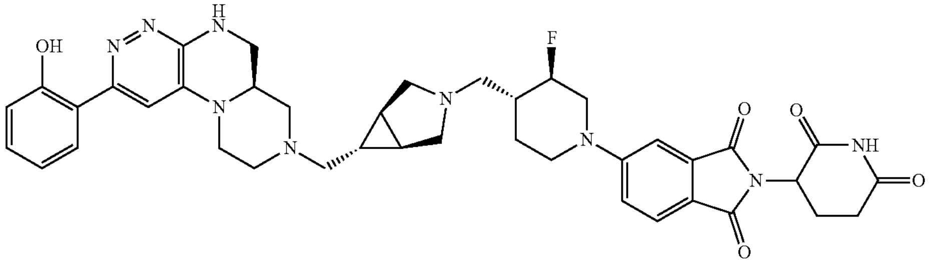 2-(2,6-dioxopiperidin-3-yl)-5-[(3R,4R)-3-fluoro-4-[[(1S,5R)-6-[[(10S)-4-(2-hydroxyphenyl)-1,5,6,8,12-pentazatricyclo[8.4.0.02,7]tetradeca-2(7),3,5-trien-12-yl]methyl]-3-azabicyclo[3.1.0]hexan-3-yl]methyl]piperidin-1-yl]isoindole-1,3-dione<br>$^1$H NMR (400 MHz, DMSO) δ 11.07 (s, 1H), 8.17 (s, 1H), 7.70 (d, J = 8.4 Hz, 1H), 7.52 (d, J = 5.7 Hz, 1H), 7.40 (t, J = 8.0 Hz, 1H), 7.29 (s, 1H), 7.04 (d, J = 8.2 Hz, 1H), 7.02-6.95 (m, 2H), 6.85 (dd, J = 8.8, 2.1 Hz, 1H), 5.36 (d, J = 53.9 Hz, 1H), 5.06 (dd, J = 12.8, 5.4 Hz, 1H), 4.38 (br, 1H), 3.85-3.73 (m, 5H), 3.71-3.57 (m, 4H), 3.52-3.38 (m, 5H) 3.38-3.21 (m, 5H), 3.16 (t, J = 10.3 Hz, 2H), 2.99-2.80 (m, 2H), 2.65-2.52 (m, 1H), 2.05-1.92 (m, 2H), 1.87 (s, 2H), 1.34 (s, 1H), 3.52-3.38 (m, 5H). | 750.3 | 750.2 |
| 195 | 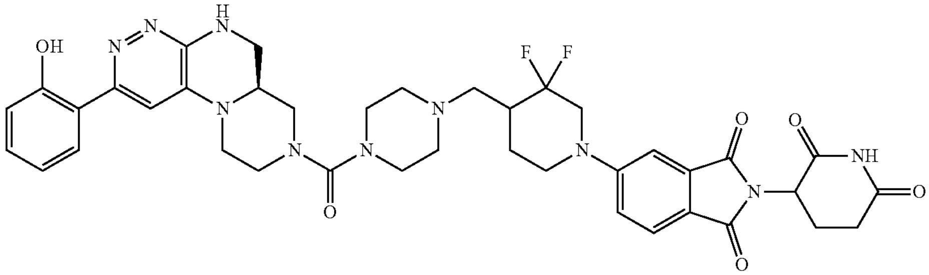 5-[3,3-difluoro-4-[[4-[(10S)-4-(2-hydroxyphenyl)-1,5,6,8,12-pentazatricyclo[8.4.0.02,7]tetradeca-2(7),3,5-triene-12-carbonyl]piperazin-1-yl]methyl]piperidin-1-yl]-2-(2,6-dioxopiperidin-3-yl)isoindole-1,3-dione | 785.3 | 785.2 |
| 196 | 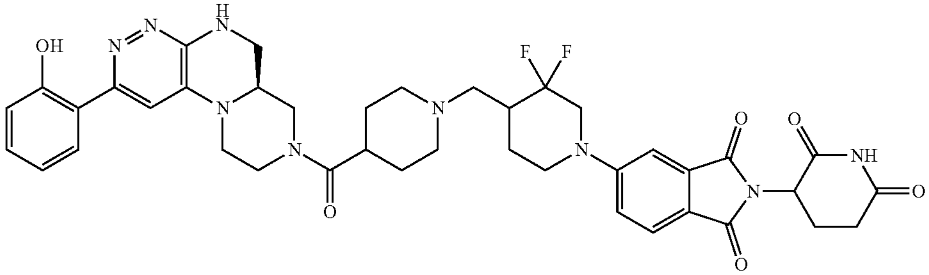 5-[3,3-difluoro-4-[[4-[(10S)-4-(2-hydroxyphenyl)-1,5,6,8,12-pentazatricyclo[8.4.0.02,7]tetradeca-2(7),3,5-triene-12-carbonyl]piperidin-1-yl]methyl]piperidin-1-yl]-2-[2,6-dioxopiperidin-3-yl)isoindole-1,3-dione | 784.3 | 784.2 |

TABLE 20-continued

| Ex. | Structure/Name | Calcd. (M + H)+ m/z | Found (M + H)+ m/z |
|---|---|---|---|
| | Examples 181, 182, 185, 186, 188, 191-196, 199-202, 206 and 276-281 | | |
| 199 | 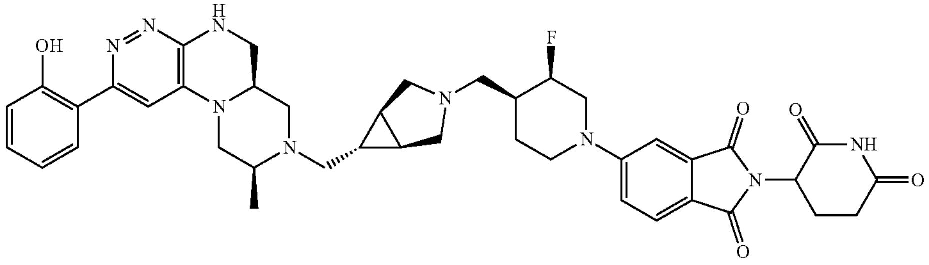 2-(2,6-dioxopiperidin-3-yl)-5-[(3R,4R)-3-fluoro-4-[[(1S,5R)-6-[[(10S,13S)-4-(2-hydroxyphenyl)-13-methyl-1,5,6,8,12-pentazatricyclo[8.4.0.02,7]tetradeca-2(7),3,5-trien-12-yl]methyl]-3-azabicyclo[3.1.0]hexan-3-yl]methyl]piperidin-1-yl]isoindole-1,3-dione | 764.4 | 764.2 |
| 200 | 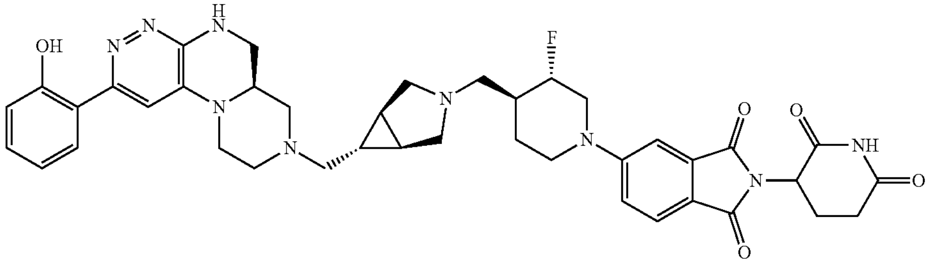 2-(2,6-dioxopiperidin-3-yl)-5-[(3S,4S)-3-fluoro-4-[[(1S,5R)-6-[[(10S)-4-(2-hydroxyphenyl)-1,5,6,8,12-pentazatricyclo[8.4.0.02,7]tetradeca-2(7),3,5-trien-12-yl]methyl]-3-azabicyclo[3.1.0]hexan-3-yl]methyl]piperidin-1-yl]isoindole-1,3-dione | 750.3 | 750.2 |
| 201 | 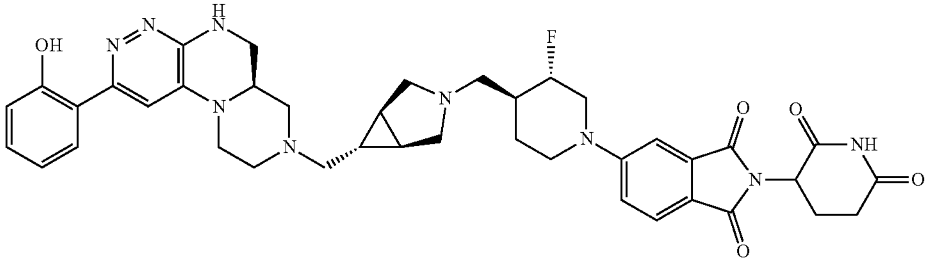 2-(2,6-dioxopiperidin-3-yl)-5-[(3S,4S)-3-fluoro-4-[[(1S,5R)-6-[[(10S)-4-(2-hydroxyphenyl)-1,5,6,8,12-pentazatricyclo[8.4.0.02,7]tetradeca-2(7),3,5-trien-12-yl]methyl]-3-azabicyclo[3.1.0]hexan-3-yl]methyl]piperidin-1-yl]isoindole-1,3-dione | 750.3 | 750.3 |
| 202 | 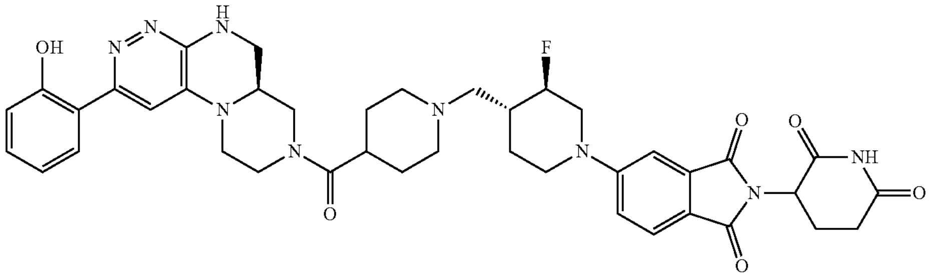 2-(2,6-dioxopiperidin-3-yl)-5-[(3R,4R)-3-fluoro-4-[[4-[(10S)-4-(2-hydroxyphenyl)-1,5,6,8,12-pentazatricyclo[8.4.0.02,7]tetradeca-2(7),3,5-triene-12-carbonyl]piperidin-1-yl]methyl]piperidin-1-yl]isoindole-1,3-dione | 766.3 | 766.2 |

TABLE 20-continued

| Ex. | Structure/Name | Calcd. (M + H)+ m/z | Found (M + H)+ m/z |
|---|---|---|---|
| | Examples 181, 182, 185, 186, 188, 191-196, 199-202, 206 and 276-281 | | |
| 206 | 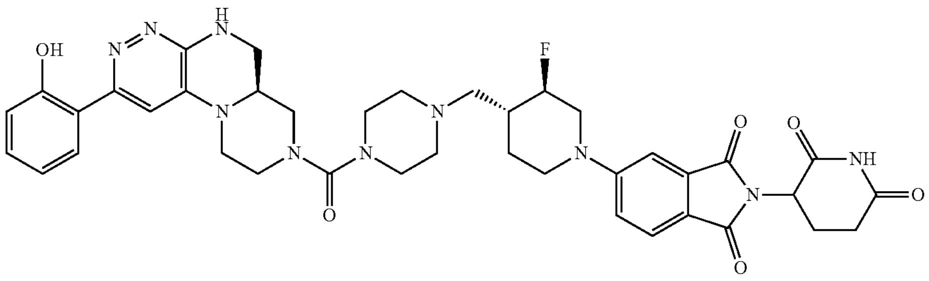 2-(2,6-dioxopiperidin-3-yl)-5-[(3R,4R)-3-fluoro-4-[[4-[(10S)-4-(2-hydroxyphenyl)-1,5,6,8,12-pentazatricyclo[8.4.0.02,7]tetradeca-2(7),3,5-triene-12-carbonyl]piperazin-1-yl]methyl]piperidin-1-yl]isoindole-1,3-dione | 767.3 | 767.2 |
| 276 | 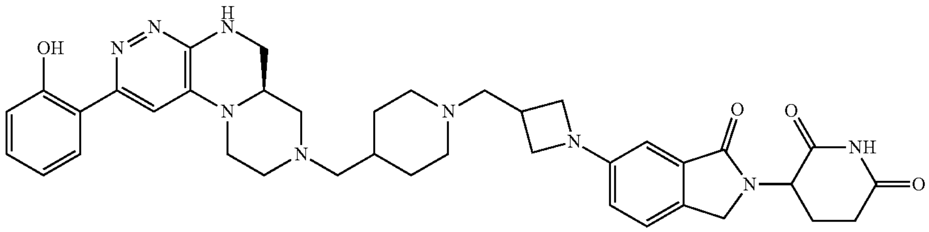 3-(6-(3-((4-(((S)-2-(2-hydroxyphenyl)-5,6,6a,7,9,10-hexahydro-8H-pyrazino[1′,2′:[4,5]pyrazino[2,3-c]pyridazin-8-yl)methyl)piperidin-1-yl)methyl)azetidin-1-yl)-1-oxoisoindolin-2-yl)piperidine-2,6-dione | 692.4 | 692.2 |
| 277 | 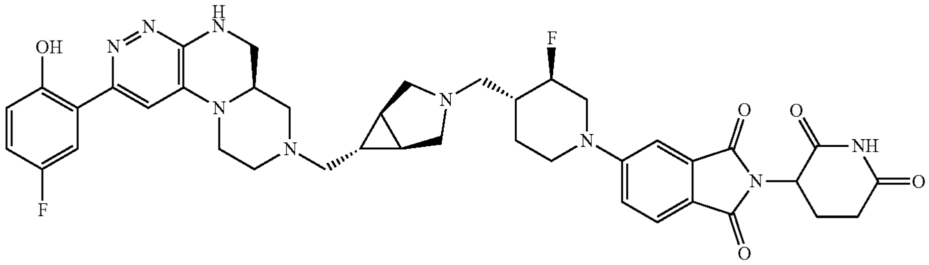 2-(2,6-dioxopiperidin-3-yl)-5-((3R,4R)-3-fluoro-4-(((1R,5S,6R)-6-(((S)-2-(5-fluoro-2-hydroxyphenyl)-5,6,6a,7,9,10-hexahydro-8H-pyrazino[1′,2′:4,5]pyrazino[2,3-c]pyridazin-8-yl)methyl)-3-azabicyclo[3.1.0]hexan-3-yl)methyl)piperidin-1-yl)isoindoline-1,3-dione | 768.3 | 768.3 |
| 278 | 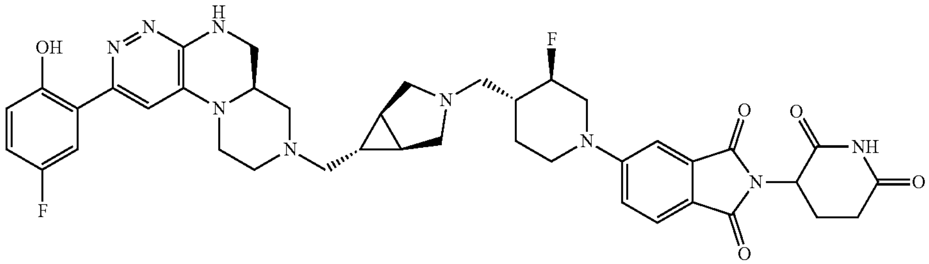 2-(2,6-dioxopiperidin-3-yl)-5-((3R,4R)-3-fluoro-4-(((1R,5S,6R)-6-(((S)-2-(5-fluoro-2-hydroxyphenyl)-5,6,6a,7,9,10-hexahydro-8H-pyrazino[1′,2′: 4,5]pyrazino[2,3-c]pyridazin-8-yl)methyl)-3-azabicyclo[3.1.0]hexan-3-yl)methyl)piperidin-1-yl)isoindoline-1,3-dione | 768.3 | 768.2 |

TABLE 20-continued

| Ex. | Structure/Name | Calcd. (M + H)+ m/z | Found (M + H)+ m/z |
|---|---|---|---|
| 279 | 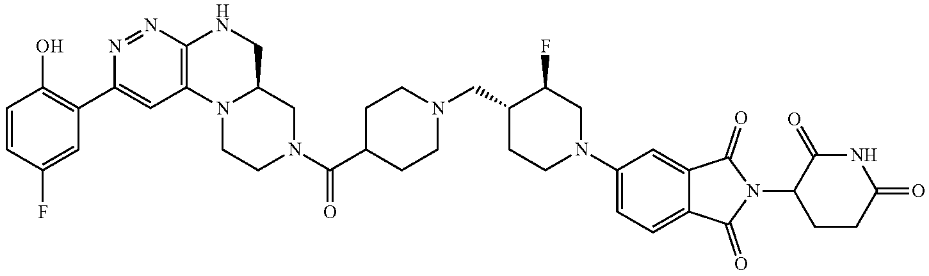 2-(2,6-dioxopiperidin-3-yl)-5-[(3R,4R)-3-fluoro-4-((4-((S)-2-(5-fluoro-2-hydroxyphenyl)-6,6a,7,8,9,10-hexahydro-5H-pyrazino[1′,2′:4,5]pyrazino[2,3-c]pyridazine-8-carbonyl)piperidin-1-yl)methyl)piperidin-1-yl)isoindoline-1,3-dione | 784.3 | 784.2 |
| 280 | 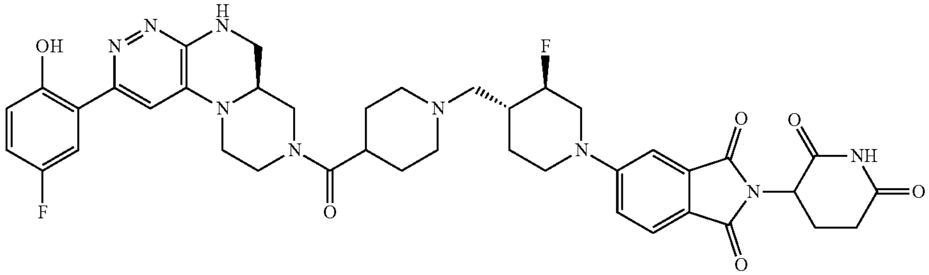 2-(2,6-dioxopiperidin-3-yl)-5-((3R,4R)-3-fluoro-4-((4-((S)-2-(5-fluoro-2-hydroxyphenyl)-6,6a,7,8,9,10-hexahydro-5H-pyrazino[1′,2′:4,5]pyrazino[2,3-c]pyridazine-8-carbonyl)piperidin-1-yl)methyl)piperidin-1-yl)isoindoline-1,3-dione | 784.3 | 784.4 |
| 281 | 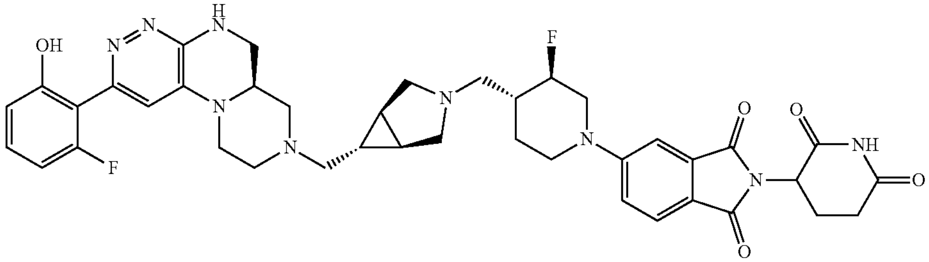 2-(2,6-dioxopiperidin-3-yl)-5-((3R,4R)-3-fluoro-4-(((1R,5S,6R)-6-(((S)-2-(2-fluoro-6-hydroxyphenyl)-5,6,6a,7,9,10-hexahydro-8H-pyrazino[1′,2′:4,5]pyrazino[2,3-c]pyridazin-8-yl)methyl)-3-azabicyclo[3.1.0]hexan-3-yl)methyl)piperidin-1-yl)isoindoline-1,3-dione | 768.3 | 768.2 |

Examples 181, 182, 185, 186, 188, 191-196, 199-202, 206 and 276-281

Example 164: 2-(2,6-dioxopiperidin-3-yl)-5-fluoro-6-[4-[[4-[[(10S)-4-(2-hydroxyphenyl)-1,5,6,8,12-pentazatricyclo[8.4.0.02,7]tetradeca-2,4,6-trien-12-yl]methyl]piperidin-1-yl]methyl]piperidin-1-yl]isoindole-1,3-dione Ex.164

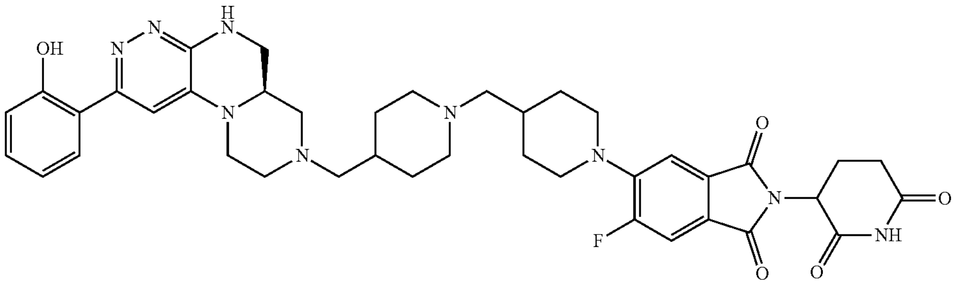

Step 1: 2-(2,6-dioxopiperidin-3-yl)-5-fluoro-6-[4-(hydroxymethyl)piperidin-1-yl]isoindole-1,3-dione

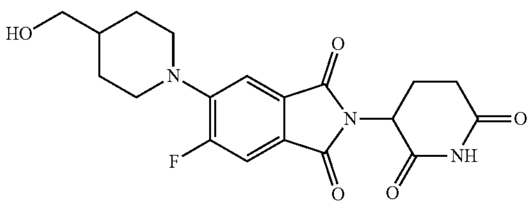 [SMILES: O=C1CCC(N2C(=O)c3cc(F)c(N4CCC(CO)CC4)cc3C2=O)C(=O)N1]

A mixture of 4-piperidinemethanol (70 mg, 0.61 mmol), 2-(2,6-dioxopiperidin-3-yl)-5,6-difluoroisoindole-1,3-dione (214 mg, 0.73 mmol) and N,N-diisopropylethylamine (0.21 mL, 1.22 mmol) in NMP (1 mL) was heated at 110° C. for 1 h. The mixture was diluted with DCM, washed with water, concentrated and purified on silica gel column (0-10% MeOH/DCM) to give 2-(2,6-dioxopiperidin-3-yl)-5-fluoro-6-[4-(hydroxymethyl)piperidin-1-yl]isoindole-1,3-dione (150 mg, 0.39 mmol, 63.4% yield). LCMS m/z calcd for $C_{19}H_{21}FN_3O_5[M+H]^+$: 390.1; found: 390.2.

Step 2: 1-[2-(2,6-dioxopiperidin-3-yl)-6-fluoro-1,3-dioxoisoindol-5-yl]piperidine-4-carbaldehyde

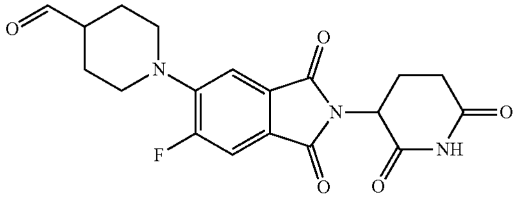 [SMILES: O=CC1CCN(c2cc3c(cc2F)C(=O)N(C2CCC(=O)NC2=O)C3=O)CC1]

2-(2,6-dioxopiperidin-3-yl)-5-fluoro-6-[4-(hydroxymethyl)piperidin-1-yl]isoindole-1,3-dione (150 mg, 0.39 mmol) was treated with Dess-Martin Periodinane (327 mg, 0.77 mmol) in DCM (5 mL) at rt for 2 h. The mixture was washed with water and purified on silica gel column (0-10% MeOH/DCM) to give 1-[2-(2,6-dioxopiperidin-3-yl)-6-fluoro-1,3-dioxoisoindol-5-yl]piperidine-4-carbaldehyde (110 mg, 0.28 mmol, 73.7% yield). LCMS m/z calcd for $C_{19}H_{19}FN_3O_5[M+H]+$: 388.1; found: 388.2.

Step 3: 2-(2,6-dioxopiperidin-3-yl)-5-fluoro-6-[4-[[4-[[(10S)-4-(2-hydroxyphenyl)-1,5,6,8,12-pentazatricyclo[8.4.0.02,7]tetradeca-2,4,6-trien-12-yl]methyl]piperidin-1-yl]methyl]piperidin-1-yl]isoindole-1,3-dione A mixture of 1-[2-(2,6-dioxopiperidin-3-yl)-1,3-dioxoisoindol-5-yl]piperidine-4-carbaldehyde (28.09 mg, 0.08 mmol), 2-[(10S)-12-[(3-methylpiperidin-4-yl)methyl]-1,5,6,8,12-pentazatricyclo[8.4.0.02,7]tetradeca-2,4,6-trien-4-yl]phenol (15.0 mg, 0.04 mmol), N,N-Diisopropylethylamine (0.02 mL, 0.11 mmol) and acetic acid (0.01 mL, 0.15 mmol) was stirred in DMF (1 mL) for 5 min then treated with sodium triacetoxyborohydride (40.3 mg, 0.19 mmol). The mixture was stirred at rt for 1 h and purified via prep-LC-MS (pH 2) to give 2-(2,6-dioxopiperidin-3-yl)-5-[4-[[4-[[(10S)-4-(2-hydroxyphenyl)-1,5,6,8,12-pentazatricyclo [8.4.0.02,7]tetradeca-2,4,6-trien-12-yl]methyl]-3-methylpiperidin-1-yl]methyl]piperidin-1-yl]isoindole-1,3-dione (5.0 mg, 0.066 mmol, 8.3% yield). LCMS m/z calcd for $C_{40}H_{47}FN_9O_5$ $[M+H]^+$: 752.4; found: 752.2.

Examples 161-163, 165-167, 169-180, 183, 184 and 263

Examples in Table 21 were prepared using the procedure described in the synthesis of Example 164 with appropriate intermediates.

TABLE 21

Examples 161-163, 165-167, 169-180, 183, 184 and 263

| Ex. | Structure/Name | Calcd. (M + H)$^+$ m/z | Found (M + H)$^+$ m/z |
|---|---|---|---|
| 161 | 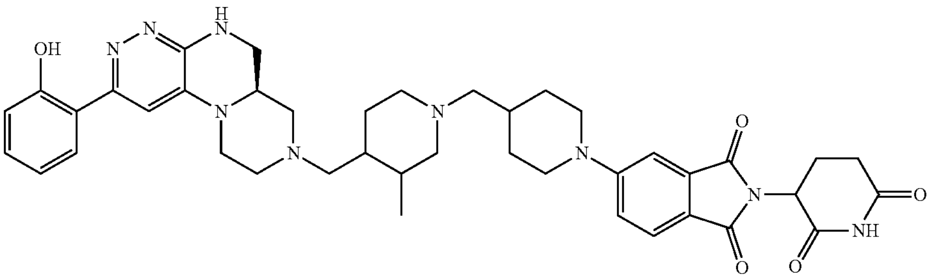 2-(2,6-dioxopiperidin-3-yl)-5-(4-((4-(((S)-2-(2-hydroxyphenyl)-5,6,6a,7,9,10-hexahydro-8H-pyrazino[1′,2′:4,5]pyrazino[2,3-c]pyridazin-8-yl)methyl)-3-methylpiperidin-1-yl)methyl)piperidin-1-yl)isoindoline-1,3-dione | 748.4 | 748.4 |

TABLE 21-continued

| Ex. | Structure/Name | Calcd. (M + H)+ m/z | Found (M + H)+ m/z |
|---|---|---|---|
| | Examples 161-163, 165-167, 169-180, 183, 184 and 263 | | |
| 162 | 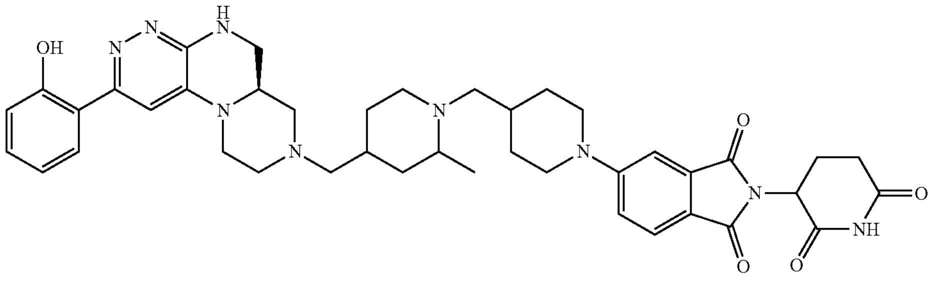 2-(2,6-dioxopiperidin-3-yl)-5-[4-[[4-[[(10S)-4-(2-hydroxyphenyl)-1,5,6,8,12-pentazatricyclo[8.4.0.02,7]tetradeca-2,4,6-trien-12-yl]methyl]-2-methylpiperidin-1-yl]methyl]piperidin-1-yl]isoindole-1,3-dione | 748.4 | 748.4 |
| 163 | 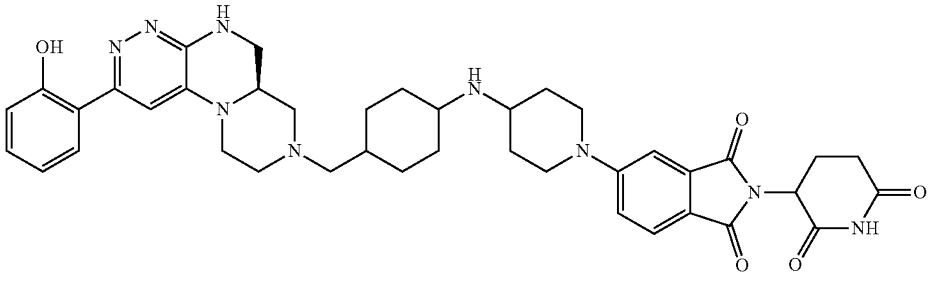 2-(2,6-dioxopiperidin-3-yl)-5-[4-[[4-[[(10S)-4-(2-hydroxyphenyl)-1,5,6,8,12-pentazatricyclo[8.4.0.02,7]tetradeca-2,4,6-trien-12-yl]methyl]cyclohexyl]amino]piperidin-1-yl]isoindole-1,3-dione | 734.4 | 734.3 |
| 165 | 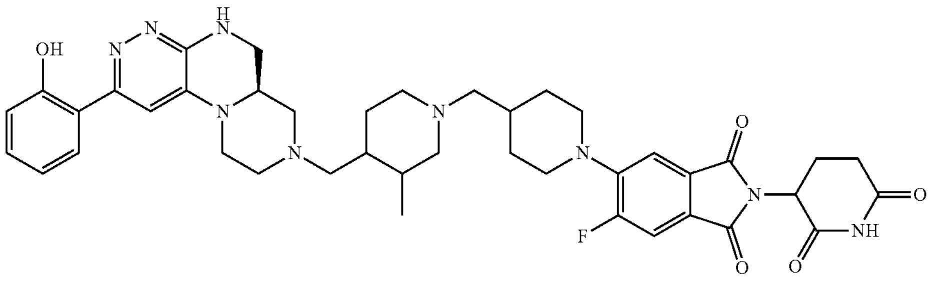 2-(2,6-dioxopiperidin-3-yl)-5-fluoro-6-[4-[[4-([[10S)-4-(2-hydroxyphenyl)-1,5,6,8,12-pentazatricyclo[8.4.0.02,7]tetradeca-2,4,6-trien-12-yl]methyl]-3-methylpiperidin-1-yl]methyl]piperidin-1-yl]isoindole-1,3-dione | 766.4 | 766.4 |
| 166 | 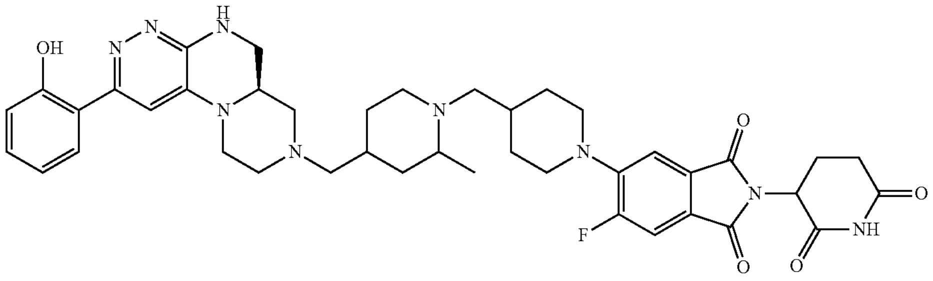 2-(2,6-dioxopiperidin-3-yl)-5-fluoro-6-[4-[[4-[[(10S)-4-(2-hydroxyphenyl)-1,5,6,8,12-pentazatricyclo[8.4.0.02,7]tetradeca-2,4,6-trien-12-yl]methyl]-2-methylpiperidin-1-yl]methyl]piperidin-1-yl]isoindole-1,3-dione | 766.4 | 766.3 |

TABLE 21-continued

Examples 161-163, 165-167, 169-180, 183, 184 and 263

| Ex. | Structure/Name | Calcd. (M + H)+ m/z | Found (M + H)+ m/z |
|---|---|---|---|
| 167 | 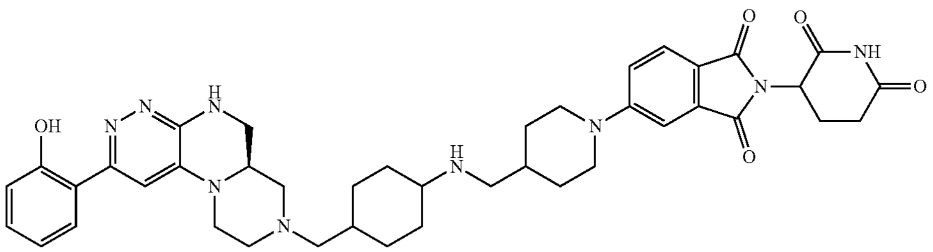 2-(2,6-dioxopiperidin-3-yl)-5-[4-[[[4-[[(10S)-4-(2-hydroxyphenyl)-1,5,6,8,12-pentazatricyclo[8.4.0.02,7]tetradeca-2,4,6-trien-12-yl]methyl]cyclohexyl]amino]methyl]piperidin-1-yl]isoindole-1,3-dione | 748.4 | 748.4 |
| 169 | 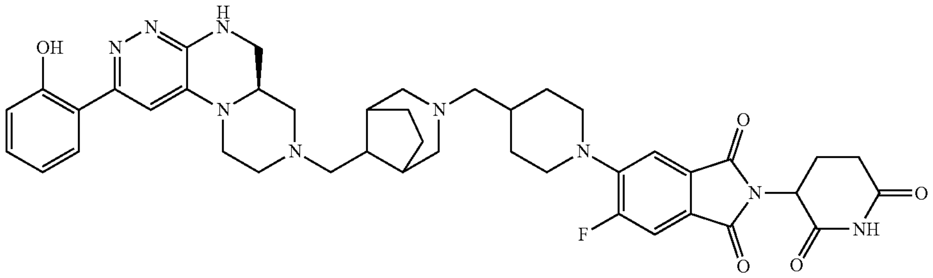 2-(2,6-dioxopiperidin-3-yl)-5-fluoro-6-[4-[[8-[[(10S)-4-(2-hydroxyphenyl)-1,5,6,8,12-pentazatricyclo[8.4.0.02,7]tetradeca-2,4,6-trien-12-yl]methyl]-3-azabicyclo[3.2.1]octan-3-yl]methyl]piperidin-1-yl]isoindole-1,3-dione | 778.4 | 778.2 |
| 170 | 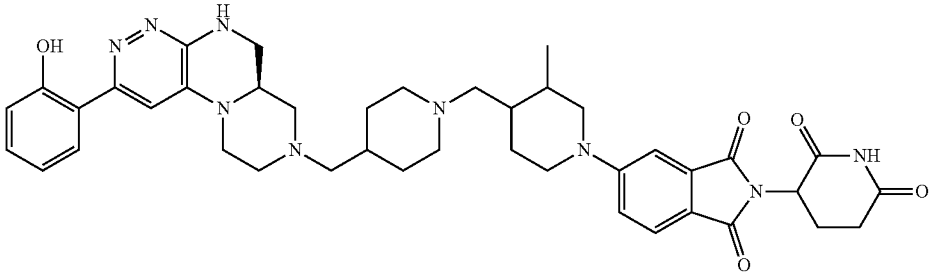 2-(2,6-dioxopiperidin-3-yl)-5-[4-[[4-[[(10S)-4-(2-hydroxyphenyl)-1,5,6,8,12-pentazatricyclo[8.4.0.02,7]tetradeca-2(7),3,5-trien-12-yl]methyl]piperidin-1-yl]methyl]-3-methylpiperidin-1-yl]isoindole-1,3-dione | 748.4 | 748.3 |
| 171 | 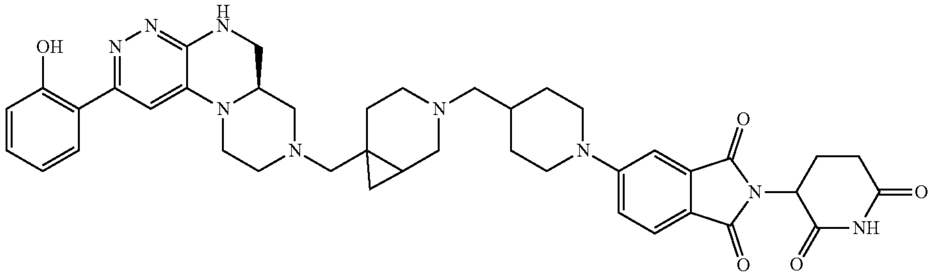 2-(2,6-dioxopiperidin-3-yl)-5-[4-[[6-[[(10S)-4-(2-hydroxyphenyl)-1,5,6,8,12-pentazatricyclo[8.4.0.02,7]tetradeca-2,4,6-trien-12-yl]methyl]-3-azabicyclo[4.1.0]heptan-3-yl]methyl]piperidin-1-yl]isoindole-1,3-dione | 746.4 | 746.2 |

TABLE 21-continued

| Ex. | Structure/Name | Calcd. (M + H)+ m/z | Found (M + H)+ m/z |
|---|---|---|---|
| | Examples 161-163, 165-167, 169-180, 183, 184 and 263 | | |
| 172 | 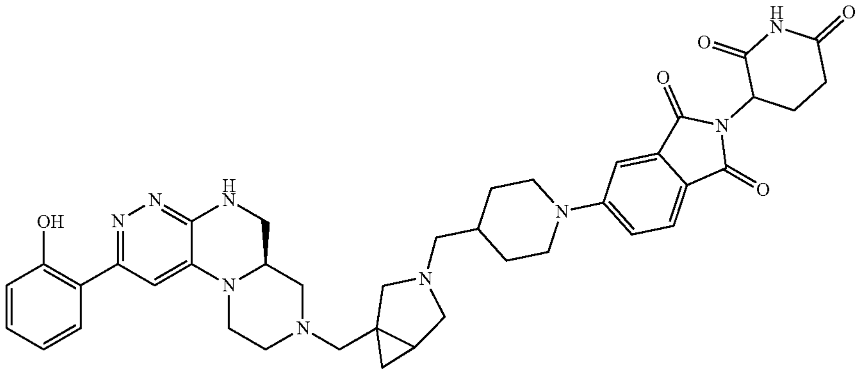 2-(2,6-dioxopiperidin-3-yl)-5-[4-[[1-[[(10S)-4-(2-hydroxyphenyl)-1,5,6,8,12-pentazatricyclo[8.4.0.02,7]tetradeca-2,4,6-trien-12-yl]methyl]-3-azabicyclo[3.1.0]hexan-3-yl]methyl]piperidin-1-yl]isoindole-1,3-dione | 732.4 | 732.2 |
| 173 | 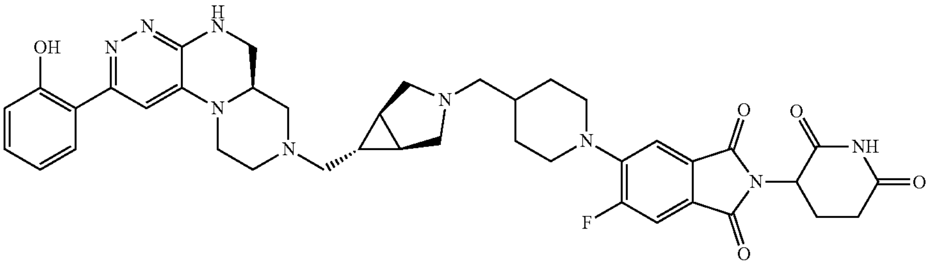 2-(2,6-dioxopiperidin-3-yl)-5-fluoro-6-[4-[[(1S,5R)-6-[[(10S)-4-(2-hydroxyphenyl)-1,5,6,8,12-pentazatricyclo[8.4.0.02,7]tetradeca-2,4,6-trien-12-yl]methyl]-3-azabicyclo[3.1.0]hexan-3-yl]methyl]piperidin-1-yl]isoindole-1,3-dione | 750.3 | 750.2 |
| 174 | 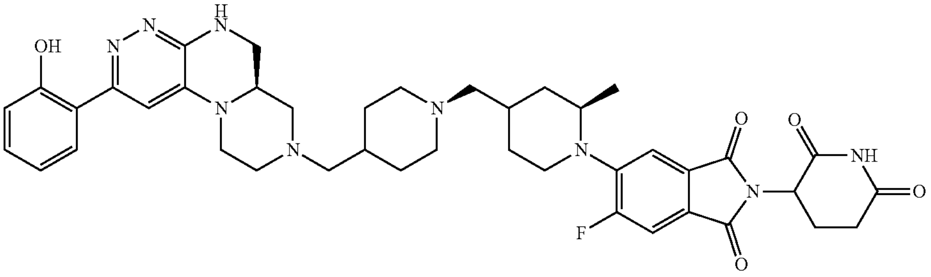 2-(2,6-dioxopiperidin-3-yl)-5-fluoro-6-[(2R,4R)-4-[[4-[[(10S)-4-(2-hydroxyphenyl)-1,5,6,8,12-pentazatricyclo[8.4.0.02,7]tetradeca-2,4,6-trien-12-yl]methyl]piperidin-1-yl]methyl]-2-methylpiperidin-1-yl]isoindole-1,3-dione | 766.4 | 766.2 |
| 175 | 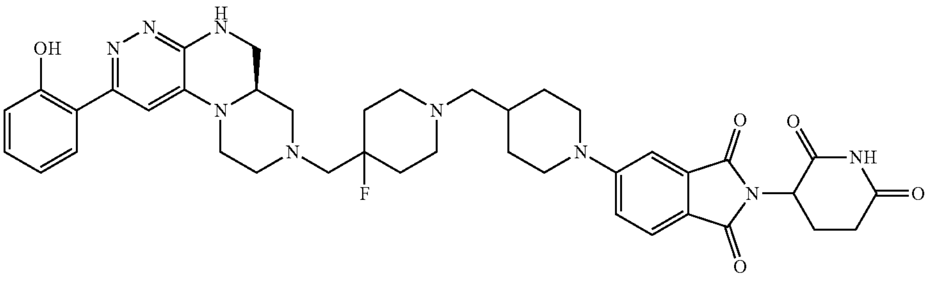 2-(2,6-dioxopiperidin-3-yl)-5-[4-[[4-fluoro-4-[[(10S)-4-(2-hydroxyphenyl)-1,5,6,8,12-pentazatricyclo[8.4.0.02,7]tetradeca-2,4,6-trien-12-yl]methyl]piperidin-1-yl]methyl]piperidin-1-yl]isoindole-1,3-dione | 752.4 | 752.2 |

TABLE 21-continued

| Ex. | Structure/Name | Calcd. (M + H)+ m/z | Found (M + H)+ m/z |
|---|---|---|---|
| | Examples 161-163, 165-167, 169-180, 183, 184 and 263 | | |
| 176 | 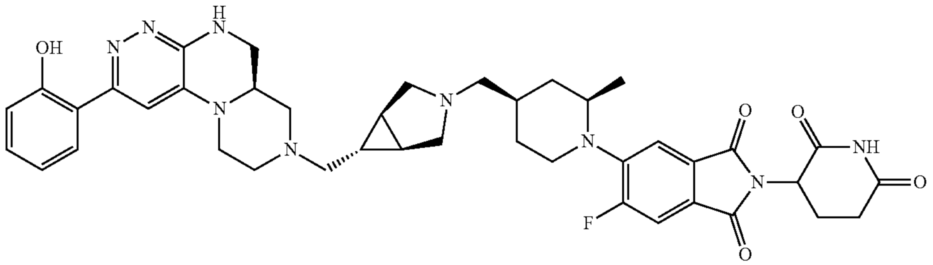 2-(2,6-dioxopiperidin-3-yl)-5-fluoro-6-[(2R,4R)-4-[[(1S,5R)-6-[[(10S)-4-(2-hydroxyphenyl)-1,5,6,8,12-pentazatricyclo[8.4.0.02,7]tetradeca-2,4,6-trien-12-yl]methyl]-3-azabicyclo[3.1.0]hexan-3-yl]methyl]-2-methylpiperidin-1-yl]isoindole-1,3-dione | 764.4 | 764.2 |
| 177 | 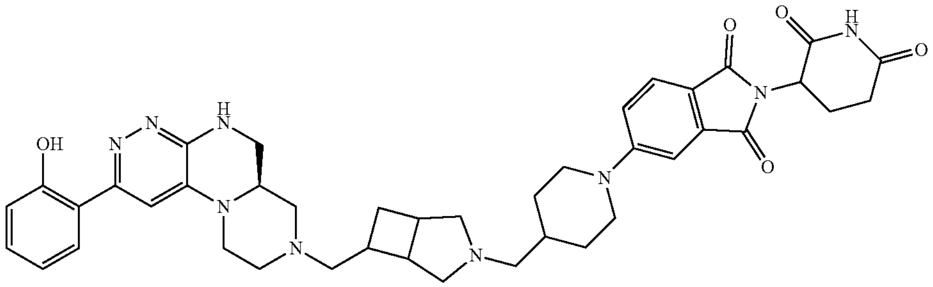 2-(2,6-dioxopiperidin-3-yl)-5-[4-[[6-[[(10S)-4-(2-hydroxyphenyl)-1,5,6,8,12-pentazatricyclo[8.4.0.02,7]tetradeca-2,4,6-trien-12-yl]methyl]-3-azabicyclo[3.2.0]heptan-3-yl]methyl]piperidin-1-yl]isoindole-1,3-dione | 746.4 | 746.2 |
| 178 | 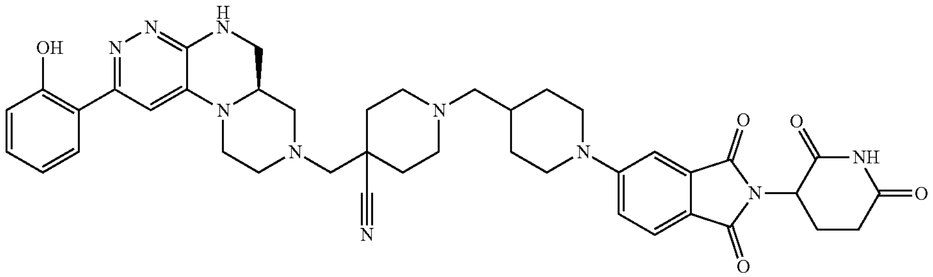 1-[[1-[2-(2,6-dioxopiperidin-3-yl)-1,3-dioxoisoindol-5-yl]piperidin-4-yl]methyl]-4-[[(10S)-4-(2-hydroxyphenyl)-1,5,6,8,12-pentazatricyclo[8.4.0.02,7]tetradeca-2,4,6-trien-12-yl]methyl]piperidine-4-carbonitrile | 759.4 | 759.2 |
| 179 | 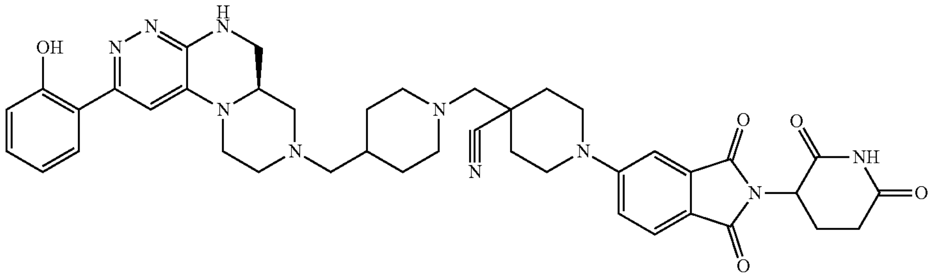 1-[2-(2,6-dioxopiperidin-3-yl)-1,3-dioxoisoindol-5-yl]-4-[[4-[[(10S)-4-(2-hydroxyphenyl)-1,5,6,8,12-pentazatricyclo[8.4.0.02,7]tetradeca-2,4,6-trien-12-yl]methyl]piperidin-1-yl]methyl]piperidine-4-carbonitrile | 759.4 | 759.4 |

TABLE 21-continued

Examples 161-163, 165-167, 169-180, 183, 184 and 263

| Ex. | Structure/Name | Calcd. $(M + H)^+$ m/z | Found $(M + H)^+$ m/z |
|---|---|---|---|
| 180 | 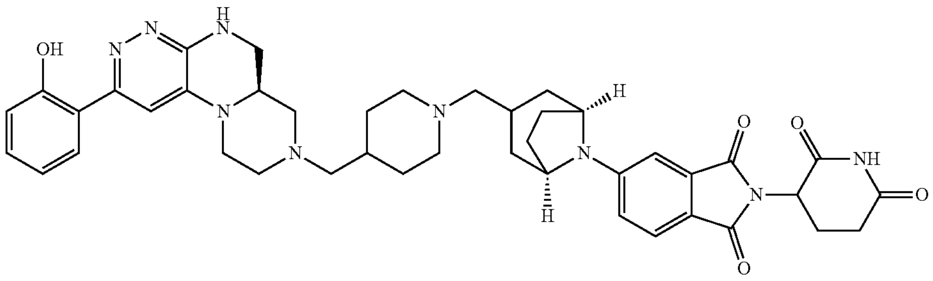 2-(2,6-dioxopiperidin-3-yl)-5-[(1S,5R)-3-[[4-[[(10S)-4-(2-hydroxyphenyl)-1,5,6,8,12-pentazatricyclo[8.4.0.02,7]tetradeca-2,4,6-trien-12-yl]methyl]piperidin-1-yl]methyl]-8-azabicyclo[3.2.1]octan-8-yl]isoindole-1,3-dione | 760.4 | 760.2 |
| 183 | 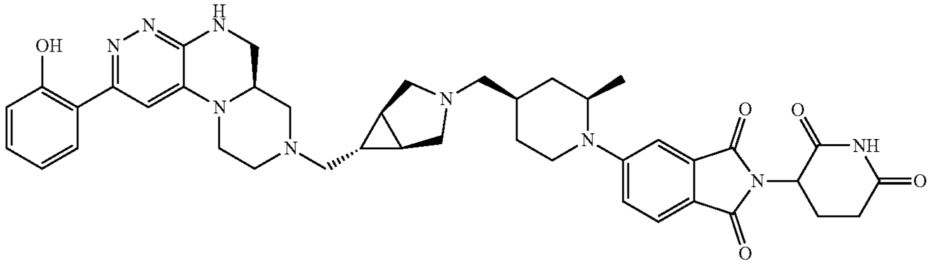 2-(2,6-dioxopiperidin-3-yl)-5-[(2R,4R)-4-[[(1S,5R)-6-[[(10S)-4-(2-hydroxyphenyl)-1,5,6,8,12-pentazatricyclo[8.4.0.02,7]tetradeca-2,4,6-trien-12-yl]methyl]-3-azabicyclo[3.1.0]hexan-3-yl]methyl]-2-methylpiperidin-1-yl]isoindole-1,3-dione | 746.4 | 746.2 |
| 184 | 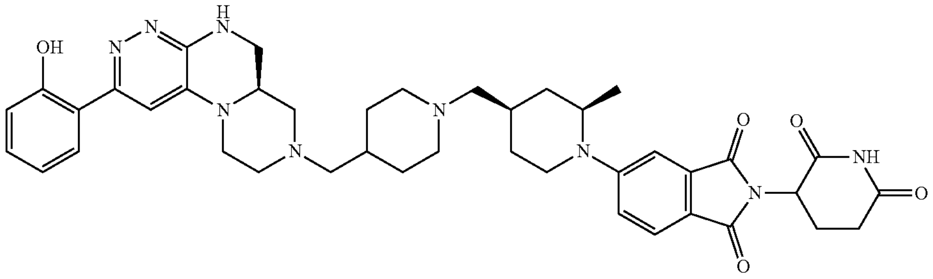 2-(2,6-dioxopiperidin-3-yl)-5-[(2R,4R)-4-[[4-[[(10S)-4-(2-hydroxyphenyl)-1,5,6,8,12-pentazatricyclo[8.4.0.02,7]tetradeca-2,4,6-trien-12-yl]methyl]piperidin-1-yl]methyl]-2-methylpiperidin-1-yl]isoindole-1,3-dione | 748.4 | 748.2 |
| 263 | 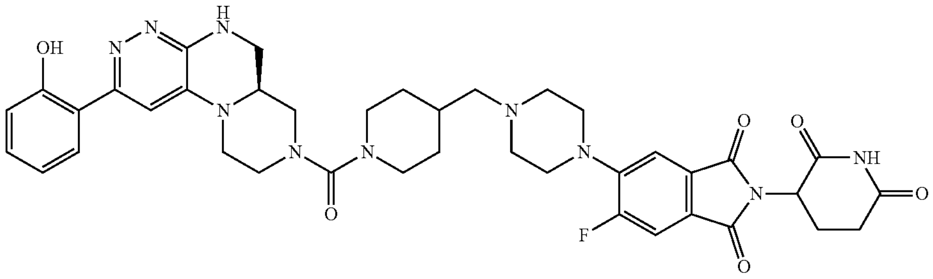 2-(2,6-dioxopiperidin-3-yl)-5-fluoro-6-(4-((1-[(S)-2-(2-hydroxyphenyl)-6,6a,7,8,9,10-hexahydro-5H-pyrazino[1′,2′:4,5]pyrazino[2,3-c]pyridazine-8-carbonyl)piperidin-4-yl)methyl)piperazin-1-yl)isoindoline-1,3-dione | 767.3 | 767.3 |

Example 187: 2-(2,6-dioxopiperidin-3-yl)-5-[[4-[[4-[[(10S)-4-(2-hydroxyphenyl)-1,5,6,8,12-pentazatricyclo[8.4.0.02,7]tetradeca-2,4,6-trien-12-yl]methyl]piperidin-1-yl]methyl]piperidin-1-yl]methyl]isoindole-1,3-dione Ex.187

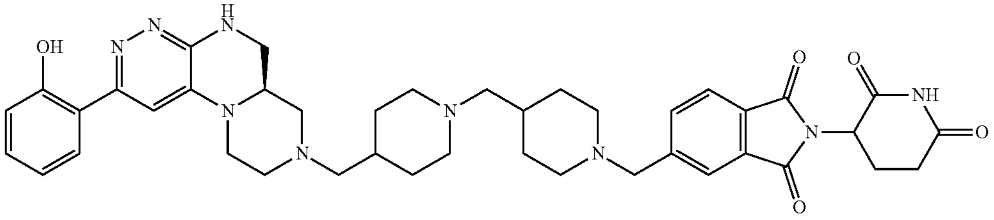

Step 1: 2-(2,6-dioxopiperidin-3-yl)-5-ethenylisoindole-1,3-dione

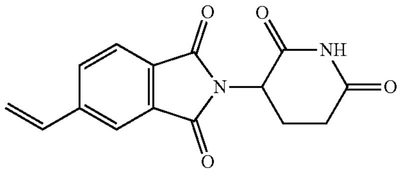 [SMILES: C=Cc1ccc2c(c1)C(=O)N(C1CCC(=O)NC1=O)C2=O]

A mixture of 5-bromo-2-(2,6-dioxopiperidin-3-yl) isoindole-1,3-dione (300 mg, 0.89 mmol), 4,4,5,5-tetramethyl-2-vinyl-1,3,2-dioxaborolane (0.3 mL, 1.78 mmol), cesium carbonate (580 mg, 1.78 mmol), and [1,1'-bis(diphenylphosphino)ferrocene]dichloropalladium(II), complex with dichloromethane (145 mg, 0.18 mmol) in 1,4-Dioxane (2.4 mL) and Water (600 μL) was stirred at 80° C. for 2 h. The reaction mixture was diluted with DCM, washed with water and purified by FCC (0-8% MeOH in DCM) to give 2-(2,6-dioxopiperidin-3-yl)-5-ethenylisoindole-1,3-dione (103 mg, 0.36 mmol, 40.7% yield).

Step 2: 2-(2,6-dioxopiperidin-3-yl)-1,3-dioxoisoindole-5-carbaldehyde

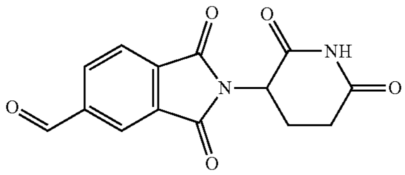 [SMILES: O=Cc1ccc2c(c1)C(=O)N(C1CCC(=O)NC1=O)C2=O]

To a solution of 2-(2,6-dioxopiperidin-3-yl)-5-ethenylisoindole-1,3-dione (203 mg, 0.71 mmol) in 1,4-dioxane (3 mL) and water (2.5 mL) at 0° C. was added sodium periodate (611 mg, 2.9 mmol), 2,6-lutidine (0.17 mL, 1.43 mmol), and potassium osmate (23.7 mg, 0.07 mmol). The reaction mixture was stirred at rt for 2 h. The reaction mixture was diluted with water, extracted with DCM, concentrated and purified by FCC (0-10% EtOAc/DCM) to give 2-(2,6-dioxopiperidin-3-yl)-1,3-dioxoisoindole-5-carbaldehyde (131 mg, 0.46 mmol, 64.1% yield). LCMS calcd for $C_{14}H_{11}N_2O_5$(M+H)+m/z: 287.1; found: 287.2.

Step 3: 2-(2,6-dioxopiperidin-3-yl)-5-[[4-(hydroxymethyl)piperidin-1-yl]methyl]isoindole-1,3-dione

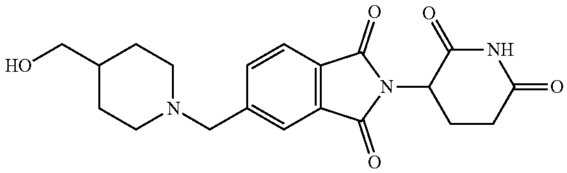 [SMILES: O=C1CCC(N2C(=O)c3ccc(CN4CCC(CO)CC4)cc3C2=O)C(=O)N1]

A mixture of 2-(2,6-dioxopiperidin-3-yl)-1,3-dioxoisoindole-5-carbaldehyde (110 mg, 0.38 mmol) and 4-Piperidinemethanol (53 mg, 0.46 mmol) in DMF (1 mL) was stirred at rt for 10 min before the addition of sodium triacetoxyborohydride (163 mg, 0.77 mmol).The mixture was stirred at rt for 1 h and then purified on silica gel column (0-15% MeOH/DCM) to give 2-(2,6-dioxopiperidin-3-yl)-5-[[4-(hydroxymethyl)piperidin-1-yl]methyl]isoindole-1,3-dione (82 mg, 0.21 mmol, 55.4% yield). LCMS calcd for $C_{20}H_{24}N_3O_5$ $[M+H]^+$ m/z=386.2; found: 386.1.

Step 4: 1-[[2-(2,6-dioxopiperidin-3-yl)-1,3-dioxoisoindol-5-yl]methyl]piperidine-4-carbaldehyde

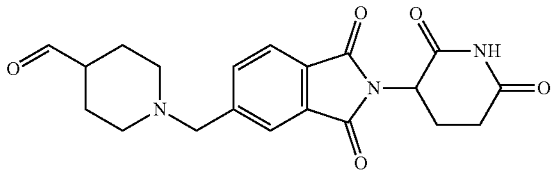 [SMILES: O=CC1CCN(Cc2ccc3c(c2)C(=O)N(C2CCC(=O)NC2=O)C3=O)CC1]

2-(2,6-dioxopiperidin-3-yl)-5-[[4-(hydroxymethyl)piperidin-1-yl]methyl]isoindole-1,3-dione (82.0 mg, 0.21 mmol) was treated with Dess-Martin Periodinane (180 mg, 0.43 mmol) in DMF (1 mL) at rt for 1 h. The reaction was quenched with water and purified on silica gel column (0-10% MeOH/DCM) to give 1-[[2-(2,6-dioxopiperidin-3-yl)-1,3-dioxoisoindol-5-yl]methyl]piperidine-4-carbaldehyde (60 mg, 0.16 mmol, 73.6% yield). LCMS calcd for $C_{20}H_{22}N_3O_5$ [M+H]+m/z=384.2; found: 384.1.

Step 5: 2-(2,6-dioxopiperidin-3-yl)-5-[[4-[[4-[[(10S)-4-(2-hydroxyphenyl)-1,5,6,8,12-pentazatricyclo[8.4.0.02,7]tetradeca-2,4,6-trien-12-yl]methyl]piperidin-1-yl]methyl]piperidin-1-yl]methyl]isoindole-1,3-dione A mixture of 1-[[2-(2,6-dioxopiperidin-3-yl)-1,3-dioxoisoindol-5-yl]methyl]piperidine-4-carbaldehyde (13.1 mg, 0.03 mmol), 2-[(10S)-12-(piperidin-4-ylmethyl)-1,5,6,8,12-pentazatricyclo[8.4.0.02,7]tetradeca-2,4,6-trien-4-yl]phenol (13.0 mg, 0.03 mmol), N,N-Diisopropylethylamine (0.02 mL, 0.14 mmol), acetic acid (0.01 mL, 0.20 mmol) and sodium triacetoxyborohydride (14.48 mg, 0.07 mmol) in DMF (1 mL) was stirred at rt for 1 h. The mixture was diluted with MeOH and purified on prep-LCMS (pH 2) to give 2-(2,6-dioxopiperidin-3-yl)-5-[[4-[[4-[[(10S)-4-(2-hydroxyphenyl)-1,5,6,8,12-pentazatricyclo [8.4.0.02,7]tetradeca-2,4,6-trien-12-yl]methyl]piperidin-1-yl]methyl]piperidin-1-yl]methyl]isoindole-1,3-dione (4.4 mg, 0.0059 mmol, 17.2% yield). LCMS calcd for $C_{41}H_{50}N_9O_5$ [M+H]+m/z=748.4; found: 748.4.

Example 207: 3-(5-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)-1-oxoisoindolin-2-yl)piperidine-2,6-dione Ex.207

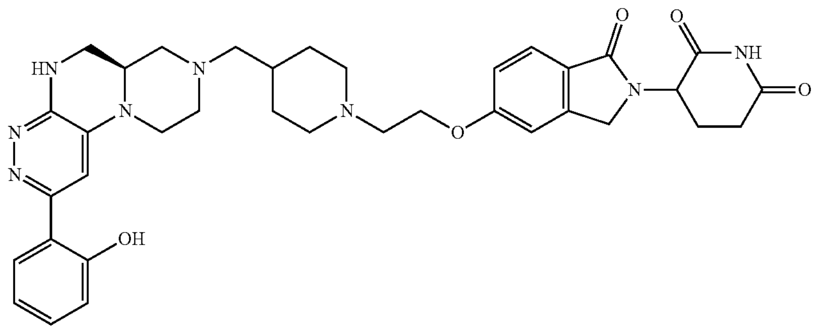

To a mixture of (S)-2-(8-(piperidin-4-ylmethyl)-6,6a,7,8,9,10-hexahydro-5H-pyrazino[1',2':4,5] pyrazino[2,3-c]pyridazin-2-yl)phenol (13.3 mg, 0.03 mmol), and 2-[[2-(2,6-dioxopiperidin-3-yl)-1-oxo-3H-isoindol-5-yl]oxy]acetaldehyde (7.94 mg, 0.03 mmol) in DMF (0.20 mL) was added AcOH (0.01 mL, 0.13 mmol). The mixture was stirred at 25° C. overnight. $NaBH(OAc)_3$ (11.1 mg, 0.05 mmol) was added. The mixture was stirred at 25° C. for 1 h. The resulted mixture was purified by Prep-(PLC on a C18 column (20-35 m, 100 A, 80 g) with mobile phase: $H_2O$ (0.1% TFA)/MeCN at flow rate: 50 mL/min, then purified by Prep-HPLC on a C18 column (20-35 μm, 100 A, 80 g) with mobile phase: $H_2O$ (0.1% $NH_4HCO_3$)/MeCN at flow rate: 50 mL/min to afford 3-(5-(2-(4-(((S)-2-(2-hydroxyphenyl)-5,6,6a,7,9,10-hexahydro-8H-pyrazino[1',2':4,5]pyrazino [2,3-c]pyridazin-8-yl)methyl)piperidin-1-yl)ethoxy)-1-oxoisoindolin-2-yl)piperidine-2,6-dione (0.80 mg, 0.0011 mmol, 440 yield). LCMS calculated for $C_{36}H_{43}N_8O_5$ $(M+H)^+$ m/z=667.3; found: 667.2.

Examples 237, 238, 255 and 256

Examples in Table 22 were prepared using the procedure described in the synthesis of Example 207 with appropriate intermediates.

TABLE 22

| Ex. | Examples 237, 238, 255 and 256<br>Structure<br>Name | Calcd. (M + H)$^+$ m/z | Found (M + H)$^+$ m/z |
|---|---|---|---|
| 237 | 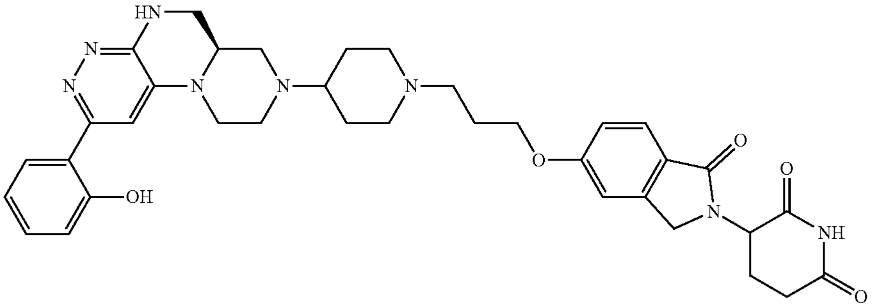<br>3-(5-(3-(4-((S)-2-(2-hydroxyphenyl)-5,6,6a,7,9,10-hexahydro-8H-pyrazino[1′,2′:4,5]pyrazino[2,3-c]pyridazin-8-yl)piperidin-1-yl)propoxy)-1-oxoisoindolin-2-yl)piperidine-2,6-dione | 667.3 | 667.4 |
| 238 | 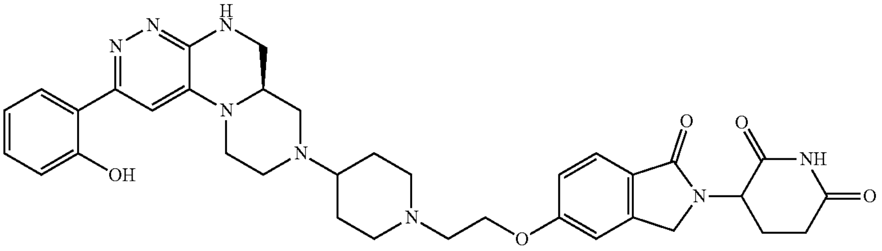<br>3-(5-(2-(4-((S)-2-(2-hydroxyphenyl)-5,6,6a,7,9,10-hexahydro-8H-pyrazino[1′,2′:4,5]pyrazino[2,3-c]pyridazin-8-yl)piperidin-1-yl)ethoxy)-1-oxoisoindolin-2-yl)piperidine-2,6-dione | 653.3 | 653.4 |
| 255 | 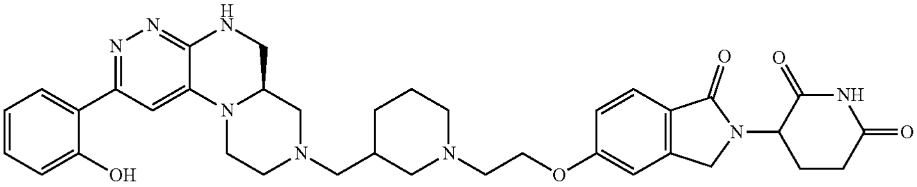<br>3-(5-(2-(3-(((S)-2-(2-hydroxyphenyl)-5,6,6a,7,9,10-hexahydro-8H-pyrazino[1′,2′:4,5]pyrazino[2,3-c]pyridazin-8-yl)methyl)piperidin-1-yl)ethoxy)-1-oxoisoindolin-2-yl)piperidine-2,6-dione | 667.3 | 667.2 |
| 256 | 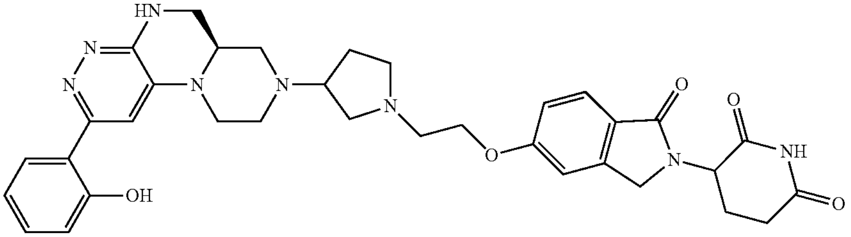<br>3-(5-(2-(3-((S)-2-(2-hydroxyphenyl)-5,6,6a,7,9,10-hexahydro-8H-pyrazino[1′,2′:4,5]pyrazino[2,3-c]pyridazin-8-yl)pyrrolidin-1-yl)ethoxy)-1-oxoisoindolin-2-yl)piperidine-2,6-dione | 639.3 | 639.2 |

Example 208: 3-(5-(1-(1-(3-((S)-2-(2-hydroxyphenyl)-5,6,6a,7,9,10-hexahydro-8H-pyrazino[1',2':4,5]pyrazino[2,3-c]pyridazin-8-yl)propyl)pyrrolidin-3-yl)piperidin-4-yl)-1-oxoisoindolin-2-yl)piperidine-2,6-dione Ex.208

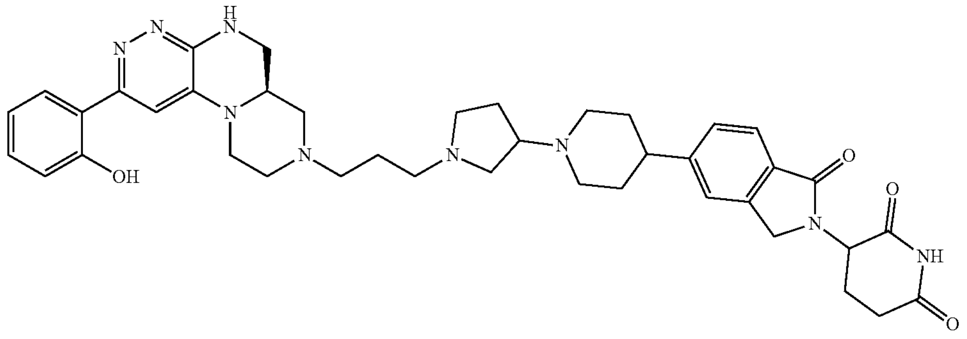

Step 1: tert-butyl 3-(4-(2-(2,6-dioxopiperidin-3-yl)-1-oxoisoindolin-5-yl)piperidin-1-yl) pyrrolidine-1-carboxylate

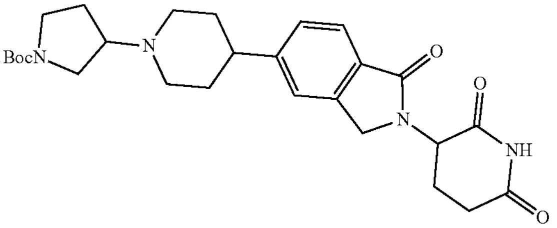 [SMILES: CC(C)(C)OC(=O)N1CCC(N2CCC(c3ccc4c(c3)CN(C3CCC(=O)NC3=O)C4=O)CC2)C1]

A mixture of 3-(3-oxo-6-piperidin-4-yl-1H-isoindol-2-yl) piperidine-2,6-dione (prepared using the procedure described in WO2019038717, 100 mg, 0.31 mmol), Boc-3-pyrrolidinone (113 mg, 0.61 mmol) and AcOH (0.09 mL, 1.53 mmol) in DMF (5 mL) was stirred at 25° C. overnight. $NaBH(OAc)_3$ (323 mg, 1.53 mmol) was added. The mixture was stirred at 25° C. for 1 h. The resulted mixture was purified by Prep-HPLC on a C18 column (20-35 μm, 100 A, 80 g) with mobile phase: $H_2O$ (0.1% TFA)/MeCN at flow rate: 50 mL/min to afford the desired product (110 mg, 0.22 mmol, 72.5% yield) as a white solid. LCMS calculated for $C_{27}H_{37}N_4O_5$ $(M+H)^+$ m/z=497.3; found: 497.2.

Step 2: 3-(1-oxo-5-(1-(pyrrolidin-3-yl)piperidin-4-yl) isoindolin-2-yl)piperidine-2,6-dione

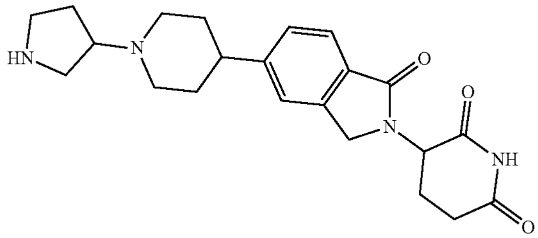 [SMILES: O=C1CCC(N2Cc3cc(C4CCN(C5CCNC5)CC4)ccc3C2=O)C(=O)N1]

A mixture of tert-butyl 3-(4-(2-(2,6-dioxopiperidin-3-yl)-1-oxoisoindolin-5-yl)piperidin-1-yl)pyrrolidine-1-carboxylate (100 mg, 0.20 mmol) and HCl in 1,4-dioxane (4 M, 0.35 mL, 1.41 mmol) in DCM (2 mL) was stirred at 25° C. for 1 h. Then the mixture was concentrated and washed with tert-butyl methyl ether to afford 3-(1-oxo-5-(1-(pyrrolidin-3-yl)piperidin-4-yl) isoindolin-2-yl)piperidine-2,6-dione (110 mg, 0.20 mmol, 98.9% yield). LCMS calculated for $C_{22}H_{29}N_4O_3$ $(M+H)^+$ m/z=397.2; found: 397.2.

Step 3: 3-(5-(1-(1-(3-((S)-2-(2-hydroxyphenyl)-5,6,6a,7,9,10-hexahydro-8H-pyrazino[1',2':4,5]pyrazino[2,3-c]pyridazin-8-yl)propyl)pyrrolidin-3-yl)piperidin-4-yl)-1-oxoisoindolin-2-yl)piperidine-2,6-dione To a mixture of (S)-2-(8-(3-bromopropyl)-6,6a,7,8,9,10-hexahydro-5H-pyrazino[1',2':4,5]pyrazino[2,3-c]pyridazin-2-yl)phenol (18.0 mg, 0.04 mmol), and 3-[3-oxo-6-(1-pyrrolidin-3-ylpiperidin-4-yl)-1H-isoindol-2-yl]piperidine-2,6-dione (17.6 mg, 0.04 mmol) in DMF (1 mL) was added DIEA (0.01 mL, 0.09 mmol). The mixture was stirred at 60° C. for 5 h. The resulted mixture was purified by Prep-HPLC on a C18 column (20-35 μm, 100 A, 80 g) with mobile phase: $H_2O$ (0.1% $NH_4HCO_3$)/MeCN at flow rate: 50 mL/min to afford the desired product (0.90 mg, 0.0010 mmol, 2.3% yield) as a white solid. LCMS calculated for $C_{40}H_{50}N_9O_4(M+H)^+$ m/z=720.4; found: 720.3.

Examples 209-213

Examples in Table 23 were prepared using the procedure described in the synthesis of Example 208 with appropriate intermediates.

TABLE 23

| Ex. | Structure Name | Calcd. (M + H)+ m/z | Found (M + H)+ m/z |
|---|---|---|---|
| | Examples 209-213 | | |
| 209 | 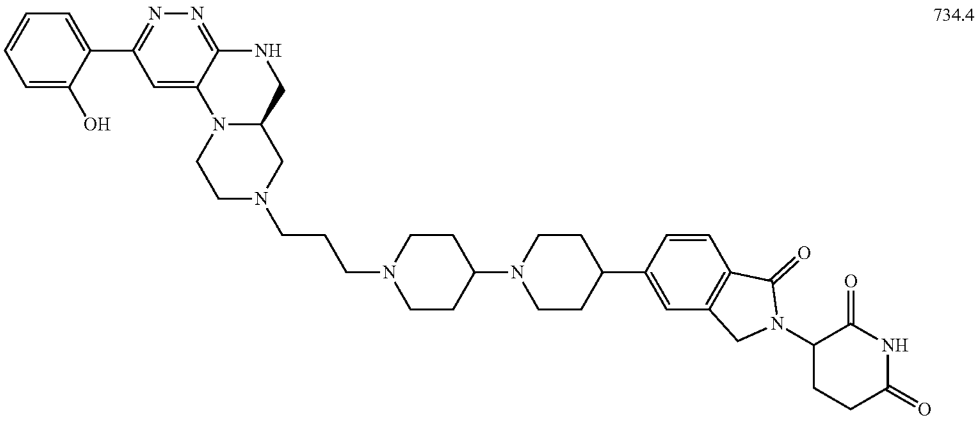 3-(5-(1'-(3-((S)-2-(2-hydroxyphenyl)-5,6,6a,7,9,10-hexahydro-8H-pyrazino[1',2':4,5]pyrazino[2,3-c]pyridazin-8-yl)propyl)-[1,4'-bipiperidin]-4-yl)-1-oxoisoindolin-2-yl)piperidine-2,6-dione | 734.4 | 734.3 |
| 210 | 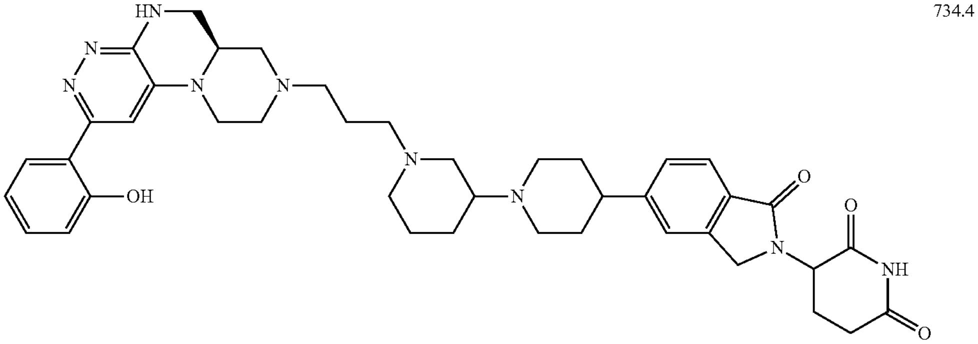 3-(5-(1'-(3-((S)-2-(2-hydroxyphenyl)-5,6,6a,7,9,10-hexahydro-8H-pyrazino[1',2':4,5]pyrazino[2,3-c] pyridazin-8-yl)propyl)-[1,3'-bipiperidin]-4-yl)-1-oxoisoindolin-2-yl)piperidine-2,6-dione | 734.4 | 734.4 |
| 211 | 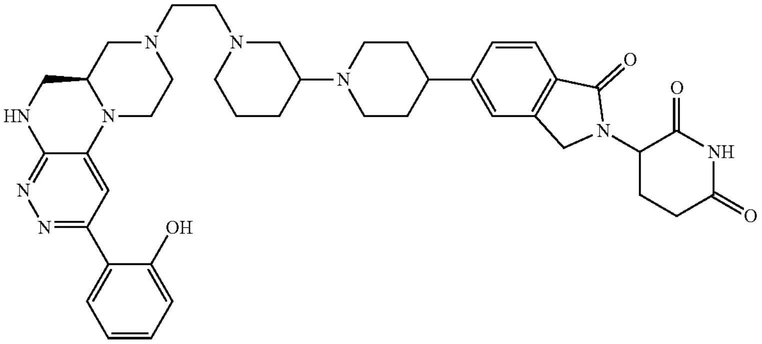 [SMILES: O=C1CCC(N2Cc3cc(C4CCN(C5CCCN(CCN6CCN7c8cc(-c9ccccc9O)nnc8NC[C@H]7C6)C5)CC4)ccc3C2=O)C(=O)N1] 3-(5-(1'-(2-((S)-2-(2-hydroxyphenyl)-5,6,6a,7,9,10-hexahydro-8H-pyrazino[1',2':4,5]pyrazino[2,3-c]pyridazin-8-yl)ethyl)-[1,3'-bipiperidin]-4-yl)-1-oxoisoindolin-2-yl)piperidine-2,6-dione | 720.4 | 720.4 |

TABLE 23-continued

| Ex. | Examples 209-213<br>Structure Name | Calcd. (M + H)+ m/z | Found (M + H)+ m/z |
|---|---|---|---|
| 212 | 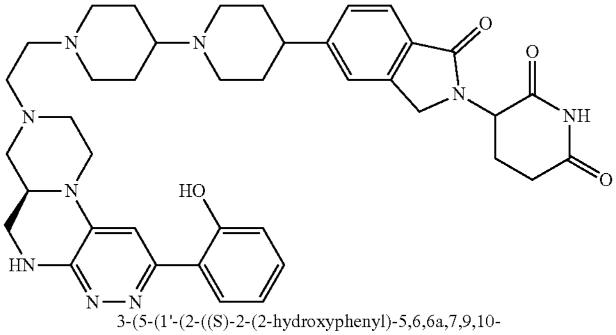<br>3-(5-(1'-(2-((S)-2-(2-hydroxyphenyl)-5,6,6a,7,9,10-hexahydro-8H-pyrazino[1',2':4,5]pyrazino[2,3-c]pyridazin-8-yl)ethyl)-[1,4'-bipiperidin]-4-yl)-1-oxoisoindolin-2-yl)piperidine-2,6-dione | 720.4 | 720.3 |
| 213 | 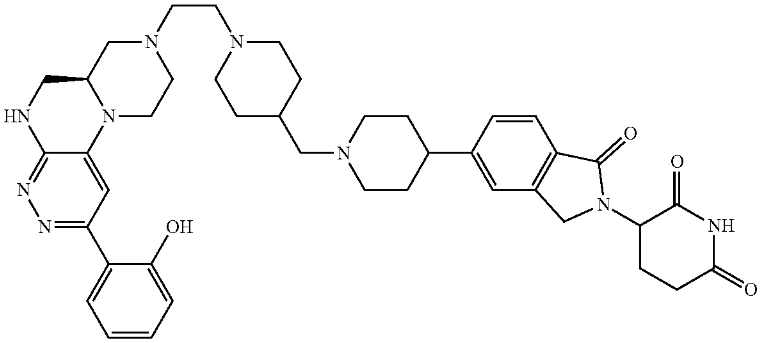 [SMILES: O=C1CCC(N2Cc3cc(C4CCN(CC5CCN(CCN6CCN7c8cc(-c9ccccc9O)nnc8NC[C@H]7C6)CC5)CC4)ccc3C2=O)C(=O)N1]<br>3-(5-(1-((1-(2-((S)-2-(2-hydroxyphenyl)-5,6,6a,7,9,10-hexahydro-8H-pyrazino[1',2':4,5]pyrazino[2,3-c]pyridazin-8-yl)ethyl)piperidin-4-yl)methyl)piperidin-4-yl)-1-oxoisoindolin-2-yl)piperidine-2,6-dione | 734.4 | 734.4 |

Example 214: (3R)-3-(5-((1-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propan-2-yl)oxy)-1-oxoisoindolin-2-yl)piperidine-2,6-dione Ex.214

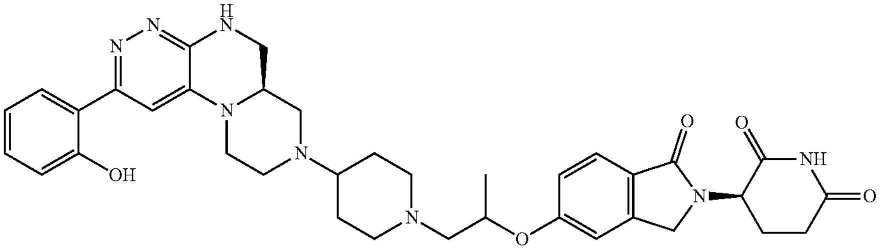

Step 1: 1-(2-hydroxypropyl)piperidin-4-one

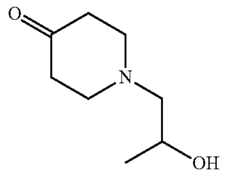

To a solution of piperidin-4-one hydrochloride (3.00 g, 22.1 mmol) and $Et_3N$ (625 mg, 7.44 mmol) in ethanol (10 mL) was added 2-methyloxirane (2.57 g, 44.3 mmol). The mixture was stirred at RT for 18 h. The resulted mixture was concentrated and purified by silica gel chromatography (PE/EA=5/1~1/1) to give 1-(2-hydroxypropyl)piperidin-4-one (1.60 g, 10.2 mmol, 46.0% yield) as a yellow oil. $^1H$ NMR (400 MHz, $CDCl_3$) δ 3.80-3.94 (m, 1H), 3.33 (s, 1H), 2.93-3.02 (m, 2H), 2.69-2.77 (m, 2H), 2.33-2.55 (m, 6H), 1.18 (d, J=6.0 Hz, 3H).

Step 2: tert-butyl (4R)-5-amino-5-oxo-4-(I-oxo-5-((1-(4-oxopiperidin-1-yl)propan-2-yl)oxy) isoindolin-2-yl)pentanoate

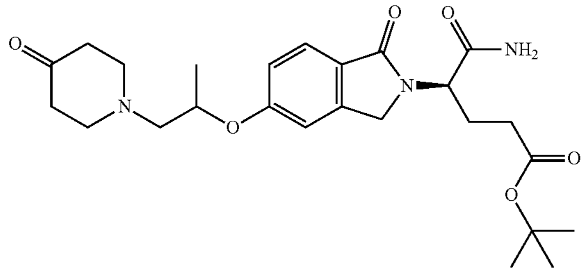 [SMILES: CC(CN1CCC(=O)CC1)Oc1ccc2c(c1)CN([C@H](CCC(=O)OC(C)(C)C)C(N)=O)C2=O]

To a mixture of 1-(2-hydroxypropyl)piperidin-4-one (254 mg, 1.61 mmol), and $PPh_3$ (59.0 mg, 0.230 mmol) in THF (10 mL) were added tert-butyl (4R)-5-amino-4-(6-hydroxy-3-oxo-1H-isoindol-2-yl)-5-oxopentanoate (450 mg, 1.35 mmol) and DIAD (51.0 mg, 1.35 mmol). The mixture was stirred at RT for 18 h. The resulted mixture was concentrated and purified by silica gel chromatography (PE/EA=5/1~ 1/1) to afford the desired product (450 mg, 0.950 mmol, 70.6% yield) as a yellow oil.

Step 3: (3R)-3-(I-oxo-5-((1-(4-oxopiperidin-1-yl) propan-2-yl)oxy) isoindolin-2-yl)piperidine-2,6-dione

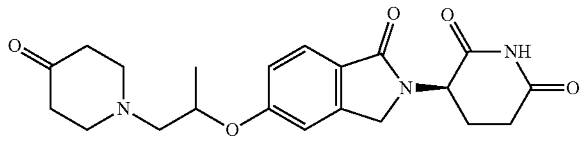 [SMILES: CC(CN1CCC(=O)CC1)Oc1ccc2c(c1)CN([C@@H]1CCC(=O)NC1=O)C2=O]

A solution of tert-butyl (4R)-5-amino-5-oxo-4-(1-oxo-5-((1-(4-oxopiperidin-1-yl)propan-2-yl)oxy) isoindolin-2-yl) pentanoate (100 mg, 0.210 mmol) and TsOH (201 mg, 1.06 mmol) in MeCN (10 mL) was stirred at 60° C. overnight. The volatiles were removed and the residue was purified by Prep-HPLC on a C18 column (20-35 uM, 100 A, 80 g) with mobile phase: $H_2O$ (0.1% TFA)/MeCN at flow rate: 50 mL/min to afford the desired product (30.0 mg, 0.0550 mmol, 26.2% yield) as a brown solid. LCMS calculated for $C_{21}H_{26}N_3O_5$ $(M+H)^+$ m/z=400.3; found: 400.2.

Step 4: (3R)-3-(5-((1-(4-((S)-2-(2-hydroxyphenyl)-5,6,6a, 7,9,1O-hexahydro-8H-pyrazino [1',2':4,5] pyrazino[2,3-c]pyridazin-8-yl)piperidin-1-yl)propan-2-yl)oxy)-1-oxoisoindolin-2-yl)piperidine-2,6-dione A solution of (3R)-3-(1-oxo-5-((1-(4-oxopiperidin-1-yl) propan-2-yl)oxy) isoindolin-2-yl)piperidine-2,6-dione (21.2 mg, 0.05 mmol), acetic acid (0.01 mL, 0.18 mmol) and (R)-2-(6,6a,7,8,9,10-hexahydro-5H-pyrazino[1',2':4,5] pyrazino[2,3-c]pyridazin-2-yl)phenol (10.0 mg, 0.04 mmol) in DMF (1 mL) was stirred at rt for 0.5 h. Sodium triacetoxyborohydride (22.0 mg, 0.11 mmol) was added. The reaction mixture was stirred at rt for additional 18 h. The resulted mixture was purified by Prep-HPLC on a C18 column (20-35 μm, 100 A, 80 g) with mobile phase: $H_2O$ (0.1% TFA)/MeCN at flow rate: 50 mL/min and purified by Prep-HPLC on a C18 column (20-35 μm, 100 A, 80 g) with mobile phase: $H_2O$ (0.1% $NH_4HCO_3$)/MeCN at flow rate: 50 mL/min to afford (3R)-3-(5-((1-(4-((S)-2-(2-hydroxyphenyl)-5,6,6a,7,9,10-hexahydro-8H-pyrazino [1',2':4,5] pyrazino[2,3-c]pyridazin-8-yl)piperidin-1-yl)propan-2-yl) oxy)-1-oxoisoindolin-2-yl)piperidine-2,6-dione (1.90 mg, 0.0027 mmol, 7.7% yield) as a white solid. LCMS calculated for $C_{36}H_{43}N_8O_5$ $(M+H)^+$ m/z=667.3; found: 667.4.

Example 215: (3R)-3-(5-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl) propoxy)-1-oxoisoindolin-2-yl)piperidine-2,6-dione Ex.215

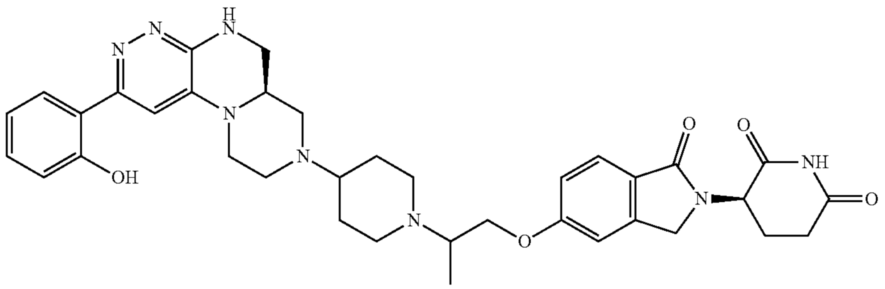

Step 1: tert-butyl (R)-5-amino-5-oxo-4-(I-oxo-5-(2-oxopropoxy) isoindolin-2-yl)pentanoate

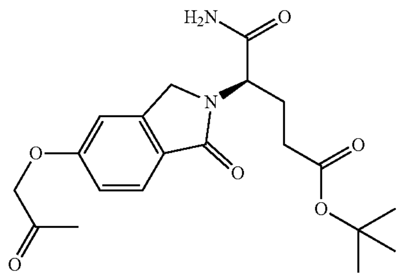 [SMILES: CC(=O)COc1ccc2c(c1)CN([C@H](CCC(=O)OC(C)(C)C)C(N)=O)C2=O]

To a mixture of tert-butyl (R)-5-amino-4-(5-hydroxy-1-oxoisoindolin-2-yl)-5-oxopentanoate (100 mg, 0.30 mmol), and 1-bromopropan-2-one (49.0 mg, 0.36 mmol) in DMF (1 mL) was added $K_2CO_3$ (124 mg, 0.90 mmol). The mixture was stirred at 25° C. overnight. The resulted mixture was concentrated and purified by silica gel chromatography (PE/EA=1/1) to afford tert-butyl (R)-5-amino-5-oxo-4-(1-oxo-5-(2-oxopropoxy) isoindolin-2-yl)pentanoate (58.0 mg, 0.150 mmol, 49.7% yield). LCMS calculated for $C_{20}H_{27}N_2O_6$ $(M+H)^+$ m/z=391.2; found: 391.2.

Step 2: (R)-3-(I-oxo-5-(2-oxopropoxy) isoindolin-2-yl)piperidine 2,6-dione

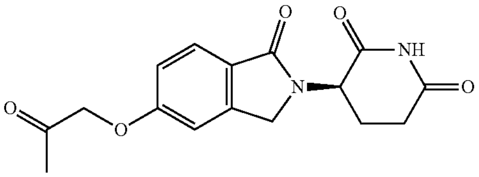 [SMILES: CC(=O)COc1ccc2c(c1)CN([C@@H]1CCC(=O)NC1=O)C2=O]

A mixture of tert-butyl (R)-5-amino-5-oxo-4-(1-oxo-5-(2-oxopropoxy) isoindolin-2-yl)pentanoate (58.0 mg, 0.150 mmol) and TsOH (256 mg, 1.49 mmol) in MeCN (10 mL) was stirred at 80° C. for 18 h. The mixture was concentrated and purified by Prep-HPLC on a C18 column (20-35 μm, 100 A, 80 g) with mobile phase: $H_2O$ (0.1% TFA)/MeOH at flow rate: 50 mL/min to afford (R)-3-(1-oxo-5-(2-oxo-propoxy) isoindolin-2-yl)piperidine-2,6-dione (48.0 mg, 0.11 mmol, 74.5% yield) as a brown solid.

Step 3: (3R)-3-(5-(2-(4-((S)-2-(2-hydroxyphenyl)-5,6,6a, 7,9,10-hexahydro-8H-pyrazino [1',2':4,5] pyrazino[2,3-c]pyridazin-8-yl)piperidin-1-yl) propoxy)-1-oxoisoindolin-2-yl)piperidine-2,6-dione A solution of (R)-3-(1-oxo-5-(2-oxopropoxy) isoindolin-2-yl)piperidine-2,6-dione (40.0 mg, 0.13 mmol), (S)-2-(8-(piperidin-4-yl)-6,6a,7,8,9,10-hexahydro-5H-pyrazino[1',2':4,5]pyrazino[2,3-c]pyridazin-2-yl)phenol hydrochloride (51.0 mg, 0.13 mmol) and acetic acid (0.04 mL, 0.63 mmol) in DMF (1 mL) was stirred at rt for 0.5 h. Sodium triacetoxyborohydride (134 mg, 0.63 mmol) was added. The reaction mixture was stirred at rt overnight. The resulted mixture was purified by Prep-HPLC on a C18 column (20-35 μm, 100 A, 80 g) with mobile phase: $H_2O$ (0.1% $NH_4HCO_3$)/MeCN at flow rate: 50 mL/min to afford the desired product (1.5 mg, 0.0023 mmol, 1.8% yield) as a white solid. LCMS calculated for $C_{36}H_{43}N_8O_5$ $(M+H)^+$ m/z=667.3; found: 667.4.

Example 239

The example in Table 24 was prepared using the procedure described in the synthesis of Example 215 with appropriate intermediates.

TABLE 24

Example 239

| Ex | Structure/Name | Calcd. $(M + H)^+$ m/z | Found $(M + H)^+$ m/z |
|---|---|---|---|
| 239 | 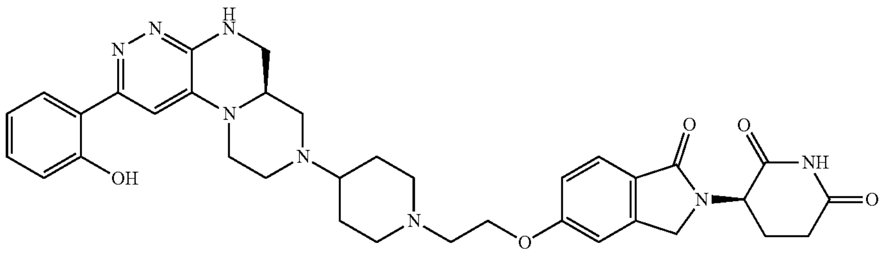 [SMILES: O=C1CC[C@@H](N2Cc3cc(OCCN4CCC(N5CCN6c7cc(-c8ccccc8O)nnc7NC[C@H]6C5)CC4)ccc3C2=O)C(=O)N1] (R)-3-(5-(2-(4-((S)-2-(2-hydroxyphenyl)-5,6,6a,7,9,10-hexahydro-8H-pyrazino[1',2':4,5]pyrazino[2,3-c] pyridazin-8-yl)piperidin-1-yl)ethoxy)-1-oxoisoindolin-2-yl)piperidine-2,6-dione | 653.3 | 653.3 |

Example 216: 2-(2,6-dioxopiperidin-3-yl)-5-((1-((1-(2-((S)-2-(2-hydroxyphenyl)-5,6,6a,7,9,10-hexahydro-8H-pyrazino[1',2':4,5]pyrazino[2,3-c]pyridazin-8-yl)ethyl) piperidin-4-yl)methyl) piperidin-4-yl)oxy) isoindoline-1,3-dione Ex.216

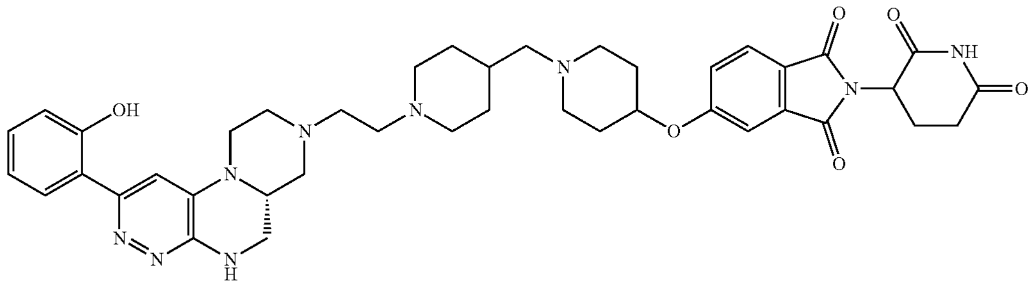

Step 1: tert-butyl 4-((4-((2-(2,6-dioxopiperidin-3-yl)-1,3-dioxoisoindolin-5-yl)oxy)piperidin-1-yl)methyl)piperidine-1-carboxylate

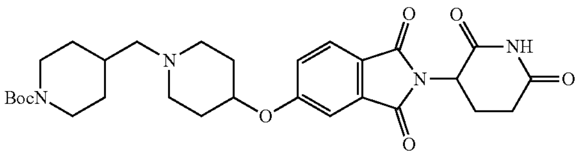 [SMILES: CC(C)(C)OC(=O)N1CCC(CN2CCC(Oc3ccc4c(c3)C(=O)N(C3CCC(=O)NC3=O)C4=O)CC2)CC1]

To a mixture of 2-(2,6-dioxopiperidin-3-yl)-5-piperidin-4-yloxyisoindole-1,3-dione (71.0 mg, 0.20 mmol), and 1-Boc-piperidine-4-carboxaldehyde (84.7 mg, 0.40 mmol) in DMF (1 mL) was added AcOH (0.06 mL, 0.99 mmol). The mixture was stirred at 25° C. for 1 h. $NaBH(OAc)_3$ (84.2 mg, 0.40 mmol) was added. The mixture was stirred at 25° C. overnight. The resulted mixture was purified by Prep-HPLC on a C18 column (20-35 μm, 100 A, 80 g) with mobile phase: $H_2O$ (0.1% TFA)/MeCN at flow rate: 50 mL/min to afford the desired product (110 mg, 0.20 mmol, 99.9% yield). LCMS calculated for $C_{29}H_{39}N_4O_7$ $(M+H)^+$ m/z=555.2; found: 555.2.

Step 2: 2-(2,6-dioxopiperidin-3-yl)-5-((1-(piperidin-4-ylmethyl)piperidin-4-yl)oxy) isoindoline-1,3-dione

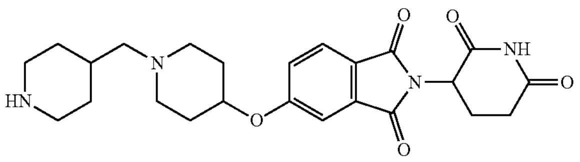 [SMILES: O=C1CCC(N2C(=O)c3ccc(OC4CCN(CC5CCNCC5)CC4)cc3C2=O)C(=O)N1]

To a stirred solution of tert-butyl 4-((4-((2-(2,6-dioxopiperidin-3-yl)-1,3-dioxoisoindolin-5-yl)oxy)piperidin-1-yl)methyl)piperidine-1-carboxylate (100 mg, 0.18 mmol) in DCM (2 mL) was added TFA (1.00 mL, 13.1 mmol) at 25° C. After 12 h, the resulted mixture was concentrated to afford the desired product (52.0 mg, 0.11 mmol, 63.4% yield). LCMS calculated for $C_{24}H_{31}N_4O_5$ $(M+H)^+$ m/z=455.2; found: 455.2.

Step 3: 2-(2,6-dioxopiperidin-3-yl)-5-((1-((1-(2-((S)-2-(2-hydroxyphenyl)-5,6,6a,7,9,10-hexahydro-8H-pyrazino[1',2':4,5]pyrazino[2,3-c]pyridazin-8-yl)ethyl)piperidin-4-yl)methyl)piperidin-4-yl)oxy) isoindoline-N, 3-dione To a stirred solution of (S)-2-(8-(2-bromoethyl)-6,6a,7,8,9,10-hexahydro-5H-pyrazino[1',2':4,5]pyrazino[2,3-c]pyridazin-2-yl)phenol (55.4 mg, 0.14 mmol), and 2-(2,6-dioxopiperidin-3-yl)-5-((1-(piperidin-4-ylmethyl)piperidin-4-yl)oxy) isoindoline-1,3-dione (64.2 mg, 0.14 mmol) in DMF (5 mL) was added DIPEA (0.07 mL, 0.43 mmol) at 25° C. After 16 h, the resulted mixture was purified by Prep-HPLC on a C18 column (20-35 μm, 100 A, 80 g) with mobile phase: $H_2O$ (0.100 $NH_4HCO_3$)/MeCN at flow rate: 50 mL/min to afford the desired product (4.5 mg, 0.0046 mmol, 3.2% yield). LCMS calculated for $C_{41}H_{50}N_9O_6$ $(M+H)^+$ m/z=764.4; found: 764.4.

Examples 155, 158 and 159

Examples in Table 25 were prepared using the procedure described in the synthesis of Example 216 with appropriate intermediates.

TABLE 25

| Ex | Structure/Name | Calcd. (M + H)+ m/z | Found (M + H)+ m/z |
|---|---|---|---|
| Examples 155, 158 and 159 | | | |
| 155 | 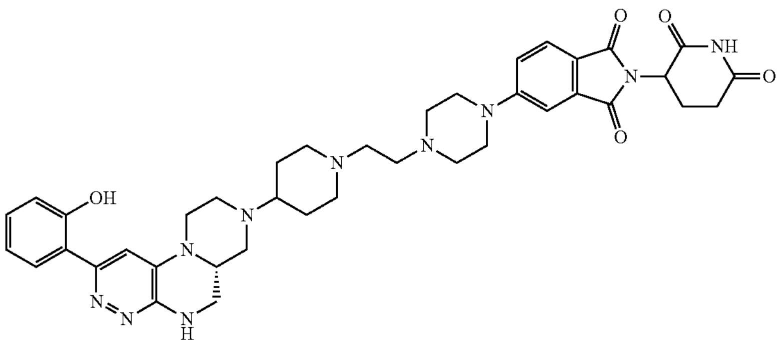 [SMILES: O=C1CCC(N2C(=O)c3ccc(N4CCN(CCN5CCC(N6CCN7c8cc(-c9ccccc9O)nnc8NC[C@H]7C6)CC5)CC4)cc3C2=O)C(=O)N1]<br>2-(2,6-dioxopiperidin-3-yl)-5-(4-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethyl)piperazin-1-yl)isoindoline-1,3-dione<br>$^1$H NMR (400 MHz, DMSO-$d_6$) δ 11.11 (s, 1H), 8.20 (s, 1H), 7.75 (d, J = 8.5 Hz, 1H), 7.51-7.38 (m, 3H), 7.33 (dd, J = 8.7, 2.2 Hz, 1H), 7.23 (s, 1H), 7.11-6.94 (m, 2H), 5.09 (dd, J = 12.9, 5.3 Hz, 1H), 3.29 (td, J = 13.1, 12.2, 5.9 Hz, 3H), 3.13-2.80 (m, 6H), 2.65-2.55 (m, 1H), 2.17-1.99 (m, 3H), 1.79 (d, J = 12.8 Hz, 2H). | 735.4 | 735.3 |
| 158 | 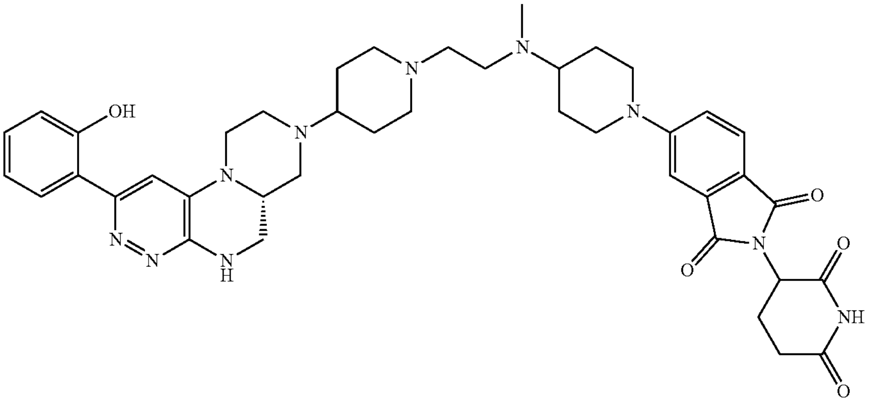 [SMILES: CN(CCN1CCC(N2CCN3c4cc(-c5ccccc5O)nnc4NC[C@H]3C2)CC1)C1CCN(c2ccc3c(c2)C(=O)N(C2CCC(=O)NC2=O)C3=O)CC1]<br>2-(2,6-dioxopiperidin-3-yl)-5-(4-((2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethyl)(methyl)amino)piperidin-1-yl)isoindoline-1,3-dione | 763.4 | 763.4 |
| 159 | 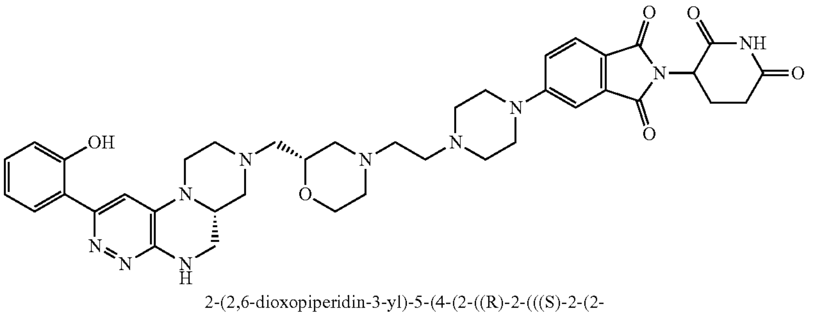<br>2-(2,6-dioxopiperidin-3-yl)-5-(4-(2-((R)-2-(((S)-2-(2-hydroxyphenyl)-5,6,6a,7,9,10-hexahydro-8H-pyrazino[1',2':4,5]pyrazino[2,3-c]pyridazin-8-yl)methyl)morpholino)ethyl)piperazin-1-yl)isoindoline-1,3-dione | 751.4 | 751.2 |

Example 217: 3-(5-(4-((1-(2-((S)-2-(2-hydroxyphenyl)-5,6,6a,7,9,10-hexahydro-8H-pyrazino [1',2':4,5] pyrazino[2,3-c]pyridazin-8-yl)ethyl)piperidin-4-yl) methyl)piperazin-1-yl)-1-oxoisoindolin-2-yl) piperidine-2,6-dione Ex.217

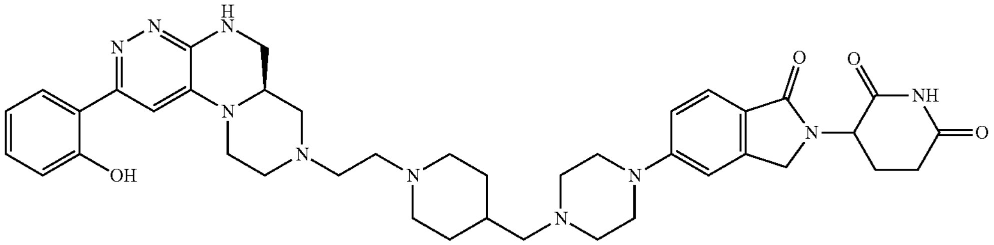

Step 1: tert-butyl 4-((4-(2-(2,6-dioxopiperidin-3-yl)-1-oxoisoindolin-5-yl)piperazin-1-yl)methyl) piperidine-1-carboxylate

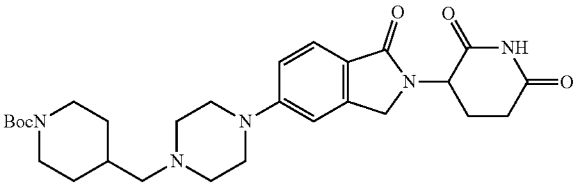 [SMILES: CC(C)(C)OC(=O)N1CCC(CN2CCN(c3ccc4c(c3)CN(C3CCC(=O)NC3=O)C4=O)CC2)CC1]

To a stirred solution of 3-(3-oxo-6-piperazin-1-yl-1H-isoindol-2-yl)piperidine-2,6-dione (prepared using the procedure described in US20180125821, 65.0 mg, 0.20 mmol), and 1-Boc-piperidine-4-carboxaldehyde (84.4 mg, 0.40 mmol) in DMF (2 mL) was added AcOH (0.06 mL, 0.99 mmol) at 25° C. After 1 h, $NaBH(OAc)_3$ (83.9 mg, 0.40 mmol) was added. After another 16 h, the resulted mixture was purified by Prep-HPLC on a C18 column (20-35 μm, 100 A, 80 g) with mobile phase: $H_2O$ (0.1% TFA)/MeCN at flow rate: 50 mL/min to afford tert-butyl 4-((4-(2-(2,6-dioxopiperidin-3-yl)-1-oxoisoindolin-5-yl)piperazin-1-yl) methyl)piperidine-1-carboxylate (72.0 mg, 0.14 mmol, 69.2% yield). LCMS calculated for $C_{28}H_{40}N_5O_5$ $(M+H)^+$ m/z=526.3; found: 426.2 (M+H−100), 470.2 (M+H−56).

Step 2: 3-(1-oxo-5-(4-(piperidin-4-ylmethyl)piperazin-1-yl) isoindolin-2-yl)piperidine-2,6-dione

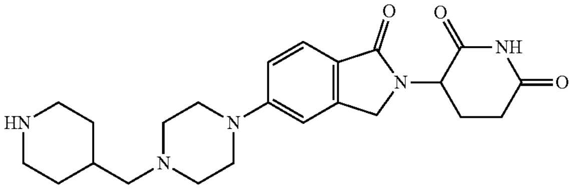 [SMILES: O=C1CCC(N2Cc3cc(N4CCN(CC5CCNCC5)CC4)ccc3C2=O)C(=O)N1]

To a stirred solution of tert-butyl 4-[[4-[2-(2,6-dioxopiperidin-3-yl)-1-oxo-3H-isoindol-5-yl]piperazin-1-yl]methyl] piperidine-1-carboxylate (40.1 mg, 0.08 mmol) in DCM (4 mL) was added TFA (1.54 mL, 20.6 mmol) at 25° C. After 5 h, volatiles were removed under reduced pressure to afford 3-(1-oxo-5-(4-(piperidin-4-ylmethyl)piperazin-1-yl) isoindolin-2-yl)piperidine-2,6-dione (30.0 mg, 0.07 mmol, 92.5% yield), which was used in next step directly.

Step 3: 3-(5-(4-((1-(2-((S)-2-(2-hydroxyphenyl)-5,6,6a, 7,9,1O-hexahydro-8H-pyrazino [1',2':4,5] pyrazino[2,3-c]pyridazin-8-yl)ethyl)piperidin-4-yl) methyl)piperazin-1-yl)-1-oxoisoindolin-2-yl) piperidine-2,6-dione To a stirred solution of (S)-2-(8-(2-bromoethyl)-6,6a,7,8,9,10-hexahydro-5H-pyrazino[1',2':4,5] pyrazino[2,3-c] pyridazin-2-yl)phenol (50.0 mg, 0.06 mmol) in DMF (1 mL) were added 3-[3-oxo-6-[4-(piperidin-4-ylmethyl)piperazin-1-yl]-1H-isoindol-2-yl]piperidine-2,6-dione (30.0 mg, 0.07 mmol) and DIPEA (0.03 mL, 0.17 mmol) at 25° C. After 24 h, the resulted mixture was purified by Prep-HPLC on a C18 column (20-35 μm, 100 A, 80 g) with mobile phase: $H_2O$ (0.1% $NH_4HCO_3$)/MeCN at flow rate: 50 mL/min to afford the desired product (1.60 mg, 0.0021 mmol, 3.7% yield) as a white solid. LCMS calculated for $C_{40}H_{51}N_{10}O_4$ $(M+H)^+$ m/z=735.4; found: 735.4.

Example 218: 2-(2,6-dioxopiperidin-3-yl)-5-(4-(((S)-2-(2-hydroxyphenyl)-5,6,6a,7,9,10-hexahydro-8H-pyrazino[1',2':4,5]pyrazino[2,3-c]pyridazin-8-yl)methyl)-[1,3'-bipiperidin]-1'-yl) isoindoline-1,3-dione Ex.218

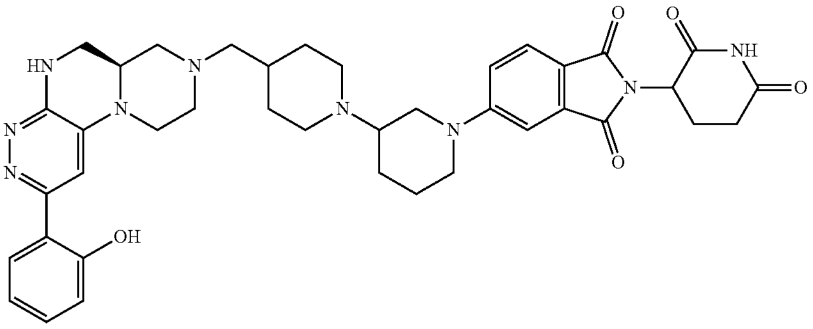

Step 1: tert-butyl 4-(((S)-2-(2-hydroxyphenyl)-5,6,6a, 7,9,10-hexahydro-8H-pyrazino[1',2':4,5]pyrazino[2,3-c]pyridazin-8-yl)methyl)-[1,3'-bipiperidine]-1'-carboxylate

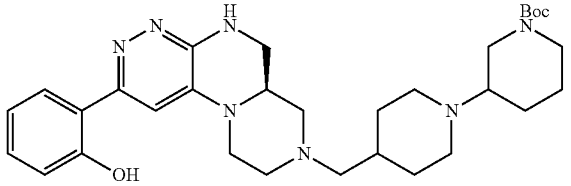 [SMILES: CC(C)(C)OC(=O)N1CCCC(N2CCC(CN3CCN4c5cc(-c6ccccc6O)nnc5NC[C@H]4C3)CC2)C1]

To a stirred solution of (S)-2-(8-(piperidin-4-ylmethyl)-6,6a,7,8,9,10-hexahydro-5H-pyrazino[1',2':4,5]pyrazino[2,3-c]pyridazin-2-yl)phenol (110 mg, 0.29 mmol), and 1-Boc-3-piperidone (115 mg, 0.58 mmol) in DMF (2 mL) was added AcOH (0.08 mL, 1.45 mmol) at 25° C. After 2 h, $NaBH(OAc)_3$ (122 mg, 0.58 mmol) was added. After another 16 h, the resulted mixture was purified by Prep-HPLC on a C18 column (20-35 μm, 100 A, 80 g) with mobile phase: $H_2O$ (0.1% TFA)/MeCN at flow rate: 30 mL/min to afford the desired product (176 mg, 0.25 mmol, 86.4% yield) as a white solid. LCMS calculated for $C_{31}H_{46}N_7O_3(M+H)^+$ m/z=564.4; found: 564.4.

Step 2: 2-((6aS)-8-([1,3'-bipiperidin]-4-ylmethyl)-6,6a, 7,8,9,1O-hexahydro-5H-pyrazino [1',2':4,5]pyrazino[2,3-c]pyridazin-2-yl)phenol

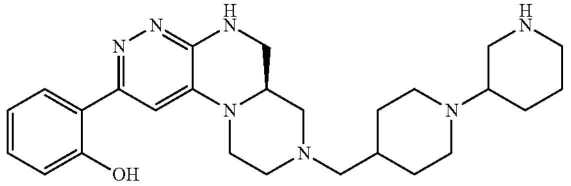 [SMILES: Oc1ccccc1-c1cc2c(nn1)NC[C@H]1CN(CC3CCN(C4CCCNC4)CC3)CCN21]

To a stirred solution of tert-butyl 4-(((S)-2-(2-hydroxyphenyl)-5,6,6a,7,9,10-hexahydro-8H-pyrazino[1',2':4,5]pyrazino[2,3-c]pyridazin-8-yl)methyl)-[1,3'-bipiperidine]-1'-carboxylate (176 mg, 0.25 mmol) in MeOH (2 mL) was added HCl in MeOH (4 M, 0.62 mL, 2.50 mmol) at 10° C. After 20 h, the volatiles were removed and the residue was purified by Prep-HPLC on a C18 column (20-35 μm, 100 A, 80 g) with mobile phase: $H_2O$ (0.1% TFA)/MeCN at flow rate: 30 mL/min to afford the desired product (22 mg, 0.033 mmol, 13.3% yield) as a white solid. LCMS calculated for $C_{26}H_{38}N_7O$ $(M+H)^+$ m/z=464.3; found: 464.4.

Step 3: 2-(2,6-dioxopiperidin-3-yl)-5-(4-(((S)-2-(2-hydroxyphenyl)-5,6,6a, 7,9,10-hexahydro-8H-pyrazino[1',2':4,5]pyrazino[2,3-c]pyridazin-8-yl)methyl)-[1,3'-bipiperidin]-1'-yl) isoindoline-1,3-dione To a stirred solution of 2-((6aS)-8-([1,3'-bipiperidin]-4-ylmethyl)-6,6a,7,8,9,10-hexahydro-5H-pyrazino[1',2':4,5]pyrazino[2,3-c]pyridazin-2-yl)phenol (22.0 mg, 0.05 mmol), and 2-(2,6-dioxopiperidin-3-yl)-5-fluoroisoindole-1,3-dione (15.9 mg, 0.06 mmol) in DMSO (0.20 mL), were added TEA (0.05 mL, 0.33 mmol) and $K_2CO_3$ (13.1 mg, 0.09 mmol) at rt. The resulted mixture was stirred at 130° C. for 1 h in a microwave reactor. The reaction mixture was purified by Prep-HPLC on a C18 column (20-35 μm, 100 A, 80 g) with mobile phase: $H_2O$ (0.1% $NH_4HCO_3$)/MeCN at flow rate: 30 mL/min to afford the desired product (1.1 mg, 0.0013 mmol, 2.800 yield) as a white solid. LCMS calculated for $C_{39}H_{46}N_9O_5$ (M+H) m/z=720.4; found: 720.2.

Examples 88-91, 147-152, 156, 157, 189, 190, 197 and 198

Examples in Table 26 were prepared using the procedure described in the synthesis of Example 218 with appropriate intermediates.

TABLE 26

| Ex | Structure/Name | Calcd. (M + H)+ m/z | Found (M + H)+ m/z |
|---|---|---|---|
| 88 | 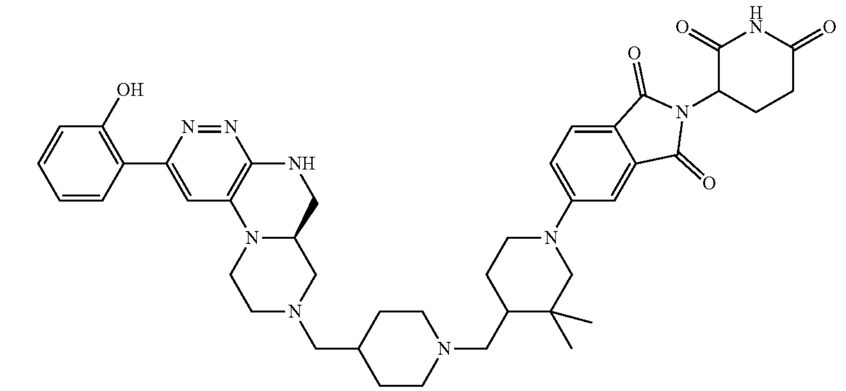 [SMILES: CC1(C)CN(c2ccc3c(c2)C(=O)N(C2CCC(=O)NC2=O)C3=O)CCC1CN1CCC(CN2CCN3c4cc(-c5ccccc5O)nnc4NC[C@H]3C2)CC1] 2-(2,6-dioxopiperidin-3-yl)-5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)-3,3-dimethylpiperidin-1-yl)isoindoline-1,3-dione $^1$H NMR (DMSO-d$_6$, 400 MHz): δ7.66-7.64 (m, 1H), 7.58-7.56 (m, 1H), 7.46-7.44(m, 1H), 7.35-7.34 (m, 2H), 7.23-7.21 (m, 1H), 7.07-7.03 (m, 2H), 5.08-5.04 (m, 1H), 4.85-4.70 (m, 1H), 4.25-4.23 (m, 1H), 4.11-4.08 (m, 1H), 3.85-3.71 (m,6H), 3.68-3.66 (m, 1H), 3.49-3.47 (m, 2H), 3.04-2.66 (m, 9H), 2.48-1.62 (m, 11H), 1.15-1.12 (m, 3H), 0.95-0.92 (m, 3H). | 761.4 | 761.3 |
| 89 | 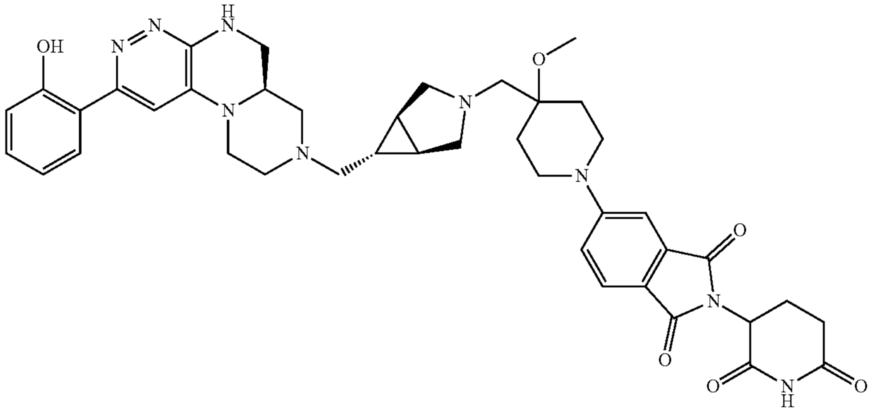 [SMILES: COC1(CN2C[C@@H]3[C@@H](CN4CCN5c6cc(-c7ccccc7O)nnc6NC[C@H]5C4)[C@@H]3C2)CCN(c2ccc3c(c2)C(=O)N(C2CCC(=O)NC2=O)C3=O)CC1] 2-(2,6-dioxopiperidin-3-yl)-5-(4-(((1R,5S,6s)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)-4-methoxypiperidin-1-yl)isoindoline-1,3-dione $^1$H NMR (DMSO-d$_6$, 400 MHz): δ 11.06 (s, 1H), 8.15 (s, 1H), 7.92-7.89 (m, 1H), 7.71-7.69 (m, 1H), 7.33 (s, 1H), 7.22-7.18 (m, 2H), 7.09-7.08 (m, 1H), 7.01 (m, 1H), 6.88-6.83 (m, 2H), 5.08-5.04 (m, 1H), 4.05-4.02 (m, 1H), 3.70-3.59 (m, 3H), 3.07-2.82 (m, 9H), 2.61-2.58 (m, 1H), 2.43-2.42 (m, 1H), 2.24-1.92 (m, 3H), 1.74-1.36 (m, 2H), 1.23-1.14 (m, 5H), 0.97-0.89 (m, 1H). | 762.4 | 762.3 |

Examples 88-91, 147-152, 156, 157, 189, 190, 197 and 198

TABLE 26-continued

| Ex | Structure/Name | Calcd. (M + H)+ m/z | Found (M + H)+ m/z |
|---|---|---|---|
| 90 | 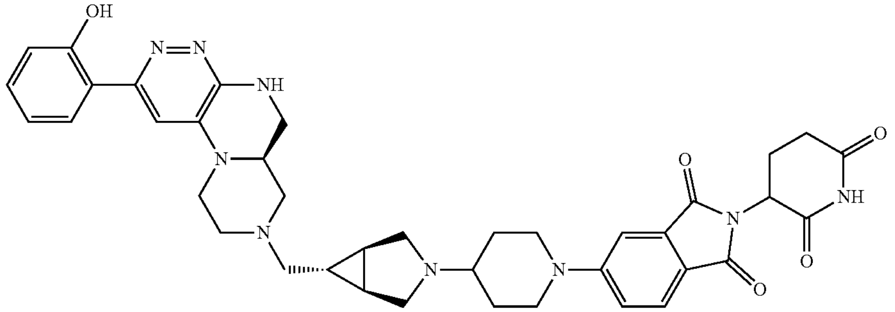 [SMILES: O=C1CCC(N2C(=O)c3ccc(N4CCC(N5C[C@@H]6[C@@H](CN7CCN8c9cc(-c%10ccccc%10O)nnc9NC[C@H]8C7)[C@@H]6C5)CC4)cc3C2=O)C(=O)N1] 2-(2,6-dioxopiperidin-3-yl)-5-(4-((1R,5S,6s)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)piperidin-1-yl)isoindoline-1,3-dione<br>$^1$H NMR (400 MHz, MeOD) δ 7.75 (d, J = 6.9 Hz, 1H), 7.68 (d, J = 8.5 Hz, 1H), 7.36 (d, J = 2.2 Hz, 1H), 7.23 (d, J = 6.7 Hz, 2H), 7.17 (s, 1H), 6.89 (d, J = 8.2 Hz, 2H), 5.06 (dd, J = 12.4, 5.4 Hz, 1H), 4.06-3.95 (m, 3H), 3.58 (dd, J = 11.5, 3.3 Hz, 1H), 3.36 (d, J = 9.9 Hz, 2H), 3.04 (s, 5H), 2.74 (d, J = 16.1 Hz, 6H), 2.39 (d, J = 6.7 Hz, 3H), 2.12-1.91 (m, 4H), 1.55 (s, 4H), 1.28 (s, 3H). | 718.3 | 718.3 |
| 91 | 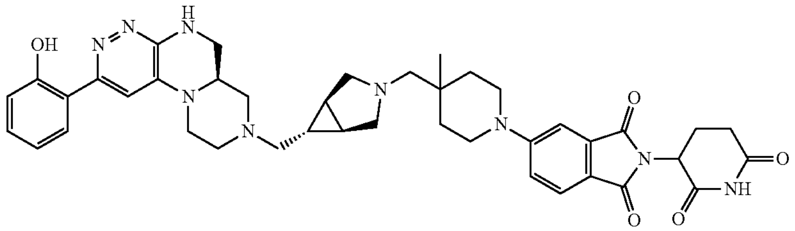 [SMILES: CC1(CN2C[C@@H]3[C@@H](CN4CCN5c6cc(-c7ccccc7O)nnc6NC[C@H]5C4)[C@@H]3C2)CCN(c2ccc3c(c2)C(=O)N(C2CCC(=O)NC2=O)C3=O)CC1] 2-(2,6-dioxopiperidin-3-yl)-5-(4-(((1R,5S,6r)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)-4-methylpiperidin-1-yl)isoindoline-1,3-dione<br>$^1$H NMR (400 MHz, DMSO-$d_6$) δ 11.06 (s, 1H), 8.45 (s, 3H), 7.91 (d, J = 8.3 Hz, 1H), 7.65 (d, J = 8.6 Hz, 1H), 7.36-7.14 (m, 5H), 6.84 (d, J = 8.1 Hz, 2H), 5.05 (dd, J = 12.9, 5.4 Hz, 1H), 4.03 (d, J = 12.0 Hz, 1H), 3.63 (s, 2H), 3.02 (dd, J = 18.9, 11.0 Hz, 6H), 2.88 (d, J = 12.4 Hz, 4H), 2.27 (dd, J = 38.2, 8.3 Hz, 4H), 2.14-1.93 (m, 3H), 1.75 (t, J = 10.6 Hz, 1H), 1.48 (s, 3H), 1.36-1.13 (m, 8H), 1.08 (s, 1H), 0.94 (s, 3H). | 745.4 | 745.4 |
| 147 | 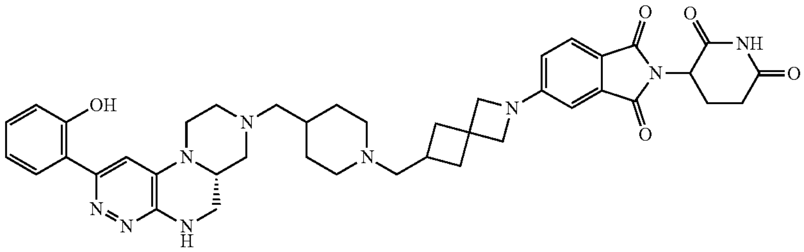 [SMILES: O=C1CCC(N2C(=O)c3ccc(N4CC5(CC(CN6CCC(CN7CCN8c9cc(-c%10ccccc%10O)nnc9NC[C@H]8C7)CC6)C5)C4)cc3C2=O)C(=O)N1] 2-(2,6-dioxopiperidin-3-yl)-5-(6-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)-2-azaspiro[3.3]heptan-2-yl)isoindoline-1,3-dione<br>$^1$H NMR ($CD_3OD$-$d_4$, 400 MHz): δ 7.63-7.64 (m, 1H), 7.55-7.57 (m, 1H), 7.43-7.47 (m, 1H), 7.27 (m, 1H), 7.05-7.06 (m, 2H), 6.80 (s, 1H), 6.63-6.65 (m, 1H), 5.05-5.08 (m, 2H), 4.32-4.35 (m, 1H), 4.15 (s, 2H), 3.96 (s, 3H), 3.73-3.76 (m,1H), 3.57 (s, 5H), 3.39-3.41 (m, 2H), 3.23-3.27 (m, 2H), 3.02 (s, 3H), 2.78-2.90 (m, 2H), 2.68-2.74 (m, 4H), 2.54 (s, 2H), 2.15-2.18 (m, 5H). | 745.4 | 745.3 |

Examples 88-91, 147-152, 156, 157, 189, 190, 197 and 198

TABLE 26-continued

| Ex | Structure/Name | Calcd. (M + H)+ m/z | Found (M + H)+ m/z |
|---|---|---|---|
| | Examples 88-91, 147-152, 156, 157, 189, 190, 197 and 198 | | |
| 148 | 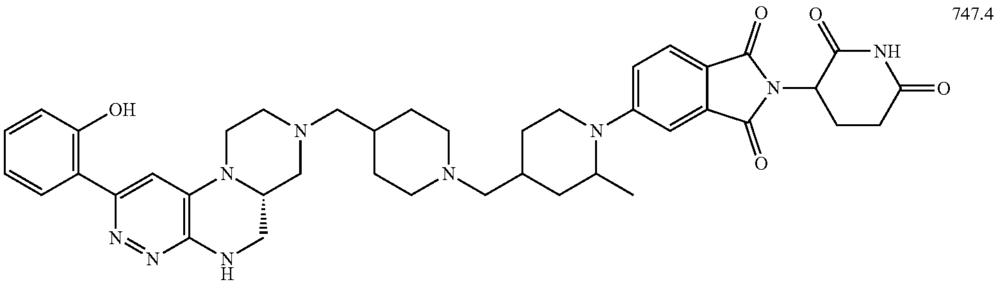<br>2-(2,6-dioxopiperidin-3-yl)-5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)-2-methylpiperidin-1-yl)isoindoline-1,3-dione<br>$^1$H NMR (CD3OD-$d_4$, 400 MHz): δ 7.68-7.70 (m, 1H), 7.56-7.58 (m, 1H), 7.25-7.46 (m, 4H), 7.03-7.07 (m, 2H), 5.05-5.09 (m, 2H), 3.67-4.53 (m,7H), 3.40-3.48 (m, 3H), 3.07-3.24 (m, 8H), 2.70-2.87 (m, 3H), 1.65-2.60 (m, 11H), 1.19-1.43 (m, 7H). | 747.4 | 747.3 |
| 149 | 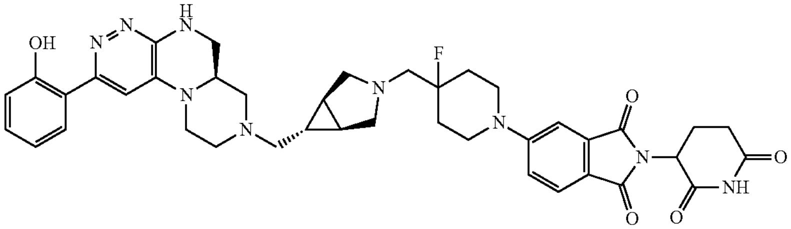 [SMILES: O=C1CCC(N2C(=O)c3ccc(N4CCC(F)(CN5C[C@@H]6[C@@H](CN7CCN8c9cc(-c%10ccccc%10O)nnc9NC[C@H]8C7)[C@@H]6C5)CC4)cc3C2=O)C(=O)N1]<br>2-(2,6-dioxopiperidin-3-yl)-5-(4-fluoro-4-(((1R,5S,6s)-6-(((S)-2-(2-hydroxyphenyl)-5,6,6a,7,9,10-hexahydro-8H-pyrazino [1',2':4,5]pyrazino[2,3-c]pyridazin-8-yl)methyl)-3-azabicyclo[3.1.0]hexan-3-yl)methyl)piperidin-1-yl)isoindoline-1,3-dione<br>$^1$H NMR ($CDCl_3$, 400 MHz): δ7.68-7.70 (m, 1H), 7.56-7.58 (m, 1H), 7.28-7.58 (m, 2H), 7.02-7.07 (m, 2H), 6.86-6.93 (m, 2H), 4.91-4.95 (m, 1H), 3.74-3.78 (m, 3H), 3.53-3.56 (m, 2H), 3.32-3.39 (m, 2H), 3.07-3.15 (m, 3H), 2.84-2.85 (m,2H), 2.64 (s, 1H), 2.58 (s, 1H), 2.49-2.52 (m, 2H), 2.34 (s, 2H), 2.11-2.14 (m, 2H), 1.93-1.97 (m, 3H), 1.58-1.75 (m,6H), 1.26 (s,3H). | 750.3 | 750.3 |
| 150 | 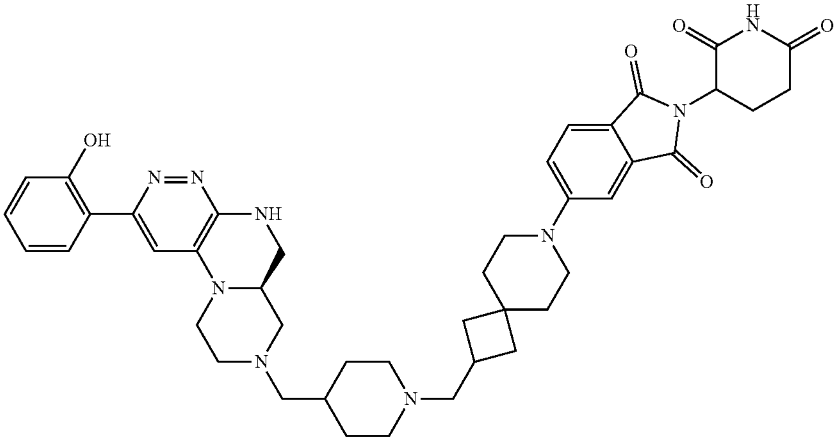 [SMILES: O=C1CCC(N2C(=O)c3ccc(N4CCC5(CC4)CC(CN4CCC(CN6CCN7c8cc(-c9ccccc9O)nnc8NC[C@H]7C6)CC4)C5)cc3C2=O)C(=O)N1]<br>2-(2,6-dioxopiperidin-3-yl)-5-(2-((4-(((S)-2-(2-hydroxyphenyl)-5,6,6a,7,9,10-hexahydro-8H-pyrazino[1',2':4,5]pyrazino[2,3-c]pyridazin-8-yl) methyl)piperidin-1-yl)methyl)-7-azaspiro[3.5]nonan-7-yl)isoindoline-1,3-dione<br>$^1$H NMR (400 MHz, MeOD) δ 7.65 (d, J = 8.6 Hz, 1H), 7.52 (d, J = 7.2 Hz, 1H), | 774.0 | 774.0 |

TABLE 26-continued

| Examples 88-91, 147-152, 156, 157, 189, 190, 197 and 198 | | | |
|---|---|---|---|
| Ex | Structure/Name | Calcd. (M + H)$^+$ m/z | Found (M + H)$^+$ m/z |
| | 7.42 (t, J = 7.6 Hz, 1H), 7.33 (s, 1H), 7.21 (d, J = 8.4 Hz, 2H), 7.03 (t, J = 8.2 Hz, 2H), 5.06 (dd, J = 12.5, 5.6 Hz, 1H), 4.21 (s, 1H), 3.87-3.36 (m, 12H), 3.23 (d, J = 6.8 Hz, 2H), 3.00-2.59 (m, 8H), 2.26-1.97 (m, 7H), 1.87-1.60 (m, 7H), 1.49 (s, 2H). | | |
| 151 | 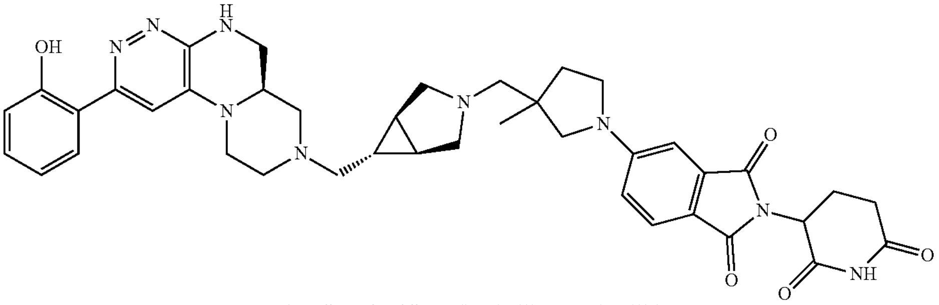 [SMILES: CC1(CN2C[C@@H]3[C@@H](CN4CCN5c6cc(-c7ccccc7O)nnc6NC[C@H]5C4)[C@@H]3C2)CCN(c2ccc3c(c2)C(=O)N(C2CCC(=O)NC2=O)C3=O)C1] 2-(2,6-dioxopiperidin-3-yl)-5-(3-(((1R,5S,6r)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)-3-methylpyrrolidin-1-yl)isoindoline-1,3-dione $^1$H NMR ($CD_3OD$, 400 MHz): δ 14.81(s, 1H), 11.05 (s, 1H), 7.92-7.90 (m, 1H), 7.64-7.62 (m, 1H), 7.34 (s, 1H), 7.22-7.20 (m, 2H), 6.89-6.83 (m, 4H), 5.06-5.01 (m, 1H), 4.06-4.01 (m, 1H), 3.47-3.44 (m, 3H),3.22 (m,1H), 3.19-3.16 (m, 2H), 3.07-3.01(m, 3H), 2.89-2.56 (m, 2H), 2.67 (m, 1H), 2.32 (m, 1H), 2.28-2.22 (m, 2H). 2.1-2.09 (m, 1H), 2.0-1.98 (m, 1H), 1.90-1.87 (m, 1H), 1.77-1.72 (m, 2H), 1.23 (s, 5H), 1.14-1.12 (m, 1H), 1.05 (m, 3H). | 732.4 | 732.4 |
| 152 | 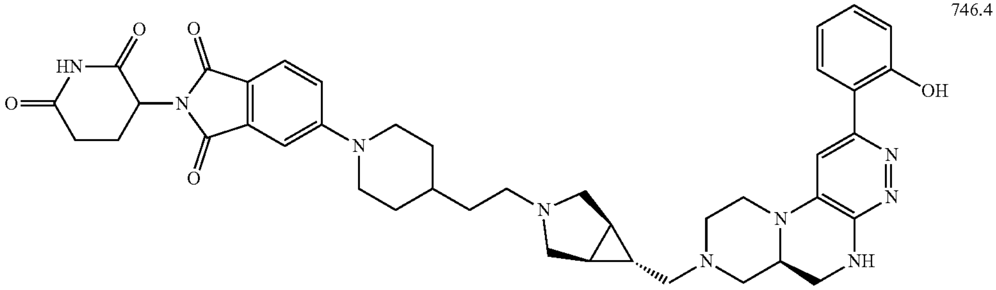 2-(2,6-dioxopiperidin-3-yl)-5-(4-(2-((1R,5S,6r)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)ethyl)piperidin-1-yl)isoindoline-1,3-dione $^1$H NMR (400 MHz, DMSO-$d_6$) δ 14.75 (s, 1H), 11.07 (s, 1H), 7.91 (d, J = 7.0 Hz, 1H), 7.64 (d, J = 8.5 Hz, 1H), 7.35 (d, J = 3.0 Hz, 1H), 7.29 (s, 1H), 7 23-7.17 (m, 3H), 6.87-6.83 (m, 2H), 5.06 (dd, J = 12.8, 5.4 Hz, 1H), 4.02 (d, J = 12.4 Hz, 3H), 3.52-3.46 (m, 1H), 3.24-2.87 (m, 10H), 2.54 (s, 2H), 2.40 (s, 2H), 2.23-2.02 (m, 5H), 1.75 (t, J = 11.0 Hz, 3H), 1.57 (s, 1H), 1.34 (d, J = 6.9 Hz, 2H), 1.17 (dd, J = 24.4, 13.0 Hz, 6H). | 746.4 | 746.4 |
| 156 | 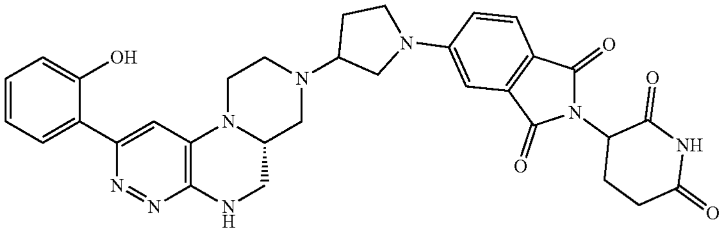 [SMILES: O=C1CCC(N2C(=O)c3ccc(N4CCC(N5CCN6c7cc(-c8ccccc8O)nnc7NC[C@H]6C5)C4)cc3C2=O)C(=O)N1] 2-(2,6-dioxopiperidin-3-yl)-5-(3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)isoindoline-1,3-dione | 609.3 | 609.3 |

TABLE 26-continued

| Ex | Structure/Name | Calcd. (M + H)+ m/z | Found (M + H)+ m/z |
|---|---|---|---|
| 157 | 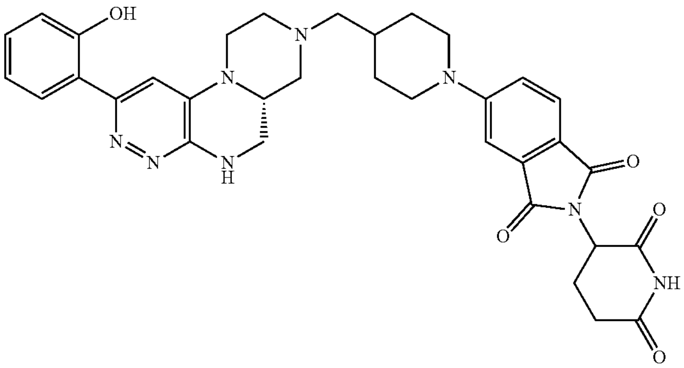 [SMILES: O=C1CCC(N2C(=O)c3ccc(N4CCC(CN5CCN6c7cc(-c8ccccc8O)nnc7NC[C@H]6C5)CC4)cc3C2=O)C(=O)N1] 2-(2,6-dioxopiperidin-3-yl)-5-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)isoindoline-1,3-dione | 637.3 | 637.4 |
| 189 | 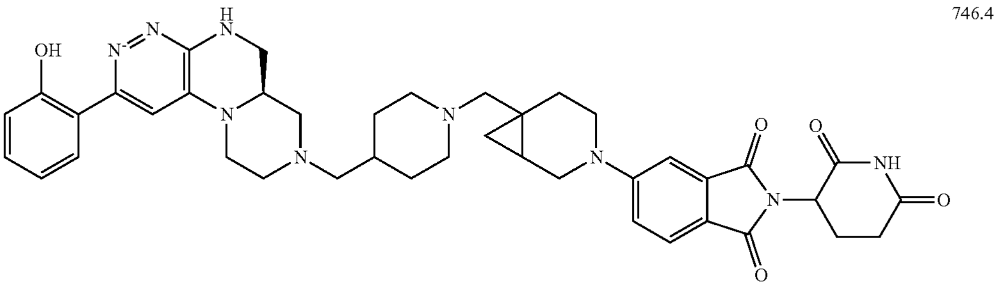 2-(2,6-dioxopiperidin-3-yl)-5-[6-[[4-[[(10S)-4-(2-hydroxyphenyl)-1,5,6,8,12-pentazatricyclo [8.4.0.02,7]tetradeca-2(7),3,5-trien-12-yl]methyl] piperidin-1-yl]methyl]-3-azabicyclo[4.1.0]heptan-3-yl]isoindole-1,3-dione | 746.4 | 746.4 |
| 190 | 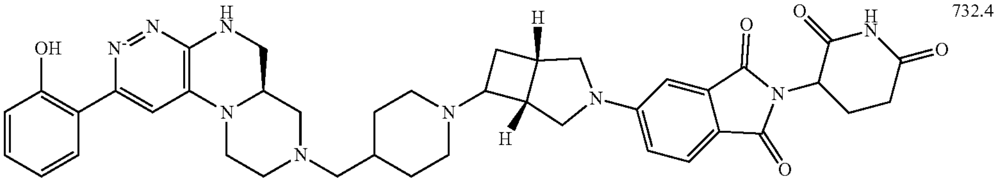 2-(2,6-dioxopiperidin-3-yl)-5-[(1S,5R)-6-[4-[[(10S)-4-(2-hydroxyphenyl)-1,5,6,8,12-pentazatricyclo [8.4.0.02,7]tetradeca-2(7),3,5-trien-12-yl]methyl] piperidin-1-yl]-3-azabicyclo[3.2.0]heptan-3-yl]isoindole-1,3-dione | 732.4 | 732.3 |
| 197 | 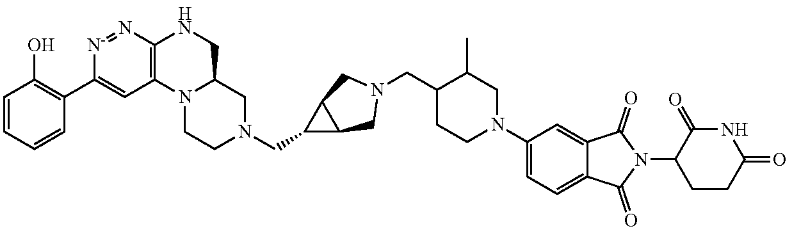 2-(2,6-dioxopiperidin-3-yl)-5-(4-(((1R,5S,6r)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)-3-methylpiperidin-1-yl)isoindoline-1,3-dione | 746.4 | 746.4 |

TABLE 26-continued

| Examples 88-91, 147-152, 156, 157, 189, 190, 197 and 198 | | | |
|---|---|---|---|
| Ex | Structure/Name | Calcd. (M + H)+ m/z | Found (M + H)+ m/z |
| 198 | 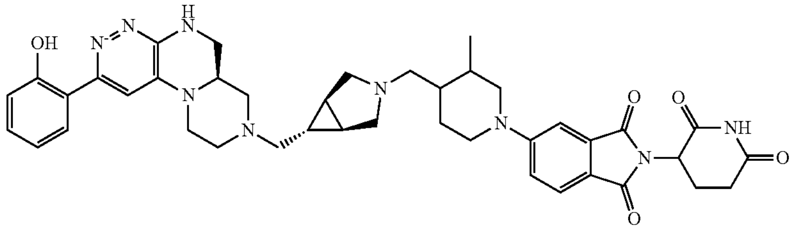 2-(2,6-dioxopiperidin-3-yl)-5-(4-(((1R,5S,6r)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)-3-methylpiperidin-1-yl)isoindoline-1,3-dione | 746.4 | 746.3 |

Example 219: 2-(2,6-dioxopiperidin-3-yl)-5-((2-(4-((S)-2-(2-hydroxyphenyl)-6,6a,7,8,9,10-hexahydro-511-pyrazino[1',2':4,5]pyrazino[2,3-c]pyridazine-8-carbonyl)piperazin-1-yl)ethyl)amino) isoindoline-1,3-dione Ex. 219

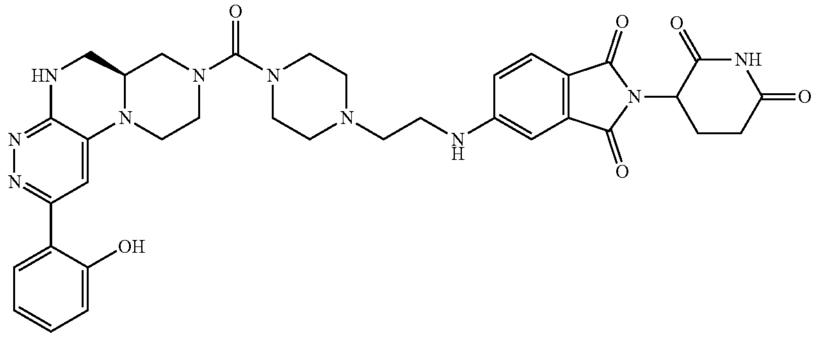

Step 1: tert-butyl 4-(2-((2-(2,6-dioxopiperidin-3-yl)-1,3-dioxoisoindolin-5-yl)amino)ethyl) piperazine-1-carboxylate

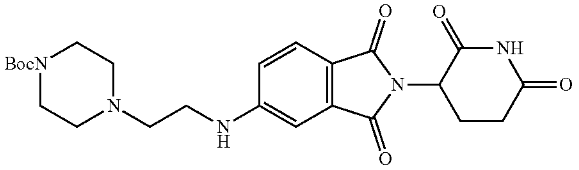 [SMILES: CC(C)(C)OC(=O)N1CCN(CCNc2ccc3c(c2)C(=O)N(C2CCC(=O)NC2=O)C3=O)CC1]

To a mixture of 2-(2,6-dioxopiperidin-3-yl)-5-fluoroisoindole-1,3-dione (220 mg, 0.80 mmol) in NMP (4 mL) were added tert-butyl 4-(2-aminoethyl)tetrahydro-1-(2H)-pyrazinecarboxylate (219 mg, 0.96 mmol) and DIPEA (0.39 mL, 2.39 mmol). The mixture was stirred at 140° C. for 1 h in microwave reactor. The resulted solution was purified by Prep-HPLC on a C18 column (20-35 μm, 100 A, 80 g) with mobile phase: $H_2O$ (0.1% TFA)/MeCN at flow rate: 30 mL/min to afford the desired product (500 mg, 0.79 mmol, 99.6% yield). LCMS calculated for $C_{24}H_{32}N_5O_6$ $(M+H)^+$ m/z=486.2; found: 486.2.

Step 2: 2-(2,6-dioxopiperidin-3-yl)-5-(2-piperazin-1-ylethylamino) isoindole-1,3-dione

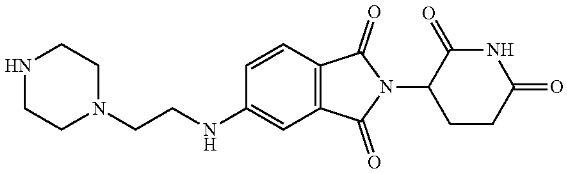 [SMILES: O=C1CCC(N2C(=O)c3ccc(NCCN4CCNCC4)cc3C2=O)C(=O)N1]

To a mixture of tert-butyl 4-(2-((2-(2,6-dioxopiperidin-3-yl)-1,3-dioxoisoindolin-5-yl)amino)ethyl)piperazine-1-carboxylate (500 mg, 1.03 mmol) in 1,4-dioxane (4 mL) was added HCl/dioxane (4 M) (2.57 mL, 10.3 mmol). The mixture was stirred at 10° C. for 20 h. The volatiles were removed under reduced pressure to afford 2-(2,6-dioxopiperidin-3-yl)-5-(2-piperazin-1-ylethylamino) isoindole-1,3-dione as its HCl salt (419 mg, 0.76 mmol, 73.9% yield). LCMS calculated for $C_{19}H_{24}N_5O_4$ $(M+H)^+$ m/z=386.0; found: 386.0.

Step 3: 2-(2,6-dioxopiperidin-3-yl)-5-((2-(4-((S)-2-(2-hydroxyphenyl)-6,6a, 7,8,9,10-hexahydro-5H-pyrazino[1',2':4,5]pyrazino[2,3-c]pyridazine-8-carbonyl)piperazin-1-yl)ethyl)amino) isoindoline-1,3-dione To a stirred solution of (R)-2-(6,6a,7,8,9,10-hexahydro-5H-pyrazino[1',2':4,5]pyrazino[2,3-c]pyridazin-2-yl)phenol (50.0 mg, 0.18 mmol) in DCM (3 mL) and DMF (1 mL) were added DIPEA (0.06 mL, 0.35 mmol) and triphosgene (26.2 mg, 0.09 mmol) at 0° C. After 2 h. 2-(2,6-Dioxopiperidin-3-yl)-5-(2-piperazin-1-ylethylamino) isoindole-1,3-dione (68.0 mg, 0.18 mmol) was added. The resulted mixture was warmed up to rt and stirred overnight. The reaction mixture was purified by Prep-HPLC on a C18 column (20-35 μm, 100 A, 80 g) with mobile phase: $H_2O$ (0.1% $NH_4HCO_3$)/MeCN at flow rate: 30 mL/min to afford the desired product (3.9 mg, 0.0044 mmol, 2.5% yield) as a white solid. LCMS calculated for $C_{35}H_{39}N_{10}O_6$ $(M+H)^+$ m/z=695.2; found: 695.0.

Example 220: 2-(2,6-dioxopiperidin-3-yl)-5-((2-((4-((S)-2-(2-hydroxyphenyl)-5,6,6a,7,9,10-hexahydro-8H-pyrazino[1',2':4,5]pyrazino[2,3-c]pyridazin-8-yl)cyclohexyl)(methyl) amino)ethyl)amino) isoindoline-1,3-dione A mixture of 2-(2,6-dioxopiperidin-3-yl)-5-fluoroisoindole-1,3-dione (500 mg, 1.81 mmol), DIPEA (0.45 mL, 3.62 mmol) and tert-butyl N-(2-aminoethyl)-N-methylcarbamate (347 mg, 1.99 mmol) in NMP (5 mL) was stirred at 120° C. under microwave irradiation for 1 h. The mixture was purified by Prep-HPLC on a C18 column (20-35 uM, 100 A, 80 g) with mobile phase: $H_2O$ (0.1% $NH_4HCO_3$)/MeCN at flow rate: 50 mL/min to afford 2-(2,6-dioxopiperidin-3-yl)-5-[2-(methylamino)ethylamino] isoindole-1,3-dione (260 mg, 0.79 mmol, 43.5% yield) as a yellow solid. LCMS calculated for $C_{16}H_{19}N_4O_4$ $(M+H)^+$ m/z=331.1; found: 331.2.

Step 2: (S)-2-(8-(1,4-dioxaspiro[4.5]decan-8-yl)-6,6a, 7,8,9,10-hexahydro-5H-pyrazino[1',2':4,5]pyrazino[2,3-c]pyridazin-2-yl)phenol

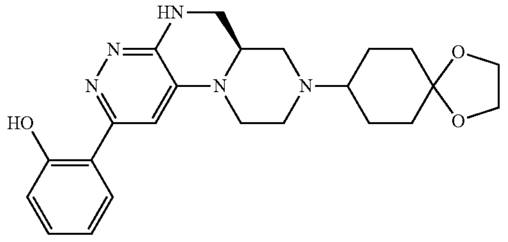

Ex. 220

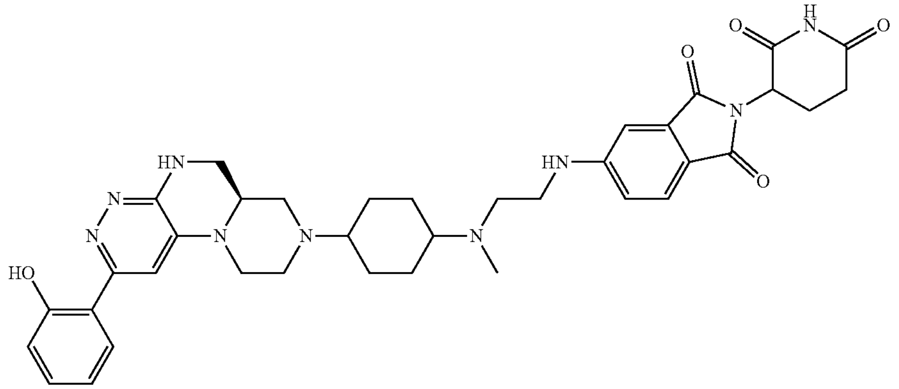

Step 1: 2-(2,6-dioxopiperidin-3-yl)-5-((2-(methylamino)ethyl)amino isoindoline-1,3-dione

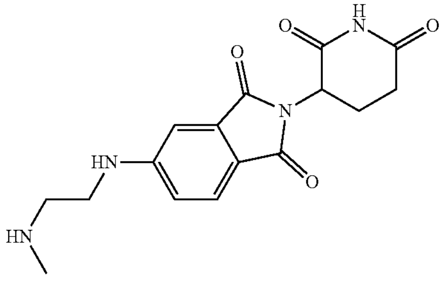 [SMILES: CNCCNc1ccc2c(c1)C(=O)N(C1CCC(=O)NC1=O)C2=O]

To a stirred solution of (R)-2-(6,6a,7,8,9,10-hexahydro-5H-pyrazino[1',2':4,5]pyrazino [2,3-c]pyridazin-2-yl) phenol hydrochloride (35 mg, 0.11 mmol) and 1,4-dioxaspiro[4,5]decan-8-one (34 mg, 0.22 mmol) in DMF (5 mL) was added acetic acid (0.02 mL, 0.36 mmol) at rt. After 2 h, sodium triacetoxyborohydride (116 mg, 0.55 mmol) was added. The resulted mixture was stirred at rt overnight. The volatiles were removed under reduced pressure and the residue was purified by Prep-HPLC on a C18 column (20-35 μm, 100 A, 40 g) with mobile phase: $H_2O$ (0.1% $NH_4HCO_3$)/MeCN at flow rate: 30 mL/min to afford the desired product (40 mg, 0.094 mmol, 86.3% yield) as a white solid. LCMS calculated for $C_{23}H_{30}N_5O_3$ $(M+H)^+$ m/z=424.2; found: 424.0.

Step 3: (S)-4-(2-(2-hydroxyphenyl)-5,6,6a, 7,9,10-hexahydro-8H-pyrazino[1',2':4,5]pyrazino[2,3-c]pyridazin-8-yl)cyclohexan-1-one

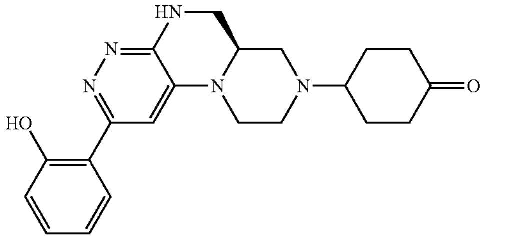 [SMILES: O=C1CCC(N2CCN3c4cc(-c5ccccc5O)nnc4NC[C@H]3C2)CC1]

To a mixture of (S)-2-(8-(1,4-dioxaspiro[4.5]decan-8-yl)-6,6a,7,8,9,10-hexahydro-5H-pyrazino[1',2':4,5]pyrazino[2,3-c]pyridazin-2-yl)phenol (40 mg, 0.09 mmol) in water (5 mL) was added formic acid (1.74 g, 37.8 mmol). The mixture was stirred at 90° C. for 18 h. The volatiles were removed to afford the crude product (35.0 mg, 0.092 mmol, 97.7% yield) as a brown oil. LCMS calculated for $C_{21}H_{26}N_5O_2$ $(M+H)^+$ m/z=380.2; found: 380.2.

Step 4: 2-(2,6-dioxopiperidin-3-yl)-5-((2-((4-((S)-2-(2-hydroxyphenyl)-5,6,6a, 7,9,10-hexahydro-8H-pyrazino[1',2':4,5]pyrazino[2,3-c]pyridazin-8-yl)cyclohexyl)(methyl)amino)ethyl) amino)isoindoline-1,3-dione To a stirred solution of (S)-4-(2-(2-hydroxyphenyl)-5,6,6a,7,9,10-hexahydro-8H-pyrazino[1',2':4,5]pyrazino[2,3-c]pyridazin-8-yl)cyclohexan-1-one (20.0 mg, 0.05 mmol) and 2-(2,6-dioxopiperidin-3-yl)-5-((2-(methylamino)ethyl)amino) isoindoline-1,3-dione (17 mg, 0.05 mmol) in DMF (5 mL) was added acetic acid (0.02 mL, 0.26 mmol) at rt. After 2 h, sodium triacetoxyborohydride (34 mg, 0.16 mmol) was added. After another 16 h, the mixture was purified by Prep-HPLC on a C18 column (20-35 μm, 100 A, 40 g) with mobile phase: $H_2O$ (0.1% $NH_4HCO_3$)/MeCN at flow rate: 30 mL/min to afford the desired product (0.8 mg, 0.001 mmol, 2.0% yield) as a white solid. LCMS calculated for $C_{37}H_{44}N_9O_5$ $(M+H)^+$ m/z=694.3; found: 694.2.

Example 68

The example in Table 27 was prepared using the procedure described in the synthesis of Example 220 with appropriate intermediates.

TABLE 27

Example 68

| Ex | Structure/Name | Calcd. $(M + H)^+$ m/z | Found $(M + H)^+$ m/z |
|---|---|---|---|
| 168 | 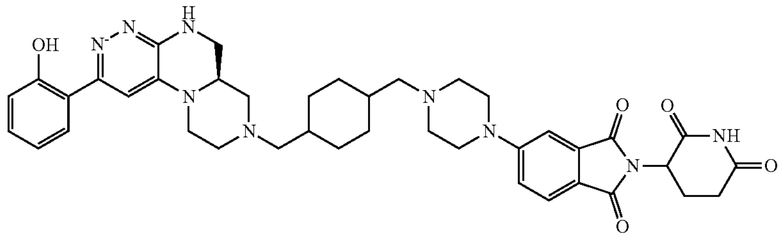 2-(2,6-dioxopiperidin-3-yl)-5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)cyclohexyl)methyl)piperazin-1-yl)isoindoline-1,3-dione | 734.4 | 734.3 |

Example 221: 2-(2,6-dioxopiperidin-3-yl)-5-(4-(1-(2-((S)-2-(2-hydroxyphenyl)-5,6,6a,7,9,10-hexahydro-8H-pyrazino[1',2':4,5]pyrazino[2,3-c]pyridazin-8-yl)ethyl)pyrrolidin-3-yl)piperazin-1-yl)isoindoline-1,3-dione Ex. 221

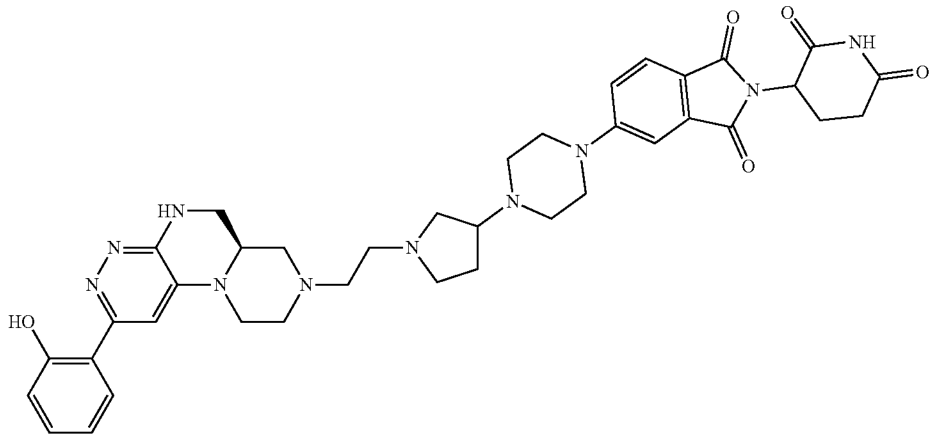

Step 1: tert-butyl 3-(4-(2-(2,6-dioxopiperidin-3-yl)-1,3-dioxoisoindolin-5-yl)piperazin-1-yl)pyrrolidine-1-carboxylate

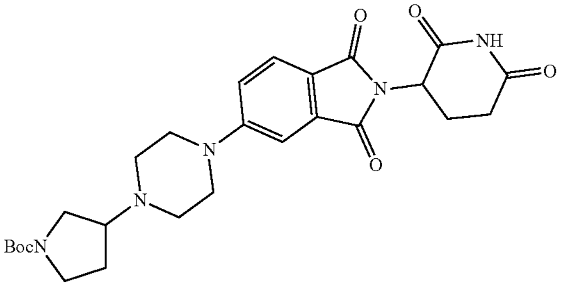 [SMILES: CC(C)(C)OC(=O)N1CCC(N2CCN(c3ccc4c(c3)C(=O)N(C3CCC(=O)NC3=O)C4=O)CC2)C1]

To a mixture of 2-(2,6-dioxopiperidin-3-yl)-5-piperazin-1-ylisoindole-1,3-dione (80.0 mg, 0.23 mmol), and Boc-3-pyrrolidinone (43.3 mg, 0.23 mmol) in DMF (1 mL), was added AcOH (0.07 mL, 1.17 mmol). The resulted mixture was stirred at 15° C. for 2 h. $NaBH(OAc)_3$ (99.0 mg, 0.47 mmol) was added. After 16 h, the reaction mixture was purified by Prep-HPLC on a C18 column (20-35 μm, 100 A, 80 g) with mobile phase: $H_2O$ (0.1% TFA)/MeCN at flow rate: 30 mL/min to afford the desired product (122 mg, 97.0% yield) as a white solid. LCMS calculated for $C_{26}H_{34}N_5O_6$ $(M+H)^+$ m/z=512.2; found: 412.1 (M+H−100).

Step 2: 2-(2,6-dioxopiperidin-3-yl)-5-(4-pyrrolidin-3-ylpiperazin-1-yl) isoindole-1,3-dione

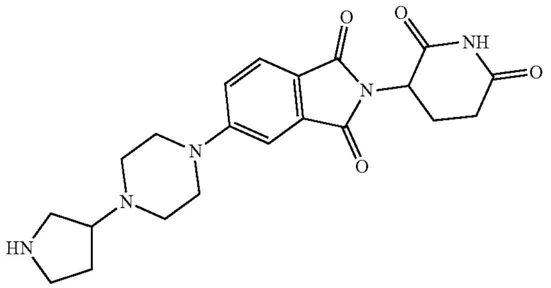 [SMILES: O=C1CCC(N2C(=O)c3ccc(N4CCN(C5CCNC5)CC4)cc3C2=O)C(=O)N1]

To a stirred solution of tert-butyl 3-(4-(2-(2,6-dioxopiperidin-3-yl)-1,3-dioxoisoindolin-5-yl)piperazin-1-yl)pyrrolidine-1-carboxylate (122 mg, 0.24 mmol) in DCM (2 mL), was added TFA (1.00 mL, 13.1 mmol) at 20° C. After 18 h, the volatiles were removed and the residue was purified by Prep-HPLC on a C18 column (20-35 μm, 100 A, 80 g) with mobile phase: $H_2O$ (0.1% TFA)/MeCN at flow rate: 30 mL/min to afford 2-(2,6-dioxopiperidin-3-yl)-5-(4-pyrrolidin-3-ylpiperazin-1-yl) isoindole-1,3-dione (94.0 mg, 96% yield) as a white solid. LCMS calculated for $C_{21}H_{26}N_5O_4$ $(M+H)^+$ m/z=412.2; found: 412.2.

Step 3: 2-(2,6-dioxopiperidin-3-yl)-5-(4-(1-(2-((S)-2-(2-hydroxyphenyl)-5,6,6a, 7,9,10-hexahydro-8H-pyrazino[1',2':4,5]pyrazino[2,3-c]pyridazin-8-yl)ethyl)pyrrolidin-3-yl)piperazin-1-yl) isoindoline-1,3-dione To a mixture of 1,2-dibromoethane (36.5 mg, 0.19 mmol) in DIPEA (0.02 mL, 0.15 mmol), was added a solution of 2-(2,6-dioxopiperidin-3-yl)-5-(4-pyrrolidin-3-ylpiperazin-1-yl) isoindole-1,3-dione (20.0 mg, 0.05 mmol) and (R)-2-(6,6a,7,8,9,10-hexahydro-5H-pyrazino[1',2':4,5]pyrazino

[2,3-c]pyridazin-2-yl)phenol (27.5 mg, 0.10 mmol) in DMF (0.40 mL). The resulted mixture was stirred at 70° C. for 1 h. The reaction mixture was purified by Prep-HPLC on a C18 column (20-35 μm, 100 A, 40 g) with mobile phase: $H_2O$ (0.1% TFA)/MeCN at flow rate: 30 mL/min to afford afford 2-(2,6-dioxopiperidin-3-yl)-5-[4-[1-[2-[(10S)-4-(2-hydroxyphenyl)-1,5,6,8,12-pentazatricyclo[8.4.0.02,7]tetradeca-2,4,6-trien-12-yl]ethyl]pyrrolidin-3-yl]piperazin-1-yl]isoindole-1,3-dione (2.00 mg, 5.6% yield). LCMS calculated for $C_{38}H_{45}N_{10}O_5$ $(M+H)^+$ m/z=721.4; found: 721.2.

Example 243

The example in Table 28 was prepared using the procedure described in the synthesis of Example 218 with appropriate intermediates.

TABLE 28

| Example 243 | | | |
|---|---|---|---|
| Ex | Structure/Name | Calcd. $(M + H)^+$ m/z | Found $(M + H)^+$ m/z |
| 243 | 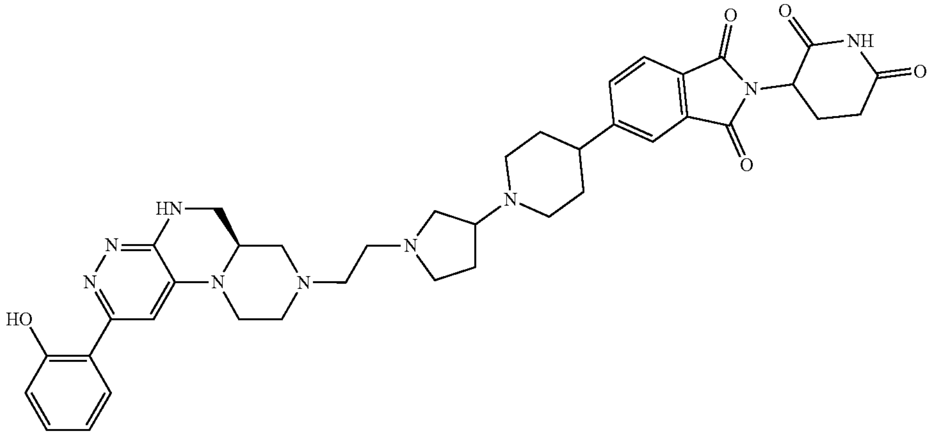 2-(2,6-dioxopiperidin-3-yl)-5-(1-(1-(2-((S)-2-(2-hydroxyphenyl)-5,6,6a,7,9,10-hexahydro-8H-pyrazino[1',2':4,5]pyrazino[2,3-c]pyridazin-8-yl)ethyl)pyrrolidin-3-yl)piperidin-4-yl)isoindoline-1,3-dione | 720.4 | 720.2 |

Example 222: 2-(2,6-dioxopiperidin-3-yl)-5-((2-(4-((S)-2-(2-hydroxyphenyl)-6,6a,7,8,9,10-hexahydro-5H-pyrazino[1',2':4,5]pyrazino[2,3-c]pyridazine-8-carbonyl)piperidin-1-yl)ethyl)(methyl)amino)isoindoline-1,3-dione Ex. 222

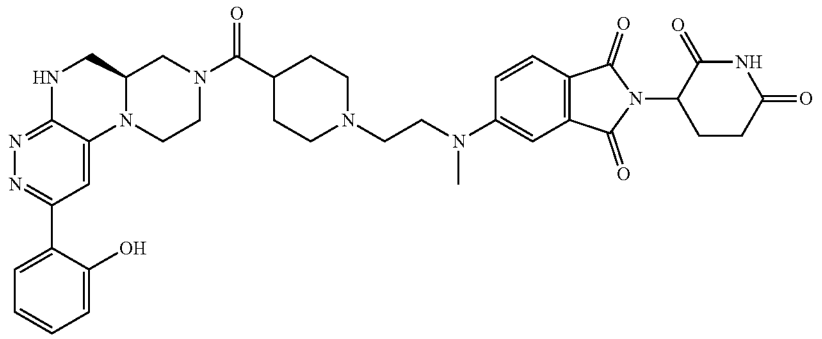

Step 1: 2-((2-(2,6-dioxopiperidin-3-yl)-1,3-dioxoisoindon-5-yl)(methyl)amino)ethyl 4-methylbenzenesulfonate

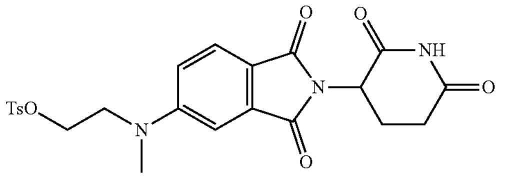 [SMILES: Cc1ccc(S(=O)(=O)OCCN(C)c2ccc3c(c2)C(=O)N(C2CCC(=O)NC2=O)C3=O)cc1]

A solution of 2-(2,6-dioxopiperidin-3-yl)-5-[2-hydroxyethyl(methyl)amino]isoindole-1,3-dione (100.0 mg, 0.30 mmol), tosyl chloride (63.3 mg, 0.33 mmol) and $Et_3N$ (0.13 mL, 0.91 mmol) in DCM (5 mL) was stirred at 25° C. overnight. The volatiles were removed and the residue was purified by Prep-HPLC on a C18 column (20-35 μm, 100 A, 80 g) with mobile phase: $H_2O$ (0.1% TFA)/MeOH at flow rate: 30 mL/min to afford the desired product (62.0 mg, 0.127 mmol, 42.3% yield) as a yellow solid. LCMS calculated for $C_{23}H_{24}N_3O_7S$ $(M+H)^+$ m/z=486.1; found: 486.2.

Step 2: 2-(2,6-dioxopiperidin-3-yl)-5-((2-(4-((S)-2-(2-hydroxyphenyl)-6,6a, 7,8,9,10-hexahydro-5H-pyrazino[1',2':4,5]pyrazino[2,3-c]pyridazine-8-carbonyl)piperidin-1-yl)ethyl)(methyl) amino) isoindoline-1,3-dione A mixture of 2-((2-(2,6-dioxopiperidin-3-yl)-1,3-dioxoisoindolin-5-yl)(methyl)amino) ethyl 4-methylbenzenesulfonate (80.0 mg, 0.16 mmol), DIEA (0.08 mL, 0.49 mmol) and KI (82.1 mg, 0.49 mmol) in DMF (2 mL) was stirred at 60° C. overnight. After being cooled down, (S)-(2-(2-hydroxyphenyl)-5,6,6a,7,9,10-hexahydro-8H-pyrazino[1',2':4,5]pyrazino[2,3-c]pyridazin-8-yl)(piperidin-4-yl)methanone (39.5 mg, 0.10 mmol) and DIEA (0.04 mL, 0.33 mmol) were added. Then the resulted mixture was stirred at 110° C. overnight. The reaction mixture was purified by Prep-HPLC on a C18 column (20-35 μm, 100 A, 80 g) with mobile phase: $H_2O$ (0.1% $NH_4HCO_3$)/MeCN at flow rate: 30 mL/min to afford the desired product (1.86 mg, 0.00263 mmol, 2.4% yield) as a yellow solid. LCMS calculated for $C_{37}H_{42}N_9O_6$ $(M+H)^+$ m/z=708.3; found: 708.1.

Examples 153, 224-229 and 245-247

Example in Table 29 were prepared using the procedure described in the synthesis of Example 222 with appropriate intermediates.

TABLE 29

Examples 153, 224-229 and 245-246, and 248

| Ex. | Structure/Name | Calcd. $(M + H)^+$ m/z | Found $(M + H)^+$ m/z |
|---|---|---|---|
| 153 | 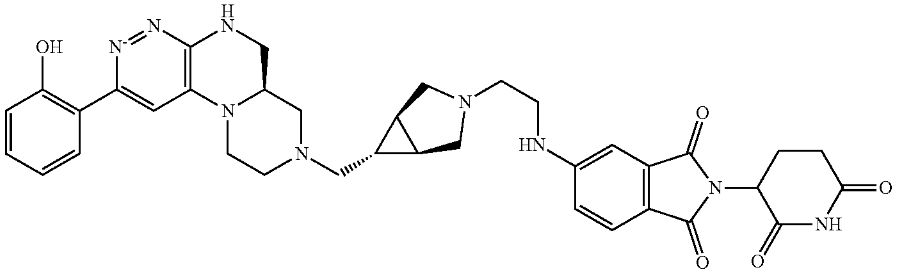 2-(2,6-dioxopiperidin-3-yl)-5-((2-((1R,5S,6r)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)ethyl)amino)isoindoline-1,3-dione $^1H$ NMR ($CD_3OD$, 400 MHz): δ 8.6-8.4 (m, 3H), 7.75 (s, 2H), 7.6 (m, 1H), 7.4-7.3 m, 4H), 7.0 (m, 2H), 6.15 (m, 1H), 4.55-4.5 (m, 3H), 4.2 (m, 1H), 3.9-3.7 (m, 4H), 3.6-3.3 (m, 18H), 3.0-2.8 (m, 4H), 2.75-2.25 (m, 8H). | 678.3 | 678.3 |

TABLE 29-continued

| Examples 153, 224-229 and 245-246, and 248 | | | |
|---|---|---|---|
| Ex. | Structure/Name | Calcd. (M + H)+ m/z | Found (M + H)+ m/z |
| 224 | 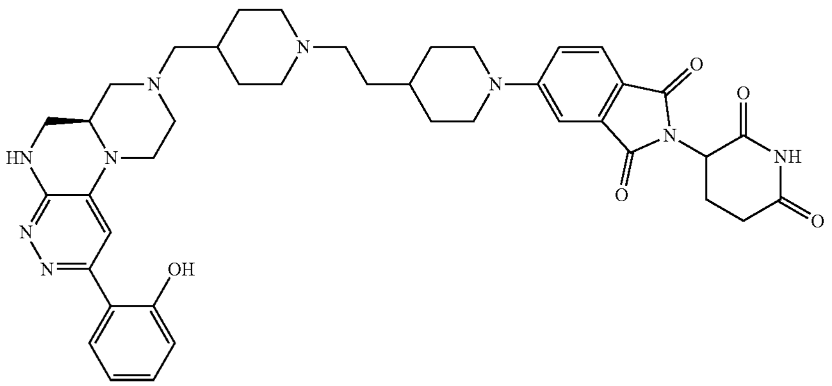 [SMILES: O=C1CCC(N2C(=O)c3ccc(N4CCC(CCN5CCC(CN6CCN7c8cc(-c9ccccc9O)nnc8NC[C@H]7C6)CC5)CC4)cc3C2=O)C(=O)N1] 2-(2,6-dioxopiperidin-3-yl)-5-(4-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethyl)piperidin-1-yl)isoindoline-1,3-dione | 748.4 | 748.2 |
| 225 | 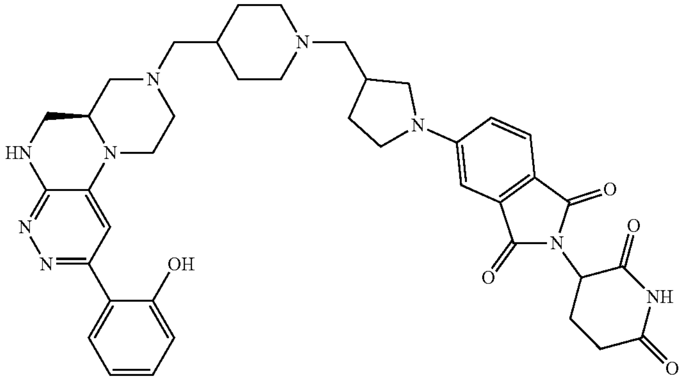 [SMILES: O=C1CCC(N2C(=O)c3ccc(N4CCC(CN5CCC(CN6CCN7c8cc(-c9ccccc9O)nnc8NC[C@H]7C6)CC5)C4)cc3C2=O)C(=O)N1] 2-(2,6-dioxopiperidin-3-yl)-5-(3-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)pyrrolidin-1-yl)isoindoline-1,3-dione | 720.4 | 720.2 |
| 226 | 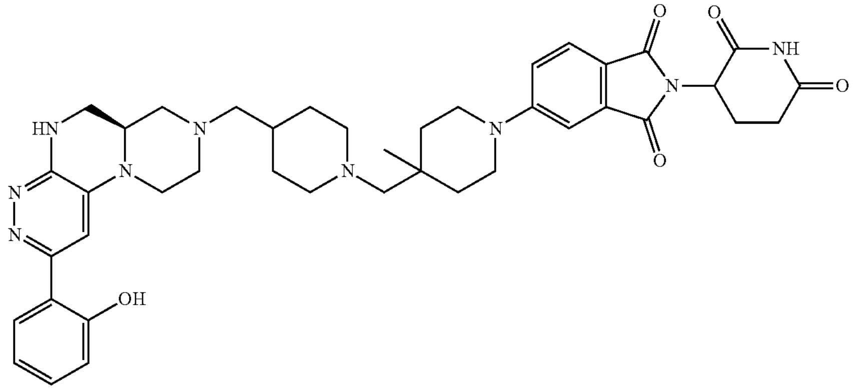 [SMILES: CC1(CN2CCC(CN3CCN4c5cc(-c6ccccc6O)nnc5NC[C@H]4C3)CC2)CCN(c2ccc3c(c2)C(=O)N(C2CCC(=O)NC2=O)C3=O)CC1] 2-(2,6-dioxopiperidin-3-yl)-5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)-4-methylpiperidin-1-yl)isoindoline-1,3-dione | 748.4 | 748.2 |

TABLE 29-continued

| Ex. | Structure/Name | Calcd. (M + H)+ m/z | Found (M + H)+ m/z |
|---|---|---|---|
| | Examples 153, 224-229 and 245-246, and 248 | | |
| 227 | 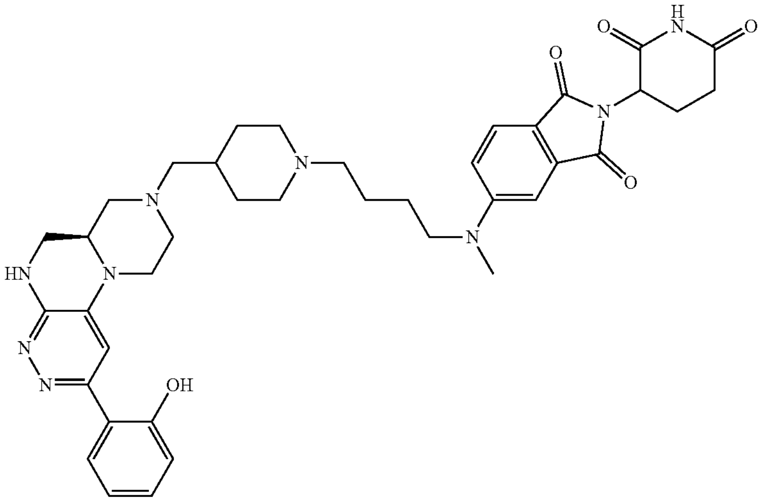 [SMILES: CN(CCCCN1CCC(CN2CCN3c4cc(-c5ccccc5O)nnc4NC[C@H]3C2)CC1)c1ccc2c(c1)C(=O)N(C1CCC(=O)NC1=O)C2=O] 2-(2,6-dioxopiperidin-3-yl)-5-((4-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)butyl)(methyl)amino)isoindoline-1,3-dione | 722.2 | 722.2 |
| 228 | 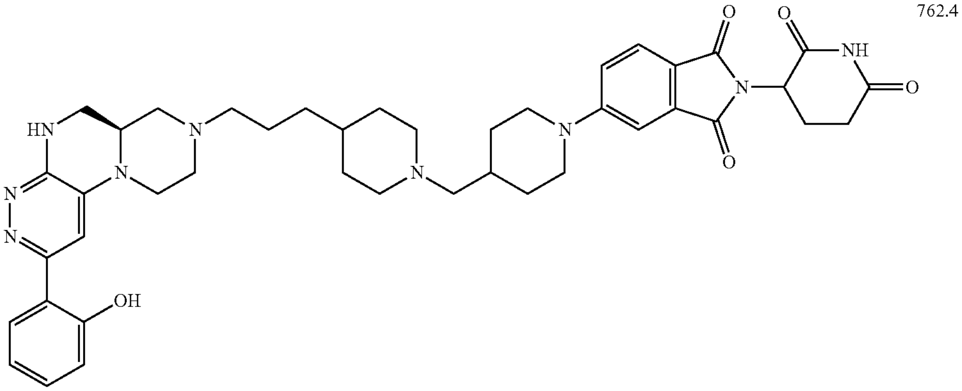 2-(2,6-dioxopiperidin-3-yl)-5-(4-((4-(3-((S)-2-(2-hydroxyphenyl)-5,6,6a,7,9,10-hexahydro-8H-pyrazino[1',2':4,5]pyrazino[2,3-c]pyridazin-8-yl)propyl)piperidin-1-yl)methyl)piperidin-1-yl)isoindoline-1,3-dione | 762.4 | 762.2 |
| 229 | 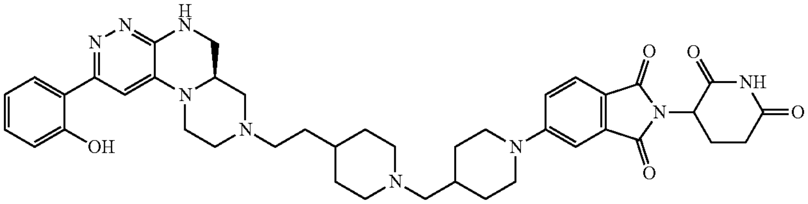 [SMILES: O=C1CCC(N2C(=O)c3ccc(N4CCC(CN5CCC(CCN6CCN7c8cc(-c9ccccc9O)nnc8NC[C@H]7C6)CC5)CC4)cc3C2=O)C(=O)N1] 2-(2,6-dioxopiperidin-3-yl)-5-(4-((4-(2-((S)-2-(2-hydroxyphenyl)-5,6,6a,7,9,10-hexahydro-8H-pyrazino[1',2':4,5]pyrazino[2,3-c]pyridazin-8-yl)ethyl)piperidin-1-yl)methyl)piperidin-1-yl)isoindoline-1,3-dione | 748.4 | 748.2 |

TABLE 29-continued

| Ex. | Structure/Name | Calcd. (M + H)+ m/z | Found (M + H)+ m/z |
|---|---|---|---|
| | Examples 153, 224-229 and 245-246, and 248 | | |
| 245 | 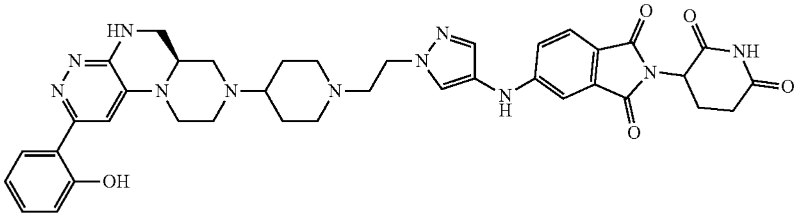 [SMILES: O=C1CCC(N2C(=O)c3ccc(Nc4cnn(CCN5CCC(N6CCN7c8cc(-c9ccccc9O)nnc8NC[C@H]7C6)CC5)c4)cc3C2=O)C(=O)N1] 2-(2,6-dioxopiperidin-3-yl)-5-((1-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethyl)-1H-pyrazol-4-yl)amino)isoindoline-1,3-dione | 732.2 | 732.2 |
| 246 | 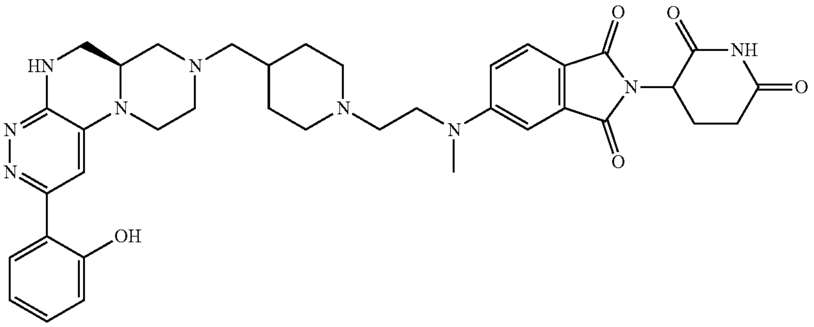 [SMILES: CN(CCN1CCC(CN2CCN3c4cc(-c5ccccc5O)nnc4NC[C@H]3C2)CC1)c1ccc2c(c1)C(=O)N(C1CCC(=O)NC1=O)C2=O] 2-(2,6-dioxopiperidin-3-yl)-5-((2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethyl)(methyl)amino)isoindoline-1,3-dione | 694.3 | 694.2 |
| 248 | 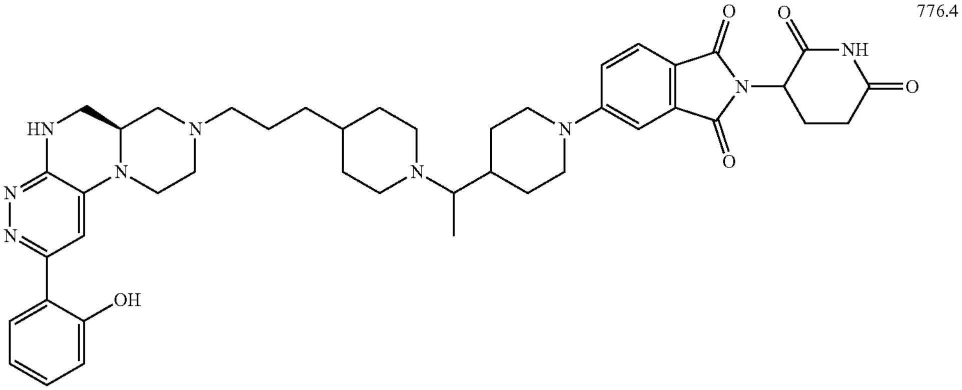 2-(2,6-dioxopiperidin-3-yl)-5-(4-(1-(4-(3-((S)-2-(2-hydroxyphenyl)-5,6,6a,7,9,10-hexahydro-8H-pyrazino[1',2':4,5]pyrazino[2,3-c]pyridazin-8-yl)propyl)piperidin-1-yl)ethyl)piperidin-1-yl)isoindoline-1,3-dione $^1$H NMR (300 MHz, MeOD) δ 7.66 (d, J = 8.3 Hz, 1H), 7.58-7.52 (m, 1H) 7.44 (td, J = 8.0, 1.5 Hz, 1H), 7.27 (s, 1H), 7.05 (t, J = 7.5 Hz, 2H), 6.84 (d, J = 1.9 Hz, 1H), 6.68 (dd, J = 8.3, 2.0 Hz, 1H), 5.07 (dd, J = 12.4, 5.4 Hz, 1H), 4.31 (dd, J = 16.6, 8.6 Hz, 3H), 3.99-3.84 (m, 3H), 3.73 (dd, J = 12.3, 3.9 Hz, 1H), 3.59 (dd, J = 24.2, 11.8 Hz, 6H), 3.40 (dd, J = 12.3, 7.6 Hz, 2H), 3.16-3.00 (m, 2H), 2.99-2.85 (m, 4H), 2.83-2.64 (m, 4H), 2.26-2.03 (m, 4H), 1.61 (d, J = 12.3 Hz, 2H). | 776.4 | 776.2 |

Example 223: 2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethyl 4-(2-(2,6-dioxopiperidin-3-yl)-1,3-dioxoisoindolin-5-yl) piperazine-1-carboxylate Ex. 223

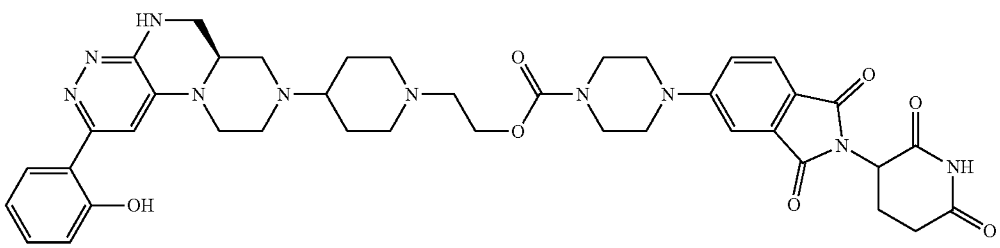

Step 1: (S)-2-(8-(1-(2-hydroxyethyl)piperidin-4-yl)-6,6a, 7,8,9,10-hexahydro-5H-pyrazino [1',2':4,5] pyrazino[2,3-c]pyridazin-2-yl)phenol

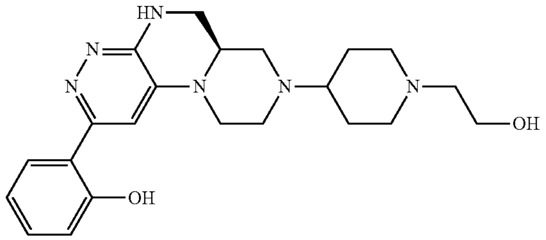 [SMILES: OCCN1CCC(N2CCN3c4cc(-c5ccccc5O)nnc4NC[C@H]3C2)CC1]

To a solution of (R)-2-(6,6a,7,8,9,10-hexahydro-5H-pyrazino[1',2':4,5]pyrazino[2,3-c]pyridazin-2-yl)phenol (70.0 mg, 0.19 mmol) in DMF (2 mL) were added 2-bromoethanol (29.4 mg, 0.24 mmol) and DIPEA (0.09 mL, 0.57 mmol). The reaction mixture was stirred at 60° C. for 16 h. The resulted mixture was purified by Prep-HPLC on a C18 column (20-35 uM, 100 A, 80 g) with mobile phase: $H_2O$ (0.1% $NH_4HCO_3$)/MeCN at flow rate: 30 mL/min to afford the desired product (34.5 mg, 44.0% yield). LCMS calculated for $C_{22}H_{31}N_6O_2$ $(M+H)^+$ m/z=411.2; found: 411.2.

Step 2: (S)-2-(4-(2-(2-hydroxyphenyl)-5,6,6a, 7,9,10-hexahydro-8H-pyrazino[1',2':4,S]pyrazino [2,3-c] pyridazin-8-yl)piperidin-1-yl)ethyl 1H-imidazole-1-carboxylate

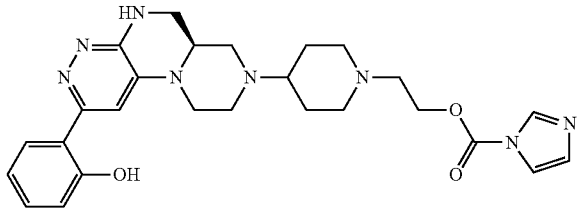 [SMILES: O=C(OCCN1CCC(N2CCN3c4cc(-c5ccccc5O)nnc4NC[C@H]3C2)CC1)n1ccnc1]

To a solution of 1,1'-carbonyldiimidazole (20.1 mg, 0.12 mmol) in DMF (2.5 mL), was added (S)-2-(8-(1-(2-hydroxyethyl)piperidin-4-yl)-6,6a,7,8,9,10-hexahydro-5H-pyrazino[1',2':4,5] pyrazino[2,3-c]pyridazin-2-yl)phenol (34.0 mg, 0.08 mmol) in portions. The reaction mixture was stirred at 30° C. for 18 h. The resulted mixture was diluted with water, and extracted with EA. The combined organic phase was washed with brine, dried over sodium sulfate, and filtered. The filtrate was concentrated to afford the desired product (17.0 mg, 41% yield), which was used directly in the next step. LCMS calculated for $C_{26}H_{33}N_8O_3$ $(M+H)^+$ m/z=505.2; found: 505.2.

Step 3: 2-(4-((S)-2-(2-hydroxyphenyl)-5,6,6a, 7,9,10-hexahydro-8H-pyrazino[1',2':4,S]pyrazino [2,3-c] pyridazin-8-yl)piperidin-1-yl)ethyl 4-(2-(2,6-dioxopiperidin-3-yl)-1,3-dioxoisoindolin-5-yl) piperazine-1-carboxylate To a solution of (S)-2-(4-(2-(2-hydroxyphenyl)-5,6,6a,7,9,10-hexahydro-8H-pyrazino[1',2':4,5] pyrazino[2,3-c] pyridazin-8-yl)piperidin-1-yl)ethyl 1H-imidazole-1-carboxylate (17.0 mg, 0.03 mmol) in THF (6 mL), was added 2-(2,6-dioxopiperidin-3-yl)-5-piperazin-1-ylisoindole-1,3-dione (11.5 mg, 0.03 mmol). The reaction mixture was stirred at 85° C. for 18 h. The volatiles were removed, and the residue was purified by Prep-HPLC on a C18 column (20-35 μm, 100 A, 80 g) with mobile phase: $H_2O$ (0.1% $NH_4HCO_3$)/MeCN at flow rate: 30 mL/min to afford the desired product (6.4 mg, 20% yield) as a white solid. LCMS calculated for $C_{40}H_{47}N_{10}O_7$ $(M+H)^+$ m/z=779.2; found: 779.2.

Example 230: 3-(5-(3-((4-(((S)-2-(2-hydroxyphenyl)-5,6,6a,7,9,10-hexahydro-8H-pyrazino[1',2':4,5] pyrazino[2,3-c]pyridazin-8-yl)methyl)piperidin-1-yl) methyl)azetidin-1-yl)-1-oxoisoindolin-2-yl) piperidine-2,6-dione

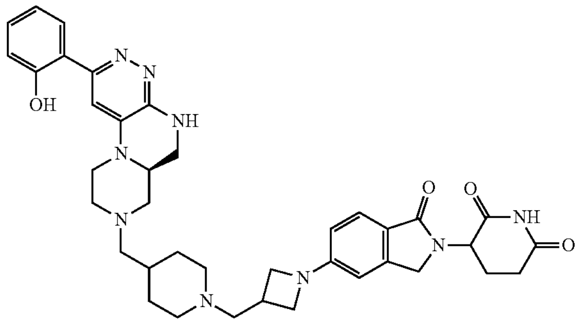 [SMILES: O=C1CCC(N2Cc3cc(N4CC(CN5CCC(CN6CCN7c8cc(-c9ccccc9O)nnc8NC[C@H]7C6)CC5)C4)ccc3C2=O)C(=O)N1]

Step 1: 1-(2-(2,6-dioxopiperidin-3-yl)-1-oxoisoindolin-5-yl)azetidine-3-carbaldehyde

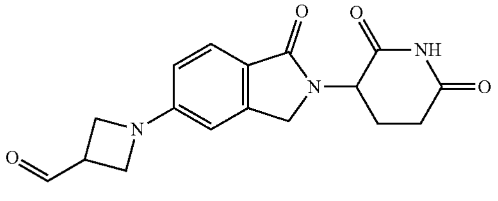 [SMILES: O=CC1CN(c2ccc3c(c2)CN(C2CCC(=O)NC2=O)C3=O)C1]

To a mixture of 3-(5-(3-(hydroxymethyl)azetidin-1-yl)-1-oxoisoindolin-2-yl)piperidine-2,6-dione (100 mg, 0.30 mmol) in DMF (4 mL) at 0° C. was added Dess-Martin periodinane (258 mg, 0.61 mmol). The mixture was stirred at RT for 2 h. Sat. $NaHCO_3$ solution was added, and the mixture was extracted with EA (50 mL×2). The combined organic layers were washed with water and brine, dried and concentrated to afford the crude product, which was used in next step without purification. LCMS calculated for $C_{17}H_{18}N_3O_4$ $(M+H)^+$ m/z=328.1; found: 328.0.

Step 2: 3-(5-(3-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)azetidin-1-yl)-1-oxoisoindolin-2-yl)piperidine-2,6-dione To a stirred solution of (S)-2-(8-(piperidin-4-ylmethyl)-6,6a,7,8,9,10-hexahydro-5H-pyrazino[1',2':4,5]pyrazino[2,3-c]pyridazin-2-yl)phenol (20 mg, 0.05 mmol) and 1-(2-(2,6-dioxopiperidin-3-yl)-1-oxoisoindolin-5-yl)azetidine-3-carbaldehyde (43 mg, 0.13 mmol) in DMF (3 mL) was added AcOH (0.02 mL, 0.26 mmol) at rt. After 1 h, sodium triacetoxyborohydride (33 mg, 0.16 mmol) was added. After 16 h, the mixture was purified by a Prep-HPLC on a C18 column (20-35 μm, 100 A, 40 g) with mobile phase: $H_2O$ (0.1% $NH_4HCO_3$)/ACN at flow rate: 30 mL/min to afford the desired product (1.1 mg, 0.00132 mmol, 2.52% yield) as a white solid. LCMS calculated for $C_{38}H_{46}N_9O_4(M+H)^+$ m/z=692.4; found: 692.2.

Examples 57, 231, 250, 251, 267 and 268

Example in Table 30 were prepared using the procedure described in the synthesis of Example 230 with appropriate intermediates.

TABLE 30

Examples 57, 231, 250, 251, 267 and 268

| Ex. | Structure/Name | Calcd. $(M + H)^+$ m/z | Found $(M + H)^+$ m/z |
|---|---|---|---|
| 57 | 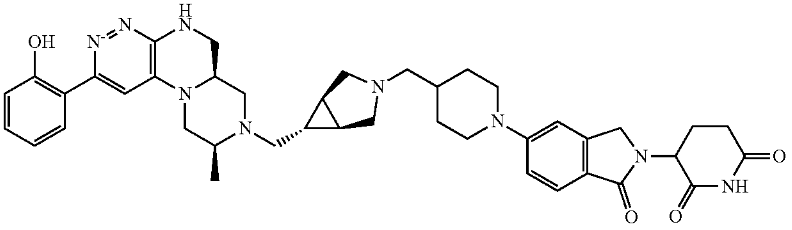 3-(5-(4-(((1R,5S,6r)-6-(((6aS,9S)-2-(2-hydroxyphenyl)-9-methyl-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)piperidin-1-yl)-1-oxoisoindolin-2-yl)piperidine-2,6-dione | 732.4 | 732.3 |
| 231 | 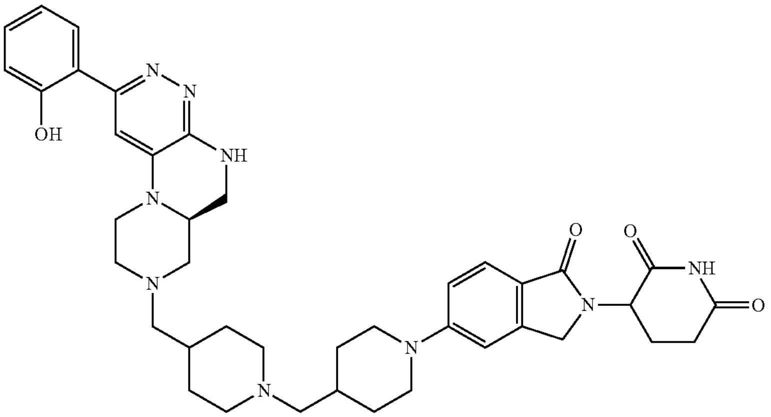 [SMILES: O=C1CCC(N2Cc3cc(N4CCC(CN5CCC(CN6CCN7c8cc(-c9ccccc9O)nnc8NC[C@H]7C6)CC5)CC4)ccc3C2=O)C(=O)N1] 3-(5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl)-1-oxoisoindolin-2-yl)piperidine-2,6-dione | 720.4 | 720.2 |

TABLE 30-continued

| Ex. | Examples 57, 231, 250, 251, 267 and 268<br>Structure/Name | Calcd. (M + H)+ m/z | Found (M + H)+ m/z |
|---|---|---|---|
| 250 | 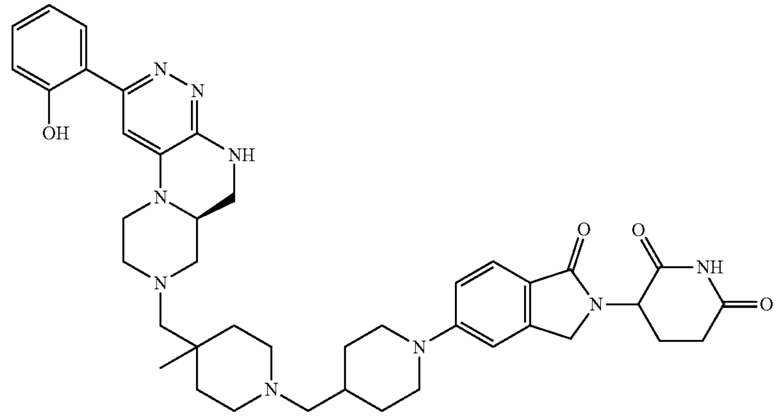 [SMILES: CC1(CN2CCN3c4cc(-c5ccccc5O)nnc4NC[C@H]3C2)CCN(CC2CCN(c3ccc4c(c3)CN(C3CCC(=O)NC3=O)C4=O)CC2)CC1]<br>3-(5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)-4-methylpiperidin-1-yl)methyl)piperidin-1-yl)-1-oxoisoindolin-2-yl)piperidine-2,6-dione | 734.4 | 734.3 |
| 251 | 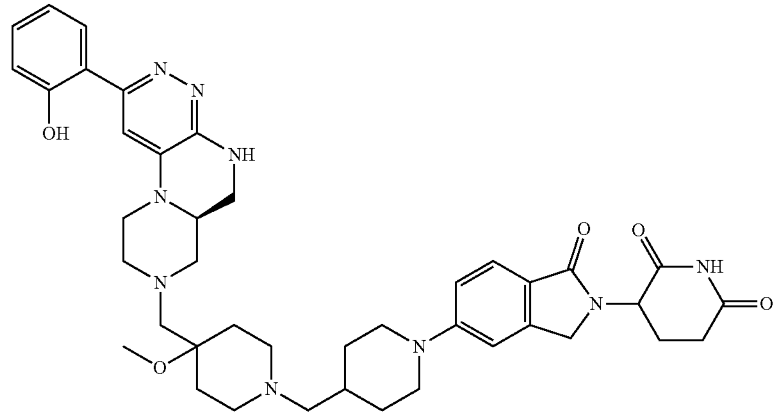 [SMILES: COC1(CN2CCN3c4cc(-c5ccccc5O)nnc4NC[C@H]3C2)CCN(CC2CCN(c3ccc4c(c3)CN(C3CCC(=O)NC3=O)C4=O)CC2)CC1]<br>3-(5-(4-((4-(((S)-2-(2-hydroxyphenyl)-5,6,6a,7,9,10-hexahydro-8H-pyrazino[1',2':4,5]pyrazino[2,3-c]pyridazin-8-yl)methyl)-4-methoxypiperidin-1-yl)methyl)piperidin-1-yl)-1-oxoisoindolin-2-yl)piperidine-2,6-dione | 750.4 | 750.2 |
| 267 | 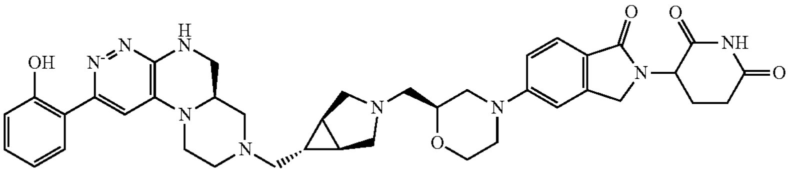<br>3-(5-((S)-2-(((1R,5S,6R)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)morpholino)-1-oxoisoindolin-2-yl)piperidine-2,6-dione | 720.4 | 720.4 |

TABLE 30-continued

| Examples 57, 231, 250, 251, 267 and 268 | | | |
|---|---|---|---|
| Ex. | Structure/Name | Calcd. (M + H)+ m/z | Found (M + H)+ m/z |
| 268 | 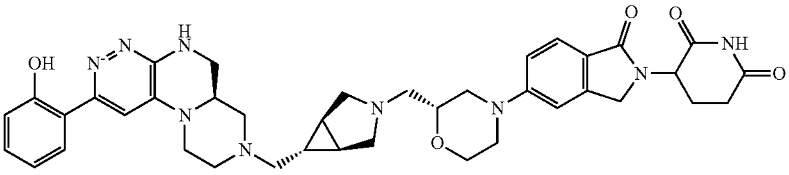 3-(5-((R)-2-(((1R,5S,6S)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)morpholino)-1-oxoisoindolin-2-yl)piperidine-2,6-dione | 720.4 | 720.3 |

Example 232: 3-(6-(4-(((1R,5S,6r)-6-(((S)-2-(2-hydroxyphenyl)-5,6,6a,7,9,10-hexahydro-8H-pyrazino[1',2':4,5]pyrazino[2,3-c]pyridazin-8-yl)methyl)-3-azabicyclo[3.1.0]hexan-3-yl)methyl)piperidin-1-yl)-1-oxoisoindolin-2-yl)piperidine-2,6-dione

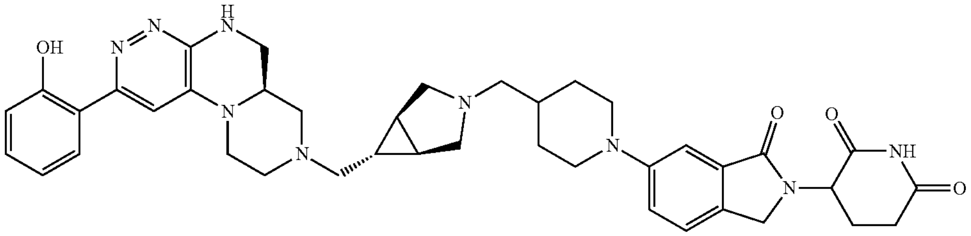

Ex. 232

To a solution of 1-(2-(2,6-dioxopiperidin-3-yl)-3-oxoisoindolin-5-yl)piperidine-4-carbaldehyde (38.0 mg, 0.11 mmol), and 2-((S)-8-(((1R,5S,6r)-3-azabicyclo[3.1.0]hexan-6-yl)methyl)-6,6a,7,8,9,10-hexahydro-5H-pyrazino[1',2':4,5]pyrazino[2,3-c]pyridazin-2-yl)phenol (15.0 mg, 0.04 mmol) in DMF (1 mL), were added DIPEA (0.04 mL, 0.24 mmol), and AcOH (0.08 mL, 1.40 mmol) at 35° C. After 1 h, $NaBH(OAc)_3$ (25.2 mg, 0.12 mmol) was added and the resulted mixture was stirred at 25° C. for additional 1 h. The reaction mixture was purified by Prep-HPLC on a C18 column (20-35 uM, 100 A, 80 g) with mobile phase: $H_2O$ (0.1% $NH_4HCO_3$)/MeCN at flow rate: 50 mL/min to afford the desired product (2.91 mg, 0.0032 mmol, 8.0% yield). LCMS calculated for $C_{40}H_{48}N_9O_4$ $(M+H)^+$ m/z=718.4; found: 718.4.

Examples 233, 235 and 252

Example in Table 31 were prepared using the procedure described in the synthesis of Example 232 with appropriate intermediates.

TABLE 31

| Examples 233, 235 and 252 | | | |
|---|---|---|---|
| Ex. | Structure/Name | Calcd. (M + H)+ m/z | Found (M + H)+ m/z |
| 233 | 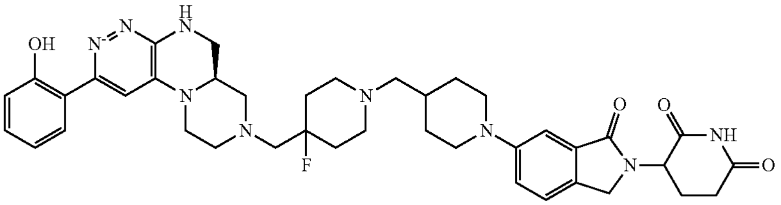 3-(6-(4-((4-fluoro-4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl)-1-oxoisoindolin-2-yl)piperidine-2,6-dione | 738.4 | 738.3 |

TABLE 31-continued

Examples 233, 235 and 252

| Ex. | Structure/Name | Calcd. (M + H)+ m/z | Found (M + H)+ m/z |
|---|---|---|---|
| 235 | 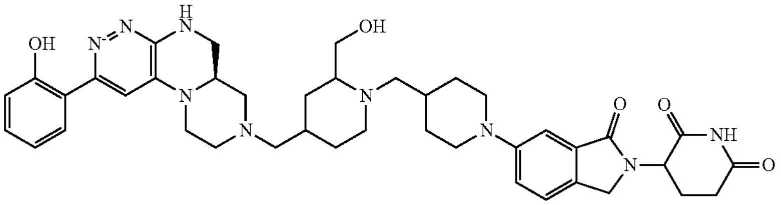 3-(6-(4-((2-(hydroxymethyl)-4-(((S)-2-(2-hydroxyphenyl)-5,6,6a,7,9,10-hexahydro-8H-pyrazino[1',2':4,5]pyrazino [2,3-c]pyridazin-8-yl)methyl)piperidin-1-yl)methyl) piperidin-1-yl)-1-oxoisoindolin-2-yl)piperidine-2,6-dione | 750.4 | 750.5 |
| 252 | 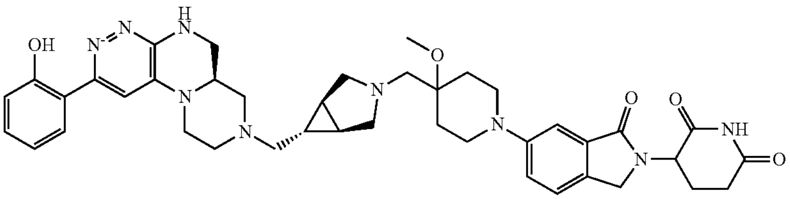 3-(6-(4-(((1R,5S,6s)-6-(((S)-2-(2-hydroxyphenyl)-5,6,6a,7,9,10-hexahydro-8H-pyrazino[1',2':4,5]pyrazino [2,3-c]pyridazin-8-yl)methyl)-3-azabicyclo[3.1.0]hexan-3-yl)methyl)-4-methoxypiperidin-1-yl)-1-oxoisoindolin-2-yl)piperidine-2,6-dione | 748.4 | 748.2 |

Example 234: 3-(6-fluoro-5-(4-((4-(((S)-2-(2-hydroxyphenyl)-5,6,6a,7,9,1O-hexahydro-8H-pyrazino [1',2':4,5]pyrazino[2,3-c]pyridazin-8-yl)methyl)piperidin-1-yl)methyl)piperidin-1-yl)-1-oxoisoindolin-2-yl)piperidine-2,6-dione Ex. 234

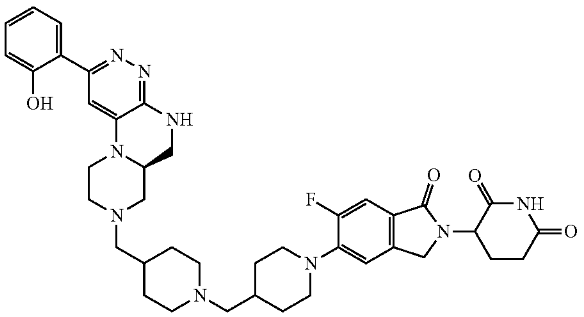

Step 1: methyl 2-bromo-5-fluoro-4-(4-(hydroxymethyl)piperidin-1-yl)benzoate

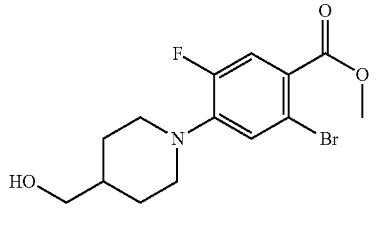 [SMILES: COC(=O)c1cc(F)c(N2CCC(CO)CC2)cc1Br]

A solution of methyl 2-bromo-4,5-difluorobenzoate (5.00 g, 19.9 mmol), DIPEA (10.4 mL, 59.8 mmol) and 4-piperidinemethanol (2.75 g, 23.9 mmol) in DMSO (20 mL) was stirred at 90° C. for 18 h. The mixture was diluted with water and extracted with EA (50 mL×2). The combined organic layers were washed with water and brine, dried and concentrated. The residue was purified by silica gel chromatography (PE/EA=2/1) to afford methyl 2-bromo-5-fluoro-4-[4-(hydroxymethyl)piperidin-1-yl]benzoate (3.90 g, 11.3 mmol, 56.6% yield) as a white solid. LCMS calculated for $C_{14}H_{18}BrFNO_3$ $(M+H)^+$ m/z=346.0; found: 346.0.

Step 2: methyl 5-fluoro-4-(4-(hydroxymethyl)piperidin-1-yl)-2-vinylbenzoate

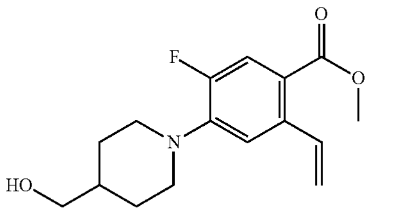 [SMILES: C=Cc1cc(N2CCC(CO)CC2)c(F)cc1C(=O)OC]

A mixture of 4,4,5,5-tetramethyl-2-vinyl-1,3,2-dioxaborolane (1.07 g, 6.93 mmol), $K_3PO_4$ (3.68 g, 17.33 mmol) and methyl 2-bromo-5-fluoro-4-(4-(hydroxymethyl)piperidin-1-yl)benzoate (2.00 g, 5.78 mmol) in 1,4-dioxane (50 mL) and water (10 mL) was stirred at 70° C. under $N_2$ atmosphere for 18 h. The reaction was diluted with water and extracted with EA (50 mL×2). The combined organic layers were washed with water and brine, dried and concentrated. The residue was purified by silica gel chromatography (PE/EA=2/1) to afford the desired product (1.00 g, 3.41 mmol, 59.0% yield). LCMS calculated for $C_{16}H_{20}FNO_3$ $(M+H)^+$ m/z=294.1; found: 294.2.

Step 3:1-(2-(2,6-dioxopiperidin-3-yl)-6-fluoro-1-oxoisoindolin-5-yl)piperidine-4-carbaldehyde

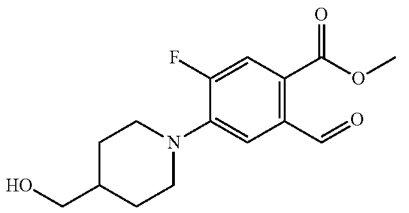 [SMILES: COC(=O)c1cc(F)c(N2CCC(CO)CC2)cc1C=O]

To a stirred solution of methyl methyl 5-fluoro-4-(4-(hydroxymethyl)piperidin-1-yl)-2-vinylbenzoate (1.00 g, 3.41 mmol) in DCM (20 mL), $O_3$ was introduced at −65° C. After 10 mins, the reaction mixture turned blue. $O_3$ was removed and 02 was continued to be introduced for another 10 mins., then dimethylsulfane (6 drops) was added, and the resulted mixture was stirred for additional 1 h at rt. The volatiles were removed, and the residue was purified by silica gel chromatography (PE/EA=2/1) to afford the desired product (280 mg, 0.95 mmol, 27.8% yield). LCMS calculated for $C_{15}H_{19}FNO_4$ $(M+H)^+$ m/z=296.1; found: 296.1.

Step 4: 3-(6-fluoro-5-(4-(hydroxymethyl)piperidin-1-yl)-1-oxoisoindolin-2-yl)piperidine-2,6-dione

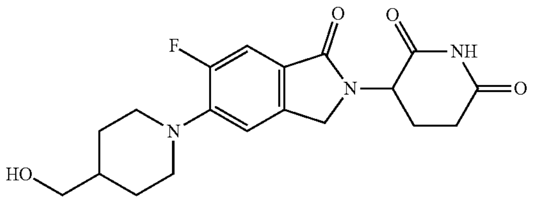 [SMILES: O=C1CCC(N2Cc3cc(N4CCC(CO)CC4)c(F)cc3C2=O)C(=O)N1]

A solution of 1-(2-(2,6-dioxopiperidin-3-yl)-6-fluoro-1-oxoisoindolin-5-yl)piperidine-4-carbaldehyde (350 mg, 1.19 mmol), 3-aminopiperidine-2,6-dione hydrochloride (234 mg, 1.42 mmol), DIEA (0.32 mL, 1.92 mmol) and AcOH (0.64 mL, 11.12 mmol) in DMF (5 mL) was stirred at 25° C. for 1 h. $NaBH(OAc)_3$ (754 mg, 3.56 mmol) was added. After 16 h, the mixture was purified by a Prep-HPLC on a C18 column (20-35 μm, 100 A, 80 g) with mobile phase: $H_2O$ (0.1% TFA)/ACN at flow rate: 50 mL/min to afford the desired product (120 mg, 0.32 mmol, 27.0% yield). LCMS calculated for $C_{19}H_{23}FN_3O_4(M+H)^+$ m/z=376.2; found: 376.0.

Step 5: 1-(2-(2,6-dioxopiperidin-3-yl)-6-fluoro-1-oxoisoindolin-5-yl)piperidine-4-carbaldehyde

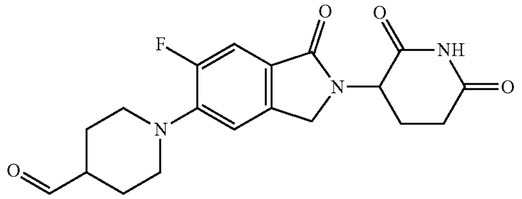 [SMILES: O=CC1CCN(c2cc3c(cc2F)C(=O)N(C2CCC(=O)NC2=O)C3)CC1]

To a stirred solution of 3-(6-fluoro-5-(4-(hydroxymethyl)piperidin-1-yl)-1-oxoisoindolin-2-yl)piperidine-2,6-dione (70 mg, 0.19 mmol) in DMF (2 mL) was added Dess-Martin periodinane (119 mg, 0.28 mmol) at rt. After 2 h, sat. aqueous $NaHCO_3$ was added and the resulted mixture was extracted with EA (50 mL×2). The combined organic layers were washed with water and brine, dried and concentrated to afford the crude product. It was used in the next step without further purification. LCMS calculated for $C_{19}H_{21}FN_3O_4$ $(M+H)^+$ m/z=374.1; found: 374.2.

Step 6: 3-(6-fluoro-5-(4-((4-(((S)-2-(2-hydroxyphenyl)-5,6,6a, 7,9,10-hexahydro-8H-pyrazino [1',2':4, 5]pyrazino[2,3-c]pyridazin-8-yl)methyl)piperidin-1-yl)methyl)piperidin-1-yl)-1-oxoisoindolin-2-yl) piperidine-2,6-dione A solution of (S)-2-(8-(piperidin-4-ylmethyl)-6,6a,7,8,9, 10-hexahydro-5H-pyrazino[1',2':4,5]pyrazino[2,3-c] pyridazin-2-yl)phenol (24 mg, 0.06 mmol), DIEA (0.04 mL, 0.48 mmol), AcOH (0.09 mL, 1.61 mmol) and 1-(2-(2,6-dioxopiperidin-3-yl)-6-fluoro-1-oxoisoindolin-5-yl)piperidine-4-carbaldehyde (60.0 mg, 0.16 mmol) in DMF (3 mL) was stirred at rt for 1 h. Sodium triacetoxyborohydride (102 mg, 0.48 mmol) was added and the reaction mixture was stirred at rt overnight. The reaction mixture was purified by a Prep-HPLC on a C18 column (20-35 μm, 100 A, 40 g) with mobile phase: $H_2O$ (0.1% TFA)/ACN at flow rate: 50 mL/min to afford the desired product (21 mg, 0.028 mmol, 17.4% yield) as a white solid. LCMS calculated for $C_{40}H_{49}FN_9O_4(M+H)^+$ m/z=738.4; found: 738.2.

Example 236: 2-(2,6-dioxopiperidin-3-yl)-5-(4-((2-(hydroxymethyl)-4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)piperidin-1-yl) isoindoline-1,3-dione Ex. 236

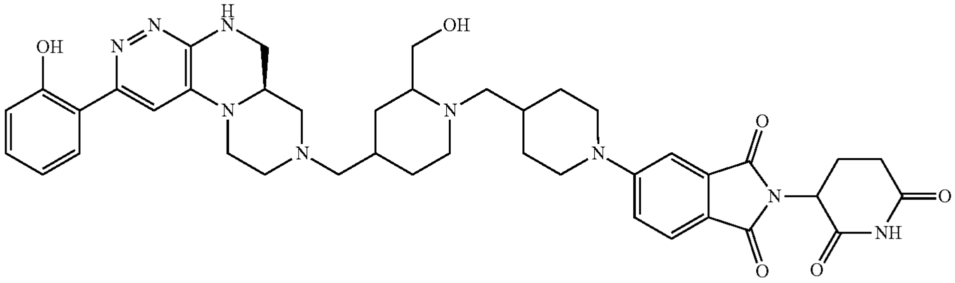

To a solution of 2-((6aS)-8-((2-(hydroxymethyl)piperidin-4-yl)methyl)-6,6a,7,8,9,10-hexahydro-5H-pyrazino[1',2':4,5]pyrazino[2,3-c]pyridazin-2-yl)phenol (28.0 mg, 0.07 mmol) and 1-(2-(2,6-dioxopiperidin-3-yl)-1,3-dioxoisoindolin-5-yl)piperidine-4-carbaldehyde (43.0 mg, 0.12 mmol in DMF (2 mL) was added AcOH (0.04 mL, 0.70 mmol) at 35° C. After 2 h, $NaBH(OAc)_3$ (43.4 mg, 0.20 mmol) was added and the resulted mixture was stirred at 25° C. for additional 2 h. The reaction mixture was purified by Prep-HPLC on a C18 column (20-35 μm, 100 A, 80 g) with mobile phase: $H_2O$ (0.1% TFA)/MeCN at flow rate: 50 mL/min to afford the desired product (20.8 mg, 0.023 mmol, 34.3% yield) as a white solid. LCMS calculated for $C_{41}H_{50}N_9O_6(M+H)^+$ m/z=764.4; found: 764.4.

Examples 154 and 249

Examples in Table 32 were prepared using the procedure described in the synthesis of Example 236 with appropriate intermediates.

TABLE 32

| Ex. | Structure/Name | Calcd. $(M + H)^+$ m/z | Found $(M + H)^+$ m/z |
|---|---|---|---|
| | Examples 154 and 249 | | |
| 154 | 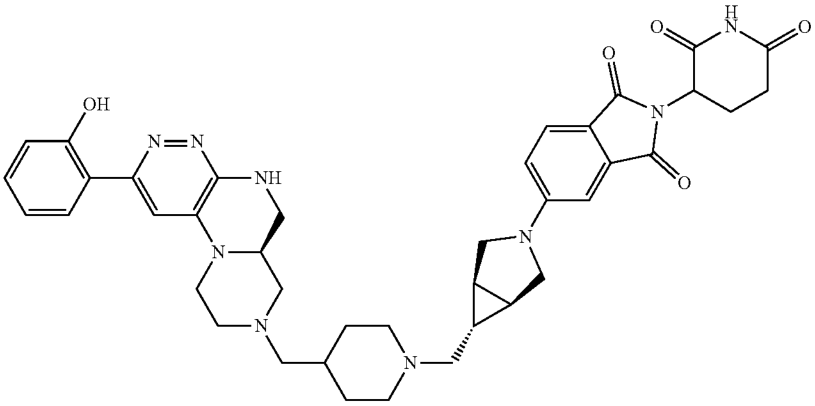 [SMILES: O=C1CCC(N2C(=O)c3ccc(N4C[C@@H]5[C@@H](CN6CCC(CN7CCN8c9cc(-c%10ccccc%10O)nnc9NC[C@H]8C7)CC6)[C@@H]5C4)cc3C2=O)C(=O)N1] 2-(2,6-dioxopiperidin-3-yl)-5-((1R,5S,6s)-6-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)-3-azabicyclo[3.1.0]hexan-3-yl)isoindoline-1,3-dione | 732.4 | 732.4 |

TABLE 32-continued

| Ex. | Structure/Name | Calcd. (M + H)+ m/z | Found (M + H)+ m/z |
|---|---|---|---|
| | Examples 154 and 249 | | |
| 249 | 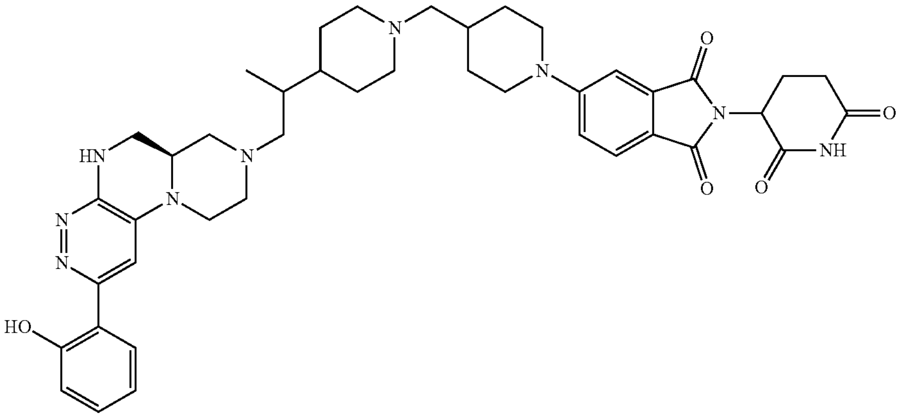 [SMILES: CC(CN1CCN2c3cc(-c4ccccc4O)nnc3NC[C@H]2C1)C1CCN(CC2CCN(c3ccc4c(c3)C(=O)N(C3CCC(=O)NC3=O)C4=O)CC2)CC1] 2-(2,6-dioxopiperidin-3-yl)-5-(4-((4-(1-((S)-2-(2-hydroxyphenyl)-5,6,6a,7,9,10-hexahydro-8H-pyrazino[1',2':4,5]pyrazino[2,3-c]pyridazin-8-yl)propan-2-yl) piperidin-1-yl)methyl)piperidin-1-yl)isoindoline-1,3-dione | 762.4 | 762.2 |

Example 240: 2-(2,6-dioxopiperidin-3-yl)-5-((4-(4-((S)-2-(2-hydroxyphenyl)-5,6,6a,7,9,10-hexahydro-8H-pyrazino[1',2':4,5]pyrazino[2,3-c]pyridazin-8-yl) piperidin-1-yl)phenyl) amino) isoindoline-1,3-dione Ex. 240

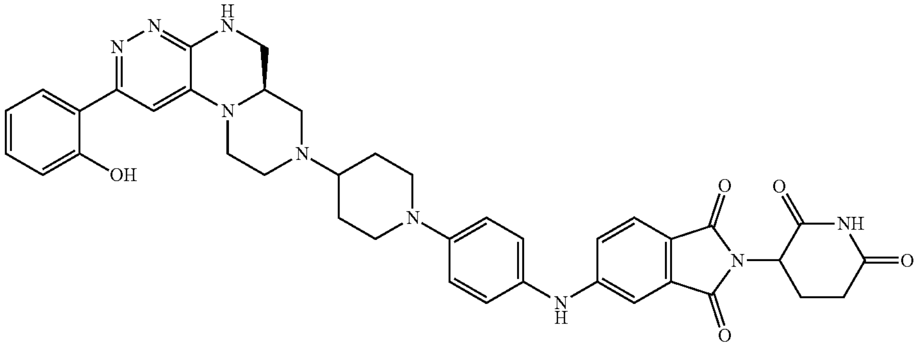

Step 1: 8-(4-nitrophenyl)-1,4-dioxa-8-azaspiro[4.5] decane

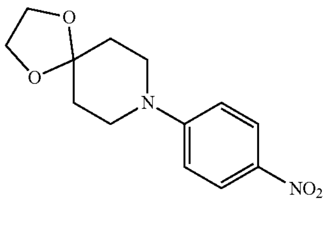

To a mixture of 1-fluoro-4-nitrobenzene (1.00 g, 7.09 mmol) and 1,4-dioxa-8-azaspiro[4,5] decane (1.22 g, 8.50 mmol) in DMF (10 mL) was added potassium carbonate (1.96 g, 14.2 mmol). The mixture was stirred at 80° C. for 2 h. Then the reaction mixture was diluted with water (50 mL), and extracted with EA (2×50 mL). The combined organic layers were washed with brine (50 mL), dried over anhydrous $Na_2SO_4$, filtered, concentrated and purified by silica gel chromatography (PE/EA=5/1) to afford 8-(4-nitrophenyl)-1,4-dioxa-8-azaspiro [4.5]decane (1.87 g, 99% yield). LCMS calculated for $C_{13}H_{17}N_2O_4$ $(M+H)^+$ m/z=265.1; found: 265.2.

Step 2: 4-(1,4-dioxa-8-azaspiro[4.5]decan-8-yl)aniline

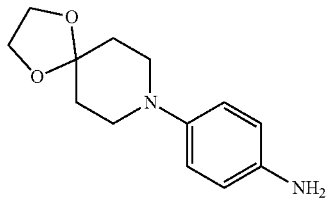 [SMILES: Nc1ccc(N2CCC3(CC2)OCCO3)cc1]

To a mixture of 8-(4-nitrophenyl)-1,4-dioxa-8-azaspiro[4.5]decane (500 mg, 1.89 mmol) in methanol (20 mL) was added Pd/C (10%, 40.1 mg, 0.38 mmol). The reaction container was purged with hydrogen for 3 times. Then the resulted mixture was stirred at 20° C. overnight. The reaction mixture was filtered and the filtrate was concentrated to give 4-(1,4-dioxa-8-azaspiro[4.5]decan-8-yl)aniline (550 mg, 95% yield) as an oil. LCMS calculated for $C_{13}H_{19}N_2O_2$ $(M+H)^+$ m/z=235.1; found: 235.2.

Step 3: 5-((4-(1,4-dioxa-8-azaspiro[4.5]decan-8-yl) phenyl)amino)-2-(2,6-dioxopiperidin-3-yl) isoindoline-1,3-dione

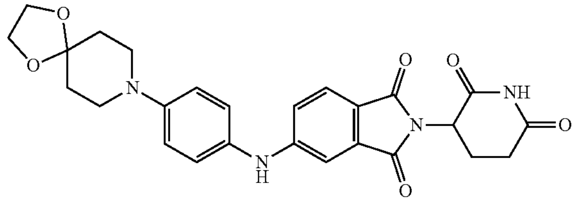 [SMILES: O=C1CCC(N2C(=O)c3ccc(Nc4ccc(N5CCC6(CC5)OCCO6)cc4)cc3C2=O)C(=O)N1]

To a mixture of 4-(1,4-dioxa-8-azaspiro[4.5]decan-8-yl) aniline (100 mg, 0.43 mmol), 5-bromo-2-(2,6-dioxopiperidin-3-yl) isoindole-1,3-dione (144 mg, 0.43 mmol), biphenyl-2-yl(dicyclohexyl) phosphine (15.0 mg, 0.04 mmol), and potassium tert-butoxide (67.1 mg, 0.60 mmol) in 1,4-dioxane (5 mL) was added palladium diacetate (19.5 mg, 0.02 mmol). The reaction mixture was bubbled with nitrogen for 3 minutes. The mixture was stirred at 100° C. under microwave irradiation for 1 hour. After that, the reaction mixture was washed with water (50 mL), and extracted with EA (2×50 mL). The combined organic layers were washed with brine (50 mL), dried over anhydrous $Na_2SO_4$, filtered and concentrated. The crude product was purified by silica gel chromatography (PE/EA=2/1), and purified by Prep-HPLC on a C18 column (20-35 μm, 100 A, 40 g) with mobile phase: $H_2O$ (0.1% $NH_4HCO_3$)/MeCN at flow rate: 30 mL/min to afford the desired product (18 mg, 8.60% yield) as a white solid. LCMS calculated for $C_{26}H_{27}N_4O_6$ $(M+H)^+$ m/z=491.2; found: 491.0.

Step 4: 2-(2,6-dioxopiperidin-3-yl)-5-[4-(4-oxopiperidin-1-yl)anilino]isoindole-1,3-dione

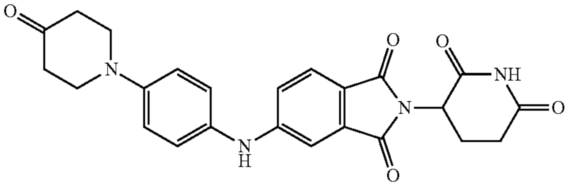 [SMILES: O=C1CCN(c2ccc(Nc3ccc4c(c3)C(=O)N(C3CCC(=O)NC3=O)C4=O)cc2)CC1]

To a mixture of formic acid (2.0 mL, 53.0 mmol) in water (5 mL) was added 5-((4-(1,4-dioxa-8-azaspiro[4.5]decan-8-yl)phenyl)amino)-2-(2,6-dioxopiperidin-3-yl) isoindoline-1,3-dione (18.0 mg, 0.04 mmol). The mixture was stirred at 90° C. for 4 h. The reaction mixture was concentrated to afford the crude product, 2-(2,6-dioxopiperidin-3-yl)-5-[4-(4-oxopiperidin-1-yl)anilino]isoindole-1,3-dione (100 mg, 0.0224 mmol, 61.0% yield). LCMS calculated for $C_{24}H_{23}N_4O_5$ $(M+H)^+$ m/z=447.17; found: 446.8, 464.8.

Step 5: 2-(2,6-dioxopiperidin-3-yl)-5-((4-(4-((S)-2-(2-hydroxyphenyl)-5,6,6a, 7,9,10-hexahydro-8H-pyrazino[1',2':4,5]pyrazino[2,3-c]pyridazin-8-yl) piperidin-1-yl)phenyl)amino) isoindoline-1,3-dione To a stirred solution of 2-(2,6-dioxopiperidin-3-yl)-5-[4-(4-oxopiperidin-1-yl)anilino]isoindole-1,3-dione (15.0 mg, 0.03 mmol) and (R)-2-(6,6a,7,8,9,10-hexahydro-5H-pyrazino [1',2':4,5]pyrazino[2,3-c]pyridazin-2-yl)phenol (19.0 mg, 0.07 mmol) in DMF (1 mL) was added AcOH (10.1 mg, 0.17 mmol) at 25° C. After 0.5 h, $NaBH(OAc)_3$ (21.4 mg, 0.10 mmol) was added. The resulted mixture was stirred at 25° C. overnight. The reaction mixture was purified by Prep-HPLC on a C18 column (20-35 μm, 100 A, 40 g) with mobile phase: $H_2O$ (0.1% $NH_4HCO_3$)/MeCN at flow rate: 30 mL/min to afford the desired product (3.7 mg, 0.0046 mmol, 13.7% yield) as a white solid. LCMS calculated for $C_{39}H_{40}N_9O_5$ $(M+H)^+$ m/z=714.3; found: 714.1.

Examples 241, 244 and 258

Examples in Table 33 were prepared using the procedure described in the synthesis of Example 232 with appropriate intermediates.

TABLE 33

| Ex. | Structure/Name | Calcd. (M + H)+ m/z | Found (M + H)+ m/z |
|---|---|---|---|
| | Examples 241, 244 and 258 | | |
| 241 | 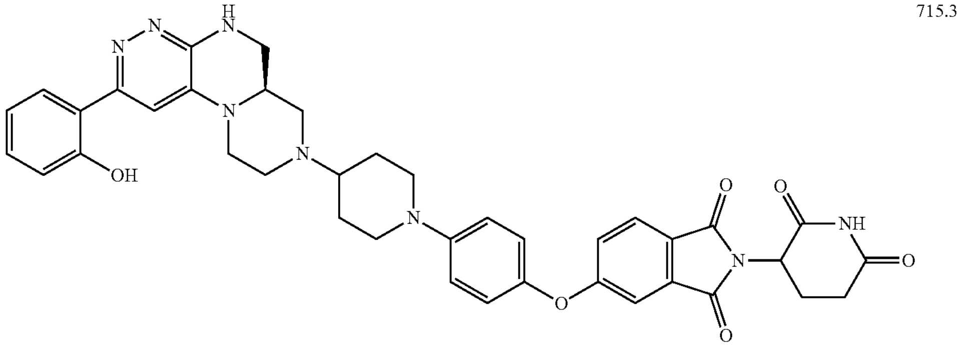 2-(2,6-dioxopiperidin-3-yl)-5-(4-(4-((S)-2-(2-hydroxyphenyl)-5,6,6a,7,9,10-hexahydro-8H-pyrazino [1',2':4,5]pyrazino[2,3-c]pyridazin-8-yl)piperidin-1-yl)phenoxy)isoindoline-1,3-dione | 715.3 | 715.3 |
| 244 | 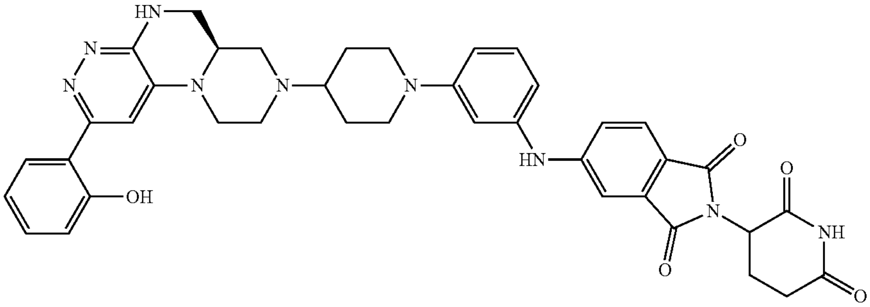 [SMILES: O=C1CCC(N2C(=O)c3ccc(Nc4cccc(N5CCC(N6CCN7c8cc(-c9ccccc9O)nnc8NC[C@H]7C6)CC5)c4)cc3C2=O)C(=O)N1] 2-(2,6-dioxopiperidin-3-yl)-5-((3-(4-((S)-2-(2-hydroxyphenyl)-5,6,6a,7,9,10-hexahydro-8H-pyrazino [1',2':4,5]pyrazino[2,3-c]pyridazin-8-yl)piperidin-1-yl)phenyl)amino)isoindoline-1,3-dione | 714.3 | 714.3 |
| 258 | 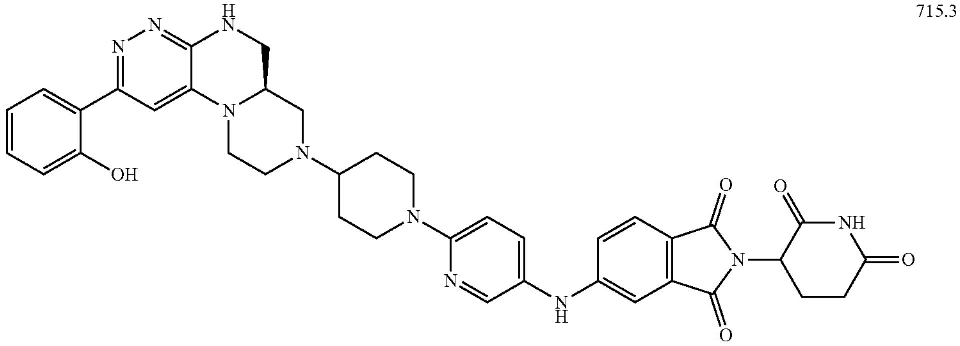 2-(2,6-dioxopiperidin-3-yl)-5-((6-(4-((S)-2-(2-hydroxyphenyl)-5,6,6a,7,9,10-hexahydro-8H-pyrazino [1',2':4,5]pyrazino[2,3-c]pyridazin-8-yl)piperidin-1-yl)pyridin-3-yl)amino)isoindoline-1,3-dione | 715.3 | 715.4 |

Example 253: 2-(2,6-dioxopiperidin-3-yl)-5-(4-((4-((2-(2-hydroxyphenyl)-6,6a,7,8,9,10-hexahydro-5H-pyrido[1',2':4,5]pyrazino[2,3-c]pyridazin-8-yl)amino)piperidin-1-yl)methyl)piperidin-1-yl)isoindoline-1,3-dione Ex. 253

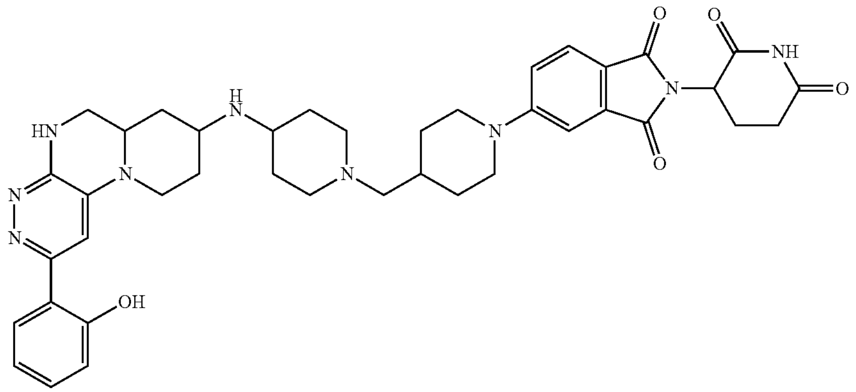

Step 1: 8-(tert-butyl) 7-methyl 1,4-dioxa-8-azaspiro[4.5]decane-7,8-dicarboxylate

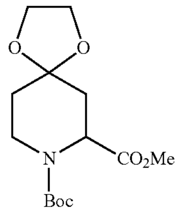 [SMILES: COC(=O)C1CC2(CCN1C(=O)OC(C)(C)C)OCCO2]

A solution of 1-(tert-butyl) 2-methyl 4-oxopiperidine-1,2-dicarboxylate (10.0 g, 38.9 mmol), ethylene glycol (8.44 g, 136 mmol) and p-toluenesulfonic acid (669 mg, 3.89 mmol) in toluene (150 mL) was refluxed overnight. The reaction mixture was concentrated, diluted with water, and extracted with DCM. The combined organic layers were washed with brine, dried by $Na_2SO_4$, concentrated and purified by column chromatography on a silica gel column (PE/EA=5/1) to afford the desired product (6.60 g, 21.9 mmol, 56.4% yield) as a yellow oil. LCMS calculated for $C_{14}H_{24}NO_6$ $(M+H)^+$ m/z=302.2; found: 202.0 (M+H−100). $^1H$ NMR (400 MHz, $CDCl_3$) δ 4.79-4.97 (m, 1H), 3.86-4.00 (m, 5H), 3.73 (s, 3H), 3.26-3.32 (m, 1H), 2.04-2.38 (m, 1H), 1.62-1.85 (m, 3H), 1.39-1.47 (m, 9H).

Step 2: 8-(tert-butoxycarbonyl)-1,4-dioxa-8-azaspiro[4.5]decane-7-carboxylic acid

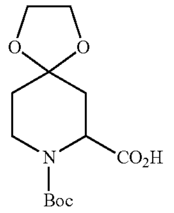 [SMILES: CC(C)(C)OC(=O)N1CCC2(CC1C(=O)O)OCCO2]

A mixture of 8-(tert-butyl) 7-methyl 1,4-dioxa-8-azaspiro[4.5]decane-7,8-dicarboxylate (6.60 g, 21.9 mmol) and LiOH (1.84 g, 43.8 mmol) in methanol (36 mL) and water (18 mL) was stirred at 25° C. overnight. The reaction mixture was extracted with EA. 1 M HCl solution was added to the aqueous layer to adjust the pH~ 4. The aqueous solution was extracted with EA. The organic phase was dried with $Na_2SO_4$, filtered, and the filtrate was concentrated to give the crude product (5.80 g, 20.2 mmol, 92.2% yield) as a colorless oil. LCMS calculated for $C_{13}H_{22}NO_6$ $(M+H)^+$ m/z=288.1; found: 188.0 (M+H−100). $^1H$ NMR (400 MHz, $CD_3OD$) δ 4.84-5.03 (m, 1H), 3.87-4.07 (m, 5H), 3.26-3.34 (m, 1H), 2.40 (t, J=14.8 Hz, 1H), 1.64-1.88 (m, 3H), 1.45-1.47 (m, 9H).

Step 3:1,4-dioxa-8-azaspiro[4.5]decane-7-carboxylic acid

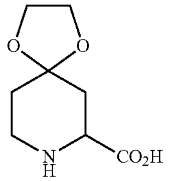 [SMILES: O=C(O)C1CC2(CCN1)OCCO2]

A solution of 8-(tert-butoxycarbonyl)-1,4-dioxa-8-azaspiro[4.5]decane-7-carboxylic acid (5.80 g, 20.2 mmol) and HCl in 1,4-dioxane (4 M, 35 mL) in DCM (50 mL) was stirred at 25° C. for 2 h. The volatiles were removed under reduced pressure to afford 1,4-dioxa-8-azaspiro[4.5]decane-7-carboxylic acid as its HCl salt (4.10 g, 20.2 mmol, 99.8% yield). LCMS calculated for $C_8H_{14}NO_4$ $(M+H)^+$ m/z=188.1; found: 188.0.

Step 4: 2-chloro-6a, 7,9,10-tetrahydrospiro[pyrido[1',2':4,5]pyrazino[2,3-c]pyridazine-8,2'-[1,3]dioxolan]-6(5H)-one

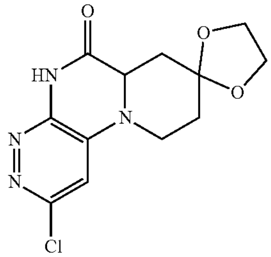 [SMILES: O=C1Nc2nnc(Cl)cc2N2CCC3(CC12)OCCO3]

A mixture of 1,4-dioxa-8-azaspiro[4.5]decane-7-carboxylic acid (300 mg, 1.60 mmol), 4-bromo-6-chloropyridazin-3-amine (735 mg, 3.53 mmol), $Cs_2CO_3$ (2.09 g, 6.41 mmol) and CuI (30.5 mg, 0.16 mmol) in DMSO (12 mL) was stirred at 130° C. in a microwave reactor for 2 h. The resulted mixture was extracted with EA. The combined organic layers were washed with brine, dried by $Na_2SO_4$, and filtered. The filtrate was concentrated and purified by Prep-HPLC on a C18 column (20-35 μm, 100 A, 80 g) with mobile phase: $H_2O$ (0.1% TFA)/MeOH at flow rate: 50 mL/min to afford 2-chloro-6a,7,9,10-tetrahydrospiro[pyrido[1',2':4,5]pyrazino[2,3-c]pyridazine-8,2'-[1,3]dioxolan]-6(5H)-one (110 mg, 0.371 mmol, 23.1% yield) as a yellow solid. LCMS calculated for $C_{12}H_{14}ClN_4O_3(M+H)^+$ m/z=297.1; found: 297.0.

Step 5: 2-chloro-5,6,6a, 7,9,10-hexahydrospiro[pyrido[1',2':4,5]pyrazino[2,3-c]pyridazine-8,2'-[1,3]dioxolane]

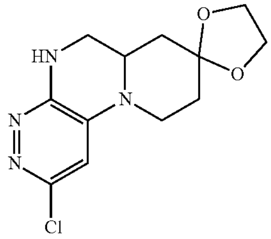 [SMILES: Clc1cc2c(nn1)NCC1CC3(CCN21)OCCO3]

A mixture of 2-chloro-6a,7,9,10-tetrahydrospiro[pyrido[1',2':4,5]pyrazino[2,3-c]pyridazine-8,2'-[1,3]dioxolan]-6(5H)-one (760 mg, 2.56 mmol) and $BH_3$·DMS (10 M, 2.56 mL, 25.6 mmol) in THF (10 mL) was stirred at 25° C. for 3 h. The reaction was quenched with MeOH (2 mL), diluted with water and extracted with EA. The combined organic layers was dried by $Na_2SO_4$ and filtered. The filtrate was concentrated and the residue was purified by Prep-HPLC on a C18 column (20-35 μm, 100 A, 80 g) with mobile phase: $H_2O$ (0.1% TFA)/MeOH at flow rate: 50 mL/min to afford the desired product (430 mg, 1.52 mmol, 59.4% yield) as a white solid. LCMS calculated for $C_{12}H_{16}ClN_4O_2$ $(M+H)^+$ m/z=283.1; found: 283.0.

Step 6: tert-butyl 4'-chlorospiro[1,3-dioxolane-2,12'-1,5,6,8-tetrazatricyclo[8.4.0.02,7]tetradeca-2(7),3,5-triene]-8'-carboxylate

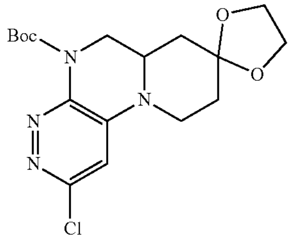 [SMILES: CC(C)(C)OC(=O)N1CC2CC3(CCN2c2cc(Cl)nnc21)OCCO3]

A mixture of 2-chloro-5,6,6a,7,9,10-hexahydrospiro[pyrido[1',2':4,5]pyrazino[2,3-c]pyridazine-8,2'-[1,3]dioxolane] (430 mg, 1.52 mmol), $Et_3N$ (1.06 mL, 7.60 mmol), $Boc_2O$ (0.7 mL, 3.04 mmol) and DMAP (19.7 mg, 0.15 mmol) in DCM (10 mL) was stirred at 25° C. overnight. The reaction mixture was diluted with DCM, washed with brine, dried by $Na_2SO_4$, and filtered. The filtrate was concentrated and the residue was purified by column chromatography on a silica gel column (PE/EA=2/1) to afford the desired product (280 mg, 0.731 mmol, 48.1% yield) as a white solid. LCMS calculated for $C_{17}H_{24}ClN_4O_4(M+H)^+$ m/z=383.2; found: 383.2.

Step 7: tert-butyl 2-(2-hydroxyphenyl)-6a, 7,9,10-tetrahydrospiro[pyrido[1',2':4,5]pyrazino[2,3-c]pyridazine-8,2'-[1,3]dioxolane]-5(6H)-carboxylate

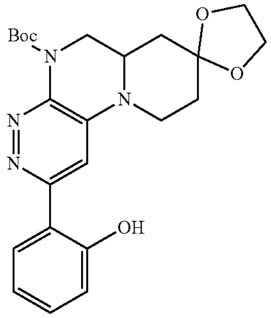 [SMILES: CC(C)(C)OC(=O)N1CC2CC3(CCN2c2cc(-c4ccccc4O)nnc21)OCCO3]

A mixture of tert-butyl 4'-chlorospiro[1,3-dioxolane-2,12'-1,5,6,8-tetrazatricyclo [8.4.0.02,7]tetradeca-2(7),3,5-triene]-8'-carboxylate (280 mg, 0.730 mmol), 2-hydroxyphenylboronic acid (110 mg, 0.80 mmol), $K_2CO_3$ (404 mg, 2.93 mmol) and $Pd(dppf)_2Cl_2$ (119 mg, 0.150 mmol) in 1,4-dioxane (4 mL) and water (2 mL) was stirred at 105° C. in a microwave reactor for 2 h. The resulted mixture was extracted with EA. The combined organic layers were washed with brine, dried by $Na_2SO_4$, and filtered. The filtrate was concentrated and the residue was purified by column chromatography on a silica gel column (PE/EA=1/1) to afford the desired product (70.0 mg, 0.159 mmol, 21.7% yield) as a white solid. LCMS calculated for $C_{23}H_{29}N_4O_5$ $(M+H)^+$ m/z=441.2; found: 441.4.

Step 8: 2-(2-hydroxyphenyl)-5,6,6a, 7,9,10-hexahydro-8H-pyrido[1',2':4,5]pyrazino[2,3-c]pyridazin-8-one

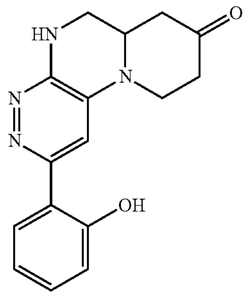 [SMILES: O=C1CCN2c3cc(-c4ccccc4O)nnc3NCC2C1]

A mixture of tert-butyl 2-(2-hydroxyphenyl)-6a,7,9,10-tetrahydrospiro[pyrido[1',2':4,5]pyrazino[2,3-c]pyridazine-8,2'-[1,3]dioxolane]-5(6H)-carboxylate (10.0 mg, 0.02 mmol) in water (1 mL) and HCOOH (0.4 mL) was stirred at 90° C. for 1 h. The volatiles were removed under reduced pressure to afford the desired product (6.40 mg, 0.0216 mmol, 95.1% yield) as a white solid, which was used in next step directly. LCMS calculated for $C_{16}H_{17}N_4O_2$ $(M+H)^+$ m/z=297.1; found: 297.2.

Step 9: tert-butyl (1-((1-(2-(2,6-dioxopiperidin-3-yl)-1,3-dioxoisoindolin-5-yl)piperidin-4-yl)methyl) piperidin-4-yl)carbamate

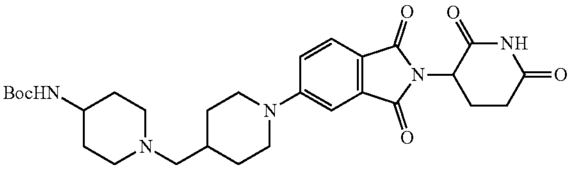 [SMILES: CC(C)(C)OC(=O)NC1CCN(CC2CCN(c3ccc4c(c3)C(=O)N(C3CCC(=O)NC3=O)C4=O)CC2)CC1]

To a stirred solution of tert-butyl N-piperidin-4-ylcarbamate (20.0 mg, 0.10 mmol), 1-(2-(2,6-dioxopiperidin-3-yl)-1,3-dioxoisoindolin-5-yl)piperidine-4-carbaldehyde (44.3 mg, 0.12 mmol) in DMF (2 mL) was added AcOH (30.0 mg, 0.50 mmol) at 25° C. After 1 h, NaBH(OAc)$_3$ (63.5 mg, 0.30 mmol) was added and the resulted mixture was stirred at 25° C. overnight. The volatiles were removed and the residue was purified by Prep-HPLC on a C18 column (20-35 μm, 100 A, 80 g) with mobile phase: $H_2O$ (0.1% TFA)/MeOH at flow rate: 50 mL/min to afford the desired product (62.0 mg, 0.112 mmol, 44.9% yield) as a brown solid. LCMS calculated for $C_{29}H_{40}N_5O_6$ $(M+H)^+$ m/z=554.3; found: 554.2.

Step 10: 5-(4-((4-aminopiperidin-1-yl)methyl)piperidin-1-yl)-2-(2,6-dioxopiperidin-3-yl) isoindoline-1,3-dione

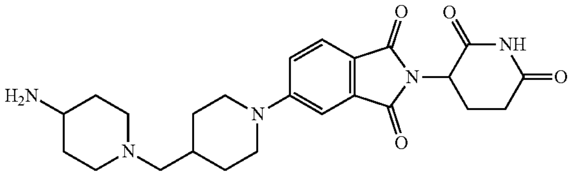 [SMILES: NC1CCN(CC2CCN(c3ccc4c(c3)C(=O)N(C3CCC(=O)NC3=O)C4=O)CC2)CC1]

A mixture of tert-butyl (1-((1-(2-(2,6-dioxopiperidin-3-yl)-1,3-dioxoisoindolin-5-yl)piperidin-4-yl)methyl)piperidin-4-yl)carbamate (86.0 mg, 0.16 mmol) and TFA (0.08 mL) in DCM (2 mL) was stirred at 25° C. for 3 h. The volatiles were removed and the residue was purified by Prep-HPLC on a C18 column (20-35 μm, 100 A, 80 g) with mobile phase: $H_2O$ (0.1% TFA)/MeOH at flow rate: 50 mL/min to afford the desired product (52.0 mg, 0.115 mmol, 73.8% yield) as a yellow solid. LCMS calculated for $C_{24}H_{32}N_5O_4$ $(M+H)^+$ m/z=454.2; found: 454.2.

Step 11: 2-(2,6-dioxopiperidin-3-yl)-5-(4-((4-((2-(2-hydroxyphenyl)-6,6a, 7,8,9,10-hexahydro-5H-pyrido [1',2':4,5]pyrazino[2,3-c]pyridazin-8-yl)amino)piperidin-1-yl)methyl)piperidin-1-yl) isoindoline-1,3-dione To a stirred solution of 5-(4-((4-aminopiperidin-1-yl) methyl)piperidin-1-yl)-2-(2,6-dioxopiperidin-3-yl) isoindoline-1,3-dione (10.0 mg, 0.02 mmol), DIEA (0.01 mL, 0.04 mmol), and 2-(2-hydroxyphenyl)-5,6,6a,7,9,10-hexahydro-8H-pyrido[1',2':4,5]pyrazino[2,3-c]pyridazin-8-one (6.53 mg, 0.02 mmol) in DMF (1 mL), AcOH (6.62 mg, 0.11 mmol) was added at 25° C. After 4 h, NaBH(OAc)$_3$ (5.56 mg, 0.07 mmol) was added. After additional 2 h, the volatiles were removed and the purified by Prep-HPLC on a C18 column (20-35 μm, 100 A, 80 g) with mobile phase: $H_2O$ (0.1% $NH_4HCO_3$)/MeCN at flow rate: 50 mL/min to afford the desired product (1.79 mg, 0.00171 mmol, 7.78% yield) as a yellow solid. LCMS calculated for $C_{40}H_{48}N_9O_5$ $(M+H)^+$ m/z=734.4; found: 734.2.

Example 254

The example in Table 34 was prepared using the procedure described in the synthesis of Example 253 with appropriate intermediates.

TABLE 34

| Ex. | Structure/Name | Calcd. (M + H)+ m/z | Found (M + H)+ m/z |
|---|---|---|---|
| Example 254 | | | |
| 254 | 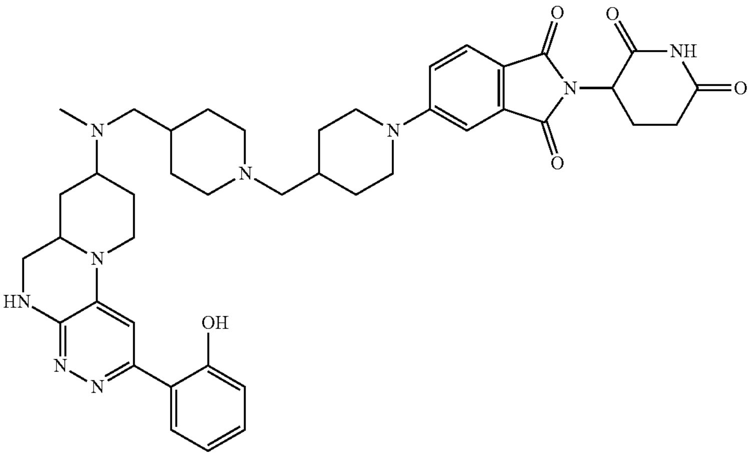 [SMILES: CN(CC1CCN(CC2CCN(c3ccc4c(c3)C(=O)N(C3CCC(=O)NC3=O)C4=O)CC2)CC1)C1CCN2c3cc(-c4ccccc4O)nnc3NCC2C1] 2-(2,6-dioxopiperidin-3-yl)-5-(4-((4-(((2-(2-hydroxyphenyl)-6,6a,7,8,9,10-hexahydro-5H-pyrido[1',2':4,5]pyrazino[2,3-c]pyridazin-8-yl)(methyl)amino)methyl)piperidin-1-yl)methyl)piperidin-1-yl)isoindoline-1,3-dione | 762.4 | 762.2 |

Example 242

The example in Table 35 was prepared using the procedure described in the synthesis of Example 219 with appropriate intermediates.

TABLE 35

| Ex. | Structure/Name | Calcd. (M + H)+ m/z | Found (M + H)+ m/z |
|---|---|---|---|
| Example 242 | | | |
| 242 | 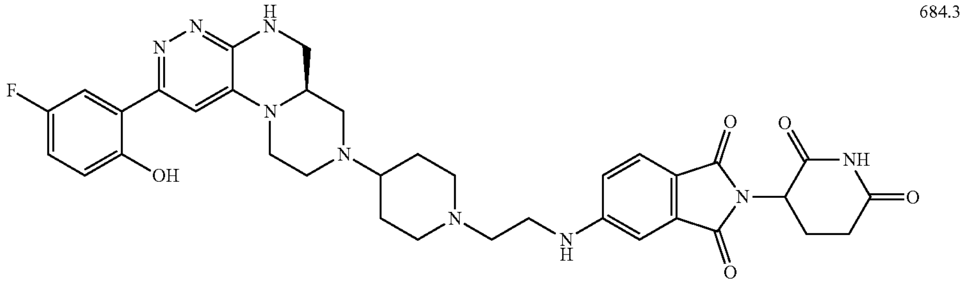 2-(2,6-dioxopiperidin-3-yl)-5-((2-(4-((S)-2-(5-fluoro-2-hydroxyphenyl)-5,6,6a,7,9,10-hexahydro-8H-pyrazino[1',2':4,5]pyrazino[2,3-c]pyridazin-8-yl)piperidin-1-yl)ethyl)amino)isoindoline-1,3-dione | 684.3 | 683.9 |

Example A: Enzymatic Activity and Cytotoxicity Studies

Compound Titration and Cell Culture

Compounds were dissolved in DMSO to make 10 mM stock and 3-fold series dilutions were further conducted keeping the highest concentration 10 μM. NCIH11693 and NCIH1520 cells were maintained in PRMI 1640 medium (Corning Cellgro, Catalog #: 10-040-CV) supplemented with 10% v/v FBS (GE Healthcare, Catalog #: SH30910.03) by splitting 1:3 twice a week.

SMACRA2 and SMARCA4 Protein Degradation $DC_{50}$ Values in NCIH1693 and NCIH520 Cells by in Cell Western (ICW) Analysis.

Cells were trypsinized and 30 thousand cells/well were seeded into 384-well plates and were allowed to grow for 1-2 hours at 37° C. Eight-point, 3-fold serial dilutions of compounds from 0.5 mM stocks were added to the cells (using digital Dispenser D300-Tecan, keeping highest concentration 1 μM and normalizing with DMSO at the highest dispensed volume). Plates were incubated at 37° C. for overnight (maximum 18 hours). Cells incubated with DMSO was used as a vehicle control.

To perform In Cell Western, medium was removed from all the wells leaving cells attached to the surface. After removing the medium, cells were fixed within the plates with 40 μL of 4% formaldehyde by incubating at room temperature for 30 minutes, and then permeabilized with wash buffer (1×PBS with 0.1% Triton X-100) by washing the plate 5 times with 50 μL/well. Before labeling with primary antibodies, cells were blocked with 30 μL/well of blocking buffer (Licor Odyssey blocking buffer PBS #927-40000) for 30 minutes at room temperature. To measure SMARCA2 or SMARCA4 proteins, cells were labeled with 20 μL/well of anti SMARCA2 or SMACRA4 antibodies (Cell Signaling BRM #11966S 1:800, Cell Signaling BRG #49360S 1:800) diluted in Li-Cor Odyssey blocking buffer-PBS #927-40000, followed by overnight incubation at 4° C.

The next day, plates were washed 5×5 minutes with 50 μL/well of washing buffer to remove all the excess primary antibody and then 20 μL from a mixture of secondary antibody and fluorescent DNA specific dye (Goat anti rabbit 1:500 IRDye-800CW #92632211, and DRAQ5™ 1:2000-#ab108410) was added to each well. Plates were incubated for 1 hour at room temperature with gentle rocking. Cells were washed 5 times with 50 μL/well wash buffer, followed by one last wash with DI water, followed by 10 mins drying at 37° C. oven before scanning. Plates were scanned using Li-Cor Odyssey CLx imaging system to acquire integrated intensities at 700 nm and 800 nm. SMARCA signals were normalized to total cell count and then these normalized values were used to calculate the percent degradation relative to DMSO control and maximum inhibition. $DC_{50}$s were calculated by using the GraphPad Prism4 program based on sigmoidal dose response equation ([Inhibitor] vs. normalized response-Variable slope).

Results of the In Cell Western analysis are summarized below in Table 36. In Table 36, the $DC_{50}/D_{max}$% (SM2_H520) refers to SMARCA2 degradation potency/maximum SMARCA2 degradation within the concentrations in H520 cells and $DC_{50}/D_{max}$% (SM4_H520) refers to SMARCA4 degradation potency/maximum SMARCA4 degradation within the concentrations tested in H520 cells.

In Table 36, A=$DC_{50}$<0.1 μM and B=0.1 μM≤$DC_{50}$<1 μM. In Table 3, A=$D_{max}$>75% and B=50%<$D_{max}$≤75%. In Table 3, NA=not applicable.

TABLE 36

Biological Data for Example A

| Example | $DC_{50}/D_{max}$ % (SM2_H520) | $DC_{50}/D_{max}$ % (SM4_H520) |
|---|---|---|
| 1 | A/A | A/A |
| 2 | A/A | A/A |
| 3 | A/A | A/A |
| 4 | A/A | A/A |
| 5 | A/A | A/A |
| 6 | A/A | A/A |
| 7 | A/A | A/A |
| 8 | A/A | A/A |
| 9 | A/A | A/B |
| 10 | A/A | A/B |
| 11 | A/A | A/A |
| 12 | A/A | A/B |
| 13 | A/A | A/A |
| 14 | A/A | A/A |
| 15 | A/B | NA |
| 16 | A/A | A/B |
| 17 | A/A | A/A |
| 18 | A/A | A/A |
| 19 | A/A | A/A |
| 20 | A/A | A/A |

TABLE 36-continued

Biological Data for Example A

| Example | $DC_{50}/D_{max}$ % (SM2_H520) | $DC_{50}/D_{max}$ % (SM4_H520) |
|---|---|---|
| 21 | A/A | A/A |
| 22 | A/A | A/A |
| 23 | A/A | NA |

Example B: SMARCA2 HiBiT and SMARCA4 HiBiT Degradation Assay

Preparation of SMARCA2/4-HiBiT Knock-In Cells

HiBiT peptide knock-in of SMARCA2 in LgBiT expressing HEK293T cells was performed by CRISPR-mediated tagging system as described Promega. The homozygous HiBiT knock-in on c-terminus SMARCA2 was confirmed by sanger sequence. SMARCA2-HiBiT knock-in Hela monoclonal cell (CS302366) and SMARCA4-HiBiT knock-in Hela monoclonal cell (CS3023226) were purchased from Promega. The heterozygous HiBiT-knock-in was confirmed by sanger sequence in both SMARCA2-HiBiT and SMARCA4-HiBiT monoclonal cells.

SMARCA2 HiBiT and SMARCA4 HiBiT Degradation Assay in HeLa Cells

Dispense 10 ul aliquot of prepared Hela-SMARCA2-HiBiT or Hela-SMARCA4-HiBiT cells (1:1 ratio of cells: Trypan Blue (#1450013, Bio-Rad)) onto cell counting slide (#145-0011, Bio-Rad) and obtain cell density and cell viability using cell counter (TC20, Bio-Rad). Remove appropriate volume of resuspended cells from culture flask to accommodate 2500 cells/well @20 μL/well. Transfer Hela-HiBiT cells to 50 mL conical (#430290, Corning). Spin down at 1000 rpm for 5 min using tabletop centrifuge (SPINCHRON 15, Beckman). Discard supernatant and resuspend cell pellet in modified EMEM (#30-2003, ATCC) cell culture media containing 10% FBS (F2422-500ML, Sigma), and 1×Penicillin/Streptomycin (200 g/L) (30-002-CI, Corning) to a cell density of 125,000 cells/mL. Dispense 20 μL of resuspended Hela-HiBit cells per well in 384-well TC treated plate (#12-565-343, Thermo Scientific) using standard cassette (#50950372, Thermo Scientific) on Multidrop Combi (#5840310, Thermo Scientific) inside laminar flow cabinet. Dispense test compounds onto plates using digital liquid dispenser (D300E, Tecan). Incubate plates in humidified tissue culture incubator @37° C. for 18 hours. Add 20 μL of prepared Nano-Glo® HiBiT Lytic detection buffer (N3050, Promega) to each well of 384-well plate using small tube cassette (#24073295, Thermo Scientific) on Multidrop Combi, incubate @RT for 30-60 min. Read plates on microplate reader (Envision 2105, PerkinElmer) using 384 well Ultra-Sensitive luminescence mode. Raw data files and compound information reports are swept into centralized data lake and deconvoluted using automated scripts designed by TetraScience, Inc. Data analysis, curve-fitting and reporting done in Dotmatics Informatics Suite using Screening Ultra module.

Results are summarized below in Table 37. In Table 37, A=$IC_{50}$ or $DC_{50}$<0.01 μM; B=0.01 μM=<$IC_{50}$ or $DC_{50}$<0.1 μM; C=0.1 μM=<$IC_{50}$ or $DC_{50}$<1 μM; D=$IC_{50}$ or $DC_{50}$>=1 μM; or A=$D_{max}$>85%; B=75%<$D_{max}$<=85%; C=50%<$D_{max}$<=75%; D=$D_{max}$<=50%.

TABLE 37

| Biological Data for Example B | | | | |
|---|---|---|---|---|
| Ex# | HeLa_HiBit-SM2 $DC_{50}$ (nM) | HeLa-HiBit-SM2 Dmax (%) | HeLa-HiBit-SM4 $DC_{50}$ (nM) | HeLa-HiBit-SM4 Dmax (%) |
| 24 | A | A | A | B |
| 25 | A | A | A | B |
| 26 | A | A | A | A |
| 27 | A | C | A | C |
| 28 | A | A | A | B |
| 29 | A | A | A | A |
| 30 | A | A | A | A |
| 31 | A | A | A | A |
| 32 | A | A | A | A |
| 33 | A | A | A | B |
| 34 | A | A | A | A |
| 35 | A | B | A | C |
| 36 | A | A | A | B |
| 37 | A | A | A | A |
| 38 | A | A | A | A |
| 39 | A | A | A | C |
| 40 | A | C | A | C |
| 41 | A | A | A | A |
| 42 | A | A | A | C |
| 43 | A | A | A | C |
| 44 | A | B | A | C |
| 45 | A | A | A | A |
| 46 | A | A | A | A |
| 47 | A | A | A | C |
| 48 | A | A | A | B |
| 49 | A | A | A | B |
| 50 | A | A | A | B |
| 51 | A | A | A | C |
| 52 | A | A | A | B |
| 53 | A | B | A | C |
| 54 | A | B | B | C |
| 55 | B | C | B | B |
| 56 | A | C | B | B |
| 57 | A | C | A | D |
| 58 | A | C | B | D |
| 59 | A | B | B | B |
| 60 | A | D | A | D |
| 61 | A | D | A | D |
| 62 | A | A | A | A |
| 63 | A | A | A | A |
| 64 | A | A | A | B |
| 65 | A | A | A | A |
| 66 | A | A | A | A |
| 67 | A | C | A | C |
| 68 | A | A | B | A |
| 69 | A | A | A | A |
| 70 | A | A | A | A |
| 71 | A | B | A | B |
| 72 | A | B | A | C |
| 73 | A | B | A | C |
| 74 | A | A | A | A |
| 75 | A | B | A | B |
| 76 | A | A | A | A |
| 77 | A | A | A | A |
| 78 | A | A | A | A |
| 79 | A | B | A | B |
| 80 | A | A | A | A |
| 81 | A | B | A | B |
| 82 | A | B | A | C |
| 83 | A | A | A | B |
| 84 | A | A | A | B |
| 85 | A | A | A | B |
| 86 | A | A | B | C |
| 87 | A | B | B | B |
| 88 | A | A | A | A |
| 89 | A | B | A | C |
| 90 | A | C | B | C |
| 91 | A | A | B | C |
| 92 | A | A | A | B |
| 93 | A | A | A | A |
| 94 | A | C | A | C |
| 95 | A | A | A | B |
| 96 | A | C | B | D |
| 97 | A | B | B | C |
| 98 | A | B | A | A |

TABLE 37-continued

| Biological Data for Example B | | | | |
|---|---|---|---|---|
| Ex# | HeLa_HiBit-SM2 $DC_{50}$ (nM) | HeLa-HiBit-SM2 Dmax (%) | HeLa-HiBit-SM4 $DC_{50}$ (nM) | HeLa-HiBit-SM4 Dmax (%) |
| 99 | A | A | B | B |
| 100 | A | B | B | B |
| 101 | A | B | B | B |
| 102 | A | A | A | B |
| 103 | A | B | B | B |
| 104 | A | A | A | B |
| 105 | A | A | A | A |
| 106 | A | A | A | B |
| 107 | A | A | B | B |
| 108 | A | A | A | A |
| 109 | A | A | A | A |
| 110 | A | A | B | B |
| 111 | A | C | B | C |
| 112 | A | A | A | B |
| 113 | A | D | B | C |
| 114 | A | A | A | B |
| 115 | A | C | A | C |
| 116 | A | B | A | C |
| 117 | A | B | B | D |
| 118 | A | A | B | A |
| 119 | A | A | A | A |
| 120 | A | A | B | A |
| 121 | A | A | B | B |
| 122 | B | A | B | B |
| 123 | A | B | A | B |
| 124 | A | C | A | C |
| 125 | A | B | A | B |
| 126 | A | A | A | B |
| 127 | A | A | A | B |
| 128 | A | A | A | A |
| 129 | A | A | A | A |
| 130 | A | A | A | A |
| 131 | A | A | A | A |
| 132 | A | A | A | B |
| 133 | A | C | A | C |
| 134 | A | B | A | C |
| 135 | A | B | A | C |
| 136 | A | A | A | A |
| 137 | A | C | B | C |
| 138 | A | A | A | A |
| 139 | A | A | A | A |
| 140 | A | B | A | B |
| 141 | A | B | B | C |
| 142 | A | B | B | C |
| 143 | A | A | B | B |
| 144 | A | B | A | B |
| 145 | A | B | B | B |
| 146 | A | A | A | A |
| 147 | A | A | A | A |
| 148 | A | A | A | A |
| 149 | A | C | B | C |
| 150 | A | A | A | A |
| 151 | A | B | B | C |
| 152 | A | C | A | C |
| 153 | A | C | B | B |
| 154 | A | C | A | C |
| 155 | A | A | A | A |
| 156 | B | B | B | C |
| 157 | A | B | B | C |
| 158 | A | A | A | A |
| 159 | A | A | A | C |
| 160 | A | B | A | C |
| 161 | A | A | A | A |
| 162 | A | A | A | A |
| 163 | A | A | A | A |
| 164 | A | A | A | B |
| 165 | A | B | A | B |
| 166 | A | A | A | A |
| 167 | A | A | A | A |
| 168 | A | A | A | B |
| 169 | A | B | B | B |
| 170 | A | A | A | A |
| 171 | A | A | A | A |
| 172 | A | B | A | C |
| 173 | A | B | B | C |

TABLE 37-continued

| Biological Data for Example B | | | | |
|---|---|---|---|---|
| Ex# | HeLa_HiBit-SM2 $DC_{50}$ (nM) | HeLa-HiBit-SM2 Dmax (%) | HeLa-HiBit-SM4 $DC_{50}$ (nM) | HeLa-HiBit-SM4 Dmax (%) |
| 174 | A | A | A | A |
| 175 | A | A | A | A |
| 176 | A | A | B | C |
| 177 | A | A | A | C |
| 178 | A | A | A | B |
| 179 | A | C | A | C |
| 180 | A | B | A | B |
| 181 | A | A | A | A |
| 182 | A | A | B | C |
| 183 | A | A | A | B |
| 184 | A | A | A | A |
| 185 | A | B | A | C |
| 186 | A | B | A | C |
| 187 | A | C | A | C |
| 188 | A | A | A | B |
| 189 | A | B | A | B |
| 190 | A | B | A | B |
| 191 | A | C | B | B |
| 192 | A | C | A | D |
| 193 | A | B | B | C |
| 194 | A | A | A | B |
| 195 | A | C | B | C |
| 196 | A | B | B | C |
| 197 | A | A | A | B |
| 198 | A | A | A | C |
| 199 | A | A | A | C |
| 200 | A | B | A | C |
| 201 | A | A | A | A |
| 202 | A | A | B | B |
| 203 | A | A | A | A |
| 204 | A | B | B | B |
| 205 | A | A | B | B |
| 206 | A | A | B | C |
| 207 | A | C | B | D |
| 208 | A | B | A | C |
| 209 | A | A | A | A |
| 210 | A | A | A | B |
| 211 | A | A | A | A |
| 212 | A | A | A | A |
| 213 | A | A | A | A |
| 214 | A | B | A | C |
| 215 | A | C | B | C |
| 216 | A | A | A | C |
| 217 | A | A | A | A |
| 218 | A | A | A | B |
| 219 | A | C | B | D |
| 220 | A | B | A | B |
| 221 | A | B | A | C |
| 222 | A | C | C | D |
| 223 | A | B | A | B |
| 224 | A | B | A | B |
| 225 | A | A | A | A |
| 226 | A | A | A | B |
| 227 | A | C | B | C |
| 228 | A | A | A | A |
| 229 | A | A | A | A |
| 230 | A | A | A | A |
| 231 | A | A | A | A |
| 232 | A | A | A | A |
| 233 | A | A | A | A |
| 234 | A | A | A | A |
| 235 | A | A | A | A |
| 236 | A | A | A | B |
| 237 | A | A | A | B |
| 238 | A | A | A | B |
| 239 | A | A | A | C |
| 240 | A | B | A | B |
| 241 | A | C | B | B |
| 242 | A | A | A | A |
| 243 | A | A | A | A |
| 244 | A | B | B | B |
| 245 | A | C | B | C |
| 246 | A | B | A | C |
| 247 | A | A | A | A |
| 248 | A | A | A | A |

TABLE 37-continued

| Biological Data for Example B | | | | |
|---|---|---|---|---|
| Ex# | HeLa_HiBit-SM2 $DC_{50}$ (nM) | HeLa-HiBit-SM2 Dmax (%) | HeLa-HiBit-SM4 $DC_{50}$ (nM) | HeLa-HiBit-SM4 Dmax (%) |
| 249 | A | A | A | A |
| 250 | A | A | A | A |
| 251 | A | A | A | A |
| 252 | A | A | A | A |
| 253 | A | C | B | C |
| 254 | A | C | B | B |
| 255 | B | B | C | D |
| 256 | B | C | B | C |
| 257 | A | A | A | A |
| 258 | A | C | B | C |
| 258 | A | A | A | B |
| 259 | A | A | A | B |
| 260 | A | B | B | B |
| 261 | A | A | B | B |
| 262 | A | A | A | A |
| 263 | A | D | B | D |
| 264 | A | A | A | B |
| 265 | A | B | B | B |
| 266 | A | A | A | A |
| 267 | A | A | A | B |
| 268 | A | B | A | C |
| 269 | A | B | B | C |
| 270 | A | A | A | A |
| 271 | A | A | A | A |
| 272 | A | A | B | B |
| 273 | A | A | A | B |
| 274 | A | A | A | C |
| 275 | A | B | A | B |
| 276 | A | A | A | A |
| 277 | A | A | A | C |
| 278 | A | A | A | A |
| 279 | A | A | A | C |
| 280 | A | A | A | B |
| 281 | A | B | B | D |
| 282 | A | A | A | B |

What is claimed:

1. A compound of Formula (I):

PTM-ULM (I)

or a pharmaceutically acceptable salt or solvate thereof, wherein PTM is a moiety of Formula IA:

(IA)

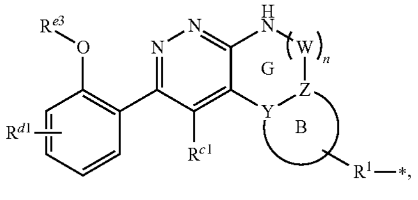

wherein $R^1$ is a chemical moiety that links PTM and ULM, wherein the chemical moiety represented by the formula:

-(A)q-, wherein:

q is an integer from 1 to 14;

each A is independently selected from the group consisting of a bond, $CR^{1a}R^{1b}$, O, S, SO, $SO_2$, $NR^{1c}$, $SO_2NR^{1c}$, $SONR^{1c}$, SO ($=NR^{1c}$), SO($=NR^{1c}$) $NR^{1d}$, $CONR^{1c}$, $NR^{1c}CONR^{1d}$, $NR^{1c}C(O)$ O, $NR^{1c}SO_2NR^{1d}$, CO, $CR^{1a}=CR^{1b}$, C≡C, $SiR^{1a}R^{1b}$, $P(O)R^{1a}$, $P(O)OR^{1a}$, $(CR^{1a}R^{1b})_{1-4}$, $-(CR^{1a}R^{1b})_{1-4}O(CR^{1a}R^{1b})_{1-4}$, $-(CR^{1a}R^{1b})_{1-4}S(CR^{1a}R^{1b})_{1-4}$, $-(CR^{1a}R^{1b})_{1-4}NR(CR^{1a}R^{1b})_{1-4}$, $NR^{1c}C(=NCN)NR^{1d}NR^{1c}C(=NCN)$, $NR^{1c}C(=CNO_2)NR^{1d}$, 3-11 membered cycloalkyl, optionally substituted with 0-6 $R^{1a}$ and/or $R^{1b}$ groups, 3-11 membered heterocyclyl optionally substituted with 0-6 $R^{1a}$ and/or $R^{1b}$ groups, aryl optionally substituted with 0-6 $R^{1a}$ and/or $R^{1b}$ groups, or heteroaryl optionally substituted with 0-6 $R^{1a}$ and/or $R^{1b}$ groups, wherein $R^{1a}$, $R^{1b}$, $R^{1c}$, $R^{1d}$ and $R^{1e}$ are each independently, —H, D,-halo, —$C_1$-$C_8$alkyl, —O—$C_1$-$C_8$alkyl, —$C_1$-$C_6$haloalkyl, —S—$C_1$-$C_8$alkyl, —NH$C_1$-$C_8$alkyl, —N($C_1$-$C_8$alkyl) 2, 3-11 membered cycloalkyl, aryl, heteroaryl, 3-11 membered heterocyclyl, —O-(3-11 membered cycloalkyl), —S-(3-11 membered cycloalkyl), NH-(3-11 membered cycloalkyl), N (3-11 membered cycloalkyl$)_2$, N-(3-11 membered cycloalkyl) ($C_1$-$C_8$alkyl), —OH, —$NH_2$, —SH, —$SO_2C_1$-$C_8$alkyl, SO(NH)$C_1$-$C_8$alkyl, P(O)(O$C_1$-$C_8$alkyl) ($C_1$-$C_8$alkyl), —P(O)(O$C_1$-$C_8$alkyl$)_2$, —C≡C—$C_1$-$C_8$alkyl, —C≡CH, —CH=CH ($C_1$-$C_8$alkyl), —C($C_1$-$C_8$alkyl)=CH ($C_1$-$C_8$alkyl), —C($C_1$-$C_8$alkyl)=C($C_1$-$C_8$alkyl$)_2$, —Si$(OH)_3$, —Si($C_1$-$C_8$alkyl$)_3$, —Si(OH)($C_1$-$C_8$alkyl$)_2$, —C(O)$C_1$-$C_8$alkyl, —$CO_2H$, —CN, —$CF_3$, —$CHF_2$, —$CH_2F$, —$NO_2$, —$SF_5$, —$SO_2NHC_1$-$C_8$alkyl, —$SO_2N$($C_1$-$C_8$alkyl$)_2$, —SO (NH)NH$C_1$-$C_8$alkyl, —SO(NH)N($C_1$-$C_8$alkyl$)_2$, —SONH$C_1$-$C_8$alkyl, —SON($C_1$-$C_8$alkyl$)_2$, —CONH$C_1$-$C_8$alkyl, —CON($C_1$-$C_8$alkyl$)_2$, —N($C_1$-$C_8$alkyl)CONH($C_1$-$C_8$alkyl), —N($C_1$-$C_8$alkyl)CON($C_1$-$C_8$alkyl)$_2$, —NHCONH($C_1$-$C_8$alkyl), —NHCON($C_1$-$C_8$alkyl)$_2$, —NHCONH$_2$, —N($C_1$-$C_8$alkyl)SO$_2$NH($C_1$-$C_8$alkyl), —N($C_1$-$C_8$alkyl)SO$_2$N($C_1$-$C_8$alkyl)$_2$, —NHSO$_2$NH($C_1$-$C_8$alkyl), —NHSO$_2$N($C_1$-$C_8$alkyl)$_2$, or —NHSO$_2$NH$_2$; and where $R^{1a}$ or $R^{1b}$, each independently may be optionally linked to other groups to form cycloalkyl and/or heterocyclyl moiety, optionally substituted with 0-4 $R^{1e}$ groups;

* is a point of attachment to ULM;

n=0-3;

each W is independently optionally substituted —CH$_2$—, —C(O)—, —S(O)—, or —S(O)$_2$—; wherein when n=2 or 3, only one W is —C(O)—, —S(O)—, or —S(O)$_2$—, and the other W are —CH$_2$— or substituted —CH$_2$—;

$R^{c1}$ and $R^{d1}$ are independently H, D, Halo, $C_{1-3}$ alkyl, $C_{1-3}$ haloalkyl, or $C_{1-4}$ alkoxyl;

$R^{e3}$ is H, —C(O) $R^f$, or —P(O)(OR$^g$)$_2$; wherein $R^f$ and $R^g$ are independently H, $C_{1-4}$ alkyl, $C_{1-4}$ substituted alkyl, $C_{3-8}$ cyclcoalkyl, $C_{3-8}$ substituted cyclcoalkyl, $C_{3-8}$ heterocyclcoalkyl, or $C_{3-8}$ substituted heterocyclcoalkyl;

Z and Y are each independently N; CR$^h$ wherein $R^h$=H or absent; or, if $R^1$ is attached to Z, then Z is C and Y is N or CR$^h$ wherein $R^h$ is H; or if $R^1$ is attached to Y, then Y is C and Z is N or CR$^h$ wherein $R^h$ is H;

B is an optionally substituted 5-7 membered cycloalkyl ring, an optionally substituted 5-7 membered heteroaryl ring, or an optionally substituted 5-7 membered heterocyclic ring, wherein ring B is fused to ring G through Y and Z; and ULM is a moiety having the Formula ULM-I (ULM-I)

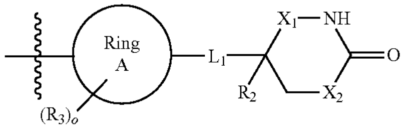

wherein:

∿∿∿ is a point of attachment to PTM;

Ring A is a monocyclic, bicyclic or tricyclic aryl, heteroaryl or heterocycle group, $L_1$ is a bond, —O—, —S—, —NR$^a$—, —C(R$^a$)$_2$—C(O) NR$^a$—;

$X_1$ is a bond, —C(O)—, —C(S)—, —CH$_2$—, —CHCF$_3$—, SO$_2$—, —S(O), P(O)R$^b$— or —P(O) OR$^b$—;

$X_2$ is —C(R$^a$)$_2$—, —NR$^a$— or —S—;

$R_2$ is H, D, optionally substituted $C_{1-4}$ alkyl, $C_{1-4}$ alkoxyl, $C_{1-4}$ haloalkyl, —CN, —OR$^a$, —OR$^b$ or —SR$^b$;

each $R^3$ is independently H, D, halogen, oxo, —OH, —CN, —NO$_2$, —$C_1$-$C_6$alkyl, —$C_2$-$C_6$alkenyl, —$C_2$-$C_6$alkynyl, $C_0$-$C_1$alk-aryl, $C_0$-$C_1$alk-heteroaryl, cycloalkyl, cycloalkenyl, heterocycloalkyl, or heterocycloalkenyl, —OR$^a$, —SR$^a$, —NR$^c$R$^d$, —NR$^a$R$^c$, —C(O)R$^b$, —OC(O)R$^a$, —C(O)OR$^a$, —C(O)NR$^c$R$^d$, —S(O)R$^b$, —S(O)$_2$NR$^c$R$^d$, —S(O)(=NR$^b$)R$^b$, —SF$_5$, —P(O)R$^b$R$^b$, —P(O)(OR$^b$)(OR$^b$), —B(OR$^d$)(OR$^c$) or —S(O)$_2$R$^b$;

each $R^a$ is independently H, D, —C(O)R$^b$, —C(O)OR$^e$, —C(O)NR$^c$R$^d$, —C(=NR$^b$)NR$^b$R$^c$, —C(=NOR$^b$) NR$^b$R$^c$, —C(=NCN)NR$^b$R$^c$, —P(OR$^c$)$_2$, —P(O) R$^c$R$^b$, —P(O)OR$^c$OR$^b$, —S(O)R$^b$, —S(O)NR$^c$R$^d$, —S(O)$_2$R$^b$, —S(O)$_2$NR$^c$R$^d$, SiR$^b_3$, —$C_1$-$C_{10}$alkyl, —$C_2$-$C_{10}$ alkenyl, —$C_2$-$C_{10}$ alkynyl, aryl, cycloalkyl, cycloalkenyl, heteroaryl, heterocycloalkyl, or heterocycloalkenyl;

each $R^b$, is independently H, D, —$C_1$-$C_6$ alkyl, —$C_2$-$C_6$ alkenyl, —$C_2$-$C_6$ alkynyl, aryl, cycloalkyl, cycloalkenyl, heteroaryl, heterocycloalkyl, or heterocycloalkenyl;

each $R^c$ or $R^d$ is independently H, D, —$C_1$-$C_{10}$ alkyl, —$C_2$-$C_6$ alkenyl, —$C_2$-$C_6$ alkynyl, —O$C_1$-$C_6$alkyl, —O-cycloalkyl, aryl, heteroaryl, cycloalkyl, cycloalkenyl, heterocycloalkyl, or heterocycloalkenyl; or $R^c$ and $R^d$, together with the atom to which they are both attached, form a monocyclic or multicyclic heterocycloalkyl, or a monocyclic or multicyclic heterocyclo-alkenyl group; and is 1, 2, 3, 4, or 5.

2. The compound according to claim 1, wherein q=5 and $R^1$ is a chemical moiety represented by the formula:-$A_1$-$A_2$-$A_3$-$A_4$-$A_5$-; wherein:

each of $A_1$, $A_3$ and $A_5$ is independently selected from the group consisting of a bond, —(CR$^{1a}$R$^{1b}$)$_{0-4}$O(CR$^{1a}$R$^{1b}$)$_{0-4}$, —(CR$^{1a}$R$^{1b}$)$_{0-4}$S(CR$^{1a}$R$^{1b}$)$_{0-4}$, —(CR$^{1a}$R$^{1b}$)$_{0-4}$NR$^{1c}$(CR$^{1a}$R$^{1b}$)$_{0-4}$, —(CR$^{1a}$R$^{1b}$)$_{0-4}$SO(CR$^{1a}$R$^{1b}$)$_{0-4}$, —(CR$^{1a}$R$^{1b}$)$_{0-4}$SO$_2$(CR$^{1a}$R$^{1b}$)$_{0-4}$, —(CR$^{1a}$R$^{1b}$)$_{0-4}$ SO$_2$NR$^{1c}$(CR$^{1a}$R$^{1b}$)$_{0-4}$, —(CR$^{1a}$R$^{1b}$)$_{0-4}$SONR$^{1c}$ (CR$^{1a}$R$^{1b}$)$_{0-4}$, —(CR$^{1a}$R$^{1b}$)$_{0-4}$SO(=NR$^{1c}$) (CR$^{1a}$R$^{1b}$)$_{0-4}$, —(CR$^{1a}$R$^{1b}$)$_{0-4}$ SO(=NR$^{1c}$)NR$^{1d}$(CR$^{1a}$R$^{1b}$)$_{0-4}$, —(CR$^{1a}$R$^{1b}$)$_{0-4}$CONR$^{1c}$(CR$^{1a}$R$^{1b}$)$_{0-4}$, —(CR$^{1a}$R$^{1b}$)$_{0-4}$ C(O)O(CR$^{1a}$R$^{1b}$)$_{0-4}$, —(CR$^{1a}$R$^{1b}$)$_{0-4}$NR$^{1c}$CONR$^{1d}$(CR$^{1a}$R$^{1b}$)$_{0-4}$, —(CR$^{1a}$R$_{1b}$)$_{0-4}$NR$^{1c}$ (O)O(CR$^{1a}$R$^{1b}$)$_{0-4}$, —(CR$^{1a}$R$_{1b}$)$_{0-4}$NR$^{1c}$SO$_2$NR$^{1d}$(CR$^{1a}$R$^{1b}$)$_{0-4}$, —(CR$^{1a}$R$^{1b}$)$_{0-4}$C(O)(CR$^{1a}$R$^{1b}$)$_{0-4}$, —(CR$^{1a}$R$^{1b}$)$_{0-4}$ CR$^{1a}$—CR$^{1b}$(CR$^{1a}$R$^{1b}$)$_{0-4}$, —(CR$^{1a}$R$^{1b}$)$_{0-4}$C≡C(CR$^{1a}$R$^{1b}$)$_{0-4}$, —(CR$^{1a}$R$^{1b}$)$_{0-4}$SiR$^{1a}$R$^{1b}$(CR$^{1a}$R$^{1b}$)$_{0-4}$, —(CR$^{1a}$R$^{1b}$)$_{0-4}$P(O)R$^{1a}$(CR$^{1a}$R$^{1b}$)$_{0-4}$, —(CR$^{1a}$R$^{1b}$)$_{0-4}$P(O)OR$^{1a}$(CR$^{1a}$R$^{1b}$)$_{0-4}$, (CR$^{1a}$R$^{1b}$)$_{1-4}$, optionally substituted 3-11 membered cycloalkyl, 3-11 membered heterocyclyl, aryl, and heteroaryl;

each of $A_2$ and $A_4$ is independently selected from the group consisting of is independently selected from the group consisting of a bond, (CR$^{1a}$R$^{1b}$)$_{1-4}$, optionally substituted 3-11 membered cycloalkyl, 3-11 membered heterocyclyl, aryl, and heteroaryl;

$R^{1a}$ and $R^{1b}$ are each independently selected from the group consisting of —H, D, -halo, —$C_1$-$C_8$alkyl, —O—$C_1$-$C_8$alkyl, —$C_1$-$C_6$haloalkyl, —S—$C_1$-$C_8$alkyl, —NH$C_1$-$C_8$alkyl, —N($C_1$-$C_8$alkyl) 2, 3-11 membered cycloalkyl, aryl, heteroaryl, 3-11 membered heterocyclyl, —O-(3-11 membered cycloalkyl), —S-(3-11 membered cycloalkyl), NH-(3-11 membered cycloalkyl), N (3-11 membered cycloalkyl)$_2$, N-(3-11 membered cycloalkyl) ($C_1$-$C_8$alkyl), —OH, —NH$_2$, —SH, —SO$_2$$C_1$-$C_8$alkyl, SO(NH)$C_1$-$C_8$alkyl, P(O)(O$C_1$-$C_8$alkyl) ($C_1$-$C_8$alkyl), —P(O)(O$C_1$-$C_8$alkyl)$_2$, —C≡C—$C_1$-$C_8$alkyl, —C≡CH, —CH=CH ($C_1$-$C_8$alkyl), —C($C_1$-$C_8$alkyl)-CH($C_1$-$C_8$alkyl), —C($C_1$-$C_8$alkyl)=C ($C_1$-$C_8$alkyl)$_2$, —Si(OH)$_3$, —Si($C_1$-$C_8$alkyl)$_3$, —Si(OH)($C_1$-$C_8$alkyl)$_2$, —C(O)$C_1$-$C_8$alkyl, —CO$_2$H, —CN, —NO$_2$, —SF$_5$, —SO$_2$NH$C_1$-$C_8$alkyl, —SO$_2$N($C_1$-$C_8$alkyl)$_2$, —SO(NH)NH$C_1$-$C_8$alkyl, —SO(NH)N($C_1$-$C_8$alkyl)$_2$, —SONH$C_1$-$C_8$alkyl, —SON($C_1$-$C_8$alkyl)$_2$, —CONH$C_1$-$C_8$alkyl, —CON($C_1$-$C_8$alkyl)$_2$, —N($C_1$-$C_8$alkyl)CONH($C_1$-$C_8$alkyl), —N($C_1$-$C_8$alkyl)CON($C_1$-$C_8$alkyl)$_2$, —NHCONH($C_1$-$C_8$alkyl), —NHCON($C_1$-$C_8$alkyl)$_2$, —NHCON$H_2$, —N($C_1$-$C_8$alkyl)$SO_2$NH($C_1$-$C_8$alkyl), —N($C_1$-$C_8$alkyl)$SO_2$N—($C_1$-$C_8$alkyl)$_2$, —NH$SO_2$NH($C_1$-$C_8$alkyl), —NH$SO_2$N($C_1$-$C_8$alkyl)$_2$, or —NH$SO_2$N$H_2$; and $R^{1c}$ and $R^{1d}$ are each independently selected from the group consisting of H, D, optionally substituted $C_{1-4}$ alkyl, $C_{3-8}$ cyclcoalkyl, $C_{3-8}$ heterocyclcoalkyl, aryl, or heteroaryl.

3. The compound according to claim 1, wherein $R^1$ is a 3-11 membered cycloalkyl optionally substituted with 0-6 $R^{1a}$ and/or $R^{1b}$ groups, 3-11 membered heterocyclyl optionally substituted with 0-6 $R^{1a}$ and/or $R^{1b}$ groups, —$(CR^{1a}R^{1b})_{1-5}$, —$(CR^{1a}$=$CR^{1b})$—, —$(CR^{1a}R^{1b})_{1-5}$-A- wherein A is O, S, or $NR^{1c}$, —$(CR^{1a}R^{1b})_{1-5}$-A-$(CR^{1a}R^{1b})_{1-5}$— wherein A is O, S, or $NR^{1c}$, —$(CR^{1a}R^{1b})_{1-5}$-A-$(CR^{1a}R^{1b})_{1-5}$-A- wherein A is O, S, or $NR^{1c}$, —$(CR^{1a}R^{1b})_{1-5}$—$(CR^{1a}$=$CR^{1b})$—$(CR^{1a}R^{1b})_{1-5}$—, —$(CR^{1a}R^{1b})_{1-5}$—$(CR^{1a}R^{1b})$—$(CR^{1a}R^{1b})_{1-5}$-A- wherein A is O, S, or $NR^{1c}$, —$(CR^{1a}R^{1b})_{1-5}$—(C≡C)—$(CR^{1a}R^{1b})_{1-5}$—, —$(CR^{1a}R^{1b})_{1-5}$—(C≡C)—$(CR^{1a}R^{1b})_{1-5}$-A- wherein A is O, S, or $NR^{1c}$, —(C≡C)—$(CR^{1a}R^{1b})_{1-5}$-A-$(CR^{1a}R^{1b})_{1-5}$— wherein A is O, S, or $NR^{1e}$, —(C≡C)—$(CR^{1a}R^{1b})_{1-5}$, —$(CR^{1a}R^{1b})_{1-5}$-(3-11 membered cycloalkyl optionally substituted with 0-6 $R^{1a}$ and/or $R^{1b}$ groups)-, $(CR^{1a}R^{1b})_{1-5}$-(3-11 membered heterocyclyl optionally substituted with 0-6 $R^{1a}$ and/or $R^{1b}$ groups)-,-(3-11 membered cycloalkyl optionally substituted with 0-6 $R^{1a}$ and/or $R^{1b}$ groups)-$(CR^{1a}R^{1b})_{1-5}$—,-(3-11 membered heterocyclyl optionally substituted with 0-6 $R^{1a}$ and/or $R^{1b}$ groups)-$(CR^{1a}R^{1b})_{1-5}$—, —$(CR^{1a}R^{1b})_{1-5}$-(3-11 membered cycloalkyl optionally substituted with 0-6 $R^{1a}$ and/or $R^{1b}$ groups)-A-, —$(CR^{1a}R^{1b})_{1-5}$-(3-11 membered heterocyclyl optionally substituted with 0-6 $R^{1a}$ and/or $R^{1b}$ groups)-A-, —$(CR^{1a}R^{1b})_{1-5}$-(3-11 membered cycloalkyl optionally substituted with 0-6 $R^{1a}$ and/or $R^{1b}$ groups)-$(CR^{1a}R^{1b})_{1-5}$, —$(CR^{1a}R^{1b})_{1-5}$-(3-11 membered cycloalkyl optionally substituted with 0-6 $R^{1a}$ and/or $R^{1b}$ groups)-A- wherein A is O, S, or $NR^{1c}$, —$(CR^{1a}R^{1b})_{1-5}$-(3-11 membered cycloalkyl optionally substituted with 0-6 $R^{1a}$ and/or $R^{1b}$ groups)-$(CR^{1a}R^{1b})_{1-5}$-A- wherein A is O, S, or $NR^{1c}$, —$(CR^{1a}R^{1b})_{1-5}$-A-(3-11 membered cycloalkyl optionally substituted with 0-6 $R^{1a}$ and/or $R^{1b}$ groups)- wherein A is O, S, or $NR^{1c}$, —$(CR^{1a}R^{1b})_{1-5}$-(3-11 membered heterocyclyl optionally substituted with 0-6 $R^{1a}$ and/or $R^{1b}$ groups)-$(CR^{1a}R^{1b})_{1-5}$, —$(CR^{1a}R^{1b})_{1-5}$-(3-11 membered heterocyclyl optionally substituted with 0-6 $R^{1a}$ and/or $R^{1b}$ groups)-$(CR^{1a}R^{1b})_{1-5}$-A- wherein A is O, S, or $NR^{1c}$, —$(CR^{1a}R^{1b})_{1-5}$-(3-11 membered heterocyclyl optionally substituted with 0-6 $R^{1a}$ and/or $R^{1b}$ groups)-A- wherein A is O, S, or $NR^{1c}$, —$(CR^{1a}R^{1b})_{1-5}$-A-(3-11 membered heterocyclyl optionally substituted with 0-6 $R^{1a}$ and/or $R^{1b}$ groups)- wherein A is O, S, or $NR^{1c}$, —$(CR^{1a}R^{1b})_{1-5}$-(3-11 membered cycloalkyl optionally substituted with 0-6 $R^{1a}$ and/or $R^{1b}$ groups)-$(CR^{1a}R^{1b})_{1-5}$-A- wherein A is O, S, or $NR^{1c}$, —$(CR^{1a}R^{1b})_{1-5}$-A-(3-11 membered cycloalkyl optionally substituted with 0-6 $R^{1a}$ and/or $R^{1b}$ groups)- wherein A is O, S, or $NR^{1c}$, —$(CR^{1a}R^{1b})_{1-5}$-A-(3-11 membered cycloalkyl optionally substituted with 0-6 $R^{1a}$ and/or $R^{1b}$ groups)-$(CR^{1a}R^{1b})_{1-5}$-A- wherein each A is independently O, S, or $NR^{1c}$, —$(CR^{1a}R^{1b})_{1-5}$-A-(3-11 membered heterocyclyl optionally substituted with 0-6 $R^{1a}$ and/or $R^{1b}$ groups)-$(CR^{1a}R^{1b})_{1-5}$-A- wherein each A is independently O, S, or $NR^{1c}$, —$(CR^{1a}R^{1b})_{1-5}$-A-$(CR^{1a}R^{1b})_{1-5}$-A- wherein A is O, S, or $NR^{1c}$, —$(CR^{1a}R^{1b})_{1-5}$-A-$(CR^{1a}R^{1b})_{1-5}$-A-$(CR^{1a}R^{1b})_{1-5}$-A-$(CR^{1a}R^{1b})_{1-5}$-A- wherein A is O, S, or $NR^{1c}$, —$(CR^{1a}R^{1b})_{1-5}$-A-(CO) wherein A is O, S, or $NR^{1c}$, —$(CR^{1a}R^{1b})_{1-5}$—$(CR^{1a}$=$CR^{1b})$—$(CR^{1a}R^{1b})_{1-5}$-A-(CO)— wherein A is O, S, or $NR^{1c}$, —$(CR^{1a}R^{1b})_{1-5}$—(C≡C)—$(CR^{1a}R^{1b})_{1-5}$-A-(CO)— wherein A is O, S, or $NR^{1c}$, —$(CR^{1a}R^{1b})_{1-5}$-(3-11 membered cycloalkyl optionally substituted with 0-6 $R^{1a}$ and/or $R^{1b}$ groups)-$(CR^{1a}R^{1b})_{1-5}$-A-(CO)— wherein A is O, S, or $NR^{1c}$, —$(CR^{1a}R^{1b})_{1-5}$-A-(CO)-(3-11 membered cycloalkyl optionally substituted with 0-6 $R^{1a}$ and/or $R^{1b}$ groups)- wherein A is O, S, or $NR^{1c}$, —$(CR^{1a}R^{1b})_{1-5}$-(3-11 membered heterocyclyl optionally substituted with 0-6 $R^{1a}$ and/or $R^{1b}$ groups)-$(CR^{1a}R^{1b})_{1-5}$-A-(CO)— wherein A is O, S, or $NR^{1c}$, —$(CR^{1a}R^{1b})_{1-5}$-A-(CO)-(3-11 membered heterocyclyl optionally substituted with 0-6 $R^{1a}$ and/or $R^{1b}$ groups)- wherein A is O, S, or $NR^{1c}$, —$(CR^{1a}R^{1b})_{1-5}$-A-(3-11 membered cycloalkyl optionally substituted with 0-6 $R^{1a}$ and/or $R^{1b}$ groups)-A-(CO)— wherein each A is independently O, S, or $NR^{1c}$, -(3-11 membered cycloalkyl optionally substituted with 0-6 $R^{1a}$ and/or $R^{1b}$ groups)-CO—$(CR^{1a}R^{1b})_{1-5}$-A- wherein A is O, S, or $NR^{1c}$, —$(CR^{1a}R^{1b})_{1-5}$-(3-11 membered cycloalkyl optionally substituted with 0-6 $R^{1a}$ and/or $R^{1b}$ groups)-$(CR^{1a}R^{1b})_{1-5}$-A-(CO)— wherein A is O, S, or $NR^{1c}$, —$(CR^{1a}R^{1b})_{1-5}$-(3-11 membered heterocyclyl optionally substituted with 0-6 $R^{1a}$ and/or $R^{1b}$ groups)-$(CR^{1a}R^{1b})_{1-5}$-A-(CO)— wherein A is O, S, or $NR^{1c}$,-(3-11 membered cycloalkyl optionally substituted with 0-6 $R^{1a}$ and/or $R^{1b}$ groups)-$(CR^{1a}R^{1b})_{1-5}$—, or -(3-11 membered heterocyclyl optionally substituted with 0-6 $R^{1a}$ and/or $R^{1b}$ groups)-$(CR^{1a}R^{1b})_{1-5}$—.

4. The compound according to claim 1, wherein the compound of Formula IA is a compound of Formula IA-1:

(IA-1)

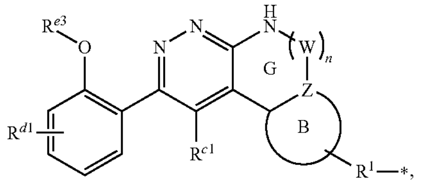

or a compound of Formula IA-2:

(IA-2)

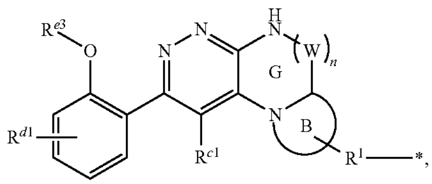

or a compound of Formula IA-3:

(IA-3)

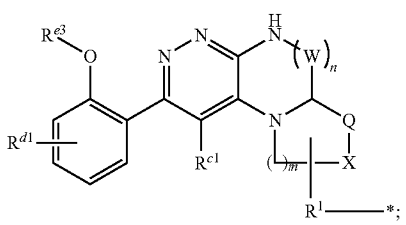

wherein m=1 to 3; and

X is optionally substituted —$CH_2$—, or NH; or, if $R^1$ is attached to X, then X is —CH— or N; and Q is optionally substituted —$CH_2$—, optionally substituted —$(CH_2)_2$—, —C(O)—, optionally substituted —$CH_2C(O)$—, —S(O)—, —$S(O)_2$—, optionally substituted —$CH_2S(O)_2$—, or optionally substituted —$CH_2S(O)$—, or a compound of Formula IA-4:

(IA-4)

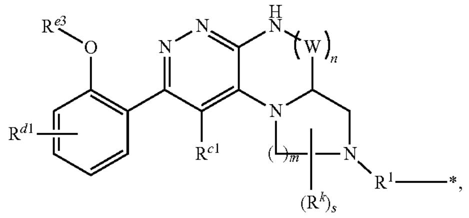

wherein m=1 to 3;

each $R^k$ is independently H, D, F, $C_{1-3}$ alkyl, $C_{1-3}$ haloalkyl, $C_{1-4}$ alkoxyl, substituted $C_{1-3}$ alkyl, substituted $C_{1-3}$ haloalkyl, or substituted $C_{1-4}$ alkoxyl; and S=0, 1, 2, 3, 4, 5, 6 or 7.

5. The compound according to claim 4, wherein the compound of Formula IA-4 is a compound of Formula IA-5:

(IA-5)

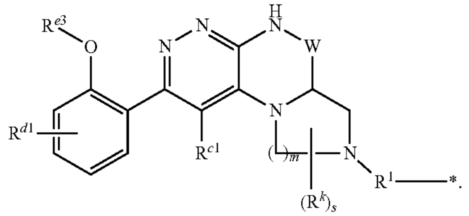

6. The compound according to claim 4, wherein m=2.

7. The compound according to claim 4, wherein at least one W is optionally substituted —$CH_2$; and wherein when n=2 or 3, only one W is —C(O)—, —S(O)—, or —$S(O)_2$— and the other W are —$CH_2$— or substituted —$CH_2$—, or at least one W is —C(O)—.

8. The compound according to claim 5, wherein the compound of Formula IA-5 is a compound of Formula IA-6, IA-6a or IA-6b:

(IA-6)

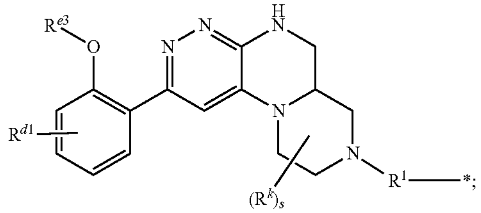

-continued (IA-6a)

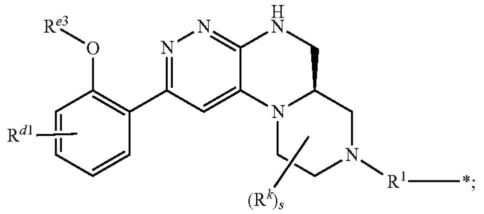

or (IA-6b)

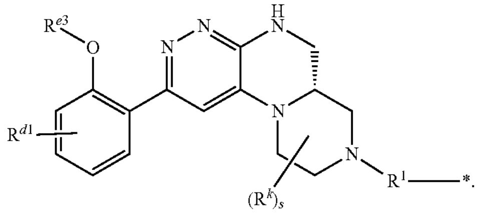

9. The compound according to claim 4, wherein $R^{e3}$ is H, $R^{d1}$ is H or $R^{c1}$ is H.

10. The compound according to claim 1, wherein ring A is monocyclic heteroaryl, bicyclic heteroaryl or tricyclic heteroaryl.

11. The compound according to claim 1, wherein $L^1$ is a bond or —$C(O)NR^a$—.

12. The compound according to claim 1, wherein $X_1$ is —C(O)—.

13. The compound according to claim 1, wherein ULM-I is a compound of formula:

(ULM-IA)

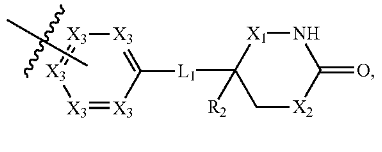

wherein each $X_3$ is independently N, N-oxide or $CR^3$ and at least one $X_3$ is N or N-oxide;

wherein ~~~~ is a point of attachment to PTM; or (ULM-IB)

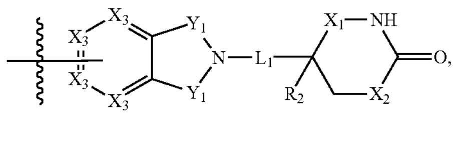

wherein each $X_3$ is independently N, N-oxide or $CR^3$;

wherein each $Y_1$ is independently —C(O)— or —$C(R^a)_2$— and at least one $Y_1$ is —C(O)—; and wherein ∿∿ is a point of attachment to PTM; or (ULM-IC)

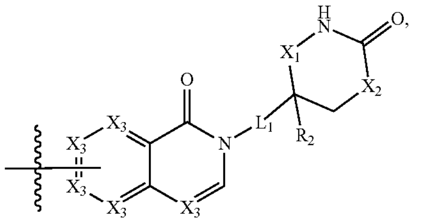

wherein each $X_3$ is independently N, N-oxide or $CR^3$ and wherein ∿∿ is a point of attachment to PTM; or (ULM-ID)

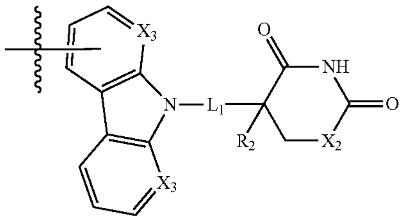

wherein each $X_3$ is independently N, N-oxide or $CR^3$ and wherein ∿∿ is a point of attachment to PTM.

14. The compound according to claim 1, wherein ring A is a monocyclic heteroaryl having at least one N atom; optionally wherein the monocyclic heteroaryl having at least one N atom is a pyridine or a pyridazine; optionally wherein ring A is

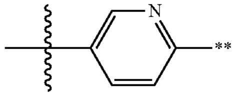 or 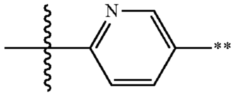

wherein ∿∿ is a point of attachment to PTM and ** is a point of attachment to $L_1$.

15. The compound according to claim 1, wherein ring A is a bicyclic heteroaryl having at least one N atom; optionally wherein the bicyclic heteroaryl having at least one N atom is an isoindolin-one, an isoindolin-dione, an isoquinolin-one or an isoquinolin-dione; optionally wherein ring A is

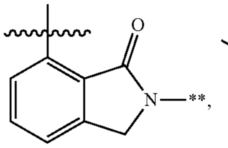
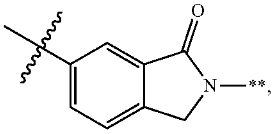
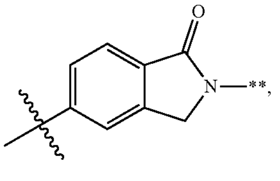
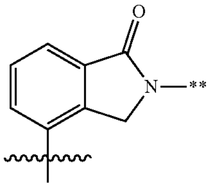 or

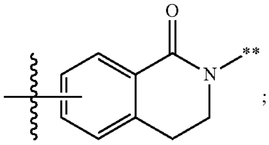;

wherein ∿∿ is a point of attachment to PTM and * is a point of attachment to $L_1$;

optionally wherein ring A is

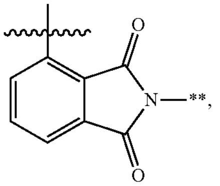
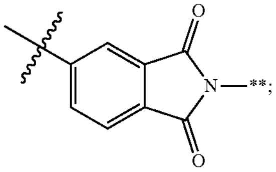

wherein ∿∿ is a point of attachment to PTM and ** is a point of attachment to $L_1$; optionally wherein ring A is

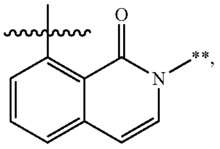
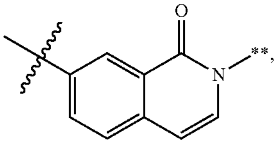

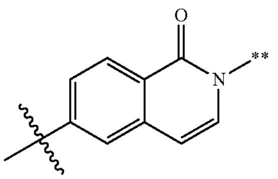 or 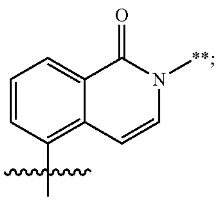

wherein ∿∿ is a point of attachment to PTM and ** is a point of attachment to $L_1$.

16. The compound according to claim 1, wherein ring A is a tricyclic heteroaryl having at least one N atom; optionally wherein the tricyclic heteroaryl having at least one N atom is a carbazole, a pyrido-indole or a pyrrolo-dipyridine; optionally wherein ring A is

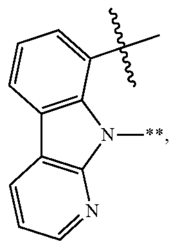
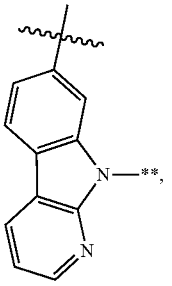
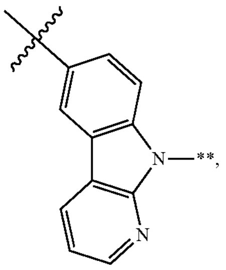
-continued
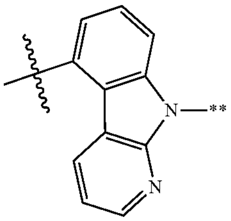 or 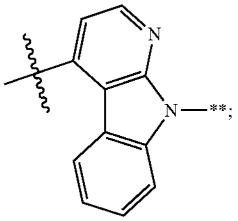
wherein ∿∿∿ is a point of attachment to PTM and * is a point of attachment to $L_1$.
17. The compound according to claim 1, wherein the compound of Formula I is a compound of Formula IA-7, Formula IA-8, Formula IA-9, Formula IA-10, Formula IA-11, Formula IA-12 or Formula IA-13:
(IA-7)
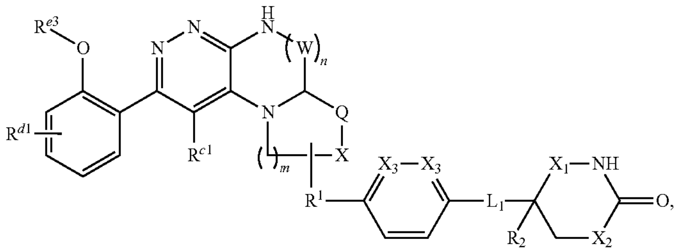
or
(IA-8)
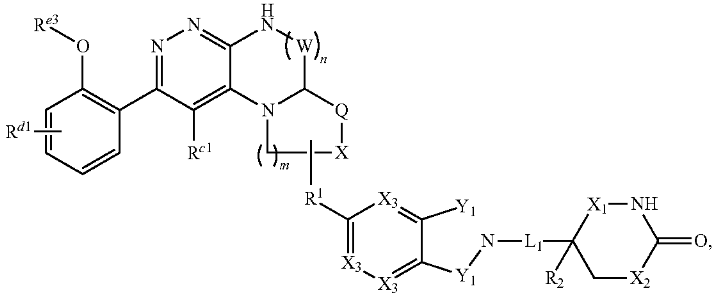
or
(IA-9)
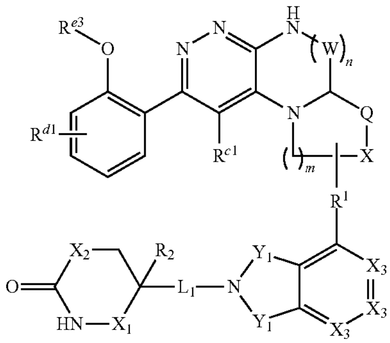
, or
(IA-10)
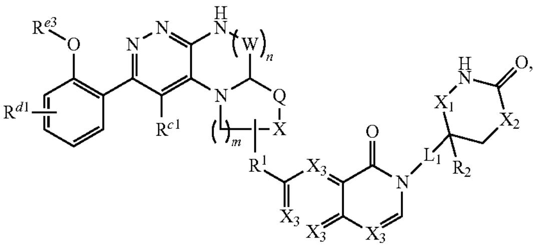
or -continued
(IA-11)
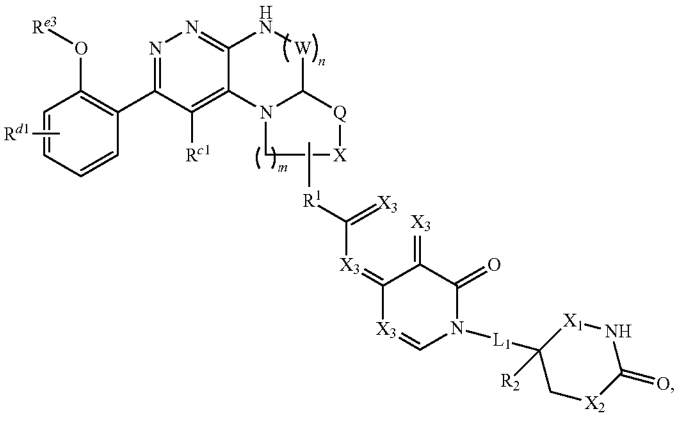
, or
(IA-12)
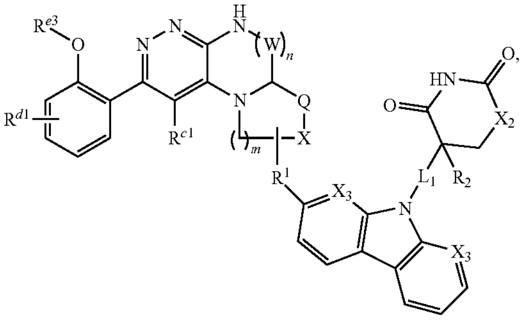
, or
(IA-13)
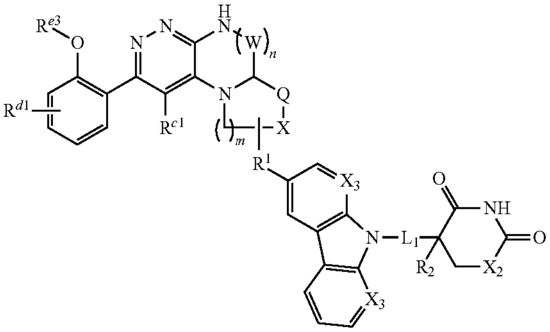
.
18. The compound according to claim 17, wherein the compound of Formula I is a compound of Formula IA-8 or IA-9.
19. The compound according to claim 17, wherein the compound of Formula I is a compound of Formula IA-7a, Formula IA-8a, Formula IA-9a, Formula IA-10a, Formula IA-11a, Formula IA-12a or Formula IA-13a:
(IA-7a)
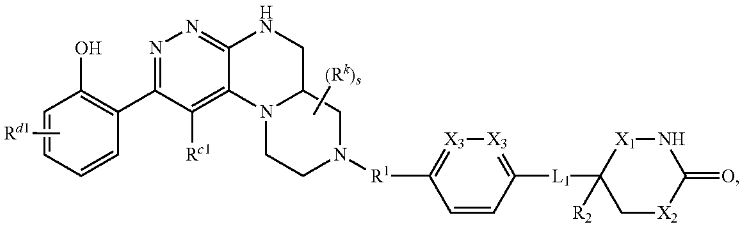
, or
(IA-8a)
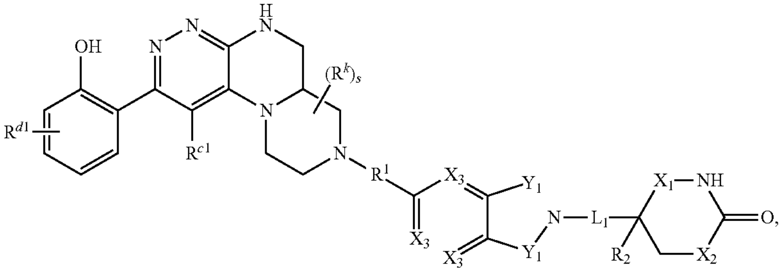
, or -continued
(IA-9a)
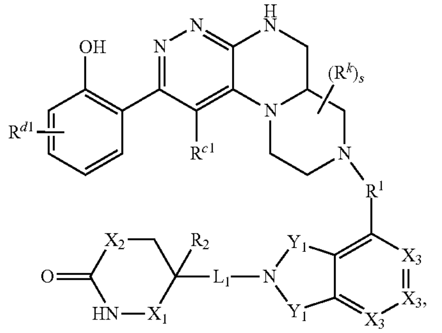
, or
(IA-10a)
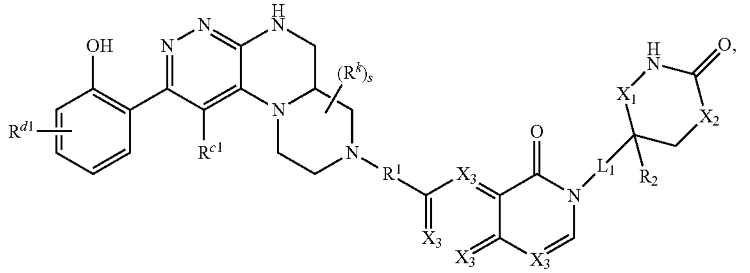
, or
(IA-11a)
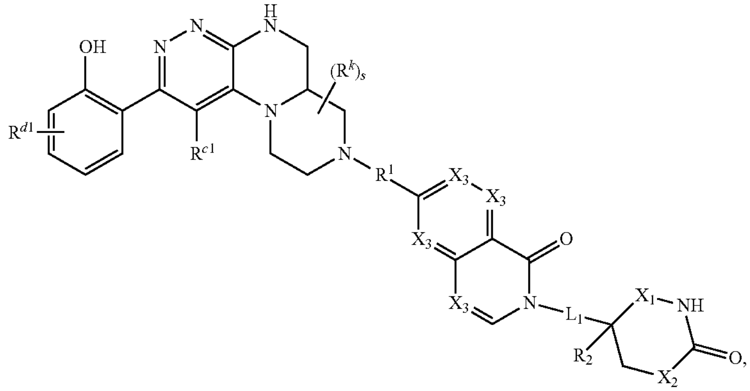
, or
(IA-12a)
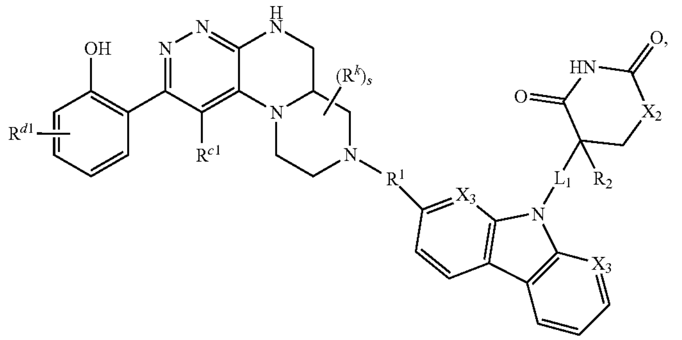
, or -continued (IA-13a)

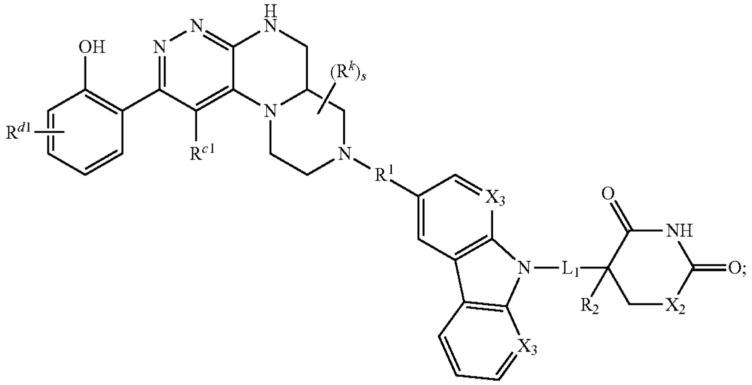

wherein each $R^k$ is independently H, D, F, $C_{1-3}$ alkyl, $C_{1-3}$ haloalkyl, $C_{1-4}$ alkoxyl, substituted $C_{1-3}$ alkyl, substituted $C_{1-3}$ haloalkyl, or substituted $C_{1-4}$ alkoxyl;

s is 0, 1, 2, 3 or 4; and each $Y_1$ is independently —C(O)— or —$CH_2$— and at least one $Y_1$ is —C(O)—.

20. The compound according to claim 19, wherein the compound of Formula I is a compound of Formula IA-7b, Formula IA-8b, Formula IA-9b, Formula IA-10b, Formula IA-11b, Formula IA-12b or Formula IA-13b:

(IA-7b)

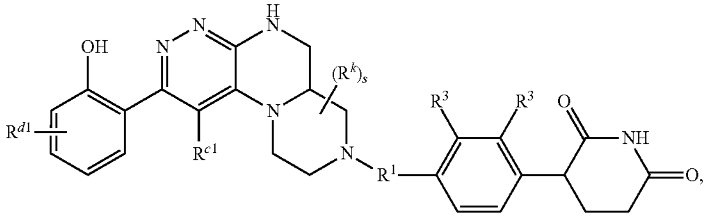

or (IA-8b)

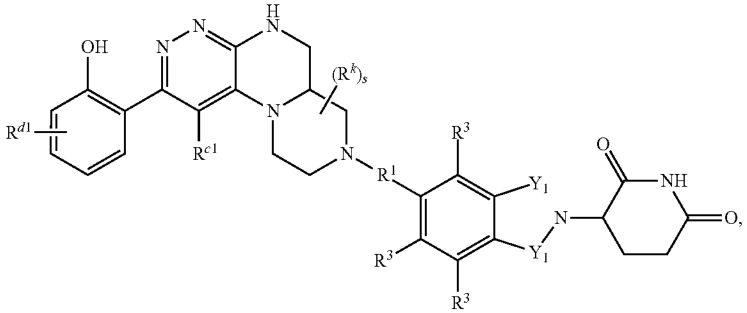

or

-continued
(IA-9b)
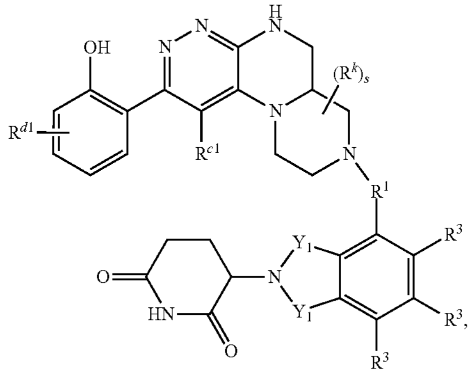
or
(IA-10b)
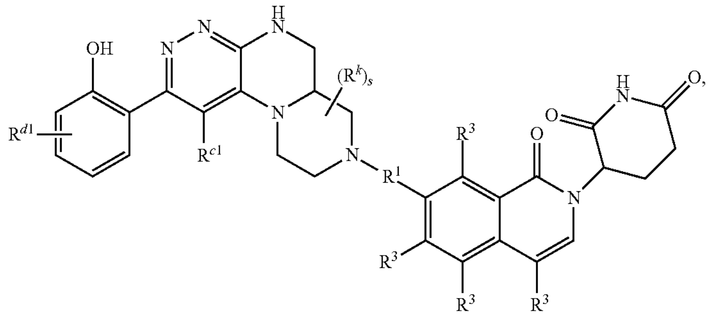
or
(IA-11b)
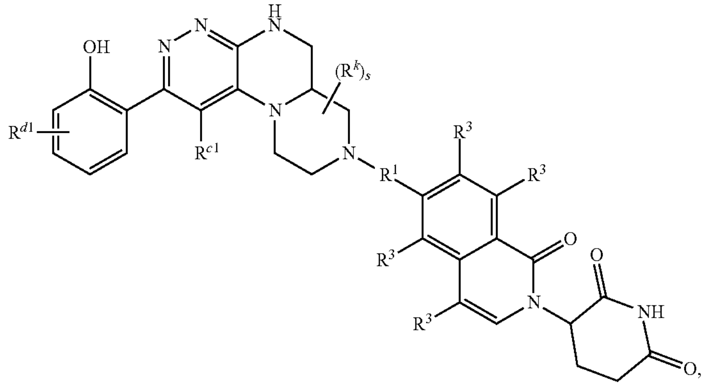
or
(IA-12b)
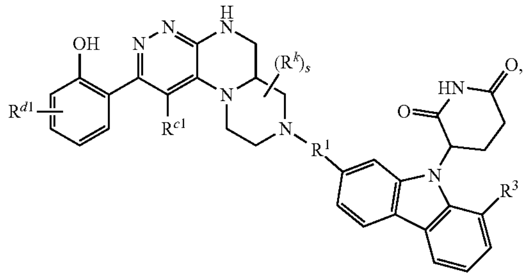
or
(IA-13b)
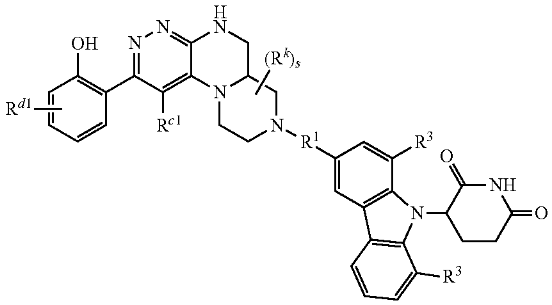
;

wherein each $R^k$ is independently H, D, F, $C_{1-3}$ alkyl, $C_{1-3}$ haloalkyl, $C_{1-4}$ alkoxyl, substituted $C_{1-3}$ alkyl, substituted $C_{1-3}$ haloalkyl, or substituted $C_{1-4}$ alkoxyl;

s is 0, 1, 2, 3 or 4; and each $Y_1$ is independently —C(O)— or —$CH_2$— and at least one $Y_1$ is —C(O)—.

21. The compound according to claim 20, wherein the compound of Formula I is a compound of Formula IA-7c, Formula IA-8c, Formula IA-9c, Formula IA-10c, Formula IA-11c, Formula IA-12c or Formula IA-13c:

(IA-7c)

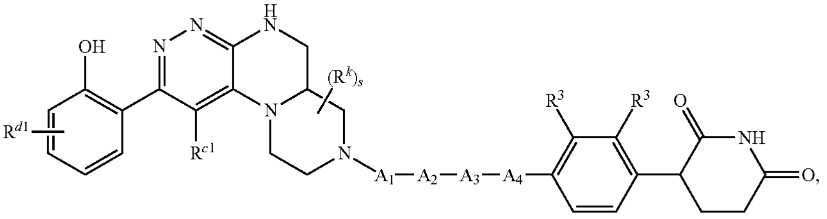

or (IA-8c)

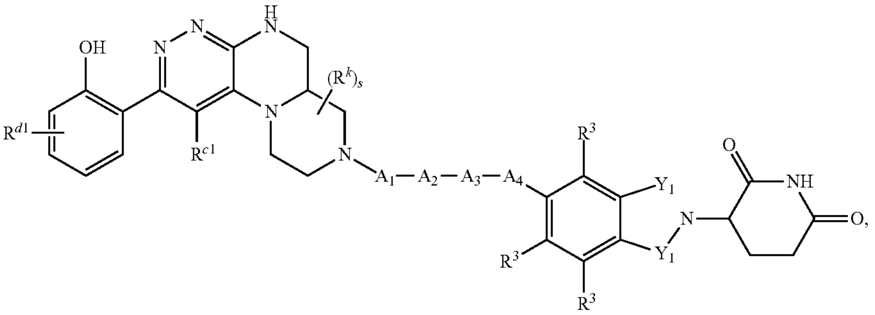

or (IA-9c)

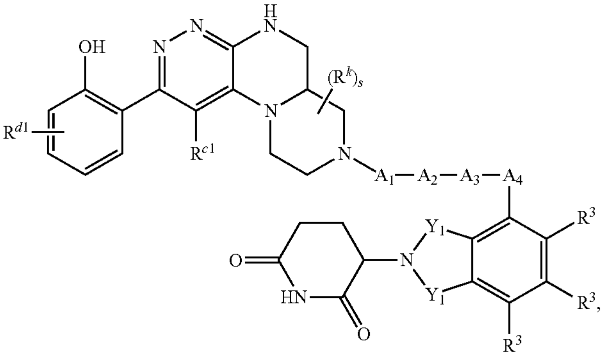

or (IA-10c)

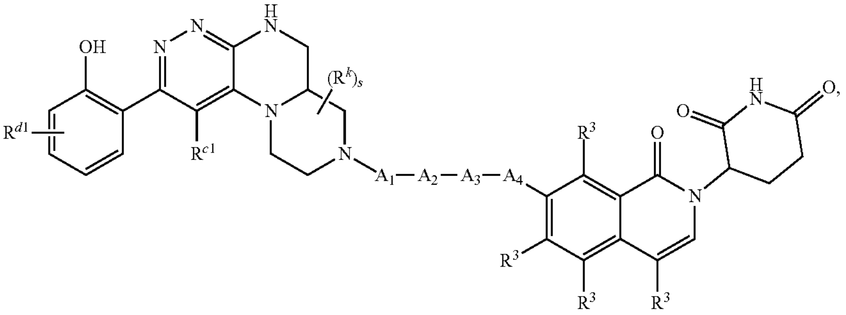

or

-continued (IA-11c)

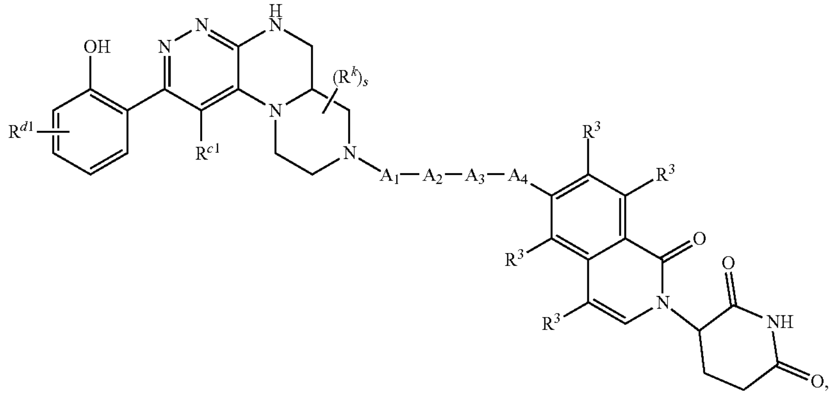

or (IA-12c)

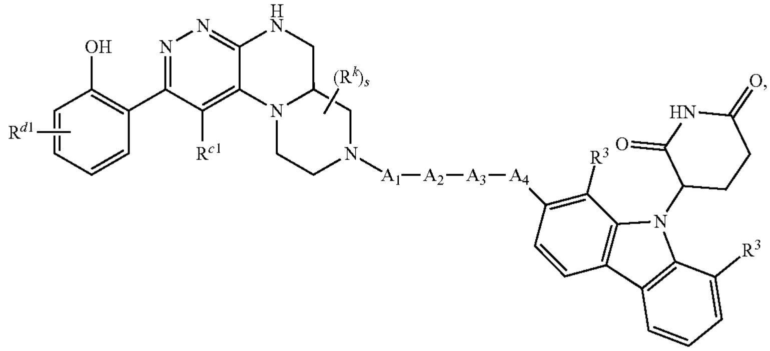

or (IA-13c)

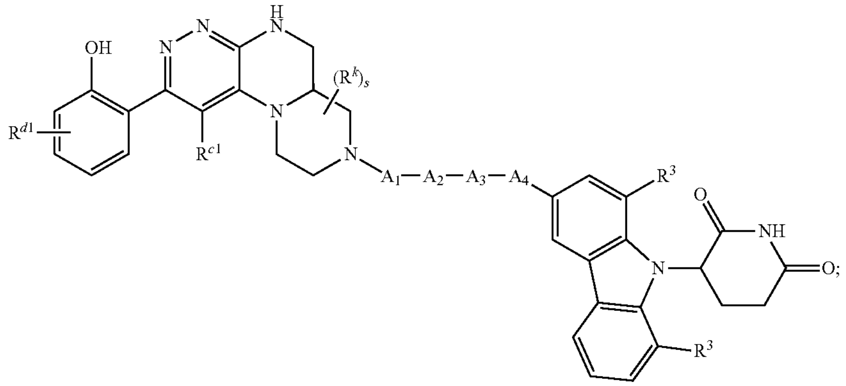

wherein each $R^k$ is independently H, D, F, $C_{1-3}$ alkyl, $C_{1-3}$ haloalkyl, $C_{1-4}$ alkoxyl, substituted $C_{1-3}$ alkyl, substituted $C_{1-3}$ haloalkyl, or substituted $C_{1-4}$ alkoxyl;

s is 0, 1, 2, 3 or 4;

each $Y_1$ is independently —C(O)— or —$CH_2$— and at least one $Y_1$ is —C(O)—;

$A_1$ is a bond, —$(CR^1R^2)_n$, —O$(CR^1R^2)_n$, —S$(CR^1R^2)_n$, —C═O, —C(═O)O, —C(═O)$NR^3$, —$SO_2$, —SO, heteroaryl, cycloalkyl, or heterocycloalkyl;

$A_2$ is a bond, alkyl, cycloalkyl, heteroaryl or heterocycloalkyl;

$A_3$ is a bond, —$(CR^1R^2)_n$, —(O—$(CR^1R^2)_n$, —S$(CR^1R^2)_n$, —C═O, —$SO_2$, SO, aryl, heteroaryl, cycloalkyl or heterocycloalkyl;

$A_4$ is a bond, alkyl, cycloalkyl, heteroaryl or heterocycloalkyl;

wherein each of $A_1$, $A_2$, $A_3$ and $A_4$ is optionally substituted with D, halo, alkyl, haloalkyl, —CN, —$OR^3$, $NR^cR^d$, $NO_2$, —$SR^3$, —C═$OR^b$, —C(═O)$OR^b$, —C(═O)$NR^3R^3$, —$SO_2R^b$, —$SOR^b$, —S(═O)(═$NR^b$)N, cycloalkyl or heterocycloalkyl; and wherein two substituents on each $A_1$, A2, $A_3$, $A_4$ optionally are joined to form an additional 3-8 membered ring.

22. The compound according to claim 21, wherein $A_1$ is —$CR_1R_2$, —C(═O) O, or —C(═O)$NR^3$;

$A_2$ is heterocycloalkyl, heteroaryl or cycloalkyl optionally substituted with D, halo, alkyl, haloalkyl, —CN or $OR^3$;

$A_3$ is —$(CR^1R^2)_n$; and $A_4$ is heterocycloalkyl or heteroaryl optionally substituted with D, halo, alkyl, haloalkyl, —CN or $OR^3$.

23. The compound according to claim 21, wherein the compound of Formula I is a compound of Formula IA-7d, Formula IA-8d1, Formula IA-8d2, Formula IA-8d3, Formula IA-9d1, Formula IA-9d2, Formula IA-9d3, Formula IA-10d, Formula IA-11d, Formula IA-12d or Formula IA-13d:
(IA-7d)
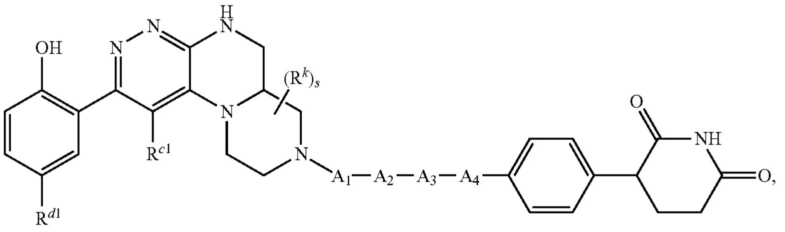
, or
(IA-8d1)
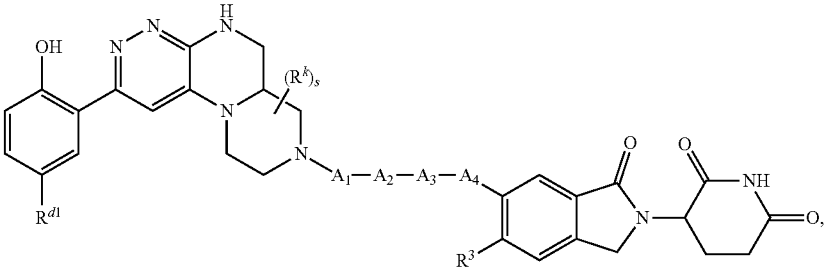
, or
(IA-8d2)
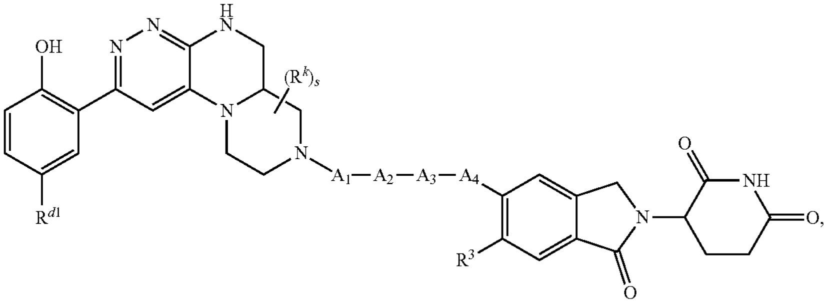
, or
(IA-8d3)
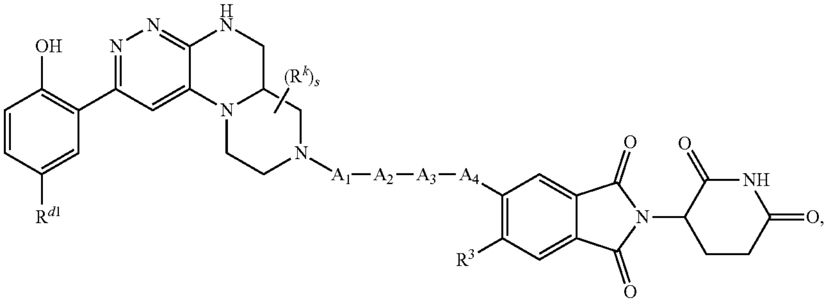
, or
(IA-9d1)
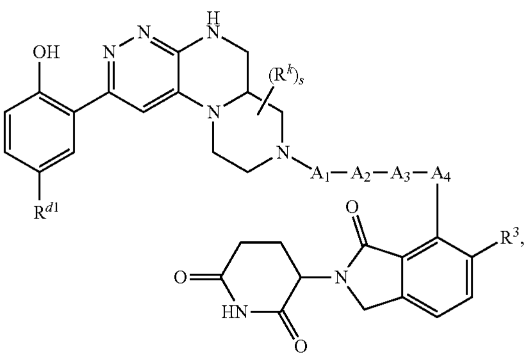
, or
(IA-9d2)
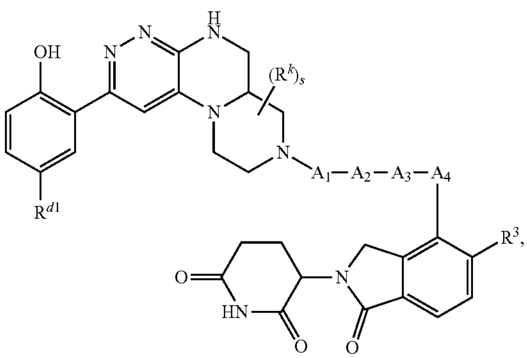
, or -continued
(IA-9d3)
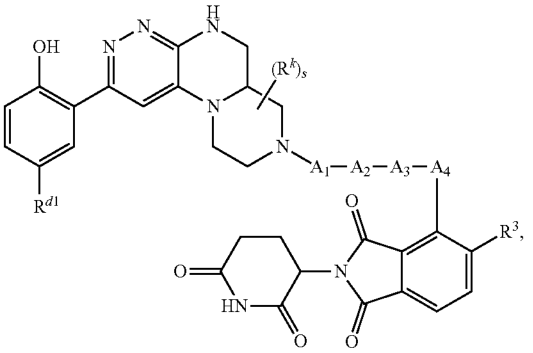
, or
(IA-10c)
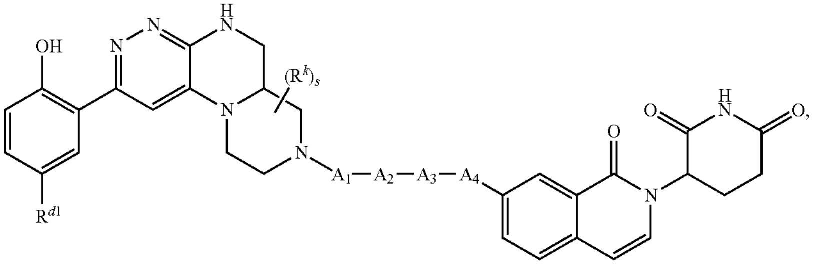
, or
(IA-IIc)
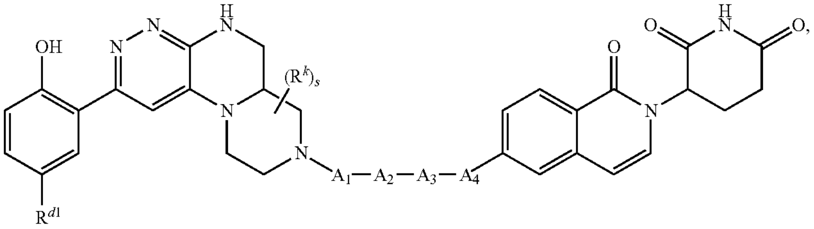
, or
(IA-12c)
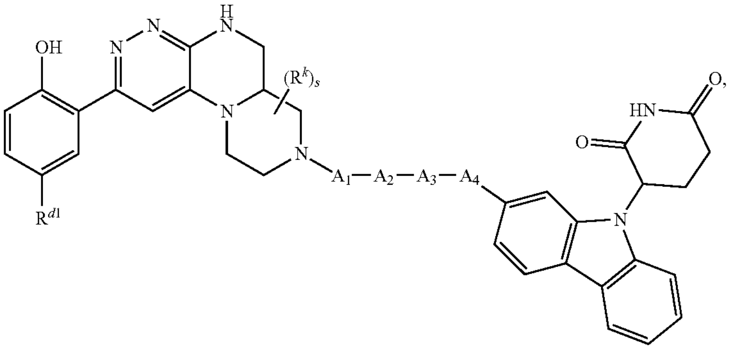
, or
(IA-13c)
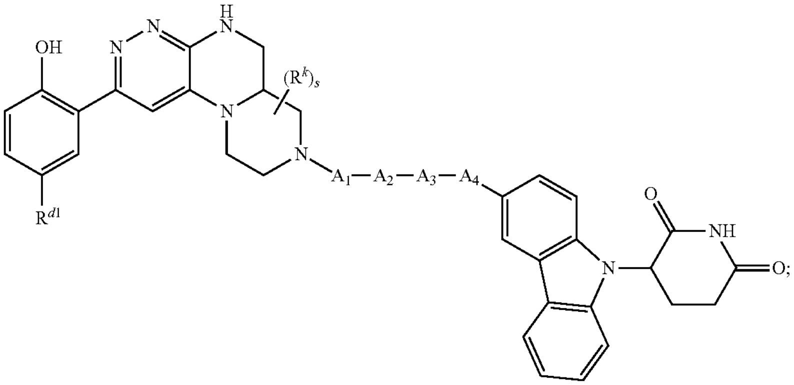
;

each $R^k$ is independently H or $C_{1-6}$alkyl;

s is 0, 1, 2, 3 or 4;

$R^{d1}$ is H or F;

$R^3$ is H or F;

$A_1$ is —$CR^1R^2$ or —C═O;

$A_2$ is a 3-8 membered heterocycloalkyl or 3-8 membered cycloalkyl;

$A_3$ is —$CR^1R^2$ or —C═O; and $A_4$ is a 3-8 membered heterocycloalkyl or 3-8 membered cycloalkyl.

24. The compound according to claim 23, wherein the compound of Formula I is a compound of Formula IA-8d1a, Formula IA-8d1b, Formula IA-8d2a, Formula IA-8d2b, Formula IA-8d3a, Formula IA-8d3b, Formula IA-9dla, Formula IA-9d1b, Formula IA-9d2a, Formula IA-9d2b, Formula IA-9d3a, or Formula IA-9d3b:

(IA-8d1a)

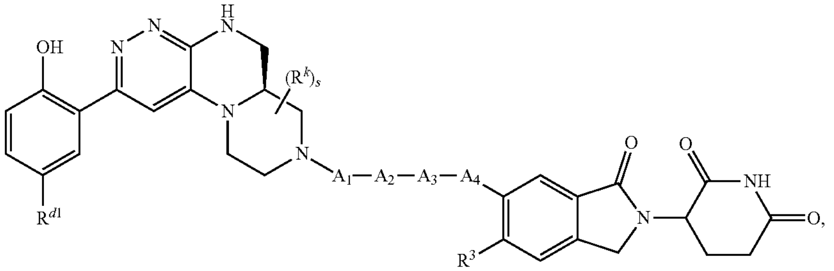

or (IA-8d1b)

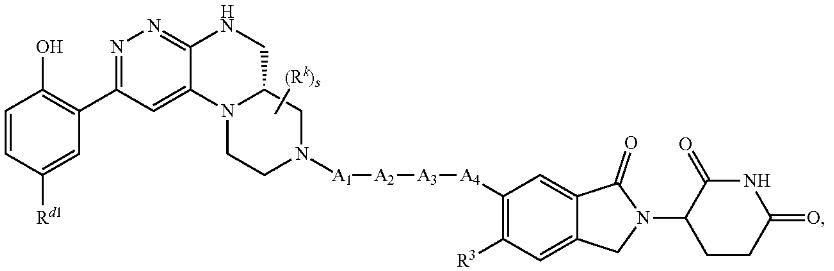

or (IA-8d2a)

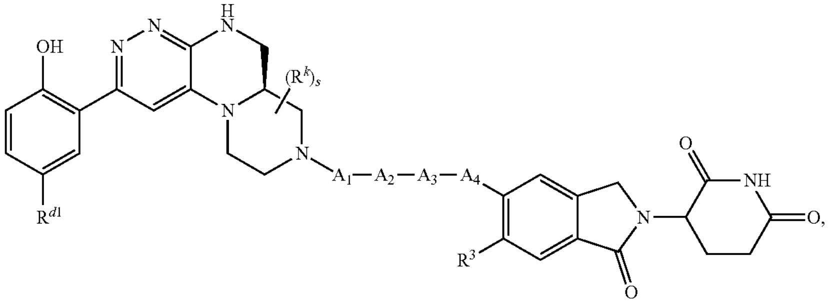

or (IA-8d2b)

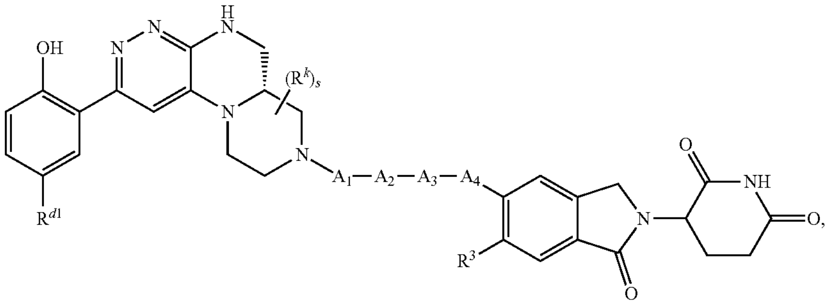

or

-continued
(IA-8d3a)
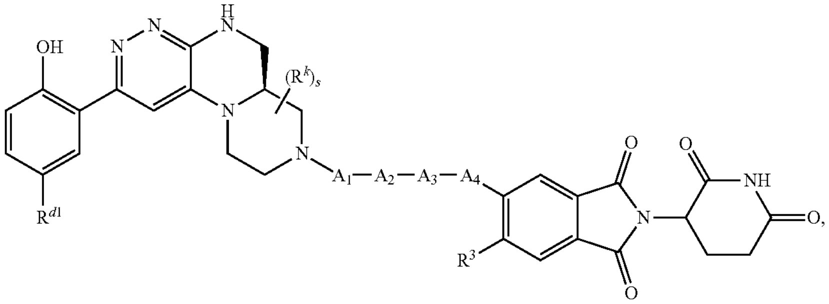
or
(IA-8d3b)
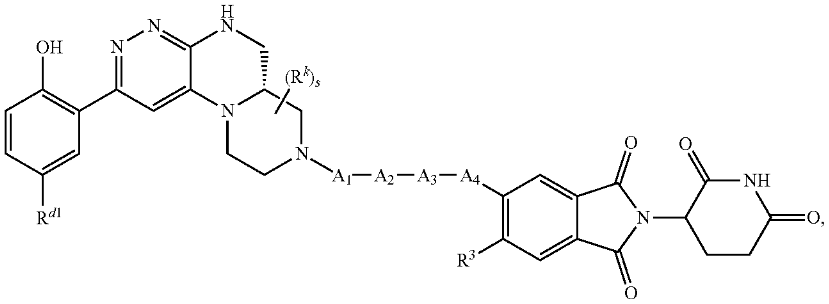
or
(IA-9d1a)
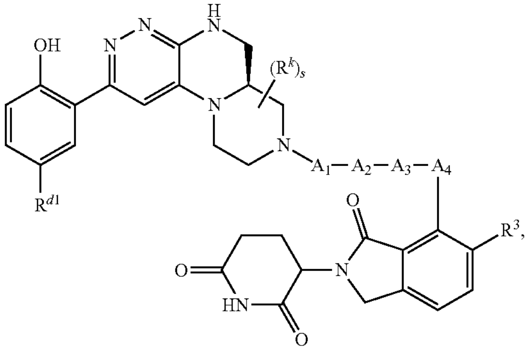
or
(IA-9d1b)
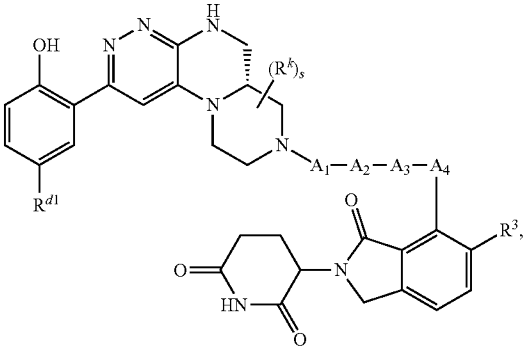
or
(IA-9d2a)
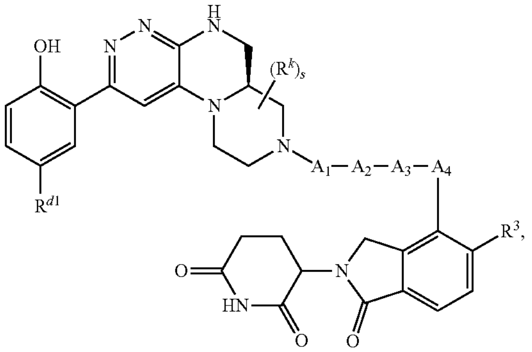
or
(IA-9d2b)
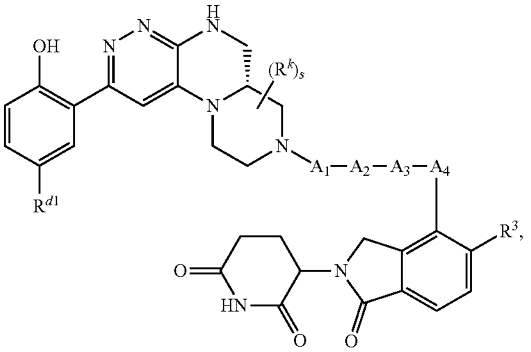
or -continued (IA-9d3a)

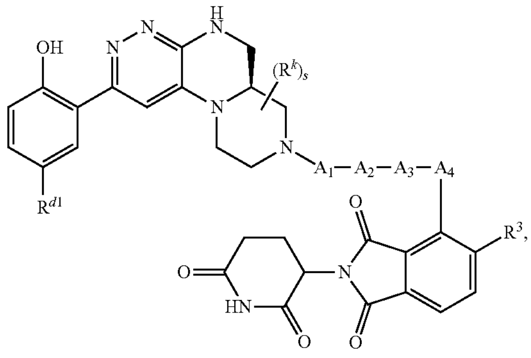

, or (IA-9d3b)

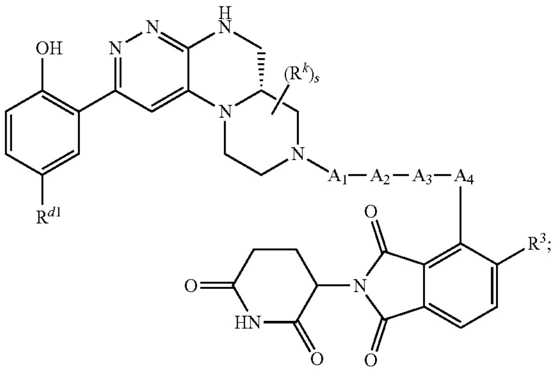

;

wherein each $R^k$ is independently H or $C_{1-6}$alkyl;

s is 0, 1, 2, 3 or 4;

$R^{d1}$ is H or F;

$R^3$ is H or F;

$A_1$ is —$CR^1R^2$ or —C═O;

$A_2$ is a 3-8 membered heterocycloalkyl or 3-8 membered cycloalkyl;

$A_3$ is —$CR^1R^2$ or —C═O; and $A_4$ is a 3-8 membered heterocycloalkyl or 3-8 membered cycloalkyl.

25. The compound according to claim 21, wherein $A_1$ is —$CH_2$ or —C═O; or $A_3$ is —$CR^1R^2$ or —C═O; or $A_2$ is a piperidine, piperazine, pyrrolidine, or azetidine; or $A_4$ is a piperidine, piperazine, pyrrolidine, or azetidine.

26. The compound according to claim 1, wherein the compound is selected from:

3-(5-(2-(4-(2-((S)-2-(2-hydroxyphenyl)-5,6,6a,7,9,10-hexahydro-8H-pyrazino[1',2': 4,5]pyrazino[2,3-c]pyridazin-8-yl)pyrimidin-5-yl) piperidin-1-yl) ethyl)-1-oxoisoindolin-2-yl) piperidine-2,6-dione;

3-(5-(3-(4-(2-((R)-2-(2-hydroxyphenyl)-5,6,6a,7,9,10-hexahydro-8H-pyrazino[1',2': 4,5]pyrazino[2,3-c]pyridazin-8-yl)pyrimidin-5-yl) piperidin-1-yl) propyl)-1-oxoisoindolin-2-yl) piperidine-2,6-dione;

3-(5-(3-(4-(2-(2-((R)-2-(2-hydroxyphenyl)-5,6,6a,7,9,10-hexahydro-8H-pyrazino [1',2': 4,5] pyrazino[2,3-c]pyridazin-8-yl)pyrimidin-5-yl)ethyl) piperidin-1-yl) propyl)-1-oxoisoindolin-2-yl) piperidine-2,6-dione;

3-(5-(2-(4-(2-((R)-2-(2-hydroxyphenyl)-5,6,6a,7,9,10-hexahydro-8H-pyrazino[1',2': 4,5]pyrazino[2,3-c]pyridazin-8-yl)pyrimidin-5-yl) piperidin-1-yl) ethyl)-1-oxoisoindolin-2-yl) piperidine-2,6-dione;

3-(5-(2-(4-(2-(2-((R)-2-(2-hydroxyphenyl)-5,6,6a,7,9,10-hexahydro-8H-pyrazino [1',2': 4,5] pyrazino[2,3-c]pyridazin-8-yl)pyrimidin-5-yl) ethyl) piperidin-1-yl) ethyl)-1-oxoisoindolin-2-yl) piperidine-2,6-dione;

3-(5-(2-(4-(2-((S)-2-(2-hydroxyphenyl)-5,6,6a,7,9,10-hexahydro-8H-pyrazino[1',2': 4,5]pyrazino[2,3-c]pyridazin-8-yl)pyrimidin-5-yl)-3,6-dihydropyridin-1 (2H)-yl) ethyl)-1-oxoisoindolin-2-yl) piperidine-2,6-dione;

3-(5-(2-(4-((E)-2-(2-((S)-2-(2-hydroxyphenyl)-5,6,6a,7,9,10-hexahydro-8H-pyrazino [1',2': 4,5] pyrazino[2,3-c]pyridazin-8-yl)pyrimidin-5-yl) vinyl) piperidin-1-yl) ethyl)-1-oxoisoindolin-2-yl) piperidine-2,6-dione;

3-(5-(2-(4-(2-(4-((S)-2-(2-hydroxyphenyl)-5,6,6a,7,9,10-hexahydro-8H-pyrazino [1',2': 4,5] pyrazino[2,3-c]pyridazin-8-yl) piperidin-1-yl)ethoxy)piperidin-1-yl) ethyl)-1-oxoisoindolin-2-yl) piperidine-2,6-dione;

3-(5-((4-(2-(4-((S)-2-(2-hydroxyphenyl)-5,6,6a,7,9,10-hexahydro-8H-pyrazino [1',2': 4,5] pyrazino[2,3-c]pyridazin-8-yl) piperidin-1-yl) ethoxy) piperidin-1-yl) methyl)-1-oxoisoindolin-2-yl) piperidine-2,6-dione;

3-(5-((4-(2-((S)-2-(2-hydroxyphenyl)-5,6,6a,7,9,10-hexahydro-8H-pyrazino[1',2': 4,5]pyrazino[2,3-c]pyridazin-8-yl)pyrimidin-5-yl) piperidin-1-yl) methyl)-1-oxoisoindolin-2-yl) piperidine-2,6-dione;

2-(2,6-Dioxopiperidin-3-yl)-5-(4-(3-(4-((S)-2-(2-hydroxyphenyl)-5,6,6a,7,9,10-hexahydro-8H-pyrazino [1',2': 4,5] pyrazino[2,3-c]pyridazin-8-yl) piperidin-1-yl) propyl) piperazin-1-yl) isoindoline-1,3-dione;

2-(2,6-Dioxopiperidin-3-yl)-5-(4-(2-(3-((S)-2-(2-hydroxyphenyl)-5,6,6a,7,9,10-hexahydro-8H-pyrazino [1',2': 4,5] pyrazino[2,3-c]pyridazin-8-yl) pyrrolidin-1-yl) ethyl) piperazin-1-yl) isoindoline-1,3-dione;

2-(2,6-Dioxopiperidin-3-yl)-5-(3-(4-((S)-2-(2-hydroxyphenyl)-5,6,6a,7,9,10-hexahydro-8H-pyrazino[1',2': 4,5] pyrazino[2,3-c]pyridazin-8-yl) piperidin-1-yl) pyrrolidin-1-yl) isoindoline-1,3-dione;

2-(2,6-dioxopiperidin-3-yl)-5-(4-((S)-2-(2-hydroxyphenyl)-5,6,6a,7,9,10-hexahydro-8H-pyrazino[1',2': 4,5] pyrazino[2,3-c]pyridazin-8-yl)-[1,4'-bipiperidin]-1'-yl) isoindoline-1,3-dione;

2-(2,6-Dioxopiperidin-3-yl)-5-(4-(2-(3-((S)-2-(2-hydroxyphenyl)-5,6,6a,7,9,10-hexahydro-8H-pyrazino [1',2': 4,5] pyrazino[2,3-c]pyridazin-8-yl) pyrrolidin-1-yl) ethoxy) piperidin-1-yl) isoindoline-1,3-dione;

2-(2,6-Dioxopiperidin-3-yl)-5-(4-(2-(4-((S)-2-(2-hydroxyphenyl)-5,6,6a,7,9,10-hexahydro-8H-pyrazino [1',2': 4,5] pyrazino[2,3-c]pyridazin-8-yl) piperidin-1-yl) ethoxy) piperidin-1-yl) isoindoline-1,3-dione;

3-(6-(4-(2-(4-((S)-2-(2-hydroxyphenyl)-5,6,6a,7,9,10-hexahydro-8H-pyrazino[1',2:4,5]pyrazino[2,3-c]pyridazin-8-yl) piperidin-1-yl) ethyl) piperazin-1-yl)-1-oxoisoindolin-2-yl) piperidine-2,6-dione;

3-(6-(3-(4-(2-((R)-2-(2-hydroxyphenyl)-5,6,6a,7,9,10-hexahydro-8H-pyrazino[1',2': 4,5]pyrazino[2,3-c]pyridazin-8-yl)pyrimidin-5-yl) piperidin-1-yl) propyl)-9H-pyrido [2,3-b] indol-9-yl) piperidine-2,6-dione;

3-(6-(3-(4-((S)-2-(2-hydroxyphenyl)-5,6,6a,7,9,10-hexahydro-8H-pyrazino[1',2': 4,5]pyrazino[2,3-c]pyridazin-8-yl) piperidin-1-yl) propyl)-9H-pyrido [2,3-b] indol-9-yl) piperidine-2,6-dione;

3-(6-(3-(4-((S)-2-(2-hydroxyphenyl)-5,6,6a, 7,9,10-hexahydro-8H-pyrazino[1',2': 4,5]pyrazino[2,3-c]

pyridazin-8-yl)-[1,4'-bipiperidin]-1'-yl) propyl)-9H-pyrido [2,3-b] indol-9-yl) piperidine-2,6-dione;

3-(6-(3-(4-(3-((S)-2-(2-hydroxyphenyl)-5,6,6a,7,9,10-hexahydro-8H-pyrazino[1',2': 4,5]pyrazino[2,3-c] pyridazin-8-yl) azetidin-1-yl) piperidin-1-yl) propyl)-9H-pyrido [2,3-b] indol-9-yl) piperidine-2,6-dione;

3-(6-(3-(4-(2-((S)-2-(2-hydroxyphenyl)-5,6,6a,7,9,10-hexahydro-8H-pyrazino[1',2': 4,5]pyrazino[2,3-c] pyridazin-8-yl) ethyl) piperazin-1-yl) propyl)-9H-pyrido [2,3-b] indol-9-yl) piperidine-2,6-dione;

3-(6-(3-(4-(2-(((6aR,8S)-2-(2-hydroxyphenyl)-5,6,6a,7,8,9-hexahydropyrrolo [1',2': 4,5]pyrazino[2,3-c] pyridazin-8-yl) oxy) pyrimidin-5-yl) piperidin-1-yl) propyl)-9H-pyrido [2,3-b] indol-9-yl) piperidine-2,6-dione;

N-(2,6-dioxopiperidin-3-yl)-5-(4-((4-((S)-2-(2-hydroxyphenyl)-5,6,6a, 7,9,10-hexahydro-8H-pyrazino[1',2': 4,5] pyrazino[2,3-c]pyridazin-8-yl) piperidin-1-yl) methyl) piperidin-1-yl) picolinamide;

3-(6-(3-(4-(2-(2-hydroxyphenyl)-6a-methyl-5,6,6a,7,9,10-hexahydro-8H-pyrazino [1',2': 4,5] pyrazino[2,3-c] pyridazin-8-yl) piperidin-1-yl) propyl)-9H-pyrido [2,3-b] indol-9-yl) piperidine-2,6-dione;

3-(6-(4-((4-((S)-2-(2-hydroxyphenyl)-5,6,6a,7,9,10-hexahydro-8H-pyrazino[1',2': 4,5]pyrazino[2,3-c] pyridazin-8-yl) piperidin-1-yl) methyl) piperidin-1-yl)-1-oxoisoquinolin-2 (1H)-yl) piperidine-2,6-dione;

3-(6-(3-(4-(4-((6aR)-2-(2-hydroxyphenyl)-5,6,6a,7,8,9-hexahydropyrrolo [1',2': 4,5]pyrazino[2,3-c]pyridazin-8-yl) piperazin-1-yl) piperidin-1-yl) propyl)-9H-pyrido [2,3-b] indol-9-yl) piperidine-2,6-dione;

2-(2,6-dioxopiperidin-3-yl)-5-(4-((4-(((6aS,9S)-2-(2-hydroxyphenyl)-9-methyl-5,6,6a, 7,9,10-hexahydro-8H-pyrazino[1',2': 4,5] pyrazino[2,3-c]pyridazin-8-yl) methyl) piperidin-1-yl) methyl) piperidin-1-yl) isoindoline-1,3-dione;

2-(2,6-dioxopiperidin-3-yl)-5-(4-((4-(((6aR)-2-(2-hydroxyphenyl)-5,6,6a, 7,8,9-hexahydropyrrolo [1',2': 4,5] pyrazino[2,3-c]pyridazin-8-yl) (methyl) amino) piperidin-1-yl) methyl) piperidin-1-yl) isoindoline-1,3-dione;

2-(2,6-dioxopiperidin-3-yl)-5-(4-((4-((S)-2-(2-hydroxyphenyl)-5,6,6a,7,9,10-hexahydro-8H-pyrazino[1',2': 4,5] pyrazino[2,3-c]pyridazin-8-yl) piperidin-1-yl) methyl) piperidin-1-yl) isoindoline-1,3-dione;

2-(2,6-dioxopiperidin-3-yl)-5-(4-((4-(((S)-2-(2-hydroxyphenyl)-5,6,6a,7,9,10-hexahydro-8H-pyrazino[1',2': 4,5] pyrazino[2,3-c]pyridazin-8-yl) methyl) piperidin-1-yl) methyl) piperidin-1-yl) isoindoline-1,3-dione;

2-(2,6-dioxopiperidin-3-yl)-5-(4-((4-(1-((S)-2-(2-hydroxyphenyl)-5,6,6a,7,9,10-hexahydro-8H-pyrazino [1',2': 4,5] pyrazino[2,3-c]pyridazin-8-yl) ethyl) piperidin-1-yl) methyl) piperidin-1-yl) isoindoline-1,3-dione;

2-(2,6-dioxopiperidin-3-yl)-5-(4-((3-(((S)-2-(2-hydroxyphenyl)-5,6,6a, 7,9,10-hexahydro-8H-pyrazino[1',2': 4,5] pyrazino[2,3-c]pyridazin-8-yl) methyl) pyrrolidin-1-yl) methyl) piperidin-1-yl) isoindoline-1,3-dione;

(3-(5-(4-((4-(((S)-2-(2-hydroxyphenyl)-5,6,6a,7,9,10-hexahydro-8H-pyrazino[1',2': 4,5]pyrazino[2,3-c] pyridazin-8-yl) methyl) piperidin-1-yl) methyl) piperidin-1-yl)-1,3-dioxoisoindolin-2-yl)-2,6-dioxopiperidin-1-yl) methyl pivalate;

2-(2,6-dioxopiperidin-3-yl)-5-(4-((3-(((S)-2-(2-hydroxyphenyl)-5,6,6a,7,9,10-hexahydro-8H-pyrazino[1',2': 4,5] pyrazino[2,3-c]pyridazin-8-yl) methyl) piperidin-1-yl) methyl) piperidin-1-yl) isoindoline-1,3-dione;

2-(2,6-dioxopiperidin-3-yl)-5-(4-((3-(((S)-2-(2-hydroxyphenyl)-5,6,6a, 7,9,10-hexahydro-8H-pyrazino[1',2': 4,5] pyrazino[2,3-c]pyridazin-8-yl) methyl) azetidin-1-yl) methyl) piperidin-1-yl) isoindoline-1,3-dione;

2-(2,6-dioxopiperidin-3-yl)-5-(4-((4-(((S)-2-(2-hydroxyphenyl)-5,6,6a,7,9,10-hexahydro-8H-pyrazino[1',2': 4,5] pyrazino[2,3-c]pyridazin-8-yl) methyl)-4-methylpiperidin-1-yl) methyl) piperidin-1-yl) isoindoline-1,3-dione;

2-(2,6-dioxopiperidin-3-yl)-5-(4-((4-hydroxy-4-(((S)-2-(2-hydroxyphenyl)-5,6,6a,7,9,10-hexahydro-8H-pyrazino[1',2': 4,5] pyrazino[2,3-c]pyridazin-8-yl) methyl) piperidin-1-yl) methyl) piperidin-1-yl) isoindoline-1,3-dione;

2-(2,6-dioxopiperidin-3-yl)-5-(4-((6-(((S)-2-(2-hydroxyphenyl)-5,6,6a,7,9,10-hexahydro-8H-pyrazino[1',2': 4,5] pyrazino[2,3-c]pyridazin-8-yl) methyl)-3-azabicyclo[3.1.1]heptan-3-yl) methyl)piperidin-1-yl) isoindoline-1,3-dione;

2-(2,6-dioxopiperidin-3-yl)-5-(4-(((3-((S)-2-(2-hydroxyphenyl)-5,6,6a,7,9,10-hexahydro-8H-pyrazino[1',2': 4,5] pyrazino[2,3-c]pyridazin-8-yl) propyl) (methyl) amino) methyl) piperidin-1-yl) isoindoline-1,3-dione;

2-(2,6-dioxopiperidin-3-yl)-5-(4-((6-(((S)-2-(2-hydroxyphenyl)-5,6,6a,7,9,10-hexahydro-8H-pyrazino[1',2': 4,5] pyrazino[2,3-c]pyridazin-8-yl) methyl)-2-azaspiro [3.3]heptan-2-yl) methyl) piperidin-1-yl) isoindoline-1,3-dione;

2-(2,6-dioxopiperidin-3-yl)-5-(4-(((1R,5S,6r)-6-(((S)-2-(2-hydroxyphenyl)-5,6,6a,7,9,10-hexahydro-8H-pyrazino[1',2': 4,5] pyrazino[2,3-c]pyridazin-8-yl) methyl)-3-azabicyclo[3.1.0]hexan-3-yl) methyl) piperidin-1-yl) isoindoline-1,3-dione;

2-(2,6-dioxopiperidin-3-yl)-5-(4-(((1R,5S,6s)-6-(((S)-2-(2-hydroxyphenyl)-5,6,6a,7,9,10-hexahydro-8H-pyrazino[1',2': 4,5] pyrazino[2,3-c]pyridazin-8-yl) methyl)-3-azabicyclo[3.1.0]hexan-3-yl) methyl) piperidin-1-yl) isoindoline-1,3-dione;

2-(2,6-dioxopiperidin-3-yl)-5-(4-(((1R,5S,6r)-6-(((6aS, 9S)-2-(2-hydroxyphenyl)-9-methyl-5,6,6a,7,9,10-hexahydro-8H-pyrazino[1',2': 4,5] pyrazino[2,3-c] pyridazin-8-yl) methyl)-3-azabicyclo[3.1.0] hexan-3-yl) methyl) piperidin-1-yl) isoindoline-1,3-dione;

2-(2,6-dioxopiperidin-3-yl)-5-(4-(((3aR,5s,6aS)-5-(((S)-2-(2-hydroxyphenyl)-5,6,6a, 7,9,10-hexahydro-8H-pyrazino[1',2': 4,5] pyrazino[2,3-c]pyridazin-8-yl) methyl) hexahydrocyclopenta[c]pyrrol-2 (1H)-yl) methyl) piperidin-1-yl) isoindoline-1,3-dione;

2-(2,6-dioxopiperidin-3-yl)-5-(4-((7-(((S)-2-(2-hydroxyphenyl)-5,6,6a,7,9,10-hexahydro-8H-pyrazino[1',2': 4,5] pyrazino[2,3-c]pyridazin-8-yl) methyl)-3-azabicyclo[4.1.0]heptan-3-yl) methyl) piperidin-1-yl) isoindoline-1,3-dione;

2-(2,6-dioxopiperidin-3-yl)-5-(4-hydroxy-4-(((1R,5S, 6s)-6-(((S)-2-(2-hydroxyphenyl)-5,6,6a, 7,9,10-hexahydro-8H-pyrazino[1',2': 4,5] pyrazino[2,3-c] pyridazin-8-yl) methyl)-3-azabicyclo[3.1.0] hexan-3-yl) methyl) piperidin-1-yl) isoindoline-1,3-dione;

2-(2,6-dioxopiperidin-3-yl)-5-(4-fluoro-4-((4-(((S)-2-(2-hydroxyphenyl)-5,6,6a,7,9,10-hexahydro-8H-pyrazino [1',2': 4,5] pyrazino[2,3-c]pyridazin-8-yl) methyl) piperidin-1-yl) methyl) piperidin-1-yl) isoindoline-1,3-dione;

2-(2,6-dioxopiperidin-3-yl)-5-(2-(((1R,5S,6s)-6-(((S)-2-(2-hydroxyphenyl)-5,6,6a,7,9,10-hexahydro-8H-pyrazino[1',2': 4,5] pyrazino[2,3-c]pyridazin-8-yl)

methyl)-3-azabicyclo[3.1.0]hexan-3-yl)methyl)morpholino) isoindoline-1,3-dione;

2-(2,6-dioxopiperidin-3-yl)-5-(4-hydroxy-4-((4-(((S)-2-(2-hydroxyphenyl)-5,6,6a,7,9,10-hexahydro-8H-pyrazino[1',2': 4,5] pyrazino[2,3-c]pyridazin-8-yl) methyl) piperidin-1-yl) methyl) piperidin-1-yl) isoindoline-1,3-dione;

2-(2,6-dioxopiperidin-3-yl)-5-((S)-2-(((1R,5S,6R)-6-(((S)-2-(2-hydroxyphenyl)-5,6,6a, 7,9,10-hexahydro-8H-pyrazino[1',2': 4,5] pyrazino[2,3-c]pyridazin-8-yl) methyl)-3-azabicyclo[3.1.0] hexan-3-yl) methyl) morpholino) isoindoline-1,3-dione;

2-(2,6-dioxopiperidin-3-yl)-5-((R)-2-(((1R,5S,6S)-6-(((S)-2-(2-hydroxyphenyl)-5,6,6a, 7,9,10-hexahydro-8H-pyrazino[1',2': 4,5] pyrazino[2,3-c]pyridazin-8-yl) methyl)-3-azabicyclo[3.1.0] hexan-3-yl) methyl) morpholino) isoindoline-1,3-dione;

2-(2,6-dioxopiperidin-3-yl)-5-(8-(((1R,5S,6r)-6-(((S)-2-(2-hydroxyphenyl)-5,6,6a,7,9,10-hexahydro-8H-pyrazino[1',2': 4,5] pyrazino[2,3-c]pyridazin-8-yl) methyl)-3-azabicyclo[3.1.0]hexan-3-yl) methyl)-3-azabicyclo[3.2.1] octan-3-yl) isoindoline-1,3-dione;

3-(6-(4-(((1R,5S,6r)-6-(((6aS,9S)-2-(2-hydroxyphenyl)-9-methyl-5,6,6a,7,9,10-hexahydro-8H-pyrazino[1',2': 4,5] pyrazino[2,3-c]pyridazin-8-yl) methyl)-3-azabicyclo[3.1.0]hexan-3-yl) methyl) piperidin-1-yl)-1-oxoisoindolin-2-yl) piperidine-2,6-dione;

5-(4,4-difluoro-3-(((1R,5S,6r)-6-(((S)-2-(2-hydroxyphenyl)-5,6,6a,7,9,10-hexahydro-8H-pyrazino[1',2': 4,5] pyrazino[2,3-c]pyridazin-8-yl) methyl)-3-azabicyclo [3.1.0] hexan-3-yl) methyl) piperidin-1-yl)-2-(2,6-dioxopiperidin-3-yl) isoindoline-1,3-dione;

2-(2,6-dioxopiperidin-3-yl)-5-(3-(((1R,5S,6r)-6-(((S)-2-(2-hydroxyphenyl)-5,6,6a,7,9,10-hexahydro-8H-pyrazino[1',2': 4,5] pyrazino[2,3-c]pyridazin-8-yl) methyl)-3-azabicyclo[3.1.0]hexan-3-yl) methyl)-4-methylpiperazin-1-yl) isoindoline-1,3-dione;

3-(5-(4-(((1R,5S,6r)-6-(((6aS,9S)-2-(2-hydroxyphenyl)-9-methyl-5,6,6a, 7,9,10-hexahydro-8H-pyrazino[1',2': 4,5] pyrazino[2,3-c]pyridazin-8-yl) methyl)-3-azabicyclo[3.1.0]hexan-3-yl) methyl) piperidin-1-yl)-1-oxoisoindolin-2-yl) piperidine-2,6-dione;

2-(2,6-dioxopiperidin-3-yl)-5-(2-((1R,5S,6s)-6-(((S)-2-(2-hydroxyphenyl)-5,6,6a,7,9,10-hexahydro-8H-pyrazino[1',2': 4,5] pyrazino[2,3-c]pyridazin-8-yl) methyl)-3-azabicyclo[3.1.0]hexan-3-yl)-5,7-dihydro-6H-pyrrolo [3,4-d]pyrimidin-6-yl) isoindoline-1,3-dione;

2-(2,6-dioxopiperidin-3-yl)-5-(2-(((1R,5S,6s)-6-(((S)-2-(2-hydroxyphenyl)-5,6,6a,7,9,10-hexahydro-8H-pyrazino[1',2': 4,5] pyrazino[2,3-c]pyridazin-8-yl) methyl)-3-azabicyclo[3.1.0]hexan-3-yl) methyl)-2-methylmorpholino) isoindoline-1,3-dione;

2-(2,6-dioxopiperidin-3-yl)-5-(4-((2-((S)-2-(2-hydroxyphenyl)-5,6,6a,7,9,10-hexahydro-8H-pyrazino[1',2': 4,5] pyrazino[2,3-c]pyridazin-8-yl)-5,8-dihydropyrido [3,4-d]pyrimidin-7 (6H)-yl) methyl) piperidin-1-yl) isoindoline-1,3-dione;

3-(6-(4-((2-((S)-2-(2-hydroxyphenyl)-5,6,6a,7,9,10-hexahydro-8H-pyrazino[1',2': 4,5]pyrazino[2,3-c] pyridazin-8-yl)-5,7-dihydro-6H-pyrrolo [3,4-d]pyrimidin-6-yl) methyl) piperidin-1-yl)-1-oxoisoindolin-2-yl) piperidine-2,6-dione;

3-(5-(2-(4-((S)-2-(2-hydroxyphenyl)-5,6,6a, 7,9,10-hexahydro-8H-pyrazino[1',2': 4,5]pyrazino[2,3-c] pyridazin-8-yl)-[1,4'-bipiperidin]-1'-yl) ethyl)-1-oxoisoindolin-2-yl) piperidine-2,6-dione;

3-(5-((4-((S)-2-(2-hydroxyphenyl)-5,6,6a,7,9,10-hexahydro-8H-pyrazino[1',2': 4,5]pyrazino[2,3-c] pyridazin-8-yl)-[1,4'-bipiperidin]-1'-yl) methyl)-1-oxoisoindolin-2-yl) piperidine-2,6-dione;

3-(5-((4-(2-(2-((S)-2-(2-hydroxyphenyl)-5,6,6a,7,9,10-hexahydro-8H-pyrazino[1',2': 4,5]pyrazino[2,3-c] pyridazin-8-yl)pyrimidin-5-yl) ethyl) piperidin-1-yl) methyl)-1-oxoisoindolin-2-yl) piperidine-2,6-dione;

3-(5-((4-(3-(4-((S)-2-(2-hydroxyphenyl)-5,6,6a,7,9,10-hexahydro-8H-pyrazino[1',2': 4,5]pyrazino[2,3-c] pyridazin-8-yl) piperidin-1-yl) propyl) piperidin-1-yl) methyl)-1-oxoisoindolin-2-yl) piperidine-2,6-dione;

2-(2,6-dioxopiperidin-3-yl)-4-(4-((S)-2-(2-hydroxyphenyl)-5,6,6a,7,9,10-hexahydro-8H-pyrazino[1',2': 4,5] pyrazino[2,3-c]pyridazin-8-yl)-[1,4'-bipiperidin]-1'-yl) isoindoline-1,3-dione;

2-(2,6-dioxopiperidin-3-yl)-4-(4-(2-(4-((S)-2-(2-hydroxyphenyl)-5,6,6a,7,9,10-hexahydro-8H-pyrazino [1',2': 4,5] pyrazino[2,3-c]pyridazin-8-yl) piperidin-1-yl) ethoxy) piperidin-1-yl) isoindoline-1,3-dione;

2-(2,6-dioxopiperidin-3-yl)-4-((2-(4-((S)-2-(2-hydroxyphenyl)-5,6,6a,7,9,10-hexahydro-8H-pyrazino[1',2': 4,5] pyrazino[2,3-c]pyridazin-8-yl) piperidin-1-yl) ethyl) (methyl) amino) isoindoline-1,3-dione;

2-(2,6-dioxopiperidin-3-yl)-4-(4-(3-(4-((S)-2-(2-hydroxyphenyl)-5,6,6a,7,9,10-hexahydro-8H-pyrazino [1',2': 4,5] pyrazino[2,3-c]pyridazin-8-yl) piperidin-1-yl) propyl) piperazin-1-yl) isoindoline-1,3-dione;

2-(2,6-dioxopiperidin-3-yl)-4-((3-(4-((S)-2-(2-hydroxyphenyl)-5,6,6a,7,9,10-hexahydro-8H-pyrazino[1',2': 4,5] pyrazino[2,3-c]pyridazin-8-yl) piperidin-1-yl) propyl) amino) isoindoline-1,3-dione;

2-(2,6-dioxopiperidin-3-yl)-4-(((S)-1-(4-((S)-2-(2-hydroxyphenyl)-5,6,6a,7,9,10-hexahydro-8H-pyrazino [1',2': 4,5] pyrazino[2,3-c]pyridazin-8-yl) piperidin-1-yl) propan-2-yl) amino) isoindoline-1,3-dione;

2-(2,6-dioxopiperidin-3-yl)-4-(4-(3-(9-((S)-2-(2-hydroxyphenyl)-5,6,6a,7,9,10-hexahydro-8H-pyrazino [1',2': 4,5] pyrazino[2,3-c]pyridazin-8-yl)-3-azaspiro [5.5] undecan-3-yl) propyl) piperidin-1-yl) isoindoline-1,3-dione;

2-(2,6-dioxopiperidin-3-yl)-4-(4-(3-(3-fluoro-4-((S)-2-(2-hydroxyphenyl)-5,6,6a,7,9,10-hexahydro-8H-pyrazino[1',2': 4,5] pyrazino[2,3-c]pyridazin-8-yl) piperidin-1-yl) propyl) piperidin-1-yl) isoindoline-1,3-dione;

2-(2,6-dioxopiperidin-3-yl)-5-(4-((S)-2-(((S)-2-(2-hydroxyphenyl)-5,6,6a,7,9,10-hexahydro-8H-pyrazino [1',2': 4,5] pyrazino[2,3-c]pyridazin-8-yl) methyl) morpholino) piperidin-1-yl) isoindoline-1,3-dione;

2-(2,6-dioxopiperidin-3-yl)-5-(4-(((R)-2-(((S)-2-(2-hydroxyphenyl)-5,6,6a,7,9,10-hexahydro-8H-pyrazino [1',2': 4,5] pyrazino[2,3-c]pyridazin-8-yl) methyl) morpholino) methyl) piperidin-1-yl) isoindoline-1,3-dione;

2-(2,6-dioxopiperidin-3-yl)-5-(4-(((1R,3s)-3-(((S)-2-(2-hydroxyphenyl)-5,6,6a,7,9,10-hexahydro-8H-pyrazino [1',2': 4,5] pyrazino[2,3-c]pyridazin-8-yl) methyl) cyclobutyl) amino) piperidin-1-yl) isoindoline-1,3-dione;

2-(2,6-dioxopiperidin-3-yl)-5-(4-(((1S,3r)-3-(((S)-2-(2-hydroxyphenyl)-5,6,6a,7,9,10-hexahydro-8H-pyrazino [1',2': 4,5] pyrazino[2,3-c]pyridazin-8-yl) methyl)cyclobutyl) amino) piperidin-1-yl) isoindoline-1,3-dione;

2-(2,6-dioxopiperidin-3-yl)-5-(4-((((1R,3s)-3-(((S)-2-(2-hydroxyphenyl)-5,6,6a,7,9,10-hexahydro-8H-pyrazino

[1',2': 4,5] pyrazino[2,3-c]pyridazin-8-yl) methyl) cyclobutyl) amino) methyl)piperidin-1-yl)isoindoline-1,3-dione;

2-(2,6-dioxopiperidin-3-yl)-5-(3-(((S)-2-(((S)-2-(2-hydroxyphenyl)-5,6,6a,7,9,10-hexahydro-8H-pyrazino [1',2': 4,5] pyrazino[2,3-c]pyridazin-8-yl) methyl)morpholino) methyl)piperidin-1-yl)isoindoline-1,3-dione;

(6aS)—N-(1-((1-(2-(2,6-dioxopiperidin-3-yl)-1,3-dioxoisoindolin-5-yl) piperidin-4-yl) methyl) piperidin-4-yl)-2-(2-hydroxyphenyl)-5,6,6a,7,9,10-hexahydro-8H-pyrazino[1',2': 4,5]pyrazino[2,3-c]pyridazine-8-carboxamide;

2-(2,6-dioxopiperidin-3-yl)-5-(4-(((4-((S)-2-(2-hydroxyphenyl)-6,6a,7,8,9,10-hexahydro-5H-pyrazino[1',2': 4,5] pyrazino[2,3-c]pyridazine-8-carbonyl) bicyclo [2.2.2] octan-1-yl) amino) methyl) piperidin-1-yl) isoindoline-1,3-dione;

2-(2,6-dioxopiperidin-3-yl)-5-(3-((4-((S)-2-(2-hydroxyphenyl)-6,6a,7,8,9,10-hexahydro-5H-pyrazino[1',2': 4,5] pyrazino[2,3-c]pyridazine-8-carbonyl) piperazin-1-yl) methyl) azetidin-1-yl) isoindoline-1,3-dione;

1-((1-(2-(2,6-dioxopiperidin-3-yl)-1-oxoisoindolin-5-yl) piperidin-4-yl) methyl) piperidin-4-yl (6aS)-2-(2-hydroxyphenyl)-5,6,6a, 7,9,10-hexahydro-8H-pyrazino [1',2': 4,5] pyrazino[2,3-c] pyridazine-8-carboxylate;

3-(5-(4-(((4-((S)-2-(2-hydroxyphenyl)-6,6a,7,8,9,10-hexahydro-5H-pyrazino[1',2': 4,5]pyrazino[2,3-c] pyridazine-8-carbonyl) bicyclo[2.2.2] octan-1-yl) amino) methyl) piperidin-1-yl)-1-oxoisoindolin-2-yl) piperidine-2,6-dione;

1-((1-(2-(2,6-dioxopiperidin-3-yl)-3-oxoisoindolin-5-yl) piperidin-4-yl) methyl) piperidin-4-yl (6aS)-2-(2-hydroxyphenyl)-5,6,6a,7,9,10-hexahydro-8H-pyrazino [1',2': 4,5] pyrazino[2,3-c] pyridazine-8-carboxylate;

2-(2,6-dioxopiperidin-3-yl)-5-(3-((4-((S)-2-(2-hydroxyphenyl)-6,6a,7,8,9,10-hexahydro-5H-pyrazino[1',2': 4,5] pyrazino[2,3-c]pyridazine-8-carbonyl) piperidin-1-yl) methyl) azetidin-1-yl) isoindoline-1,3-dione;

3-(5-(4-((4-((S)-2-(2-hydroxyphenyl)-6,6a,7,8,9,10-hexahydro-5H-pyrazino[1',2': 4,5]pyrazino[2,3-c] pyridazine-8-carbonyl)-1,4-diazepan-1-yl) methyl) piperidin-1-yl)-1-oxoisoindolin-2-yl) piperidine-2,6-dione;

2-(2,6-dioxopiperidin-3-yl)-5-(4-((4-(((S)-2-(2-hydroxyphenyl)-5,6,6a,7,9,10-hexahydro-8H-pyrazino[1',2': 4,5] pyrazino[2,3-c]pyridazin-8-yl) methyl) piperidin-1-yl) methyl)-3,3-dimethylpiperidin-1-yl) isoindoline-1,3-dione;

2-(2,6-dioxopiperidin-3-yl)-5-(4-(((1R,5S,6s)-6-(((S)-2-(2-hydroxyphenyl)-5,6,6a,7,9,10-hexahydro-8H-pyrazino[1',2': 4,5] pyrazino[2,3-c]pyridazin-8-yl) methyl)-3-azabicyclo[3.1.0]hexan-3-yl) methyl)-4-methoxypiperidin-1-yl) isoindoline-1,3-dione;

2-(2,6-dioxopiperidin-3-yl)-5-(4-((1R,5S,6s)-6-(((S)-2-(2-hydroxyphenyl)-5,6,6a,7,9,10-hexahydro-8H-pyrazino[1',2': 4,5] pyrazino[2,3-c]pyridazin-8-yl) methyl)-3-azabicyclo[3.1.0]hexan-3-yl) piperidin-1-yl) isoindoline-1,3-dione;

2-(2,6-dioxopiperidin-3-yl)-5-(4-(((1R,5S,6r)-6-(((S)-2-(2-hydroxyphenyl)-5,6,6a,7,9,10-hexahydro-8H-pyrazino[1',2': 4,5] pyrazino[2,3-c]pyridazin-8-yl) methyl)-3-azabicyclo[3.1.0]hexan-3-yl) methyl)-4-methylpiperidin-1-yl) isoindoline-1,3-dione;

3-(5-(4-(((1R,5S,6r)-6-(((S)-2-(2-hydroxyphenyl)-5,6,6a, 7,9,10-hexahydro-8H-pyrazino [1',2': 4,5] pyrazino[2, 3-c]pyridazin-8-yl) methyl)-3-azabicyclo[3.1.0]hexan-3-yl) methyl) piperidin-1-yl)-1-oxoisoindolin-2-yl) piperidine-2,6-dione;

2-(2,6-dioxopiperidin-3-yl)-5-(2-((1R,5S,6s)-6-(((S)-2-(2-hydroxyphenyl)-5,6,6a,7,9,10-hexahydro-8H-pyrazino[1',2': 4,5] pyrazino[2,3-c]pyridazin-8-yl) methyl)-3-azabicyclo[3.1.0]hexan-3-yl)-7-azaspiro [3.5] nonan-7-yl) isoindoline-1,3-dione;

2-(2,6-dioxopiperidin-3-yl)-5-(9-(2-((S)-2-(2-hydroxyphenyl)-5,6,6a,7,9,10-hexahydro-8H-pyrazino[1',2': 4,5] pyrazino[2,3-c]pyridazin-8-yl) ethyl)-2,9-diazaspiro [5.5] undecan-2-yl) isoindoline-1,3-dione;

3-(6-(4-((4-((S)-2-(2-hydroxyphenyl)-6,6a,7,8,9,10-hexahydro-5H-pyrazino[1',2': 4,5]pyrazino[2,3-c] pyridazine-8-carbonyl) piperazin-1-yl) methyl) piperidin-1-yl)-1-oxoisoindolin-2-yl) piperidine-2,6-dione;

3-(6-(4-(((1R,5S,6r)-6-((S)-2-(2-hydroxyphenyl)-6,6a,7,8,9,10-hexahydro-5H-pyrazino [1',2': 4,5] pyrazino[2,3-c]pyridazine-8-carbonyl)-3-azabicyclo[3.1.0] hexan-3-yl) methyl) piperidin-1-yl)-1-oxoisoindolin-2-yl) piperidine-2,6-dione;

2-(2,6-dioxopiperidin-3-yl)-5-((3aS, 7aS)-2-(4-((S)-2-(2-hydroxyphenyl)-6,6a,7,8,9,10-hexahydro-5H-pyrazino [1',2': 4,5] pyrazino[2,3-c]pyridazine-8-carbonyl) cyclohexyl) octahydro-5H-pyrrolo [3,4-c]pyridin-5-yl) isoindoline-1,3-dione;

2-(2,6-dioxopiperidin-3-yl)-5-((3aS,6aS)-5-(4-((S)-2-(2-hydroxyphenyl)-6,6a,7,8,9,10-hexahydro-5H-pyrazino [1',2': 4,5] pyrazino[2,3-c]pyridazine-8-carbonyl) cyclohexyl) hexahydropyrrolo [3,4-c] pyrrol-2 (1H)-yl) isoindoline-1,3-dione;

3-(6-(4-((4-((6aS,9S)-2-(2-hydroxyphenyl)-9-methyl-6, 6a,7,8,9,10-hexahydro-5H-pyrazino[1',2': 4,5] pyrazino[2,3-c]pyridazine-8-carbonyl) piperazin-1-yl) methyl)piperidin-1-yl)-1-oxoisoindolin-2-yl)piperidine-2,6-dione;

3-(6-(4-((4-((S)-2-(2-hydroxyphenyl)-6,6a,7,8,9,10-hexahydro-5H-pyrazino[1',2': 4,5]pyrazino[2,3-c] pyridazine-8-carbonyl)-3-(trifluoromethyl) piperazin-1-yl) methyl) piperidin-1-yl)-1-oxoisoindolin-2-yl) piperidine-2,6-dione;

3-(6-(4-(((6-((S)-2-(2-hydroxyphenyl)-6,6a,7,8,9,10-hexahydro-5H-pyrazino[1',2': 4,5]pyrazino[2,3-c] pyridazine-8-carbonyl)-2,6-diazaspiro [3.3]heptan-2-yl) methyl) piperidin-1-yl)-1-oxoisoindolin-2-yl) piperidine-2,6-dione;

3-(6-(4-((4-((S)-2-(2-hydroxyphenyl)-6,6a,7,8,9,10-hexahydro-5H-pyrazino[1',2': 4,5]pyrazino[2,3-c] pyridazine-8-carbonyl)-2-(trifluoromethyl) piperazin-1-yl) methyl) piperidin-1-yl)-1-oxoisoindolin-2-yl) piperidine-2,6-dione;

3-(6-(4-((3-((S)-2-(2-hydroxyphenyl)-6,6a,7,8,9,10-hexahydro-5H-pyrazino[1',2': 4,5]pyrazino[2,3-c] pyridazine-8-carbonyl)-3,8-diazabicyclo[3.2.1] octan-8-yl) methyl) piperidin-1-yl)-1-oxoisoindolin-2-yl) piperidine-2,6-dione;

3-(6-(4-((4-((S)-2-(2-hydroxyphenyl)-6,6a,7,8,9,10-hexahydro-5H-pyrazino[1',2': 4,5]pyrazino[2,3-c] pyridazine-8-carbonyl)-3-methylpiperazin-1-yl) methyl) piperidin-1-yl)-1-oxoisoindolin-2-yl) piperidine-2,6-dione;

3-(6-(4-((4-((S)-2-(2-hydroxyphenyl)-6,6a,7,8,9,10-hexahydro-5H-pyrazino[1',2': 4,5]pyrazino[2,3-c] pyridazine-8-carbonyl)-3,3-dimethylpiperazin-1-yl) methyl) piperidin-1-yl)-1-oxoisoindolin-2-yl) piperidine-2,6-dione;

3-(6-(4-((4-((S)-2-(2-hydroxyphenyl)-6,6a,7,8,9,10-hexahydro-5H-pyrazino[1',2': 4,5]pyrazino[2,3-c]pyridazine-8-carbonyl)-2-methylpiperazin-1-yl) methyl) piperidin-1-yl)-1-oxoisoindolin-2-yl) piperidine-2,6-dione;

3-(6-(3-((4-((S)-2-(2-hydroxyphenyl)-6,6a,7,8,9,10-hexahydro-5H-pyrazino[1',2': 4,5]pyrazino[2,3-c]pyridazine-8-carbonyl) piperazin-1-yl) methyl) azetidin-1-yl)-1-oxoisoindolin-2-yl) piperidine-2,6-dione;

3-(6-(3-(((1R,5S,6r)-6-(((S)-2-(2-hydroxyphenyl)-5,6,6a,7,9,10-hexahydro-8H-pyrazino [1',2': 4,5] pyrazino[2,3-c]pyridazin-8-yl) methyl)-3-azabicyclo[3.1.0] hexan-3-yl) methyl) azetidin-1-yl)-1-oxoisoindolin-2-yl) piperidine-2,6-dione;

2-(2,6-dioxopiperidin-3-yl)-5-(3-(((1R,5S,6r)-6-(((S)-2-(2-hydroxyphenyl)-5,6,6a, 7,9,10-hexahydro-8H-pyrazino[1',2': 4,5] pyrazino[2,3-c]pyridazin-8-yl) methyl)-3-azabicyclo[3.1.0]hexan-3-yl)methyl)azetidin-1-yl)isoindoline-1,3-dione;

3-(6-(4-((3-(hydroxymethyl)-4-((S)-2-(2-hydroxyphenyl)-6,6a,7,8,9,10-hexahydro-5H-pyrazino[1',2': 4,5] pyrazino[2,3-c]pyridazine-8-carbonyl) piperazin-1-yl) methyl) piperidin-1-yl)-1-oxoisoindolin-2-yl) piperidine-2,6-dione;

3-(6-(2-((4-((S)-2-(2-hydroxyphenyl)-6,6a,7,8,9,10-hexahydro-5H-pyrazino[1',2': 4,5]pyrazino[2,3-c]pyridazine-8-carbonyl) piperazin-1-yl) methyl) morpholino)-1-oxoisoindolin-2-yl) piperidine-2,6-dione;

3-(6-(4-(((S)-4-((S)-2-(2-hydroxyphenyl)-6,6a,7,8,9,10-hexahydro-5H-pyrazino [1',2': 4,5] pyrazino[2,3-c]pyridazine-8-carbonyl)-3-methylpiperazin-1-yl) methyl) piperidin-1-yl)-1-oxoisoindolin-2-yl) piperidine-2,6-dione;

3-(6-(2-((4-((S)-2-(2-hydroxyphenyl)-6,6a,7,8,9,10-hexahydro-5H-pyrazino[1',2': 4,5]pyrazino[2,3-c]pyridazine-8-carbonyl) piperidin-1-yl) methyl) morpholino)-1-oxoisoindolin-2-yl) piperidine-2,6-dione;

3-(6-(4-(((R)-4-((S)-2-(2-hydroxyphenyl)-6,6a,7,8,9,10-hexahydro-5H-pyrazino [1',2': 4,5] pyrazino[2,3-c]pyridazine-8-carbonyl)-3-methylpiperazin-1-yl) methyl) piperidin-1-yl)-1-oxoisoindolin-2-yl) piperidine-2,6-dione;

2-(2,6-dioxopiperidin-3-yl)-5-(4-(((R)-4-((S)-2-(2-hydroxyphenyl)-6,6a, 7,8,9,10-hexahydro-5H-pyrazino [1',2': 4,5] pyrazino[2,3-c]pyridazine-8-carbonyl)-3-methylpiperazin-1-yl) methyl) piperidin-1-yl) isoindoline-1,3-dione;

2-(2,6-dioxopiperidin-3-yl)-5-(4-(((S)-4-((S)-2-(2-hydroxyphenyl)-6,6a,7,8,9,10-hexahydro-5H-pyrazino [1',2': 4,5] pyrazino[2,3-c]pyridazine-8-carbonyl)-3-methylpiperazin-1-yl) methyl) piperidin-1-yl) isoindoline-1,3-dione;

2-(2,6-dioxopiperidin-3-yl)-5-(2-((4-((S)-2-(2-hydroxyphenyl)-6,6a,7,8,9,10-hexahydro-5H-pyrazino[1',2': 4,5] pyrazino[2,3-c]pyridazine-8-carbonyl) piperazin-1-yl) methyl) morpholino) isoindoline-1,3-dione;

3-(6-(1-(2-(4-((S)-2-(2-hydroxyphenyl)-5,6,6a,7,9,10-hexahydro-8H-pyrazino[1',2': 4,5]pyrazino[2,3-c]pyridazin-8-yl) piperidin-1-yl) ethyl) piperidin-4-yl)-1-oxoisoindolin-2-yl) piperidine-2,6-dione;

3-(6-(4-(2-(4-(((S)-2-(2-hydroxyphenyl)-5,6,6a,7,9,10-hexahydro-8H-pyrazino[1',2': 4,5]pyrazino[2,3-c]pyridazin-8-yl) methyl) piperidin-1-yl) ethyl) piperazin-1-yl)-1-oxoisoindolin-2-yl) piperidine-2,6-dione;

3-(6-(1-(2-(4-(((S)-2-(2-hydroxyphenyl)-5,6,6a,7,9,10-hexahydro-8H-pyrazino[1',2': 4,5]pyrazino[2,3-c]pyridazin-8-yl) methyl) piperidin-1-yl) ethyl) piperidin-4-yl)-1-oxoisoindolin-2-yl) piperidine-2,6-dione;

3-(6-(4-(3-(4-(((S)-2-(2-hydroxyphenyl)-5,6,6a,7,9,10-hexahydro-8H-pyrazino[1',2': 4,5]pyrazino[2,3-c]pyridazin-8-yl) methyl) piperidin-1-yl) propyl) piperazin-1-yl)-1-oxoisoindolin-2-yl) piperidine-2,6-dione;

3-(6-(1-(3-(4-(((S)-2-(2-hydroxyphenyl)-5,6,6a,7,9,10-hexahydro-8H-pyrazino[1',2': 4,5]pyrazino[2,3-c]pyridazin-8-yl) methyl) piperidin-1-yl) propyl) piperidin-4-yl)-1-oxoisoindolin-2-yl) piperidine-2,6-dione;

(3-(4-(4-((S)-2-(2-hydroxyphenyl)-5,6,6a,7,9,10-hexahydro-8H-pyrazino[1',2': 4,5]pyrazino[2,3-c]pyridazin-8-yl)-[1,4'-bipiperidin]-1'-yl)-1,3-dioxoisoindolin-2-yl)-2,6-dioxopiperidin-1-yl) methyl pivalate;

2-(2,6-dioxopiperidin-3-yl)-4-(4-(3-(4-((S)-2-(2-hydroxyphenyl)-5,6,6a,7,9,10-hexahydro-8H-pyrazino [1',2': 4,5] pyrazino[2,3-c]pyridazin-8-yl)-3-methylpiperidin-1-yl) propyl) piperidin-1-yl) isoindoline-1,3-dione;

2-(2,6-dioxopiperidin-3-yl)-4-(4-(3-(3-((S)-2-(2-hydroxyphenyl)-5,6,6a,7,9,10-hexahydro-8H-pyrazino [1',2': 4,5] pyrazino[2,3-c]pyridazin-8-yl)-8-azabicyclo [3.2.1] octan-8-yl) propyl) piperidin-1-yl) isoindoline-1,3-dione;

2-(2,6-dioxopiperidin-3-yl)-4-(4-(3-(4-((S)-2-(2-hydroxyphenyl)-5,6,6a,7,9,10-hexahydro-8H-pyrazino [1',2': 4,5] pyrazino[2,3-c]pyridazin-8-yl)-2-methylpiperidin-1-yl) propyl) piperidin-1-yl) isoindoline-1,3-dione;

2-(2,6-dioxopiperidin-3-yl)-4-(4-((4-(((S)-2-(2-hydroxyphenyl)-5,6,6a,7,9,10-hexahydro-8H-pyrazino[1',2': 4,5] pyrazino[2,3-c]pyridazin-8-yl) methyl) piperidin-1-yl) methyl) piperidin-1-yl) isoindoline-1,3-dione;

2-(2,6-dioxopiperidin-3-yl)-5-(4-((4-((6-ethyl-2-(2-hydroxyphenyl)-5,6,6a, 7,9,10-hexahydro-8H-pyrazino [1',2': 4,5] pyrazino[2,3-c]pyridazin-8-yl) methyl) piperidin-1-yl) methyl) piperidin-1-yl) isoindoline-1,3-dione;

(3-(5-(4-((4-(((S)-2-(2-hydroxyphenyl)-5,6,6a,7,9,10-hexahydro-8H-pyrazino[1',2': 4,5]pyrazino[2,3-c]pyridazin-8-yl) methyl) piperidin-1-yl) methyl) piperidin-1-yl)-1,3-dioxoisoindolin-2-yl)-2,6-dioxopiperidin-1-yl) methyl dihydrogen phosphate;

(3-(5-(4-((4-(((S)-2-(2-hydroxyphenyl)-5,6,6a,7,9,10-hexahydro-8H-pyrazino[1',2': 4,5]pyrazino[2,3-c]pyridazin-8-yl) methyl) piperidin-1-yl) methyl) piperidin-1-yl)-1,3-dioxoisoindolin-2-yl)-2,6-dioxopiperidin-1-yl) methyl 1-hydroxycyclopropane-1-carboxylate;

(3-(5-(4-((4-(((S)-2-(2-hydroxyphenyl)-5,6,6a,7,9,10-hexahydro-8H-pyrazino[1',2': 4,5]pyrazino[2,3-c]pyridazin-8-yl) methyl) piperidin-1-yl) methyl) piperidin-1-yl)-1,3-dioxoisoindolin-2-yl)-2,6-dioxopiperidin-1-yl) methyl 1-aminocyclopropane-1-carboxylate;

2-(2,6-dioxopiperidin-3-yl)-5-(4-((9-(((S)-2-(2-hydroxyphenyl)-5,6,6a,7,9,10-hexahydro-8H-pyrazino[1',2': 4,5] pyrazino[2,3-c]pyridazin-8-yl) methyl)-3-oxa-7-azabicyclo[3.3.1] nonan-7-yl) methyl) piperidin-1-yl) isoindoline-1,3-dione;

2-(2,6-dioxopiperidin-3-yl)-5-(4-((7-(((S)-2-(2-hydroxyphenyl)-5,6,6a, 7,9,10-hexahydro-8H-pyrazino[1',2': 4,5] pyrazino[2,3-c]pyridazin-8-yl) methyl)-3-oxa-9-azabicyclo[3.3.1] nonan-9-yl) methyl) piperidin-1-yl) isoindoline-1,3-dione;

2-(2,6-dioxopiperidin-3-yl)-5-(4-(((3-(((S)-2-(2-hydroxyphenyl)-5,6,6a,7,9,10-hexahydro-8H-pyrazino[1',2': 4,5] pyrazino[2,3-c]pyridazin-8-yl) methyl) bicyclo [1.1.1] pentan-1-yl) amino) methyl) piperidin-1-yl) isoindoline-1,3-dione;

2-(2,6-dioxopiperidin-3-yl)-5-(4-((3-(((S)-2-(2-hydroxyphenyl)-5,6,6a,7,9,10-hexahydro-8H-pyrazino[1',2': 4,5] pyrazino[2,3-c]pyridazin-8-yl) methyl) bicyclo [1.1.1] pentan-1-yl) amino) piperidin-1-yl) isoindoline-1,3-dione;

2-(2,6-dioxopiperidin-3-yl)-5-(4-((5-(((S)-2-(2-hydroxyphenyl)-5,6,6a,7,9,10-hexahydro-8H-pyrazino[1',2': 4,5] pyrazino[2,3-c]pyridazin-8-yl) methyl)-2-azabicyclo[2.2.1]heptan-2-yl) methyl) piperidin-1-yl) isoindoline-1,3-dione;

2-(2,6-dioxopiperidin-3-yl)-5-(4-((4-(((S)-2-(2-hydroxyphenyl)-5,6,6a,7,9,10-hexahydro-8H-pyrazino[1',2': 4,5] pyrazino[2,3-c]pyridazin-8-yl) sulfonyl) piperidin-1-yl) methyl) piperidin-1-yl) isoindoline-1,3-dione;

(6aS)—N-(1-((1-(2-(2,6-dioxopiperidin-3-yl)-1,3-dioxoisoindolin-5-yl) piperidin-4-yl) methyl) piperidin-4-yl)-2-(2-hydroxyphenyl)-N-methyl-5,6,6a,7,9,10-hexahydro-8H-pyrazino[1',2': 4,5] pyrazino[2,3-c] pyridazine-8-carboxamide;

(6aS)—N-(1-((1-(2-(2,6-dioxopiperidin-3-yl)-1-oxoisoindolin-5-yl) piperidin-4-yl) methyl) piperidin-4-yl)-2-(2-hydroxyphenyl)-N-methyl-5,6,6a,7,9,10-hexahydro-8H-pyrazino[1',2': 4,5]pyrazino[2,3-c] pyridazine-8-carboxamide;

2-(2,6-dioxopiperidin-3-yl)-5-(4-(((1-((S)-2-(2-hydroxyphenyl)-6,6a,7,8,9,10-hexahydro-5H-pyrazino[1',2': 4,5] pyrazino[2,3-c]pyridazine-8-carbonyl) piperidin-4-yl) amino) methyl) piperidin-1-yl) isoindoline-1,3-dione;

2-(2,6-dioxopiperidin-3-yl)-5-(4-((1-((S)-2-(2-hydroxyphenyl)-6,6a, 7,8,9,10-hexahydro-5H-pyrazino[1',2': 4,5] pyrazino[2,3-c]pyridazine-8-carbonyl) piperidin-4-yl) amino) piperidin-1-yl) isoindoline-1,3-dione;

2-(2,6-dioxopiperidin-3-yl)-5-(4-((1-((S)-2-(2-hydroxyphenyl)-6,6a,7,8,9,10-hexahydro-5H-pyrazino[1',2': 4,5] pyrazino[2,3-c]pyridazine-8-carbonyl) piperidin-4-yl) methyl) piperazin-1-yl) isoindoline-1,3-dione;

3-(6-(1-((1-((S)-2-(2-hydroxyphenyl)-6,6a,7,8,9,10-hexahydro-5H-pyrazino[1',2': 4,5]pyrazino[2,3-c] pyridazine-8-carbonyl) piperidin-4-yl) methyl) piperidin-4-yl)-1-oxoisoindolin-2-yl) piperidine-2,6-dione;

2-(2,6-dioxopiperidin-3-yl)-5-(1-((1-((S)-2-(2-hydroxyphenyl)-6,6a,7,8,9,10-hexahydro-5H-pyrazino[1',2': 4,5] pyrazino[2,3-c]pyridazine-8-carbonyl) piperidin-4-yl) methyl) piperidin-4-yl) isoindoline-1,3-dione;

2-(2,6-dioxopiperidin-3-yl)-5-((1-((1-((S)-2-(2-hydroxyphenyl)-6,6a,7,8,9,10-hexahydro-5H-pyrazino[1',2': 4,5] pyrazino[2,3-c]pyridazine-8-carbonyl) piperidin-4-yl) methyl) piperidin-4-yl) oxy) isoindoline-1,3-dione;

3-(6-(4-((1-((S)-2-(2-hydroxyphenyl)-6,6a,7,8,9,10-hexahydro-5H-pyrazino[1',2': 4,5]pyrazino[2,3-c] pyridazine-8-carbonyl) piperidin-4-yl) methyl) piperazin-1-yl)-1-oxoisoindolin-2-yl) piperidine-2,6-dione;

2-(2,6-dioxopiperidin-3-yl)-5-(6-((4-(((S)-2-(2-hydroxyphenyl)-5,6,6a,7,9,10-hexahydro-8H-pyrazino[1',2': 4,5] pyrazino[2,3-c]pyridazin-8-yl) methyl) piperidin-1-yl) methyl)-2-azaspiro [3.3]heptan-2-yl) isoindoline-1,3-dione;

2-(2,6-dioxopiperidin-3-yl)-5-(4-((4-(((S)-2-(2-hydroxyphenyl)-5,6,6a,7,9,10-hexahydro-8H-pyrazino[1',2': 4,5] pyrazino[2,3-c]pyridazin-8-yl) methyl) piperidin-1-yl) methyl)-2-methylpiperidin-1-yl) isoindoline-1,3-dione;

2-(2,6-dioxopiperidin-3-yl)-5-(4-fluoro-4-(((1R,5S,6s)-6-(((S)-2-(2-hydroxyphenyl)-5,6,6a, 7,9,10-hexahydro-8H-pyrazino[1',2': 4,5] pyrazino[2,3-c]pyridazin-8-yl) methyl)-3-azabicyclo[3.1.0] hexan-3-yl) methyl) piperidin-1-yl) isoindoline-1,3-dione;

2-(2,6-dioxopiperidin-3-yl)-5-(2-((4-(((S)-2-(2-hydroxyphenyl)-5,6,6a,7,9,10-hexahydro-8H-pyrazino[1',2': 4,5] pyrazino[2,3-c]pyridazin-8-yl) methyl) piperidin-1-yl) methyl)-7-azaspiro [3.5] nonan-7-yl) isoindoline-1,3-dione;

2-(2,6-dioxopiperidin-3-yl)-5-(3-(((1R,5S,6r)-6-(((S)-2-(2-hydroxyphenyl)-5,6,6a,7,9,10-hexahydro-8H-pyrazino[1',2': 4,5] pyrazino[2,3-c]pyridazin-8-yl) methyl)-3-azabicyclo [3.1.0] hexan-3-yl) methyl)-3-methylpyrrolidin-1-yl) isoindoline-1,3-dione;

2-(2,6-dioxopiperidin-3-yl)-5-(4-(2-((1R,5S,6r)-6-(((S)-2-(2-hydroxyphenyl)-5,6,6a, 7,9,10-hexahydro-8H-pyrazino[1',2': 4,5] pyrazino[2,3-c]pyridazin-8-yl) methyl)-3-azabicyclo[3.1.0] hexan-3-yl) ethyl) piperidin-1-yl) isoindoline-1,3-dione;

2-(2,6-dioxopiperidin-3-yl)-5-((2-((1R,5S,6r)-6-(((S)-2-(2-hydroxyphenyl)-5,6,6a,7,9,10-hexahydro-8H-pyrazino[1',2': 4,5] pyrazino[2,3-c]pyridazin-8-yl) methyl)-3-azabicyclo[3.1.0] hexan-3-yl) ethyl) amino) isoindoline-1,3-dione;

2-(2,6-dioxopiperidin-3-yl)-5-((1R,5S,6s)-6-((4-(((S)-2-(2-hydroxyphenyl)-5,6,6a,7,9,10-hexahydro-8H-pyrazino[1',2': 4,5] pyrazino[2,3-c]pyridazin-8-yl) methyl) piperidin-1-yl) methyl)-3-azabicyclo[3.1.0] hexan-3-yl) isoindoline-1,3-dione;

2-(2,6-dioxopiperidin-3-yl)-5-(4-(2-(4-((S)-2-(2-hydroxyphenyl)-5,6,6a,7,9,10-hexahydro-8H-pyrazino [1',2': 4,5] pyrazino[2,3-c]pyridazin-8-yl) piperidin-1-yl) ethyl) piperazin-1-yl) isoindoline-1,3-dione;

2-(2,6-dioxopiperidin-3-yl)-5-(3-((S)-2-(2-hydroxyphenyl)-5,6,6a,7,9,10-hexahydro-8H-pyrazino[1',2': 4,5] pyrazino[2,3-c]pyridazin-8-yl) pyrrolidin-1-yl) isoindoline-1,3-dione;

2-(2,6-dioxopiperidin-3-yl)-5-(4-(((S)-2-(2-hydroxyphenyl)-5,6,6a,7,9,10-hexahydro-8H-pyrazino[1',2': 4,5] pyrazino[2,3-c]pyridazin-8-yl) methyl) piperidin-1-yl) isoindoline-1,3-dione;

2-(2,6-dioxopiperidin-3-yl)-5-(4-((2-(4-((S)-2-(2-hydroxyphenyl)-5,6,6a,7,9,10-hexahydro-8H-pyrazino [1',2': 4,5] pyrazino[2,3-c]pyridazin-8-yl) piperidin-1-yl)ethyl) (methyl) amino) piperidin-1-yl) isoindoline-1,3-dione;

2-(2,6-dioxopiperidin-3-yl)-5-(4-(2-((R)-2-(((S)-2-(2-hydroxyphenyl)-5,6,6a,7,9,10-hexahydro-8H-pyrazino [1',2': 4,5] pyrazino[2,3-c]pyridazin-8-yl) methyl) morpholino) ethyl) piperazin-1-yl) isoindoline-1,3-dione;

2-(2,6-dioxopiperidin-3-yl)-5-[4-[1-[4-[[(10S)-4-(2-hydroxyphenyl)-1,5,6,8,12-pentazatricyclo [8.4.0.02,7] tetradeca-2 (7),3,5-trien-12-yl]methyl] piperidin-1-yl] ethyl] piperidin-1-yl] isoindole-1,3-dione;

2-(2,6-dioxopiperidin-3-yl)-5-(4-((4-(((S)-2-(2-hydroxyphenyl)-5,6,6a,7,9,10-hexahydro-8H-pyrazino[1',2': 4,5] pyrazino[2,3-c]pyridazin-8-yl) methyl)-3-methylpiperidin-1-yl) methyl) piperidin-1-yl) isoindoline-1,3-dione;

2-(2,6-dioxopiperidin-3-yl)-5-[4-[[4-[[(10S)-4-(2-hydroxyphenyl)-1,5,6,8,12-pentazatricyclo[8.4.0.02,7] tetradeca-2,4,6-trien-12-yl]methyl]-2-methylpiperidin-1-yl]methyl] piperidin-1-yl] isoindole-1,3-dione;

2-(2,6-dioxopiperidin-3-yl)-5-[4-[[4-[[(10S)-4-(2-hydroxyphenyl)-1,5,6,8,12-pentazatricyclo[8.4.0.02,7] tetradeca-2,4,6-trien-12-yl]methyl] cyclohexyl] amino] piperidin-1-yl] isoindole-1,3-dione;

2-(2,6-dioxopiperidin-3-yl)-5-fluoro-6-[4-[[4-[[(10S)-4-(2-hydroxyphenyl)-1,5,6,8,12-pentazatricyclo [8.4.0.02,7] tetradeca-2,4,6-trien-12-yl]methyl] piperidin-1-yl]methyl] piperidin-1-yl] isoindole-1,3-dione;

2-(2,6-dioxopiperidin-3-yl)-5-fluoro-6-[4-[[4-[(10S)-4-(2-hydroxyphenyl)-1,5,6,8,12-pentazatricyclo [8.4.0.02,7] tetradeca-2,4,6-trien-12-yl]methyl]-3-methylpiperidin-1-yl]methyl] piperidin-1-yl] isoindole-1,3-dione;

2-(2,6-dioxopiperidin-3-yl)-5-fluoro-6-[4-[[4-[[(10S)-4-(2-hydroxyphenyl)-1,5,6,8,12-pentazatricyclo [8.4.0.02,7] tetradeca-2,4,6-trien-12-yl]methyl]-2-methylpiperidin-1-yl]methyl] piperidin-1-yl] isoindole-1,3-dione;

2-(2,6-dioxopiperidin-3-yl)-5-[4-[[[4-[[(10S)-4-(2-hydroxyphenyl)-1,5,6,8,12-pentazatricyclo [8.4.0.02,7] tetradeca-2,4,6-trien-12-yl]methyl] cyclohexyl] amino] methyl] piperidin-1-yl] isoindole-1,3-dione;

2-(2,6-dioxopiperidin-3-yl)-5-(4-((4-(((S)-2-(2-hydroxyphenyl)-5,6,6a,7,9,10-hexahydro-8H-pyrazino[1',2':4,5] pyrazino[2,3-c]pyridazin-8-yl) methyl) cyclohexyl) methyl) piperazin-1-yl) isoindoline-1,3-dione;

2-(2,6-dioxopiperidin-3-yl)-5-fluoro-6-[4-[[8-[[(10S)-4-(2-hydroxyphenyl)-1,5,6,8,12-pentazatricyclo [8.4.0.02,7] tetradeca-2,4,6-trien-12-yl]methyl]-3-azabicyclo[3.2.1] octan-3-yl]methyl]piperidin-1-yl] isoindole-1,3-dione;

2-(2,6-dioxopiperidin-3-yl)-5-[4-[[4-[[(10S)-4-(2-hydroxyphenyl)-1,5,6,8,12-pentazatricyclo[8.4.0.02,7] tetradeca-2 (7),3,5-trien-12-yl]methyl] piperidin-1-yl] methyl]-3-methylpiperidin-1-yl] isoindole-1,3-dione;

2-(2,6-dioxopiperidin-3-yl)-5-[4-[6-[[(10S)-4-(2-hydroxyphenyl)-1,5,6,8,12-pentazatricyclo[8.4.0.02,7] tetradeca-2,4,6-trien-12-yl]methyl]-3-azabicyclo [4.1.0]heptan-3-yl] methyl]piperidin-1-yl] isoindole-1,3-dione;

2-(2,6-dioxopiperidin-3-yl)-5-[4-[[1-[[(10S)-4-(2-hydroxyphenyl)-1,5,6,8,12-pentazatricyclo[8.4.0.02,7] tetradeca-2,4,6-trien-12-yl]methyl]-3-azabicyclo [3.1.0] hexan-3-yl]methyl] piperidin-1-yl] isoindole-1,3-dione;

2-(2,6-dioxopiperidin-3-yl)-5-fluoro-6-[4-[[(1S,5R)-6-[[(10S)-4-(2-hydroxyphenyl)-1,5,6,8,12-pentazatricyclo[8.4.0.02,7] tetradeca-2,4,6-trien-12-yl]methyl]-3-azabicyclo[3.1.0]hexan-3-yl]methyl] piperidin-1-yl] isoindole-1,3-dione;

2-(2,6-dioxopiperidin-3-yl)-5-fluoro-6-[(2R,4R)-4-[[4-[[(10S)-4-(2-hydroxyphenyl)-1,5,6,8,12-pentazatricyclo [8.4.0.02,7] tetradeca-2,4,6-trien-12-yl]methyl] piperidin-1-yl]methyl]-2-methylpiperidin-1-yl] isoindole-1,3-dione;

2-(2,6-dioxopiperidin-3-yl)-5-[4-[[4-fluoro-4-[[(10S)-4-(2-hydroxyphenyl)-1,5,6,8,12-pentazatricyclo [8.4.0.02,7] tetradeca-2,4,6-trien-12-yl]methyl] piperidin-1-yl]methyl] piperidin-1-yl] isoindole-1,3-dione;

2-(2,6-dioxopiperidin-3-yl)-5-fluoro-6-[(2R,4R)-4-[[(1S,5R)-6-[[(10S)-4-(2-hydroxyphenyl)-1,5,6,8,12-pentazatricyclo[8.4.0.02,7] tetradeca-2,4,6-trien-12-yl] methyl]-3-azabicyclo[3.1.0] hexan-3-yl]methyl]-2-methylpiperidin-1-yl] isoindole-1,3-dione;

2-(2,6-dioxopiperidin-3-yl)-5-[4-[[6-[[(10S)-4-(2-hydroxyphenyl)-1,5,6,8,12-pentazatricyclo[8.4.0.02,7] tetradeca-2,4,6-trien-12-yl]methyl]-3-azabicyclo [3.2.0]heptan-3-yl] methyl] piperidin-1-yl] isoindole-1,3-dione;

1-[[1-[2-(2,6-dioxopiperidin-3-yl)-1,3-dioxoisoindol-5-yl] piperidin-4-yl]methyl]-4-[[(10S)-4-(2-hydroxyphenyl)-1,5,6,8,12-pentazatricyclo [8.4.0.02,7] tetradeca-2,4,6-trien-12-yl]methyl] piperidine-4-carbonitrile;

1-[2-(2,6-dioxopiperidin-3-yl)-1,3-dioxoisoindol-5-yl]-4-[[4-[(10S)-4-(2-hydroxyphenyl)-1,5,6,8,12-pentazatricyclo[8.4.0.02,7] tetradeca-2,4,6-trien-12-yl]methyl] piperidin-1-yl]methyl] piperidine-4-carbonitrile;

2-(2,6-dioxopiperidin-3-yl)-5-[(1S,5R)-3-[[4-[[(10S)-4-(2-hydroxyphenyl)-1,5,6,8,12-pentazatricyclo [8.4.0.02,7] tetradeca-2,4,6-trien-12-yl]methyl] piperidin-1-yl]methyl]-8-azabicyclo[3.2.1] octan-8-yl] isoindole-1,3-dione;

5-[3,3-difluoro-4-[[4-[[(10S)-4-(2-hydroxyphenyl)-1,5,6,8,12-pentazatricyclo [8.4.0.02,7] tetradeca-2 (7),3,5-trien-12-yl]methyl] piperidin-1-yl]methyl] piperidin-1-yl]-2-(2,6-dioxopiperidin-3-yl) isoindole-1,3-dione;

5-[3,3-difluoro-4-[[(1S,5R)-6-[(10S)-4-(2-hydroxyphenyl)-1,5,6,8,12-pentazatricyclo [8.4.0.02,7] tetradeca-2 (7),3,5-trien-12-yl]methyl]-3-azabicyclo[3.1.0] hexan-3-yl] methyl] piperidin-1-yl]-2-(2,6-dioxopiperidin-3-yl) isoindole-1,3-dione;

2-(2,6-dioxopiperidin-3-yl)-5-[(2R,4R)-4-[[(1S,5R)-6-[[(10S)-4-(2-hydroxyphenyl)-1,5,6,8,12-pentazatricyclo[8.4.0.02,7] tetradeca-2,4,6-trien-12-yl]methyl]-3-azabicyclo[3.1.0]hexan-3-yl]methyl]-2-methylpiperidin-1-yl] isoindole-1,3-dione;

2-(2,6-dioxopiperidin-3-yl)-5-[(2R,4R)-4-[[4-[(10S)-4-(2-hydroxyphenyl)-1,5,6,8,12-pentazatricyclo [8.4.0.02,7] tetradeca-2,4,6-trien-12-yl]methyl] piperidin-1-yl]methyl]-2-methylpiperidin-1-yl] isoindole-1,3-dione;

2-(2,6-dioxopiperidin-3-yl)-5-[(3S,4R)-3-fluoro-4-[4-[(10S)-4-(2-hydroxyphenyl)-1,5,6,8,12-pentazatricyclo[8.4.0.02,7] tetradeca-2 (7),3,5-trien-12-yl]methyl] piperidin-1-yl]methyl] piperidin-1-yl] isoindole-1,3-dione;

2-(2,6-dioxopiperidin-3-yl)-5-[(3S,4R)-3-fluoro-4-[(1S,5R)-6-[[(10S)-4-(2-hydroxyphenyl)-1,5,6,8,12-pentazatricyclo[8.4.0.02,7] tetradeca-2 (7),3,5-trien-12-yl] methyl]-3-azabicyclo[3.1.0] hexan-3-yl]methyl] piperidin-1-yl] isoindole-1,3-dione;

2-(2,6-dioxopiperidin-3-yl)-5-[[4-[[4-[[(10S)-4-(2-hydroxyphenyl)-1,5,6,8,12-pentazatricyclo[8.4.0.02,7] tetradeca-2,4,6-trien-12-yl]methyl] piperidin-1-yl] methyl] piperidin-1-yl]methyl] isoindole-1,3-dione;

5-[3,3-difluoro-4-[6-[(10S)-4-(2-hydroxyphenyl)-1,5,6,8,12-pentazatricyclo [8.4.0.02, 7] tetradeca-2 (7),3,5-trien-12-yl]methyl]-3-azabicyclo[3.2.0]heptan-3-yl] methyl] piperidin-1-yl]-2-(2,6-dioxopiperidin-3-yl) isoindole-1,3-dione;

2-(2,6-dioxopiperidin-3-yl)-5-[6-[[4-[[(10S)-4-(2-hydroxyphenyl)-1,5,6,8,12-pentazatricyclo[8.4.0.02,7] tetradeca-2 (7),3,5-trien-12-yl]methyl] piperidin-1-yl] methyl]-3-azabicyclo[4.1.0]heptan-3-yl] isoindole-1,3-dione;

2-(2,6-dioxopiperidin-3-yl)-5-[(1S,5R)-6-[4-[[(10S)-4-(2-hydroxyphenyl)-1,5,6,8,12-pentazatricyclo [8.4.0.02,7] tetradeca-2 (7),3,5-trien-12-yl]methyl] piperidin-1-yl]-3-azabicyclo [3.2.0]heptan-3-yl] isoindole-1,3-dione;

5-[3,3-difluoro-4-[[4-[[(10S)-4-(2-hydroxyphenyl)-1,5,6,8,12-pentazatricyclo [8.4.0.02, 7] tetradeca-2 (7),3,5-trien-12-yl]methyl] piperidin-1-yl]methyl] pyrrolidin-1-yl]-2-(2,6-dioxopiperidin-3-yl) isoindole-1,3-dione;

2-(2,6-dioxopiperidin-3-yl)-5-[(3R,4S)-3-fluoro-4-[(1S,5R)-6-[(10S)-4-(2-hydroxyphenyl)-1,5,6,8,12-pentazatricyclo[8.4.0.02,7] tetradeca-2 (7),3,5-trien-12-yl] methyl]-3-azabicyclo[3.1.0] hexan-3-yl]methyl] piperidin-1-yl] isoindole-1,3-dione;

2-(2,6-dioxopiperidin-3-yl)-5-[(3R,4R)-3-fluoro-4-[[(1S,5R)-6-[(10S)-4-(2-hydroxyphenyl)-1,5,6,8,12-pentazatricyclo[8.4.0.02,7] tetradeca-2 (7),3,5-trien-12-yl] methyl]-3-azabicyclo[3.1.0] hexan-3-yl]methyl] piperidin-1-yl] isoindole-1,3-dione;

2-(2,6-dioxopiperidin-3-yl)-5-[(3R,4R)-3-fluoro-4-[[(1S,5R)-6-[(10S)-4-(2-hydroxyphenyl)-1,5,6,8,12-pentazatricyclo[8.4.0.02,7] tetradeca-2 (7),3,5-trien-12-yl] methyl]-3-azabicyclo[3.1.0] hexan-3-yl]methyl] piperidin-1-yl] isoindole-1,3-dione;

5-[3,3-difluoro-4-[[4-[(10S)-4-(2-hydroxyphenyl)-1,5,6,8,12-pentazatricyclo [8.4.0.02, 7] tetradeca-2 (7),3,5-triene-12-carbonyl] piperazin-1-yl]methyl] piperidin-1-yl]-2-(2,6-dioxopiperidin-3-yl) isoindole-1,3-dione;

5-[3,3-difluoro-4-[4-[(10S)-4-(2-hydroxyphenyl)-1,5,6,8,12-pentazatricyclo[8.4.0.02,7] tetradeca-2 (7),3,5-triene-12-carbonyl] piperidin-1-yl]methyl] piperidin-1-yl]-2-(2,6-dioxopiperidin-3-yl) isoindole-1,3-dione;

2-(2,6-dioxopiperidin-3-yl)-5-(4-(((1R,5S,6r)-6-(((S)-2-(2-hydroxyphenyl)-5,6,6a,7,9,10-hexahydro-8H-pyrazino[1',2': 4,5] pyrazino[2,3-c]pyridazin-8-yl) methyl)-3-azabicyclo[3.1.0] hexan-3-yl) methyl)-3-methylpiperidin-1-yl) isoindoline-1,3-dione;

2-(2,6-dioxopiperidin-3-yl)-5-(4-(((1R,5S,6r)-6-(((S)-2-(2-hydroxyphenyl)-5,6,6a, 7,9,10-hexahydro-8H-pyrazino[1',2': 4,5] pyrazino[2,3-c]pyridazin-8-yl) methyl)-3-azabicyclo[3.1.0] hexan-3-yl) methyl)-3-methylpiperidin-1-yl) isoindoline-1,3-dione;

2-(2,6-dioxopiperidin-3-yl)-5-[(3R,4R)-3-fluoro-4-[[(1S,5R)-6-[(10S, 13S)-4-(2-hydroxyphenyl)-13-methyl-1,5,6,8,12-pentazatricyclo [8.4.0.02,7] tetradeca-2 (7),3,5-trien-12-yl]methyl]-3-azabicyclo[3.1.0] hexan-3-yl] methyl] piperidin-1-yl] isoindole-1,3-dione;

2-(2,6-dioxopiperidin-3-yl)-5-[(3S,4S)-3-fluoro-4-[(1S,5R)-6-[(10S)-4-(2-hydroxyphenyl)-1,5,6,8,12-pentazatricyclo[8.4.0.02,7] tetradeca-2 (7),3,5-trien-12-yl] methyl]-3-azabicyclo[3.1.0] hexan-3-yl]methyl] piperidin-1-yl] isoindole-1,3-dione;

2-(2,6-dioxopiperidin-3-yl)-5-[(3S,4S)-3-fluoro-4-[[(1S,5R)-6-[(10S)-4-(2-hydroxyphenyl)-1,5,6,8,12-pentazatricyclo[8.4.0.02,7] tetradeca-2 (7),3,5-trien-12-yl] methyl]-3-azabicyclo[3.1.0] hexan-3-yl]methyl] piperidin-1-yl] isoindole-1,3-dione;

2-(2,6-dioxopiperidin-3-yl)-5-[(3R,4R)-3-fluoro-4-[4-[(10S)-4-(2-hydroxyphenyl)-1,5,6,8,12-pentazatricyclo[8.4.0.02,7] tetradeca-2 (7),3,5-triene-12-carbonyl] piperidin-1-yl] methyl] piperidin-1-yl] isoindole-1,3-dione;

3-(6-((3R,4R)-3-fluoro-4-(((1R,5S,6R)-6-(((S)-2-(2-hydroxyphenyl)-5,6,6a,7,9,10-hexahydro-8H-pyrazino [1',2': 4,5] pyrazino[2,3-c]pyridazin-8-yl) methyl)-3-azabicyclo[3.1.0]hexan-3-yl) methyl) piperidin-1-yl)-1-oxoisoindolin-2-yl) piperidine-2,6-dione;

3-[5-[(3R,4R)-3-fluoro-4-[[(1S,5R)-6-[[(10S, 13S)-4-(2-hydroxyphenyl)-13-methyl-1,5,6,8,12-pentazatricyclo [8.4.0.02, 7] tetradeca-2,4,6-trien-12-yl]methyl]-3-azabicyclo[3.1.0]hexan-3-yl]methyl] piperidin-1-yl]-3-oxo-1H-isoindol-2-yl] piperidine-2,6-dione;

3-[5-[(3R,4R)-3-fluoro-4-[[4-[(10S)-4-(2-hydroxyphenyl)-1,5,6,8,12-pentazatricyclo [8.4.0.02, 7] tetradeca-2,4,6-triene-12-carbonyl] piperazin-1-yl]methyl] piperidin-1-yl]-3-oxo-1H-isoindol-2-yl] piperidine-2,6-dione;

2-(2,6-dioxopiperidin-3-yl)-5-[(3R,4R)-3-fluoro-4-[[4-[(10S)-4-(2-hydroxyphenyl)-1,5,6,8,12-pentazatricyclo[8.4.0.02, 7] tetradeca-2 (7),3,5-triene-12-carbonyl] piperazin-1-yl] methyl] piperidin-1-yl] isoindole-1,3-dione;

3-(5-(2-(4-(((S)-2-(2-hydroxyphenyl)-5,6,6a,7,9,10-hexahydro-8H-pyrazino[1',2': 4,5] pyrazino[2,3-c] pyridazin-8-yl) methyl) piperidin-1-yl) ethoxy)-1-oxoisoindolin-2-yl) piperidine-2,6-dione;

3-(5-(1-(1-(3-((S)-2-(2-hydroxyphenyl)-5,6,6a,7,9,10-hexahydro-8H-pyrazino[1',2': 4,5]pyrazino[2,3-c] pyridazin-8-yl) propyl) pyrrolidin-3-yl) piperidin-4-yl)-1-oxoisoindolin-2-yl) piperidine-2,6-dione;

3-(5-(1'-(3-((S)-2-(2-hydroxyphenyl)-5,6,6a,7,9,10-hexahydro-8H-pyrazino[1',2': 4,5]pyrazino[2,3-c] pyridazin-8-yl) propyl)-[1,4'-bipiperidin]-4-yl)-1-oxoisoindolin-2-yl) piperidine-2,6-dione;

3-(5-(1'-(3-((S)-2-(2-hydroxyphenyl)-5,6,6a,7,9,10-hexahydro-8H-pyrazino[1',2': 4,5]pyrazino[2,3-c] pyridazin-8-yl) propyl)-[1,3'-bipiperidin]-4-yl)-1-oxoisoindolin-2-yl) piperidine-2,6-dione;

3-(5-(1'-(2-((S)-2-(2-hydroxyphenyl)-5,6,6a,7,9,10-hexahydro-8H-pyrazino[1',2': 4,5]pyrazino[2,3-c] pyridazin-8-yl) ethyl)-[1,3'-bipiperidin]-4-yl)-1-oxoisoindolin-2-yl) piperidine-2,6-dione;

3-(5-(1'-(2-((S)-2-(2-hydroxyphenyl)-5,6,6a,7,9,10-hexahydro-8H-pyrazino[1',2': 4,5] pyrazino[2,3-c] pyridazin-8-yl) ethyl)-[1,4'-bipiperidin]-4-yl)-1-oxoisoindolin-2-yl) piperidine-2,6-dione;

3-(5-(1-((1-(2-((S)-2-(2-hydroxyphenyl)-5,6,6a, 7,9,10-hexahydro-8H-pyrazino[1',2': 4,5]pyrazino[2,3-c] pyridazin-8-yl) ethyl) piperidin-4-yl) methyl) piperidin-4-yl)-1-oxoisoindolin-2-yl) piperidine-2,6-dione;

(3R)-3-(5-((1-(4-((S)-2-(2-hydroxyphenyl)-5,6,6a,7,9,10-hexahydro-8H-pyrazino [1',2': 4,5] pyrazino[2,3-c] pyridazin-8-yl) piperidin-1-yl) propan-2-yl) oxy)-1-oxoisoindolin-2-yl) piperidine-2,6-dione;

(3R)-3-(5-(2-(4-((S)-2-(2-hydroxyphenyl)-5,6,6a,7,9,10-hexahydro-8H-pyrazino [1',2': 4,5] pyrazino[2,3-c] pyridazin-8-yl) piperidin-1-yl) propoxy)-1-oxoisoindolin-2-yl) piperidine-2,6-dione;

2-(2,6-dioxopiperidin-3-yl)-5-((1-((1-(2-((S)-2-(2-hydroxyphenyl)-5,6,6a,7,9,10-hexahydro-8H-pyrazino [1',2': 4,5] pyrazino[2,3-c]pyridazin-8-yl) ethyl) piperidin-4-yl) methyl) piperidin-4-yl) oxy) isoindoline-1,3-dione;

3-(5-(4-((1-(2-((S)-2-(2-hydroxyphenyl)-5,6,6a,7,9,10-hexahydro-8H-pyrazino[1',2': 4,5]pyrazino[2,3-c] pyridazin-8-yl) ethyl) piperidin-4-yl) methyl) piperazin-1-yl)-1-oxoisoindolin-2-yl) piperidine-2,6-dione;

2-(2,6-dioxopiperidin-3-yl)-5-(4-(((S)-2-(2-hydroxyphenyl)-5,6,6a,7,9,10-hexahydro-8H-pyrazino[1',2': 4,5] pyrazino[2,3-c]pyridazin-8-yl) methyl)-[1,3'-bipiperidin]-1'-yl) isoindoline-1,3-dione;

2-(2,6-dioxopiperidin-3-yl)-5-((2-(4-((S)-2-(2-hydroxyphenyl)-6,6a,7,8,9,10-hexahydro-5H-pyrazino[1',2': 4,5] pyrazino[2,3-c]pyridazine-8-carbonyl) piperazin-1-yl) ethyl) amino) isoindoline-1,3-dione;

2-(2,6-dioxopiperidin-3-yl)-5-((2-((4-((S)-2-(2-hydroxyphenyl)-5,6,6a,7,9,10-hexahydro-8H-pyrazino[1',2': 4,5] pyrazino[2,3-c]pyridazin-8-yl) cyclohexyl) (methyl) amino) ethyl) amino) isoindoline-1,3-dione;

2-(2,6-dioxopiperidin-3-yl)-5-(4-(1-(2-((S)-2-(2-hydroxyphenyl)-5,6,6a,7,9,10-hexahydro-8H-pyrazino

[1',2': 4,5] pyrazino[2,3-c]pyridazin-8-yl) ethyl) pyrrolidin-3-yl) piperazin-1-yl) isoindoline-1,3-dione;

2-(2,6-dioxopiperidin-3-yl)-5-((2-(4-((S)-2-(2-hydroxyphenyl)-6,6a,7,8,9,10-hexahydro-5H-pyrazino[1',2': 4,5] pyrazino[2,3-c]pyridazine-8-carbonyl) piperidin-1-yl) ethyl) (methyl) amino) isoindoline-1,3-dione;

2-(4-((S)-2-(2-hydroxyphenyl)-5,6,6a,7,9,10-hexahydro-8H-pyrazino[1',2': 4,5] pyrazino [2,3-c]pyridazin-8-yl) piperidin-1-yl) ethyl 4-(2-(2,6-dioxopiperidin-3-yl)-1,3-dioxoisoindolin-5-yl) piperazine-1-carboxylate;

2-(2,6-dioxopiperidin-3-yl)-5-(4-(2-(4-(((S)-2-(2-hydroxyphenyl)-5,6,6a,7,9,10-hexahydro-8H-pyrazino [1',2': 4,5] pyrazino[2,3-c]pyridazin-8-yl) methyl) piperidin-1-yl) ethyl) piperidin-1-yl) isoindoline-1,3-dione;

2-(2,6-dioxopiperidin-3-yl)-5-(3-((4-(((S)-2-(2-hydroxyphenyl)-5,6,6a,7,9,10-hexahydro-8H-pyrazino[1',2': 4,5] pyrazino[2,3-c]pyridazin-8-yl) methyl) piperidin-1-yl) methyl) pyrrolidin-1-yl) isoindoline-1,3-dione;

2-(2,6-dioxopiperidin-3-yl)-5-(4-((4-(((S)-2-(2-hydroxyphenyl)-5,6,6a,7,9,10-hexahydro-8H-pyrazino[1',2': 4,5] pyrazino[2,3-c]pyridazin-8-yl) methyl) piperidin-1-yl) methyl)-4-methylpiperidin-1-yl) isoindoline-1,3-dione;

2-(2,6-dioxopiperidin-3-yl)-5-((4-(4-(((S)-2-(2-hydroxyphenyl)-5,6,6a,7,9,10-hexahydro-8H-pyrazino[1',2': 4,5] pyrazino[2,3-c]pyridazin-8-yl) methyl) piperidin-1-yl) butyl) (methyl) amino) isoindoline-1,3-dione;

2-(2,6-dioxopiperidin-3-yl)-5-(4-((4-(3-((S)-2-(2-hydroxyphenyl)-5,6,6a,7,9,10-hexahydro-8H-pyrazino [1',2': 4,5] pyrazino[2,3-c]pyridazin-8-yl) propyl) piperidin-1-yl)methyl) piperidin-1-yl)isoindoline-1,3-dione;

2-(2,6-dioxopiperidin-3-yl)-5-(4-((4-(2-((S)-2-(2-hydroxyphenyl)-5,6,6a,7,9,10-hexahydro-8H-pyrazino [1',2': 4,5] pyrazino[2,3-c]pyridazin-8-yl) ethyl) piperidin-1-yl) methyl) piperidin-1-yl)isoindoline-1,3-dione;

3-(5-(3-((4-(((S)-2-(2-hydroxyphenyl)-5,6,6a,7,9,10-hexahydro-8H-pyrazino[1',2': 4,5]pyrazino[2,3-c] pyridazin-8-yl) methyl) piperidin-1-yl) methyl) azetidin-1-yl)-1-oxoisoindolin-2-yl) piperidine-2,6-dione;

3-(5-(4-((4-(((S)-2-(2-hydroxyphenyl)-5,6,6a,7,9,10-hexahydro-8H-pyrazino[1',2': 4,5]pyrazino[2,3-c] pyridazin-8-yl) methyl) piperidin-1-yl) methyl) piperidin-1-yl)-1-oxoisoindolin-2-yl) piperidine-2,6-dione;

3-(6-(4-(((1R,5S,6r)-6-(((S)-2-(2-hydroxyphenyl)-5,6,6a,7,9,10-hexahydro-8H-pyrazino [1',2': 4,5] pyrazino[2,3-c]pyridazin-8-yl) methyl)-3-azabicyclo[3.1.0] hexan-3-yl) methyl) piperidin-1-yl)-1-oxoisoindolin-2-yl) piperidine-2,6-dione;

3-(6-(4-((4-fluoro-4-(((S)-2-(2-hydroxyphenyl)-5,6,6a,7,9,10-hexahydro-8H-pyrazino [1',2': 4,5] pyrazino[2,3-c]pyridazin-8-yl) methyl) piperidin-1-yl) methyl) piperidin-1-yl)-1-oxoisoindolin-2-yl) piperidine-2,6-dione;

3-(6-fluoro-5-(4-((4-(((S)-2-(2-hydroxyphenyl)-5,6,6a,7,9,10-hexahydro-8H-pyrazino [1',2': 4,5] pyrazino[2,3-c]pyridazin-8-yl) methyl) piperidin-1-yl) methyl) piperidin-1-yl)-1-oxoisoindolin-2-yl) piperidine-2,6-dione;

3-(6-(4-((2-(hydroxymethyl)-4-(((S)-2-(2-hydroxyphenyl)-5,6,6a,7,9,10-hexahydro-8H-pyrazino[1',2': 4,5] pyrazino[2,3-c]pyridazin-8-yl) methyl) piperidin-1-yl) methyl) piperidin-1-yl)-1-oxoisoindolin-2-yl) piperidine-2,6-dione;

2-(2,6-dioxopiperidin-3-yl)-5-(4-((2-(hydroxymethyl)-4-(((S)-2-(2-hydroxyphenyl)-5,6,6a, 7,9,10-hexahydro-8H-pyrazino[1',2': 4,5] pyrazino[2,3-c]pyridazin-8-yl) methyl) piperidin-1-yl) methyl) piperidin-1-yl) isoindoline-1,3-dione;

3-(5-(3-(4-((S)-2-(2-hydroxyphenyl)-5,6,6a,7,9,10-hexahydro-8H-pyrazino[1',2': 4,5]pyrazino[2,3-c] pyridazin-8-yl) piperidin-1-yl) propoxy)-1-oxoisoindolin-2-yl) piperidine-2,6-dione;

3-(5-(2-(4-((S)-2-(2-hydroxyphenyl)-5,6,6a,7,9,10-hexahydro-8H-pyrazino[1',2': 4,5]pyrazino[2,3-c] pyridazin-8-yl) piperidin-1-yl) ethoxy)-1-oxoisoindolin-2-yl) piperidine-2,6-dione;

(R)-3-(5-(2-(4-((S)-2-(2-hydroxyphenyl)-5,6,6a,7,9,10-hexahydro-8H-pyrazino[1',2': 4,5]pyrazino[2,3-c] pyridazin-8-yl) piperidin-1-yl) ethoxy)-1-oxoisoindolin-2-yl) piperidine-2,6-dione;

2-(2,6-dioxopiperidin-3-yl)-5-((4-(4-((S)-2-(2-hydroxyphenyl)-5,6,6a,7,9,10-hexahydro-8H-pyrazino[1',2': 4,5] pyrazino[2,3-c]pyridazin-8-yl) piperidin-1-yl) phenyl) amino) isoindoline-1,3-dione;

2-(2,6-dioxopiperidin-3-yl)-5-(4-(4-((S)-2-(2-hydroxyphenyl)-5,6,6a,7,9,10-hexahydro-8H-pyrazino[1',2': 4,5] pyrazino[2,3-c]pyridazin-8-yl) piperidin-1-yl) phenoxy) isoindoline-1,3-dione;

2-(2,6-dioxopiperidin-3-yl)-5-((2-(4-((S)-2-(5-fluoro-2-hydroxyphenyl)-5,6,6a, 7,9,10-hexahydro-8H-pyrazino[1',2': 4,5] pyrazino[2,3-c]pyridazin-8-yl) piperidin-1-yl) ethyl) amino) isoindoline-1,3-dione;

2-(2,6-dioxopiperidin-3-yl)-5-(1-(1-(2-((S)-2-(2-hydroxyphenyl)-5,6,6a,7,9,10-hexahydro-8H-pyrazino [1',2': 4,5] pyrazino[2,3-c]pyridazin-8-yl) ethyl) pyrrolidin-3-yl) piperidin-4-yl) isoindoline-1,3-dione;

2-(2,6-dioxopiperidin-3-yl)-5-((3-(4-((S)-2-(2-hydroxyphenyl)-5,6,6a,7,9,10-hexahydro-8H-pyrazino[1',2': 4,5] pyrazino[2,3-c]pyridazin-8-yl) piperidin-1-yl) phenyl) amino) isoindoline-1,3-dione;

2-(2,6-dioxopiperidin-3-yl)-5-((1-(2-(4-((S)-2-(2-hydroxyphenyl)-5,6,6a,7,9,10-hexahydro-8H-pyrazino [1',2': 4,5] pyrazino[2,3-c]pyridazin-8-yl) piperidin-1-yl) ethyl)-1H-pyrazol-4-yl) amino) isoindoline-1,3-dione;

2-(2,6-dioxopiperidin-3-yl)-5-((2-(4-(((S)-2-(2-hydroxyphenyl)-5,6,6a,7,9,10-hexahydro-8H-pyrazino[1',2': 4,5] pyrazino[2,3-c]pyridazin-8-yl) methyl) piperidin-1-yl) ethyl) (methyl) amino) isoindoline-1,3-dione;

2-(2,6-dioxopiperidin-3-yl)-5-(4-(1-(4-(3-((S)-2-(2-hydroxyphenyl)-5,6,6a,7,9,10-hexahydro-8H-pyrazino [1',2': 4,5] pyrazino[2,3-c]pyridazin-8-yl) propyl)piperidin-1-yl) ethyl) piperidin-1-yl) isoindoline-1,3-dione;

2-(2,6-dioxopiperidin-3-yl)-5-(4-(1-(4-(3-((S)-2-(2-hydroxyphenyl)-5,6,6a,7,9,10-hexahydro-8H-pyrazino [1',2': 4,5] pyrazino[2,3-c]pyridazin-8-yl) propyl) piperidin-1-yl) ethyl) piperidin-1-yl) isoindoline-1,3-dione;

2-(2,6-dioxopiperidin-3-yl)-5-(4-((4-(1-((S)-2-(2-hydroxyphenyl)-5,6,6a,7,9,10-hexahydro-8H-pyrazino [1',2': 4,5] pyrazino[2,3-c]pyridazin-8-yl) propan-2-yl) piperidin-1-yl) methyl)piperidin-1-yl)isoindoline-1,3-dione;

3-(5-(4-((4-(((S)-2-(2-hydroxyphenyl)-5,6,6a,7,9,10-hexahydro-8H-pyrazino[1',2': 4,5]pyrazino[2,3-c] pyridazin-8-yl) methyl)-4-methylpiperidin-1-yl) methyl) piperidin-1-yl)-1-oxoisoindolin-2-yl) piperidine-2,6-dione;

3-(5-(4-((4-(((S)-2-(2-hydroxyphenyl)-5,6,6a,7,9,10-hexahydro-8H-pyrazino[1',2': 4,5]pyrazino[2,3-c]

pyridazin-8-yl) methyl)-4-methoxypiperidin-1-yl) methyl) piperidin-1-yl)-1-oxoisoindolin-2-yl) piperidine-2,6-dione;

3-(6-(4-(((1R,5S,6s)-6-(((S)-2-(2-hydroxyphenyl)-5,6,6a, 7,9,10-hexahydro-8H-pyrazino [1',2': 4,5] pyrazino[2, 3-c]pyridazin-8-yl) methyl)-3-azabicyclo[3.1.0] hexan-3-yl) methyl)-4-methoxypiperidin-1-yl)-1-oxoisoindolin-2-yl) piperidine-2,6-dione;

2-(2,6-dioxopiperidin-3-yl)-5-(4-((4-((2-(2-hydroxyphenyl)-6,6a, 7,8,9,10-hexahydro-5H-pyrido [1',2': 4,5] pyrazino[2,3-c]pyridazin-8-yl) amino) piperidin-1-yl) methyl) piperidin-1-yl) isoindoline-1,3-dione;

2-(2,6-dioxopiperidin-3-yl)-5-(4-((4-(((2-(2-hydroxyphenyl)-6,6a,7,8,9,10-hexahydro-5H-pyrido [1',2': 4,5] pyrazino[2,3-c]pyridazin-8-yl) (methyl) amino) methyl) piperidin-1-yl) methyl) piperidin-1-yl) isoindoline-1,3-dione;

3-(5-(2-(3-(((S)-2-(2-hydroxyphenyl)-5,6,6a,7,9,10-hexahydro-8H-pyrazino[1',2': 4,5]pyrazino[2,3-c] pyridazin-8-yl) methyl) piperidin-1-yl) ethoxy)-1-oxoisoindolin-2-yl) piperidine-2,6-dione;

3-(5-(2-(3-((S)-2-(2-hydroxyphenyl)-5,6,6a, 7,9,10-hexahydro-8H-pyrazino[1',2': 4,5]pyrazino[2,3-c] pyridazin-8-yl) pyrrolidin-1-yl) ethoxy)-1-oxoisoindolin-2-yl) piperidine-2,6-dione;

2-(2,6-dioxopiperidin-3-yl)-5-(4-((4-(((S)-2-(2-hydroxyphenyl)-5,6,6a,7,9,10-hexahydro-8H-pyrazino[1',2': 4,5] pyrazino[2,3-c]pyridazin-8-yl) methyl)-3,3-dimethylpiperidin-1-yl) methyl) piperidin-1-yl) isoindoline-1,3-dione;

2-(2,6-dioxopiperidin-3-yl)-5-(4-((6-(((S)-2-(2-hydroxyphenyl)-5,6,6a,7,9,10-hexahydro-8H-pyrazino[1',2': 4,5] pyrazino[2,3-c]pyridazin-8-yl) methyl)-1-methyl-3-azabicyclo[3.1.0]hexan-3-yl) methyl) piperidin-1-yl) isoindoline-1,3-dione;

2-(2,6-dioxopiperidin-3-yl)-5-(6-((1R,5S,6s)-6-(((S)-2-(2-hydroxyphenyl)-5,6,6a,7,9,10-hexahydro-8H-pyrazino[1',2': 4,5] pyrazino[2,3-c]pyridazin-8-yl) methyl)-3-azabicyclo[3.1.0]hexan-3-yl)-2-azaspiro [3.3]heptan-2-yl)isoindoline-1,3-dione;

5-(4-((3,3-difluoro-4-(((S)-2-(2-hydroxyphenyl)-5,6,6a, 7,9,10-hexahydro-8H-pyrazino [1',2': 4,5] pyrazino[2, 3-c]pyridazin-8-yl) methyl) piperidin-1-yl) methyl) piperidin-1-yl)-2-(2,6-dioxopiperidin-3-yl) isoindoline-1,3-dione;

3-(6-((3R,4R)-3-fluoro-4-((4-((S)-2-(2-hydroxyphenyl)-6,6a,7,8,9,10-hexahydro-5H-pyrazino[1',2': 4,5] pyrazino[2,3-c]pyridazine-8-carbonyl) piperidin-1-yl) methyl) piperidin-1-yl)-1-oxoisoindolin-2-yl) piperidine-2,6-dione;

3-(6-(4-((4-((S)-2-(2-hydroxyphenyl)-6,6a,7,8,9,10-hexahydro-5H-pyrazino[1',2': 4,5]pyrazino[2,3-c] pyridazine-8-carbonyl)-4,7-diazaspiro [2.5] octan-7-yl) methyl) piperidin-1-yl)-1-oxoisoindolin-2-yl) piperidine-2,6-dione;

2-(2,6-dioxopiperidin-3-yl)-5-fluoro-6-(4-((1-((S)-2-(2-hydroxyphenyl)-6,6a,7,8,9,10-hexahydro-5H-pyrazino [1',2': 4,5] pyrazino[2,3-c]pyridazine-8-carbonyl) piperidin-4-yl) methyl) piperazin-1-yl) isoindoline-1,3-dione;

3-(6-(4-((4-((S)-2-(2-hydroxyphenyl)-6,6a,7,8,9,10-hexahydro-5H-pyrazino[1',2': 4,5]pyrazino[2,3-c] pyridazine-8-carbonyl)-3-methylpiperidin-1-yl) methyl) piperidin-1-yl)-1-oxoisoindolin-2-yl) piperidine-2,6-dione;

3-(6-(4-((4-((S)-2-(2-hydroxyphenyl)-6,6a,7,8,9,10-hexahydro-5H-pyrazino[1',2': 4,5]pyrazino[2,3-c] pyridazine-8-carbonyl)-2-methylpiperidin-1-yl) methyl) piperidin-1-yl)-1-oxoisoindolin-2-yl) piperidine-2,6-dione;

3-(6-(4-((4-((S)-2-(2-hydroxyphenyl)-6,6a,7,8,9,10-hexahydro-5H-pyrazino[1',2': 4,5]pyrazino[2,3-c] pyridazine-8-carbonyl)-3,5-dimethylpiperazin-1-yl) methyl) piperidin-1-yl)-1-oxoisoindolin-2-yl) piperidine-2,6-dione;

3-(5-((S)-2-(((1R,5S,6R)-6-(((S)-2-(2-hydroxyphenyl)-5, 6,6a,7,9,10-hexahydro-8H-pyrazino[1',2': 4,5] pyrazino[2,3-c]pyridazin-8-yl) methyl)-3-azabicyclo [3.1.0] hexan-3-yl) methyl) morpholino)-1-oxoisoindolin-2-yl) piperidine-2,6-dione;

3-(5-((R)-2-(((1R,5S,6S)-6-(((S)-2-(2-hydroxyphenyl)-5, 6,6a,7,9,10-hexahydro-8H-pyrazino[1',2': 4,5] pyrazino[2,3-c]pyridazin-8-yl) methyl)-3-azabicyclo [3.1.0] hexan-3-yl) methyl) morpholino)-1-oxoisoindolin-2-yl) piperidine-2,6-dione;

2-(2,6-dioxopiperidin-3-yl)-5-(4-((3-ethyl-4-((S)-2-(2-hydroxyphenyl)-6,6a,7,8,9,10-hexahydro-5H-pyrazino [1',2': 4,5] pyrazino[2,3-c]pyridazine-8-carbonyl) piperazin-1-yl) methyl) piperidin-1-yl) isoindoline-1,3-dione;

3-(6-(4-((3-ethyl-4-((S)-2-(2-hydroxyphenyl)-6,6a,7,8,9, 10-hexahydro-5H-pyrazino [1',2': 4,5] pyrazino[2,3-c] pyridazine-8-carbonyl) piperazin-1-yl) methyl) piperidin-1-yl)-1-oxoisoindolin-2-yl) piperidine-2,6-dione;

3-(6-(4-((3-ethyl-4-((S)-2-(2-hydroxyphenyl)-6,6a,7,8,9, 10-hexahydro-5H-pyrazino [1',2': 4,5] pyrazino[2,3-c] pyridazine-8-carbonyl) piperazin-1-yl) methyl) piperidin-1-yl)-1-oxoisoindolin-2-yl) piperidine-2,6-dione;

2-(2,6-dioxopiperidin-3-yl)-5-(4-((1-((S)-2-(2-hydroxyphenyl)-6,6a, 7,8,9,10-hexahydro-5H-pyrazino[1',2': 4,5] pyrazino[2,3-c]pyridazine-8-carbonyl) piperidin-4-yl) methyl)-2-methylpiperazin-1-yl) isoindoline-1,3-dione;

2-(2,6-dioxopiperidin-3-yl)-5-(4-((4-((S)-2-(2-hydroxyphenyl)-6,6a,7,8,9,10-hexahydro-5H-pyrazino[1',2': 4,5] pyrazino[2,3-c]pyridazine-8-carbonyl)-3,5-dimethylpiperazin-1-yl) methyl) piperidin-1-yl) isoindoline-1,3-dione;

2-(2,6-dioxopiperidin-3-yl)-5-(3-((4-((S)-2-(2-hydroxyphenyl)-6,6a,7,8,9,10-hexahydro-5H-pyrazino[1',2': 4,5] pyrazino[2,3-c]pyridazine-8-carbonyl)-3,5-dimethylpiperazin-1-yl) methyl) azetidin-1-yl) isoindoline-1,3-dione;

2-(2,6-dioxopiperidin-3-yl)-5-(3-(2-(4-(((S)-2-(2-hydroxyphenyl)-5,6,6a,7,9,10-hexahydro-8H-pyrazino [1',2': 4,5] pyrazino[2,3-c]pyridazin-8-yl) methyl) piperidin-1-yl) ethyl) azetidin-1-yl) isoindoline-1,3-dione;

3-(6-(3-((4-(((S)-2-(2-hydroxyphenyl)-5,6,6a,7,9,10-hexahydro-8H-pyrazino[1',2': 4,5]pyrazino[2,3-c] pyridazin-8-yl) methyl) piperidin-1-yl) methyl) azetidin-1-yl)-1-oxoisoindolin-2-yl)piperidine-2,6-dione;

2-(2,6-dioxopiperidin-3-yl)-5-((3R,4R)-3-fluoro-4-(((1R, 5S,6R)-6-(((S)-2-(5-fluoro-2-hydroxyphenyl)-5,6,6a,7, 9,10-hexahydro-8H-pyrazino[1',2': 4,5] pyrazino[2,3-c]pyridazin-8-yl)methyl)-3-azabicyclo[3.1.0] hexan-3-yl) methyl) piperidin-1-yl) isoindoline-1,3-dione;

2-(2,6-dioxopiperidin-3-yl)-5-((3R,4R)-3-fluoro-4-(((1R, 5S,6R)-6-(((S)-2-(5-fluoro-2-hydroxyphenyl)-5,6,6a, 7,9,10-hexahydro-8H-pyrazino[1',2': 4,5] pyrazino[2, 3-c]pyridazin-8-yl)methyl)-3-azabicyclo[3.1.0] hexan-3-yl) methyl) piperidin-1-yl) isoindoline-1,3-dione;

2-(2,6-dioxopiperidin-3-yl)-5-((3R,4R)-3-fluoro-4-((4-((S)-2-(5-fluoro-2-hydroxyphenyl)-6,6a,7,8,9,10-hexahydro-5H-pyrazino[1',2': 4,5] pyrazino[2,3-c]

pyridazine-8-carbonyl)piperidin-1-yl)methyl) piperidin-1-yl)isoindoline-1,3-dione;

2-(2,6-dioxopiperidin-3-yl)-5-((3R,4R)-3-fluoro-4-((4-((S)-2-(5-fluoro-2-hydroxyphenyl)-6,6a, 7,8,9,10-hexahydro-5H-pyrazino[1',2': 4,5] pyrazino[2,3-c] pyridazine-8-carbonyl) piperidin-1-yl) methyl) piperidin-1-yl) isoindoline-1,3-dione;

2-(2,6-dioxopiperidin-3-yl)-5-((3R,4R)-3-fluoro-4-(((1R, 5S,6R)-6-(((S)-2-(2-fluoro-6-hydroxyphenyl)-5,6,6a,7, 9,10-hexahydro-8H-pyrazino[1',2': 4,5] pyrazino[2,3-c]pyridazin-8-yl) methyl)-3-azabicyclo[3.1.0] hexan-3-yl) methyl) piperidin-1-yl) isoindoline-1,3-dione;

3-(6-(4-((4-((S)-2-(5-fluoro-2-hydroxyphenyl)-6,6a,7,8, 9,10-hexahydro-5H-pyrazino[1',2': 4,5] pyrazino[2,3-c]pyridazine-8-carbonyl) piperazin-1-yl) methyl) piperidin-1-yl)-1-oxoisoindolin-2-yl) piperidine-2,6-dione;

or a pharmaceutically acceptable salt thereof.

27. A pharmaceutical composition comprising a compound according to claim 1 and a pharmaceutically acceptable excipient.

28. A method of treating cancer in a subject in need thereof comprising administering to the subject a compound of claim 1; optionally wherein the cancer is SMARCA4 deleted cancer; optionally wherein the cancer is squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas; or optionally wherein the cancer is T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

29. The method of claim 28 wherein the lung cancer is SMARCA4 deficient non-small cell lung cancer.

* * * * *